US011970486B2

(12) United States Patent
Le Bourdonnec et al.

(10) Patent No.: US 11,970,486 B2
(45) Date of Patent: Apr. 30, 2024

(54) COMPOUNDS AND USES THEREOF

(71) Applicant: JANSSEN PHARMACEUTICA NV, Beerse (BE)

(72) Inventors: Bertrand Le Bourdonnec, Northborough, MA (US); Matthew Lucas, Lexington, MA (US); Kerem Ozboya, Cambridge, MA (US); Bhaumik Pandya, Bedford, MA (US); Parcharee Tivitmahaisoon, Boston, MA (US); Iwona Wrona, Sharon, MA (US)

(73) Assignee: Janssen Pharmaceutica NV, Beerse (BE)

(*) Notice: Subject to any disclaimer, the term of this patent is extended or adjusted under 35 U.S.C. 154(b) by 0 days.

(21) Appl. No.: 16/344,195

(22) PCT Filed: Oct. 24, 2017

(86) PCT No.: PCT/US2017/058144
§ 371 (c)(1),
(2) Date: Apr. 23, 2019

(87) PCT Pub. No.: WO2018/081167
PCT Pub. Date: May 3, 2018

(65) Prior Publication Data
US 2020/0010462 A1 Jan. 9, 2020

Related U.S. Application Data

(60) Provisional application No. 62/534,990, filed on Jul. 20, 2017, provisional application No. 62/443,040, filed on Jan. 6, 2017, provisional application No. 62/412,119, filed on Oct. 24, 2016.

(51) Int. Cl.
*C07D 413/14* (2006.01)
*C07D 413/04* (2006.01)
*C07D 417/04* (2006.01)
*C07D 417/14* (2006.01)
*C07D 471/04* (2006.01)

(52) U.S. Cl.
CPC ......... *C07D 413/14* (2013.01); *C07D 413/04* (2013.01); *C07D 417/04* (2013.01); *C07D 417/14* (2013.01); *C07D 471/04* (2013.01)

(58) Field of Classification Search
CPC .. C07D 413/14; C07D 413/04; C07D 417/04; C07D 417/14; C07D 471/04
See application file for complete search history.

(56) References Cited

U.S. PATENT DOCUMENTS

| 4,782,071 A | 11/1988 | Butler et al. |
| 5,780,472 A * | 7/1998 | Cho ..................... C07D 213/40 514/253.12 |
| 6,727,247 B2 * | 4/2004 | Flohr ..................... A61P 25/36 544/70 |
| 7,074,809 B2 | 7/2006 | Arora et al. |
| 7,132,424 B2 | 11/2006 | Picard |
| 7,381,749 B2 | 6/2008 | Malecha et al. |
| 7,767,677 B2 | 8/2010 | Kamboj et al. |
| 7,790,408 B1 | 9/2010 | Ntambi et al. |
| 8,063,224 B2 | 11/2011 | Lachance et al. |
| 8,129,376 B2 | 3/2012 | Sundaresan et al. |
| 8,207,147 B2 | 6/2012 | Fyfe et al. |
| 8,207,199 B2 | 6/2012 | Aoki et al. |
| 8,258,160 B2 | 9/2012 | Dales et al. |
| 8,314,138 B2 | 11/2012 | Dales et al. |
| 8,563,539 B2 | 10/2013 | Baldino et al. |
| 8,673,917 B2 | 3/2014 | Zoller et al. |
| 8,791,136 B2 | 7/2014 | Goff et al. |
| 8,946,225 B2 | 2/2015 | Dupont-Passelaigue et al. |
| 9,266,832 B2 | 2/2016 | Griffioen et al. |
| 9,290,465 B2 | 3/2016 | Derryberry et al. |
| 9,296,711 B2 | 3/2016 | Erickson et al. |
| 10,941,134 B2 | 3/2021 | Goff et al. |
| 10,973,810 B2 | 4/2021 | Vincent et al. |
| 2002/0019389 A1 | 2/2002 | Kim et al. |
| 2002/0133005 A1 | 9/2002 | Iino et al. |
| 2004/0023973 A1 | 2/2004 | Nagato et al. |
| 2004/0097483 A1* | 5/2004 | Zeng ..................... C07D 417/14 514/210.21 |
| 2004/0127521 A1* | 7/2004 | Cai ..................... A61P 17/00 514/341 |
| 2004/0146872 A1 | 7/2004 | Winther et al. |
| 2005/0119242 A1 | 6/2005 | Deluca et al. |
| 2005/0256068 A1 | 11/2005 | McSwiggen et al. |

(Continued)

FOREIGN PATENT DOCUMENTS

| CN | 1177352 A | 3/1998 |
| CN | 1630650 A | 6/2005 |

(Continued)

OTHER PUBLICATIONS

Berlin et al., 16(4) Bioorg. & Med. Chem. Letts., 989-994 (2006) (Year: 2006).*
Huestis et al., "The Vinyl Moiety as a Handle for regiocontrol in the Preparation of Unsymmetrical 2,3-Aliphatic-Substituted Indoles and Pyrroles," Agnew Chem Int Edit. 50(6):1338-41 (2011).
International Preliminary Report on Patentability for International Application No. PCT/US2017/058144, dated May 9, 2019 (7 pages).
International Search Report and Written Opinion for International Patent Application No. PCT/US2017/058144, dated Mar. 9, 2018 (17 pages).

(Continued)

*Primary Examiner* — Timothy R Rozof
(74) *Attorney, Agent, or Firm* — Wan Chieh Lee; Haug Partners LLP

(57) ABSTRACT

The present invention features compounds useful in the treatment of neurological disorders. The compounds of the invention, alone or in combination with other pharmaceutically active agents, can be used for treating or preventing neurological disorders.

12 Claims, 13 Drawing Sheets

Specification includes a Sequence Listing.

(56) References Cited

U.S. PATENT DOCUMENTS

| | | |
|---|---|---|
| 2006/0116382 A1 | 6/2006 | Yao et al. |
| 2006/0167044 A1 | 7/2006 | Arnaiz et al. |
| 2006/0270686 A1 | 11/2006 | Kelly et al. |
| 2007/0087363 A1 | 4/2007 | Bartel et al. |
| 2008/0015230 A1 | 1/2008 | Kamboj et al. |
| 2008/0021028 A1* | 1/2008 | Swinnen .......... A61P 1/16 514/235.8 |
| 2008/0132542 A1 | 6/2008 | Lachance et al. |
| 2008/0207587 A1 | 8/2008 | Kamboj et al. |
| 2008/0249100 A1 | 10/2008 | Chisholm et al. |
| 2008/0255130 A1 | 10/2008 | Koltun et al. |
| 2008/0255161 A1 | 10/2008 | Koltun et al. |
| 2008/0280891 A1 | 11/2008 | Kelly et al. |
| 2009/0098105 A1 | 4/2009 | Hopf et al. |
| 2009/0118296 A1 | 5/2009 | Black et al. |
| 2009/0149466 A1 | 6/2009 | Gillespie et al. |
| 2009/0163545 A1 | 6/2009 | Goldfarb |
| 2009/0170822 A1 | 7/2009 | DeLuca et al. |
| 2009/0170828 A1 | 7/2009 | Isabel et al. |
| 2009/0221597 A1 | 9/2009 | Hadida et al. |
| 2009/0239810 A1 | 9/2009 | Sundaresan et al. |
| 2009/0246137 A1 | 10/2009 | Hadida Ruah et al. |
| 2009/0253693 A1 | 10/2009 | Koltun et al. |
| 2009/0253738 A1 | 10/2009 | Koltun et al. |
| 2009/0325956 A1 | 12/2009 | Taniguchi et al. |
| 2010/0022486 A1 | 1/2010 | Bouillot et al. |
| 2010/0029722 A1 | 2/2010 | Dales et al. |
| 2010/0041696 A1 | 2/2010 | Daugan et al. |
| 2010/0160323 A1 | 6/2010 | Bischoff et al. |
| 2010/0210649 A1 | 8/2010 | Djaballah et al. |
| 2012/0010186 A1 | 1/2012 | Lachance et al. |
| 2012/0178678 A1 | 7/2012 | Dupont-Passelaigue et al. |
| 2012/0196844 A1 | 8/2012 | Alper et al. |
| 2012/0252850 A1 | 10/2012 | Milne et al. |
| 2012/0316182 A1 | 12/2012 | Whitten et al. |
| 2013/0011361 A1 | 1/2013 | Dales et al. |
| 2013/0225529 A1 | 8/2013 | Rigas |
| 2013/0317020 A1 | 11/2013 | Ruah et al. |
| 2014/0364393 A1 | 12/2014 | Yang et al. |
| 2015/0051206 A1 | 2/2015 | Loren et al. |
| 2015/0087673 A1 | 3/2015 | Hitoshi et al. |
| 2015/0246893 A1 | 9/2015 | Devaraj et al. |
| 2015/0252032 A1 | 9/2015 | Bolli et al. |
| 2016/0223559 A1 | 8/2016 | Devaraj et al. |
| 2016/0251336 A1 | 9/2016 | Yang et al. |
| 2016/0332989 A1 | 11/2016 | Wu et al. |
| 2017/0174699 A1 | 6/2017 | Hadari et al. |
| 2018/0015068 A1 | 1/2018 | Inoue et al. |
| 2018/0193325 A1 | 7/2018 | Vincent et al. |
| 2019/0302121 A1 | 10/2019 | Copland, III et al. |
| 2019/0330198 A1 | 10/2019 | Wrona et al. |
| 2020/0010462 A1 | 1/2020 | Lucas et al. |
| 2020/0262828 A1 | 8/2020 | Lucas et al. |
| 2021/0139471 A1 | 5/2021 | Wrona et al. |
| 2022/0040167 A1 | 2/2022 | Vincent et al. |

FOREIGN PATENT DOCUMENTS

| | | |
|---|---|---|
| CN | 101083994 A | 12/2007 |
| CN | 101128435 A | 2/2008 |
| CN | 101137363 A | 3/2008 |
| CN | 101589039 A | 11/2009 |
| CN | 101641347 A | 2/2010 |
| CN | 101835776 A | 9/2010 |
| CN | 103221408 A | 7/2013 |
| CN | 103328482 A | 9/2013 |
| CN | 103619825 A | 3/2014 |
| CN | 103748087 A | 4/2014 |
| CN | 104163794 | 11/2014 |
| EP | 1193255 | 4/2002 |
| EP | 1737451 A2 | 1/2007 |
| EP | 2455080 | 5/2012 |
| EP | 2455081 | 5/2012 |
| EP | 2598483 | 6/2013 |
| EP | 2462121 | 2/2015 |
| EP | 2980077 A1 | 2/2016 |
| EP | 2990400 | 3/2016 |
| EP | 3284738 A1 | 2/2018 |
| EP | 3381908 A1 | 10/2018 |
| JP | H11501021 A | 1/1999 |
| JP | 2005213233 | 8/2005 |
| JP | 2008513514 A | 5/2008 |
| JP | 2008525478 A | 7/2008 |
| JP | 2008526796 A | 7/2008 |
| JP | 2008539275 | 11/2008 |
| JP | 2008545760 A | 12/2008 |
| JP | 2009019013 | 1/2009 |
| JP | 2009501733 A | 3/2009 |
| JP | 201043052 | 2/2010 |
| JP | 2010506859 A | 3/2010 |
| JP | 2010510272 | 4/2010 |
| JP | 2010510993 A | 4/2010 |
| JP | 2010513400 | 4/2010 |
| JP | 2010516714 A | 5/2010 |
| JP | 2010535847 A | 11/2010 |
| JP | 2011516420 | 5/2011 |
| JP | 2011529102 A | 12/2011 |
| JP | 2012518603 A | 8/2012 |
| JP | 2013537180 A | 9/2013 |
| JP | 2014501274 A | 1/2014 |
| JP | 2014509600 A | 4/2014 |
| JP | 2014510708 A | 5/2014 |
| JP | 2014513071 A | 5/2014 |
| JP | 2014518240 A | 7/2014 |
| KR | 20150014719 | 2/2015 |
| KR | 20150015305 | 2/2015 |
| KR | 20160020616 | 2/2016 |
| WO | WO-96/26937 A1 | 9/1996 |
| WO | WO 9963979 | 12/1999 |
| WO | WO-00/20414 A1 | 4/2000 |
| WO | WO-0114339 | 3/2001 |
| WO | WO-0105769 | 11/2001 |
| WO | WO-02066470 | 8/2002 |
| WO | WO-03070885 | 8/2003 |
| WO | WO-03/084948 A1 | 10/2003 |
| WO | WO-2004014892 | 2/2004 |
| WO | WO-2005011654 | 2/2005 |
| WO | WO-2005011655 | 2/2005 |
| WO | WO-2005011656 | 2/2005 |
| WO | WO-2005011657 | 2/2005 |
| WO | WO-2005014607 | 2/2005 |
| WO | WO-2005023833 | 3/2005 |
| WO | WO-2005026137 | 3/2005 |
| WO | WO-2006012325 | 2/2006 |
| WO | WO-2006014168 | 2/2006 |
| WO | WO-2006015621 | 2/2006 |
| WO | WO-2006/034440 A2 | 3/2006 |
| WO | WO-2006022442 | 3/2006 |
| WO | WO 2006022442 A1 | 3/2006 |
| WO | WO-2006034279 | 3/2006 |
| WO | WO-2006034312 | 3/2006 |
| WO | WO-2006034315 | 3/2006 |
| WO | WO-2006034338 | 3/2006 |
| WO | WO-2006034341 | 3/2006 |
| WO | WO-2006034441 | 3/2006 |
| WO | WO-2006034446 | 3/2006 |
| WO | WO-2006057902 | 6/2006 |
| WO | WO-2006067531 | 6/2006 |
| WO | WO-2006/071730 A1 | 7/2006 |
| WO | WO-2006/072436 A1 | 7/2006 |
| WO | WO-2006074025 | 7/2006 |
| WO | WO-2006086445 | 8/2006 |
| WO | WO-2006086447 | 8/2006 |
| WO | WO-2006116713 | 11/2006 |
| WO | WO-2006125179 | 11/2006 |
| WO | WO-2006125181 | 11/2006 |
| WO | WO-2006125194 | 11/2006 |
| WO | WO-2006/130986 A1 | 12/2006 |
| WO | WO-2007/009236 A1 | 1/2007 |
| WO | WO-2007044085 | 4/2007 |
| WO | WO-2007046868 | 4/2007 |
| WO | WO-2007056846 | 5/2007 |
| WO | WO-2007/076055 A2 | 7/2007 |

(56) References Cited

FOREIGN PATENT DOCUMENTS

| | | |
|---|---|---|
| WO | WO-2007079180 | 7/2007 |
| WO | WO-2007/120702 A2 | 10/2007 |
| WO | WO-2007130075 | 11/2007 |
| WO | WO-2007134457 | 11/2007 |
| WO | WO-2007136746 | 11/2007 |
| WO | WO-2007143597 | 12/2007 |
| WO | WO-2007143823 | 12/2007 |
| WO | WO-2007143824 | 12/2007 |
| WO | WO-2008003753 | 1/2008 |
| WO | WO-2008008059 | 1/2008 |
| WO | WO 2008008852 A2 | 1/2008 |
| WO | WO 2008008854 A2 | 1/2008 |
| WO | WO-2008017161 | 2/2008 |
| WO | WO-2008023720 A1 | 2/2008 |
| WO | WO-2008024139 | 2/2008 |
| WO | WO-2008024390 | 2/2008 |
| WO | WO-2008029266 A1 | 3/2008 |
| WO | WO-2008036715 | 3/2008 |
| WO | WO-2008/046226 A1 | 4/2008 |
| WO | WO-2008043087 | 4/2008 |
| WO | WO-2008044767 | 4/2008 |
| WO | WO-2008056687 | 5/2008 |
| WO | WO-2008057280 | 5/2008 |
| WO | WO2008061795 | 5/2008 |
| WO | WO-2008062276 | 5/2008 |
| WO | WO-2008/064474 A1 | 6/2008 |
| WO | WO-2008074824 | 6/2008 |
| WO | WO-2008074832 | 6/2008 |
| WO | WO-2008074833 | 6/2008 |
| WO | WO-2008074834 | 6/2008 |
| WO | WO-2008074835 | 6/2008 |
| WO | WO-2008076356 | 6/2008 |
| WO | WO-2008/089580 A1 | 7/2008 |
| WO | WO-2008096746 | 8/2008 |
| WO | WO-2008104524 | 9/2008 |
| WO | WO-2008116898 | 10/2008 |
| WO | WO-2008120744 | 10/2008 |
| WO | WO-2008120759 | 10/2008 |
| WO | WO-2008123469 | 10/2008 |
| WO | WO-2008127349 | 10/2008 |
| WO | WO-2008128335 | 10/2008 |
| WO | WO-2008139845 | 11/2008 |
| WO | WO-2008141455 | 11/2008 |
| WO | WO-2008157844 | 12/2008 |
| WO | WO-2009010560 | 1/2009 |
| WO | WO-2009012573 | 1/2009 |
| WO | WO-2009/021990 A1 | 2/2009 |
| WO | WO-2009016216 | 2/2009 |
| WO | WO-2009019566 | 2/2009 |
| WO | WO-2009037542 | 3/2009 |
| WO | WO-2009/060053 A1 | 5/2009 |
| WO | WO-2009056556 | 5/2009 |
| WO | WO-2009060054 | 5/2009 |
| WO | WO-2009070533 | 6/2009 |
| WO | WO-2009073973 | 6/2009 |
| WO | WO-2009103739 | 8/2009 |
| WO | WO-2009106991 | 9/2009 |
| WO | WO-2009117659 | 9/2009 |
| WO | WO-2009123896 | 10/2009 |
| WO | WO-2009124259 | 10/2009 |
| WO | WO-2009129625 | 10/2009 |
| WO | WO-2009150196 | 12/2009 |
| WO | WO-2009156484 | 12/2009 |
| WO | WO-2010006962 | 1/2010 |
| WO | WO-2010007482 | 1/2010 |
| WO | WO-2010007966 A1 | 1/2010 |
| WO | WO-2010/013037 A1 | 2/2010 |
| WO | WO-2010/022055 A2 | 2/2010 |
| WO | WO-2010025553 | 3/2010 |
| WO | WO-2010/039186 A2 | 4/2010 |
| WO | WO-2010035052 | 4/2010 |
| WO | WO-2010037225 | 4/2010 |
| WO | WO-2010043052 | 4/2010 |
| WO | WO 2010043052 A1 | 4/2010 |
| WO | WO-2010045371 | 4/2010 |
| WO | WO-2010045374 | 4/2010 |
| WO | WO-2010056230 | 5/2010 |
| WO | WO-2010057833 | 5/2010 |
| WO | WO-2010060996 | 6/2010 |
| WO | WO-2010/094126 A1 | 8/2010 |
| WO | WO-2010094120 | 8/2010 |
| WO | WO-2010/108268 A1 | 9/2010 |
| WO | WO-2010101964 | 9/2010 |
| WO | WO-2010112520 | 10/2010 |
| WO | WO-2011011506 | 1/2011 |
| WO | WO-2011011508 | 1/2011 |
| WO | WO-2011011872 | 2/2011 |
| WO | WO-2011015629 | 2/2011 |
| WO | WO-2011/025690 A1 | 3/2011 |
| WO | WO-2011030312 | 3/2011 |
| WO | WO-2011039358 | 4/2011 |
| WO | WO-2011047481 | 4/2011 |
| WO | WO-2011109059 | 9/2011 |
| WO | WO-2011123681 | 10/2011 |
| WO | WO-2011131593 | 10/2011 |
| WO | WO-2011157793 | 12/2011 |
| WO | WO-2012009134 | 1/2012 |
| WO | WO-2012016217 | 2/2012 |
| WO | WO-2012/035023 A1 | 3/2012 |
| WO | WO-2012046681 | 4/2012 |
| WO | WO-2012/066077 A1 | 5/2012 |
| WO | WO-2012080729 | 6/2012 |
| WO | WO-2012082817 | 6/2012 |
| WO | WO-2012/093809 A2 | 7/2012 |
| WO | WO-2012/123449 A1 | 9/2012 |
| WO | WO-2012/136492 A1 | 10/2012 |
| WO | WO-2012/169649 A1 | 12/2012 |
| WO | WO-2013/004642 A1 | 1/2013 |
| WO | WO-2013/026587 A1 | 2/2013 |
| WO | WO-2013/056148 A2 | 4/2013 |
| WO | WO 2013046136 A1 | 4/2013 |
| WO | WO 2013070660 A1 | 5/2013 |
| WO | WO-2013085954 | 6/2013 |
| WO | WO-2013085957 | 6/2013 |
| WO | WO 2013098373 A1 | 7/2013 |
| WO | WO-2013134546 | 9/2013 |
| WO | WO-2013160811 | 10/2013 |
| WO | WO-2013170072 | 11/2013 |
| WO | WO-2014003153 | 1/2014 |
| WO | WO-2014031928 | 2/2014 |
| WO | WO-2014/092104 A1 | 6/2014 |
| WO | WO-2014116386 | 7/2014 |
| WO | WO-2015048547 | 4/2015 |
| WO | WO-2015101293 A1 | 7/2015 |
| WO | WO 2015113920 A1 | 8/2015 |
| WO | WO-2015/140130 A1 | 9/2015 |
| WO | WO-2015132610 | 9/2015 |
| WO | WO-2015137385 | 9/2015 |
| WO | WO-2016022626 | 2/2016 |
| WO | WO-2016022955 | 2/2016 |
| WO | WO-2016/049586 A2 | 3/2016 |
| WO | WO-2016040794 | 3/2016 |
| WO | WO 2016098005 A1 | 6/2016 |
| WO | WO-2016107603 | 7/2016 |
| WO | WO-2017066705 | 4/2017 |
| WO | WO-2017093263 | 6/2017 |
| WO | WO 2017112777 A1 | 6/2017 |
| WO | WO-2017212425 | 12/2017 |
| WO | WO 2018026663 A1 | 2/2018 |
| WO | WO-2018/081167 A1 | 5/2018 |
| WO | WO-2018112077 | 6/2018 |
| WO | WO-2018129403 | 7/2018 |
| WO | WO-2018160717 | 9/2018 |
| WO | WO-2018161033 | 9/2018 |
| WO | WO 2018195450 A1 | 10/2018 |
| WO | WO-2019018795 | 1/2019 |
| WO | WO-2019084157 | 5/2019 |
| WO | WO-2019123375 | 6/2019 |
| WO | WO-2019123378 | 6/2019 |
| WO | WO-2019140188 | 7/2019 |
| WO | WO-2019173394 | 9/2019 |
| WO | WO-2019183587 | 9/2019 |
| WO | WO-2019209948 | 10/2019 |
| WO | WO-2019209962 | 10/2019 |

(56) References Cited

FOREIGN PATENT DOCUMENTS

| | | |
|---|---|---|
| WO | WO-2020023657 | 1/2020 |
| WO | WO-2020132378 | 6/2020 |
| WO | WO-2020154571 | 7/2020 |
| WO | WO-2020198026 | 10/2020 |
| WO | WO-2021092240 | 5/2021 |
| WO | WO-2021092262 | 5/2021 |
| WO | WO-2021097240 | 5/2021 |
| WO | WO-2021139595 | 7/2021 |
| WO | WO-2021154571 | 8/2021 |

OTHER PUBLICATIONS

Jarvis et al., "A-803467, a potent and selective Nav1.8 sodium channel blocker, attenuates neuropathic and inflammatory pain in the rat," Proc Natl Acad Sci U.S.A. 104(20):8520-5 (2007).
PubChem Compound Summary for CID 126485826, dated Apr. 22, 2017 (6 pages).
PubChem Compound Summary for CID 127012056, dated Jun. 2, 2017 (12 pages).
PubChem Compound Summary for CID 127868748, dated Jun. 18, 2017 (9 pages).
PubChem Compound Summary for CID 53003909, dated Jun. 21, 2011 (7 pages).
PubChem Compound Summary for CID 56980069, dated Jun. 13, 2012 (11 pages).
PubChem Compound Summary for CID 7059272, dated Jul. 29, 2006 (12 pages).
Invitation Pursuant to Rule 63(1) for European Application No. 17863983.7, dated Mar. 20, 2020 (6 pages).
PubChem Compound Summary for CID 15985883, "5-[5-[4-[(4-Chlorophenyl)methyl]piperidin-1-yl]-5-oxopentyl]-1H-pyridin-2-one," created Mar. 27, 2007, retrieved Mar. 25, 2020 (7 pages).
International Preliminary Report on Patentability for International Application No. PCT/US2018/043136, dated Jan. 21, 2020 (7 pages).
International Search Report and Written Opinion for International Application No. PCT/US18/43136, dated Oct. 10, 2018 (24 pages).
Communication pursuant to Rule 164(1) EPC for European Patent Application No. 17863983.7, dated Sep. 9, 2020 (35 pages).
Extended European Search Report for European Patent Application No. 17863983.7, dated Nov. 25, 2020 (31 pages).
Horan et al., "Piperazinyl-oxadiazoles as selective sphingosine-1-phosphate receptor agonists," Bioorg Med Chem Lett. 24(20):4807-11 (2014) (5 pages).
Krasavin et al., "Antiproliferative 4-(1,2,4-oxadiazol-5-yl)piperidine-1-carboxamides, a new tubulin inhibitor chemotype," Bioorg Med Chem Lett. 24(18): 4477-4481 (2014) (5 pages).
Muraglia et al., "N-(2-alkylaminoethyl)-4-(1,2,4-oxadiazol-5-yl)piperazine-1-carboxamides as highly potent smoothened antagonists," Bioorg Med Chem Lett. 21(18): 5283-8 (2011) (6 pages).
Ontoria et al., "Identification of a series of 4-[3-(quinolin-2-yl)-1,2,4-oxadiazol-5-yl]piperazinyl ureas as potent smoothened antagonist hedgehog pathway inhibitors," 21(18): 5274-82 (2011) (9 pages).
Tiwari et al., "Synthesis of 3-(5-bromo-2,3-dimethoxy-phenyl)-[1,2,4] oxadiazole analogues and their evaluation as anti-Parkinson's agents," Med Chem Res. 17:386-398 (2008) (12 pages).
PubChem Compound Summary for CID 71908265, retrieved from <https://pubchem.ncbi.nlm.nih.gov/compound/71908265>, created Nov. 29, 2013, retrieved Jan. 4, 2021 (8 pages).
Database Registry Chemical Abstracts Service, RN 887202-53-1, entered STN: Jun. 8, 2006 (3 pages).
Kumar et al., "Design and Synthesis of 3,5-Disubstituted-1,2,4-Oxadiazoles as Potent Inhibitors of Phosphodiesterase4B2," Chem Biol Drug Des. 79(5):810-8 (2012).
Registry, Database Registry (online). Retrieved from STN, 2012. Search Date: Jul. 21, 2021 (13 pages).
Shen et al., "Discovery of a Highly Potent, Selective, and Bioavailable Soluble Epoxide Hydrolase Inhibitor with Excellent Ex Vivo Target Engagement," J Med Chem. 52(16):5009-12 (2009).
Database Registry Chemical Abstracts Service, Accession No. RN 276236-86-3, entered STN Jul. 11, 2000 (71 pages).
"List of neurological conditions and disorders," <https://en.wikipedia.org/wiki/List_of_neurological_conditions_and_disorders>, retrieved on Jun. 27, 2019 (12 pages).
Astarita et al., "Elevated stearoyl-CoA desaturase in brains of patients with Alzheimer's disease," PLoS One. 6(10):e24777 (2011) (9 pages).
Bähler et al., "Heterologous modules for efficient and versatile PCR-based gene targeting in Schizosaccharomyces pombe." Yeast. 14(10):943-51 (1998).
Berge et al., "Pharmaceutical salts," J Pharm Sci. 66(1):1-19 (1977).
Black et al., "Advances and limitations in the evaluation of analgesic combination therapy," Neurology. 65(12 Suppl 4):S3-6 (2005) (14 pages).
Chung et al., "Identification and rescue of alpha-synuclein toxicity in Parkinson patient-drived neurons," available in PMC Nov. 22, 2014, published in final edited form as: Science. 342(6161):983-7 (2013) (12 pages).
Cingolani et al., "A program for annotating and predicting the effects of single nucleotide polymorphisms, SnpEff: SNPs in the genome of Drosophila melanogaster strain w1118; iso-2; iso- 3," Fly(Austin). 6(2):80-92 (2012).
Cooper et al., "Alpha-synuclein blocks ER-Golgi traffic and Rab1 rescues neuron loss in Parkinson's models," available in PMC Sep. 19, 2007, published in final edited form as: Science. 313(5785):324-8 (2006) (12 pages).
Crews et al., "Role of Synucleins in Alzheimer's Disease," Neurotox Res. 16(3):306-317 (2009).
Dai et al., "SCD1 Confes Temozolomide Resistance to Human Glioma Cells via Akt/GSK3β/β-Catenin Signaling Axis," Frontiers in Pharmacology, vol. 8, Art. 960 (2018).
Debenham et al., "Discovery of N-[Bis(4-methoxyphenyl)methyl]-4-hydroxy-2-(pyridazin-3-yl)pyrimidine-5-carboxamide (MK-8617), an Orally Active Pan-Inhibitor of Hypoxia-Inducible Factor Prolyl Hydroxylase1-3 (HIF PHD1-3) for the Treatment of Anemia," J. Med. Chem. 59, 11039-11049 (2016).
Dillon et al., "Development of a novel LC(MS method to quantitate cellular stearoyl-CoA desaturase activity," Anal Chim Acta. 627(1):99-104 (2008).
Fatutta et al.: "Comportamento di alcune idrazidi di fronte a composti y-dicarbonilici. (*)", Gazzetta Chimica Italiana, Societa Chimica Italiana, IT, vol. 90, Jan. 1, 1960 (Jan. 1, 1960), pp. 1645-1657, XP009532381.
Friedrich et al., "Mechanism of amyloid plaque formation suggests an intracellular basis of Abeta pathogenicity," Proc Natl Acad Sci U.S.A. 107(5):1942-7 (2010).
Garrison et al., "Haplotype-based variant detection from short-read sequencing," <https://arxiv.org/pdf/1207.3907.pdf>. retrieved Apr. 23, 2018 (2012) (9 pages).
Gietz, "Yeast transformation by the LiAc/SS carrier DNA/PEG method," Methods Mol Biol. 1205:1- 12 (2014).
Goedert, M., "Parkinson's disease and other alpha-synucleinopathies," Clin Chem Lab Med. 39(4):308-12 (2001) (Abstract only).
Hamilton et al., "Aberrant Lipid Metabolism in the Forebrain Niche Suppresses Adult Neural Stem Cell Proliferation in an Animal Model of Alzheimer's Disease," Cell Stem Cell. 17(4):397-411 (2015) (16 pages).
Kamboh et al., "A novel mutation in the apolipoprotein E gene (APOE*4 Pittsburgh) is associated with the risk of late-onset Alzheimer's disease " Neurosci Lett. 263(2-3):129-32 (1999).
Larson et al., "Soluble α-synuclein is a novel modulator of Alzheimer's disease pathophysiology," Available in PMC Jan. 25, 2013, published in final edited form as: J Neurosci. 32(30): 10253-66 (2012) (28 pages).
Li et al., "Fast and accurate long-read alignment with Burrows-Wheeler transform," Bioinformatics. 26(5):589-95 (2010).
Li et al., "Fast and accurate short read alignment with Burrows-Wheeler transform," Bioinformatics. 25(14):1754-60 (2009).
Li et al., "The sequence alignment/map format and SAMtools," Bioinformatics. 25(16):2078-9 (2009).

(56) References Cited

OTHER PUBLICATIONS

Longtine et al., "Additional modules for versatile and economical PCR-based gene deletion and modification in *Saccharomyces cerevisiae*," Yeast. 14(10):953-61 (1998).
Maya S. Salnikova, Rational Development of Protein Formulations in Solid and Solution States.
Mikolaenko et al., "Alpha-synuclein lesions in normal aging, Parkinson disease, and Alzheimer disease: evidence from the Baltimore Longitudinal Study of Aging (BLSA)," J Neuropathol Exp Neurol. 64(2):156-62 (2005}.
Miyazaki et al., "The biosynthesis of hepatic cholesterol esters and triglycerides is impaired in mice with a disruption of the gene for stearoyl-CoA desaturase 1," J Biol Chem. 275(39):30132-8 (2000).
Ng Davis et al: "Reviewing editor", Jul. 20, 2016 (Jul. 20, 2016), pp. 1-33, XP055921015,Retrieved from the Internet: URL:https://www.ncbi.nlm.nih.gov/pmc/articles/PMC4954757/pdf/elife-11878.pdf [retrieved on May 13, 2022].
Oatman et al. "Mechanisms of stearoyl CoA desaturase inhibitor sensitivity and acquired resistance in cancer" Science Advances. Feb. 10, 2021 (Feb. 10, 2021) vol. 7, p. 1-19.
Pankratz et al., "Presence of an APOE4 Allele Results in Significantly Earlier Onset of Parkinson's Disease and a Higher Risk With Dementia," Mov Disord. 21(1):45-49 (2006).
Piotrowski et al., "Plant-derived antifungal agent poacic acid targets beta-1,3-glucan," Proc Natl Acad Sci U S A. 112(12):E1490-7 (2015).
Ponomarenko et al., "The Size of the Human Proteome: The Width and Depth," Int J Anal Chem. 2016:7426849 (2016) (6 pages).
Shanklin et al., "Stearoyl-acyl-carrier-protein desaturase from higher plants is structurally unrelated to the animal and fungal homologs," Proc Natl Acad Sci US A. 88(6):2510-4 (1991 ).
Simon et al., "Total ApoE and ApoE4 isoform assays in an Alzheimer's disease case-control study by targeted mass spectrometry (n=669): a pilot assay for methionine-containing proteotypic peptides." Mol Cell Proteomics. 11(11):1389-403 (2012).
Sinner et al., "StearoylCoA Desaturase-5: A novel regulator of neuronal cell proliferation and differentiation" PLOS One. 7(6):e39787 (2012) (12 pages).
Skedelj Veronika et al: "ATP-Binding Site of Bacterial Enzymes as a Target for Antibacterial Drug Design", Journal of Medicinal Chemistry, vol. 54, No. 4, Jan. 14, 2011 (Jan. 14, 2011), pp. 915-929, XP055922741.
Soulard et al., "Development of a high-throughput screening assay for stearoyl-CoA desaturase using rat liver microsomes, deuterium labeled stearoyl-CoA and mass spectrometry," Anal Chim Acta. 627(1):105-11 (2008).
Su et al., "Compounds from an unbiased chemical screen reverse both ER-to-Golgi trafficking defects and mitochondrial dysfunction in Parkinson's disease models," Dis Model Mech. 3(3-4):194-208 (2010).
Suzuki et al., "Knocking out multi-gene redundancies via cycles of sexual assortment and fluorescence selection," available in PMC Aug. 1, 2011, published in final edited form as: Nat Methods. 8(2): 159-64 (2011) (15 pages).
Tafesse et al., "Disruption of Sphingolipid Biosynthesis Blocks Phagocytosis of *Candida albicans*," PLOS Pathog. 11(10):e1005188 (2015) (27 pages).
Terry-Kantor et al., "Rapid Alpha-Synuclein Toxicity in a Neural Cell Model and Its Rescue by a Stearoyl-CoA Desaturase Inhibitor," Int. J. Mol. Sci., 21, 5193, 1-16 (Jul. 22. 2020).
Tesfay et al., "Steroyl-CoA Desaturase (SCD1) protects ovarian cancer cells from ferroptotic cell death," Cancer Res. 79(20): 5355-5366 (Oct. 15, 2019).
Tindale et al., "Rare and common variants in the Apolipoprotein E gene in healthy oldest old," Neurobiol Aging. 35(3):727.e1-3 (2014) (3 pages).
Verghese et al.," Roles of Apolipoprotein E in Alzheimer's disease and other neurological disorders," Lancet Neurol. 10(3):241-252 (2011 ).
Wang et al., "Characterization of HSCD5, a novel human stearoyl-CoA desaturase unique to primates," Biochem Biophys Res Commun. 332(3):735-42 (2005).
Zhang et al., "Revisiting the Medical Management of Parkinson's Disease: Levodopa Versus Dopamine Agonist," Curr Neuropharmacol. 14(4):356-363 (2016).
Zhang et al., "Opportunities and Challenges in Develping Stearoyl-Coenzyme A Desaturase-1 Inhibitors as Novel Therapeutics for Human Disease," J. Med. Chem., 57, 5039-5056 (2014).
Zhou, Youping, Zhong, et al. Inhibition of stearoyl-coenzyme A desaturase 1 ameliorates hepatic steatosis by inducing AMPK-mediated lipophagy. Aging, 12(8):7350-7362 (Apr. 23, 2020).
NCBI, Gene ID: 79966, "SCD5 stearoyl-CoA desaturase 5 [Homo sapiens (human)]," <https://web.archive.org/web/20150828032953/http://www.ncbi.nlm.nih.gov:80/gene/79966>, last modified Jul. 23, 2015 (5 pages).
PubChem CID 91412014, Create Date: Mar. 17, 2015 (Mar. 17, 2015), p. 2, Fig.
Registry (STN) [online] and Feb. 29, 2012 [the date of search Jul. 19, 2021] CAS Registration No. 1358463-36-1 etc.
RN1266245-83-3, registry database compound, 2011.
Madia Valentina Noemi et al., "Novel Benzazole Derivatives Endowed with Potent Antiheparanase Activity", Journal of Medicinal Chemistry, vol. 61, No. 15, Jul. 16, 2018 (Jul. 16, 2018), pp. 6918-6936, XP093025853, US.
Trivedi Prakruti et al., "Design, synthesis and biological screening of 2-aminobenzamides as selective HDAC3 inhibitors with promising anticancer effects", European Journal of Pharmaceutical Sciences, Elsevier Amsterdam, NL, vol. 124, Aug. 29, 2018 (Aug. 29, 2018), pp. 165-181, XP085483648.
Tang Qidong et al., "Discovery of novel 7-azaindole derivatives bearing dihydropyridazine moiety as c-Met kinase inhibitors", European Journal of Medicinal Chemistry, vol. 133, Jun. 1, 2017 (Jun. 1, 2017), pp. 97-106, XP093026184.
Wang Lin Xiao et al., "Discovery of novel pyrrolo-pyridine/pyrimidine derivatives bearing pyridazinone moiety as c-Met kinase inhibitors", European Journal of Medicinal Chemistry, vol. 141, Oct. 13, 2017 (Oct. 13, 2017), pp. 538-551, XP085259430.
Byrd Katherine M. et al., "Synthesis and Biological Evaluation of Stilbene Analogues as Hsp90 C-Terminal Inhibitors", ChemMedChem Communications, vol. 12, No. 24, Nov. 30, 2017 (Nov. 30, 2017), pp. 2022-2029, XP093025869.
Vincent et al. "Inhibiting Stearoyl-CoA Desaturase Ameliorates a-Synuclein Cytotoxicity," Cell Reports, 25: 2742-2754 (2018).

\* cited by examiner

SEQUENCE LISTING

```
<160> NUMBER OF SEQ ID NOS: 1

<210> SEQ ID NO 1
<211> LENGTH: 510
<212> TYPE: PRT
<213> ORGANISM: Saccharomyces cerevisiae

<400> SEQUENCE: 1

Met Pro Thr Ser Gly Thr Thr Ile Glu Leu Ile Asp Asp Gln Phe Pro
1               5                   10                  15

Lys Asp Asp Ser Ala Ser Ser Gly Ile Val Asp Glu Val Asp Leu Thr
            20                  25                  30

Glu Ala Asn Ile Leu Ala Thr Gly Leu Asn Lys Lys Ala Pro Arg Ile
        35                  40                  45

Val Asn Gly Phe Gly Ser Leu Met Gly Ser Lys Glu Met Val Ser Val
    50                  55                  60

Glu Phe Asp Lys Lys Gly Asn Glu Lys Ser Asn Leu Asp Arg Leu
65                  70                  75                  80

Leu Glu Lys Asp Asn Gln Glu Lys Glu Glu Ala Lys Thr Lys Ile His
            85                  90                  95

Ile Ser Glu Gln Pro Trp Thr Leu Asn Asn Trp His Gln His Leu Asn
        100                 105                 110

Trp Leu Asn Met Val Leu Val Cys Gly Met Pro Met Ile Gly Trp Tyr
    115                 120                 125

Phe Ala Leu Ser Gly Lys Val Pro Leu His Leu Asn Val Phe Leu Phe
    130                 135                 140

Ser Val Phe Tyr Tyr Ala Val Gly Gly Val Ser Ile Thr Ala Gly Tyr
145                 150                 155                 160

His Arg Leu Trp Ser His Arg Ser Tyr Ser Ala His Trp Pro Leu Arg
            165                 170                 175

Leu Phe Tyr Ala Ile Phe Gly Cys Ala Ser Val Glu Gly Ser Ala Lys
        180                 185                 190
```

-continued

```
Trp Trp Gly His Ser His Arg Ile His His Arg Tyr Thr Asp Thr Leu
        195                 200                 205

Arg Asp Pro Tyr Asp Ala Arg Arg Gly Leu Trp Tyr Ser His Met Gly
    210                 215                 220

Trp Met Leu Leu Lys Pro Asn Pro Lys Tyr Lys Ala Arg Ala Asp Ile
225                 230                 235                 240

Thr Asp Met Thr Asp Asp Trp Thr Ile Arg Phe Gln His Arg His Tyr
            245                 250                 255

Ile Leu Leu Met Leu Leu Thr Ala Phe Val Ile Pro Thr Leu Ile Cys
                260                 265                 270

Gly Tyr Phe Phe Asn Asp Tyr Met Gly Gly Leu Ile Tyr Ala Gly Phe
            275                 280                 285

Ile Arg Val Phe Val Ile Gln Gln Ala Thr Phe Cys Ile Asn Ser Leu
        290                 295                 300

Ala His Tyr Ile Gly Thr Gln Pro Phe Asp Asp Arg Arg Thr Pro Arg
305                 310                 315                 320

Asp Asn Trp Ile Thr Ala Ile Val Thr Phe Gly Glu Gly Tyr His Asn
                325                 330                 335

Phe His His Glu Phe Pro Thr Asp Tyr Arg Asn Ala Ile Lys Trp Tyr
            340                 345                 350

Gln Tyr Asp Pro Thr Lys Val Ile Ile Tyr Leu Thr Ser Leu Val Gly
        355                 360                 365

Leu Ala Tyr Asp Leu Lys Lys Phe Ser Gln Asn Ala Ile Glu Glu Ala
    370                 375                 380

Leu Ile Gln Gln Glu Gln Lys Lys Ile Asn Lys Lys Ala Lys Ile
385                 390                 395                 400

Asn Trp Gly Pro Val Leu Thr Asp Leu Pro Met Trp Asp Lys Gln Thr
                405                 410                 415

Phe Leu Ala Lys Ser Lys Glu Asn Lys Gly Leu Val Ile Ile Ser Gly
            420                 425                 430

Ile Val His Asp Val Ser Gly Tyr Ile Ser Glu His Pro Gly Gly Glu
        435                 440                 445

Thr Leu Ile Lys Thr Ala Leu Gly Lys Asp Ala Thr Lys Ala Phe Ser
    450                 455                 460

Gly Gly Val Tyr Arg His Ser Asn Ala Ala Gln Asn Val Leu Ala Asp
465                 470                 475                 480

Met Arg Val Ala Val Ile Lys Glu Ser Lys Asn Ser Ala Ile Arg Met
                485                 490                 495

Ala Ser Lys Arg Gly Glu Ile Tyr Glu Thr Gly Lys Phe Phe
            500                 505                 510
```

COMPOUNDS AND USES THEREOF

PRIORITY CLAIM

This application is a § 371 national phase filing of PCT Application No. PCT/US2017/058144 filed Oct. 24, 2017, published on May 3, 2018 under PCT Patent Application Publication No. WO 2018/081167 A1, which claims priority to U.S. Provisional Application Ser. No. 62/412,119 filed Oct. 24, 2016, U.S. Provisional Application Ser. No. 62/443,040 filed Jan. 6, 2017, and U.S. Provisional Application Ser. No. 62/534,990 filed Jul. 20, 2017, the entire contents of each of these applications identified above are hereby incorporated by reference herein in their entirety.

SEQUENCE LISTING

The instant application contains a Sequence Listing which has been submitted electronically in ASCII format and is hereby incorporated by reference in its entirety. Said ASCII copy, created Apr. 22, 2019, is named 51061-021004_Sequence_Listing_04.22.19 and is 4,782 bytes in size.

BACKGROUND

An incomplete understanding of the molecular perturbations that cause disease, as well as a limited arsenal of robust model systems, has contributed to a failure to generate successful disease-modifying therapies against common and progressive neurological disorders, such as Parkinson's Disease (PD) and Alzheimer's Disease (AD). Progress is being made on many fronts to find agents that can arrest the progress of these disorders. However, the present therapies for most, if not all, of these diseases provide very little relief. Accordingly, a need exists to develop therapies that can alter the course of neurodegenerative diseases. More generally, a need exists for better methods and compositions for the treatment of neurodegenerative diseases in order to improve the quality of the lives of those afflicted by such diseases.

SUMMARY OF THE INVENTION

This disclosure provides a compound, or a pharmaceutically acceptable salt thereof, having the structure of Formula I:

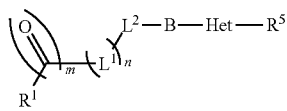

Formula Ia wherein B is absent or has the structure:

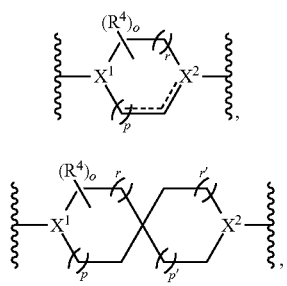

Formula Ib

Formula Ic

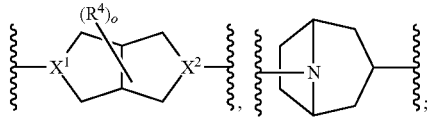

Formula Id

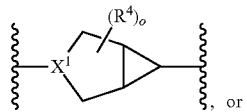

Formula Ie

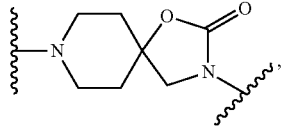

Formula If the dashed lines represent an optional double bond;

Het is —C(O)NH— or an optionally substituted $C_2$-$C_9$ heteroaryl;

m is 0 or 1;

n is 0, 1, or 2;

is 0, 1, 2, 3, 4, 5, 6, 7, or 8;

p, p', r, and r' are, independently, 0 or 1;

$X^1$ and $X^2$ are each, independently, N or $CR^6$;

$L^1$ is —O—, —$SO_2$—, $NR^2$, optionally substituted $C_1$-$C_6$ alkylene, optionally substituted $C_1$-$C_6$ alkenylene, optionally substituted $C_1$-$C_6$ heteroalkylene, optionally substituted $C_3$-$C_7$ cycloalkyl, optionally substituted $C_2$-$C_9$ heteroaryl, an optionally substituted $C_6$-$C_{10}$ aryl, or optionally substituted $C_2$-$C_9$ heterocycle;

$L^2$ is absent, —O—, —$SO_2$—, $NR^2$, or —$CR^2R^3$—;

$R^1$ is hydrogen, amino, hydroxy, optionally substituted $C_1$-$C_6$ alkyl, optionally substituted $C_1$-$C_6$ heteroalkyl, optionally substituted $C_6$-$C_{10}$ aryl, optionally substituted $C_6$-$C_{10}$ aryl $C_1$-$C_6$ alkyl, optionally substituted $C_3$-$C_7$ cycloalkyl, optionally substituted $C_3$-$C_7$ cycloalkyl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocycle, or optionally substituted $C_2$-$C_9$ heterocycle $C_1$-$C_6$ alkyl;

$R^2$ and $R^3$ are each, independently, hydrogen, halogen, hydroxyl, optionally substituted $C_1$-$C_6$ alkyl, optionally substituted $C_1$-$C_6$ heteroalkyl, or combine with the carbon to which they are attached to form a carbonyl or an optionally substituted $C_3$-$C_7$ cycloalkyl;

each $R^4$ is, independently, halogen, hydroxyl, optionally substituted $C_1$-$C_6$ alkyl, optionally substituted $C_1$-$C_6$ heteroalkyl, or two $R^4$ combine with the carbon two which they are attached to form a carbonyl or optionally substituted $C_3$-$C_7$ cycloalkyl;

$R^5$ is optionally substituted $C_1$-$C_6$ heteroalkyl, optionally substituted $C_1$-$C_6$ alkyl, optionally substituted $C_6$-$C_{10}$ aryl, optionally substituted $C_2$-$C_9$ heteroaryl, optionally substituted $C_2$-$C_9$ heterocycle, optionally substituted $C_6$-$C_{10}$ aryl $C_1$-$C_6$ alkyl, optionally substituted $C_2$-$C_9$ heterocycle $C_1$-$C_6$ alkyl, or optionally substituted $C_2$-$C_9$ heteroaryl $C_1$-$C_6$ alkyl; and each $R^6$ is, independently, hydrogen, halogen, hydroxy, optionally substituted $C_1$-$C_6$ heteroalkyl, or optionally substituted $C_1$-$C_6$ alkyl.

In some embodiments, B is absent.

In some embodiments, B has the structure of Formula Ib:

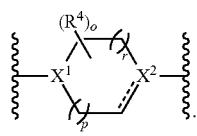

In some embodiments, $X^1$ is N and $X^2$ is $CR^6$. In some embodiments, o is 0, 1, or 2. In some embodiments, $R^4$ is halogen (e.g., fluoro), optionally substituted $C_1$-$C_6$ alkyl (e.g., methyl), or two $R^4$ combine with the carbon two which they are attached to form a carbonyl. In some embodiments, $R^6$ is hydrogen. In some embodiments, $R^6$ is halogen (e.g., fluoro). In some embodiments, $R^6$ is optionally substituted $C_1$-$C_6$ alkyl (e.g., methyl). In some embodiments, the dashed line represents a double bond. In some embodiments, both dashed lines represent a single bond. In some embodiments, p is 1 and r is 1. In some embodiments, p is 1 and r is 0. In some embodiments, p is 0 and r is 0. In some embodiments, B has the structure:

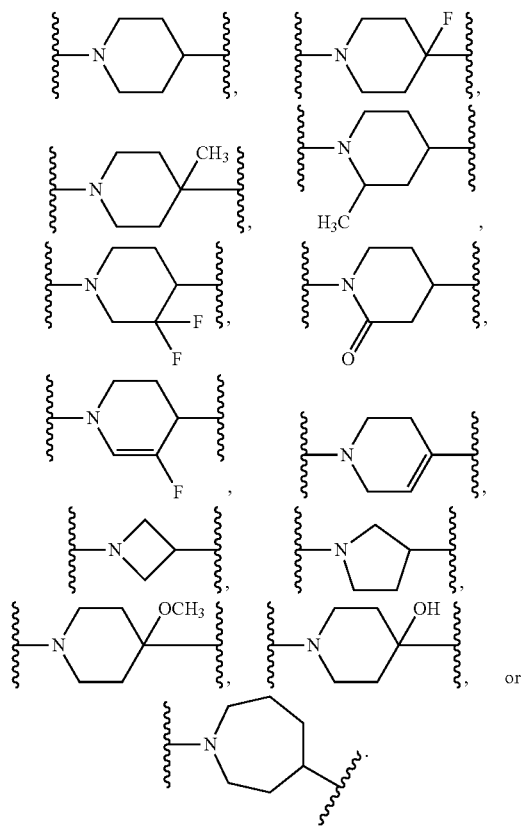

In some embodiments, $X^1$ is $CR^6$ and $X^2$ is N. In some embodiments, o is 0, 1, or 2. In some embodiments, $R^4$ is halogen (e.g., fluoro), optionally substituted $C_1$-$C_6$ alkyl (e.g., methyl), or two $R^4$ combine with the carbon two which they are attached to form a carbonyl. In some embodiments, $R^6$ is hydrogen. In some embodiments, $R^6$ is halogen (e.g., fluoro). In some embodiments, $R^6$ is optionally substituted $C_1$-$C_6$ alkyl (e.g., methyl). In some embodiments, the dashed line represents a double bond. In some embodiments, the dashed line represents a single bond. In some embodiments, p is 1 and r is 1. In some embodiments, p is 1 and r is 0. In some embodiments, p is 0 and r is 0. In some embodiments, B has the structure:

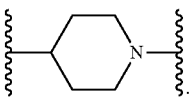

In some embodiments, $X^1$ is N and $X^2$ is N. In some embodiments, o is 0, 1, or 2. In some embodiments, $R^4$ is halogen (e.g., fluoro), optionally substituted $C_1$-$C_6$ alkyl (e.g., methyl), or two $R^4$ combine with the carbon two which they are attached to form a carbonyl. In some embodiments, the dashed line represents a double bond. In some embodiments, the dashed line represents a single bond. In some embodiments, p is 1 and r is 1. In some embodiments, p is 1 and r is 0. In some embodiments, p is 0 and r is 0. In some embodiments, o is 1 and r is 2. In some embodiments. B has the structure:

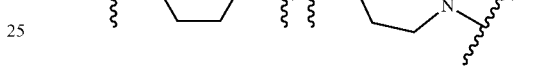

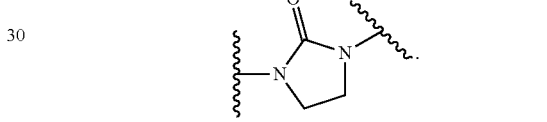

In some embodiments, $X^1$ is $CR^6$ and $X^2$ is $CR^6$. In some embodiments, o is 0, 1, or 2. In some embodiments, $R^4$ is halogen (e.g., fluoro), optionally substituted $C_1$-$C_6$ alkyl (e.g., methyl), or two $R^4$ combine with the carbon two which they are attached to form a carbonyl. In some embodiments, the dashed line represents a double bond. In some embodiments, the dashed line represents a single bond. In some embodiments, p is 1 and r is 1. In some embodiments, p is 1 and r is 0. In some embodiments, p is 0 and r is 0. In some embodiments, B has the structure:

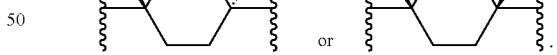

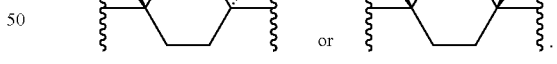

In some embodiments, B has the structure of Formula Ic:

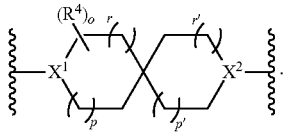

In some embodiments, $X^1$ is N and $X^2$ is N. In some embodiments, o is 0. In some embodiments, p, p', r, and r' are 0. In some embodiments, p and r are each 1 and p' and r' are 0. In some embodiments, B has the structure:

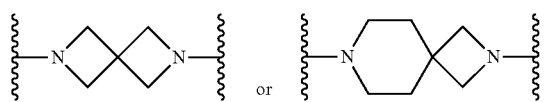 or 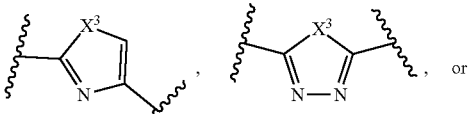.

In some embodiments, B has the structure of Formula Id:

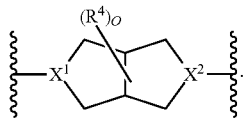

In some embodiments, $X^1$ is N and $X^2$ is N. In some embodiments, o is 0. In some embodiments, B has the structure:

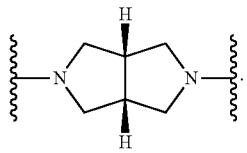 [SMILES: *N1C[C@H]2CN(*)C[C@H]2C1]

In some embodiments, B has the structure of Formula Ie:

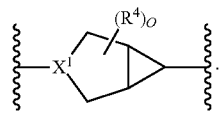

In some embodiments, $X^1$ is N and $X^2$ is N. In some embodiments, o is 0. In some embodiments, B has the structure:

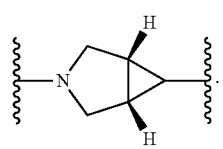 [SMILES: *C1[C@H]2CN(*)C[C@@H]12]

In some embodiments, B has the structure of Formula If:

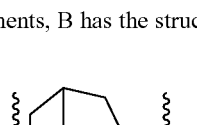

In some embodiments of any of the foregoing compounds, Het is —C(O)NH— or:

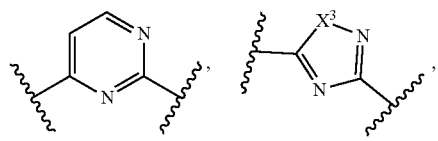

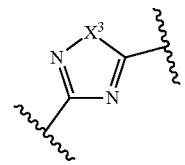, or wherein $X^3$ is O or S.

In some embodiments, Het is —C(O)NH—.
In some embodiments, Het is

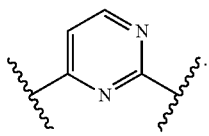 [SMILES: *c1ccnc(*)n1]

In some embodiments, Het is

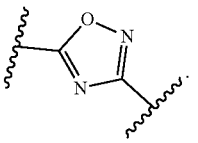 [SMILES: *c1noc(*)n1]

In some embodiments, Het is

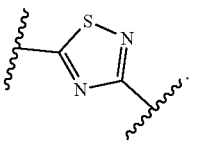 [SMILES: *c1nsc(*)n1]

In some embodiments, Het is

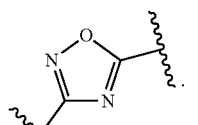

In some embodiments, $L^2$ is absent. In some embodiments, $L^2$ is —$NR^2$— (e.g., —NH—). In some embodiments, $L^2$ is —O—. In some embodiments, $L^2$ is —$SO_2$—. In some embodiments, $L^2$ is —$CR^2R^3$—. In some embodiments, $R^2$ and $R^3$ combine with the carbon to which they are attached to form a carbonyl. In some embodiments, $R^2$ and $R^3$ combine with the carbon to which they are attached to form an optionally substituted $C_3$-$C_7$ cycloalkyl (e.g., cyclopropyl). In some embodiments, $R^2$ and $R^3$ are both hydrogen. In some embodiments, $R^2$ is hydrogen and $R^3$ is optionally substituted $C_1$-$C_6$ alkylene (e.g., methylene).

In some embodiments, n is 0. In some embodiments, n is 1. In some embodiments, $L^1$ is —$NR^2$— (e.g., ~NH— or —N(Et)-). In some embodiments, $L^1$ is —O—. In some embodiments, $L^1$ is —$SO_2$—. In some embodiments, $L^1$ is optionally substituted $C_1$-$C_6$ alkylene (e.g., methylene or hydroxy-methylene). In some embodiments, $L^1$ is optionally substituted $C_1$-$C_6$ heteroalkylene (e.g., ~NH—$CH_2$—, —O—$CH_2$—, —O—$CH_2$—$CH_2$—, —$CH_2$—O—$CH_2$—, —$CH_2$—O—,

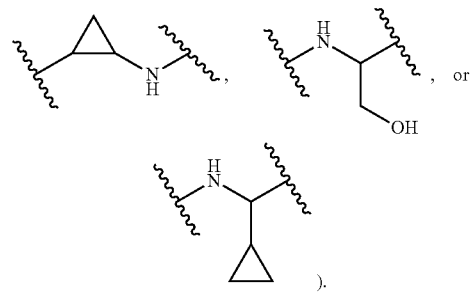

In some embodiments, $L^1$ is optionally substituted $C_2$-$C_9$ heterocycle (e.g.,

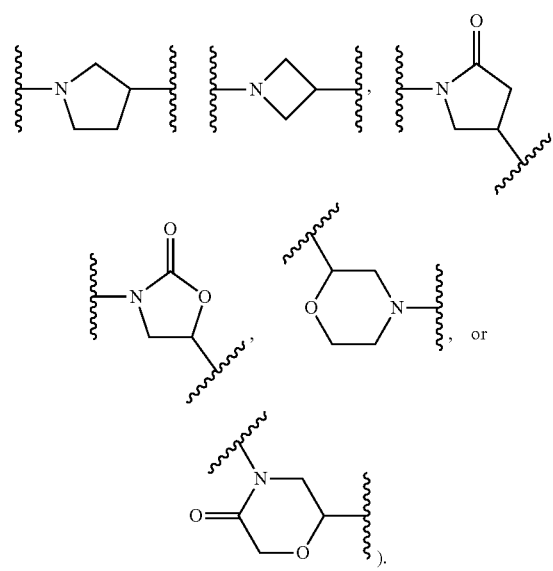

In some embodiments, $R^1$ is cyano, optionally substituted $C_1$-$C_6$ alkyl (e.g., methyl, ethyl, isopropyl, tert-butyl, trifluoromethyl, trifluoroethyl, pentafluoro-ethyl, 2-chloro-ethyl, 1-chloro-3-hydroxy-isopropyl, 2-methoxy-ethyl, or hexafluoro-isopropyl). In some embodiments, $R^1$ is optionally substituted $C_6$-$C_{10}$ aryl (e.g., phenyl, 2-chloro-phenyl, 3-chloro-phenyl, 4-chloro-phenyl, 2-trifluoromethyl-phenyl, 3-trifluoromethyl-phenyl, 4-trifluoromethyl-phenyl, 2-cyano-phenyl, 3-cyano-phenyl, 4-cyano-phenyl, 3-isopropyl-phenyl, 4-isopropyl-phenyl, 2-fluoro-phenyl, 3-fluoro-phenyl, 4-fluoro-phenyl, 4-methoxy-phenyl, 4-difluoromethoxy-phenyl, 4-trifluoromethoxy-phenyl, 2-chloro-5-fluoro-phenyl, 2-fluoro-4-chloro-phenyl, 3-fluoro-4-chloro-phenyl, 2-bromo-4-methoxy-phenyl, 2-trifluoromethyl-5-fluoro-phenyl, 2-trifluoromethyl-5-chloro-phenyl,

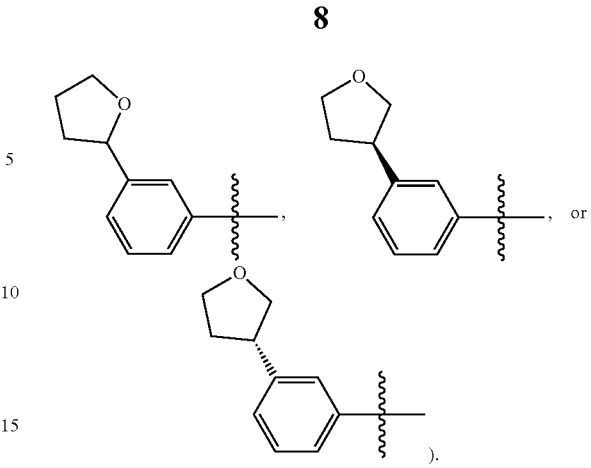

In some embodiments, $R^1$ is optionally substituted $C_6$-$C_{10}$ aryl $C_1$-$C_6$ alkyl (e.g., naphthylmethyl). In some embodiments, $R^1$ is optionally substituted $C_3$-$C_7$ cycloalkyl (e.g., cyclopropyl, cyclohexyl, 6-methoxy-cyclohexyl, 1-cyano-cyclopropyl, bicycle[1.1.1]pentane, 1-methyl-cyclopropyl, 1-ethyl-cyclopropyl, 1-fluoro-cyclopropyl, 1-methoxy-cyclopropyl, 1-hydroxy-cyclopropyl, 2,2-dimethyl-cyclopropyl, 2,2-difluoro-cyclopropyl, cyclobutyl,

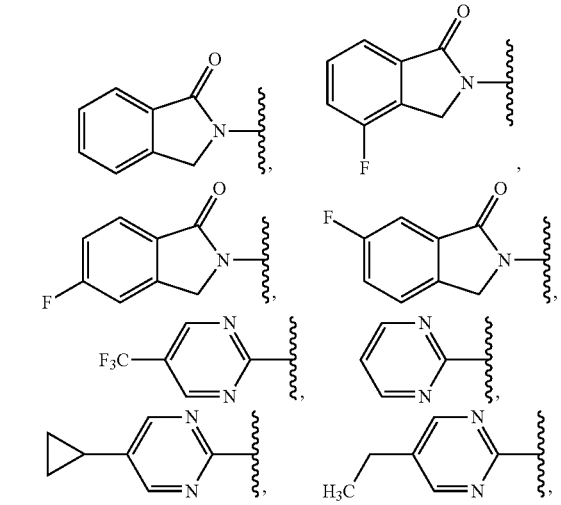

In some embodiments, $R^1$ is optionally substituted $C_3$-$C_7$ cycloalkyl $C_1$-$C_6$ alkyl (cyclopropylmethyl). In some embodiments, $R^1$ is optionally substituted $C_2$-$C_9$ heteroaryl (e.g.,

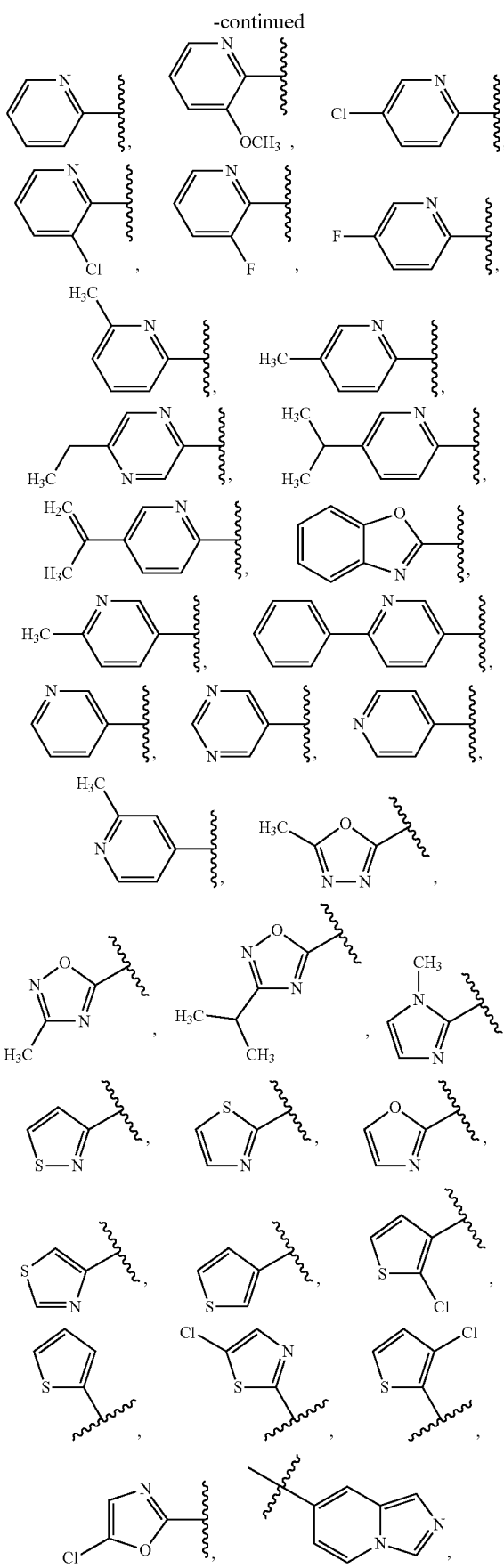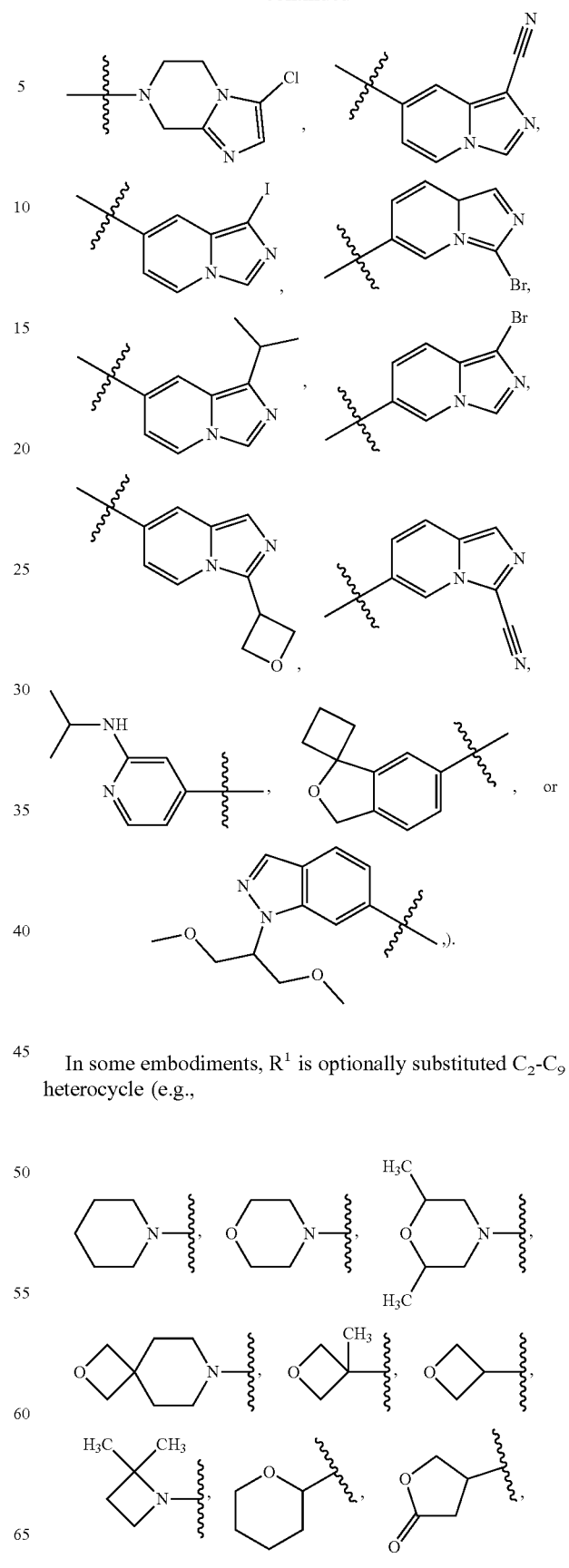
In some embodiments, $R^1$ is optionally substituted $C_2$-$C_9$ heterocycle (e.g.,

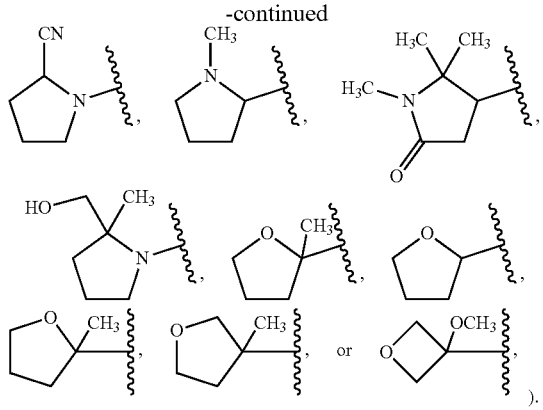

In some embodiments, R¹ is optionally substituted $C_2$-$C_9$ heterocycle $C_1$-$C_6$ alkyl (e.g.,

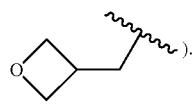
).

In some embodiments, R⁵ is optionally substituted $C_6$-$C_{10}$ aryl (e.g., phenyl, 3,4-dimethoxy-phenyl, 3-methoxy-4-ethoxy-phenyl, 3,5-dimethoxy-phenyl, 3-methoxy-4-cyclopropoxy-phenyl, 3-methoxy-4-trifluoromethoxy-phenyl, 3-isopropoxy-4-methoxy-phenyl,

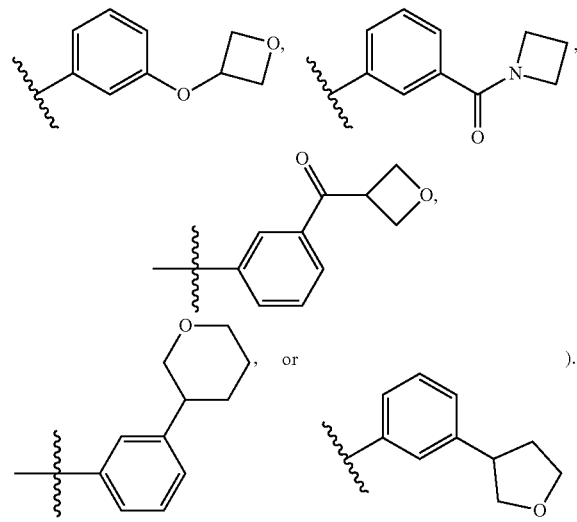

In some embodiments, R⁵ is optionally substituted $C_2$-$C_9$ heteroaryl (e.g.,

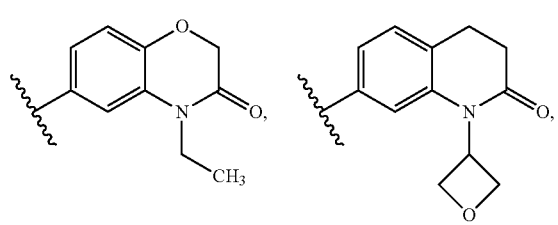

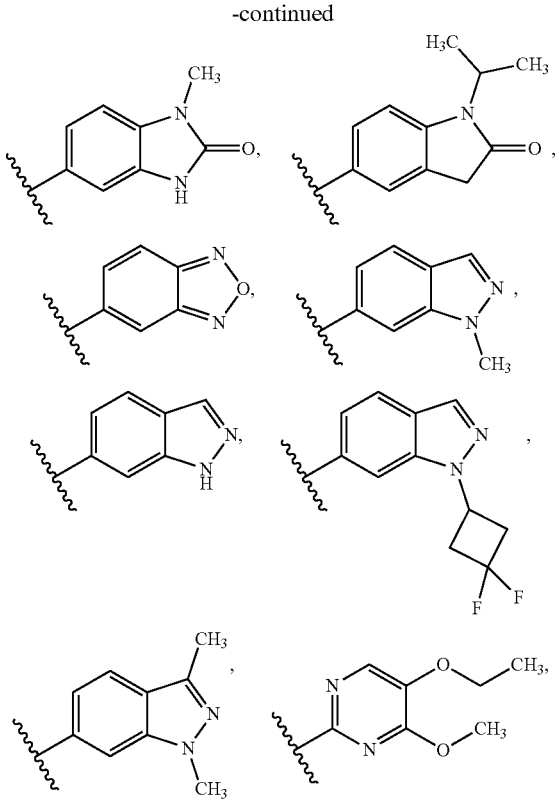

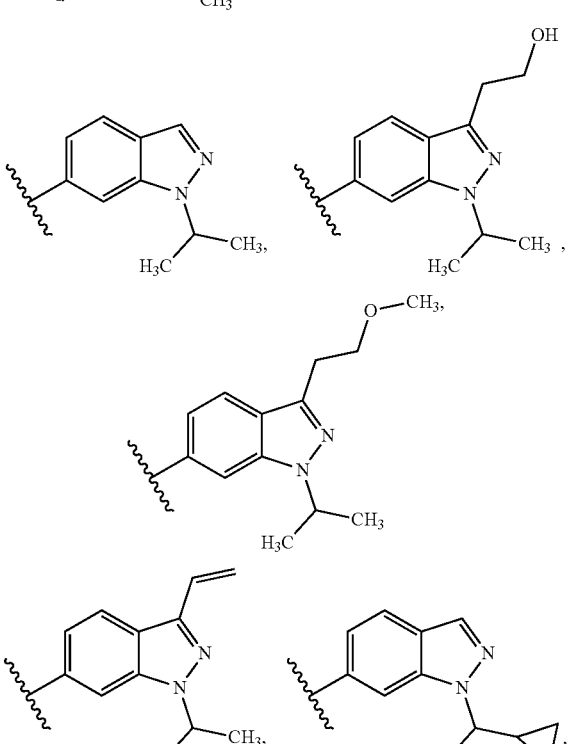

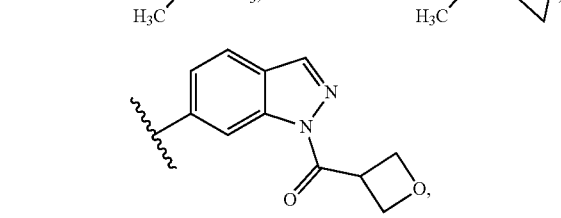

-continued
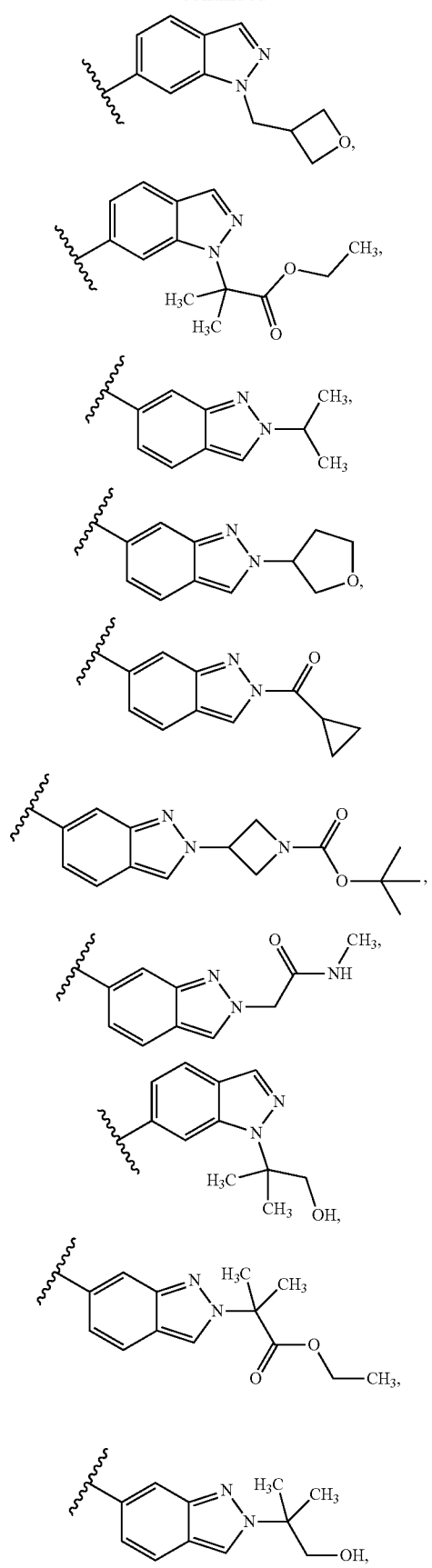
-continued
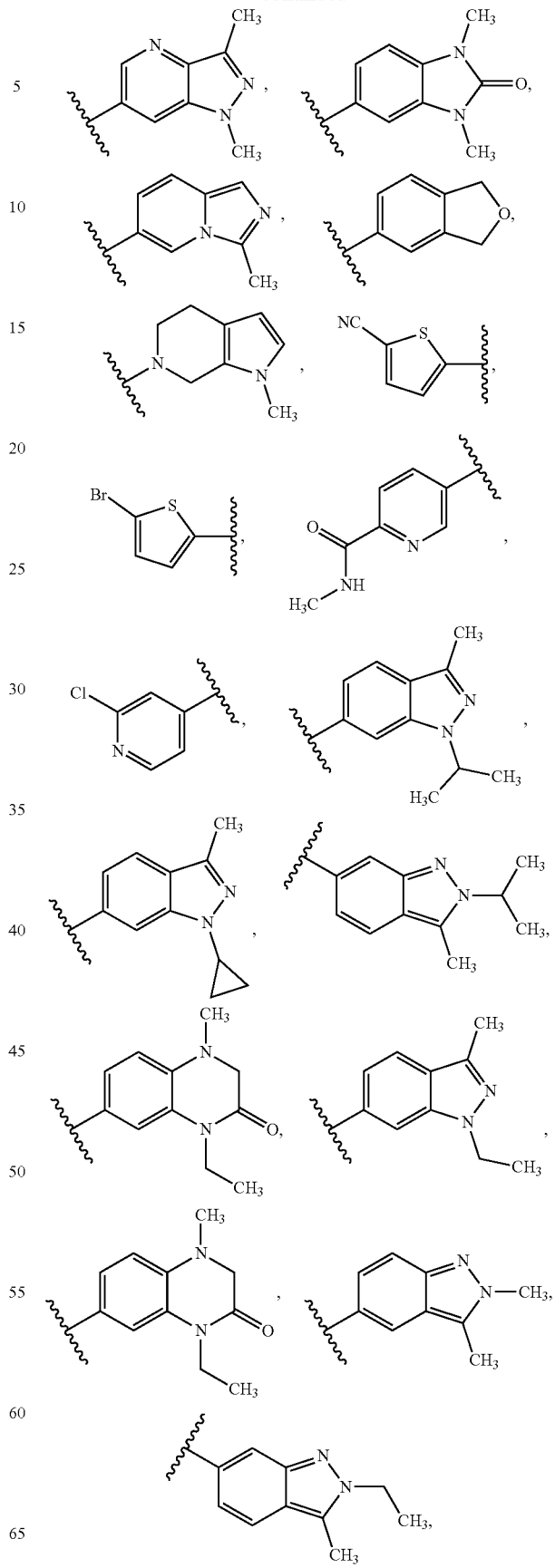

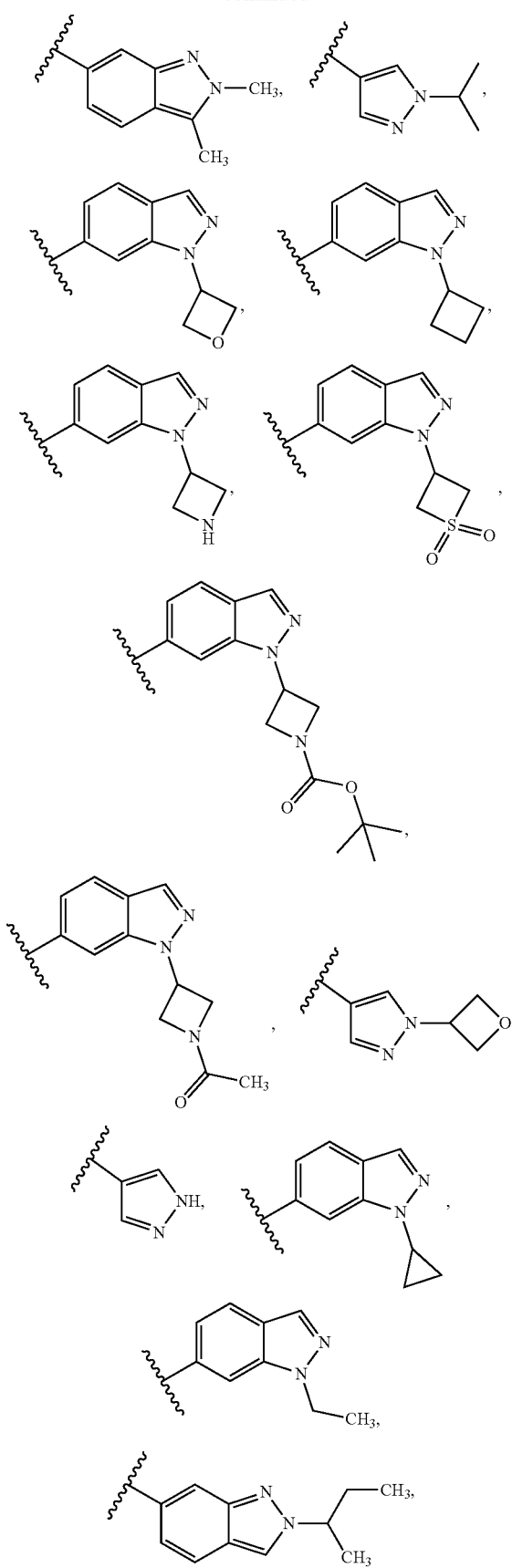
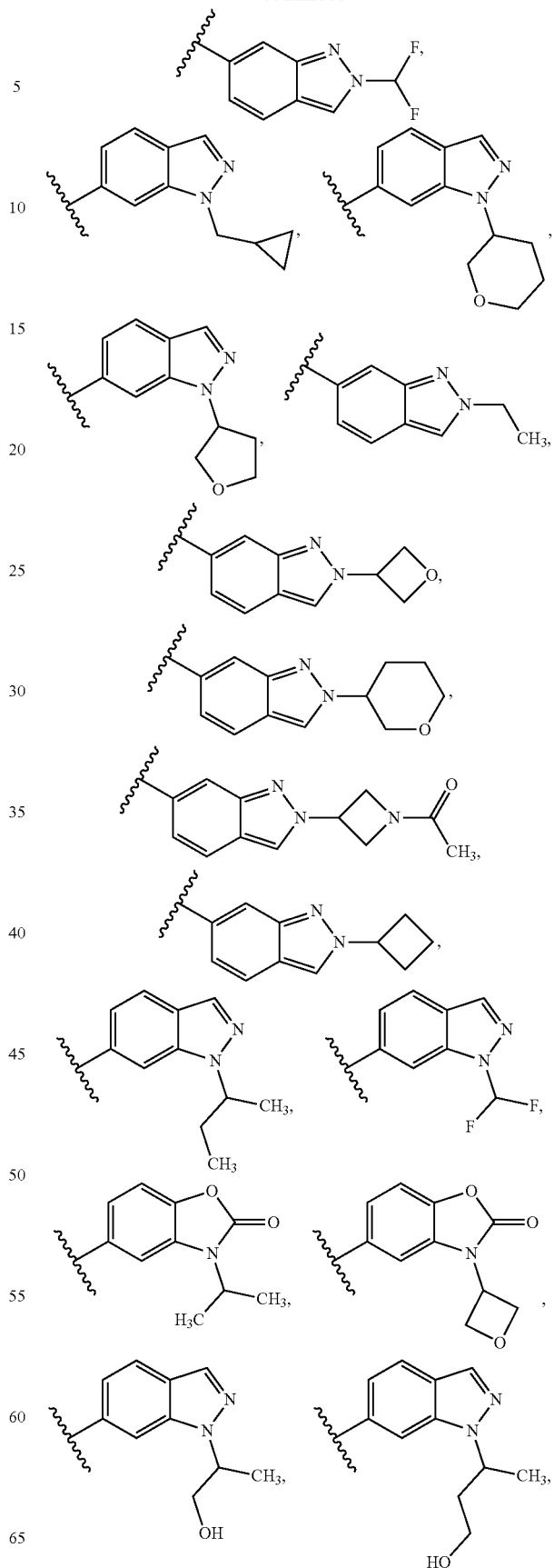

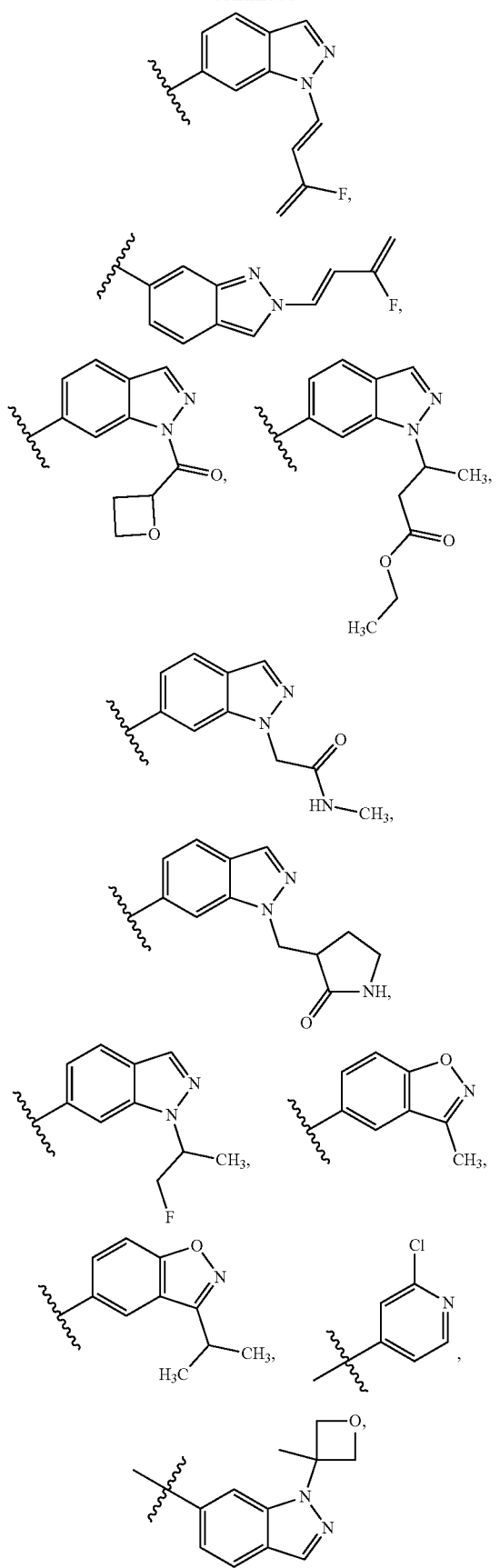
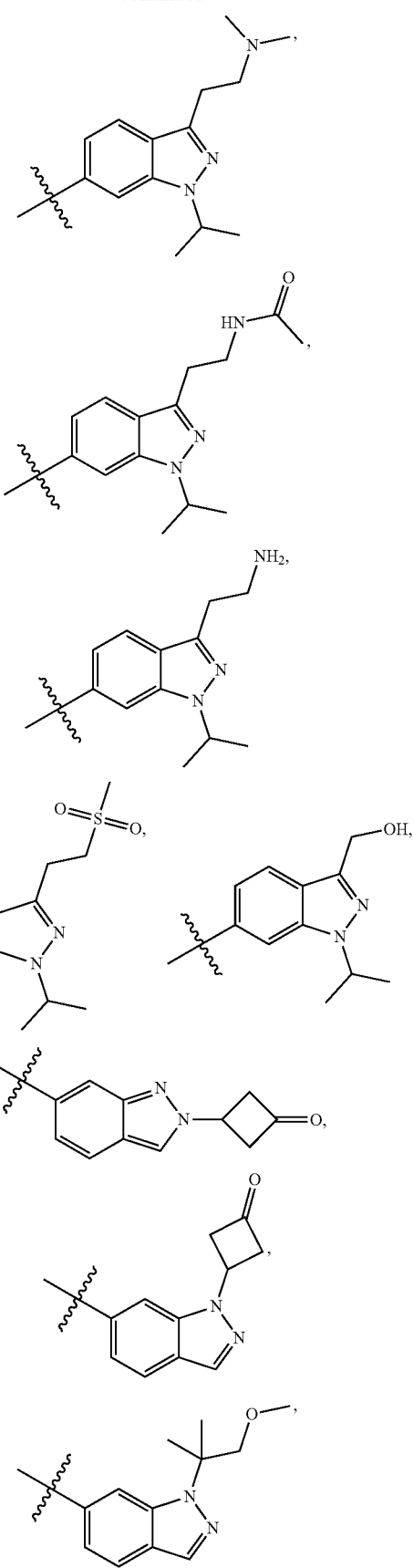

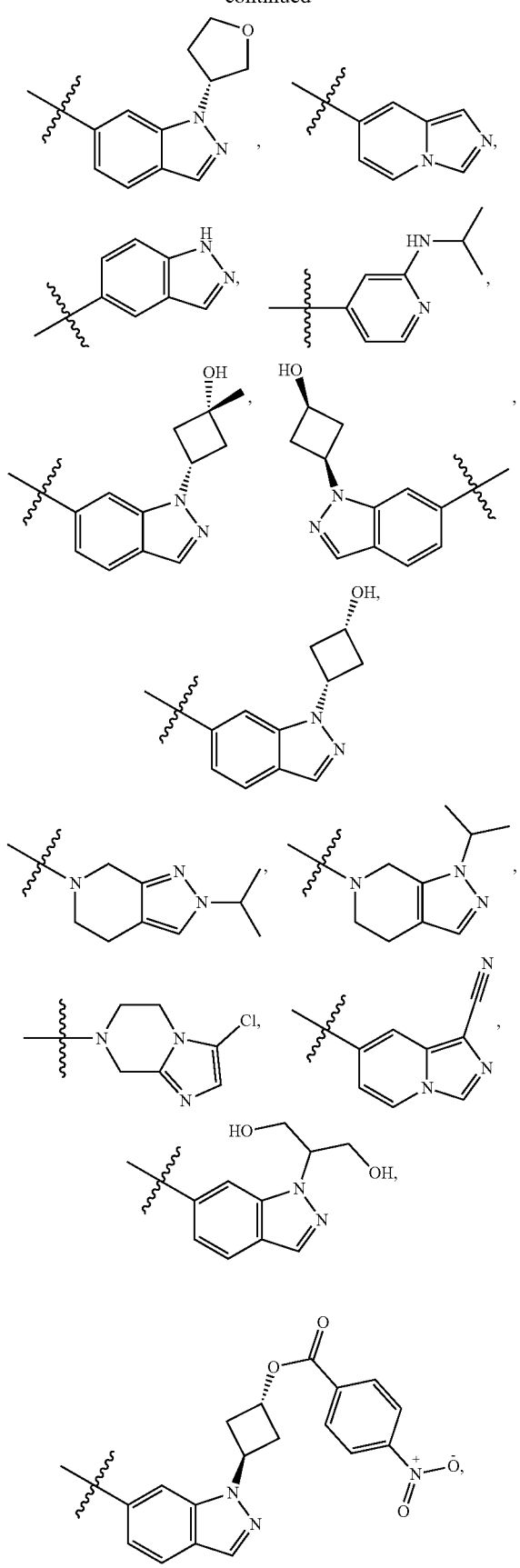
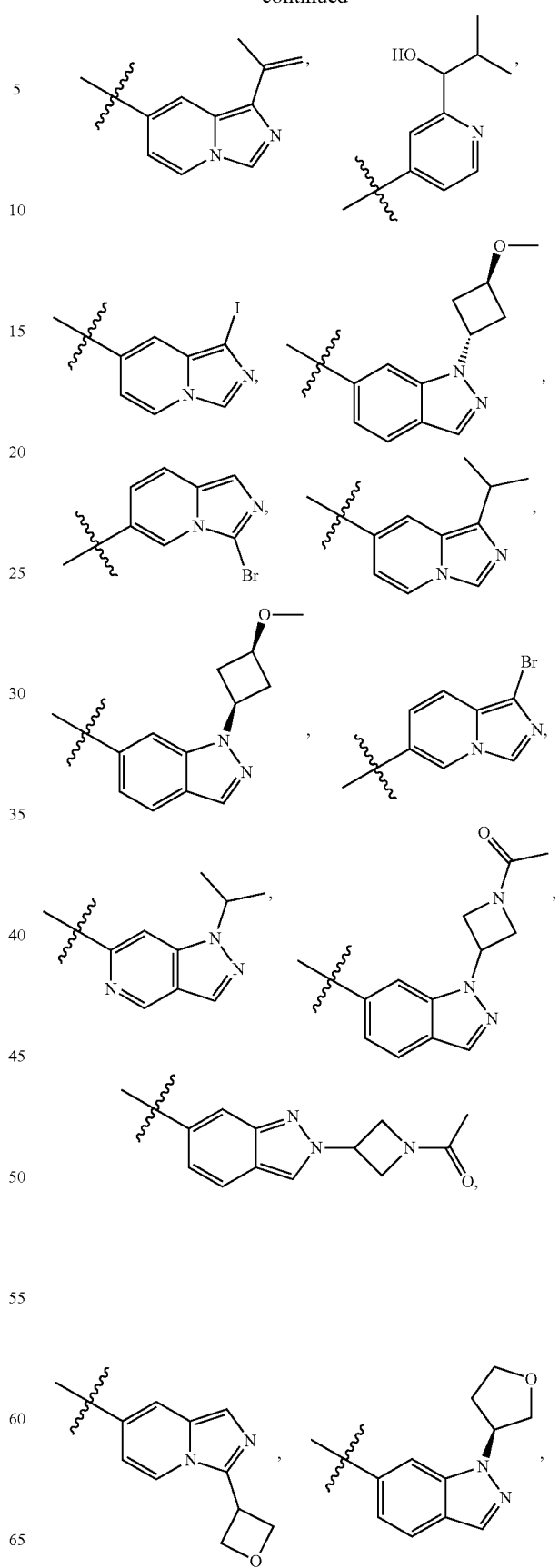

-continued

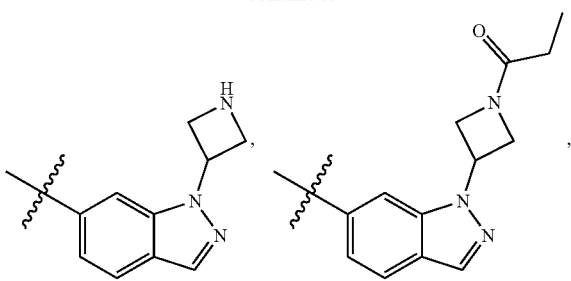

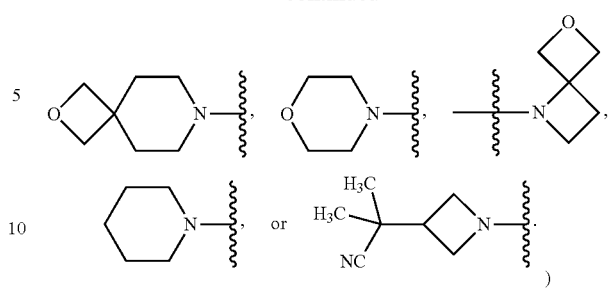

In some embodiments, $R^5$ is optionally substituted $C_2$-$C_9$ heteroaryl $C_1$-$C_6$ alkyl (e.g.,

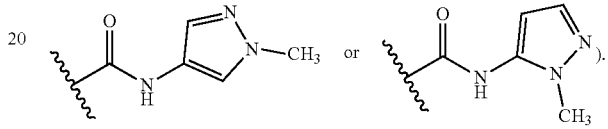

).

In some embodiments, $R^5$ is a bicyclic heterocyle. For example, a bicyclic heterocycle such as an indazole. In some embodiments, $R^5$ is an indazole having the structure:

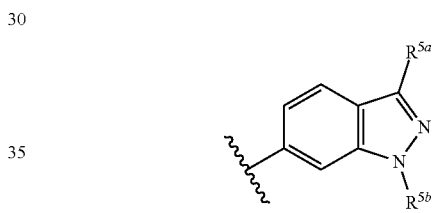

wherein $R^{5a}$ is hydrogen or optionally substituted $C_1$-$C_6$ alkyl (e.g., methyl) and $R^{5b}$ is optionally substituted $C_1$-$C_6$ alkyl (e.g., methyl or iso-propyl), optionally substituted $C_2$-$C_9$ heterocyclyl (e.g., oxetane), or optionally substituted $C_3$-$C_7$ cycloalkyl (e.g., cyclopropyl).

In some embodiments, B has the structure:

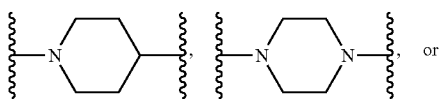

In some embodiments, $R^1$ is optionally substituted $C_1$-$C_6$ alkyl (e.g., methyl, ethyl, iso-propyl, or tert-butyl), optionally substituted $C_6$-$C_{10}$ aryl, or optionally substituted $C_2$-$C_9$ heteroaryl.

In some embodiments, m is 0, n is 1, $L^1$ is —O—, and $L^2$ is —C(O)—. In some embodiments, m is 0, n is 0, and $L^2$ is —C(O)—. In some embodiments, m is 0, n is 1, $L^1$ is In some embodiments, $R^5$ is an optionally substituted indazole. In some embodiments, $R^5$ is optionally substituted $C_2$-$C_9$ heterocycle (e.g., a nitrogen containing heterocycle such as

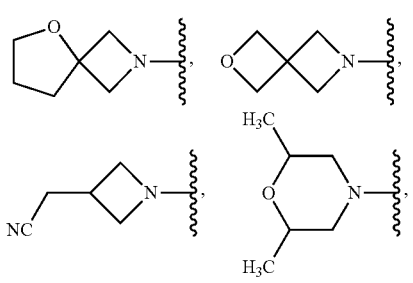

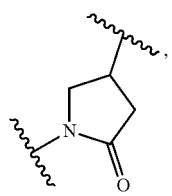 [SMILES: *C1CC(=O)N(*)C1]

and L² is —C(O)—. In some embodiments, m is 1, n is 1, L¹ is

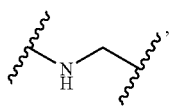

and L² is —C(O)—.

In some embodiments, R⁵ is an indazole having the structure:

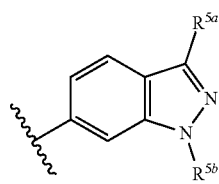

wherein $R^{5a}$ is hydrogen or optionally substituted $C_1$-$C_6$ alkyl (e.g., methyl) and $R^{5b}$ is optionally substituted $C_1$-$C_6$ alkyl (e.g., methyl or iso-propyl), optionally substituted $C_2$-$C_9$ heterocyclyl (e.g., oxetane), or optionally substituted $C_3$-$C_7$ cycloalkyl (e.g., cyclopropyl); B has the structure:

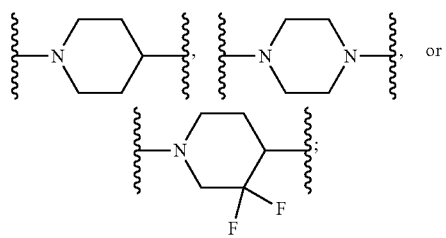

$R^1$ is optionally substituted $C_1$-$C_6$ alkyl (e.g., methyl, ethyl, iso-propyl, or tert-butyl), optionally substituted $C_6$-$C_{10}$ aryl, or optionally substituted $C_2$-$C_9$ heteroaryl; and m is 0, n is 1, L¹ is —O—, and L² is —C(O)—, m is 0, n is 0, and L² is —C(O)—, m is 0, n is 1, L¹ is

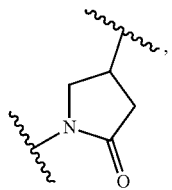 [SMILES: *C1CC(=O)N(*)C1]

and L² is —C(O)—, or m is 1, n is 1, L¹ is

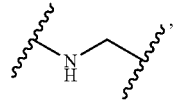 [SMILES: *CN*]

and L² is —C(O)—.

In some embodiments, m is 0, n is 1, L¹ is —O—, L² is —C(O)— and $R^1$ is optionally substituted $C_1$-$C_6$ alkyl (e.g., methyl, ethyl, iso-propyl, or tert-butyl).

In some embodiments, m is 0, n is 0, L² is —C(O)—, and $R^1$ is optionally substituted $C_6$-$C_{10}$ aryl.

In some embodiments, m is 0, n is 1, L¹ is

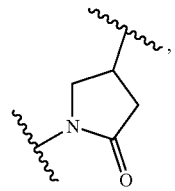

L² is —C(O)—, and $R^1$ is optionally substituted $C_6$-$C_{10}$ aryl, or optionally substituted $C_2$-$C_9$ heteroaryl.

In some embodiments, m is 1, n is 1, L¹ is

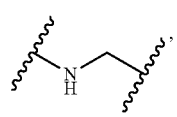 [SMILES: *CN*]

L² is —C(O)—, and $R^1$ is optionally substituted $C_6$-$C_{10}$ aryl.

In some embodiments, the compound has the structure of Formula Ig:

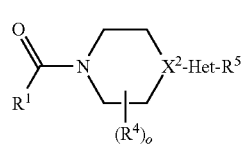

Formula Ig wherein Het is an optionally substituted oxadiazole;
is 0, 1, 2, 3, 4, 5, 6, 7, or 8;
$X^2$ is N or $CR^6$;
$R^1$ is optionally substituted $C_1$-$C_6$ alkyl, optionally substituted $C_1$-$C_6$ heteroalkyl, optionally substituted $C_6$-$C_{10}$ aryl, optionally substituted $C_6$-$C_{10}$ aryl $C_1$-$C_6$ alkyl, optionally substituted $C_3$-$C_7$ cycloalkyl, optionally substituted $C_3$-$C_7$ cycloalkyl $C_1$-$C_6$ alkyl, optionally substituted $C_2$-$C_9$ heteroaryl, optionally substituted $C_2$-$C_9$ heteroaryl $C_1$-$C_6$ alkyl, optionally substituted $C_2$-$C_9$ heterocycle, or optionally substituted $C_2$-$C_9$ heterocycle $C_1$-$C_6$ alkyl;
each $R^4$ is, independently, halogen, hydroxyl, optionally substituted $C_1$-$C_6$ alkyl, optionally substituted $C_1$-$C_6$ heteroalkyl, or two $R^4$ combine with the carbon two which they are attached to form a carbonyl or optionally substituted $C_3$-$C_7$ cycloalkyl;
$R^5$ is optionally substituted $C_1$-$C_6$ heteroalkyl, optionally substituted $C_1$-$C_6$ alkyl, optionally substituted $C_6$-$C_{10}$ aryl, optionally substituted $C_2$-$C_9$ heteroaryl, optionally substituted C$_2$-C$_9$ heterocycle, optionally substituted C$_6$-C$_{10}$ aryl C$_1$-C$_6$ alkyl, optionally substituted C$_2$-C$_9$ heterocycle C$_1$-C$_6$ alkyl, or optionally substituted C$_2$-C$_9$ heteroaryl C$_1$-C$_6$ alkyl; and each R$^6$ is, independently, hydrogen, halogen, optionally substituted C$_1$-C$_6$ heteroalkyl, or optionally substituted C$_1$-C$_6$ alkyl.

In some embodiments, Het is

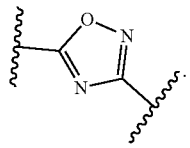 [SMILES: *c1noc(*)n1]

In some embodiments, Het is

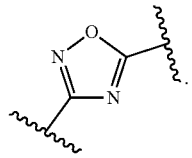 [SMILES: *c1noc(*)n1]

In some embodiments, X$^2$ is N or CH. In some embodiments, X$^2$ is N. In some embodiments, X$^2$ is CH.

In some embodiments, R$^1$ is optionally substituted C$_1$-C$_6$ alkyl, optionally substituted C$_1$-C$_6$ heteroalkyl, or optionally substituted C$_6$-C$_{10}$ aryl.

In some embodiments, R$^5$ is optionally substituted C$_6$-C$_{10}$ aryl or optionally substituted C$_2$-C$_9$ heteroaryl (e.g., bicyclic heteroaryl such as an indazole). In some embodiments, R$^5$ has the structure:

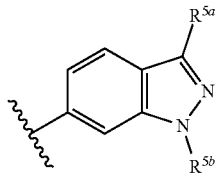

wherein R$^{5a}$ is hydrogen or optionally substituted C$_1$-C$_6$ alkyl (e.g., methyl) and R$^{5b}$ is optionally substituted C$_1$-C$_6$ alkyl (e.g., methyl or iso-propyl), optionally substituted C$_2$-C$_9$ heterocyclyl (e.g., oxetane), or optionally substituted C$_3$-C$_7$ cycloalkyl (e.g., cyclopropyl). In some embodiments, R$^{5a}$ is hydrogen.

In some embodiments, Het is

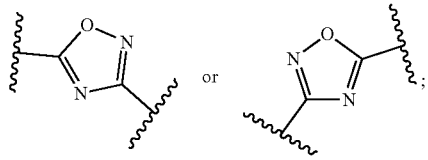 [SMILES: *c1noc(*)n1 ; *c1noc(*)n1]

o is 0; X$^2$ is N or CH; R$^1$ is optionally substituted C$_1$-C$_6$ alkyl, optionally substituted C$_1$-C$_6$ heteroalkyl (e.g., C$_1$-C$_6$ alkoxy or C$_1$-C$_6$ alkylamino), or optionally substituted C$_6$-C$_{10}$ aryl; and R$^5$ has the structure:

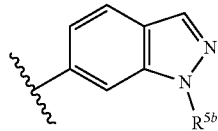

wherein R$^{5b}$ is optionally substituted C$_1$-C$_6$ alkyl (e.g., methyl or iso-propyl), optionally substituted C$_2$-C$_9$ heterocyclyl (e.g., oxetane), or optionally substituted C$_3$-C$_7$ cycloalkyl (e.g., cyclopropyl).

In some embodiments the compound has the structure of Formula I:

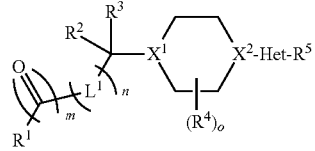

Formula I wherein Het is an optionally substituted optionally substituted C$_2$-C$_9$ heteroaryl;

m is 0 or 1;

n is 0, 1, or 2;

is 0, 1, 2, 3, 4, 5, 6, 7, or 8;

X$^1$ and X$^2$ are each, independently, N or CR$^6$;

L$^1$ is optionally substituted C$_1$-C$_6$ alkylene, optionally substituted C$_1$-C$_6$ alkenylene, optionally substituted C$_1$-C$_6$ heteroalkylene, optionally substituted C$_3$-C$_7$ cycloalkyl, optionally substituted C$_2$-C$_9$ heteroaryl, or optionally substituted C$_2$-C$_9$ heterocycle;

R$^1$ is optionally substituted C$_1$-C$_6$ alkyl, optionally substituted C$_1$-C$_6$ heteroalkyl, optionally substituted C$_6$-C$_{10}$ aryl, optionally substituted C$_3$-C$_7$ cycloalkyl, optionally substituted C$_2$-C$_9$ heteroaryl, or optionally substituted C$_2$-C$_9$ heterocycle;

R$^2$ and R$^3$ are each, independently, hydrogen, optionally substituted C$_1$-C$_6$ alkyl, or combine with the carbon to which they are attached to form a carbonyl;

each R$^4$ is, independently, halogen, hydroxyl, optionally substituted C$_1$-C$_6$ alkyl, optionally substituted C$_1$-C$_6$ heteroalkyl, or two R$^4$ combine with the carbon two which they are attached to form a carbonyl;

R$^5$ is optionally substituted C$_6$-C$_{10}$ aryl or optionally substituted C$_2$-C$_9$ heteroaryl; and each R$^6$ is, independently, hydrogen or optionally substituted C$_1$-C$_6$ alkyl.

In some embodiments of any of the foregoing compounds, R$^2$ and R$^3$ combine with the carbon to which they are attached to form a carbonyl. In some embodiments of any of the foregoing compounds, R$^2$ and R$^3$ are both hydrogen.

In some embodiments of any of the foregoing compounds, Het is:

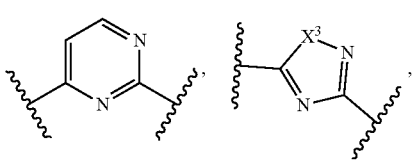

-continued

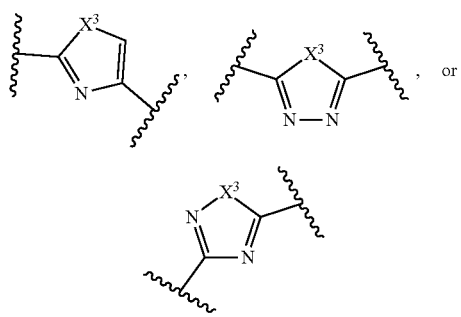

wherein $X^3$ is O or S.

In some embodiments, the compound has the structure of Formula II or IIa:

Formula II

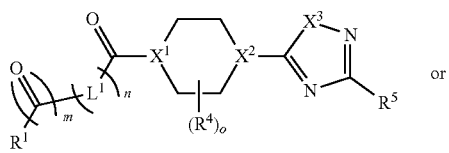

or

Formula IIa

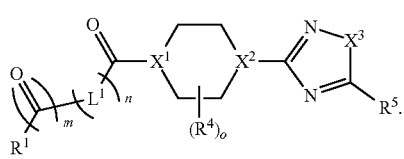

In some embodiments of any of the foregoing compounds, $X^3$ is O. In some embodiments of any of the foregoing compounds, $X^3$ is S.

In some embodiments of any of the foregoing compounds, $X^1$ is N and $X^2$ is $CR^6$. In some embodiments of any of the foregoing compounds, $X^1$ is N and $X^2$ is N. In some embodiments of any of the foregoing compounds, $X^1$ is $CR^6$ and $X^2$ is N. In some embodiments of any of the foregoing compounds, $R^6$ is hydrogen.

In some embodiments of any of the foregoing compounds, $R^5$ is optionally substituted $C_6$-$C_{10}$ aryl. For example, in some embodiments, $R^5$ is a $C_6$-$C_{10}$ aryl substituted with 1, 2, 3, or 4 substituents independently selected from $C_1$-$C_6$ alkyl (e.g., methyl), halogen (e.g., fluoro, chloro, or bromo), $C_1$-$C_6$ alkoxy (e.g., methoxy or ethoxy), nitrile, or two substituents combine to form a 5 or 6-membered heterocycle (e.g., 2,2-difluoro-1,3-benzodioxole). In some embodiments of any of the foregoing compounds, $R^5$ is phenyl, 2-methyl-phenyl, 3-methyl-phenyl, 4-methyl-phenyl, 3,4-dimethyl-phenyl, 2-methoxy-phenyl, 3-methoxy-phenyl, 4-methoxy-phenyl, 3,4-dimethoxy-phenyl, 2-fluoro-phenyl, 3-fluoro-phenyl, 4-fluoro-phenyl, 3,4-di fluoro-phenyl, 3,4-dichloro-phenyl, 3-methoxy-4-ethoxy-phenyl, 3-chloro-4-ethoxy-phenyl, 3-fluoro-4-ethoxy-phenyl, 3-bromo-4-ethoxy-phenyl, 3-cyano-4-ethoxy-phenyl, or 2,2-difluoro-1,3-benzodioxole.

In some embodiments, the compound has the structure of Formula III or IIIa:

Formula III

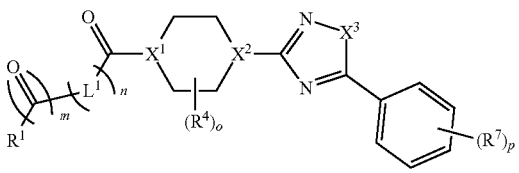

Formula IIIa wherein p is 1, 2, 3, 4, or 5;

each $R^7$ is, independently, halogen, nitrile, $OR^8$, or optionally substituted $C_1$-$C_6$ alkyl; and each $R^8$ is, independently, hydrogen or optionally substituted $C_1$-$C_6$ alkyl.

In some embodiments, the compound has the structure of Formula IV or IVa:

Formula IV

Formula IVa

In some embodiments, each $R^7$ is $OR^8$. In some embodiments, each $R^8$ is optionally substituted $C_1$-$C_6$ alkyl (e.g., methyl or ethyl).

In some embodiments of any of the foregoing compounds, $R^5$ is optionally substituted $C_2$-$C_9$ heteroaryl (e.g., bicyclic heteroaryl). In some embodiments of any of the foregoing compounds, $R^5$ is:

-continued

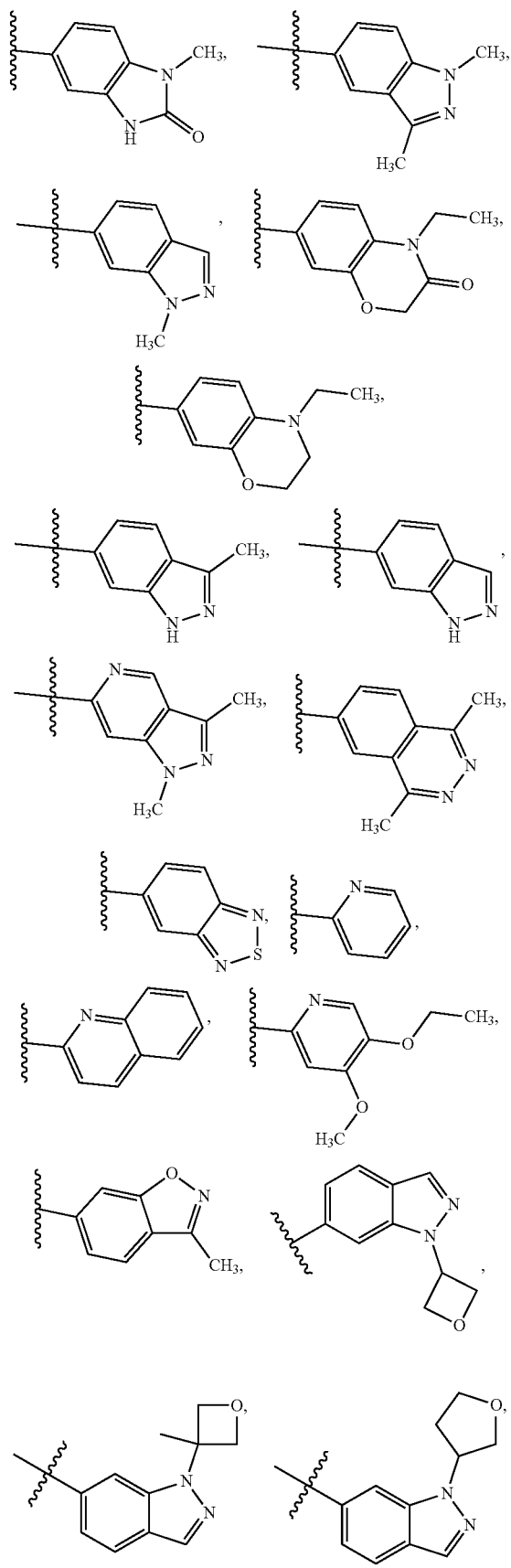

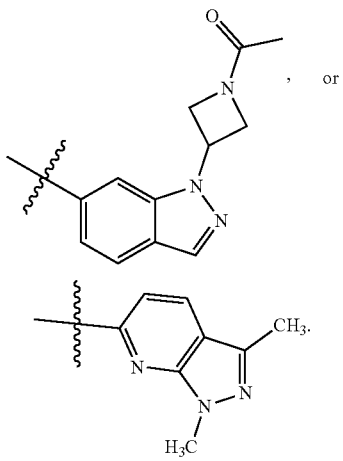

In some embodiments of any of the forgoing compounds, R⁵ is:

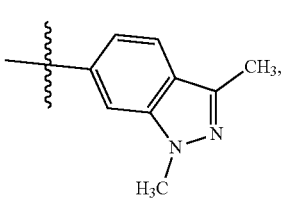

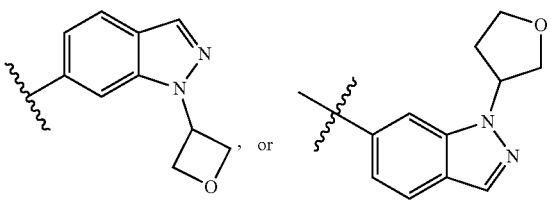

In some embodiments of any of the foregoing compounds, $R^1$ is optionally substituted $C_6$-$C_{10}$ aryl or optionally substituted $C_2$-$C_9$ heteroaryl. In some embodiments, $R^1$ is optionally substituted $C_6$-$C_{10}$ aryl. For example, phenyl or a $C_6$-$C_{10}$ aryl substituted with 1, 2, 3, 4, or 5 substituents independently selected from $C_1$-$C_6$ alkyl (e.g., methyl or iso-propyl), $C_1$-$C_6$ alkoxy (e.g., methoxy), or halogen (e.g., chloro). In some embodiments of any of the foregoing compounds $R^1$ is 2-methoxy-phenyl, 3-methoxy-phenyl, 4-methoxy-phenyl, 3,4-dimethoxy-phenyl, phenyl, 3-methyl-phenyl, 4-methyl-phenyl, 3,4-methyl-phenyl, 4-iso-propyl-phenyl, 2-chloro-phenyl, 3-chloro-phenyl, or 4-chloro-phenyl. In some embodiments of any of the foregoing compounds, $R^1$ is a bicyclic $C_6$-$C_{10}$ aryl (e.g., naphthalene). In some embodiments of any of the foregoing compounds, $R^1$ is $C_3$-$C_7$ cycloalkyl (e.g., cyclohexyl). In some embodiments of any of the foregoing compounds, $R^1$ is optionally substituted $C_2$-$C_9$ heteroaryl or optionally substituted $C_2$-$C_9$ heterocycle. For example, in some embodiments, $R^1$ is:

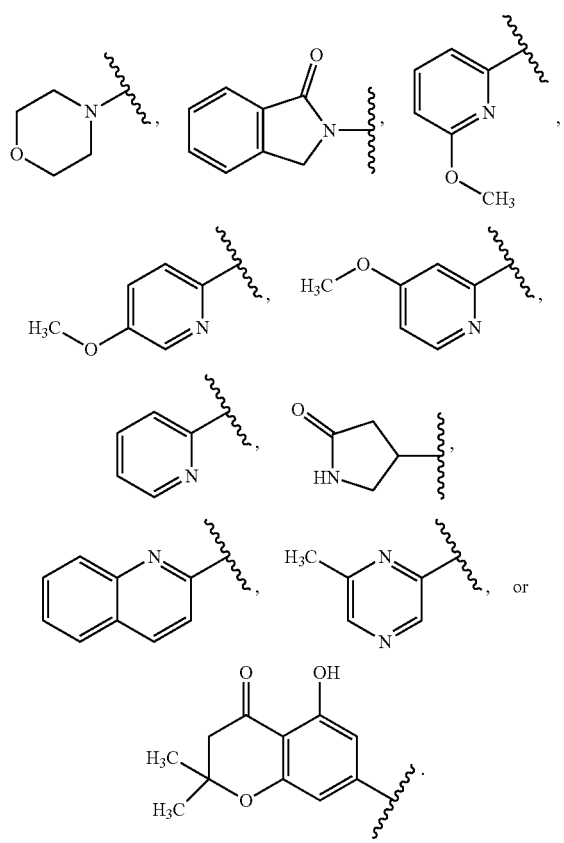

In some embodiments of any of the foregoing compounds, the compound has the structure of Formula V or Va:

Formula V

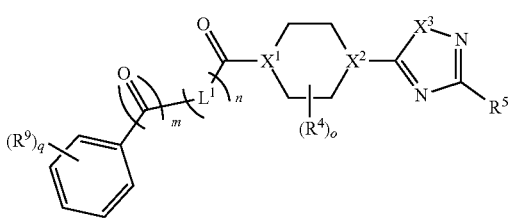

Formula Va

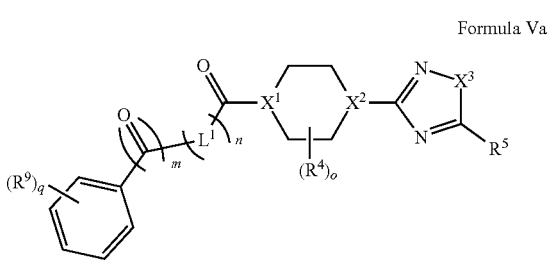

wherein q is 1, 2, 3, 4, or 5; and $R^9$ is halogen or optionally substituted $C_1$-$C_6$ alkyl.

In some embodiments of any of the foregoing compounds, the compound has the structure of Formula VI or VIa:

Formula VI

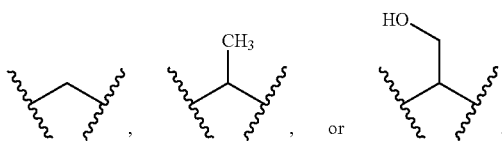

Formula VIa

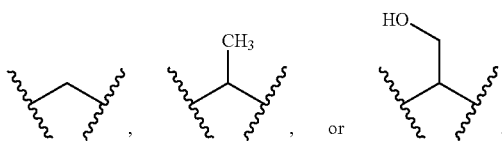

In some embodiments of any of the foregoing compounds, n is 1. In some embodiments of any of the foregoing compounds, n is 0.

In some embodiments of any of the foregoing compounds, $L^1$ is optionally substituted $C_1$-$C_6$ alkyl. For example, $L^1$ has the structure:

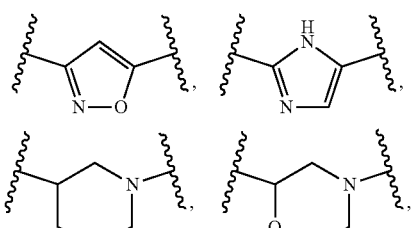

In some embodiments of any of the foregoing compounds, $L^1$ is optionally substituted $C_1$-$C_6$ alkenylene (e.g., ethenylene).

In some embodiments of any of the foregoing compounds, $L^1$ is optionally substituted $C_2$-$C_9$ heterocyclene or optionally substituted $C_2$-$C_9$ heteroarylene. For example,

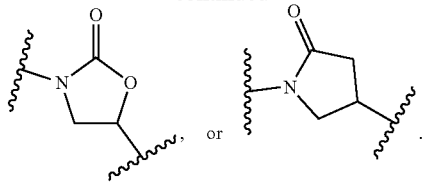

In some embodiments, L¹ is

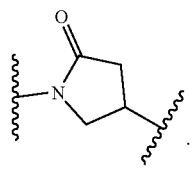 [SMILES: *C1CC(=O)N(*)C1]

In some embodiments of any of the foregoing compounds, L¹ is optionally substituted $C_1$-$C_6$ heteroalkylene. For example, in some embodiments, L¹ is:

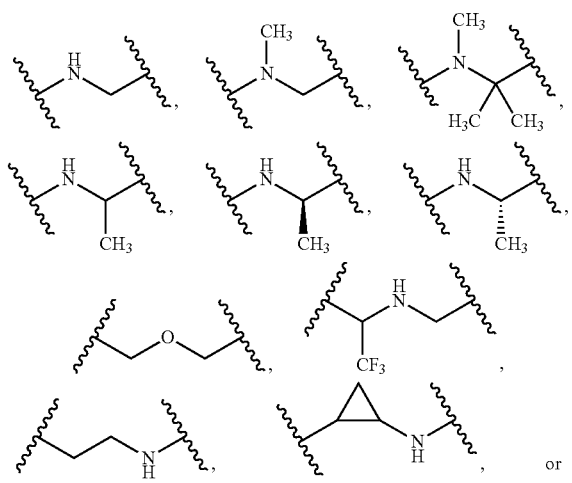

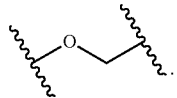

In some embodiments of any of the foregoing compounds, L¹ is ~NH—(CR¹⁰R¹¹)$_r$—, wherein r is 1, 2, 3, 4, 5, or 6, and each R¹⁰ and R¹¹ is, independently, hydrogen or optionally substituted $C_1$-$C_6$ alkyl. For example, in some embodiments, L¹ is ~NH—CH₂—, ~NH—CR¹⁰R¹¹—, wherein each of R¹⁰ and R¹¹ is methyl, or ~NH—CHR¹¹—, wherein R¹¹ is methyl.

In some embodiments of any of the foregoing compounds, m is 1. In some embodiments of any of the foregoing compounds, m is 0.

In another aspect, the disclosure provides a compound, or pharmaceutically acceptable salt thereof, having the structure of any one of compounds 1-966 in Table 1. In some embodiments, the compound is any one of compounds 1-264, 266-271, 274-276, 278-299, 302-318, 320-329, 331-340, 344-354, 358, 362-364, 367, 369, 371-378, 385, 388-392, 396, 397, 399-401, 403, 406-411, 414, 418-420, 422, 425-432, 434-436, 438, 440-444, 446, 450-454, 456, 458, 460, 461, 464, 466, 470, 472-474, 476, 477, or 481-746 in Table 1. In some embodiments, the compound is any one of compounds 1-347, 349, 350, or 354-746 in Table 1. In some embodiments, the compound is any one of compounds 1-387, 389, 393-405, 407-430, 432-439, 441-449, 452, 454-457, 459-472, 475, 477-480, 482-487, or 489-746 in Table 1, In some embodiments, the compound is any one of compounds 1-483 or 491-746 in Table 1. In some embodiments, the compound is any one of compounds 747-966. In some embodiments, the compound is any one of compounds 27, 40, 96, 128, 140, 168, 184, 204, 226, 244, 265, 268, 269, 284, 286 291, 294, 302, 305, 306, 308, 317, 319, 343, 344, 345, 346, 349, 355-357, or 359-364. In some embodiments, the compound is any one of compounds 244, 265, 269, 319, 345, 349, 355-357, 361, or 364. In some embodiments, the compound is any one of compounds 750, 767, 775-778, 780, 784, 785, 789-792, 795, 799, 812, 813, 817, 828, 838, 839, 842-844, 846, 848, 850, 851, 853, 854, 861, 862, 865, 874-881, 884-888, 890-898, 902, 903, 907, 910, 916, 928, 932, 934, 953, 957, 960, 964, or 965.

TABLE 1

| Compounds of the Invention | |
|---|---|
| # | Structure |
| 1 | |

TABLE 1-continued
Compounds of the Invention
| # | Structure |
|---|---|
| 2 | 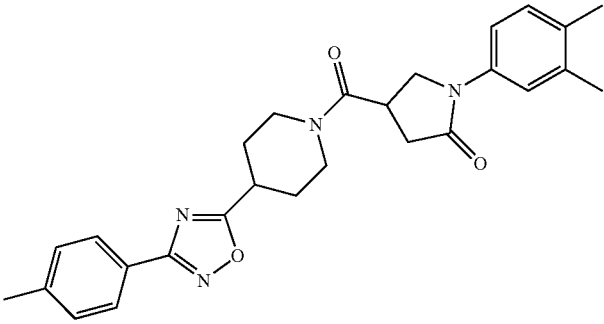 |
| 3 | 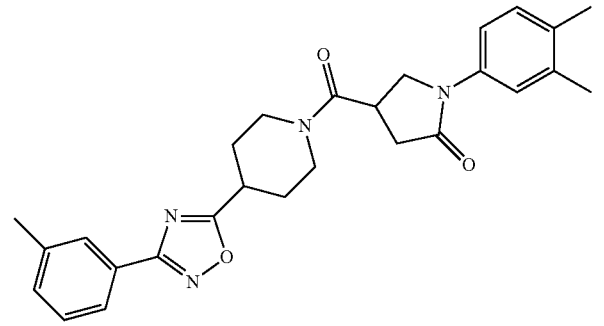 |
| 4 | 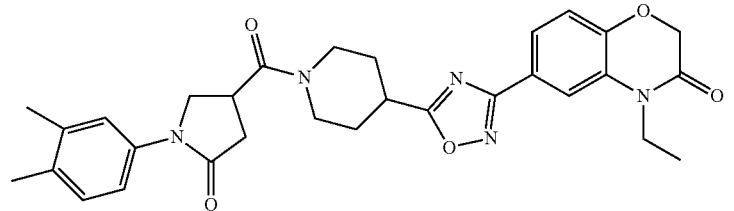 [SMILES: CCN1C(=O)COc2ccc(-c3noc(C4CCN(C(=O)C5CC(=O)N(c6ccc(C)c(C)c6)C5)CC4)n3)cc21] |
| 5 | 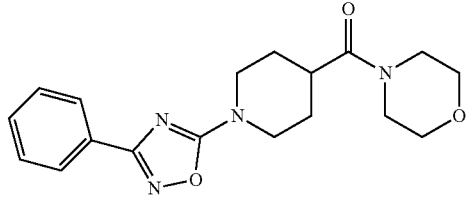 [SMILES: O=C(C1CCN(c2nc(-c3ccccc3)no2)CC1)N1CCOCC1] |
| 6 | 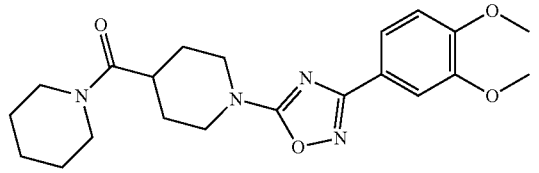 [SMILES: COc1ccc(-c2noc(N3CCC(C(=O)N4CCCCC4)CC3)n2)cc1OC] |
| 7 | 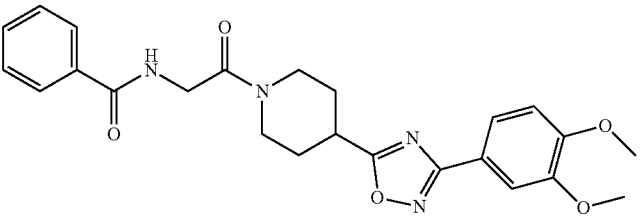 [SMILES: COc1ccc(-c2noc(C3CCN(C(=O)CNC(=O)c4ccccc4)CC3)n2)cc1OC] |

TABLE 1-continued
Compounds of the Invention
| # | Structure |
|---|---|
| 8 | 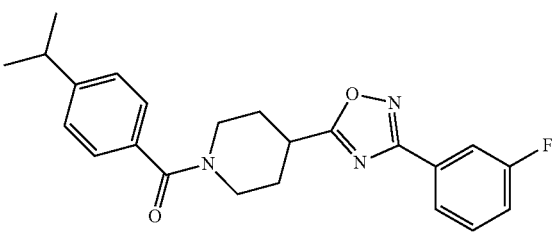 [SMILES: CC(C)c1ccc(C(=O)N2CCC(c3nc(-c4cccc(F)c4)no3)CC2)cc1] |
| 9 | 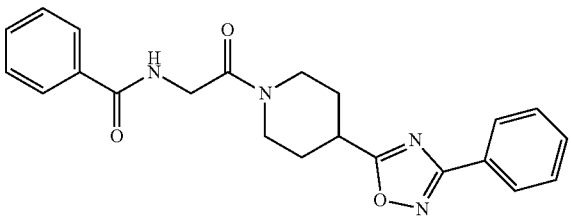 [SMILES: O=C(NCC(=O)N1CCC(c2nc(-c3ccccc3)no2)CC1)c1ccccc1] |
| 10 | 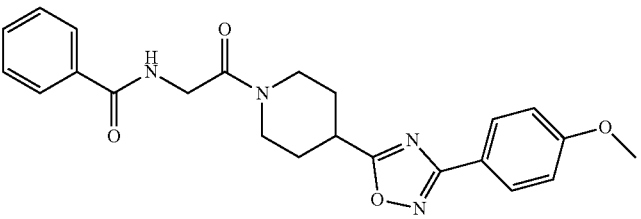 [SMILES: COc1ccc(-c2noc(C3CCN(C(=O)CNC(=O)c4ccccc4)CC3)n2)cc1] |
| 11 | 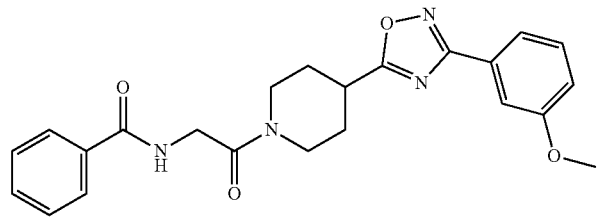 [SMILES: COc1cccc(-c2noc(C3CCN(C(=O)CNC(=O)c4ccccc4)CC3)n2)c1] |
| 12 | 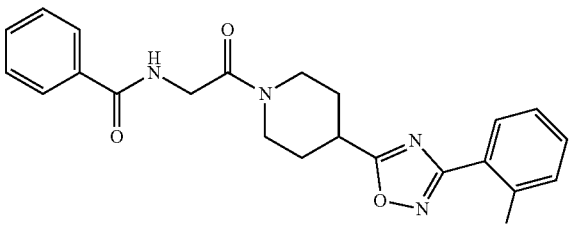 |
| 13 | 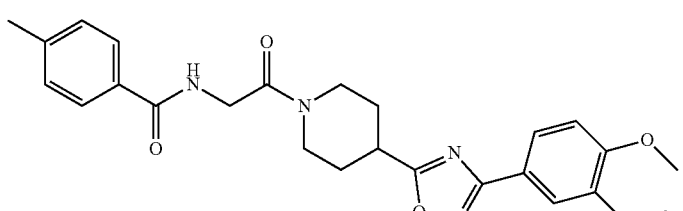 |

TABLE 1-continued

Compounds of the Invention

| # | Structure |
|---|---|
| 14 | 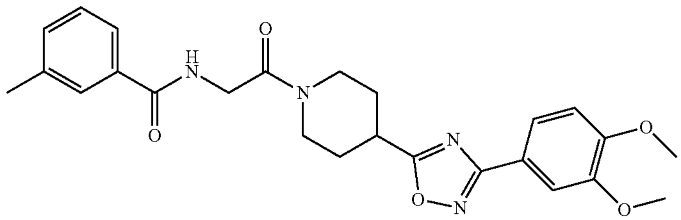 |
| 15 | 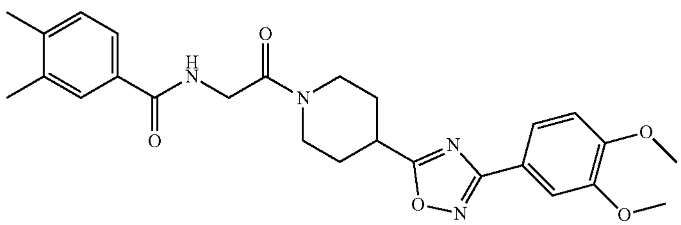 |
| 16 | 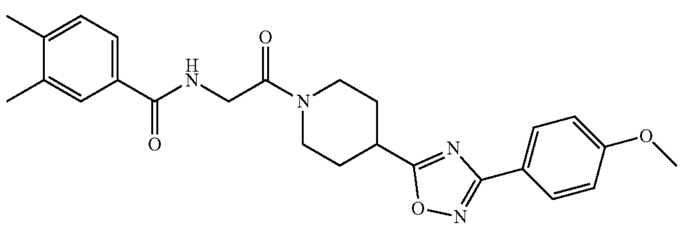 |
| 17 | 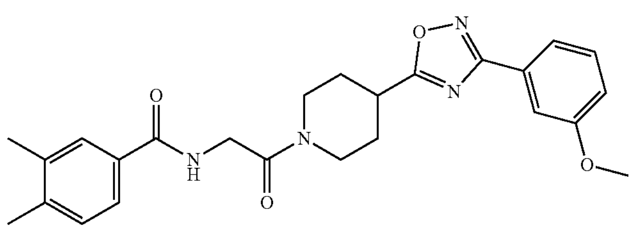 |
| 18 | 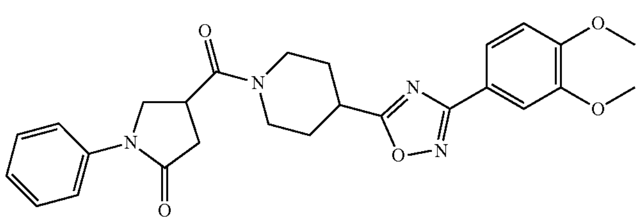 [SMILES: COc1ccc(-c2noc(C3CCN(C(=O)C4CC(=O)N(c5ccccc5)C4)CC3)n2)cc1OC] |
| 19 | 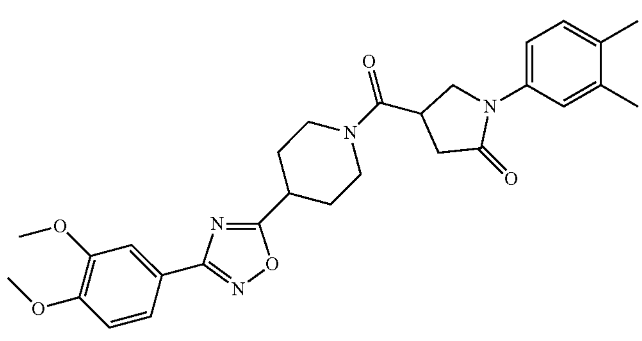 |

TABLE 1-continued

Compounds of the Invention

| # | Structure |
|---|---|
| 20 | 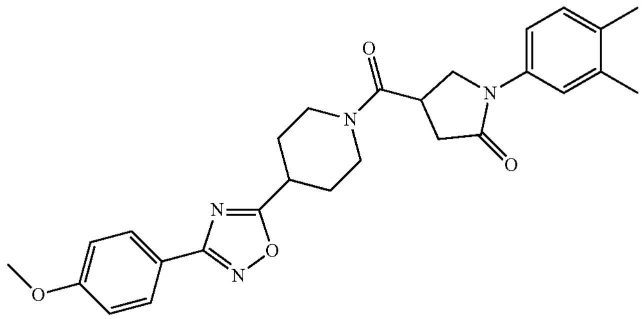 |
| 21 | 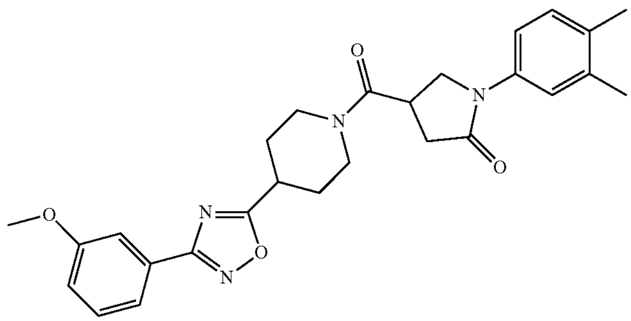 |
| 22 | 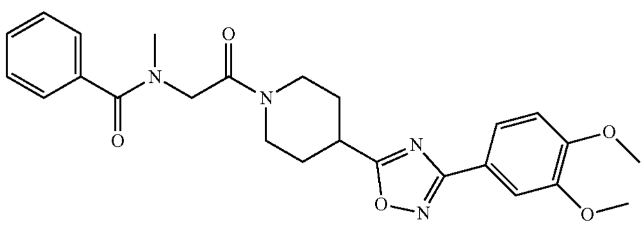 [SMILES: COc1ccc(-c2noc(C3CCN(C(=O)CN(C)C(=O)c4ccccc4)CC3)n2)cc1OC] |
| 23 | 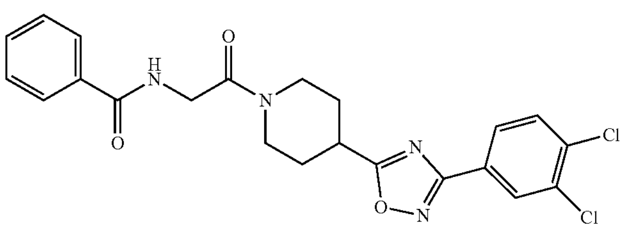 [SMILES: O=C(NCC(=O)N1CCC(c2nc(-c3ccc(Cl)c(Cl)c3)no2)CC1)c1ccccc1] |
| 24 | 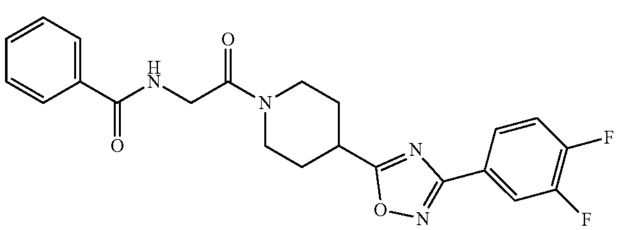 [SMILES: O=C(NCC(=O)N1CCC(c2nc(-c3ccc(F)c(F)c3)no2)CC1)c1ccccc1] |
| 25 | 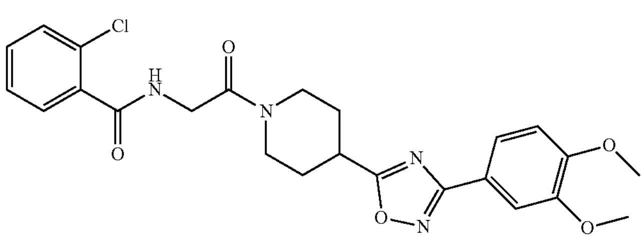 [SMILES: COc1ccc(-c2noc(C3CCN(C(=O)CNC(=O)c4ccccc4Cl)CC3)n2)cc1OC] |

TABLE 1-continued

Compounds of the Invention

| # | Structure |
|---|---|
| 26 | 3-chlorobenzoyl-Gly-piperidinyl-[3-(3,4-dimethoxyphenyl)-1,2,4-oxadiazol-5-yl] |
| 27 | 4-chlorobenzoyl-Gly-piperidinyl-[3-(3,4-dimethoxyphenyl)-1,2,4-oxadiazol-5-yl] |
| 28 | benzoyl-Ala-piperidinyl-[3-(3,4-dimethoxyphenyl)-1,2,4-oxadiazol-5-yl] |
| 29 | benzoyl-Aib-piperidinyl-[3-(3,4-dimethoxyphenyl)-1,2,4-oxadiazol-5-yl] |
| 30 | benzylamino-acetyl-piperidinyl-[3-(3,4-dimethoxyphenyl)-1,2,4-oxadiazol-5-yl] |
| 31 | benzyloxy-acetyl-piperidinyl-[3-(3,4-dimethoxyphenyl)-1,2,4-oxadiazol-5-yl] |

TABLE 1-continued
Compounds of the Invention
| # | Structure |
|---|---|
| 32 | 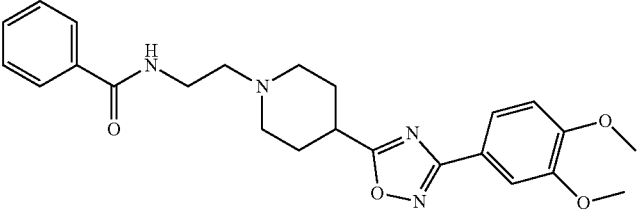 [SMILES: COc1ccc(-c2noc(C3CCN(CCNC(=O)c4ccccc4)CC3)n2)cc1OC] |
| 33 | 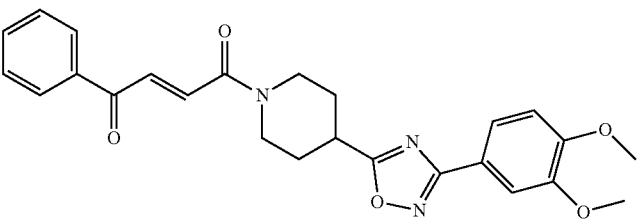 [SMILES: COc1ccc(-c2noc(C3CCN(C(=O)/C=C/C(=O)c4ccccc4)CC3)n2)cc1OC] |
| 34 | 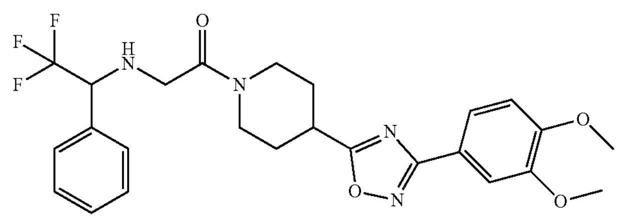 [SMILES: COc1ccc(-c2noc(C3CCN(C(=O)CNC(c4ccccc4)C(F)(F)F)CC3)n2)cc1OC] |
| 35 | 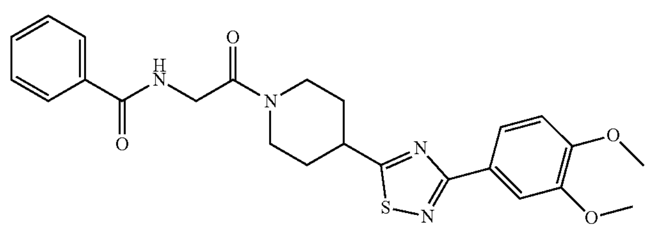 |
| 36 | 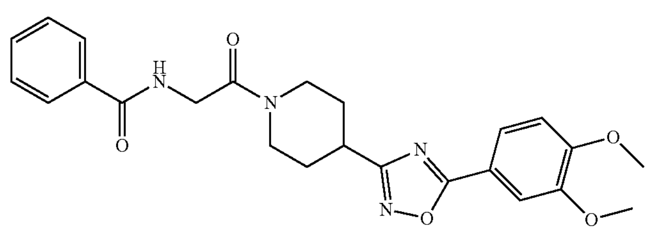 [SMILES: COc1ccc(-c2nc(C3CCN(C(=O)CNC(=O)c4ccccc4)CC3)no2)cc1OC] |
| 37 | 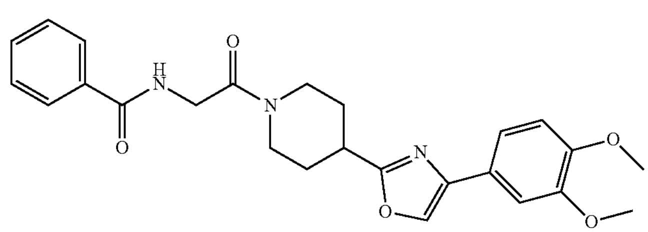 [SMILES: COc1ccc(-c2coc(C3CCN(C(=O)CNC(=O)c4ccccc4)CC3)n2)cc1OC] |

TABLE 1-continued

Compounds of the Invention

| # | Structure |
|---|---|
| 38 | (structure) |
| 39 | (structure) |
| 40 | (structure) |
| 41 | (structure) |
| 42 | (structure) |
| 43 | (structure) |
| 44 | (structure) |

TABLE 1-continued

Compounds of the Invention

| # | Structure |
|---|-----------|
| 45 | 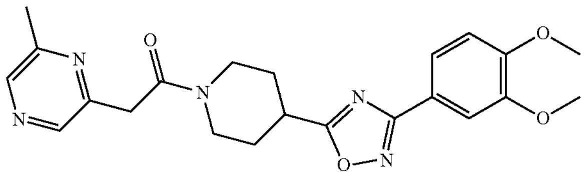 [SMILES: COc1ccc(-c2noc(C3CCN(C(=O)Cc4cncc(C)n4)CC3)n2)cc1OC] |
| 46 | 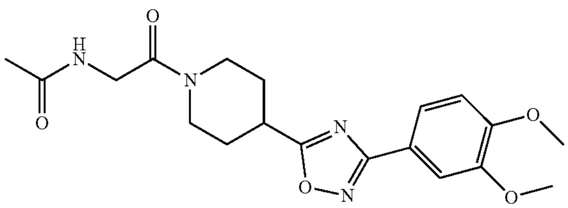 [SMILES: COc1ccc(-c2noc(C3CCN(C(=O)CNC(C)=O)CC3)n2)cc1OC] |
| 47 | 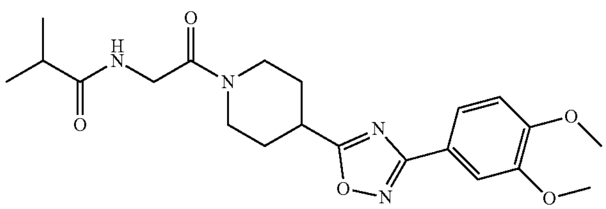 [SMILES: COc1ccc(-c2noc(C3CCN(C(=O)CNC(=O)C(C)C)CC3)n2)cc1OC] |
| 48 | 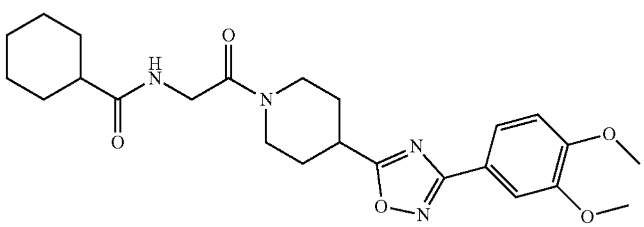 [SMILES: COc1ccc(-c2noc(C3CCN(C(=O)CNC(=O)C4CCCCC4)CC3)n2)cc1OC] |
| 49 | 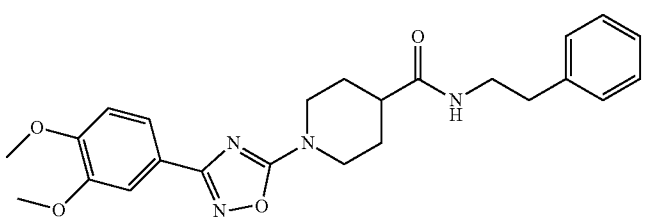 [SMILES: COc1ccc(-c2noc(N3CCC(C(=O)NCCc4ccccc4)CC3)n2)cc1OC] |
| 50 | 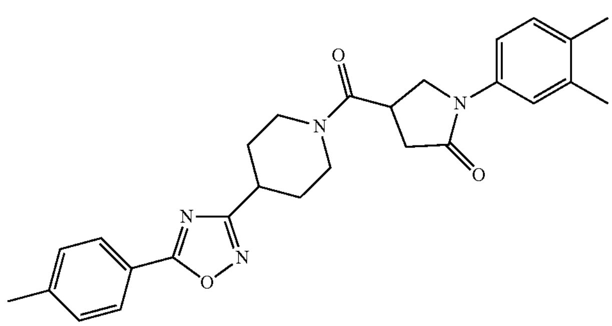 |

TABLE 1-continued
Compounds of the Invention
| # | Structure |
|---|---|
| 51 | 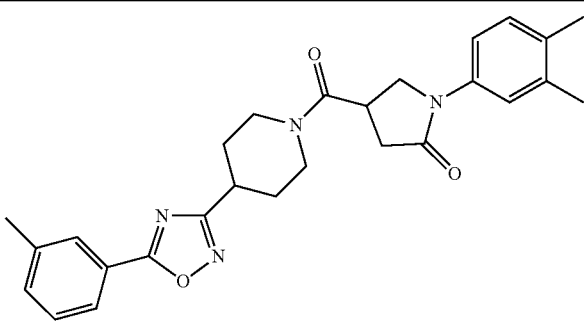 |
| 52 | 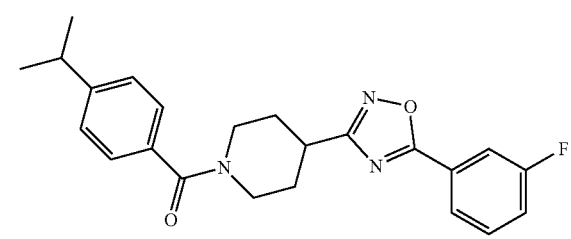 [SMILES: CC(C)c1ccc(C(=O)N2CCC(c3noc(-c4cccc(F)c4)n3)CC2)cc1] |
| 53 | 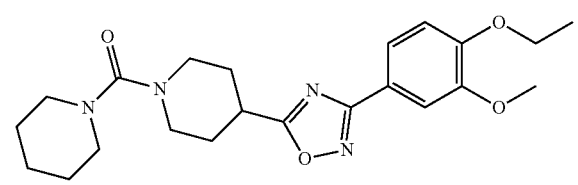 [SMILES: CCOc1ccc(-c2noc(C3CCN(C(=O)N4CCCCC4)CC3)n2)cc1OC] |
| 54 | 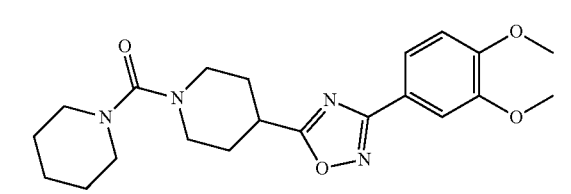 [SMILES: COc1ccc(-c2noc(C3CCN(C(=O)N4CCCCC4)CC3)n2)cc1OC] |
| 55 | 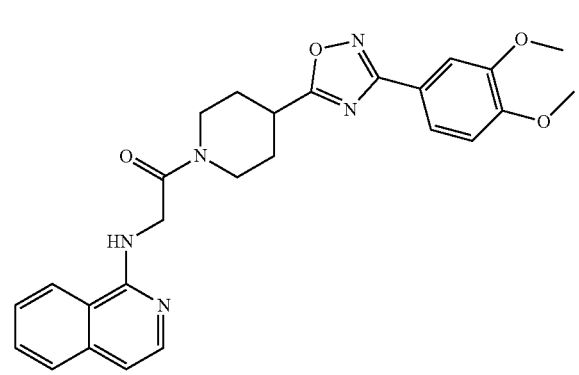 [SMILES: COc1ccc(-c2noc(C3CCN(C(=O)CNc4nccc5ccccc45)CC3)n2)cc1OC] |
| 56 | 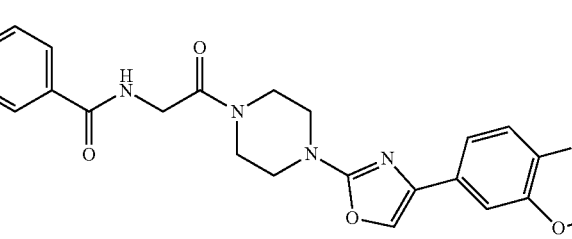 |

US 11,970,486 B2
TABLE 1-continued
Compounds of the Invention
| # | Structure |
|---|---|
| 57 | 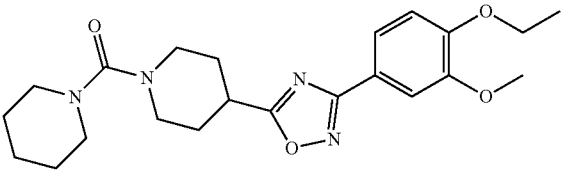 [SMILES: CCOc1ccc(-c2noc(C3CCN(C(=O)N4CCCCC4)CC3)n2)cc1OC] |
| 58 | 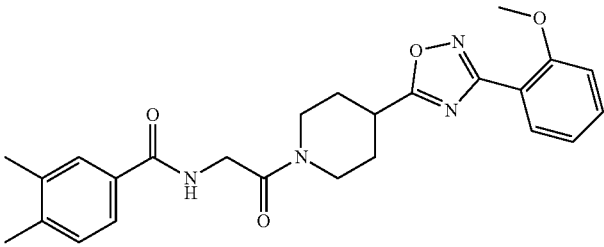 [SMILES: COc1ccccc1-c1noc(C2CCN(C(=O)CNC(=O)c3ccc(C)c(C)c3)CC2)n1] |
| 59 | 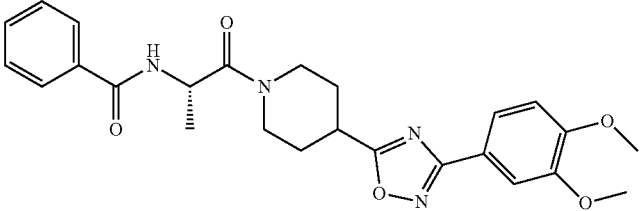 |
| 60 | 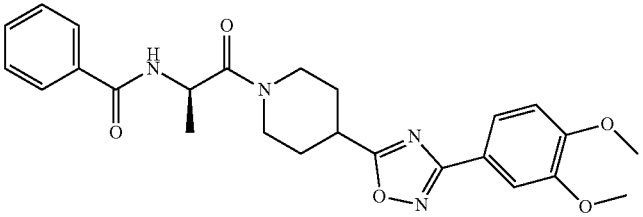 [SMILES: COc1ccc(-c2noc(C3CCN(C(=O)[C@@H](C)NC(=O)c4ccccc4)CC3)n2)cc1OC] |
| 61 | 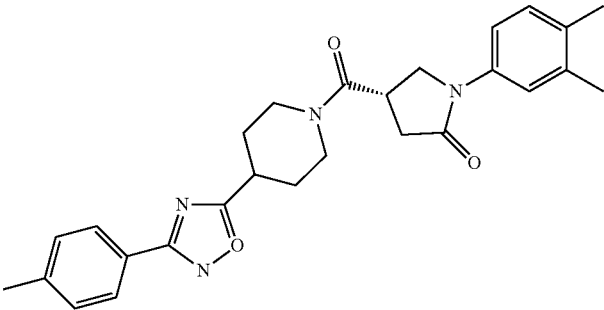 |
| 62 | 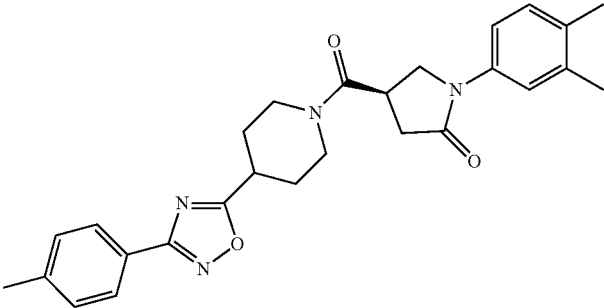 |

TABLE 1-continued
Compounds of the Invention
| # | Structure |
|---|---|
| 63 | 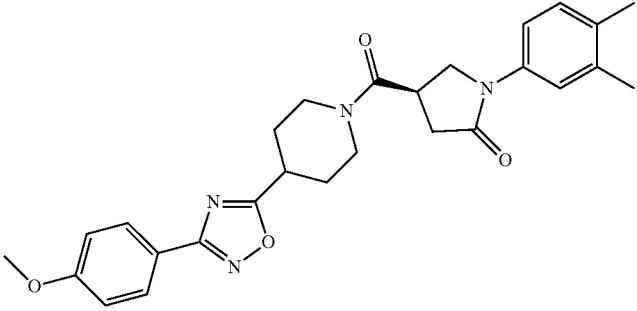 |
| 64 | 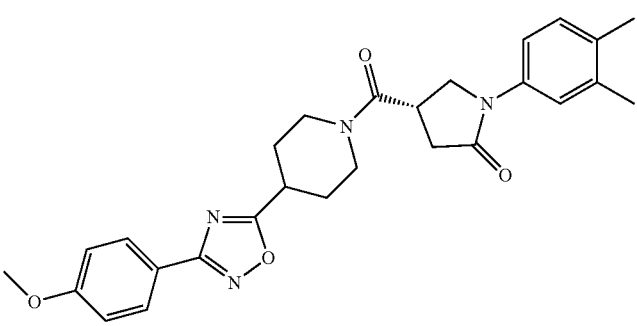 |
| 65 | 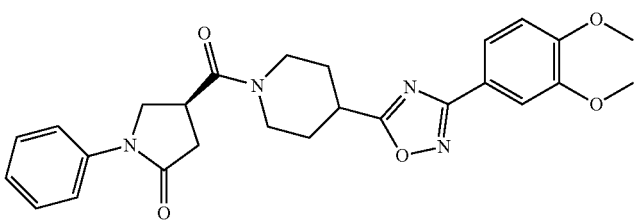 [SMILES: COc1ccc(-c2noc(C3CCN(C(=O)[C@H]4CC(=O)N(c5ccccc5)C4)CC3)n2)cc1OC] |
| 66 | 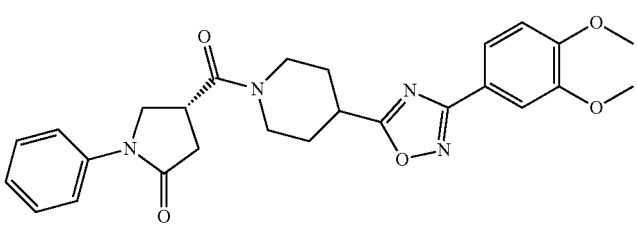 [SMILES: COc1ccc(-c2noc(C3CCN(C(=O)[C@@H]4CC(=O)N(c5ccccc5)C4)CC3)n2)cc1OC] |
| 67 | 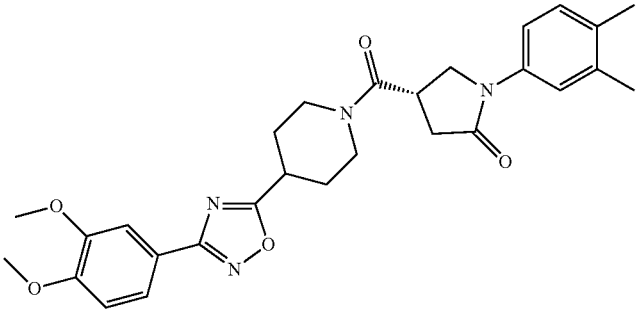 |

TABLE 1-continued

Compounds of the Invention

| # | Structure |
|---|-----------|
| 68 | 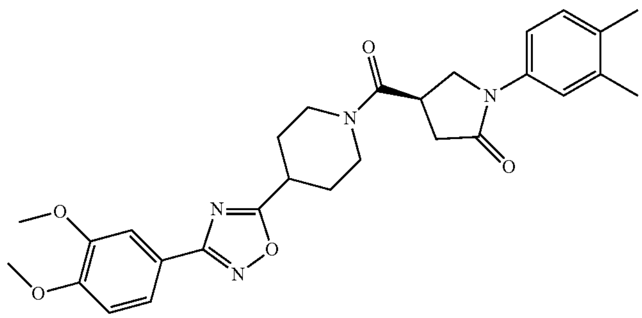 |
| 69 | 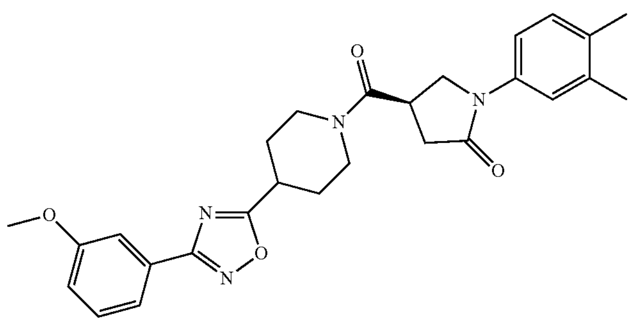 |
| 70 | 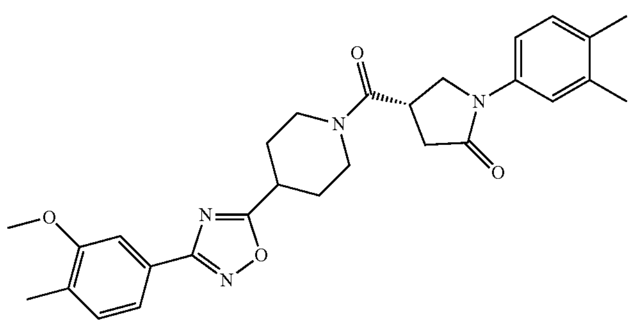 |
| 71 | 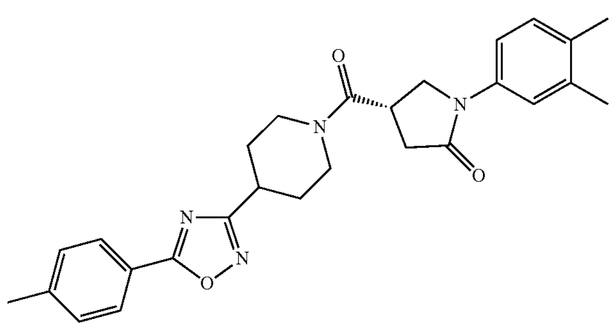 |

TABLE 1-continued

Compounds of the Invention

| # | Structure |
|---|---|
| 72 | 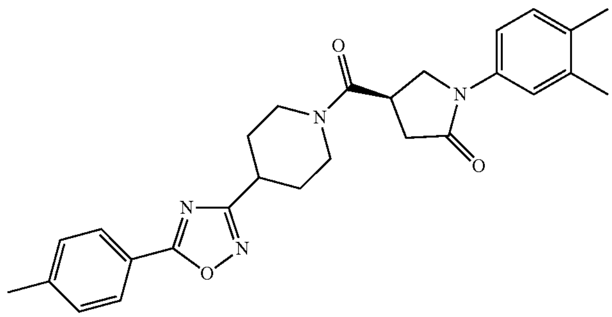 |
| 73 | 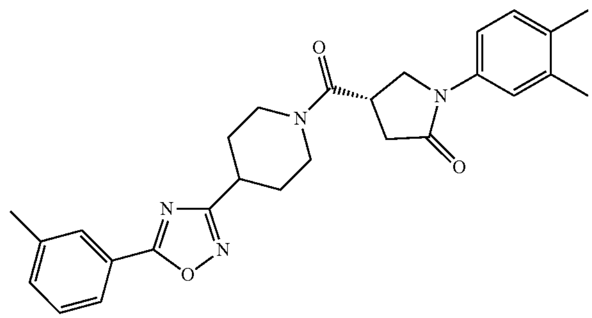 |
| 74 | 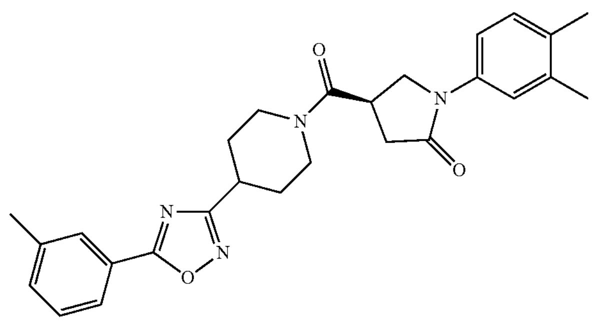 |
| 75 | 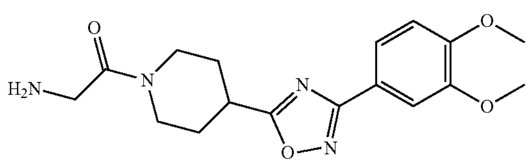 [SMILES: COc1ccc(-c2noc(C3CCN(C(=O)CN)CC3)n2)cc1OC] |
| 76 | 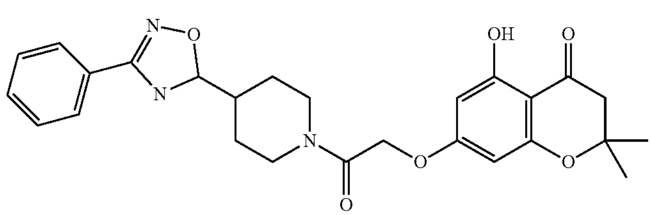 [SMILES: CC1(C)CC(=O)c2c(O)cc(OCC(=O)N3CCC(C4NC(c5ccccc5)=NO4)CC3)cc2O1] |
| 77 | 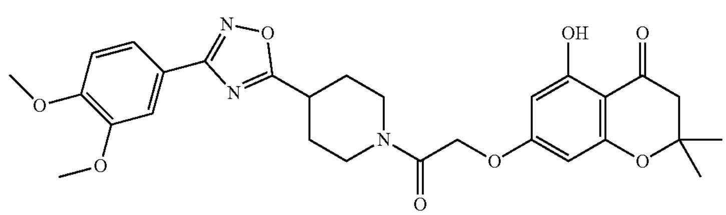 |

TABLE 1-continued
Compounds of the Invention
| # | Structure |
|---|---|
| 78 | 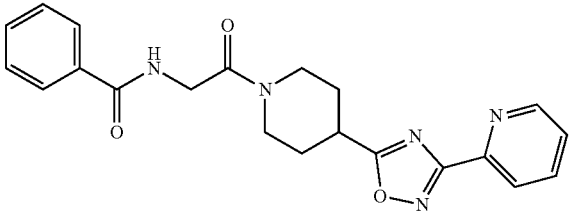 [SMILES: O=C(NCC(=O)N1CCC(c2nc(-c3ccccn3)no2)CC1)c1ccccc1] |
| 79 | 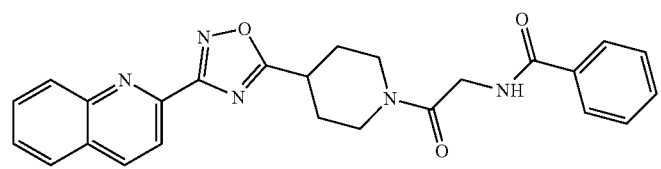 [SMILES: O=C(NCC(=O)N1CCC(c2nc(-c3ccc4ccccc4n3)no2)CC1)c1ccccc1] |
| 80 | 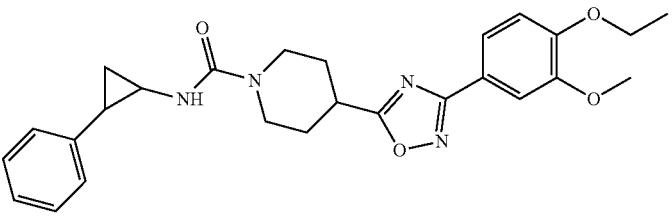 [SMILES: CCOc1ccc(-c2noc(C3CCN(C(=O)NC4CC4c4ccccc4)CC3)n2)cc1OC] |
| 81 | 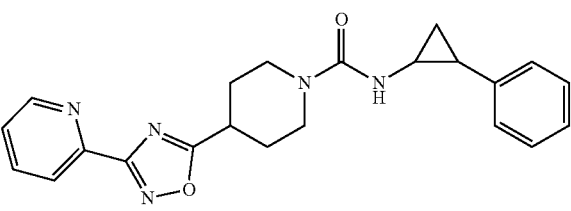 [SMILES: O=C(NC1CC1c1ccccc1)N1CCC(c2nc(-c3ccccn3)no2)CC1] |
| 82 | 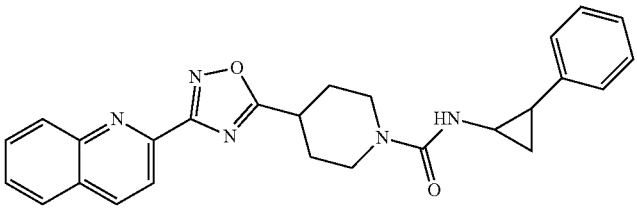 [SMILES: O=C(NC1CC1c1ccccc1)N1CCC(c2nc(-c3ccc4ccccc4n3)no2)CC1] |
| 83 | 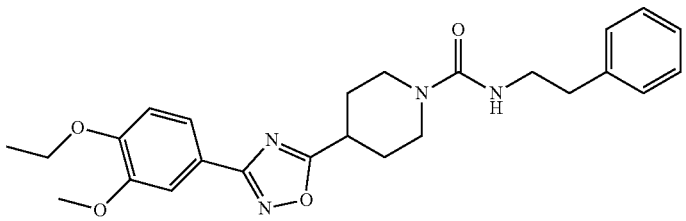 [SMILES: CCOc1ccc(-c2noc(C3CCN(C(=O)NCCc4ccccc4)CC3)n2)cc1OC] |
| 84 | 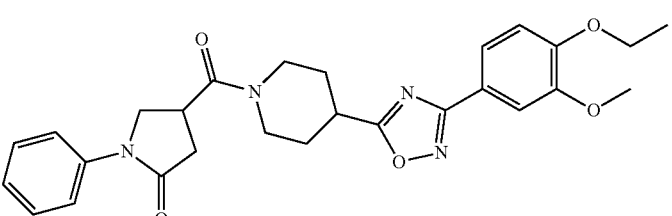 |

TABLE 1-continued

Compounds of the Invention

| # | Structure |
|---|---|
| 85 | 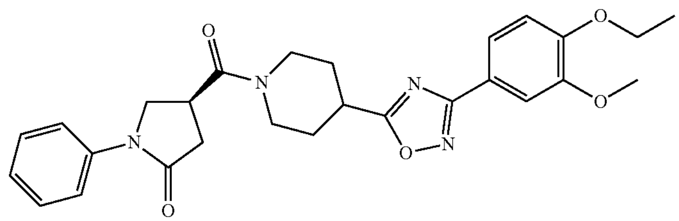 |
| 86 | 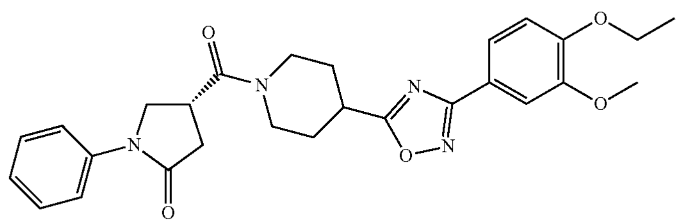 [SMILES: CCOc1ccc(-c2noc(C3CCN(C(=O)C4CC(=O)N(c5ccccc5)C4)CC3)n2)cc1OC] |
| 87 | 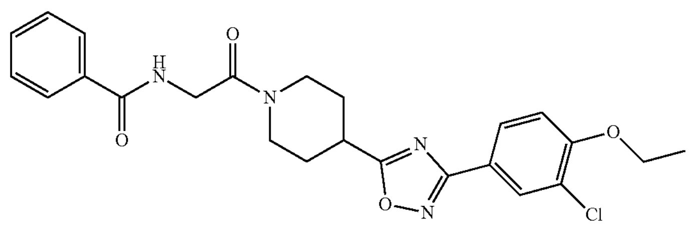 |
| 88 | 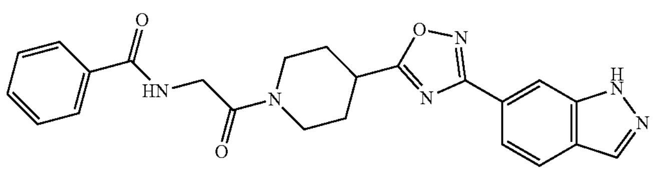 [SMILES: O=C(NCC(=O)N1CCC(c2nc(-c3ccc4cn[nH]c4c3)no2)CC1)c1ccccc1] |
| 89 | 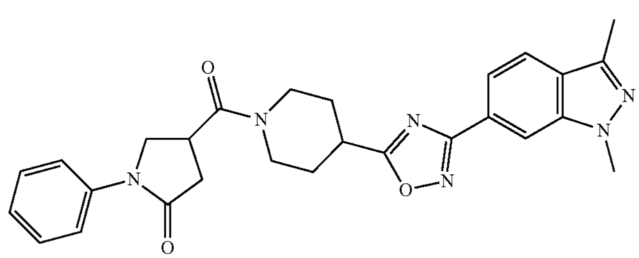 [SMILES: Cc1nn(C)c2cc(-c3noc(C4CCN(C(=O)C5CC(=O)N(c6ccccc6)C5)CC4)n3)ccc12] |
| 90 | 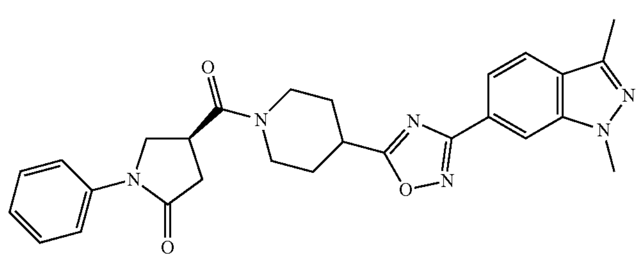 [SMILES: Cc1nn(C)c2cc(-c3noc(C4CCN(C(=O)[C@H]5CC(=O)N(c6ccccc6)C5)CC4)n3)ccc12] |

TABLE 1-continued

Compounds of the Invention

| # | Structure |
|---|-----------|
| 91 | 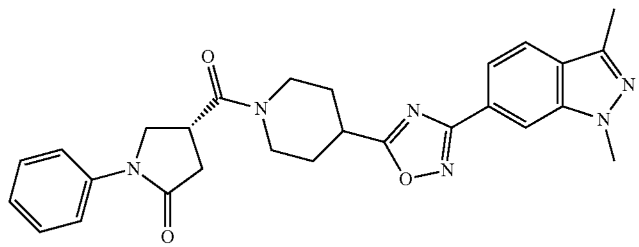 [SMILES: Cc1nn(C)c2cc(-c3noc(C4CCN(C(=O)[C@@H]5CC(=O)N(c6ccccc6)C5)CC4)n3)ccc12] |
| 92 | 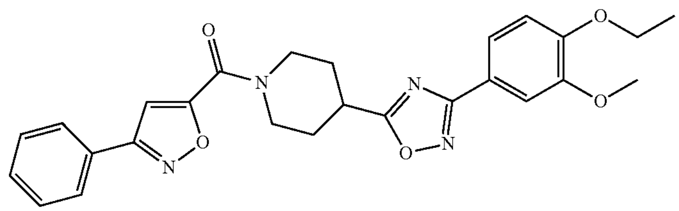 [SMILES: CCOc1ccc(-c2noc(C3CCN(C(=O)c4cc(-c5ccccc5)no4)CC3)n2)cc1OC] |
| 93 | 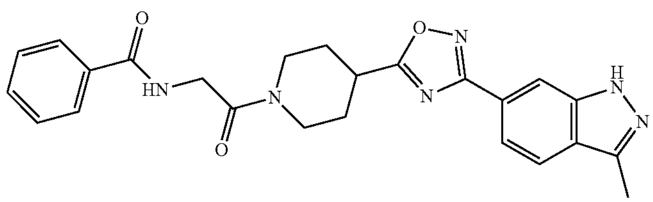 [SMILES: Cc1n[nH]c2cc(-c3noc(C4CCN(C(=O)CNC(=O)c5ccccc5)CC4)n3)ccc12] |
| 94 | 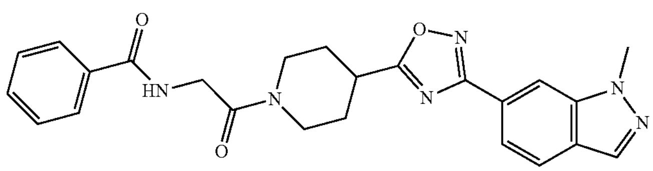 [SMILES: Cn1ncc2ccc(-c3noc(C4CCN(C(=O)CNC(=O)c5ccccc5)CC4)n3)cc21] |
| 95 | 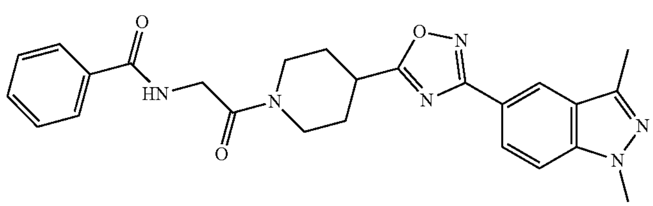 [SMILES: Cc1nn(C)c2ccc(-c3noc(C4CCN(C(=O)CNC(=O)c5ccccc5)CC4)n3)cc12] |
| 96 | 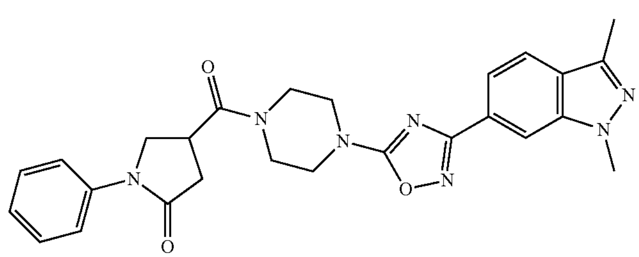 [SMILES: Cc1nn(C)c2cc(-c3noc(N4CCN(C(=O)C5CC(=O)N(c6ccccc6)C5)CC4)n3)ccc12] |
| 97 | 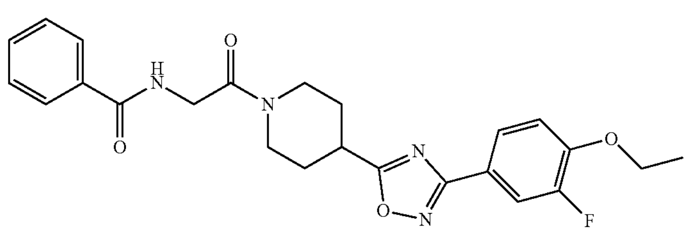 [SMILES: CCOc1ccc(-c2noc(C3CCN(C(=O)CNC(=O)c4ccccc4)CC3)n2)cc1F] |

TABLE 1-continued

Compounds of the Invention

| # | Structure |
|---|---|
| 98 | 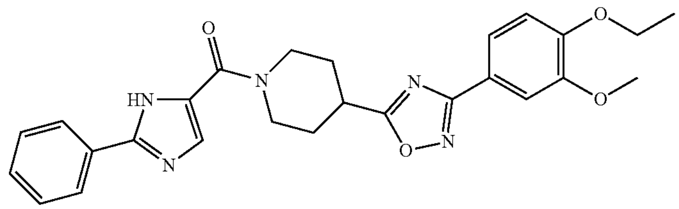 [SMILES: CCOc1ccc(-c2noc(C3CCN(C(=O)c4cnc(-c5ccccc5)[nH]4)CC3)n2)cc1OC] |
| 99 | 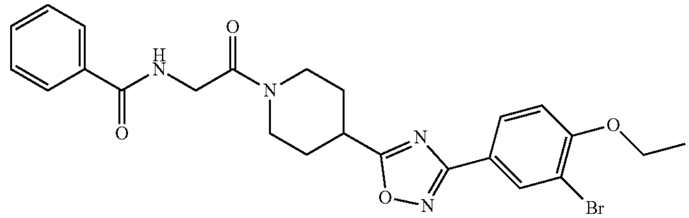 |
| 100 | 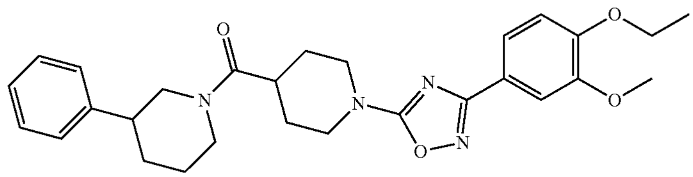 |
| 101 | 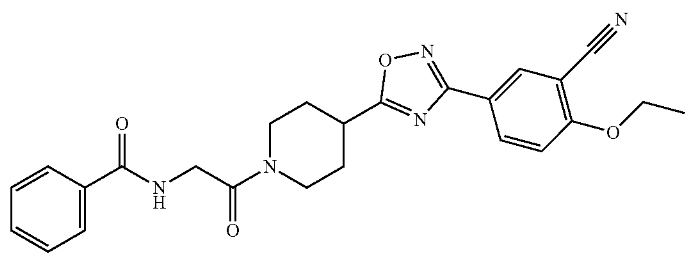 [SMILES: CCOc1ccc(-c2noc(C3CCN(C(=O)CNC(=O)c4ccccc4)CC3)n2)cc1C#N] |
| 102 | 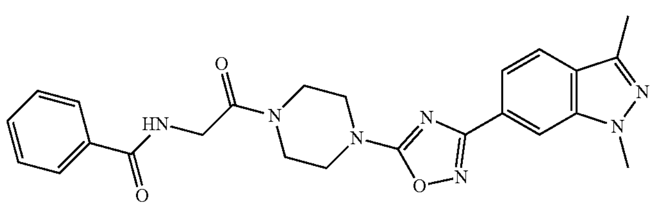 [SMILES: Cc1nn(C)c2cc(-c3noc(N4CCN(C(=O)CNC(=O)c5ccccc5)CC4)n3)ccc12] |
| 103 | 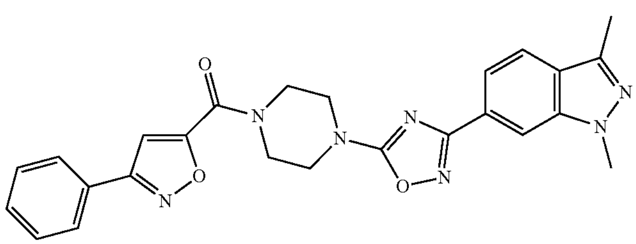 [SMILES: Cc1nn(C)c2cc(-c3noc(N4CCN(C(=O)c5cc(-c6ccccc6)no5)CC4)n3)ccc12] |
| 104 | 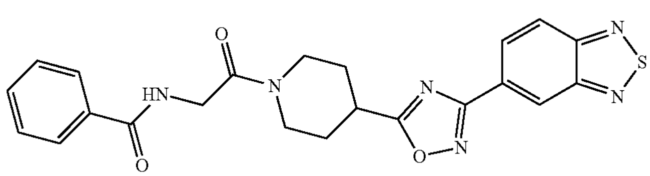 [SMILES: O=C(NCC(=O)N1CCC(c2nc(-c3ccc4nsnc4c3)no2)CC1)c1ccccc1] |

TABLE 1-continued

Compounds of the Invention

| # | Structure |
|---|---|
| 105 | 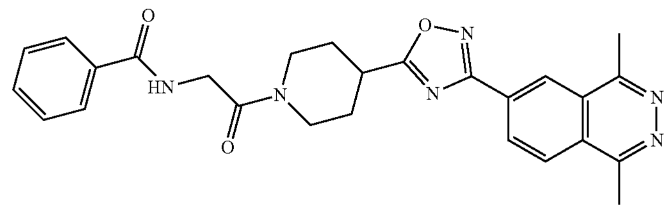 [SMILES: Cc1nnc(C)c2cc(-c3noc(C4CCN(C(=O)CNC(=O)c5ccccc5)CC4)n3)ccc12] |
| 106 | 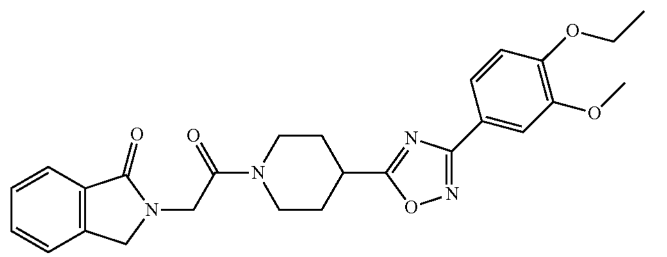 [SMILES: CCOc1ccc(-c2noc(C3CCN(C(=O)CN4Cc5ccccc5C4=O)CC3)n2)cc1OC] |
| 107 | 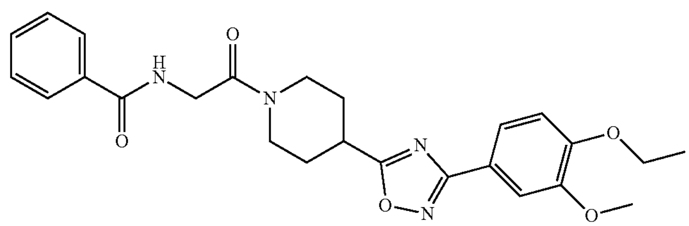 [SMILES: CCOc1ccc(-c2noc(C3CCN(C(=O)CNC(=O)c4ccccc4)CC3)n2)cc1OC] |
| 108 | 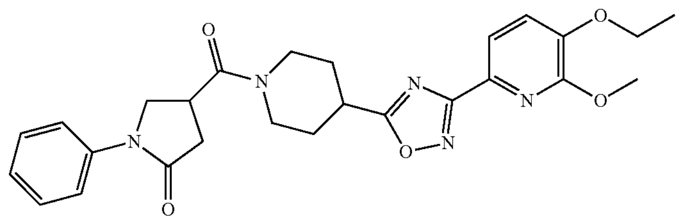 |
| 109 | 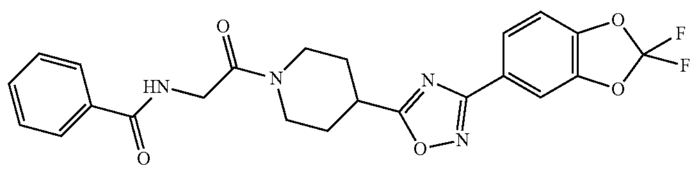 [SMILES: O=C(NCC(=O)N1CCC(c2nc(-c3ccc4c(c3)OC(F)(F)O4)no2)CC1)c1ccccc1] |
| 110 | 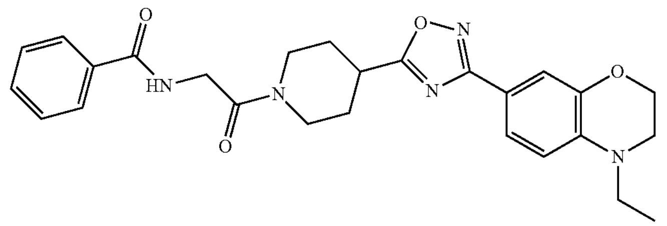 [SMILES: CCN1CCOc2cc(-c3noc(C4CCN(C(=O)CNC(=O)c5ccccc5)CC4)n3)ccc21] |
| 111 | 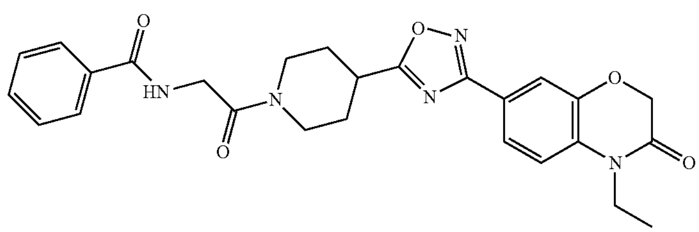 [SMILES: CCN1C(=O)COc2cc(-c3noc(C4CCN(C(=O)CNC(=O)c5ccccc5)CC4)n3)ccc21] |

TABLE 1-continued
Compounds of the Invention
| # | Structure |
|---|---|
| 112 | 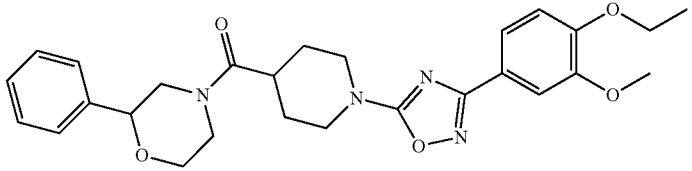 [SMILES: CCOc1ccc(-c2noc(N3CCC(C(=O)N4CCOC(c5ccccc5)C4)CC3)n2)cc1OC] |
| 113 | 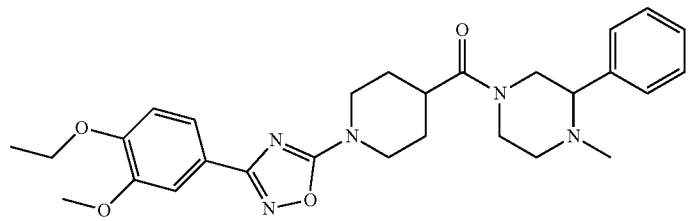 [SMILES: CCOc1ccc(-c2noc(N3CCC(C(=O)N4CCN(C)C(c5ccccc5)C4)CC3)n2)cc1OC] |
| 114 | 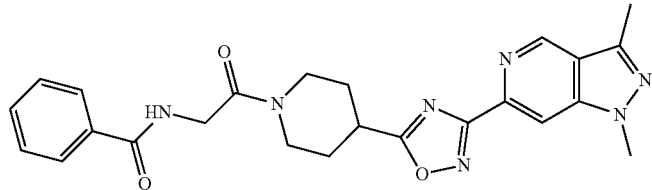 [SMILES: Cc1nn(C)c2cc(-c3noc(C4CCN(C(=O)CNC(=O)c5ccccc5)CC4)n3)ncc12] |
| 115 | 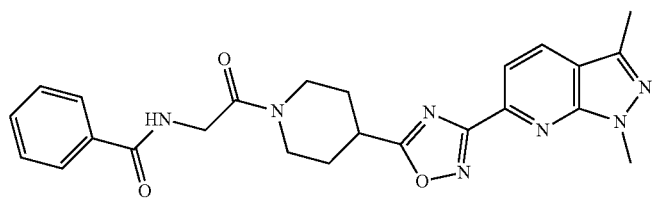 [SMILES: Cc1nn(C)c2nc(-c3noc(C4CCN(C(=O)CNC(=O)c5ccccc5)CC4)n3)ccc12] |
| 116 | 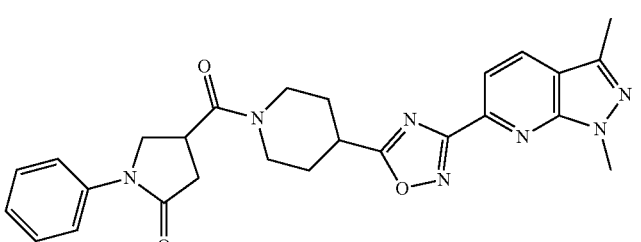 |
| 117 | 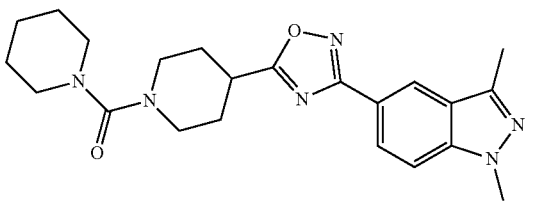 [SMILES: Cc1nn(C)c2ccc(-c3noc(C4CCN(C(=O)N5CCCCC5)CC4)n3)cc12] |
| 118 | 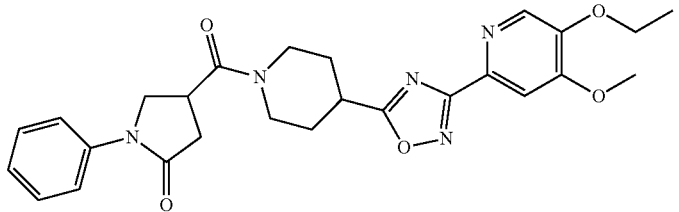 [SMILES: CCOc1cnc(-c2noc(C3CCN(C(=O)C4CC(=O)N(c5ccccc5)C4)CC3)n2)cc1OC] |

TABLE 1-continued

Compounds of the Invention

| # | Structure |
|---|---|
| 119 | 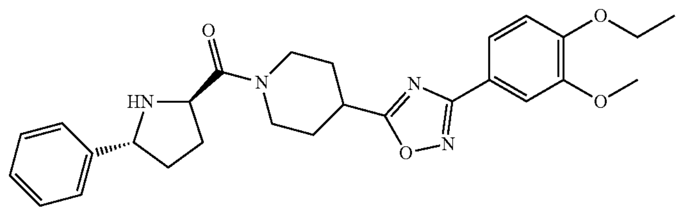 [SMILES: CCOc1ccc(-c2noc(C3CCN(C(=O)[C@H]4CC[C@H](c5ccccc5)N4)CC3)n2)cc1OC] |
| 120 | 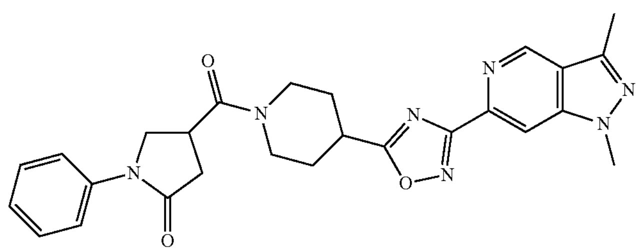 [SMILES: Cc1nn(C)c2cc(-c3noc(C4CCN(C(=O)C5CC(=O)N(c6ccccc6)C5)CC4)n3)ncc12] |
| 121 | 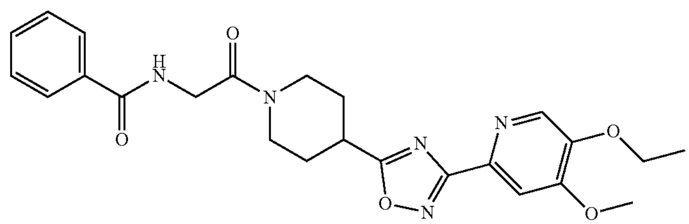 [SMILES: CCOc1cnc(-c2noc(C3CCN(C(=O)CNC(=O)c4ccccc4)CC3)n2)cc1OC] |
| 122 | 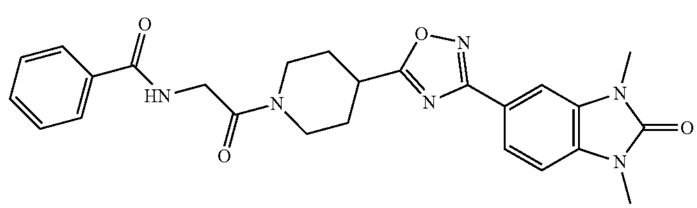 [SMILES: Cn1c(=O)n(C)c2cc(-c3noc(C4CCN(C(=O)CNC(=O)c5ccccc5)CC4)n3)ccc21] |
| 123 | 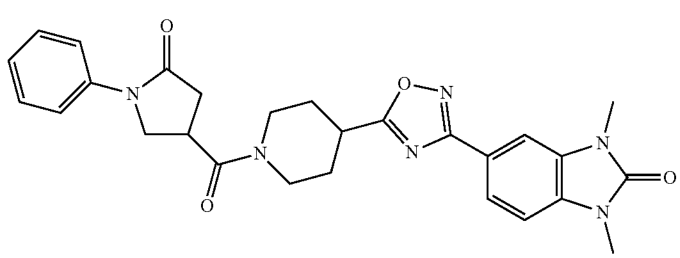 [SMILES: Cn1c(=O)n(C)c2cc(-c3noc(C4CCN(C(=O)C5CC(=O)N(c6ccccc6)C5)CC4)n3)ccc21] |
| 124 | 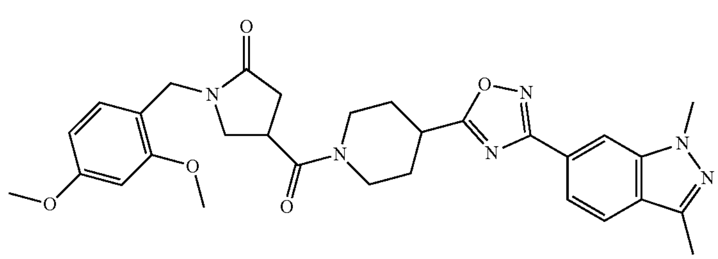 [SMILES: COc1ccc(CN2CC(C(=O)N3CCC(c4nc(-c5ccc6c(C)nn(C)c6c5)no4)CC3)CC2=O)c(OC)c1] |

TABLE 1-continued

Compounds of the Invention

| # | Structure |
|---|---|
| 125 | 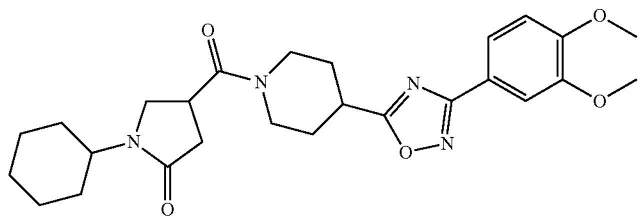 [SMILES: COc1ccc(-c2noc(C3CCN(C(=O)C4CC(=O)N(C5CCCCC5)C4)CC3)n2)cc1OC] |
| 126 | 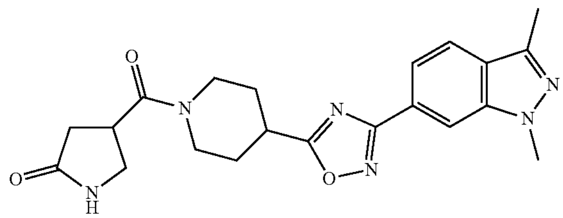 [SMILES: Cc1nn(C)c2cc(-c3noc(C4CCN(C(=O)C5CNC(=O)C5)CC4)n3)ccc12] |
| 127 | 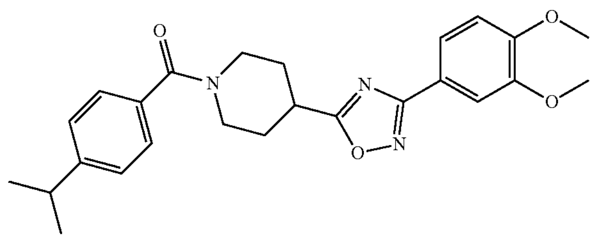 [SMILES: COc1ccc(-c2noc(C3CCN(C(=O)c4ccc(C(C)C)cc4)CC3)n2)cc1OC] |
| 128 | 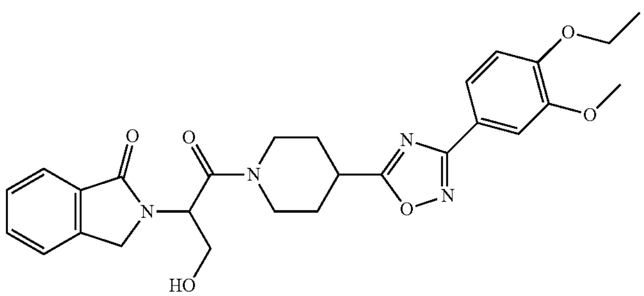 [SMILES: CCOc1ccc(-c2noc(C3CCN(C(=O)C(CO)N4Cc5ccccc5C4=O)CC3)n2)cc1OC] |
| 129 | 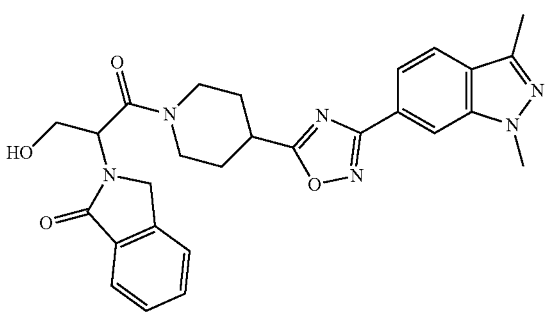 [SMILES: Cc1nn(C)c2cc(-c3noc(C4CCN(C(=O)C(CO)N5Cc6ccccc6C5=O)CC4)n3)ccc12] |
| 130 | 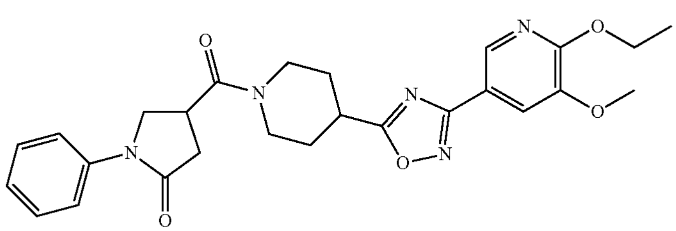 [SMILES: CCOc1ncc(-c2noc(C3CCN(C(=O)C4CC(=O)N(c5ccccc5)C4)CC3)n2)cc1OC] |

US 11,970,486 B2
77                                                    78
TABLE 1-continued
Compounds of the Invention
| # | Structure |
|---|---|
| 131 | 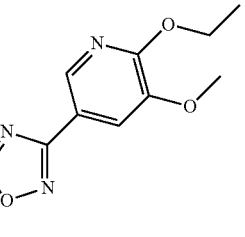 |
| 132 | 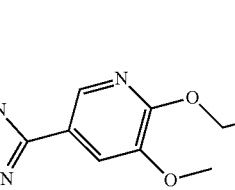 |
| 133 | 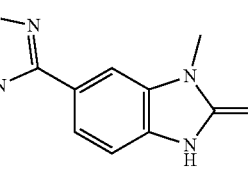 |
| 134 | 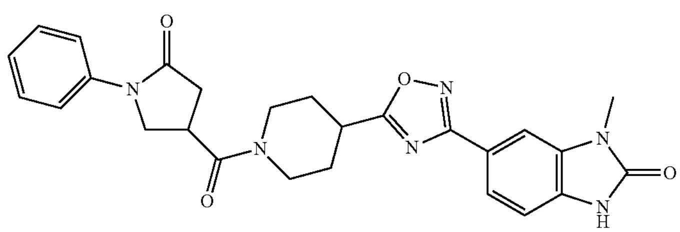 [SMILES: Cn1c(=O)[nH]c2ccc(-c3noc(C4CCN(C(=O)C5CC(=O)N(c6ccccc6)C5)CC4)n3)cc21] |
| 135 | 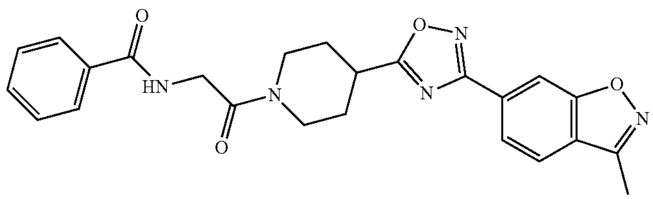 [SMILES: Cc1noc2cc(-c3noc(C4CCN(C(=O)CNC(=O)c5ccccc5)CC4)n3)ccc12] |
| 136 | 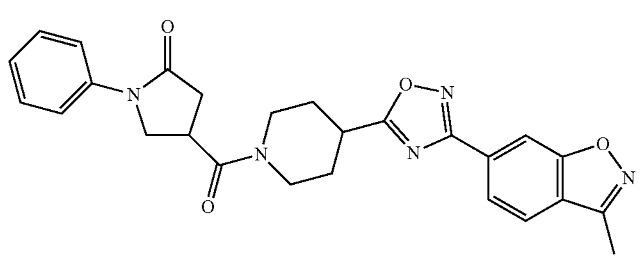 [SMILES: Cc1noc2cc(-c3noc(C4CCN(C(=O)C5CC(=O)N(c6ccccc6)C5)CC4)n3)ccc12] |
| 137 | 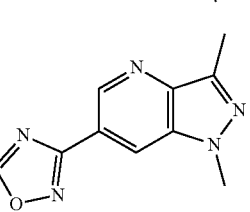 |

TABLE 1-continued

Compounds of the Invention

| # | Structure |
|---|-----------|
| 138 | 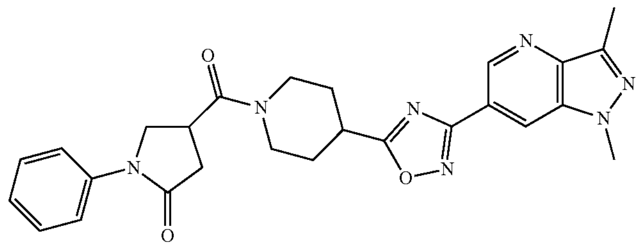 [SMILES: Cc1nn(C)c2cc(-c3noc(C4CCN(C(=O)C5CC(=O)N(c6ccccc6)C5)CC4)n3)cnc12] |
| 139 | 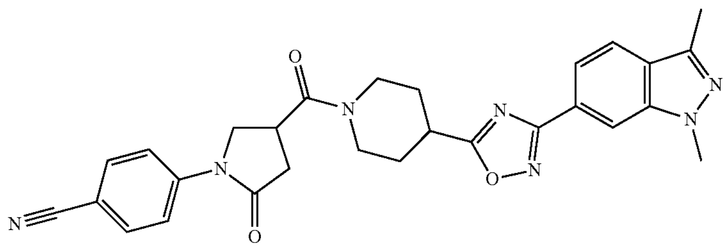 [SMILES: Cc1nn(C)c2cc(-c3noc(C4CCN(C(=O)C5CC(=O)N(c6ccc(C#N)cc6)C5)CC4)n3)ccc12] |
| 140 | 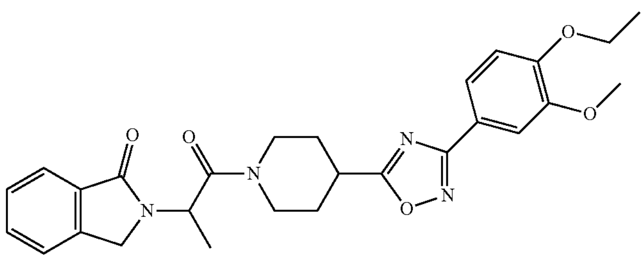 |
| 141 | 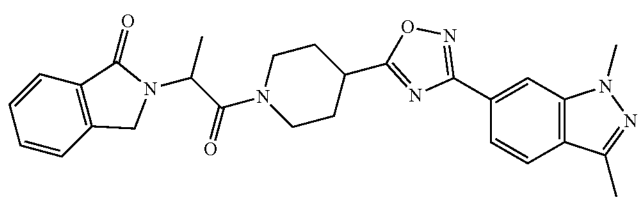 [SMILES: Cc1nn(C)c2cc(-c3noc(C4CCN(C(=O)C(C)N5Cc6ccccc6C5=O)CC4)n3)ccc12] |
| 142 | 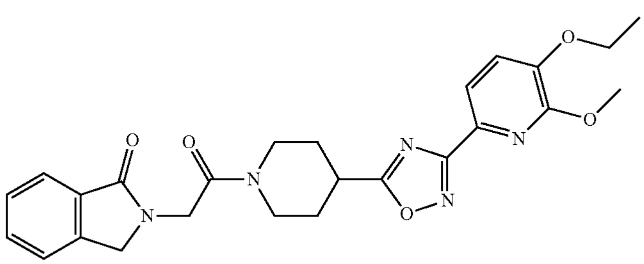 |
| 143 | 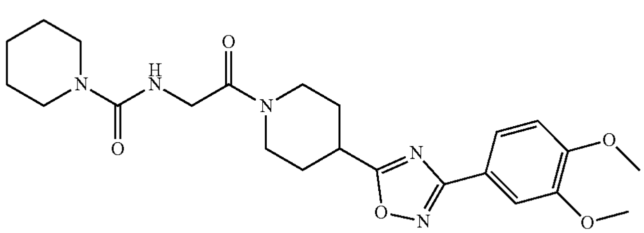 [SMILES: COc1ccc(-c2noc(C3CCN(C(=O)CNC(=O)N4CCCCC4)CC3)n2)cc1OC] |

TABLE 1-continued
Compounds of the Invention
| # | Structure |
|---|---|
| 144 | 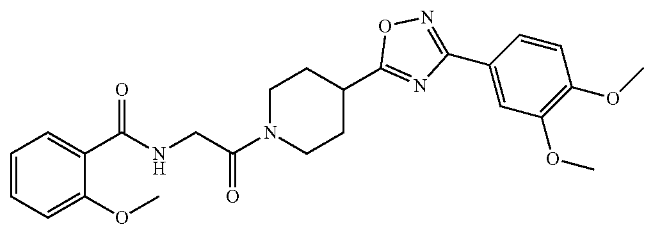 [SMILES: COc1ccc(-c2noc(C3CCN(C(=O)CNC(=O)c4ccccc4OC)CC3)n2)cc1OC] |
| 145 | 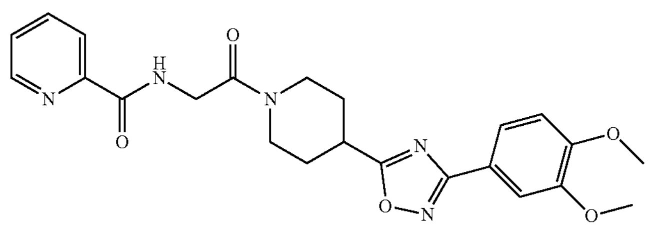 |
| 146 | 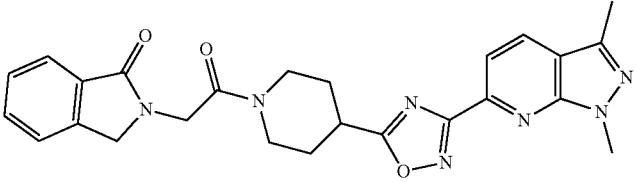 [SMILES: Cc1nn(C)c2nc(-c3noc(C4CCN(C(=O)CN5Cc6ccccc6C5=O)CC4)n3)ccc12] |
| 147 | 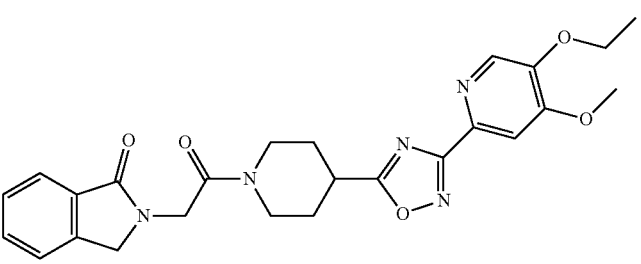 |
| 148 | 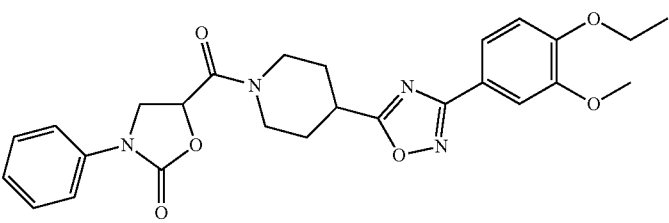 [SMILES: CCOc1ccc(-c2noc(C3CCN(C(=O)C4CN(c5ccccc5)C(=O)O4)CC3)n2)cc1OC] |
| 149 | 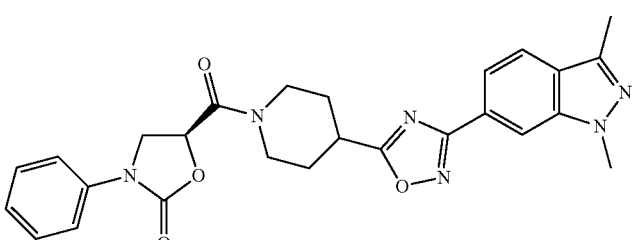 |

TABLE 1-continued
Compounds of the Invention
| # | Structure |
|---|---|
| 150 | 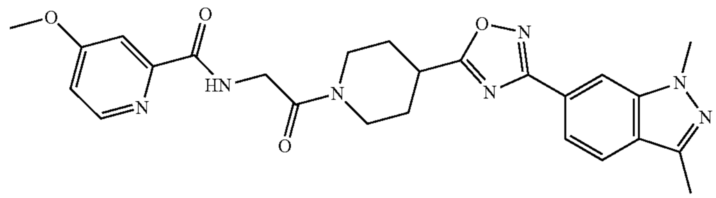 [SMILES: COc1ccnc(C(=O)NCC(=O)N2CCC(c3nc(-c4ccc5c(C)nn(C)c5c4)no3)CC2)c1] |
| 151 | 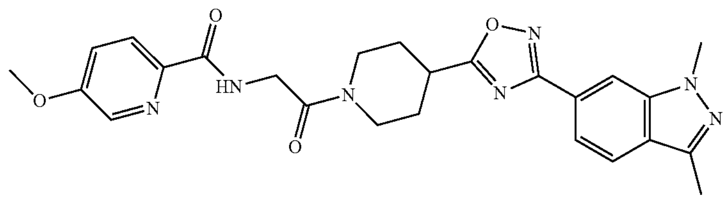 [SMILES: COc1ccc(C(=O)NCC(=O)N2CCC(c3nc(-c4ccc5c(C)nn(C)c5c4)no3)CC2)nc1] |
| 152 | 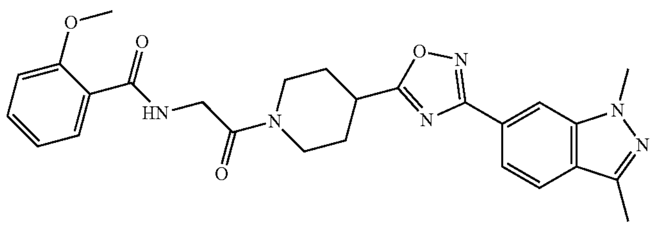 [SMILES: COc1ccccc1C(=O)NCC(=O)N1CCC(c2nc(-c3ccc4c(C)nn(C)c4c3)no2)CC1] |
| 153 | 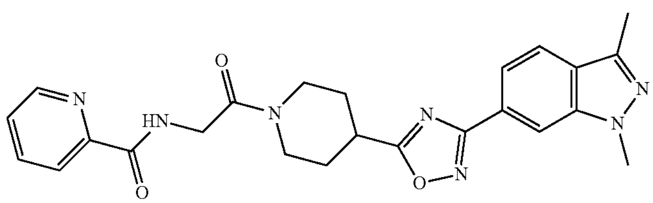 |
| 154 | 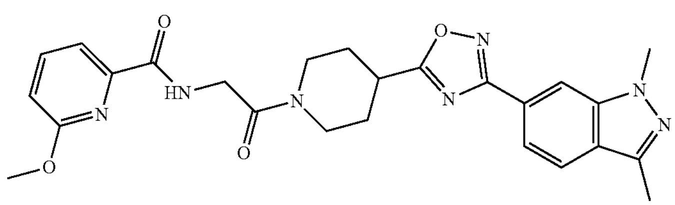 [SMILES: COc1cccc(C(=O)NCC(=O)N2CCC(c3nc(-c4ccc5c(C)nn(C)c5c4)no3)CC2)n1] |
| 155 | |
| 156 | 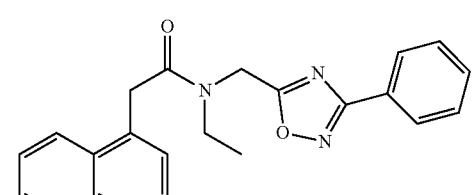 |
| 157 | 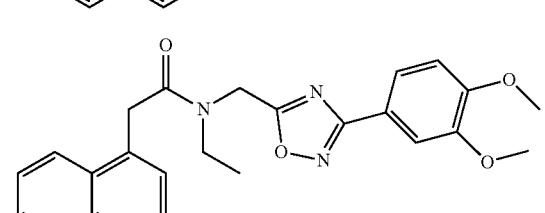 |

TABLE 1-continued
Compounds of the Invention
| # | Structure |
|---|---|
| 158 | 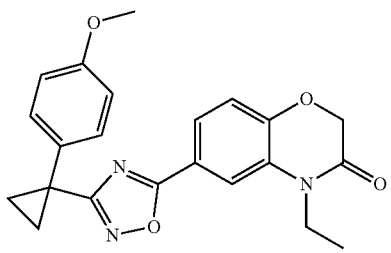 [SMILES: CCN1C(=O)COc2ccc(-c3nc(C4(c5ccc(OC)cc5)CC4)no3)cc21] |
| 159 | 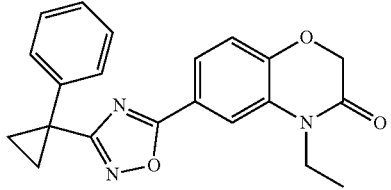 [SMILES: CCN1C(=O)COc2ccc(-c3nc(C4(c5ccccc5)CC4)no3)cc21] |
| 160 | 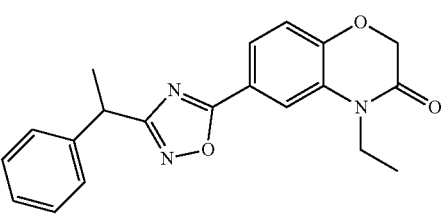 [SMILES: CCN1C(=O)COc2ccc(-c3nc(C(C)c4ccccc4)no3)cc21] |
| 161 | 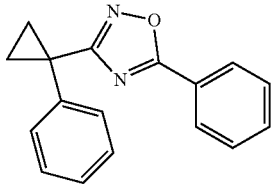 [SMILES: c1ccc(-c2nc(C3(c4ccccc4)CC3)no2)cc1] |
| 162 | 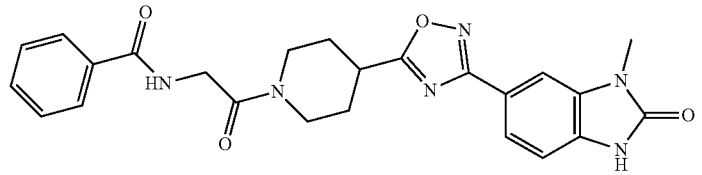 [SMILES: Cn1c(=O)[nH]c2ccc(-c3noc(C4CCN(C(=O)CNC(=O)c5ccccc5)CC4)n3)cc21] |
| 163 | 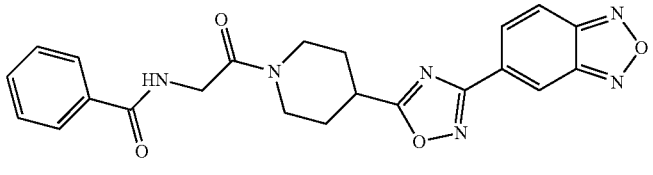 [SMILES: O=C(NCC(=O)N1CCC(c2nc(-c3ccc4nonc4c3)no2)CC1)c1ccccc1] |
| 164 | 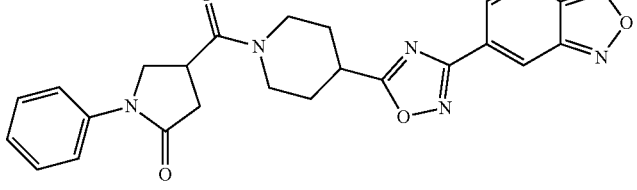 |

TABLE 1-continued
Compounds of the Invention
| # | Structure |
|---|---|
| 165 | 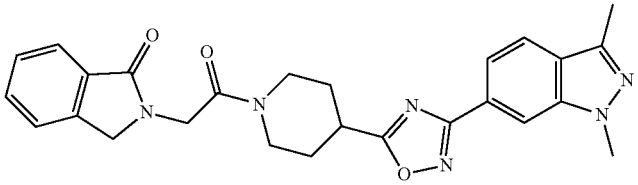 [SMILES: Cc1nn(C)c2cc(-c3noc(C4CCN(C(=O)CN5Cc6ccccc6C5=O)CC4)n3)ccc12] |
| 166 | 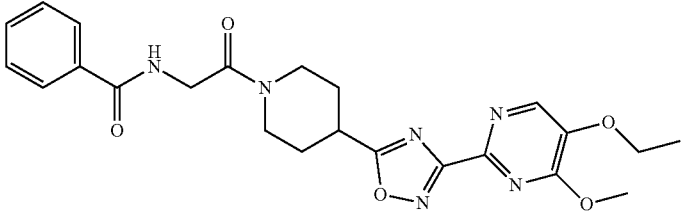 [SMILES: CCOc1cnc(-c2noc(C3CCN(C(=O)CNC(=O)c4ccccc4)CC3)n2)nc1OC] |
| 167 | 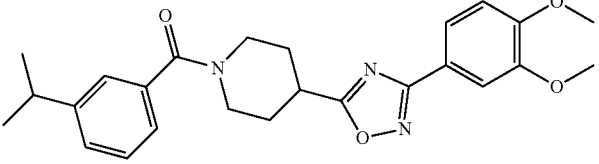 |
| 168 | 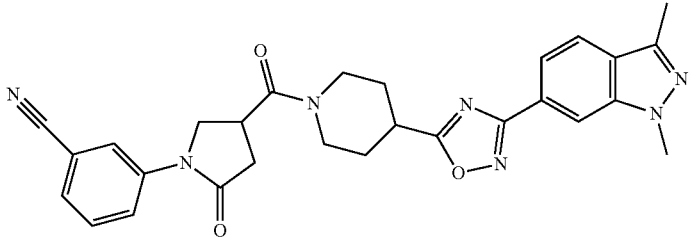 [SMILES: Cc1nn(C)c2cc(-c3noc(C4CCN(C(=O)C5CC(=O)N(c6cccc(C#N)c6)C5)CC4)n3)ccc12] |
| 169 | 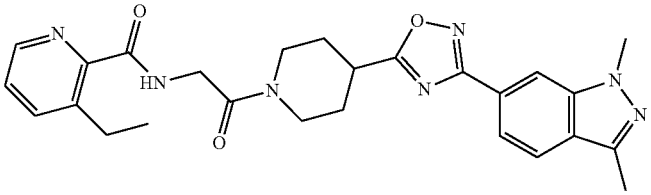 [SMILES: CCc1cccnc1C(=O)NCC(=O)N1CCC(c2nc(-c3ccc4c(C)nn(C)c4c3)no2)CC1] |
| 170 | 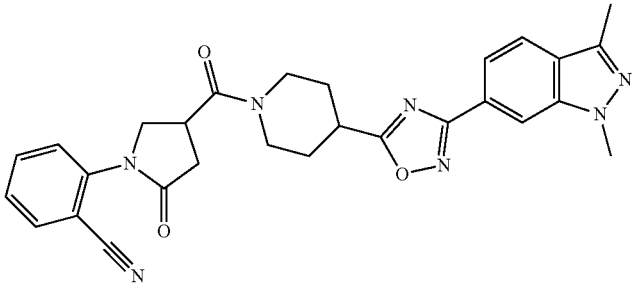 [SMILES: Cc1nn(C)c2cc(-c3noc(C4CCN(C(=O)C5CC(=O)N(c6ccccc6C#N)C5)CC4)n3)ccc12] |
| 171 | 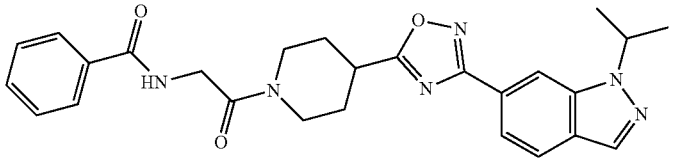 [SMILES: CC(C)n1ncc2ccc(-c3noc(C4CCN(C(=O)CNC(=O)c5ccccc5)CC4)n3)cc21] |

TABLE 1-continued

Compounds of the Invention

| # | Structure |
|---|---|
| 172 | 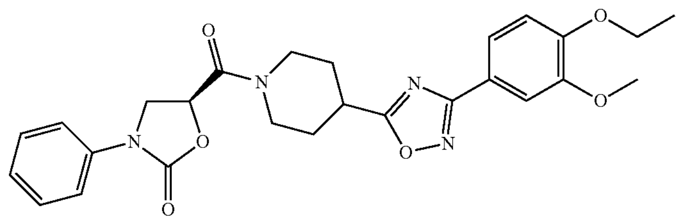 [SMILES: CCOc1ccc(-c2noc(C3CCN(C(=O)[C@@H]4CN(c5ccccc5)C(=O)O4)CC3)n2)cc1OC] |
| 173 | 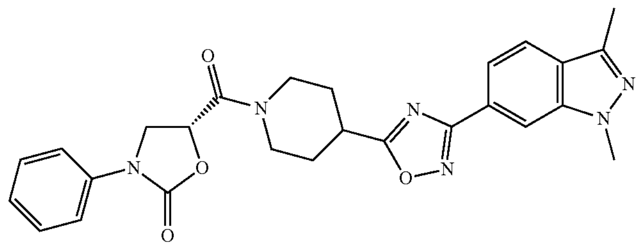 |
| 174 | 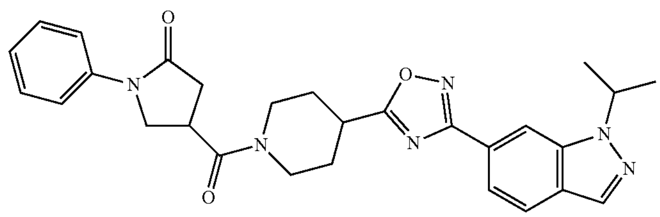 [SMILES: CC(C)n1ncc2ccc(-c3noc(C4CCN(C(=O)C5CC(=O)N(c6ccccc6)C5)CC4)n3)cc21] |
| 175 | 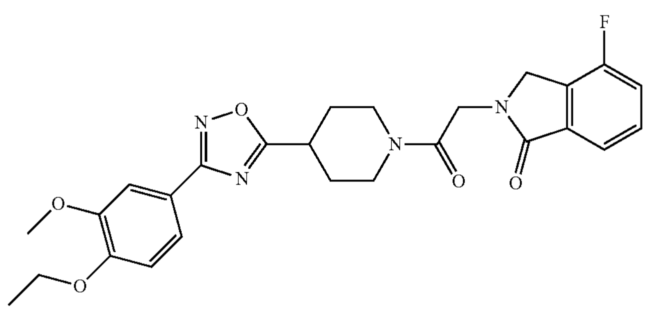 [SMILES: CCOc1ccc(-c2noc(C3CCN(C(=O)CN4Cc5c(F)cccc5C4=O)CC3)n2)cc1OC] |
| 176 | 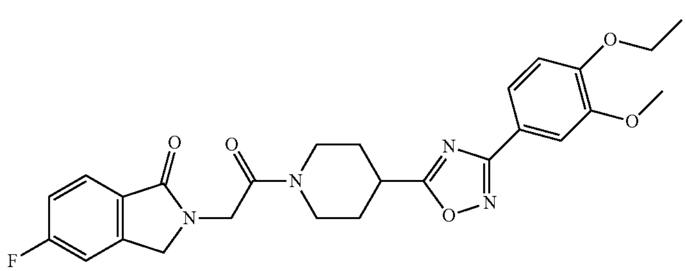 [SMILES: CCOc1ccc(-c2noc(C3CCN(C(=O)CN4Cc5cc(F)ccc5C4=O)CC3)n2)cc1OC] |
| 177 | 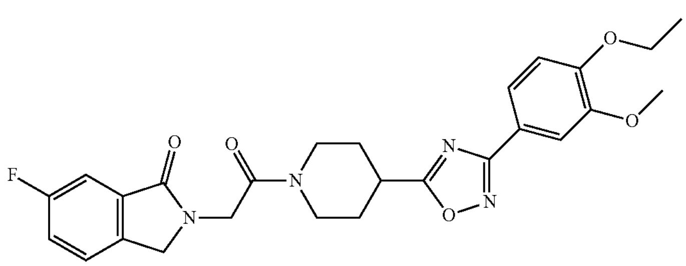 [SMILES: CCOc1ccc(-c2noc(C3CCN(C(=O)CN4Cc5ccc(F)cc5C4=O)CC3)n2)cc1OC] |

TABLE 1-continued
Compounds of the Invention
| # | Structure |
|---|---|
| 178 | 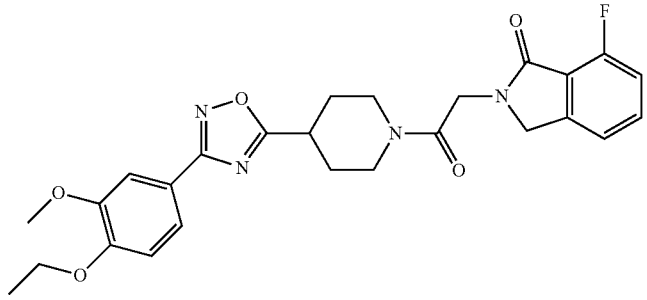 [SMILES: CCOc1ccc(-c2noc(C3CCN(C(=O)CN4Cc5cccc(F)c5C4=O)CC3)n2)cc1OC] |
| 179 | 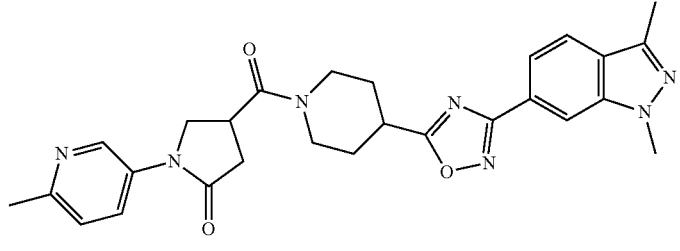 [SMILES: Cc1ccc(N2CC(C(=O)N3CCC(c4nc(-c5ccc6c(C)nn(C)c6c5)no4)CC3)CC2=O)cn1] |
| 180 | 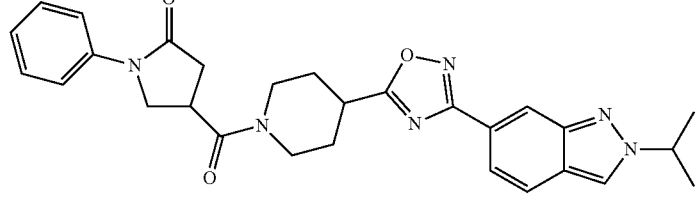 |
| 181 | 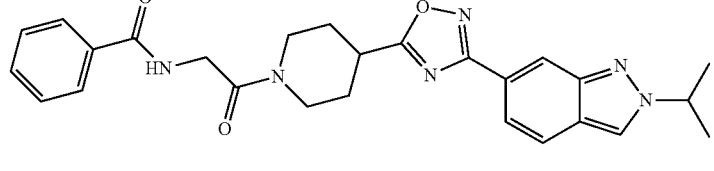 |
| 182 | 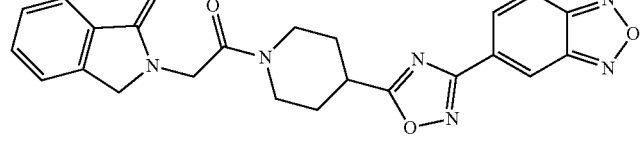 |
| 183 | 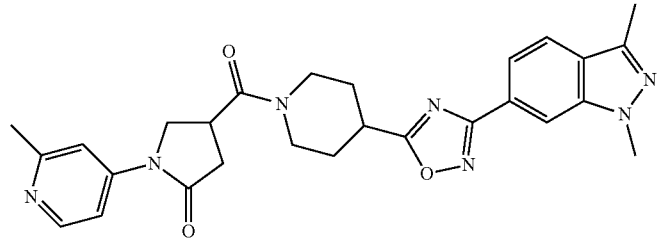 [SMILES: Cc1cc(N2CC(C(=O)N3CCC(c4nc(-c5ccc6c(C)nn(C)c6c5)no4)CC3)CC2=O)ccn1] |

TABLE 1-continued

Compounds of the Invention

| # | Structure |
|---|---|
| 184 | 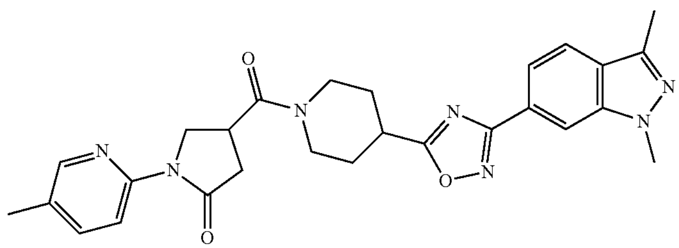 [SMILES: Cc1ccc(N2CC(C(=O)N3CCC(c4nc(-c5ccc6c(C)nn(C)c6c5)no4)CC3)CC2=O)nc1] |
| 185 | 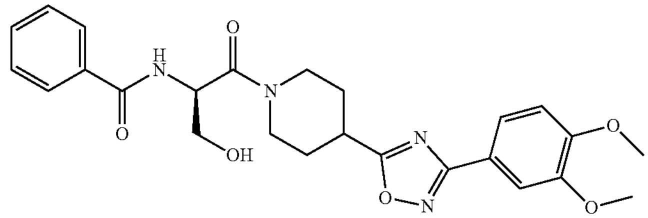 [SMILES: COc1ccc(-c2noc(C3CCN(C(=O)[C@@H](CO)NC(=O)c4ccccc4)CC3)n2)cc1OC] |
| 186 | 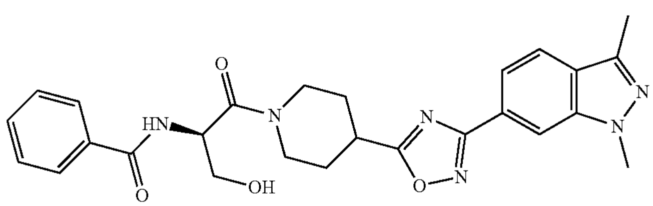 [SMILES: Cc1nn(C)c2cc(-c3noc(C4CCN(C(=O)[C@@H](CO)NC(=O)c5ccccc5)CC4)n3)ccc12] |
| 187 | 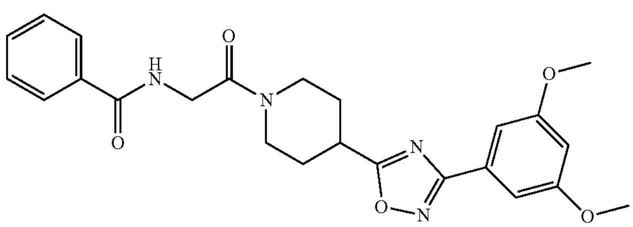 [SMILES: COc1cc(OC)cc(-c2noc(C3CCN(C(=O)CNC(=O)c4ccccc4)CC3)n2)c1] |
| 188 | 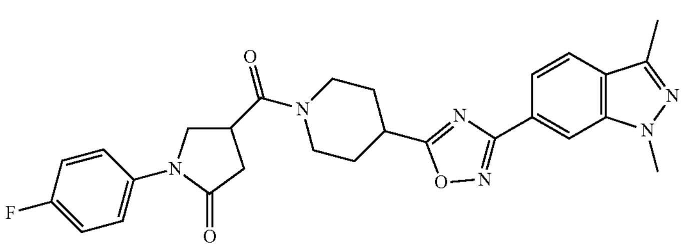 [SMILES: Cc1nn(C)c2cc(-c3noc(C4CCN(C(=O)C5CC(=O)N(c6ccc(F)cc6)C5)CC4)n3)ccc12] |
| 189 | 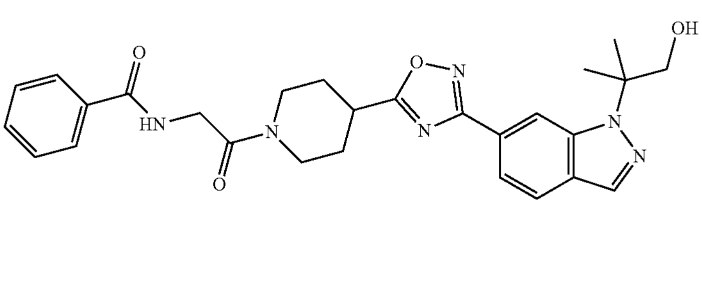 [SMILES: CC(C)(CO)n1ncc2ccc(-c3noc(C4CCN(C(=O)CNC(=O)c5ccccc5)CC4)n3)cc21] |

TABLE 1-continued

Compounds of the Invention

| # | Structure |
|---|---|
| 190 | 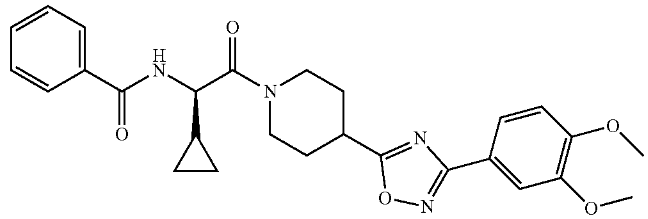 [SMILES: COc1ccc(-c2noc(C3CCN(C(=O)[C@H](NC(=O)c4ccccc4)C4CC4)CC3)n2)cc1OC] |
| 191 | 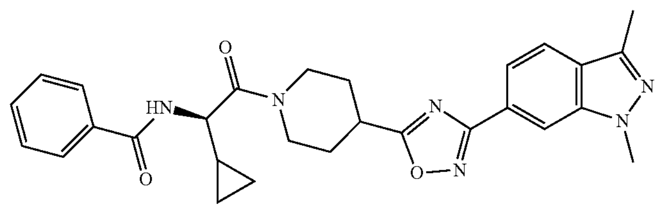 [SMILES: Cc1nn(C)c2cc(-c3noc(C4CCN(C(=O)[C@H](NC(=O)c5ccccc5)C5CC5)CC4)n3)ccc12] |
| 192 | 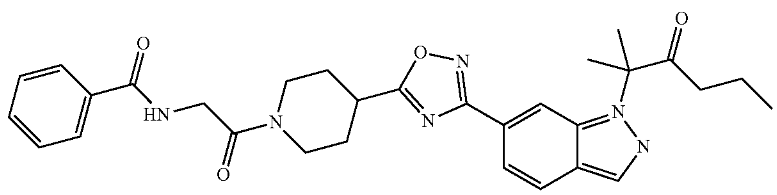 |
| 193 | 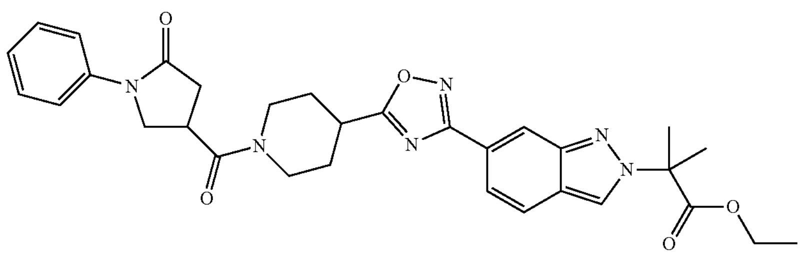 [SMILES: CCOC(=O)C(C)(C)n1cc2ccc(-c3noc(C4CCN(C(=O)C5CC(=O)N(c6ccccc6)C5)CC4)n3)cc2n1] |
| 194 | 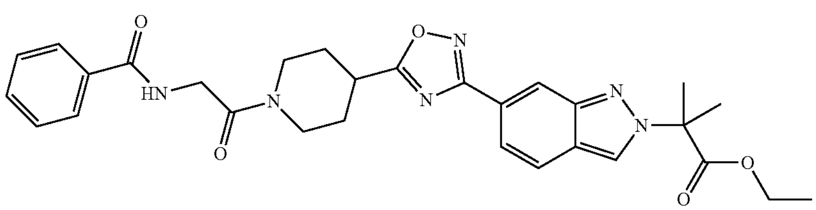 [SMILES: CCOC(=O)C(C)(C)n1cc2ccc(-c3noc(C4CCN(C(=O)CNC(=O)c5ccccc5)CC4)n3)cc2n1] |
| 195 | 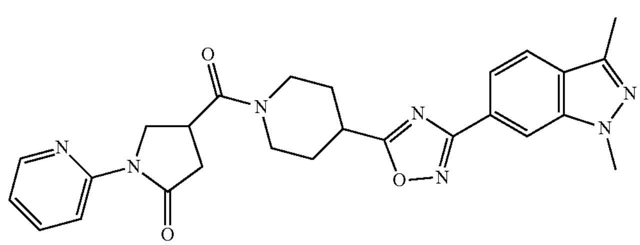 [SMILES: Cc1nn(C)c2cc(-c3noc(C4CCN(C(=O)C5CC(=O)N(c6ccccn6)C5)CC4)n3)ccc12] |
| 196 | 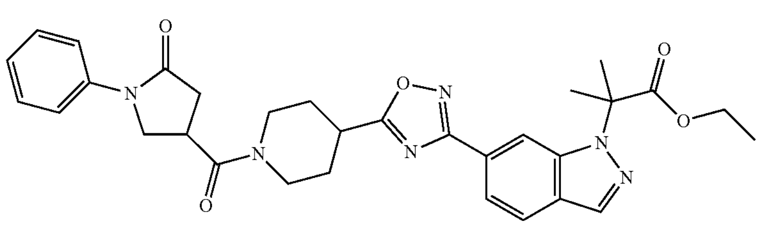 [SMILES: CCOC(=O)C(C)(C)n1ncc2ccc(-c3noc(C4CCN(C(=O)C5CC(=O)N(c6ccccc6)C5)CC4)n3)cc21] |

US 11,970,486 B2
97                                                                    98
TABLE 1-continued
Compounds of the Invention
| # | Structure |
|---|-----------|
197 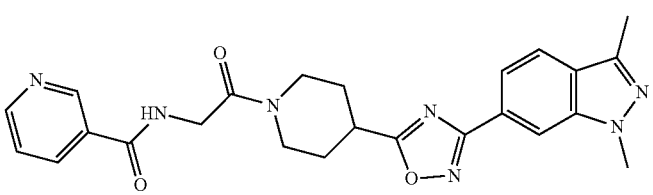 [SMILES: Cc1nn(C)c2cc(-c3noc(C4CCN(C(=O)CNC(=O)c5cccnc5)CC4)n3)ccc12]
198 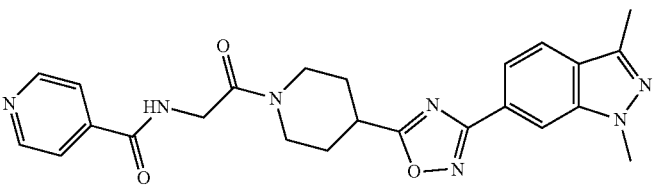 [SMILES: Cc1nn(C)c2cc(-c3noc(C4CCN(C(=O)CNC(=O)c5ccncc5)CC4)n3)ccc12]
199 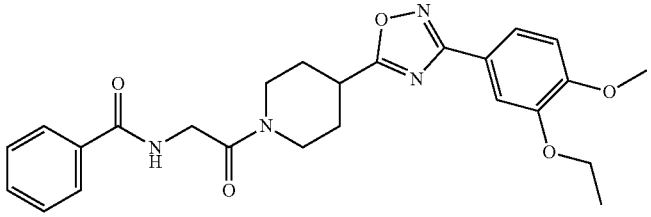 [SMILES: CCOc1cc(-c2noc(C3CCN(C(=O)CNC(=O)c4ccccc4)CC3)n2)ccc1OC]
200 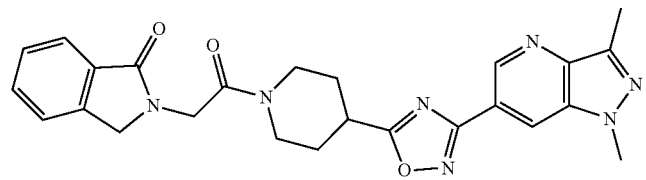 [SMILES: Cc1nn(C)c2cc(-c3noc(C4CCN(C(=O)CN5Cc6ccccc6C5=O)CC4)n3)cnc12]
201 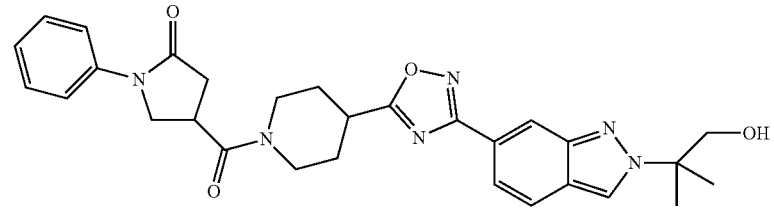 [SMILES: CC(C)(CO)n1cc2ccc(-c3noc(C4CCN(C(=O)C5CC(=O)N(c6ccccc6)C5)CC4)n3)cc2n1]
202 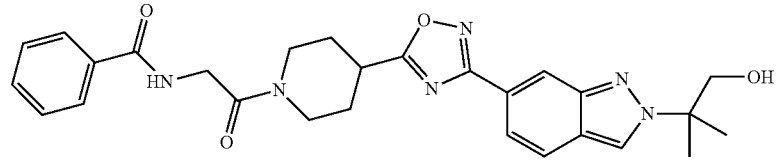 [SMILES: CC(C)(CO)n1cc2ccc(-c3noc(C4CCN(C(=O)CNC(=O)c5ccccc5)CC4)n3)cc2n1]
203 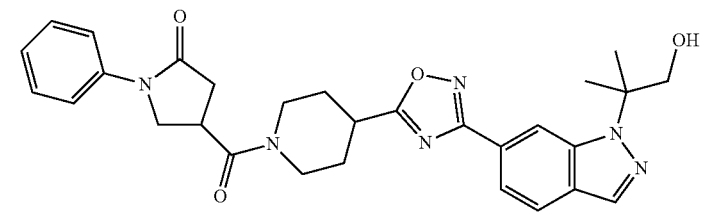 [SMILES: CC(C)(CO)n1ncc2ccc(-c3noc(C4CCN(C(=O)C5CC(=O)N(c6ccccc6)C5)CC4)n3)cc21]

TABLE 1-continued

Compounds of the Invention

| # | Structure |
|---|---|
| 204 | 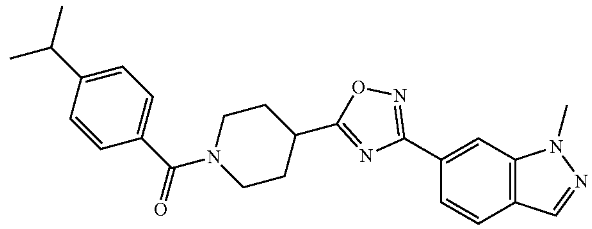 [SMILES: CC(C)c1ccc(C(=O)N2CCC(c3nc(-c4ccc5cnn(C)c5c4)no3)CC2)cc1] |
| 205 | 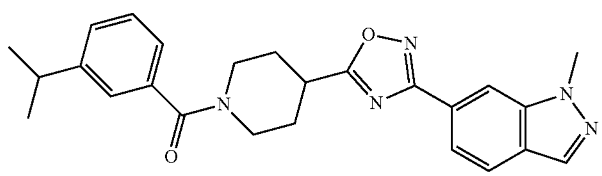 [SMILES: CC(C)c1cccc(C(=O)N2CCC(c3nc(-c4ccc5cnn(C)c5c4)no3)CC2)c1] |
| 206 | 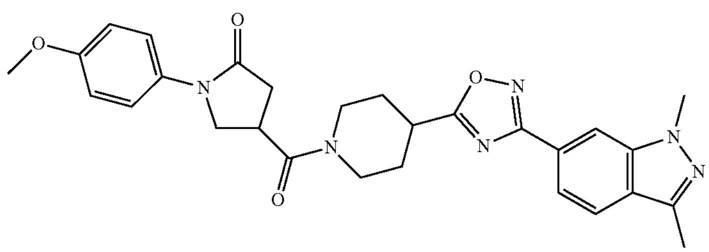 [SMILES: COc1ccc(N2CC(C(=O)N3CCC(c4nc(-c5ccc6c(C)nn(C)c6c5)no4)CC3)CC2=O)cc1] |
| 207 | 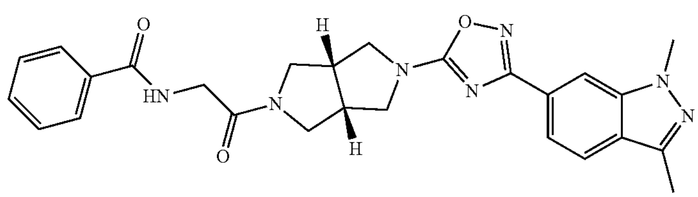 [SMILES: Cc1nn(C)c2cc(-c3noc(N4C[C@H]5CN(C(=O)CNC(=O)c6ccccc6)C[C@H]5C4)n3)ccc12] |
| 208 | 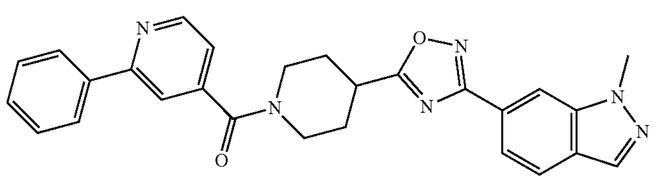 [SMILES: Cn1ncc2ccc(-c3noc(C4CCN(C(=O)c5ccnc(-c6ccccc6)c5)CC4)n3)cc21] |
| 209 | 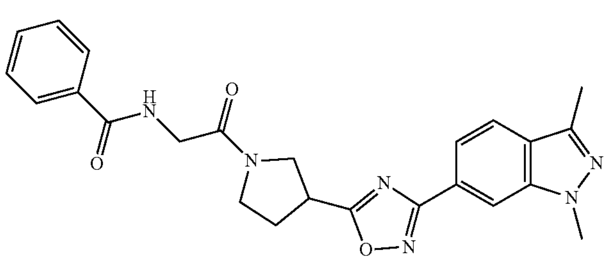 [SMILES: Cc1nn(C)c2cc(-c3noc(C4CCN(C(=O)CNC(=O)c5ccccc5)C4)n3)ccc12] |
| 210 | 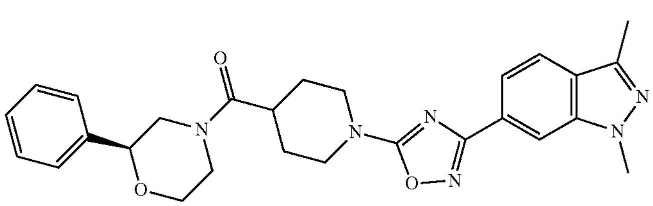 [SMILES: Cc1nn(C)c2cc(-c3noc(N4CCC(C(=O)N5CCO[C@@H](c6ccccc6)C5)CC4)n3)ccc12] |

TABLE 1-continued

Compounds of the Invention

| # | Structure |
|---|---|
| 211 | 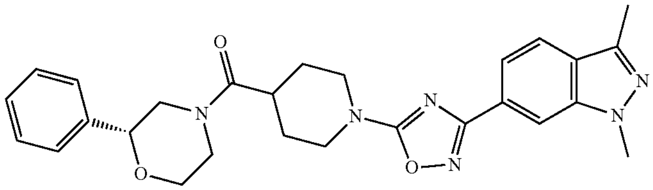 [SMILES: Cc1nn(C)c2cc(-c3noc(N4CCC(C(=O)N5CCO[C@H](c6ccccc6)C5)CC4)n3)ccc12] |
| 212 | 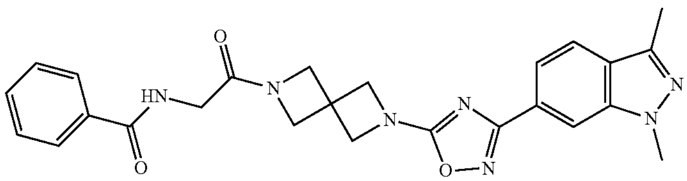 [SMILES: Cc1nn(C)c2cc(-c3noc(N4CC5(CN(C(=O)CNC(=O)c6ccccc6)C5)C4)n3)ccc12] |
| 213 | 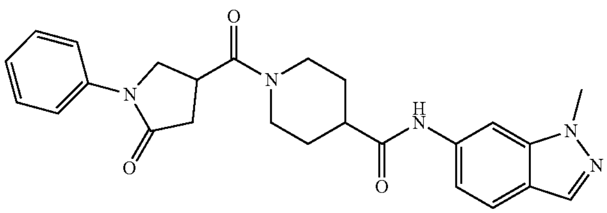 [SMILES: Cn1ncc2ccc(NC(=O)C3CCN(C(=O)C4CC(=O)N(c5ccccc5)C4)CC3)cc21] |
| 214 | 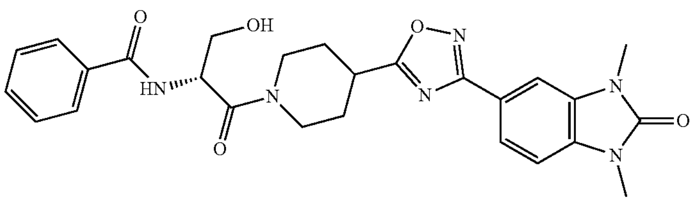 [SMILES: Cn1c(=O)n(C)c2cc(-c3noc(C4CCN(C(=O)[C@@H](CO)NC(=O)c5ccccc5)CC4)n3)ccc21] |
| 215 | 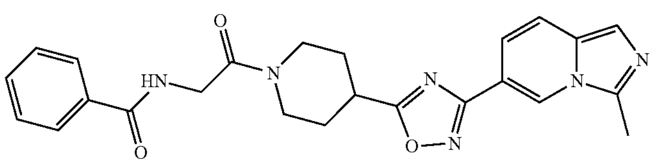 [SMILES: Cc1ncc2ccc(-c3noc(C4CCN(C(=O)CNC(=O)c5ccccc5)CC4)n3)cn12] |
| 216 | 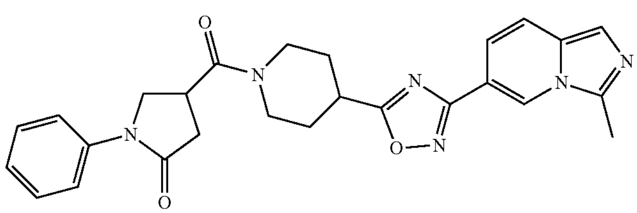 [SMILES: Cc1ncc2ccc(-c3noc(C4CCN(C(=O)C5CC(=O)N(c6ccccc6)C5)CC4)n3)cn12] |
| 217 | 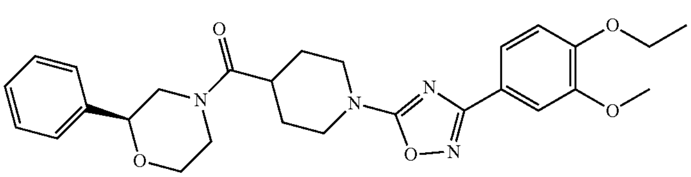 [SMILES: CCOc1ccc(-c2noc(N3CCC(C(=O)N4CCO[C@@H](c5ccccc5)C4)CC3)n2)cc1OC] |
| 218 | 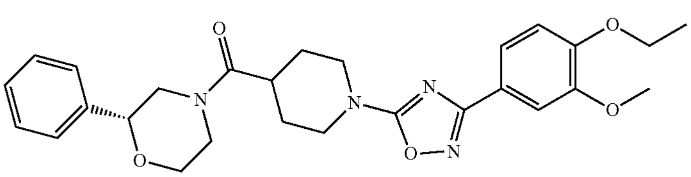 [SMILES: CCOc1ccc(-c2noc(N3CCC(C(=O)N4CCO[C@H](c5ccccc5)C4)CC3)n2)cc1OC] |

TABLE 1-continued
Compounds of the Invention
| # | Structure |
|---|---|
| 219 | 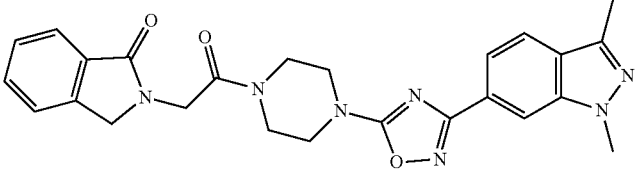 [SMILES: Cc1nn(C)c2cc(-c3noc(N4CCN(C(=O)CN5Cc6ccccc6C5=O)CC4)n3)ccc12] |
| 220 | 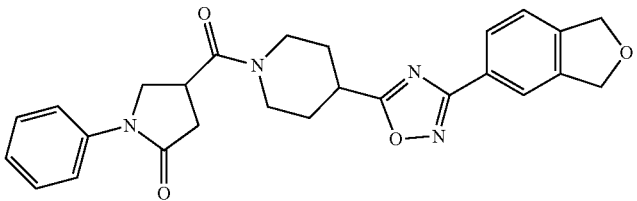 [SMILES: O=C(C1CC(=O)N(c2ccccc2)C1)N1CCC(c2nc(-c3ccc4c(c3)COC4)no2)CC1] |
| 221 | 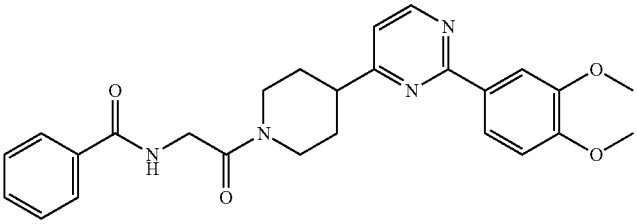 [SMILES: COc1ccc(-c2nccc(C3CCN(C(=O)CNC(=O)c4ccccc4)CC3)n2)cc1OC] |
| 222 | 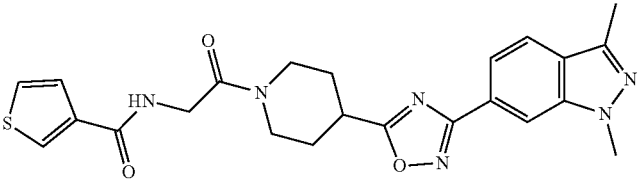 [SMILES: Cc1nn(C)c2cc(-c3noc(C4CCN(C(=O)CNC(=O)c5ccsc5)CC4)n3)ccc12] |
| 223 | 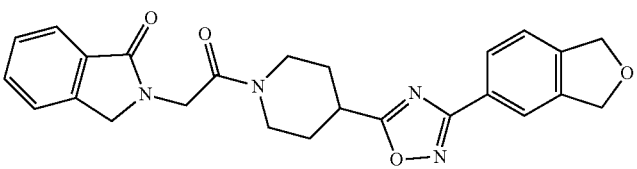 [SMILES: O=C(CN1Cc2ccccc2C1=O)N1CCC(c2nc(-c3ccc4c(c3)COC4)no2)CC1] |
| 224 | 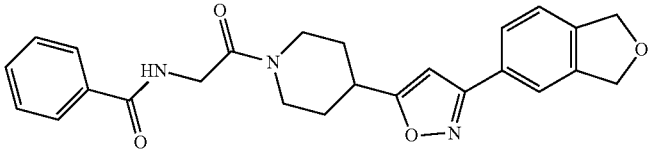 [SMILES: O=C(NCC(=O)N1CCC(c2cc(-c3ccc4c(c3)COC4)no2)CC1)c1ccccc1] |
| 225 | 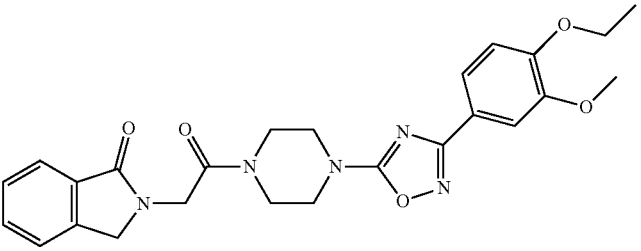 [SMILES: CCOc1ccc(-c2noc(N3CCN(C(=O)CN4Cc5ccccc5C4=O)CC3)n2)cc1OC] |

TABLE 1-continued
Compounds of the Invention
| # | Structure |
|---|---|
| 226 | 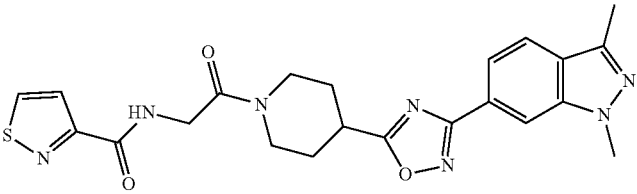 [SMILES: Cc1nn(C)c2cc(-c3noc(C4CCN(C(=O)CNC(=O)c5ccsn5)CC4)n3)ccc12] |
| 227 | 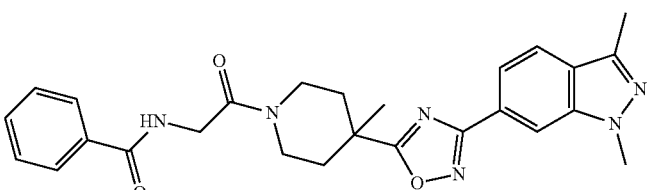 |
| 228 | 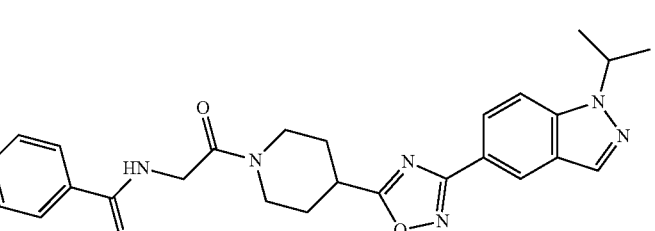 |
| 229 | 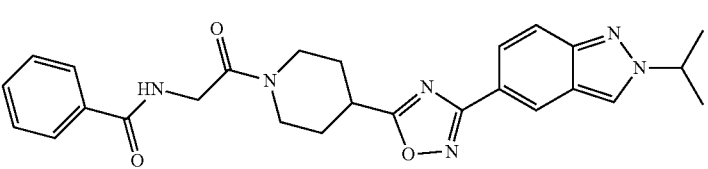 [SMILES: CC(C)n1cc2cc(-c3noc(C4CCN(C(=O)CNC(=O)c5ccccc5)CC4)n3)ccc2n1] |
| 230 | 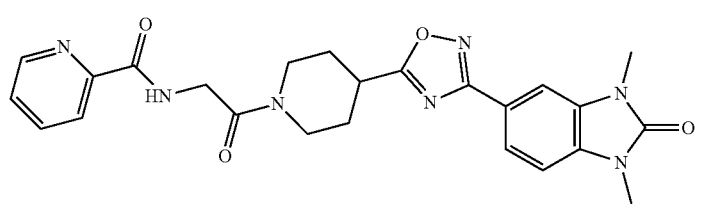 [SMILES: Cn1c(=O)n(C)c2cc(-c3noc(C4CCN(C(=O)CNC(=O)c5ccccn5)CC4)n3)ccc21] |
| 231 | 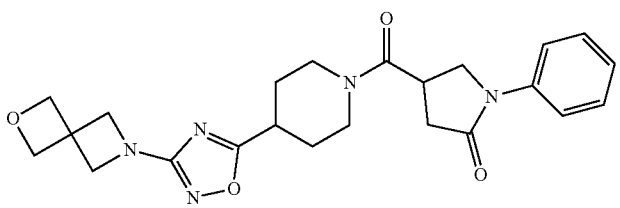 [SMILES: O=C(C1CC(=O)N(c2ccccc2)C1)N1CCC(c2nc(N3CC4(COC4)C3)no2)CC1] |
| 232 | 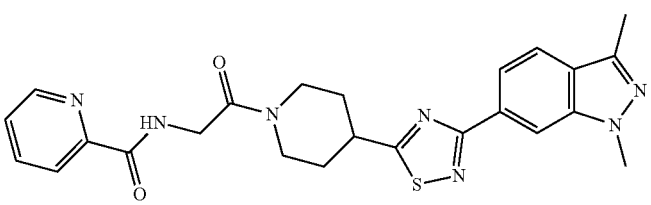 [SMILES: Cc1nn(C)c2cc(-c3nsc(C4CCN(C(=O)CNC(=O)c5ccccn5)CC4)n3)ccc12] |

TABLE 1-continued

Compounds of the Invention

| # | Structure |
|---|-----------|
| 233 | 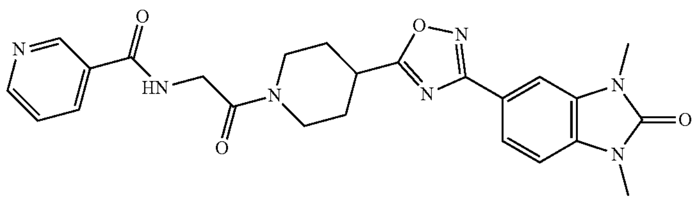 [SMILES: Cn1c(=O)n(C)c2cc(-c3noc(C4CCN(C(=O)CNC(=O)c5cccnc5)CC4)n3)ccc21] |
| 234 | 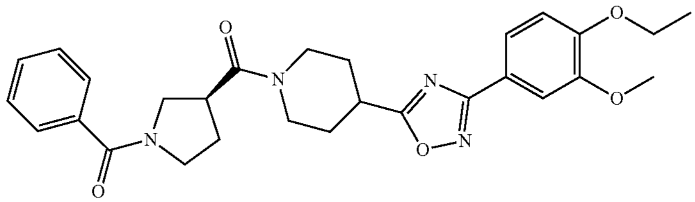 [SMILES: CCOc1ccc(-c2noc(C3CCN(C(=O)[C@H]4CCN(C(=O)c5ccccc5)C4)CC3)n2)cc1OC] |
| 235 | 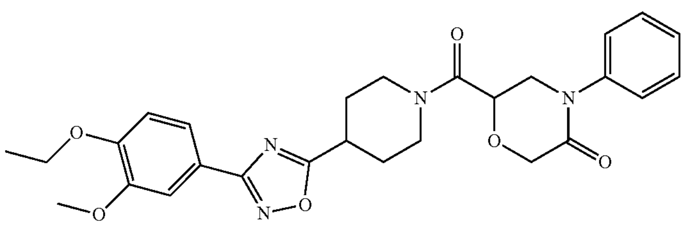 [SMILES: CCOc1ccc(-c2noc(C3CCN(C(=O)C4CN(c5ccccc5)C(=O)CO4)CC3)n2)cc1OC] |
| 236 | 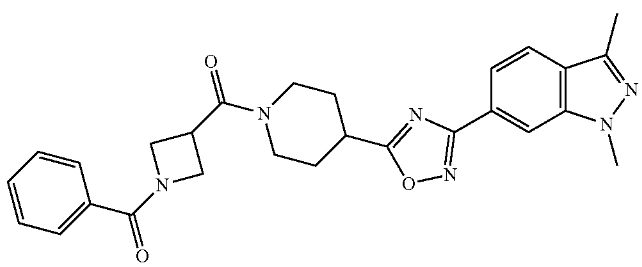 [SMILES: Cc1nn(C)c2cc(-c3noc(C4CCN(C(=O)C5CN(C(=O)c6ccccc6)C5)CC4)n3)ccc12] |
| 237 | 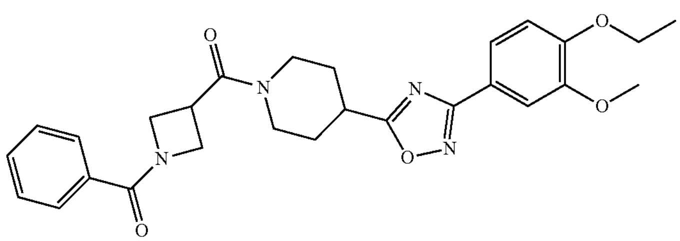 [SMILES: CCOc1ccc(-c2noc(C3CCN(C(=O)C4CN(C(=O)c5ccccc5)C4)CC3)n2)cc1OC] |
| 238 | 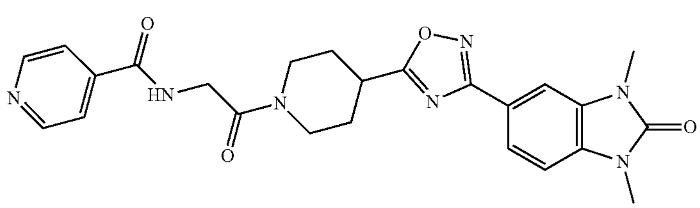 [SMILES: Cn1c(=O)n(C)c2cc(-c3noc(C4CCN(C(=O)CNC(=O)c5ccncc5)CC4)n3)ccc21] |

TABLE 1-continued

Compounds of the Invention

| # | Structure |
|---|-----------|
| 239 | 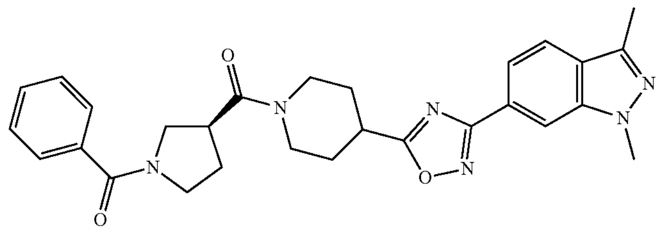 [SMILES: Cc1nn(C)c2cc(-c3noc(C4CCN(C(=O)[C@H]5CCN(C(=O)c6ccccc6)C5)CC4)n3)ccc12] |
| 240 | 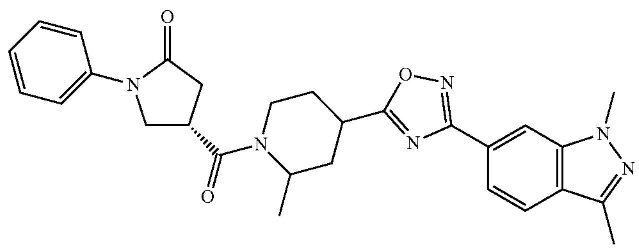 [SMILES: Cc1nn(C)c2cc(-c3noc(C4CCN(C(=O)[C@H]5CC(=O)N(c6ccccc6)C5)C(C)C4)n3)ccc12] |
| 241 | 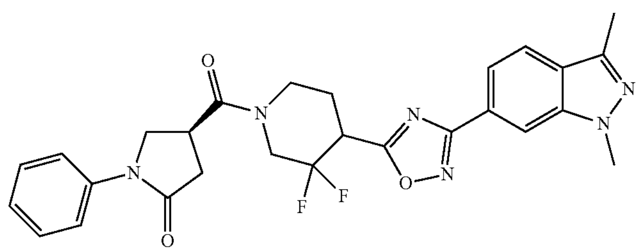 [SMILES: Cc1nn(C)c2cc(-c3noc(C4CCN(C(=O)[C@H]5CC(=O)N(c6ccccc6)C5)CC4(F)F)n3)ccc12] |
| 242 | 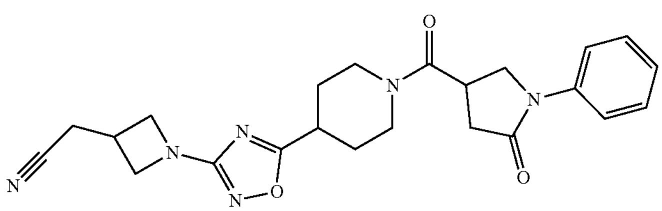 [SMILES: N#CCC1CN(c2noc(C3CCN(C(=O)C4CC(=O)N(c5ccccc5)C4)CC3)n2)C1] |
| 243 | 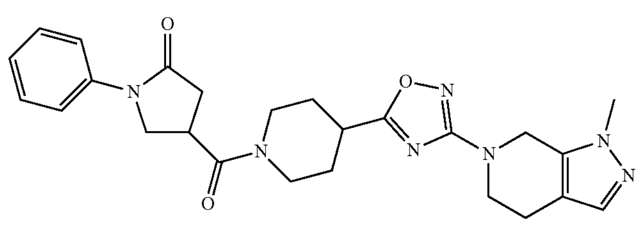 [SMILES: Cn1ncc2c1CN(c1noc(C3CCN(C(=O)C4CC(=O)N(c5ccccc5)C4)CC3)n1)CC2] |
| 244 | 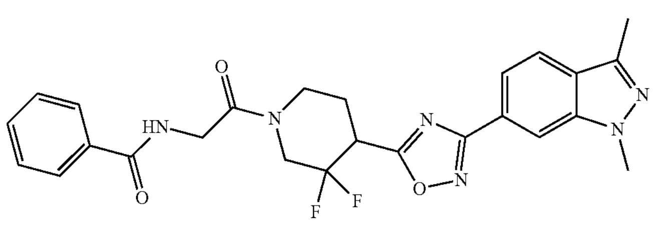 [SMILES: Cc1nn(C)c2cc(-c3noc(C4CCN(C(=O)CNC(=O)c5ccccc5)CC4(F)F)n3)ccc12] |

TABLE 1-continued

Compounds of the Invention

| # | Structure |
|---|---|
| 245 | 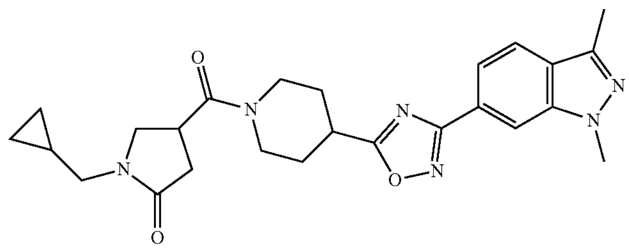 [SMILES: Cc1nn(C)c2cc(-c3noc(C4CCN(C(=O)C5CC(=O)N(CC6CC6)C5)CC4)n3)ccc12] |
| 246 | 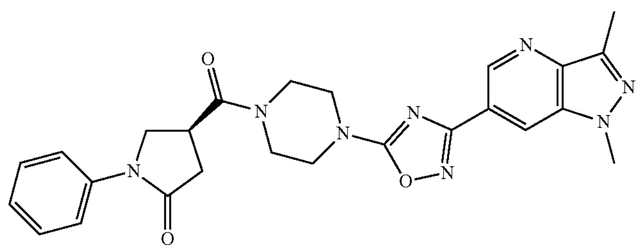 [SMILES: Cc1nn(C)c2cc(-c3noc(N4CCN(C(=O)[C@H]5CC(=O)N(c6ccccc6)C5)CC4)n3)cnc12] |
| 247 | 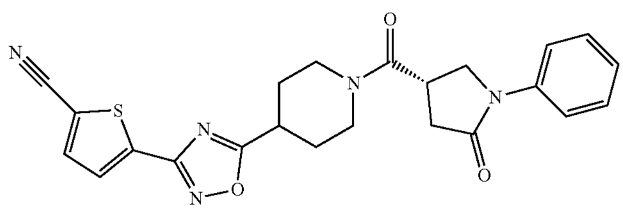 [SMILES: N#Cc1ccc(-c2noc(C3CCN(C(=O)[C@H]4CC(=O)N(c5ccccc5)C4)CC3)n2)s1] |
| 248 | 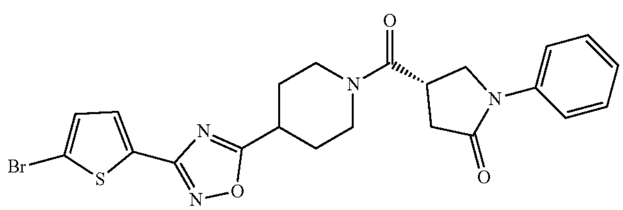 [SMILES: O=C([C@H]1CC(=O)N(c2ccccc2)C1)N1CCC(c2nc(-c3ccc(Br)s3)no2)CC1] |
| 249 | 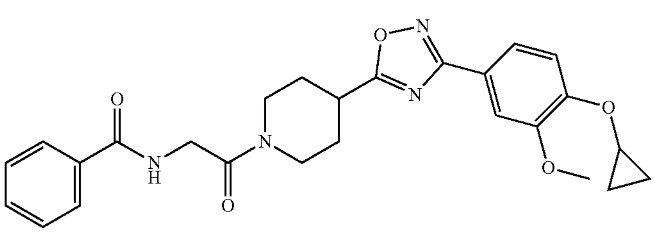 [SMILES: COc1cc(-c2noc(C3CCN(C(=O)CNC(=O)c4ccccc4)CC3)n2)ccc1OC1CC1] |
| 250 | 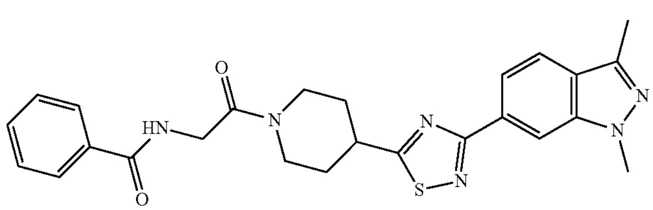 [SMILES: Cc1nn(C)c2cc(-c3nsc(C4CCN(C(=O)CNC(=O)c5ccccc5)CC4)n3)ccc12] |

TABLE 1-continued
Compounds of the Invention
| # | Structure |
|---|---|
| 251 | 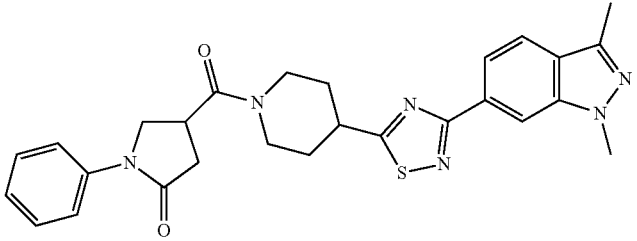 [SMILES: Cc1nn(C)c2cc(-c3nsc(C4CCN(C(=O)C5CC(=O)N(c6ccccc6)C5)CC4)n3)ccc12] |
| 252 | 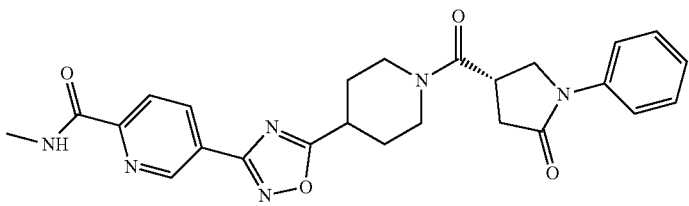 [SMILES: CNC(=O)c1ccc(-c2noc(C3CCN(C(=O)[C@H]4CC(=O)N(c5ccccc5)C4)CC3)n2)cn1] |
| 253 | 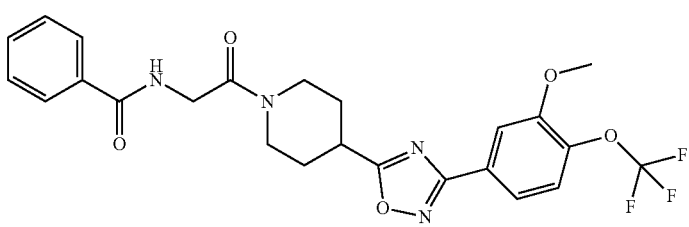 [SMILES: COc1cc(-c2noc(C3CCN(C(=O)CNC(=O)c4ccccc4)CC3)n2)ccc1OC(F)(F)F] |
| 254 | 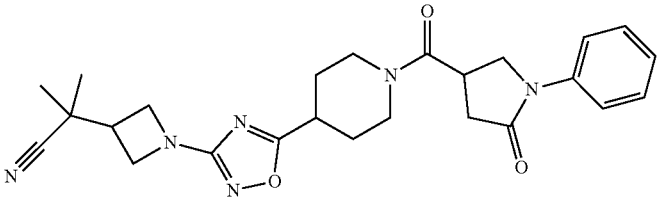 [SMILES: CC(C)(C#N)C1CN(c2noc(C3CCN(C(=O)C4CC(=O)N(c5ccccc5)C4)CC3)n2)C1] |
| 255 | 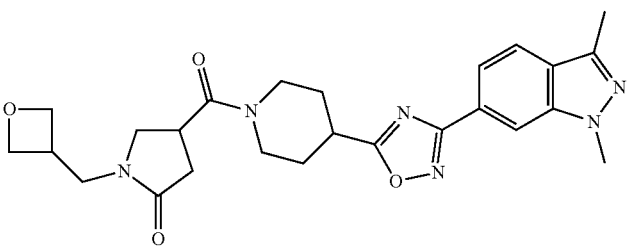 [SMILES: Cc1nn(C)c2cc(-c3noc(C4CCN(C(=O)C5CC(=O)N(CC6COC6)C5)CC4)n3)ccc12] |
| 256 | 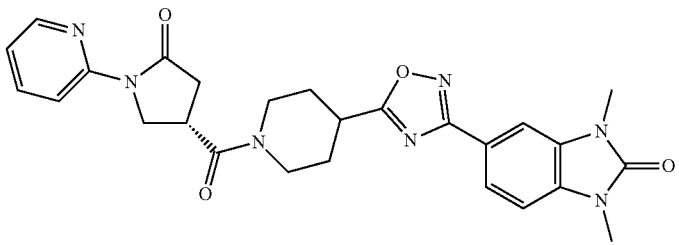 [SMILES: Cn1c(=O)n(C)c2cc(-c3noc(C4CCN(C(=O)[C@H]5CC(=O)N(c6ccccn6)C5)CC4)n3)ccc21] |

TABLE 1-continued

Compounds of the Invention

| # | Structure |
|---|---|
| 257 | 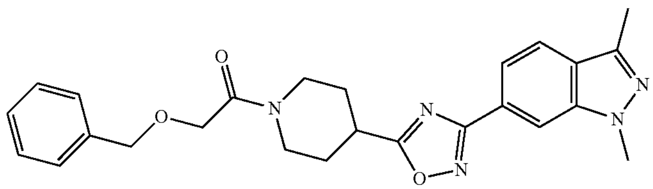 [SMILES: Cc1nn(C)c2cc(-c3noc(C4CCN(C(=O)COCc5ccccc5)CC4)n3)ccc12] |
| 258 | 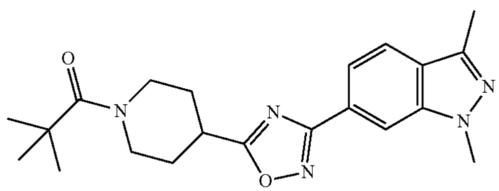 [SMILES: Cc1nn(C)c2cc(-c3noc(C4CCN(C(=O)C(C)(C)C)CC4)n3)ccc12] |
| 259 | 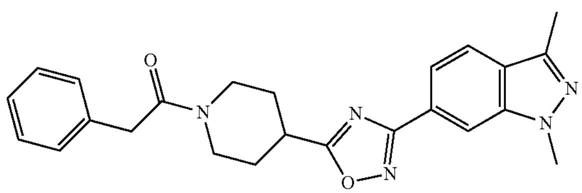 [SMILES: Cc1nn(C)c2cc(-c3noc(C4CCN(C(=O)Cc5ccccc5)CC4)n3)ccc12] |
| 260 | 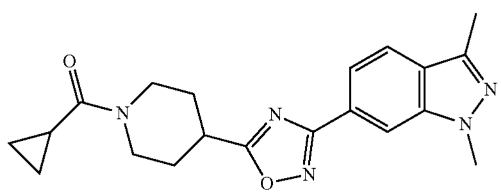 [SMILES: Cc1nn(C)c2cc(-c3noc(C4CCN(C(=O)C5CC5)CC4)n3)ccc12] |
| 261 | 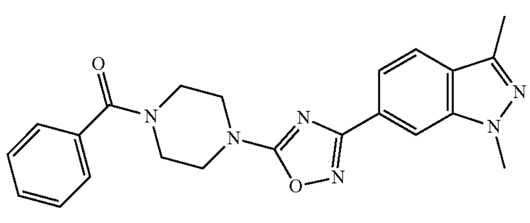 [SMILES: Cc1nn(C)c2cc(-c3noc(N4CCN(C(=O)c5ccccc5)CC4)n3)ccc12] |
| 262 | 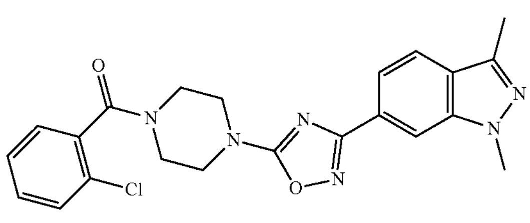 [SMILES: Cc1nn(C)c2cc(-c3noc(N4CCN(C(=O)c5ccccc5Cl)CC4)n3)ccc12] |
| 263 | 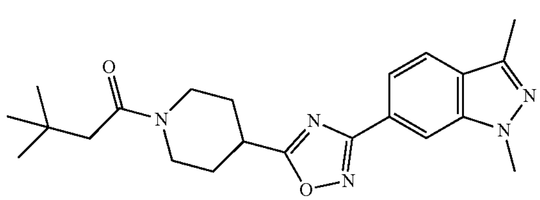 [SMILES: Cc1nn(C)c2cc(-c3noc(C4CCN(C(=O)CC(C)(C)C)CC4)n3)ccc12] |

TABLE 1-continued

Compounds of the Invention

| # | Structure |
|---|---|
| 264 | 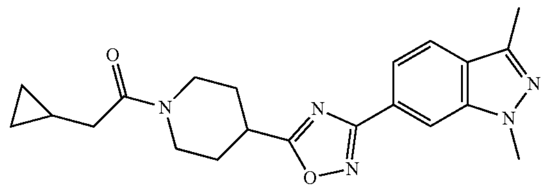 [SMILES: Cc1nn(C)c2cc(-c3noc(C4CCN(C(=O)CC5CC5)CC4)n3)ccc12] |
| 265 | 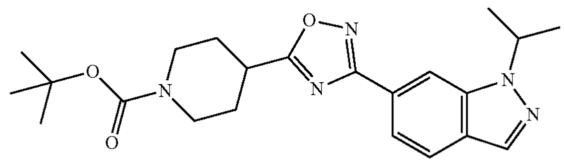 |
| 266 | 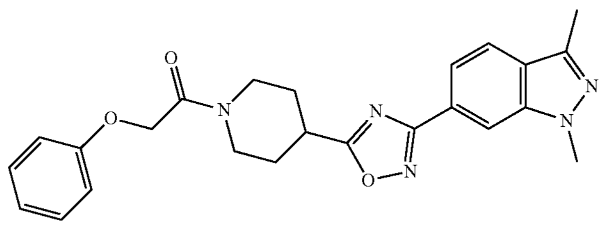 [SMILES: Cc1nn(C)c2cc(-c3noc(C4CCN(C(=O)COc5ccccc5)CC4)n3)ccc12] |
| 267 | 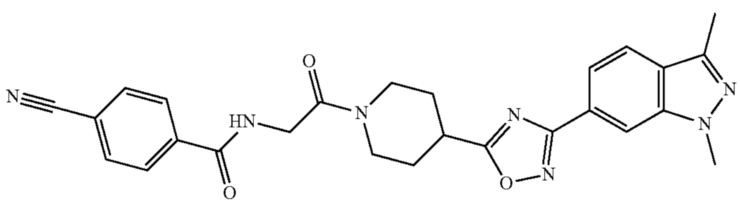 [SMILES: Cc1nn(C)c2cc(-c3noc(C4CCN(C(=O)CNC(=O)c5ccc(C#N)cc5)CC4)n3)ccc12] |
| 268 | 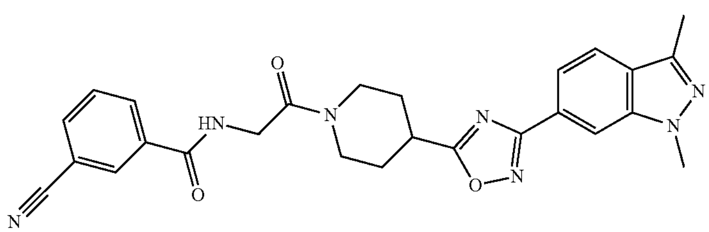 |
| 269 | 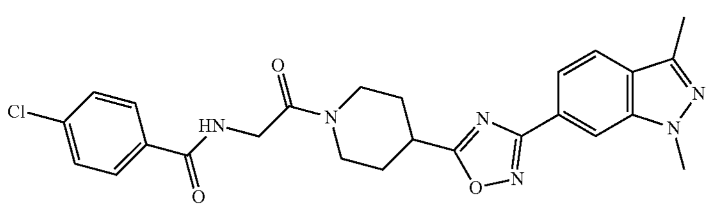 [SMILES: Cc1nn(C)c2cc(-c3noc(C4CCN(C(=O)CNC(=O)c5ccc(Cl)cc5)CC4)n3)ccc12] |
| 270 | 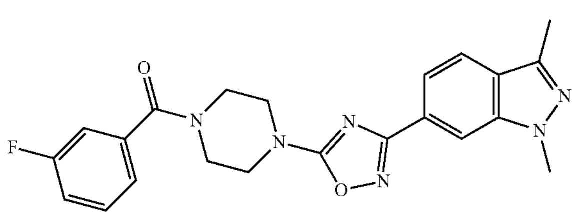 [SMILES: Cc1nn(C)c2cc(-c3noc(N4CCN(C(=O)c5cccc(F)c5)CC4)n3)ccc12] |

TABLE 1-continued

Compounds of the Invention

| # | Structure |
|---|---|
| 271 | 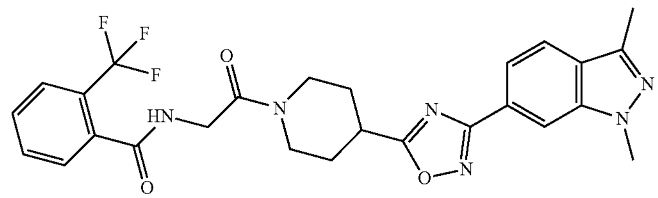 [SMILES: Cc1nn(C)c2cc(-c3noc(C4CCN(C(=O)CNC(=O)c5ccccc5C(F)(F)F)CC4)n3)ccc12] |
| 272 | 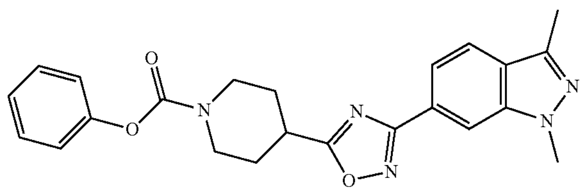 |
| 273 | 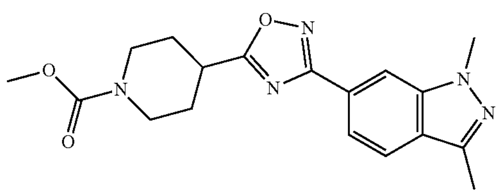 [SMILES: COC(=O)N1CCC(c2nc(-c3ccc4c(C)nn(C)c4c3)no2)CC1] |
| 274 | 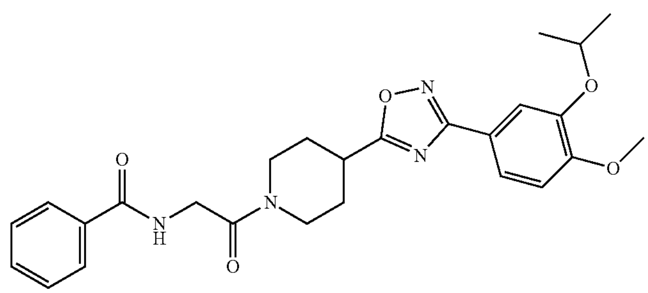 [SMILES: COc1ccc(-c2noc(C3CCN(C(=O)CNC(=O)c4ccccc4)CC3)n2)cc1OC(C)C] |
| 275 | 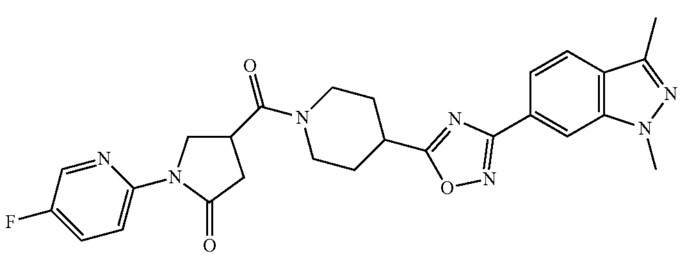 [SMILES: Cc1nn(C)c2cc(-c3noc(C4CCN(C(=O)C5CC(=O)N(c6ccc(F)cn6)C5)CC4)n3)ccc12] |
| 276 | 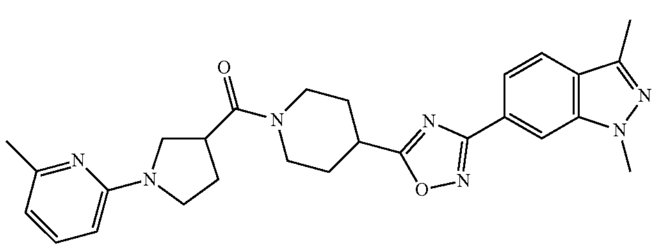 [SMILES: Cc1cccc(N2CCC(C(=O)N3CCC(c4nc(-c5ccc6c(C)nn(C)c6c5)no4)CC3)C2)n1] |
| 277 | 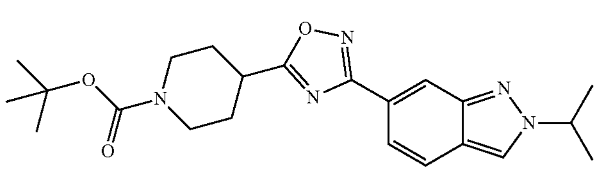 [SMILES: CC(C)n1cc2ccc(-c3noc(C4CCN(C(=O)OC(C)(C)C)CC4)n3)cc2n1] |

TABLE 1-continued

Compounds of the Invention

| # | Structure |
|---|---|
| 278 | 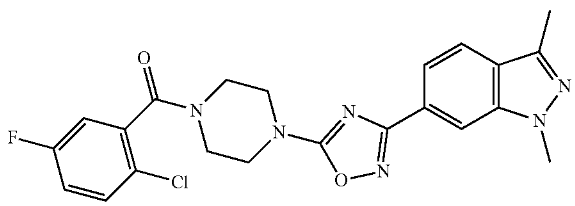 [SMILES: Cc1nn(C)c2cc(-c3noc(N4CCN(C(=O)c5cc(F)ccc5Cl)CC4)n3)ccc12] |
| 279 | 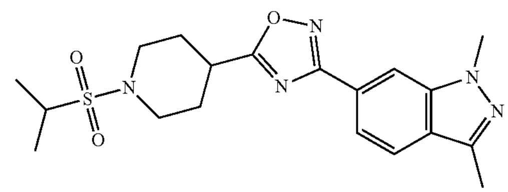 [SMILES: Cc1nn(C)c2cc(-c3noc(C4CCN(S(=O)(=O)C(C)C)CC4)n3)ccc12] |
| 280 | 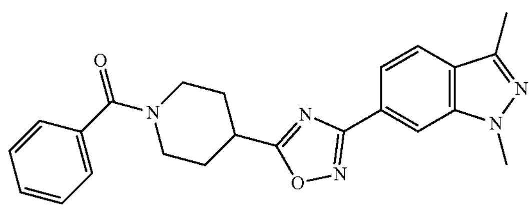 [SMILES: Cc1nn(C)c2cc(-c3noc(C4CCN(C(=O)c5ccccc5)CC4)n3)ccc12] |
| 281 | 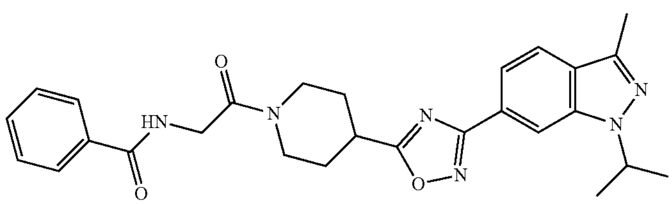 [SMILES: Cc1nn(C(C)C)c2cc(-c3noc(C4CCN(C(=O)CNC(=O)c5ccccc5)CC4)n3)ccc12] |
| 282 | 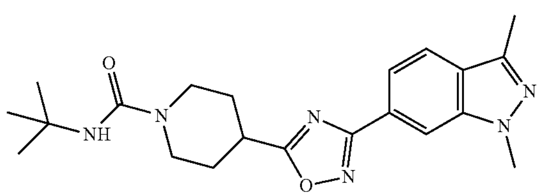 [SMILES: Cc1nn(C)c2cc(-c3noc(C4CCN(C(=O)NC(C)(C)C)CC4)n3)ccc12] |
| 283 | 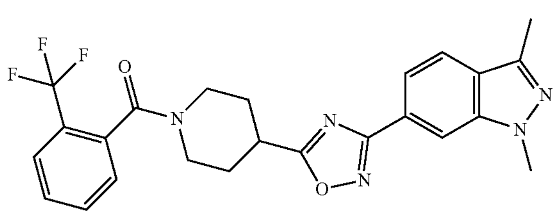 [SMILES: Cc1nn(C)c2cc(-c3noc(C4CCN(C(=O)c5ccccc5C(F)(F)F)CC4)n3)ccc12] |
| 284 | 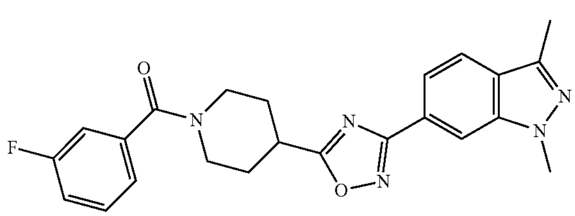 [SMILES: Cc1nn(C)c2cc(-c3noc(C4CCN(C(=O)c5cccc(F)c5)CC4)n3)ccc12] |

TABLE 1-continued

Compounds of the Invention

| # | Structure |
|---|---|
| 285 | 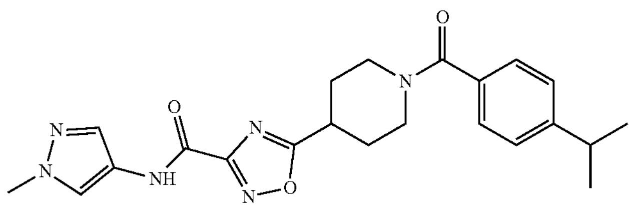 [SMILES: CC(C)c1ccc(C(=O)N2CCC(c3nc(C(=O)Nc4cnn(C)c4)no3)CC2)cc1] |
| 286 | 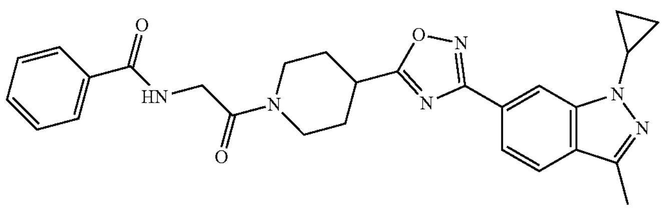 [SMILES: Cc1nn(C2CC2)c2cc(-c3noc(C4CCN(C(=O)CNC(=O)c5ccccc5)CC4)n3)ccc12] |
| 287 | 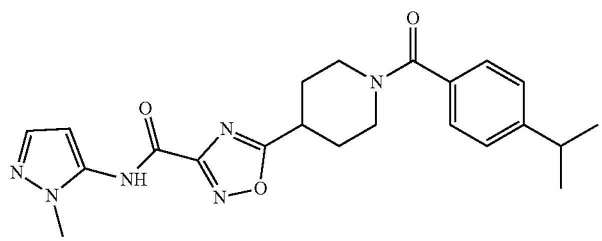 [SMILES: CC(C)c1ccc(C(=O)N2CCC(c3nc(C(=O)Nc4ccnn4C)no3)CC2)cc1] |
| 288 | 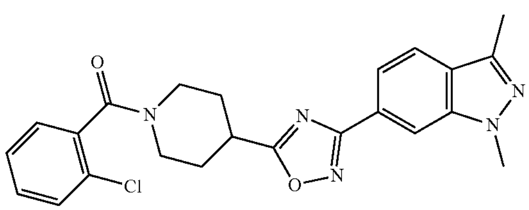 [SMILES: Cc1nn(C)c2cc(-c3noc(C4CCN(C(=O)c5ccccc5Cl)CC4)n3)ccc12] |
| 289 | 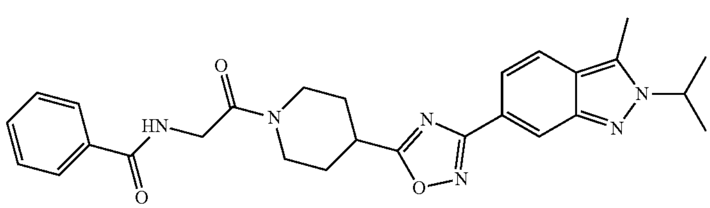 [SMILES: Cc1c2ccc(-c3noc(C4CCN(C(=O)CNC(=O)c5ccccc5)CC4)n3)cc2nn1C(C)C] |
| 290 | 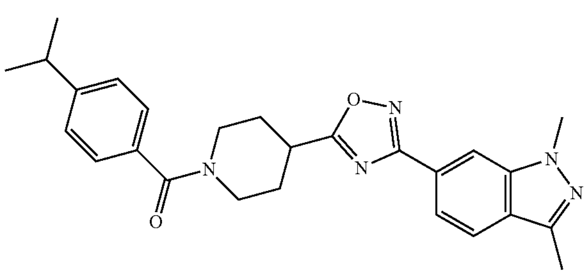 [SMILES: Cc1nn(C)c2cc(-c3noc(C4CCN(C(=O)c5ccc(C(C)C)cc5)CC4)n3)ccc12] |

TABLE 1-continued

Compounds of the Invention

| # | Structure |
|---|---|
| 291 | 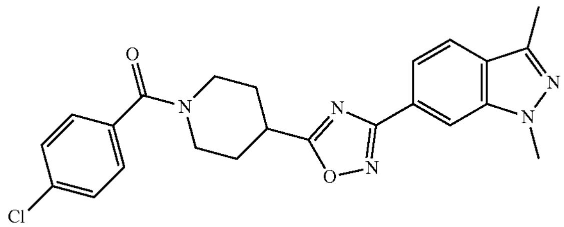 [SMILES: Cc1nn(C)c2cc(-c3noc(C4CCN(C(=O)c5ccc(Cl)cc5)CC4)n3)ccc12] |
| 292 | 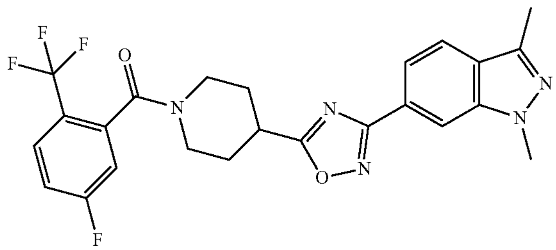 [SMILES: Cc1nn(C)c2cc(-c3noc(C4CCN(C(=O)c5cc(F)ccc5C(F)(F)F)CC4)n3)ccc12] |
| 293 | 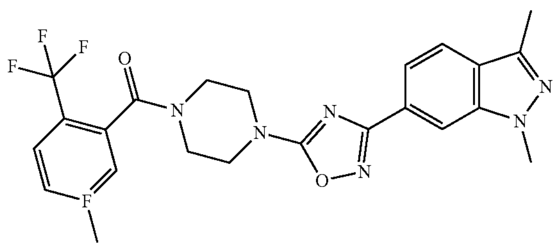 |
| 294 | 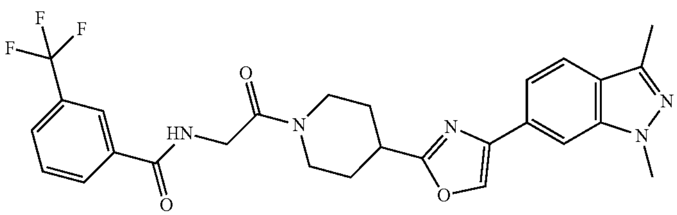 [SMILES: Cc1nn(C)c2cc(-c3coc(C4CCN(C(=O)CNC(=O)c5cccc(C(F)(F)F)c5)CC4)n3)ccc12] |
| 295 | 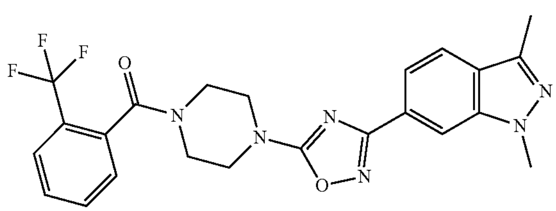 [SMILES: Cc1nn(C)c2cc(-c3noc(N4CCN(C(=O)c5ccccc5C(F)(F)F)CC4)n3)ccc12] |
| 296 | 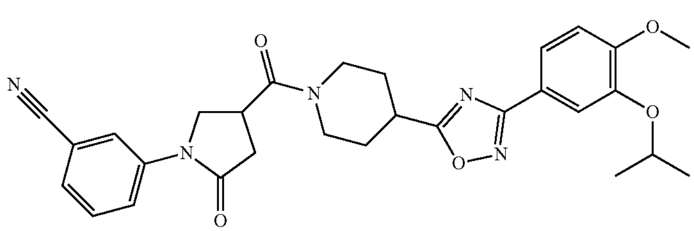 [SMILES: COc1ccc(-c2noc(C3CCN(C(=O)C4CC(=O)N(c5cccc(C#N)c5)C4)CC3)n2)cc1OC(C)C] |

TABLE 1-continued

Compounds of the Invention

| # | Structure |
|---|---|
| 297 | 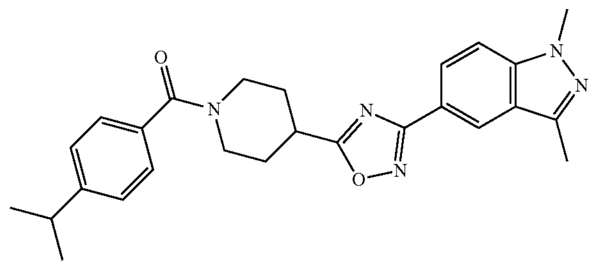 [SMILES: Cc1nn(C)c2ccc(-c3noc(C4CCN(C(=O)c5ccc(C(C)C)cc5)CC4)n3)cc12] |
| 298 | 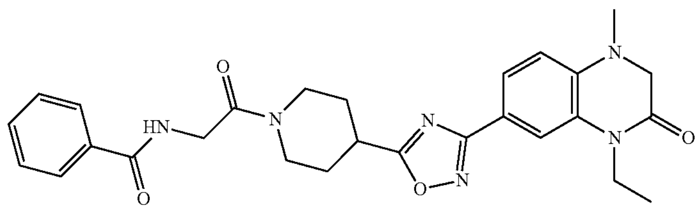 [SMILES: CCN1C(=O)CN(C)c2ccc(-c3noc(C4CCN(C(=O)CNC(=O)c5ccccc5)CC4)n3)cc21] |
| 299 | 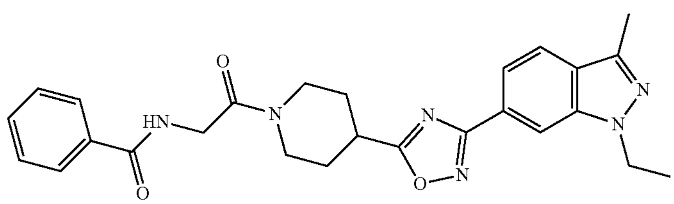 [SMILES: CCn1nc(C)c2ccc(-c3noc(C4CCN(C(=O)CNC(=O)c5ccccc5)CC4)n3)cc21] |
| 300 | 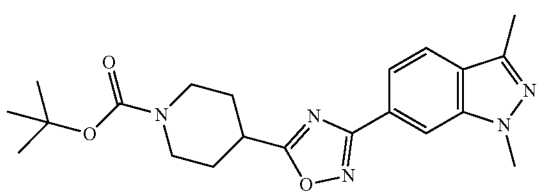 [SMILES: Cc1nn(C)c2cc(-c3noc(C4CCN(C(=O)OC(C)(C)C)CC4)n3)ccc12] |
| 301 | 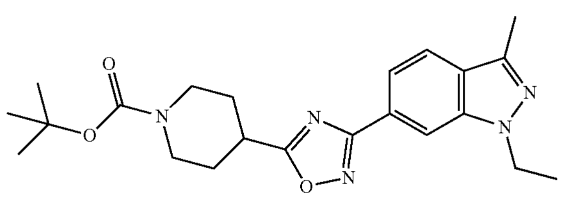 [SMILES: CCn1nc(C)c2ccc(-c3noc(C4CCN(C(=O)OC(C)(C)C)CC4)n3)cc21] |
| 302 | 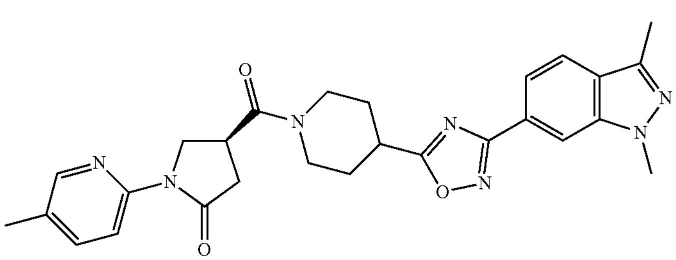 [SMILES: Cc1ccc(N2C[C@@H](C(=O)N3CCC(c4nc(-c5ccc6c(C)nn(C)c6c5)no4)CC3)CC2=O)nc1] |

TABLE 1-continued
Compounds of the Invention
| # | Structure |
|---|---|
| 303 | 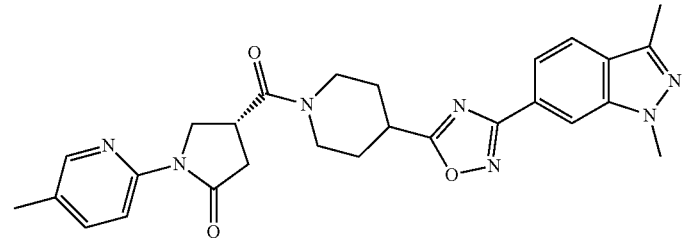 |
| 304 | 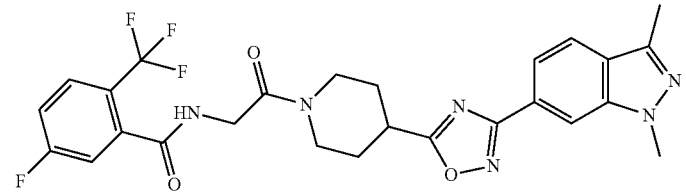 [SMILES: Cc1nn(C)c2cc(-c3noc(C4CCN(C(=O)CNC(=O)c5cc(F)ccc5C(F)(F)F)CC4)n3)ccc12] |
| 305 | 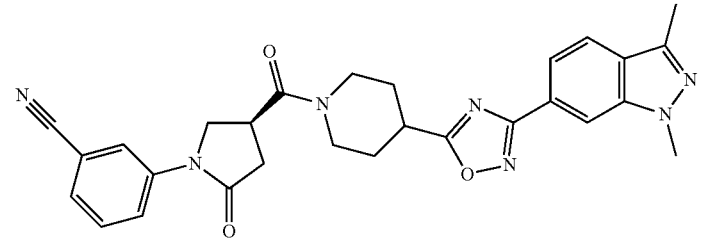 [SMILES: Cc1nn(C)c2cc(-c3noc(C4CCN(C(=O)[C@H]5CC(=O)N(c6cccc(C#N)c6)C5)CC4)n3)ccc12] |
| 306 | 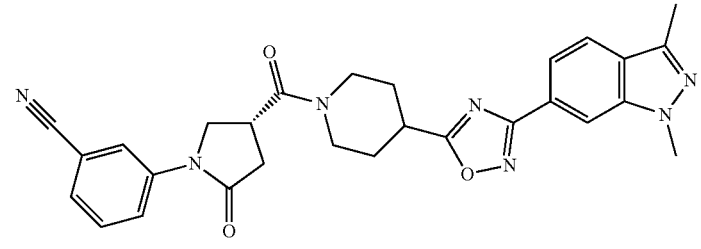 [SMILES: Cc1nn(C)c2cc(-c3noc(C4CCN(C(=O)[C@@H]5CC(=O)N(c6cccc(C#N)c6)C5)CC4)n3)ccc12] |
| 307 | 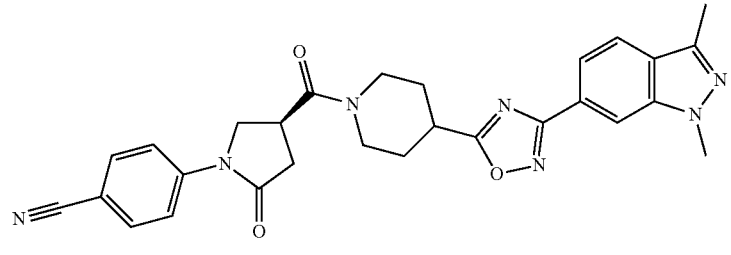 [SMILES: Cc1nn(C)c2cc(-c3noc(C4CCN(C(=O)[C@H]5CC(=O)N(c6ccc(C#N)cc6)C5)CC4)n3)ccc12] |
| 308 | 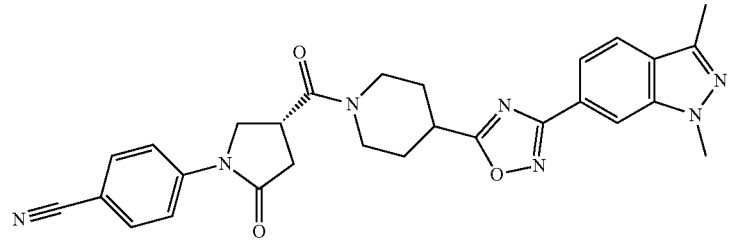 |

TABLE 1-continued

Compounds of the Invention

| # | Structure |
|---|---|
| 309 | 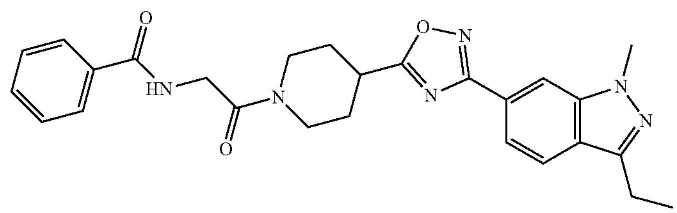 [SMILES: CCc1nn(C)c2cc(-c3noc(C4CCN(C(=O)CNC(=O)c5ccccc5)CC4)n3)ccc12] |
| 310 | 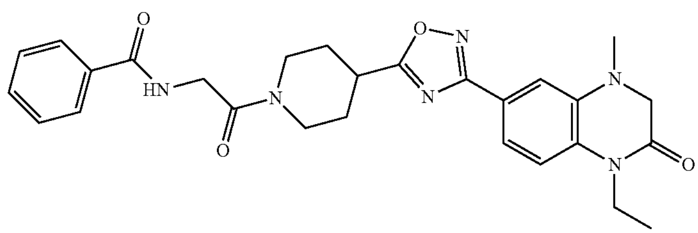 [SMILES: CCN1C(=O)CN(C)c2cc(-c3noc(C4CCN(C(=O)CNC(=O)c5ccccc5)CC4)n3)ccc21] |
| 311 | 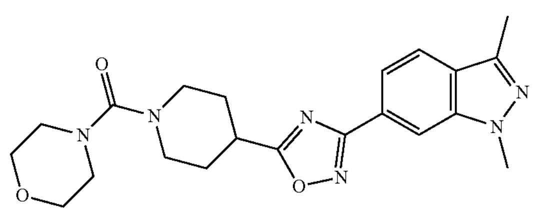 |
| 312 | 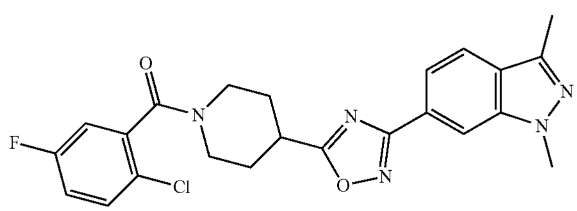 [SMILES: Cc1nn(C)c2cc(-c3noc(C4CCN(C(=O)c5cc(F)ccc5Cl)CC4)n3)ccc12] |
| 313 | 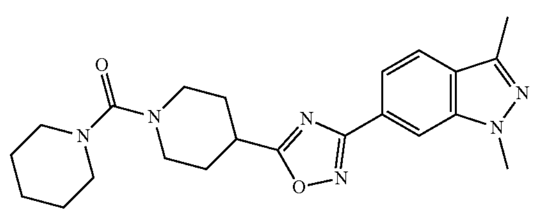 [SMILES: Cc1nn(C)c2cc(-c3noc(C4CCN(C(=O)N5CCCCC5)CC4)n3)ccc12] |
| 314 | 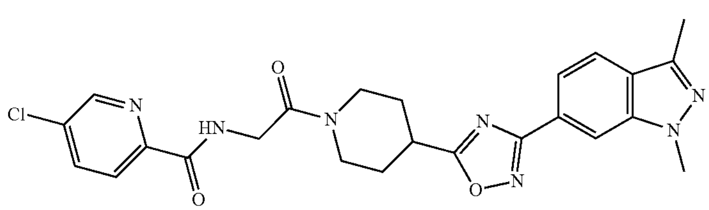 [SMILES: Cc1nn(C)c2cc(-c3noc(C4CCN(C(=O)CNC(=O)c5ccc(Cl)cn5)CC4)n3)ccc12] |
| 315 | 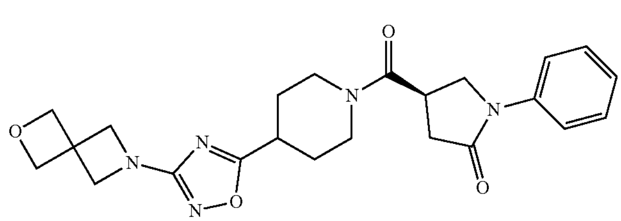 [SMILES: O=C([C@@H]1CC(=O)N(c2ccccc2)C1)N1CCC(c2nc(N3CC4(COC4)C3)no2)CC1] |

TABLE 1-continued

Compounds of the Invention

| # | Structure |
|---|---|
| 316 | (structure) |
| 317 | (structure) |
| 318 | (structure) |
| 319 | (structure) |
| 320 | (structure) |
| 321 | (structure) |
| 322 | (structure) |

TABLE 1-continued
Compounds of the Invention
| # | Structure |
|---|---|
| 323 | 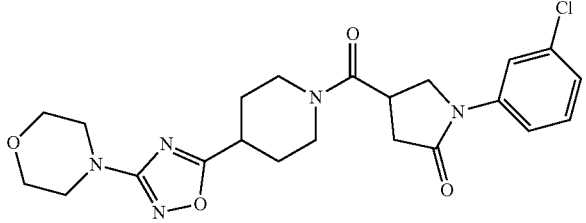 [SMILES: O=C(C1CC(=O)N(c2cccc(Cl)c2)C1)N1CCC(c2nc(N3CCOCC3)no2)CC1] |
| 324 | 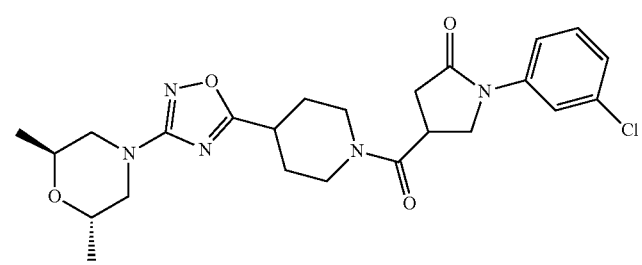 [SMILES: C[C@H]1CN(c2noc(C3CCN(C(=O)C4CC(=O)N(c5cccc(Cl)c5)C4)CC3)n2)C[C@H](C)O1] |
| 325 | 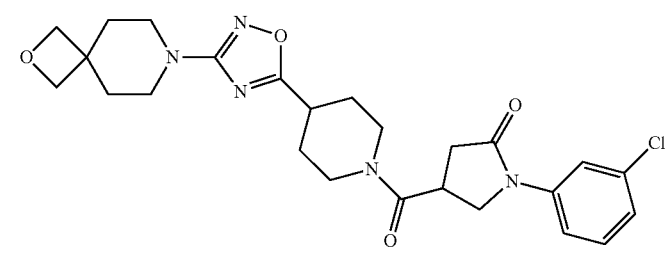 [SMILES: O=C(C1CC(=O)N(c2cccc(Cl)c2)C1)N1CCC(c2nc(N3CCC4(CC3)COC4)no2)CC1] |
| 326 | 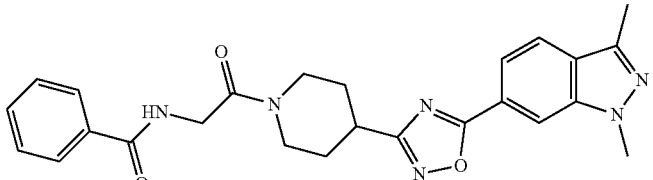 |
| 327 | 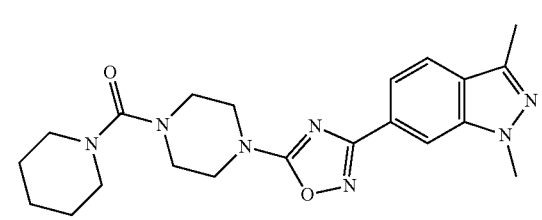 [SMILES: Cc1nn(C)c2cc(-c3noc(N4CCN(C(=O)N5CCCCC5)CC4)n3)ccc12] |
| 328 | 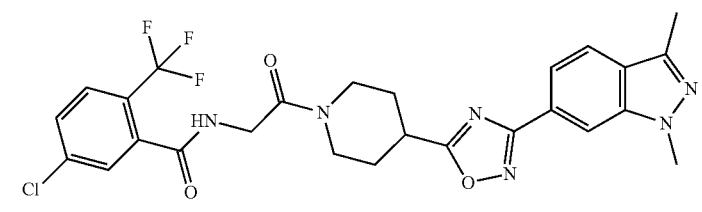 [SMILES: Cc1nn(C)c2cc(-c3noc(C4CCN(C(=O)CNC(=O)c5cc(Cl)ccc5C(F)(F)F)CC4)n3)ccc12] |

TABLE 1-continued

Compounds of the Invention

| # | Structure |
|---|---|
| 329 | 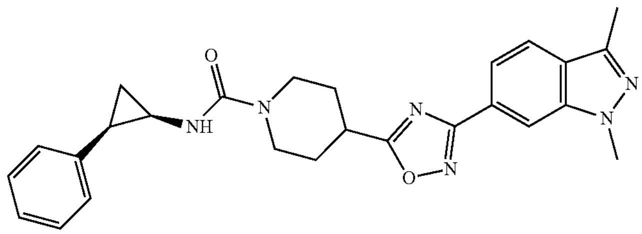 [SMILES: Cc1nn(C)c2cc(-c3noc(C4CCN(C(=O)N[C@@H]5C[C@@H]5c5ccccc5)CC4)n3)ccc12] |
| 330 | 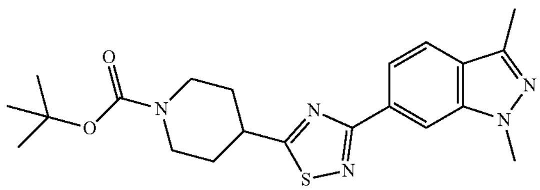 |
| 331 | 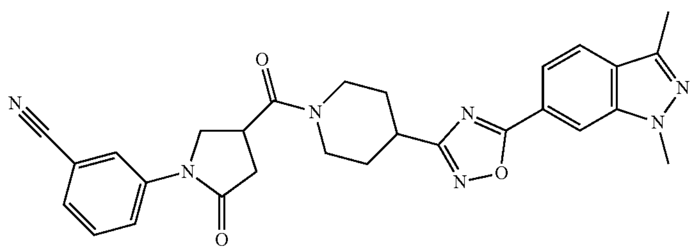 [SMILES: Cc1nn(C)c2cc(-c3nc(C4CCN(C(=O)C5CC(=O)N(c6cccc(C#N)c6)C5)CC4)no3)ccc12] |
| 332 | 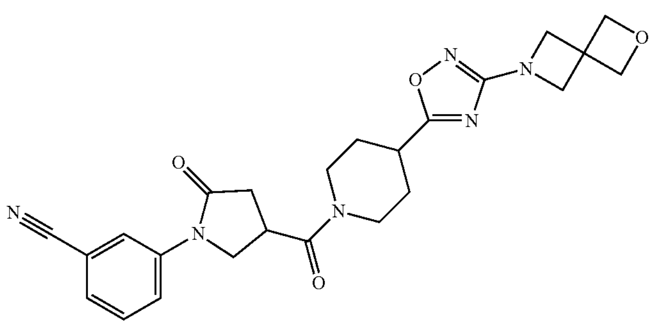 [SMILES: N#Cc1cccc(N2CC(C(=O)N3CCC(c4nc(N5CC6(COC6)C5)no4)CC3)CC2=O)c1] |
| 333 | 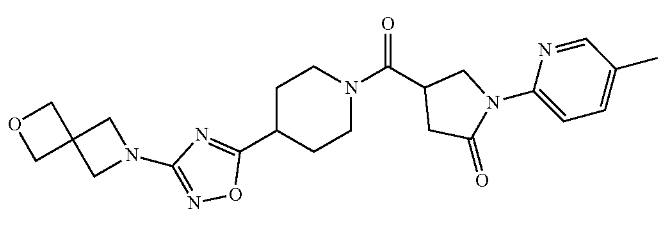 [SMILES: Cc1ccc(N2CC(C(=O)N3CCC(c4nc(N5CC6(COC6)C5)no4)CC3)CC2=O)nc1] |
| 334 | 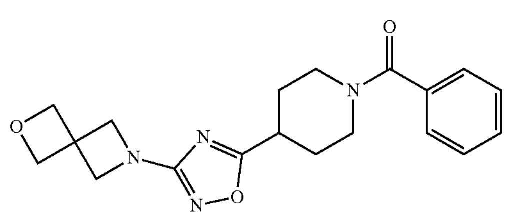 [SMILES: O=C(c1ccccc1)N1CCC(c2nc(N3CC4(COC4)C3)no2)CC1] |

TABLE 1-continued

| Compounds of the Invention | |
|---|---|
| # | Structure |

335

336

337

338

339

340

TABLE 1-continued

Compounds of the Invention

| # | Structure |
|---|---|
| 341 | 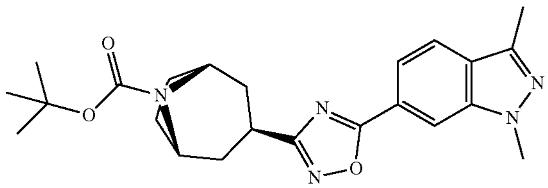 |
| 342 | 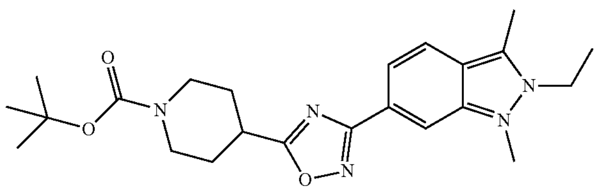 |
| 343 | 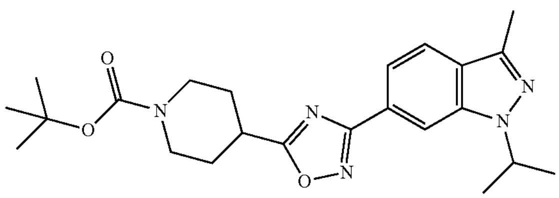 [SMILES: Cc1nn(C(C)C)c2cc(-c3noc(C4CCN(C(=O)OC(C)(C)C)CC4)n3)ccc12] |
| 344 | 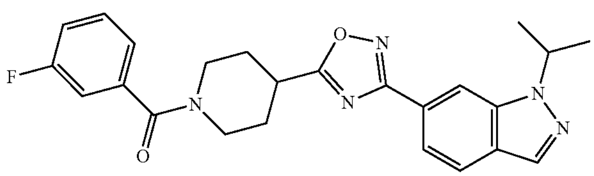 [SMILES: CC(C)n1ncc2ccc(-c3noc(C4CCN(C(=O)c5cccc(F)c5)CC4)n3)cc21] |
| 345 | 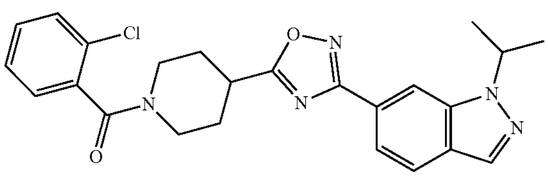 |
| 346 | 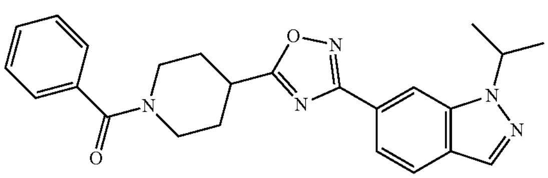 [SMILES: CC(C)n1ncc2ccc(-c3noc(C4CCN(C(=O)c5ccccc5)CC4)n3)cc21] |
| 347 | 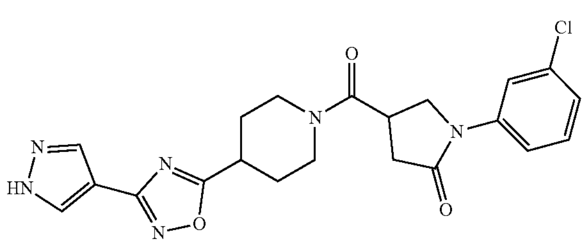 [SMILES: O=C(C1CC(=O)N(c2cccc(Cl)c2)C1)N1CCC(c2nc(-c3cn[nH]c3)no2)CC1] |

TABLE 1-continued

Compounds of the Invention

| # | Structure |
|---|---|
| 348 | 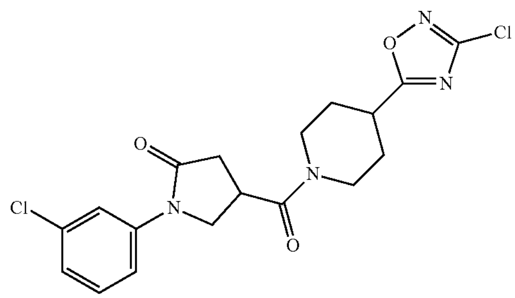 [SMILES: O=C(C1CC(=O)N(c2cccc(Cl)c2)C1)N1CCC(c2nc(Cl)no2)CC1] |
| 349 | 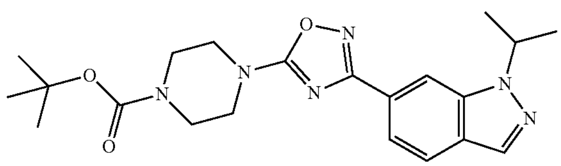 |
| 350 | 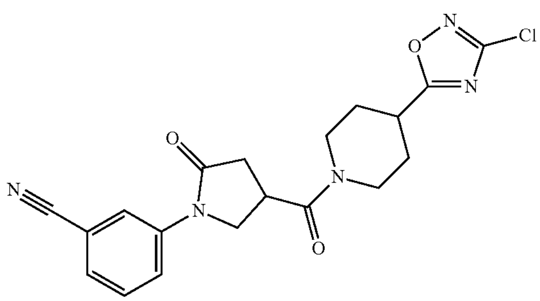 [SMILES: N#Cc1cccc(N2CC(C(=O)N3CCC(c4nc(Cl)no4)CC3)CC2=O)c1] |
| 351 | 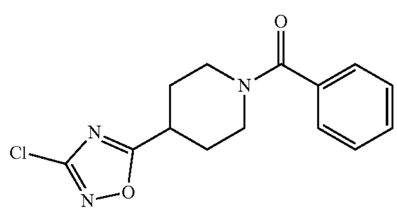 [SMILES: O=C(c1ccccc1)N1CCC(c2nc(Cl)no2)CC1] |
| 352 | 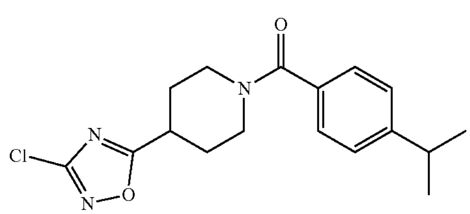 [SMILES: CC(C)c1ccc(C(=O)N2CCC(c3nc(Cl)no3)CC2)cc1] |
| 353 | 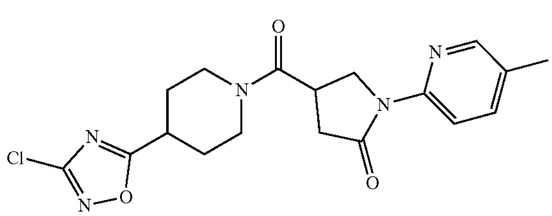 [SMILES: Cc1ccc(N2CC(C(=O)N3CCC(c4nc(Cl)no4)CC3)CC2=O)nc1] |

TABLE 1-continued

Compounds of the Invention

| # | Structure |
|---|-----------|
| 354 | 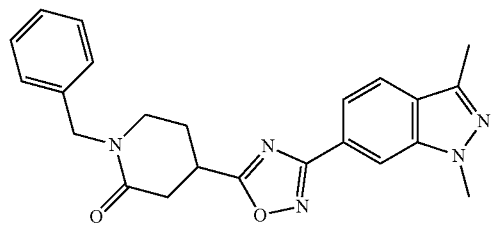 [SMILES: Cc1nn(C)c2cc(-c3noc(C4CCN(Cc5ccccc5)C(=O)C4)n3)ccc12] |
| 355 | 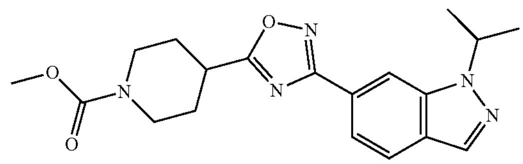 [SMILES: COC(=O)N1CCC(c2nc(-c3ccc4cnn(C(C)C)c4c3)no2)CC1] |
| 356 | 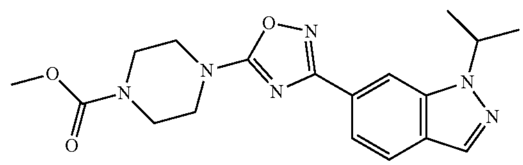 [SMILES: COC(=O)N1CCN(c2nc(-c3ccc4cnn(C(C)C)c4c3)no2)CC1] |
| 357 | 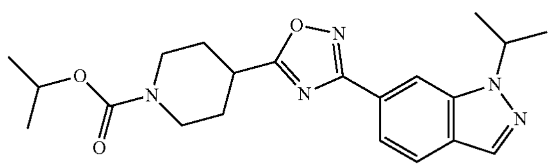 [SMILES: CC(C)OC(=O)N1CCC(c2nc(-c3ccc4cnn(C(C)C)c4c3)no2)CC1] |
| 358 | 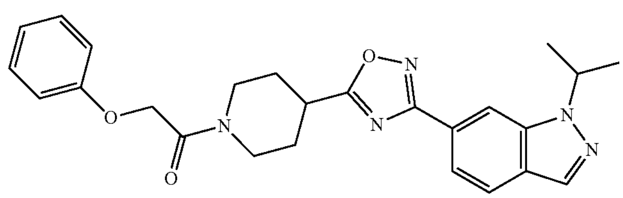 [SMILES: CC(C)n1ncc2ccc(-c3noc(C4CCN(C(=O)COc5ccccc5)CC4)n3)cc21] |
| 359 | 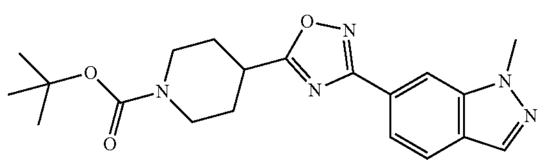 [SMILES: Cn1ncc2ccc(-c3noc(C4CCN(C(=O)OC(C)(C)C)CC4)n3)cc21] |
| 360 | 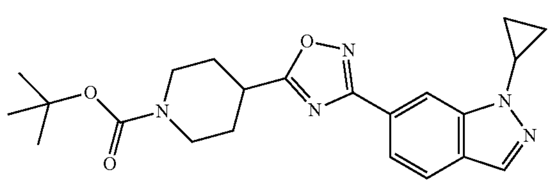 [SMILES: CC(C)(C)OC(=O)N1CCC(c2nc(-c3ccc4cnn(C5CC5)c4c3)no2)CC1] |
| 361 | 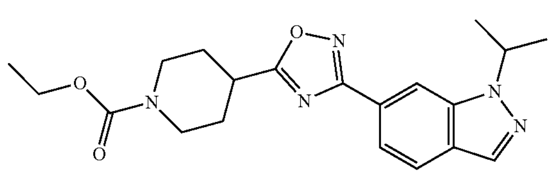 [SMILES: CCOC(=O)N1CCC(c2nc(-c3ccc4cnn(C(C)C)c4c3)no2)CC1] |

TABLE 1-continued

Compounds of the Invention

| # | Structure |
|---|---|
| 362 | 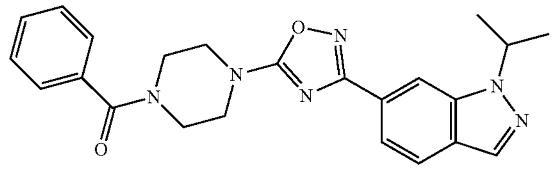 [SMILES: CC(C)n1ncc2ccc(-c3noc(N4CCN(C(=O)c5ccccc5)CC4)n3)cc21] |
| 363 | 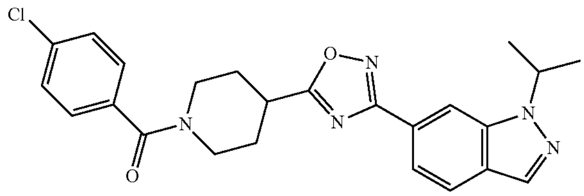 [SMILES: CC(C)n1ncc2ccc(-c3noc(C4CCN(C(=O)c5ccc(Cl)cc5)CC4)n3)cc21] |
| 364 | 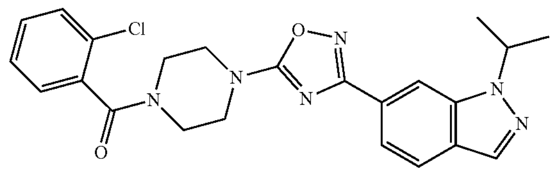 [SMILES: CC(C)n1ncc2ccc(-c3noc(N4CCN(C(=O)c5ccccc5Cl)CC4)n3)cc21] |
| 365 | 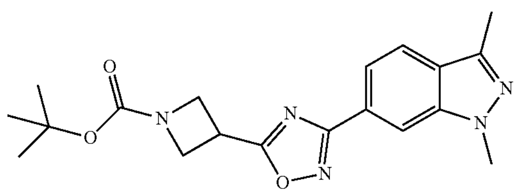 [SMILES: Cc1nn(C)c2cc(-c3noc(C4CN(C(=O)OC(C)(C)C)C4)n3)ccc12] |
| 366 | 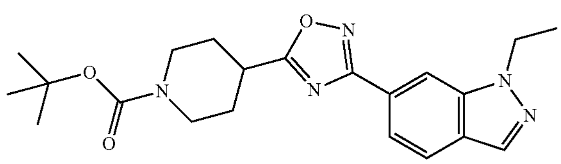 [SMILES: CCn1ncc2ccc(-c3noc(C4CCN(C(=O)OC(C)(C)C)CC4)n3)cc21] |
| 367 | 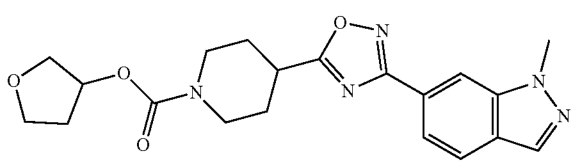 [SMILES: Cn1ncc2ccc(-c3noc(C4CCN(C(=O)OC5CCOC5)CC4)n3)cc21] |
| 368 | 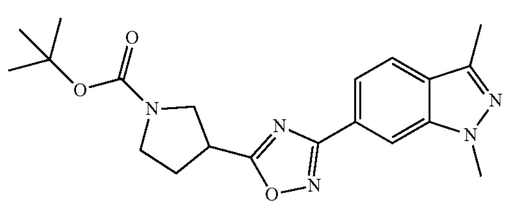 [SMILES: Cc1nn(C)c2cc(-c3noc(C4CCN(C(=O)OC(C)(C)C)C4)n3)ccc12] |
| 369 | 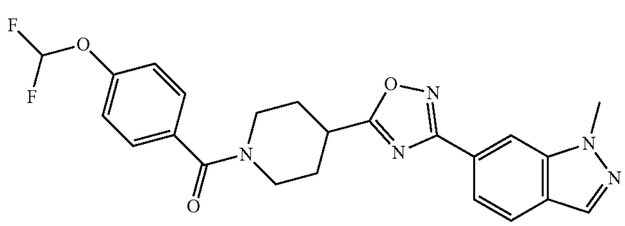 [SMILES: Cn1ncc2ccc(-c3noc(C4CCN(C(=O)c5ccc(OC(F)F)cc5)CC4)n3)cc21] |

TABLE 1-continued
Compounds of the Invention
| # | Structure |
|---|---|
| 370 | 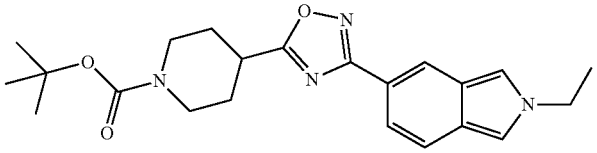 [SMILES: CCn1cc2ccc(-c3noc(C4CCN(C(=O)OC(C)(C)C)CC4)n3)cc2c1] |
| 371 | 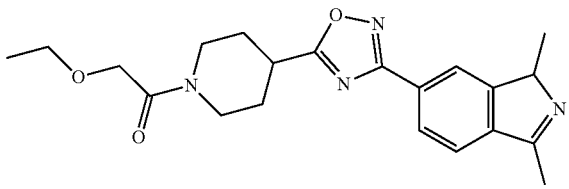 [SMILES: CCOCC(=O)N1CCC(c2nc(-c3ccc4c(c3)C(C)N=C4C)no2)CC1] |
| 372 | 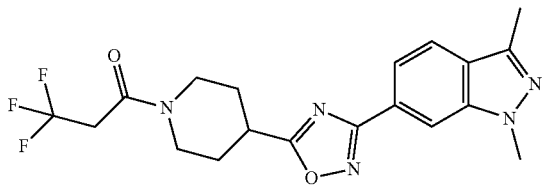 [SMILES: Cc1nn(C)c2cc(-c3noc(C4CCN(C(=O)CC(F)(F)F)CC4)n3)ccc12] |
| 373 | 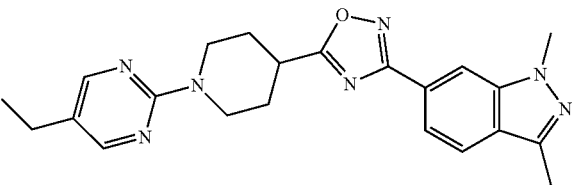 [SMILES: CCc1cnc(N2CCC(c3nc(-c4ccc5c(C)nn(C)c5c4)no3)CC2)nc1] |
| 374 | 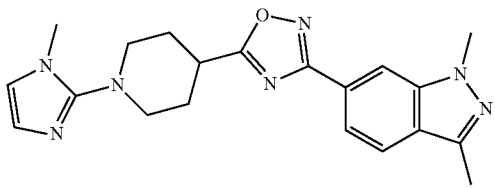 [SMILES: Cc1nn(C)c2cc(-c3noc(C4CCN(c5nccn5C)CC4)n3)ccc12] |
| 375 | 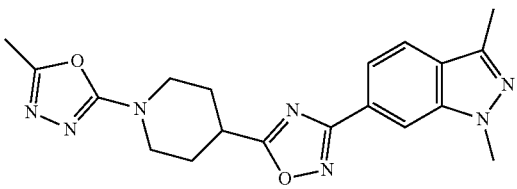 [SMILES: Cc1nnc(N2CCC(c3nc(-c4ccc5c(C)nn(C)c5c4)no3)CC2)o1] |
| 376 | 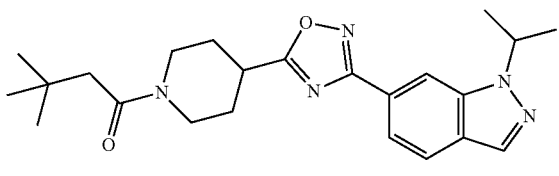 [SMILES: CC(C)n1ncc2ccc(-c3noc(C4CCN(C(=O)CC(C)(C)C)CC4)n3)cc21] |
| 377 | 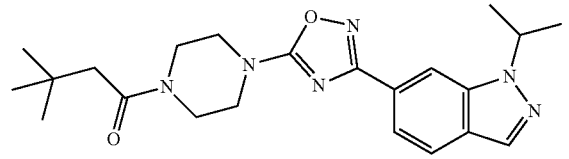 |

TABLE 1-continued
Compounds of the Invention
| # | Structure |
|---|---|
| 378 | 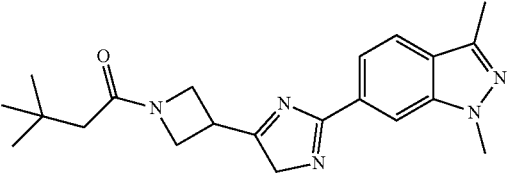 [SMILES: Cc1nn(C)c2cc(C3=NCC(C4CN(C(=O)CC(C)(C)C)C4)=N3)ccc12] |
| 379 | 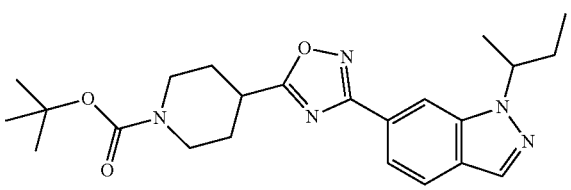 [SMILES: CCC(C)n1ncc2ccc(-c3noc(C4CCN(C(=O)OC(C)(C)C)CC4)n3)cc21] |
| 380 | 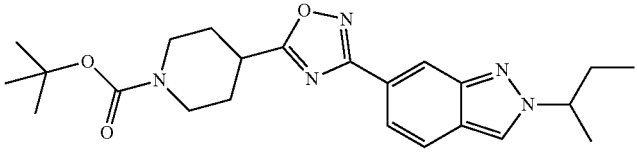 [SMILES: CCC(C)n1cc2ccc(-c3noc(C4CCN(C(=O)OC(C)(C)C)CC4)n3)cc2n1] |
| 381 | 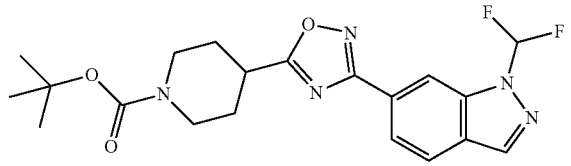 [SMILES: CC(C)(C)OC(=O)N1CCC(c2nc(-c3ccc4cnn(C(F)F)c4c3)no2)CC1] |
| 382 | 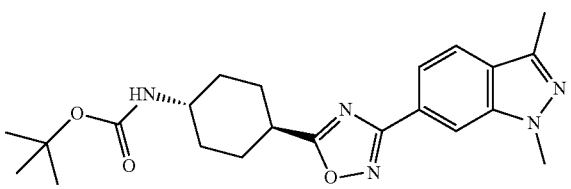 [SMILES: Cc1nn(C)c2cc(-c3noc([C@H]4CC[C@H](NC(=O)OC(C)(C)C)CC4)n3)ccc12] |
| 383 | 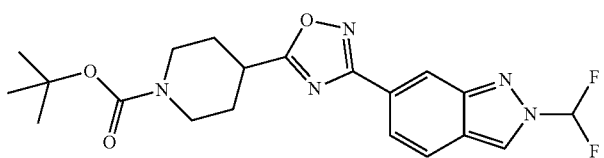 [SMILES: CC(C)(C)OC(=O)N1CCC(c2nc(-c3ccc4cn(C(F)F)nc4c3)no2)CC1] |
| 384 | 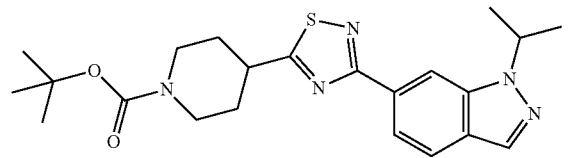 [SMILES: CC(C)n1ncc2ccc(-c3nsc(C4CCN(C(=O)OC(C)(C)C)CC4)n3)cc21] |
| 385 | 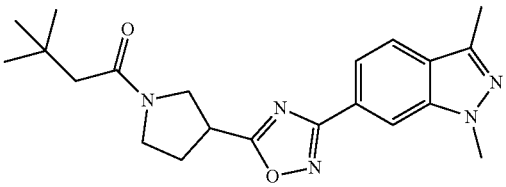 [SMILES: Cc1nn(C)c2cc(-c3noc(C4CCN(C(=O)CC(C)(C)C)C4)n3)ccc12] |

TABLE 1-continued

Compounds of the Invention

| # | Structure |
|---|---|
| 386 | 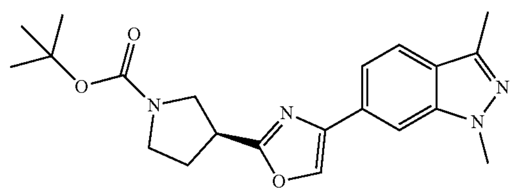 [SMILES: Cc1nn(C)c2cc(-c3coc([C@H]4CCN(C(=O)OC(C)(C)C)C4)n3)ccc12] |
| 387 | 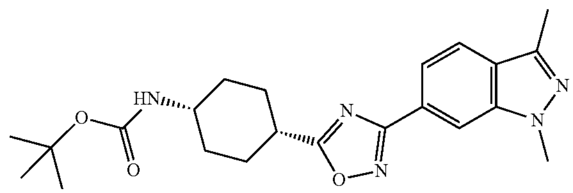 [SMILES: Cc1nn(C)c2cc(-c3noc([C@H]4CC[C@@H](NC(=O)OC(C)(C)C)CC4)n3)ccc12] |
| 388 | 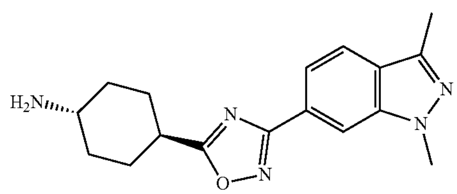 [SMILES: Cc1nn(C)c2cc(-c3noc([C@H]4CC[C@H](N)CC4)n3)ccc12] |
| 389 | 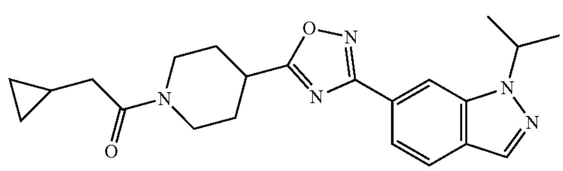 [SMILES: CC(C)n1ncc2ccc(-c3noc(C4CCN(C(=O)CC5CC5)CC4)n3)cc21] |
| 390 | 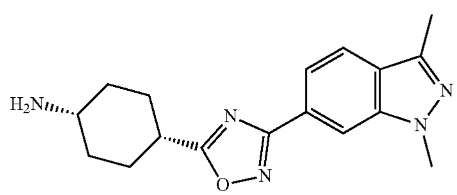 [SMILES: Cc1nn(C)c2cc(-c3noc([C@H]4CC[C@@H](N)CC4)n3)ccc12] |
| 391 | 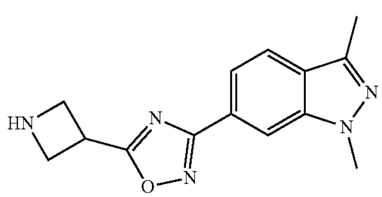 [SMILES: Cc1nn(C)c2cc(-c3noc(C4CNC4)n3)ccc12] |
| 392 | 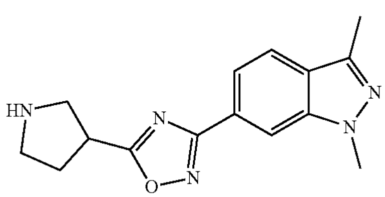 [SMILES: Cc1nn(C)c2cc(-c3noc(C4CCNC4)n3)ccc12] |
| 393 | 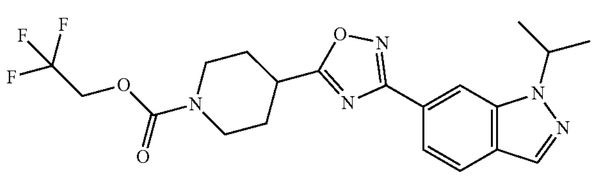 [SMILES: CC(C)n1ncc2ccc(-c3noc(C4CCN(C(=O)OCC(F)(F)F)CC4)n3)cc21] |

TABLE 1-continued

Compounds of the Invention

| # | Structure |
|---|---|
| 394 | 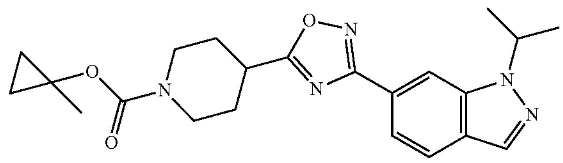 [SMILES: CC(C)n1ncc2ccc(-c3noc(C4CCN(C(=O)OC5(C)CC5)CC4)n3)cc21] |
| 395 | 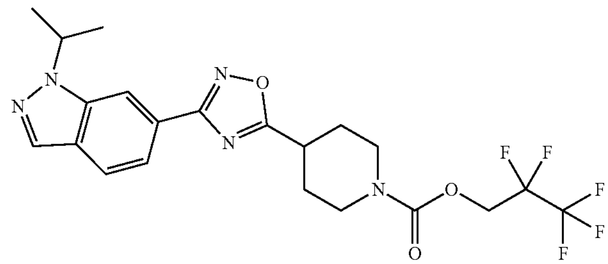 [SMILES: CC(C)n1ncc2ccc(-c3noc(C4CCN(C(=O)OCC(F)(F)C(F)(F)F)CC4)n3)cc21] |
| 396 | 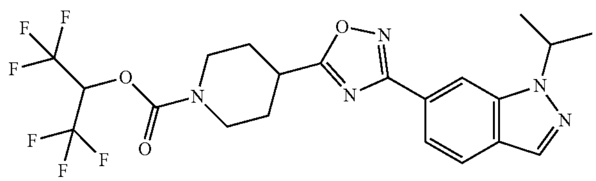 [SMILES: CC(C)n1ncc2ccc(-c3noc(C4CCN(C(=O)OC(C(F)(F)F)C(F)(F)F)CC4)n3)cc21] |
| 397 | 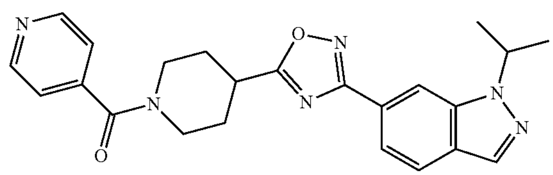 [SMILES: CC(C)n1ncc2ccc(-c3noc(C4CCN(C(=O)c5ccncc5)CC4)n3)cc21] |
| 398 | 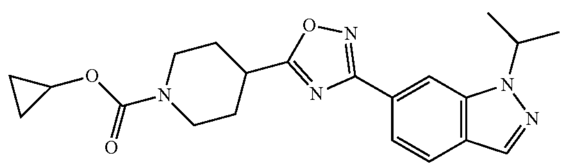 [SMILES: CC(C)n1ncc2ccc(-c3noc(C4CCN(C(=O)OC5CC5)CC4)n3)cc21] |
| 399 | 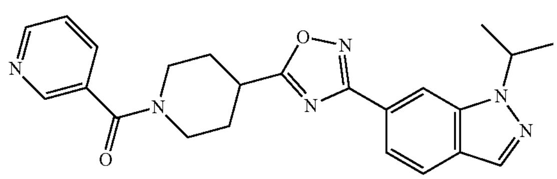 [SMILES: CC(C)n1ncc2ccc(-c3noc(C4CCN(C(=O)c5cccnc5)CC4)n3)cc21] |
| 400 | 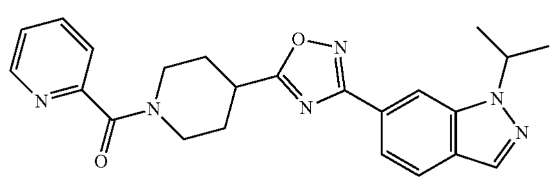 [SMILES: CC(C)n1ncc2ccc(-c3noc(C4CCN(C(=O)c5ccccn5)CC4)n3)cc21] |
| 401 | 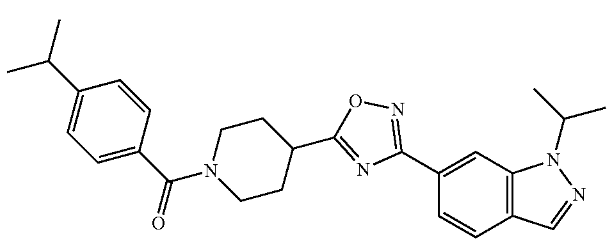 [SMILES: CC(C)c1ccc(C(=O)N2CCC(c3nc(-c4ccc5cnn(C(C)C)c5c4)no3)CC2)cc1] |

US 11,970,486 B2
157                                                           158
TABLE 1-continued
Compounds of the Invention
| # | Structure |
|---|-----------|
| 402 | 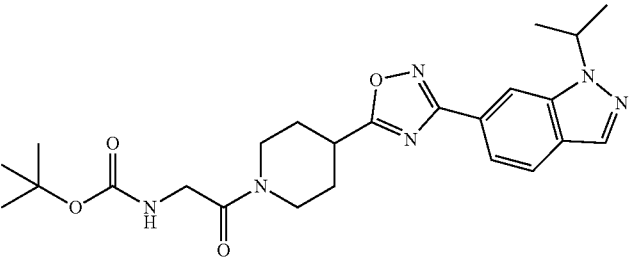 [SMILES: CC(C)n1ncc2ccc(-c3noc(C4CCN(C(=O)CNC(=O)OC(C)(C)C)CC4)n3)cc21] |
| 403 | 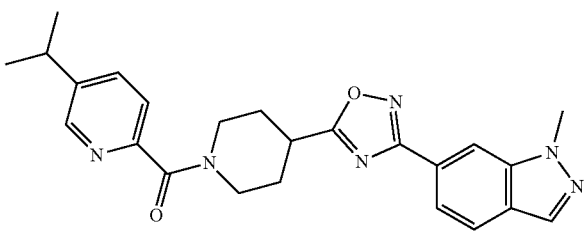 [SMILES: CC(C)c1ccc(C(=O)N2CCC(c3nc(-c4ccc5cnn(C)c5c4)no3)CC2)nc1] |
| 404 | 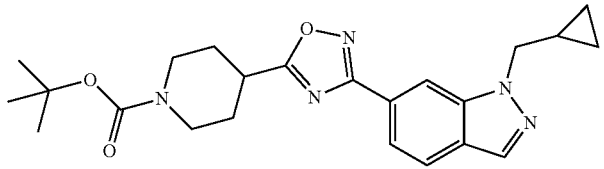 [SMILES: CC(C)(C)OC(=O)N1CCC(c2nc(-c3ccc4cnn(CC5CC5)c4c3)no2)CC1] |
| 405 | 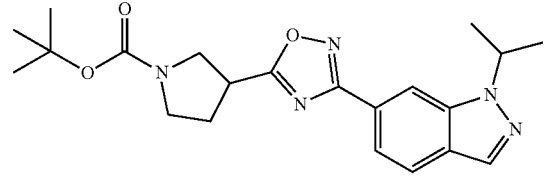 [SMILES: CC(C)n1ncc2ccc(-c3noc(C4CCN(C(=O)OC(C)(C)C)C4)n3)cc21] |
| 406 | 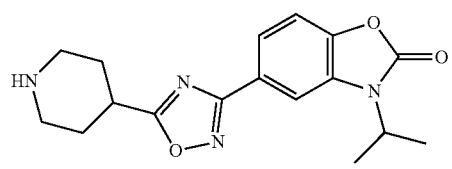 [SMILES: CC(C)n1c(=O)oc2ccc(-c3noc(C4CCNCC4)n3)cc21] |
| 407 | 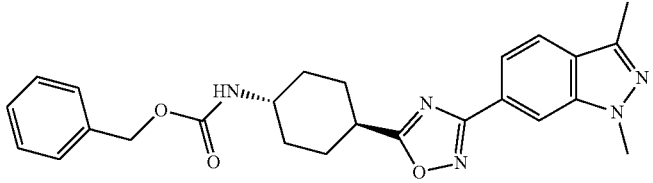 [SMILES: Cc1nn(C)c2cc(-c3noc([C@H]4CC[C@H](NC(=O)OCc5ccccc5)CC4)n3)ccc12] |
| 408 | 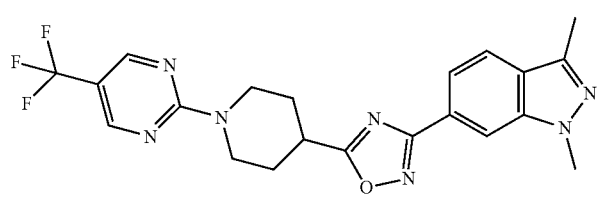 [SMILES: Cc1nn(C)c2cc(-c3noc(C4CCN(c5ncc(C(F)(F)F)cn5)CC4)n3)ccc12] |

TABLE 1-continued

Compounds of the Invention

| # | Structure |
|---|---|
| 409 | 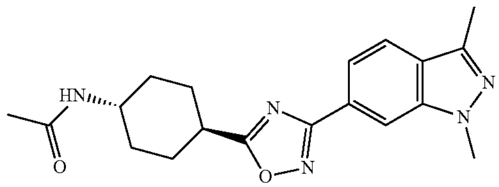 [SMILES: CC(=O)N[C@H]1CC[C@H](c2nc(-c3ccc4c(C)nn(C)c4c3)no2)CC1] |
| 410 | 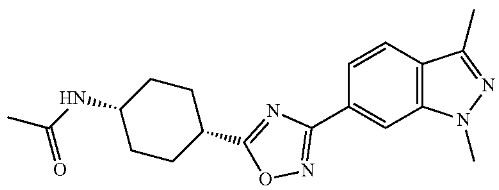 [SMILES: CC(=O)N[C@H]1CC[C@@H](c2nc(-c3ccc4c(C)nn(C)c4c3)no2)CC1] |
| 411 | 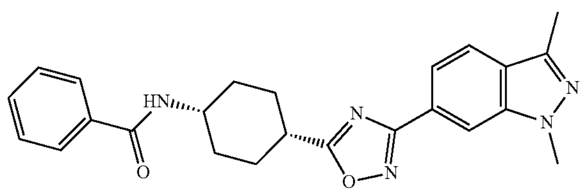 [SMILES: Cc1nn(C)c2cc(-c3noc([C@H]4CC[C@@H](NC(=O)c5ccccc5)CC4)n3)ccc12] |
| 412 | 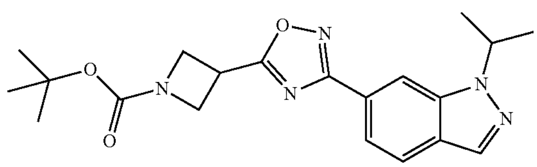 [SMILES: CC(C)n1ncc2ccc(-c3noc(C4CN(C(=O)OC(C)(C)C)C4)n3)cc21] |
| 413 | 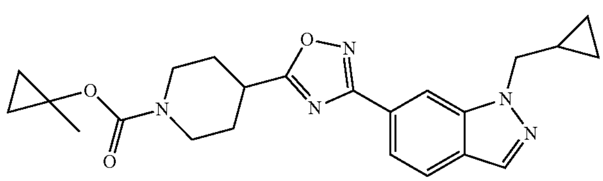 [SMILES: CC1(OC(=O)N2CCC(c3nc(-c4ccc5cnn(CC6CC6)c5c4)no3)CC2)CC1] |
| 414 | 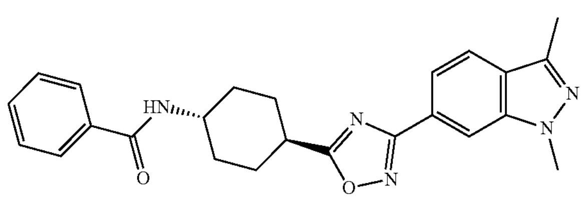 [SMILES: Cc1nn(C)c2cc(-c3noc([C@H]4CC[C@H](NC(=O)c5ccccc5)CC4)n3)ccc12] |
| 415 | 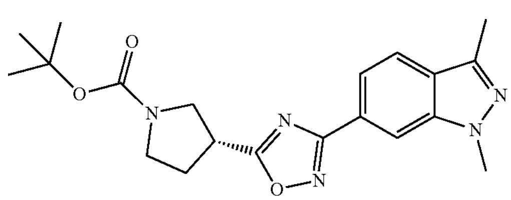 [SMILES: Cc1nn(C)c2cc(-c3noc([C@@H]4CCN(C(=O)OC(C)(C)C)C4)n3)ccc12] |

TABLE 1-continued
Compounds of the Invention
| # | Structure |
|---|-----------|
| 416 | 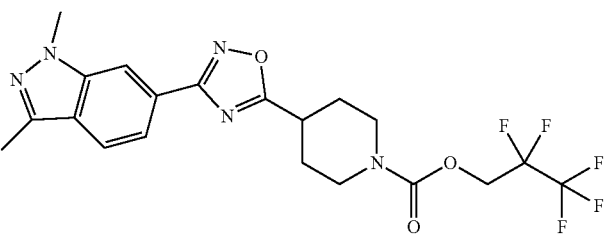 [SMILES: Cc1nn(C)c2cc(-c3noc(C4CCN(C(=O)OCC(F)(F)C(F)(F)F)CC4)n3)ccc12] |
| 417 | 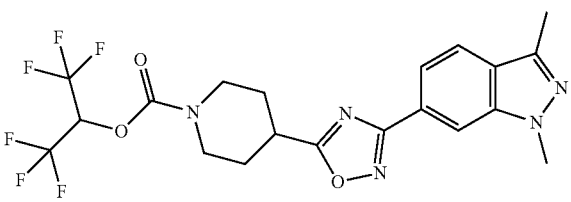 [SMILES: Cc1nn(C)c2cc(-c3noc(C4CCN(C(=O)OC(C(F)(F)F)C(F)(F)F)CC4)n3)ccc12] |
| 418 | 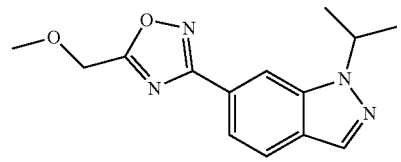 [SMILES: COCc1nc(-c2ccc3cnn(C(C)C)c3c2)no1] |
| 419 | 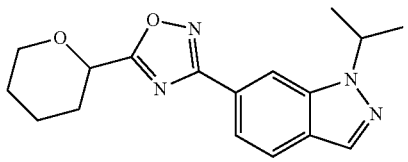 [SMILES: CC(C)n1ncc2ccc(-c3noc(C4CCCCO4)n3)cc21] |
| 420 | 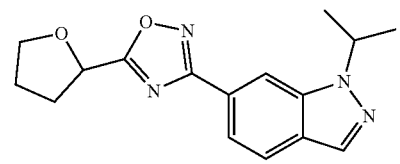 [SMILES: CC(C)n1ncc2ccc(-c3noc(C4CCCO4)n3)cc21] |
| 421 | 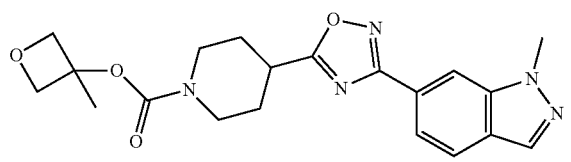 [SMILES: Cn1ncc2ccc(-c3noc(C4CCN(C(=O)OC5(C)COC5)CC4)n3)cc21] |
| 422 | 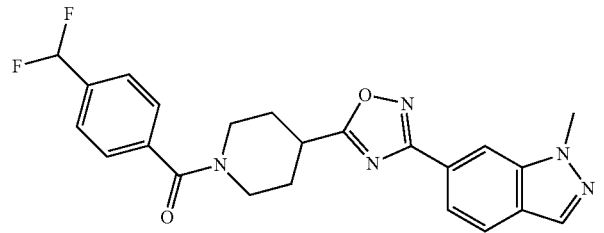 [SMILES: Cn1ncc2ccc(-c3noc(C4CCN(C(=O)c5ccc(C(F)F)cc5)CC4)n3)cc21] |
| 423 | 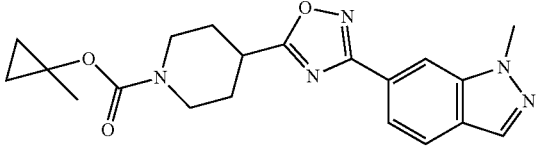 [SMILES: Cn1ncc2ccc(-c3noc(C4CCN(C(=O)OC5(C)CC5)CC4)n3)cc21] |

TABLE 1-continued

Compounds of the Invention

| # | Structure |
|---|---|
| 424 | 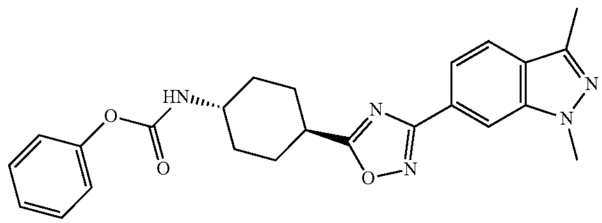 [SMILES: Cc1nn(C)c2cc(-c3noc([C@H]4CC[C@H](NC(=O)Oc5ccccc5)CC4)n3)ccc12] |
| 425 | 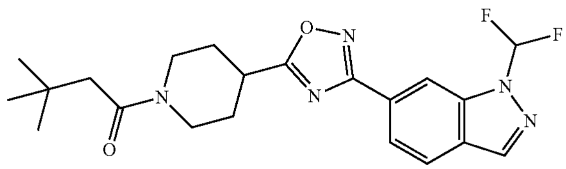 [SMILES: CC(C)(C)CC(=O)N1CCC(c2nc(-c3ccc4cnn(C(F)F)c4c3)no2)CC1] |
| 426 | 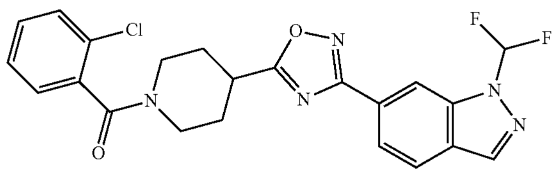 [SMILES: O=C(c1ccccc1Cl)N1CCC(c2nc(-c3ccc4cnn(C(F)F)c4c3)no2)CC1] |
| 427 | 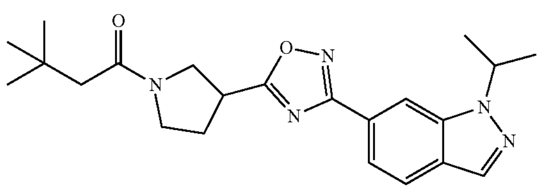 [SMILES: CC(C)n1ncc2ccc(-c3noc(C4CCN(C(=O)CC(C)(C)C)C4)n3)cc21] |
| 428 | 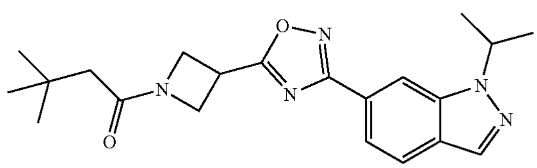 [SMILES: CC(C)n1ncc2ccc(-c3noc(C4CN(C(=O)CC(C)(C)C)C4)n3)cc21] |
| 429 | 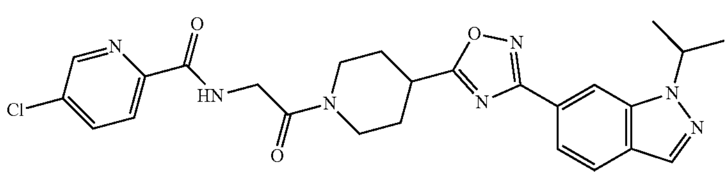 [SMILES: CC(C)n1ncc2ccc(-c3noc(C4CCN(C(=O)CNC(=O)c5ccc(Cl)cn5)CC4)n3)cc21] |
| 430 | 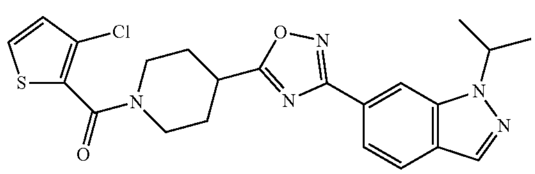 [SMILES: CC(C)n1ncc2ccc(-c3noc(C4CCN(C(=O)c5sccc5Cl)CC4)n3)cc21] |
| 431 | 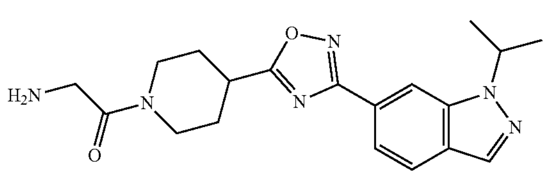 [SMILES: CC(C)n1ncc2ccc(-c3noc(C4CCN(C(=O)CN)CC4)n3)cc21] |

TABLE 1-continued

Compounds of the Invention

| # | Structure |
|---|---|
| 432 | 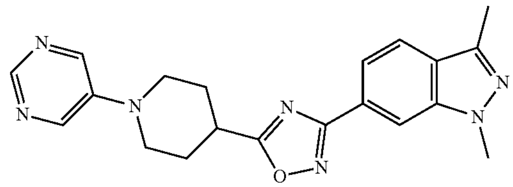 [SMILES: Cc1nn(C)c2cc(-c3noc(C4CCN(c5cncnc5)CC4)n3)ccc12] |
| 433 | 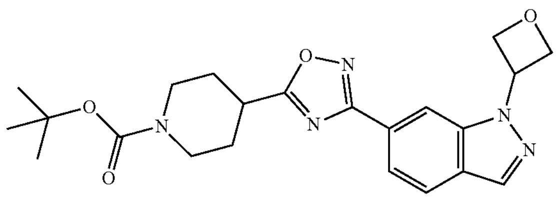 [SMILES: CC(C)(C)OC(=O)N1CCC(c2nc(-c3ccc4cnn(C5COC5)c4c3)no2)CC1] |
| 434 | 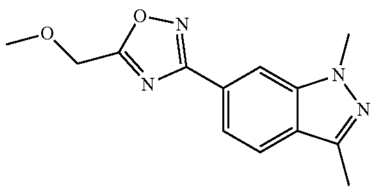 [SMILES: COCc1nc(-c2ccc3c(C)nn(C)c3c2)no1] |
| 435 | 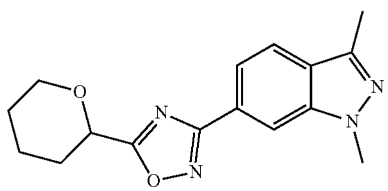 [SMILES: Cc1nn(C)c2cc(-c3noc(C4CCCCO4)n3)ccc12] |
| 436 | 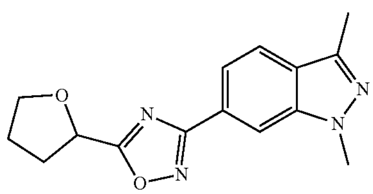 [SMILES: Cc1nn(C)c2cc(-c3noc(C4CCCO4)n3)ccc12] |
| 437 | 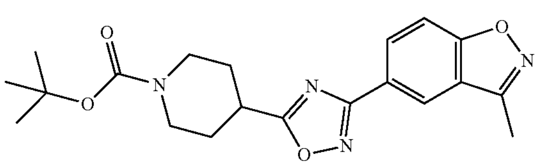 [SMILES: Cc1noc2ccc(-c3noc(C4CCN(C(=O)OC(C)(C)C)CC4)n3)cc12] |
| 438 | 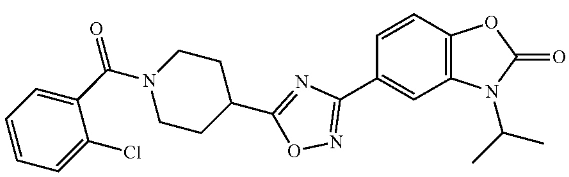 [SMILES: CC(C)n1c(=O)oc2ccc(-c3noc(C4CCN(C(=O)c5ccccc5Cl)CC4)n3)cc21] |
| 439 | 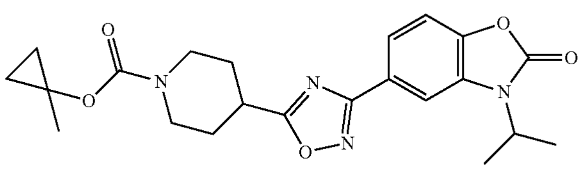 [SMILES: CC(C)n1c(=O)oc2ccc(-c3noc(C4CCN(C(=O)OC5(C)CC5)CC4)n3)cc21] |

TABLE 1-continued
Compounds of the Invention
| # | Structure |
|---|---|
| 440 | 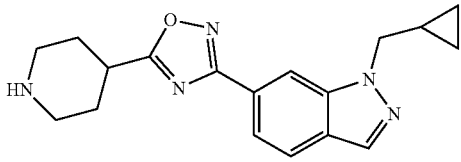 [SMILES: c1cc2cnn(CC3CC3)c2cc1-c1noc(C2CCNCC2)n1] |
| 441 | 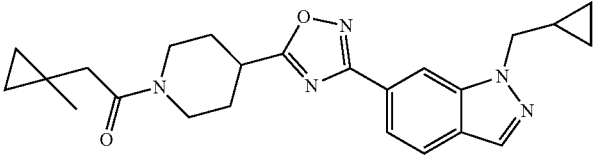 [SMILES: CC1(CC(=O)N2CCC(c3nc(-c4ccc5cnn(CC6CC6)c5c4)no3)CC2)CC1] |
| 442 | 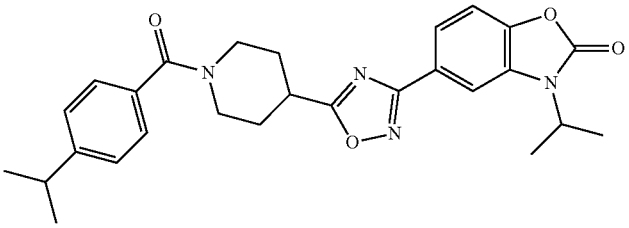 [SMILES: CC(C)c1ccc(C(=O)N2CCC(c3nc(-c4ccc5oc(=O)n(C(C)C)c5c4)no3)CC2)cc1] |
| 443 | 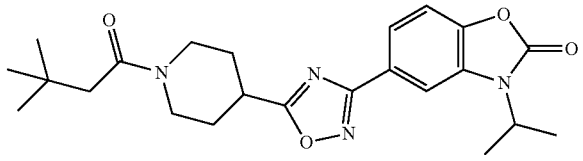 [SMILES: CC(C)n1c(=O)oc2ccc(-c3noc(C4CCN(C(=O)CC(C)(C)C)CC4)n3)cc21] |
| 444 | 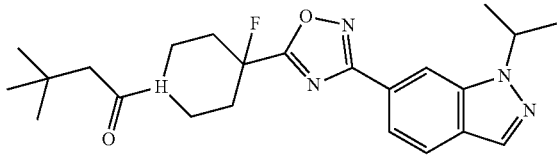 |
| 445 | 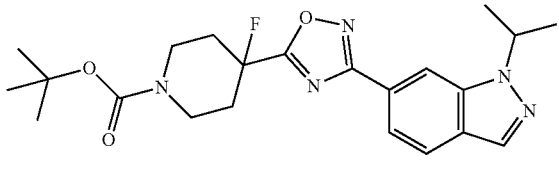 [SMILES: CC(C)n1ncc2ccc(-c3noc(C4(F)CCN(C(=O)OC(C)(C)C)CC4)n3)cc21] |
| 446 | 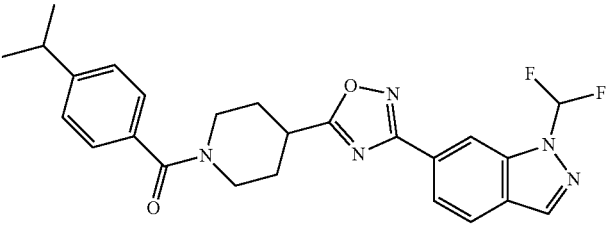 [SMILES: CC(C)c1ccc(C(=O)N2CCC(c3nc(-c4ccc5cnn(C(F)F)c5c4)no3)CC2)cc1] |
| 447 | 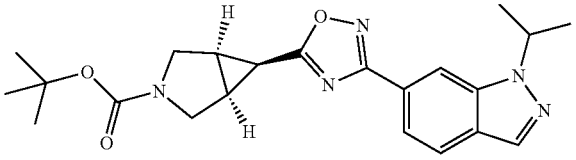 [SMILES: CC(C)n1ncc2ccc(-c3noc([C@@H]4[C@@H]5CN(C(=O)OC(C)(C)C)C[C@@H]54)n3)cc21] |

TABLE 1-continued

Compounds of the Invention

| # | Structure |
|---|-----------|
| 448 | 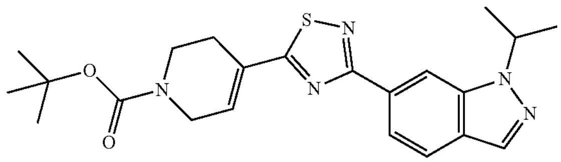 [SMILES: CC(C)n1ncc2ccc(-c3nsc(C4=CCN(C(=O)OC(C)(C)C)CC4)n3)cc21] |
| 449 | 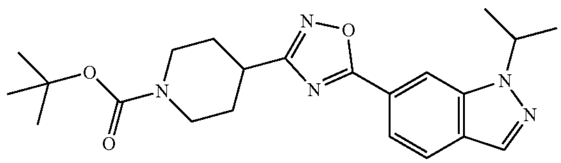 [SMILES: CC(C)n1ncc2ccc(-c3nc(C4CCN(C(=O)OC(C)(C)C)CC4)no3)cc21] |
| 450 | 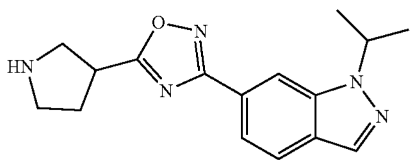 [SMILES: CC(C)n1ncc2ccc(-c3noc(C4CCNC4)n3)cc21] |
| 451 | 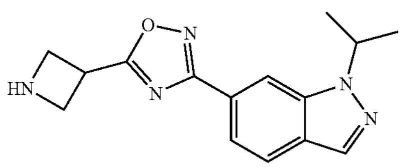 [SMILES: CC(C)n1ncc2ccc(-c3noc(C4CNC4)n3)cc21] |
| 452 | 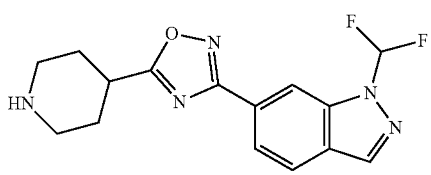 [SMILES: FC(F)n1ncc2ccc(-c3noc(C4CCNCC4)n3)cc21] |
| 453 | 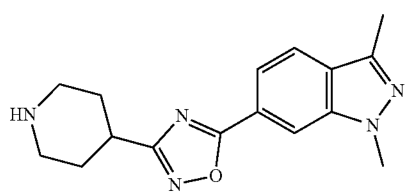 [SMILES: Cc1nn(C)c2cc(-c3nc(C4CCNCC4)no3)ccc12] |
| 454 | 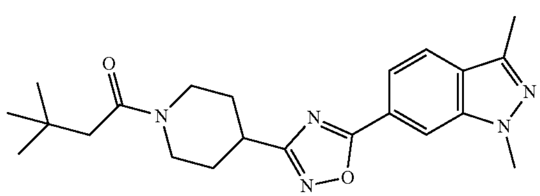 [SMILES: Cc1nn(C)c2cc(-c3nc(C4CCN(C(=O)CC(C)(C)C)CC4)no3)ccc12] |
| 455 | 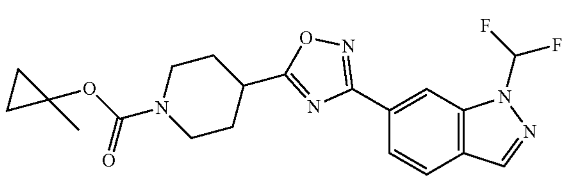 [SMILES: CC1(OC(=O)N2CCC(c3nc(-c4ccc5cnn(C(F)F)c5c4)no3)CC2)CC1] |

TABLE 1-continued

Compounds of the Invention

| # | Structure |
|---|---|
| 456 | 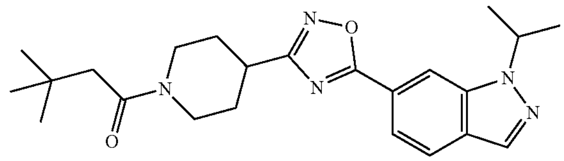 [SMILES: CC(C)n1ncc2ccc(-c3nc(C4CCN(C(=O)CC(C)(C)C)CC4)no3)cc21] |
| 457 | 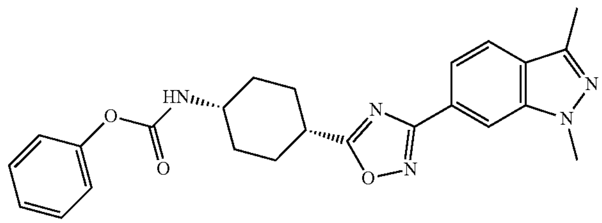 [SMILES: Cc1nn(C)c2cc(-c3noc([C@H]4CC[C@@H](NC(=O)Oc5ccccc5)CC4)n3)ccc12] |
| 458 | 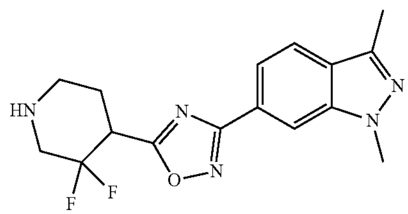 [SMILES: Cc1nn(C)c2cc(-c3noc(C4CCNCC4(F)F)n3)ccc12] |
| 459 | 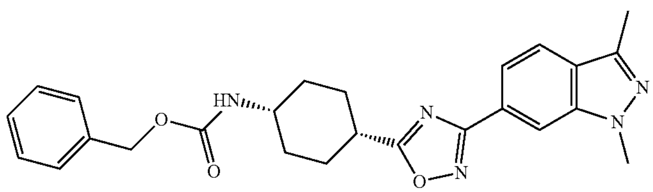 [SMILES: Cc1nn(C)c2cc(-c3noc([C@H]4CC[C@@H](NC(=O)OCc5ccccc5)CC4)n3)ccc12] |
| 460 | 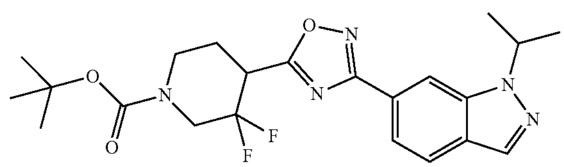 [SMILES: CC(C)n1ncc2ccc(-c3noc(C4CCN(C(=O)OC(C)(C)C)CC4(F)F)n3)cc21] |
| 461 | 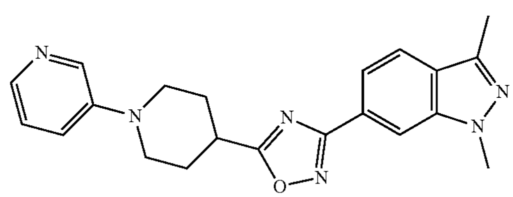 [SMILES: Cc1nn(C)c2cc(-c3noc(C4CCN(c5cccnc5)CC4)n3)ccc12] |
| 462 | 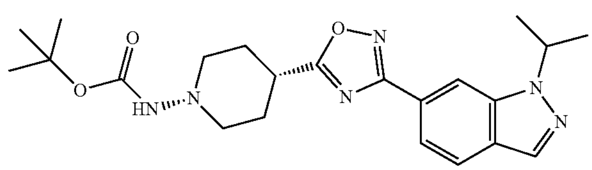 |
| 463 | 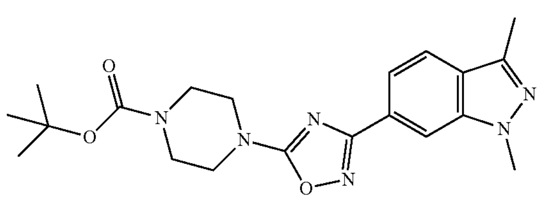 [SMILES: Cc1nn(C)c2cc(-c3noc(N4CCN(C(=O)OC(C)(C)C)CC4)n3)ccc12] |

TABLE 1-continued

Compounds of the Invention

| # | Structure |
|---|---|
| 464 | 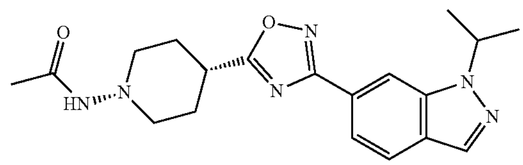 |
| 465 | 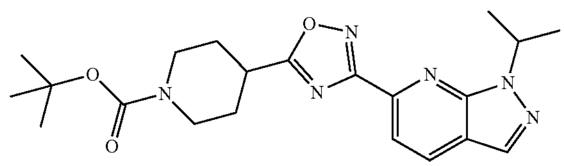 [SMILES: CC(C)n1ncc2ccc(-c3noc(C4CCN(C(=O)OC(C)(C)C)CC4)n3)nc21] |
| 466 | 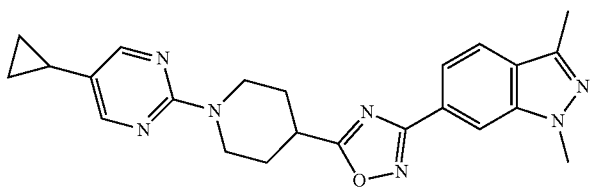 [SMILES: Cc1nn(C)c2cc(-c3noc(C4CCN(c5ncc(C6CC6)cn5)CC4)n3)ccc12] |
| 467 | 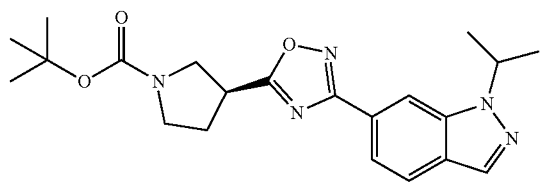 [SMILES: CC(C)n1ncc2ccc(-c3noc([C@H]4CCN(C(=O)OC(C)(C)C)C4)n3)cc21] |
| 468 | 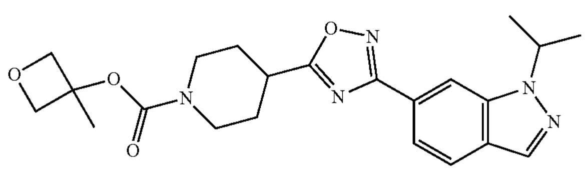 [SMILES: CC(C)n1ncc2ccc(-c3noc(C4CCN(C(=O)OC5(C)COC5)CC4)n3)cc21] |
| 469 | 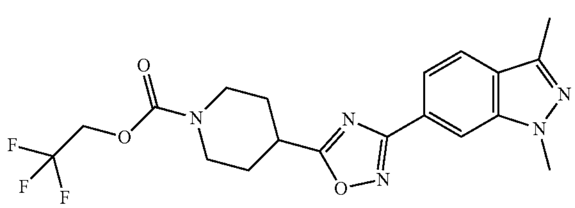 |
| 470 | 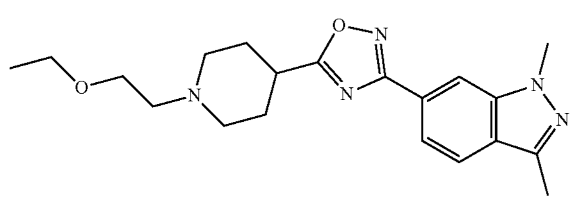 [SMILES: CCOCCN1CCC(c2nc(-c3ccc4c(C)nn(C)c4c3)no2)CC1] |
| 471 | 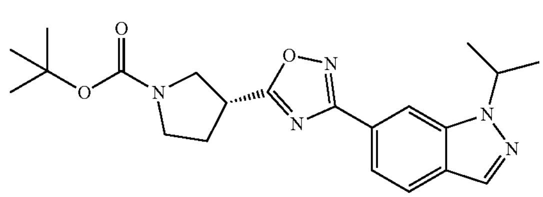 [SMILES: CC(C)n1ncc2ccc(-c3noc([C@@H]4CCN(C(=O)OC(C)(C)C)C4)n3)cc21] |

TABLE 1-continued

Compounds of the Invention

| # | Structure |
|---|---|
| 472 | 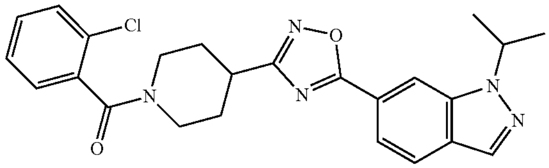 [SMILES: CC(C)n1ncc2ccc(-c3nc(C4CCN(C(=O)c5ccccc5Cl)CC4)no3)cc21] |
| 473 | 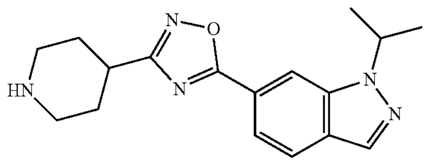 [SMILES: CC(C)n1ncc2ccc(-c3nc(C4CCNCC4)no3)cc21] |
| 474 | 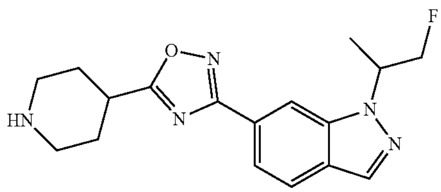 [SMILES: CC(CF)n1ncc2ccc(-c3noc(C4CCNCC4)n3)cc21] |
| 475 | 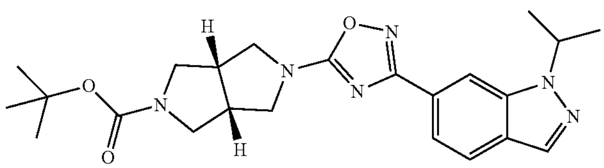 [SMILES: CC(C)n1ncc2ccc(-c3noc(N4C[C@H]5CN(C(=O)OC(C)(C)C)C[C@H]5C4)n3)cc21] |
| 476 | 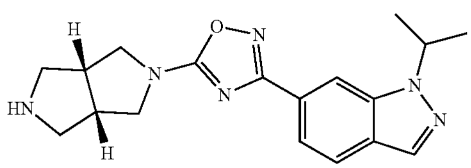 [SMILES: CC(C)n1ncc2ccc(-c3noc(N4C[C@H]5CNC[C@H]5C4)n3)cc21] |
| 477 | 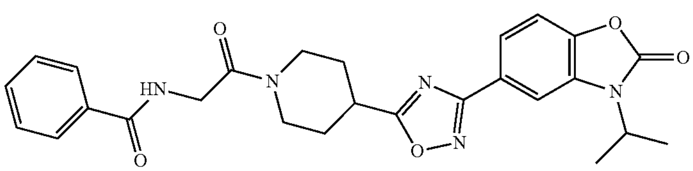 [SMILES: CC(C)n1c(=O)oc2ccc(-c3noc(C4CCN(C(=O)CNC(=O)c5ccccc5)CC4)n3)cc21] |
| 478 | 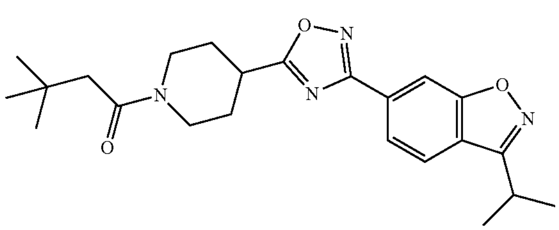 [SMILES: CC(C)c1noc2cc(-c3noc(C4CCN(C(=O)CC(C)(C)C)CC4)n3)ccc12] |
| 479 | 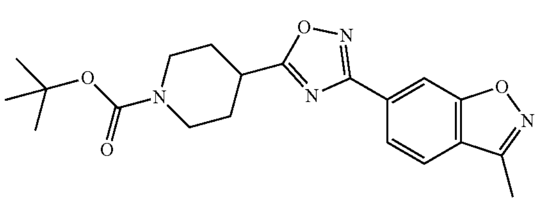 [SMILES: Cc1noc2cc(-c3noc(C4CCN(C(=O)OC(C)(C)C)CC4)n3)ccc12] |

TABLE 1-continued
Compounds of the Invention
| # | Structure |
|---|---|
| 480 | 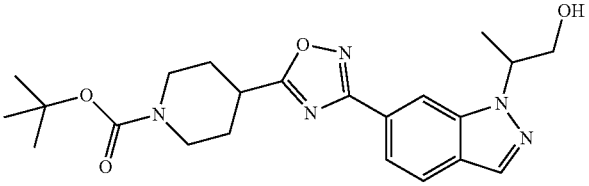 [SMILES: CC(CO)n1ncc2ccc(-c3noc(C4CCN(C(=O)OC(C)(C)C)CC4)n3)cc21] |
| 481 | 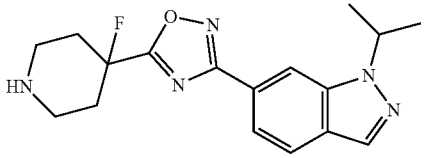 [SMILES: CC(C)n1ncc2ccc(-c3noc(C4(F)CCNCC4)n3)cc21] |
| 482 | 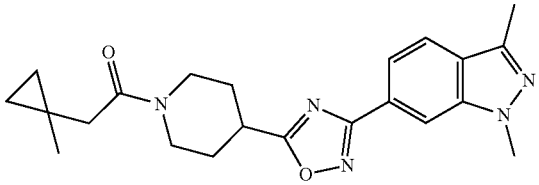 [SMILES: Cc1nn(C)c2cc(-c3noc(C4CCN(C(=O)CC5(C)CC5)CC4)n3)ccc12] |
| 483 | 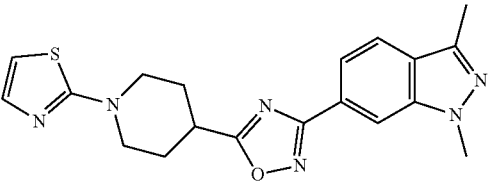 [SMILES: Cc1nn(C)c2cc(-c3noc(C4CCN(c5nccs5)CC4)n3)ccc12] |
| 484 | 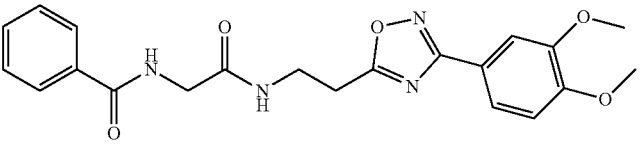 [SMILES: COc1ccc(-c2noc(CCNC(=O)CNC(=O)c3ccccc3)n2)cc1OC] |
| 485 | 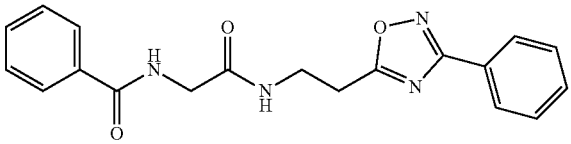 [SMILES: O=C(CNC(=O)c1ccccc1)NCCc1nc(-c2ccccc2)no1] |
| 486 | 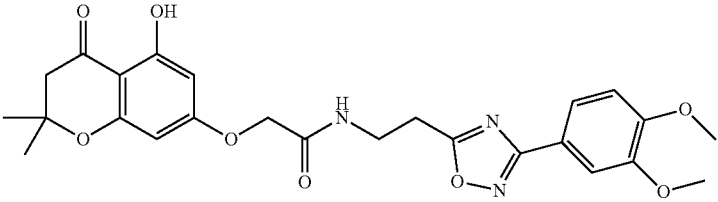 |
| 487 | 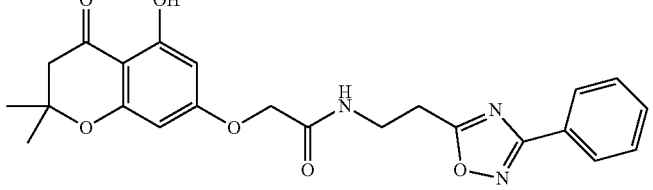 |

TABLE 1-continued

Compounds of the Invention

| # | Structure |
|---|---|
| 488 | 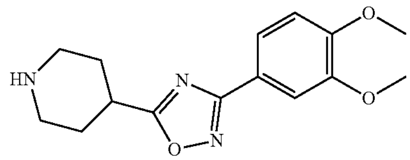 [SMILES: COc1ccc(-c2noc(C3CCNCC3)n2)cc1OC] |
| 489 | 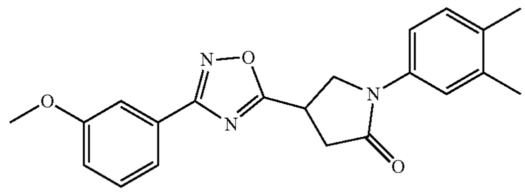 |
| 490 | 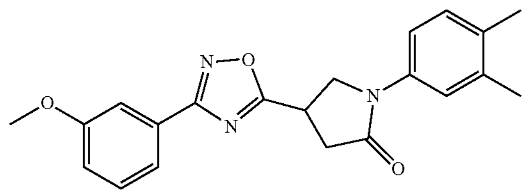 |
| 491 | 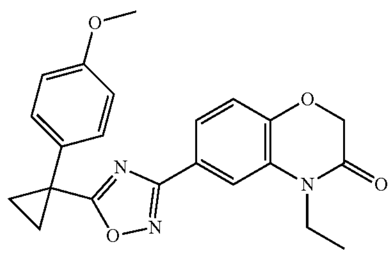 [SMILES: CCN1C(=O)COc2ccc(-c3noc(C4(c5ccc(OC)cc5)CC4)n3)cc21] |
| 492 | 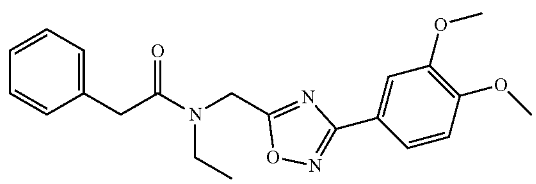 [SMILES: CCN(Cc1nc(-c2ccc(OC)c(OC)c2)no1)C(=O)Cc1ccccc1] |
| 493 | 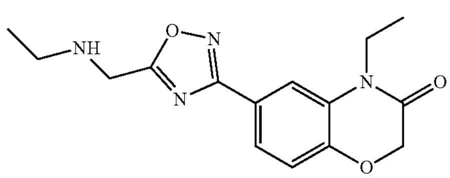 [SMILES: CCNCc1nc(-c2ccc3c(c2)N(CC)C(=O)CO3)no1] |
| 494 | 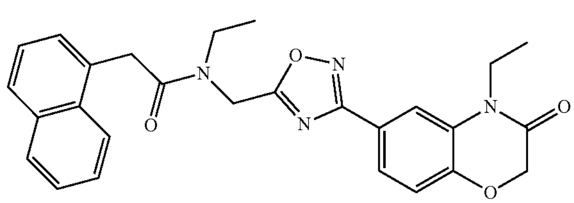 [SMILES: CCN(Cc1nc(-c2ccc3c(c2)N(CC)C(=O)CO3)no1)C(=O)Cc1cccc2ccccc12] |
| 495 | 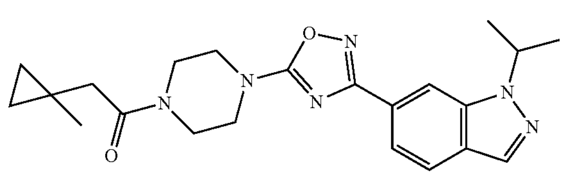 [SMILES: CC(C)n1ncc2ccc(-c3noc(N4CCN(C(=O)CC5(C)CC5)CC4)n3)cc21] |

TABLE 1-continued

Compounds of the Invention

| # | Structure |
|---|---|
| 496 | 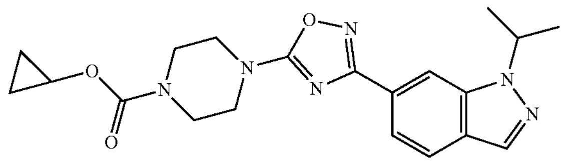 [SMILES: CC(C)n1ncc2ccc(-c3noc(N4CCN(C(=O)OC5CC5)CC4)n3)cc21] |
| 497 | 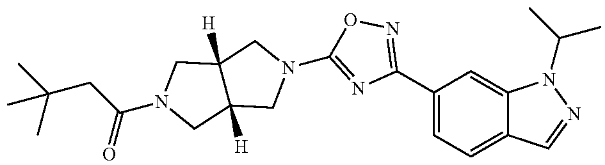 [SMILES: CC(C)n1ncc2ccc(-c3noc(N4C[C@H]5CN(C(=O)CC(C)(C)C)C[C@H]5C4)n3)cc21] |
| 498 | 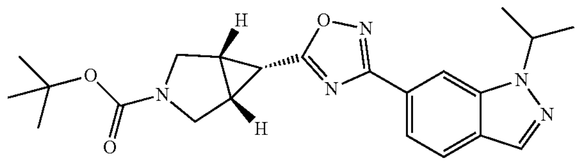 [SMILES: CC(C)n1ncc2ccc(-c3noc([C@@H]4[C@@H]5CN(C(=O)OC(C)(C)C)C[C@@H]54)n3)cc21] |
| 499 | 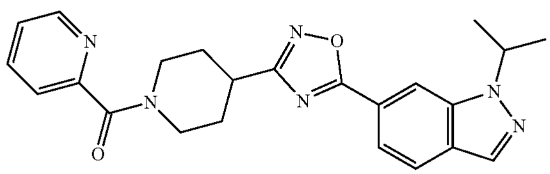 |
| 500 | 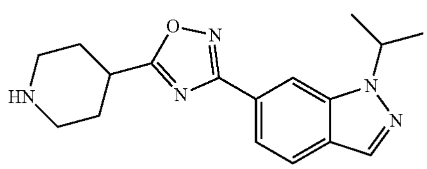 [SMILES: CC(C)n1ncc2ccc(-c3noc(C4CCNCC4)n3)cc21] |
| 501 | 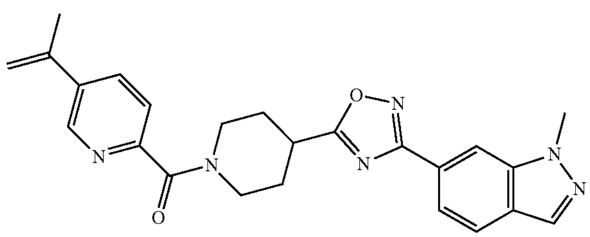 [SMILES: C=C(C)c1ccc(C(=O)N2CCC(c3nc(-c4ccc5cnn(C)c5c4)no3)CC2)nc1] |
| 502 | 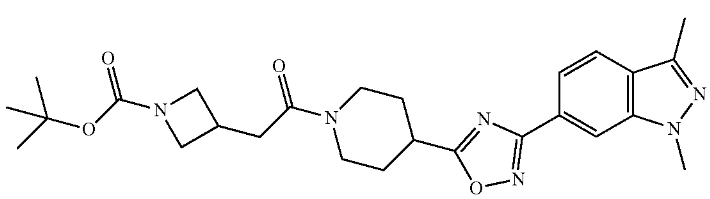 [SMILES: Cc1nn(C)c2cc(-c3noc(C4CCN(C(=O)CC5CN(C(=O)OC(C)(C)C)C5)CC4)n3)ccc12] |
| 503 | 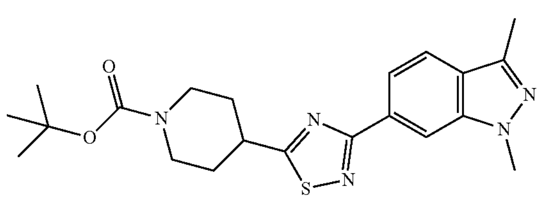 |

TABLE 1-continued

Compounds of the Invention

| # | Structure |
|---|---|
| 504 | 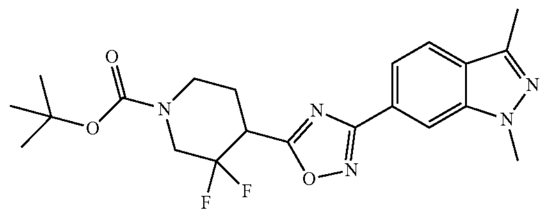 [SMILES: Cc1nn(C)c2cc(-c3noc(C4CCN(C(=O)OC(C)(C)C)CC4(F)F)n3)ccc12] |
| 505 | 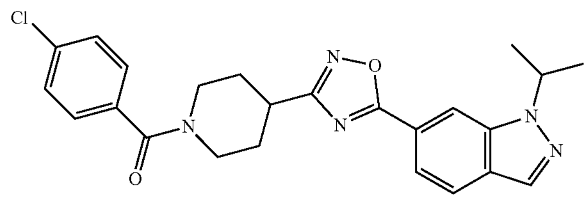 [SMILES: CC(C)n1ncc2ccc(-c3nc(C4CCN(C(=O)c5ccc(Cl)cc5)CC4)no3)cc21] |
| 506 | 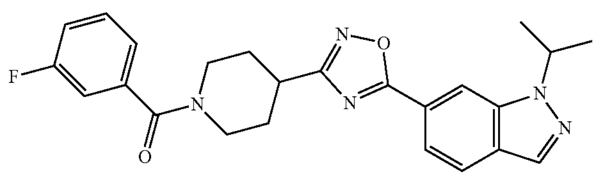 [SMILES: CC(C)n1ncc2ccc(-c3nc(C4CCN(C(=O)c5cccc(F)c5)CC4)no3)cc21] |
| 507 | 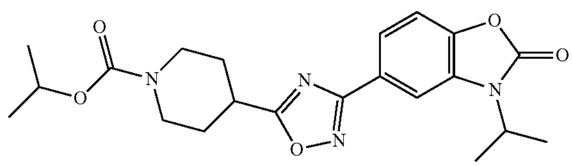 [SMILES: CC(C)OC(=O)N1CCC(c2nc(-c3ccc4oc(=O)n(C(C)C)c4c3)no2)CC1] |
| 508 | 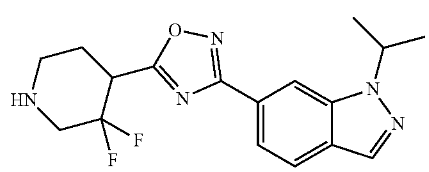 [SMILES: CC(C)n1ncc2ccc(-c3noc(C4CCNCC4(F)F)n3)cc21] |
| 509 | 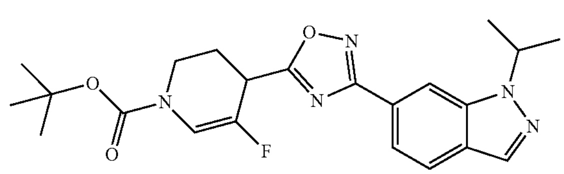 [SMILES: CC(C)n1ncc2ccc(-c3noc(C4CCN(C(=O)OC(C)(C)C)C=C4F)n3)cc21] |
| 510 | 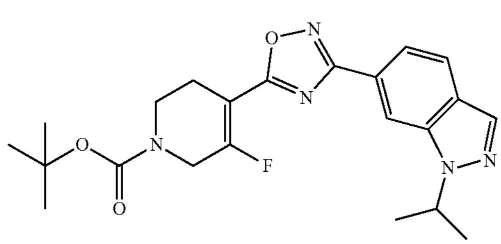 [SMILES: CC(C)n1ncc2ccc(-c3noc(C4=C(F)CN(C(=O)OC(C)(C)C)CC4)n3)cc21] |

TABLE 1-continued
Compounds of the Invention
| # | Structure |
|---|---|
| 511 | 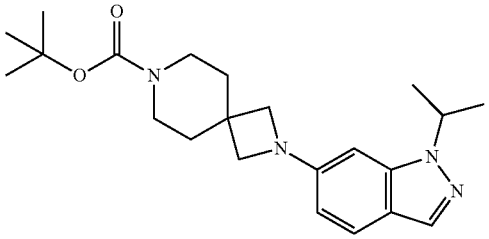 [SMILES: CC(C)n1ncc2ccc(N3CC4(CCN(C(=O)OC(C)(C)C)CC4)C3)cc21] |
| 512 | 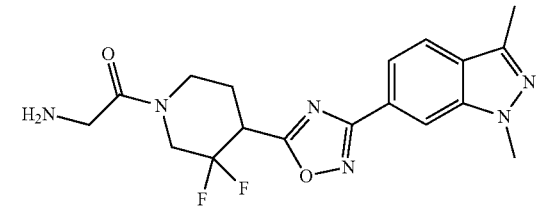 [SMILES: Cc1nn(C)c2cc(-c3noc(C4CCN(C(=O)CN)CC4(F)F)n3)ccc12] |
| 513 | 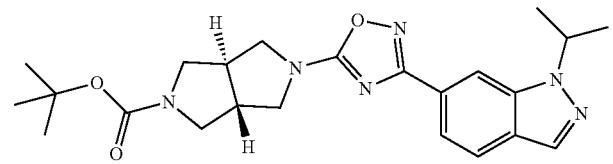 [SMILES: CC(C)n1ncc2ccc(-c3noc(N4C[C@@H]5CN(C(=O)OC(C)(C)C)C[C@H]5C4)n3)cc21] |
| 514 | 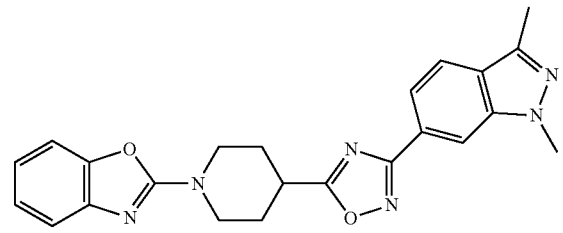 [SMILES: Cc1nn(C)c2cc(-c3noc(C4CCN(c5nc6ccccc6o5)CC4)n3)ccc12] |
| 515 | 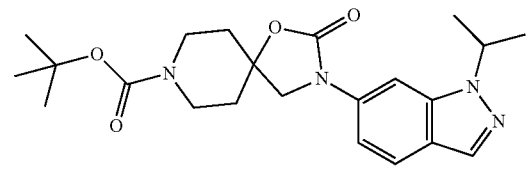 [SMILES: CC(C)n1ncc2ccc(N3CC4(CCN(C(=O)OC(C)(C)C)CC4)OC3=O)cc21] |
| 516 | 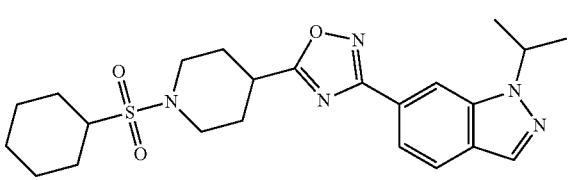 [SMILES: CC(C)n1ncc2ccc(-c3noc(C4CCN(S(=O)(=O)C5CCCCC5)CC4)n3)cc21] |
| 517 | 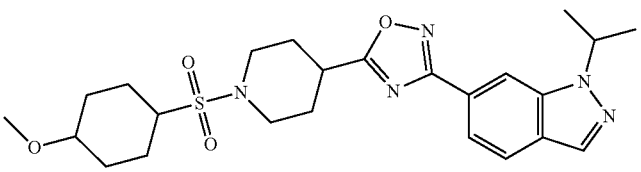 [SMILES: COC1CCC(S(=O)(=O)N2CCC(c3nc(-c4ccc5cnn(C(C)C)c5c4)no3)CC2)CC1] |

TABLE 1-continued

Compounds of the Invention

| # | Structure |
|---|---|
| 518 | 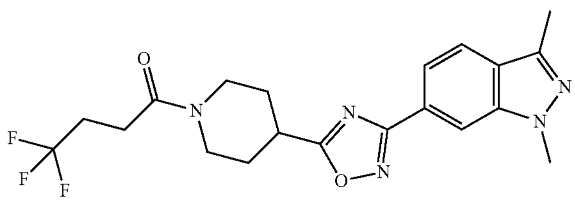 [SMILES: Cc1nn(C)c2cc(-c3noc(C4CCN(C(=O)CCC(F)(F)F)CC4)n3)ccc12] |
| 519 | 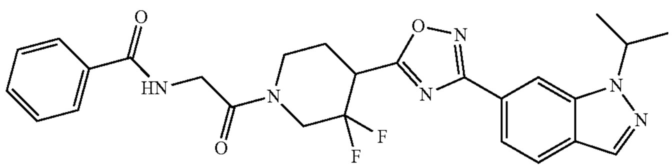 [SMILES: CC(C)n1ncc2ccc(-c3noc(C4CCN(C(=O)CNC(=O)c5ccccc5)CC4(F)F)n3)cc21] |
| 520 | 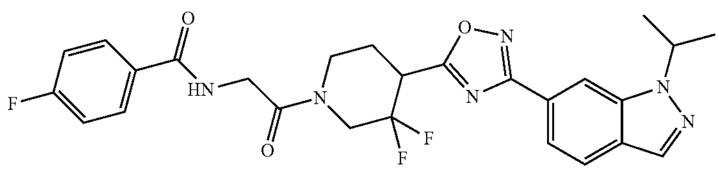 [SMILES: CC(C)n1ncc2ccc(-c3noc(C4CCN(C(=O)CNC(=O)c5ccc(F)cc5)CC4(F)F)n3)cc21] |
| 521 | 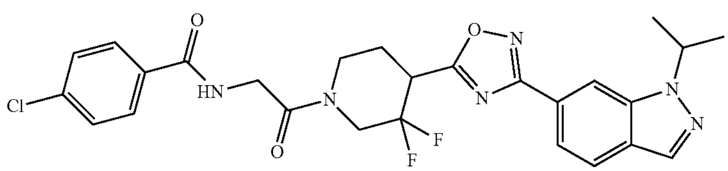 [SMILES: CC(C)n1ncc2ccc(-c3noc(C4CCN(C(=O)CNC(=O)c5ccc(Cl)cc5)CC4(F)F)n3)cc21] |
| 522 | 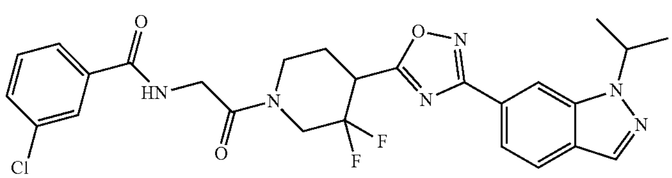 [SMILES: CC(C)n1ncc2ccc(-c3noc(C4CCN(C(=O)CNC(=O)c5cccc(Cl)c5)CC4(F)F)n3)cc21] |
| 523 | 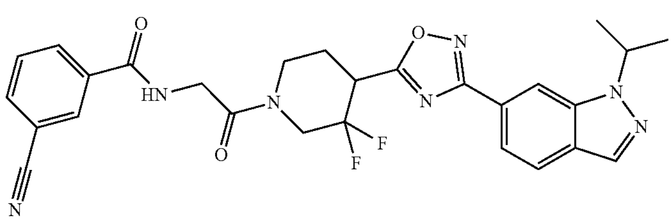 [SMILES: CC(C)n1ncc2ccc(-c3noc(C4CCN(C(=O)CNC(=O)c5cccc(C#N)c5)CC4(F)F)n3)cc21] |
| 524 | 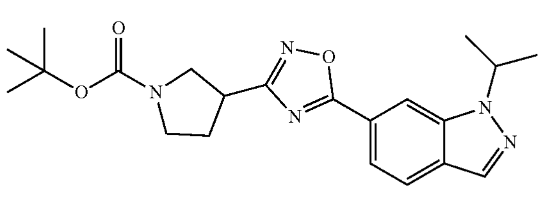 [SMILES: CC(C)n1ncc2ccc(-c3nc(C4CCN(C(=O)OC(C)(C)C)C4)no3)cc21] |

TABLE 1-continued

Compounds of the Invention

| # | Structure |
|---|---|
| 525 | 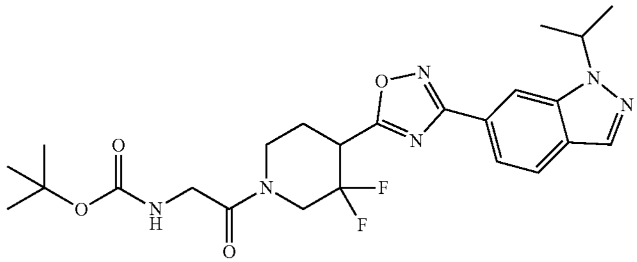 [SMILES: CC(C)n1ncc2ccc(-c3noc(C4CCN(C(=O)CNC(=O)OC(C)(C)C)CC4(F)F)n3)cc21] |
| 526 | 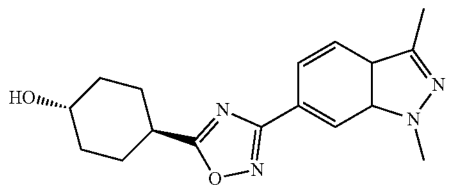 [SMILES: CC1=NN(C)C2C=C(c3noc([C@H]4CC[C@H](O)CC4)n3)C=CC12] |
| 527 | 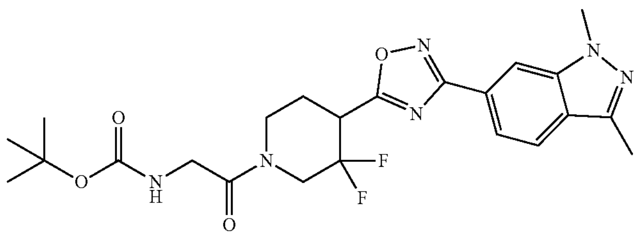 [SMILES: Cc1nn(C)c2cc(-c3noc(C4CCN(C(=O)CNC(=O)OC(C)(C)C)CC4(F)F)n3)ccc12] |
| 528 | 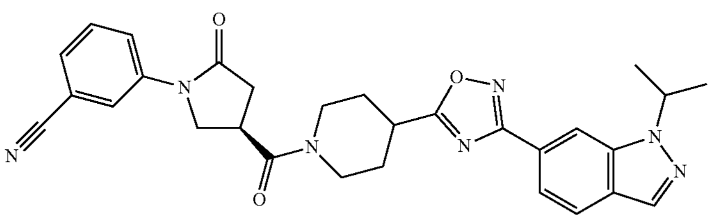 [SMILES: CC(C)n1ncc2ccc(-c3noc(C4CCN(C(=O)[C@@H]5CC(=O)N(c6cccc(C#N)c6)C5)CC4)n3)cc21] |
| 529 | 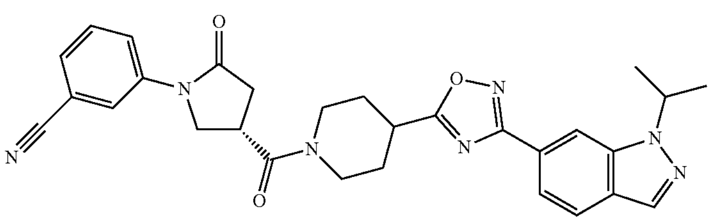 [SMILES: CC(C)n1ncc2ccc(-c3noc(C4CCN(C(=O)[C@H]5CC(=O)N(c6cccc(C#N)c6)C5)CC4)n3)cc21] |
| 530 | 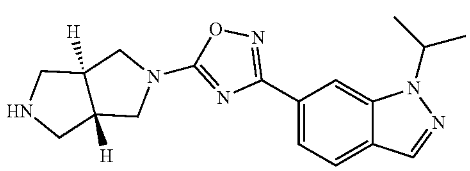 [SMILES: CC(C)n1ncc2ccc(-c3noc(N4C[C@@H]5CNC[C@H]5C4)n3)cc21] |
| 531 | 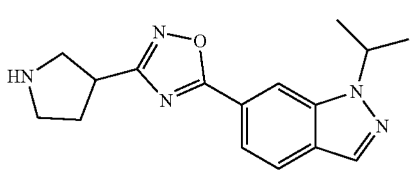 [SMILES: CC(C)n1ncc2ccc(-c3nc(C4CCNC4)no3)cc21] |

TABLE 1-continued

Compounds of the Invention

| # | Structure |
|---|---|
| 532 | 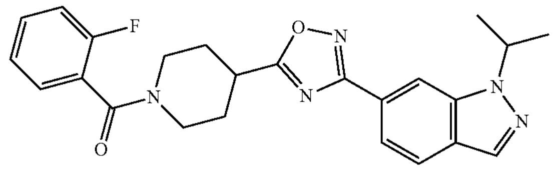 [SMILES: CC(C)n1ncc2ccc(-c3noc(C4CCN(C(=O)c5ccccc5F)CC4)n3)cc21] |
| 533 | 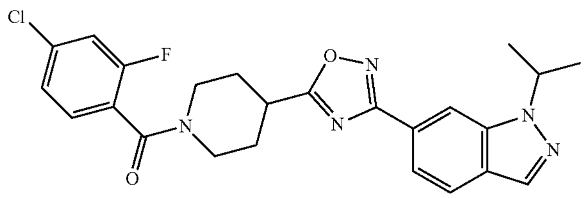 [SMILES: CC(C)n1ncc2ccc(-c3noc(C4CCN(C(=O)c5ccc(Cl)cc5F)CC4)n3)cc21] |
| 534 | 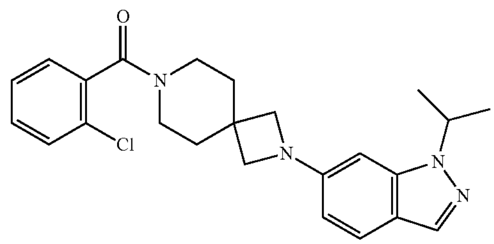 [SMILES: CC(C)n1ncc2ccc(N3CC4(CCN(C(=O)c5ccccc5Cl)CC4)C3)cc21] |
| 535 | 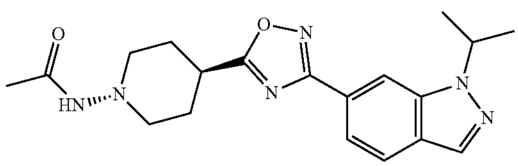 |
| 536 | 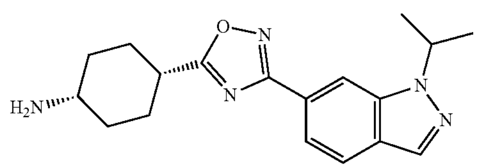 [SMILES: CC(C)n1ncc2ccc(-c3noc([C@H]4CC[C@@H](N)CC4)n3)cc21] |
| 537 | 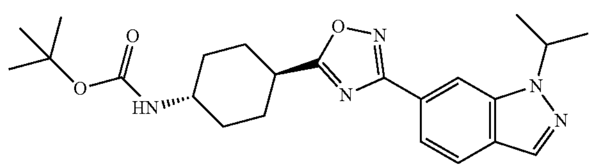 [SMILES: CC(C)n1ncc2ccc(-c3noc([C@H]4CC[C@H](NC(=O)OC(C)(C)C)CC4)n3)cc21] |
| 538 | 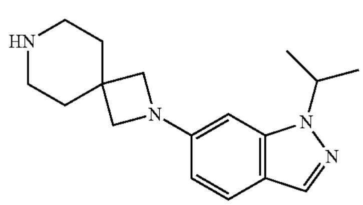 [SMILES: CC(C)n1ncc2ccc(N3CC4(CCNCC4)C3)cc21] |
| 539 | 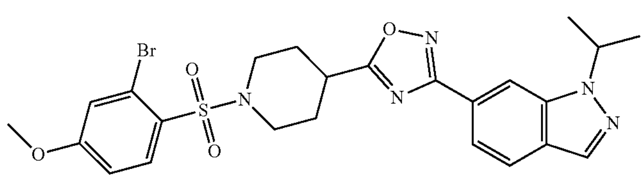 [SMILES: COc1ccc(S(=O)(=O)N2CCC(c3nc(-c4ccc5cnn(C(C)C)c5c4)no3)CC2)c(Br)c1] |

TABLE 1-continued

Compounds of the Invention

| # | Structure |
|---|---|
| 540 | 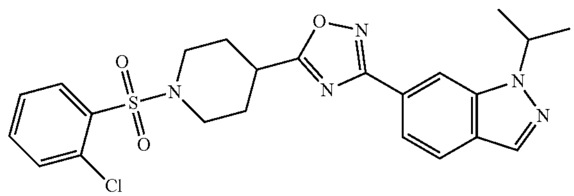 [SMILES: CC(C)n1ncc2ccc(-c3noc(C4CCN(S(=O)(=O)c5ccccc5Cl)CC4)n3)cc21] |
| 541 | 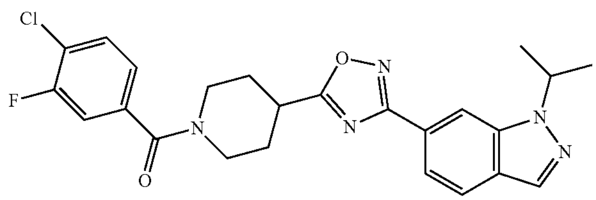 [SMILES: CC(C)n1ncc2ccc(-c3noc(C4CCN(C(=O)c5ccc(Cl)c(F)c5)CC4)n3)cc21] |
| 542 | 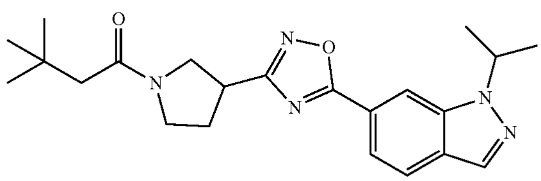 [SMILES: CC(C)n1ncc2ccc(-c3nc(C4CCN(C(=O)CC(C)(C)C)C4)no3)cc21] |
| 543 | 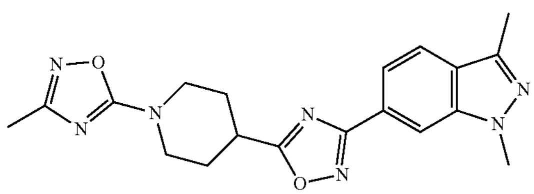 [SMILES: Cc1noc(N2CCC(c3nc(-c4ccc5c(C)nn(C)c5c4)no3)CC2)n1] |
| 544 | 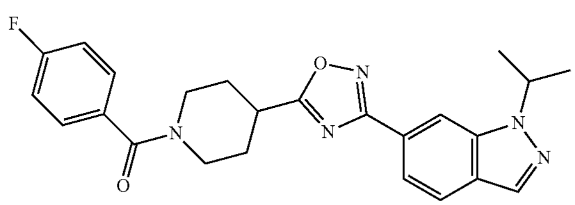 [SMILES: CC(C)n1ncc2ccc(-c3noc(C4CCN(C(=O)c5ccc(F)cc5)CC4)n3)cc21] |
| 545 | 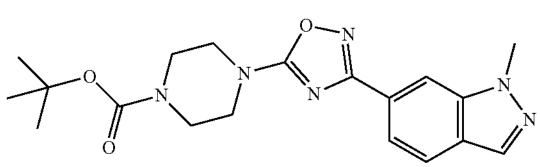 [SMILES: Cn1ncc2ccc(-c3noc(N4CCN(C(=O)OC(C)(C)C)CC4)n3)cc21] |
| 546 | 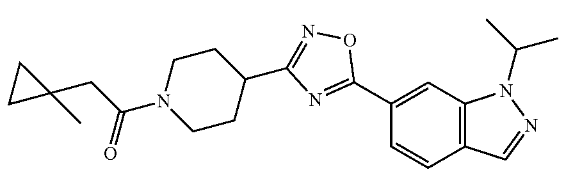 |
| 547 | 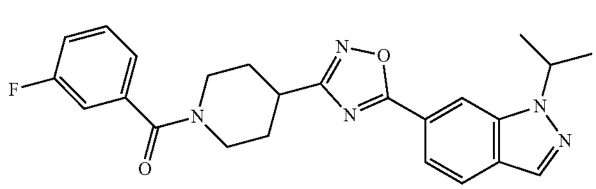 [SMILES: CC(C)n1ncc2ccc(-c3nc(C4CCN(C(=O)c5cccc(F)c5)CC4)no3)cc21] |

TABLE 1-continued

Compounds of the Invention

| # | Structure |
|---|---|
| 548 | 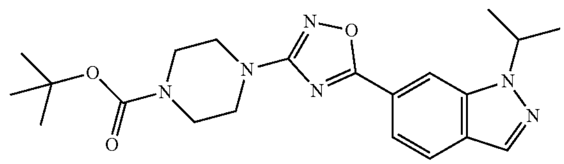 [SMILES: CC(C)n1ncc2ccc(-c3nc(N4CCN(C(=O)OC(C)(C)C)CC4)no3)cc21] |
| 549 | 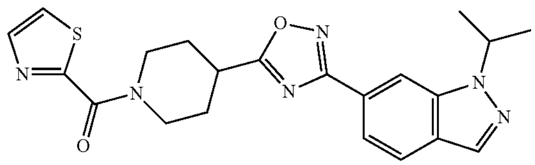 [SMILES: CC(C)n1ncc2ccc(-c3noc(C4CCN(C(=O)c5nccs5)CC4)n3)cc21] |
| 550 | 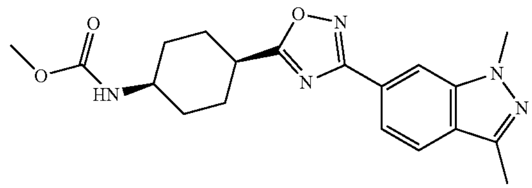 [SMILES: COC(=O)N[C@H]1CC[C@@H](c2nc(-c3ccc4c(C)nn(C)c4c3)no2)CC1] |
| 551 | 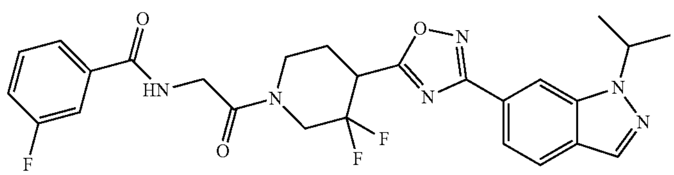 [SMILES: CC(C)n1ncc2ccc(-c3noc(C4CCN(C(=O)CNC(=O)c5cccc(F)c5)CC4(F)F)n3)cc21] |
| 552 | 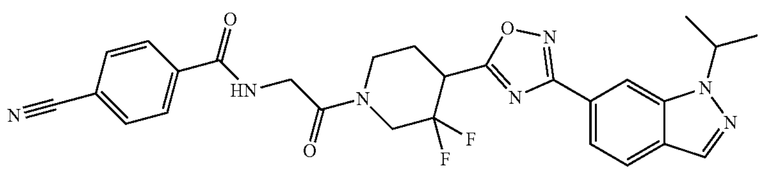 [SMILES: CC(C)n1ncc2ccc(-c3noc(C4CCN(C(=O)CNC(=O)c5ccc(C#N)cc5)CC4(F)F)n3)cc21] |
| 553 | 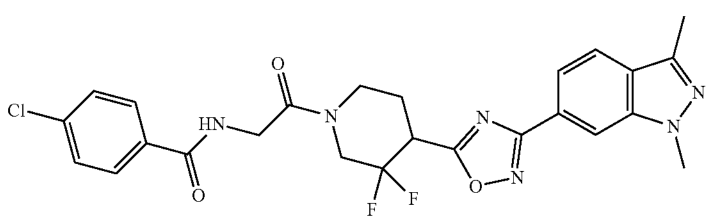 [SMILES: Cc1nn(C)c2cc(-c3noc(C4CCN(C(=O)CNC(=O)c5ccc(Cl)cc5)CC4(F)F)n3)ccc12] |
| 554 | 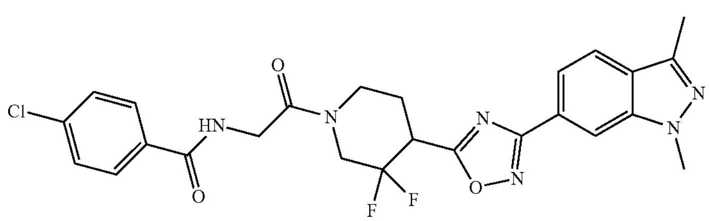 [SMILES: Cc1nn(C)c2cc(-c3noc(C4CCN(C(=O)CNC(=O)c5ccc(Cl)cc5)CC4(F)F)n3)ccc12] |
| 555 | 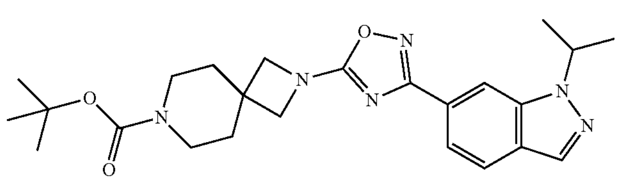 [SMILES: CC(C)n1ncc2ccc(-c3noc(N4CC5(CCN(C(=O)OC(C)(C)C)CC5)C4)n3)cc21] |

TABLE 1-continued

Compounds of the Invention

| # | Structure |
|---|---|
| 556 | (structure) |
| 557 | (structure) |
| 558 | (structure) |
| 559 | (structure) |
| 560 | (structure) |
| 561 | (structure) |
| 562 | (structure) |

US 11,970,486 B2
199
200
TABLE 1-continued
Compounds of the Invention
| # | Structure |
|---|---|
| 563 | 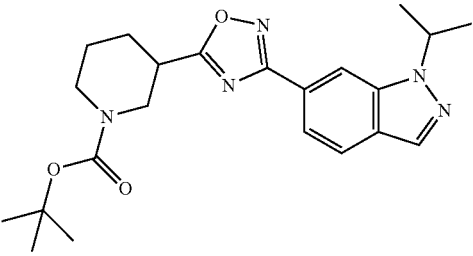 [SMILES: CC(C)n1ncc2ccc(-c3noc(C4CCCN(C(=O)OC(C)(C)C)C4)n3)cc21] |
| 564 | 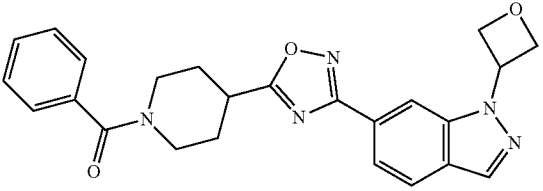 [SMILES: O=C(c1ccccc1)N1CCC(c2nc(-c3ccc4cnn(C5COC5)c4c3)no2)CC1] |
| 565 | 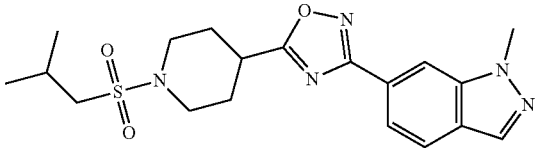 [SMILES: CC(C)CS(=O)(=O)N1CCC(c2nc(-c3ccc4cnn(C)c4c3)no2)CC1] |
| 566 | 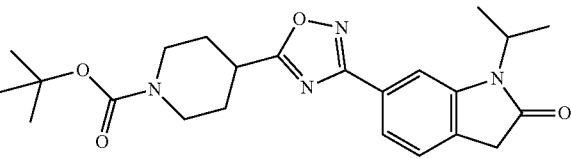 [SMILES: CC(C)N1C(=O)Cc2ccc(-c3noc(C4CCN(C(=O)OC(C)(C)C)CC4)n3)cc21] |
| 567 | 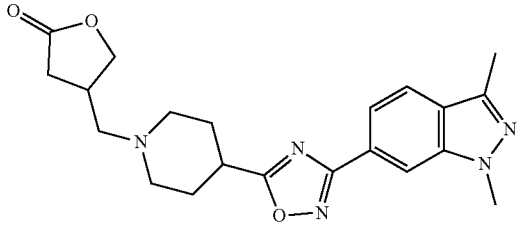 [SMILES: Cc1nn(C)c2cc(-c3noc(C4CCN(CC5COC(=O)C5)CC4)n3)ccc12] |
| 568 | 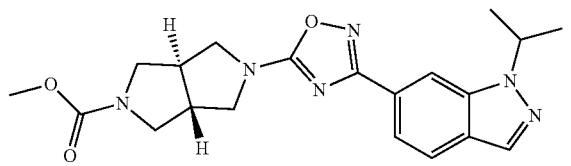 [SMILES: COC(=O)N1C[C@H]2CN(c3nc(-c4ccc5cnn(C(C)C)c5c4)no3)C[C@@H]2C1] |
| 569 | 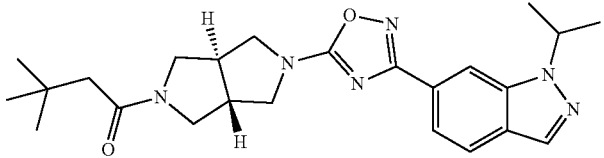 [SMILES: CC(C)n1ncc2ccc(-c3noc(N4C[C@@H]5CN(C(=O)CC(C)(C)C)C[C@H]5C4)n3)cc21] |
| 570 | 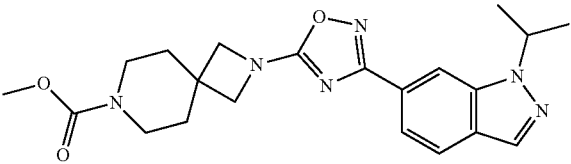 [SMILES: COC(=O)N1CCC2(CC1)CN(c1nc(-c3ccc4cnn(C(C)C)c4c3)no1)C2] |

TABLE 1-continued
Compounds of the Invention
| # | Structure |
|---|---|
| 571 | 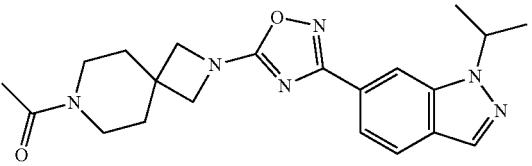 [SMILES: CC(=O)N1CCC2(CC1)CN(c1nc(-c3ccc4cnn(C(C)C)c4c3)no1)C2] |
| 572 | 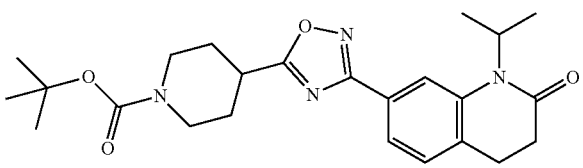 [SMILES: CC(C)N1C(=O)CCc2ccc(-c3noc(C4CCN(C(=O)OC(C)(C)C)CC4)n3)cc21] |
| 573 | 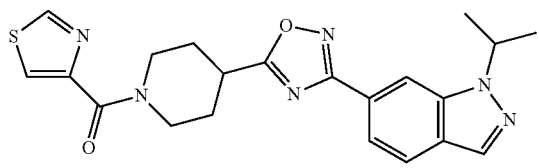 [SMILES: CC(C)n1ncc2ccc(-c3noc(C4CCN(C(=O)c5cscn5)CC4)n3)cc21] |
| 574 | 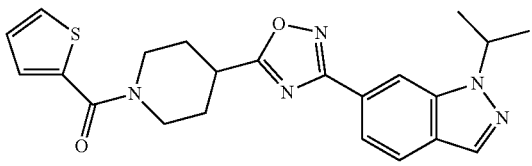 [SMILES: CC(C)n1ncc2ccc(-c3noc(C4CCN(C(=O)c5cccs5)CC4)n3)cc21] |
| 575 | 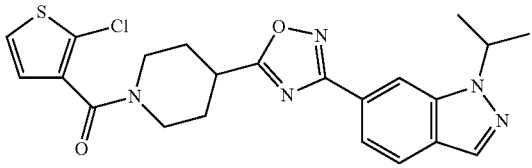 [SMILES: CC(C)n1ncc2ccc(-c3noc(C4CCN(C(=O)c5ccsc5Cl)CC4)n3)cc21] |
| 576 | 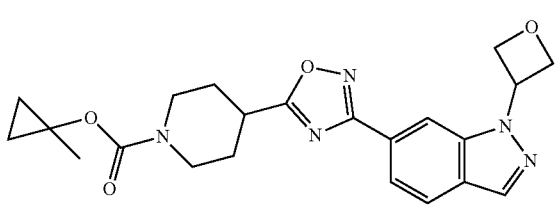 [SMILES: CC1(OC(=O)N2CCC(c3nc(-c4ccc5cnn(C6COC6)c5c4)no3)CC2)CC1] |
| 577 | 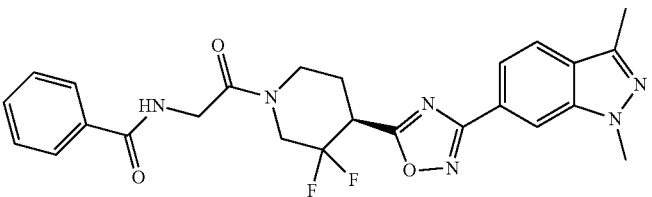 [SMILES: Cc1nn(C)c2cc(-c3noc([C@@H]4CCN(C(=O)CNC(=O)c5ccccc5)CC4(F)F)n3)ccc12] |
| 578 | 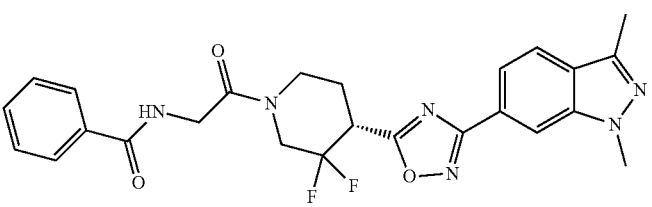 [SMILES: Cc1nn(C)c2cc(-c3noc([C@H]4CCN(C(=O)CNC(=O)c5ccccc5)CC4(F)F)n3)ccc12] |

TABLE 1-continued

Compounds of the Invention

| # | Structure |
|---|---|
| 579 | 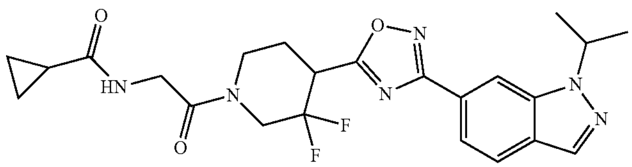 [SMILES: CC(C)n1ncc2ccc(-c3noc(C4CCN(C(=O)CNC(=O)C5CC5)CC4(F)F)n3)cc21] |
| 580 | 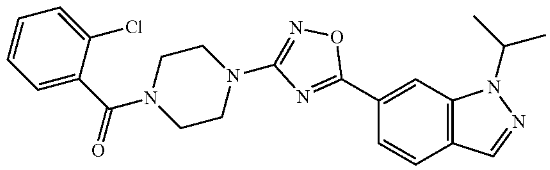 [SMILES: CC(C)n1ncc2ccc(-c3nc(N4CCN(C(=O)c5ccccc5Cl)CC4)no3)cc21] |
| 581 | 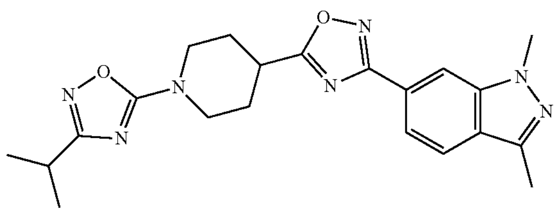 [SMILES: Cc1nn(C)c2cc(-c3noc(C4CCN(c5nc(C(C)C)no5)CC4)n3)ccc12] |
| 582 | 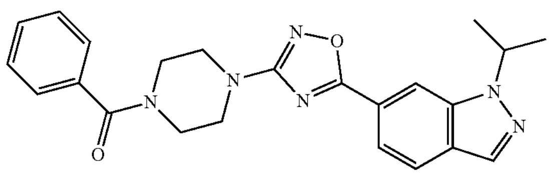 [SMILES: CC(C)n1ncc2ccc(-c3nc(N4CCN(C(=O)c5ccccc5)CC4)no3)cc21] |
| 583 | 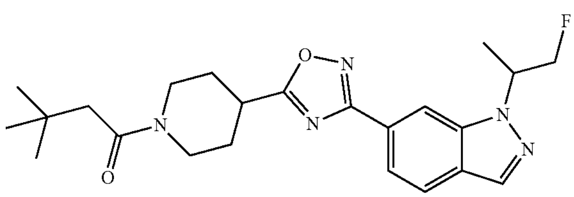 [SMILES: CC(CF)n1ncc2ccc(-c3noc(C4CCN(C(=O)CC(C)(C)C)CC4)n3)cc21] |
| 584 | 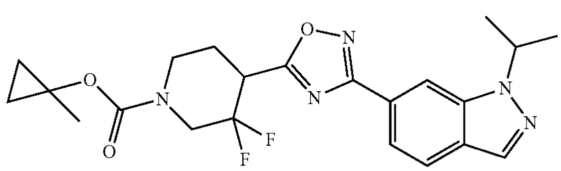 [SMILES: CC(C)n1ncc2ccc(-c3noc(C4CCN(C(=O)OC5(C)CC5)CC4(F)F)n3)cc21] |
| 585 | 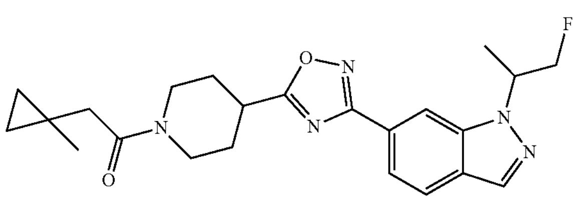 |
| 586 | 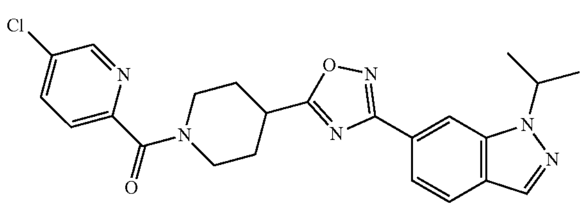 |

TABLE 1-continued

Compounds of the Invention

| # | Structure |
|---|---|
| 587 | 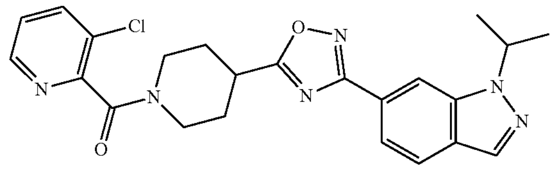 [SMILES: CC(C)n1ncc2ccc(-c3noc(C4CCN(C(=O)c5ncccc5Cl)CC4)n3)cc21] |
| 588 | 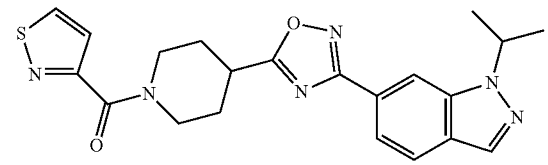 [SMILES: CC(C)n1ncc2ccc(-c3noc(C4CCN(C(=O)c5ccsn5)CC4)n3)cc21] |
| 589 | 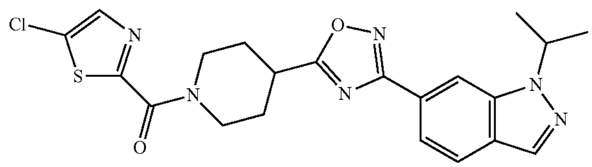 [SMILES: CC(C)n1ncc2ccc(-c3noc(C4CCN(C(=O)c5ncc(Cl)s5)CC4)n3)cc21] |
| 590 | 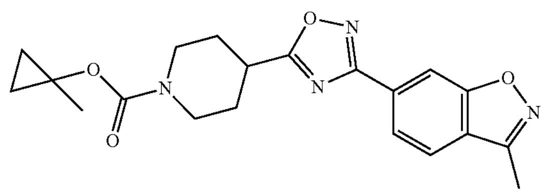 [SMILES: Cc1noc2cc(-c3noc(C4CCN(C(=O)OC5(C)CC5)CC4)n3)ccc12] |
| 591 | 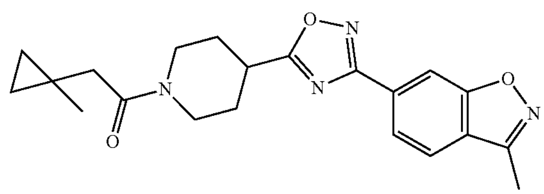 |
| 592 | 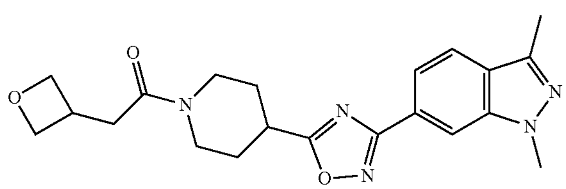 [SMILES: Cc1nn(C)c2cc(-c3noc(C4CCN(C(=O)CC5COC5)CC4)n3)ccc12] |
| 593 | 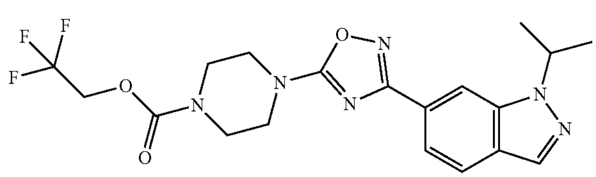 [SMILES: CC(C)n1ncc2ccc(-c3noc(N4CCN(C(=O)OCC(F)(F)F)CC4)n3)cc21] |
| 594 | 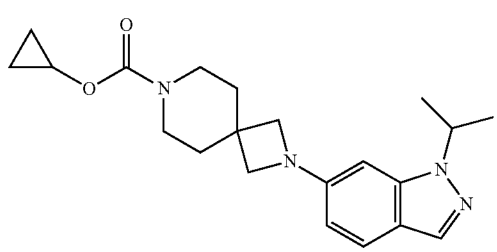 [SMILES: CC(C)n1ncc2ccc(N3CC4(CCN(C(=O)OC5CC5)CC4)C3)cc21] |

TABLE 1-continued

Compounds of the Invention

| # | Structure |
|---|---|
| 595 | 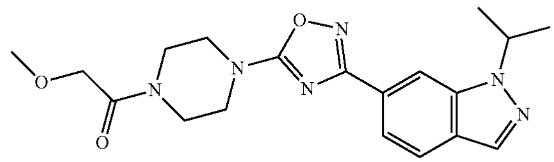 [SMILES: COCC(=O)N1CCN(c2nc(-c3ccc4cnn(C(C)C)c4c3)no2)CC1] |
| 596 | 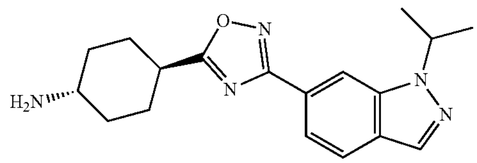 [SMILES: CC(C)n1ncc2ccc(-c3noc([C@H]4CC[C@H](N)CC4)n3)cc21] |
| 597 | 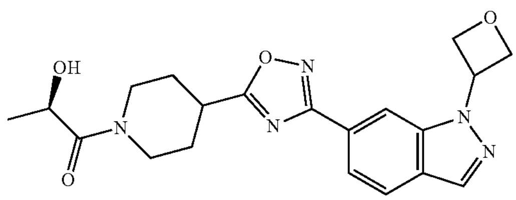 [SMILES: C[C@@H](O)C(=O)N1CCC(c2nc(-c3ccc4cnn(C5COC5)c4c3)no2)CC1] |
| 598 | 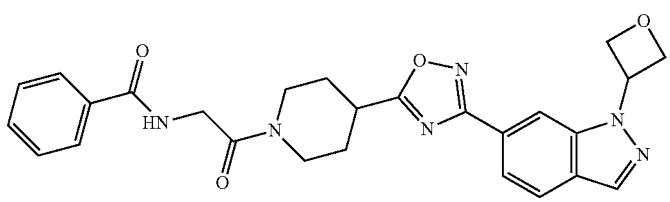 [SMILES: O=C(NCC(=O)N1CCC(c2nc(-c3ccc4cnn(C5COC5)c4c3)no2)CC1)c1ccccc1] |
| 599 | 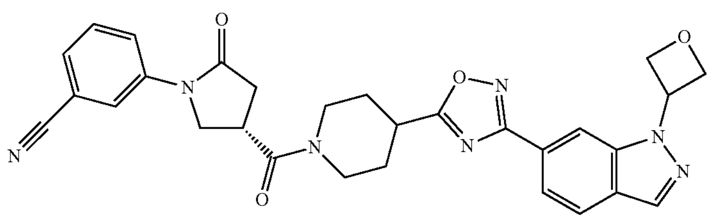 [SMILES: N#Cc1cccc(N2C[C@@H](C(=O)N3CCC(c4nc(-c5ccc6cnn(C7COC7)c6c5)no4)CC3)CC2=O)c1] |
| 600 | 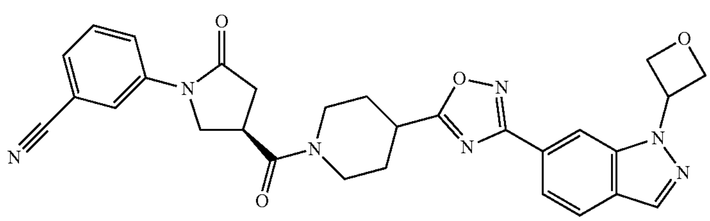 [SMILES: N#Cc1cccc(N2C[C@H](C(=O)N3CCC(c4nc(-c5ccc6cnn(C7COC7)c6c5)no4)CC3)CC2=O)c1] |
| 601 | 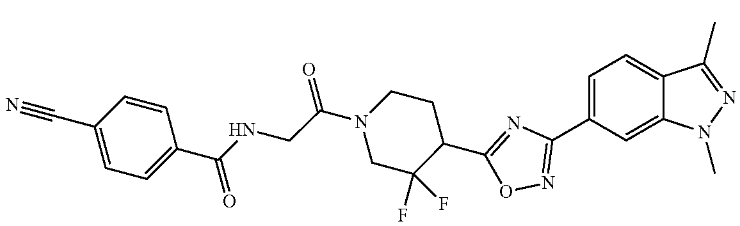 [SMILES: Cc1nn(C)c2cc(-c3noc(C4CCN(C(=O)CNC(=O)c5ccc(C#N)cc5)CC4(F)F)n3)ccc12] |

TABLE 1-continued

Compounds of the Invention

| # | Structure |
|---|-----------|
| 602 | 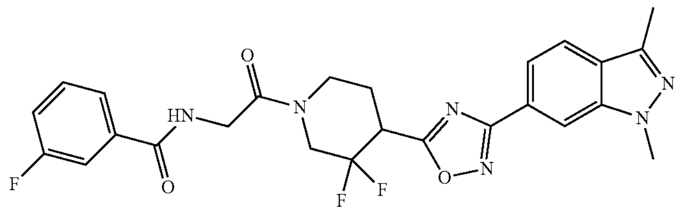 [SMILES: Cc1nn(C)c2cc(-c3noc(C4CCN(C(=O)CNC(=O)c5cccc(F)c5)CC4(F)F)n3)ccc12] |
| 603 | 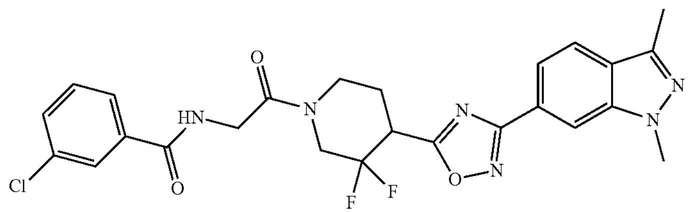 [SMILES: Cc1nn(C)c2cc(-c3noc(C4CCN(C(=O)CNC(=O)c5cccc(Cl)c5)CC4(F)F)n3)ccc12] |
| 604 | 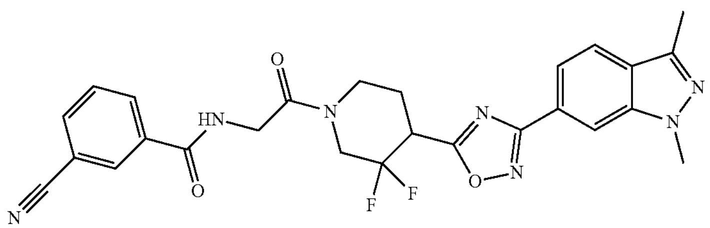 [SMILES: Cc1nn(C)c2cc(-c3noc(C4CCN(C(=O)CNC(=O)c5cccc(C#N)c5)CC4(F)F)n3)ccc12] |
| 605 | 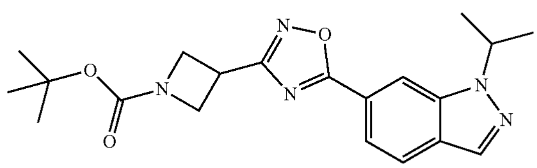 |
| 606 | 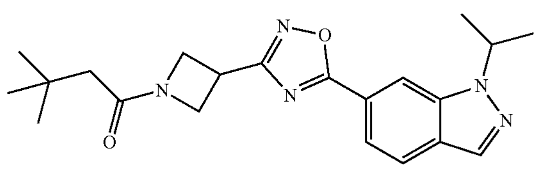 [SMILES: CC(C)n1ncc2ccc(-c3nc(C4CN(C(=O)CC(C)(C)C)C4)no3)cc21] |
| 607 | 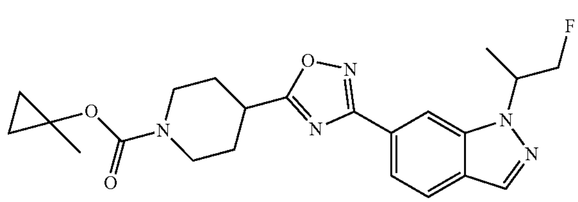 [SMILES: CC(CF)n1ncc2ccc(-c3noc(C4CCN(C(=O)OC5(C)CC5)CC4)n3)cc21] |
| 608 | 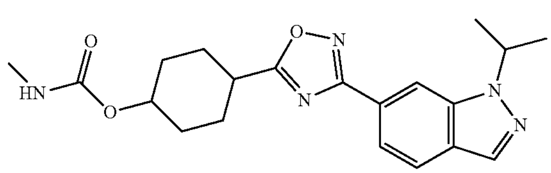 [SMILES: CNC(=O)OC1CCC(c2nc(-c3ccc4cnn(C(C)C)c4c3)no2)CC1] |

TABLE 1-continued

Compounds of the Invention

| # | Structure |
|---|---|
| 609 | 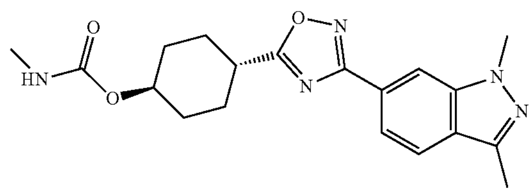 [SMILES: CNC(=O)O[C@H]1CC[C@H](c2nc(-c3ccc4c(C)nn(C)c4c3)no2)CC1] |
| 610 | 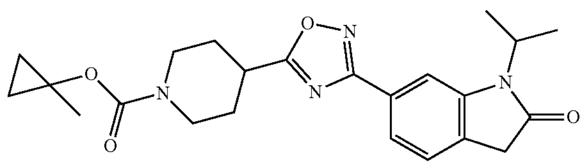 [SMILES: CC(C)N1C(=O)Cc2ccc(-c3noc(C4CCN(C(=O)OC5(C)CC5)CC4)n3)cc21] |
| 611 | 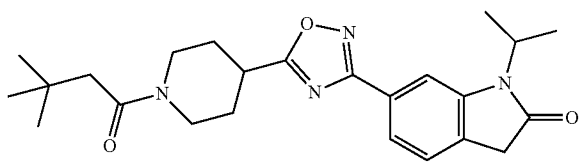 |
| 612 | 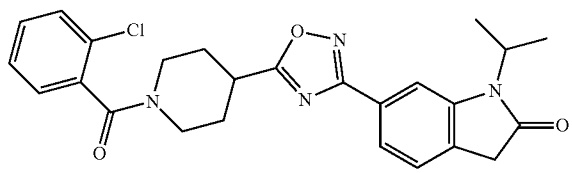 [SMILES: CC(C)N1C(=O)Cc2ccc(-c3noc(C4CCN(C(=O)c5ccccc5Cl)CC4)n3)cc21] |
| 613 | 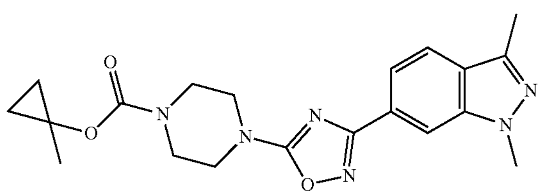 |
| 614 | 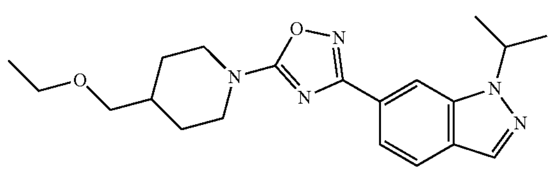 [SMILES: CCOCC1CCN(c2nc(-c3ccc4cnn(C(C)C)c4c3)no2)CC1] |
| 615 | 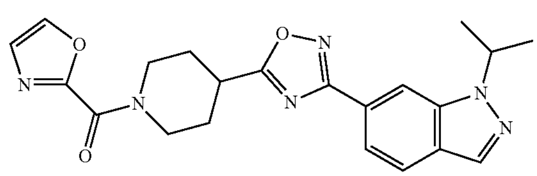 |
| 616 | 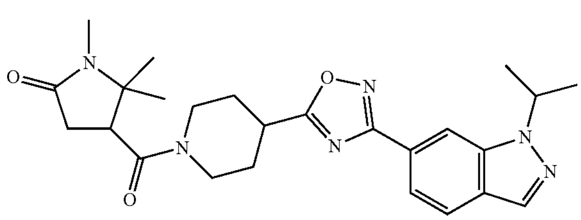 [SMILES: CC(C)n1ncc2ccc(-c3noc(C4CCN(C(=O)C5CC(=O)N(C)C5(C)C)CC4)n3)cc21] |

TABLE 1-continued

Compounds of the Invention

| # | Structure |
|---|---|
| 617 | 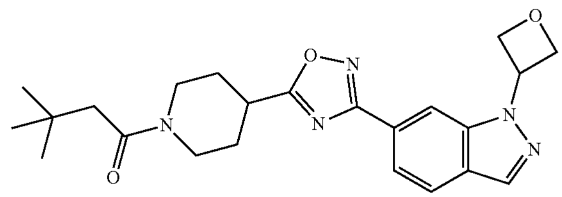 [SMILES: CC(C)(C)CC(=O)N1CCC(c2nc(-c3ccc4cnn(C5COC5)c4c3)no2)CC1] |
| 618 | 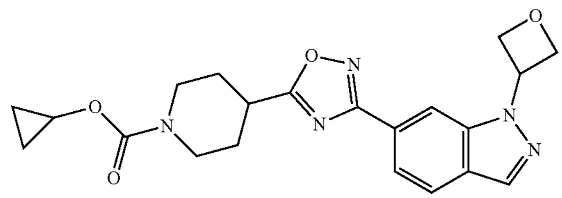 |
| 619 | 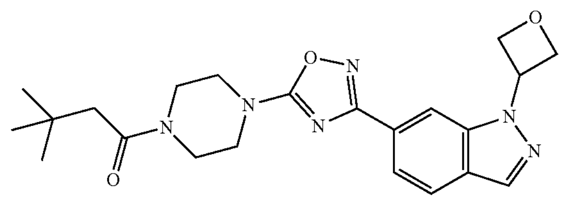 [SMILES: CC(C)(C)CC(=O)N1CCN(c2nc(-c3ccc4cnn(C5COC5)c4c3)no2)CC1] |
| 620 | 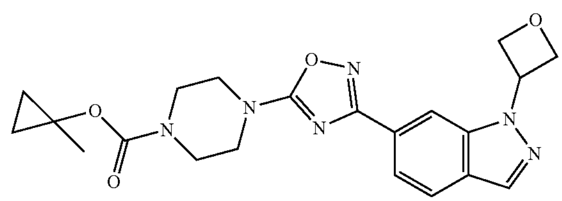 [SMILES: CC1(OC(=O)N2CCN(c3nc(-c4ccc5cnn(C6COC6)c5c4)no3)CC2)CC1] |
| 621 | 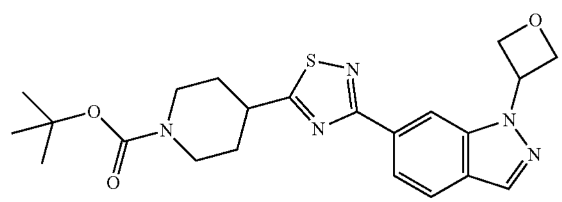 [SMILES: CC(C)(C)OC(=O)N1CCC(c2nc(-c3ccc4cnn(C5COC5)c4c3)ns2)CC1] |
| 622 | 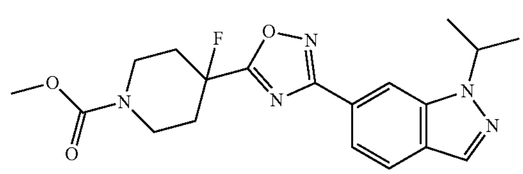 |
| 623 | 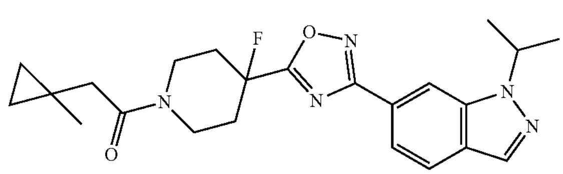 [SMILES: CC(C)n1ncc2ccc(-c3noc(C4(F)CCN(C(=O)CC5(C)CC5)CC4)n3)cc21] |
| 624 | 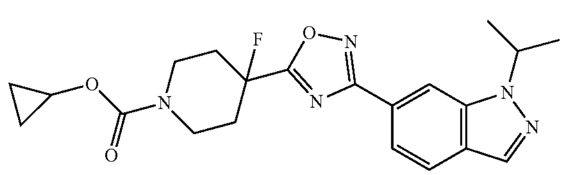 [SMILES: CC(C)n1ncc2ccc(-c3noc(C4(F)CCN(C(=O)OC5CC5)CC4)n3)cc21] |

TABLE 1-continued

Compounds of the Invention

| # | Structure |
|---|---|
| 625 | 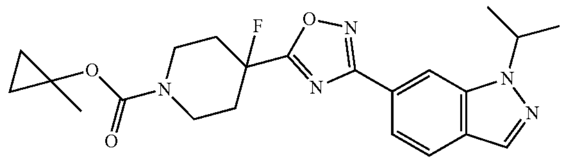 [SMILES: CC(C)n1ncc2ccc(-c3noc(C4(F)CCN(C(=O)OC5(C)CC5)CC4)n3)cc21] |
| 626 | 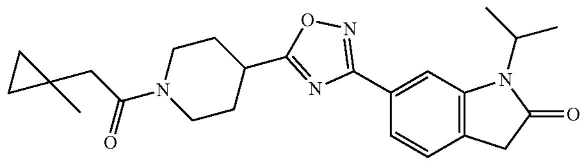 |
| 627 | 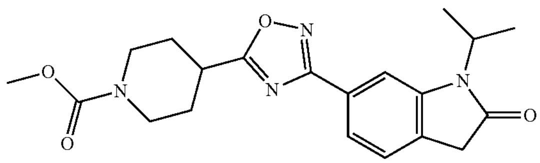 [SMILES: COC(=O)N1CCC(c2nc(-c3ccc4c(c3)N(C(C)C)C(=O)C4)no2)CC1] |
| 628 | 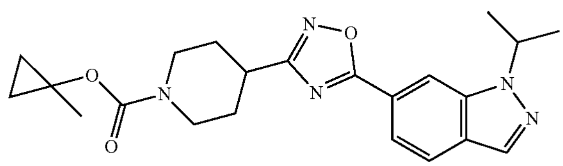 [SMILES: CC(C)n1ncc2ccc(-c3nc(C4CCN(C(=O)OC5(C)CC5)CC4)no3)cc21] |
| 629 | 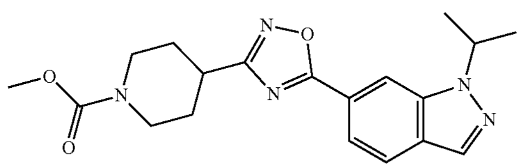 |
| 630 | 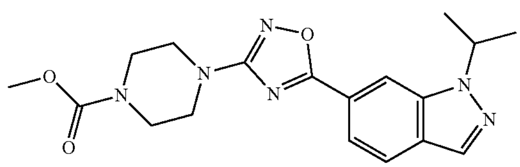 [SMILES: COC(=O)N1CCN(c2noc(-c3ccc4cnn(C(C)C)c4c3)n2)CC1] |
| 631 | 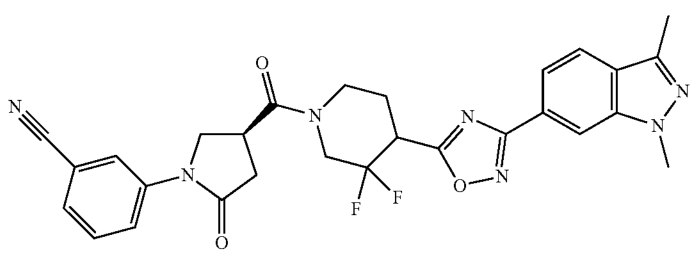 [SMILES: Cc1nn(C)c2cc(-c3noc(C4CCN(C(=O)[C@H]5CC(=O)N(c6cccc(C#N)c6)C5)CC4(F)F)n3)ccc12] |
| 632 | 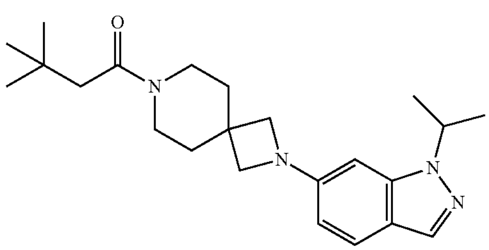 [SMILES: CC(C)n1ncc2ccc(N3CC4(CCN(C(=O)CC(C)(C)C)CC4)C3)cc21] |

TABLE 1-continued
Compounds of the Invention
| # | Structure |
|---|---|
| 633 | 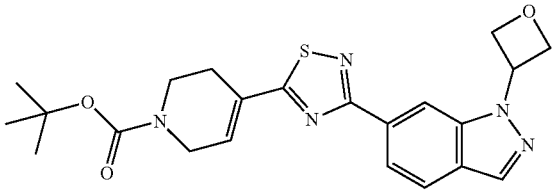 [SMILES: CC(C)(C)OC(=O)N1CC=C(c2nc(-c3ccc4cnn(C5COC5)c4c3)ns2)CC1] |
| 634 | 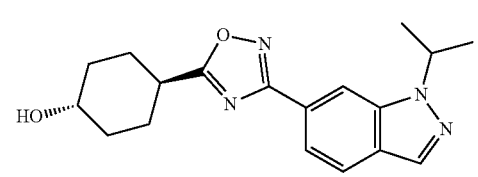 [SMILES: CC(C)n1ncc2ccc(-c3noc([C@H]4CC[C@H](O)CC4)n3)cc21] |
| 635 | 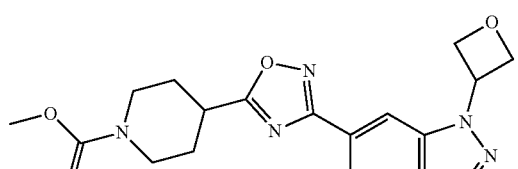 |
| 636 | 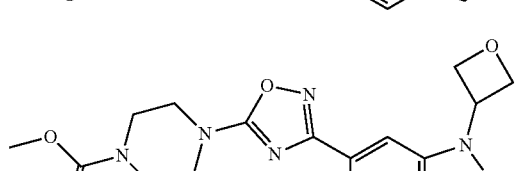 |
| 637 | 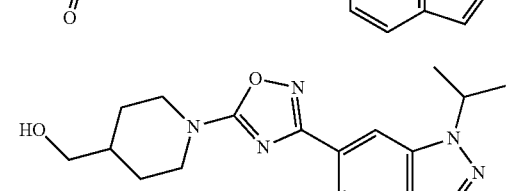 |
| 638 | 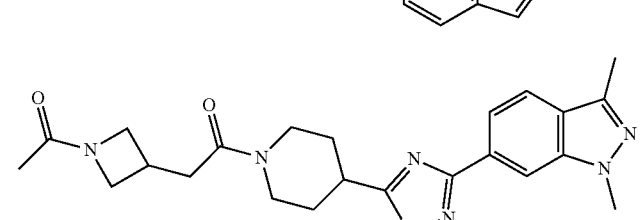 |
| 639 | 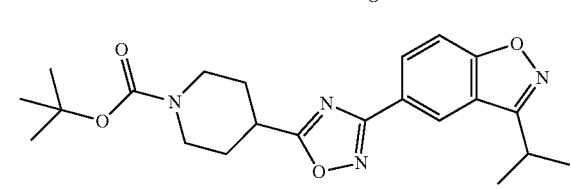 |
| 640 | 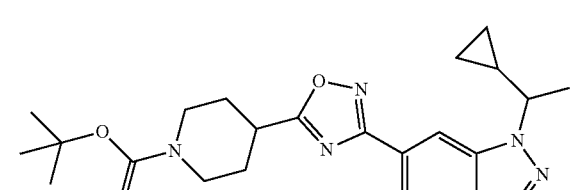 |

TABLE 1-continued
Compounds of the Invention
| # | Structure |
|---|---|
| 641 | 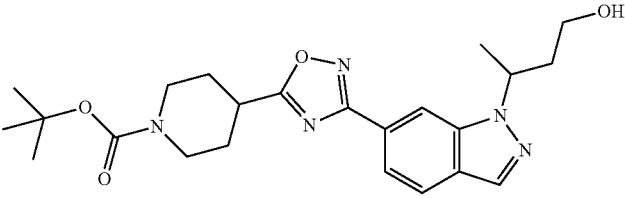 [SMILES: CC(CCO)n1ncc2ccc(-c3noc(C4CCN(C(=O)OC(C)(C)C)CC4)n3)cc21] |
| 642 | 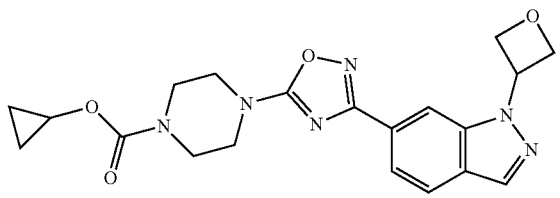 |
| 643 | 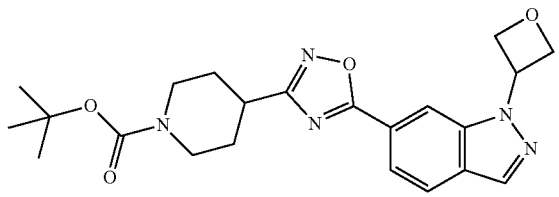 [SMILES: CC(C)(C)OC(=O)N1CCC(c2noc(-c3ccc4cnn(C5COC5)c4c3)n2)CC1] |
| 644 | 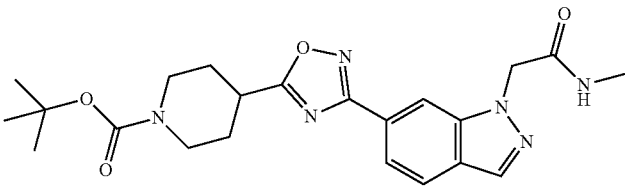 [SMILES: CNC(=O)Cn1ncc2ccc(-c3noc(C4CCN(C(=O)OC(C)(C)C)CC4)n3)cc21] |
| 645 | 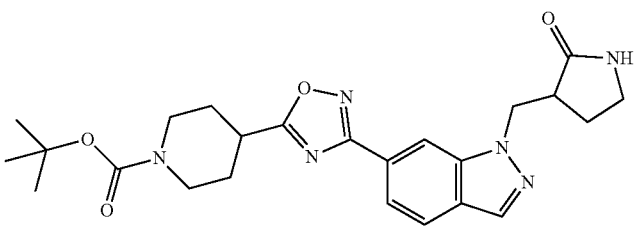 [SMILES: CC(C)(C)OC(=O)N1CCC(c2nc(-c3ccc4cnn(CC5CCNC5=O)c4c3)no2)CC1] |
| 646 | 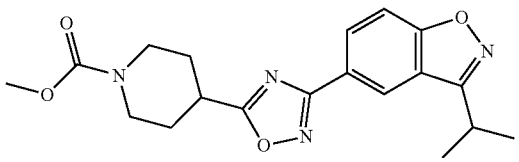 [SMILES: COC(=O)N1CCC(c2nc(-c3ccc4onc(C(C)C)c4c3)no2)CC1] |
| 647 | 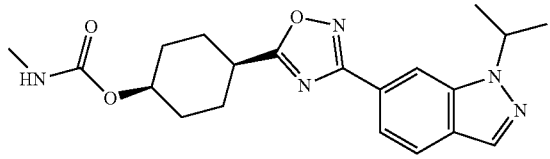 [SMILES: CNC(=O)O[C@H]1CC[C@@H](c2nc(-c3ccc4cnn(C(C)C)c4c3)no2)CC1] |

TABLE 1-continued

Compounds of the Invention

| # | Structure |
|---|---|
| 648 | 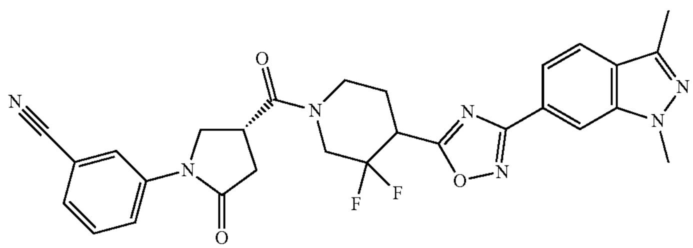 [SMILES: Cc1nn(C)c2cc(-c3noc(C4CCN(C(=O)[C@@H]5CC(=O)N(c6cccc(C#N)c6)C5)CC4(F)F)n3)ccc12] |
| 649 | 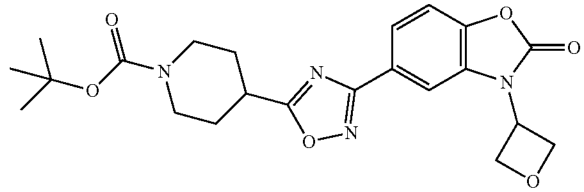 [SMILES: CC(C)(C)OC(=O)N1CCC(c2nc(-c3ccc4oc(=O)n(C5COC5)c4c3)no2)CC1] |
| 650 | 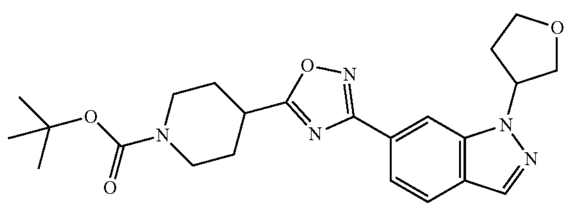 [SMILES: CC(C)(C)OC(=O)N1CCC(c2nc(-c3ccc4cnn(C5CCOC5)c4c3)no2)CC1] |
| 651 | 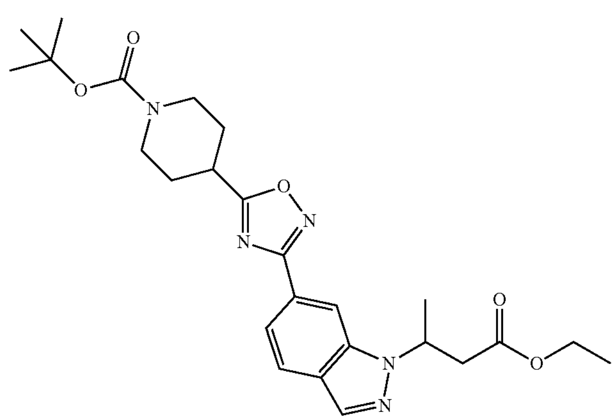 [SMILES: CCOC(=O)CC(C)n1ncc2ccc(-c3noc(C4CCN(C(=O)OC(C)(C)C)CC4)n3)cc21] |
| 652 | 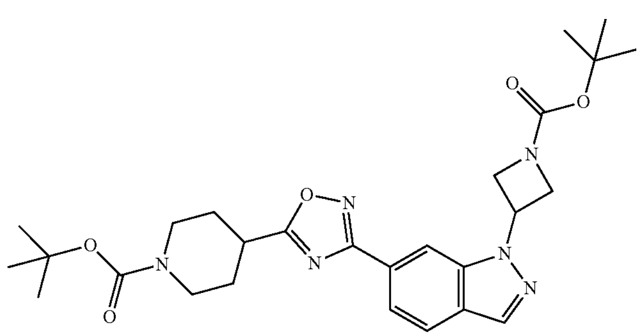 [SMILES: CC(C)(C)OC(=O)N1CCC(c2nc(-c3ccc4cnn(C5CN(C(=O)OC(C)(C)C)C5)c4c3)no2)CC1] |

TABLE 1-continued
Compounds of the Invention
| # | Structure |
|---|---|
| 653 | 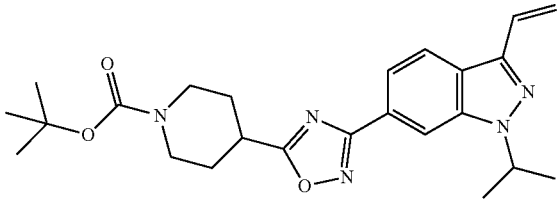 [SMILES: C=Cc1nn(C(C)C)c2cc(-c3noc(C4CCN(C(=O)OC(C)(C)C)CC4)n3)ccc12] |
| 654 | 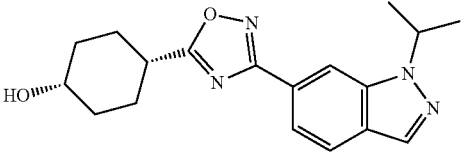 [SMILES: CC(C)n1ncc2ccc(-c3noc([C@H]4CC[C@@H](O)CC4)n3)cc21] |
| 655 | 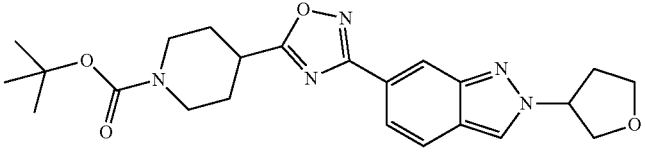 [SMILES: CC(C)(C)OC(=O)N1CCC(c2nc(-c3ccc4cn(C5CCOC5)nc4c3)no2)CC1] |
| 656 | 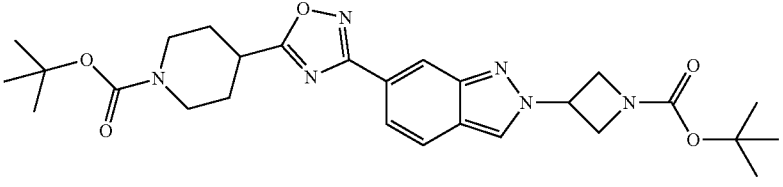 [SMILES: CC(C)(C)OC(=O)N1CCC(c2nc(-c3ccc4cn(C5CN(C(=O)OC(C)(C)C)C5)nc4c3)no2)CC1] |
| 657 | 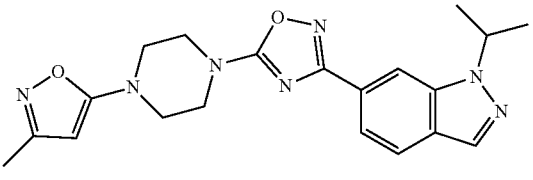 [SMILES: Cc1cc(N2CCN(c3nc(-c4ccc5cnn(C(C)C)c5c4)no3)CC2)on1] |
| 658 | 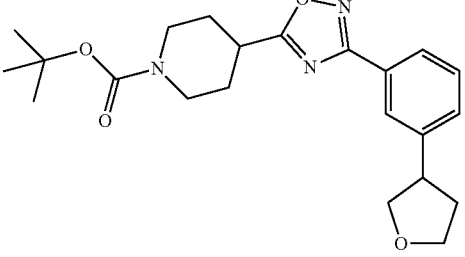 |
| 659 | 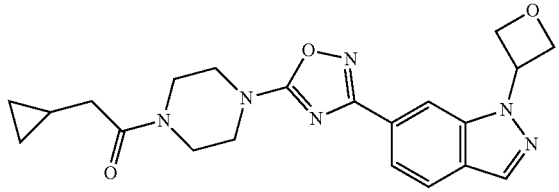 [SMILES: O=C(CC1CC1)N1CCN(c2nc(-c3ccc4cnn(C5COC5)c4c3)no2)CC1] |

TABLE 1-continued
Compounds of the Invention
| # | Structure |
|---|---|
| 660 | 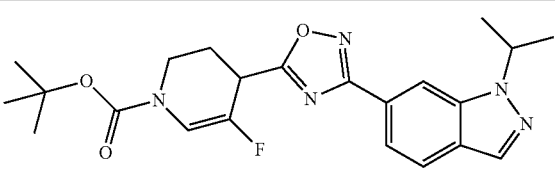 [SMILES: CC(C)n1ncc2ccc(-c3noc(C4CCN(C(=O)OC(C)(C)C)C=C4F)n3)cc21] |
| 661 | 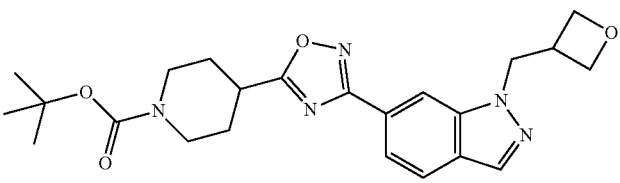 [SMILES: CC(C)(C)OC(=O)N1CCC(c2nc(-c3ccc4cnn(CC5COC5)c4c3)no2)CC1] |
| 662 | 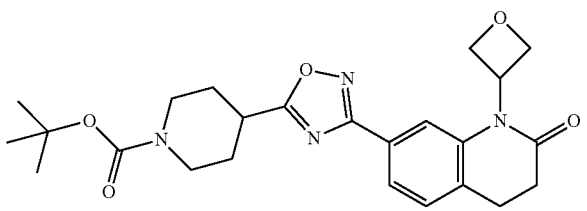 [SMILES: CC(C)(C)OC(=O)N1CCC(c2nc(-c3ccc4c(c3)N(C3COC3)C(=O)CC4)no2)CC1] |
| 663 | 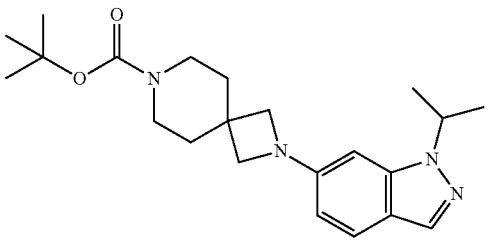 [SMILES: CC(C)n1ncc2ccc(N3CC4(CCN(C(=O)OC(C)(C)C)CC4)C3)cc21] |
| 664 | 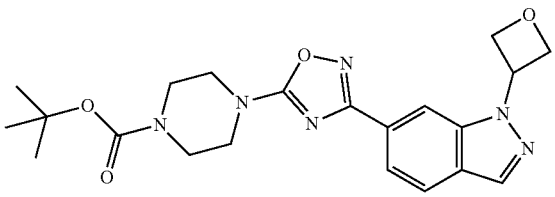 [SMILES: CC(C)(C)OC(=O)N1CCN(c2nc(-c3ccc4cnn(C5COC5)c4c3)no2)CC1] |
| 665 | 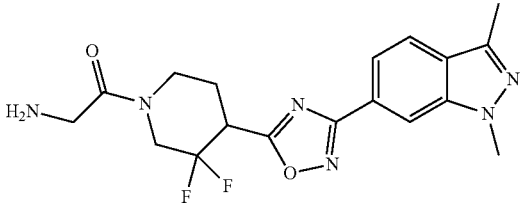 [SMILES: Cc1nn(C)c2cc(-c3noc(C4CCN(C(=O)CN)CC4(F)F)n3)ccc12] |
| 666 | 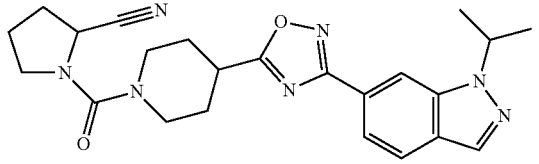 [SMILES: CC(C)n1ncc2ccc(-c3noc(C4CCN(C(=O)N5CCCC5C#N)CC4)n3)cc21] |

TABLE 1-continued

Compounds of the Invention

| # | Structure |
|---|---|
| 667 | 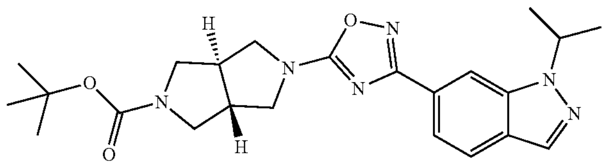 [SMILES: CC(C)n1ncc2ccc(-c3noc(N4C[C@@H]5CN(C(=O)OC(C)(C)C)C[C@H]5C4)n3)cc21] |
| 668 | 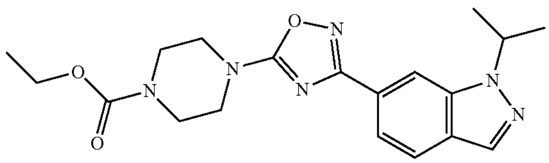 |
| 669 | 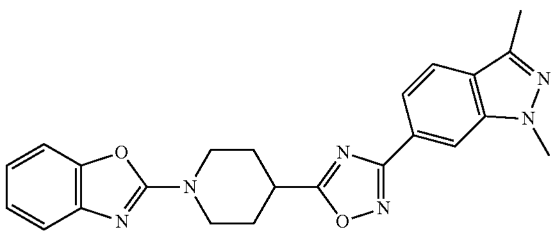 [SMILES: Cc1nn(C)c2cc(-c3noc(C4CCN(c5nc6ccccc6o5)CC4)n3)ccc12] |
| 670 | 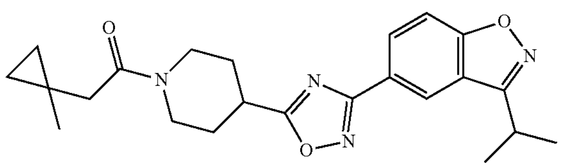 [SMILES: CC(C)c1noc2ccc(-c3noc(C4CCN(C(=O)CC5(C)CC5)CC4)n3)cc12] |
| 671 | 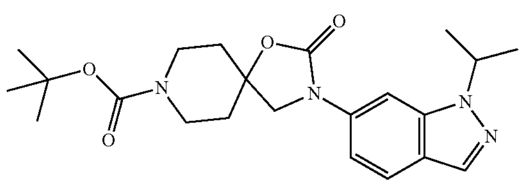 [SMILES: CC(C)n1ncc2ccc(N3CC4(CCN(C(=O)OC(C)(C)C)CC4)OC3=O)cc21] |
| 672 | 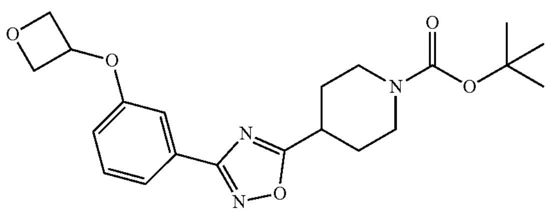 [SMILES: CC(C)(C)OC(=O)N1CCC(c2nc(-c3cccc(OC4COC4)c3)no2)CC1] |
| 673 | 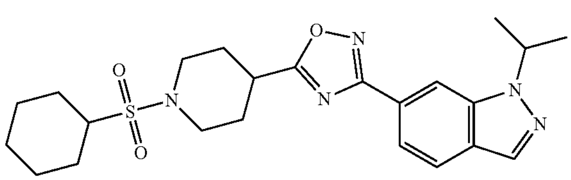 [SMILES: CC(C)n1ncc2ccc(-c3noc(C4CCN(S(=O)(=O)C5CCCCC5)CC4)n3)cc21] |
| 674 | 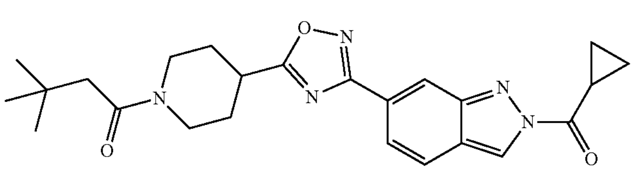 [SMILES: CC(C)(C)CC(=O)N1CCC(c2nc(-c3ccc4cn(C(=O)C5CC5)nc4c3)no2)CC1] |

TABLE 1-continued

Compounds of the Invention

| # | Structure |
|---|-----------|
| 675 | 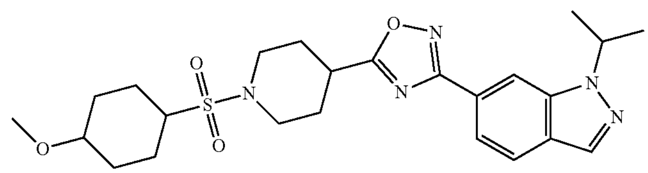 [SMILES: COC1CCC(S(=O)(=O)N2CCC(c3nc(-c4ccc5cnn(C(C)C)c5c4)no3)CC2)CC1] |
| 676 | 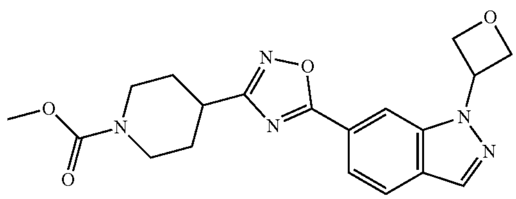 [SMILES: COC(=O)N1CCC(c2noc(-c3ccc4cnn(C5COC5)c4c3)n2)CC1] |
| 677 | 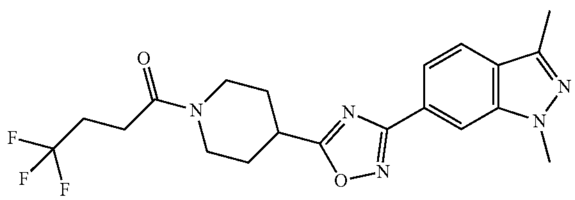 [SMILES: Cc1nn(C)c2cc(-c3noc(C4CCN(C(=O)CCC(F)(F)F)CC4)n3)ccc12] |
| 678 | 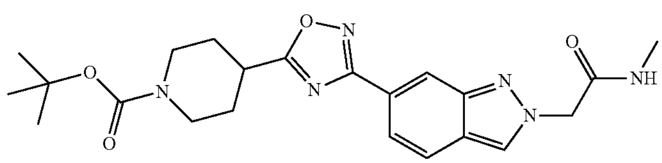 [SMILES: CNC(=O)Cn1cc2ccc(-c3noc(C4CCN(C(=O)OC(C)(C)C)CC4)n3)cc2n1] |
| 679 | 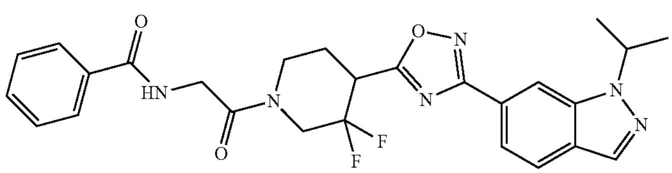 [SMILES: CC(C)n1ncc2ccc(-c3noc(C4CCN(C(=O)CNC(=O)c5ccccc5)CC4(F)F)n3)cc21] |
| 680 | 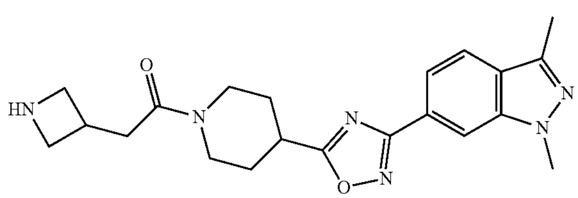 [SMILES: Cc1nn(C)c2cc(-c3noc(C4CCN(C(=O)CC5CNC5)CC4)n3)ccc12] |
| 681 | 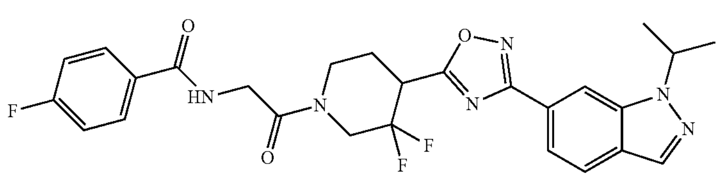 [SMILES: CC(C)n1ncc2ccc(-c3noc(C4CCN(C(=O)CNC(=O)c5ccc(F)cc5)CC4(F)F)n3)cc21] |
| 682 | 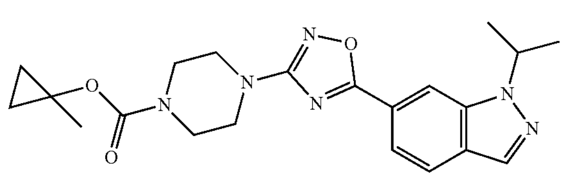 |

TABLE 1-continued

Compounds of the Invention

| # | Structure |
|---|---|
| 683 | 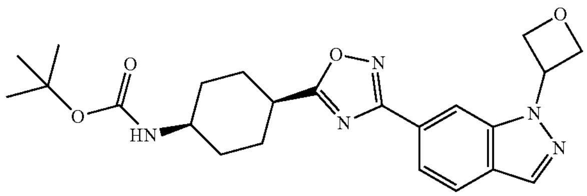 [SMILES: CC(C)(C)OC(=O)N[C@H]1CC[C@@H](c2nc(-c3ccc4cnn(C5COC5)c4c3)no2)CC1] |
| 684 | 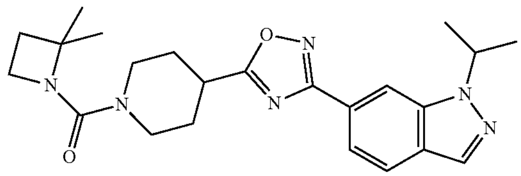 [SMILES: CC(C)n1ncc2ccc(-c3noc(C4CCN(C(=O)N5CCC5(C)C)CC4)n3)cc21] |
| 685 | 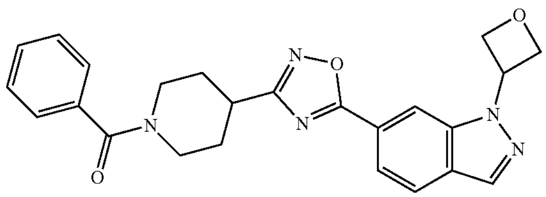 [SMILES: O=C(c1ccccc1)N1CCC(c2noc(-c3ccc4cnn(C5COC5)c4c3)n2)CC1] |
| 686 | 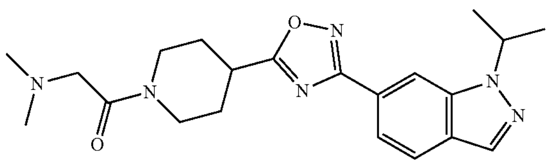 |
| 687 | 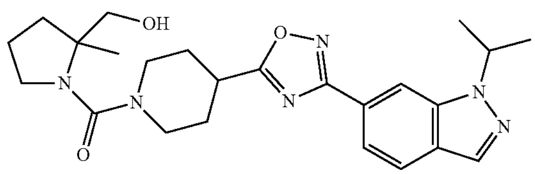 [SMILES: CC(C)n1ncc2ccc(-c3noc(C4CCN(C(=O)N5CCCC5(C)CO)CC4)n3)cc21] |
| 688 | 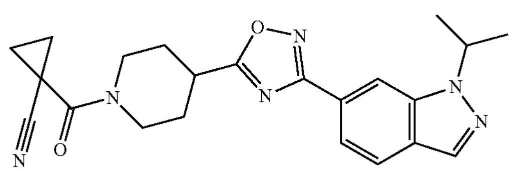 [SMILES: CC(C)n1ncc2ccc(-c3noc(C4CCN(C(=O)C5(C#N)CC5)CC4)n3)cc21] |
| 689 | 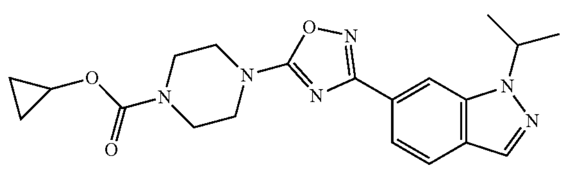 [SMILES: CC(C)n1ncc2ccc(-c3noc(N4CCN(C(=O)OC5CC5)CC4)n3)cc21] |
| 690 | 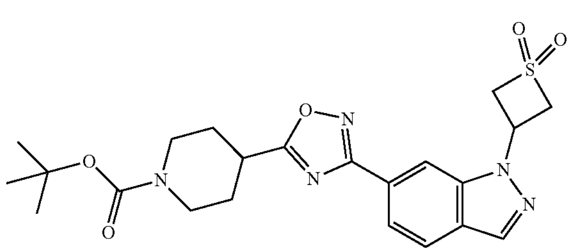 [SMILES: CC(C)(C)OC(=O)N1CCC(c2nc(-c3ccc4cnn(C5CS(=O)(=O)C5)c4c3)no2)CC1] |

US 11,970,486 B2
233                                                                234
TABLE 1-continued
Compounds of the Invention
| # | Structure |
|---|---|
| 691 | 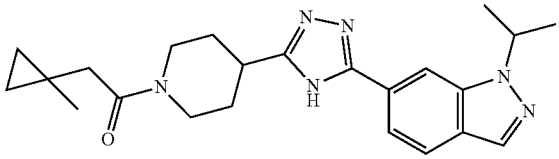 [SMILES: CC(C)n1ncc2ccc(-c3nnc(C4CCN(C(=O)CC5(C)CC5)CC4)[nH]3)cc21] |
| 692 | 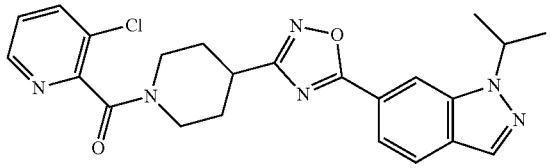 |
| 693 | 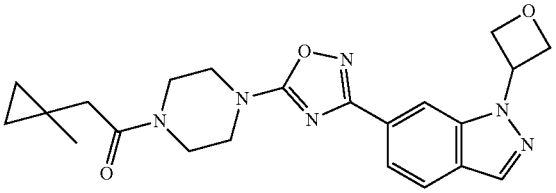 |
| 694 | 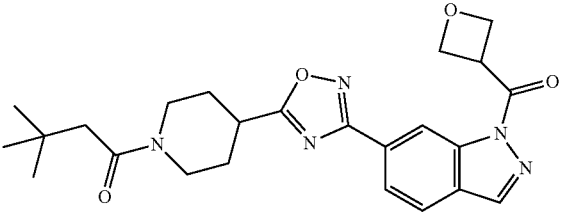 [SMILES: CC(C)(C)CC(=O)N1CCC(c2nc(-c3ccc4cnn(C(=O)C5COC5)c4c3)no2)CC1] |
| 695 | 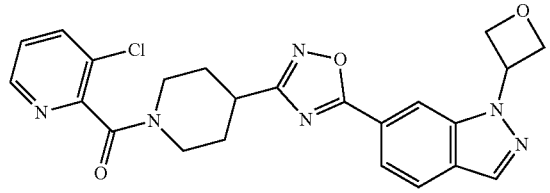 [SMILES: O=C(c1ncccc1Cl)N1CCC(c2noc(-c3ccc4cnn(C5COC5)c4c3)n2)CC1] |
| 696 | 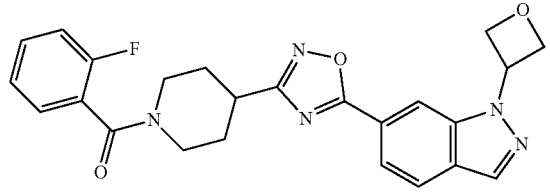 [SMILES: O=C(c1ccccc1F)N1CCC(c2noc(-c3ccc4cnn(C5COC5)c4c3)n2)CC1] |
| 697 | 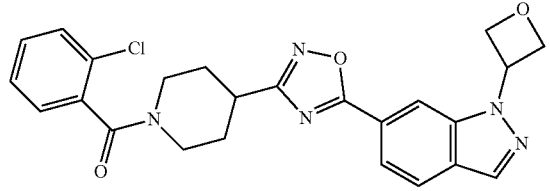 [SMILES: O=C(c1ccccc1Cl)N1CCC(c2noc(-c3ccc4cnn(C5COC5)c4c3)n2)CC1] |

TABLE 1-continued
Compounds of the Invention
| # | Structure |
|---|---|
| 698 | 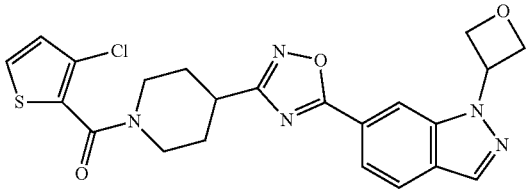 [SMILES: O=C(c1sccc1Cl)N1CCC(c2noc(-c3ccc4cnn(C5COC5)c4c3)n2)CC1] |
| 699 | 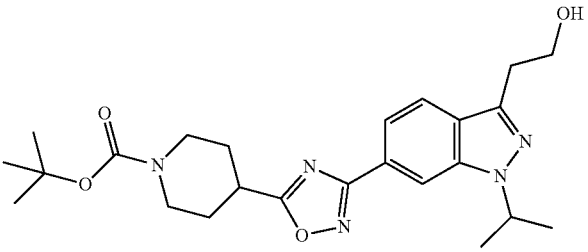 [SMILES: CC(C)n1nc(CCO)c2ccc(-c3noc(C4CCN(C(=O)OC(C)(C)C)CC4)n3)cc21] |
| 700 | 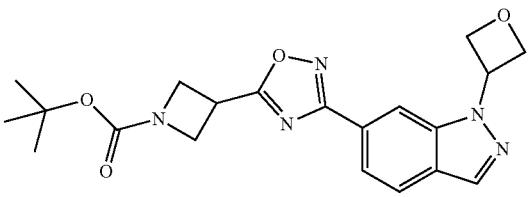 |
| 701 | 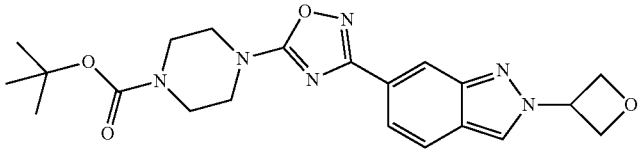 [SMILES: CC(C)(C)OC(=O)N1CCN(c2nc(-c3ccc4cn(C5COC5)nc4c3)no2)CC1] |
| 702 | 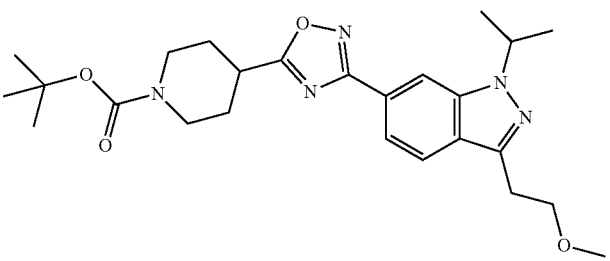 [SMILES: COCCc1nn(C(C)C)c2cc(-c3noc(C4CCN(C(=O)OC(C)(C)C)CC4)n3)ccc12] |
| 703 | 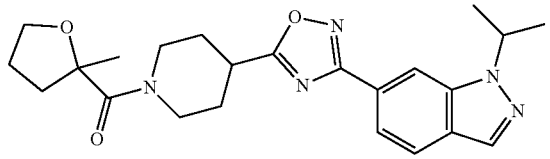 [SMILES: CC(C)n1ncc2ccc(-c3noc(C4CCN(C(=O)C5(C)CCCO5)CC4)n3)cc21] |
| 704 | 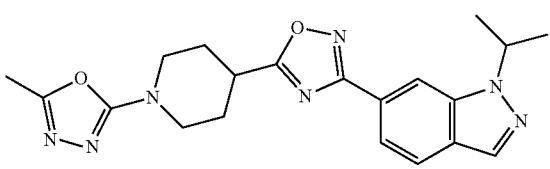 [SMILES: Cc1nnc(N2CCC(c3nc(-c4ccc5cnn(C(C)C)c5c4)no3)CC2)o1] |

US 11,970,486 B2
237                                                                 238
TABLE 1-continued
Compounds of the Invention
| # | Structure |
|---|---|
| 705 | 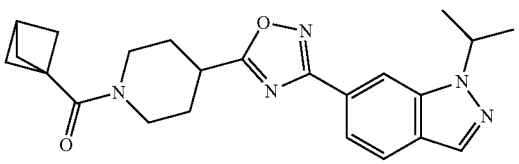 [SMILES: CC(C)n1ncc2ccc(-c3noc(C4CCN(C(=O)C56CC(C5)C6)CC4)n3)cc21] |
| 706 | 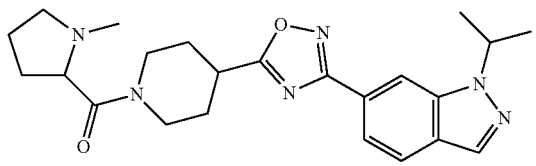 [SMILES: CC(C)n1ncc2ccc(-c3noc(C4CCN(C(=O)C5CCCN5C)CC4)n3)cc21] |
| 707 | 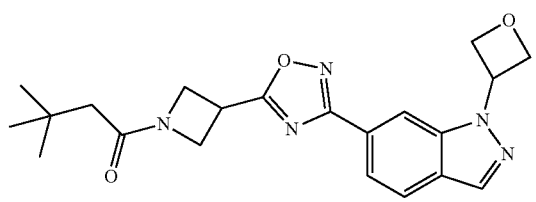 [SMILES: CC(C)(C)CC(=O)N1CC(c2nc(-c3ccc4cnn(C5COC5)c4c3)no2)C1] |
| 708 | 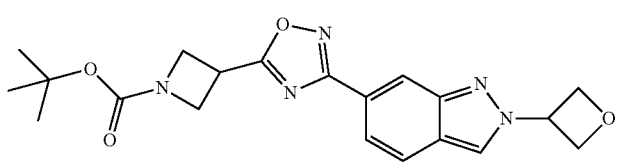 [SMILES: CC(C)(C)OC(=O)N1CC(c2nc(-c3ccc4cn(C5COC5)nc4c3)no2)C1] |
| 709 | 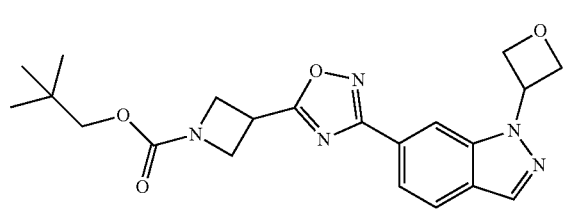 [SMILES: CC(C)(C)COC(=O)N1CC(c2nc(-c3ccc4cnn(C5COC5)c4c3)no2)C1] |
| 710 | 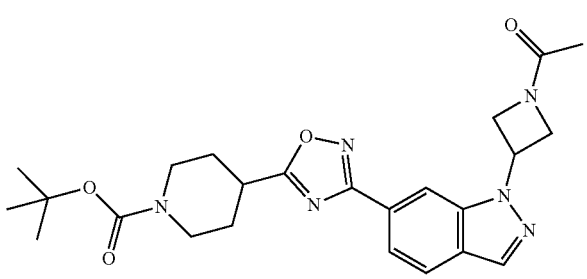 [SMILES: CC(=O)N1CC(n2ncc3ccc(-c4noc(C5CCN(C(=O)OC(C)(C)C)CC5)n4)cc32)C1] |
| 711 | 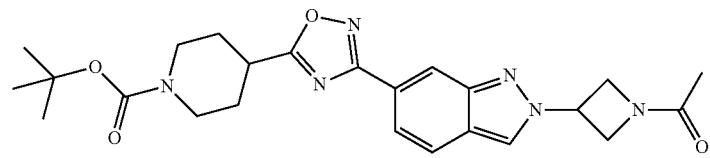 [SMILES: CC(=O)N1CC(n2cc3ccc(-c4noc(C5CCN(C(=O)OC(C)(C)C)CC5)n4)cc3n2)C1] |
| 712 | 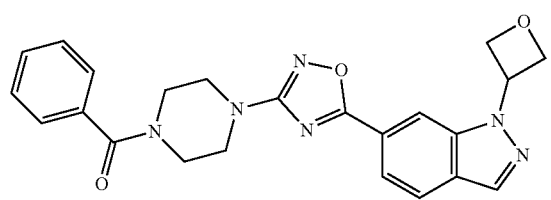 [SMILES: O=C(c1ccccc1)N1CCN(c2noc(-c3ccc4cnn(C5COC5)c4c3)n2)CC1] |

TABLE 1-continued

Compounds of the Invention

| # | Structure |
|---|---|
| 713 | 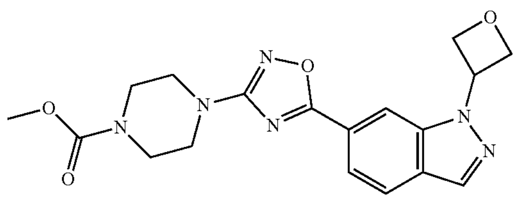 [SMILES: COC(=O)N1CCN(c2noc(-c3ccc4cnn(C5COC5)c4c3)n2)CC1] |
| 714 | 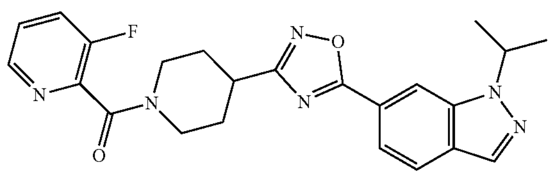 [SMILES: CC(C)n1ncc2ccc(-c3nc(C4CCN(C(=O)c5ncccc5F)CC4)no3)cc21] |
| 715 | 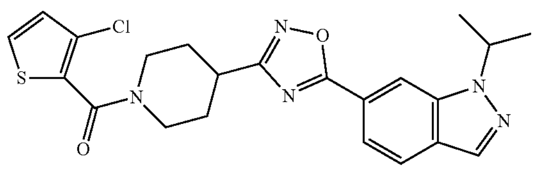 [SMILES: CC(C)n1ncc2ccc(-c3nc(C4CCN(C(=O)c5sccc5Cl)CC4)no3)cc21] |
| 716 | 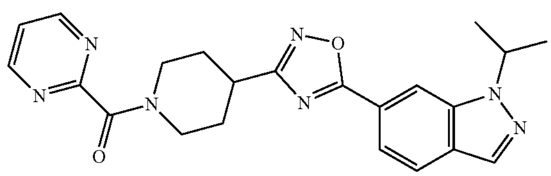 [SMILES: CC(C)n1ncc2ccc(-c3nc(C4CCN(C(=O)c5ncccn5)CC4)no3)cc21] |
| 717 | 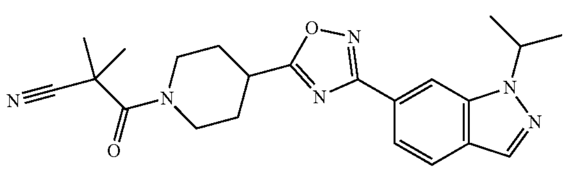 [SMILES: CC(C)n1ncc2ccc(-c3noc(C4CCN(C(=O)C(C)(C)C#N)CC4)n3)cc21] |
| 718 | 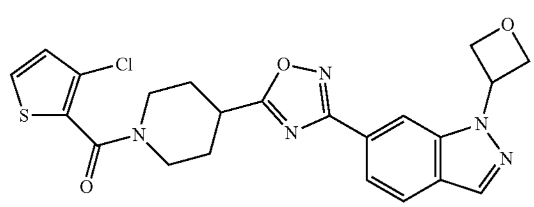 [SMILES: O=C(c1sccc1Cl)N1CCC(c2nc(-c3ccc4cnn(C5COC5)c4c3)no2)CC1] |
| 719 | 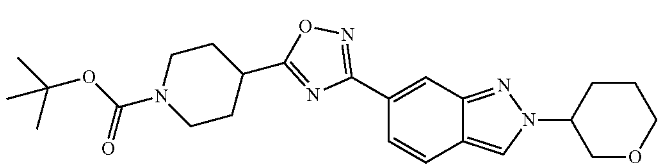 [SMILES: CC(C)(C)OC(=O)N1CCC(c2nc(-c3ccc4cn(C5CCCOC5)nc4c3)no2)CC1] |
| 720 | 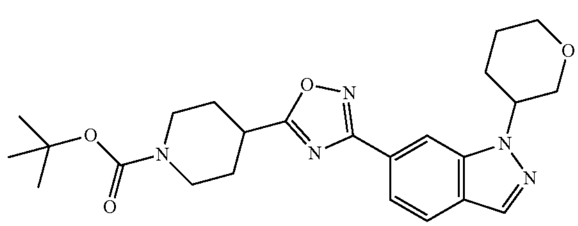 [SMILES: CC(C)(C)OC(=O)N1CCC(c2nc(-c3ccc4cnn(C5CCCOC5)c4c3)no2)CC1] |

TABLE 1-continued

Compounds of the Invention

| # | Structure |
|---|---|
| 721 | 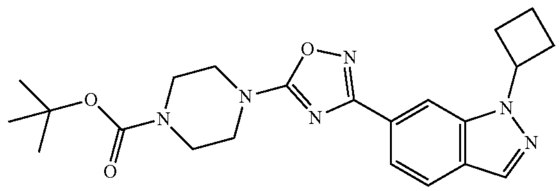 [SMILES: CC(C)(C)OC(=O)N1CCN(c2nc(-c3ccc4cnn(C5CCC5)c4c3)no2)CC1] |
| 722 | 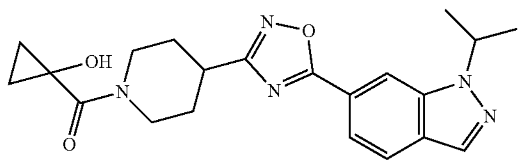 [SMILES: CC(C)n1ncc2ccc(-c3nc(C4CCN(C(=O)C5(O)CC5)CC4)no3)cc21] |
| 723 | 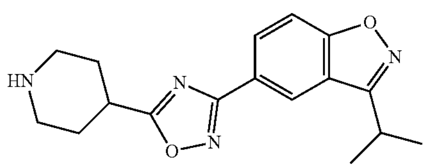 [SMILES: CC(C)c1noc2ccc(-c3noc(C4CCNCC4)n3)cc12] |
| 724 | 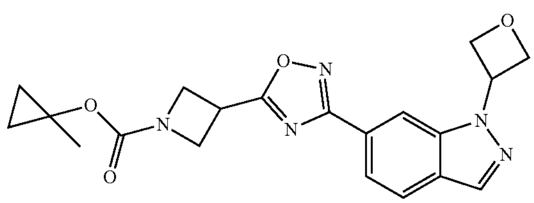 [SMILES: CC1(OC(=O)N2CC(c3nc(-c4ccc5cnn(C6COC6)c5c4)no3)C2)CC1] |
| 725 | 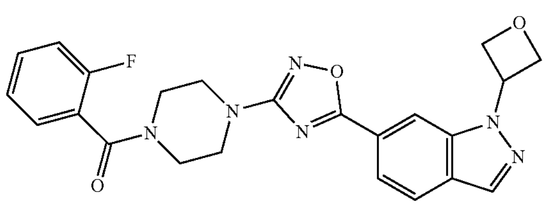 [SMILES: O=C(c1ccccc1F)N1CCN(c2noc(-c3ccc4cnn(C5COC5)c4c3)n2)CC1] |
| 726 | 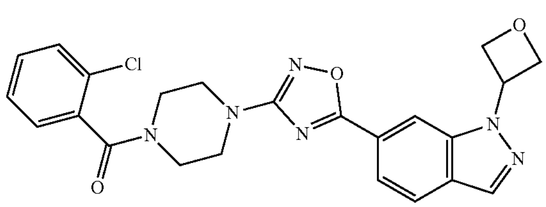 [SMILES: O=C(c1ccccc1Cl)N1CCN(c2noc(-c3ccc4cnn(C5COC5)c4c3)n2)CC1] |
| 727 | 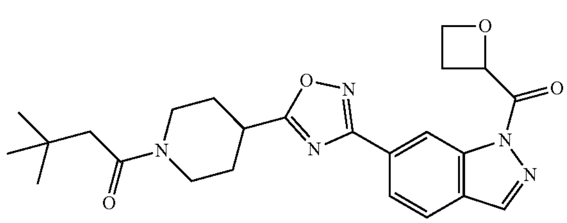 [SMILES: CC(C)(C)CC(=O)N1CCC(c2nc(-c3ccc4cnn(C(=O)C5CCO5)c4c3)no2)CC1] |

US 11,970,486 B2
243                                                                244
TABLE 1-continued
Compounds of the Invention
| # | Structure |
|---|-----------|
| 728 | 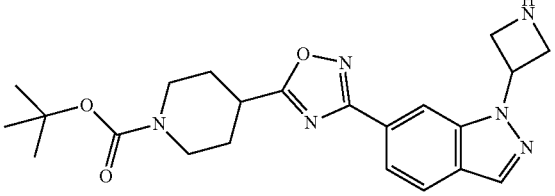 |
| 729 | 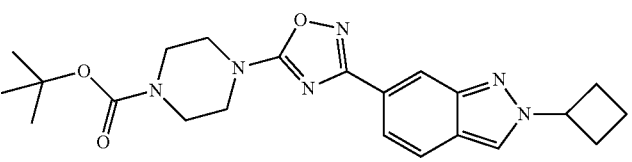 [SMILES: CC(C)(C)OC(=O)N1CCN(c2nc(-c3ccc4cn(C5CCC5)nc4c3)no2)CC1] |
| 730 | 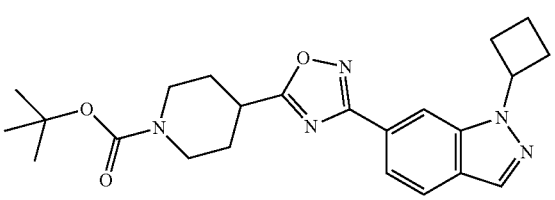 [SMILES: CC(C)(C)OC(=O)N1CCC(c2nc(-c3ccc4cnn(C5CCC5)c4c3)no2)CC1] |
| 731 | 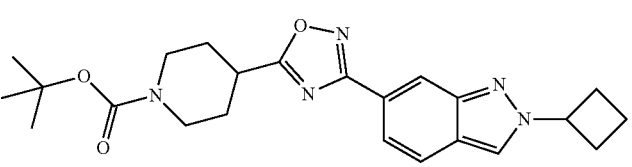 [SMILES: CC(C)(C)OC(=O)N1CCC(c2nc(-c3ccc4cn(C5CCC5)nc4c3)no2)CC1] |
| 732 | 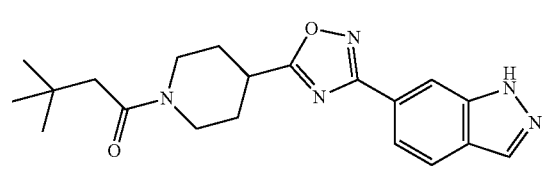 [SMILES: CC(C)(C)CC(=O)N1CCC(c2nc(-c3ccc4cn[nH]c4c3)no2)CC1] |
| 733 | 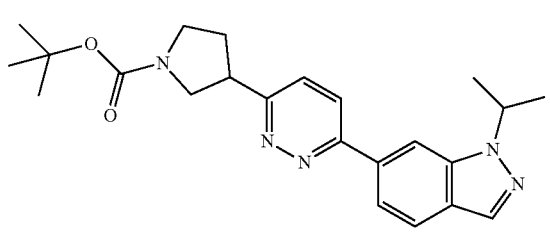 [SMILES: CC(C)n1ncc2ccc(-c3ccc(C4CCN(C(=O)OC(C)(C)C)C4)nn3)cc21] |
| 734 | 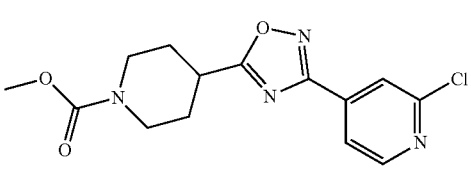 [SMILES: COC(=O)N1CCC(c2nc(-c3ccnc(Cl)c3)no2)CC1] |
| 735 | 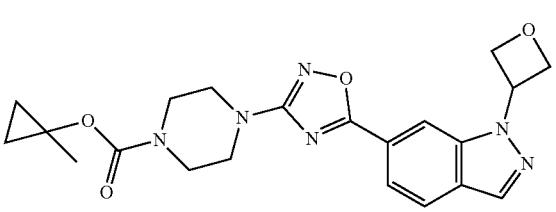 [SMILES: CC1(OC(=O)N2CCN(c3noc(-c4ccc5cnn(C6COC6)c5c4)n3)CC2)CC1] |

US 11,970,486 B2
TABLE 1-continued
Compounds of the Invention
| # | Structure |
|---|---|
| 736 | 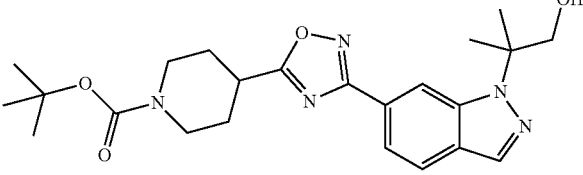 |
| 737 | 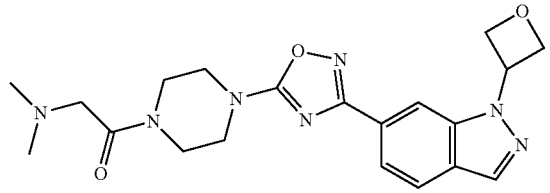 [SMILES: CN(C)CC(=O)N1CCN(c2nc(-c3ccc4cnn(C5COC5)c4c3)no2)CC1] |
| 738 | 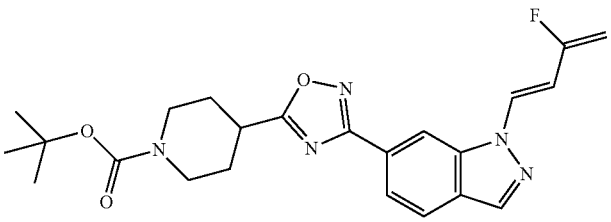 [SMILES: C=C(F)/C=C/n1ncc2ccc(-c3noc(C4CCN(C(=O)OC(C)(C)C)CC4)n3)cc21] |
| 739 | 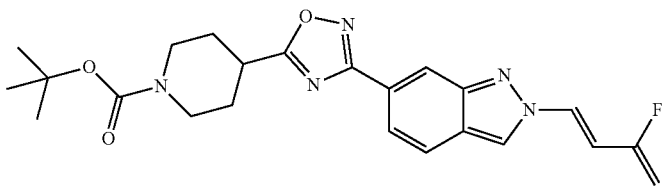 [SMILES: C=C(F)/C=C/n1cc2ccc(-c3noc(C4CCN(C(=O)OC(C)(C)C)CC4)n3)cc2n1] |
| 740 | 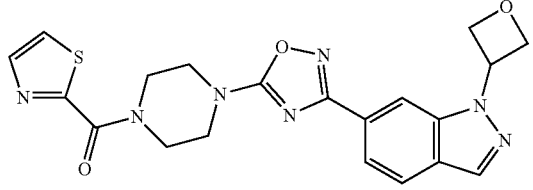 [SMILES: O=C(c1nccs1)N1CCN(c2nc(-c3ccc4cnn(C5COC5)c4c3)no2)CC1] |
| 741 | 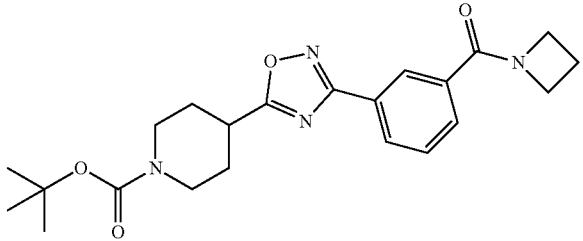 [SMILES: CC(C)(C)OC(=O)N1CCC(c2nc(-c3cccc(C(=O)N4CCC4)c3)no2)CC1] |
| 742 | 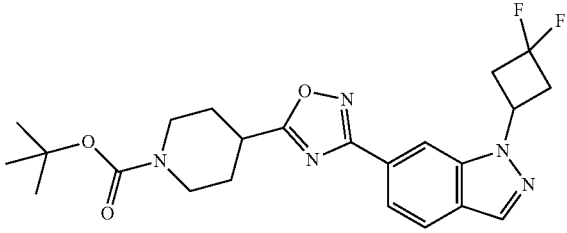 [SMILES: CC(C)(C)OC(=O)N1CCC(c2nc(-c3ccc4cnn(C5CC(F)(F)C5)c4c3)no2)CC1] |

247

TABLE 1-continued

Compounds of the Invention

| # | Structure |
|---|---|
| 743 | 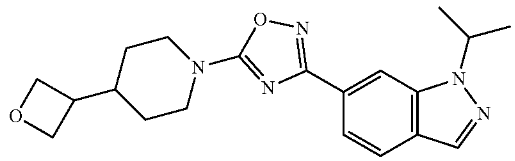 [SMILES: CC(C)n1ncc2ccc(-c3noc(N4CCC(C5COC5)CC4)n3)cc21] |
| 744 | 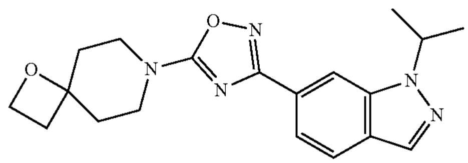 [SMILES: CC(C)n1ncc2ccc(-c3noc(N4CCC5(CCO5)CC4)n3)cc21] |
| 745 | 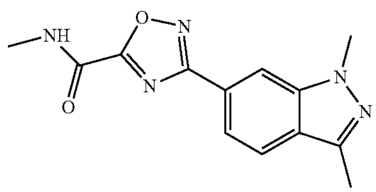 [SMILES: CNC(=O)c1nc(-c2ccc3c(C)nn(C)c3c2)no1] |
| 746 | 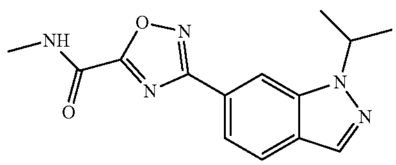 [SMILES: CNC(=O)c1nc(-c2ccc3cnn(C(C)C)c3c2)no1] |

TABLE 2

Compounds of the Invention

| # | Structure |
|---|---|
| 747 | 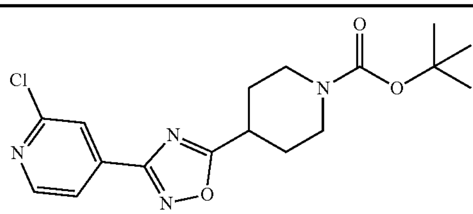 |
| 748 | 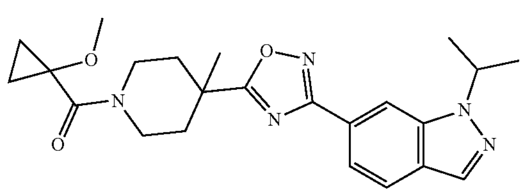 [SMILES: COC1(C(=O)N2CCC(C)(c3nc(-c4ccc5cnn(C(C)C)c5c4)no3)CC2)CC1] |
| 749 | 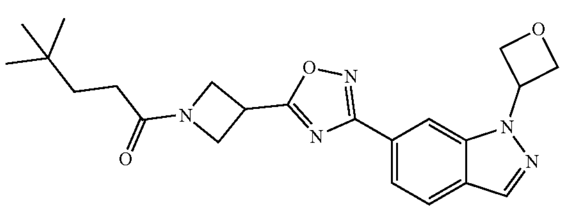 [SMILES: CC(C)(C)CCC(=O)N1CC(c2nc(-c3ccc4cnn(C5COC5)c4c3)no2)C1] |

248

US 11,970,486 B2
249                                                                                     250
TABLE 2-continued
Compounds of the Invention
| # | Structure |
|---|-----------|
| 750 | 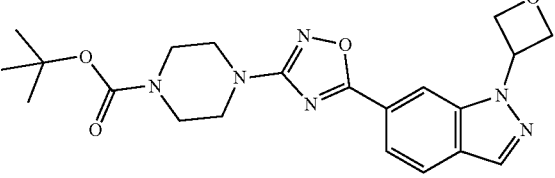 |
| 751 | 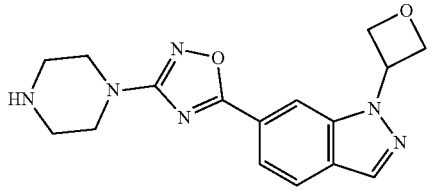 |
| 752 | 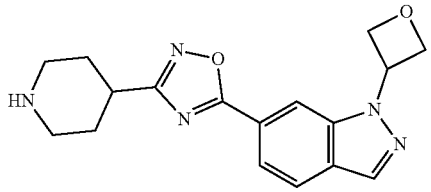 [SMILES: c1cc2cnn(C3COC3)c2cc1-c1nc(N2CCNCC2)no1] |
| 753 | 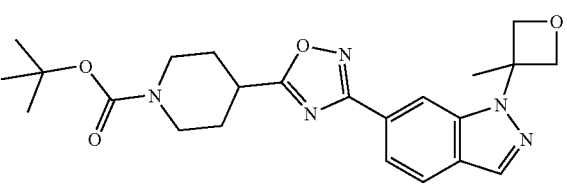 [SMILES: CC(C)(C)OC(=O)N1CCC(c2nc(-c3ccc4cnn(C5(C)COC5)c4c3)no2)CC1] |
| 754 | 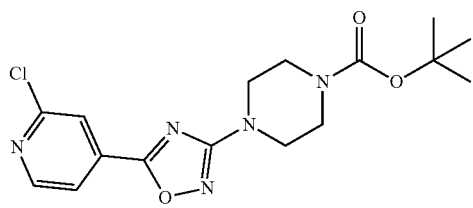 [SMILES: CC(C)(C)OC(=O)N1CCN(c2noc(-c3ccnc(Cl)c3)n2)CC1] |
| 755 | 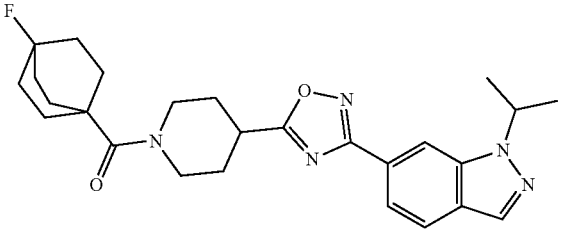 [SMILES: CC(C)n1ncc2ccc(-c3noc(C4CCN(C(=O)C56CCC(F)(CC5)CC6)CC4)n3)cc21] |
| 756 | 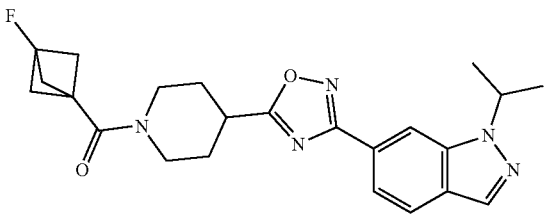 [SMILES: CC(C)n1ncc2ccc(-c3noc(C4CCN(C(=O)C56CC(F)(C5)C6)CC4)n3)cc21] |

TABLE 2-continued

| Compounds of the Invention | |
|---|---|
| # | Structure |
| 757 | |
| 758 | |
| 759 | |
| 760 | |
| 761 | |
| 762 | |

TABLE 2-continued

| # | Structure |
|---|---|
| 763 | (structure) |
| 764 | (structure) |
| 765 | (structure) |
| 766 | (structure) |
| 767 | (structure) |
| 768 | (structure) |

TABLE 2-continued

Compounds of the Invention

| # | Structure |
|---|---|
| 769 | *(structure)* |
| 770 | *(structure)* |
| 771 | *(structure)* |
| 772 | *(structure)* |
| 773 | *(structure)* |
| 774 | *(structure)* |

TABLE 2-continued

Compounds of the Invention

| # | Structure |
|---|-----------|
| 775 | 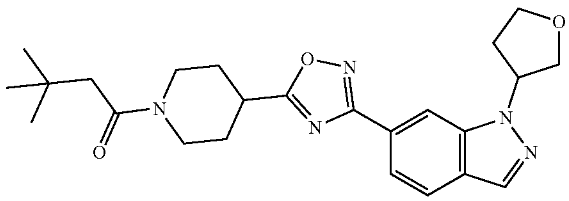 [SMILES: CC(C)(C)CC(=O)N1CCC(c2nc(-c3ccc4cnn(C5CCOC5)c4c3)no2)CC1] |
| 776 | 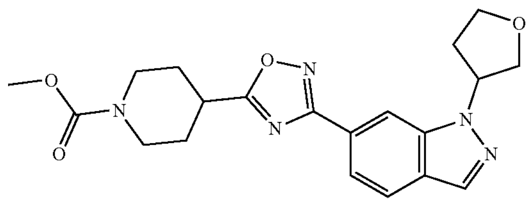 [SMILES: COC(=O)N1CCC(c2nc(-c3ccc4cnn(C5CCOC5)c4c3)no2)CC1] |
| 777 | 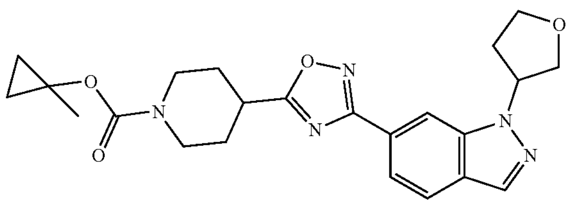 [SMILES: CC1(OC(=O)N2CCC(c3nc(-c4ccc5cnn(C6CCOC6)c5c4)no3)CC2)CC1] |
| 778 | 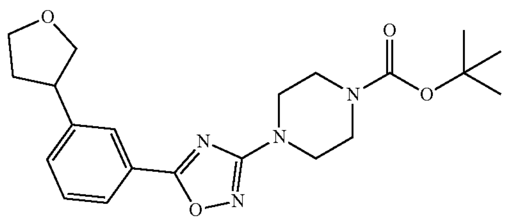 [SMILES: CC(C)(C)OC(=O)N1CCN(c2noc(-c3cccc(C4CCOC4)c3)n2)CC1] |
| 779 | 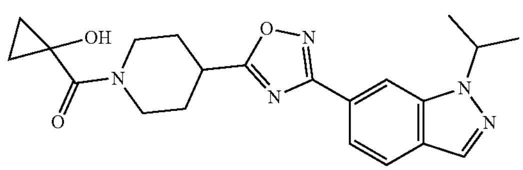 [SMILES: CC(C)n1ncc2ccc(-c3noc(C4CCN(C(=O)C5(O)CC5)CC4)n3)cc21] |
| 780 | 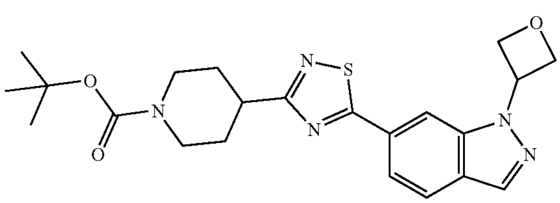 [SMILES: CC(C)(C)OC(=O)N1CCC(c2nsc(-c3ccc4cnn(C5COC5)c4c3)n2)CC1] |
| 781 | 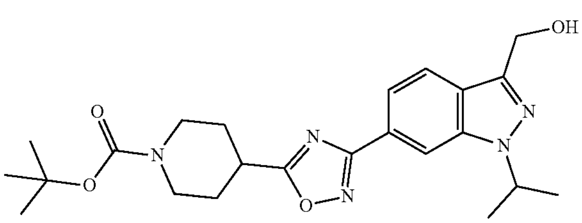 [SMILES: CC(C)n1nc(CO)c2ccc(-c3noc(C4CCN(C(=O)OC(C)(C)C)CC4)n3)cc21] |

TABLE 2-continued

Compounds of the Invention

| # | Structure |
|---|---|
| 782 | 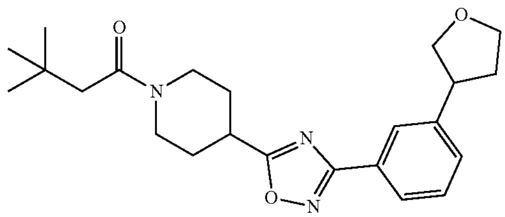 [SMILES: CC(C)(C)CC(=O)N1CCC(c2nc(-c3cccc(C4CCOC4)c3)no2)CC1] |
| 783 | 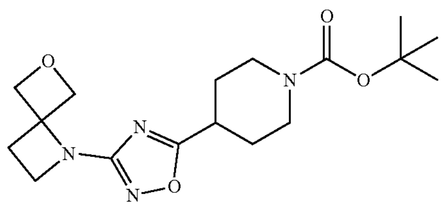 [SMILES: CC(C)(C)OC(=O)N1CCC(c2nc(N3CCC34COC4)no2)CC1] |
| 784 | 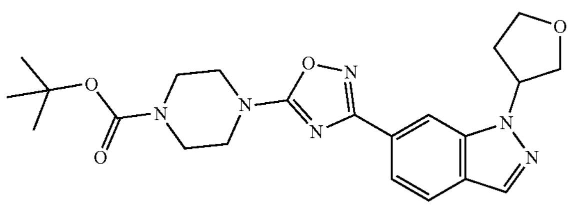 [SMILES: CC(C)(C)OC(=O)N1CCN(c2nc(-c3ccc4cnn(C5CCOC5)c4c3)no2)CC1] |
| 785 | 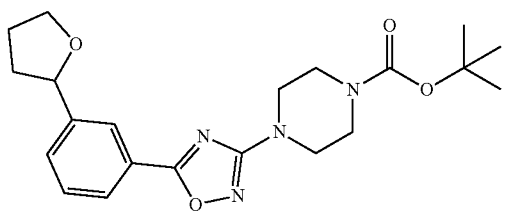 [SMILES: CC(C)(C)OC(=O)N1CCN(c2noc(-c3cccc(C4CCCO4)c3)n2)CC1] |
| 786 | 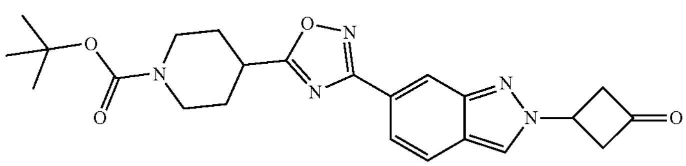 [SMILES: CC(C)(C)OC(=O)N1CCC(c2nc(-c3ccc4cn(C5CC(=O)C5)nc4c3)no2)CC1] |
| 787 | 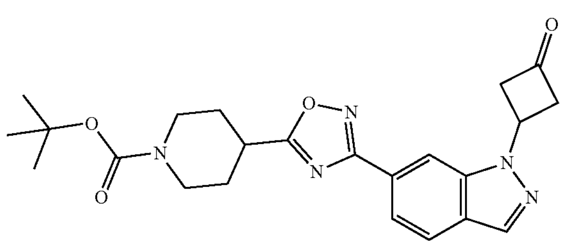 [SMILES: CC(C)(C)OC(=O)N1CCC(c2nc(-c3ccc4cnn(C5CC(=O)C5)c4c3)no2)CC1] |
| 788 | 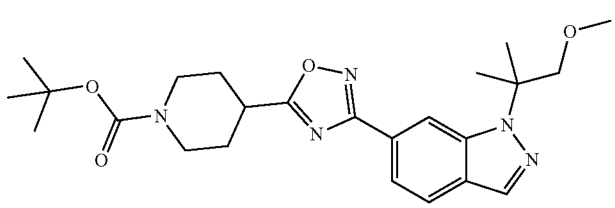 [SMILES: COCC(C)(C)n1ncc2ccc(-c3noc(C4CCN(C(=O)OC(C)(C)C)CC4)n3)cc21] |

TABLE 2-continued

| Compounds of the Invention | |
|---|---|
| # | Structure |
| 789 | |
| 790 | |
| 791 | |
| 792 | |
| 793 | |
| 794 | |
| 795 | |

TABLE 2-continued
Compounds of the Invention
| # | Structure |
|---|---|
| 796 | 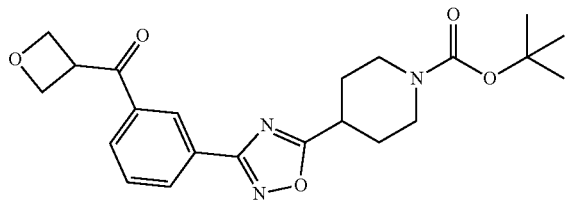 [SMILES: CC(C)(C)OC(=O)N1CCC(c2nc(-c3cccc(C(=O)C4COC4)c3)no2)CC1] |
| 797 | 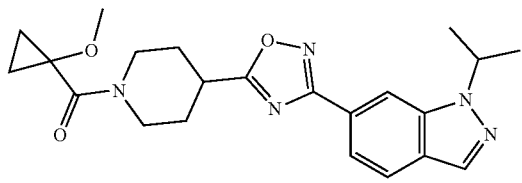 |
| 798 | 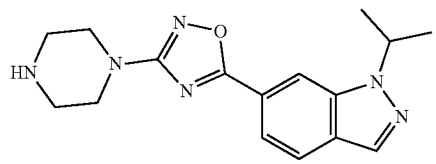 [SMILES: CC(C)n1ncc2ccc(-c3nc(N4CCNCC4)no3)cc21] |
| 799 | 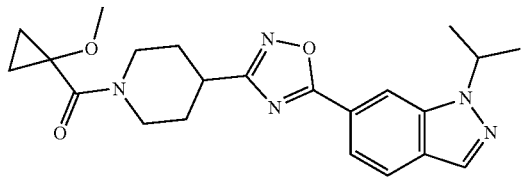 [SMILES: COC1(C(=O)N2CCC(c3noc(-c4ccc5cnn(C(C)C)c5c4)n3)CC2)CC1] |
| 801 | 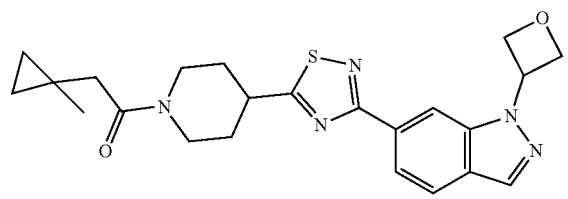 [SMILES: CC1(CC(=O)N2CCC(c3nc(-c4ccc5cnn(C6COC6)c5c4)ns3)CC2)CC1] |
| 802 | 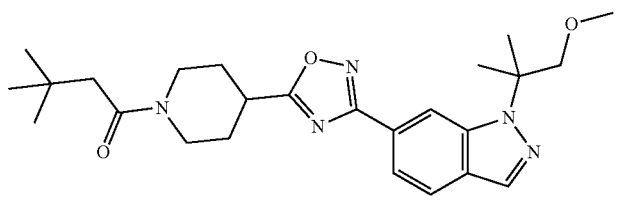 [SMILES: COCC(C)(C)n1ncc2ccc(-c3noc(C4CCN(C(=O)CC(C)(C)C)CC4)n3)cc21] |
| 803 | 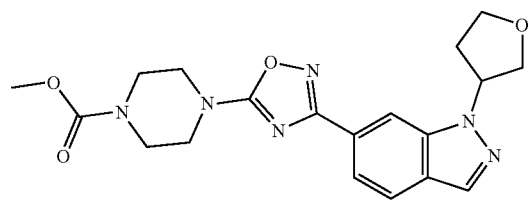 [SMILES: COC(=O)N1CCN(c2nc(-c3ccc4cnn(C5CCOC5)c4c3)no2)CC1] |

TABLE 2-continued

| # | Structure |
|---|---|
| 804 | 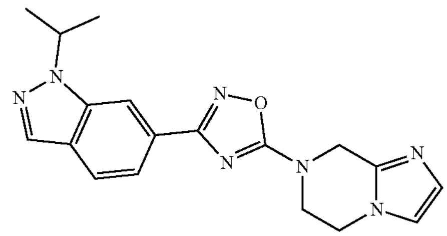 [SMILES: CC(C)n1ncc2ccc(-c3noc(N4CCn5ccnc5C4)n3)cc21] |
| 805 | 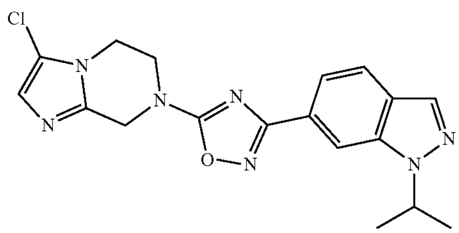 [SMILES: CC(C)n1ncc2ccc(-c3noc(N4CCn5c(Cl)cnc5C4)n3)cc21] |
| 806 | 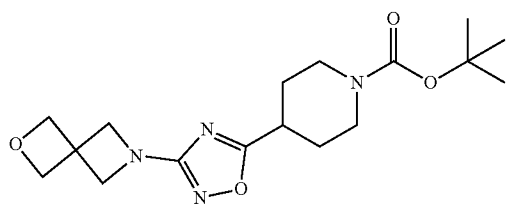 [SMILES: CC(C)(C)OC(=O)N1CCC(c2nc(N3CC4(COC4)C3)no2)CC1] |
| 807 | 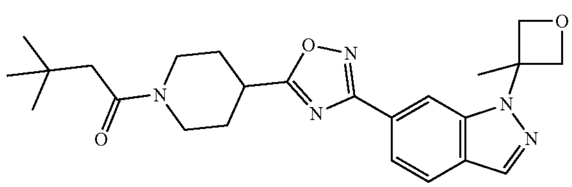 [SMILES: CC(C)(C)CC(=O)N1CCC(c2nc(-c3ccc4cnn(C5(C)COC5)c4c3)no2)CC1] |
| 808 | 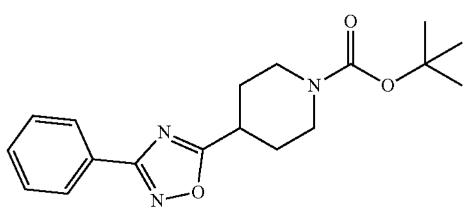 [SMILES: CC(C)(C)OC(=O)N1CCC(c2nc(-c3ccccc3)no2)CC1] |
| 809 | 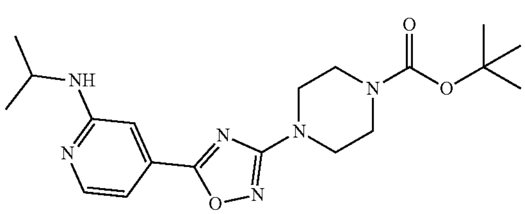 [SMILES: CC(C)Nc1cc(-c2nc(N3CCN(C(=O)OC(C)(C)C)CC3)no2)ccn1] |
| 810 | 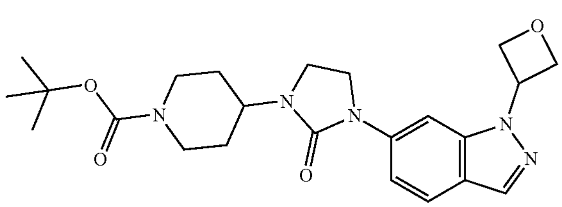 [SMILES: CC(C)(C)OC(=O)N1CCC(N2CCN(c3ccc4cnn(C5COC5)c4c3)C2=O)CC1] |

TABLE 2-continued

Compounds of the Invention

| # | Structure |
|---|---|
| 811 | 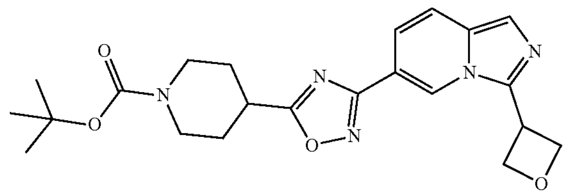 [SMILES: CC(C)(C)OC(=O)N1CCC(c2nc(-c3ccc4cnc(C5COC5)n4c3)no2)CC1] |
| 812 | 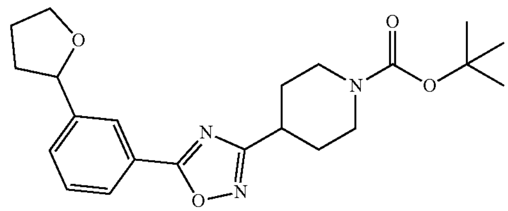 [SMILES: CC(C)(C)OC(=O)N1CCC(c2noc(-c3cccc(C4CCCO4)c3)n2)CC1] |
| 813 | 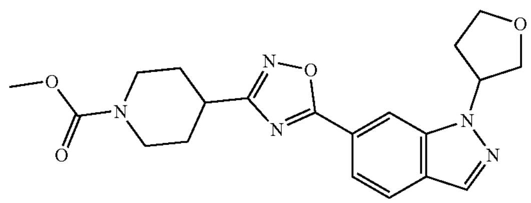 [SMILES: COC(=O)N1CCC(c2noc(-c3ccc4cnn(C5CCOC5)c4c3)n2)CC1] |
| 814 | 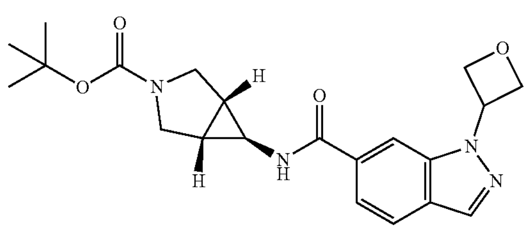 [SMILES: CC(C)(C)OC(=O)N1C[C@@H]2[C@H](C1)[C@H]2NC(=O)c1ccc2cnn(C3COC3)c2c1] |
| 815 | 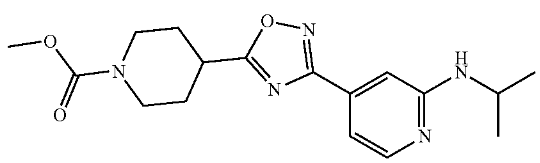 [SMILES: COC(=O)N1CCC(c2nc(-c3ccnc(NC(C)C)c3)no2)CC1] |
| 816 | 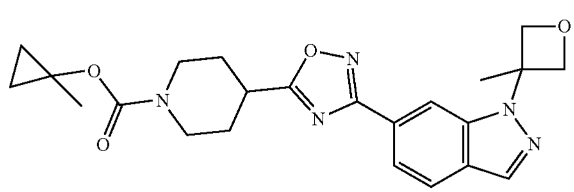 [SMILES: CC1(OC(=O)N2CCC(c3nc(-c4ccc5cnn(C6(C)COC6)c5c4)no3)CC2)CC1] |
| 817 | 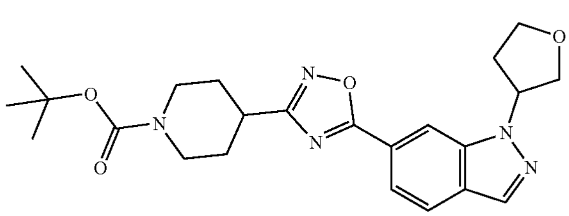 [SMILES: CC(C)(C)OC(=O)N1CCC(c2noc(-c3ccc4cnn(C5CCOC5)c4c3)n2)CC1] |

TABLE 2-continued

Compounds of the Invention

| # | Structure |
|---|---|
| 818 | 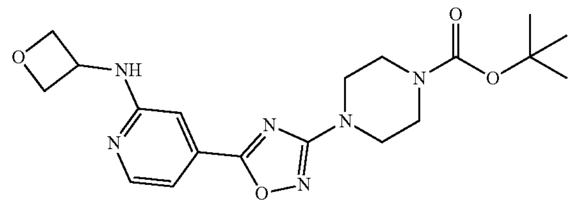 [SMILES: CC(C)(C)OC(=O)N1CCN(c2noc(-c3ccnc(NC4COC4)c3)n2)CC1] |
| 819 | 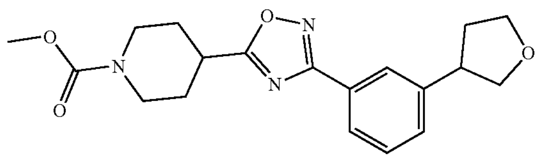 [SMILES: COC(=O)N1CCC(c2nc(-c3cccc(C4CCOC4)c3)no2)CC1] |
| 820 | 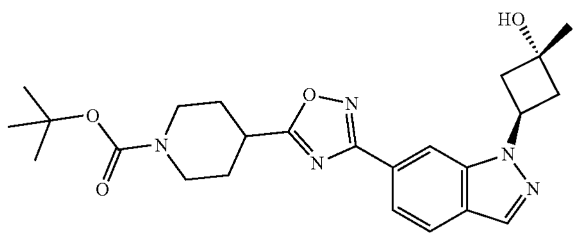 [SMILES: CC(C)(C)OC(=O)N1CCC(c2nc(-c3ccc4cnn([C@H]5C[C@](C)(O)C5)c4c3)no2)CC1] |
| 821 | 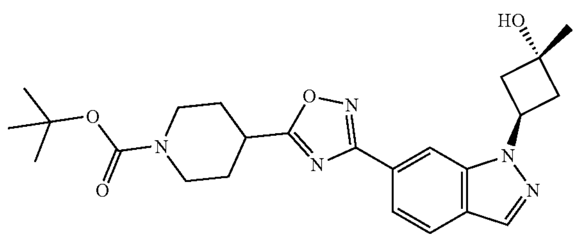 [SMILES: CC(C)(C)OC(=O)N1CCC(c2nc(-c3ccc4cnn([C@H]5C[C@](C)(O)C5)c4c3)no2)CC1] |
| 822 | 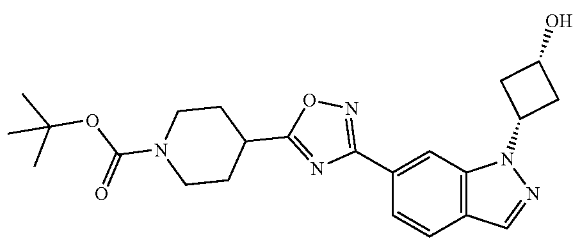 [SMILES: CC(C)(C)OC(=O)N1CCC(c2nc(-c3ccc4cnn([C@H]5C[C@@H](O)C5)c4c3)no2)CC1] |
| 823 | 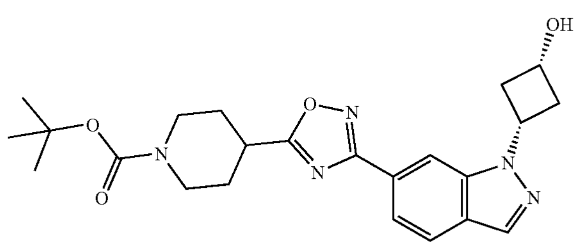 [SMILES: CC(C)(C)OC(=O)N1CCC(c2nc(-c3ccc4cnn([C@H]5C[C@@H](O)C5)c4c3)no2)CC1] |
| 824 | 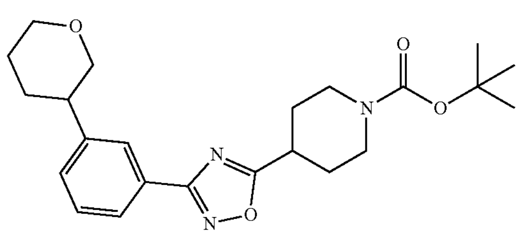 [SMILES: CC(C)(C)OC(=O)N1CCC(c2nc(-c3cccc(C4CCCOC4)c3)no2)CC1] |

TABLE 2-continued

Compounds of the Invention

| # | Structure |
|---|---|
| 825 | (structure) |
| 826 | (structure) |
| 827 | (structure) |
| 828 | (structure) |
| 829 | (structure) |
| 830 | (structure) |
| 831 | (structure) |
| 832 | (structure) |

TABLE 2-continued
Compounds of the Invention
| # | Structure |
|---|---|
| 833 | 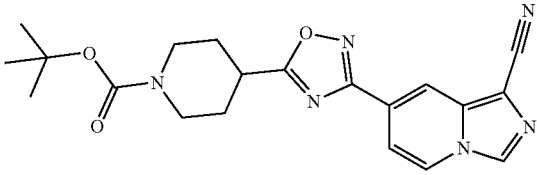 [SMILES: CC(C)(C)OC(=O)N1CCC(c2nc(-c3ccn4cnc(C#N)c4c3)no2)CC1] |
| 834 | 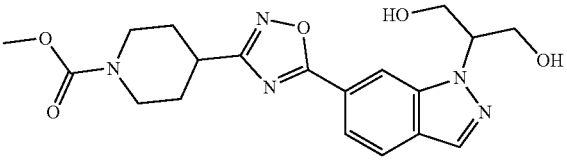 [SMILES: COC(=O)N1CCC(c2noc(-c3ccc4cnn(C(CO)CO)c4c3)n2)CC1] |
| 835 | 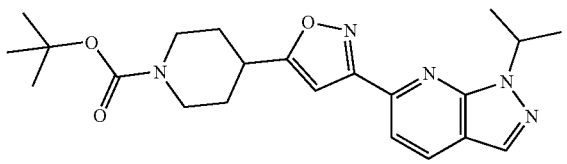 [SMILES: CC(C)n1ncc2ccc(-c3cc(C4CCN(C(=O)OC(C)(C)C)CC4)on3)nc21] |
| 836 | 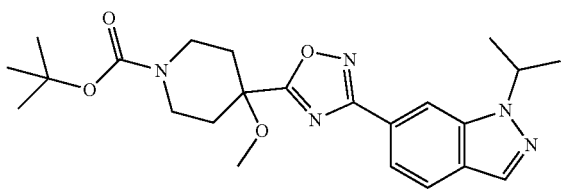 [SMILES: COC1(c2nc(-c3ccc4cnn(C(C)C)c4c3)no2)CCN(C(=O)OC(C)(C)C)CC1] |
| 837 | 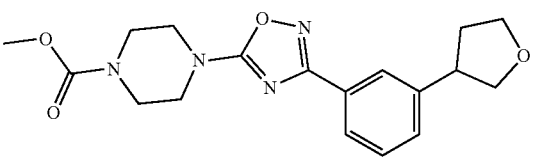 [SMILES: COC(=O)N1CCN(c2nc(-c3cccc(C4CCOC4)c3)no2)CC1] |
| 838 | 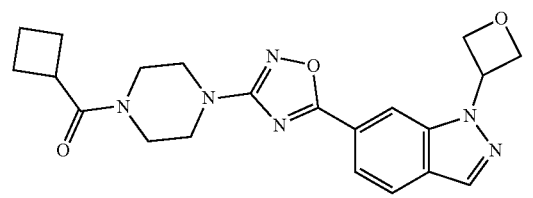 [SMILES: O=C(C1CCC1)N1CCN(c2noc(-c3ccc4cnn(C5COC5)c4c3)n2)CC1] |
| 839 | 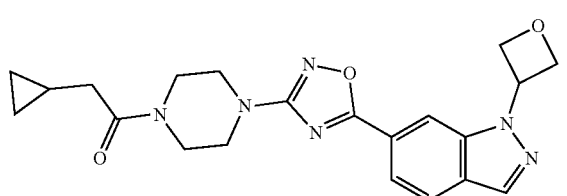 |
| 840 | 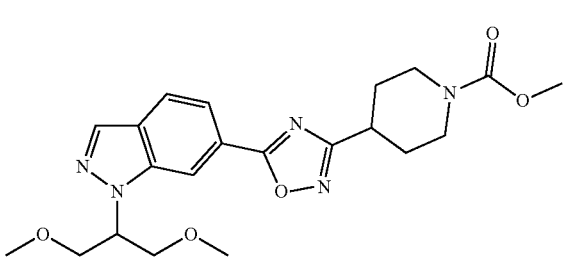 |

TABLE 2-continued

Compounds of the Invention

| # | Structure |
|---|---|
| 841 | 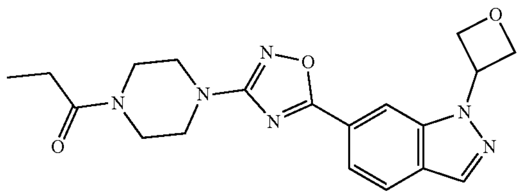 [SMILES: CCC(=O)N1CCN(c2noc(-c3ccc4cnn(C5COC5)c4c3)n2)CC1] |
| 842 | 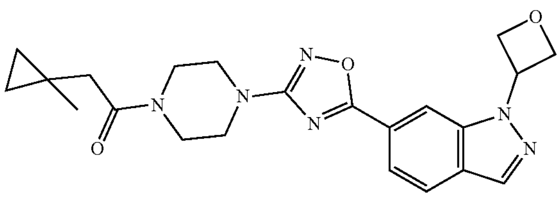 [SMILES: CC1(CC(=O)N2CCN(c3noc(-c4ccc5cnn(C6COC6)c5c4)n3)CC2)CC1] |
| 843 | 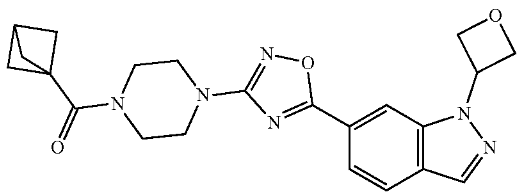 [SMILES: O=C(N1CCN(c2noc(-c3ccc4cnn(C5COC5)c4c3)n2)CC1)C12CC(C1)C2] |
| 844 | 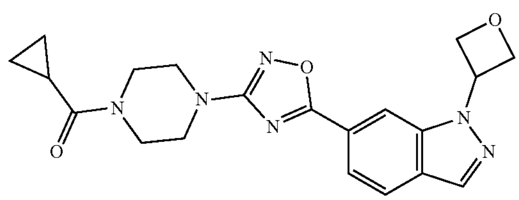 |
| 845 | 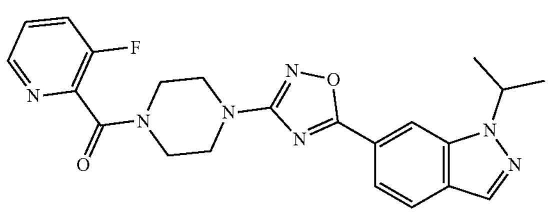 [SMILES: CC(C)n1ncc2ccc(-c3nc(N4CCN(C(=O)c5ncccc5F)CC4)no3)cc21] |
| 846 | 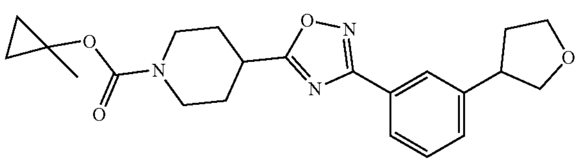 [SMILES: CC1(OC(=O)N2CCC(c3nc(-c4cccc(C5CCOC5)c4)no3)CC2)CC1] |
| 847 | 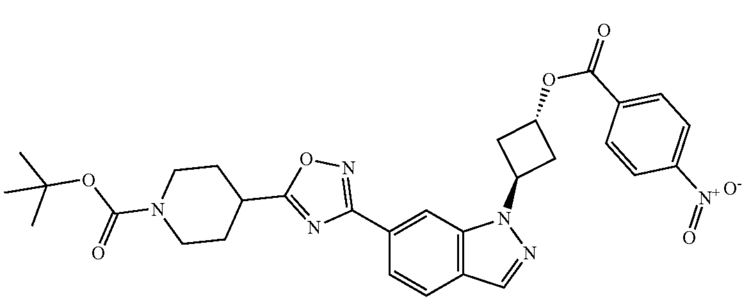 |

TABLE 2-continued
Compounds of the Invention
| # | Structure |
|---|---|
| 848 | 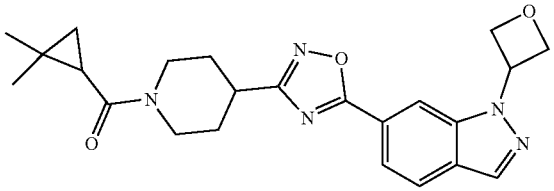 [SMILES: CC1(C)CC1C(=O)N1CCC(c2noc(-c3ccc4cnn(C5COC5)c4c3)n2)CC1] |
| 849 | 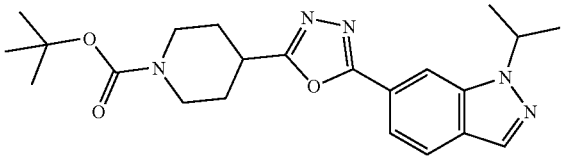 [SMILES: CC(C)n1ncc2ccc(-c3nnc(C4CCN(C(=O)OC(C)(C)C)CC4)o3)cc21] |
| 850 | 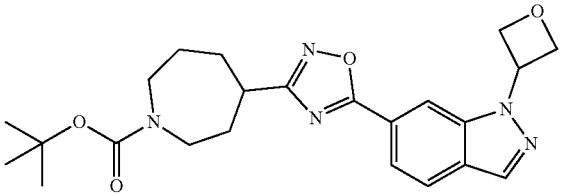 |
| 851 | 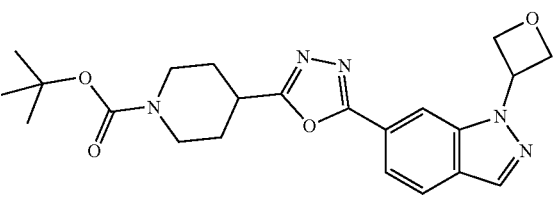 [SMILES: CC(C)(C)OC(=O)N1CCC(c2nnc(-c3ccc4cnn(C5COC5)c4c3)o2)CC1] |
| 852 | 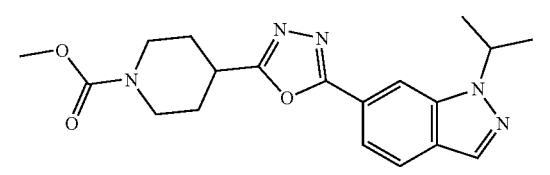 [SMILES: COC(=O)N1CCC(c2nnc(-c3ccc4cnn(C(C)C)c4c3)o2)CC1] |
| 853 | 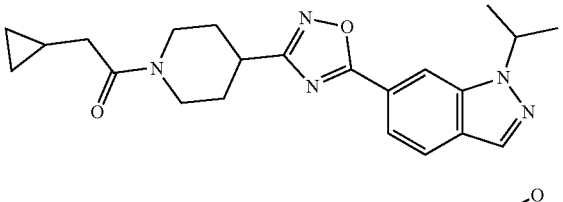 |
| 854 | 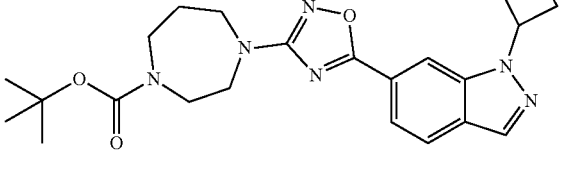 |
| 855 | 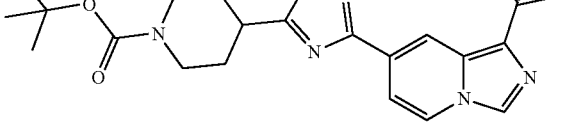 |

TABLE 2-continued

Compounds of the Invention

| # | Structure |
|---|---|
| 856 | 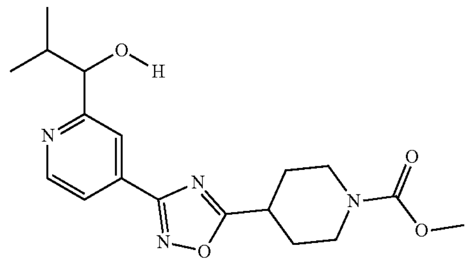 [SMILES: COC(=O)N1CCC(c2nc(-c3ccnc(C(O)C(C)C)c3)no2)CC1] |
| 857 | 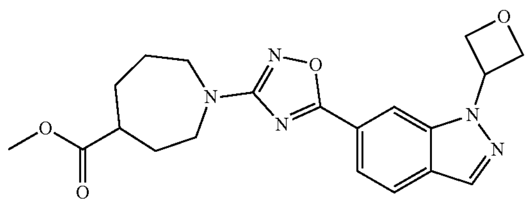 [SMILES: COC(=O)C1CCCN(c2noc(-c3ccc4cnn(C5COC5)c4c3)n2)CC1] |
| 858 | 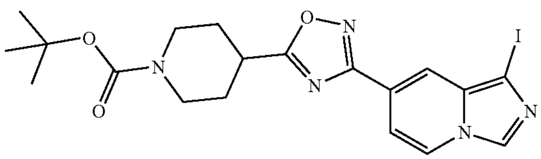 [SMILES: CC(C)(C)OC(=O)N1CCC(c2nc(-c3ccn4cnc(I)c4c3)no2)CC1] |
| 859 | 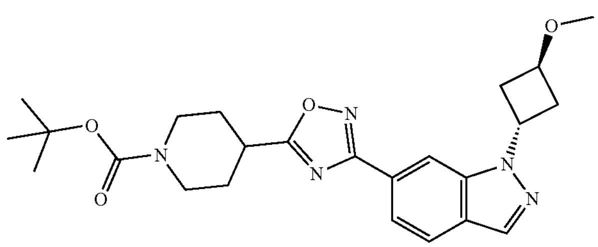 [SMILES: CO[C@H]1C[C@H](n2ncc3ccc(-c4noc(C5CCN(C(=O)OC(C)(C)C)CC5)n4)cc32)C1] |
| 860 | 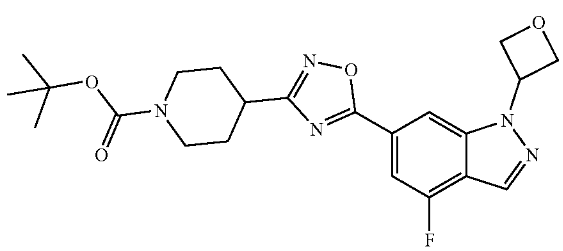 [SMILES: CC(C)(C)OC(=O)N1CCC(c2noc(-c3cc(F)c4cnn(C5COC5)c4c3)n2)CC1] |
| 861 | 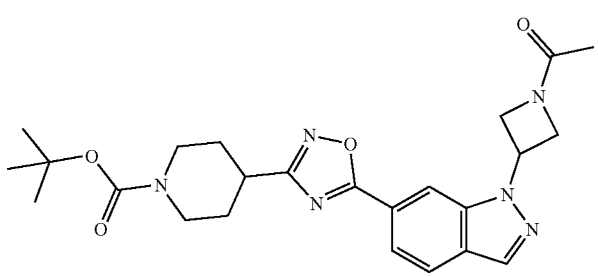 [SMILES: CC(=O)N1CC(n2ncc3ccc(-c4nc(C5CCN(C(=O)OC(C)(C)C)CC5)no4)cc32)C1] |
| 862 | 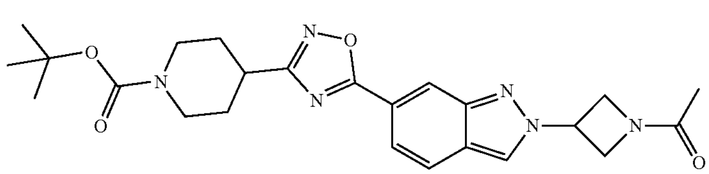 [SMILES: CC(=O)N1CC(n2cc3ccc(-c4nc(C5CCN(C(=O)OC(C)(C)C)CC5)no4)cc3n2)C1] |

TABLE 2-continued
Compounds of the Invention
| # | Structure |
|---|---|
| 863 | 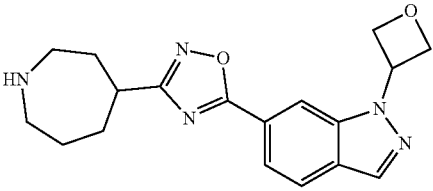 [SMILES: c1cc2cnn(C3COC3)c2cc1-c1nc(C2CCCNCC2)no1] |
| 864 | 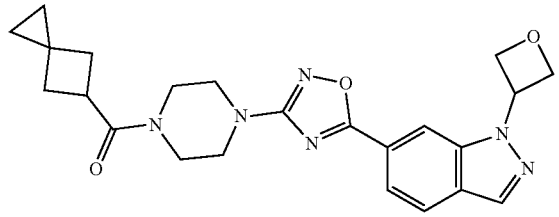 [SMILES: O=C(C1CC2(CC2)C1)N1CCN(c2noc(-c3ccc4cnn(C5COC5)c4c3)n2)CC1] |
| 865 | 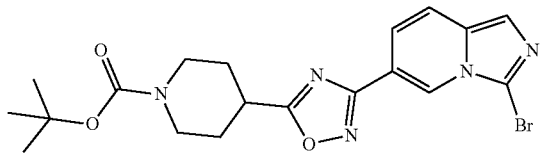 [SMILES: CC(C)(C)OC(=O)N1CCC(c2nc(-c3ccc4cnc(Br)n4c3)no2)CC1] |
| 866 | 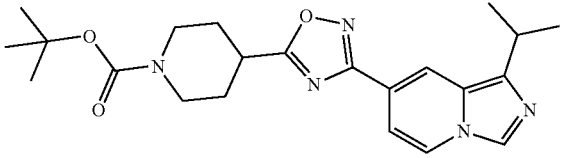 [SMILES: CC(C)c1ncn2ccc(-c3noc(C4CCN(C(=O)OC(C)(C)C)CC4)n3)cc12] |
| 867 | 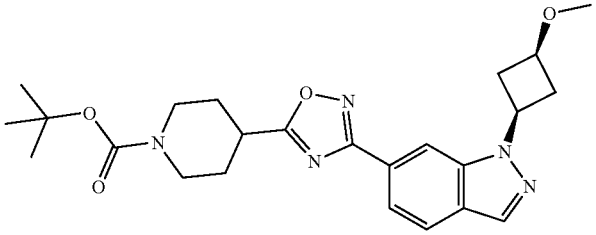 [SMILES: CO[C@H]1C[C@@H](n2ncc3ccc(-c4noc(C5CCN(C(=O)OC(C)(C)C)CC5)n4)cc32)C1] |
| 868 | 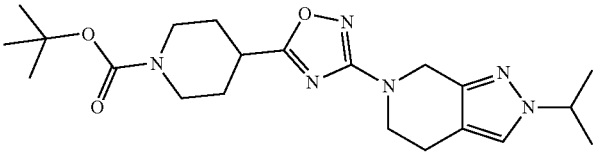 [SMILES: CC(C)n1cc2c(n1)CN(c1noc(C3CCN(C(=O)OC(C)(C)C)CC3)n1)CC2] |
| 869 | 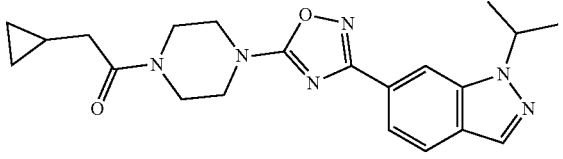 [SMILES: CC(C)n1ncc2ccc(-c3noc(N4CCN(C(=O)CC5CC5)CC4)n3)cc21] |
| 870 | 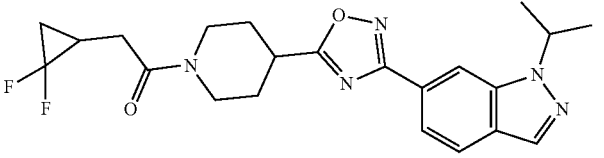 [SMILES: CC(C)n1ncc2ccc(-c3noc(C4CCN(C(=O)CC5CC5(F)F)CC4)n3)cc21] |

US 11,970,486 B2
283
TABLE 2-continued
284
| Compounds of the Invention | |
|---|---|
| # | Structure |
| 871 | 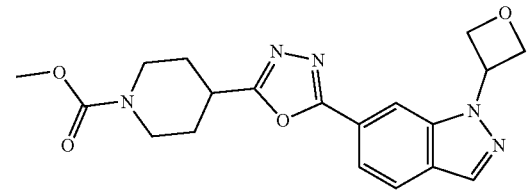 [SMILES: COC(=O)N1CCC(c2nnc(-c3ccc4cnn(C5COC5)c4c3)o2)CC1] |
| 872 | 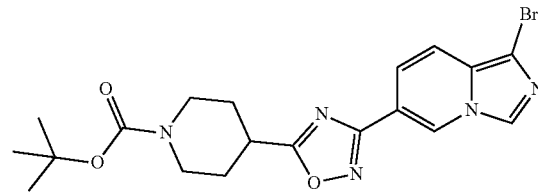 |
| 873 | 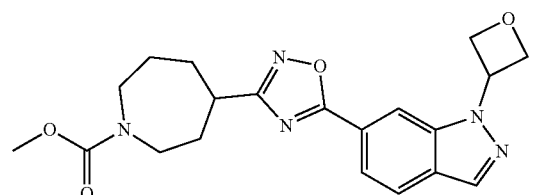 |
| 874 | 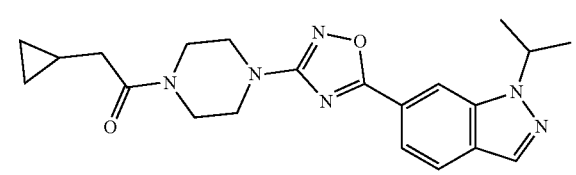 [SMILES: CC(C)n1ncc2ccc(-c3nc(N4CCN(C(=O)CC5CC5)CC4)no3)cc21] |
| 875 | 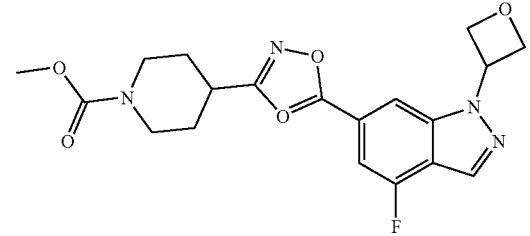 |
| 876 | 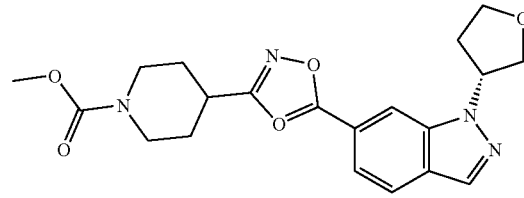 |
| 877 | 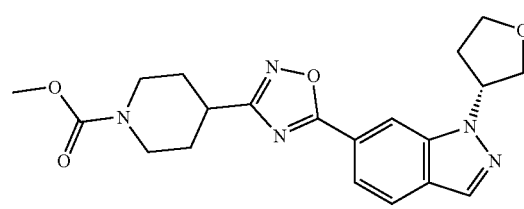 |

TABLE 2-continued

Compounds of the Invention

| # | Structure |
|---|---|
| 878 | 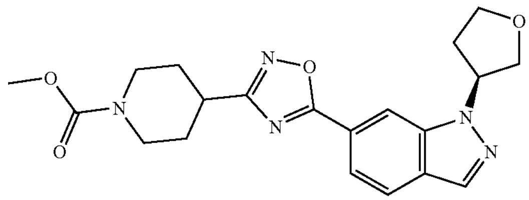 [SMILES: COC(=O)N1CCC(c2noc(-c3ccc4cnn([C@H]5CCOC5)c4c3)n2)CC1] |
| 879 | 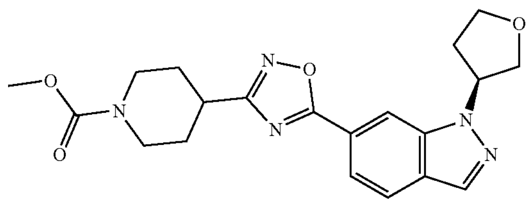 [SMILES: COC(=O)N1CCC(c2noc(-c3ccc4cnn([C@H]5CCOC5)c4c3)n2)CC1] |
| 880 | 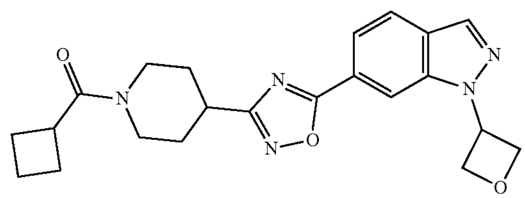 [SMILES: O=C(C1CCC1)N1CCC(c2noc(-c3ccc4cnn(C5COC5)c4c3)n2)CC1] |
| 881 | 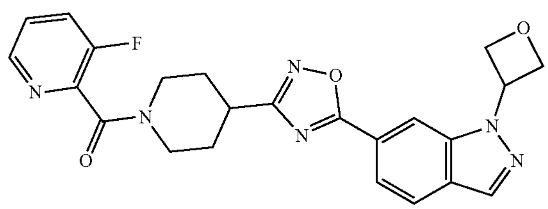 [SMILES: O=C(c1ncccc1F)N1CCC(c2noc(-c3ccc4cnn(C5COC5)c4c3)n2)CC1] |
| 882 | 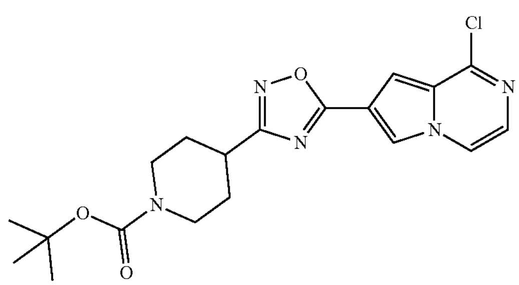 [SMILES: CC(C)(C)OC(=O)N1CCC(c2noc(-c3cc4c(Cl)nccn4c3)n2)CC1] |
| 883 | 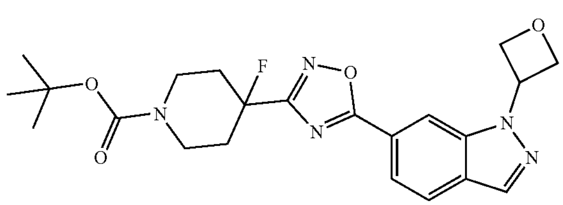 [SMILES: CC(C)(C)OC(=O)N1CCC(F)(c2noc(-c3ccc4cnn(C5COC5)c4c3)n2)CC1] |
| 884 | 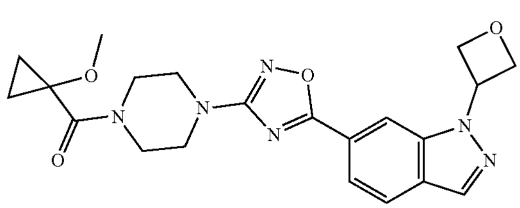 [SMILES: COC1(C(=O)N2CCN(c3noc(-c4ccc5cnn(C6COC6)c5c4)n3)CC2)CC1] |

287
288
TABLE 2-continued
Compounds of the Invention
| # | Structure |
|---|---|
| 885 | 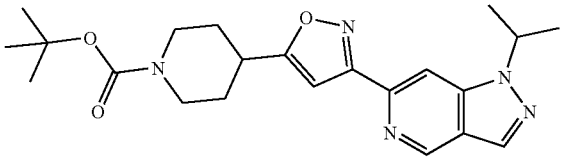 [SMILES: CC(C)n1ncc2cnc(-c3cc(C4CCN(C(=O)OC(C)(C)C)CC4)on3)cc21] |
| 886 | 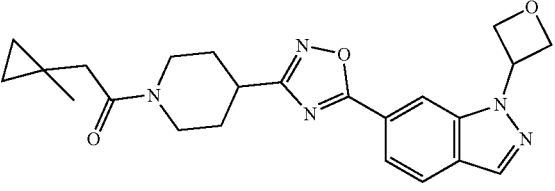 [SMILES: CC1(CC(=O)N2CCC(c3noc(-c4ccc5cnn(C6COC6)c5c4)n3)CC2)CC1] |
| 887 | 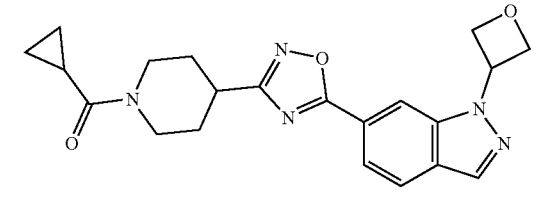 [SMILES: O=C(C1CC1)N1CCC(c2noc(-c3ccc4cnn(C5COC5)c4c3)n2)CC1] |
| 888 | 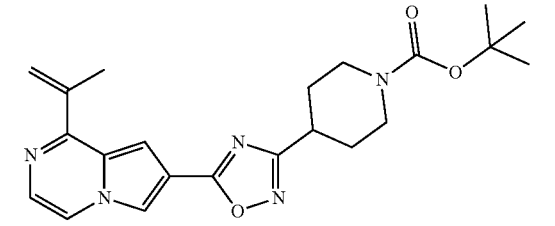 [SMILES: C=C(C)c1nccn2cc(-c3nc(C4CCN(C(=O)OC(C)(C)C)CC4)no3)cc12] |
| 889 | 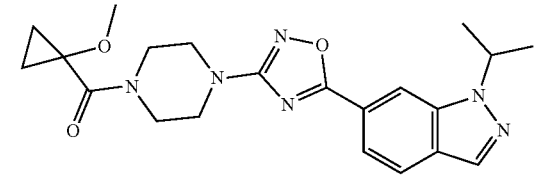 [SMILES: COC1(C(=O)N2CCN(c3noc(-c4ccc5cnn(C(C)C)c5c4)n3)CC2)CC1] |
| 890 | 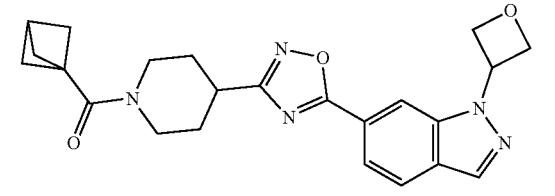 [SMILES: O=C(N1CCC(c2noc(-c3ccc4cnn(C5COC5)c4c3)n2)CC1)C12CC(C1)C2] |
| 891 | 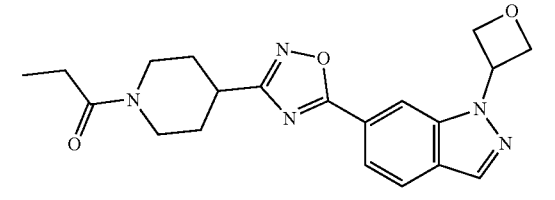 [SMILES: CCC(=O)N1CCC(c2noc(-c3ccc4cnn(C5COC5)c4c3)n2)CC1] |

TABLE 2-continued

Compounds of the Invention

| # | Structure |
|---|---|
| 892 | 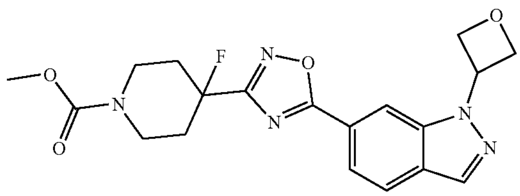 [SMILES: COC(=O)N1CCC(F)(c2noc(-c3ccc4cnn(C5COC5)c4c3)n2)CC1] |
| 893 | 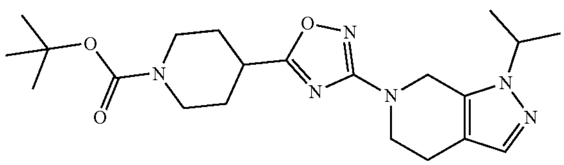 [SMILES: CC(C)n1ncc2c1CN(c1noc(C3CCN(C(=O)OC(C)(C)C)CC3)n1)CC2] |
| 894 | 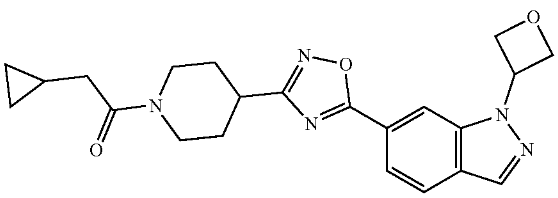 [SMILES: O=C(CC1CC1)N1CCC(c2noc(-c3ccc4cnn(C5COC5)c4c3)n2)CC1] |
| 895 | 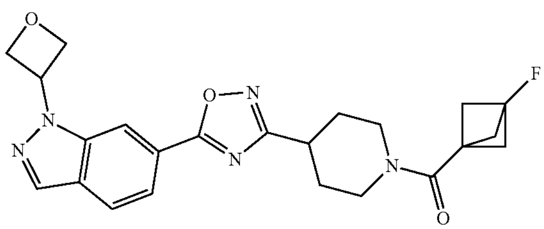 [SMILES: O=C(N1CCC(c2noc(-c3ccc4cnn(C5COC5)c4c3)n2)CC1)C12CC(F)(C1)C2] |
| 896 | 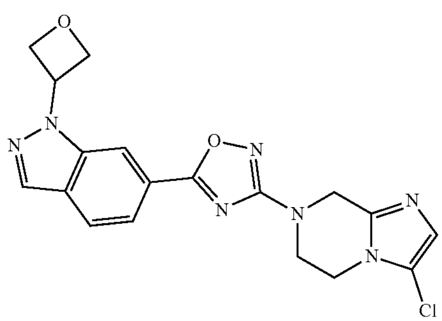 [SMILES: Clc1cnc2n1CCN(c1noc(-c3ccc4cnn(C5COC5)c4c3)n1)C2] |
| 897 | 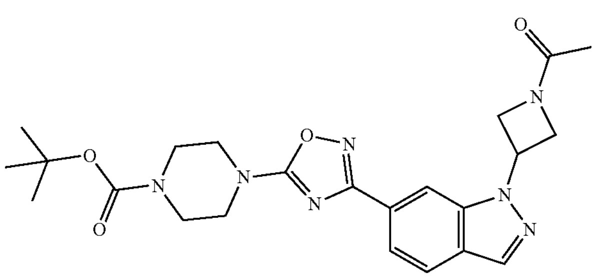 [SMILES: CC(=O)N1CC(n2ncc3ccc(-c4noc(N5CCN(C(=O)OC(C)(C)C)CC5)n4)cc32)C1] |
| 898 | 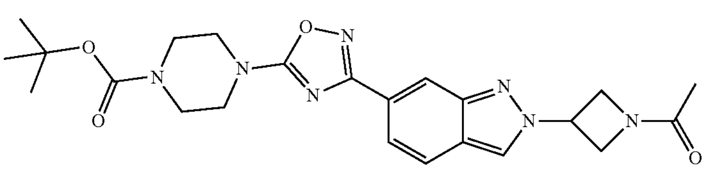 [SMILES: CC(=O)N1CC(n2cc3ccc(-c4noc(N5CCN(C(=O)OC(C)(C)C)CC5)n4)cc3n2)C1] |

TABLE 2-continued
Compounds of the Invention
| # | Structure |
|---|---|
| 899 | 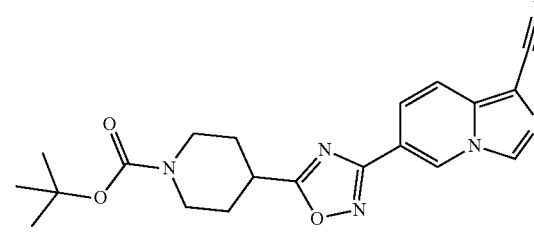 |
| 900 | 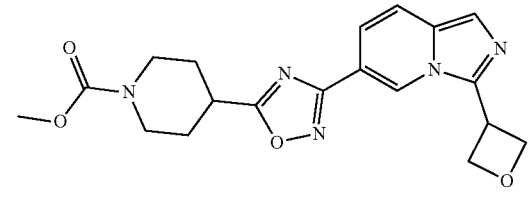 [SMILES: COC(=O)N1CCC(c2nc(-c3ccc4cnc(C5COC5)n4c3)no2)CC1] |
| 901 | 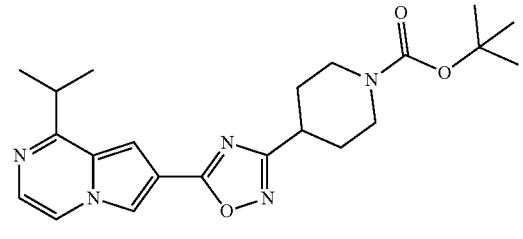 [SMILES: CC(C)c1nccn2cc(-c3nc(C4CCN(C(=O)OC(C)(C)C)CC4)no3)cc12] |
| 902 | 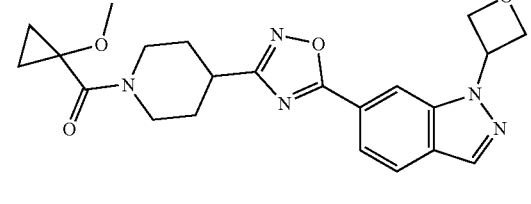 |
| 903 | 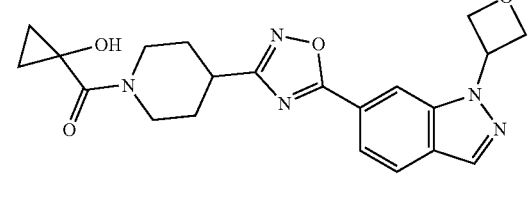 |
| 904 | 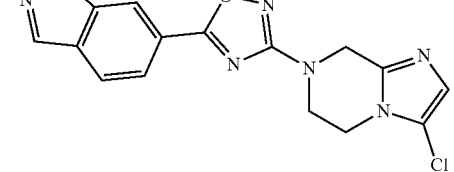 |

TABLE 2-continued

Compounds of the Invention

| # | Structure |
|---|---|
| 905 | 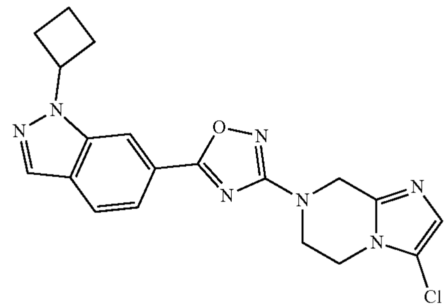 [SMILES: Clc1cnc2n1CCN(c1noc(-c3ccc4cnn(C5CCC5)c4c3)n1)C2] |
| 906 | 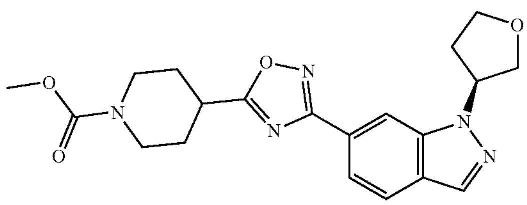 [SMILES: COC(=O)N1CCC(c2nc(-c3ccc4cnn([C@H]5CCOC5)c4c3)no2)CC1] |
| 907 | 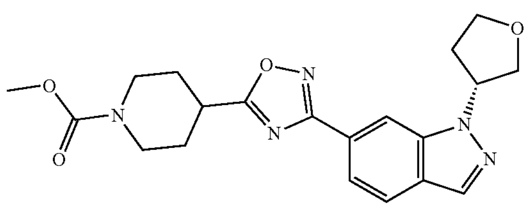 [SMILES: COC(=O)N1CCC(c2nc(-c3ccc4cnn([C@@H]5CCOC5)c4c3)no2)CC1] |
| 908 | 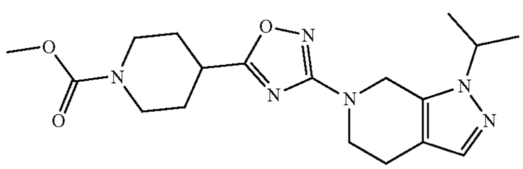 [SMILES: COC(=O)N1CCC(c2nc(N3CCc4cnn(C(C)C)c4C3)no2)CC1] |
| 909 | 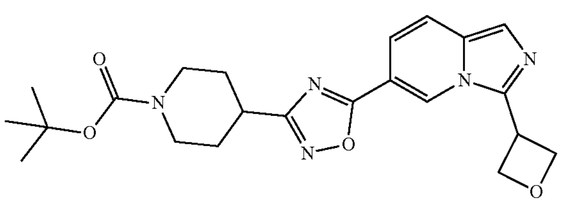 [SMILES: CC(C)(C)OC(=O)N1CCC(c2noc(-c3ccc4cnc(C5COC5)n4c3)n2)CC1] |
| 910 | 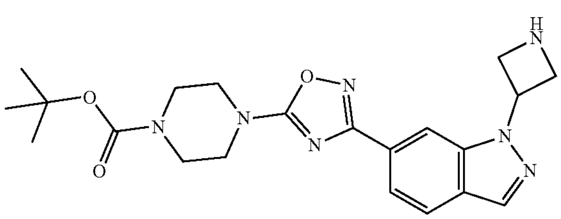 [SMILES: CC(C)(C)OC(=O)N1CCN(c2nc(-c3ccc4cnn(C5CNC5)c4c3)no2)CC1] |
| 911 | 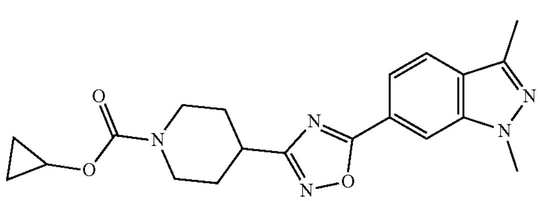 [SMILES: Cc1nn(C)c2cc(-c3nc(C4CCN(C(=O)OC5CC5)CC4)no3)ccc12] |

TABLE 2-continued
Compounds of the Invention
| # | Structure |
|---|---|
| 912 | 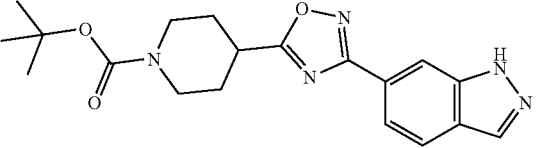 [SMILES: CC(C)(C)OC(=O)N1CCC(c2nc(-c3ccc4cn[nH]c4c3)no2)CC1] |
| 913 | 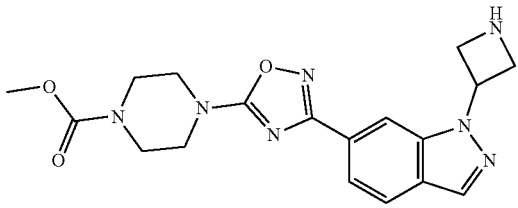 [SMILES: COC(=O)N1CCN(c2nc(-c3ccc4cnn(C5CNC5)c4c3)no2)CC1] |
| 914 | 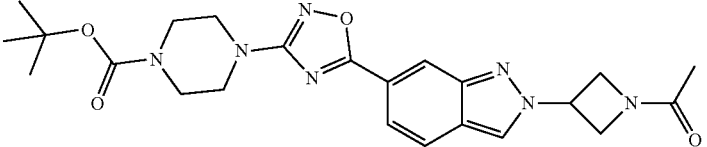 [SMILES: CC(=O)N1CC(n2cc3ccc(-c4nc(N5CCN(C(=O)OC(C)(C)C)CC5)no4)cc3n2)C1] |
| 915 | 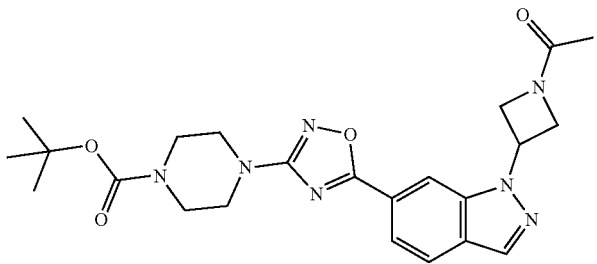 [SMILES: CC(=O)N1CC(n2ncc3ccc(-c4nc(N5CCN(C(=O)OC(C)(C)C)CC5)no4)cc32)C1] |
| 916 | 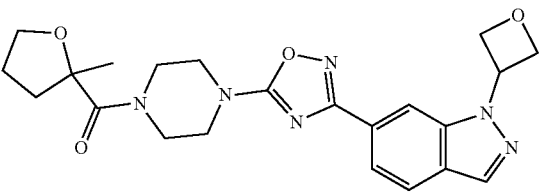 [SMILES: CC1(C(=O)N2CCN(c3nc(-c4ccc5cnn(C6COC6)c5c4)no3)CC2)CCCO1] |
| 917 | 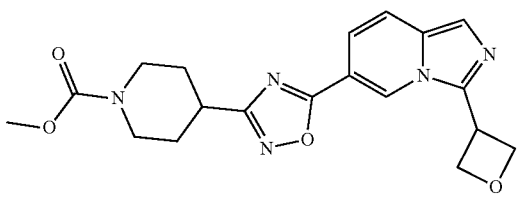 [SMILES: COC(=O)N1CCC(c2noc(-c3ccc4cnc(C5COC5)n4c3)n2)CC1] |
| 918 | 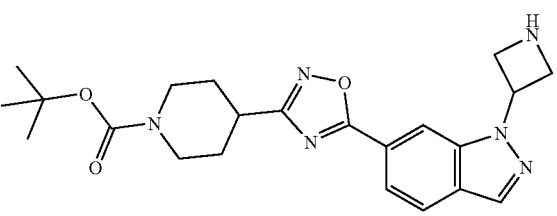 [SMILES: CC(C)(C)OC(=O)N1CCC(c2noc(-c3ccc4cnn(C5CNC5)c4c3)n2)CC1] |

TABLE 2-continued

Compounds of the Invention

| # | Structure |
|---|---|
| 919 | 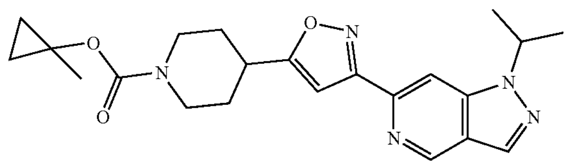 [SMILES: CC(C)n1ncc2cnc(-c3cc(C4CCN(C(=O)OC5(C)CC5)CC4)on3)cc21] |
| 920 | 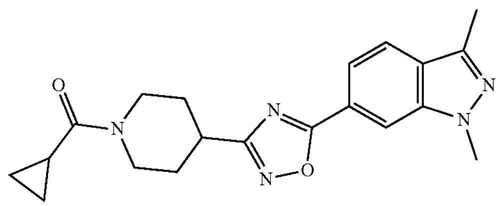 [SMILES: Cc1nn(C)c2cc(-c3nc(C4CCN(C(=O)C5CC5)CC4)no3)ccc12] |
| 921 | 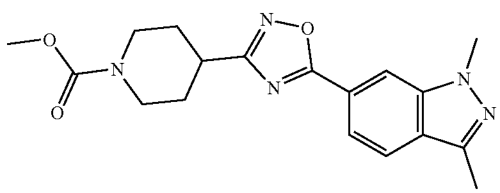 [SMILES: COC(=O)N1CCC(c2noc(-c3ccc4c(C)nn(C)c4c3)n2)CC1] |
| 922 | 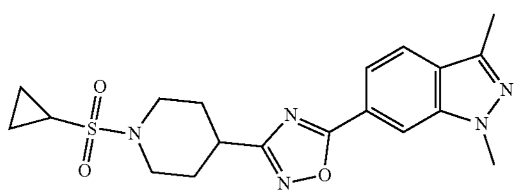 [SMILES: Cc1nn(C)c2cc(-c3nc(C4CCN(S(=O)(=O)C5CC5)CC4)no3)ccc12] |
| 923 | 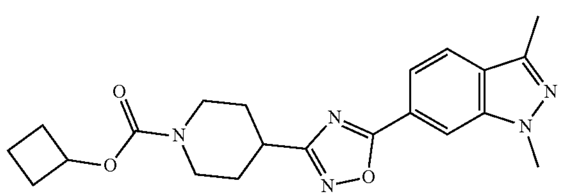 [SMILES: Cc1nn(C)c2cc(-c3nc(C4CCN(C(=O)OC5CCC5)CC4)no3)ccc12] |
| 924 | 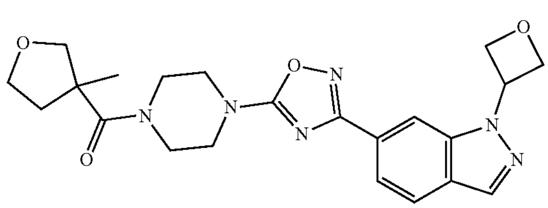 [SMILES: CC1(C(=O)N2CCN(c3nc(-c4ccc5cnn(C6COC6)c5c4)no3)CC2)CCOC1] |

TABLE 2-continued
Compounds of the Invention
| # | Structure |
|---|---|
| 925 | 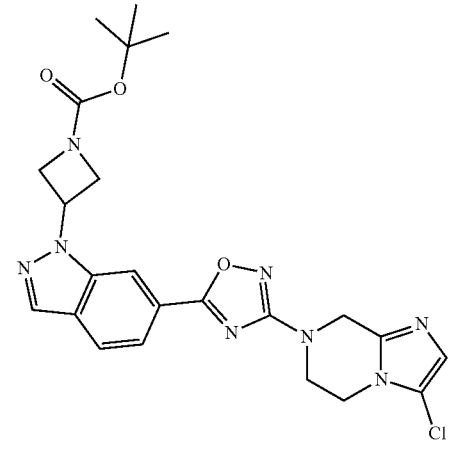 [SMILES: CC(C)(C)OC(=O)N1CC(n2ncc3ccc(-c4nc(N5CCn6c(Cl)cnc6C5)no4)cc32)C1] |
| 926 | 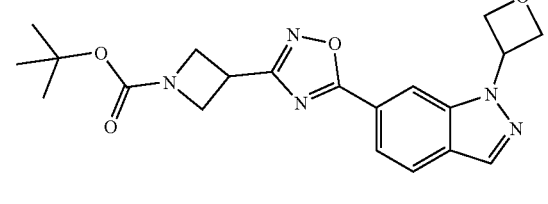 |
| 927 | 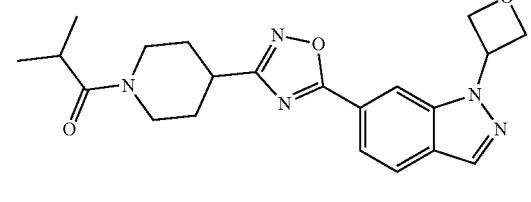 |
| 928 | 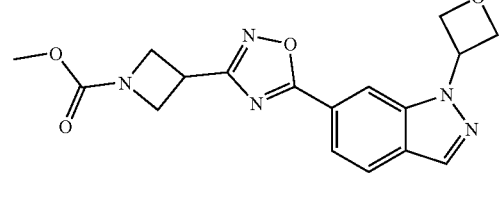 |
| 929 | 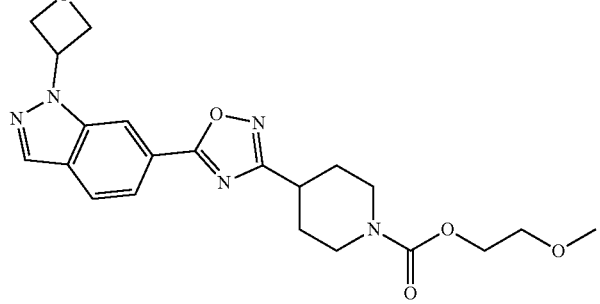 |

TABLE 2-continued

Compounds of the Invention

| # | Structure |
|---|---|
| 930 | 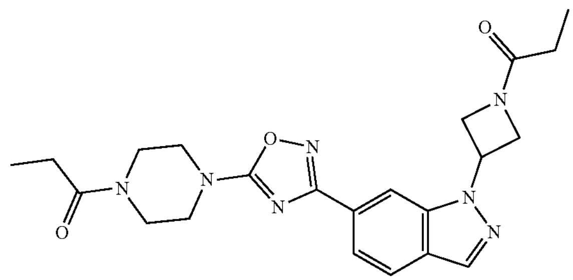 [SMILES: CCC(=O)N1CCN(c2nc(-c3ccc4cnn(C5CN(C(=O)CC)C5)c4c3)no2)CC1] |
| 931 | 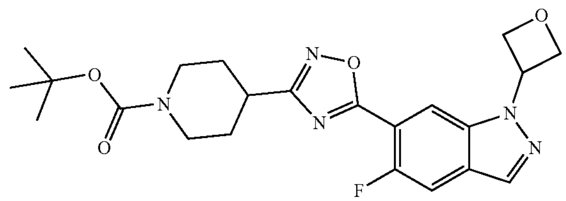 [SMILES: CC(C)(C)OC(=O)N1CCC(c2noc(-c3cc4c(cnn4C4COC4)cc3F)n2)CC1] |
| 932 | 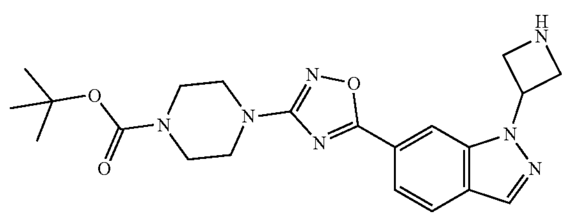 [SMILES: CC(C)(C)OC(=O)N1CCN(c2noc(-c3ccc4cnn(C5CNC5)c4c3)n2)CC1] |
| 933 | 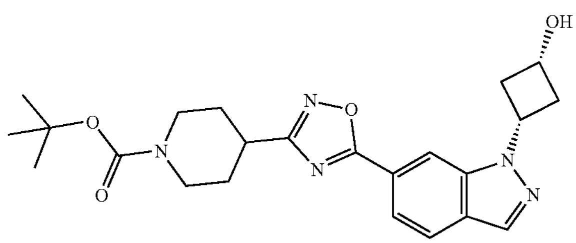 [SMILES: CC(C)(C)OC(=O)N1CCC(c2noc(-c3ccc4cnn([C@H]5C[C@@H](O)C5)c4c3)n2)CC1] |
| 934 | 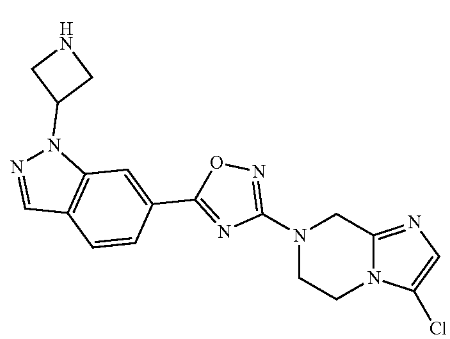 [SMILES: Clc1cnc2n1CCN(c1noc(-c3ccc4cnn(C5CNC5)c4c3)n1)C2] |

TABLE 2-continued

Compounds of the Invention

| # | Structure |
|---|---|
| 935 | 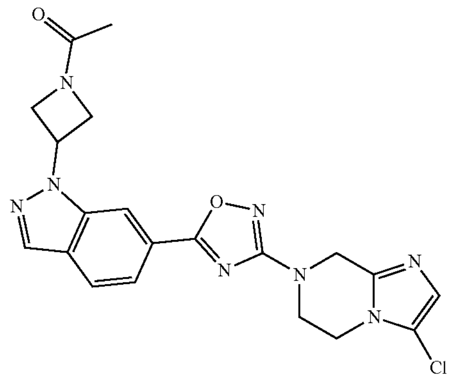 [SMILES: CC(=O)N1CC(n2ncc3ccc(-c4nc(N5CCn6c(Cl)cnc6C5)no4)cc32)C1] |
| 936 | 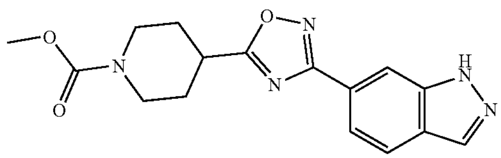 [SMILES: COC(=O)N1CCC(c2nc(-c3ccc4cn[nH]c4c3)no2)CC1] |
| 937 | 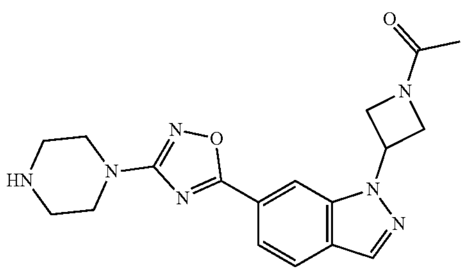 [SMILES: CC(=O)N1CC(n2ncc3ccc(-c4nc(N5CCNCC5)no4)cc32)C1] |
| 938 | 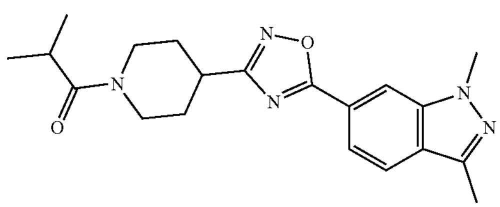 [SMILES: Cc1nn(C)c2cc(-c3nc(C4CCN(C(=O)C(C)C)CC4)no3)ccc12] |
| 939 | 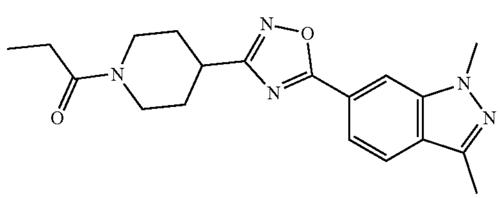 [SMILES: CCC(=O)N1CCC(c2noc(-c3ccc4c(C)nn(C)c4c3)n2)CC1] |
| 940 | 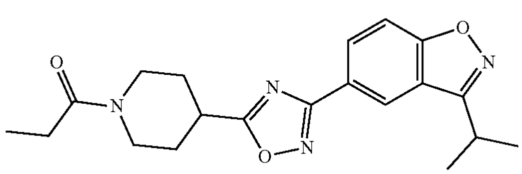 [SMILES: CCC(=O)N1CCC(c2nc(-c3ccc4onc(C(C)C)c4c3)no2)CC1] |
| 941 | 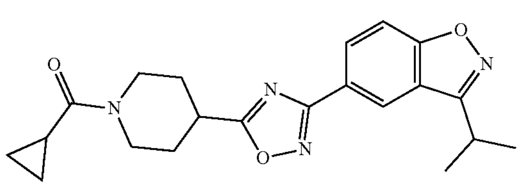 [SMILES: CC(C)c1noc2ccc(-c3noc(C4CCN(C(=O)C5CC5)CC4)n3)cc12] |

TABLE 2-continued

Compounds of the Invention

| # | Structure |
|---|---|
| 942 | 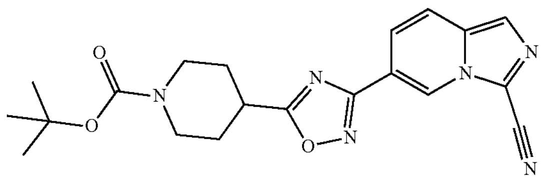 [SMILES: CC(C)(C)OC(=O)N1CCC(c2nc(-c3ccc4cnc(C#N)n4c3)no2)CC1] |
| 943 | 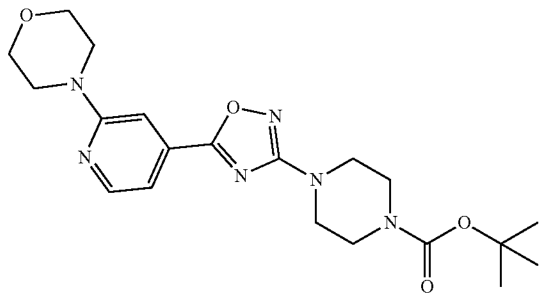 [SMILES: CC(C)(C)OC(=O)N1CCN(c2noc(-c3ccnc(N4CCOCC4)c3)n2)CC1] |
| 944 | 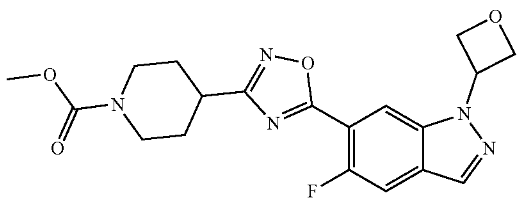 [SMILES: COC(=O)N1CCC(c2noc(-c3cc4c(cnn4C4COC4)cc3F)n2)CC1] |
| 945 | 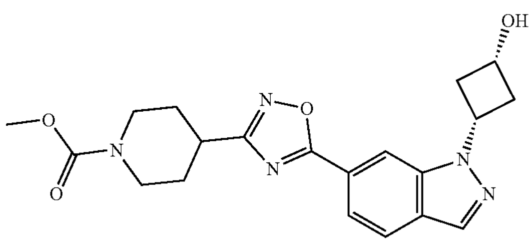 [SMILES: COC(=O)N1CCC(c2noc(-c3ccc4cnn([C@H]5C[C@@H](O)C5)c4c3)n2)CC1] |
| 946 | 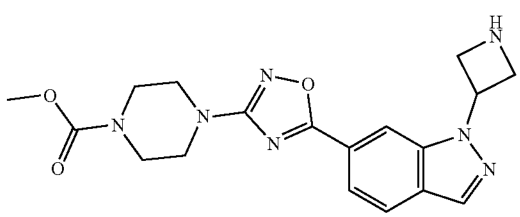 [SMILES: COC(=O)N1CCN(c2noc(-c3ccc4cnn(C5CNC5)c4c3)n2)CC1] |
| 947 | 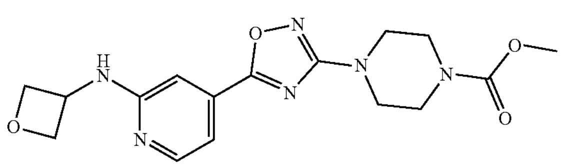 [SMILES: COC(=O)N1CCN(c2noc(-c3ccnc(NC4COC4)c3)n2)CC1] |
| 948 | 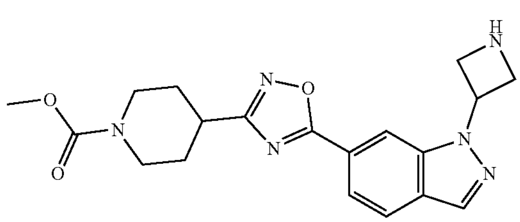 [SMILES: COC(=O)N1CCC(c2noc(-c3ccc4cnn(C5CNC5)c4c3)n2)CC1] |

TABLE 2-continued

Compounds of the Invention

| # | Structure |
|---|---|
| 949 | 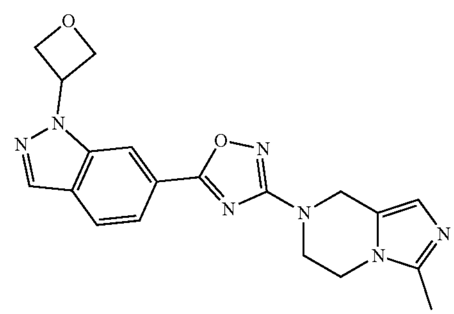 [SMILES: Cc1ncc2n1CCN(c1noc(-c3ccc4cnn(C5COC5)c4c3)n1)C2] |
| 950 | 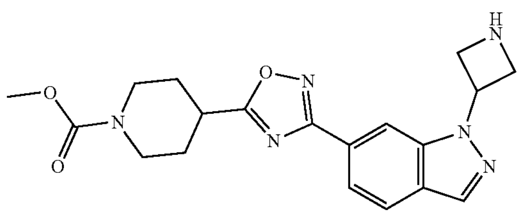 [SMILES: COC(=O)N1CCC(c2nc(-c3ccc4cnn(C5CNC5)c4c3)no2)CC1] |
| 951 | 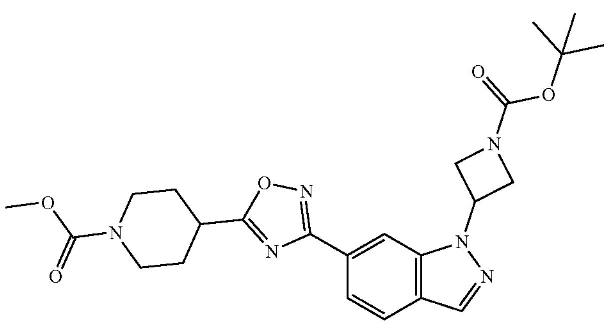 [SMILES: COC(=O)N1CCC(c2nc(-c3ccc4cnn(C5CN(C(=O)OC(C)(C)C)C5)c4c3)no2)CC1] |
| 952 | 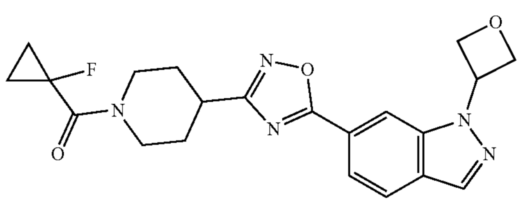 [SMILES: O=C(N1CCC(c2noc(-c3ccc4cnn(C5COC5)c4c3)n2)CC1)C1(F)CC1] |
| 953 | 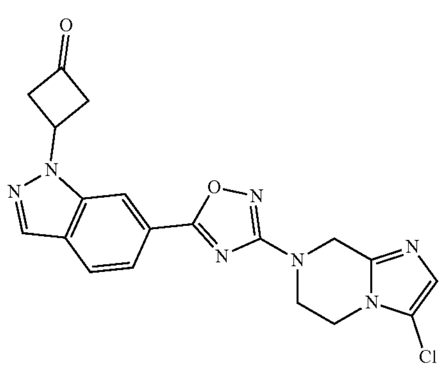 [SMILES: O=C1CC(n2ncc3ccc(-c4nc(N5CCn6c(Cl)cnc6C5)no4)cc32)C1] |

TABLE 2-continued

Compounds of the Invention

| # | Structure |
|---|---|
| 954 | 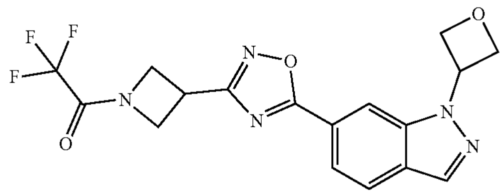 [SMILES: O=C(N1CC(c2noc(-c3ccc4cnn(C5COC5)c4c3)n2)C1)C(F)(F)F] |
| 955 | 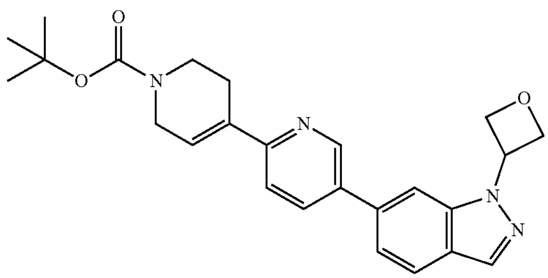 [SMILES: CC(C)(C)OC(=O)N1CC=C(c2ccc(-c3ccc4cnn(C5COC5)c4c3)cn2)CC1] |
| 956 | 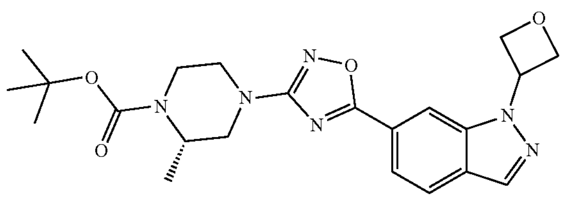 [SMILES: C[C@H]1CN(c2noc(-c3ccc4cnn(C5COC5)c4c3)n2)CCN1C(=O)OC(C)(C)C] |
| 957 | 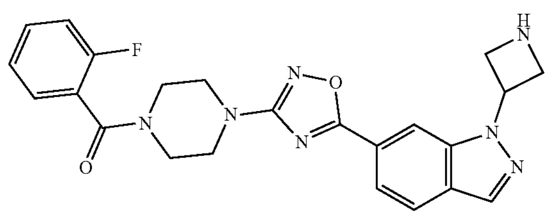 [SMILES: O=C(c1ccccc1F)N1CCN(c2noc(-c3ccc4cnn(C5CNC5)c4c3)n2)CC1] |
| 958 | 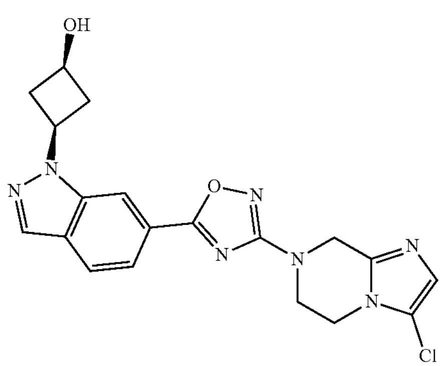 [SMILES: O[C@H]1C[C@@H](n2ncc3ccc(-c4nc(N5CCn6c(Cl)cnc6C5)no4)cc32)C1] |
| 959 | 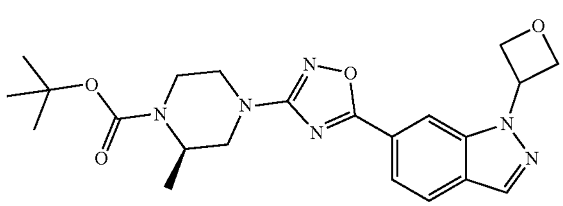 [SMILES: C[C@@H]1CN(c2noc(-c3ccc4cnn(C5COC5)c4c3)n2)CCN1C(=O)OC(C)(C)C] |

311
312
TABLE 2-continued
Compounds of the Invention
| # | Structure |
|---|---|
| 960 | 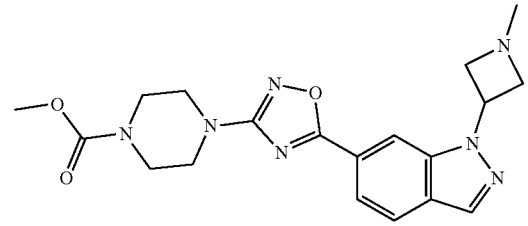 [SMILES: COC(=O)N1CCN(c2noc(-c3ccc4cnn(C5CN(C)C5)c4c3)n2)CC1] |
| 961 | 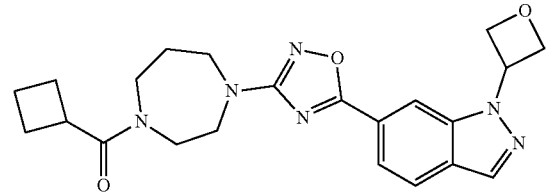 [SMILES: O=C(C1CCC1)N1CCCN(c2noc(-c3ccc4cnn(C5COC5)c4c3)n2)CC1] |
| 962 | 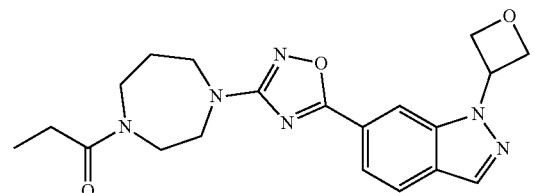 |
| 963 | 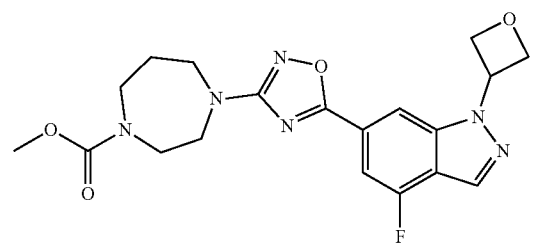 [SMILES: COC(=O)N1CCCN(c2noc(-c3cc(F)c4cnn(C5COC5)c4c3)n2)CC1] |
| 964 | 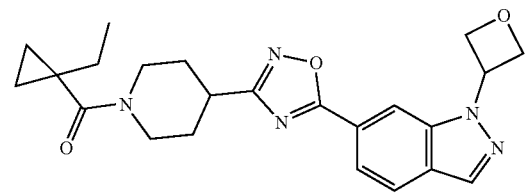 [SMILES: CCC1(C(=O)N2CCC(c3noc(-c4ccc5cnn(C6COC6)c5c4)n3)CC2)CC1] |
| 965 | 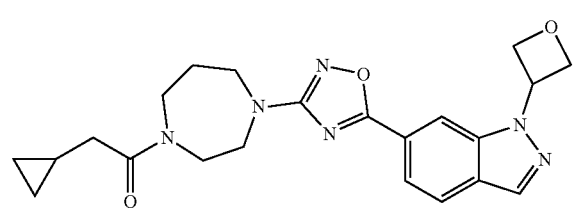 [SMILES: O=C(CC1CC1)N1CCCN(c2noc(-c3ccc4cnn(C5COC5)c4c3)n2)CC1] |

TABLE 2-continued

Compounds of the Invention

| # | Structure |
|---|---|
| 966 | 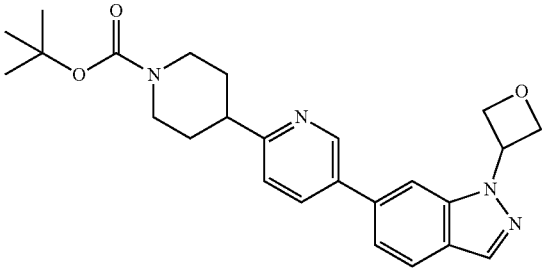 [SMILES: CC(C)(C)OC(=O)N1CCC(c2ccc(-c3ccc4cnn(C5COC5)c4c3)cn2)CC1] |

In another aspect, the disclosure provides pharmaceutical composition comprising any of the foregoing compounds, or pharmaceutically acceptable salts thereof and a pharmaceutically acceptable excipient.

In another aspect, the disclosure provides a method of treating a neurological disorder in a subject in need thereof, the method comprising administering an effective amount of any of the foregoing compounds, or pharmaceutically acceptable salts thereof, or any of the foregoing pharmaceutical compositions.

In another aspect, the disclosure provides a method of inhibiting toxicity in a cell (e.g., a mammalian neural cell) related to a protein (e.g., toxicity related to protein misfolding and/or aggregation such as protein aggregation related to misfolding of proteins such as α-synuclein or ApoE4), the method comprising administering, or contacting the cell with, an effective amount of any of the foregoing compounds, or pharmaceutically acceptable salts thereof. In some embodiments, the toxicity is α-synuclein-related toxicity. In some embodiments, the toxicity is ApoE4-related toxicity.

Non-limiting exemplary neurological disorders include, but are not limited to Alexander disease, Alper's disease, AD, amyotrophic lateral sclerosis, ataxia telangiectasia, Canavan disease, Cockayne syndrome, corticobasal degeneration, Creutzfeldt-Jakob disease, Huntington disease, Kennedy's disease, Krabbe disease, Lewy body dementia, Machado-Joseph disease, multiple sclerosis, PD, Pelizaeus-Merzbacher disease, Pick's disease, primary lateral sclerosis, Refsum's disease, Sandhoff disease, Schilder's disease, Steele-Richardson-Olszewski disease, tabes *dorsalis*, frontal temporal dementia, vascular dementia, Down's syndrome, and Guillain-Barre Syndrome.

In another aspect, the disclosure provides a method of treating a stearoyl-CoA desaturase (SCD)-associated disorder in a subject in need thereof, the method comprising administering, or contacting the cell with, an effective amount of any of the foregoing compounds, or pharmaceutically acceptable salts thereof.

Non-limiting exemplary SCD-associated disorders include, but are not limited to metabolic disorders (e.g., diabetes (e.g., Type I diabetes and Type II diabetes), hyperglycemia, metabolic syndrome, obesity, lipid disorders, fatty liver, nonalcoholic steatohepatitis (NASH), nonalcoholic fatty liver disease (NAFLD), and hypertension), cancer, cardiovascular diseases, cerebrovascular diseases, kidney diseases, liver diseases, skin disorders (e.g., acne (e.g., acne vulgaris)), central nervous system (CNS) disorders, dementia, multiple sclerosis, schizophrenia, mild cognitive impairment, Alzheimer's Disease, cerebral amyloid angiopathy, and dementia associated with Down Syndrome.

Chemical Terms

It is to be understood that the terminology employed herein is for the purpose of describing particular embodiments and is not intended to be limiting.

The term "acyl," as used herein, represents a hydrogen or an alkyl group, as defined herein, that is attached to a parent molecular group through a carbonyl group, as defined herein, and is exemplified by formyl (i.e., a carboxyaldehyde group), acetyl, trifluoroacetyl, propionyl, and butanoyl. Exemplary unsubstituted acyl groups include from 1 to 6, from 1 to 11, or from 1 to 21 carbons.

The term "alkyl," as used herein, refers to a branched or straight-chain monovalent saturated aliphatic hydrocarbon radical of 1 to 20 carbon atoms (e.g., 1 to 16 carbon atoms, 1 to 10 carbon atoms, or 1 to 6 carbon atoms). An alkylene is a divalent alkyl group.

The term "alkenyl," as used herein, alone or in combination with other groups, refers to a straight-chain or branched hydrocarbon residue having a carbon-carbon double bond and having 2 to 20 carbon atoms (e.g., 2 to 16 carbon atoms, 2 to 10 carbon atoms, 2 to 6, or 2 carbon atoms).

The term "alkynyl," as used herein, alone or in combination with other groups, refers to a straight-chain or branched hydrocarbon residue having a carbon-carbon triple bond and having 2 to 20 carbon atoms (e.g., 2 to 16 carbon atoms, 2 to 10 carbon atoms, 2 to 6, or 2 carbon atoms).

The term "amino," as used herein, represents —N($R^{N1}$)$_2$, wherein each $R^{N1}$ is, independently, H, OH, NO$_2$, N($R^{N2}$)$_2$, SO$_2$OR$^{N2}$, SO$_2$R$^{N2}$, SOR$^{N2}$, an N-protecting group, alkyl, alkoxy, aryl, arylalkyl, cycloalkyl, acyl (e.g., acetyl, trifluoroacetyl, or others described herein), wherein each of these recited $R^{N1}$ groups can be optionally substituted; or two $R^{N1}$ combine to form an alkylene or heteroalkylene, and wherein each $R^{N2}$ is, independently, H, alkyl, or aryl. The amino groups of the invention can be an unsubstituted amino (i.e., —NH$_2$) or a substituted amino (i.e., —N($R^{N1}$)$_2$).

The term "aryl," as used herein, refers to an aromatic mono- or polycarbocyclic radical of 6 to 12 carbon atoms having at least one aromatic ring. Examples of such groups include, but are not limited to, phenyl, naphthyl, 1,2,3,4-tetrahydronaphthyl, 1,2-dihydronaphthyl, indanyl, and 1H-indenyl.

The term "arylalkyl," as used herein, represents an alkyl group substituted with an aryl group. Exemplary unsubstituted arylalkyl groups are from 7 to 30 carbons (e.g., from 7 to 16 or from 7 to 20 carbons, such as $C_{1-6}$ alkyl $C_{6-10}$ aryl, $C_{1-10}$ alkyl $C_{6-10}$ aryl, or $C_{1-20}$ alkyl $C_{6-10}$ aryl), such as, benzyl and phenethyl. In some embodiments, the alkyl and the aryl each can be further substituted with 1, 2, 3, or 4 substituent groups as defined herein for the respective groups.

The term "azido," as used herein, represents a —$N_3$ group.

The term "cyano," as used herein, represents a —CN group.

The terms "carbocyclyl," as used herein, refer to a non-aromatic $C_{3-12}$ monocyclic, bicyclic, or tricyclic structure in which the rings are formed by carbon atoms. Carbocyclyl structures include cycloalkyl groups and unsaturated carbocyclyl radicals.

The term "cycloalkyl," as used herein, refers to a saturated, non-aromatic, monovalent mono- or polycarbocyclic radical of three to ten, preferably three to six carbon atoms. This term is further exemplified by radicals such as cyclopropyl, cyclobutyl, cyclopentyl, cyclohexyl, cycloheptyl, norbornyl, and adamantyl.

The term "halogen," as used herein, means a fluorine (fluoro), chlorine (chloro), bromine (bromo), or iodine (iodo) radical.

The term "heteroalkyl," as used herein, refers to an alkyl group, as defined herein, in which one or more of the constituent carbon atoms have been replaced by nitrogen, oxygen, or sulfur. In some embodiments, the heteroalkyl group can be further substituted with 1, 2, 3, or 4 substituent groups as described herein for alkyl groups. Examples of heteroalkyl groups are an "alkoxy" which, as used herein, refers alkyl-O— (e.g., methoxy and ethoxy). A heteroalkylene is a divalent heteroalkyl group.

The term "heteroalkenyl," as used herein, refers to an alkenyl group, as defined herein, in which one or more of the constituent carbon atoms have been replaced by nitrogen, oxygen, or sulfur. In some embodiments, the heteroalkenyl group can be further substituted with 1, 2, 3, or 4 substituent groups as described herein for alkenyl groups. Examples of heteroalkenyl groups are an "alkenoxy" which, as used herein, refers alkenyl-O—. A heteroalkenylene is a divalent heteroalkenyl group.

The term "heteroalkynyl," as used herein, refers to an alkynyl group, as defined herein, in which one or more of the constituent carbon atoms have been replaced by nitrogen, oxygen, or sulfur. In some embodiments, the heteroalkynyl group can be further substituted with 1, 2, 3, or 4 substituent groups as described herein for alkynyl groups. Examples of heteroalkynyl groups are an "alkynoxy" which, as used herein, refers alkynyl-O—. A heteroalkynylene is a divalent heteroalkynyl group.

The term "heteroaryl," as used herein, refers to an aromatic mono- or polycyclic radical of 5 to 12 atoms having at least one aromatic ring containing one, two, or three ring heteroatoms selected from N, O, and S, with the remaining ring atoms being C. One or two ring carbon atoms of the heteroaryl group may be replaced with a carbonyl group. Examples of heteroaryl groups are pyridyl, pyrazoyl, benzooxazolyl, benzoimidazolyl, benzothiazolyl, imidazolyl, oxaxolyl, and thiazolyl.

The term "heteroarylalkyl," as used herein, represents an alkyl group substituted with a heteroaryl group. Exemplary unsubstituted heteroarylalkyl groups are from 7 to 30 carbons (e.g., from 7 to 16 or from 7 to 20 carbons, such as $C_{1-6}$ alkyl $C_{2-9}$ heteroaryl, $C_{1-10}$ alkyl $C_{2-9}$ heteroaryl, or $C_{1-20}$ alkyl $C_{2-9}$ heteroaryl). In some embodiments, the alkyl and the heteroaryl each can be further substituted with 1, 2, 3, or 4 substituent groups as defined herein for the respective groups.

The term "heterocyclyl," as used herein, denotes a mono- or polycyclic radical having 3 to 12 atoms having at least one ring containing one, two, three, or four ring heteroatoms selected from N, O or S, wherein no ring is aromatic. Examples of heterocyclyl groups include, but are not limited to, morpholinyl, thiomorpholinyl, furyl, piperazinyl, piperidinyl, pyranyl, pyrrolidinyl, tetrahydropyranyl, tetrahydrofuranyl, and 1,3-dioxanyl.

The term "heterocyclylalkyl," as used herein, represents an alkyl group substituted with a heterocyclyl group. Exemplary unsubstituted heterocyclylalkyl groups are from 7 to 30 carbons (e.g., from 7 to 16 or from 7 to 20 carbons, such as $C_{1-6}$ alkyl $C_{2-9}$ heterocyclyl, $C_{1-10}$ alkyl $C_{2-9}$ heterocyclyl, or $C_{1-20}$ alkyl $C_{2-9}$ heterocyclyl). In some embodiments, the alkyl and the heterocyclyl each can be further substituted with 1, 2, 3, or 4 substituent groups as defined herein for the respective groups.

The term "hydroxyl," as used herein, represents an —OH group.

The term "N-protecting group," as used herein, represents those groups intended to protect an amino group against undesirable reactions during synthetic procedures. Commonly used N-protecting groups are disclosed in Greene, "Protective Groups in Organic Synthesis," $3^{rd}$ Edition (John Wiley & Sons, New York, 1999). N-protecting groups include acyl, aryloyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, and phenylalanine; sulfonyl-containing groups such as benzenesulfonyl, and p-toluenesulfonyl; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyloxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl, arylalkyl groups such as benzyl, triphenylmethyl, and benzyloxymethyl, and silyl groups, such as trimethylsilyl. Preferred N-protecting groups are alloc, formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an —$NO_2$ group.

The term "thiol," as used herein, represents an —SH group.

The alkyl, alkenyl, alkynyl, heteroalkyl, heteroalkenyl, heteroalkynyl, carbocyclyl (e.g., cycloalkyl), aryl, heteroaryl, and heterocyclyl groups may be substituted or unsubstituted. When substituted, there will generally be 1 to 4 substituents present, unless otherwise specified. Substituents include, for example: aryl (e.g., substituted and unsubstituted phenyl), carbocyclyl (e.g., substituted and unsubstituted cycloalkyl), halogen (e.g., fluoro), hydroxyl, heteroalkyl (e.g., substituted and unsubstituted methoxy, ethoxy, or thioalkoxy), heteroaryl, heterocyclyl, amino (e.g., $NH_2$ or mono- or dialkyl amino), azido, cyano, nitro, or thiol. Aryl, carbocyclyl (e.g., cycloalkyl), heteroaryl, and heterocyclyl groups may also be substituted with alkyl (unsubstituted and substituted such as arylalkyl (e.g., substituted and unsubstituted benzyl)).

Compounds of the invention can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbents or eluant). That is, certain of the disclosed compounds may exist in various stereoisomeric forms. Stereoisomers are compounds that differ only in their spatial arrangement. Enantiomers are pairs of stereoisomers whose mirror images are not superimposable, most commonly because they contain an asymmetrically substituted carbon atom that acts as a chiral center. "Enantiomer" means one of a pair of molecules that are mirror images of each other and are not superimposable. Diastereomers are stereoisomers that are not related as mirror images, most commonly because they contain two or more asymmetrically substituted carbon atoms and represent the configuration of substituents around one or more chiral carbon atoms. Enantiomers of a compound can be prepared, for example, by separating an enantiomer from a racemate using one or more well-known techniques and methods, such as, for example, chiral chromatography and separation methods based thereon. The appropriate technique and/or method for separating an enantiomer of a compound described herein from a racemic mixture can be readily determined by those of skill in the art. "Racemate" or "racemic mixture" means a compound containing two enantiomers, wherein such mixtures exhibit no optical activity; i.e., they do not rotate the plane of polarized light. "Geometric isomer" means isomers that differ in the orientation of substituent atoms in relationship to a carbon-carbon double bond, to a cycloalkyl ring, or to a bridged bicyclic system. Atoms (other than H) on each side of a carbon-carbon double bond may be in an E (substituents are on opposite sides of the carbon-carbon double bond) or Z (substituents are oriented on the same side) configuration. "R," "S," "S*," "R*," "E," "Z," "cis," and "trans," indicate configurations relative to the core molecule. Certain of the disclosed compounds may exist in atropisomeric forms. Atropisomers are stereoisomers resulting from hindered rotation about single bonds where the steric strain barrier to rotation is high enough to allow for the isolation of the conformers. The compounds of the invention may be prepared as individual isomers by either isomer-specific synthesis or resolved from an isomeric mixture. Conventional resolution techniques include forming the salt of a free base of each isomer of an isomeric pair using an optically active acid (followed by fractional crystallization and regeneration of the free base), forming the salt of the acid form of each isomer of an isomeric pair using an optically active amine (followed by fractional crystallization and regeneration of the free acid), forming an ester or amide of each of the isomers of an isomeric pair using an optically pure acid, amine or alcohol (followed by chromatographic separation and removal of the chiral auxiliary), or resolving an isomeric mixture of either a starting material or a final product using various well known chromatographic methods. When the stereochemistry of a disclosed compound is named or depicted by structure, the named or depicted stereoisomer is at least 60%, 70%, 80%, 90%, 99% or 99.9%) by weight relative to the other stereoisomers. When a single enantiomer is named or depicted by structure, the depicted or named enantiomer is at least 60%, 70%, 80%, 90%, 99% or 99.9% by weight optically pure. When a single diastereomer is named or depicted by structure, the depicted or named diastereomer is at least 60%, 70%, 80%, 90%, 99% or 99.9% by weight pure. Percent optical purity is the ratio of the weight of the enantiomer or over the weight of the enantiomer plus the weight of its optical isomer. Diastereomeric purity by weight is the ratio of the weight of one diastereomer or over the weight of all the diastereomers. When the stereochemistry of a disclosed compound is named or depicted by structure, the named or depicted stereoisomer is at least 60%, 70%, 80%, 90%, 99% or 99.9% by mole fraction pure relative to the other stereoisomers. When a single enantiomer is named or depicted by structure, the depicted or named enantiomer is at least 60%, 70%, 80%, 90%, 99% or 99.9% by mole fraction pure. When a single diastereomer is named or depicted by structure, the depicted or named diastereomer is at least 60%, 70%, 80%, 90%, 99% or 99.9% by mole fraction pure. Percent purity by mole fraction is the ratio of the moles of the enantiomer or over the moles of the enantiomer plus the moles of its optical isomer. Similarly, percent purity by moles fraction is the ratio of the moles of the diastereomer or over the moles of the diastereomer plus the moles of its isomer. When a disclosed compound is named or depicted by structure without indicating the stereochemistry, and the compound has at least one chiral center, it is to be understood that the name or structure encompasses either enantiomer of the compound free from the corresponding optical isomer, a racemic mixture of the compound or mixtures enriched in one enantiomer relative to its corresponding optical isomer. When a disclosed compound is named or depicted by structure without indicating the stereochemistry and has two or more chiral centers, it is to be understood that the name or structure encompasses a diastereomer free of other diastereomers, a number of diastereomers free from other diastereomeric pairs, mixtures of diastereomers, mixtures of diastereomeric pairs, mixtures of diastereomers in which one diastereomer is enriched relative to the other diastereomer(s) or mixtures of diastereomers in which one or more diastereomer is enriched relative to the other diastereomers. The invention embraces all of these forms.

Definitions

In the practice of the methods of the present invention, an "effective amount" of any one of the compounds of the invention or a combination of any of the compounds of the invention or a pharmaceutically acceptable salt thereof, is administered via any of the usual and acceptable methods known in the art, either singly or in combination.

The term "pharmaceutical composition," as used herein, represents a composition containing a compound described herein formulated with a pharmaceutically acceptable excipient, and manufactured or sold with the approval of a governmental regulatory agency as part of a therapeutic regimen for the treatment of disease in a mammal. Pharmaceutical compositions can be formulated, for example, for oral administration in unit dosage form (e.g., a tablet, capsule, caplet, gelcap, or syrup); for topical administration (e.g., as a cream, gel, lotion, or ointment); for intravenous administration (e.g., as a sterile solution free of particulate emboli and in a solvent system suitable for intravenous use); or in any other pharmaceutically acceptable formulation.

A "pharmaceutically acceptable excipient," as used herein, refers any ingredient other than the compounds described herein (for example, a vehicle capable of suspending or dissolving the active compound) and having the properties of being substantially nontoxic and non-inflammatory in a patient. Excipients may include, for example: antiadherents, antioxidants, binders, coatings, compression aids, disintegrants, dyes (colors), emollients, emulsifiers, fillers (diluents), film formers or coatings, flavors, fragrances, glidants (flow enhancers), lubricants, preservatives, printing inks, sorbents, suspensing or dispersing agents, sweeteners, and waters of hydration. Exemplary excipients include, but are not limited to: butylated hydroxytoluene (BHT), calcium carbonate, calcium phosphate (dibasic), calcium stearate, croscarmellose, crosslinked polyvinyl pyrrolidone, citric acid, crospovidone, cysteine, ethylcellulose, gelatin, hydroxypropyl cellulose, hydroxypropyl methylcellulose, lactose, magnesium stearate, maltitol, mannitol, methionine, methylcellulose, methyl paraben, microcrystalline cellulose, polyethylene glycol, polyvinyl pyrrolidone, povidone, pregelatinized starch, propyl paraben, retinyl palmitate, shellac, silicon dioxide, sodium carboxymethyl cellulose, sodium citrate, sodium starch glycolate, sorbitol, starch (corn), stearic acid, sucrose, talc, titanium dioxide, vitamin A, vitamin E, vitamin C, and xylitol.

As used herein, the term "pharmaceutically acceptable salt" means any pharmaceutically acceptable salt of the compound of formula (I). For example pharmaceutically acceptable salts of any of the compounds described herein include those that are within the scope of sound medical judgment, suitable for use in contact with the tissues of humans and animals without undue toxicity, irritation, allergic response and are commensurate with a reasonable benefit/risk ratio. Pharmaceutically acceptable salts are well known in the art. For example, pharmaceutically acceptable salts are described in: Berge et al., *J. Pharmaceutical Sciences* 66:1-19, 1977 and in *Pharmaceutical Salts: Properties, Selection, and Use*, (Eds. P. N. Stahl and C. G. Wermuth), Wiley-VCH, 2008. The salts can be prepared in situ during the final isolation and purification of the compounds described herein or separately by reacting a free base group with a suitable organic acid.

The compounds of the invention may have ionizable groups so as to be capable of preparation as pharmaceutically acceptable salts. These salts may be acid addition salts involving inorganic or organic acids or the salts may, in the case of acidic forms of the compounds of the invention be prepared from inorganic or organic bases. Frequently, the compounds are prepared or used as pharmaceutically acceptable salts prepared as addition products of pharmaceutically acceptable acids or bases. Suitable pharmaceutically acceptable acids and bases and methods for preparation of the appropriate salts are well-known in the art. Salts may be prepared from pharmaceutically acceptable non-toxic acids and bases including inorganic and organic acids and bases.

Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, and valerate salts. Representative alkali or alkaline earth metal salts include sodium, lithium, potassium, calcium, and magnesium, as well as nontoxic ammonium, quaternary ammonium, and amine cations, including, but not limited to ammonium, tetramethylammonium, tetraethylammonium, methylamine, dimethylamine, trimethylamine, triethylamine, and ethylamine.

As used herein, the term "stearoyl-CoA desaturase (SCD)-associated disorder" refers to an undesired physiological condition, disorder, or disease that is associated with and/or mediated at least in part by an SCD protein. In some instances, SCD-associated disorders are associated with excess SCD levels and/or activity. SCDs introduce a double bond in the C9-C10 position of saturated fatty acids such as palmitoyl-CoA and stearoyl-CoA which are converted to palmitoleoyl-CoA and oleoyl-CoA, respectively. One SCD gene, SCD1, has been characterized in humans for which there are two isoforms, SCD1 and SODS. An SCD-associated disorder may be associated with and/or mediated at least in part by SCD1 and/or SODS. Exemplary SCD-associated disorders include SCD-associated disorders include, but are not limited to metabolic disorders (e.g., diabetes (e.g., Type I diabetes and Type II diabetes), hyperglycemia, metabolic syndrome, obesity, lipid disorders, fatty liver, nonalcoholic steatohepatitis (NASH), nonalcoholic fatty liver disease (NAFLD), and hypertension), cancer, cardiovascular diseases, cerebrovascular diseases, kidney diseases, liver diseases, skin disorders (e.g., acne (e.g., acne vulgaris)), central nervous system (CNS) disorders, dementia, multiple sclerosis, schizophrenia, mild cognitive impairment, Alzheimer's Disease, cerebral amyloid angiopathy, and dementia associated with Down Syndrome. Additional SCD-associated disorders are described herein or known in the art.

As used herein, the term "subject" refers to any organism to which a composition in accordance with the invention may be administered, e.g., for experimental, diagnostic, prophylactic, and/or therapeutic purposes. Typical subjects include any animal (e.g., mammals such as mice, rats, rabbits, non-human primates, and humans). A subject may seek or be in need of treatment, require treatment, be receiving treatment, be receiving treatment in the future, or be a human or animal who is under care by a trained professional for a particular disease or condition.

As used herein, the terms "treat," "treated," or "treating" mean both therapeutic treatment and prophylactic or preventative measures wherein the object is to prevent or slow down (lessen) an undesired physiological condition, disorder, or disease, or obtain beneficial or desired clinical results. Beneficial or desired clinical results include, but are not limited to, alleviation of symptoms; diminishment of the extent of a condition, disorder, or disease; stabilized (i.e., not worsening) state of condition, disorder, or disease; delay in onset or slowing of condition, disorder, or disease progression; amelioration of the condition, disorder, or disease state or remission (whether partial or total), whether detectable or undetectable; an amelioration of at least one measurable physical parameter, not necessarily discernible by the patient; or enhancement or improvement of condition, disorder, or disease. Treatment includes eliciting a clinically significant response without excessive levels of side effects. Treatment also includes prolonging survival as compared to expected survival if not receiving treatment.

BRIEF DESCRIPTION OF THE DRAWINGS

(FIG. 1A) Compound 7, a representative 1,2,4-oxadiazole, was profiled in ApoE4 (top) and control (bottom) non-inducing conditions at 12-point dose (x-axis). The Y-axis shows raw $OD_{600}$. Compound 7 exhibited a bell-shaped dose-response curve (DRC) in the ApoE4 model. Rescue decreased at concentrations just above the maximal efficacy (Emax). In the control condition (bottom panel), growth decreased at this same concentration. (FIG. 1B) The relationship between Emax (rescue in ApoE4) and growth inhibition (in control condition) correlated across 34 tested 1,2,4-oxadiazoles. The maximal rescue dose (EC100) is shown on the y-axis for ApoE4 and minimal inhibitory dose (IC100) in the control condition is shown on the x-axis. This correlation indicates that growth inhibition is caused by the same on-target activity that rescues ApoE4 toxicity.

(FIG. 2A) Growth inhibition (24 h) of strain GM yap1 flr1 by Ole1/SCD-targeting 1,2,4-oxadiazoles is reversed by exogenous 0.5 mM oleic/palmitoleic acid, which did not affect growth inhibition by other compounds (black dots indicate other scaffolds tested). Maximal growth inhibition across a dose range from 33 nM to 33 µM is plotted. (FIG. 2B) Rescue (40 h) of the yeast alpha-synuclein ("aSyn") model by 1,2,4-oxadiazoles was reversed by exogenous 0.5 mM oleic/palmitoleic acid, which did not affect rescue by other scaffolds. Maximal model rescue across a dose range from 33 nM to 33 µM is plotted.

(FIG. 3A) Yeast cells deleted for the chromosomal copy of OLE1 and expressing OLE1 (wild-type), ole1P123T, or ole1E188Q mutants from a pRS316-based plasmid were grown in complete synthetic medium (CSM)-glucose media at the indicated doses of 1,2,4-oxadiazole Compound 95 for 24 h. Growth was normalized to samples treated with the solvent control dimethyl sulfoxide (DMSO), set as "1". (FIG. 3B) Yeast cells deleted for the chromosomal copy of OLE1 and expressing OLE1 (Wild-type), ole1P123T, or ole1E188Q mutants from a pRS316-based plasmid were grown in CSM-galactose media (inducing expression of alpha-Synuclein) at the indicated doses of the 1,2,4-oxadiazole Compound 95 for 40 h. Growth was normalized to samples treated with the solvent control DMSO, where rescue is set as "1".

DETAILED DESCRIPTION OF THE INVENTION

Figure 1A:
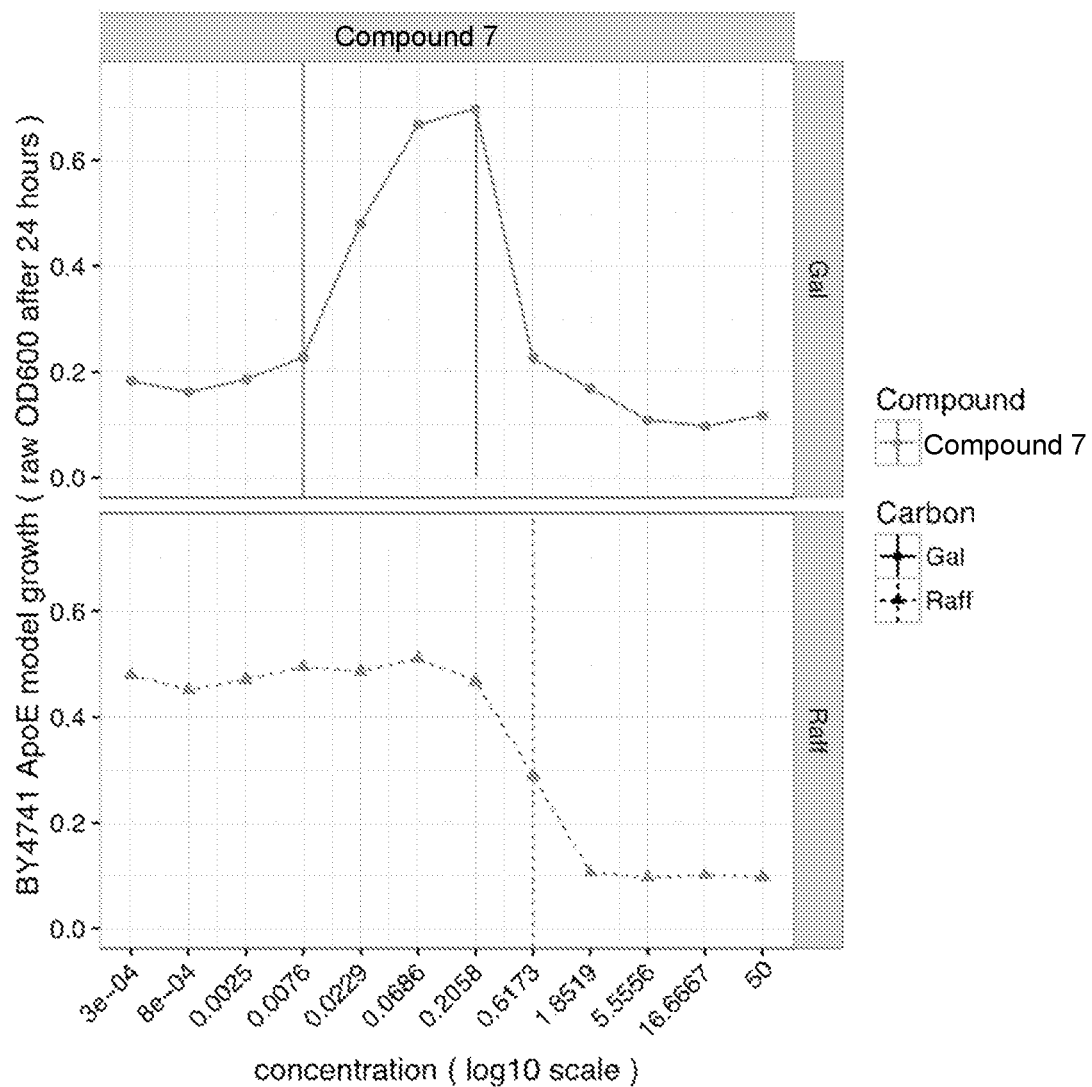
FIGS. 1A and 1B are graphs showing that growth inhibition by 1,2,4-oxadiazoles occurs through same mechanism as the rescue of toxicity in the apolipoprotein E4 (ApoE4) Alzheimer's disease yeast model.

The invention features compounds useful for the treatment of neurological disorders, e.g., by inhibiting α-synuclein toxicity in a cell such as a neural cell. Exemplary compounds described herein include compounds having a structure according to formula I or formula Ia:

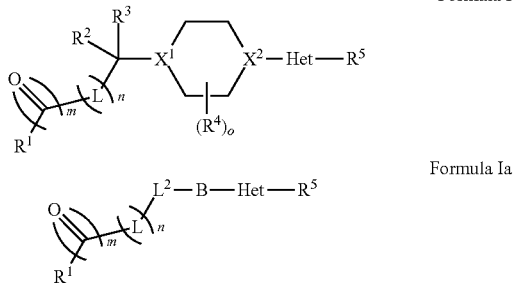

or pharmaceutically acceptable salts thereof.

In some embodiments, the compound has the structure of any one of compounds 1-746 in Table 1.

Other embodiments, as well as exemplary methods for the synthesis or production of these compounds, are described herein.

Pharmaceutical Uses

The compounds described herein are useful in the methods of the invention and, while not bound by theory, are believed to exert their desirable effects through their ability to inhibit toxicity caused by protein aggregation, e.g., α-synuclein aggregation, in a cell.

Another aspect of the present invention relates to methods of treating and/or preventing a neurological disorders such as neurodegenerative diseases in a subject in need thereof. The pathology of neurodegenerative disease, may be characterized by the presence of inclusion bodies in brain tissue of affected patients.

In certain embodiments, neurological disorders that may be treated and/or prevented by the inventive methods include, but are not limited to, Alexander disease, Alper's disease, AD, amyotrophic lateral sclerosis, ataxia telangiectasia, Canavan disease, Cockayne syndrome, corticobasal degeneration, Creutzfeldt-Jakob disease, Huntington disease, Kennedy's disease, Krabbe disease, Lewy body dementia, Machado-Joseph disease, multiple sclerosis, PD, Pelizaeus-Merzbacher disease, Pick's disease, primary lateral sclerosis, Ref sum's disease, Sandhoff disease, Schilder's disease, Steele-Richardson-Olszewski disease, tabes *dorsalis*, and Guillain-Barre Syndrome.

The compounds described herein are useful as inhibitors of stearoyl-CoA desaturase (SCD), including SCD1 and/or SCD5. SCD inhibitors are known in the art to be useful in methods of treating and/or preventing SCD-associated disorders. SCD-associated disorders are described, for example, in U.S. Pat. No. 8,148,378, and in International Patent Application Publication Nos. WO 2011/047481, WO 2010/112520, WO 2010/045374, WO 2010/028761; WO 2009150196, and WO 2009/106991. Accordingly, another aspect of the present invention relates to methods of treating and/or preventing an SCD-associated disorder in a subject in need thereof.

SCD-associated disorders include metabolic disorders (e.g., insulin resistance, diabetes mellitus (e.g., Type I diabetes, Type II diabetes, non-insulin-dependent diabetes mellitus, gestational diabetes, and diabetic complications (e.g., diabetic peripheral neuropathy, diabetic nephropathy diseases, diabetic retinopathy, diabetic macroangiopathy, vascular complications of diabetes, and diabetic arteriosclerosis)), hyperglycemia, metabolic syndrome, hyperinsulinanemia, glucose intolerance, impaired glucose tolerance, body weight disorders (e.g., obesity (e.g., abdominal obesity), overweight, cachexia, body mass index, and anorexia), lipid disorders (e.g., abnormal lipid levels (e.g., elevated lipid levels, for example, in plasma), dyslipidemia (e.g., diabetic dyslipidemia), mixed dyslipidemia, hyperlipidemia, hypertriglyceridemia, hypoalphalipoproteinemia, hyperbetalipoproteinemia, atherosclerosis, hypercholesterolemia (e.g., familial hypercholesterolemia), low HDL, high LDL, diseases related to accumulation of lipids in liver, familial histiocytic reticulosis, lipoprotein lipase deficiency, polyunsaturated fatty acid (PUFA) disorder, fatty acid desaturation index (e.g. the ratio of 18:1/18:0 fatty acids, or other fatty acids), and abnormal lipid metabolism disorders), disorders of abnormal plasma lipoprotein, disorders of pancreatic beta cell regeneration, fatty liver, nonalcoholic steatohepatitis (NASH), nonalcoholic fatty liver disease (NAFLD), hypertension, and microalbuminemia, leptin related diseases, hyperleptinaemia, appetite disorder, essential fatty acid deficiency, and adverse weight gain associated with a drug therapy).

Additional SCD-associated disorders include cancer, including solid tumors or hematological malignancies (e.g., esophageal cancer, pancreatic cancer, endometrial cancer, kidney cancer, hepatoma, thyroid cancer, gallbladder cancer, prostate cancer, leukemia (e.g., lymphomas and myelomas), ENT-related cancer, brain cancer, colon cancer, rectal cancer, colorectal cancer, ovarian cancer, uterine cancer, breast cancer, skin cancer, and prostate cancer), neoplasia, malignancy, metastases, tumors (benign or malignant), carcinogenesis, and hepatomas.

Further SCD-associated disorders include cardiovascular disease (e.g., heart disease, atherosclerosis, hypertension, lipidemia, dyslipidemia, elevated blood pressure, microalbuminemia, hyperuricaemia, hypercholesterolemia, hyperlipidemias, hypertriglyceridemias, arteriosclerosis, coronary artery disease, myocardial infarction, vascular complications of diabetes, and diabetic arteriosclerosis), inflammation, sinusitis, asthma, pancreatitis, osteoarthritis, rheumatoid arthritis, hepatitis (e.g., sexual hepatitis), meibomitis, cystic fibrosis, pre-menstrual syndrome, osteoporosis, thrombosis, cardiovascular risks, weight loss, angina, high blood pressure, ischemia, cardiac ischemia, reperfusion injury, angioplastic restenosis, infertility, liver disease (e.g., fatty liver, cirrhosis, nonalcoholic steatohepatitis, liver fibrosis, and hepatitis C related steatosis), kidney disease (e.g., tubulointerstitial fibrosis, kidney lipid accumulation, glomerular sclerosis, and proteinuria), osteoarthritis (e.g., osteoarthritis of the knee), gastro-esophageal disease, sleep apnea, secondary hyperparathyroidism of renal osteodystrophy, peripheral vascular disease, cerebrovascular disease (e.g., stroke, ischemic stroke and transient ischemic attack (TIA), and ischemic retinopathy), hyperandrogenism, malignant syndrome, extrapyramidal symptoms, hyperuricemia, hypercoagulability, syndrome X, cataract, polycystic ovary syndrome, breathing abnormalities, sleep-disordered breathing, low back pain, gout, gallstone disease, myopathies, lipid myopathies (e.g., carnitine palmitoyltransferase deficiency (CPT I or CPT II)), autoimmune diseases (e.g., lupus, host versus graft rejection, and rejection of organ transplants), asthma, inflammatory bowel diseases, nephropathy, retinopathy, erythrohepatic protoporphyria, iron overload disorders, and hereditary hemochromatosis.

Still further SCD-associated disorders include central nervous system (CNS) disorders, dementia, schizophrenia, mild cognitive impairment, Alzheimer's Disease, cerebral amyloid angiopathy, dementia associated with Down Syndrome, other neurodegenerative diseases, psychiatric disorders, eye diseases, immune disorders, multiple sclerosis, neuropathy, and depression.

Additional SCD-associated disorders include skin disorders (e.g., acne (e.g., acne vulgaris), psoriasis, hirsutism, rosacea, seborrheic skin, oily skin (syn seborrhea), seborrheic dermatitis, hyperseborrhea, eczema, keloid scar, skin ageing, diseases related to production or secretions from mucous membranes, wrinkles, lack of adequate skin firmness, lack of adequate dermal hydration, insufficient sebum secretion, oily hair, shiny skin, greasy-looking skin, greasy-looking hair, and other skin conditions caused by lipid imbalance).

An SCD-associated disorder can also include a disease or condition which is, or is related to, viral diseases or infections.

In some embodiments, the SCD-associated disorder is acne (e.g., acne vulgaris). In some embodiments, the SCD-associated disorder is diabetes (e.g., type II diabetes, including diabetes with inadequate glycemic control). In some embodiments, the SCD-associated disorder is nonalcoholic fatty liver disease (NAFLD). In some embodiments, the SCD-associated disorder is nonalcoholic steatohepatitis (NASH). In some embodiments, the SCD-associated disorder is cancer. In some embodiments, the SCD-associated disorder is obesity. In some embodiments, the SCD-associated disorder is metabolic syndrome (e.g., dyslipidemia, obesity, insulin resistance, hypertension, microalbuminemia, hyperuricaemia, and hypercoagulability), syndrome X, diabetes, insulin resistance, decreased glucose tolerance, non-insulin-dependent diabetes mellitus, Type II diabetes, Type I diabetes, diabetic complications, body weight disorders (e.g., obesity, overweight, cachexia, and anorexia), weight loss, body mass index, leptin related diseases, or a skin disorder (e.g., eczema, acne, psoriasis, and keloid scar). In some embodiments, the SCD-associated disorder is diabetes, metabolic syndrome, insulin resistance, obesity, a cardiovascular disorder, a CNS disorder, schizophrenia, or Alzheimer's disease.

Combination Formulations and Uses Thereof

The compounds of the invention can be combined with one or more therapeutic agents. In particular, the therapeutic agent can be one that treats or prophylactically treats any neurological disorder described herein.

Combination Therapies

A compound of the invention can be used alone or in combination with other agents that treat neurological disorders or symptoms associated therewith, or in combination with other types of treatment to treat, prevent, and/or reduce the risk of any neurological disorders. In combination treatments, the dosages of one or more of the therapeutic compounds may be reduced from standard dosages when administered alone. For example, doses may be determined empirically from drug combinations and permutations or may be deduced by isobolographic analysis (e.g., Black et al., Neurology 65:S3-S6, 2005). In this case, dosages of the compounds when combined should provide a therapeutic effect.

Pharmaceutical Compositions

The compounds of the invention are preferably formulated into pharmaceutical compositions for administration to human subjects in a biologically compatible form suitable for administration in vivo. Accordingly, in another aspect, the present invention provides a pharmaceutical composition comprising a compound of the invention in admixture with a suitable diluent, carrier, or excipient.

The compounds of the invention may be used in the form of the free base, in the form of salts, solvates, and as prodrugs. All forms are within the scope of the invention. In accordance with the methods of the invention, the described compounds or salts, solvates, or prodrugs thereof may be administered to a patient in a variety of forms depending on the selected route of administration, as will be understood by those skilled in the art. The compounds of the invention may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound of the invention may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, a compound of the invention may be incorporated with an excipient and used in the form of ingestible tablets, buccal tablets, troches, capsules, elixirs, suspensions, syrups, and wafers.

A compound of the invention may also be administered parenterally. Solutions of a compound of the invention can be prepared in water suitably mixed with a surfactant, such as hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2003, 20th ed.) and in The United States Pharmacopeia: The National Formulary (USP 24 NF19), published in 1999.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe.

Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve which is intended for disposal after use. Where the dosage form comprises an aerosol dispenser, it will contain a propellant, which can be a compressed gas, such as compressed air or an organic propellant, such as fluorochlorohydrocarbon. The aerosol dosage forms can also take the form of a pump-atomizer.

Compositions suitable for buccal or sublingual administration include tablets, lozenges, and pastilles, where the active ingredient is formulated with a carrier, such as sugar, acacia, tragacanth, gelatin, and glycerine. Compositions for rectal administration are conveniently in the form of suppositories containing a conventional suppository base, such as cocoa butter.

The compounds of the invention may be administered to an animal, e.g., a human, alone or in combination with pharmaceutically acceptable carriers, as noted herein, the proportion of which is determined by the solubility and chemical nature of the compound, chosen route of administration, and standard pharmaceutical practice.

Dosages

The dosage of the compounds of the invention, and/or compositions comprising a compound of the invention, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds of the invention may be administered initially in a suitable dosage that may be adjusted as required, depending on the clinical response. In general, satisfactory results may be obtained when the compounds of the invention are administered to a human at a daily dosage of, for example, between 0.05 mg and 3000 mg (measured as the solid form). Dose ranges include, for example, between 10-1000 mg (e.g., 50-800 mg). In some embodiments, 50, 100, 150, 200, 250, 300, 350, 400, 450, 500, 550, 600, 650, 700, 750, 800, 850, 900, 950, or 1000 mg of the compound is administered. Preferred dose ranges include, for example, between 0.05-15 mg/kg or between 0.5-15 mg/kg.

Alternatively, the dosage amount can be calculated using the body weight of the patient. For example, the dose of a compound, or pharmaceutical composition thereof, administered to a patient may range from 0.1-50 mg/kg (e.g., 0.25-25 mg/kg). In exemplary, non-limiting embodiments, the dose may range from 0.5-5.0 mg/kg (e.g., 0.5, 1.0, 1.5, 2.0, 2.5, 3.0, 3.5, 4.0, 4.5, or 5.0 mg/kg) or from 5.0-20 mg/kg (e.g., 5.5, 6.0, 6.5, 7.0, 7.5, 8.0, 8.5, 9.0, 9.5, 10, 11, 12, 13, 14, 15, 16, 17, 18, 19, or 20 mg/kg).

EXAMPLES

The synthesis of compounds of this invention can be synthesized according to one or more of the general schemes 1-10 shown below. The variables recited in the general schemes below are as defined for Formulae I, II, III, and IV.

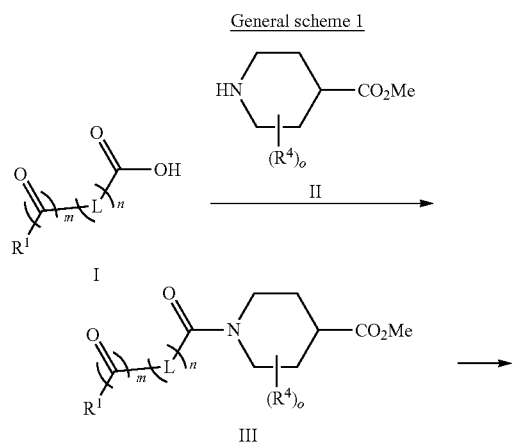

General scheme 1

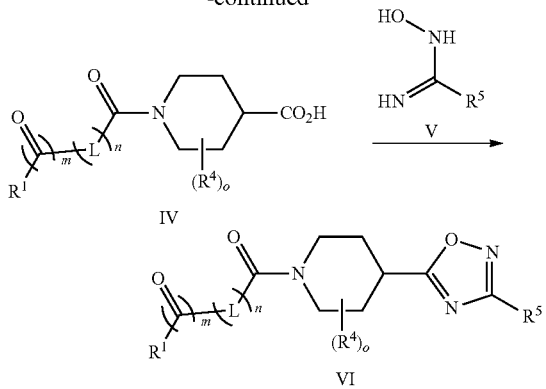

An appropriately substituted carboxylic acid I can be coupled with an appropriately substituted piperidine II to provide ester III. This can be hydrolysed under variety of conditions to provide carboxylic acid intermediate IV. This can be condensed with a substituted N-hydroxyimidamide V to give the desired 1,2,4-oxadiazole compound VI.

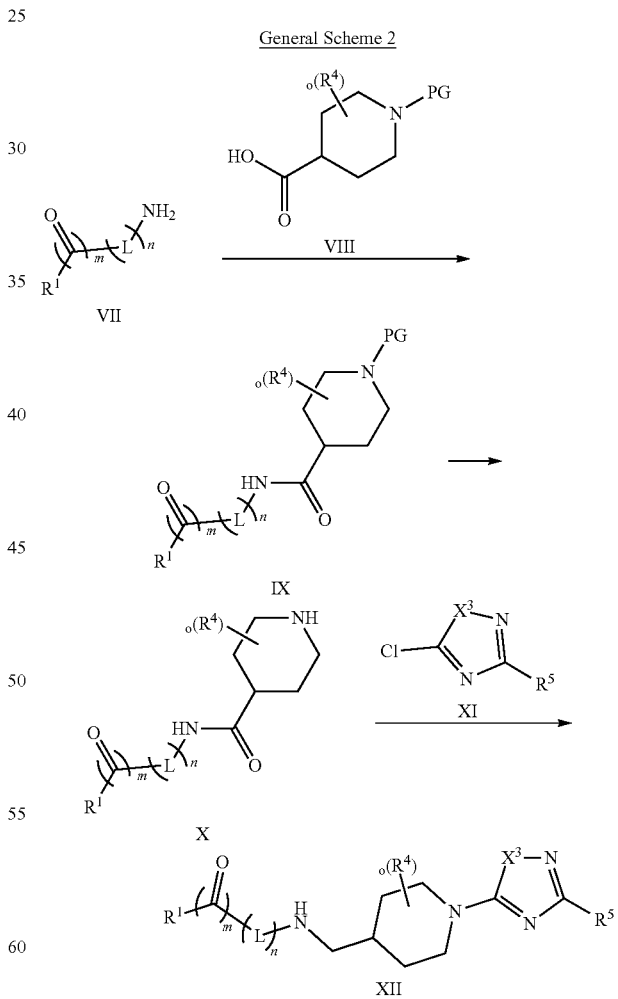

General Scheme 2

An appropriately substituted carboxylic acid VII can be coupled with an appropriately protected (where PG is an N-protecting group) and substituted piperidine carboxylic acid VIII to provide intermediate IX. This can be deprotected using a variety of conditions to provide free amine intermediate X. This compound can be coupled using metal catalysis or under thermal conditions with a halogenated heterocycle such as XI to give the desired 1,2,4-oxadiazole ($X^3$=O) or 1,2,4-thiadiazole ($X^3$=S) compound XII.

General scheme 3

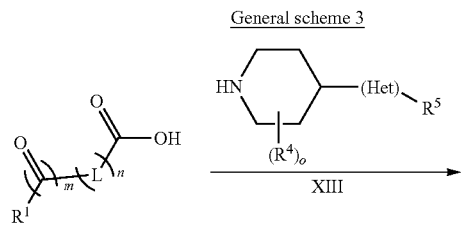

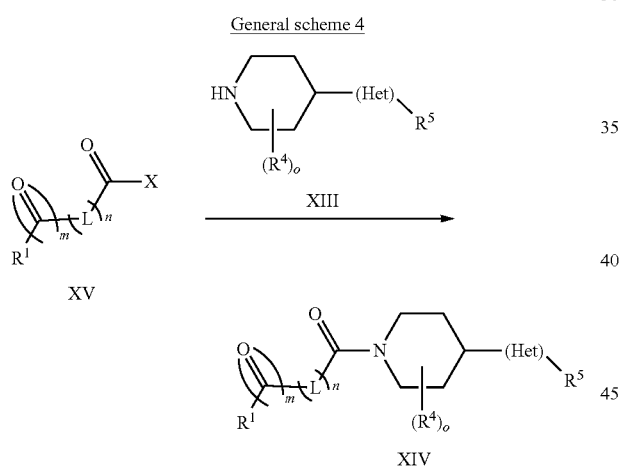

An appropriately substituted carboxylic acid I can be coupled with an appropriately substituted piperidine XIII to provide the desired heterocyclic compound XIV.

General scheme 4

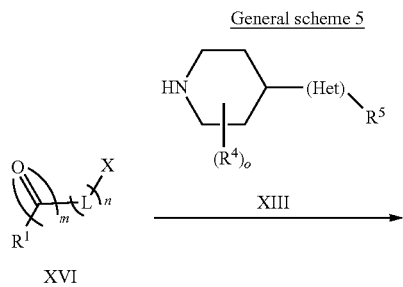

An appropriately substituted acyl halide XV (where X is a halogen atom, e.g., chlorine) can be coupled with an appropriately substituted piperidine XIII to provide the desired heterocyclic compound XIV.

General scheme 5

-continued

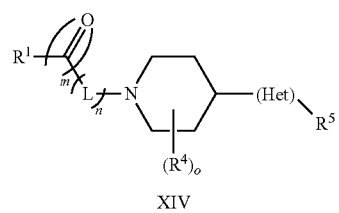
XIV

An appropriately substituted alkyl intermediate XVI (where X is a good leaving group, e.g., a halogen atom or triflate) can undergo nucleophilic displacement with an appropriately substituted piperidine XIII to provide the desired heterocyclic compound XIV.

General scheme 6

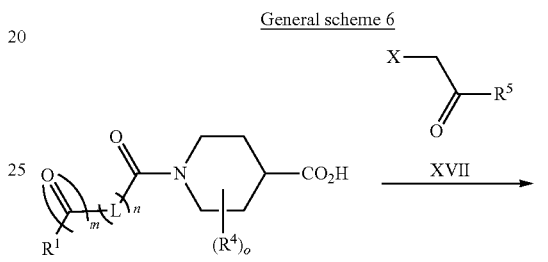

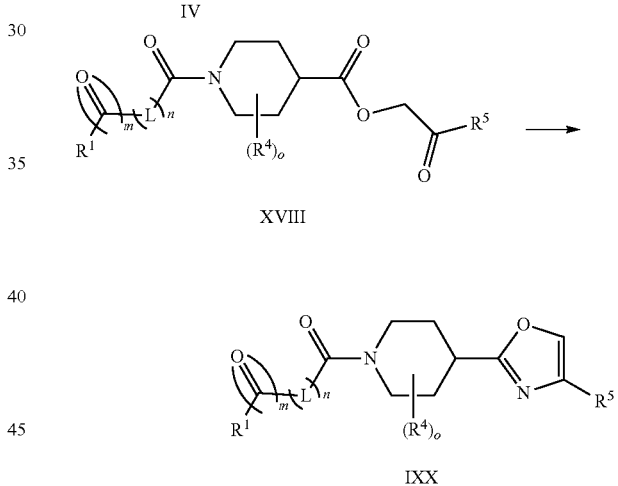

An appropriately substituted carboxylic acid IV can be coupled with an appropriately substituted ketone XVII (where X is a leaving group, e.g., bromine) to provide the intermediate compound XVII. This compound can be condensed with ammonium acetate to provide oxazole IXX.

General scheme 7

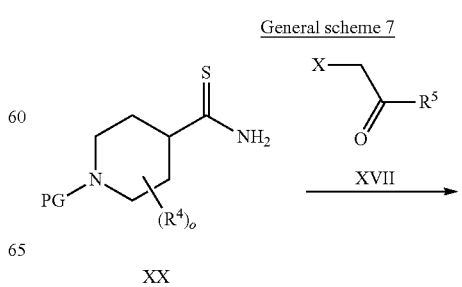

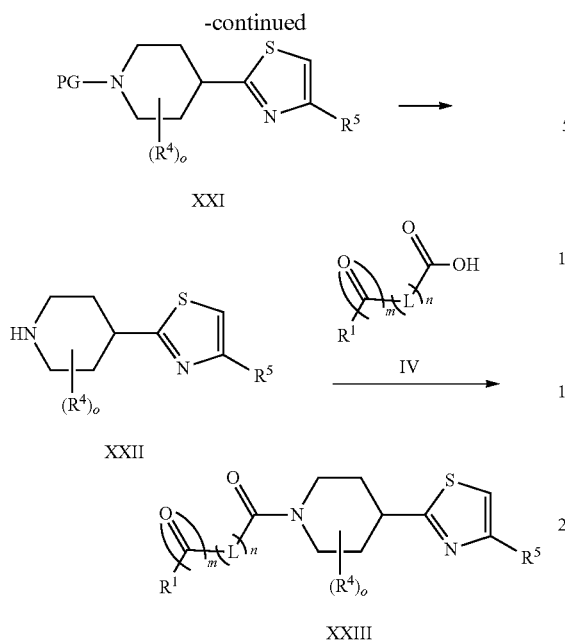

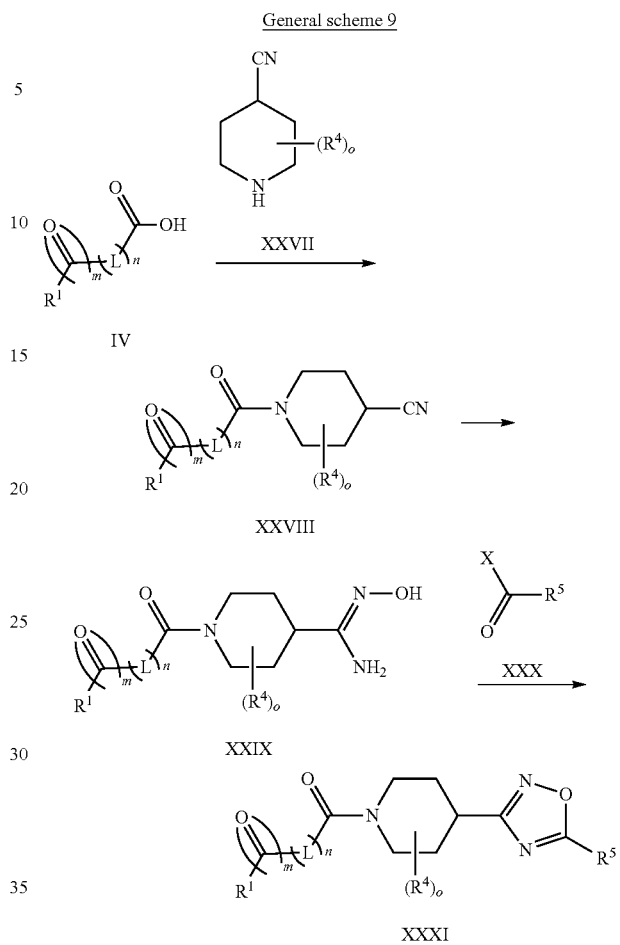

An appropriately protected and substituted thiomide XX can be coupled with an appropriately substituted ketone XVII (where X is a leaving group, most commonly bromine) to provide the protected (where PG is an amine protecting group, such as tert-butoxycarbonyl) thiazole compound XXI. This compound can be deprotected under appropriate conditions to give intermediate piperidine XXII. This can be coupled with and appropriately substituted carboxylic acid IV to provide thiazole XXIII.

General scheme 8

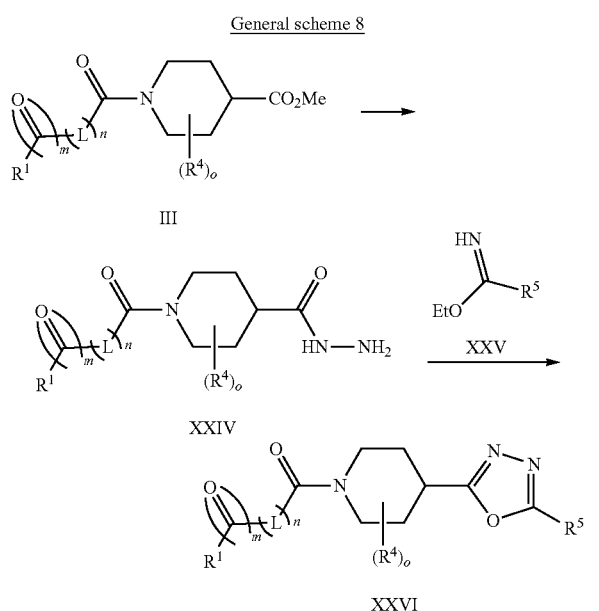

An appropriately protected and substituted ester III can be treated with hydrazine to provide the hydrazide compound XXIV. This compound can coupled with an appropriately substituted acetamidate XXV to provide 1,3,4-oxadiazole XXVI.

An appropriately substituted carboxylic acid IV can be couple with and appropriately substituted piperidine compound XXVII to give a compound XXVIII. This compound can be converted to the corresponding hydroxyimidamide compound XXIX. This is can be treated with an appropriately substituted acid halide (most commonly an acid chloride, where X=Cl) XXX to provide 1,2,4-oxadiazole XXXI.

General scheme 10

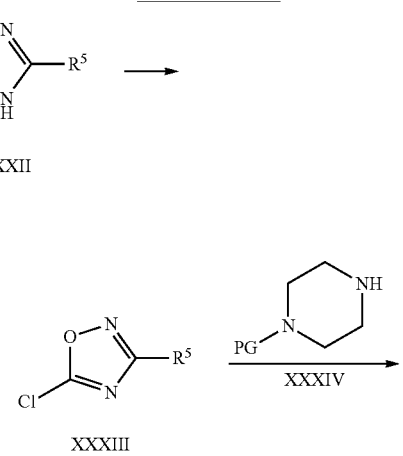

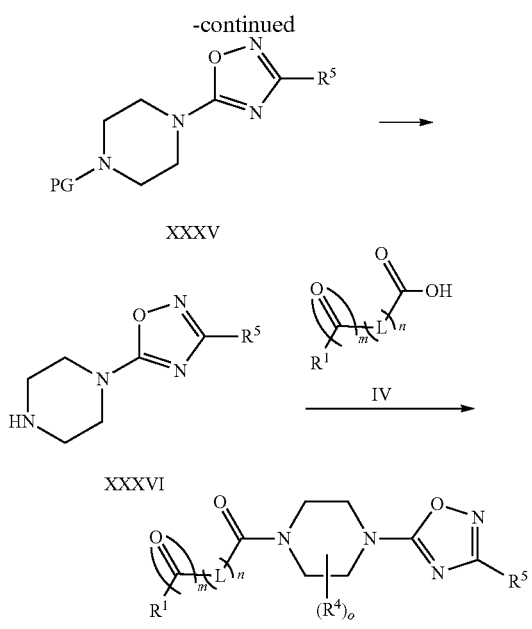

An appropriately substituted oxadiazolone XXXII can be converted to the appropriately substituted compound XXXIII. This compound can be coupled with the appropriate protected piperazine compound XXXIV (where PG is an N-protecting group, for example, a tert-butyloxycarbonyl group) to give compound XXXV. This compound can be deprotected under the appropriate conditions to give piperazine compound XXXVI. This can be coupled with a carboxylic acid IV to provide 1,2,4-oxadiazole XXXVII.

Experimental Procedures

The compounds of the invention can be synthesized according to the following procedures.

In the examples below, when purification by preparative HPLC was performed, a Gilson 281 semi-preparative HPLC system was used, using a variety of stationary and mobile phases which are described in the experimental section. For example, (column: Waters X bridge 150×2.5 mm 5 μm; mobile phase: [water (10 mM NH$_4$OAc)-acetonitrile]; B %: 36%-66%, 12 min) indicates that the following purification conditions were used:

Mobile phase: A: 10 mM NH$_4$OAc in H$_2$O; B: acetonitrile
Column: Waters Xbridge 150×2.5 mm dimensions, 5 μm particle size
Flow rate: 25 mL/min
Monitor wavelength: 220&254 nm
Gradient:

| Time/minutes | B % |
|---|---|
| 0.0 | 36 |
| 12.0 | 66 |
| 12.2 | 100 |
| 14.0 | 100 |
| 14.2 | 36 |
| 16.0 | 36 |

Example 1. Preparation of 1-(3,4-dimethylphenyl)-4-(4-(3-phenyl-1,2,4-oxadiazol-5-yl)piperidine-1-carbonyl)pyrrolidin-2-one

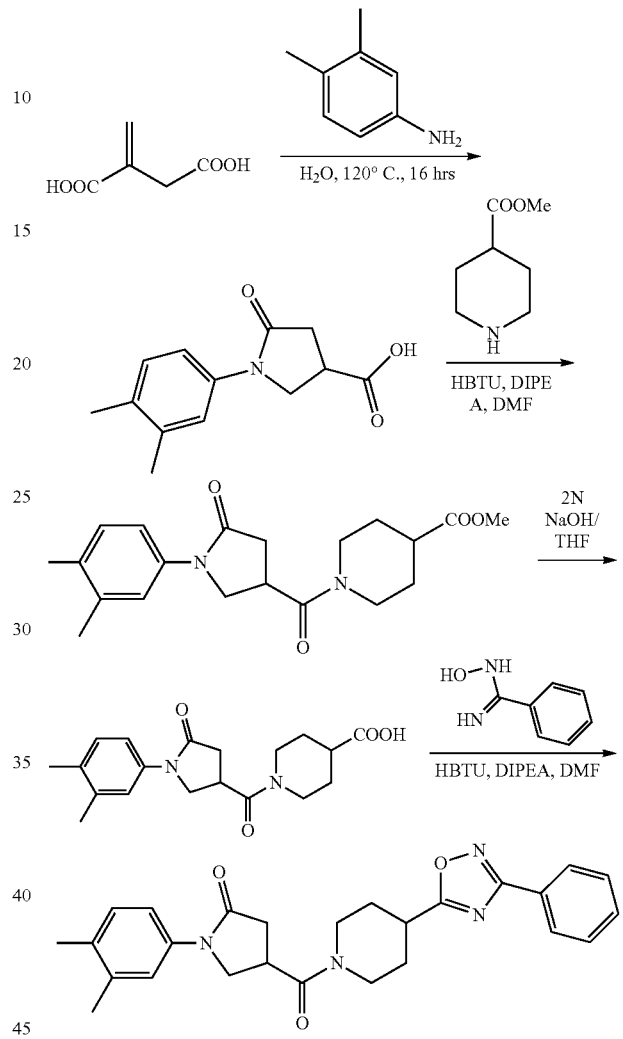

Step 1: Preparation of 1-(3,4-dimethylphenyl)-5-oxopyrrolidine-3-carboxylic acid

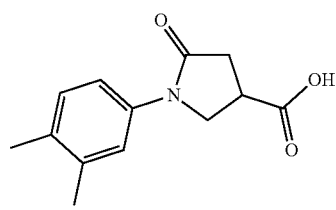 [SMILES: Cc1ccc(N2CC(C(=O)O)CC2=O)cc1C]

A mixture of 2-methylenesuccinic acid (2.0 g, 1.27 mL, 15.37 mmol) and 3,4-dimethylaniline (1.86 g, 15.37 mmol) in water (20 mL) was stirred at 120° C. (reflux) for 16 h. The mixture was cooled to 25° C. and filtered. The filter cake was washed with cold water (5 mL) to give 1-(3,4-dimethylphenyl)-5-oxopyrrolidine-3-carboxylic acid (3.0 g, 12.9 mmol, 84%) as a yellow solid. This material was used directly in the next step without further purification. $^1$H NMR (400 MHz, DMSO-d6) δ 7.40-7.35 (m, 2H), 7.13-7.11 (d, 1H), 4.01-3.93 (m, 2H), 3.34-3.30 (m, 1H), 2.75-2.67 (m, 2H), 2.22 (s, 3H) 2.19 (s, 3H); LCMS (ESI) m/z: [M−H]⁻=232.1.

Step 2: Preparation of methyl 1-(1-(3,4-dimethylphenyl)-5-oxopyrrolidine-3-carbonyl)piperidine-4-carboxylate

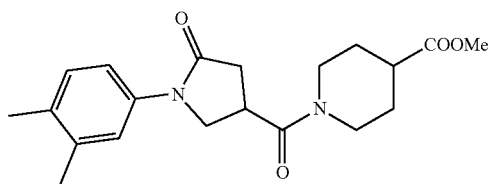 [SMILES: COC(=O)C1CCN(C(=O)C2CC(=O)N(c3ccc(C)c(C)c3)C2)CC1]

To a stirred solution of 1-(3,4-dimethylphenyl)-5-oxopyrrolidine-3-carboxylic acid (1.0 g, 4.29 mmol) and methyl piperidine-4-carboxylate (737 mg, 5.15 mmol) in N,N-dimethylformamide (10 mL) was added (2-(1H-benzotriazol-1-yl)-1,1,3,3-tetramethyluronium hexafluorophosphate) (1.63 g, 4.29 mmol) and N-ethyl-N-(propan-2-yl)propan-2-amine (1.11 g, 8.58 mmol, 1.50 mL). After stirring at 15° C. for 16 h, to the mixture was added water (20 mL) and the mixture extracted with ethyl acetate (20 mL×4). The organic layer was washed with water (10 mL), saturated aqueous sodium chloride solution (10 mL), then dried over anhydrous sodium sulfate, filtered and concentrated to give crude product that was purified by chromatography on silica gel eluted with Petroleum ether/ethyl acetate from 1/1 to 0/1 to give methyl 1-(1-(3,4-dimethylphenyl)-5-oxopyrrolidine-3-carbonyl)piperidine-4-carboxylate (1.90 g, 5.30 mmol, quantitative) as a red oil. LCMS (ESI) m/z: [M+H]+=359.3.

Step 3: Preparation of 1-(1-(3,4-dimethylphenyl)-5-oxopyrrolidine-3-carbonyl)piperidine-4-carboxylic acid

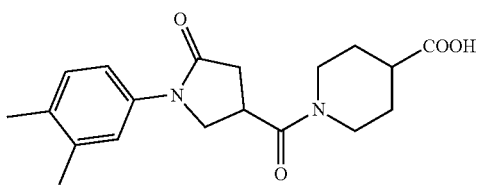 [SMILES: Cc1ccc(N2CC(C(=O)N3CCC(C(=O)O)CC3)CC2=O)cc1C]

To a stirred solution of methyl 1-(1-(3,4-dimethylphenyl)-5-oxopyrrolidine-3-carbonyl)piperidine-4-carboxylate (400 mg, 1.12 mmol) in tetrahydrofuran (4 mL) was added aqueous sodium hydroxide (2 M, 1.68 mL). The mixture was stirred at 40° C. for 2 h, then the mixture was acidified with concentrated hydrochloric acid until pH 1. The mixture was extracted with dichloromethane (20 mL×3), then the organic layer was washed with saturated aqueous sodium chloride solution (10 mL), dried over anhydrous sodium sulfate, filtered and concentrated to give 1-(1-(3,4-dimethylphenyl)-5-oxopyrrolidine-3-carbonyl)piperidine-4-carboxylic acid (300 mg, 871 µmol, 78%) as a white solid that was used directly without further purification.

Step 4: Preparation of 1-(3,4-dimethylphenyl)-4-(4-(3-phenyl-1,2,4-oxadiazol-5-yl)piperidine-1-carbonyl)pyrrolidin-2-one

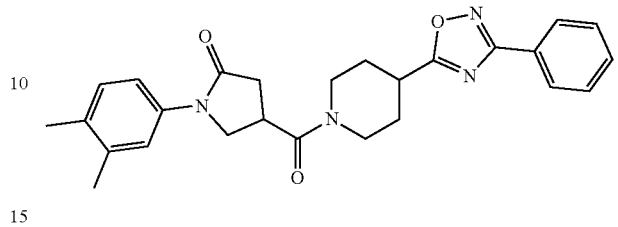

To a stirred solution of 1-(1-(3,4-dimethylphenyl)-5-oxopyrrolidine-3-carbonyl)piperidine-4-carboxylic acid (253 mg, 734 µmol) in N,N-dimethylformamide (1 mL) was added (2-(1H-benzotriazol-1-yl)-1,1,3,3-tetramethyluronium hexafluorophosphate) (279 mg, 734 µmol) and N-ethyl-N-(propan-2-yl)propan-2-amine (285 mg, 2.20 mmol, 384 µL). The mixture was stirred at 25° C. for 5 min, then N-hydroxybenzimidamide (100 mg, 734 µmol) was added. The mixture was warmed to 25° C., stirred for 16 h, then the mixture was diluted with water (5 mL) and extracted with ethyl acetate (20 mL×3). The organic layers were combined and washed with water (5 mL×2) and saturated aqueous sodium chloride solution (5 mL), then dried over anhydrous sodium sulfate, filtered and concentrated to give a crude product which was dissolved in N,N-dimethylformamide (2 mL) and then heated at 120° C. for 3 h. Without any additional work-up, the mixture was purified by prep-HPLC (Waters X bridge 150×25 5 µm column; 36-66% acetonitrile in a 10 mM ammonium acetate solution in water, 12 min gradient) to give 1-(3,4-dimethylphenyl)-4-(4-(3-phenyl-1,2,4-oxadiazol-5-yl)piperidine-1-carbonyl)pyrrolidin-2-one (73 mg, 164 µmol, 22%) as a white solid. $^1$H NMR (400 MHz, CDCl₃) δ 8.10-8.09 (m, 2H), 7.55-7.49 (m, 3H), 7.39 (s, 1H), 7.30 (s, 1H), 7.15-7.13 (d, 1H), 4.54-4.53 (m, 1H), 4.31-4.27 (m, 1H), 3.98-3.90 (m., 2H), 3.60-3.56 (m, 1H), 3.42-3.36 (m, 2H). 3.15-2.95 (m, 2H), 2.86-2.79 (m, 1H), 2.29-2.26 (m, 8H), 2.03-1.97 (m, 2H); LCMS (ESI) m/z: [M+H]+=445.3.

Example 2: Preparation of 1-(3,4-dimethylphenyl)-4-(4-(3-(p-tolyl)-1,2,4-oxadiazol-5-yl)piperidine-1-carbonyl)pyrrolidin-2-one

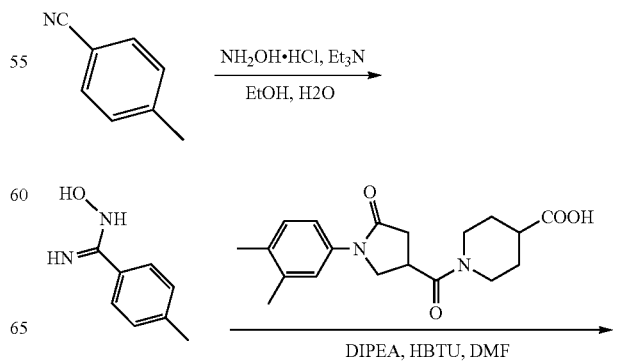

-continued

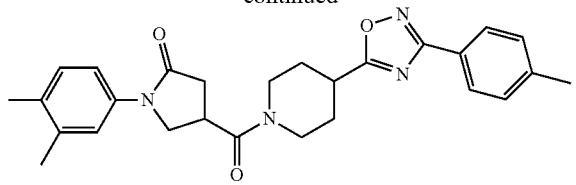

Step 1: Preparation of
N-hydroxy-4-methylbenzimidamide

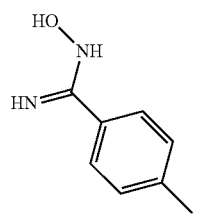

To a stirred solution of 4-methylbenzonitrile (1.0 g, 8.54 mmol, 1.02 mL) in ethanol (10 mL) and water (1 mL) was added hydroxylamine hydrochloride (1.19 g, 17.1 mmol) and triethylamine (1.73 g, 17.1 mmol, 2.37 mL). The mixture was heated at 75° C. for 16 h, then the reaction mixture was concentrated under reduced pressure to give a residue that was diluted with water (5 mL), and then extracted with dichloromethane (8 mL×10). The combined organic layers were washed with saturated aqueous sodium chloride solution (8 mL×5), dried over anhydrous sodium sulfate, filtered, and concentrated under reduced pressure to give a N-hydroxy-4-methylbenzimidamide (900 mg, 5.99 mmol, 70%) as a light green solid. $^1$H NMR (400 MHz, METHANOL-d4) d=7.49 (d, J=8.2 Hz, 2H), 7.18 (d, J=7.9 Hz, 2H), 2.33 (s, 3H).

Step 2: Preparation of methyl 1-(3,4-dimethylphenyl)-4-(4-(3-(p-tolyl)-1,2,4-oxadiazol-5-yl)piperidine-1-carbonyl)pyrrolidin-2-one

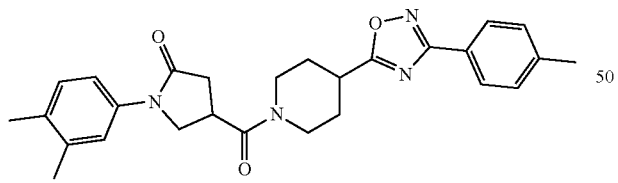

To a stirred solution of methyl 1-(1-(3,4-dimethylphenyl)-5-oxopyrrolidine-3-carbonyl)piperidine-4-carboxylate (229 mg, 666 μmol) in N,N-dimethylformamide (1 mL) was added (2-(1H-benzotriazol-1-yl)-1,1,3,3-tetramethyluronium hexafluorophosphate) (253 mg, 666 μmol) and N-ethyl-N-(propan-2-yl)propan-2-amine (258 mg, 2.00 mmol, 349 μL). The mixture was stirred at 25° C. for 5 mins, then N-hydroxy-4-methylbenzimidamide (100 mg, 666 μmol) was added. After 16 h, the reaction mixture was extracted with ethyl acetate (5 mL×3). The organic layers were combined, washed with saturated aqueous sodium chloride solution (5 mL×2), dried over anhydrous sodium sulfate, filtered, and concentrated under reduced pressure to give a residue that was purified by prep-HPLC (column: Waters Xbridge 150×25 5 μm; mobile phase: [water(10 mM NH$_4$HCO$_3$)-acetonitrile]; B %: 40%-70%, 12 min) to give 1-(3,4-dimethylphenyl)-4-(4-(3-(p-tolyl)-1,2,4-oxadiazol-5-yl)piperidine-1-carbonyl)pyrrolidin-2-one (38 mg, 81 μmol, 12%, 98.4% purity) as a white solid. $^1$H NMR (400 MHz, CHLOROFORM-d) δ 7.89 (d, J=7.1 Hz, 2H), 7.29 (s. 1H), 7.22 (t. J=7.9 Hz, 3H), 7.05 (d, J=8.2 Hz, 1H), 4.50-4.38 (m, 1H), 4.20 (t, J=8.4 Hz, 1H), 3.95-3.79 (m, 2H), 3.49 (td, J=8.5, 16.9 Hz, 1H), 3.36-3.20 (m, 2H), 3.12-2.97 (m, 1H), 2.89 (td, J=8.7, 17.1 Hz, 1H), 2.79-2.69 (m, 1H), 2.35 (s, 3H), 2.18 (d, J=13.0 Hz, 7H), 2.00-1.82 (m, 2H); LCMS (ESI) m/z: [M+H]$^+$=459.3.

Example 3: Preparation of 1-(3,4-dimethylphenyl)-4-[4-[3-(m-tolyl)-1,2,4-oxadiazol-5-yl]piperidine-1-carbonyl]pyrrolidin-2-one

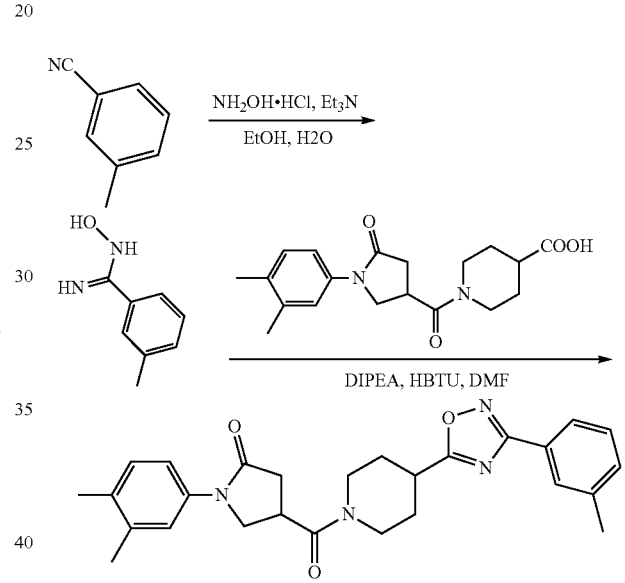

Step 1: Preparation of
N-hydroxy-3-methylbenzimidamide

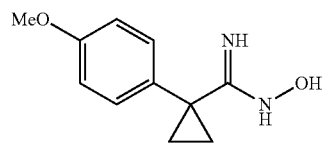 [SMILES: COc1ccc(C2(C(=N)NO)CC2)cc1]

To a stirred solution of 3-methylbenzonitrile (1.0 g, 8.54 mmol, 1.02 mL) in ethanol (10 mL) and water (1 mL) was added hydroxylamine hydrochloride (1.19 g, 17.1 mmol) and triethylamine (1.73 g, 17.1 mmol, 2.37 mL). The mixture was heated at 75° C. for 16 h and then concentrated under reduced pressure to give a residue that was then diluted with dichloromethane. The organic phase was washed with saturated aqueous sodium chloride solution (5 mL×2), dried over anhydrous sodium sulfate, filtered and concentrated to give N-hydroxy-3-methyl-benzamidine (1.05 g, solid) as a crude solid that was used directly in the next step without further purification. $^1$H NMR (400 MHz, CHLOROFORM-d) δ=7.42-7.31 (m, 2H), 7.24-7.12 (m, 2H), 4.93-4.71 (s, 1H), 3.67-3.58 (m, 1H), 2.97 (q, J=7.3 Hz, 1H), 2.30 (s, 3H), 1.32-1.23 (m, 1H), 1.18-1.11 (m, 1H).

Step 2: Preparation of 1-(3,4-dimethylphenyl)-4-(4-(3-(m-tolyl)-1,2,4-oxadiazol-5-yl)piperidine-1-carbonyl)pyrrolidin-2-one

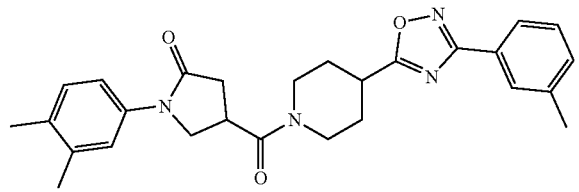 [SMILES: Cc1cccc(-c2noc(C3CCN(C(=O)C4CC(=O)N(c5ccc(C)c(C)c5)C4)CC3)n2)c1]

To a stirred solution of 1-[1-(3,4-dimethylphenyl)-5-oxo-pyrrolidine-3-carbonyl]piperidine-4-carboxylic acid (229 mg, 666 μmol) in N,N-dimethylformamide (1 mL) was added (2-(1H-benzotriazol-1-yl)-1,1,3,3-tetramethyluronium hexafluorophosphate) (253 mg, 666 μmol) and N-ethyl-N-(propan-2-yl)propan-2-amine (258 mg, 2.00 mmol, 349 μL). The mixture was stirred at 25° C. for 5 mins then N-hydroxy-3-methyl-benzamidine (100 mg, 666 μmol) was added. After 16 h, the reaction mixture was diluted with water (1 mL) extracted with ethyl acetate (5 mL×3). The organic layers were combined, washed with saturated aqueous sodium chloride solution (5 mL×2), dried over anhydrous sodium sulfate, filtered, and concentrated under reduced pressure to give a crude residue that was purified by prep-HPLC (Waters X bridge 150×25 5 μm column, 41%-71% acetonitrile in an a 10 mM ammonium acetate solution in water, 12 min gradient) to give 1-(3,4-dimethylphenyl)-4-[4-[3-(m-tolyl)-1,2,4-oxadiazol-5-yl]piperidine-1-carbonyl]pyrrolidin-2-one (118 mg, 266 μmol, 38%) as a yellow solid. $^1$H NMR (400 MHz, CHLOROFORM-d) δ=7.93-7.83 (m, 1H), 7.40-7.30 (m, 3H), 7.16-7.07 (m, 1H), 4.58-4.45 (m, 1H), 4.29-4.25 (m 1H), 4.00-3.90 (m, 2H), 3.59-3.55 (m, 1H), 3.43-3.24 (m, 2H), 3.19-3.01 (m, 1H), 3.01-2.89 (m, 1H), 2.87-2.74 (m, 1H), 2.43 (s, 3H), 2.27-2.22 (m, 8H), 2.07-1.90 (m, 2H); LCMS (ESI) m/z: [M+H]$^+$=459.3.

Example 4. 6-(5-(1-(1-(3,4-Dimethylphenyl)-5-oxopyrrolidine-3-carbonyl)piperidin-4-yl)-1,2,4-oxadiazol-3-yl)-4-ethyl-2H-benzo[b][1,4]oxazin-3 (4H)-one

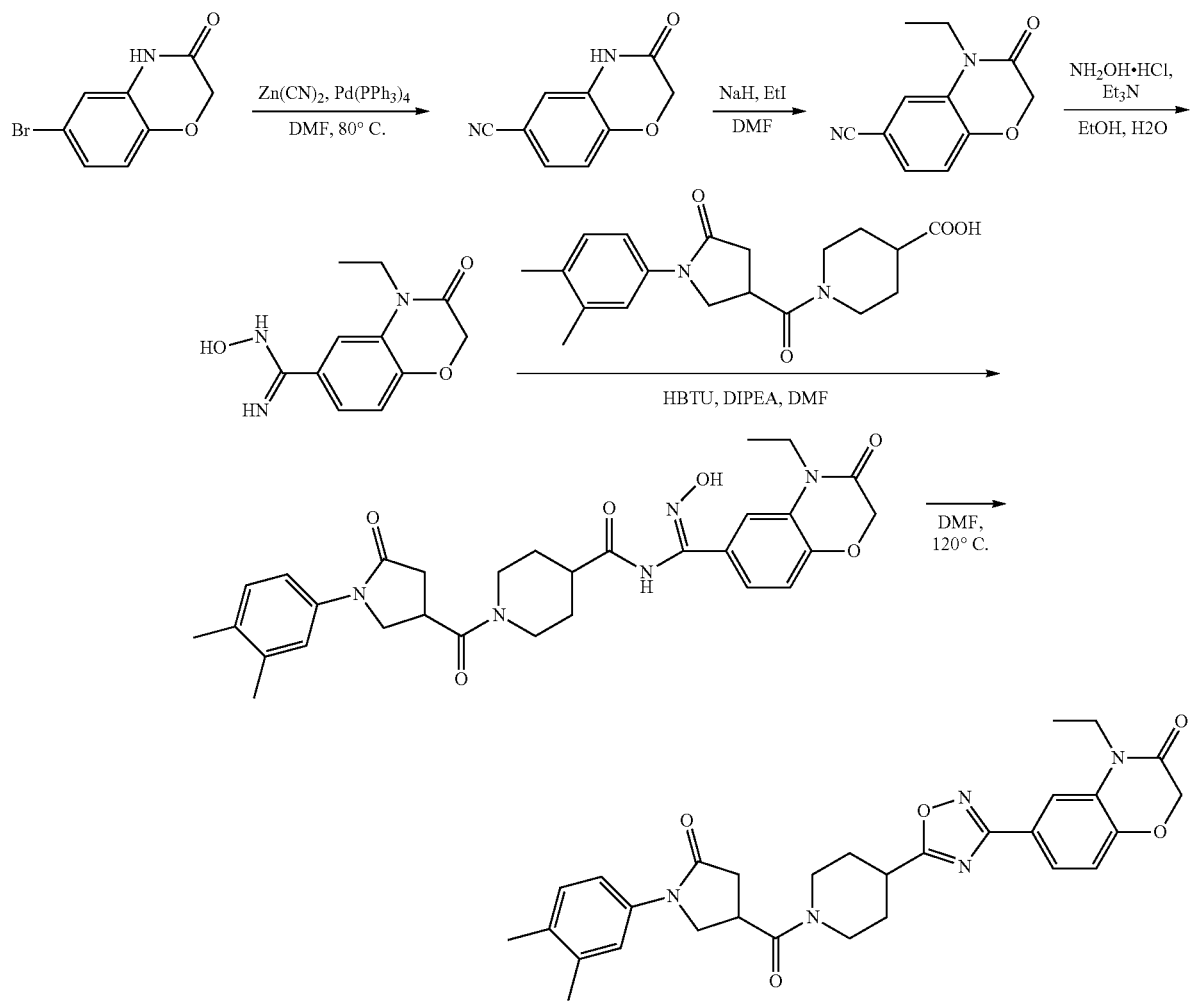

Step 1: Preparation of 3-oxo-3,4-dihydro-2H-benzo[b][1,4]oxazine-6-carbonitrile

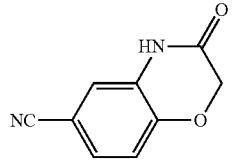 [SMILES: N#Cc1ccc2c(c1)NC(=O)CO2]

To a stirred solution of 6-bromo-2H-benzo[b][1,4]oxazin-3(4H)-one (3.0 g, 13.2 mmol) in N,N-dimethylformamide (35 mL) was added zinc cyanide (1.24 g, 10.5 mmol, 668 μL) and tetrakis(triphenylphosphine)palladium(0) (760 mg, 658 μmol) under nitrogen. The mixture was then stirred at 80° C. for 16 h, cooled to room temperature, and extracted with ethyl acetate (60 mL×4). The combined organic layers were washed with saturated aqueous sodium chloride solution (15 mL) and dried over anhydrous sodium sulfate. The combined organic layers were concentrated to dryness to give the crude product. The crude product was further purified by trituration in ethyl acetate and used in the next step without further purification. 3-oxo-3,4-dihydro-2H-benzo[b][1,4]oxazine-6-carbonitrile (3.40 g) was obtained as a white solid. LCMS (ESI) m/z: [M+H]$^+$=175.0.

Step 2: Preparation of 4-ethyl-3-oxo-3,4-dihydro-2H-benzo[b][1,4]oxazine-6-carbonitrile

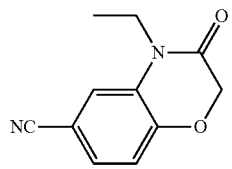

To a stirred solution of 3-oxo-3,4-dihydro-2H-benzo[b][1,4]oxazine-6-carbonitrile (3.30 g, 19.0 mmol) in N,N-dimethylformamide (35 mL) was added sodium hydride (758 mg, 19 mmol, 60% dispersion in mineral oil) and iodoethane (3.84 g, 25 mmol, 1.97 mL) at 0° C. The mixture was warmed to 20° C. After 3 h, the mixture was cooled to 0° C., quenched by addition of water (50 mL), and extracted with ethyl acetate (60 mL×4). The combined organic phases were washed with saturated aqueous sodium chloride solution (20 mL), dried over anhydrous sodium sulfate, filtered, and concentrated to give crude product that was purified by chromatography (silica, petroleumether:ethylacetate=50:1 to 5:1) to give 4-ethyl-3-oxo-3,4-dihydro-2H-benzo[b][1,4]oxazine-6-carbonitrile (1.30 g, 6.43 mmol, 34%) as a white solid. $^1$H NMR (400 MHz, CDCl$_3$) δ 7.25 (dd, J=1.8, 8.3 Hz, 1H), 7.17 (d, J=1.8 Hz, 1H), 6.98 (d, J=8.3 Hz, 1H), 4.62 (s, 2H), 3.93 (q, J=7.2 Hz, 2H), 1.23 (t, J=7.2 Hz, 3H); LCMS (ESI) m/z: 203.1 [M+H]$^+$.

Step 3: Preparation of 4-ethyl-N-hydroxy-3-oxo-3,4-dihydro-2H-benzo[b][1,4]oxazine-6-carboximidamide

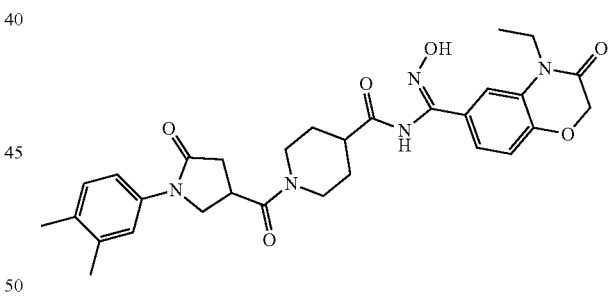

To a stirred solution of 4-ethyl-3-oxo-3,4-dihydro-2H-benzo[b][1,4]oxazine-6-carbonitrile (1.20 g, 5.93 mmol) in ethanol (20 mL) was added hydroxylamine hydrochloride (825 mg, 11.9 mmol), triethylamine (1.20 g, 11.9 mmol, 1.64 mL) and water (2 mL), then the mixture was heated at 75° C. After 5 h, the mixture was cooled to 20° C. and water (20 mL) added. The mixture was extracted with ethyl acetate (30 mL×3), then the combined organic layers were washed with saturated aqueous sodium chloride solution (20 mL), dried over anhydrous sodium sulfate, filtered, and concentrated to give 4-ethyl-N-hydroxy-3-oxo-3,4-dihydro-2H-benzo[b][1,4]oxazine-6-carboximidamide (1.20 g, 5.10 mmol, 86%) as a white solid that was used directly without further purification. $^1$H NMR (400 MHz, DMSO-d6) δ 9.61 (s, 1H), 7.44 (d, J=1.6 Hz, 1H), 7.35 (dd, J=1.8, 8.4 Hz, 1H), 7.00 (d, J=8.4 Hz, 1H), 5.87 (s, 2H), 4.66 (s, 2H), 3.96 (q, J=7.0 Hz, 2H), 1.18 (t, J=7.0 Hz, 3H).

Step 4: Preparation of (E)-1-(1-(3,4-dimethylphenyl)-5-oxopyrrolidine-3-carbonyl)-N-((4-ethyl-3-oxo-3,4-dihydro-2H-benzo[b][1,4]oxazin-6-yl)(hydroxyimino)methyl)piperidine-4-carboxamide To a stirred solution of 4-ethyl-N-hydroxy-3-oxo-3,4-dihydro-2H-benzo[b][1,4]oxazine-6-carboximidamide (150 mg, 638 μmol) in N,N-dimethylformamide (5 mL) was added 1-(1-(3,4-dimethylphenyl)-5-oxopyrrolidine-3-carbonyl)piperidine-4-carboxylic acid (220 mg, 638 μmol), (2-(1H-benzotriazol-1-yl)-1,1,3,3-tetramethyluronium hexafluorophosphate) (242 mg, 638 μmol) and N-ethyl-N-(propan-2-yl)propan-2-amine (247 mg, 1.91 mmol, 334 μL). After 16 h at 20° C., the reaction mixture was quenched with water (10 mL). The mixture was extracted with ethyl acetate (20 mL×4), then the combined organic phases were washed with saturated aqueous sodium chloride solution (5 mL), dried over anhydrous sodium sulfate, filtered, and concentrated to give (E)-1-(1-(3,4-dimethylphenyl)-5-oxopyrrolidine-3-carbonyl)-N-((4-ethyl-3-oxo-3,4-dihydro-2H-benzo[b][1,4]oxazin-6-yl)(hydroxyimino)methyl)piperidine-4- carboxamide (450 mg) as a yellow oil. This material was used directly without further purification. LCMS (ESI) m/z=562.3 [M+H]$^+$.

Step 5: Preparation of 6-(5-(1-(1-(3,4-dimethylphenyl)-5-oxopyrrolidine-3-carbonyl)piperidin-4-yl)-1,2,4-oxadiazol-3-yl)-4-ethyl-2H-benzo[b][1,4]oxazin-3(4H)-one (E)-1-(1-(3,4-dimethylphenyl)-5-oxopyrrolidine-3-carbonyl)-N-((4-ethyl-3-oxo-3,4-dihydro-2H-benzo[b][1,4]oxazin-6-yl)(hydroxyimino)methyl)piperidine-4-carboxamide (450 mg, 801 µmol) was heated in N,N-dimethylformamide (3 mL) at 120° C. for 3 h. The mixture was cooled and purified directly by prep-HPLC (column: Luna C8 100×30 5 µm; mobile phase: [water (10 mM ammonium carbonate)-acetonitrile]; B %: 40%-65%, 12 min) to give 6-(5-(1-(1-(3,4-dimethylphenyl)-5-oxopyrrolidine-3-carbonyl)piperidin-4-yl)-1,2,4-oxadiazol-3-yl)-4-ethyl-2H-benzo[b][1,4]oxazin-3(4H)-one (142 mg, 255 µmol, 32%) as a white solid. $^1$H NMR (400 MHz, CDCl$_3$) δ 7.70-7.60 (m, 2H), 7.29 (s, 1H), 7.22-7.19 (m, 1H), 7.03 (dd, J=8.3, 16.9 Hz, 2H), 4.60 (s, 2H), 4.56-4.40 (m, 1H), 4.21 (d, J=7.3 Hz, 1H), 4.00 (d, J=6.5 Hz, 2H), 3.96-3.78 (m, 2H), 3.49 (quin, J=8.3 Hz, 1H), 3.37-3.19 (m, 2H), 3.09-2.82 (m, 2H), 2.81-2.69 (m, 1H), 2.18 (d, J=12.8 Hz, 8H), 1.98-1.82 (m, 2H), 1.26 (t, J=6.8 Hz, 3H); LCMS (ESI) [M+H]$^+$=544.2.

Example 5: Morpholino(1-(3-phenyl-1,2,4-oxadiazol-5-yl)piperidin-4-yl)methanone

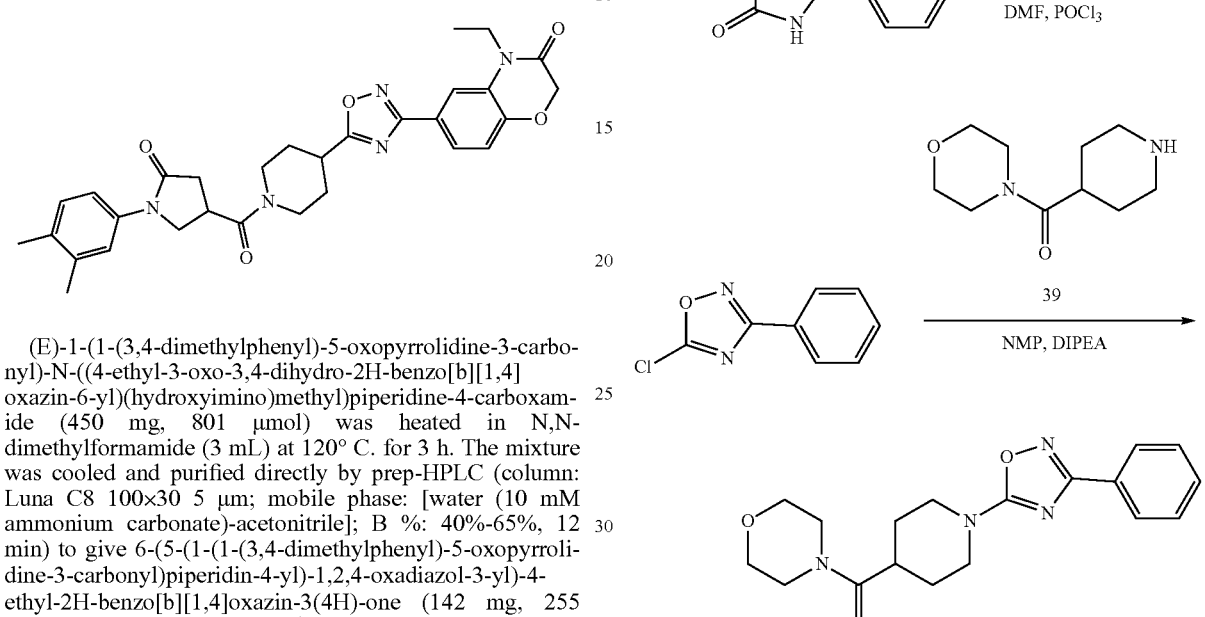

Step 1: Preparation of tert-butyl 4-(morpholine-4-carbonyl)piperidine-1-carboxylate

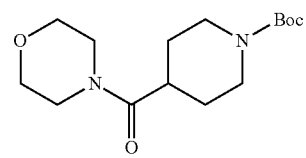 [SMILES: CC(C)(C)OC(=O)N1CCC(C(=O)N2CCOCC2)CC1]

To a stirred solution of 1-(tert-butoxycarbonyl)piperidine-4-carboxylic acid (300 mg, 1.31 mmol) in N,N-dimethylformamide (10 mL) was added morpholine (136 mg, 1.57 mmol, 138 µL), (2-(1H-benzotriazol-1-yl)-1,1,3,3-tetramethyluronium hexafluorophosphate) (496 mg, 1.31 mmol) and N-ethyl-N-(propan-2-yl)propan-2-amine (338 mg, 2.62 mmol, 457 µL). The mixture was stirred at 20° C. for 16 h, then quenched with water (10 mL) and extracted with ethyl acetate (20 mL×4). The combined organic phases were washed with saturated aqueous sodium chloride solution (10 mL), dried over anhydrous sodium sulfate, filtered and concentrated to give tert-butyl 4-(morpholine-4-carbonyl)piperidine-1-carboxylate (700 mg) as a yellow oil. This material was used directly without further purification. $^1$H NMR (400 MHz, CDCl$_3$) δ 3.72-3.51 (m, 5H), 3.45 (br. s., 1H), 3.18-3.05 (m, 1H), 2.93-2.86 (m, 3H), 2.81 (s, 3H), 2.75-2.71 (m, 2H), 2.59-2.48 (m, 1H), 1.39 (s, 9H).

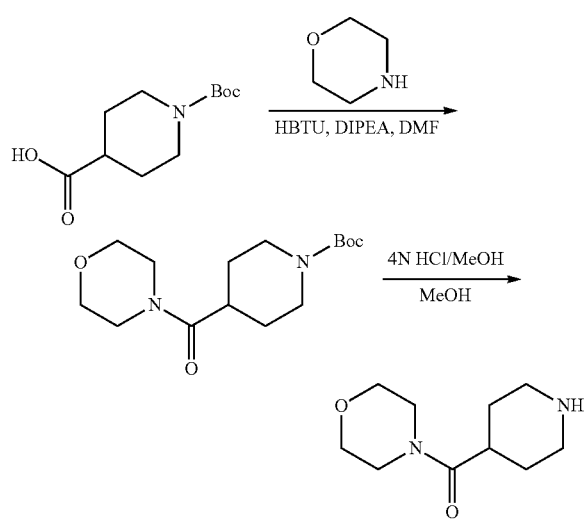

Step 2: Preparation of morpholino(piperidin-4-yl)methanone

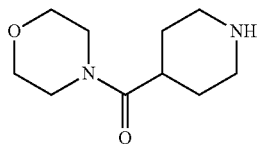 [SMILES: O=C(C1CCNCC1)N1CCOCC1]

To a stirred solution of tert-butyl 4-(morpholine-4-carbonyl)piperidine-1-carboxylate (700 mg, 2.35 mmol) in methanol (5 mL) was added 4N hydrochloric acid in methanol (15 mL). The mixture was stirred at 20° C. for 16 h then concentrated under reduced pressure to give morpholino(4-piperidyl)methanone (300 mg) as a colorless oil that was used directly without further purification. LCMS (ESI) [M+H]+=199.1.

Step 3: Preparation of 3-phenyl-1,2,4-oxadiazol-5(4H)-one

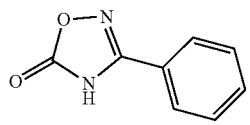 [SMILES: O=c1[nH]c(-c2ccccc2)no1]

To a stirred solution of N-hydroxybenzamidine (2.0 g, 14.69 mmol) in dioxane (10 mL) was added 1,8-diazabicyclo[5.4.0]undec-7-ene (2.46 g, 16 mmol, 2.44 mL) and 1,1'-carbonyldiimidazole (3.57 g, 22 mmol). The mixture was stirred at 110° C. for 16 h, then cooled and quenched with water (10 mL). The mixture was extracted with dichloromethane (50 mL×4), then the combined organic phases were washed with saturated aqueous sodium chloride solution (20 mL), dried over anhydrous sodium sulfate, filtered, and concentrated to give crude product that was purified by chromatography (silica, petroleum ether:ethyl acetate=1:1) to give 3-phenyl-1,2,4-oxadiazol-5(4H)-one (1.30 g, 8.02 mmol, 55%) as a yellow solid. $^1$H NMR (400 MHz, Methanol-d4) δ 7.83-7.75 (m, 2H), 7.66-7.52 (m, 3H); LCMS (ESI) m/z=163.2 [M+H]+.

Step 4: Preparation of 5-chloro-3-phenyl-1,2,4-oxadiazole

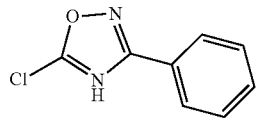 [SMILES: Clc1nc(-c2ccccc2)no1]

To a stirred solution of 3-phenyl-1,2,4-oxadiazol-5(4H)-one (500 mg, 3.08 mmol) equipped with calcium chloride tube was added N,N-dimethylformamide (1 mL). Phosphoryl chloride (10 mL) was added dropwise, and the resulting mixture was heated at 110° C. for 16 h. The reaction mixture was cooled to 20° C. and poured onto ice water (100 mL), and the resulting mixture was stirred for 30 min. The mixture was extracted with dichloromethane (20 mL×5), then the combined organic phases were washed with saturated aqueous sodium chloride solution (10 mL), dried over anhydrous sodium sulfate, filtered, and concentrated to give crude product that was purified by chromatography (silica, petroleum ether:ethyl acetate=50:1) to give 5-chloro-3-phenyl-1,2,4-oxadiazole (180 mg, 997 μmol, 32%) as a yellow oil. $^1$H NMR (400 MHz, CDCl$_3$) δ 8.10-7.98 (m, 2H), 7.57-7.46 (m, 3H).

Step 5: Preparation of morpholino(1-(3-phenyl-1,2,4-oxadiazol-5-yl)piperidin-4-yl)methanone

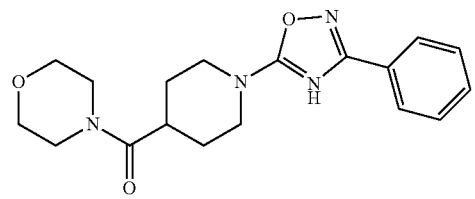 [SMILES: O=C(C1CCN(c2nc(-c3ccccc3)no2)CC1)N1CCOCC1]

To a stirred solution of morpholino(piperidin-4-yl)methanone (180 mg, 908 μmol) in N-methyl-2-pyrrolidone (5 mL) was added 5-chloro-3-phenyl-1,2,4-oxadiazole (163 mg, 908 μmol) and N-ethyl-N-(propan-2-yl)propan-2-amine (234 mg, 1.82 mmol, 317 μL). The mixture was stirred at 120° C. for 16 h then cooled and purified directly by prep-HPLC (column: Waters Xbridge 150×25 5 μm; mobile phase: [water (10 mM ammonium carbonate)-acetonitrile]; B %: 20%-50%, 12 min) to give morpholino(1-(3-phenyl-1,2,4-oxadiazol-5-yl)piperidin-4-yl)methanone (130 mg, 380 μmol, 42%) as a yellow solid. $^1$H NMR (400 MHz, Methanol-d4) δ 8.00-7.94 (m, 2H), 7.55-7.45 (m, 3H), 4.26 (d, J=13.3 Hz, 2H), 3.74-3.59 (m, 8H), 3.32-3.26 (m, 2H), 3.08-2.98 (m, 1H), 1.92-1.75 ppm (m, 4H); LCMS (ESI) [M+H]+=343.2.

Example 6: (1-(3-(3,4-dimethoxyphenyl)-1,2,4-oxadiazol-5-yl)piperidin-4-yl)(piperidin-1-yl)methanone

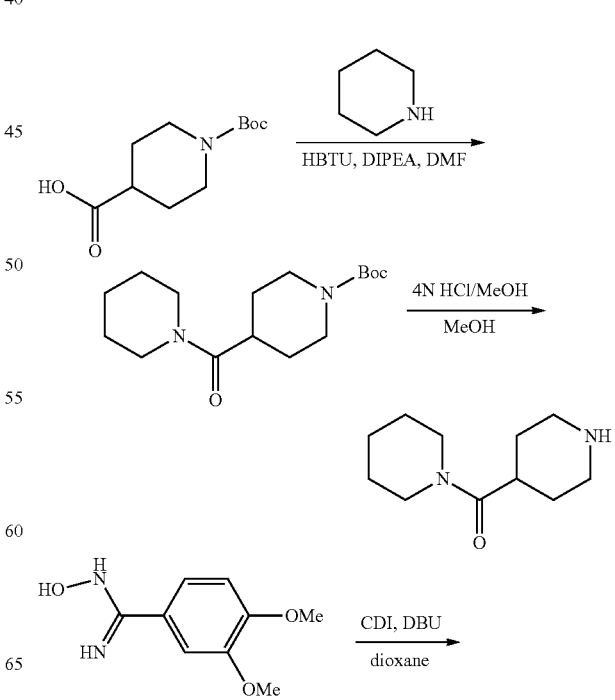

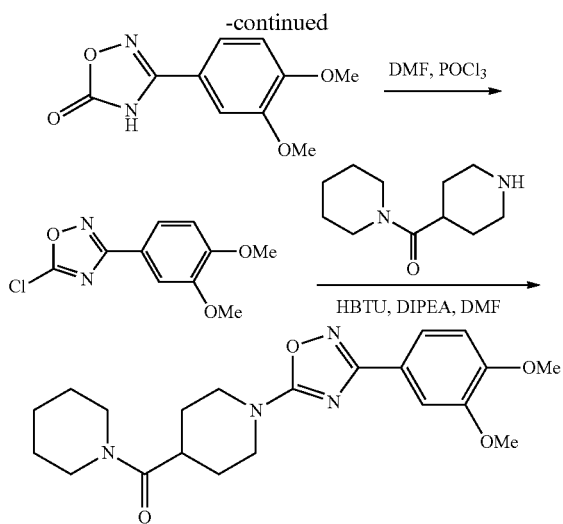

Step 1: Preparation of tert-butyl 4-(piperidine-1-carbonyl)piperidine-1-carboxylate

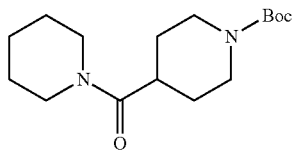 [SMILES: CC(C)(C)OC(=O)N1CCC(C(=O)N2CCCCC2)CC1]

To a mixture of 1-(tert-butoxycarbonyl)piperidine-4-carboxylic acid (300 mg, 1.31 mmol), (2-(1H-benzotriazol-1-yl)-1,1,3,3-tetramethyluronium hexafluorophosphate) (496 mg, 1.31 mmol) and N-ethyl-N-(propan-2-yl)propan-2-amine (338 mg, 2.62 mmol, 457 μL) in N,N-dimethylformamide (1 mL) was added piperidine (133 mg, 1.57 mmol, 155 μL) at 0° C. The mixture was stirred at 25° C. for 2 h. The residue was poured into water (5 mL). The aqueous phase was extracted with ethyl acetate (10 mL×3). The combined organic phases were washed with saturated aqueous sodium chloride solution (5 mL), dried over anhydrous sodium sulfate, filtered, and concentrated in vacuo to give tert-butyl 4-(piperidine-1-carbonyl)piperidine-1-carboxylate (600 mg) as a yellow oil. This material was used directly without further purification. $^1$H NMR (400 MHz, CDCl$_3$) δ 3.73 (dd, J=6.4, 9.9 Hz, 1H), 3.55 (br. s., 2H), 3.44 (br. s., 2H), 3.29-3.15 (m, 2H), 2.68-2.57 (m, 1H), 1.96-1.83 (m, 1H), 1.77-1.62 (m, 8H), 1.56 (br. s., 4H), 1.46 (s, 9H); LCMS (ESI) m/z=297.3 [M+H]$^+$.

Step 2: Preparation of piperidin-1-yl(piperidin-4-yl)methanone

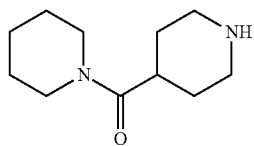 [SMILES: O=C(C1CCNCC1)N1CCCCC1]

To a mixture of tert-butyl 4-(piperidine-1-carbonyl)piperidine-1-carboxylate (500 mg, 1.69 mmol) in methanol (5 mL) was added 4M methanolic hydrochloric acid (10 mL) at 0° C. The mixture was stirred at 25° C. for 2 h. The mixture was concentrated in vacuo to give piperidin-1-yl(piperidin-4-yl)methanone (300 mg) as a yellow oil which was used in the next step directly without further purification. LCMS (ESI) [M+H]$^+$=197.3.

Step 3: Preparation of 3-(3,4-dimethoxyphenyl)-1,2,4-oxadiazol-5(4H)-one

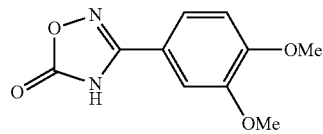 [SMILES: COc1ccc(-c2noc(=O)[nH]2)cc1OC]

A mixture of N-hydroxy-3,4-dimethoxybenzimidamide (1.0 g, 5.10 mmol), 1,8-diazabicyclo[5.4.0]undec-7-ene (853 mg, 5.61 mmol, 845 μL) and 1,1'-carbonyldiimidazole (1.24 g, 7.65 mmol) in dioxane (10 mL) was prepared at 15° C. The mixture was warmed to 110° C. for 12 h. The mixture was cooled to 15° C. and then poured into water (5 mL). The aqueous phase was extracted with dichloromethane (10 mL×5), then the combined organic phases were washed with saturated aqueous sodium chloride solution (5 mL), dried over anhydrous sodium sulfate, filtered and concentrated in vacuo to afford 3-(3,4-dimethoxyphenyl)-1,2,4-oxadiazol-5(4H)-one (800 mg) as a yellow solid. $^1$H NMR (400 MHz, CDCl$_3$) δ 7.60-7.52 (m, 2H), 6.88 (d, J=8.8 Hz, 1H), 3.91 (d, J=6.1 Hz, 6H); LCMS (ESI) m/z=223.2 [M+H]$^+$.

Step 4: Preparation of 5-chloro-3-(3,4-dimethoxyphenyl)-1,2,4-oxadiazole

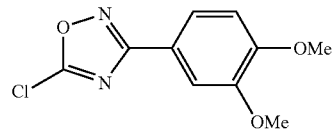 [SMILES: COc1ccc(-c2noc(Cl)n2)cc1OC]

3-(3,4-Dimethoxyphenyl)-1,2,4-oxadiazol-5(4H)-one (500 mg, 2.25 mmol) was added to a mixture of phosphoryl chloride (13.2 g, 86.1 mmol, 8 mL) and N,N-dimethylformamide (1 mL). The mixture was equipped with a calcium chloride tube and heated at 100° C. for 16 h, at which time the mixture was cooled and concentrated in vacuo at 45° C. The residue was poured into ice-water (w/w=10/1) (11 mL) and stirred for 10 min. The mixture was extracted with dichloromethane (10 mL×5), then the combined organic phases were washed with saturated aqueous sodium chloride solution (2 mL), dried over anhydrous sodium sulfate, filtered, and concentrated in vacuo. The residue was purified by chromatography (silica, petroleumether:ethylacetate=5:1 to 1:1 gradient) to afford 5-chloro-3-(3,4-dimethoxyphenyl)-1,2,4-oxadiazole (200 mg, 0.83 mmol, 37%) as a yellow solid. $^1$H NMR (400 MHz, CDCl$_3$) δ 7.67 (dd, J=2.0, 8.4 Hz, 1H), 7.53 (d, J=2.0 Hz, 1H), 6.97 (d, J=8.4 Hz, 1H), 3.96 (d, J=2.4 Hz, 6H); LCMS (ESI) m/z=241.1 [M+H]$^+$.

Step 5: Preparation of (1-(3-(3,4-dimethoxyphenyl)-1,2,4-oxadiazol-5-yl)piperidin-4-yl)(piperidin-1-yl)methanone

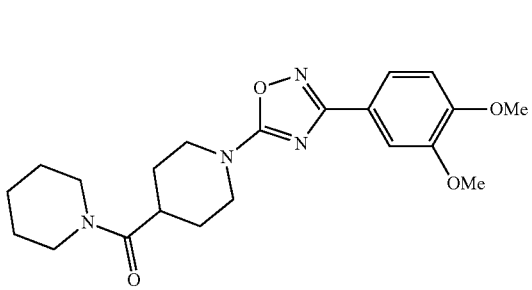 [SMILES: COc1ccc(-c2noc(N3CCC(C(=O)N4CCCCC4)CC3)n2)cc1OC]

To a stirred solution of 5-chloro-3-(3,4-dimethoxyphenyl)-1,2,4-oxadiazole (200 mg, 831 µmol) and triethylamine (252 mg, 2.49 mmol, 345 µL) in dichloromethane (2 mL) was added piperidin-1-yl(piperidin-4-yl)methanone (163 mg, 831 µmol) at 0° C. The mixture was warmed to 15° C. and stirred for 2 h, then concentrated in vacuo to afford crude product. The residue was purified by prep-HPLC (column: Luna C8 100×30 5 µm; mobile phase: [water (10 mM ammonium carbonate)-acetonitrile]; B %: 20%-55%, 12 min) to give (1-(3-(3,4-dimethoxyphenyl)-1,2,4-oxadiazol-5-yl)piperidin-4-yl)(piperidin-1-yl)methanone (36 mg, 89.7 µmol, 11%) as a yellow solid. $^1$H NMR (400 MHz, CDCl$_3$) δ 7.61 (d, J=8.4 Hz, 1H), 7.51 (s, 1H), 6.92 (d, J=8.4 Hz, 1H), 4.28 (d, J=13.2 Hz, 2H), 3.95 (d, J=8.8 Hz, 6H), 3.65-3.41 (m, 4H), 3.30-3.15 (m, 2H), 2.85-2.69 (m, 1H), 2.01-1.89 (m, 2H), 1.88-1.79 (m, 2H), 1.68 (d, J=4.9 Hz, 2H), 1.61 (br. s., 1H); LCMS (ESI) m/z=[M+H]$^+$: 401.2.

Example 7: N-(2-(4-(3-(3,4-dimethoxyphenyl)-1,2,4-oxadiazol-5-yl)piperidin-1-yl)-2-oxoethyl)benzamide

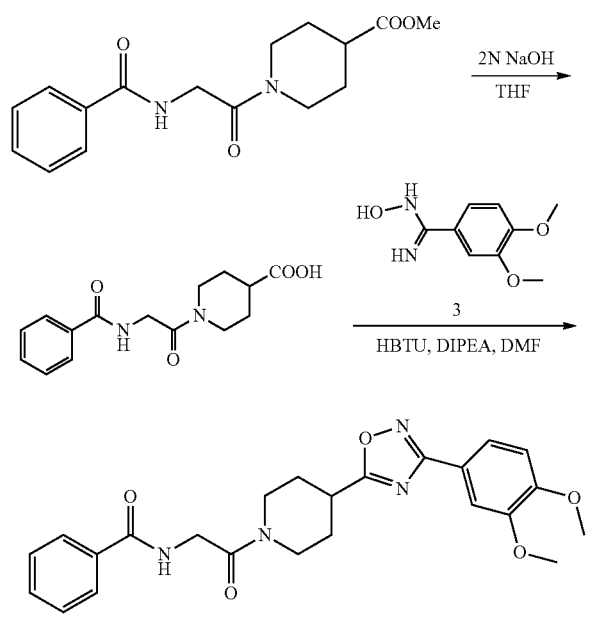

Step 1: Preparation of 1-(2-benzamidoacetyl)piperidine-4-carboxylic acid

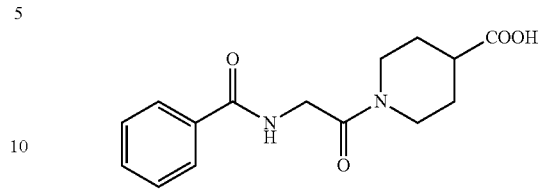

To a stirred solution of methyl 1-(2-benzamidoacetyl)piperidine-4-carboxylate (5.0 g, 16.4 mmol) in tetrahydrofuran (50 mL) was added aqueous sodium hydroxide (2 M, 16.4 mL). The mixture was stirred at 20° C. for 2 h and then acidified by the addition of concentrated hydrochloric acid until pH 1. The mixture was extracted with dichloromethane (80 mL×3). The combined organic phases were washed with saturated aqueous sodium chloride solution (30 mL), dried over anhydrous sodium sulfate, filtered, and concentrated to give crude product 1-(2-benzamidoacetyl)piperidine-4-carboxylic acid (3.25 g, 11.2 mmol, 68%) as a yellow solid. $^1$H NMR (400 MHz, Methanol-d4) δ 7.87 (d, J=7.5 Hz, 2H), 7.59-7.42 (m, 3H), 4.39-4.20 (m, 3H), 3.92 (d, J=14.1 Hz, 1H), 3.24 (t, J=11.5 Hz, 1H), 2.98-2.88 (m, 1H), 2.62 (s, 1H), 2.08-1.89 (m, 2H), 1.81-1.53 (m, 2H).

Step 2: Preparation of N-(2-(4-(3-(3,4-dimethoxyphenyl)-1,2,4-oxadiazol-5-yl)piperidin-1-yl)-2-oxoethyl)benzamide

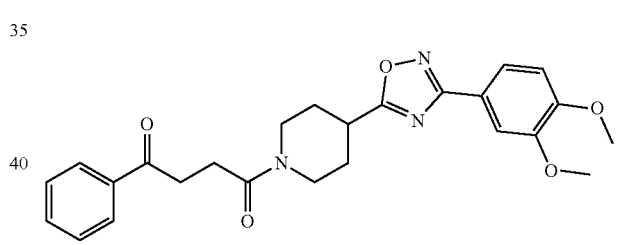

To a stirred solution of 1-(2-benzamidoacetyl)piperidine-4-carboxylic acid (2.0 g, 6.89 mmol) in N,N-dimethylformamide (30 mL) was added N-hydroxy-3,4-dimethoxybenzimidamide (1.62 g, 8.27 mmol), N-ethyl-N-(propan-2-yl)propan-2-amine (2.67 g, 20.67 mmol, 3.61 mL) and 1-[bis(dimethylamino)methylene]-1H-1,2,3-triazolo[4,5-b]pyridinium 3-oxide hexafluorophosphate (2.62 g, 6.89 mmol). The mixture was stirred at 20° C. for 2 h and then warmed at 120° C. for 2 h. The reaction mixture was quenched by addition of water (40 mL), then the mixture was extracted with ethyl acetate (80 mL×3). The combined organic phases were washed with saturated aqueous sodium chloride solution (30 mL), dried over anhydrous sodium sulfate, filtered, and concentrated to give crude product that was purified by chromatography (silica, petroleumether:ethylacetate=20:1 to 1:2) to give a yellow solid. The yellow solid was washed with ethyl acetate (30 mL), then the mixture was filtered, and the filter cake was dried in vacuo to give N-(2-(4-(3-(3,4-dimethoxyphenyl)-1,2,4-oxadiazol-5-yl)piperidin-1-yl)-2-oxoethyl)benzamide (1.29 g, 2.86 mmol, 42%) as a white solid. $^1$H NMR (400 MHz, CDCl$_3$) δ 7.92-7.84 (m, 2H), 7.80 (s, 1H), 7.58-7.44 (m, 3H), 7.41-7.35 (m, 1H), 7.28-7.26 (m, 2H), 6.92 (d, J=8.9 Hz, 1H), 4.58-4.47 (m, 1H), 4.32 (d, J=3.9 Hz, 2H), 3.99-3.88 (m, 7H), 3.37-3.06 (m, 3H), 2.28-2.13 (m, 2H), 2.07-1.89 (m, 2H); LCMS (ESI) [M+H]$^+$=451.3.

Example 8: (4-(3-(3-fluorophenyl)-1,2,4-oxadiazol-5-yl)piperidin-1-yl)(4-isopropylphenyl)methanone

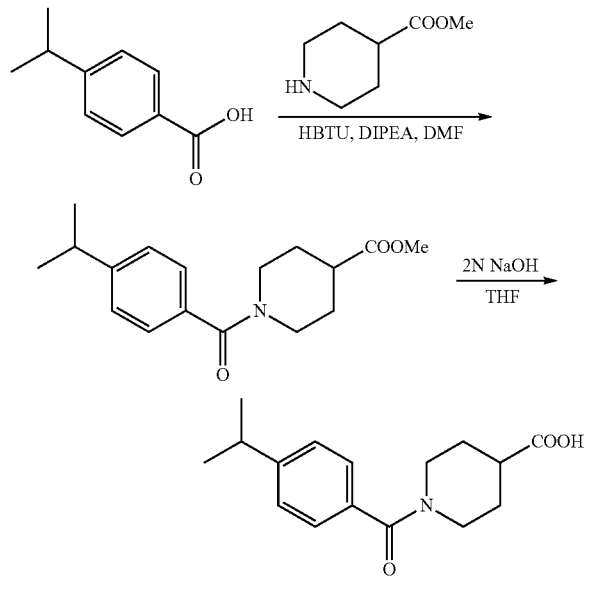

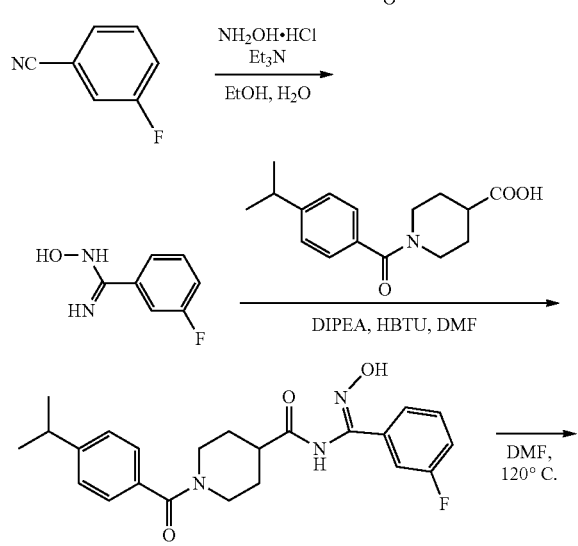

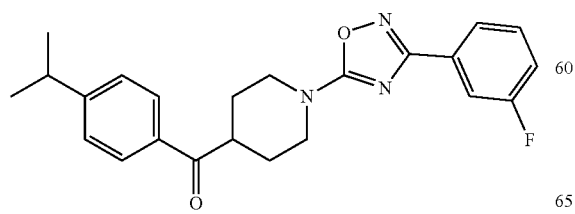

Step 1: Preparation of methyl 1-(4-isopropylbenzoyl)piperidine-4-carboxylate

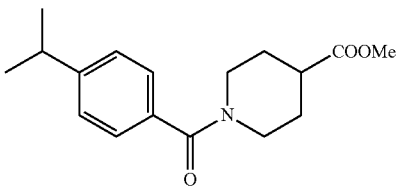 [SMILES: COC(=O)C1CCN(C(=O)c2ccc(C(C)C)cc2)CC1]

To a stirred solution of 4-isopropylbenzoic acid (250 mg, 1.52 mmol) in N,N-dimethylformamide (10 mL) was added methyl piperidine-4-carboxylate (261 mg, 1.82 mmol), (2-(1H-benzotriazol-1-yl)-1,1,3,3-tetramethyluronium hexafluorophosphate) (576 mg, 1.52 mmol) and N-ethyl-N-(propan-2-yl)propan-2-amine (392 mg, 3.04 mmol, 530 µL). The mixture was stirred at 20° C. for 16 h. The reaction mixture was quenched with water (10 mL), then the mixture was extracted with ethyl acetate (20 mL×4). The combined organic phases were washed with saturated aqueous sodium chloride solution (10 mL), dried over anhydrous sodium sulfate, filtered, and concentrated to give crude product methyl 1-(4-isopropylbenzoyl)piperidine-4-carboxylate (900 mg) as a yellow oil. LCMS (ESI) m/z: 290.3 [M+H]$^+$.

Step 2: Preparation of 1-(4-isopropylbenzoyl)piperidine-4-carboxylic acid

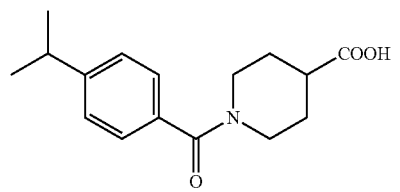 [SMILES: CC(C)c1ccc(C(=O)N2CCC(C(=O)O)CC2)cc1]

To a stirred solution of methyl 1-(4-isopropylbenzoyl)piperidine-4-carboxylate (900 mg, 3.11 mmol) in tetrahydrofuran (10 mL) was added aqueous sodium hydroxide (2 M, 3.11 mL). The mixture was stirred at 20° C. for 16 h. The mixture was acidified to pH 1 by dropwise addition of concentrated hydrochloric acid. The mixture was extracted with dichloromethane (20 mL×4). The combined organic phases were washed with saturated aqueous sodium chloride solution (5 mL), dried over anhydrous sodium sulfate, filtered, and concentrated to give crude product 1-(4-isopropylbenzoyl)piperidine-4-carboxylic acid (400 mg) as a yellow solid. LCMS (ESI) [M+H]$^+$=276.2.

Step 3: Preparation of 3-fluoro-N-hydroxybenzimidamide

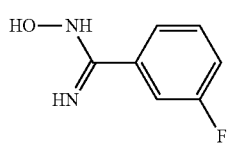 [SMILES: N=C(NO)c1cccc(F)c1]

To a stirred solution of 3-fluorobenzonitrile (1.0 g, 8.26 mmol, 884 µL) in ethanol (10 mL) were added hydroxylamine hydrochloride (1.15 g, 16.5 mmol), triethylamine (2.09 g, 20.7 mmol, 2.86 mL), and water (1 mL). Then the mixture was heated at 75° C. for 16 h. After cooling to 20° C., water (10 mL) was added to the solution. The mixture was extracted with ethyl acetate (20 mL×5). The combined organic layers were washed with saturated aqueous sodium chloride solution (10 mL), dried over anhydrous sodium sulfate, filtered, and concentrated in vacuo to give 3-fluoro-N-hydroxybenzimidamide (2.0 g) as a green solid that was used directly in the next step without further purification. LCMS (ESI) m/z: 155.1 [M+H]$^+$.

Step 4: Preparation of (E)-N-((3-fluorophenyl)(hydroxyimino)methyl)-1-(4-isopropylbenzoyl)piperidine-4-carboxamide

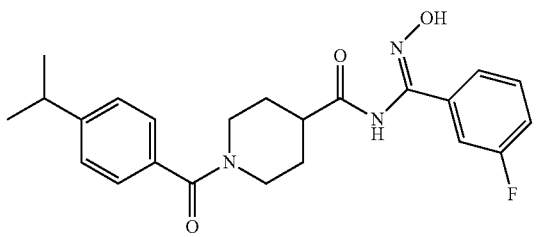 [SMILES: CC(C)c1ccc(C(=O)N2CCC(C(=O)N/C(=N/O)c3cccc(F)c3)CC2)cc1]

To a stirred solution of 1-(4-isopropylbenzoyl)piperidine-4-carboxylic acid (400 mg, 1.45 mmol) in N,N-dimethylformamide (10 mL) were added 3-fluoro-N-hydroxybenzimidamide (223 mg, 1.45 mmol), (2-(1H-benzotriazol-1-yl)-1,1,3,3-tetramethyluronium hexafluorophosphate) (550 mg, 1.45 mmol) and N-ethyl-N-(propan-2-yl)propan-2-amine (563 mg, 4.36 mmol, 761 µL). The mixture was stirred at 20° C. for 16 h. The reaction mixture was quenched with water (10 mL) and then extracted with ethyl acetate (20 mL×4). The combined organic phases were washed with saturated aqueous sodium chloride solution (10 mL), dried over anhydrous sodium sulfate, filtered, and concentrated to give (E)-N-((3-fluorophenyl)(hydroxyimino)methyl)-1-(4-isopropylbenzoyl)piperidine-4-carboxamide (350 mg) as a yellow oil. LCMS (ESI) m/z: 412.3 [M+H]$^+$.

Step 5: Preparation of (4-(3-(3-fluorophenyl)-1,2,4-oxadiazol-5-yl)piperidin-1-yl)(4-isopropylphenyl)methanone

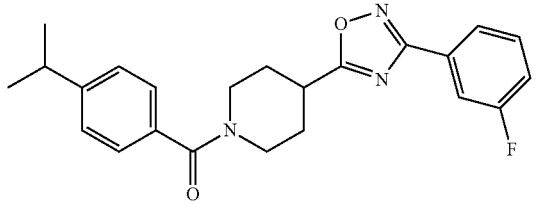 [SMILES: CC(C)c1ccc(C(=O)N2CCC(c3nc(-c4cccc(F)c4)no3)CC2)cc1]

(E)-N-((3-Fluorophenyl)(hydroxyimino)methyl)-1-(4-isopropylbenzoyl)piperidine-4-carboxamide (350 mg, 851 µmol) was added to N,N-dimethylformamide (3 mL), and the mixture was stirred at 120° C. for 16 h. The reaction mixture was cooled and purified by direct injection and prep-HPLC (column: Waters Xbridge 150×2.5 mm 5 µm; mobile phase: [water (10 mM ammonium carbonate)-acetonitrile]; B %: 50%-80%, 12 min) to give (4-(3-(3-fluorophenyl)-1,2,4-oxadiazol-5-yl)piperidin-1-yl)(4-isopropylphenyl)methanone (82 mg, 210 µmol, 25%) as a yellow oil. $^1$H NMR (400 MHz, Methanol-d4) δ 7.92 (d, J=7.8 Hz, 1H), 7.79 (d, J=9.7 Hz, 1H), 7.57 (d, J=5.6 Hz, 1H), 7.42-7.28 (m, 5H), 4.69-4.50 (m, 1H), 3.89 (br. s., 1H), 3.53-3.42 (m, 1H), 3.39-3.34 (m, 1H), 3.32-3.28 (m, 1H), 2.99 (td, J=6.9, 13.8 Hz, 1H), 2.43-2.09 (m, 2H), 2.07-1.83 (m, 2H), 1.30 (s, 3H), 1.29 (s, 3H); LCMS (ESI) m/z [M+H]$^+$=394.2.

Example 9: N-(2-oxo-2-(4-(3-phenyl-1,2,4-oxadiazol-5-yl)piperidin-1-yl)ethyl)benzamide

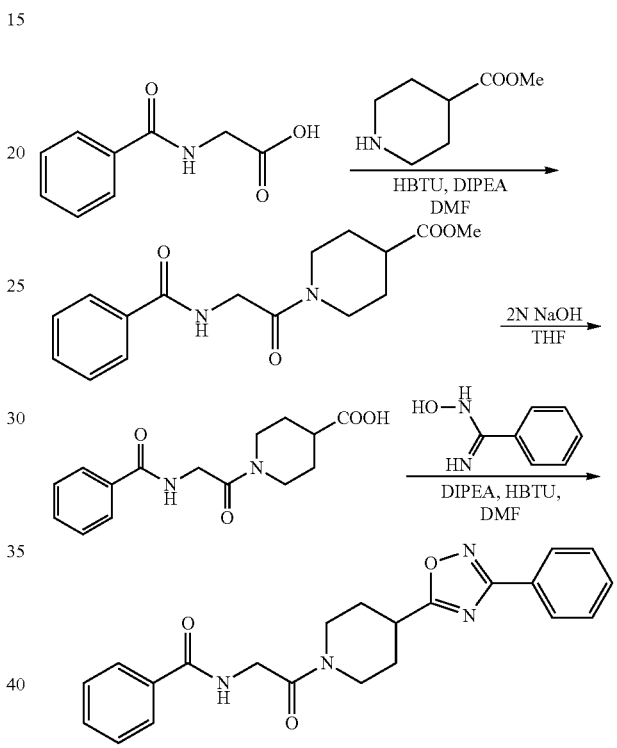

Step 1: Preparation of methyl 1-(2-benzamidoacetyl)piperidine-4-carboxylate

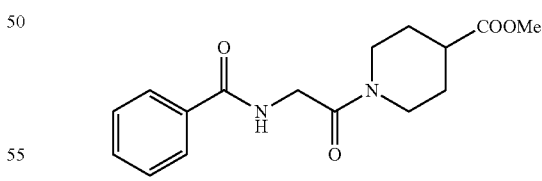

To a stirred solution of 2-benzamidoacetic acid (3.0 g, 16.7 mmol) in N,N-dimethylformamide (30 mL) were added methyl piperidine-4-carboxylate (2.88 g, 20.09 mmol), (2-(1H-benzotriazol-1-yl)-1,1,3,3-tetramethyluronium hexafluorophosphate) (6.35 g, 16.7 mmol), and N-ethyl-N-(propan-2-yl)propan-2-amine (6.49 g, 50.2 mmol, 8.77 mL). The mixture was stirred at 20° C. for 3 h and then quenched by addition of water (40 mL). The mixture was extracted with ethyl acetate (80 mL×4). The combined organic phases were washed with saturated aqueous sodium chloride solution (30 mL), dried over anhydrous sodium sulfate, filtered, and concentrated to give crude product that was purified by chromatography (silica, petroleumether:ethylacetate=5:1 to 1:1) to give methyl 1-(2-benzamidoacetyl)piperidine-4-carboxylate (7.0 g, 23.0 mmol, quantitative), as a yellow oil. LCMS (ESI) m/z=305.1 [M+H]+.

Step 2: Preparation of 1-(2-benzamidoacetyl)piperidine-4-carboxylic acid

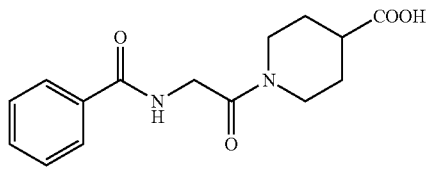 [SMILES: O=C(NCC(=O)N1CCC(C(=O)O)CC1)c1ccccc1]

To a stirred solution of methyl 1-(2-benzamidoacetyl) piperidine-4-carboxylate (7.0 g, 23.0 mmol) in tetrahydrofuran (50 mL) was added aqueous sodium hydroxide (2 M, 23 mL). The mixture was then stirred at 20° C. for 16 h. The mixture was then acidified to pH 1 using concentrated hydrochloric acid and then extracted with dichloromethane (80 mL×4). The organic phases were combined, washed with saturated aqueous sodium chloride solution (30 mL), dried over anhydrous sodium sulfate, filtered, and concentrated to give 1-(2-benzamidoacetyl)piperidine-4-carboxylic acid (4.20 g, 14.47 mmol, 63%) as a yellow solid. This was used directly in the next step without further purification. $^1$H NMR (400 MHz, Methanol-d4) δ 7.93-7.85 (m, 2H), 7.59-7.54 (m, 1H), 7.52-7.46 (m, 2H), 4.42-4.33 (m, 1H), 4.29 (s, 2H), 4.01-3.87 (m, 1H), 3.30-3.20 (m, 1H), 2.97-2.88 (m, 1H), 2.63-2.52 (m, 1H), 2.06-1.92 (m, 2H), 1.80-1.55 (m, 2H).

Step 3: Preparation of N-(2-oxo-2-(4-(3-phenyl-1,2,4-oxadiazol-5-yl)piperidin-1-yl)ethyl)benzamide

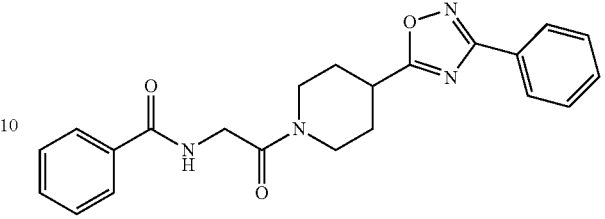

To a stirred solution of 1-(2-benzamidoacetyl)piperidine-4-carboxylic acid (200 mg, 689 μmol) in N,N-dimethylformamide (4 mL) were added N-hydroxybenzamidine (112 mg, 826 μmol), N,N,N',N'-tetramethyl-O-(1H-benzotriazol-1-yl)uronium hexafluorophosphate (261 mg, 689 μmol), and N,N-diisopropylethylamine (267 mg, 2.07 mmol, 360.96 μL). The reaction mixture was then stirred at 20° C. for 2 h, quenched by addition of water (5 mL), and extracted with ethyl acetate (20 mL×4). The organic extracts were combined, washed with saturated aqueous sodium chloride solution, dried over anhydrous sodium sulfate, and concentrated in vacuo to provide a crude residue. To the residue was added N,N-dimethylformamide (4 mL), and the resulting mixture was stirred at 120° C. for 2 h, concentrated under vacuum, and purified by prep-HPLC (column: Luna C8 100×30 5 μm; mobile phase: [water (10 mM ammonium carbonate)-acetonitrile]; B %: 30%-60%, 12 min) to give N-(2-oxo-2-(4-(3-phenyl-1,2,4-oxadiazol-5-yl)piperidin-1-yl)ethyl)benzamide (74 mg, 189 μmol, 27%) as a white solid. $^1$H NMR (400 MHz, CDCl$_3$) δ 8.13-8.08 (m, 2H), 7.88 (d, J=7.2 Hz, 2H), 7.55-7.46 (m, 6H), 7.36 (br. s., 1H), 4.51 (d, J=13.7 Hz, 1H), 4.33 (d, J=3.8 Hz, 2H), 3.94 (d, J=13.3 Hz, 1H), 3.42-3.32 (m, 2H), 3.20 (t, J=10.5 Hz, 1H), 2.28 (br. s., 2H), 2.11-1.96 (m, 2H); LCMS (ESI) m/z: [M+H]+=391.1.

Example 10: N-(2-(4-(3-(4-methoxyphenyl)-1,2,4-oxadiazol-5-yl)piperidin-1-yl)-2-oxoethyl)benzamide

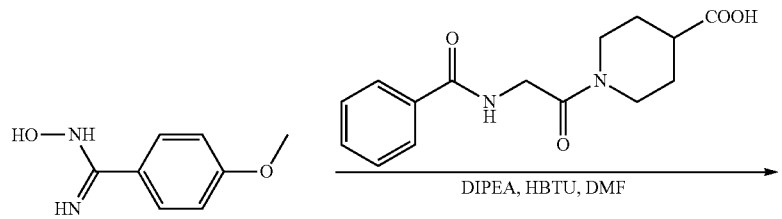

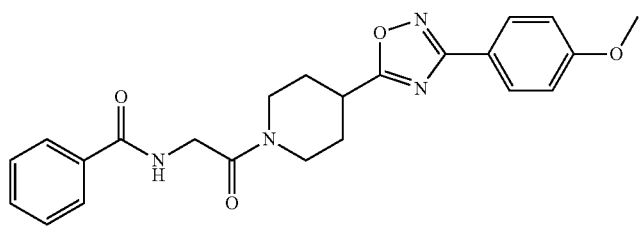

Step 1: Preparation of N-(2-(4-(3-(4-methoxyphenyl)-1,2,4-oxadiazol-5-yl)piperidin-1-yl)-2-oxoethyl)benzamide

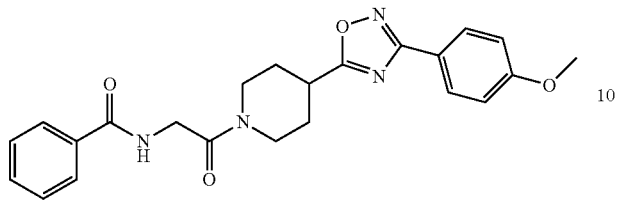

To a stirred solution of 1-(2-benzamidoacetyl)piperidine-4-carboxylic acid (120 mg, 413 μmol) and N-hydroxy-4-methoxybenzimidamide (82 mg, 496 μmol) in N,N-dimethylformamide (2 mL) were added N,N-diisopropylamine (106 mg, 827 μmol, 144 μL) and (2-(1H-benzotriazol-1-yl)-1,1,3,3-tetramethyluronium hexafluorophosphate) (156 mg, 413 μmol) at 15° C., then the mixture was stirred for 15 h. The mixture was heated to 110° C. and stirred for 5 h. After cooling, the mixture was purified directly by prep-HPLC (column: Luna C8 100×30 5 μm; mobile phase: [water (10 mM ammonium carbonate)-acetonitrile]; B %: 30%-65%, 12 min) to give N-(2-(4-(3-(4-methoxyphenyl)-1,2,4-oxadiazol-5-yl)piperidin-1-yl)-2-oxoethyl)benzamide (87 mg, 205 μmol, 50%) as a yellow solid. $^1$H NMR (400 MHz, Methanol-d4) δ 7.98 (d, J=8.8 Hz, 2H), 7.88 (d, J=7.5 Hz, 2H), 7.60-7.51 (m, 1H), 7.51-7.38 (m, 2H), 7.04 (d, J=8.4 Hz, 2H), 4.46 (d, J=13.2 Hz, 1H), 4.38-4.21 (m, 2H), 4.04 (d, J=13.7 Hz, 1H), 3.86 (s, 3H), 3.47-3.34 (m, 2H), 3.07 (t, J=11.9 Hz, 1H), 2.31-2.15 (m, 2H), 2.05-1.80 (m, 2H); LCMS (ESI) m/z [M+H]$^+$=421.1.

Example 11

Step 1: Preparation of N-hydroxy-3-methoxybenzimidamide

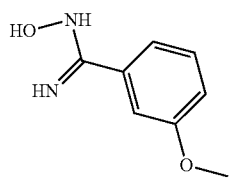

To a stirred solution of 3-methoxybenzonitrile (2.0 g, 15.0 mmol, 1.83 mL) in ethanol (20 mL) was added hydroxylamine hydrochloride (2.09 g, 30.0 mmol), triethylamine (3.04 g, 30.0 mmol, 4.16 mL) and water (2 mL). Then the mixture was heated at 75° C. for 5 h. After cooling to 20° C., water (20 mL) was added to the solution. The mixture was extracted with dichloromethane (40 mL×4). The combined organic layers were washed with saturated aqueous sodium chloride solution (20 mL) and dried over anhydrous sodium sulfate. The combined organic phases were concentrated in vacuo to give N-hydroxy-3-methoxybenzimidamide (2.60 g) as a white solid. This was used directly without further purification. $^1$H NMR (400 MHz, DMSO-d6) δ 9.67 (s, 1H), 7.37-7.24 (m, 3H), 7.10-6.88 (m, 1H), 5.84 (br. s., 2H), 3.82 (s, 3H).

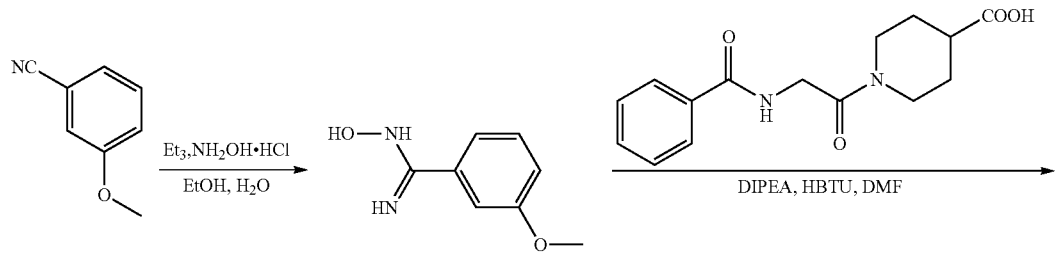

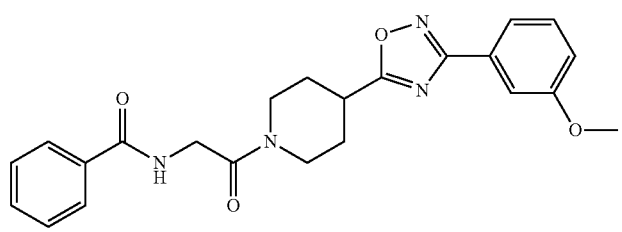

Step 2: Preparation of N-(2-(4-(3-(3-methoxyphenyl)-1,2,4-oxadiazol-5-yl)piperidin-1-yl)-2-oxoethyl)benzamide

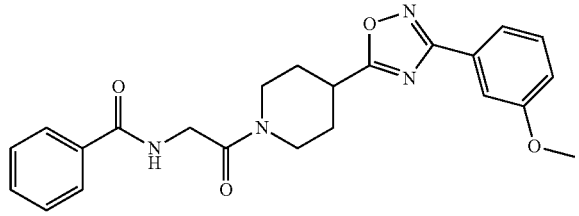 [SMILES: COc1cccc(-c2noc(C3CCN(C(=O)CNC(=O)c4ccccc4)CC3)n2)c1]

To a stirred solution of 1-(2-benzamidoacetyl)piperidine-4-carboxylic acid (120 mg, 413 μmol) in N,N-dimethylformamide (3 mL) were added N-hydroxy-3-methoxybenzimidamide (82 mg, 496 μmol), (2-(1H-benzotriazol-1-yl)-1,1,3,3-tetramethyluronium hexafluorophosphate) (156 mg, 413 μmol), and N-ethyl-N-(propan-2-yl)propan-2-amine (160 mg, 1.24 mmol, 216 μL). The mixture was stirred at 20° C. for 2 h, then heated at 120° C. for 2 h. The reaction mixture was cooled and purified directly by prep-HPLC (column: Luna C8 100×30 5 μm; mobile phase: [water (10 mM ammonium carbonate)-acetonitrile]; B %: 35%-60%, 12 min) to give N-(2-(4-(3-(3-methoxyphenyl)-1,2,4-oxadiazol-5-yl)piperidin-1-yl)-2-oxoethyl)benzamide (83 mg, 198 μmol, 48%) as a yellow solid. $^1$H NMR (400 MHz, CDCl$_3$) δ 7.91-7.85 (m, 2H), 7.72-7.68 (m, 1H), 7.62 (dd, J=1.5, 2.5 Hz, 1H), 7.57-7.52 (m, 1H), 7.51-7.45 (m, 2H), 7.42 (t, J=8.0 Hz, 1H), 7.38-7.32 (m, 1H), 7.08 (ddd, J=0.9, 2.6, 8.3 Hz, 1H), 4.52 (d, J=13.6 Hz, 1H), 4.33 (d, J=4.0 Hz, 2H), 3.95 (br. s., 1H), 3.91 (s, 3H), 3.42-3.32 (m, 2H), 3.25-3.13 (m, 1H), 2.33-2.22 (m, 2H), 2.11-1.94 (m, 2H); LCMS (ESI) m/z: [M+H]$^+$=421.2.

Example 12: N-(2-(4-(3-(2-methoxyphenyl)-1,2,4-oxadiazol-5-yl)piperidin-1-yl)-2-oxoethyl)benzamide

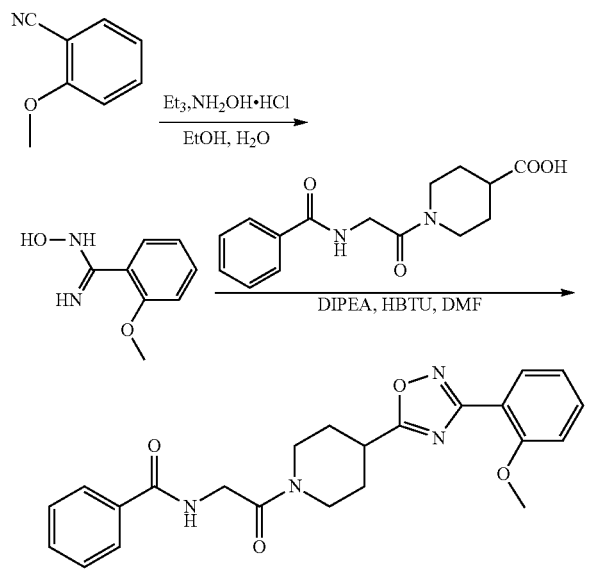

Step 1: Preparation of N-hydroxy-2-methoxybenzimidamide

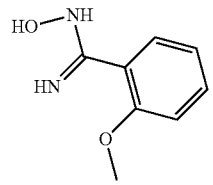

To a stirred solution of 2-methoxybenzonitrile (2.0 g, 15.0 mmol, 1.83 mL) in ethanol (20 mL) were added hydroxylamine hydrochloride (2.09 g, 30.0 mmol), triethylamine (3.04 g, 30.0 mmol, 4.16 mL), and water (2 mL), then the mixture was heated to 70° C. for 15 h. The mixture was cooled and quenched with water (20 mL), extracted with dichloromethane (30 mL×3), and the combined organic phases were washed with water (20 mL), saturated aqueous sodium chloride solution (20 mL), dried over anhydrous sodium sulfate, filtered, and concentrated to give N-hydroxy-2-methoxybenzimidamide (2.80 g) as a light green solid, which was used in next step directly. $^1$H NMR (400 MHz, Methanol-d4) δ 7.47-7.30 (m, 2H), 7.06 (d, J=8.4 Hz, 1H), 6.95 (t, J=7.5 Hz, 1H), 3.86 (s, 3H).

Step 2: Preparation of N-(2-(4-(3-(2-methoxyphenyl)-1,2,4-oxadiazol-5-yl)piperidin-1-yl)-2-oxoethyl)benzamide

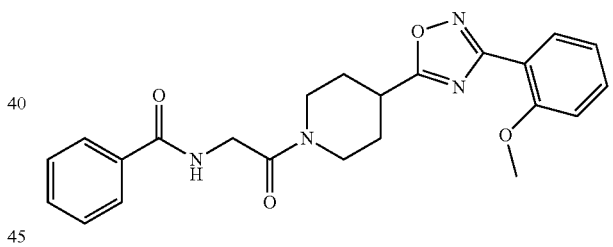

To a stirred solution of 1-(2-benzamidoacetyl)piperidine-4-carboxylic acid (120 mg, 413 μmol) and N-hydroxy-2-methoxybenzimidamide (68 mg, 413 μmol) in N,N-dimethylformamide (2 mL) were added N-ethyl-N-(propan-2-yl)propan-2-amine (106 mg, 826 μmol, 144 μL) and (2-(1H-benzotriazol-1-yl)-1,1,3,3-tetramethyluronium hexafluorophosphate) (156 mg, 413 μmol), and the mixture was stirred for 15 h at 15° C. The mixture was then heated to 110° C. and stirred for 5 h. After cooling, the mixture was purified directly by prep-HPLC (column: Luna C8 100×30 5 μm; mobile phase: [water (10 mM ammonium carbonate)-acetonitrile]; B %: 25%-60%, 12 min) to give N-(2-(4-(3-(2-methoxyphenyl)-1,2,4-oxadiazol-5-yl)piperidin-1-yl)-2-oxoethyl)benzamide (90 mg, 212 μmol, 51%) as a yellow solid. $^1$H NMR (400 MHz, Methanol-d4) δ 7.96 (d, J=7.5 Hz, 1H), 7.88 (d, J=7.9 Hz, 2H), 7.61-7.41 (m, 4H), 7.18 (d, J=8.8 Hz, 1H), 7.09 (t, J=7.5 Hz, 1H), 4.47 (d, J=13.2 Hz, 1H), 4.37-4.23 (m, 2H), 4.12-4.00 (m, 1H), 3.93 (s, 3H), 3.50-3.35 (m, 2H), 3.08 (t, J=11.5 Hz, 1H), 2.33-2.15 (m, 2H), 2.12-1.79 (m, 2H); LCMS (ESI) m/z: [M+H]$^+$=421.1.

Example 13: N-[2-[4-[3-(3,4-dimethoxyphenyl)-1,2,4-oxadiazol-5-yl]-1-piperidyl]-2-oxo-ethyl]-4-methyl-benzamide J=6.0 Hz, 2H), 4.05 (d, J=14.1 Hz, 1H), 3.89 (s, 6H), 3.50-3.34 (m, 3H), 3.06 (t, J=12.0 Hz, 1H), 2.40 (s, 3H), 2.32-2.13 (t, 2H), 2.07-1.79 (m, 3H); LCMS (ESI) m/z: [M+H]$^+$=465.3.

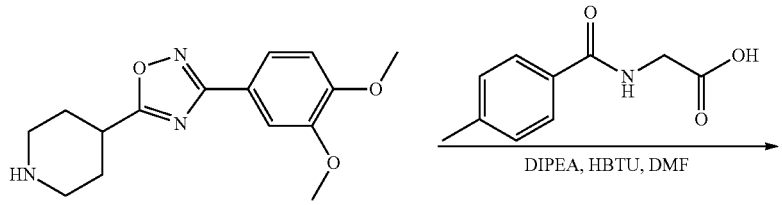

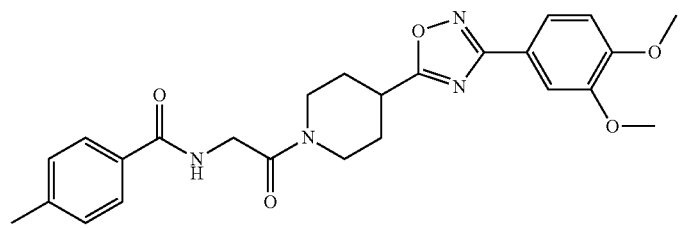

Step 1: Preparation of N-(2-(4-(3-(3,4-dimethoxyphenyl)-1,2,4-oxadiazol-5-yl)piperidin-1-yl)-2-oxoethyl)-4-methylbenzamide

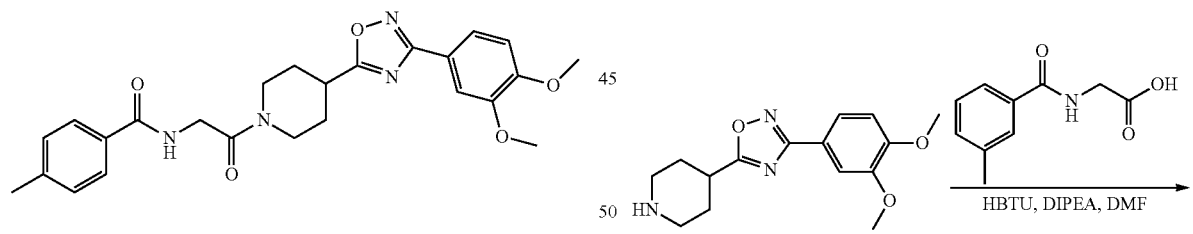

To a stirred solution of 3-(3,4-dimethoxyphenyl)-5-(4-piperidyl)-1,2,4-oxadiazole (150 mg, 518 μmol) in N,N-dimethylformamide (2 mL) were added (2-(1H-benzotriazol-1-yl)-1,1,3,3-tetramethyluronium hexafluorophosphate) (196 mg, 518 μmol) and N-ethyl-N-(propan-2-yl)propan-2-amine (201 mg, 1.56 mmol, 271 μL) and 2-[(4-methylbenzoyl)amino]acetic acid (105 mg, 544 μmol). The mixture was stirred at 20° C. for 5 h. The crude product was purified by prep-HPLC (column: Luna C8 100×30 mm 5 μm; mobile phase: [water (10 mM ammonium carbonate)-acetonitrile]; B %: 30%-60%, 12 min) to give N-(2-(4-(3-(3,4-dimethoxyphenyl)-1,2,4-oxadiazol-5-yl)piperidin-1-yl)-2-oxoethyl)-4-methylbenzamide. $^1$H NMR (400 MHz, METHANOL-d4) δ=7.77 (d, J=7.5 Hz, 2H), 7.66 (d, J=8.2 Hz, 1H), 7.59 (s, 1H), 7.29 (d, J=7.7 Hz, 2H), 7.08 (d, J=8.4 Hz, 1H), 4.47 (d, J=12.8 Hz, 1H), 4.29 (m,

Example 14: N-(2-(4-(3-(3,4-dimethoxyphenyl)-1,2,4-oxadiazol-5-yl)piperidin-1-yl)-2-oxoethyl)-3-methylbenzamide

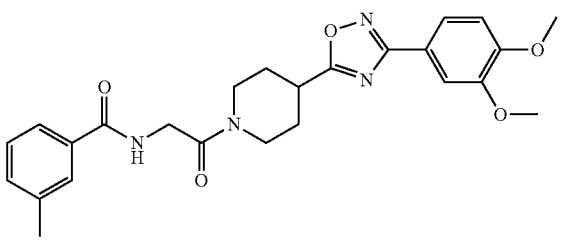

363

Preparation of N-(2-(4-(3-(3,4-dimethoxyphenyl)-1,2,4-oxadiazol-5-yl)piperidin-1-yl)-2-oxoethyl)-3-methylbenzamide

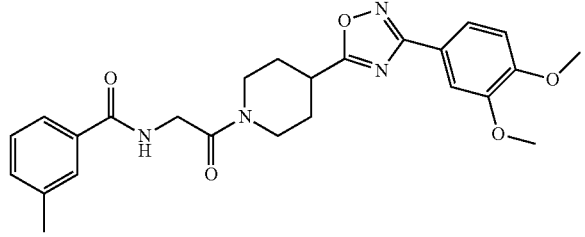 [SMILES: COc1ccc(-c2noc(C3CCN(C(=O)CNC(=O)c4cccc(C)c4)CC3)n2)cc1OC]

To a stirred solution of 3-(3,4-dimethoxyphenyl)-5-(4-piperidyl)-1,2,4-oxadiazole (200 mg, 691 µmol) in N,N-dimethylformamide (2 mL) was added N-ethyl-N-(propan-2-yl)propan-2-amine (268 mg, 2.07 mmol, 362 µL), (2-(1H-benzotriazol-1-yl)-1,1,3,3-tetramethyluronium hexafluorophosphate) (262 mg, 691 µmol) and 2-[(3-methylbenzoyl)amino]acetic acid (133 mg, 691 µmol). The mixture was stirred at 20° C. for 16 h. The crude product was purified by prep-HPLC (column: Luna C8 100×30 5 µm; mobile phase: [water (10 mM ammonium carbonate)-acetonitrile]; B %: 30%-60%, 12 min) to give N-[2-[4-[3-(3,4-dimethoxyphenyl)-1,2,4-oxadiazol-5-yl]-1-piperidyl]-2-oxo-ethyl]-3-methyl-benzamide (157 mg, 338 µmol, 49%) as a white solid. $^1$H NMR (400 MHz, DMSO-d6) δ=8.48 (t, J=5.5 Hz, 1H), 7.72-7.63 (m, 2H), 7.58 (dd, J=2.0, 8.4 Hz, 1H), 7.46 (d, J=1.8 Hz, 1H), 7.34 (d, J=4.9 Hz, 2H), 7.11 (d, J=8.4 Hz, 1H), 4.32 (br d, J=13.0 Hz, 1H), 4.15 (dd, J=2.3, 5.4 Hz, 2H), 3.96 (d, J=13.7 Hz, 1H), 3.87-3.77 (m, 6H), 3.51-3.39 (m, 1H), 3.24 (s, 1H), 2.90 (t, J=11.6 Hz, 1H), 2.35 (s, 3H), 2.20-2.04 (m, 2H), 1.89-1.75 (m, 1H), 1.72-1.54 (m, 1H); LCMS (ESI) m/z: [M+H]$^+$=465.3.

Example 15: N-(2-(4-(3-(3,4-dimethoxyphenyl)-1,2,4-oxadiazol-5-yl)piperidin-1-yl)-2-oxoethyl)-3,4-dimethylbenzamide

364

Preparation of N-(2-(4-(3-(3,4-dimethoxyphenyl)-1,2,4-oxadiazol-5-yl)piperidin-1-yl)-2-oxoethyl)-3,4-dimethylbenzamide

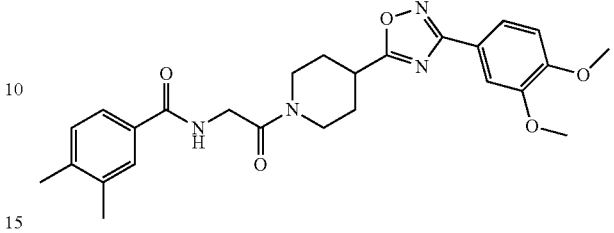

To a stirred solution of 1-[2-[(3,4-dimethylbenzoyl)amino]acetyl]piperidine-4-carboxylic acid (200 mg, 628 µmol) and N-hydroxy-3,4-dimethoxy-benzamidine (184 mg, 942 µmol) in N,N-dimethylformamide (1.50 mL) were added (2-(1H-benzotriazol-1-yl)-1,1,3,3-tetramethyluronium hexafluorophosphate) (238 mg, 628 µmol) and N-ethyl-N-(propan-2-yl)propan-2-amine (243 mg, 1.88 mmol, 329 µL). The mixture was stirred at 20° C. for 16 h. The reaction mixture was diluted with water (5 mL) and extracted with ethyl acetate (10 mL×3). The combined organic layers were washed with saturated aqueous sodium chloride solution (10 mL×2), dried over anhydrous sodium sulfate, filtered, and concentrated under reduced pressure to give a residue. N,N-Dimethylformamide (2 mL) was added, then the mixture was heated to 120° C. and stirred for a further 4 h. The mixture was cooled to 25° C., then water (5 mL) was added, and the mixture extracted with ethyl acetate (10 mL×3). The combined organic layers were washed with saturated aqueous sodium chloride solution (10 mL×2), dried over anhydrous sodium sulfate, filtered, and concentrated under reduced pressure to give a residue. This residue was purified by prep-HPLC (column: Luna C8 100×30 5 µm; mobile phase: [water (10 mM ammonium carbonate)-acetonitrile]; B %: 30%-65%, 12 min) to give N-[2-[4-[3-(3,4-dimethoxyphenyl)-1,2,4-oxadiazol-5-yl]-1-piperidyl]-2-oxo-ethyl]-3,4-dimethyl-benzamide (209 mg, 436 µmol,

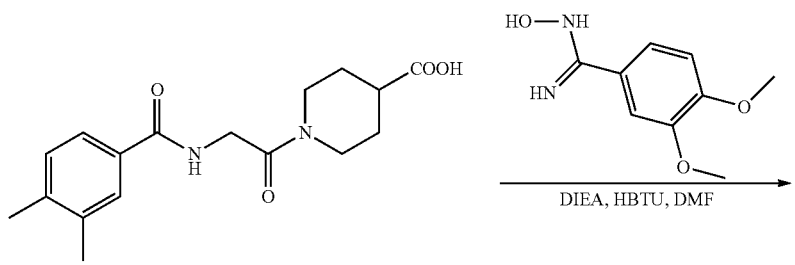

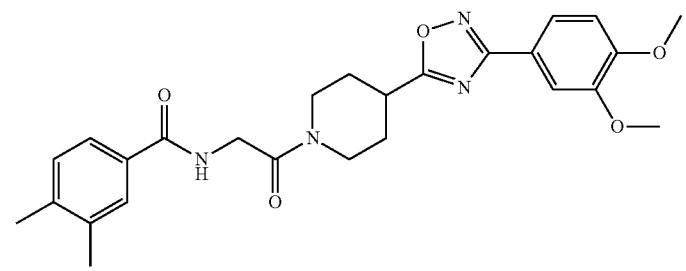

69%) as a yellow solid. $^1$H NMR (400 MHz, DMSO-d6) δ=8.40 (s, 1H), 7.66 (s, 1H), 7.59 (br d, J=7.9 Hz, 2H), 7.46 (s, 1H), 7.21 (br d, J=7.7 Hz, 1H), 7.11 (br d, J=8.4 Hz, 1H), 4.32 (br d, J=12.6 Hz, 1H), 4.14 (br s, 2H), 3.96 (br d, J=13.5 Hz, 1H), 3.89-3.72 (m, 6H), 3.43 (br t, J=10.8 Hz, 1H), 3.28-3.17 (m, 1H), 2.90 (br t, J=11.5 Hz, 1H), 2.26 (s, 6H), 2.20-2.10 (m, 2H), 1.80 (br d, J=10.4 Hz, 1H), 1.64 (br d, J=10.1 Hz, 1H). (ESI) m/z: [M+H]$^+$=479.3.
Example 16: N-(2-(4-(3-(4-methoxyphenyl)-1,2,4-oxadiazol-5-yl)piperidin-1-yl)-2-oxoethyl)-3,4-dimethylbenzamide
Step 1: Preparation of tert-butyl 2-(3,4-dimethylbenzamido)acetate
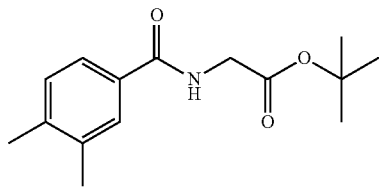 [SMILES: Cc1ccc(C(=O)NCC(=O)OC(C)(C)C)cc1C]
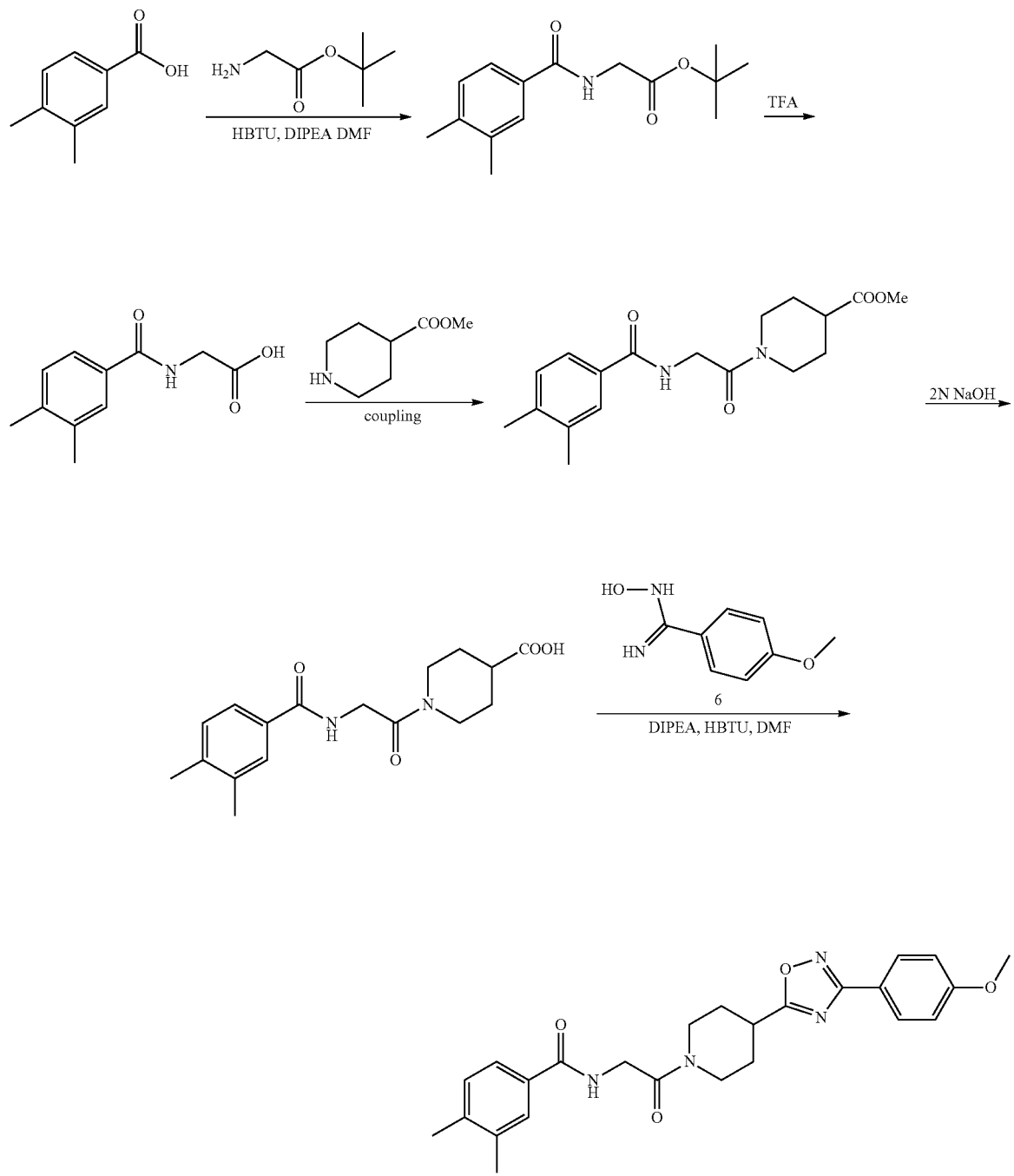

To a stirred solution of 3,4-dimethylbenzoic acid (2.0 g, 13.3 mmol) and tert-butyl 2-aminoacetate (1.92 g, 14.7 mmol) in N,N-dimethylformamide (20 mL) were added N-ethyl-N-(propan-2-yl)propan-2-amine (3.44 g, 26.6 mmol, 4.65 mL) and 1-[bis(dimethylamino)methylene]-1H-1,2,3-triazolo[4,5-b]pyridinium 3-oxide hexafluorophosphate (5.06 g, 13.3 mmol). After stirring at 15° C. for 3 h, the mixture was treated with water (30 mL), extracted with ethyl acetate (30 mL×3), and the combined organic phases were washed with water (20 mL), 1N hydrochloric acid (30 mL), saturated aqueous sodium hydrogen carbonate (30 mL), saturated aqueous sodium chloride solution (30 mL), dried over anhydrous sodium sulfate, filtered, and concentrated to give tert-butyl 2-(3,4-dimethylbenzamido)acetate (4.0 g) as light brown oil, which was used in the next step directly without further purification. ¹H NMR (400 MHz, CDCl₃) δ 7.52 (d, J=1.6 Hz, 1H), 7.46 (dd, J=1.9, 7.9 Hz, 1H), 7.11 (d, J=7.8 Hz, 1H), 4.08-4.04 (m, 2H), 2.23 (s, 6H), 1.44 (s, 9H).

Step 2: Preparation of 2-(3,4-dimethylbenzamido)acetic acid

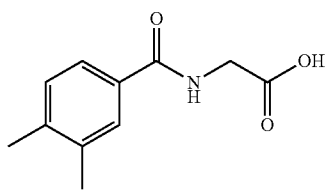

A solution of tert-butyl 2-(3,4-dimethylbenzamido)acetate (4.0 g, 15.2 mmol) in TFA (20 mL) and dichloromethane (20 mL) was stirred for 20 h at 15° C. The mixture was concentrated, and the residue was treated with water (10 mL) and extracted with dichloromethane/methanol (20/1, 20 mL×3). The combined organic phase was dried over anhydrous sodium sulfate, filtered, and concentrated to give 2-(3,4-dimethylbenzamido)acetic acid (3.20 g) as a yellow oil, which was used in next step directly without further purification.

Step 3: Preparation of methyl 1-(2-(3,4-dimethylbenzamido)acetyl)piperidine-4-carboxylate

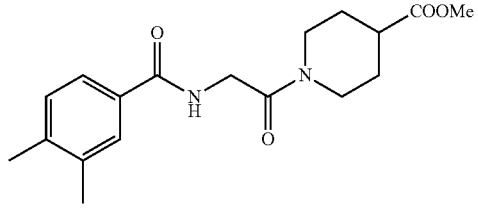 [SMILES: COC(=O)C1CCN(C(=O)CNC(=O)c2ccc(C)c(C)c2)CC1]

To a stirred solution of 2-(3,4-dimethylbenzamido)acetic acid (3.20 g, 15.4 mmol) and methyl piperidine-4-carboxylate (2.65 g, 18.5 mmol) in N,N-dimethylformamide (20 mL) were added N-ethyl-N-(propan-2-yl)propan-2-amine (3.99 g, 30.9 mmol, 5.39 mL) and (2-(1H-benzotriazol-1-yl)-1,1,3,3-tetramethyluronium hexafluorophosphate) (5.86 g, 15.4 mmol) at 0° C., then the mixture was warmed slowly to 15° C. and stirred for 15 h. The mixture was treated with water (30 mL) at 0° C., extracted with ethyl acetate (50 mL×3). The combined organic phase was washed with water (20 mL), 1N hydrochloric acid (30 mL), saturated aqueous sodium hydrogen carbonate solution (30 mL), saturated aqueous sodium chloride solution (30 mL), and dried over anhydrous sodium sulfate, filtered, and concentrated to give a crude product. Purification by chromatography (silica, petroleum ether/ethyl acetate from 10:1 to 1:2) gave methyl 1-(2-(3,4-dimethylbenzamido)acetyl)piperidine-4-carboxylate (3.50 g, 10.5 mmol, 68%) as a white solid. ¹H NMR (400 MHz, CDCl₃) δ 7.62 (s, 1H), 7.57 (d, J=7.9 Hz, 1H), 7.28 (m, 1H), 7.19 (d, J=7.5 Hz, 1H), 4.39 (d, J=13.2 Hz, 1H), 4.24 (d, J=3.5 Hz, 2H), 3.78 (d, J=13.7 Hz, 1H), 3.71 (s, 3H), 3.17 (t, J=11.0 Hz, 1H), 3.02-2.91 (m, 1H), 2.67-2.54 (m, 1H), 2.30 (s, 6H), 1.98 (m, 2H), 1.80-1.64 (m, 2H).

Step 4: Preparation of 1-(2-(3,4-dimethylbenzamido)acetyl)piperidine-4-carboxylic acid

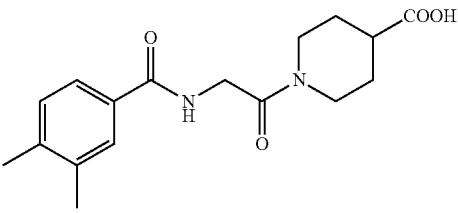 [SMILES: Cc1ccc(C(=O)NCC(=O)N2CCC(C(=O)O)CC2)cc1C]

To a stirred solution of methyl 1-(2-(3,4-dimethylbenzamido)acetyl)piperidine-4-carboxylate (3.50 g, 10.5 mmol) in tetrahydrofuran (20 mL) and methanol (20 mL) was added aqueous sodium hydroxide (2 M, 7.90 mL), and the mixture was stirred at 15° C. for 5 h. The mixture was concentrated to remove tetrahydrofuran and methanol, then then residue was acidified by 1N hydrochloric acid to pH=2-3 at 0° C. The mixture was then extracted with dichloromethane (20 mL×3), dried over anhydrous sodium sulfate, filtered, concentrated, and purified by prep-HPLC (column: Phenomenex luna C18 250×50 mm 10 µm; mobile phase: [water (0.1% TFA)-acetonitrile]; B %: 10%-40%, 20 min) to give 1-(2-(3,4-dimethylbenzamido)acetyl)piperidine-4-carboxylic acid (1.80 g, 5.65 mmol, 54%) as a white solid. ¹H NMR (400 MHz, DMSO-d6) δ8.39 (s, 1H), 7.67 (s, 1H), 7.61 (d, J=7.7 Hz, 1H), 7.24 (d, J=7.7 Hz, 1H), 4.21 (d, J=12.7 Hz, 1H), 4.12 (d, J=4.9 Hz, 2H), 3.85 (d, J=13.8 Hz, 1H), 3.14 (t, J=11.7 Hz, 1H), 2.79 (t, J=11.5 Hz, 1H), 2.28 (s, 6H), 1.86 (m, 2H), 1.63-1.32 (m, 2H).

Step 5: Preparation of N-(2-(4-(3-(4-methoxyphenyl)-1,2,4-oxadiazol-5-yl)piperidin-1-yl)-2-oxoethyl)-3,4-dimethylbenzamide

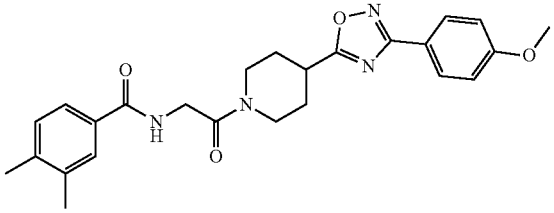

To a stirred solution of 1-(2-(3,4-dimethylbenzamido)acetyl)piperidine-4-carboxylic acid (150 mg, 471 μmol) and N-hydroxy-4-methoxybenzimidamide (93 mg, 565 μmol) in N,N-dimethylformamide (2 mL) was added N-ethyl-N-(propan-2-yl)propan-2-amine (121 mg, 942 μmol, 164 μL) and (2-(1H-benzotriazol-1-yl)-1,1,3,3-tetramethyluronium hexafluorophosphate) (178 mg, 471 μmol) at 15° C. After 15 h, the mixture was heated to 110° C. and stirred for 5 h. The mixture was cooled and directly purified by prep-HPLC (column: Waters Xbridge 150×25 5 μm; mobile phase: [water (10 mM ammonium carbonate)-acetonitrile]; B %: 40%-70%, 12 min) to give N-(2-(4-(3-(4-methoxyphenyl)-1,2,4-oxadiazol-5-yl)piperidin-1-yl)-2-oxoethyl)-3,4-dimethylbenzamide (110 mg, 244 μmol, 52%) as a light yellow solid. $^1$H NMR (400 MHz, Methanol-d4) δ 7.98 (d, J=9.3 Hz, 2H), 7.66 (s, 1H), 7.60 (d, J=7.5 Hz, 1H), 7.23 (d, J=7.9 Hz, 1H), 7.05 (d, J=9.3 Hz, 2H), 4.46 (d, J=13.2 Hz, 1H), 4.34-4.23 (m, 2H), 4.04 (d, J=13.7 Hz, 1H), 3.86 (s, 3H), 3.47-3.36 (m, 2H), 3.07 (t, J=11.0 Hz, 1H), 2.42-2.26 (s, 6H), 2.21 (d, J=17.6 Hz, 2H), 2.04-1.82 (m, 2H); LCMS (ESI) m/z: [M+H]$^+$=449.2.

Example 17: N-(2-(4-(3-(3-methoxyphenyl)-1,2,4-oxadiazol-5-yl)piperidin-1-yl)-2-oxoethyl)-3,4-dimethylbenzamide

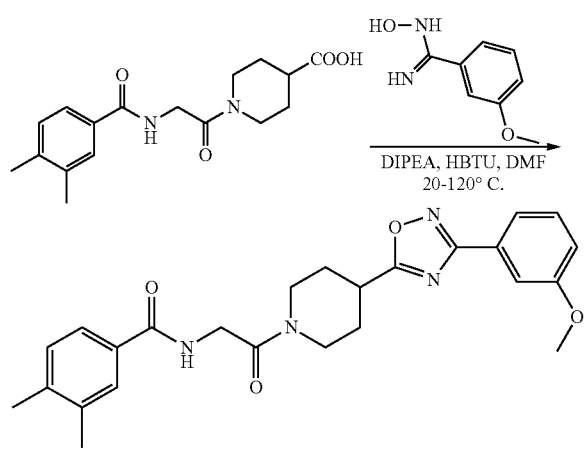

Step 1: Preparation of N-(2-(4-(3-(3-methoxyphenyl)-1,2,4-oxadiazol-5-yl)piperidin-1-yl)-2-oxoethyl)-3,4-dimethylbenzamide

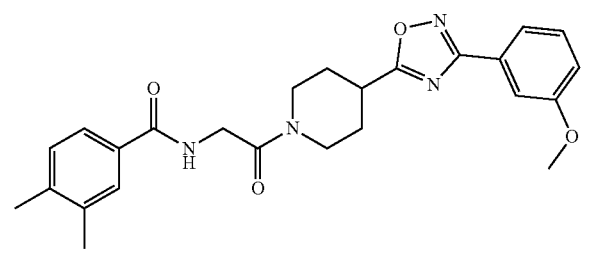 [SMILES: COc1cccc(-c2noc(C3CCN(C(=O)CNC(=O)c4ccc(C)c(C)c4)CC3)n2)c1]

To a stirred solution of 1-(2-(3,4-dimethylbenzamido)acetyl)piperidine-4-carboxylic acid (150 mg, 471 μmol) in N,N-dimethylformamide (3 mL) were added N-hydroxy-3-methoxybenzimidamide (93 mg, 565 μmol), (2-(1H-benzotriazol-1-yl)-1,1,3,3-tetramethyluronium hexafluorophosphate) (178 mg, 471 μmol) and N-ethyl-N-(propan-2-yl)propan-2-amine (182 mg, 1.41 mmol, 246 μL). The mixture was stirred at 20° C. for 2 h and then heated at 120° C. for 2 h. The reaction mixture was cooled and then purified directly by prep-HPLC (column: Luna C8 100×30 5 μm; mobile phase: [water (10 mM ammonium carbonate)-acetonitrile]; B %: 40%-70%, 12 min) to give N-(2-(4-(3-(3-methoxyphenyl)-1,2,4-oxadiazol-5-yl)piperidin-1-yl)-2-oxoethyl)-3,4-dimethylbenzamide (119 mg, 263 μmol, 56%) as a white solid. $^1$H NMR (400 MHz, CDCl$_3$) δ 7.63-7.47 (m, 4H), 7.32 (t, J=7.9 Hz, 1H), 7.23-7.20 (m, 1H), 7.15-7.10 (m, 1H), 6.98 (dd, J=1.8, 8.3 Hz, 1H), 4.48-4.37 (m, 1H), 4.22 (d, J=3.9 Hz, 2H), 3.88-3.82 (m, 1H), 3.81 (s, 3H), 3.31-3.22 (m, 2H), 3.13-3.04 (m, 1H), 2.24 (s, 6H), 2.22-2.12 (m, 2H), 2.00-1.87 (m, 2H); LCMS (ESI) m/z: [M+H]$^+$=449.3.

Example 18: 4-(4-(3-(3,4-dimethoxyphenyl)-1,2,4-oxadiazol-5-yl)piperidine-1-carbonyl)-1-phenylpyrrolidin-2-one

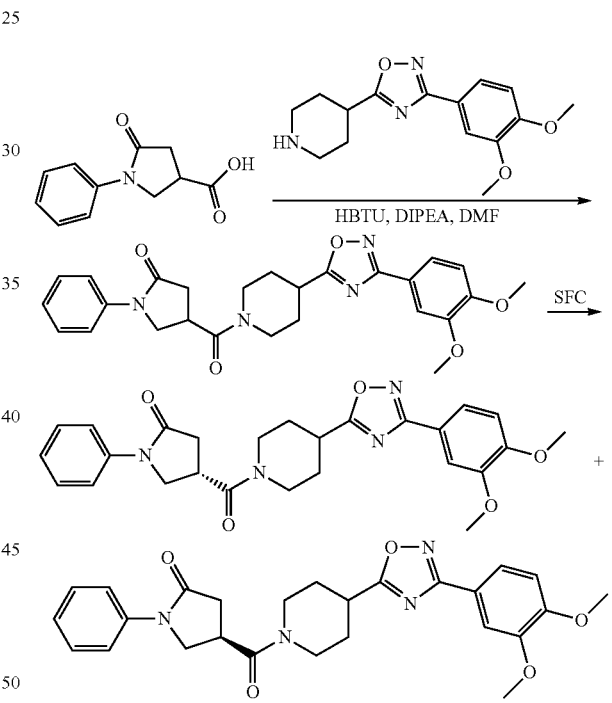

Step 1: Preparation of 4-(4-(3-(3,4-dimethoxyphenyl)-1,2,4-oxadiazol-5-yl)piperidine-1-carbonyl)-1-phenylpyrrolidin-2-one

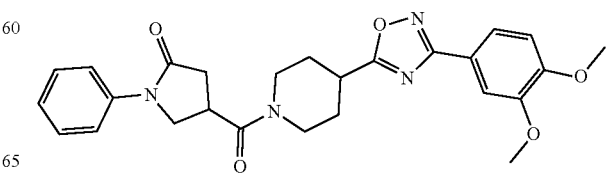

To a stirred solution of 3-(3,4-dimethoxyphenyl)-5-(4-piperidyl)-1,2,4-oxadiazole (150 mg, 518 μmol) in N,N-dimethylformamide (1.5 mL) were added (2-(1H-benzotriazol-1-yl)-1,1,3,3-tetramethyluronium hexafluorophosphate) (196 mg, 518 μmol), N-ethyl-N-(propan-2-yl)propan-2-amine (201 mg, 1.56 mmol, 271 μL) and 5-oxo-1-phenyl-pyrrolidine-3-carboxylic acid (111 mg, 544 μmol). The mixture was stirred at 20° C. for 16 h. The mixture was filtered, and the filtrate was purified directly by prep-HPLC (column: Luna C8 100×30 5 μm; mobile phase: [water (10 mM ammonium carbonate)-acetonitrile]; B %: 30%-60%, 12 min) to give 4-[4-[3-(3,4-dimethoxyphenyl)-1,2,4-oxadiazol-5-yl]piperidine-1-carbonyl]-1-phenyl-pyrrolidin-2-one (86 mg, 181 μmol, 35%) as a white solid. $^1$H NMR (400 MHz, METHANOL-d4) δ=7.69-7.56 (m, 4H), 7.38 (br t, J=7.2 Hz, 2H), 7.22-7.16 (m, 1H), 7.08 (br d, J=8.4 Hz, 1H), 4.56-4.42 (m, 1H), 4.19-4.04 (m, 3H), 3.89 (s, 6H), 3.86-3.81 (m, 1H), 3.50-3.37 (m, 2H), 3.14-3.00 (m, 1H), 2.94-2.78 (m, 2H), 2.31-2.16 (m, 2H), 2.01-1.81 (m, 2H); LCMS (ESI) m/z: [M+H]$^+$=477.3.

Example 19: 4-(4-(3-(3,4-dimethoxyphenyl)-1,2,4-oxadiazol-5-yl)piperidine-1-carbonyl)-1-(3,4-dimethylphenyl)pyrrolidin-2-one Step 1: Preparation of 4-(4-(3-(3,4-dimethoxyphenyl)-1,2,4-oxadiazol-5-yl)piperidine-1-carbonyl)-1-(3,4-dimethylphenyl)pyrrolidin-2-one

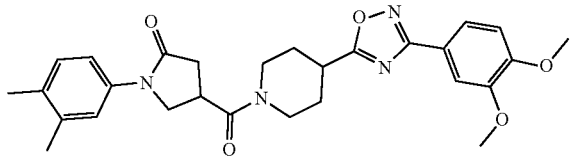

To a stirred solution of 1-[1-(3,4-dimethylphenyl)-5-oxo-pyrrolidine-3-carbonyl]piperidine-4-carboxylic acid (200 mg, 581 μmol) in N,N-dimethylformamide (1.5 mL) were added (2-(1H-benzotriazol-1-yl)-1,1,3,3-tetramethyluronium hexafluorophosphate) (220 mg, 581 μmol), N-ethyl-N-(propan-2-yl)propan-2-amine (225 mg, 1.74 mmol, 304 μL), and N-hydroxy-3,4-dimethoxy-benzamidine (125 mg, 639 μmol). The mixture was stirred at 20° C. for 12 h. The reaction mixture was diluted with water (5 mL) and extracted with ethyl acetate (10 mL×3). The combined organic layers were washed with saturated aqueous sodium chloride solution (10 mL×2), dried over anhydrous sodium sulfate, filtered, and concentrated under reduced pressure to give a residue. The residue was dissolved in N,N-dimethylformamide (2 mL) then heated at 120° C. for 5 h. The mixture was cooled to 25° C. then diluted with water (5 mL) and extracted with ethyl acetate (10 mL×3). The combined organic layers were washed with saturated aqueous sodium chloride solution (10 mL×2), dried over anhydrous sodium sulfate, filtered, and concentrated under reduced pressure to give a residue that was purified by prep-HPLC (column: Waters Xbridge 150×25 5 μm; mobile phase: [water (10 mM ammonium carbonate)-acetonitrile]; B %: 35%-65%, 12 min), to give 4-[4-[3-(3,4-dimethoxyphenyl)-1,2,4-oxadiazol-5-yl]piperidine-1-carbonyl]-1-(3,4-dimethylphenyl)pyrrolidin-2-one (7 mg, 15 μmol, 3%) as a pink solid. $^1$H NMR (400 MHz, METHANOL-d4) δ=7.66 (br d, J=8.2 Hz, 1H), 7.58 (s, 1H), 7.36 (s, 1H), 7.27 (br d, J=8.2 Hz, 1H), 7.16-7.04 (m, 2H), 4.49 (br d, J=8.4 Hz, 1H), 4.18-3.98 (m, 3H), 3.93-3.77 (m, 7H), 3.48-3.36 (m, 2H), 3.12-2.97 (m, 1H), 2.92-2.78 (m, 2H), 2.32-2.14 (m, 8H), 2.01-1.79 (m, 2H); LCMS (ESI) m/z: [M+H]$^+$=505.4.

Example 20: 1-(3,4-dimethylphenyl)-4-(4-(3-(4-methoxyphenyl)-1,2,4-oxadiazol-5-yl)piperidine-1-carbonyl)pyrrolidin-2-one

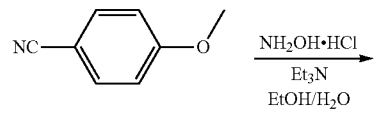

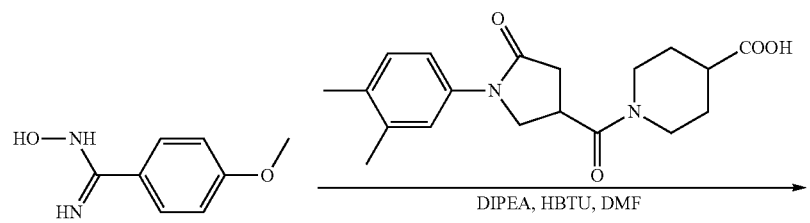

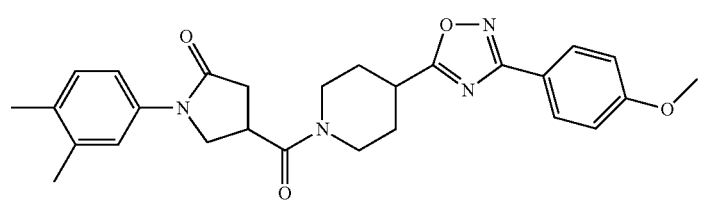

Step 1: Preparation of N-hydroxy-4-methoxybenzimidamide

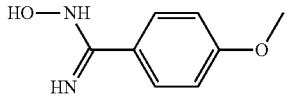

To a stirred solution of 4-methoxybenzonitrile (2.0 g, 15.02 mmol) in ethanol (20 mL) was added hydroxylamine hydrochloride (2.09 g, 30.0 mmol) and triethylamine (3.04 g, 30.0 mmol, 4.16 mL) and water (2 mL), then the mixture was heated to 70° C. for 15 h. The mixture was treated with water (20 mL) and extracted with dichloromethane (30 mL×3). The combined organic phases were washed with water (20 mL), saturated aqueous sodium chloride solution (20 mL), dried over anhydrous sodium sulfate, filtered, and concentrated to give crude N-hydroxy-4-methoxybenzimidamide (2.50 g) as a white solid, which was used in the next step directly. $^1$H NMR (400 MHz, Methanol-d4) δ 7.61-7.48 (m, 2H), 6.98-6.85 (m, 2H), 3.81 (s, 3H).

Step 2: Preparation of 1-(3,4-dimethylphenyl)-4-(4-(3-(4-methoxyphenyl)-1,2,4-oxadiazol-5-yl)piperidine-1-carbonyl)pyrrolidin-2-one

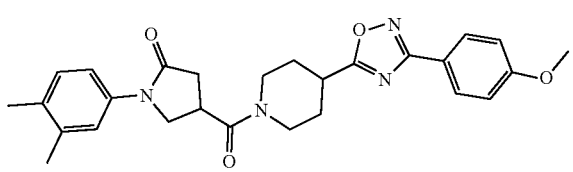

To a stirred solution of 1-(1-(3,4-dimethylphenyl)-5-oxopyrrolidine-3-carbonyl)piperidine-4-carboxylic acid (250 mg, 726 μmol) and N-hydroxy-4-methoxybenzimidamide (120 mg, 726 μmol) in N,N-dimethylformamide (3 mL) was added N-ethyl-N-(propan-2-yl)propan-2-amine (187 mg, 1.45 mmol, 253 μL) and (2-(1H-benzotriazol-1-yl)-1,1,3,3-tetramethyluronium hexafluorophosphate) (275 mg, 726 μmol), After 15 h at 15° C., the mixture was heated to 110° C. and stirred for 5 h. The reaction mixture was cooled and purified directly by prep-HPLC (column: Waters Xbridge 150×25 5 μm; mobile phase: [water (10 mM ammonium carbonate)-acetonitrile]; B %: 36%-66%, 12 min) to give 1-(3,4-dimethylphenyl)-4-(4-(3-(4-methoxyphenyl)-1,2,4-oxadiazol-5-yl)piperidine-1-carbonyl)pyrrolidin-2-one (101 mg, 213 μmol, 29%) as a light yellow solid. $^1$H NMR (400 MHz, Methanol-d4) δ 7.98 (d, J=7.5 Hz, 2H), 7.36 (s, 1H), 7.27 (d, J=7.9 Hz, 1H), 7.13 (d, J=8.4 Hz, 1H), 7.04 (d, J=8.4 Hz, 2H), 4.47 (m., 1H), 4.19-3.96 (m, 3H), 3.86 (s, 3H), 3.84-3.78 (m, 1H), 3.42 (m, 2H), 3.16-2.98 (m, 1H), 2.93-2.74 (m, 2H), 2.37-2.10 (m, 8H), 2.02-1.78 (m, 2H); LCMS (ESI) m/z: [M+H]$^+$=475.3.

Example 21: 1-(3,4-dimethylphenyl)-4-(4-(3-(3-methoxyphenyl)-1,2,4-oxadiazol-5-yl)piperidine-1-carbonyl)pyrrolidin-2-one

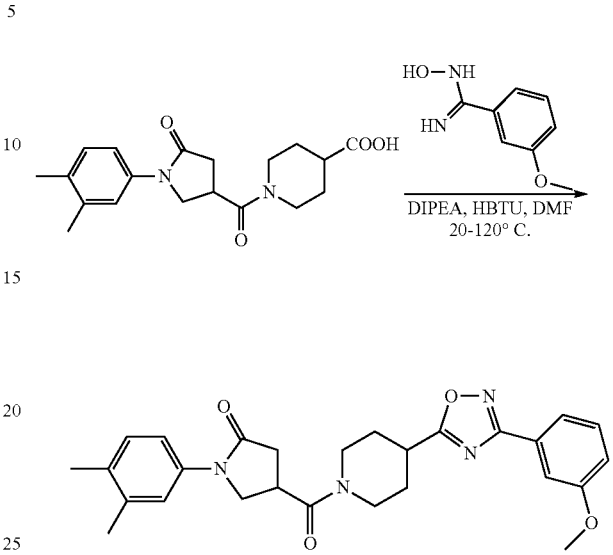

Step 1: Preparation of 1-(3,4-dimethylphenyl)-4-(4-(3-(3-methoxyphenyl)-1,2,4-oxadiazol-5-yl)piperidine-1-carbonyl)pyrrolidin-2-one

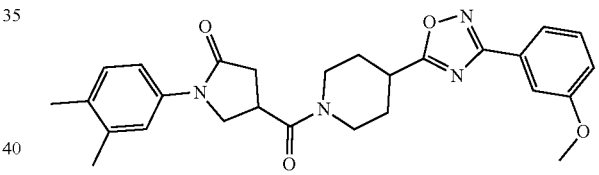

To a stirred solution of 1-(1-(3,4-dimethylphenyl)-5-oxopyrrolidine-3-carbonyl)piperidine-4-carboxylic acid (200 mg, 581 μmol) in N,N-dimethylformamide (3 mL) was added N-hydroxy-3-methoxybenzimidamide (96 mg, 581 μmol), (2-(1H-benzotriazol-1-yl)-1,1,3,3-tetramethyluronium hexafluorophosphate) (220 mg, 581 μmol) and N-ethyl-N-(propan-2-yl)propan-2-amine (225 mg, 1.74 mmol, 304 μL). The mixture was stirred at 20° C. for 2 h, then heated at 120° C. for 2 h. The reaction mixture was purified directly by prep-HPLC (column: Luna C8 100×30 5 μm; mobile phase: [water (10 mM ammonium carbonate)-acetonitrile]; B %: 40%-60%, 12 min) to give 1-(3,4-dimethylphenyl)-4-(4-(3-(3-methoxyphenyl)-1,2,4-oxadiazol-5-yl)piperidine-1-carbonyl)pyrrolidin-2-one (80 mg, 168 μmol, 29%) as a yellow solid. $^1$H NMR (400 MHz, CDCl$_3$) δ 7.72-7.67 (m, 1H), 7.62 (s, 1H), 7.45-7.37 (m, 2H), 7.30 (d, J=2.3 Hz, 1H), 7.15 (d, J=8.3 Hz, 1H), 7.11-7.06 (m, 1H), 4.61-4.47 (m, 1H), 4.30 (dd, J=7.3, 9.5 Hz, 1H), 3.91 (s, 5H), 3.64-3.54 (m, 1H), 3.46-3.30 (m, 2H), 3.21-3.05 (m, 1H), 3.03-2.92 (m, 1H), 2.89-2.79 (m, 1H), 2.28 (d, J=13.1 Hz, 8H), 2.10-1.90 (m, 2H); LCMS (ESI) m/z: [M+H]$^+$=475.3.

Example 22: N-(2-(4-(3-(3,4-dimethoxyphenyl)-1,2,4-oxadiazol-5-yl)piperidin-1-yl)-2-oxoethyl)-N-methylbenzamide

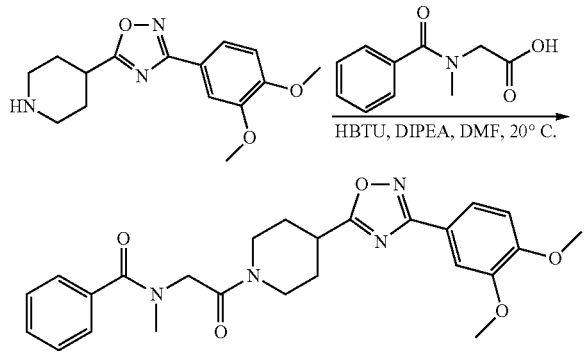

dimethylformamide (2 mL) was added (2-(1H-benzotriazol-1-yl)-1,1,3,3-tetramethyluronium hexafluorophosphate) (196 mg, 518 μmol) and N-ethyl-N-(propan-2-yl)propan-2-amine (201 mg, 1.56 mmol, 271 μL) and 2-[benzoyl(methyl)amino]acetic acid (105 mg, 544 μmol). The mixture was stirred at 20° C. for 5 h, then cooled and purified directly by prep-HPLC (column: Luna C8 100×30 5 μm; mobile phase: [water (10 mM ammonium carbonate)-acetonitrile]; B %: 30%-60%, 12 min) to give N-[2-[4-[3-(3,4-dimethoxyphenyl)-1,2,4-oxadiazol-5-yl]-1-piperidyl]-2-oxo-ethyl]-N-methyl-benzamide (133 mg, 282 μmol, 54%) as a white solid. $^1$H NMR (400 MHz, DMSO-$d_6$) δ=7.59 (dd, J=1.8, 8.4 Hz, 1H), 7.49-7.32 (m, 5H), 7.27 (br d, J=6.8 Hz, 1H), 7.16-7.08 (m, 1H), 4.44-4.24 (m, 2H), 4.21-4.03 (m, 1H), 4.02-3.88 (m, 1H), 3.88-3.74 (m, 6H), 3.56 (br d, J=13.7 Hz, 1H), 3.48-3.33 (m, 1H), 3.11-2.77 (m, 5H), 2.20-1.99 (m, 2H), 1.86 (br t, J=12.6 Hz, 1H), 1.74-1.48 (m, 2H), 1.43-1.26 (m, 1H); LCMS (ESI) m/z: [M+H]$^+$=465.3.

Example 23: N-(2-(4-(3-(3,4-dichlorophenyl)-1,2,4-oxadiazol-5-yl)piperidin-1-yl)-2-oxoethyl)benzamide

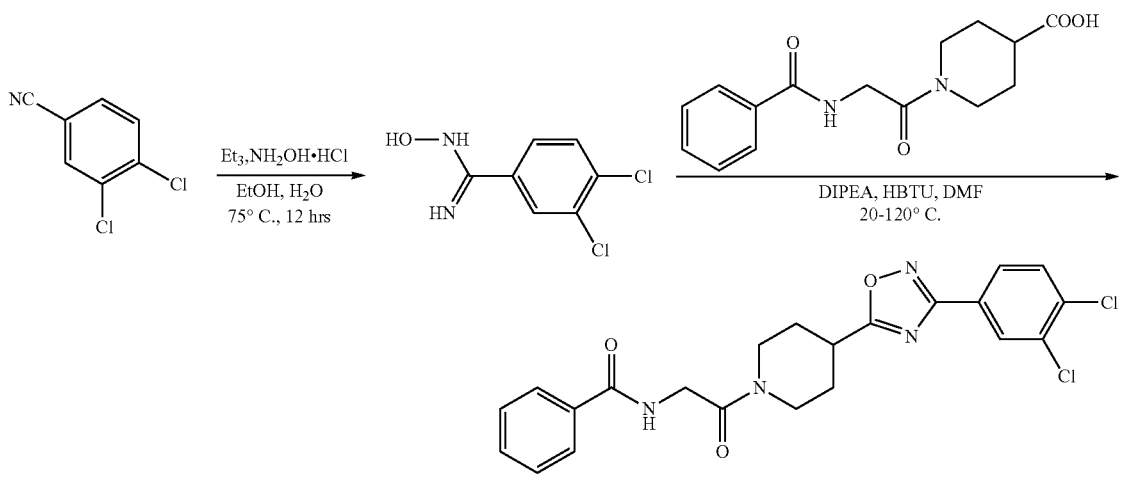

Step 1: Preparation of N-(2-(4-(3-(3,4-dimethoxyphenyl)-1,2,4-oxadiazol-5-yl)piperidin-1-yl)-2-oxoethyl)-N-methylbenzamide

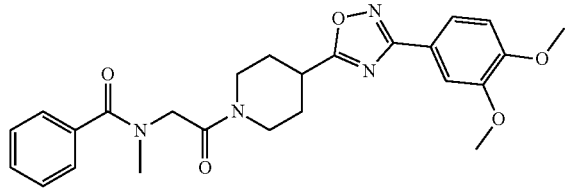 [SMILES: COc1ccc(-c2noc(C3CCN(C(=O)CN(C)C(=O)c4ccccc4)CC3)n2)cc1OC]

To a stirred solution of 3-(3,4-dimethoxyphenyl)-5-(4-piperidyl)-1,2,4-oxadiazole (150 mg, 518 μmol) in N,N-

Step 1: Preparation of 3,4-dichloro-N-hydroxybenzimidamide

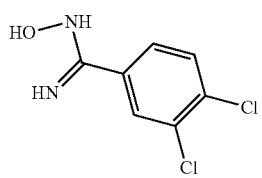 [SMILES: N=C(NO)c1ccc(Cl)c(Cl)c1]

To a stirred solution of 3,4-dichlorobenzonitrile (1.0 g, 5.81 mmol) in ethanol (20 mL) was added hydroxylamine hydrochloride (807 mg, 11.6 mmol), triethylamine (1.18 g, 11.6 mmol, 1.61 mL) and water (2 mL). The mixture was heated at 75° C. for 5 h, then cooled to 20° C. Water (20 mL) was added to the solution. The mixture was extracted with dichloromethane (40 mL×4). The combined organic layers were washed with saturated aqueous sodium chloride solution (20 mL) and dried over anhydrous sodium sulfate, then filtered and concentrated in vacuo to give 3,4-dichloro-N- hydroxybenzimidamide (1.20 g) as a white solid. This was used directly without further purification. ¹H NMR (400 MHz, DMSO-d₆) δ 9.86 (s, 1H), 7.87 (d, J=1.8 Hz, 1H), 7.69-7.58 (m, 2H), 5.95 (s, 2H).

Step 2: Preparation of N-(2-(4-(3-(3,4-dichlorophenyl)-1,2,4-oxadiazol-5-yl)piperidin-1-yl)-2-oxoethyl)benzamide

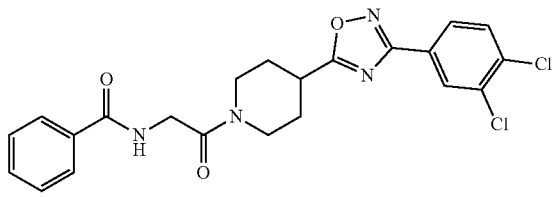 [SMILES: O=C(NCC(=O)N1CCC(c2nc(-c3ccc(Cl)c(Cl)c3)no2)CC1)c1ccccc1]

To a stirred solution of 1-(2-benzamidoacetyl)piperidine-4-carboxylic acid (200 mg, 688.92 µmol) in N,N-dimethylformamide (4 mL) was added 3,4-dichloro-N-hydroxybenzimidamide (169 mg, 826 µmol), (2-(1H-benzotriazol-1-yl)-1,1,3,3-tetramethyluronium hexafluorophosphate) (261 mg, 688.92 µmol) and N-ethyl-N-(propan-2-yl)propan-2-amine (267 mg, 2.07 mmol, 360 µL). The mixture was stirred at 20° C. for 2 h, then heated at 120° C. for 2 h. The reaction mixture cooled then purified directly by prep-HPLC (column: Waters Xbridge 150×2.5 mm 5 µm; mobile phase: [water (10 mM ammonium carbonate)-acetonitrile]; B %: 40%-70%, 12 min) to give N-(2-(4-(3-(3,4-dichlorophenyl)-1,2,4-oxadiazol-5-yl)piperidin-1-yl)-2-oxoethyl)benzamide (92 mg, 201 µmol, 29%) as a white solid. ¹H NMR (400 MHz, CDCl₃) δ 8.14-8.09 (m, 1H), 7.85 (dd, J=2.0, 8.2 Hz, 1H), 7.78 (d, J=7.1 Hz, 2H), 7.39 (s, 4H), 7.25 (br. s., 1H), 4.43 (d, J=13.7 Hz, 1H), 4.24 (d, J=3.5 Hz, 2H), 3.84 (d, J=14.1 Hz, 1H), 3.33-3.22 (m, 2H), 3.14-3.03 (m, 1H), 2.23-2.13 (m, 2H), 1.99-1.86 (m, 2H); LCMS (ESI) m/z: [M+H]⁺=459.1.

Example 24: N-(2-(4-(3-(3,4-difluorophenyl)-1,2,4-oxadiazol-5-yl)piperidin-1-yl)-2-oxoethyl)benzamide Step 1: Preparation of 3,4-difluoro-N-hydroxybenzimidamide

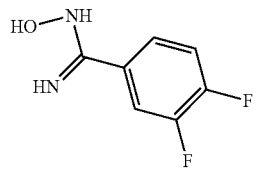 [SMILES: N=C(NO)c1ccc(F)c(F)c1]

To a stirred solution of 3,4-difluorobenzonitrile (1.0 g, 7.19 mmol) in ethanol (20 mL) were added hydroxylamine hydrochloride (999 mg, 14.4 mmol), triethylamine (1.46 g, 14.4 mmol, 1.99 mL), and water (2 mL). The mixture was heated at 75° C. for 2 h. After cooling to 20° C., water (20 mL) was added to the solution. The mixture was extracted with dichloromethane (30 mL×4). The combined organic layers were washed with saturated aqueous sodium chloride solution (20 mL), dried over anhydrous sodium sulfate, then filtered, and concentrated in vacuo to give 3,4-difluoro-N-hydroxybenzimidamide (1.24 g) as a white solid. This was used directly without further purification. ¹H NMR (400 MHz, DMSO-d6) δ 9.79 (s, 1H), 7.68 (ddd, J=2.0, 8.0, 12.2 Hz, 1H), 7.55 (br. s., 1H), 7.50-7.39 (m, 1H), 5.92 (br. s., 2H).

Step 2: Preparation of N-(2-(4-(3-(3,4-difluorophenyl)-1,2,4-oxadiazol-5-yl)piperidin-1-yl)-2-oxoethyl)benzamide

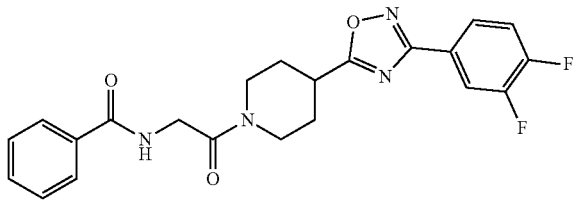 [SMILES: O=C(NCC(=O)N1CCC(c2nc(-c3ccc(F)c(F)c3)no2)CC1)c1ccccc1]

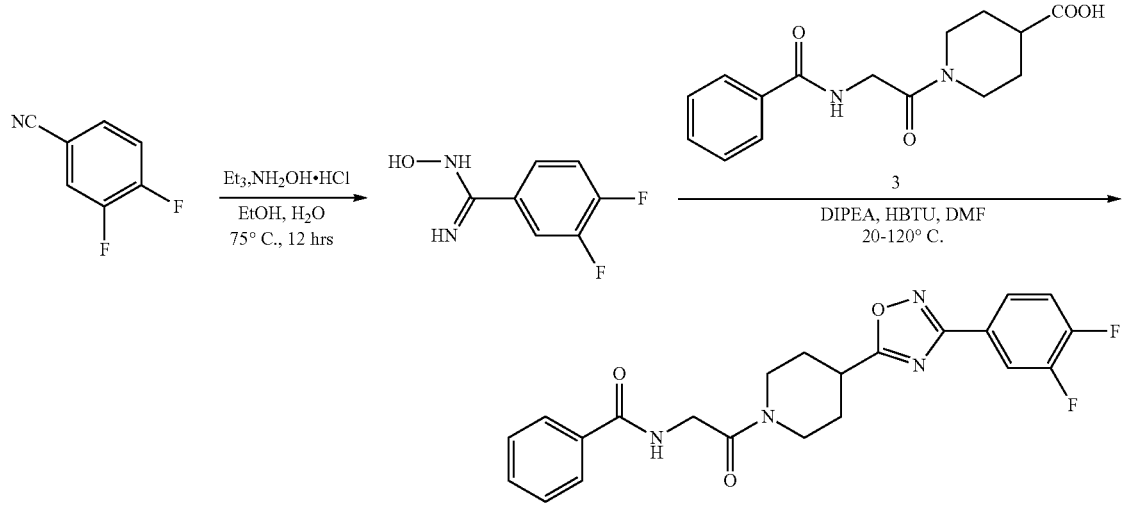

To a stirred solution of 1-(2-benzamidoacetyl)piperidine-4-carboxylic acid (120 mg, 413 µmol) in N,N-dimethylformamide (4 mL) were added 3,4-difluoro-N-hydroxybenzimidamide (85 mg, 496 µmol), (2-(1H-benzotriazol-1-yl)-1,1,3,3-tetramethyluronium hexafluorophosphate) (156 mg, 413 µmol), and N-ethyl-N-(propan-2-yl)propan-2-amine (160 mg, 1.24 mmol, 216 µL). The mixture was stirred at 20° C. for 2 h, then heated at 120° C. for 2 h. The reaction mixture was cooled then purified directly by prep-HPLC (column: Luna C8 100×30 5 µm; mobile phase: [water (10 mM ammonium carbonate)-acetonitrile]; B %: 35%-60%, 12 min) to give N-(2-(4-(3-(3,4-difluorophenyl)-1,2,4-oxadiazol-5-yl)piperidin-1-yl)-2-oxoethyl)benzamide (50 mg, 118 µmol, 28%) as a white solid. $^1$H NMR (400 MHz, CDCl$_3$) δ 7.78 (d, J=7.1 Hz, 4H), 7.44 (d, J=7.1 Hz, 1H), 7.42-7.35 (m, 2H), 7.23 (d, J=8.4 Hz, 2H), 4.43 (d, J=13.7 Hz, 1H), 4.23 (d, J=4.0 Hz, 2H), 3.84 (d, J=13.7 Hz, 1H), 3.32-3.21 (m, 2H), 3.13-3.03 (m, 1H), 2.23-2.12 (m, 2H), 1.99-1.84 (m, 2H); LCMS (ESI) m/z: [M+H]$^+$=427.2.

Example 25: 2-chloro-N-(2-(4-(3-(3,4-dimethoxyphenyl)-1,2,4-oxadiazol-5-yl)piperidin-1-yl)-2-oxoethyl)benzamide

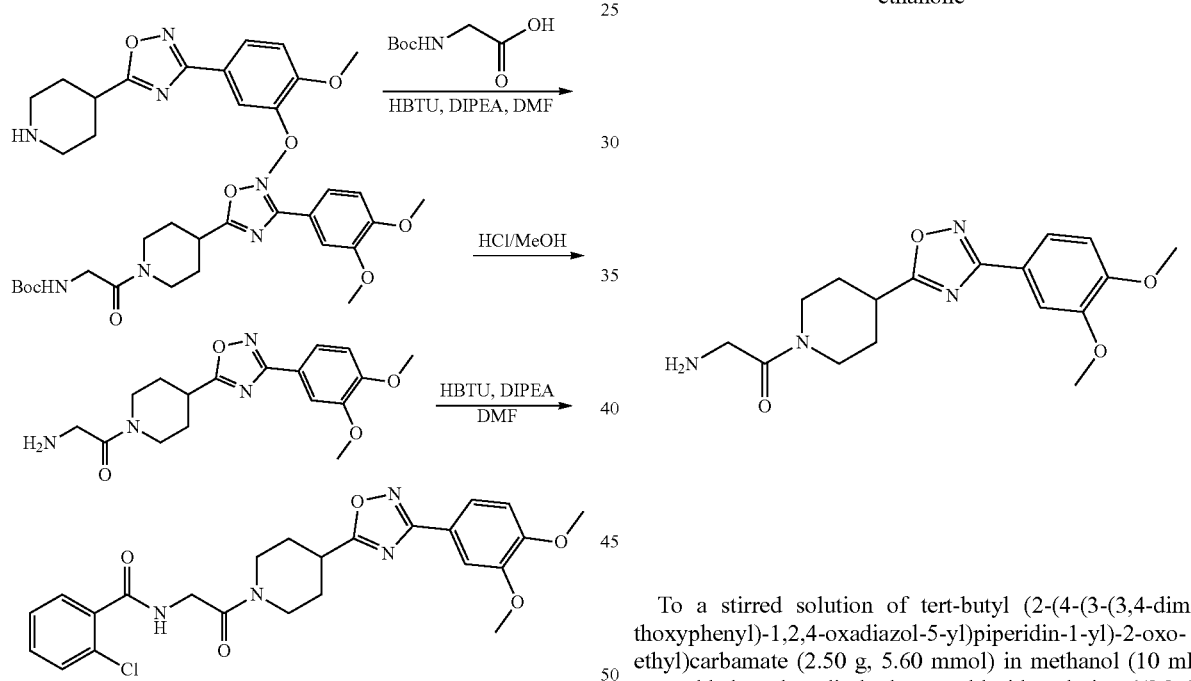

Step 1: Preparation of tert-butyl (2-(4-(3-(3,4-dimethoxyphenyl)-1,2,4-oxadiazol-5-yl)piperidin-1-yl)-2-oxoethyl)carbamate

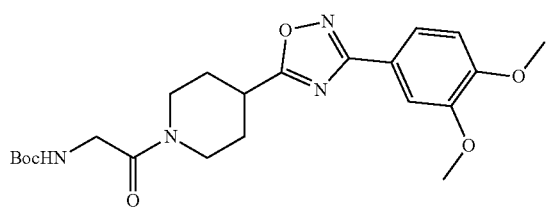 [SMILES: COc1ccc(-c2noc(C3CCN(C(=O)CNC(=O)OC(C)(C)C)CC3)n2)cc1OC]

To a stirred solution of 3-(3,4-dimethoxyphenyl)-5-(piperidin-4-yl)-1,2,4-oxadiazole (2.0 g, 6.91 mmol) in N,N-dimethylformamide (20 mL) was added 2-(tert-butoxycarbonylamino)acetic acid (1.21 g, 6.91 mmol), (2-(1H-benzotriazol-1-yl)-1,1,3,3-tetramethyluronium hexafluorophosphate (2.62 g, 6.91 mmol) and N-ethyl-N-(propan-2-yl)propan-2-amine (2.68 g, 20.7 mmol, 3.62 mL). The mixture was stirred at 15° C. for 2 h. The reaction mixture was quenched by addition of water (20 mL), then the mixture was extracted with ethyl acetate (60 mL×4). The combined organic phases were washed with saturated aqueous sodium chloride solution (20 mL), dried over anhydrous sodium sulfate, filtered, and concentrated to give a crude residue. Purification by chromatography (silica, petroleum ether:ethyl acetate=5:1 to 1:1) gave tert-butyl (2-(4-(3-(3,4-dimethoxyphenyl)-1,2,4-oxadiazol-5-yl)piperidin-1-yl)-2-oxoethyl)carbamate (2.60 g, 5.82 mmol, 84%) as a brown solid that was used directly without further purification. LCMS (ESI) m/z: [M+H]$^+$=447.2.

Step 2: Preparation of 2-amino-1-(4-(3-(3,4-dimethoxyphenyl)-1,2,4-oxadiazol-5-yl)piperidin-1-yl)ethanone To a stirred solution of tert-butyl (2-(4-(3-(3,4-dimethoxyphenyl)-1,2,4-oxadiazol-5-yl)piperidin-1-yl)-2-oxoethyl)carbamate (2.50 g, 5.60 mmol) in methanol (10 mL) was added methanolic hydrogen chloride solution (4M, 30 mL). The mixture was stirred at 20° C. for 1 h. The reaction mixture was concentrated to give crude product. A part of crude product (0.1 g) was purified by prep-HPLC (column: Waters Xbridge 150×2.5 mm 5 µm; mobile phase: [water (10 mM ammonium carbonate)-acetonitrile]; B %: 20%-50%, 12 min) to give 2-amino-1-(4-(3-(3,4-dimethoxyphenyl)-1,2,4-oxadiazol-5-yl)piperidin-1-yl)ethanone (32 mg) for analysis. The remaining crude 2-amino-1-(4-(3-(3,4-dimethoxyphenyl)-1,2,4-oxadiazol-5-yl)piperidin-1-yl)ethanone (1.90 g, 5.49 mmol, 98%), obtained as a brown solid, was used directly. $^1$H NMR (400 MHz, CDCl$_3$) δ 7.73-7.67 (m, 1H), 7.58 (d, J=1.5 Hz, 1H), 6.98 (d, J=8.4 Hz, 1H), 4.54 (d, J=12.2 Hz, 1H), 3.98 (d, J=7.2 Hz, 6H), 3.84 (d, J=12.0 Hz, 1H), 3.54 (s, 2H), 3.34-3.21 (m, 2H), 3.08 (d, J=12.3 Hz, 1H), 2.21 (d, J=13.1 Hz, 2H), 1.98 (d, J=9.4 Hz, 2H); LCMS (ESI) m/z: [M+H]$^+$=347.1.

Step 3: Preparation of 2-chloro-N-(2-(4-(3-(3,4-dimethoxyphenyl)-1,2,4-oxadiazol-5-yl)piperidin-1-yl)-2-oxoethyl)benzamide

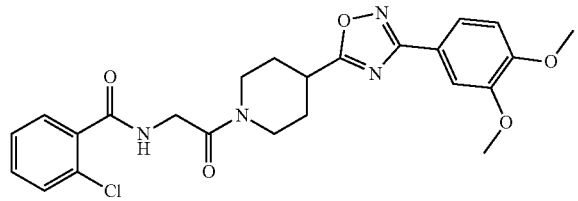 [SMILES: COc1ccc(-c2noc(C3CCN(C(=O)CNC(=O)c4ccccc4Cl)CC3)n2)cc1OC]

To a stirred solution of 2-amino-1-(4-(3-(3,4-dimethoxyphenyl)-1,2,4-oxadiazol-5-yl)piperidin-1-yl)ethanone (185 mg, 537 µmol) in N,N-dimethylformamide (3 mL) was added 2-chlorobenzoic acid (70 mg, 447 µmol), (2-(1H-benzotriazol-1-yl)-1,1,3,3-tetramethyluronium hexafluorophosphate) (169 mg, 447 µmol), and N-ethyl-N-(propan-2-yl)propan-2-amine (231 mg, 1.79 mmol, 312 µL). The mixture was stirred at 20° C. for 2 h, then purified directly by prep-HPLC (column: Waters Xbridge 150×2.5 mm 5 µm; mobile phase: [water (10 mM ammonium carbonate)-acetonitrile]; B %: 26%-56%, 12 min) to give 2-chloro-N-(2-(4-(3-(3,4-dimethoxyphenyl)-1,2,4-oxadiazol-5-yl)piperidin-1-yl)-2-oxoethyl)benzamide (124 mg, 256 µmol, 57%) as a pink solid. $^1$H NMR (400 MHz, CDCl$_3$) δ 7.72 (ddd, J=1.9, 6.3, 7.9 Hz, 2H), 7.59 (d, J=1.9 Hz, 1H), 7.49-7.33 (m, 4H), 6.98 (d, J=8.4 Hz, 1H), 4.52 (d, J=13.6 Hz, 1H), 4.36 (d, J=4.0 Hz, 2H), 3.99 (d, J=7.8 Hz, 6H), 3.92 (d, J=13.8 Hz, 1H), 3.41-3.30 (m, 2H), 3.16 (t, J=10.9 Hz, 1H), 2.33-2.21 (m, 2H), 2.11-1.94 (m, 2H); LCMS (ESI) m/z: [M+H]$^+$=485.2.

Example 26: 3-chloro-N-(2-(4-(3-(3,4-dimethoxyphenyl)-1,2,4-oxadiazol-5-yl)piperidin-1-yl)-2-oxoethyl)benzamide

Step 1: Preparation of 3-chloro-N-(2-(4-(3-(3,4-dimethoxyphenyl)-1,2,4-oxadiazol-5-yl)piperidin-1-yl)-2-oxoethyl)benzamide

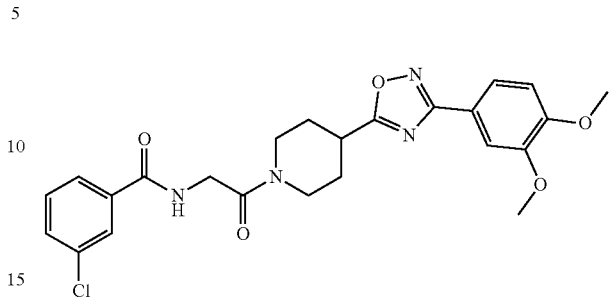

To a stirred solution of 2-amino-1-(4-(3-(3,4-dimethoxyphenyl)-1,2,4-oxadiazol-5-yl)piperidin-1-yl)ethanone (185 mg, 537 µmol) in N,N-dimethylformamide (3 mL) were added 3-chlorobenzoic acid (70 mg, 447 µmol), (2-(1H-benzotriazol-1-yl)-1,1,3,3-tetramethyluronium hexafluorophosphate) (169 mg, 447 µmol), and N-ethyl-N-(propan-2-yl)propan-2-amine (231 mg, 1.79 mmol, 312 µL). The mixture was stirred at 20° C. for 2 h. The reaction mixture was purified directly by prep-HPLC (column: Waters Xbridge 150×2.5 mm 5 µm; mobile phase: [water (10 mM ammonium carbonate)-acetonitrile]; B %: 26%-56%, 12 min) to give 3-chloro-N-(2-(4-(3-(3,4-dimethoxyphenyl)-1,2,4-oxadiazol-5-yl)piperidin-1-yl)-2-oxoethyl)benzamide (126 mg, 261 µmol, 58%) as a white solid. $^1$H NMR (400 MHz, CDCl$_3$) δ 7.89-7.86 (m, 1H), 7.72 (d, J=2.0 Hz, 2H), 7.59 (d, J=1.9 Hz, 1H), 7.54-7.50 (m, 1H), 7.45-7.39 (m, 1H), 7.34 (br. s., 1H), 6.98 (d, J=8.5 Hz, 1H), 4.53 (d, J=14.3 Hz, 1H), 4.31 (d, J=3.9 Hz, 2H), 3.98 (d, J=7.4 Hz, 6H), 3.96-3.87 (m, 1H), 3.41-3.30 (m, 2H), 3.18 (t, J=10.9 Hz, 1H), 2.33-2.22 (m, 2H), 2.10-1.94 (m, 2H); LCMS (ESI) m/z: [M+H]$^+$=485.3.

Example 27: 4-chloro-N-(2-(4-(3-(3,4-dimethoxyphenyl)-1,2,4-oxadiazol-5-yl)piperidin-1-yl)-2-oxoethyl)benzamide

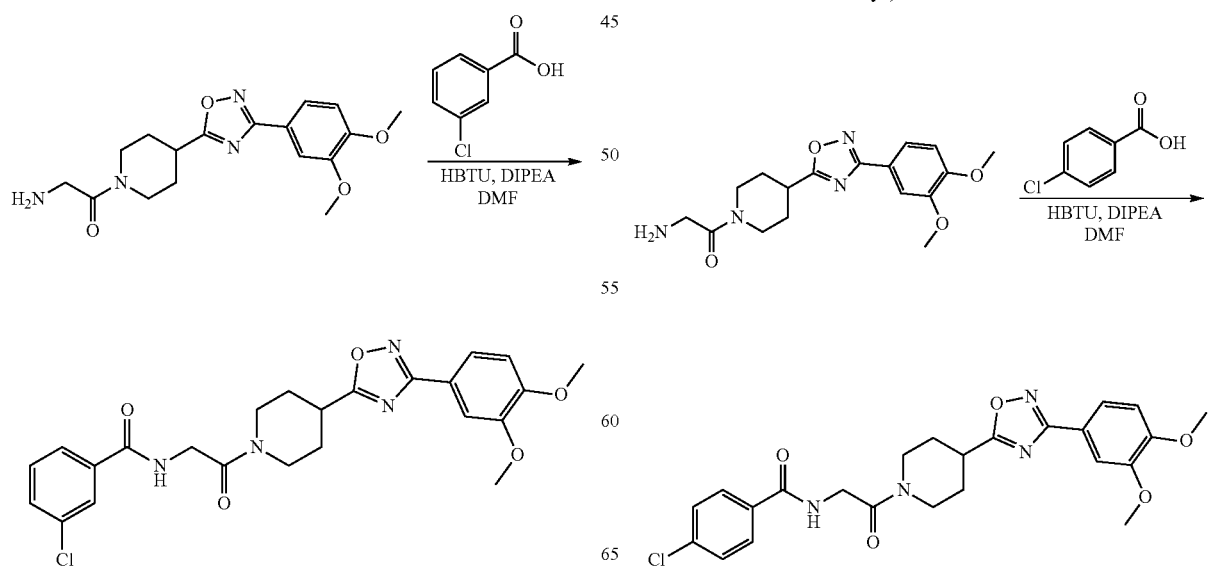

Step 1: Preparation of 4-chloro-N-(2-(4-(3-(3,4-dimethoxyphenyl)-1,2,4-oxadiazol-5-yl)piperidin-1-yl)-2-oxoethyl)benzamide

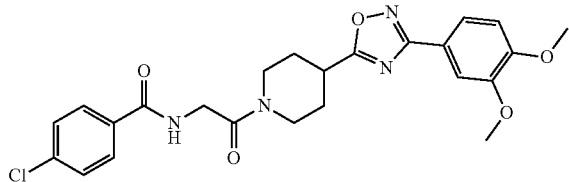 [SMILES: COc1ccc(-c2noc(C3CCN(C(=O)CNC(=O)c4ccc(Cl)cc4)CC3)n2)cc1OC]

To a stirred solution of 2-amino-1-(4-(3-(3,4-dimethoxyphenyl)-1,2,4-oxadiazol-5-yl)piperidin-1-yl)ethanone (185 mg, 536.5 μmol) in N,N-dimethylformamide (3 mL) were added 4-chlorobenzoic acid (70 mg, 447 μmol), (2-(1H-benzotriazol-1-yl)-1,1,3,3-tetramethyluronium hexafluorophosphate) (169 mg, 447 μmol) and N-ethyl-N-(propan-2-yl)propan-2-amine (231 mg, 1.79 mmol, 312 μL). The mixture was stirred at 20° C. for 2 h. The reaction mixture was purified directly by prep-HPLC (column: Waters Xbridge 150×2.5 mm 5 μm; mobile phase: [water (10 mM ammonium carbonate)-acetonitrile]; B %: 30%-60%, 12 min) to give 4-chloro-N-(2-(4-(3-(3,4-dimethoxyphenyl)-1,2,4-oxadiazol-5-yl)piperidin-1-yl)-2-oxoethyl)benzamide (144 mg, 294 μmol, 66%) as a white solid. $^1$H NMR (400 MHz, CDCl$_3$) δ 7.82 (d, J=8.5 Hz, 2H), 7.71 (dd, J=1, 9, 8.3 Hz, 1H), 7.59 (d, J=1.8 Hz, 1H), 7.45 (d, J=8.5 Hz, 2H), 7.33 (br, s., 1H), 6.98 (d, J=8.4 Hz, 1H), 4.52 (d, J=14.2 Hz, 1H), 4.31 (d, J=3.9 Hz, 2H), 3.98 (d, J=7.3 Hz, 6H), 3.92 (d, J=13.7 Hz, 1H), 3.41-3.30 (m, 2H), 3.17 (t, J=10.7 Hz, 1H), 2.34-2.21 (m, 2H), 2.10-1.94 (m, 2H); LCMS (ESI) m/z: [M+H]$^+$=485.2.

Example 28: N-(1-(4-(3-(3,4-dimethoxyphenyl)-1,2,4-oxadiazol-5-yl)piperidin-1-yl)-1-oxopropan-2-yl)benzamide

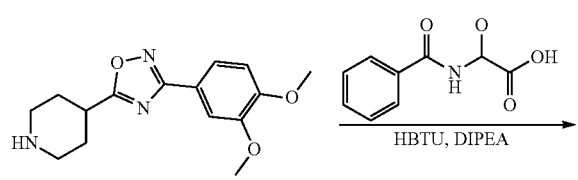

Step 1: Preparation of N-(1-(4-(3-(3,4-dimethoxyphenyl)-1,2,4-oxadiazol-5-yl)piperidin-1-yl)-1-oxopropan-2-yl)benzamide

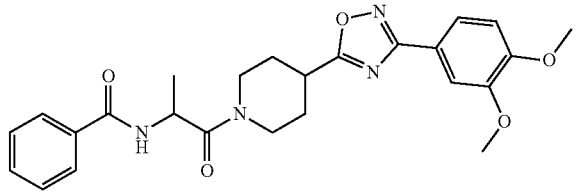 [SMILES: COc1ccc(-c2noc(C3CCN(C(=O)C(C)NC(=O)c4ccccc4)CC3)n2)cc1OC]

To a stirred solution of 3-(3,4-dimethoxyphenyl)-5-(4-piperidyl)-1,2,4-oxadiazole (150 mg, 518 μmol) in N,N-dimethylformamide (2 mL) were added (2-(1H-benzotriazol-1-yl)-1,1,3,3-tetramethyluronium hexafluorophosphate) (196 mg, 518 μmol), N-ethyl-N-(propan-2-yl)propan-2-amine (201 mg, 1.56 mmol, 271 μL), and 2-benzamidopropanoic acid (105 mg, 544 μmol). The mixture was stirred at 20° C. for 7 h, then the crude product was purified directly by prep-HPLC (column: Luna C8 100×30 5 μm; mobile phase: [water (10 mM ammonium carbonate)-acetonitrile; B %: 35%-60%, 12 min] to give N-[2-[4-[3-(3,4-dimethoxyphenyl)-1,2,4-oxadiazol-5-yl]-1-piperidyl]-1-methyl-2-oxo-ethyl]benzamide (52 mg, 112 μmol, 22%) as a white solid. $^1$H NMR (400 MHz, DMSO-d6) δ=8.63 (br dd, J=7.3, 16.1 Hz, 1H), 7.88 (br d, J=7.3 Hz, 2H), 7.66-7.34 (m, 5H), 7.11 (br d, J=7.9 Hz, 1H), 4.97 (br d, J=6.0 Hz, 1H), 4.45-4.22 (m, 1H), 4.08-3.94 (m, 1H), 3.82 (s, 6H), 3.42 (br t, J=10.7 Hz, 1H), 3.29-3.21 (m, 1H), 3.00-2.80 (m, 1H), 2.09 (br d, J=11.9 Hz, 2H), 1.87-1.56 (m, 1H), 1.29 (s, 3H); LCMS (ESI) m/z: [M+H]$^+$=465.3.

Example 29: N-(1-(4-(3-(3,4-dimethoxyphenyl)-1,2,4-oxadiazol-5-yl)piperidin-1-yl)-2-methyl-1-oxopropan-2-yl)benzamide

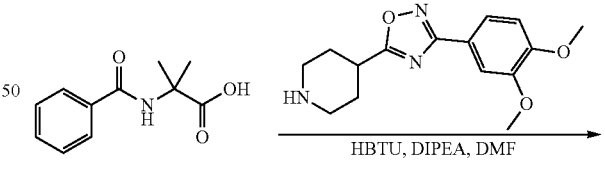

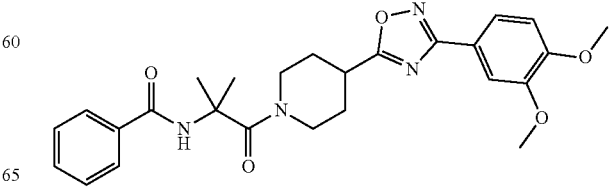

Step 1: Preparation of N-(1-(4-(3-(3,4-dimethoxyphenyl)-1,2,4-oxadiazol-5-yl)piperidin-1-yl)-2-methyl-1-oxopropan-2-yl)benzamide

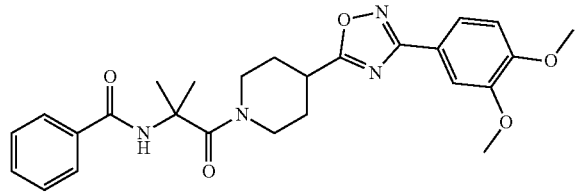 [SMILES: COc1ccc(-c2noc(C3CCN(C(=O)C(C)(C)NC(=O)c4ccccc4)CC3)n2)cc1OC]

To a stirred solution of 3-(3,4-dimethoxyphenyl)-5-(4-piperidyl)-1,2,4-oxadiazole (150 mg, 518 μmol) in N,N-dimethylformamide (2 mL) was added (2-(1H-benzotriazol-1-yl)-1,1,3,3-tetramethyluronium hexafluorophosphate) (196 mg, 518 μmol), N-ethyl-N-(propan-2-yl)propan-2-amine (201 mg, 1.56 mmol, 271 μL) and 2-benzamido-2-methyl-propanoic acid (112 mg, 544 μmol). The mixture was stirred at 20° C. for 5 h. The crude product was purified directly by prep-HPLC (column: Waters Xbridge 150×25 5 μm; mobile phase: [water (10 mM ammonium carbonate)-acetonitrile]; B %: 27%-57%, 12 min) to give N-[2-[4-[3-(3,4-dimethoxyphenyl)-1,2,4-oxadiazol-5-yl]-1-piperidyl]-1,1-dimethyl-2-oxo-ethyl]benzamide (47 mg, 99 μmol, 19%) as a pale yellow solid. $^1$H NMR (400 MHz, METHANOL-d4) δ=7.88-7.81 (m, 2H), 7.62 (dd, J=2.0, 8.4 Hz, 1H), 7.57-7.51 (m, 2H), 7.49-7.42 (m, 2H), 7.06 (d, J=8.4 Hz, 1H), 4.61-4.45 (m, 2H), 3.88 (d, J=5.1 Hz, 6H), 3.13 (s, 3H), 2.08 (br s, 2H), 1.90-1.74 (m, 2H), 1.60 (s, 6H); LCMS (ESI) m/z: [M+H]$^+$=477.1.

Example 30: 2-(benzylamino)-1-(4-(3-(3,4-dimethoxyphenyl)-1,2,4-oxadiazol-5-yl)piperidin-1-yl)ethanone Step 1: Preparation of 2-(benzylamino)-1-(4-(3-(3,4-dimethoxyphenyl)-1,2,4-oxadiazol-5-yl)piperidin-1-yl)ethanone

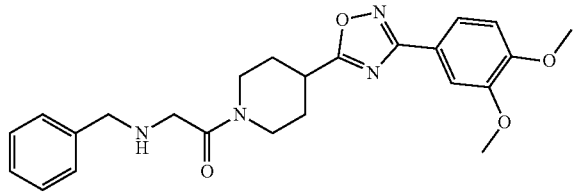 [SMILES: COc1ccc(-c2noc(C3CCN(C(=O)CNCc4ccccc4)CC3)n2)cc1OC]

To a stirred solution of 3-(3,4-dimethoxyphenyl)-5-(4-piperidyl)-1,2,4-oxadiazole (150 mg, 518 μmol) in N,N-dimethylformamide (1.50 mL) were added (2-(1H-benzotriazol-1-yl)-1,1,3,3-tetramethyluronium hexafluorophosphate) (196 mg, 518 μmol), N-ethyl-N-(propan-2-yl)propan-2-amine (201 mg, 1.56 mmol, 271 μL), and 2-(benzylamino)acetic acid (89 mg, 544 μmol). The mixture was stirred at 20° C. for 16 h and filtered, and the crude filtrate was purified directly by prep-HPLC (column: Luna C8 100×30 5 μm; mobile phase: [water (10 mM ammonium carbonate)-acetonitrile]; B %: 30%-60%, 12 min) to give 2-(benzylamino)-1-[4-[3-(3,4-dimethoxyphenyl)-1,2,4-oxadiazol-5-yl]-1-piperidyl]ethanone (48 mg, 110 μmol, 21%) as a yellow solid. $^1$H NMR (400 MHz, METHANOL-d4) δ=7.65 (dd, J=1.8, 8.2 Hz, 1H), 7.57 (d, J=1.8 Hz, 1H), 7.40-7.30 (m, 4H), 7.28-7.22 (m, 1H), 7.06 (d, J=8.4 Hz, 1H), 4.45 (br d, J=13.7 Hz, 1H), 3.94-3.83 (m, 7H), 3.78 (s, 2H), 3.57-3.44 (m, 2H), 3.40-3.33 (m, 1H), 3.27-3.20 (m, 1H), 3.01 (t, J=11.2 Hz, 1H), 2.17 (dd, J=2.8, 13.3 Hz, 2H), 1.93-1.73 (m, 2H); LCMS (ESI) m/z: [M+H]$^+$=437.3.

Example 31: 2-(benzyloxy)-1-(4-(3-(3,4-dimethoxyphenyl)-1,2,4-oxadiazol-5-yl)piperidin-1-yl)ethanone

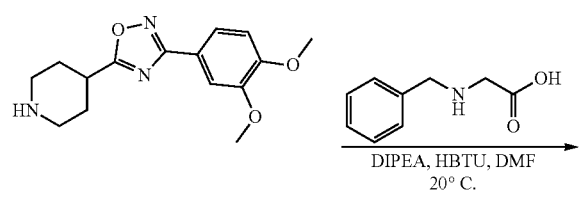

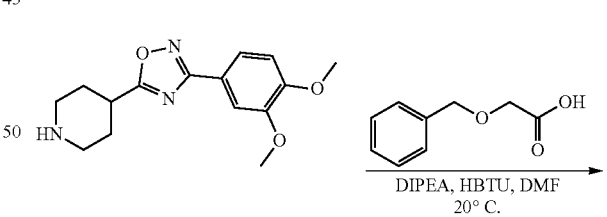

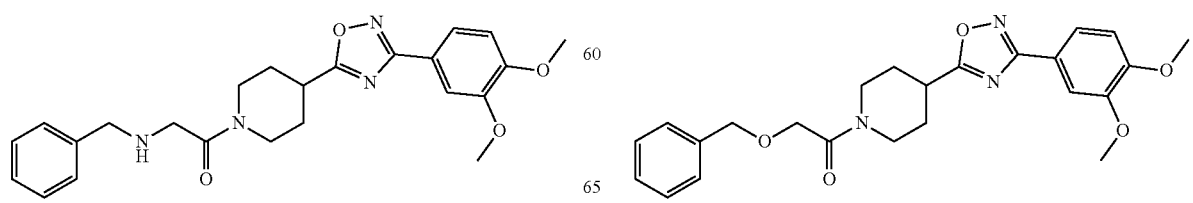

Step 1: Preparation of 2-(benzyloxy)-1-(4-(3-(3,4-dimethoxyphenyl)-1,2,4-oxadiazol-5-yl)piperidin-1-yl)ethanone

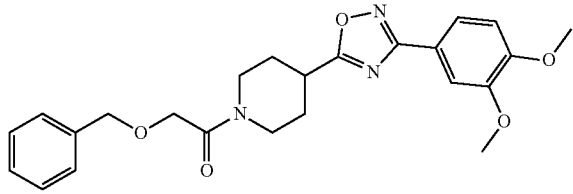 [SMILES: COc1ccc(-c2noc(C3CCN(C(=O)COCc4ccccc4)CC3)n2)cc1OC]

To a stirred solution of 3-(3,4-dimethoxyphenyl)-5-(4-piperidyl)-1,2,4-oxadiazole (150 mg, 518 μmol) in N,N-dimethylformamide (2 mL) were added (2-(1H-benzotriazol-1-yl)-1,1,3,3-tetramethyluronium hexafluorophosphate) (196 mg, 518 μmol), N-ethyl-N-(propan-2-yl)propan-2-amine (201 mg, 1.56 mmol, 271 μL), and 2-benzyloxyacetic acid (90 mg, 544 μmol, 77 μL). The mixture was stirred at 20° C. for 5 h. The crude product was purified directly by prep-HPLC (column: Waters Xbridge 150×25 5 μm; mobile phase: [water (10 mM ammonium carbonate)-acetonitrile]; B %: 32%-62%, 12 min) to give 2-benzyloxy-1-[4-[3-(3,4-dimethoxyphenyl)-1,2,4-oxadiazol-5-yl]-1-piperidyl]ethanone (68 mg, 157 μmol, 30%) as a white solid. $^1$H NMR (400 MHz, DMSO-d6) δ=7.60 (dd, J=1.9, 8.3 Hz, 1H), 7.48 (d, J=1.9 Hz, 1H), 7.40-7.35 (m, 4H), 7.34-7.26 (m, 1H), 7.14 (d, J=8.4 Hz, 1H), 4.54 (s, 2H), 4.33 (br d, J=13.2 Hz, 1H), 4.25 (br d, J=7.8 Hz, 2H), 3.93-3.78 (m, 7H), 3.43 (tt, J=3.9, 11.0 Hz, 1H), 3.22 (br t, J=11.7 Hz, 1H), 2.90 (br t, J=11.7 Hz, 1H), 2.17-2.04 (m, 2H), 1.88-1.59 (m, 2H); LCMS (ESI) m/z: [M+H]$^+$=438.3.

Example 32: N-[2-[4-[3-(3,4-dimethoxyphenyl)-1,2,4-oxadiazol-5-yl]-1-piperidyl]ethyl]benzamide

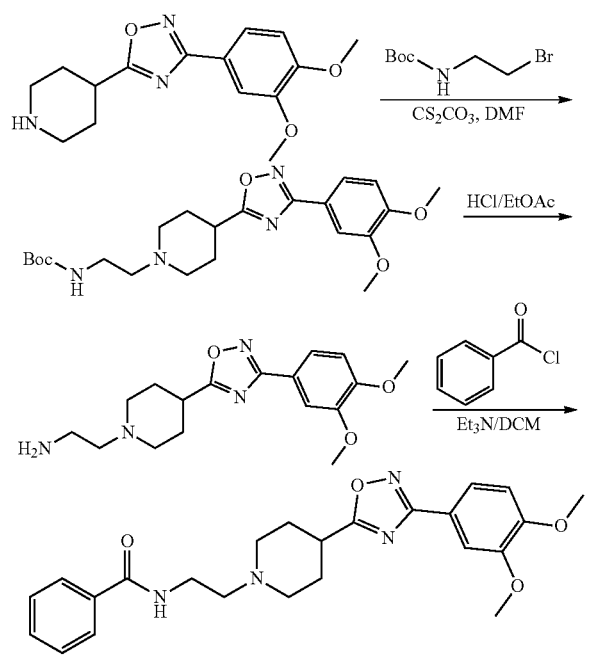

Step 1: Preparation of tert-butyl (2-(4-(3-(3,4-dimethoxyphenyl)-1,2,4-oxadiazol-5-yl)piperidin-1-yl)ethyl)carbamate

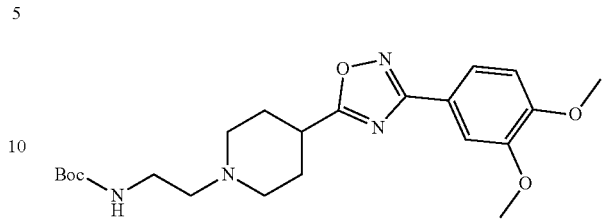

To a stirred solution of 3-(3,4-dimethoxyphenyl)-5-(4-piperidyl)-1,2,4-oxadiazole (750 mg, 2.59 mmol) in N,N-dimethylformamide (1 mL) were added cesium carbonate (844 mg, 2.59 mmol) and tert-butyl N-(2-bromoethyl)carbamate (871 mg, 3.89 mmol). The mixture was stirred at 50° C. for 16 h. The reaction mixture was cooled then extracted with ethyl acetate (5 mL×2). The combined organic extracts were washed with saturated aqueous sodium chloride solution (10 mL), dried over anhydrous sodium sulfate, filtered, and concentrated under reduced pressure to give tert-butyl N-[2-[4-[3-(3,4-dimethoxyphenyl)-1,2,4-oxadiazol-5-yl]-1-piperidyl]ethyl]carbamate (1.30 g) which was used directly without further purification. LCMS (ESI) m/z=433.3 [M+H]$^+$.

Step 2: Preparation of 2-(4-(3-(3,4-dimethoxyphenyl)-1,2,4-oxadiazol-5-yl)piperidin-1-yl)ethanamine

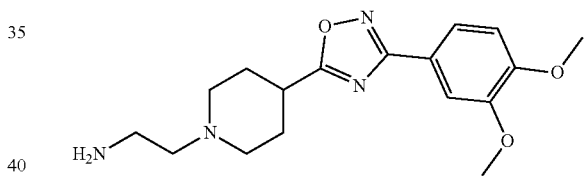

A solution of tert-butyl N-[2-[4-[3-(3,4-dimethoxyphenyl)-1,2,4-oxadiazol-5-yl]-1-piperidyl]ethyl]carbamate (1.0 g, 2.31 mmol) in hydrochloric acid/ethyl acetate (4M, 25 mL) was stirred at 25° C. for 30 mins. The reaction mixture was concentrated under reduced pressure to give 2-[4-[3-(3,4-dimethoxyphenyl)-1,2,4-oxadiazol-5-yl]-1-piperidyl]ethanamine (750 mg) which was used directly without further purification. LCMS (ESI) m/z=333.1 [M+H]$^+$.

Step 3: Preparation of N-(2-(4-(3-(3,4-dimethoxyphenyl)-1,2,4-oxadiazol-5-yl)piperidin-1-yl)ethyl)benzamide

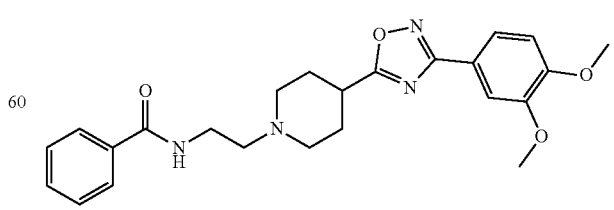

To a mixture of 2-[4-[3-(3,4-dimethoxyphenyl)-1,2,4-oxadiazol-5-yl]-1-piperidyl]ethanamine (200 mg, 602 μmol)

and benzoyl chloride (109 mg, 782 µmol, 90 µL) in dichloromethane (1 mL) was added triethylamine (182 mg, 1.81 mmol, 250 µL) at 0° C. The mixture was stirred at 20° C. for 5 h, then purified directly by prep-HPLC (column: Luna C8 100×30 5 µm; mobile phase: [water (10 mM ammonium carbonate)-acetonitrile]; B %: 35%-50%, 12 min) to give N-[2-[4-[3-(3,4-dimethoxyphenyl)-1,2,4-oxadiazol-5-yl]-1-piperidyl]ethyl]benzamide (25 mg, 56 µmol, 9%) as a white solid. $^1$H NMR (400 MHz, METHANOL-d4) δ=7.86-7.79 (m, 2H), 7.66 (dd, J=1.8, 8.4 Hz, 1H), 7.58 (d, J=1.8 Hz, 1H), 7.55-7.43 (m, 3H), 7.07 (d, J=8.6 Hz, 1H), 3.89 (s, 6H), 3.58 (t, J=6.8 Hz, 2H), 3.16-3.09 (m, 2H), 2.67 (t, J=6.8 Hz, 2H), 2.37-2.29 (m, 2H), 2.18 (br d, J=11.2 Hz, 2H), 2.07-1.91 (m, 3H); LCMS (ESI) m/z: [M+H]$^+$=437.3.

Example 33: (E)-1-(4-(3-(3,4-dimethoxyphenyl)-1,2,4-oxadiazol-5-yl)piperidin-1-yl)-4-phenylbut-2-ene-1,4-dione

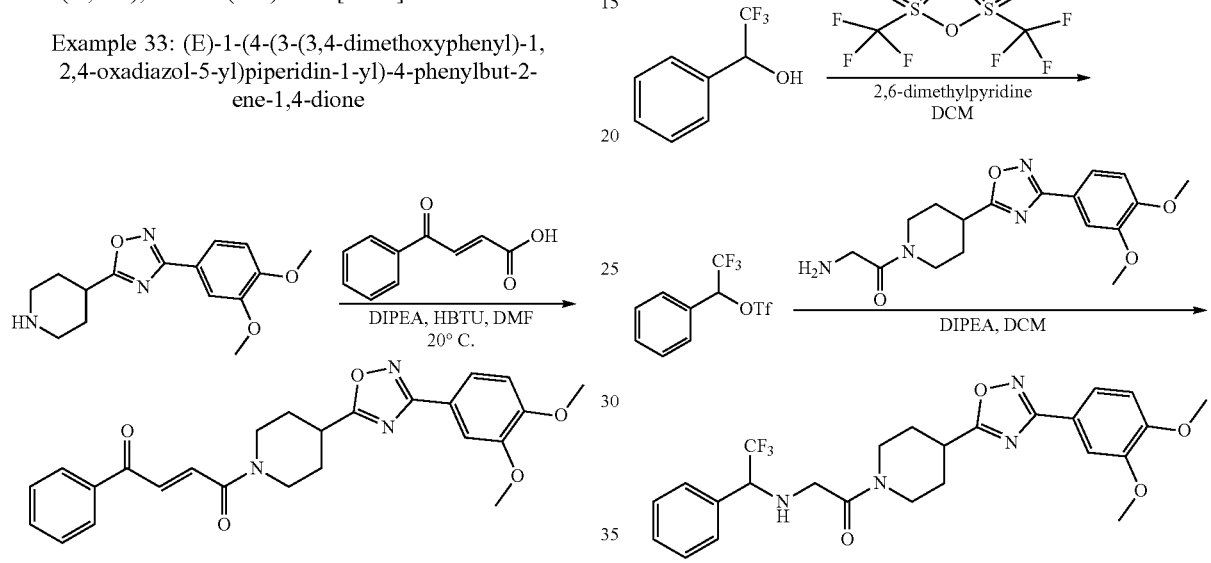

Step 1: Preparation of (E)-1-(4-(3-(3,4-dimethoxyphenyl)-1,2,4-oxadiazol-5-yl)piperidin-1-yl)-4-phenylbut-2-ene-1,4-dione

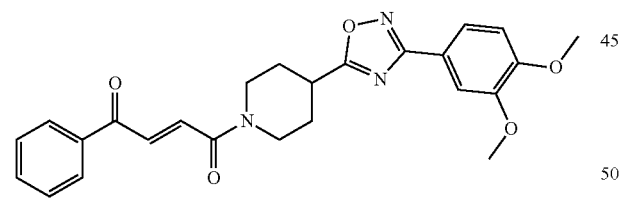

To a stirred solution of 3-(3,4-dimethoxyphenyl)-5-(4-piperidyl)-1,2,4-oxadiazole (250 mg, 864 µmol) in N,N-dimethylformamide (4 mL) were added (2-(1H-benzotriazol-1-yl)-1,1,3,3-tetramethyluronium hexafluorophosphate) (327 mg, 864 µmol), N-ethyl-N-(propan-2-yl)propan-2-amine (335 mg, 2.59 mmol, 452 µL) and (E)-4-oxo-4-phenyl-but-2-enoic acid (152 mg, 864 µmol). The mixture was stirred at 20° C. for 5 h, then the crude mixture was purified directly by prep-HPLC (column: Luna C8 100×30 5 µm; mobile phase: [water (10 mM ammonium carbonate)-acetonitrile]; B %: 40%-70%, 12 min) to give (E)-1-[4-[3-(3,4-dimethoxyphenyl)-1,2,4-oxadiazol-5-yl]-1-piperidyl]-4-phenyl-but-2-ene-1,4-dione (118 mg, 251 µmol, 29%) as a yellow solid. $^1$H NMR (400 MHz, DMSO-d6) δ=8.03 (br d, J=7.3 Hz, 2H), 7.75 (d, J=15.4 Hz, 1H), 7.71-7.65 (m, 1H), 7.61-7.53 (m, 3H), 7.51-7.43 (m, 2H), 7.11 (d, J=8.4 Hz, 1H), 4.41 (br d, J=13.2 Hz, 1H), 4.11-3.99 (m, 1H), 3.88-3.77 (m, 6H), 3.54-3.34 (m, 2H), 3.02 (br t, J=11.2 Hz, 1H), 2.15 (br d, J=13.0 Hz, 2H), 1.88-1.67 (m, 2H); LCMS (ESI) m/z: [M+H]$^+$=448.2.

Example 34: 1-(4-(3-(3,4-dimethoxyphenyl)-1,2,4-oxadiazol-5-yl)piperidin-1-yl)-2-((2,2,2-trifluoro-1-phenylethyl)amino)ethanone Step 1: Preparation of 2,2,2-trifluoro-1-phenylethyl trifluoromethanesulfonate To a stirred solution of 2,2,2-trifluoro-1-phenylethanol (100 mg, 568 µmol, 76 µL) in dichloromethane (2 mL) were added 2,6-dimethylpyridine (121 mg, 1.14 mmol, 132 µL) and trifluoromethanesulfonic anhydride (288 mg, 1.02 mmol, 168 µL) at 0° C. The mixture was stirred at 0° C. for 0.5 h and then diluted with dichloromethane (5 mL) and water (5 mL), and the phases separated. The aqueous phase was extracted with dichloromethane (15 mL×2), then the combined organic phases were dried over anhydrous sodium sulfate, filtered, and concentrated to give 2,2,2-trifluoro-1-phenylethyl trifluoromethanesulfonate (380 mg) as a brown oil. This material was used directly without further purification.

Step 2: Preparation of 1-(4-(3-(3,4-dimethoxyphenyl)-1,2,4-oxadiazol-5-yl)piperidin-1-yl)-2-((2,2,2-trifluoro-1-phenylethyl)amino)ethanone

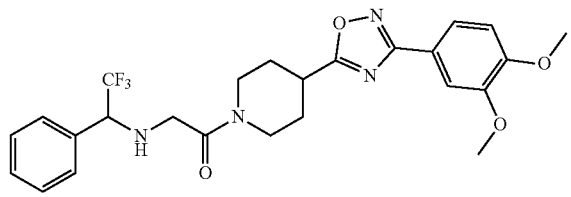 [SMILES: COc1ccc(-c2noc(C3CCN(C(=O)CNC(c4ccccc4)C(F)(F)F)CC3)n2)cc1OC]

To a stirred solution of 2-amino-1-(4-(3-(3,4-dimethoxyphenyl)-1,2,4-oxadiazol-5-yl)piperidin-1-yl)ethanone (120 mg, 346 μmol) in dichloromethane (2.5 mL) was added 2,2,2-trifluoro-1-phenylethyl trifluoromethanesulfonate (213 mg, 692.88 μmol) and N-ethyl-N-(propan-2-yl)propan-2-amine (179 mg, 1.39 mmol, 242 μL). The mixture was stirred at 40° C. for 16 h. The reaction mixture was concentrated in vacuo to give a crude product that was purified by prep-HPLC (column: Waters Xbridge 150×2.5 mm 5 μm; mobile phase: [water (10 mM ammonium carbonate)-acetonitrile]; B %: 40%-70%, 12 min) to give 1-(4-(3-(3,4-dimethoxyphenyl)-1,2,4-oxadiazol-5-yl)piperidin-1-yl)-2-((2,2,2-trifluoro-1-phenylethyl)amino)ethanone (52 mg, 101 μmol, 29%) as a yellow solid. $^1$H NMR (400 MHz, DMSO-d6) δ 7.63-7.56 (m, 1H), 7.51-7.37 (m, 6H), 7.14 (d, J=8.4 Hz, 1H), 4.53-4.43 (m, 1H), 4.30 (br. s., 1H), 3.84 (s, 6H), 3.71 (d, J=10.2 Hz, 1H), 3.44-3.36 (m, 2H), 3.18-3.07 (m, 1H), 2.99 (d, J=5.5 Hz, 1H), 2.87 (br. s., 1H), 2.08 (d, J=12.5 Hz, 2H), 1.75-1.56 (m, 2H); LCMS (ESI) m/z: [M+H]$^+$ =505.3.

Example 35: N-(2-(4-(3-(3,4-dimethoxyphenyl)-1,2,4-thiadiazol-5-yl)piperidin-1-yl)-2-oxoethyl)benzamide

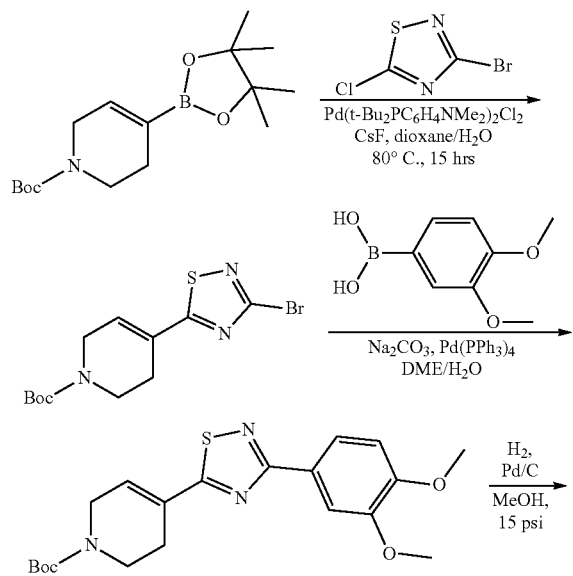

Step 1: Preparation of tert-butyl 4-(3-bromo-1,2,4-thiadiazol-5-yl)-5,6-dihydropyridine-1(2H)-carboxylate

A mixture of 3-bromo-5-chloro-1,2,4-thiadiazole (500 mg, 2.51 mmol), tert-butyl 4-(4,4,5,5-tetramethyl-1,3,2-dioxaborolan-2-yl)-3,6-dihydro-2H-pyridine-1-carboxylate (931 mg, 3.01 mmol), cesium fluoride (762 mg, 5.02 mmol, 185 μL) in dioxane (3.5 mL) was degassed and purged with nitrogen 3 times, then 4-ditert-butylphosphanyl-N,N-dimethyl-aniline; dichloropalladium (88 mg, 125.50 μmol, 88 μL, 0.05 eq) was added. The mixture was stirred at 80° C. for 2 h under an atmosphere of nitrogen. The mixture was cooled to 25° C. and concentrated in vacuo at 40° C. The residue was poured into water (15 mL), the aqueous phase was extracted with dichloromethane (20 mL×3). The combined organic phases were washed with saturated aqueous sodium chloride solution (20 mL), dried over anhydrous sodium sulfate, filtered, and concentrated in vacuo to afford crude product. The crude product was purified by chromatography (silica, petroleum ether/ethyl acetate (from 20/1 to 2/1) to give tert-butyl 4-(3-bromo-1,2,4-thiadiazol-5-yl)-3,6-dihydro-2H-pyridine-1-carboxylate (260 mg, 750.92 μmol, 30%) as a yellow oil. LCMS (ESI) m/z: 368.3 [M+Na]$^+$.

Step 2: Preparation of tert-butyl 4-(3-(3,4-dimethoxyphenyl)-1,2,4-thiadiazol-5-yl)-5,6-dihydropyridine-1(2H)-carboxylate

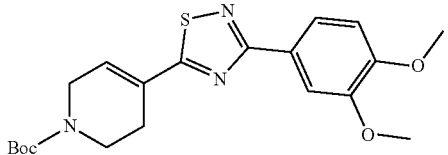 [SMILES: COc1ccc(-c2nsc(C3=CCN(C(=O)OC(C)(C)C)CC3)n2)cc1OC]

A mixture of tert-butyl 4-(3-bromo-1,2,4-thiadiazol-5-yl)-3,6-dihydro-2H-pyridine-1-carboxylate (260 mg, 751 µmol), (3,4-dimethoxyphenyl)boronic acid (163 mg, 901 µmol), and sodium carbonate (103 mg, 976 µmol) in water (400 µL) and dimethoxyethane (1.2 mL) was degassed and purged with nitrogen 3 times, and then tetrakis(triphenylphosphine)palladium(0) (17 mg, 15 µmol) was added. The mixture was stirred at 100° C. for 6 h under a nitrogen atmosphere. The mixture was cooled to 25° C. and concentrated in vacuo at 40° C. The residue was poured into water (5 mL), and the aqueous phase was extracted with dichloromethane (10 mL×3). The combined organic phases were washed with saturated aqueous sodium chloride solution (10 mL), dried over anhydrous sodium sulfate, filtered, and concentrated in vacuo to afford crude product. The crude residue was purified by prep-TLC (silica, petroleum ether/ethyl acetate=3:1) to give tert-butyl 4-[3-(3,4-dimethoxyphenyl)-1,2,4-thiadiazol-5-yl]-3,6-dihydro-2H-pyridine-1-carboxylate (122 mg, 303 µmol, 40%) as a yellow oil. LCMS (ESI) m/z: 404.1 [M+H]$^+$.

Step 3: Preparation of tert-butyl 4-(3-(3,4-dimethoxyphenyl)-1,2,4-thiadiazol-5-yl)piperidine-1-carboxylate

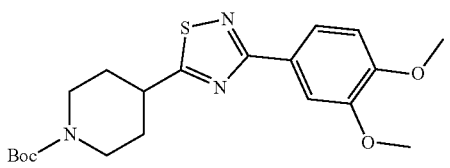 [SMILES: COc1ccc(-c2nsc(C3CCN(C(=O)OC(C)(C)C)CC3)n2)cc1OC]

To a stirred solution of tert-butyl 4-[3-(3,4-dimethoxyphenyl)-1,2,4-thiadiazol-5-yl]-3,6-dihydro-2H-pyridine-1-carboxylate (100 mg, 248 µmol) in methanol (10 mL) was added palladium(0) on carbon (10%, 150 mg) under nitrogen. The suspension was degassed under vacuum and purged with hydrogen three times. The mixture was stirred under hydrogen (15 psi) at 20° C. for 48 h. The reaction mixture was filtered and concentrated under reduced pressure to give tert-butyl 4-[3-(3,4-dimethoxyphenyl)-1,2,4-thiadiazol-5-yl]piperidine-1-carboxylate (79 mg) that was used into the next step without further purification. LCMS (ESI) m/z: 406.2 [M+H]$^+$.

Step 4: Preparation of 3-(3,4-dimethoxyphenyl)-5-(piperidin-4-yl)-1,2,4-thiadiazole

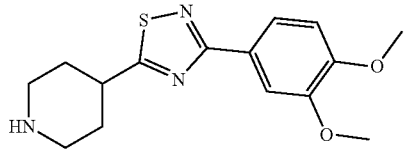 [SMILES: COc1ccc(-c2nsc(C3CCNCC3)n2)cc1OC]

A solution of tert-butyl 4-[3-(3,4-dimethoxyphenyl)-1,2,4-thiadiazol-5-yl]piperidine-1-carboxylate (79 mg, 195 µmol) in hydrochloric acid/ethyl acetate (4M, 15 mL) was stirred at 20° C. for 3 h. The reaction mixture was concentrated in vacuo to give 3-(3,4-dimethoxyphenyl)-5-(4-piperidyl)-1,2,4-thiadiazole (65 mg) that was used into the next step without further purification.

Step 5: Preparation of N-(2-(4-(3-(3,4-dimethoxyphenyl)-1,2,4-thiadiazol-5-yl)piperidin-1-yl)-2-oxoethyl)benzamide

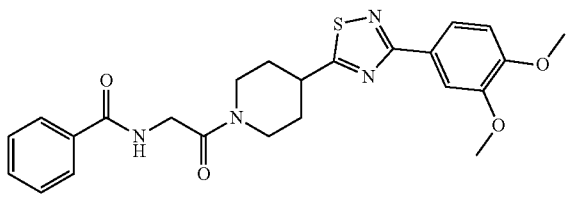 [SMILES: COc1ccc(-c2nsc(C3CCN(C(=O)CNC(=O)c4ccccc4)CC3)n2)cc1OC]

To a stirred solution of 3-(3,4-dimethoxyphenyl)-5-(4-piperidyl)-1,2,4-thiadiazole (65 mg, 214 µmol) and 2-benzamidoacetic acid (46 mg, 257 µmol) in N,N-dimethylformamide (1 mL) were added (2-(1H-benzotriazol-1-yl)-1,1,3,3-tetramethyluronium hexafluorophosphate) (81 mg, 214 µmol) and N-ethyl-N-(propan-2-yl)propan-2-amine (69 mg, 536 µmol, 93 µL). After 2 h, the reaction mixture purified directly by prep-HPLC (column: Waters Xbridge 150×25 5 µm; mobile phase: [water (10 mM ammonium carbonate)-acetonitrile]; B %: 26%-56%, 12 min) to give N-[2-[4-[3-(3,4-dimethoxyphenyl)-1,2,4-thiadiazol-5-yl]-1-piperidyl]-2-oxo-ethyl]benzamide (10 mg, 22 µmol, 10%) as a yellow solid. $^1$H NMR (400 MHz, METHANOL-d4) δ=7.92-7.82 (m, 4H), 7.59-7.52 (m, 1H), 7.51-7.44 (m, 2H), 7.06 (d, J=8.4 Hz, 1H), 4.61 (d, J=12.9 Hz, 1H), 4.41-4.24 (m, 2H), 4.11 (br d, J=14.9 Hz, 1H), 3.98-3.84 (m, 6H), 3.63-3.52 (m, 1H), 3.39 (br t, J=11.7 Hz, 1H), 2.99 (br t, J=11.6 Hz, 1H), 2.35-2.20 (m, 2H), 2.03-1.74 (m, 2H); LCMS (ESI) m/z: [M+H]$^+$=467.2.

Example 36: N-(2-(4-(5-(3,4-dimethoxyphenyl)-1,2,4-oxadiazol-3-yl)piperidin-1-yl)-2-oxoethyl)benzamide

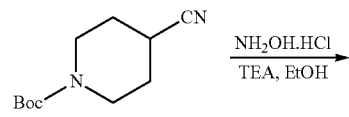

Step 1: Preparation of (Z)-tert-butyl 4-(N'-hydroxy-carbamimidoyl)piperidine-1-carboxylate

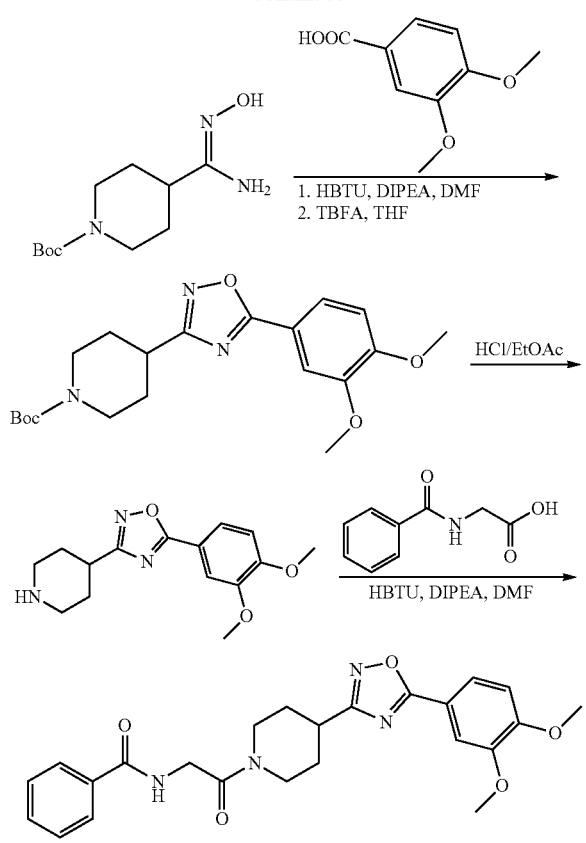

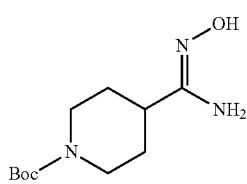 [SMILES: CC(C)(C)OC(=O)N1CCC(/C(N)=N/O)CC1]

A mixture of tert-butyl 4-cyanopiperidine-1-carboxylate (2.0 g, 9.51 mmol), hydroxylamine hydrochloride (1.32 g, 19.0 mmol), and triethylamine (1.92 g, 19.0 mmol, 2.64 mL) in ethanol (20 mL) and water (2 mL) was heated at 75° C. for 16 h. The reaction mixture was cooled, diluted with water (10 mL), and extracted with ethyl acetate (15 mL×3). The combined organic phases were washed with saturated aqueous sodium chloride solution (10 mL×2), dried over anhydrous sodium sulfate, filtered, and concentrated under reduced pressure to give tert-butyl 4-[(Z)—N'-hydroxycar-bamimidoyl]piperidine-1-carboxylate (1.90 g) which was used directly without further purification. $^1$H NMR (400 MHz, METHANOL-d4) δ=4.15 (br d, J=13.3 Hz, 2H), 2.78 (br s, 2H), 2.27 (tt, J=3.6, 12.1 Hz, 1H), 1.84-1.70 (m, 2H), 1.62 (dq, J=4.3, 12.6 Hz, 2H), 1.53-1.39 (m, 9H).

Step 2: Preparation of tert-butyl 4-(5-(3,4-dimethoxyphenyl)-1,2,4-oxadiazol-3-yl)piperidine-1-carboxylate

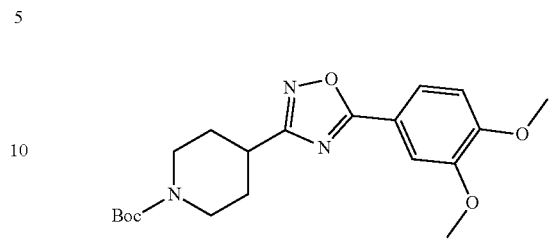

To a stirred solution of tert-butyl 4-[(Z)—N'-hydroxycar-bamimidoyl]piperidine-1-carboxylate (750 mg, 3.08 mmol) in N,N-dimethylformamide (5 mL) was added (2-(1H-benzotriazol-1-yl)-1,1,3,3-tetramethyluronium hexafluorophosphate) (1.17 g, 3.08 mmol), N-ethyl-N-(propan-2-yl)propan-2-amine (1.19 g, 9.24 mmol, 1.61 mL) and 3,4-dimethoxybenzoic acid (561 mg, 3.08 mmol). The mixture was stirred at 20° C. for 16 h. The reaction mixture was diluted with water (10 mL) and extracted with ethyl acetate (15 mL×3). The combined organic phases were washed with saturated aqueous sodium chloride solution (10 mL×2), dried over anhydrous sodium sulfate, filtered, and concentrated under reduced pressure to give a residue. Tetrahydrofuran (500 μL) and tetrabutylammonium fluoride/tetrahydrofuran (1 M, 4.62 mL) were added to the residue, and the resulting mixture was heated at 50° C. for 16 h. The residue was purified by chromatography (silica, petroleum ether/ethyl acetate=5:1) to give tert-butyl 4-[5-(3,4-dimethoxyphenyl)-1,2,4-oxadiazol-3-yl]piperidine-1-carboxylate (970 mg, 2.49 mmol, 81%) as a white solid. LCMS (ESI) m/z: 412.3 [M+Na]$^+$=334.2.

Step 3: Preparation of 5-(3,4-dimethoxyphenyl)-3-(piperidin-4-yl)-1,2,4-oxadiazole

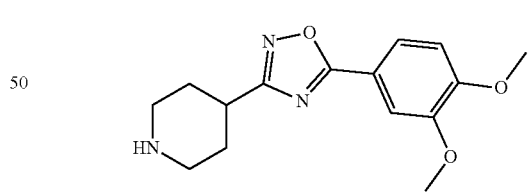

A solution of tert-butyl 4-[5-(3,4-dimethoxyphenyl)-1,2,4-oxadiazol-3-yl]piperidine-1-carboxylate (750 mg, 1.93 mmol) in hydrochloric acid/ethyl acetate (4M, 30 mL) was stirred at 20° C. for 0.5 h. The reaction mixture was concentrated under reduced pressure to give 5-(3,4-dimethoxyphenyl)-3-(4-piperidyl)-1,2,4-oxadiazole (683 mg) that was used directly without further purification.

Step 4: Preparation of N-(2-(4-(5-(3,4-dimethoxyphenyl)-1,2,4-oxadiazol-3-yl)piperidin-1-yl)-2-oxoethyl)benzamide

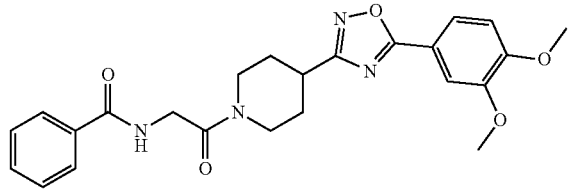 [SMILES: COc1ccc(-c2nc(C3CCN(C(=O)CNC(=O)c4ccccc4)CC3)no2)cc1OC]

To a stirred solution of 5-(3,4-dimethoxyphenyl)-3-(4-piperidyl)-1,2,4-oxadiazole (180 mg, 622 μmol) in N,N-dimethylformamide (2 mL) were added 2-benzamidoacetic acid (111 mg, 622 μmol), (2-(1H-benzotriazol-1-yl)-1,1,3,3-tetramethyluronium hexafluorophosphate) (235 mg, 622 μmol), and N-ethyl-N-(propan-2-yl)propan-2-amine (241 mg, 1.87 mmol, 325 μL). The mixture was stirred at 20° C. for 16 h. The crude product was purified by prep-HPLC (column: Waters Xbridge 150×25 5 μm; mobile phase: [water (10 mM ammonium carbonate)-acetonitrile]; B %: 30%-60%, 12 min) to give N-[2-[4-[5-(3,4-dimethoxyphenyl)-1,2,4-oxadiazol-3-yl]-1-piperidyl]-2-oxo-ethyl]benzamide (169 mg, 376 μmol, 60%) as a white solid. $^1$H NMR (400 MHz, DMSO-d6) δ=8.55 (br t, J=5.4 Hz, 1H), 7.87 (br d, J=7.5 Hz, 2H), 7.70 (br d, J=8.4 Hz, 1H), 7.57-7.41 (m, 4H), 7.17 (br d, J=8.4 Hz, 1H), 4.34 (br d, J=12.3 Hz, 1H), 4.16 (br d, J=4.2 Hz, 2H), 3.97 (br d, J=13.0 Hz, 1H), 3.90-3.74 (m, 6H), 3.27-3.09 (m, 2H), 2.88 (br t, J=11.6 Hz, 1H), 2.03 (br t, J=11.8 Hz, 2H), 1.75 (br d, J=10.4 Hz, 1H), 1.59 (br d, J=9.9 Hz, 1H); LCMS (ESI) m/z: [M+H]$^+$=451.2.

Example 37: N-(2-(4-(4-(3,4-dimethoxyphenyl)oxazol-2-yl)piperidin-1-yl)-2-oxoethyl)benzamide

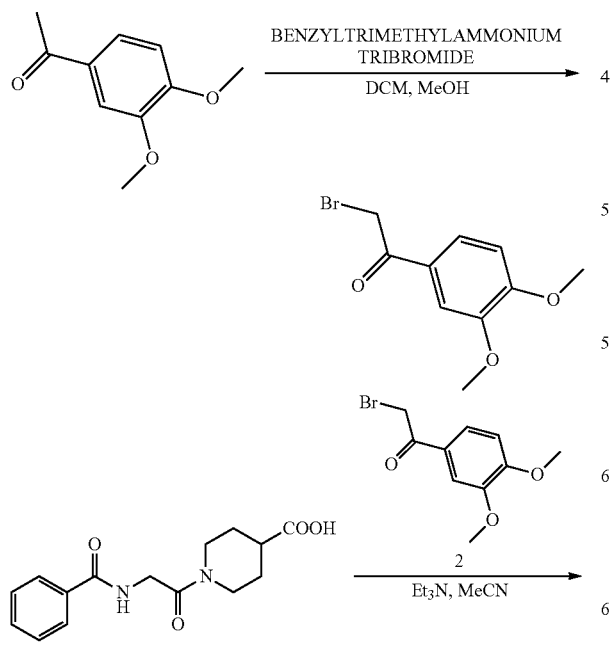

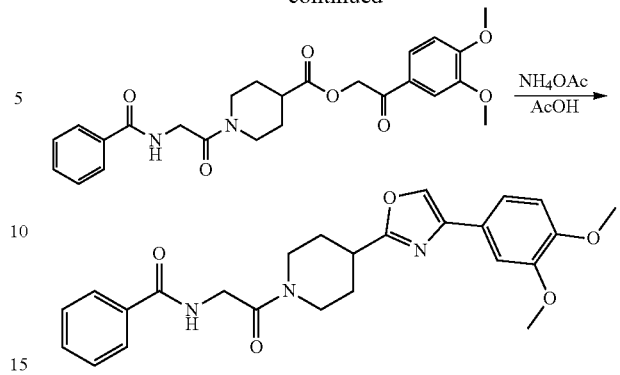

Step 1: Preparation of 2-bromo-1-(3,4-dimethoxyphenyl)ethanone

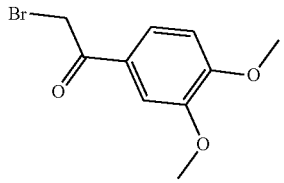

To a stirred solution of 1-(3,4-dimethoxyphenyl)ethanone (1.0 g, 5.55 mmol) in dichloromethane (6 mL) and methanol (3 mL) was added benzyltrimethylammonium tribromide (2.16 g, 5.55 mmol). After 16 h, the mixture was diluted with dichloromethane (80 mL) and water (40 mL), the organic layer was separated, and the water phase was extracted with dichloromethane (80 mL×2). The combined organic phases were dried over anhydrous sodium sulfate, filtered, and concentrated to give 2-bromo-1-(3,4-dimethoxyphenyl)ethanone (1.20 g, 4.63 mmol, 83%) as a brown solid. $^1$H NMR (400 MHz, CDCl$_3$) δ 7.63 (s, 1H), 7.57 (d, J=2.1 Hz, 1H), 6.94 (d, J=8.4 Hz, 1H), 4.43 (s, 2H), 3.98 (d, J=8.4 Hz, 6H).

Step 2: Preparation of 2-(3,4-dimethoxyphenyl)-2-oxoethyl 1-(2-benzamidoacetyl)piperidine-4-carboxylate

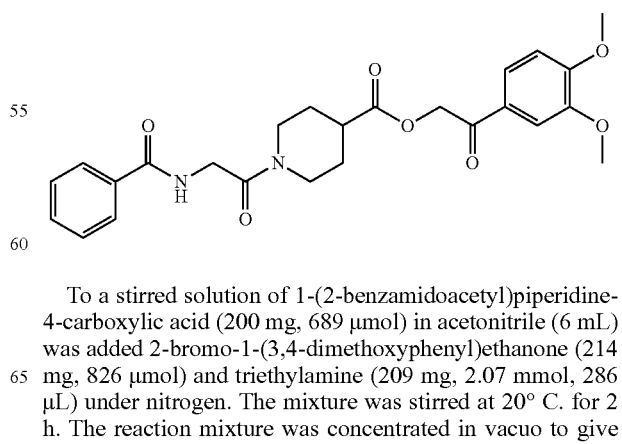

To a stirred solution of 1-(2-benzamidoacetyl)piperidine-4-carboxylic acid (200 mg, 689 μmol) in acetonitrile (6 mL) was added 2-bromo-1-(3,4-dimethoxyphenyl)ethanone (214 mg, 826 μmol) and triethylamine (209 mg, 2.07 mmol, 286 μL) under nitrogen. The mixture was stirred at 20° C. for 2 h. The reaction mixture was concentrated in vacuo to give 2-(3,4-dimethoxyphenyl)-2-oxoethyl 1-(2-benzamidoacetyl)piperidine-4-carboxylate (233 mg, 497 µmol, 72%) as a yellow solid. This was used directly without further purification. LCMS (ESI) m/z: [M+H]$^+$=469.3.

Step 3: Preparation of N-(2-(4-(4-(3,4-dimethoxyphenyl)oxazol-2-yl)piperidin-1-yl)-2-oxoethyl)benzamide

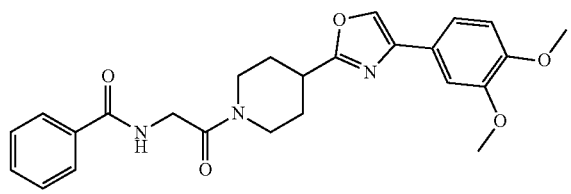 [SMILES: COc1ccc(-c2coc(C3CCN(C(=O)CNC(=O)c4ccccc4)CC3)n2)cc1OC]

To a stirred solution of 2-(3,4-dimethoxyphenyl)-2-oxoethyl 1-(2-benzamidoacetyl)piperidine-4-carboxylate (180 mg, 384 µmol) in acetic acid (8 mL) was added ammonium acetate (148 mg, 1.92 mmol) under nitrogen, then the mixture was heated at 100° C. for 16 h. The reaction mixture was concentrated in vacuo to give crude product that was purified by prep-HPLC (column: Waters Xbridge 150×2.5 mm 5 µm; mobile phase: [water (10 mM ammonium carbonate)-acetonitrile]; B %: 30%-55%, 12 min) to give N-(2-(4-(4-(3,4-dimethoxyphenyl)oxazol-2-yl)piperidin-1-yl)-2-oxoethyl)benzamide (55 mg, 120 µmol, 31%) as a pink solid. $^1$H NMR (400 MHz, CDCl$_3$) δ 7.92-7.84 (m, 2H), 7.80 (s, 1H), 7.58-7.44 (m, 3H), 7.41-7.35 (m, 1H), 7.28-7.26 (m, 2H), 6.92 (d, J=8.9 Hz, 1H), 4.58-4.47 (m, 1H), 4.32 (d, J=3.9 Hz, 2H), 3.99-3.88 (m, 7H), 3.37-3.06 (m, 3H), 2.28-2.13 (m, 2H), 2.07-1.89 (m, 2H); LCMS (ESI) m/z: [M+H]$^+$=450.3.

Example 38: N-(2-(4-(4-(3,4-dimethoxyphenyl)thiazol-2-yl)piperidin-1-yl)-2-oxoethyl)benzamide

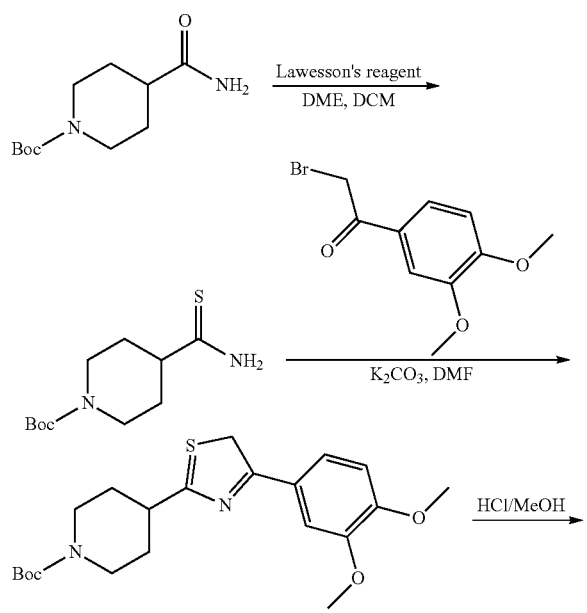

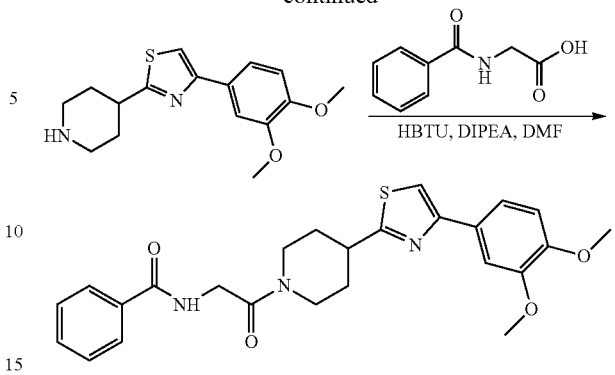

Step 1: Preparation of tert-butyl 4-carbamothioylpiperidine-1-carboxylate

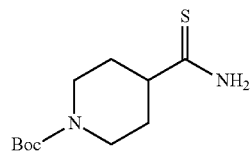 [SMILES: CC(C)(C)OC(=O)N1CCC(C(N)=S)CC1]

To a stirred solution of tert-butyl 4-carbamoylpiperidine-1-carboxylate (1.0 g, 4.38 mmol) in a mixture of dimethoxyethane (16 mL) and dichloromethane (8 mL) was added 2,4-bis(4-methoxyphenyl)-1,3,2,4-dithiadiphosphetane-2,4-disulfide (885 mg, 2.19 mmol). The mixture was stirred at 20° C. for 16 h, then concentrated in vacuo. The residue dissolved in ethyl acetate and washed with saturated aqueous potassium carbonate (10 mL×2). The organic layer was separated, dried over sodium sulfate and concentrated in vacuo to give tert-butyl 4-carbamothioylpiperidine-1-carboxylate (1.0 g) as a yellow solid. This was used directly without further purification. $^1$H NMR (400 MHz, DMSO-d6) δ 9.45 (br. s., 1H), 9.17 (br. s., 1H), 4.14-3.98 (m, 2H), 3.91-3.79 (m, 1H), 2.80-2.66 (m, 2H), 1.74-1.55 (m, 4H), 1.46 (s, 9H).

Step 2: Preparation of tert-butyl 4-(4-(3,4-dimethoxyphenyl)thiazol-2-yl)piperidine-1-carboxylate

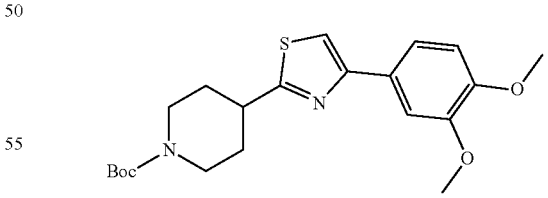

To a stirred solution of tert-butyl 4-carbamothioylpiperidine-1-carboxylate (200 mg, 818.5 µmol) in N,N-dimethylformamide (5 mL) was added 2-bromo-1-(3,4-dimethoxyphenyl)ethanone (212 mg, 818.50 µmol) and potassium carbonate (124 mg, 900 µmol). The mixture was stirred at 110° C. for 16 h. The reaction mixture was quenched with water (10 mL) and extracted with ethyl acetate (40 mL×3). The combined organic phases were washed with saturated aqueous sodium chloride solution (10 mL), dried over anhydrous sodium sulfate, filtered, and concentrated to give tert-butyl 4-(4-(3,4-dimethoxyphenyl)thiazol-2-yl)piperidine-1-carboxylate (300 mg, 742 μmol, 91%) as a yellow solid. This was used directly without further purification. LCMS (ESI) m/z: [M+H]⁺=405.3.

Step 3: Preparation of 4-(3,4-dimethoxyphenyl)-2-(piperidin-4-yl)thiazole

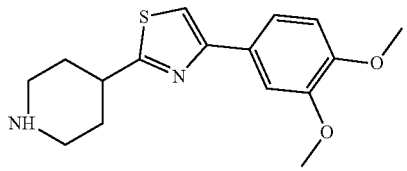 [SMILES: COc1ccc(-c2csc(C3CCNCC3)n2)cc1OC]

To a stirred solution of tert-butyl 4-(4-(3,4-dimethoxyphenyl)thiazol-2-yl)piperidine-1-carboxylate (300 mg, 742 μmol) in methanol (3 mL) was added methanolic hydrogen chloride solution (4M, 10 mL). The mixture was stirred at 20° C. for 1 h. The reaction mixture was concentrated under reduced pressure to provide 4-(3,4-dimethoxyphenyl)-2-(piperidin-4-yl)thiazole (260 mg) as a yellow solid. LCMS (ESI) m/z: [M+H]⁺=305.1.

Step 4: Preparation of N-(2-(4-(4-(3,4-dimethoxyphenyl)thiazol-2-yl)piperidin-1-yl)-2-oxoethyl)benzamide

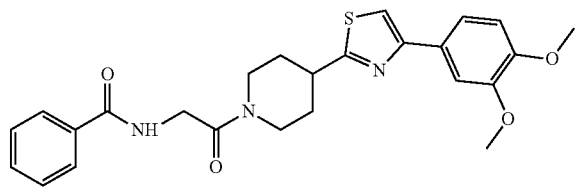 [SMILES: COc1ccc(-c2csc(C3CCN(C(=O)CNC(=O)c4ccccc4)CC3)n2)cc1OC]

To a stirred solution of 4-(3,4-dimethoxyphenyl)-2-(piperidin-4-yl)thiazole (203 mg, 670 μmol) in N,N-dimethylformamide (4 mL) were added 2-benzamidoacetic acid (100 mg, 558 μmol), (2-(1H-benzotriazol-1-yl)-1,1,3,3-tetramethyluronium hexafluorophosphate) (211 mg, 558 μmol) and N-ethyl-N-(propan-2-yl)propan-2-amine (288 mg, 2.23 mmol, 389 μL). The mixture was stirred at 20° C. for 16 h. The reaction mixture was purified directly by prep-HPLC (column: Waters Xbridge 150×2.5 mm 5 μm; mobile phase: [water (10 mM ammonium carbonate)-acetonitrile]; B %: 30%-60%, 12 min) to give N-(2-(4-(4-(3,4-dimethoxyphenyl)thiazol-2-yl)piperidin-1-yl)-2-oxoethyl)benzamide (111 mg, 239 μmol, 43%) as a yellow solid. ¹H NMR (400 MHz, CDCl₃) δ 7.91-7.85 (m, 2H), 7.57-7.42 (m, 5H), 7.39 (br. s., 1H), 6.94 (d, J=8.2 Hz, 1H), 4.70 (d, J=13.6 Hz, 1H), 4.40-4.26 (m, 2H), 3.97 (d, J=19.7 Hz, 7H), 3.43-3.26 (m, 2H), 3.05-2.95 (m, 1H), 2.37-2.23 (m, 2H), 1.98-1.83 (m, 2H); LCMS (ESI) m/z: [M+H]⁺=466.3.

Example 39: N-(2-(4-(5-(3,4-dimethoxyphenyl)-1,3,4-oxadiazol-2-yl)piperidin-1-yl)-2-oxoethyl)benzamide

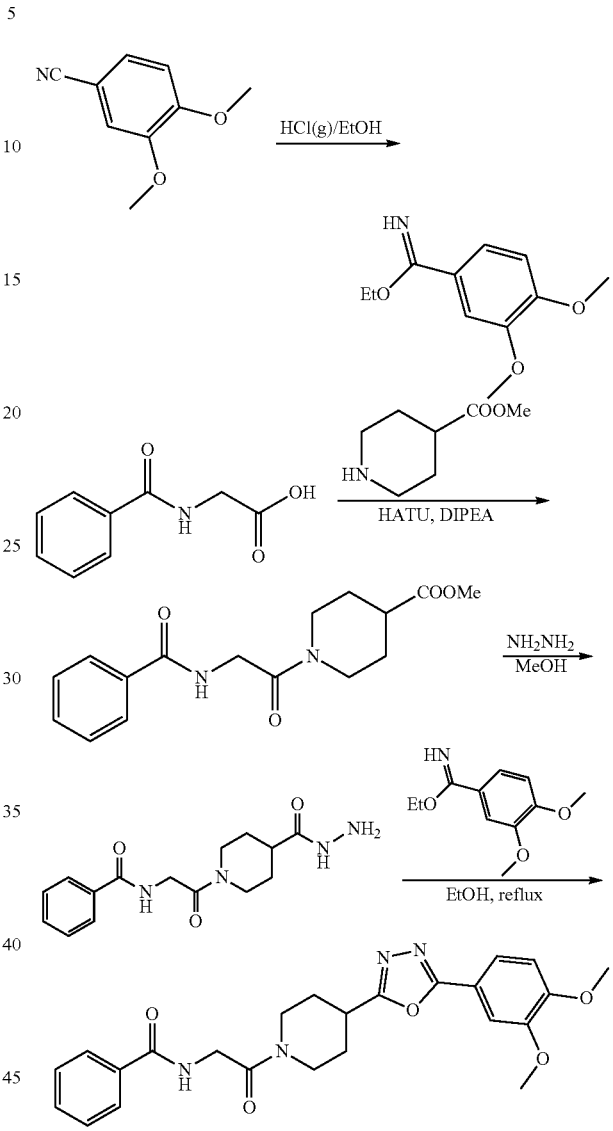

Step 1: Ethyl 3,4-dimethoxybenzimidate

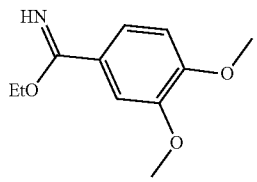

To a stirred solution of 3,4-dimethoxybenzonitrile (2.0 g, 12.3 mmol) in dry ethanol (50 mL) was added dropwise acetyl chloride (7.70 g, 98.1 mmol, 7.0 mL) at 0° C., after complete addition, the mixture was warmed to 15° C. and stirred for 30 h. The reaction was concentrated in vacuo, and then saturated hydrochloric acid in ethanol (50 mL) was added. After 5 h, the mixture was concentrated in vacuo to give crude ethyl 3,4-dimethoxybenzenecarboximidate (2.50 g) as a light yellow solid, which was used in next step directly.

Step 2: methyl 1-(2-benzamidoacetyl)piperidine-4-carboxylate

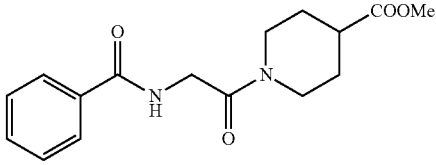 [SMILES: COC(=O)C1CCN(C(=O)CNC(=O)c2ccccc2)CC1]

To a stirred solution of 2-benzamidoacetic acid (3.0 g, 16.7 mmol) and methyl piperidine-4-carboxylate (3.60 g, 25.1 mmol) in dry N,N-dimethylformamide (50 mL) was added N-ethyl-N-(propan-2-yl)propan-2-amine (4.33 g, 33.5 mmol, 5.9 mL) and 1-[bis(dimethylamino)methylene]-1H-1,2,3-triazolo[4,5-b]pyridinium 3-oxide hexafluorophosphate (7.0 g, 18.4 mmol) at 0° C., then the mixture was warmed to 15° C. and stirred for 15 h. The mixture was poured into ice water (100 mL) then extracted with ethyl acetate (50 mL×3). The combined organic phases were washed with 1N hydrochloric acid (30 mL×2), saturated aqueous sodium carbonate (30 mL), and saturated aqueous sodium chloride solution (30 mL), then dried over anhydrous sodium sulfate, filtered and concentrated to give a crude methyl 1-(2-benzamidoacetyl)piperidine-4-carboxylate (5.30 g) as a brown oil, which was used in next step directly. $^1$H NMR (400 MHz, Methanol-d4) δ 7.87 (d, J=7.1 Hz, 2H), 7.58-7.51 (m, 1H), 7.49-7.40 (m, 2H), 4.39-4.29 (m, 1H), 4.28-4.17 (m, 2H), 3.96-3.84 (m, 1H), 3.68 (s, 3H), 3.28-3.17 (m, 1H), 2.96-2.86 (m, 1H), 2.69-2.62 (m, 1H), 2.00-1.88 (m, 2H), 1.78-1.51 (m, 2H).

Step 3: N-(2-(4-(hydrazinecarbonyl)piperidin-1-yl)-2-oxoethyl)benzamide

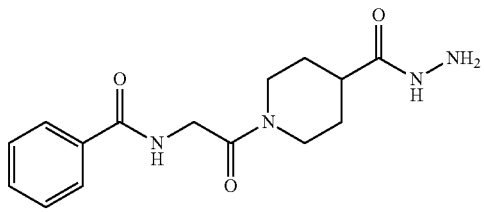 [SMILES: NNC(=O)C1CCN(C(=O)CNC(=O)c2ccccc2)CC1]

A solution of methyl 1-(2-benzamidoacetyl)piperidine-4-carboxylate (500 mg, 1.64 mmol) and hydrazine hydrate (328 mg, 6.56 mmol, 318 μL) in methanol (3 mL) was heated to 80° C. for 15 h. The mixture was concentrated in vacuo to give a crude residue that was washed with tert-butyl methyl ether (10 mL) to obtain N-[2-[4-(hydrazinecarbonyl)-1-piperidyl]-2-oxo-ethyl]benzamide (500 mg) as a light yellow solid that was used directly without further purification. $^1$H NMR (400 MHz, DMSO-d$_6$) δ 9.03 (s, 1H), 8.54 (t, J=5.6 Hz, 1H), 7.94-7.82 (m, 2H), 7.60-7.43 (m, 3H), 4.41-4.29 (m, 1H), 4.13 (d, J=5.6 Hz, 2H), 3.93 (d, J=12.9 Hz, 1H), 3.05 (t, J=11.9 Hz, 1H), 2.68-2.57 (m, 2H), 2.34 (tdd, J=3.9, 7.5, 11.2 Hz, 1H), 1.73-1.34 (m, 4H).

Step 4: N-(2-(4-(5-(3,4-dimethoxyphenyl)-1,3,4-oxadiazol-2-yl)piperidin-1-yl)-2-oxoethyl)benzamide

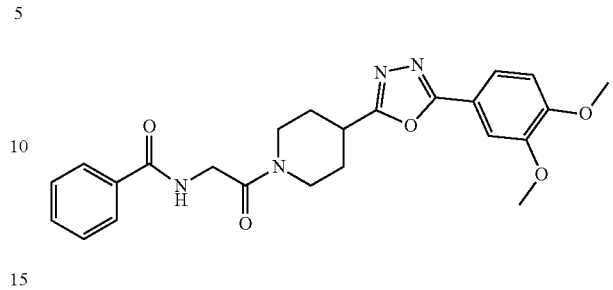

A solution of N-[2-[4-(hydrazinecarbonyl)-1-piperidyl]-2-oxo-ethyl]benzamide (200 mg, 657 μmol) and ethyl 3,4-dimethoxybenzenecarboximidate (151 mg, 723 μmol) in ethanol (4 mL) was heated to 80° C. for 15 h. The mixture was concentrated to give a crude product, which was purified by prep-HPLC (column: Waters Xbridge 150×25 5 μm; mobile phase: [water (10 mM ammonium carbonate)-acetonitrile]; B %: 20%-35%, 12 min) to give N-[2-[4-[5-(3,4-dimethoxyphenyl)-1,3,4-oxadiazol-2-yl]-1-piperidyl]-2-oxo-ethyl]benzamide (23 mg, 48 μmol, 7%) as a white solid. $^1$H NMR (400 MHz, Methanol-d4) δ 7.92-7.82 (m, 2H), 7.62 (dd, J=1.8, 8.4 Hz, 1H), 7.59-7.52 (m, 2H), 7.51-7.44 (m, 2H), 7.12 (d, J=8.4 Hz, 1H), 4.49 (d, J=13.2 Hz, 1H), 4.38-4.24 (m, 2H), 4.06 (d, J=13.7 Hz, 1H), 3.97-3.80 (m, 6H), 3.48-3.34 (m, 2H), 3.06 (t, J=11.2 Hz, 1H), 2.33-2.15 (m, 2H), 2.06-1.94 (m, 1H), 1.92-1.75 (m, 1H); LCMS (ESI) m/z: [M+H]$^+$=451.2.

Example 40: N-(2-(4-(3-(1,3-dimethyl-1H-indazol-6-yl)-1,2,4-oxadiazol-5-yl)piperidin-1-yl)-2-oxoethyl)benzamide

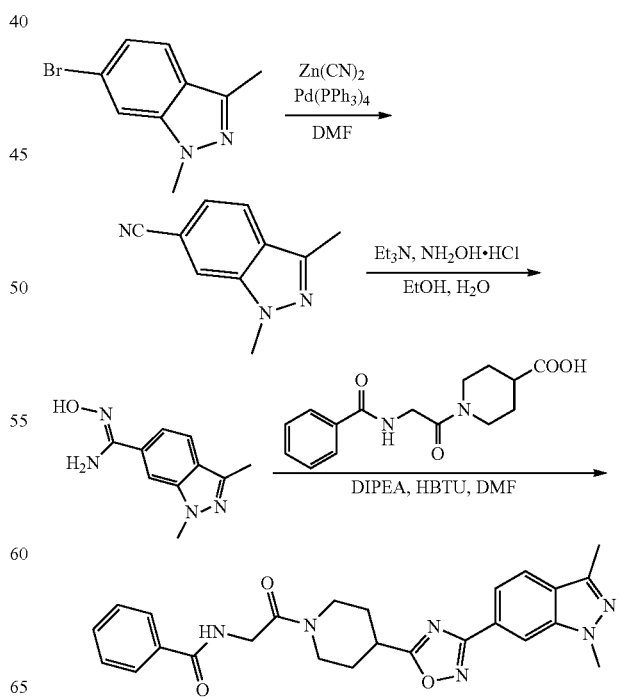

Step 1: Preparation of 1,3-dimethyl-1H-indazole-6-carbonitrile

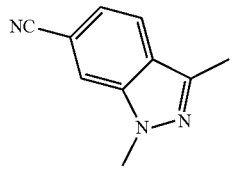

To a stirred solution of 6-bromo-1,3-dimethyl-1H-indazole (400 mg, 1.78 mmol) in N,N-dimethylformamide (5 mL) was added zinc cyanide (209 mg, 1.78 mmol, 112 μL) and tetrakis(triphenylphosphine)palladium(0) (205 mg, 178 μmol, 0.10 eq) under nitrogen. The mixture was heated at 100° C. for 16 h, then cooled to 20° C., water (10 mL) added, and the resulting mixture was extracted with ethyl acetate (40 mL×3). The combined organic phases were washed with saturated aqueous sodium chloride solution (15 mL) and dried over anhydrous sodium sulfate. The organic phase was filtered and concentrated in vacuo to give crude product. Petroleum ether (40 mL) was added to the crude product, then the mixture was filtered, and the filter cake dried in vacuo to give 1,3-dimethyl-1H-indazole-6-carbonitrile (250 mg, 1.46 mmol, 82%) as a white solid. $^1$H NMR (400 MHz, CDCl$_3$) δ 7.78-7.71 (m, 2H), 7.34 (dd, J=1.3, 8.3 Hz, 1H), 4.07 (s, 3H), 2.61 (s, 3H).

Step 2: Preparation of (Z)—N'-hydroxy-1,3-dimethyl-1H-indazole-6-carboximidamide

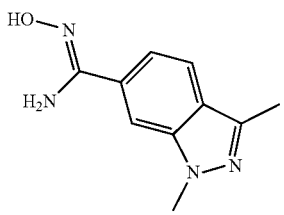

To a stirred solution of 1,3-dimethyl-1H-indazole-6-carbonitrile (100 mg, 584 μmol) in ethanol (2 mL) was added hydroxylamine hydrochloride (81 mg, 1.17 mmol), triethylamine (118 mg, 1.17 mmol, 161 μL) and water (200 μL). The mixture was heated at 75° C. for 2 h. After cooling to 20° C., water (5 mL) was added to the solution. The mixture was extracted with dichloromethane (30 mL×3). The combined organic phases were washed with saturated aqueous sodium chloride solution (5 mL) and dried over anhydrous sodium sulfate, then filtered and concentrated in vacuo to give (Z)—N'-hydroxy-1,3-dimethyl-1H-indazole-6-carboximidamide (140 mg) as a white solid. LCMS (ESI) m/z: [M+H]$^+$=205.1.

Step 3: Preparation of N-(2-(4-(3-(1,3-dimethyl-1H-indazol-6-yl)-1,2,4-oxadiazol-5-yl)piperidin-1-yl)-2-oxoethyl)benzamide

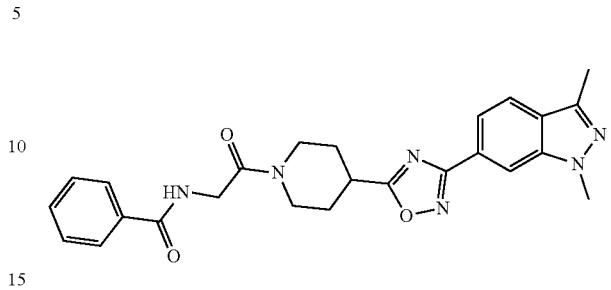

To a stirred solution of 1-(2-benzamidoacetyl)piperidine-4-carboxylic acid (120 mg, 413 μmol) in N,N-dimethylformamide (2 mL) was added (Z)—N'-hydroxy-1,3-dimethyl-1H-indazole-6-carboximidamide (101 mg, 496 μmol), (2-(1H-benzotriazol-1-yl)-1,1,3,3-tetramethyluronium hexafluorophosphate) (156 mg, 413 μmol) and N-ethyl-N-(propan-2-yl)propan-2-amine (160 mg, 1.24 mmol, 216 μL). The mixture was stirred at 20° C. for 2 h, then heated at 120° C. for 2 h. The reaction mixture cooled then purified directly by prep-HPLC (column: Waters Xbridge 150×2.5 mm 5 μm; mobile phase: [water (10 mM ammonium carbonate)-acetonitrile]; B %: 30%-65%, 12 min) to give N-(2-(4-(3-(1,3-dimethyl-1H-indazol-6-yl)-1,2,4-oxadiazol-5-yl)piperidin-1-yl)-2-oxoethyl)benzamide (46 mg, 101 μmol, 25%) as a yellow solid. $^1$H NMR (400 MHz, CDCl$_3$) δ 8.02 (s, 1H), 7.81-7.73 (m, 3H), 7.66 (dd, J=0.6, 8.4 Hz, 1H), 7.48-7.42 (m, 1H), 7.42-7.35 (m, 2H), 7.26 (br. s., 1H), 4.46 (d, J=14.1 Hz, 1H), 4.24 (d, J=3.9 Hz, 2H), 4.01 (s, 3H), 3.86 (d, J=13.7 Hz, 1H), 3.29 (ddd, J=3.6, 10.5, 14.2 Hz, 2H), 3.13-3.04 (m, 1H), 2.53 (s, 3H), 2.26-2.15 (m, 2H), 2.04-1.89 (m, 2H); LCMS (ESI) m/z: [M+H]$^+$=459.3.

Example 41: N-(2-(4-(3-(4-fluorophenyl)-1,2,4-oxadiazol-5-yl)piperidin-1-yl)-2-oxoethyl)benzamide

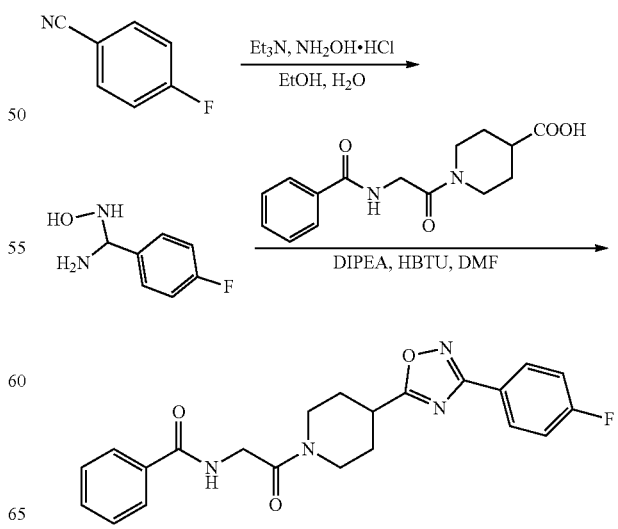

Step 1: Preparation of 4-fluoro-N-hydroxybenzimidamide

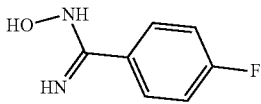

To a stirred solution of 4-fluorobenzonitrile (1.0 g, 8.26 mmol) in ethanol (10 mL) was added hydroxylamine hydrochloride (1.15 g, 16.5 mmol), triethylamine (1.67 g, 16.52 mmol, 2.29 mL) and water (1 mL). The mixture was heated at 75° C. for 2 h. After cooling to 20° C., water (20 mL) was added to the solution. The mixture was extracted with dichloromethane (40 mL×4). The combined organic phases were washed with saturated aqueous sodium chloride solution (20 mL) and dried over anhydrous sodium sulfate, then filtered and concentrated in vacuo to give 4-fluoro-N-hydroxybenzimidamide (1.0 g, 6.49 mmol, 79%) as a white solid. $^1$H NMR (400 MHz, DMSO-d6) δ 9.64 (s, 1H), 7.85-7.64 (m, 2H), 7.21 (t, J=8.9 Hz, 2H), 5.84 (br. s., 2H).

Step 2: Preparation of N-(2-(4-(3-(4-fluorophenyl)-1,2,4-oxadiazol-5-yl)piperidin-1-yl)-2-oxoethyl)benzamide

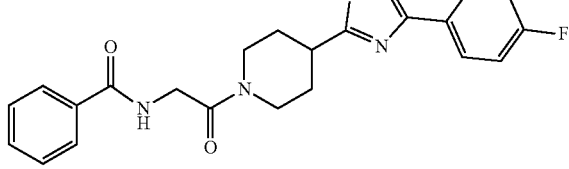

To a stirred solution of 1-(2-benzamidoacetyl)piperidine-4-carboxylic acid (120 mg, 413 μmol) in N,N-dimethylformamide (3 mL) was added 4-fluoro-N-hydroxybenzimidamide (76 mg, 496 μmol), (2-(1H-benzotriazol-1-yl)-1,1,3,3-tetramethyluronium hexafluorophosphate) (156 mg, 413 μmol) and N-ethyl-N-(propan-2-yl)propan-2-amine (160 mg, 1.24 mmol, 216 μL). The mixture was stirred at 20° C. for 2 h, then heated at 120° C. for 2 h. The reaction mixture cooled then purified directly by prep-HPLC (column: Luna C18 150×2.5 mm 5 μm; mobile phase: [water (0.225% FA)-acetonitrile]; B %: 35%-65%, 12 min) to give N-(2-(4-(3-(4-fluorophenyl)-1,2,4-oxadiazol-5-yl)piperidin-1-yl)-2-oxoethyl)benzamide (56 mg, 135 μmol, 33%) as a white solid. $^1$H NMR (400 MHz, CDCl$_3$) δ 8.13-8.07 (m, 2H), 7.90-7.86 (m, 2H), 7.58-7.52 (m, 1H), 7.51-7.45 (m, 2H), 7.35 (br. s., 1H), 7.23-7.16 (m, 2H), 4.56-4.47 (m, 1H), 4.33 (d, J=3.9 Hz, 2H), 3.93 (d, J=13.9 Hz, 1H), 3.41-3.31 (m, 2H), 3.23-3.13 (m, 1H), 2.33-2.21 (m, 2H), 2.02 (ddq, J=4.1, 10.5, 14.2 Hz, 2H); LCMS (ESI) m/z: [M+H]$^+$=409.2.

Example 42: N-(2-(4-(3-(3-fluorophenyl)-1,2,4-oxadiazol-5-yl)piperidin-1-yl)-2-oxoethyl)benzamide

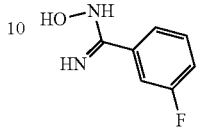

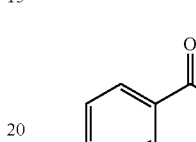

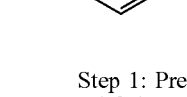

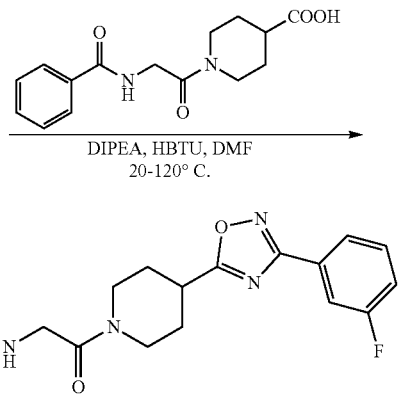

Step 1: Preparation of N-(2-(4-(3-(3-fluorophenyl)-1,2,4-oxadiazol-5-yl)piperidin-1 oxoethyl)benzamide

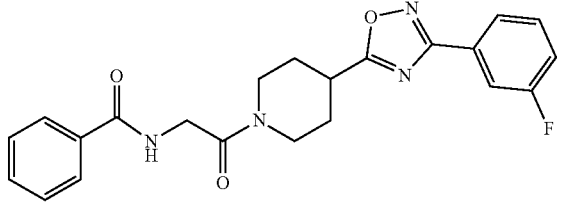 [SMILES: O=C(NCC(=O)N1CCC(c2nc(-c3cccc(F)c3)no2)CC1)c1ccccc1]

To a stirred solution of 1-(2-benzamidoacetyl)piperidine-4-carboxylic acid (120 mg, 413 μmol) in N,N-dimethylformamide (4 mL) was added 3-fluoro-N-hydroxybenzimidamide (76 mg, 496 μmol), (2-(1H-benzotriazol-1-yl)-1,1,3,3-tetramethyluronium hexafluorophosphate) (156 mg, 413 μmol) and N-ethyl-N-(propan-2-yl)propan-2-amine (160 mg, 1.24 mmol, 216 μL). The mixture was stirred at 20° C. for 2 h, then heated at 120° C. for 2 h. The reaction mixture was cooled then purified directly by prep-HPLC (column: Luna C8 100*30 5 μm; mobile phase: [water (10 mM ammonium carbonate)-acetonitrile]; B %: 35%-60%, 12 min) to give N-(2-(4-(3-(3-fluorophenyl)-1,2,4-oxadiazol-5-yl)piperidin-1-yl)-2-oxoethyl)benzamide (59 mg, 145 μmol, 35%) as a yellow solid. $^1$H NMR (400 MHz, CDCl$_3$) δ 7.85-7.76 (m, 3H), 7.71 (d, J=9.3 Hz, 1H), 7.49-7.35 (m, 4H), 7.26 (br. s., 1H), 7.15 (s, 1H), 4.43 (d, J=13.7 Hz, 1H), 4.24 (d, J=3.5 Hz, 2H), 3.84 (d, J=14.1 Hz, 1H), 3.33-3.22 (m, 2H), 3.14-3.04 (m, 1H), 2.26-2.13 (m, 2H), 2.00-1.85 ppm (m, 2H); LCMS (ESI) m/z: [M+H]$^+$=409.2.

Example 43: N-(2-(4-(3-(2-fluorophenyl)-1,2,4-oxadiazol-5-yl)piperidin-1-yl)-2-oxoethyl)benzamide

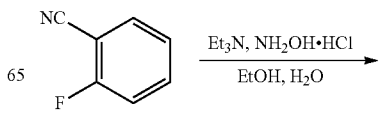

-continued

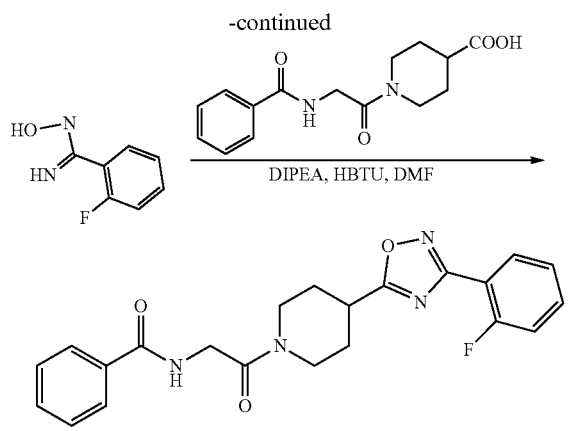

DIPEA, HBTU, DMF

Step 1: Preparation of 2-fluoro-N-hydroxybenzimidamide

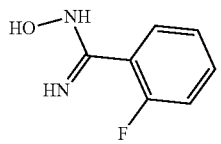 [SMILES: N=C(NO)c1ccccc1F]

To a stirred solution of 2-fluorobenzonitrile (1.0 g, 8.26 mmol, 877 μL) in ethanol (10 mL) was added hydroxylamine hydrochloride (1.15 g, 16.5 mmol), triethylamine (1.67 g, 16.5 mmol, 2.29 mL) and water (1 mL). The mixture was heated at 75° C. for 2 h. After cooling to 20° C., water (20 mL) was added. The mixture was extracted with dichloromethane (40 mL×4). The combined organic phases were washed with saturated aqueous sodium chloride solution (20 mL) and dried over anhydrous sodium sulfate, then filtered and concentrated in vacuo to give 2-fluoro-N-hydroxybenzimidamide (1.20 g, 7.79 mmol, 94%) as a white solid. LCMS (ESI) m/z: [M+H]$^+$=155.1.

Step 2: Preparation of N-(2-(4-(3-(2-fluorophenyl)-1,2,4-oxadiazol-5-yl)piperidin-1-yl)-2-oxoethyl)benzamide

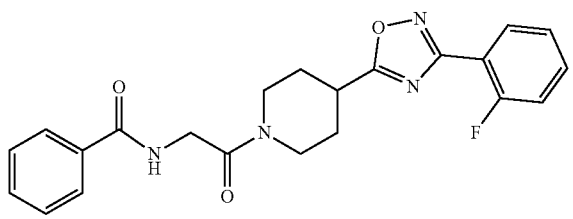 [SMILES: O=C(NCC(=O)N1CCC(c2nc(-c3ccccc3F)no2)CC1)c1ccccc1]

To a stirred solution of 1-(2-benzamidoacetyl)piperidine-4-carboxylic acid (150 mg, 516.7 μmol) in N,N-dimethylformamide (4 mL) was added 2-fluoro-N-hydroxybenzimidamide (95 mg, 620 μmol), (2-(1H-benzotriazol-1-yl)-1,1,3,3-tetramethyluronium hexafluorophosphate) (195 mg, 516.7 μmol) and N-ethyl-N-(propan-2-yl)propan-2-amine (200 mg, 1.55 mmol, 270 μL). The mixture was stirred at 20° C. for 2 h, then heated at 120° C. for 2 h. The reaction mixture was cooled then purified directly by prep-HPLC (column: Luna C8 100*30 5 μm; mobile phase: [water (10 mM ammonium carbonate)-acetonitrile]; B %: 30%-60%, 12 min) to give N-(2-(4-(3-(2-fluorophenyl)-1,2,4-oxadiazol-5-yl)piperidin-1-yl)-2-oxoethyl)benzamide (85 mg, 208.6 μmol, 40%) as a yellow solid. $^1$H NMR (400 MHz, CDCl$_3$) δ 7.98 (s, 1H), 7.81-7.75 (m, 2H), 7.48-7.34 (m, 4H), 7.28-7.20 (m, 2H), 7.16 (d, J=8.5 Hz, 1H), 4.42 (d, J=14.1 Hz, 1H), 4.23 (d, J=3.9 Hz, 2H), 3.84 (d, J=13.9 Hz, 1H), 3.29 (dt, J=4.1, 10.4 Hz, 2H), 3.14-3.04 (m, 1H), 2.25-2.13 (m, 2H), 2.02-1.86 (m, 2H); LCMS (ESI) m/z: [M+H]$^+$=409.2.

Example 44: 1-(4-(3-(3,4-dimethoxyphenyl)-1,2,4-oxadiazol-5-yl)piperidin-1-yl)-2-phenylethanone

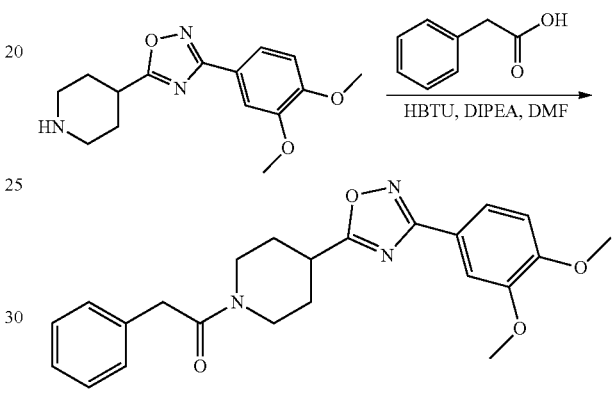

Step 1: Preparation of 1-(4-(3-(3,4-dimethoxyphenyl)-1,2,4-oxadiazol-5-yl)piperidin-1-yl)-2-phenylethanone

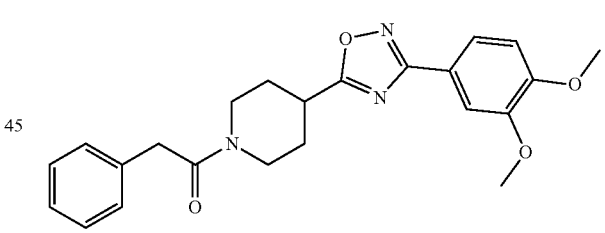

To a stirred solution of 3-(3,4-dimethoxyphenyl)-5-(4-piperidyl)-1,2,4-oxadiazole (150 mg, 518 μmol) in N,N-dimethylformamide (1.50 mL) was added (2-(1H-benzotriazol-1-yl)-1,1,3,3-tetramethyluronium hexafluorophosphate) (196 mg, 518 μmol), N-ethyl-N-(propan-2-yl)propan-2-amine (201 mg, 1.56 mmol, 271 μL) and 2-phenylacetic acid (74 mg, 544 μmol, 68 μL). The mixture was stirred at 20° C. for 16 h. The crude product was purified directly by prep-HPLC (column: Luna C8 100×30 5 μm; mobile phase: [water (10 mM ammonium carbonate)-acetonitrile]; B %: 35%-65%, 12 min) to give 1-[4-[3-(3,4-dimethoxyphenyl)-1,2,4-oxadiazol-5-yl]-1-piperidyl]-2-phenyl-ethanone (24 mg, 59 μmol, 11%) as a white solid. $^1$H NMR (400 MHz, METHANOL-d4) δ=7.63 (dd, J=2.0, 8.4 Hz, 1H), 7.55 (d, J=1.8 Hz, 1H), 7.39-7.20 (m, 5H), 7.05 (d, J=8.4 Hz, 1H), 4.49 (br d, J=13.5 Hz, 1H), 4.04 (br d, J=13.2 Hz, 1H), 3.88 (s, 6H), 3.82 (s, 2H), 3.34 (br d, J=2.6 Hz, 1H), 3.29-3.23 (m, 1H), 3.05-2.95 (m, 1H), 2.19-2.11 (m, 1H), 2.06-1.98 (m, 1H), 1.83-1.71 (m, 1H), 1.67-1.54 (m, 1H); LCMS (ESI) m/z: [M+H]⁺=408.3.

Example 45: 1-(4-(3-(3,4-dimethoxyphenyl)-1,2,4-oxadiazol-5-yl)piperidin-1-yl)-2-(6-methylpyrazin-2-yl)ethanone

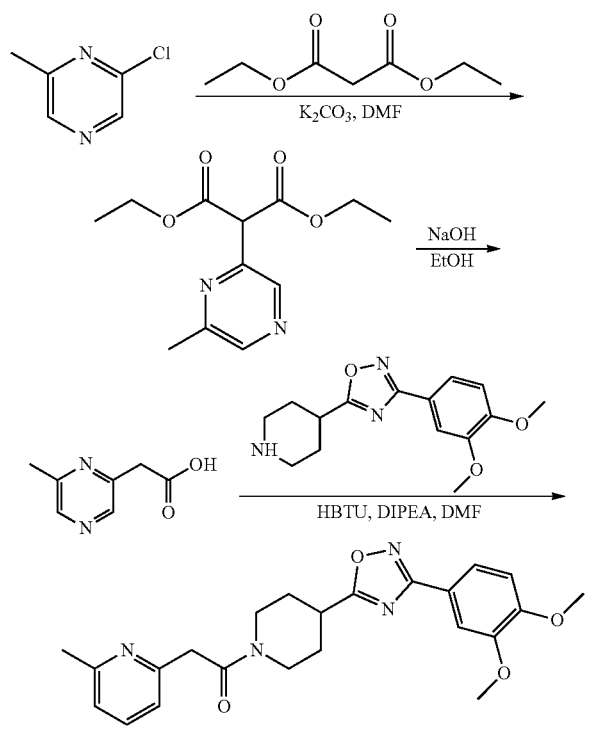

Step 1: Preparation of diethyl 2-(6-methylpyrazin-2-yl)malonate

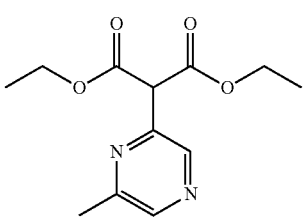 [SMILES: CCOC(=O)C(C(=O)OCC)c1cncc(C)n1]

To a stirred solution of 2-chloro-6-methylpyrazine (1.0 g, 7.78 mmol) in N,N-dimethylformamide (20 mL) was added diethyl malonate (3.12 g, 19.5 mmol, 2.94 mL) and potassium carbonate (2.69 g, 19.5 mmol), then the mixture was stirred at 110° C. for 16 h. The reaction mixture was cooled to 20° C., quenched with water (20 mL), and then extracted with ethyl acetate (60 mL×3). The combined organic phases were washed with saturated aqueous sodium chloride solution (20 mL), dried over anhydrous sodium sulfate, filtered and concentrated under reduced pressure. Purification by chromatography (silica, petroleumether:ethylacetate=50:1 to 10:1) gave diethyl 2-(6-methylpyrazin-2-yl)malonate (180 mg, 713.5 μmol, 9%) as a green oil. ¹H NMR (400 MHz, CDCl₃) δ 8.58 (s, 1H), 8.44 (s, 1H), 4.91 (s, 1H), 4.20-4.15 (q, J=7.2 Hz, 4H), 2.58 (s, 3H), 1.25-1.22 (t, J=7.2 Hz, 6H); LCMS (ESI) m/z: 253.1 [M+H]⁺.

Step 2: Preparation of 2-(6-methylpyrazin-2-yl)acetic acid

To a stirred solution of diethyl 2-(6-methylpyrazin-2-yl) malonate (180 mg, 713.5 μmol) in ethanol (10 mL) was added sodium hydroxide (2 M, 1.96 mL) and the mixture warmed at 60° C. for 2 h. The reaction was cooled to 20° C., and acidified with 1 M hydrochloric acid (5 mL). The mixture was concentrated in vacuo to give 2-(6-methylpyrazin-2-yl) acetic acid (1.42 g) as a light yellow solid that was used directly without further purification.

Step 3: Preparation of 1-(4-(3-(3,4-dimethoxyphenyl)-1,2,4-oxadiazol-5-yl)piperidin-1-yl)-2-(6-methylpyrazin-2-yl)ethanone To a stirred solution of 2-(6-methylpyrazin-2-yl)acetic acid (1.05 g, 415 μmol, purity 6%) in N,N-dimethylformamide (4 mL) was added 3-(3,4-dimethoxyphenyl)-5-(piperidin-4-yl)-1,2,4-oxadiazole (120 mg, 415 μmol), (2-(1H-benzotriazol-1-yl)-1,1,3,3-tetramethyluronium hexafluorophosphate) (157 mg, 415 μmol) and N-ethyl-N-(propan-2-yl)propan-2-amine (214 mg, 1.66 mmol, 289 μL). The mixture was stirred at 20° C. for 4 h. The reaction mixture was purified directly by prep-HPLC (column: Waters Xbridge 150×2.5 mm 5 μm; mobile phase: [water (10 mM ammonium carbonate)-acetonitrile]; B %: 25%-50%, 12 min) to give 1-(4-(3-(3,4-dimethoxyphenyl)-1,2,4-oxadiazol-5-yl)piperidin-1-yl)-2-(6-methylpyrazin-2-yl)ethanone (26 mg, 62 μmol, 15%) as a yellow solid. ¹H NMR (400 MHz, Methanol-d4) δ 8.41 (s, 2H), 7.68 (dd, J=1.9, 8.3 Hz, 1H), 7.61 (d, J=1.8 Hz, 1H), 7.10 (d, J=8.4 Hz, 1H), 4.51 (d, J=13.4 Hz, 1H), 4.22 (d, J=13.9 Hz, 1H), 4.12-3.93 (m, 2H), 3.92 (s, 6H), 3.52-3.38 (m, 2H), 3.12-3.02 (m, 1H), 2.57 (s, 3H), 2.28-2.17 (m, 2H), 2.04-1.80 (m, 2H); LCMS (ESI) m/z: [M+H]⁺=424.2.

Example 46: N-(2-(4-(3-(3,4-dimethoxyphenyl)-1,2,4-oxadiazol-5-yl)piperidin-1-yl)-2-oxoethyl)acetamide

Example 47: N-(2-(4-(3-(3,4-dimethoxyphenyl)-1,2,4-oxadiazol-5-yl)piperidin-1-yl)-2-oxoethyl)isobutyramide

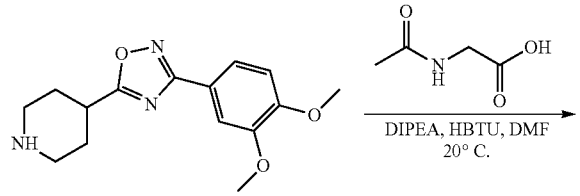

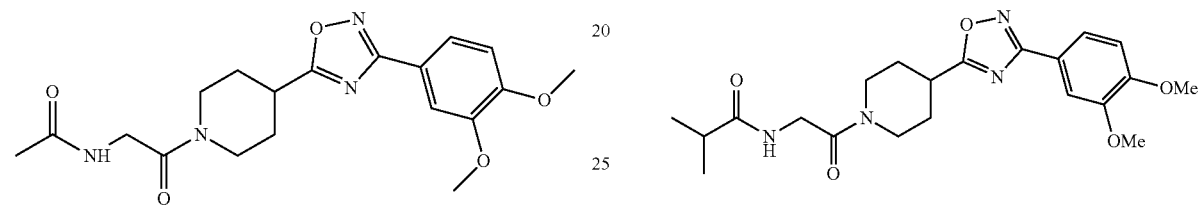

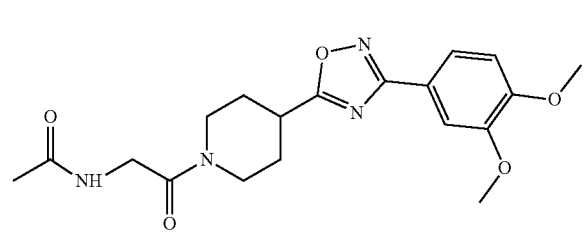 [SMILES: COc1ccc(-c2noc(C3CCN(C(=O)CNC(C)=O)CC3)n2)cc1OC]

Step 1: Preparation of N-(2-(4-(3-(3,4-dimethoxyphenyl)-1,2,4-oxadiazol-5-yl)piperidin-1-yl)-2-oxoethyl)acetamide

Step 1: Preparation of N-(2-(4-(3-(3,4-dimethoxyphenyl)-1,2,4-oxadiazol-5-yl)piperidin-1-yl)-2-oxoethyl)isobutyramide To a stirred solution of 3-(3,4-dimethoxyphenyl)-5-(4-piperidyl)-1,2,4-oxadiazole (250 mg, 864 μmol) in N,N-dimethylformamide (1.5 mL) was added (2-(1H-benzotriazol-1-yl)-1,1,3,3-tetramethyluronium hexafluorophosphate) (327 mg, 864 μmol), N-ethyl-N-(propan-2-yl)propan-2-amine (335 mg, 2.59 mmol, 452 μL) and 2-acetamidoacetic acid (106 mg, 907 μmol). The mixture was stirred at 20° C. for 16 h. The crude product was purified by prep-HPLC (column: Luna C8 100×30 5 μm; mobile phase: [water (10 mM ammonium carbonate)-acetonitrile]; B %: 20%-50%, 12 min) to give N-[2-[4-[3-(3,4-dimethoxyphenyl)-1,2,4-oxadiazol-5-yl]-1-piperidyl]-2-oxo-ethyl]acetamide (36 mg, 94 μmol, 11%) as a white solid. $^1$H NMR (400 MHz, METHANOL-d4) δ=7.69 (dd, J=1.9, 8.3 Hz, 1H), 7.61 (d, J=1.9 Hz, 1H), 7.10 (d, J=8.4 Hz, 1H), 4.47 (br d, J=14.2 Hz, 1H), 4.21-4.06 (m, 2H), 3.98 (br d, J=13.1 Hz, 1H), 3.92 (s, 6H), 3.47-3.38 (m, 2H), 3.13-3.00 (m, 1H), 2.31-2.16 (m, 2H), 2.05 (s, 3H), 2.00-1.79 (m, 2H); LCMS (ESI) m/z: [M+H]$^+$=389.2.

To a stirred solution of 2-amino-1-(4-(3-(3,4-dimethoxyphenyl)-1,2,4-oxadiazol-5-yl)piperidin-1-yl)ethanone (150 mg, 433 μmol) in dichloromethane (3 mL) was added isobutyryl chloride (55 mg, 520 μmol, 54 μL) and triethylamine (131 mg, 1.30 mmol, 180 μL) at 0° C. The mixture was warmed and stirred at 20° C. for 1 h. The reaction mixture was concentrated in vacuo to give crude product that was purified by HPLC prep-HPLC (column: Waters Xbridge 150×2.5 mm 5 μm; mobile phase: [water (10 mM ammonium carbonate)-acetonitrile]; B %: 23%-53%, 12 min) to give N-(2-(4-(3-(3,4-dimethoxyphenyl)-1,2,4-oxadiazol-5-yl)piperidin-1-yl)-2-oxoethyl)isobutyramide (85 mg, 204 μmol, 47%) as a white solid. $^1$H NMR (400 MHz, CDCl$_3$) δ 7.74-7.68 (m, 1H), 7.58 (d, J=1.9 Hz, 1H), 6.98 (d, J=8.4 Hz, 1H), 6.63 (br. s., 1H), 4.49 (d, J=13.3 Hz, 1H), 4.12 (d, J=4.0 Hz, 2H), 3.98 (d, J=7.3 Hz, 6H), 3.87 (d, J=14.1 Hz, 1H), 3.36-3.26 (m, 2H), 3.13 (t, J=10.9 Hz, 1H), 2.50 (td, J=6.9, 13.8 Hz, 1H), 2.23 (br. s., 2H), 2.06-1.92 (m, 2H), 1.22 (d, J=6.9 Hz, 6H); LCMS (ESI) m/z: [M+H]$^+$=417.3.

Example 48: N-(2-(4-(3-(3,4-dimethoxyphenyl)-1,2,4-oxadiazol-5-yl)piperidin-1-yl)-2-oxoethyl)cyclohexanecarboxamide

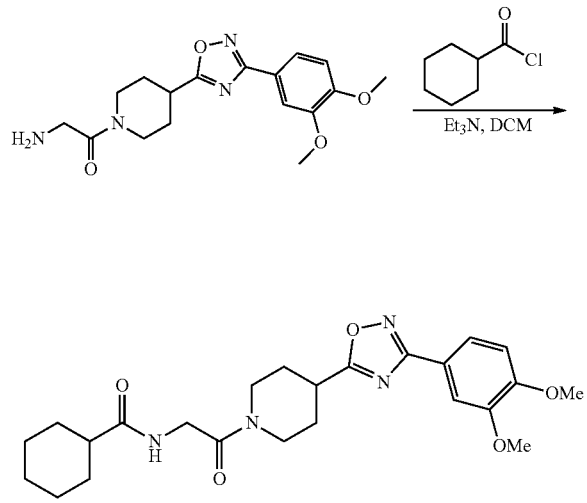

Step 1: Preparation of N-(2-(4-(3-(3,4-dimethoxyphenyl)-1,2,4-oxadiazol-5-yl)piperidin-1-yl)-2-oxoethyl)cyclohexanecarboxamide

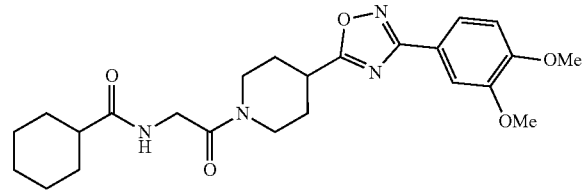 [SMILES: COc1ccc(-c2noc(C3CCN(C(=O)CNC(=O)C4CCCCC4)CC3)n2)cc1OC]

To a stirred solution of 2-amino-1-(4-(3-(3,4-dimethoxyphenyl)-1,2,4-oxadiazol-5-yl)piperidin-1-yl)ethanone (150 mg, 433 μmol) in dichloromethane (3 mL) was added cyclohexanecarbonyl chloride (76 mg, 520 μmol, 69 μL) and triethylamine (131 mg, 1.30 mmol, 180 μL) at 0° C. The mixture was warmed and stirred at 20° C. for 1 h. The reaction mixture was concentrated in vacuo to give a crude product that was purified by prep-HPLC (column: Waters Xbridge 150×2.5 mm 5 μm; mobile phase: [water (10 mM ammonium carbonate)-acetonitrile]; B %: 23%-53%, 12 min) to give N-(2-(4-(3-(3,4-dimethoxyphenyl)-1,2,4-oxadiazol-5-yl)piperidin-1-yl)-2-oxoethyl)cyclohexanecarboxamide (78 mg, 171 μmol, 39%) as a white solid. $^1$H NMR (400 MHz, CDCl$_3$) δ 7.73-7.68 (m, 1H), 7.60-7.57 (m, 1H), 6.98 (d, J=8.4 Hz, 1H), 6.64-6.59 (m, 1H), 4.53-4.45 (m, 1H), 4.11 (d, J=4.0 Hz, 2H), 3.98 (d, J=7.2 Hz, 6H), 3.86 (d, J=13.3 Hz, 1H), 3.36-3.26 (m, 2H), 3.12 (t, J=10.7 Hz, 1H), 2.28-2.18 (m, 3H), 2.05-1.89 (m, 4H), 1.82 (d, J=12.3 Hz, 2H), 1.71 (d, J=10.9 Hz, 2H), 1.54-1.42 (m, 2H), 1.37-1.22 (m, 3H); LCMS (ESI) m/z: [M+H]$^+$=457.3.

Example 49: 1-[3-(3,4-dimethoxyphenyl)-1,2,4-oxadiazol-5-yl]-N-(2-phenylethyl)piperidine-4-carboxamide

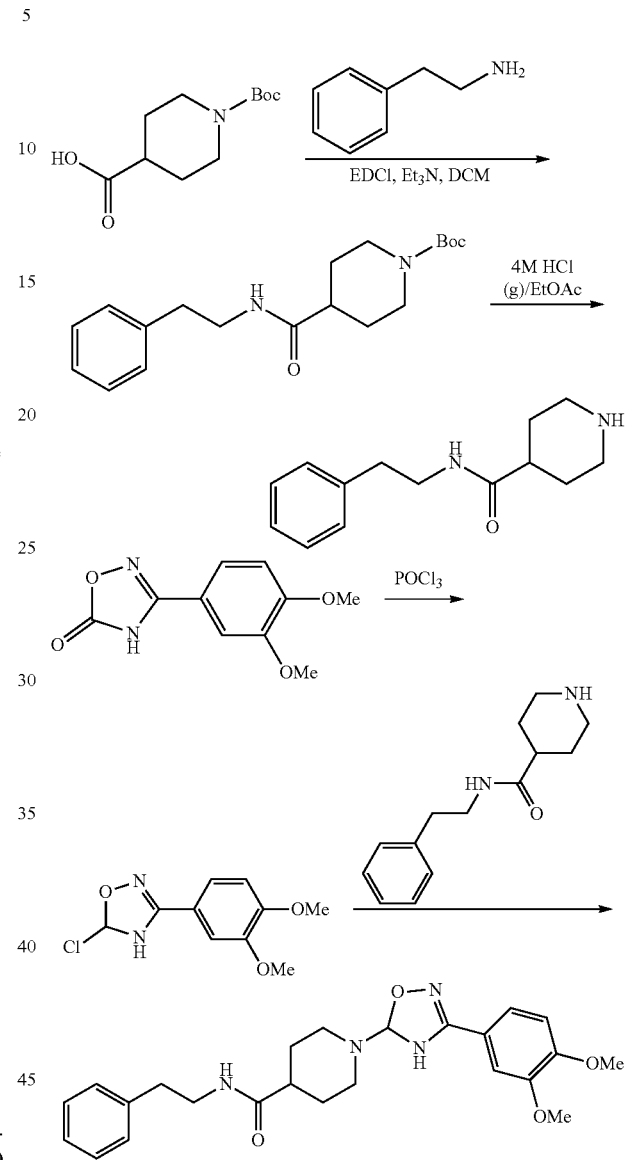

Step 1: Preparation of tert-butyl 4-(phenethylcarbamoyl)piperidine-1-carboxylate

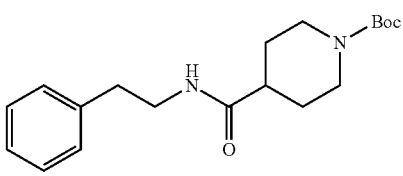 [SMILES: CC(C)(C)OC(=O)N1CCC(C(=O)NCCc2ccccc2)CC1]

To a stirred solution of 1-tert-butoxycarbonylpiperidine-4-carboxylic acid (1.0 g, 4.36 mmol) in dichloromethane (15 mL) was added 2-phenylethanamine (528 mg, 4.36 mmol, 544 μL), 1-ethyl-3-(3-dimethylaminopropyl)carbodiimide (835 mg, 4.36 mmol) and triethylamine (44 mg, 436 µmol, 60 µL). The mixture was stirred at 20° C. for 5 h. The reaction mixture was concentrated in vacuo to give a crude product that was purified by chromatography (silica, petroleum ether/ethyl acetate from 10/1 to 1/1) to give tert-butyl 4-(2-phenylethylcarbamoyl)piperidine-1-carboxylate (800 mg, 2.41 mmol, 55%) as a white solid. LCMS (ESI) m/z: 355.2 [M+Na]+.

Step 2: Preparation of N-phenethylpiperidine-4-carboxamide

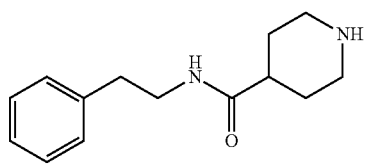 [SMILES: O=C(NCCc1ccccc1)C1CCNCC1]

A solution of tert-butyl 4-(2-phenylethylcarbamoyl)piperidine-1-carboxylate (800 mg, 2.41 mmol) in 4N hydrochloric acid/ethyl acetate (10 mL) was stirred at 20° C. for 0.5 h. The reaction mixture was concentrated in vacuo to give N-(2-phenylethyl)piperidine-4-carboxamide (720 mg) as a hydrochloric acid salt and as a white solid.

Step 3: Preparation of 5-chloro-3-(3,4-dimethoxyphenyl)-1,2,4-oxadiazole

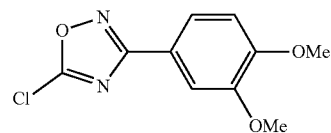

3-(3,4-dimethoxyphenyl)-4H-1,2,4-oxadiazol-5-one (900 mg, 4.05 mmol) was added to a mixture of N,N-dimethylformamide (2 mL) and phosphoryl chloride (24.8 g, 161.4 mmol, 15 mL). The mixture was equipped with calcium chloride tube and the mixture was heated at 100° C. for 16 h. The mixture was cooled to 0° C. and concentrated under reduced pressure. The residue was poured into ice-water (20 mL) and stirred for 10 min, then the aqueous phase was extracted with dichloromethane (10 mL×5). The combined organic phases were washed with saturated aqueous sodium chloride solution (10 mL), dried over anhydrous sodium sulfate, filtered and concentrated in vacuo. The residue was purified by chromatography (silica, petroleum ether/ethyl acetate=5/1, 1/1) to give 5-chloro-3-(3,4-dimethoxyphenyl)-1,2,4-oxadiazole (104 mg, 432 µmol, 11%) as a white solid.

Step 4: Preparation of 1-(3-(3,4-dimethoxyphenyl)-1,2,4-oxadiazol-5-yl)-N-phenethylpiperidine-4-carboxamide

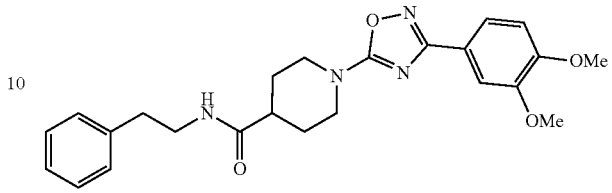

To a stirred solution of 5-chloro-3-(3,4-dimethoxyphenyl)-1,2,4-oxadiazole (95 mg, 395 µmol) in N-methyl-2-pyrrolidone (2 mL) was added N-(2-phenylethyl)piperidine-4-carboxamide (110 mg, 474 µmol) and N-ethyl-N-(propan-2-yl)propan-2-amine (102 mg, 790 µmol, 137 µL) at 20° C. Then the mixture was heated to 120° C. and stirred for 5 h. The crude product was purified by prep-HPLC (column: Luna C8 100×30 5 µm; mobile phase: [water (10 mM ammonium carbonate)-acetonitrile]; B %: 25%-65%, 12 min), Compound 1-[3-(3,4-dimethoxyphenyl)-1,2,4-oxadiazol-5-yl]-N-(2-phenylethyl)piperidine-4-carboxamide (117 mg, 266 µmol, 67%) as a white solid. 1H NMR (400 MHz, METHANOL-d4) δ=7.57 (dd, J=2.0, 8.4 Hz, 1H), 7.51 (d, J=1.9 Hz, 1H), 7.33-7.27 (m, 2H), 7.25-7.18 (m, 3H), 7.06 (d, J=8.4 Hz, 1H), 4.22 (br d, J=13.3 Hz, 2H), 3.90 (s, 6H), 3.44 (t, J=7.3 Hz, 2H), 3.27-3.17 (m, 2H), 2.82 (t, J=7.2 Hz, 2H), 2.51-2.40 (m, 1H), 1.92-1.67 (m, 4H); LCMS (ESI) m/z: [M+H]+=437.3.

Example 50: 1-(3,4-dimethylphenyl)-4-(4-(5-(p-tolyl)-1,2,4-oxadiazol-3-yl)piperidine-1-carbonyl)pyrrolidin-2-one

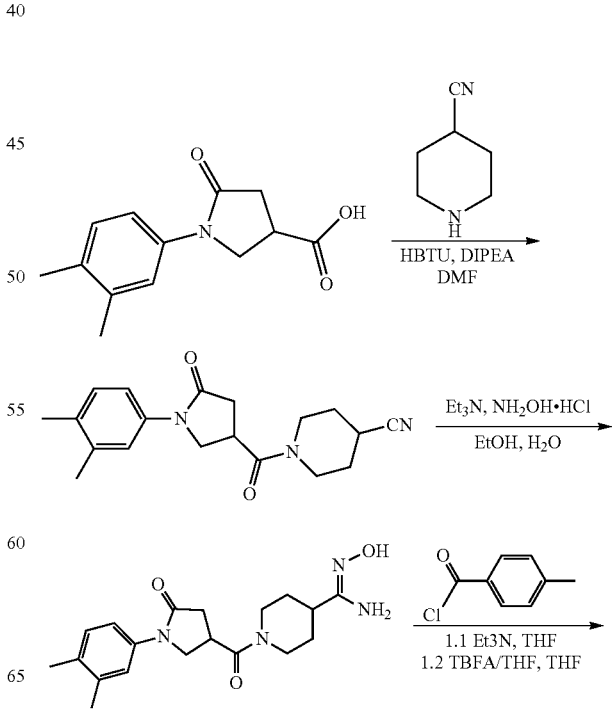

-continued

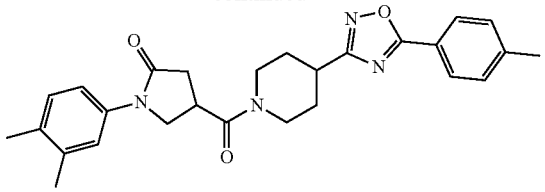

Step 1: Preparation of 1-(1-(3,4-dimethylphenyl)-5-oxopyrrolidine-3-carbonyl)piperidine-4-carbonitrile

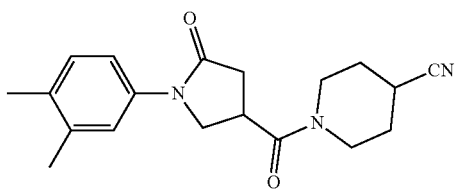 [SMILES: Cc1ccc(N2CC(C(=O)N3CCC(C#N)CC3)CC2=O)cc1C]

To a stirred solution of 1-(3,4-dimethylphenyl)-5-oxopyrrolidine-3-carboxylic acid (1.0 g, 4.29 mmol) in N,N-dimethylformamide (10 mL) was added piperidine-4-carbonitrile (567 mg, 5.15 mmol), (2-(1H-benzotriazol-1-yl)-1,1,3,3-tetramethyluronium hexafluorophosphate) (1.63 g, 4.29 mmol) and N-ethyl-N-(propan-2-yl)propan-2-amine (1.66 g, 12.87 mmol, 2.25 mL). The mixture was stirred at 20° C. for 16 h. The reaction mixture was quenched with water (10 mL), then the mixture was extracted with ethyl acetate (20 mL×4). The combined organic phases were washed with saturated aqueous sodium chloride solution (5 mL), dried over anhydrous sodium sulfate, filtered and concentrated in vacuo to a yellow oil (1.6 g). A portion of the crude product (0.3 g) was purified by prep-HPLC (column: Waters Xbridge 150×2.5 mm 5 μm; mobile phase: [water (10 mM ammonium carbonate)-acetonitrile]; B %: 20%-50%, 12 min) to give 1-(1-(3,4-dimethylphenyl)-5-oxopyrrolidine-3-carbonyl)piperidine-4-carbonitrile for analysis (144 mg). The remainder of the crude product was used directly without purification. $^1$H NMR (400 MHz, Methanol-d4) δ 7.37 (d, J=2.5 Hz, 1H), 7.31-7.25 (m, 1H), 7.15 (d, J=8.2 Hz, 1H), 4.08 (d, J=7.0 Hz, 5H), 3.59-3.37 (m, 2H), 3.16-3.03 (m, 1H), 2.91-2.79 (m, 2H), 2.28 (d, J=10.2 Hz, 6H), 2.10-1.72 (m, 4H); LCMS (ESI) m/z: [M+H]$^+$=326.2.

Step 2: Preparation of (Z)-1-(1-(3,4-dimethylphenyl)-5-oxopyrrolidine-3-carbonyl)-N'-hydroxypiperidine-4-carboximidamide

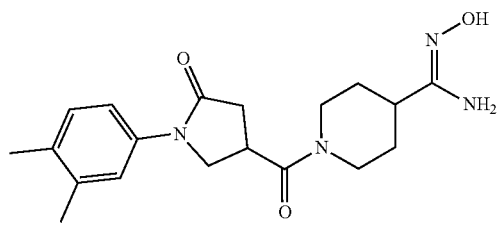 [SMILES: Cc1ccc(N2CC(C(=O)N3CCC(/C(N)=N/O)CC3)CC2=O)cc1C]

To a stirred solution of 1-(1-(3,4-dimethylphenyl)-5-oxopyrrolidine-3-carbonyl)piperidine-4-carbonitrile (1.30 g, 4.00 mmol) in ethanol (10 mL) was added hydroxylamine hydrochloride (555 mg, 8.00 mmol), triethylamine (809 mg, 8.00 mmol, 1.11 mL) and water (1 mL). The mixture was heated at 75° C. for 2 h. After cooling to 20° C., water (20 mL) was added to the solution. The mixture was extracted with dichloromethane (40 mL×4). The combined organic phases were washed with saturated aqueous sodium chloride solution (20 mL) and dried over anhydrous sodium sulfate, filtered and concentrated in vacuo to give a brown solid (1.4 g). A portion of crude product (0.3 g) was purified by prep-HPLC (column: Luna C18 150×2.5 mm 5 μm; mobile phase: [water (0.225% TFA)-acetonitrile]; B %: 15%-40%, 12 min) to give (Z)-1-(1-(3,4-dimethylphenyl)-5-oxopyrrolidine-3-carbonyl)-N'-hydroxypiperidine-4-carboximidamide. The remainder was used directly in the next step. $^1$H NMR (400 MHz, DMSO-d6) δ 8.86-8.77 (m, 1H), 8.15 (s, 1H), 7.45-7.33 (m, 2H), 7.12 (dd, J=8.2, 2.4 Hz, 1H), 5.36 (br. s., 2H), 4.47-4.32 (m, 1H), 4.06-3.86 (m, 3H), 3.75-3.60 (m, 1H), 3.07 (br. s., 1H), 2.80-2.57 (m, 3H), 2.36-2.24 (m, 1H), 2.21 (d, J=11.8 Hz, 6H), 1.83-1.67 (m, 2H), 1.56 ppm (br. s., 2H); LCMS (ESI) m/z: [M+H]$^+$=359.3.

Step 3: Preparation of 1-(3,4-dimethylphenyl)-4-(4-(5-(p-tolyl)-1,2,4-oxadiazol-3-yl)piperidine-1-carbonyl)pyrrolidin-2-one

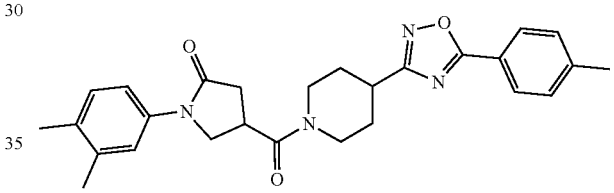

To a stirred solution of (Z)-1-(1-(3,4-dimethylphenyl)-5-oxopyrrolidine-3-carbonyl)-N'-hydroxypiperidine-4-carboximidamide (300 mg, 837 μmol) in tetrahydrofuran (8 mL) was added 4-methylbenzoyl chloride (155 mg, 1.00 mmol, 132 μL) and triethylamine (254 mg, 2.51 mmol, 348 μL) at 0° C., then the mixture was warmed at 20° C. After 3 h, to the reaction mixture was added ethyl acetate and water and the organic phase was separated. The organic phase was washed with water and saturated aqueous sodium chloride solution and then dried over anhydrous sodium sulfate. The mixture was filtered and concentrated under reduced pressure. To the residue were added tetrahydrofuran (8 mL) and a tetrabutylammonium fluoride in tetrahydrofuran (1 M, 2.51 mL) solution, and the mixture warmed at 50° C. for 16 h. The reaction mixture was concentrated in vacuo to give a crude product that was purified by prep-HPLC (column: Luna C18 100*30 5 μm; mobile phase: [water (0.225% TFA)-acetonitrile]; B %: 45%-75%, 12 min) to give the racemic of 1-(3,4-dimethylphenyl)-4-(4-(5-(p-tolyl)-1,2,4-oxadiazol-3-yl)piperidine-1-carbonyl)pyrrolidin-2-one (106 mg, 0.23 mmol, 28%) as a white solid. $^1$H NMR (400 MHz, CDCl$_3$) δ 8.06-7.99 (m, 2H), 7.41-7.33 (m, 3H), 7.31 (d, J=2.0 Hz, 1H), 7.15 (d, J=8.0 Hz, 1H), 4.60 (t, J=13.2 Hz, 1H), 4.30 (dd, J=7.4, 9.5 Hz, 1H), 4.04-3.88 (m, 2H), 3.60 (quin, J=8.5 Hz, 1H), 3.42-3.31 (m, 1H), 3.25-3.14 (m, 1H), 3.11-2.94 (m, 2H), 2.88-2.78 (m, 1H), 2.47 (s, 3H), 2.32-2.12 (m, 8H), 2.03-1.86 (m, 2H); LCMS (ESI) m/z: [M+H]$^+$=459.3.

Example 51: 1-(3,4-dimethylphenyl)-4-(4-(5-(m-tolyl)-1,2,4-oxadiazol-3-yl)piperidine-1-carbonyl)pyrrolidin-2-one

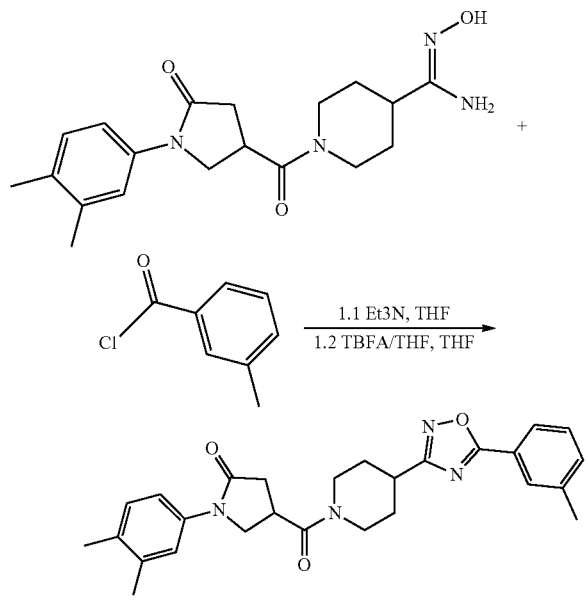

Step 1: Preparation of 1-(3,4-dimethylphenyl)-4-(4-(5-(m-tolyl)-1,2,4-oxadiazol-3-yl)piperidine-1-carbonyl)pyrrolidin-2-one

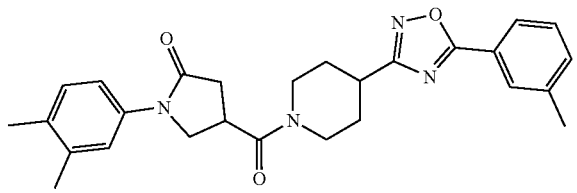 [SMILES: Cc1cccc(-c2nc(C3CCN(C(=O)C4CC(=O)N(c5ccc(C)c(C)c5)C4)CC3)no2)c1]

To a stirred solution of (Z)-1-(1-(3,4-dimethylphenyl)-5-oxopyrrolidine-3-carbonyl)-N'-hydroxypiperidine-4-carboximidamide (280 mg, 781 μmol) in tetrahydrofuran (8 mL) was added 3-methylbenzoyl chloride (144 mg, 937 μmol, 123 μL) and triethylamine (237 mg, 2.34 mmol, 324 μL) at 0° C., the mixture was stirred at 20° C. for 3 h. To the reaction mixture was added ethyl acetate and water and the organic phase was separated. The organic phase was washed with water and saturated aqueous sodium chloride solution, then dried over anhydrous sodium sulfate, filtered and evaporated under reduced pressure. To the residue were added tetrahydrofuran (8 mL) and a tetrabutylammonium fluoride in tetrahydrofuran solution (1 M, 2.34 mL). The mixture was warmed to 50° C. and stirred for 16 h. The reaction mixture was cooled and concentrated in vacuo to give a crude product that was purified by prep-HPLC (column: Luna C8 100×30 5 μm; mobile phase: [water (10 mM ammonium carbonate)-acetonitrile]; B %: 40%-75%, 12 min) to give the racemic of 1-(3,4-dimethylphenyl)-4-(4-(5-(m-tolyl)-1,2,4-oxadiazol-3-yl)piperidine-1-carbonyl)pyrrolidin-2-one (156 mg, 0.34 mmol, 44%) as a white solid. $^1$H NMR (400 MHz, CDCl$_3$) δ 7.99-7.91 (m, 2H), 7.43 (d, J=1.0 Hz, 3H), 7.32-7.29 (m, 1H), 7.15 (d, J=8.3 Hz, 1H), 4.60 (t, J=14.1 Hz, 1H), 4.30 (dd, J=7.3, 9.6 Hz, 1H), 4.04-3.88 (m, 2H), 3.65-3.54 (m, 1H), 3.37 (d, J=7.0 Hz, 1H), 3.21 (d, J=3.5 Hz, 1H), 3.11-2.94 (m, 2H), 2.88-2.78 (m, 1H), 2.48 (s, 3H), 2.32-2.13 (m, 8H), 1.93 (d, J=12.2 Hz, 2H); LCMS (ESI) m/z: [M+H]$^+$=459.3.

Example 52: (4-(5-(3-fluorophenyl)-1,2,4-oxadiazol-3-yl)piperidin-1-yl)(4-isopropylphenyl)methanone

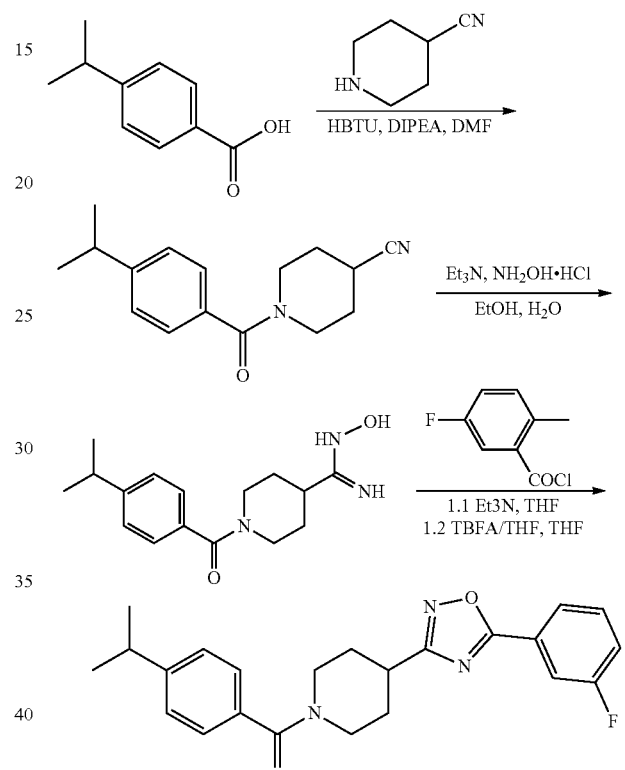

Step 1: Preparation of 1-(4-isopropylbenzoyl)piperidine-4-carbonitrile

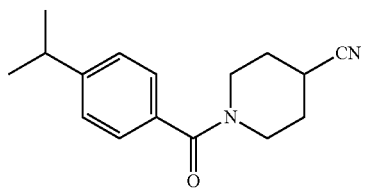 [SMILES: CC(C)c1ccc(C(=O)N2CCC(C#N)CC2)cc1]

To a stirred solution of 4-isopropylbenzoic acid (1.0 g, 6.09 mmol) in N,N-dimethylformamide (10 mL) was added piperidine-4-carbonitrile (805 mg, 7.31 mmol), (2-(1H-benzotriazol-1-yl)-1,1,3,3-tetramethyluronium hexafluorophosphate) (2.31 g, 6.09 mmol) and N-ethyl-N-(propan-2-yl)propan-2-amine (2.36 g, 18.27 mmol, 3.19 mL). The mixture was stirred at 20° C. for 16 h. The reaction mixture was quenched with water (10 mL), then the mixture was extracted with ethyl acetate (40 mL×4). The combined organic phases were washed with saturated aqueous sodium chloride solution (10 mL), dried over anhydrous sodium sulfate, filtered and concentrated to give yellow oil (1.8 g). A portion of crude product (0.2 g) was purified by prep-HPLC (column: Waters Xbridge 150×2.5 mm 5 μm; mobile phase: [water (10 mM ammonium carbonate)-acetonitrile]; B %: 25%-55%, 12 min) to give 1-(4-isopropylbenzoyl) piperidine-4-carbonitrile (115 mg) as a sample for analysis. The remainder was used directly. $^1$H NMR (400 MHz, Methanol-d4) δ 7.37 (s, 4H), 4.16-3.40 (m, 4H), 3.15-3.07 (m, 1H), 3.02-2.93 (m, 1H), 2.10-1.76 (m, 4H), 1.31-1.26 (m, 6H); LCMS (ESI) m/z: [M+H]$^+$=257.2.

Step 2: Preparation of N-hydroxy-1-(4-isopropylbenzoyl)piperidine-4-carboximidamide

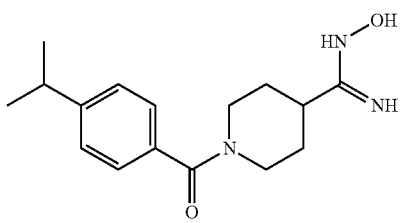 [SMILES: CC(C)c1ccc(C(=O)N2CCC(C(=N)NO)CC2)cc1]

To a stirred solution of 1-(4-isopropylbenzoyl)piperidine-4-carbonitrile (1.60 g, 6.24 mmol) in ethanol (15 mL) was added hydroxylamine hydrochloride (867 mg, 12.5 mmol), triethylamine (1.26 g, 12.48 mmol, 1.73 mL) and water (1.50 mL). The mixture was heated at 75° C. for 2 h. After cooling to 20° C., water (20 mL) was added to the solution. The mixture was extracted with dichloromethane (40 mL×4). The combined organic phases were washed with saturated aqueous sodium chloride solution (20 mL) and dried over anhydrous sodium sulfate, then filtered and concentrated in vacuo to give N-hydroxy-1-(4-isopropylbenzoyl)piperidine-4-carboximidamide (1.60 g, 5.53 mmol, 89%) as a white solid that was used directly without further purification. $^1$H NMR (400 MHz, Methanol-d4) δ 7.40-7.33 (m, 4H), 4.78-4.58 (m, 1H), 3.94-3.73 (m, 1H), 3.22 (d, J=7.3 Hz, 2H), 3.02-2.95 (m, 1H), 2.50-2.35 (m, 1H), 1.96-1.67 (m, 4H), 1.31-1.27 (m, 6H).

Step 3: Preparation of (4-(5-(3-fluorophenyl)-1,2,4-oxadiazol-3-yl)piperidin-1-yl)(4-isopropylphenyl) methanone

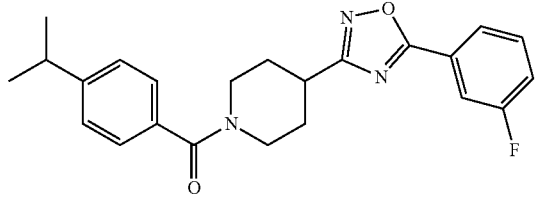 [SMILES: CC(C)c1ccc(C(=O)N2CCC(c3noc(-c4cccc(F)c4)n3)CC2)cc1]

To a stirred solution of N-hydroxy-1-(4-isopropylbenzoyl)piperidine-4-carboximidamide (200 mg, 691 μmol) in tetrahydrofuran (5 mL) was added 3-fluorobenzoyl chloride (131 mg, 829 μmol, 99 μL) and triethylamine (209 mg, 2.07 mmol, 287 μL) at 0° C. The mixture was warmed and then stirred at 20° C. for 16 h. To the reaction mixture was added ethyl acetate and water and the organic phase was separated. The organic phase was washed with water and saturated aqueous sodium chloride solution, then dried over anhydrous sodium sulfate, filtered and concentrated in vacuo. To the obtained residue were added tetrahydrofuran (5 mL) and a solution of tetrabutylammonium fluoride in tetrahydrofuran (1 M, 2.07 mL), then the mixture was warmed at 50° C. for 16 h. The reaction mixture was concentrated in vacuo to give a crude product that was purified by prep-HPLC (column: Waters Xbridge 150×2.5 mm 5 μm; mobile phase: [water (10 mM ammonium carbonate)-acetonitrile]; B %: 50%-80%, 12 min) to give (4-(5-(3-fluorophenyl)-1,2,4-oxadiazol-3-yl)piperidin-1-yl)(4-isopropylphenyl)methanone (76 mg, 193.5 μmol, 28%) as a yellow oil. $^1$H NMR (400 MHz, CDCl$_3$) δ 7.85 (d, J=7.7 Hz, 1H), 7.78-7.72 (m, 1H), 7.45 (dt, J=5.6, 8.0 Hz, 1H), 7.32-7.27 (m, 2H), 7.26-7.20 (m, 2H), 7.18 (s, 1H), 4.76-3.64 (m, 2H), 3.20-2.97 (m, 3H), 2.86 (td, J=6.9, 13.8 Hz, 1H), 2.18-1.74 (m, 4H), 1.19 (d, J=6.9 Hz, 6H); LCMS (ESI) m/z: [M+H]$^+$=394.2.

Example 53: (4-(3-(4-ethoxy-3-methoxyphenyl)-1,2,4-oxadiazol-5-yl)piperidin-1-yl)(piperidin-1-yl) methanone

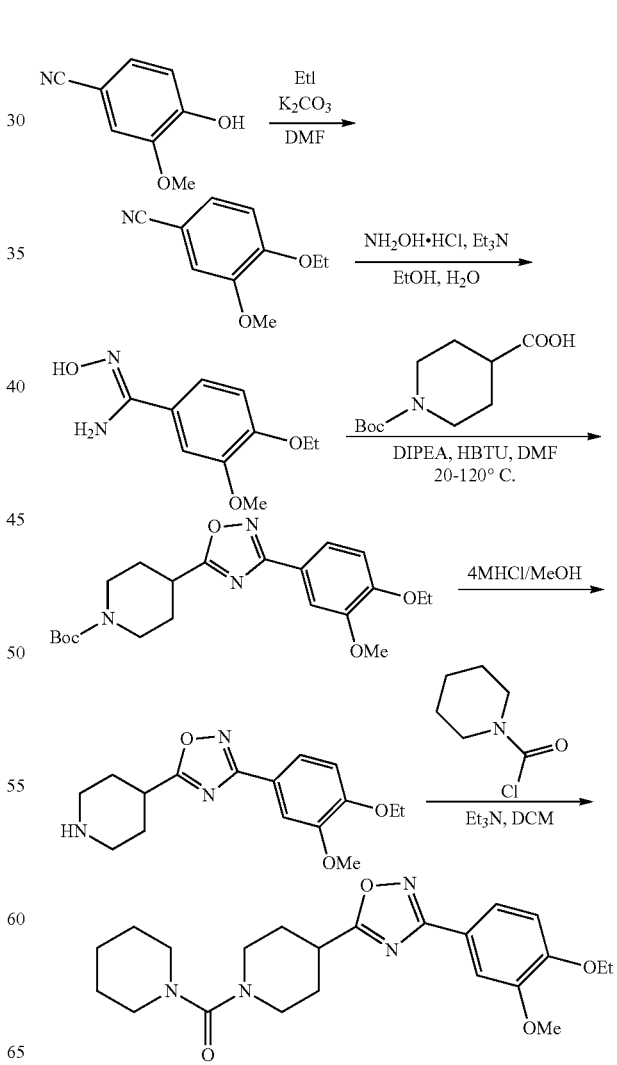

Step 1: Preparation of 4-ethoxy-3-methoxybenzonitrile

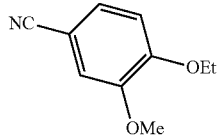 [SMILES: CCOc1ccc(C#N)cc1OC]

To a stirred solution of 4-hydroxy-3-methoxybenzonitrile (5.0 g, 33.5 mmol) in N,N-dimethylformamide (50 mL) was added iodoethane (6.27 g, 40.2 mmol, 3.22 mL) and potassium carbonate (9.27 g, 67.0 mmol) at 0° C., then the reaction was warmed and stirred at 40° C. for 16 h. The reaction mixture was quenched by addition of water (50 mL) then the mixture was extracted with ethyl acetate (80 mL×3). The combined organic phases were washed with saturated aqueous sodium chloride solution (50 mL), dried over anhydrous sodium sulfate, filtered and concentrated to give 4-ethoxy-3-methoxybenzonitrile (5.80 g, 32.7 mmol, 98%) as a white solid. $^1$H NMR (400 MHz, CDCl$_3$) δ 7.20-7.16 (m, 1H), 7.00 (d, J=1.9 Hz, 1H), 6.81 (d, J=8.4 Hz, 1H), 4.07 (q, J=6.9 Hz, 2H), 3.82 (s, 3H), 1.45-1.39 (m, 3H).

Step 2: Preparation of (Z)-4-ethoxy-N'-hydroxy-3-methoxybenzimidamide

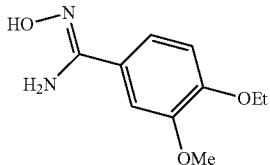 [SMILES: CCOc1ccc(/C(N)=N/O)cc1OC]

To a stirred solution of 4-ethoxy-3-methoxybenzonitrile (5.80 g, 32.7 mmol) in ethanol (50 mL) was added hydroxylamine hydrochloride (4.55 g, 65.5 mmol), triethylamine (6.62 g, 65.46 mmol, 9.07 mL) and water (5 mL). The mixture was heated at 75° C. for 2 h. After cooling to 20° C., the solvents were evaporated under vacuum, and water (20 mL) was added to the solution. The mixture was extracted with dichloromethane (60 mL×3). The combined organic extracts were washed with saturated aqueous sodium chloride solution (20 mL), dried over anhydrous sodium sulfate, and then filtered and concentrated in vacuo to give (Z)-4-ethoxy-N'-hydroxy-3-methoxybenzimidamide (5.96 g, 28.4 mmol, 87%) as a white solid. $^1$H NMR (400 MHz, DMSO-d6) δ 9.44 (br. s., 1H), 7.28-7.14 (m, 2H), 6.90 (d, J=8.4 Hz, 1H), 5.73 (s, 2H), 4.00 (q, J=6.9 Hz, 2H), 3.75 (s, 3H), 1.31 (t, J=7.1 Hz, 3H).

Step 3: Preparation of tert-butyl 4-(3-(4-ethoxy-3-methoxyphenyl)-1,2,4-oxadiazol-5-yl)piperidine-1-carboxylate

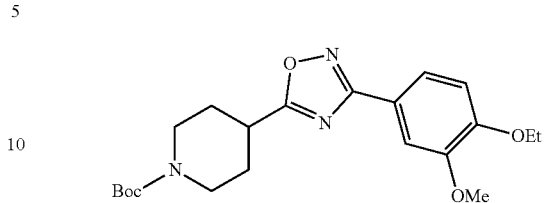

To a stirred solution of (Z)-4-ethoxy-N'-hydroxy-3-methoxybenzimidamide (1.0 g, 4.76 mmol) in N,N-dimethylformamide (15 mL) was added 1-(tert-butoxycarbonyl)piperidine-4-carboxylic acid (1.09 g, 4.76 mmol), (2-(1H-benzotriazol-1-yl)-1,1,3,3-tetramethyluronium hexafluorophosphate) (1.81 g, 4.76 mmol) and N-ethyl-N-(propan-2-yl)propan-2-amine (1.85 g, 14.28 mmol, 2.49 mL). The mixture was stirred at 20° C. for 16 h then heated at 120° C. for 2 h. The reaction mixture was cooled then quenched by addition of water (40 mL), then the mixture was extracted with ethyl acetate (80 mL×4). The combined organic phases were washed with saturated aqueous sodium chloride solution (30 mL), dried over anhydrous sodium sulfate, filtered and concentrated to give tert-butyl 4-(3-(4-ethoxy-3-methoxyphenyl)-1,2,4-oxadiazol-5-yl)piperidine-1-carboxylate (2.56 g) as a yellow oil. LCMS (ESI) m/z: [M+H]$^+$=404.3.

Step 4: Preparation of 3-(4-ethoxy-3-methoxyphenyl)-5-(piperidin-4-yl)-1,2,4-oxadiazole

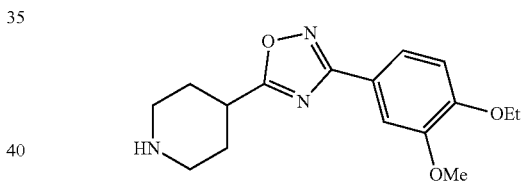

To a stirred solution of tert-butyl 4-(3-(4-ethoxy-3-methoxyphenyl)-1,2,4-oxadiazol-5-yl)piperidine-1-carboxylate (1.0 g, 2.48 mmol) in methanol (5 mL) was added 4 M methanolic hydrochloric acid (20 mL). The mixture was stirred at 20° C. for 16 h. The reaction mixture was concentrated under reduced pressure to provide the crude 3-(4-ethoxy-3-methoxyphenyl)-5-(piperidin-4-yl)-1,2,4-oxadiazole (900 mg) as a yellow solid that was used directly without further purification. LCMS (ESI) m/z: [M+H]$^+$=304.1

Step 5: Preparation of (4-(3-(4-ethoxy-3-methoxyphenyl)-1,2,4-oxadiazol-5-yl)piperidin-1-yl)(piperidin-1-yl)methanone

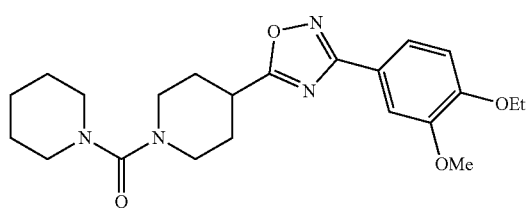 [SMILES: CCOc1ccc(-c2noc(C3CCN(C(=O)N4CCCCC4)CC3)n2)cc1OC]

To a stirred solution of 3-(4-ethoxy-3-methoxyphenyl)-5-(piperidin-4-yl)-1,2,4-oxadiazole (200 mg, 659 μmol) in dichloromethane (3 mL) was added piperidine-1-carbonyl chloride (116 mg, 791 μmol, 98 μL) and triethylamine (200 mg, 1.98 mmol, 274 μL) at 0° C. The mixture was stirred at 20° C. for 1 h. The reaction mixture was concentrated in vacuo to give a crude product that was purified by prep-HPLC (column: Waters Xbridge 150×2.5 mm 5 μm; mobile phase: [water (10 mM ammonium carbonate)-acetonitrile]; B %: 40%-70%, 12 min) to give (4-(3-(4-ethoxy-3-methoxyphenyl)-1,2,4-oxadiazol-5-yl)piperidin-1-yl)(piperidin-1-yl)methanone (65 mg, 158 μmol, 24%) as a yellow solid. ¹H NMR (400 MHz, CDCl₃) δ 7.71-7.66 (m, 1H), 7.59 (d, J=1.9 Hz, 1H), 6.96 (d, J=8.4 Hz, 1H), 4.19 (q, J=6.9 Hz, 2H), 3.98 (s, 3H), 3.75 (d, J=13.6 Hz, 2H), 3.29-3.13 (m, 5H), 3.04-2.94 (m, 2H), 2.17 (dd, J=3.1, 13.3 Hz, 2H), 2.05-1.93 (m, 2H), 1.60 (d, J=8.4 Hz, 6H), 1.53 (t, J=7.0 Hz, 3H); LCMS (ESI) m/z: [M+H]⁺=415.3.

Example 54: (4-(3-(3,4-dimethoxyphenyl)-1,2,4-oxadiazol-5-yl)piperidin-1-yl)(piperidin-1-yl)methanone

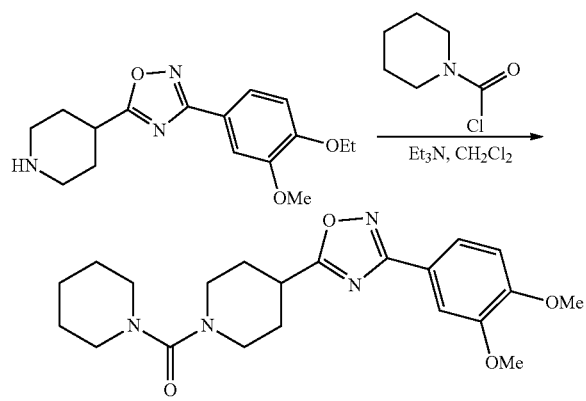

Step 1: Preparation of (4-(3-(3,4-dimethoxyphenyl)-1,2,4-oxadiazol-5-yl)piperidin-1-yl)(piperidin-1-yl)methanone

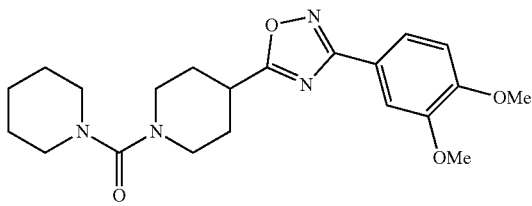 [SMILES: COc1ccc(-c2noc(C3CCN(C(=O)N4CCCCC4)CC3)n2)cc1OC]

To a stirred solution of 3-(3,4-dimethoxyphenyl)-5-(piperidin-4-yl)-1,2,4-oxadiazole (100 mg, 346 μmol) in dichloromethane (3 mL) was added piperidine-1-carbonyl chloride (61 mg, 415 μmol, 51 μL) and triethylamine (104 mg, 1.04 mmol, 143 μL) at 0° C. The mixture was stirred at 20° C. for 1 h. The reaction mixture was concentrated in vacuo to give a crude product that was purified by prep-HPLC (column: Waters Xbridge 150×2.5 mm 5 μm; mobile phase: [water (10 mM ammonium carbonate)-acetonitrile]; B %: 35%-65%, 12 min) to give (4-(3-(3,4-dimethoxyphenyl)-1,2,4-oxadiazol-5-yl)piperidin-1-yl)(piperidin-1-yl)methanone (81 mg, 202 μmol, 58%) as a white solid. ¹H NMR (400 MHz, CDCl₃) δ 7.74-7.68 (m, 1H), 7.59 (d, J=1.9 Hz, 1H), 6.98 (d, J=8.4 Hz, 1H), 3.98 (d, J=8.4 Hz, 6H), 3.76 (d, J=13.4 Hz, 2H), 3.29-3.14 (m, 5H), 3.04-2.95 (m, 2H), 2.17 (dd, J=13.3, 3.4 Hz, 2H), 2.05-1.94 (m, 2H), 1.60 ppm (d, J=8.5 Hz, 6H); LCMS (ESI) m/z: [M+H]⁺=401.3.

Example 55: 1-(4-(3-(3,4-dimethoxyphenyl)-1,2,4-oxadiazol-5-yl)piperidin-1-yl)-2-(isoquinolin-1-ylamino)ethanone

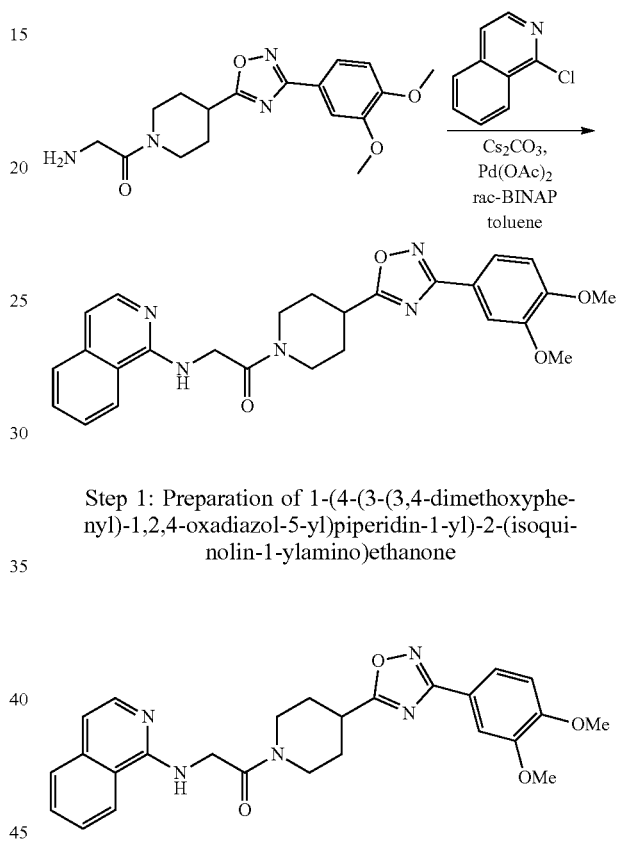

Step 1: Preparation of 1-(4-(3-(3,4-dimethoxyphenyl)-1,2,4-oxadiazol-5-yl)piperidin-1-yl)-2-(isoquinolin-1-ylamino)ethanone

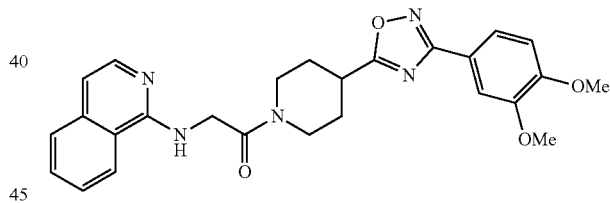

To a stirred solution of 2-amino-1-(4-(3-(3,4-dimethoxyphenyl)-1,2,4-oxadiazol-5-yl)piperidin-1-yl)ethanone (150 mg, 433 μmol) in toluene (2 mL) was added 1-chloroisoquinoline (70 mg, 433 μmol), cesium carbonate (423 mg, 1.30 mmol), (±)-2,2'-bis(diphenylphosphino)-1,1'-binaphthalene (26 mg, 43 μmol, 0.10 eq), and palladium(II) acetate (9 mg, 43 μmol, 0.10 eq) under nitrogen. The mixture was stirred at 100° C. for 16 h. The reaction mixture was filtered through diatomaceous earth and the filtrate was concentrated in vacuo to give a crude product that was purified by prep-HPLC (column: Luna C8 100*30 5 μm; mobile phase: [water (10 mM ammonium carbonate)-acetonitrile]; B %: 40%-70%, 12 min) to give 1-(4-(3-(3,4-dimethoxyphenyl)-1,2,4-oxadiazol-5-yl)piperidin-1-yl)-2-(isoquinolin-1-ylamino)ethanone (57 mg, 119 μmol, 27%) as a white solid. ¹H NMR (400 MHz, CDCl₃) δ 8.04-7.96 (m, 2H), 7.75-7.50 (m, 5H), 7.03-6.95 (m, 2H), 6.66 (br. s., 1H). 4.60 (d, J=13.7 Hz, 1H), 4.45 (br. s., 2H), 4.08 (d, J=12.5 Hz, 1H), 3.98 (d, J=7.9 Hz, 6H), 3.46-3.30 (m, 2H), 3.24-3.13 (m, 1H), 2.28 (br. s., 2H), 2.13-1.97 (m, 2H); LCMS (ESI) m/z: [M+H]⁺=474.3.

429

Example 56: N-(2-(4-(3-(3,4-dimethoxyphenyl)-1,2,4-oxadiazol-5-yl)piperazin-1-yl)-2-oxoethyl)benzamide

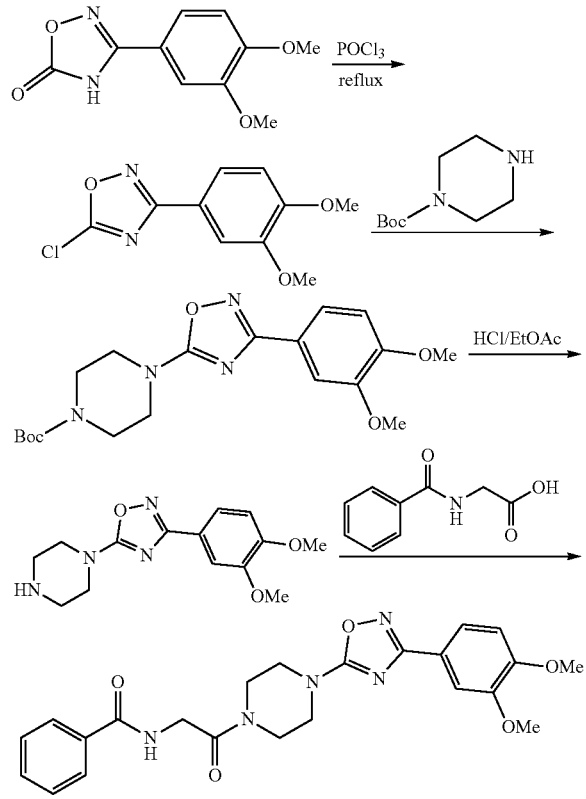

Step 1: Preparation of 5-chloro-3-(3,4-dimethoxyphenyl)-1,2,4-oxadiazole

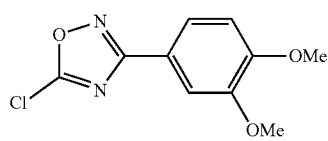 [SMILES: COc1ccc(-c2noc(Cl)n2)cc1OC]

To a mixture of N,N-dimethylformamide (1 mL) and phosphoryl chloride (8.25 g, 53.8 mmol, 5 mL) was added 3-(3,4-dimethoxyphenyl)-4H-1,2,4-oxadiazol-5-one (300 mg, 1.35 mmol) at 25° C. under calcium chloride tube. The mixture was heated to 100° C. and stirred for 16 h. The mixture was cooled to 25° C. and concentrated in vacuo carefully. The residue was poured into ice-water (20 mL) and stirred for 10 min. The aqueous phase was extracted with dichloromethane (10 mL×5). The combined organic phases were washed with saturated aqueous sodium chloride solution (10 mL), dried over anhydrous sodium sulfate, filtered and concentrated in vacuo. The residue was purified by chromatography (petroleum ether/ethyl acetate=5/1 to 1/1) to afford 5-chloro-3-(3,4-dimethoxyphenyl)-1,2,4-oxadiazole (99 mg, 414 µmol, 31%) as a white solid. LCMS (ESI) m/z: 241.1 [M+H]$^+$.

430

Step 2: Preparation of tert-butyl 4-(3-(3,4-dimethoxyphenyl)-1,2,4-oxadiazol-5-yl)piperazine-1-carboxylate

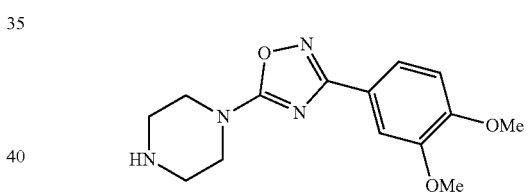

To a stirred solution of 5-chloro-3-(3,4-dimethoxyphenyl)-1,2,4-oxadiazole (90 mg, 374 µmol) and tert-butyl piperazine-1-carboxylate (83 mg, 448.80 µmol) in N-methyl-2-pyrrolidone (1.50 mL) was added N-ethyl-N-(propan-2-yl)propan-2-amine (96 mg, 748 µmol, 130 µL). The mixture was stirred at 120° C. for 2 h. The mixture was cooled to 25° C. and concentrated in vacuo at 40° C. The residue was poured into water (10 mL) then the aqueous phase was extracted with ethyl acetate (10 mL×3). The combined organic phases were washed with saturated aqueous sodium chloride solution (10 mL), dried over anhydrous sodium sulfate, filtered and concentrated in vacuo to afford tert-butyl 4-[3-(3,4-dimethoxyphenyl)-1,2,4-oxadiazol-5-yl]piperazine-1-carboxylate (900 mg) that was used directly without further purification.

Step 3: Preparation of 3-(3,4-dimethoxyphenyl)-5-(piperazin-1-yl)-1,2,4-oxadiazole

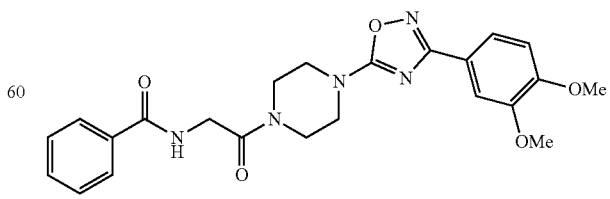

A solution of tert-butyl 4-[3-(3,4-dimethoxyphenyl)-1,2,4-oxadiazol-5-yl]piperazine-1-carboxylate (146 mg, 374 µmol) in hydrochloric acid/ethyl acetate (4M, 10 mL) was stirred at 20° C. for 2 h. The reaction mixture was concentrated in vacuo to give 3-(3,4-dimethoxyphenyl)-5-piperazin-1-yl-1,2,4-oxadiazole hydrochloride (900 mg) which was used directly without further purification.

Step 4: Preparation of N-(2-(4-(3-(3,4-dimethoxyphenyl)-1,2,4-oxadiazol-5-yl)piperazin-1-yl)-2-oxoethyl)benzamide To a stirred solution of 3-(3,4-dimethoxyphenyl)-5-piperazin-1-yl-1,2,4-oxadiazole hydrochloride (667 mg, 306

µmol,) and 2-benzamidoacetic acid (137 mg, 765 µmol) in N,N-dimethylformamide (2 mL) was added (2-(1H-benzotriazol-1-yl)-1,1,3,3-tetramethyluronium hexafluorophosphate) (174 mg, 459 µmol) and N-ethyl-N-(propan-2-yl)propan-2-amine (118 mg, 918.51 µmol, 160 µL) at 20° C. The mixture was stirred at 20° C. for 5 h. The reaction mixture was purified directly by prep-HPLC (column: Waters Xbridge 150×25 5 µm; mobile phase: [water (10 mM ammonium carbonate)-acetonitrile]; B %: 25%-60%, 12 min) to give N-[2-[4-[3-(3,4-dimethoxyphenyl)-1,2,4-oxadiazol-5-yl]piperazin-1-yl]-2-oxo-ethyl]benzamide (55 mg, 121 µmol, 39%) as a yellow solid. $^1$H NMR (400 MHz, DMSO-d6) δ=8.59 (br t, J=5.6 Hz, 1H), 7.93-7.83 (m, 2H), 7.60-7.44 (m, 4H), 7.39 (d, J=1.9 Hz, 1H), 7.08 (d, J=8.5 Hz, 1H), 4.20 (d, J=5.6 Hz, 2H), 3.81 (d, J=1.1 Hz, 6H), 3.73-3.58 (m, 8H); LCMS (ESI) m/z: [M+H]$^+$=452.2.

Example 57: (1-(3-(4-ethoxy-3-methoxyphenyl)-1,2,4-oxadiazol-5-yl)piperidin-4-yl)(piperidin-1-yl)methanone

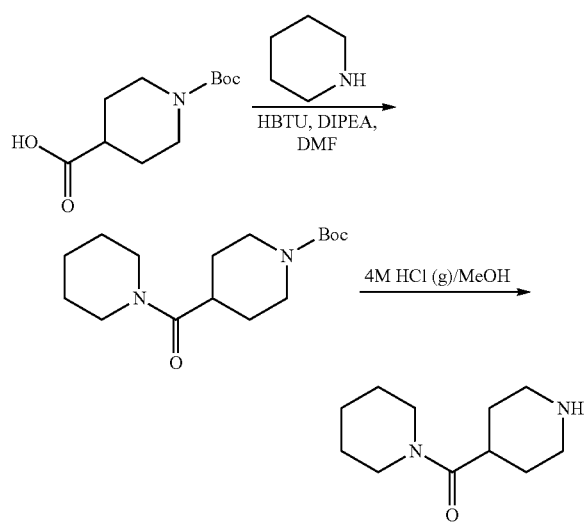

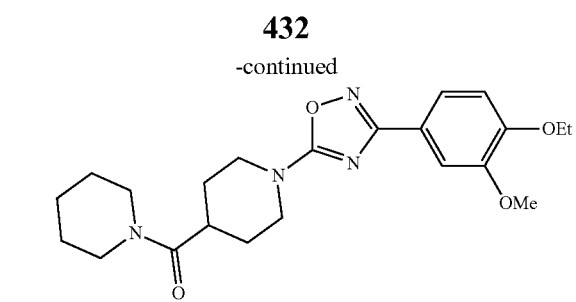

Step 1: Preparation of tert-butyl 4-(piperidine-1-carbonyl)piperidine-1-carboxylate

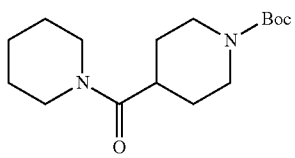 [SMILES: CC(C)(C)OC(=O)N1CCC(C(=O)N2CCCCC2)CC1]

To a stirred solution of 1-(tert-butoxycarbonyl)piperidine-4-carboxylic acid (1.0 g, 4.36 mmol) in N,N-dimethylformamide (15 mL) was added piperidine (445 mg, 5.23 mmol, 518 µL), 1-[bis(dimethylamino)methylene]-1H-1,2,3-triazolo[4,5-b]pyridinium 3-oxide hexafluorophosphate (1.99 g, 5.23 mmol) and N-ethyl-N-(propan-2-yl)propan-2-amine (1.69 g, 13.1 mmol, 2.29 mL). The mixture was stirred at 20° C. for 3 h. The reaction mixture was quenched by addition of water (20 mL) then the mixture was extracted with ethyl acetate (40 mL×4), then the combined organic phases were washed with saturated aqueous sodium chloride solution (20 mL), dried over anhydrous sodium sulfate, filtered and concentrated to give tert-butyl 4-(piperidine-1-carbonyl)piperidine-1-carboxylate (1.90 g) as a yellow oil. This was used directly without further purification. LCMS (ESI) m/z: [M+H]$^+$=297.2

Step 2: Preparation of piperidin-1-yl(piperidin-4-yl)methanone

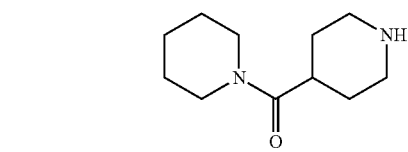 [SMILES: O=C(C1CCNCC1)N1CCCCC1]

To a stirred solution of tert-butyl 4-(piperidine-1-carbonyl)piperidine-1-carboxylate (500 mg, 1.69 mmol) in methanol (5 mL) was added 4N methanolic hydrogen chloride solution (15 mL). The mixture was stirred at 20° C. for 16 h. The reaction mixture was concentrated under reduced pressure to provide piperidin-1-yl(piperidin-4-yl)methanone (400 mg) as a colorless oil. $^1$H NMR (400 MHz, DMSO-d6) δ 3.51-3.36 (m, 4H), 3.28-3.18 (m, 2H), 2.90 (s, 4H), 1.82-1.68 (m, 4H), 1.64-1.37 (m, 6H).

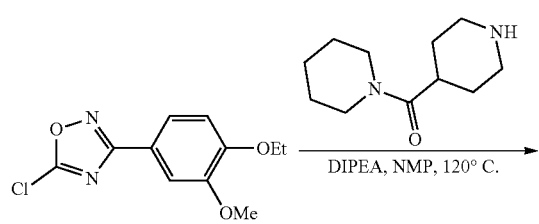

Step 3: Preparation of 3-(4-ethoxy-3-methoxyphenyl)-1,2,4-oxadiazol-5(4H)-one

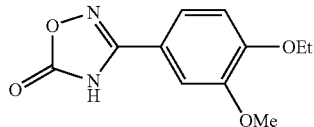 [SMILES: CCOc1ccc(-c2noc(=O)[nH]2)cc1OC]

To a stirred solution of 4-ethoxy-N-hydroxy-3-methoxybenzimidamide (800 mg, 3.81 mmol) in dioxane (8 mL) was added 1,8-diazabicyclo[5.4.0]undec-7-ene (638 mg, 4.19 mmol, 631 μL) and 1,1'-carbonyldiimidazole (926 mg, 5.72 mmol). The mixture was stirred at 110° C. for 16 h. The reaction mixture was quenched with water (10 mL), then the mixture was extracted with dichloromethane (50 mL×4). The combined organic phases were washed with saturated aqueous sodium chloride solution (20 mL), dried over anhydrous sodium sulfate, filtered and concentrated in vacuo. Purification by chromatography (silica, dichloromethane:methanol=50:1) gave 3-(4-ethoxy-3-methoxyphenyl)-1,2,4-oxadiazol-5(4H)-one (1.20 g, quant.) as a yellow oil. LCMS (ESI) m/z: [M+H]$^+$=237.1.

Step 4: Preparation of 5-chloro-3-(4-ethoxy-3-methoxyphenyl)-1,2,4-oxadiazole

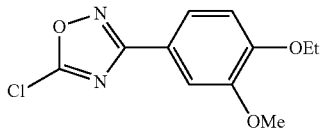 [SMILES: CCOc1ccc(-c2noc(Cl)n2)cc1OC]

To a stirred mixture of 3-(4-ethoxy-3-methoxyphenyl)-1,2,4-oxadiazol-5(4H)-one (500 mg, 2.12 mmol) and N,N-dimethylformamide (1 mL) was equipped with calcium chloride tube and phosphoryl chloride (10 mL) was added dropwise. The mixture was heated at 110° C. for 16 h. The reaction mixture was cooled to 20° C., then poured onto ice water (100 mL), and stirred for 30 min. The mixture was extracted with dichloromethane (20 mL×5), then the combined organic phases were washed with saturated aqueous sodium chloride solution (10 mL), dried over anhydrous sodium sulfate, filtered and concentrated to give 5-chloro-3-(4-ethoxy-3-methoxyphenyl)-1,2,4-oxadiazole (360 mg, 1.41 mmol, 67%) as a brown solid. LCMS (ESI) m/z: [M+H]$^+$=255.1

Step 5: Preparation of (1-(3-(4-ethoxy-3-methoxyphenyl)-1,2,4-oxadiazol-5-yl)piperidin-4-yl)(piperidin-1-yl)methanone

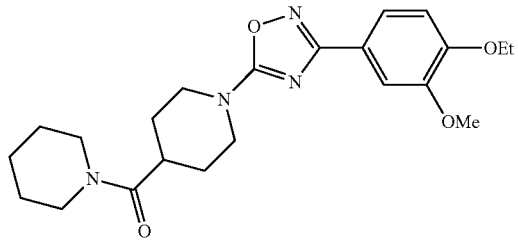 [SMILES: CCOc1ccc(-c2noc(N3CCC(C(=O)N4CCCCC4)CC3)n2)cc1OC]

To a stirred solution of piperidin-1-yl(piperidin-4-yl)methanone (100 mg, 509 μmol) in N-methyl-2-pyrrolidone (4 mL) was added 5-chloro-3-(4-ethoxy-3-methoxyphenyl)-1,2,4-oxadiazole (194 mg, 764 μmol) and N-ethyl-N-(propan-2-yl)propan-2-amine (131 mg, 1.02 mmol, 177 μL). The mixture was stirred at 120° C. for 16 h. The reaction mixture was purified directly by prep-HPLC (column: Luna C8 100*30 5 μm; mobile phase: [water (10 mM ammonium carbonate)-acetonitrile]; B %: 35%-65%, 12 min) to give (1-(3-(4-ethoxy-3-methoxyphenyl)-1,2,4-oxadiazol-5-yl)piperidin-4-yl)(piperidin-1-yl)methanone (61 mg, 147.6 μmol, 29%) as a yellow solid. $^1$H NMR (400 MHz, CDCl$_3$) δ 7.53-7.47 (m, 1H), 7.42 (d, J=1.9 Hz, 1H), 6.84 (d, J=8.5 Hz, 1H), 4.24-4.16 (m, 2H), 4.08 (q, J=6.9 Hz, 2H), 3.87 (s, 3H), 3.50 (br. s., 2H), 3.40 (br. s., 2H), 3.19-3.09 (m, 2H), 2.69 (tt, J=3.8, 10.7 Hz, 1H), 1.94-1.71 (m, 4H), 1.63-1.48 (m, 6H), 1.42 (t, J=7.0 Hz, 3H); LCMS (ESI) m/z: [M+H]$^+$=415.3.

Example 58: N-(2-(4-(3-(2-methoxyphenyl)-1,2,4-oxadiazol-5-yl)piperidin-1-yl)-2-oxoethyl)-3,4-dimethylbenzamide

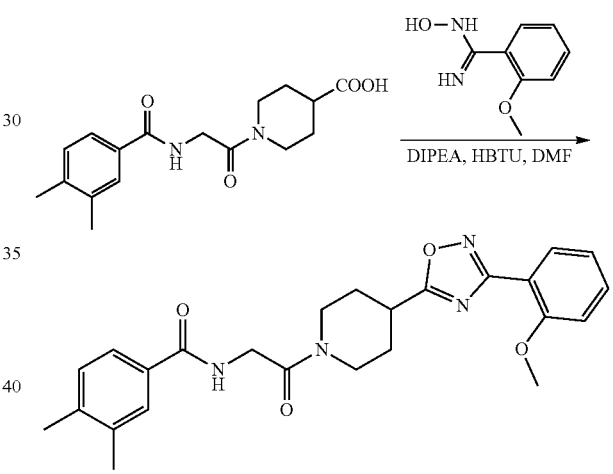

Step 1: N-(2-(4-(3-(2-methoxyphenyl)-1,2,4-oxadiazol-5-yl)piperidin-1-yl)-2-oxoethyl)-3,4-dimethylbenzamide

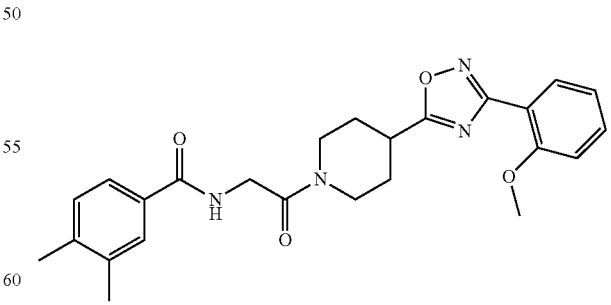

To a stirred solution of 1-(2-(3,4-dimethylbenzamido)acetyl)piperidine-4-carboxylic acid (150 mg, 471 μmol) and N-hydroxy-2-methoxybenzimidamide (78 mg, 471 μmol) in N,N-dimethylformamide (2 mL) was added N-ethyl-N-(propan-2-yl)propan-2-amine (121 mg, 942 μmol, 164 μL) and (2-(1H-benzotriazol-1-yl)-1,1,3,3-tetramethyluronium hexafluorophosphate) (178 mg, 471 µmol) at 15° C. The mixture was stirred for 15 h, then the mixture was heated to 110° C. and stirred for 5 h. The mixture was cooled and then purified by prep-HPLC (column: Waters Xbridge 150×25 5 µm; mobile phase: [water (10 mM ammonium carbonate)-acetonitrile]; B %: 37%-67%, 12 min) to obtain N-(2-(4-(3-(2-methoxyphenyl)-1,2,4-oxadiazol-5-yl)piperidin-1-yl)-2-oxoethyl)-3,4-dimethylbenzamide (110 mg, 244 µmol, 52%) as yellow solid. $^1$H NMR (400 MHz, Methanol-d4) δ 7.96 (dd, J=1.5, 7.7 Hz, 1H), 7.66 (s, 1H), 7.60 (d, J=7.9 Hz, 1H), 7.56-7.49 (m, 1H), 7.23 (d, J=7.5 Hz, 1H), 7.18 (d, J=8.4 Hz, 1H), 7.09 (t, J=7.5 Hz, 1H), 4.47 (d, J=12.8 Hz, 1H), 4.35-4.23 (m, 2H), 4.04 (d, J=13.7 Hz, 1H), 3.92 (s, 3H), 3.49-3.35 (m, 2H), 3.07 (t, J=11.0 Hz, 1H), 2.32 (s, 6H), 2.27-2.10 (m, 2H), 2.06-1.83 (m, 2H); LCMS (ESI) m/z: [M+H]$^+$=449.3.

Example 59: N-[2-[4-[3-(3,4-dimethoxyphenyl)-1,2,4-oxadiazol-5-yl]-1-piperidyl]-1-methyl-2-oxo-ethyl]benzamide, Enantiomer 1 and Example 60: N-[2-[4-[3-(3,4-dimethoxyphenyl)-1,2,4-oxadiazol-5-yl]-1-piperidyl]-1-methyl-2-oxo-ethyl]benzamide, Enantiomer 2

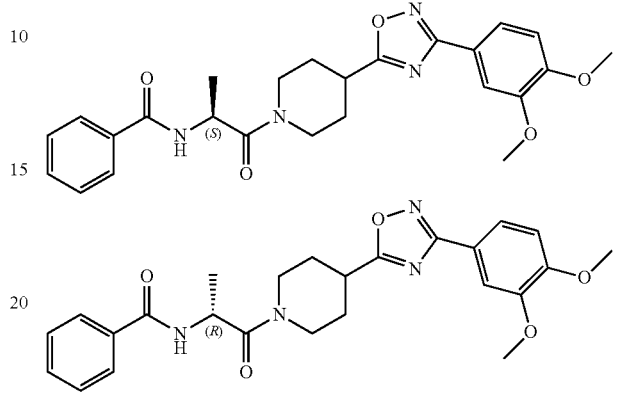

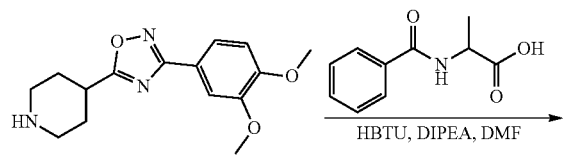

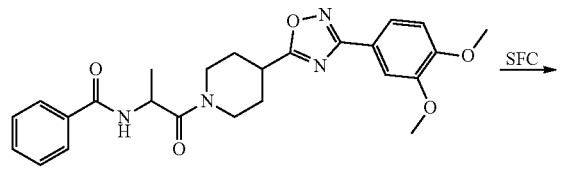

+

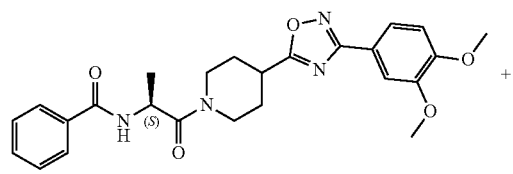

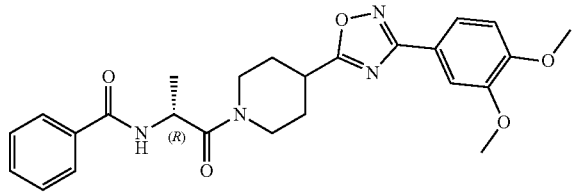

Step 1: Preparation of N-[(R)-2-[4-[3-(3,4-dimethoxyphenyl)-1,2,4-oxadiazol-5-yl]-1-piperidyl]-1-methyl-2-oxo-ethyl]benzamide and N-[(S)-2-[4-[3-(3,4-dimethoxyphenyl)-1,2,4-oxadiazol-5-yl]-1-piperidyl]-1-methyl-2-oxo-ethyl]benzamide To a stirred solution of 3-(3,4-dimethoxyphenyl)-5-(4-piperidyl)-1,2,4-oxadiazole (150 mg, 518 µmol) and 2-benzamidopropanoic acid (105 mg, 544 µmol) in N,N-dimethylformamide (2 mL) was added (2-(1H-benzotriazol-1-yl)-1,1,3,3-tetramethyluronium hexafluorophosphate) (196 mg, 518 µmol) and N-ethyl-N-(propan-2-yl)propan-2-amine (201 mg, 1.56 mmol, 271 µL). The mixture was stirred at 20° C. for 5 h. The crude product was purified by prep-HPLC (column: Luna C18 150×25 5 µm; mobile phase: [water (10 mM ammonium carbonate)-acetonitrile]; B %: 35%-65%, 12 min) to give rac-N-(1-(4-(3-(3,4-dimethoxyphenyl)-1,2,4-oxadiazol-5-yl)piperidin-1-yl)-1-oxopropan-2-yl)benzamide then the product purified by SFC separation (column: AD(250×30 mm, 5 µm); mobile phase: [Neu-IPA]; B %: 42%-42%, min) to give N-[2-[4-[3-(3,4-dimethoxyphenyl)-1,2,4-oxadiazol-5-yl]-1-piperidyl]-1-methyl-2-oxo-ethyl]benzamide, Enantiomer 1 (63 mg, 134.93 µmol, 26%) as a white solid and N-[2-[4-[3-(3,4-dimethoxyphenyl)-1,2,4-oxadiazol-5-yl]-1-piperidyl]-1-methyl-2-oxo-ethyl]benzamide, Enantiomer 2 (56 mg, 120 µmol, 23% as a white solid.

N-[2-[4-[3-(3,4-dimethoxyphenyl)-1,2,4-oxadiazol-5-yl]-1-piperidyl]-1-methyl-2-oxo-ethyl]benzamide, Enantiomer 1

$^1$H NMR (400 MHz, DMSO-d$_6$) δ=8.63 (br dd, J=7.3, 16.1 Hz, 1H), 7.88 (br d, J=7.5 Hz, 2H), 7.62-7.41 (m, 5H), 7.11 (br d, J=8.2 Hz, 1H), 4.97 (br d, J=6.4 Hz, 1H), 4.43-4.24 (m, 1H), 4.10-3.95 (m, 1H), 3.82 (s, 6H), 3.42 (br t, J=10.8 Hz, 1H), 3.30-3.21 (m, 1H), 2.99-2.83 (m, 1H), 2.09 (br d, J=11.9 Hz, 2H), 1.83-1.60 (m, 2H), 1.30 (br s, 3H); LCMS (ESI) m/z: [M+H]$^+$=465.3. ee=100%.

N-[2-[4-[3-(3,4-dimethoxyphenyl)-1,2,4-oxadiazol-5-yl]-1-piperidyl]-1-methyl-2-oxo-ethyl]benzamide, Enantiomer 2

$^1$H NMR (400 MHz, DMSO-d$_6$) δ=8.65 (br dd, J=7.6, 16.1 Hz, 1H), 7.98-7.86 (m, 2H), 7.70-7.41 (m, 5H), 7.13 (br d, J=8.2 Hz, 1H), 5.00 (br d, J=5.5 Hz, 1H), 4.49-4.24 (m, 1H), 4.12-3.96 (m, 1H), 3.85 (s, 6H), 3.45 (br t, J=10.7 Hz,

1H), 3.27 (br s, 1H), 3.05-2.83 (m, 1H), 2.12 (br d, J=12.5 Hz, 2H), 1.89-1.61 (m, 2H), 1.32 (br s, 3H); LCMS (ESI) m/z: [M+H]$^+$=465.3. ee=99.6

Example 61: (2-methyl-4-(2-oxo-4-(4-(3-(p-tolyl)-1,2,4-oxadiazol-5-yl)piperidine-1-carbonyl)pyrrolidin-1-yl)phenyl)methylium, Enantiomer 1 and Example 62: (2-methyl-4-(2-oxo-4-(4-(3-(p-tolyl)-1,2,4-oxadiazol-5-yl)piperidine-1-carbonyl)pyrrolidin-1-yl)phenyl)methylium, Enantiomer 2

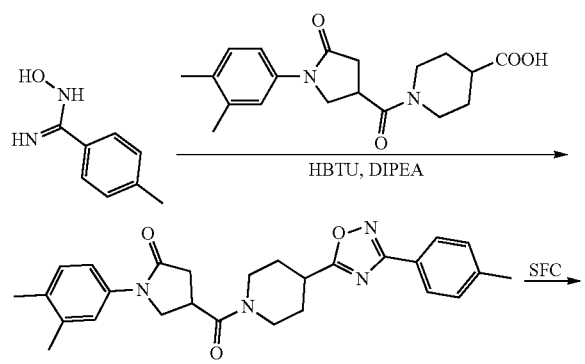

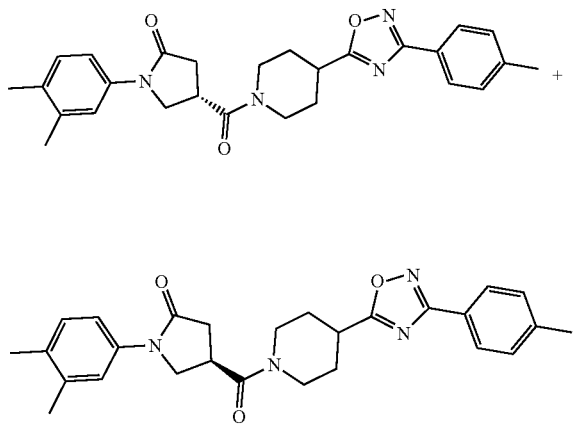

Step 1: Preparation of (2-methyl-4-(2-oxo-4-(4-(3-(p-tolyl)-1,2,4-oxadiazol-5-yl)piperidine-1-carbonyl)pyrrolidin-1-yl)phenyl)methylium, Enantiomer 1 and (2-methyl-4-(2-oxo-4-(4-(3-(p-tolyl)-1,2,4-oxadiazol-5-yl)piperidine-1-carbonyl)pyrrolidin-1-yl)phenyl)methylium, Enantiomer 2

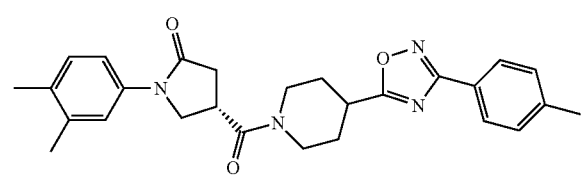

-continued

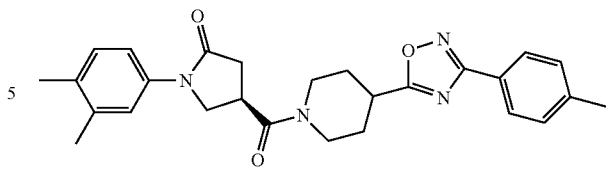

To a stirred solution of N-hydroxy-4-methylbenzimidamide (300 mg, 2.0 mmol), (2-(1H-benzotriazol-1-yl)-1,1,3,3-tetramethyluronium hexafluorophosphate) (834 mg, 2.20 mmol) and 1-(1-(3,4-dimethylphenyl)-5-oxopyrrolidine-3-carbonyl)piperidine-4-carboxylic acid (688 mg, 2.00 mmol) in N,N-dimethylformamide (10 mL) were added N-ethyl-N-(propan-2-yl)propan-2-amine (516 mg, 4.00 mmol, 698 µL) at 0° C. Then the reaction was warmed to 25° C. After 17 h, the reaction was warmed to 90° C. After 3 h, the mixture was cooled, diluted with water (10 mL), and extracted with ethyl acetate (30 mL×3). The combined organic phases were washed with saturated aqueous sodium chloride solution (40 mL), dried over anhydrous sodium sulfate, filtered and concentrated to give a crude residue that was purified by prep-HPLC (column: Phenomenex luna(2) C18 250×50 10 µm; mobile phase: [water (0.1% TFA)-acetonitrile]; B %: 40%-70%, 20 min) to give the racemic of 1-(3,4-dimethylphenyl)-4-(4-(3-(p-tolyl)-1,2,4-oxadiazol-5-yl)piperidine-1-carbonyl)pyrrolidin-2-one (600 mg, 1.31 mmol, 65%). This was purified by SFC (column: AS(250× 30 mm, 5 µm); mobile phase: [CO$_2$ base-methanol]; B %: 40%-40%) to give (2-methyl-4-(2-oxo-4-(4-(3-(p-tolyl)-1,2,4-oxadiazol-5-yl)piperidine-1-carbonyl)pyrrolidin-1-yl)phenyl)methylium, Enantiomer 1 (193 mg, 421 µmol, 21%) as a white solid, and (2-methyl-4-(2-oxo-4-(4-(3-(p-tolyl)-1,2,4-oxadiazol-5-yl)piperidine-1-carbonyl)pyrrolidin-1-yl)phenyl)methylium, Enantiomer 2 (199 mg, 433 µmol, 22%) as a white solid.

(2-methyl-4-(2-oxo-4-(4-(3-(p-tolyl)-1,2,4-oxadiazol-5-yl)piperidine-1-carbonyl)pyrrolidin-1-yl)phenyl)methylium, Enantiomer 1

$^1$H NMR (400 MHz, DMSO-d6) δ=7.91 (br d, J=6.9 Hz, 2H), 7.43 (br s, 1H), 7.38 (br d, J=8.0 Hz, 3H), 7.12 (br d, J=6.3 Hz, 1H), 4.35 (br s, 1H), 4.09-3.98 (m, 2H), 3.92 (td, J=5.0, 10.0 Hz, 1H), 3.80-3.63 (m, 1H), 3.45 (br t, J=10.8 Hz, 1H), 3.36 (br s, 1H), 3.00-2.90 (m, 1H), 2.82-2.65 (m, 2H), 2.39 (s, 3H), 2.27-2.10 (m, 8H), 1.91-1.61 (m, 2H); LCMS (ESI) m/z: [M+H]$^+$=459.3; ee=98.6

(2-methyl-4-(2-oxo-4-(4-(3-(p-tolyl)-1,2,4-oxadiazol-5-yl)piperidine-1-carbonyl)pyrrolidin-1-yl)phenyl)methylium, Enantiomer 2

$^1$H NMR (400 MHz, DMSO-d6) δ=7.91 (br d, J=6.9 Hz, 2H), 7.43 (br s, 1H), 7.38 (br d, J=8.0 Hz, 3H), 7.12 (br d, J=6.4 Hz, 1H), 4.35 (br s, 1H), 4.11-3.97 (m, 2H), 3.92 (td, J=5.0, 9.9 Hz, 1H), 3.81-3.68 (m, 1H), 3.53-3.37 (m, 1H), 3.36 (br s, 1H), 3.02-2.90 (m, 1H), 2.82-2.65 (m, 2H), 2.39 (s, 3H), 2.25-2.09 (m, 8H), 1.89-1.62 (m, 2H); LCMS (ESI) m/z: [M+H]$^+$=459.3; ee=99%.

Example 63: 1-(3,4-dimethylphenyl)-4-(4-(3-(4-methoxyphenyl)-1,2,4-oxadiazol-5-yl)piperidine-1-carbonyl)pyrrolidin-2-one, Enantiomer 1 and
Example 64: 1-(3,4-dimethylphenyl)-4-(4-(3-(4-methoxyphenyl)-1,2,4-oxadiazol-5-yl)piperidine-1-carbonyl)pyrrolidin-2-one, Enantiomer 2

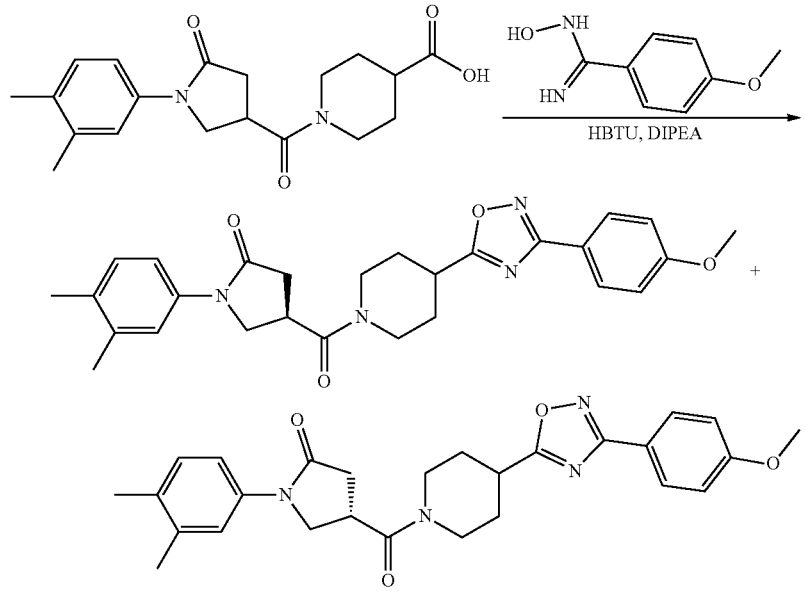

Step 1: Preparation of 1-(3,4-dimethylphenyl)-4-(4-(3-(4-methoxyphenyl)-1,2,4-oxadiazol-5-yl)piperidine-1-carbonyl)pyrrolidin-2-one, Enantiomer 1 and 1-(3,4-dimethylphenyl)-4-(4-(3-(4-methoxyphenyl)-1,2,4-oxadiazol-5-yl)piperidine-1-carbonyl)pyrrolidin-2-one, Enantiomer 2

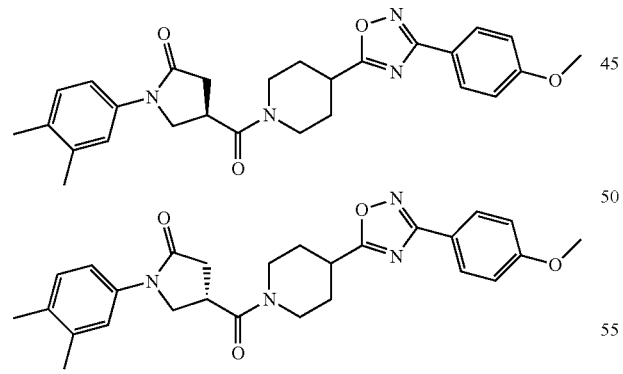

To a stirred solution of 1-(1-(3,4-dimethylphenyl)-5-oxopyrrolidine-3-carbonyl)piperidine-4-carboxylic acid (350 mg, 1.02 mmol) and N-hydroxy-4-methoxybenzimidamide (168 mg, 1.02 mmol) in N,N-dimethylformamide (3 mL) was added N-ethyl-N-(propan-2-yl)propan-2-amine (262 mg, 2.03 mmol, 354 µL) and (2-(1H-benzotriazol-1-yl)-1,1,3,3-tetramethyluronium hexafluorophosphate) (385 mg, 1.02 mmol), then the mixture was stirred for 15 h at 15° C. The the mixture was then heated to 110° C. and stirred for 5 h. The mixture was cooled and purified by prep-HPLC (column: Waters Xbridge 150×25 5 µm; mobile phase: [water (10 mM ammonium carbonate)-acetonitrile]; B %: 37%-67%, 12 min) to give racemic 1-(3,4-dimethylphenyl)-4-(4-(3-(4-methoxyphenyl)-1,2,4-oxadiazol-5-yl)piperidine-1-carbonyl)pyrrolidin-2-one (0.2 g) as a white solid. This was purified by SFC separation: (column: OJ(250×30 mm, 10 µm); mobile phase: [$CO_2$ base-ethanol]; B %: 45%-45%) to give ((1-(3,4-dimethylphenyl)-4-(4-(3-(4-methoxyphenyl)-1,2,4-oxadiazol-5-yl)piperidine-1-carbonyl)pyrrolidin-2-one, Enantiomer 1 (84 mg, 177 µmol, 17%) as a white solid and 1-(3,4-dimethylphenyl)-4-(4-(3-(4-methoxyphenyl)-1,2,4-oxadiazol-5-yl)piperidine-1-carbonyl)pyrrolidin-2-one, Enantiomer 2 (96 mg, 198 µmol, 19%) as a yellow solid 1-(3,4-dimethylphenyl)-4-(4-(3-(4-methoxyphenyl)-1,2,4-oxadiazol-5-yl)piperidine-1-carbonyl)pyrrolidin-2-one, Enantiomer 1

$^1$H NMR (400 MHz, Methanol-d4) δ 7.98 (dd, J=2.2, 8.8 Hz, 2H), 7.36 (s, 1H), 7.27 (d, J=7.9 Hz, 1H), 7.13 (d, J=8.4 Hz, 1H), 7.04 (d, J=7.1 Hz, 2H), 4.53-4.43 (m, 1H), 4.18-3.99 (m, 3H), 3.95-3.73 (m, 4H), 3.49-3.36 (m, 2H), 3.14-3.01 (m, 1H), 2.93-2.77 (m, 2H), 2.47-2.04 (m, 8H), 2.01-1.80 (m, 2H); LCMS (ESI) m/z: [M+H]$^+$=475.3; ee=100%.

1-(3,4-dimethylphenyl)-4-(4-(3-(4-methoxyphenyl)-1,2,4-oxadiazol-5-yl)piperidine-1-carbonyl)pyrrolidin-2-one, Enantiomer 2

$^1$H NMR (400 MHz, Methanol-d4) δ 7.98 (dd, J=2.4, 9.0 Hz, 2H), 7.36 (s, 1H), 7.27 (d, J=8.4 Hz, 1H), 7.13 (d, J=8.4 Hz, 1H), 7.04 (d, J=7.1 Hz, 2H), 4.48 (d, J=7.5 Hz, 1H), 4.16-4.00 (m, 3H), 3.92-3.74 (m, 4H), 3.49-3.37 (m, 2H), 3.13-3.03 (m, 1H), 2.91-2.80 (m, 2H), 2.34-2.11 (m, 8H), 1.98-1.83 (m, 2H); LCMS (ESI) m/z: [M+H]$^+$=475.3; ee=100%.

Example 65: (4S)-4-[4-[3-(3,4-dimethoxyphenyl)-1,2,4-oxadiazol-5-yl]piperidine-1-carbonyl]-1-phenyl-pyrrolidin-2-one

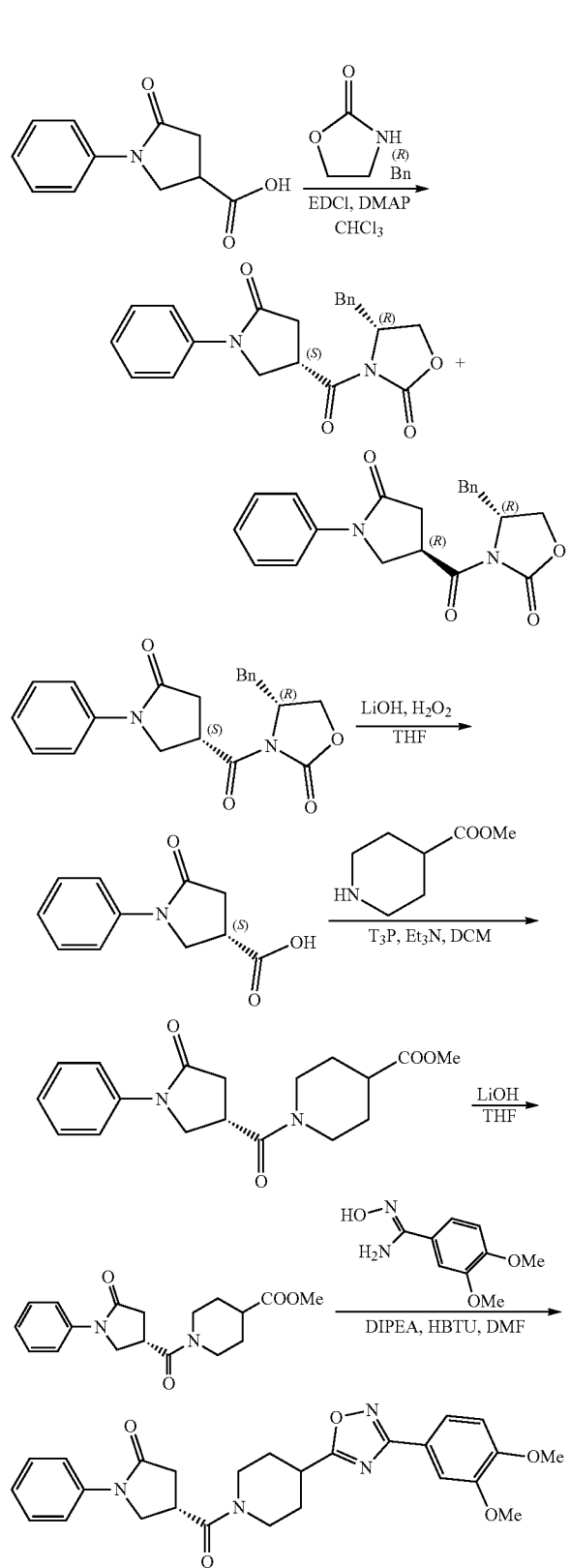

Step 1: (4R)-4-benzyl-3-[(3S)-5-oxo-1-phenyl-pyrrolidine-3-carbonyl]oxazolidin-2-one

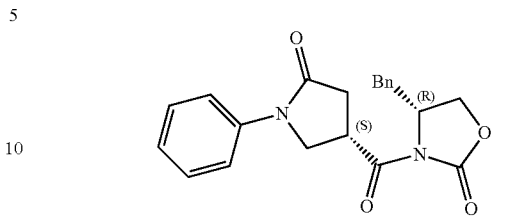

To a stirred solution of 5-oxo-1-phenyl-pyrrolidine-3-carboxylic acid (20.0 g, 97.5 mmol) in chloroform (100 mL) was added (4R)-4-benzyloxazolidin-2-one (20.72 g, 117 mmol), 1-ethyl-3-(3-dimethylaminopropyl)carbodiimide (20.74 g, 108.2 mmol) and DMAP (6.43 g, 52.6 mmol) at 0° C. After addition, the mixture was stirred for 15 min, then warmed and stirred at 20° C. for 18 h. The residue was purified by chromatography (silica, petroleum ether/ethyl acetate=1/1 to 1:9) to give (4R)-4-benzyl-3-[(3S)-5-oxo-1-phenyl-pyrrolidine-3-carbonyl]oxazolidin-2-one (10.0 g, 27.4 mmol, 28%) and (4R)-4-benzyl-3-[(3R)-5-oxo-1-phenyl-pyrrolidine-3-carbonyl]oxazolidin-2-one (10.0 g, 27 mmol, 28%) each as a white solid. LCMS (ESI) m/z: 365.1 [M+H]$^+$.

Step 2: (3S)-5-oxo-1-phenyl-pyrrolidine-3-carboxylic acid

To a stirred solution of lithium hydroxide monohydrate (2.63 g, 62.8 mmol) in water (30 mL) was added dropwise hydrogen peroxide (15.5 g, 456.6 mmol, 13.2 mL) at 0° C. The mixture was stirred for 30 min. To the mixture was then added tetrahydrofuran (80 mL), water (30 mL) followed by a solution of 3-[(3S)-5-oxo-1-phenyl-pyrrolidine-3-carbonyl]-4-phenyl-oxazolidin-2-one (10.0 g, 28.5 mmol) in tetrahydrofuran (80 mL) dropwise. The mixture was stirred at 0° C. for 1 h, quenched by addition of a sodium sulfate solution in water (10 mL) at 0° C., and made basic (pH 11) by addition of an aqueous sodium carbonate solution. The mixture was extracted with ethyl acetate (100 mL), acidified to pH 2 using 1M HCl, and extracted again with ethyl acetate (100 mL). The organic layers were washed with a saturated aqueous sodium chloride solution (100 mL), dried over sodium sulfate, filtered and concentrated under reduced pressure to give (3S)-5-oxo-1-phenyl-pyrrolidine-3-carboxylic acid (4.80 g, 23.39 mmol, 82%) as a white solid. $^1$H NMR (400 MHz, CHLOROFORM-d) δ 7.57 (dd, J=0.9, 8.6 Hz, 2H), 7.40-7.34 (m, 2H), 7.20-7.15 (m, 1H), 4.18-4.13 (m, 1H), 4.10-4.04 (m, 1H), 3.45-3.35 (m, 1H), 3.03-2.86 (m, 2H).

Step 3: methyl 1-[(3S)-5-oxo-1-phenyl-pyrrolidine-3-carbonyl]piperidine-4-carboxylate

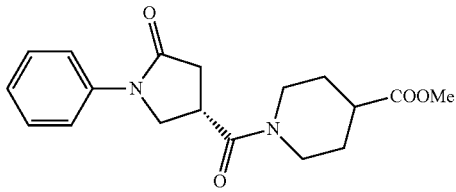 [SMILES: COC(=O)C1CCN(C(=O)[C@H]2CC(=O)N(c3ccccc3)C2)CC1]

A mixture of (3S)-5-oxo-1-phenyl-pyrrolidine-3-carboxylic acid (4.50 g, 21.93 mmol), methyl piperidine-4-carboxylate (3.77 g, 26.32 mmol), 2,4,6-tripropyl-1,3,5,2,4,6-trioxatriphosphinane 2,4,6-trioxide in ethyl acetate (27.91 g, 43.86 mmol, 26.08 mL, 50% purity), triethylamine (44.38 g, 438.60 mmol, 60 mL) in dichloromethane (60 mL) was degassed, purged with nitrogen 3 times, and then the mixture was stirred at 20° C. for 16 h under a nitrogen atmosphere. The reaction mixture was diluted with water (30 mL) and extracted with dichloromethane (50 mL). The organic layers were washed with saturated aqueous sodium chloride solution (50 mL), dried over $Na_2SO_4$, filtered, concentrated under reduced pressure and purified by chromatography (silica, petroleum ether/ethyl acetate=1:1) to give methyl 1-[(3S)-5-oxo-1-phenyl-pyrrolidine-3-carbonyl]piperidine-4-carboxylate (4.70 g, 14.2 mmol, 65%) as a white solid. $^1$H NMR (400 MHz, CHLOROFORM-d) δ 7.56 (d, J=7.7 Hz, 2H), 7.35 (t, J=7.5 Hz, 2H), 7.16-7.11 (m, 1H), 4.47-4.34 (m, 1H), 4.24 (dd, J=7.3, 9.5 Hz, 1H), 3.91-3.81 (m, 2H), 3.69 (s, 3H), 3.52 (quin, J=8.5 Hz, 1H), 3.24-3.12 (m, 1H), 2.98-2.87 (m, 2H), 2.80-2.73 (m, 1H), 2.64-2.52 (m, 1H), 1.97 (br dd, J=4.3, 8.3 Hz, 2H), 1.73-1.63 (m, 2H).

Step 4: 1-[(3)-5-oxo-1-phenyl-pyrrolidine-3-carbonyl]piperidine-4-carboxylic acid

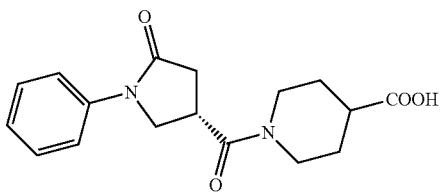 [SMILES: O=C(O)C1CCN(C(=O)[C@H]2CC(=O)N(c3ccccc3)C2)CC1]

To a stirred solution of methyl 1-[(3S)-5-oxo-1-phenyl-pyrrolidine-3-carbonyl]piperidine-4-carboxylate (3.00 g, 9.08 mmol) in tetrahydrofuran (60 mL) was added a solution of lithium hydroxide monohydrate (0.5 M, 21.79 mL) in water. The mixture was then stirred at 0° C. for 2 h. The mixture was acidified to pH 4-5 using 1M HCl, and then extracted with dichloromethane (60 mL; 30 mL×2). The combined organic phases were washed with saturated aqueous sodium chloride solution 40 mL; 20 mL×2), dried over sodium sulfate, filtered and concentrated under reduced pressure to give 1-[(3S)-5-oxo-1-phenyl-pyrrolidine-3-carbonyl]piperidine-4-carboxylic acid (2.70 g, 8.53 mmol, 94%) as a white solid.

Step 5: (4S)-4-[4-[3-(3,4-dimethoxyphenyl)-1,2,4-oxadiazol-5-yl]piperidine-1-carbonyl]-1-phenyl-pyrrolidin-2-one

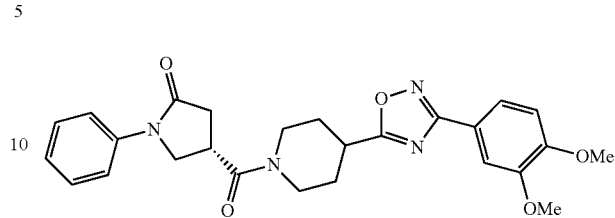

A mixture of N'-hydroxy-3,4-dimethoxy-benzamidine (1.04 g, 5.32 mmol), 1-[(3S)-5-oxo-1-phenyl-pyrrolidine-3-carbonyl]piperidine-4-carboxylic acid (1.40 g, 4.43 mmol), (2-(1H-benzotriazol-1-yl)-1,1,3,3-tetramethyluronium hexafluorophosphate) (2.18 g, 5.76 mmol) and N-ethyl-N-(propan-2-yl)propan-2-amine (1.72 g, 13.29 mmol, 2.32 mL) in N,N-dimethylformamide (8.00 mL), was stirred at 20° C. for 15 h and at 110° C. for 1 h. The mixture was cooled to room temperature, concentrated under reduced pressure to give a residue purified by prep-HPLC [column: Phenomenex luna C18 250×50 mm×10 μm; mobile phase: water/ammonium carbonate (10 mM)/acetonitrile]; B %: 30%-60%, 30 min. The desired compound (4S)-4-[4-[3-(3,4-dimethoxyphenyl)-1,2,4-oxadiazol-5-yl]piperidine-1-carbonyl]-1-phenyl-pyrrolidin-2-one was isolated as a light yellow solid (608 mg, 1.28 mmol, 29%). $^1$H NMR (400 MHz, CHLOROFORM-d) δ 7.68 (br d, J=8.2 Hz, 1H), 7.61-7.53 (m, 3H), 7.40-7.33 (m, 2H), 7.18-7.12 (m, 1H), 6.95 (d, J=8.4 Hz, 1H), 4.61-4.46 (m, 1H), 4.30 (dd, J=7.2, 9.6 Hz, 1H), 4.01-3.92 (m, 8H), 3.57 (quin, J=8.4 Hz, 1H), 3.43-3.26 (m, 2H), 3.14-2.91 (m, 2H), 2.86-2.80 (m, 1H), 2.23 (br t, J=13.1 Hz, 2H), 2.02-1.93 (m, 2H); LCMS (ESI) m/z: [M+H]$^+$=477.3.

Example 66 [(4R)-4-[4-[3-(3,4-dimethoxyphenyl)-1,2,4-oxadiazol-5-yl]piperidine-1-carbonyl]-1-phenyl-pyrrolidin-2-one]

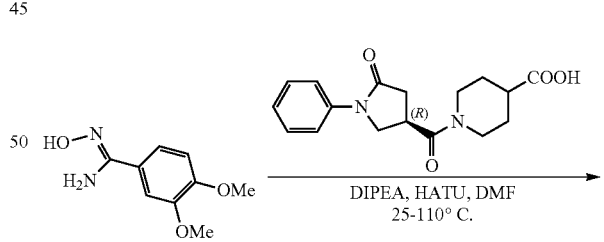

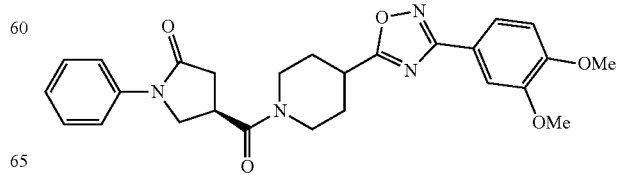

Step 1: Preparation of (4R)-4-[4-[3-(3,4-dimethoxyphenyl)-1,2,4-oxadiazol-5-yl]piperidine-1-carbonyl]-1-phenyl-pyrrolidin-2-one

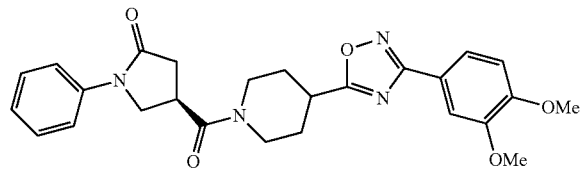 [SMILES: COc1ccc(-c2noc(C3CCN(C(=O)[C@@H]4CC(=O)N(c5ccccc5)C4)CC3)n2)cc1OC]

To a stirred solution of 1-[(3R)-5-oxo-1-phenyl-pyrrolidine-3-carbonyl]piperidine-4-carboxylic acid (115 mg, 363.52 µmol) and N'-hydroxy-3,4-dimethoxy-benzamidine (71 mg, 363.52 µmol) in N,N-dimethylformamide (500 µL) was added (2-(1H-benzotriazol-1-yl)-1,1,3,3-tetramethyluronium hexafluorophosphate) (137 mg, 363.52 µmol) and N-ethyl-N-(propan-2-yl)propan-2-amine (93 mg, 727 µmol, 126 µL) at 25° C. The mixture was then stirred at 25° C. for 2 h, and at 110° C. for 2 h. The mixture was concentrated under reduced pressure and the resulting crude product was purified by chromatography (column: Waters Xbridge 150× 2.5 mm 5 µm; mobile phase: water/ammonium carbonate (10 mM)/acetonitrile]; B %: 25%-60%, 12 min to give (4R)-4-[4-[3-(3,4-dimethoxyphenyl)-1,2,4-oxadiazol-5-yl]piperidine-1-carbonyl]-1-phenyl-pyrrolidin-2-one (32 mg, 67.45 µmol, 19%) as a yellow solid. $^1$H NMR (400 MHz, CHLOROFORM-d) δ=7.68 (br d, J=8.2 Hz, 1H), 7.61-7.55 (t, 3H), 7.37 (t, J=7.8 Hz, 2H), 7.19-7.14 (t, 1H), 6.95 (d, J=8.4 Hz, 1H), 4.60-4.46 (m, 1H), 4.31 (dd, J=7.2, 9.6 Hz, 1H), 3.98-3.94 (m, 7H), 3.98-3.92 (m, 1H), 3.58 (quin, J=8.5 Hz, 1H), 3.43-3.26 (m, 2H), 3.16-2.91 (m, 2H), 2.88-2.79 (m, 1H), 2.24 (br t, J=13.3 Hz, 2H), 2.06-1.88 (m, 2H); LCMS (ESI) m/z: [M+H]$^+$=477.3.

Examples 67: 4-(4-(3-(3,4-dimethoxyphenyl)-1,2,4-oxadiazol-5-yl)piperidine-1-carbonyl)-1-(3,4-dimethylphenyl)pyrrolidin-2-one, Enantiomer 1 and
Example 68: 4-(4-(3-(3,4-dimethoxyphenyl)-1,2,4-oxadiazol-5-yl)piperidine-1-carbonyl)-1-(3,4-dimethylphenyl)pyrrolidin-2-one, Enantiomer 2

Step 1: Preparation of 4-(4-(3-(3,4-dimethoxyphenyl)-1,2,4-oxadiazol-5-yl)piperidine-1-carbonyl)-1-(3,4-dimethylphenyl)pyrrolidin-2-one

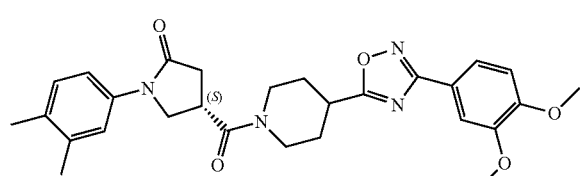

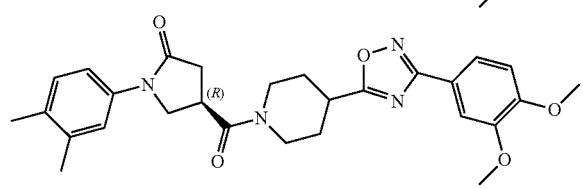

To a stirred solution of 1-[1-(3,4-dimethylphenyl)-5-oxo-pyrrolidine-3-carbonyl]piperidine-4-carboxylic acid (351 mg, 1.02 mmol) in N,N-dimethylformamide (1.50 mL) was added (2-(1H-benzotriazol-1-yl)-1,1,3,3-tetramethyluronium hexafluorophosphate) (386 mg, 1.02 mmol), N-ethyl-N-(propan-2-yl)propan-2-amine (395 mg, 3.06 mmol, 534 µL) and N-hydroxy-3,4-dimethoxy-benzamidine (200 mg, 1.02 mmol). The mixture was stirred at 20° C. for 12 h. The reaction mixture was then diluted with water (5 mL) and extracted with ethyl acetate (10 mL×3). The combined organic phases were washed with saturated aqueous sodium chloride solution (10 mL×2), dried over anhydrous sodium sulfate, filtered and concentrated under reduced pressure to give a residue. N,N-dimethylformamide (2 mL) was added to the residue and the resulting mixture was heated at 120° C. for 5 h. The mixture was cooled to 25° C., diluted by addition of water (5 mL) and extracted with ethyl acetate (10 mL×3). The combined organic phases were washed with saturated aqueous sodium chloride solution (10 mL×2), dried over anhydrous sodium sulfate, filtered and concentrated under reduced pressure to give a residue that was purified by prep-HPLC (column: Waters Xbridge 150×25 µm; mobile phase: water/ammonium carbonate (10 mM)/acetonitrile]; B %: 33%-63%, 12 min) to give racemic 4-(4-(3-(3,4-dimethoxyphenyl)-1,2,4-oxadiazol-5-yl)piperidine-1-carbonyl)-1-(3,4-dimethylphenyl)pyrrolidin-2-one.

This was separated by chiral-SFC (column: AS(250×30 mm, 10 µm); mobile phase: [CO$_2$ base-methanol]; B %: 40%-40%, min) to give firstly 4-[4-[3-(3,4-dimethoxyphenyl)-1,2,4-oxadiazol-5-yl]piperidine-1-carbonyl]-1-(3,4-dimethylphenyl)pyrrolidin-2-one, Enantiomer 1 (51 mg, 102 µmol, 10%) as a white solid. $^1$H NMR (400 MHz, DMSO-d6) δ=7.61 (br d, J=8.4 Hz, 1H), 7.48 (s, 1H), 7.43 (br s, 1H), 7.38 (br d, J=7.5 Hz, 1H), 7.16-7.10 (m, 2H), 4.37 (br s, 1H), 4.08-3.99 (m, 2H), 3.96-3.88 (m, 1H), 3.85 (s, 6H), 3.79-3.67 (m, 1H), 3.45 (br t, J=10.8 Hz, 1H), 3.32-3.28 (m, 1H), 3.02-2.87 (m, 1H), 2.82-2.70 (m, 2H), 2.24-2.18 (m, 6H), 2.18-2.10 (m, 2H), 1.91-1.61 (m, 2H); LCMS (ESI) m/z: [M+H]$^+$=505.4 and secondly 4-[4-[3-(3,4-dimethoxyphenyl)-1,2,4-oxadiazol-5-yl]piperidine-1-carbonyl]-1-(3,4-dimethylphenyl)pyrrolidin-2-one, Enantiomer 2 (48 mg, 95 µmol, 9%) also as a white solid. $^1$H NMR (400 MHz, DMSO-d6) δ=7.61 (br d, J=8.4 Hz, 1H), 7.48 (s, 1H), 7.43 (br s, 1H), 7.41-7.35 (m, 1H), 7.17-7.10 (m, 2H), 4.37 (br s, 1H), 4.09-3.99 (m, 2H), 3.98-3.89 (m, 1H), 3.85 (s, 6H), 3.78-3.68 (m, 1H), 3.50-3.39 (m, 1H), 3.35 (br s, 1H), 3.00-2.88 (m, 1H), 2.81-2.70 (m, 2H), 2.26-2.19 (m, 6H), 2.17-2.09 (m, 2H), 1.88-1.63 (m, 2H); LCMS (ESI) m/z: [M+H]$^+$=505.4

Example 69 1-(3,4-dimethylphenyl)-4-(4-(3-(3-methoxyphenyl)-1,2,4-oxadiazol-5-yl)piperidine-1-carbonyl)pyrrolidin-2-one, Enantiomer 1 and
Example 70 1-(3,4-dimethylphenyl)-4-(4-(3-(3-methoxyphenyl)-1,2,4-oxadiazol-5-yl)piperidine-1-carbonyl)pyrrolidin-2-one, Enantiomer 2

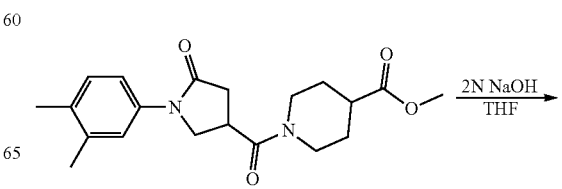

-continued

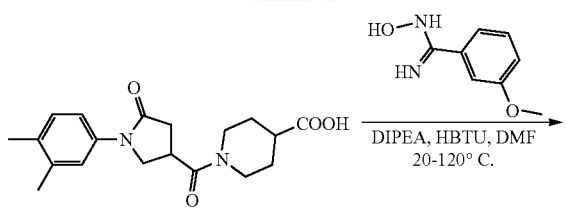

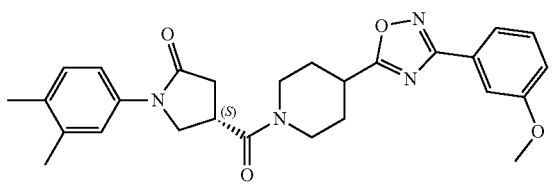

Step 1: Preparation of 1-(1-(3,4-dimethylphenyl)-5-oxopyrrolidine-3-carbonyl)piperidine-4-carboxylic acid

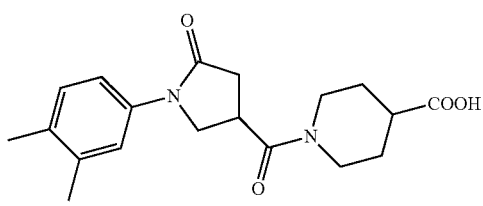 [SMILES: Cc1ccc(N2CC(C(=O)N3CCC(C(=O)O)CC3)CC2=O)cc1C]

To a stirred solution of methyl 1-(1-(3,4-dimethylphenyl)-5-oxopyrrolidine-3-carbonyl)piperidine-4-carboxylate (470 mg, 1.31 mmol) in tetrahydrofuran (5 mL) was added sodium hydroxide (2 M, 1.31 mL). The mixture was stirred at 20° C. for 16 h. The mixture was acidified with concentrated hydrochloric acid until pH=1. The mixture was extracted with dichloromethane (20 mL×4). The organic layers were combined and washed with saturated aqueous sodium chloride solution (5 mL), dried over anhydrous sodium sulfate, filtered and concentrated to give 1-(1-(3,4-dimethylphenyl)-5-oxopyrrolidine-3-carbonyl)piperidine-4-carboxylic acid (300 mg) as a brown solid. LCMS (ESI) m/z: [M+H]$^+$=345.2.

Step 2: Preparation of 1-(3,4-dimethylphenyl)-4-(4-(3-(3-methoxyphenyl)-1,2,4-oxadiazol-5-yl)piperidine-1-carbonyl)pyrrolidin-2-one, Enantiomer 1 and 1-(3,4-dimethylphenyl)-4-(4-(3-(3-methoxyphenyl)-1,2,4-oxadiazol-5-yl)piperidine-1-carbonyl)pyrrolidin-2-one, Enantiomer 2

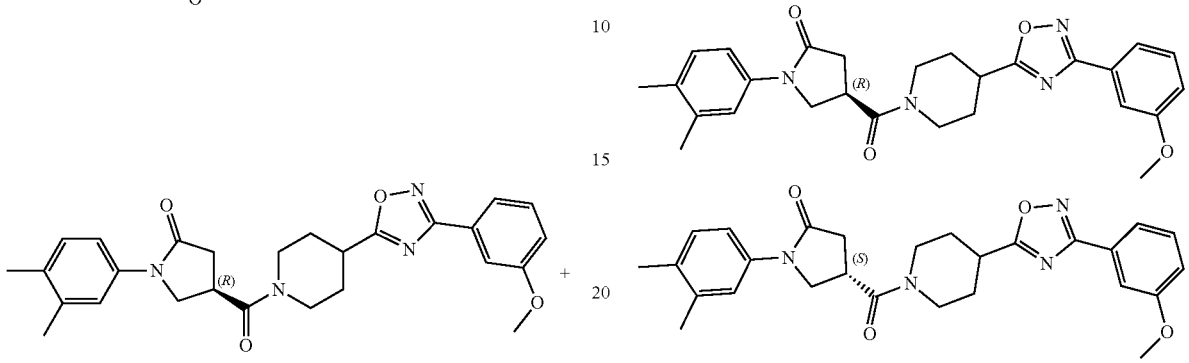

To a stirred solution of 1-(1-(3,4-dimethylphenyl)-5-oxopyrrolidine-3-carbonyl)piperidine-4-carboxylic acid (300 mg, 871 μmol) in N,N-dimethylformamide (4 mL) was added N-hydroxy-3-methoxy-benzamidine (173 mg, 1.05 mmol), (2-(1H-benzotriazol-1-yl)-1,1,3,3-tetramethyluronium hexafluorophosphate) (330 mg, 871 μmol) and N-ethyl-N-(propan-2-yl)propan-2-amine (337 mg, 2.61 mmol, 456 μL). The mixture was stirred at 20° C. for 2 h and then at 120° C. for 2 h. The reaction mixture was cooled, concentrated under reduced pressure and purified directly by preparative HPLC (column: Luna C8 100*30 5 μm; mobile phase: [water (10 mM ammonium carbonate)-acetonitrile]; B %: 45%-65%, 12 min) to give (rac)-1-(3,4-dimethylphenyl)-4-(4-(3-(3-methoxyphenyl)-1,2,4-oxadiazol-5-yl)piperidine-1-carbonyl) pyrrolidin-2-one that was purified by chiral-SFC (column: AD(250 mm*30 mm, 5 mm); mobile phase: [Base-isopropanol]; B %: 42%-42%, min) to give firstly 1-(3,4-dimethylphenyl)-4-(4-(3-(3-methoxyphenyl)-1,2,4-oxadiazol-5-yl)piperidine-1-carbonyl) yrrolidin-2-one, Enantiomer 1 (75 mg, 158.7 μmol, 18%, ee 100%) as a white solid, then 1-(3,4-dimethylphenyl)-4-(4-(3-(3-methoxyphenyl)-1,2,4-oxadiazol-5-yl)piperidine-1-carbonyl)pyrrolidin-2-one, Enantiomer 2 (75 mg, 160 μmol, 18%, ee 99.7%) as a yellow solid.

1-(3,4-dimethylphenyl)-4-(4-(3-(3-methoxyphenyl)-1,2,4-oxadiazol-5-yl)piperidine-1-carbonyl)pyrrolidin-2-one, Enantiomer 1

$^1$H NMR (400 MHz, CDCl$_3$) δ 7.63-7.57 (m, 1H), 7.55-7.50 (m, 1H), 7.31 (d, J=12.3 Hz, 2H), 7.22-7.19 (m, 1H), 7.05 (d, J=8.2 Hz, 1H), 7.00 (d, J=1.8 Hz, 1H), 4.53-4.37 (m, 1H), 4.21 (dd, J=7.3, 9.6 Hz, 1H), 3.95-3.77 (m, 5H), 3.49 (td, J=8.6, 16.9 Hz, 1H), 3.36-3.20 (m, 2H), 3.12-2.96 (m, 1H), 2.89 (td, J=8.3, 16.9 Hz, 1H), 2.79-2.70 (m, 1H), 2.18 (d, J=13.1 Hz, 8H), 1.99-1.83 (m, 2H); LCMS (ESI) m/z: [M+H]$^+$=475.1.

1-(3,4-dimethylphenyl)-4-(4-(3-(3-methoxyphenyl)-1,2,4-oxadiazol-5-yl)piperidine-1-carbonyl)pyrrolidin-2-one, Enantiomer 2

$^1$H NMR (400 MHz, CDCl$_3$) δ 7.63-7.57 (m, 1H), 7.53 (s, 1H), 7.36-7.27 (m, 2H), 7.21 (d, J=2.0 Hz, 1H), 7.05 (d,

J=8.0 Hz, 1H), 7.00 (d, J=2.0 Hz, 1H), 4.53-4.37 (m, 1H), 4.21 (dd, J=7.3, 9.5 Hz, 1H), 3.96-3.77 (m, 5H), 3.55-3.44 (m, 1H), 3.37-3.19 (m, 2H), 3.12-2.82 (m, 2H), 2.76 (d, J=9.4 Hz, 1H), 2.18 (d, J=13.1 Hz, 8H), 1.92 (br. s., 2H); LCMS (ESI) m/z: [M+H]$^+$=475.1.

Example 71 (1-(3,4-dimethylphenyl)-4-(4-(5-(p-tolyl)-1,2,4-oxadiazol-3-yl)piperidine-1-carbonyl) pyrrolidin-2-one), Enantiomer 1 and Example 72 (1-(3,4-dimethylphenyl)-4-(4-(5-(p-tolyl)-1,2,4-oxadiazol-3-yl)piperidine-1-carbonyl)pyrrolidin-2-one), Enantiomer 2

Racemic 1-(3,4-dimethylphenyl)-4-(4-(5-(p-tolyl)-1,2,4-oxadiazol-3-yl)piperidine-1-carbonyl)pyrrolidin-2-one (80 mg) was purified by SFC separation (column: AD (250×30 mm, 5 µm); mobile phase: [CO$_2$ base-isopropanol]; B %: 50%-50%, min) to give firstly 1-(3,4-dimethylphenyl)-4-(4-(5-(p-tolyl)-1,2,4-oxadiazol-3-yl)piperidine-1-carbonyl) pyrrolidin-2-one, Enantiomer 1 (26 mg, 59 µmol, 7%) as a white solid and secondly 1-(3,4-dimethylphenyl)-4-(4-(5-(p-tolyl)-1,2,4-oxadiazol-3-yl)piperidine-1-carbonyl)pyrrolidin-2-one, Enantiomer 2 as a white solid (23 mg, 52 µmol, 6%). 1-(3,4-dimethylphenyl)-4-(4-(5-(p-tolyl)-1,2,4-oxadiazol-3ll)piperidine-1-carbonyl)pyrrolidin-2-one, Enantiomer 1.

$^1$H NMR (400 MHz, CDCl$_3$) δ 8.06-8.00 (m, 2H), 7.41-7.33 (m, 3H), 7.32-7.29 (m, 1H), 7.15 (d, J=8.3 Hz, 1H), 4.66-4.54 (m, 1H), 4.30 (dd, J=7.4, 9.5 Hz, 1H), 4.05-3.88 (m, 2H), 3.65-3.55 (m, 1H), 3.43-3.30 (m, 1H), 3.20 (d, J=3.4 Hz, 1H), 3.12-2.94 (m, 2H), 2.85 (d, J=9.7 Hz, 1H), 2.47 (s, 3H), 2.32-2.14 (m, 8H), 1.94 (br. s., 2H); LCMS (ESI) m/z: [M+H]$^+$=459.3.

1-(3,4-dimethylphenyl)-4-(4-(5-(p-tolyl)-1,2,4-oxadiazol-3-yl)piperidine-1-carbonyl)pyrrolidin-2-one, Enantiomer 2

$^1$H NMR (400 MHz, CDCl$_3$) δ 7.96-7.90 (m, 2H), 7.32-7.24 (m, 3H), 7.22-7.19 (m, 1H), 7.05 (d, J=8.2 Hz, 1H), 4.58-4.43 (m, 1H), 4.20 (s, 1H), 3.94-3.79 (m, 2H), 3.50 (quin, J=8.5 Hz, 1H), 3.28 (br. s., 1H), 3.10 (d, J=3.9 Hz, 1H), 3.02-2.84 (m, 2H), 2.78-2.68 (m, 1H), 2.38 (s, 3H), 2.23-2.03 (m, 8H), 1.83 (d, J=10.8 Hz, 2H); LCMS (ESI) m/z: [M+H]$^+$=459.3

Examples 73 1-(3,4-dimethylphenyl)-4-(4-(5-(m-tolyl)-1,2,4-oxadiazol-3-yl)piperidine-1-carbonyl) pyrrolidin-2-one, Enantiomer 1 and Example 74 1-(3,4-dimethylphenyl)-4-(4-(5-(m-tolyl)-1,2,4-oxadiazol-3-yl)piperidine-1-carbonyl)pyrrolidin-2-one, Enantiomer 2

Racemic 1-(3,4-dimethylphenyl)-4-(4-(5-(m-tolyl)-1,2,4-oxadiazol-3-yl)piperidine-1-carbonyl)pyrrolidin-2-one (120 mg) was purified by SFC separation (column: OJ(250 mm×30 mm, 5 mm); mobile phase: [CO$_2$ base-ethanol]; B %: 30%-30%, min) to give firstly 1-(3,4-dimethylphenyl)-4-(4-(5-(m-tolyl)-1,2,4-oxadiazol-3-yl)piperidine-1-carbonyl)pyrrolidin-2-one, Enantiomer 1 (39 mg, 86.7 µmol, 11%) as a pink solid and secondly 1-(3,4-dimethylphenyl)-4-(4-(5-(m-tolyl)-1,2,4-oxadiazol-3-yl)piperidine-1-carbonyl)pyrrolidin-2-one, Enantiomer 2 (36 mg, 77.9 µmol, 10%) as a pink solid.

1-(3,4-dimethylphenyl)-4-(4-(5-(m-tolyl)-1,2,4-oxadiazol-3-yl)piperidine-1-carbonyl)pyrrolidin-2-one, Enantiomer 1

$^1$H NMR (400 MHz, CDCl$_3$) δ 7.94 (br. s., 2H), 7.39 (d, J=15.0 Hz, 3H), 7.29 (br. s., 1H), 7.12 (d, J=8.4 Hz, 1H), 4.58 (t, J=13.9 Hz, 1H), 4.28 (t, J=8.6 Hz, 1H), 4.01-3.87 (m, 2H), 3.62-3.53 (m, 1H), 3.35 (br. s., 1H), 3.19 (br. s., 1H), 3.08-2.93 (m, 2H), 2.86-2.76 (m, 1H), 2.45 (s, 3H), 2.32-2.11 (m, 8H), 1.90 (d, J=13.7 Hz, 2H); LCMS (ESI) m/z: [M+H]$^+$=459.3.

1-(3,4-dimethylphenyl)-4-(4-(5-(m-tolyl)-1,2,4-oxadiazol-3-yl)piperidine-1-carbonyl)pyrrolidin-2-one, Enantiomer 2

$^1$H NMR (400 MHz, Methanol-d4) δ8.00-7.90 (m, 2H), 7.53-7.45 (m, 2H), 7.41-7.37 (m, 1H), 7.32-7.27 (m, 1H), 7.19-7.13 (m, 1H), 4.53 (dd, J=3.5, 13.2 Hz, 1H), 4.19-4.03 (m, 3H), 3.90-3.80 (m, 1H), 3.49-3.39 (m, 1H), 3.30-3.20 (m, 1H), 3.12-3.00 (m, 1H), 2.94-2.82 (m, 2H), 2.47 (s, 3H), 2.35-2.11 (m, 8H), 1.99-1.77 (m, 2H); LCMS (ESI) m/z: [M+H]$^+$=459.3.

Example 75: (2-amino-1-(4-(3-(3,4-dimethoxyphenyl)-1,2,4-oxadiazol-5-yl)piperidin-1-yl)ethanone)

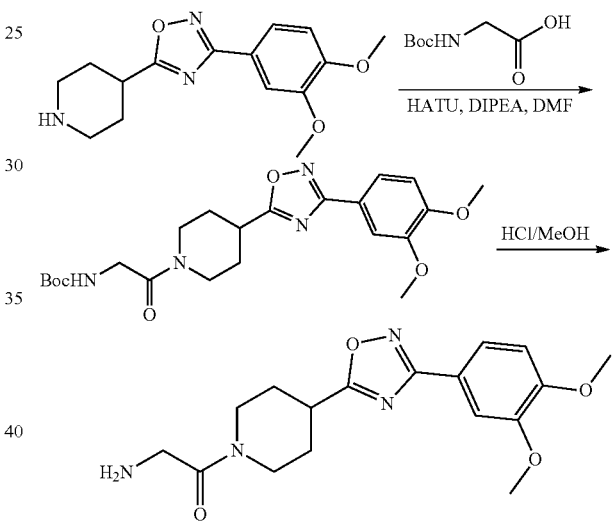

Step 1: Preparation of tert-butyl (2-(4-(3-(3,4-dimethoxyphenyl)-1,2,4-oxadiazol-5-yl)piperidin-1-yl)-2-oxoethyl)carbamate

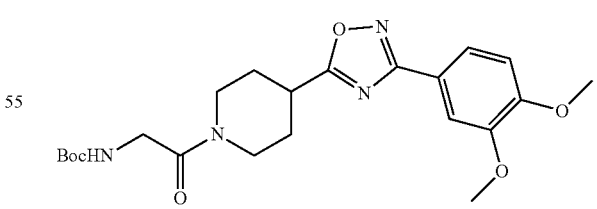

To a stirred solution of 3-(3,4-dimethoxyphenyl)-5-(piperidin-4-yl)-1,2,4-oxadiazole (2.0 g, 6.91 mmol) in N,N-dimethylformamide (20 mL) was added 2-(tert-butoxycarbonylamino)acetic acid (1.21 g, 6.91 mmol), (2-(1H-benzotriazol-1-yl)-1,1,3,3-tetramethyluronium hexafluorophosphate) (2.62 g, 6.91 mmol) and N-ethyl-N-(propan-2-yl)propan-2-amine (2.68 g, 20.7 mmol, 3.62 mL).

The mixture was stirred at 15° C. for 2 h. The reaction mixture was quenched by addition of water (20 mL) then the mixture was extracted with ethyl acetate (60 mL×4). The combined organic phases were washed with saturated aqueous sodium chloride solution (20 mL), dried over anhydrous sodium sulfate, filtered and concentrated to give a crude material that was purified by chromatography (silica, petroleum ether:ethyl acetate=5:1 to 1:1) to give tert-butyl (2-(4-(3-(3,4-dimethoxyphenyl)-1,2,4-oxadiazol-5-yl)piperidin-1-yl)-2-oxoethyl)carbamate (2.60 g, 5.82 mmol, 84%) as a brown solid. LCMS (ESI) m/z: [M+H]$^+$=447.2.

Step 2: Preparation of 2-amino-1-(4-(3-(3,4-dimethoxyphenyl)-1,2,4-oxadiazol-5-yl)piperidin-1-yl)ethanone

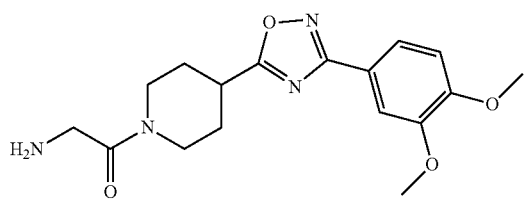 [SMILES: COc1ccc(-c2noc(C3CCN(C(=O)CN)CC3)n2)cc1OC]

To a stirred solution of tert-butyl (2-(4-(3-(3,4-dimethoxyphenyl)-1,2,4-oxadiazol-5-yl)piperidin-1-yl)-2-oxoethyl)carbamate (2.50 g, 5.60 mmol) in methanol (10 mL) was added methanolic hydrogen chloride solution (30 mL). The mixture was stirred at 20° C. for 1 h and then concentrated to give 2-amino-1-(4-(3-(3,4-dimethoxyphenyl)-1,2,4-oxadiazol-5-yl)piperidin-1-yl)ethanone (1.90 g, 5.49 mmol, 97.95%), isolated as a brown solid and used for the next step without further purification. A small amount (0.1 g) of the crude product was purified by prep-HPLC (column: Waters Xbridge 150×2.5 mm 5 μm; mobile phase: [water (10 mM ammonium carbonate)-acetonitrile]; B %: 20%-50%, 12 min) to give a pure sample for analysis: 2-amino-1-(4-(3-(3,4-dimethoxyphenyl)-1,2,4-oxadiazol-5-yl)piperidin-1-yl)ethanone (32 mg). $^1$H NMR (400 MHz, CDCl$_3$) δ 7.73-7.67 (m, 1H), 7.58 (d, J=1.5 Hz, 1H), 6.98 (d, J=8.4 Hz, 1H), 4.54 (d, J=12.2 Hz, 1H), 3.98 (d, J=7.2 Hz, 6H), 3.84 (d, J=12.0 Hz, 1H), 3.54 (s, 2H), 3.34-3.21 (m, 2H), 3.08 (d, J=12.3 Hz, 1H), 2.21 (d, J=13.1 Hz, 2H), 1.98 (d, J=9.4 Hz, 2H); LCMS (ESI) m/z: [M+H]$^+$=347.1.

Example 76: (5-hydroxy-2,2-dimethyl-7-(2-oxo-2-(4-(3-phenyl-1,2,4-oxadiazol-5-yl)piperidin-1-yl)ethoxy)choman-4-one)

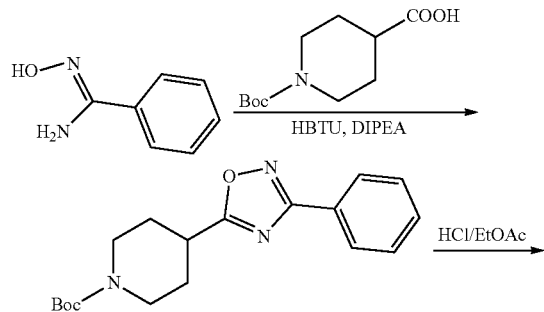

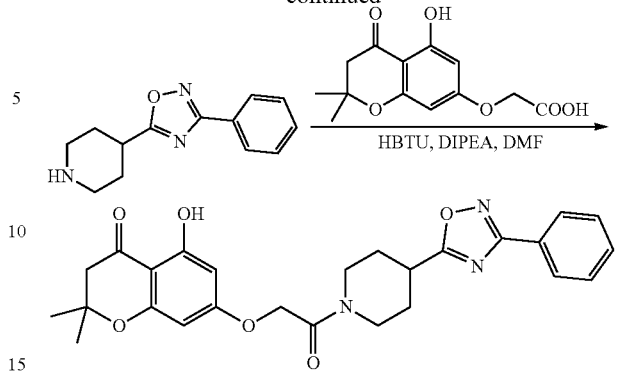

Step 1: Preparation of tert-butyl 4-(3-phenyl-1,2,4-oxadiazol-5-yl)piperidine-1-carboxylate

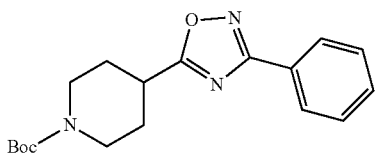 [SMILES: CC(C)(C)OC(=O)N1CCC(c2nc(-c3ccccc3)no2)CC1]

To a stirred solution of (Z)—N'-hydroxybenzimidamide (214 mg, 1.57 mmol) in N,N-dimethylformamide (5 mL) was added 1-(tert-butoxycarbonyl)piperidine-4-carboxylic acid (300 mg, 1.31 mmol), (2-(1H-benzotriazol-1-yl)-1,1,3,3-tetramethyluronium hexafluorophosphate) (496 mg, 1.31 mmol) and N-ethyl-N-(propan-2-yl)propan-2-amine (507 mg, 3.93 mmol, 686 μL). The mixture was stirred at 20° C. for 2 h, and then heated at 120° C. for 2 h. The reaction mixture was quenched with water (10 mL), then the mixture was extracted with ethyl acetate (30 mL×3). The combined organic phases were washed with saturated aqueous sodium chloride solution (10 mL), dried over anhydrous sodium sulfate, filtered and concentrated to give the crude product. The crude product was extracted with petroleum ether (30 mL×2). The combined organic extracts were concentrated under reduced pressure to give tert-butyl 4-(3-phenyl-1,2,4-oxadiazol-5-yl)piperidine-1-carboxylate (310 mg, 941 μmol, 72%) as a yellow oil. This product was used in the next step without further purification.

Step 2: Preparation of 3-phenyl-5-(piperidin-4-yl)-1,2,4-oxadiazole

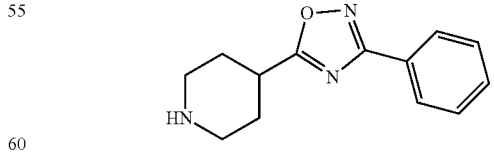

To a stirred solution of tert-butyl 4-(3-phenyl-1,2,4-oxadiazol-5-yl)piperidine-1-carboxylate (310 mg, 941 μmol) in ethyl acetate (2 mL) was added an anhydrous solution of hydrochloric acid in ethyl acetate (20 mL). The mixture was stirred at 20° C. for 1 h. The reaction mixture was concentrated under reduced pressure to provide the crude 3-phenyl- 5-(piperidin-4-yl)-1,2,4-oxadiazole (233 mg) as a yellow solid that was used for the next step without further purification. LCMS (ESI) m/z: [M+H]⁺=230.2.

Step 3: Preparation of 5-hydroxy-2,2-dimethyl-7-(2-oxo-2-(4-(3-phenyl-1,2,4-oxadiazol-5-yl)piperidin-1-yl)ethoxy)choman-4-one

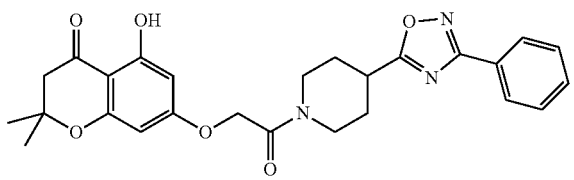 [SMILES: CC1(C)CC(=O)c2c(O)cc(OCC(=O)N3CCC(c4nc(-c5ccccc5)no4)CC3)cc2O1]

To a stirred solution of 2-((5-hydroxy-2,2-dimethyl-4-oxochoman-7-yl)oxy)acetic acid (150 mg, 563 μmol) in N,N-dimethylformamide (2 mL) was added 3-phenyl-5-(piperidin-4-yl)-1,2,4-oxadiazole (142 mg, 620 μmol), (2-(1H-benzotriazol-1-yl)-1,1,3,3-tetramethyluronium hexafluorophosphate) (213 mg, 563 μmol) and N-ethyl-N-(propan-2-yl)propan-2-amine (291 mg, 2.25 mmol, 393 μL). The mixture was stirred at 20° C. for 2 h. The reaction mixture was concentrated under reduced pressure and the resulting residue purified by prep-HPLC (column: Waters Xbridge 150×2.5 mm 5 μm; mobile phase: [water (10 mM ammonium carbonate)-acetonitrile]; B %: 45%-75%, 12 min) to give 5-hydroxy-2,2-dimethyl-7-(2-oxo-2-(4-(3-phenyl-1,2,4-oxadiazol-5-yl)piperidin-1-yl)ethoxy)choman-4-one (120 mg, 250.6 μmol, 44%) as a white solid. ¹H NMR (400 MHz, CDCl₃) δ 12.00 (s, 1H), 8.12-8.07 (m, 2H), 7.56-7.48 (m, 3H), 6.07 (d, J=2.4 Hz, 1H), 6.04 (d, J=2.3 Hz, 1H), 4.74 (s, 2H), 4.46 (d, J=13.8 Hz, 1H), 3.98 (d, J=13.1 Hz, 1H), 3.42-3.28 (m, 2H), 3.13 (t, J=11.1 Hz, 1H), 2.71 (s, 2H), 2.23 (br. s., 2H), 2.07-1.92 (m, 2H), 1.49-1.46 (m, 6H); LCMS (ESI) m/z: [M+H]⁺=478.2.

Example 77 (7-(2-(4-(3-(3,4-dimethoxyphenyl)-1,2,4-oxadiazol-5-yl)piperidin-1-yl)-2-oxoethoxy)-5-hydroxy-2,2-dimethylchroman-4-one)

Step 1: Preparation of 7-(2-(4-(3-(3,4-dimethoxyphenyl)-1,2,4-oxadiazol-5-yl)piperidin-1-yl)-2-oxoethoxy)-5-hydroxy-2,2-dimethylchoman-4-one

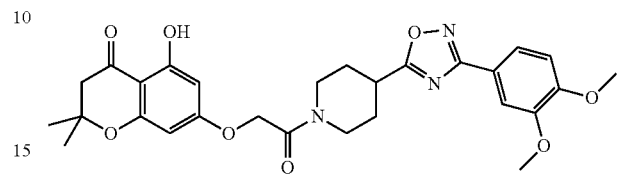

To a stirred solution of 2-((5-hydroxy-2,2-dimethyl-4-oxochoman-7-yl)oxy)acetic acid (150 mg, 563 μmol) in N,N-dimethylformamide (2 mL) was added 3-(3,4-dimethoxyphenyl)-5-(piperidin-4-yl)-1,2,4-oxadiazole (195 mg, 676 μmol), (2-(1H-benzotriazol-1-yl)-1,1,3,3-tetramethyluronium hexafluorophosphate) (213 mg, 563 μmol) and N-ethyl-N-(propan-2-yl)propan-2-amine (291 mg, 2.25 mmol, 393 μL). The mixture was stirred at 20° C. for 2 h. The reaction mixture was concentrated under reduced pressure. The resulting residue was purified by prep-HPLC (column: Waters Xbridge 150×2.5 mm 5 μm; mobile phase: [water (10 mM ammonium carbonate)-acetonitrile]; B %: 40%-70%, 12 min) to give 7-(2-(4-(3-(3,4-dimethoxyphenyl)-1,2,4-oxadiazol-5-yl)piperidin-1-yl)-2-oxoethoxy)-5-hydroxy-2,2-dimethylchoman-4-one (133 mg, 245.66 μmol, 44%) as a white solid. ¹H NMR (400 MHz, CDCl₃) δ 12.00 (s, 1H), 7.71 (dd, J=1.9, 8.3 Hz, 1H), 7.58 (d, J=1.9 Hz, 1H), 6.98 (d, J=8.4 Hz, 1H), 6.06 (d, J=2.4 Hz, 1H), 6.03 (d, J=2.4 Hz, 1H), 4.74 (s, 2H), 4.47 (d, J=14.2 Hz, 1H), 4.01-3.94 (m, 7H), 3.41-3.26 (m, 2H), 3.11 (t, J=11.0 Hz, 1H), 2.71 (s, 2H), 2.22 (br. s., 2H), 2.06-1.93 (m, 2H), 1.47 (s, 6H); LCMS (ESI) m/z: [M+H]⁺=538.3.

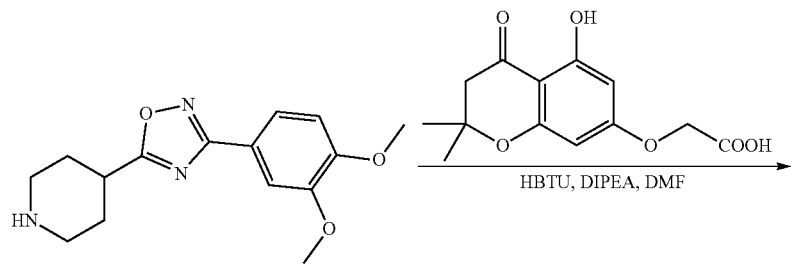

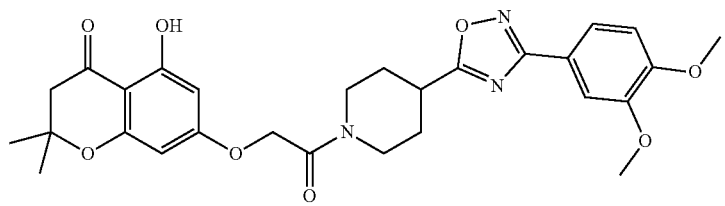

Example 78: (N-(2-oxo-2-(4-(3-(pyridin-2-yl)-1,2,4-oxadiazol-5-yl)piperidin-1-yl)ethyl)benzamide

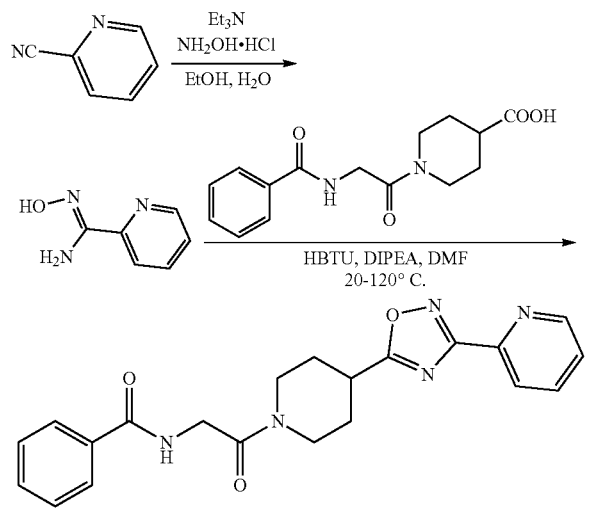

Step 1: Preparation of (Z)—N'-hydroxypicolinimidamide

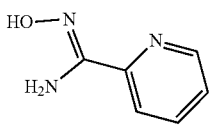

To a stirred solution of picolinonitrile (3.0 g, 28.8 mmol, 2.78 mL) in ethanol (30 mL) was added hydroxylamine hydrochloride (4.01 g, 57.6 mmol), triethylamine (5.83 g, 57.6 mmol, 8.0 mL) and water (5 mL). The mixture was heated at 75° C. for 5 h. The mixture was then concentrated to give a residue. The solid residue was triturated with water (30 mL), filtered, and dried under reduced pressure to give (Z)—N'-hydroxypicolinimidamide (2.0 g, 14.6 mmol, 51%) as a white solid. $^1$H NMR (400 MHz, DMSO-d6) δ 9.93 (s, 1H), 8.57 (d, J=4.5 Hz, 1H), 7.92-7.75 (m, 2H), 7.47-7.35 (m, 1H), 5.85 (br. s., 2H).

Step 2: Preparation of N-(2-oxo-2-(4-(3-(pyridin-2-yl)-1,2,4-oxadiazol-5-yl)piperidin-1-yl)ethyl)benzamide

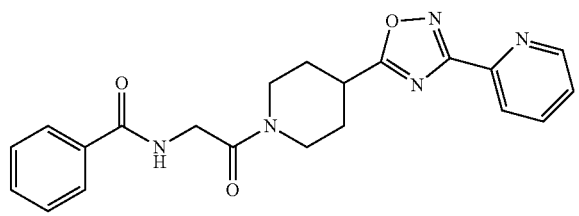 [SMILES: O=C(NCC(=O)N1CCC(c2nc(-c3ccccn3)no2)CC1)c1ccccc1]

To a stirred solution of 1-(2-benzamidoacetyl)piperidine-4-carboxylic acid (120 mg, 413 μmol) in N,N-dimethylformamide (2 mL) was added (Z)—N'-hydroxypicolinimidamide (56 mg, 413 μmol), N-ethyl-N-(propan-2-yl)propan-2-amine (160 mg, 1.24 mmol, 216 μL) and (2-(1H-benzotriazol-1-yl)-1,1,3,3-tetramethyluronium hexafluorophosphate) (156 mg, 413 μmol). The mixture was stirred at 20° C. for 2 h, then heated at 120° C. for 2 h. The reaction mixture was cooled, concentrated under reduced pressure and the resulting residue was purified by prep-HPLC (column: Waters Xbridge 150×2.5 mm 5 μm; mobile phase: [water (10 mM ammonium carbonate)-acetonitrile]; B %: 20%-55%, 12 min) to give N-(2-oxo-2-(4-(3-(pyridin-2-yl)-1,2,4-oxadiazol-5-yl)piperidin-1-yl)ethyl)benzamide (75 mg, 192 μmol, 47%) as a yellow solid. $^1$H NMR (400 MHz, CDCl$_3$) δ 8.84 (td, J=0.8, 4.0 Hz, 1H), 8.18-8.12 (m, 1H), 7.93-7.84 (m, 3H), 7.58-7.43 (m, 4H), 7.35 (br. s., 1H), 4.53 (d, J=13.6 Hz, 1H), 4.32 (t, J=3.5 Hz, 2H), 3.93 (d, J=14.1 Hz, 1H), 3.45-3.31 (m, 2H), 3.21-3.10 (m, 1H), 2.37-2.24 (m, 2H), 2.15-1.98 (m, 2H); LCMS (ESI) m/z: [M+H]$^+$=392.2.

Example 79: N-(2-oxo-2-(4-(3-(quinolin-2-yl)-1,2,4-oxadiazol-5-yl)piperidin-1-yl)ethyl)benzamide

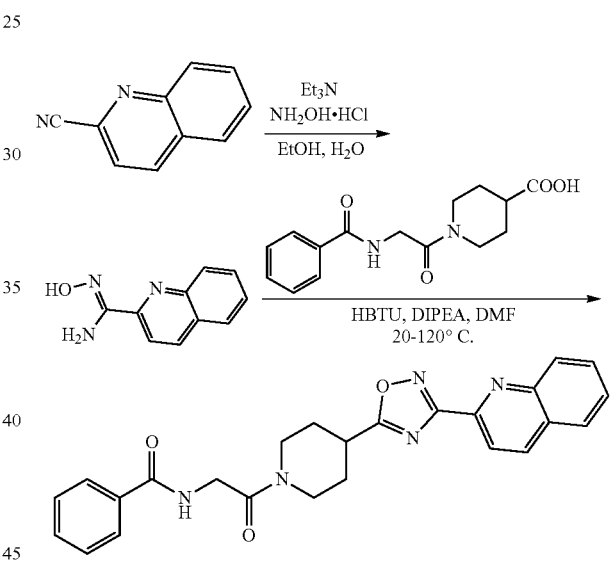

Step 1: Preparation of (Z)—N'-hydroxyquinoline-2-carboximidamide

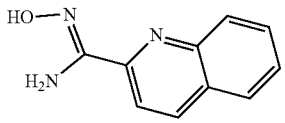 [SMILES: N/C(=N\O)c1ccc2ccccc2n1]

To a stirred solution of quinoline-2-carbonitrile (900 mg, 5.84 mmol) in ethanol (10 mL) was added hydroxylamine hydrochloride (811 mg, 11.7 mmol), triethylamine (1.18 g, 11.7 mmol, 1.6 mL) and water (1 mL). The mixture was heated at 75° C. for 5 h. The reaction mixture was cooled and filtered, and the filter cake dried in vacuo to give (Z)—N'-hydroxyquinoline-2-carboximidamide (1.0 g, 5.34 mmol, 91%) as a light yellow solid. This was used directly without further purification. $^1$H NMR (400 MHz, DMSO-d6) δ 10.23

(s, 1H), 8.34 (d, J=8.7 Hz, 1H), 8.10-7.93 (m, 3H), 7.80 (s, 1H), 7.67-7.59 (m, 1H), 6.02 (br. s., 2H).

Step 2: Preparation of N-(2-oxo-2-(4-(3-(quinolin-2-yl)-1,2,4-oxadiazol-5-yl)piperidin-1-yl)ethyl)benzamide

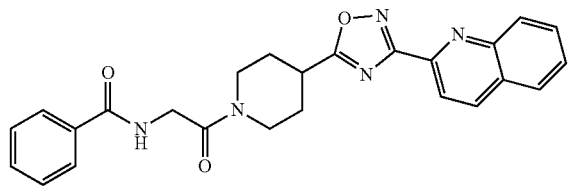 [SMILES: O=C(NCC(=O)N1CCC(c2nc(-c3ccc4ccccc4n3)no2)CC1)c1ccccc1]

To a stirred solution of 1-(2-benzamidoacetyl)piperidine-4-carboxylic acid (120 mg, 413 µmol) in N,N-dimethylformamide (2 mL) was added (Z)—N'-hydroxyquinoline-2-carboximidamide (77 mg, 413 µmol), N-ethyl-N-(propan-2-yl)propan-2-amine (160 mg, 1.24 mmol, 216 µL) and (2-(1H-benzotriazol-1-yl)-1,1,3,3-tetramethyluronium hexafluorophosphate) (156 mg, 413 µmol). The mixture was stirred at 20° C. for 2 h firstly, then heated at 120° C. for 2 h. The reaction mixture was cooled and purified directly by prep-HPLC (column: Waters Xbridge 150×2.5 mm 5 µm; mobile phase: [water (10 mM ammonium carbonate)-acetonitrile]; B %: 30%-60%, 12 min) to give N-(2-oxo-2-(4-(3-(quinolin-2-yl)-1,2,4-oxadiazol-5-yl)piperidin-1-yl)ethyl)benzamide (66 mg, 150 µmol, 36%) as a yellow solid. $^1$H NMR (400 MHz, CDCl$_3$) δ 8.26 (dd, J=2.1, 8.5 Hz, 2H), 8.14 (d, J=8.5 Hz, 1H), 7.86-7.77 (m, 3H), 7.72 (dt, J=1.3, 7.7 Hz, 1H), 7.61-7.53 (m, 1H), 7.49-7.34 (m, 3H), 7.27 (br. s., 1H), 4.50 (d, J=13.8 Hz, 1H), 4.24 (d, J=3.6 Hz, 2H), 3.87 (d, J=13.8 Hz, 1H), 3.42-3.22 (m, 2H), 3.09-2.98 (m, 1H), 2.31-2.16 (m, 2H), 2.10-1.91 (m, 2H); LCMS (ESI) m/z: [M+H]$^+$=442.2.

Example 80: 4-(3-(4-ethoxy-3-methoxyphenyl)-1,2,4-oxadiazol-5-yl)-N-(2-phenylcyclopropyl)piperidine-1-carboxamide

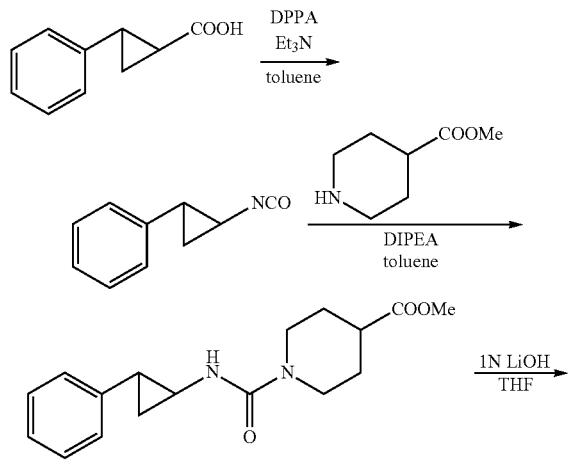

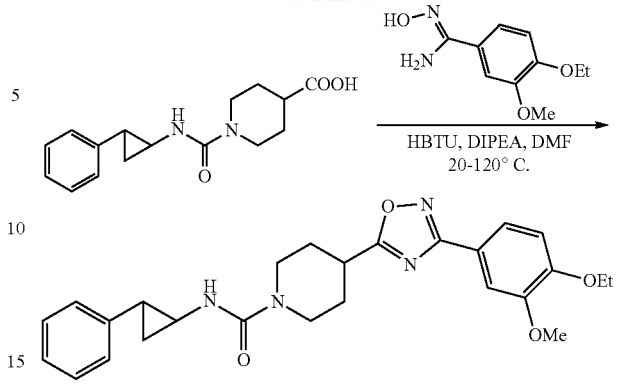

Step 1: (2-isocyanatocyclopropyl)benzene

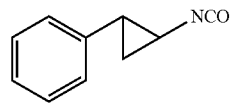

To a stirred solution of 2-phenylcyclopropanecarboxylic acid (1.0 g, 6.17 mmol) in toluene (10 mL) was added diphenylphosphoryl azide (2.04 g, 7.40 mmol, 1.60 mL) and triethylamine (935 mg, 9.25 mmol, 1.28 mL) under nitrogen. The mixture was stirred at 120° C. for 2 h. The reaction mixture was cooled then concentrated in vacuo to give (2-isocyanatocyclopropyl)benzene (2.0 g) as a yellow oil that was used directly without purification.

Step 2: Preparation of methyl 1-((2-phenylcyclopropyl)carbamoyl)piperidine-4-carboxylate

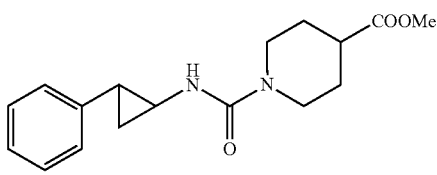 [SMILES: COC(=O)C1CCN(C(=O)NC2CC2c2ccccc2)CC1]

To a stirred solution of methyl piperidine-4-carboxylate (800 mg, 5.59 mmol) in toluene (10 mL) was added (2-isocyanatocyclopropyl)benzene (2.0 g, 12.58 mmol, 2.25 eq) and N-ethyl-N-(propan-2-yl)propan-2-amine (722 mg, 5.59 mmol, 975 µL). After 16 h, the reaction mixture was quenched with water (10 mL). The mixture was extracted with ethyl acetate (50 mL×3), then the combined organic phases were washed with saturated aqueous sodium chloride solution (20 mL), dried over anhydrous sodium sulfate, filtered and concentrated to a residue which was purified by chromatography (silica, petroleumether:ethylacetate=50:1 to 2:1) to give methyl 1-((2-phenylcyclopropyl)carbamoyl)piperidine-4-carboxylate (820 mg, 2.71 mmol, 48%) as a yellow oil. $^1$H NMR (400 MHz, CDCl$_3$) δ 7.22-7.19 (m, 1H), 7.17 (s, 1H), 7.10 (d, J=7.4 Hz, 3H), 4.75 (br. s., 1H), 3.79 (d, J=13.3 Hz, 2H), 3.63 (s, 3H), 2.89-2.73 (m, 3H), 2.47-2.33 (m, 1H), 2.02-1.78 (m, 3H), 1.61 (dd, J=2.1, 13.1 Hz, 2H), 1.16-1.11 (m, 1H), 1.08-1.03 (m, 1H).

Step 3: Preparation of 1-((2-phenylcyclopropyl) carbamoyl)piperidine-4-carboxylic acid

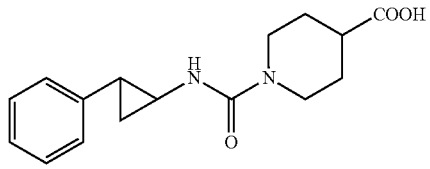 [SMILES: O=C(O)C1CCN(C(=O)NC2CC2c2ccccc2)CC1]

To a stirred solution of methyl 1-((2-phenylcyclopropyl) carbamoyl)piperidine-4-carboxylate (770 mg, 2.55 mmol) in tetrahydrofuran (10 mL) was added lithium hydroxide (1 M, 5.10 mL). After 2 h, the reaction was acidified with 1 M hydrochloric acid (8 mL). The mixture was extracted with dichloromethane (40 mL×3). The organic phases were combined and washed with saturated aqueous sodium chloride solution (10 mL), then dried over anhydrous sodium sulfate, filtered, and concentrated to give 1-((2-phenylcyclopropyl) carbamoyl)piperidine-4-carboxylic acid (660 mg, 2.29 mmol, 90%) as a yellow solid that was used directly without further purification. $^1$H NMR (400 MHz, DMSO-d6) δ 12.22 (s, 1H), 7.33-7.01 (m, 5H), 6.78 (d, J=2.5 Hz, 1H), 3.85 (d, J=13.3 Hz, 2H), 2.81-2.66 (m, 3H), 2.40 (br. s., 1H), 1.95-1.69 (m, 3H), 1.39 (d, J=12.0 Hz, 2H), 1.21-1.13 (m, 1H), 1.10-1.04 (m, 1H).

Step 4: Preparation of 4-(3-(4-ethoxy-3-methoxyphenyl)-1,2,4-oxadiazol-5-yl)-N-(2-phenylcyclopropyl)piperidine-1-carboxamide

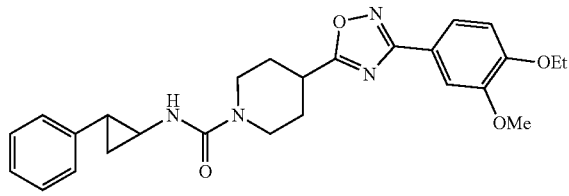 [SMILES: CCOc1ccc(-c2noc(C3CCN(C(=O)NC4CC4c4ccccc4)CC3)n2)cc1OC]

To a stirred solution of 1-((2-phenylcyclopropyl)carbamoyl)piperidine-4-carboxylic acid (100 mg, 347 μmol) in N,N-dimethylformamide (2 mL) was added (Z)-4-ethoxy-N'-hydroxy-3-methoxybenzimidamide (72 mg, 347 μmol), (2-(1H-benzotriazol-1-yl)-1,1,3,3-tetramethyluronium hexafluorophosphate) (131 mg, 347 μmol) and N-ethyl-N-(propan-2-yl)propan-2-amine (134 mg, 1.04 mmol, 181 μL). The mixture was stirred at 20° C. for 2 h, then heated at 120° C. for 2 h. The reaction mixture was cooled then purified by prep-HPLC (column: Waters Xbridge 150×2.5 mm 5 μm; mobile phase: [water (10 mM ammonium carbonate)-acetonitrile]; B %: 40%-75%, 12 min) to give 4-(3-(4-ethoxy-3-methoxyphenyl)-1,2,4-oxadiazol-5-yl)-N-(2-phenylcyclopropyl)piperidine-1-carboxamide (81 mg, 173 μmol, 50%) as a yellow solid. $^1$H NMR (400 MHz, CDCl$_3$) δ 7.70-7.66 (m, 1H), 7.58 (d, J=1.9 Hz, 1H), 7.31 (s, 1H), 7.27 (s, 1H), 7.23-7.17 (m, 3H), 6.97 (d, J=8.5 Hz, 1H), 4.91 (s, 1H), 4.19 (q, J=7.0 Hz, 2H), 3.98 (s, 5H), 3.25-3.16 (m, 1H), 3.13-3.03 (m, 2H), 2.91-2.85 (m, 1H), 2.18 (dd, J=3.5, 13.4 Hz, 2H), 2.07 (ddd, J=3.3, 6.2, 9.5 Hz, 1H), 2.03-1.91 (m, 2H), 1.53 (t, J=7.0 Hz, 3H), 1.28-1.22 (m, 1H), 1.17 (td, J=5.0, 9.7 Hz, 1H); LCMS (ESI) m/z: [M+H]$^+$=463.2.

Example 81: N-(2-phenylcyclopropyl)-4-(3-(pyridin-2-yl)-1,2,4-oxadiazol-5-yl)piperidine-1-carboxamide

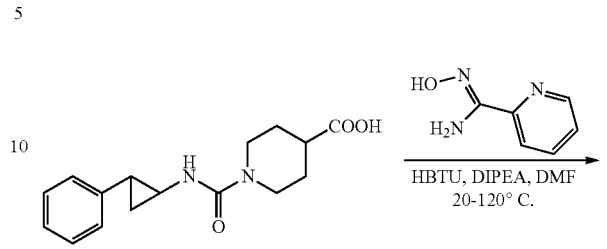


Step 1: Preparation of N-(2-phenylcyclopropyl)-4-(3-(pyridin-2-yl)-1,2,4-oxadiazol-5-yl)piperidine-1-carboxamide

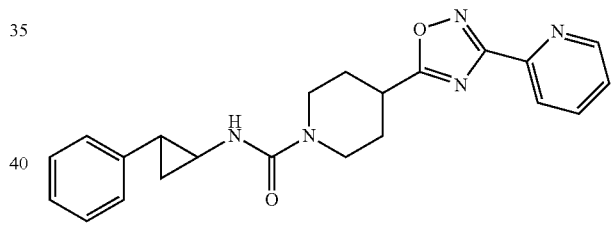

To a stirred solution of 1-((2-phenylcyclopropyl)carbamoyl)piperidine-4-carboxylic acid (130 mg, 451 μmol) in N,N-dimethylformamide (1 mL) was added (Z)—N'-hydroxypicolinimidamide (74 mg, 541 μmol), (2-(1H-benzotriazol-1-yl)-1,1,3,3-tetramethyluronium hexafluorophosphate) (170 mg, 451 μmol) and N-ethyl-N-(propan-2-yl) propan-2-amine (174 mg, 1.35 mmol, 236 μL). The mixture was stirred at 20° C. for 2 h, then heated at 110° C. for 2 h. The reaction mixture was cooled then purified by prep-HPLC (column: Waters Xbridge 150×2.5 mm 5 μm; mobile phase: [water (10 mM ammonium carbonate)-acetonitrile]; B %: 30%-60%, 12 min) to give N-(2-phenylcyclopropyl)-4-(3-(pyridin-2-yl)-1,2,4-oxadiazol-5-yl)piperidine-1-carboxamide (47 mg, 121.6 μmol, 27%) as a yellow solid. $^1$H NMR (400 MHz, DMSO-d6) δ 8.76 (d, J=4.0 Hz, 1H), 8.12-7.97 (m, 2H), 7.65-7.55 (m, 1H), 7.30-7.19 (m, 2H), 7.18-7.05 (m, 3H), 6.87 (br. s., 1H), 3.96 (d, J=13.2 Hz, 2H), 2.93 (t, J=11.7 Hz, 2H), 2.71 (d, J=3.1 Hz, 1H), 2.06 (d, J=11.5 Hz, 2H), 1.89 (br. s., 1H), 1.68 (d, J=11.9 Hz, 3H), 1.20-1.04 (m, 2H); LCMS (ESI) m/z: [M+H]$^+$=390.1.

Example 82: N-(2-phenylcyclopropyl)-4-(3-(quinolin-2-yl)-1,2,4-oxadiazol-5-yl)piperidine-1-carboxamide

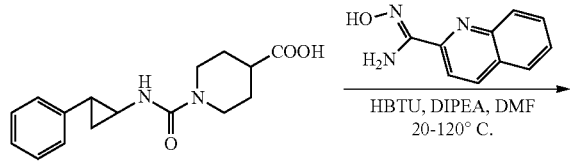

Step 1: Preparation of N-(2-phenylcyclopropyl)-4-(3-(quinolin-2-yl)-1,2,4-oxadiazol-5-yl)piperidine-1-carboxamide

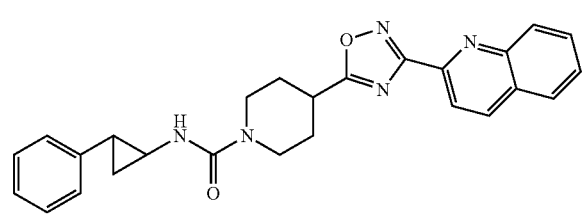 [SMILES: O=C(NC1CC1c1ccccc1)N1CCC(c2nc(-c3ccc4ccccc4n3)no2)CC1]

To a stirred solution of 1-[(2-phenylcyclopropyl)carbamoyl]piperidine-4-carboxylic acid (130 mg, 451 μmol) in N,N-dimethylformamide (2 mL) was added (Z)—N'-hydroxyquinoline-2-carboximidamide (101 mg, 541 μmol), (2-(1H-benzotriazol-1-yl)-1,1,3,3-tetramethyluronium hexafluorophosphate) (170 mg, 451 μmol) and N-ethyl-N-(propan-2-yl)propan-2-amine (174 mg, 1.35 mmol, 236 μL). The mixture was stirred at 20° C. for 2 h, and then heated at 120° C. for 2 h. The reaction mixture was cooled then purified by prep-HPLC (column: Waters Xbridge 150×2.5 mm 5 μm; mobile phase: [water (10 mM ammonium carbonate)-acetonitrile]; B %: 40%-70%, 12 min) to give N-(2-phenylcyclopropyl)-4-(3-(quinolin-2-yl)-1,2,4-oxadiazol-5-yl)piperidine-1-carboxamide (34 mg, 77 μmol, 17%) as a yellow solid. $^1$H NMR (400 MHz, DMSO-d6) δ 8.60 (s, 1H), 8.22-8.07 (m, 3H), 7.88 (br. s., 1H), 7.74 (d, J=7.5 Hz, 1H), 7.30-7.20 (m, 2H), 7.18-7.06 (m, 3H), 6.89 (br. s., 1H), 3.99 (d, J=13.7 Hz, 2H), 3.45-3.37 (m, 1H), 2.94 (t, J=11.7 Hz, 2H), 2.72 (d, J=3.5 Hz, 1H), 2.10 (d, J=11.0 Hz, 2H), 1.89 (br. s., 1H), 1.72 (d, J=11.5 Hz, 2H), 1.18 (td, J=4.6, 9.3 Hz, 1H), 1.11-1.05 (m, 1H); LCMS (ESI) m/z: [M+H]$^+$=440.1.

Example 83: 4-(3-(4-ethoxy-3-methoxyphenyl)-1,2,4-oxadiazol-5-yl)-N-phenethylpiperidine-1-carboxamide

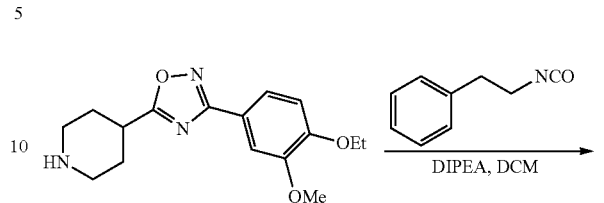

Step 1: Preparation of 4-(3-(4-ethoxy-3-methoxyphenyl)-1,2,4-oxadiazol-5-yl)-N-phenethylpiperidine-1-carboxamide

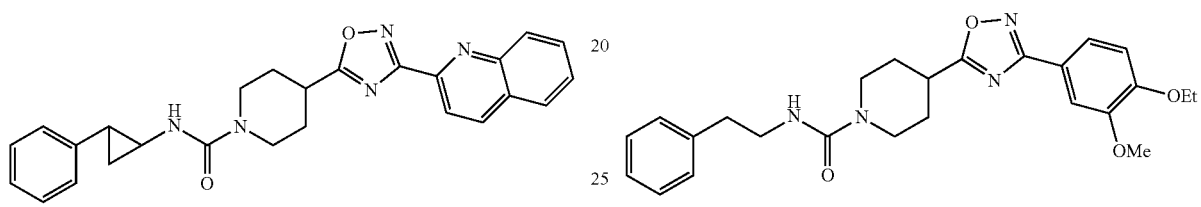

To a stirred solution of (2-isocyanatoethyl)benzene (72 mg, 494 μmol, 68 μL) in toluene (2 mL) was added 3-(4-ethoxy-3-methoxyphenyl)-5-(piperidin-4-yl)-1,2,4-oxadiazole (150 mg, 494 μmol) and N-ethyl-N-(propan-2-yl)propan-2-amine (63 mg, 494 μmol, 86 μL). Then mixture was stirred at 20° C. for 16 h. The reaction mixture was concentrated in vacuo to give a crude product that was purified by prep-HPLC (column: Waters Xbridge 150×2.5 mm 5 μm; mobile phase: [water (10 mM ammonium carbonate)-acetonitrile]; B %: 35%-60%, 12 min) to give 4-(3-(4-ethoxy-3-methoxyphenyl)-1,2,4-oxadiazol-5-yl)-N-phenethylpiperidine-1-carboxamide (58 mg, 130 μmol, 26%) as a white solid. $^1$H NMR (400 MHz, CDCl$_3$) δ 7.59 (dd, J=2.0, 8.4 Hz, 1H), 7.49 (d, J=1.9 Hz, 1H), 7.28-7.22 (m, 2H), 7.18-7.12 (m, 3H), 6.87 (d, J=8.4 Hz, 1H), 4.40 (br. s., 1H), 4.10 (q, J=7.0 Hz, 2H), 3.88 (s, 3H), 3.86-3.80 (m, 2H), 3.48-3.41 (m, 2H), 3.14-3.05 (m, 1H), 2.97-2.88 (m, 2H), 2.78 (t, J=6.8 Hz, 2H), 2.04 (dd, J=3.2, 13.1 Hz, 2H), 1.89-1.77 (m, 2H), 1.43 (t, J=7.0 Hz, 3H); LCMS (ESI) m/z: [M+H]$^+$=451.3.

Example 84: 4-(4-(3-(4-ethoxy-3-methoxyphenyl)-1,2,4-oxadiazol-5-yl)piperidine-1-carbonyl)-1-phenylpyrrolidin-2-one, Example 85: (R)-4-(4-(3-(4-ethoxy-3-methoxyphenyl)-1,2,4-oxadiazol-5-yl)piperidine-1-carbonyl)-1-phenylpyrrolidin-2-one, and Example 86: (S)-4-(4-(3-(4-ethoxy-3-methoxyphenyl)-1,2,4-oxadiazol-5-yl)piperidine-1-carbonyl)-1-phenylpyrrolidin-2-one

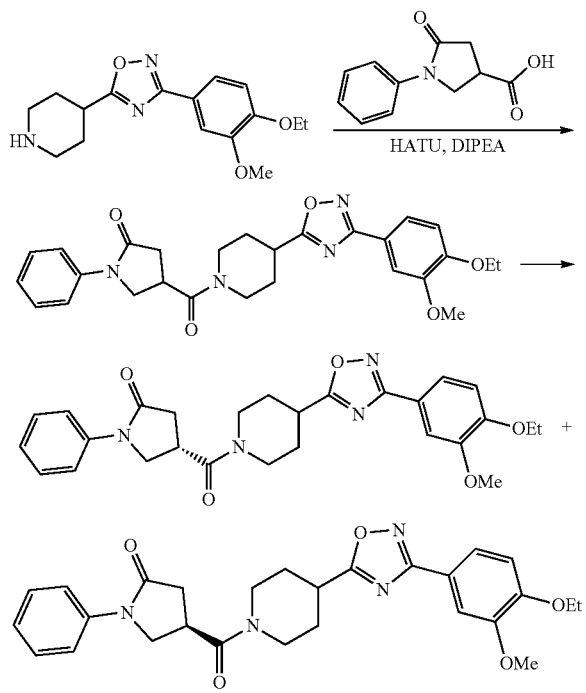

Step 1: Preparation of 4-(4-(3-(4-ethoxy-3-methoxyphenyl)-1,2,4-oxadiazol-5-yl)piperidine-1-carbonyl)-1-phenylpyrrolidin-2-one, (S)-4-(4-(3-(4-ethoxy-3-methoxyphenyl)-1,2,4-oxadiazol-5-yl)piperidine-1-carbonyl)-1-phenylpyrrolidin-2-one, and (R)-4-(4-(3-(4-ethoxy-3-methoxyphenyl)-1,2,4-oxadiazol-5-yl)piperidine-1-carbonyl)-1-phenylpyrrolidin-2-one

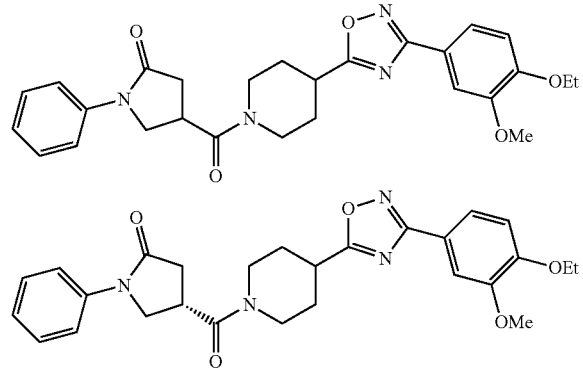

-continued

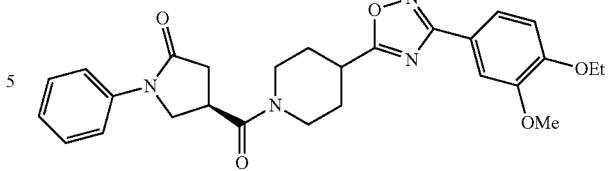

To a stirred solution of 5-oxo-1-phenyl-pyrrolidine-3-carboxylic acid (200 mg, 975 μmol) in N,N-dimethylformamide (4 mL) was added 3-(4-ethoxy-3-methoxy-phenyl)-5-(4-piperidyl)-1,2,4-oxadiazole (295 mg, 975 μmol), (2-(1H-benzotriazol-1-yl)-1,1,3,3-tetramethyluronium hexafluorophosphate) (369 mg, 975 μmol) and N-ethyl-N-(propan-2-yl)propan-2-amine (377 mg, 2.92 mmol, 510 μL). The mixture was stirred at 20° C. for 1 h. The reaction mixture was purified by prep-HPLC (column: Waters Xbridge 150×2.5 mm 5 μm; mobile phase: [water (10 mM ammonium carbonate)-acetonitrile]; B %: 40%-70%, 12 min) to give racemic 4-(4-(3-(4-ethoxy-3-methoxyphenyl)-1,2,4-oxadiazol-5-yl)piperidine-1-carbonyl)-1-phenylpyrrolidin-2-one (151 mg, 31%). A portion of this racemic mixture (140 mg) underwent SFC separation (column: OJ(250× 30 mm, 5 μm); mobile phase: [CO₂ base-isopropanol]; B %: 45%-45%, min]) to give (R)-4-(4-(3-(4-ethoxy-3-methoxyphenyl)-1,2,4-oxadiazol-5-yl)piperidine-1-carbonyl)-1-phenylpyrrolidin-2-one (64 mg, 132 μmol, 14%, 99.7% purity) as a white solid then (S)-4-(4-(3-(4-ethoxy-3-methoxyphenyl)-1,2,4-oxadiazol-5-yl)piperidine-1-carbonyl)-1-phenylpyrrolidin-2-one (65 mg, 133.9 μmol, 14%, 99.58% purity) also as a white solid.

4-(4-(3-(4-ethoxy-3-methoxyphenyl)-1,2,4-oxadiazol-5-yl)piperidine-1-carbonyl)-1-phenylpyrrolidin-2-one $^{1}$H NMR (400 MHz, DMSO-d6) δ 7.68 (d, J=8.0 Hz, 2H), 7.62-7.56 (m, 1H), 7.48 (s, 1H), 7.39 (t, J=6.7 Hz, 2H), 7.19-7.09 (m, 2H), 4.38 (d, J=13.8 Hz, 1H), 4.14-3.93 (m, 5H), 3.85 (s, 3H), 3.80-3.71 (m, 1H), 3.51-3.40 (m, 1H), 3.30 (br. s., 1H), 3.00-2.89 (m, 1H), 2.83-2.73 (m, 2H), 2.22-2.09 (m, 2H), 1.90-1.64 (m, 2H), 1.37 (t, J=7.0 Hz, 3H); LCMS (ESI) m/z: [M+H]⁺=491.2.

(R)-4-(4-(3-(4-ethoxy-3-methoxyphenyl)-1,2,4-oxadiazol-5-yl)piperidine-1-carbonyl)-1-phenylpyrrolidin-2-one $^{1}$H NMR (400 MHz, DMSO-d6) δ 7.68 (d, J=7.9 Hz, 2H), 7.62-7.56 (m, 1H), 7.51-7.46 (m, 1H), 7.39 (t, J=6.7 Hz, 2H), 7.19-7.09 (m, 2H), 4.38 (d, J=13.4 Hz, 1H), 4.13-3.95 (m, 5H), 3.85 (s, 3H), 3.80-3.71 (m, 1H), 3.44 (d, J=10.0 Hz, 2H), 2.94 (br. s., 1H), 2.81-2.74 (m, 2H), 2.16 (t, J=13.6 Hz, 2H), 1.91-1.64 (m, 2H), 1.37 (t, J=6.9 Hz, 3H); LCMS (ESI) m/z: [M+H]⁺=491.1.

(S)-4-(4-(3-(4-ethoxy-3-methoxyphenyl)-1,2,4-oxadiazol-5-yl)piperidine-1-carbonyl)-1-phenylpyrrolidin-2-one $^{1}$H NMR (400 MHz, DMSO-d6) δ 7.66 (d, J=6.6 Hz, 2H), 7.57 (d, J=8.4 Hz, 1H), 7.46 (s, 1H), 7.41-7.33 (m, 2H), 7.17-7.07 (m, 2H), 4.37 (d, J=12.8 Hz, 1H), 4.12-3.92 (m, 5H), 3.83 (s, 3H), 3.78-3.69 (m, 1H), 3.43 (t, J=10.6 Hz, 1H), 3.28 (br. s., 1H), 2.92 (t, J=13.0 Hz, 1H), 2.81-2.70 (m, 2H), 2.14 (t, J=13.5 Hz, 2H), 1.88-1.78 (m, 1H), 1.74-1.64 (m, 1H), 1.35 (t, J=7.1 Hz, 3H); LCMS (ESI) m/z: C27H30N4O5 [M+H]⁺=491.1

Alternatively, Example 85: (4R)-4-[4-[3-(4-ethoxy-3-methoxy-phenyl)-1,2,4-oxadiazol-5-yl]piperidine-1-carbonyl]-1-phenyl-pyrrolidin-2-One can be Prepared in an Enantioselective Fashion as Follows Example 87: N-(2-(4-(3-(3-chloro-4-ethoxyphenyl)-1,2,4-oxadiazol-5-yl)piperidin-1-yl)-2-oxoethyl)benzamide

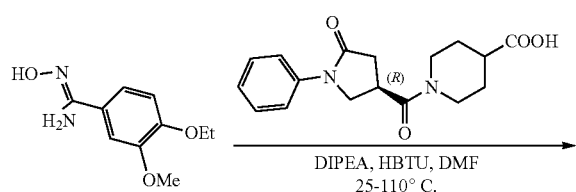

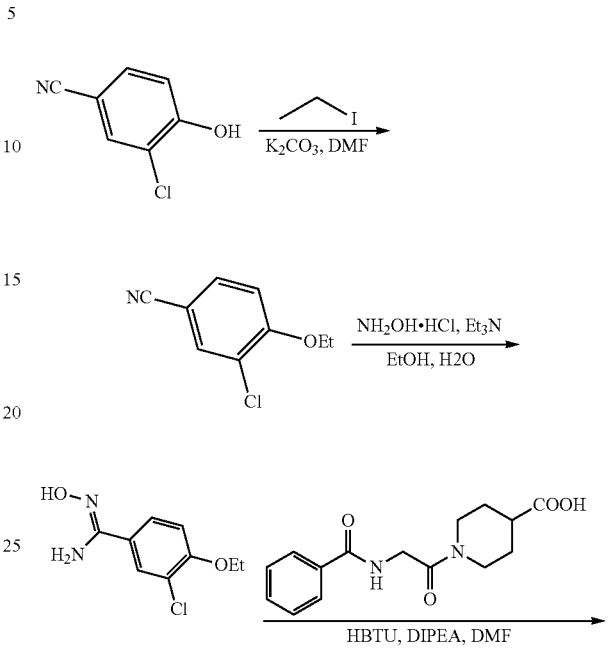

Step 1: Preparation of (4R)-4-[4-[3-(4-ethoxy-3-methoxy-phenyl)-1,2,4-oxadiazol-5-yl]piperidine-1-carbonyl]-1-phenyl-pyrrolidin-2-one

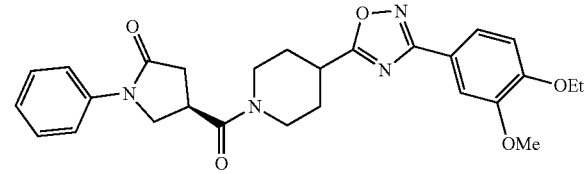

To a stirred solution of 1-[(3R)-5-oxo-1-phenyl-pyrrolidine-3-carbonyl]piperidine-4-carboxylic acid (100 mg, 316 μmol) and 4-ethoxy-N'-hydroxy-3-methoxy-benzamidine (66 mg, 316 μmol) in DMF (1.50 mL) was added (2-(1H-benzotriazol-1-yl)-1,1,3,3-tetramethyluronium hexafluorophosphate) (119 mg, 316 μmol) and N-ethyl-N-(propan-2-yl)propan-2-amine (81 mg, 632 μmol, 110 μL) at 25° C. After 12 h, the mixture was heated and stirred at 110° C. for 1 h. The mixture was cooled then purified by prep_HPLC (Waters Xbridge 150×25 5 μm; mobile phase: [water (10 mM ammonium carbonate)-acetonitrile]; B %: 25%-65%, 12 min) to give (4R)-4-[4-[3-(4-ethoxy-3-methoxy-phenyl)-1,2,4-oxadiazol-5-yl]piperidine-1-carbonyl]-1-phenyl-pyrrolidin-2-one (59 mg, 122 μmol, 39%) as a pink solid. $^1$H NMR (400 MHz, CHLOROFORM-d) δ=7.66 (br d, J=8.2 Hz, 1H), 7.61-7.54 (m, 3H), 7.37 (m, J=7.9 Hz, 2H), 7.19-7.14 (m, 1H), 6.94 (d, J=8.4 Hz, 1H), 4.59-4.46 (m, 1H), 4.31 (dd, J=7.3, 9.7 Hz, 1H), 4.17 (q, J=7.0 Hz, 2H), 3.99-3.90 (m, 5H), 3.58 (quin, J=8.4 Hz, 1H), 3.43-3.26 (m, 2H), 3.16-2.92 (m, 2H), 2.88-2.79 (m, 1H), 2.24 (br t, J=12.9 Hz, 2H), 2.05-1.89 (m, 2H), 1.50 (t, J=6.9 Hz, 3H); LCMS (ESI) m/z: [M+H]$^+$=491.3.

Step 1: Preparation of 3-chloro-4-ethoxybenzonitrile

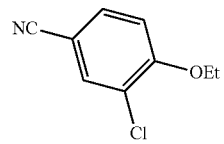 [SMILES: CCOc1ccc(C#N)cc1Cl]

To a stirred solution of 3-chloro-4-hydroxybenzonitrile (2.0 g, 13.0 mmol) in N,N-dimethylformamide (20 mL) was added iodoethane (2.44 g, 15.6 mmol, 1.25 mL) and potassium carbonate (3.60 g, 26.1 mmol) at 0° C. The reaction was warmed to 40° C. After 16 h, the reaction mixture was quenched by addition of water (30 mL) then the mixture was extracted with ethyl acetate (60 mL×3). The combined organic phases were washed with saturated aqueous sodium chloride solution (30 mL), dried over anhydrous sodium sulfate, filtered and concentrated in vacuo to give crude 3-chloro-4-ethoxybenzonitrile (2.50 g) as a yellow solid. $^1$H NMR (400 MHz, CDCl$_3$) δ 7.57 (d, J=1.9 Hz, 1H), 7.45 (dd, J=2.0, 8.7 Hz, 1H), 6.88 (d, J=8.5 Hz, 1H), 4.10 (q, J=7.0 Hz, 2H), 1.43 (t, J=7.0 Hz, 3H).

Step 2: Preparation of (Z)-3-chloro-4-ethoxy-N'-hydroxybenzimidamide

To a stirred solution of 3-chloro-4-ethoxybenzonitrile (2.40 g, 13.2 mmol) in ethanol (30 mL) was added hydroxylamine hydrochloride (1.84 g, 26.4 mmol), triethylamine (2.67 g, 26.4 mmol, 3.66 mL) and water (3 mL). The mixture was heated at 80° C. for 2 h. The reaction mixture was filtered and the filter cake dried in vacuo to give (Z)-3-chloro-4-ethoxy-N'-hydroxybenzimidamide (700 mg, 3.62 mmol, 69%) as a brown oil. $^1$H NMR (400 MHz, DMSO-d6) δ 9.59 (s, 1H), 7.72 (d, J=2.0 Hz, 2H), 7.14 (d, J=8.8 Hz, 1H), 5.83 (s, 2H), 4.14 (q, J=6.9 Hz, 2H), 1.45-1.30 (m, 3H).

Step 3: Preparation of N-(2-(4-(3-(3-chloro-4-ethoxyphenyl)-1,2,4-oxadiazol-5-yl)piperidin-1-yl)-2-oxoethyl)benzamide

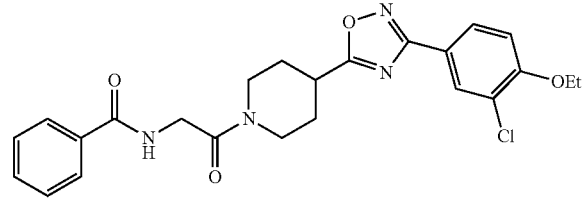 [SMILES: CCOc1ccc(-c2noc(C3CCN(C(=O)CNC(=O)c4ccccc4)CC3)n2)cc1Cl]

To a stirred solution of 1-(2-benzamidoacetyl)piperidine-4-carboxylic acid (120 mg, 413 μmol) in N,N-dimethylformamide (2 mL) was added (Z)-3-chloro-4-ethoxy-N'-hydroxybenzimidamide (97 mg, 455 μmol), (2-(1H-benzotriazol-1-yl)-1,1,3,3-tetramethyluronium hexafluorophosphate) (156 mg, 413 μmol) and N-ethyl-N-(propan-2-yl)propan-2-amine (160 mg, 1.24 mmol, 216 μL). The mixture was stirred at 20° C. for 2 h, then heated at 120° C. for 2 h. The reaction mixture was cooled then purified by prep-HPLC (column: Waters Xbridge 150×2.5 mm 5 μm; mobile phase: [water (10 mM ammonium carbonate)-acetonitrile]; B %: 45%-80%, 12 min) to give N-(2-(4-(3-(3-chloro-4-ethoxyphenyl)-1,2,4-oxadiazol-5-yl)piperidin-1-yl)-2-oxoethyl)benzamide (104 mg, 223 μmol, 54%) as a yellow solid. $^1$H NMR (400 MHz, CDCl$_3$) δ 8.12 (d, J=2.0 Hz, 1H), 7.95 (dd, J=2.1, 8.6 Hz, 1H), 7.91-7.86 (m, 2H), 7.58-7.44 (m, 3H), 7.35 (br. s., 1H), 7.02 (d, J=8.7 Hz, 1H), 4.51 (d, J=13.7 Hz, 1H), 4.33 (d, J=3.9 Hz, 2H), 4.21 (q, J=7.0 Hz, 2H), 3.93 (d, J=13.9 Hz, 1H), 3.41-3.29 (m, 2H), 3.18 (t, J=10.8 Hz, 1H), 2.33-2.20 (m, 2H), 2.09-1.93 (m, 2H), 1.53 (t, J=7.0 Hz, 3H); LCMS (ESI) m/z: [M+H]$^+$=469.3.

Example 88: N-(2-(4-(3-($^1$H-indazol-6-yl)-1,2,4-oxadiazol-5-yl)piperidin-1-yl)-2-oxoethyl)benzamide

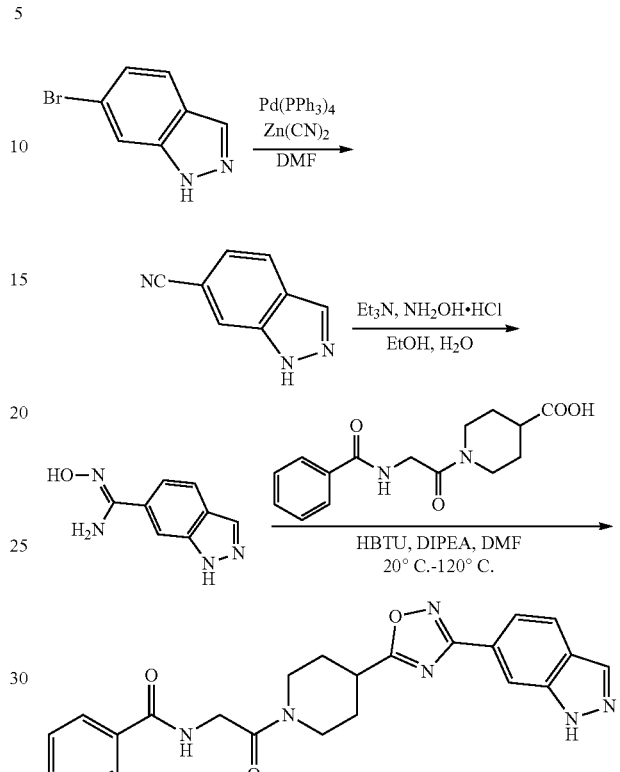

Step 1: Preparation of $^1$H-indazole-6-carbonitrile

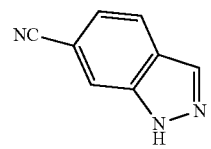 [SMILES: N#Cc1ccc2cn[nH]c2c1]

To a stirred solution of 6-bromo-1H-indazole (1.0 g, 5.08 mmol) in N,N-dimethylformamide (12 mL) was added zinc cyanide (595 mg, 5.08 mmol, 322 μL) and tetrakis(triphenylphosphine)palladium(0) (586 mg, 508 μmol), and the mixture was degassed with nitrogen three times. The mixture heated at 100° C. for 4 h under nitrogen. The reaction cooled to 20° C., water (15 mL) was added, and the reaction mixture was extracted with ethyl acetate (40 mL×3). The combined organic extracts were washed with saturated aqueous sodium chloride solution (20 mL), dried over anhydrous sodium sulfate, filtered and concentrated in vacuo to give crude product. This was triturated with petroleum ether (30 mL) and dichloromethane (5 mL), and the mixture filtered. The filter cake was dried in vacuo to give 1H-indazole-6-carbonitrile (880 mg) as a yellow solid that was used directly without further purification. $^1$H NMR (400 MHz, DMSO-d6) δ 13.65 (br. s., 1H), 8.33-8.12 (m, 2H), 7.99 (d, J=8.4 Hz, 1H), 7.88-7.80 (m, 1H).

Step 2: Preparation of (Z)—N'-hydroxy-1H-indazole-6-carboximidamide

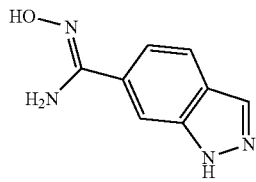 [SMILES: N/C(=N\O)c1ccc2cn[nH]c2c1]

To a stirred solution of 1H-indazole-6-carbonitrile (800 mg, 5.59 mmol) in ethanol (1 mL) was added hydroxylamine hydrochloride (776 mg, 11.18 mmol), triethylamine (1.13 g, 11.18 mmol, 1.55 mL) and water (100 µL). The mixture was heated at 80° C. for 2 h. The reaction mixture was cooled, concentrated under reduced pressure, and then diluted with water (5 mL). The solid that formed was filtered and the filter cake was dried under reduced pressure to give (Z)—N'-hydroxy-1H-indazole-6-carboximidamide (500 mg, 2.84 mmol, 51%) as a yellow solid that was used directly without further purification. $^1$H NMR (400 MHz, DMSO-d6) δ 13.22-13.10 (m, 1H), 9.68 (br. s., 1H), 8.04 (s, 1H), 7.78 (s, 1H), 7.70-7.66 (m, 1H), 7.47-7.42 (m, 1H), 5.87 (br. s., 2H).

Step 3: Preparation of N-(2-(4-(3-($^1$H-indazol-6-yl)-1,2,4-oxadiazol-5-yl)piperidin-1-yl)-2-oxoethyl)benzamide

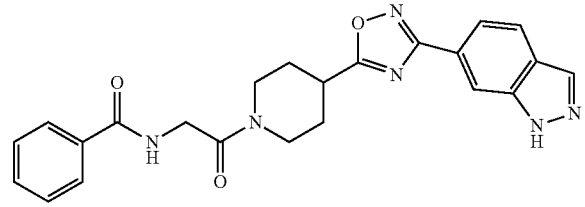 [SMILES: O=C(NCC(=O)N1CCC(c2nc(-c3ccc4cn[nH]c4c3)no2)CC1)c1ccccc1]

To a stirred solution of 1-(2-benzamidoacetyl)piperidine-4-carboxylic acid (120 mg, 413 µmol) in N,N-dimethylformamide (2 mL) was added (Z)—N'-hydroxy-1H-indazole-6-carboximidamide (94 mg, 537 µmol), (2-(1H-benzotriazol-1-yl)-1,1,3,3-tetramethyluronium hexafluorophosphate) (156 mg, 413 µmol) and N-ethyl-N-(propan-2-yl)propan-2-amine (160 mg, 1.24 mmol, 216 µL). The mixture was stirred at 20° C. for 1 h, then heated at 110° C. for 1 h. The reaction mixture was purified directly by prep-HPLC (column: Luna C18 100*30 5 µm; mobile phase: [water (0.225% TFA)-acetonitrile]; B %: 30%-55%, 12 min) to give N-(2-(4-(3-($^1$H-indazol-6-yl)-1,2,4-oxadiazol-5-yl)piperidin-1-yl)-2-oxoethyl)benzamide (21 mg, 44 µmol, 11%) as a brown solid. $^1$H NMR (400 MHz, DMSO-d6) δ 13.34 (br s, 1H), 8.55 (t, J=5.6 Hz, 1H), 8.18-8.16 (m, 1H), 7.94-7.89 (m, 1H), 7.88-7.83 (m, 2H), 7.72 (dd, J=1.1, 8.4 Hz, 1H), 7.54-7.41 (m, 3H), 4.36-4.27 (m, 1H), 4.16 (d, J=5.7 Hz, 2H), 3.97 (br d, J=14.1 Hz, 1H), 3.59 (br s, 1H), 3.47 (s, 1H), 3.34-3.24 (m, 1H), 2.98-2.88 (m, 1H), 2.20-2.08 (m, 2H), 1.89-1.77 (m, 1H), 1.66 (br d, J=11.5 Hz, 1H); LCMS (ESI) m/z: [M+H]$^+$=431.1.

Example 89: 4-(4-(3-(1,3-dimethyl-1H-indazol-6-yl)-1,2,4-oxadiazol-5-yl)piperidine-1-carbonyl)-1-phenylpyrrolidin-2-one, example 90: 4-(4-(3-(1,3-dimethyl-1H-indazol-6-yl)-1,2,4-oxadiazol-5-yl)piperidine-1-carbonyl)-1-phenylpyrrolidin-2-one, Enantiomer 1 and Example 91: (R)-4-(4-(3-(1,3-dimethyl-1H-indazol-6-yl)-1,2,4-oxadiazol-5-yl)piperidine-1-carbonyl)-1-phenylpyrrolidin-2-one, Enantiomer 2

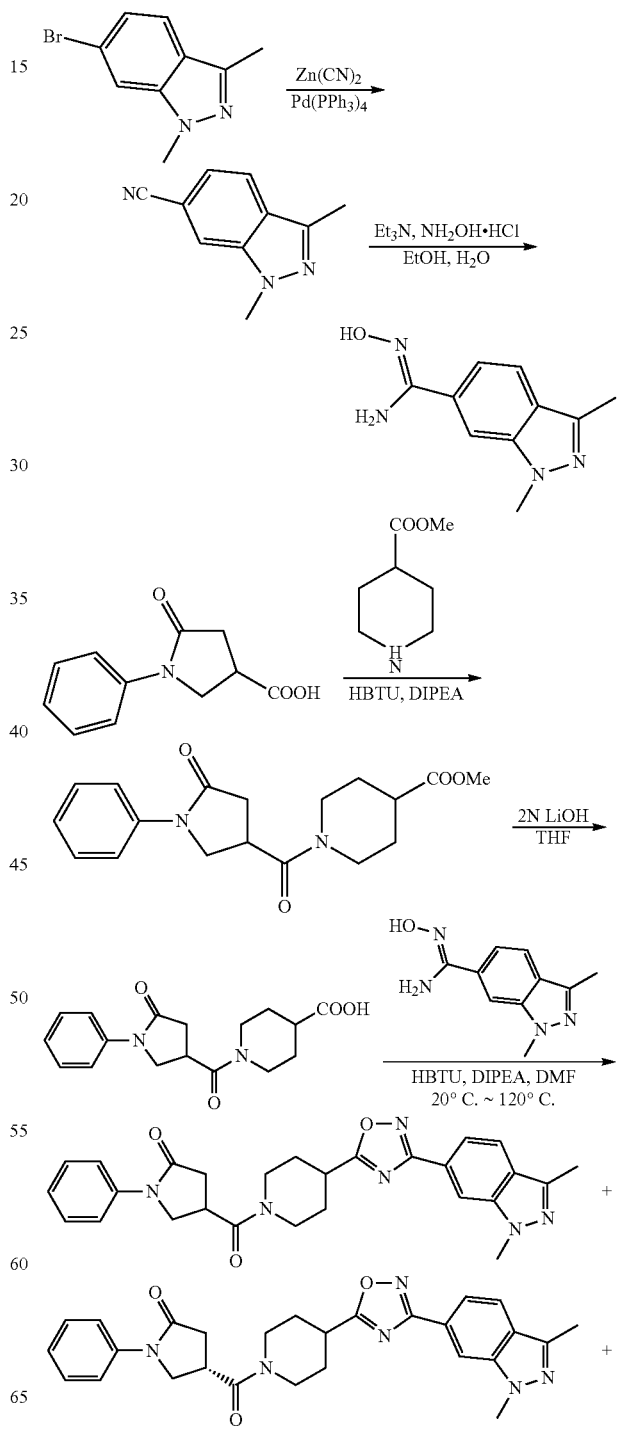

-continued

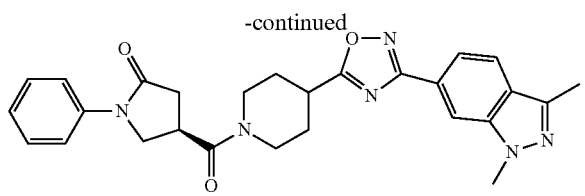

Step 1: Preparation of 1,3-dimethyl-1H-indazole-6-carbonitrile

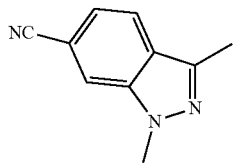

To a stirred solution of 6-bromo-1,3-dimethyl-1H-indazole (480 mg, 2.13 mmol) in N,N-dimethylformamide (5 mL) was added zinc cyanide (250 mg, 2.13 mmol) and tetrakis(triphenylphosphine)palladium(0) (246 mg, 213 μmol) under nitrogen, then the mixture was heated to 100° C. After 16 h, the reaction was cooled to 20° C., water (10 mL) was added, and the reaction mixture extracted with ethyl acetate (40 mL×3). The combined organic phases were washed with saturated aqueous sodium chloride solution (15 mL), dried over anhydrous sodium sulfate, filtered and then concentrated in vacuo to give crude product. The residue was triturated with petroleum ether (30 mL), then filtered and the filter cake dried in vacuo to give 1,3-dimethyl-1H-indazole-6-carbonitrile (300 mg, 1.75 mmol, 82%) as a yellow solid. $^1$H NMR (400 MHz, CDCl$_3$) δ 7.78-7.71 (m, 2H), 7.38-7.31 (m, 1H), 4.08 (s, 3H), 2.61 (s, 3H).

Step 2: Preparation of (Z)—N'-hydroxy-1,3-dimethyl-1H-indazole-6-carboximidamide

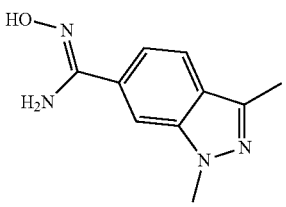

To a stirred solution of 1,3-dimethyl-1H-indazole-6-carbonitrile (300 mg, 1.75 mmol) in ethanol (5 mL) was added hydroxylamine hydrochloride (243 mg, 3.50 mmol), triethylamine (354 mg, 3.50 mmol, 485 μL) and water (500 μL). The mixture was heated at 80° C. for 5 h, then cooled and filtered, and the filter cake was dried in vacuo to give (Z)—N'-hydroxy-1,3-dimethyl-1H-indazole-6-carboximidamide (290 mg, 1.42 mmol, 81%) as a white solid that was used directly without further purification. $^1$H NMR (400 MHz, DMSO-d6) δ 9.71 (s, 1H), 7.86 (s, 1H), 7.65 (d, J=8.5 Hz, 1H), 7.49 (d, J=8.5 Hz, 1H), 5.90 (s, 2H), 3.97 (s, 3H), 2.47 (s, 3H).

Step 3: Preparation of methyl 1-(5-oxo-1-phenylpyrrolidine-3-carbonyl)piperidine-4-carboxylate

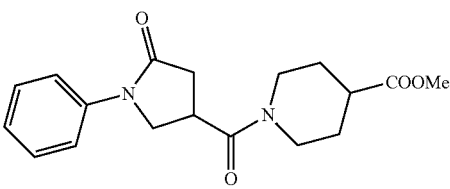 [SMILES: COC(=O)C1CCN(C(=O)C2CC(=O)N(c3ccccc3)C2)CC1]

To a stirred solution of 5-oxo-1-phenylpyrrolidine-3-carboxylic acid (500 mg, 2.44 mmol) in N,N-dimethylformamide (10 mL) was added methyl piperidine-4-carboxylate (349 mg, 2.44 mmol), (2-(1H-benzotriazol-1-yl)-1,1,3,3-tetramethyluronium hexafluorophosphate) (925 mg, 2.44 mmol) and N-ethyl-N-(propan-2-yl)propan-2-amine (946 mg, 7.32 mmol, 1.28 mL). The mixture was stirred at 20° C. for 2 h. The reaction mixture was quenched by addition of water (20 mL) then extracted with ethyl acetate (40 mL×3). The combined organic phases were washed with saturated aqueous sodium chloride solution (20 mL), dried over anhydrous sodium sulfate, filtered and concentrated in vacuo. Purification by chromatography (silica, petroleumether:ethylacetate=20:1 to 1:1) gave methyl 1-(5-oxo-1-phenylpyrrolidine-3-carbonyl)piperidine-4-carboxylate (940 mg) as a yellow oil.

Step 4: Preparation of 1-(5-oxo-1-phenylpyrrolidine-3-carbonyl)piperidine-4-carboxylic acid

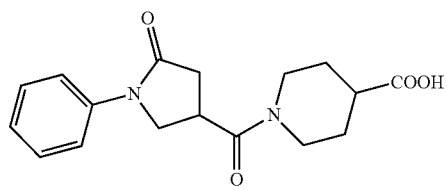 [SMILES: O=C(O)C1CCN(C(=O)C2CC(=O)N(c3ccccc3)C2)CC1]

To a stirred solution of methyl 1-(5-oxo-1-phenylpyrrolidine-3-carbonyl)piperidine-4-carboxylate (900 mg, 2.72 mmol) in tetrahydrofuran (10 mL) was added lithium hydroxide (2 M, 2.72 mL). After 2 h, the reaction mixture was acidified to pH 1 with 1 M hydrochloric acid (6 mL). The mixture was extracted with ethyl acetate (40 mL×3). The organic extracts were combined and washed with saturated aqueous sodium chloride solution (10 mL), dried over anhydrous sodium sulfate, filtered, and concentrated to give 1-(5-oxo-1-phenylpyrrolidine-3-carbonyl)piperidine-4-carboxylic acid (600 mg, 1.90 mmol, 70%) as a yellow solid. $^1$H NMR (400 MHz, DMSO-d6) δ 12.37-12.17 (m, 1H), 7.66 (dd, J=5.8, 7.2 Hz, 2H), 7.38 (t, J=7.9 Hz, 2H), 7.19-7.09 (m, 1H), 4.28-4.19 (m, 1H), 4.04 (s, 1H), 3.93 (br. s., 2H), 3.76-3.66 (m, 1H), 3.18 (br. s., 1H), 2.86-2.67 (m, 4H), 1.87 (t, J=13.2 Hz, 2H), 1.61-1.35 (m, 2H).

Step 5: Preparation of 4-(4-(3-(1,3-dimethyl-1H-indazol-6-yl)-1,2,4-oxadiazol-5-yl)piperidine-1-carbonyl)-1-phenylpyrrolidin-2-one, 4-(4-(3-(1,3-dimethyl-1H-indazol-6-yl)-1,2,4-oxadiazol-5-yl)piperidine-1-carbonyl)-1-phenylpyrrolidin-2-one, Enantiomer 1 and 4-(4-(3-(1,3-dimethyl-1H-indazol-6-yl)-1,2,4-oxadiazol-5-yl)piperidine-1-carbonyl)-1-phenylpyrrolidin-2-one, Enantiomer 2

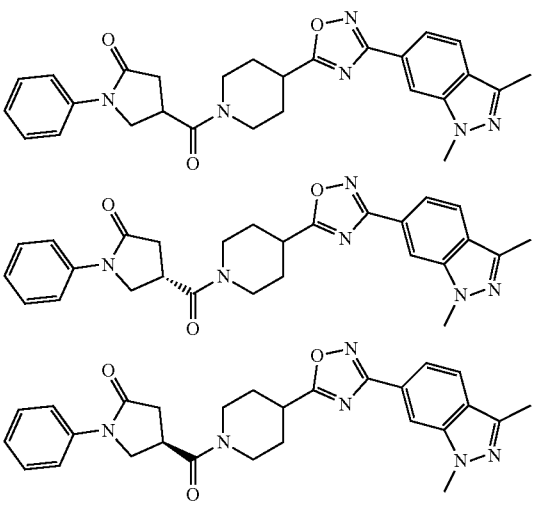

To a stirred solution of 1-(5-oxo-1-phenyl-pyrrolidine-3-carbonyl)piperidine-4-carboxylic acid (150 mg, 474 µmol) in N,N-dimethylformamide (2 mL) was added N'-hydroxy-1,3-dimethyl-indazole-6-carboxamidine (96 mg, 474 µmol), (2-(1H-benzotriazol-1-yl)-1,1,3,3-tetramethyluronium hexafluorophosphate) (179 mg, 474 µmol) and N-ethyl-N-(propan-2-yl)propan-2-amine (183 mg, 1.42 mmol, 248 µL). The mixture was stirred at 20° C. for 2 h, then heated at 120° C. for 1 h. The reaction mixture was cooled then purified by prep-HPLC (column: Waters Xbridge 150×2.5 mm 5 µm; mobile phase: [water (10 mM ammonium carbonate)-acetonitrile]; B %: 30%-55%, 12 min) to give the racemic of 4-(4-(3-(1,3-dimethyl-1H-indazol-6-yl)-1,2,4-oxadiazol-5-yl)piperidine-1-carbonyl)-1-phenylpyrrolidin-2-one (85 mg) as a white solid. A portion (25 mg, 53 µmol, 11%, 99.83% purity) was retained for analysis. The remainder (60 mg) was purified by SFC (column: OJ (250×30 mm, 5 µm); mobile phase: [CO$_2$ base-methanol]; B %: 45%-45%, min) to give 4-(4-(3-(1,3-dimethyl-1H-indazol-6-yl)-1,2,4-oxadiazol-5-yl)piperidine-1-carbonyl)-1-phenylpyrrolidin-2-one, Enatiomer 1 (27 mg, 56 µmol, 12%) as a brown solid then 4-(4-(3-(1,3-dimethyl-1H-indazol-6-yl)-1,2,4-oxadiazol-5-yl)piperidine-1-carbonyl)-1-phenylpyrrolidin-2-one, Enantiomer 2 (26 mg, 55 µmol, 12%) as a white solid.

4-(4-(3-(1,3-dimethyl-1H-indazol-6-yl)-1,2,4-oxadiazol-5-yl)piperidine-1-carbonyl)-1-phenylpyrrolidin-2-one $^1$H NMR (400 MHz, CDCl$_3$) δ 8.13-8.07 (m, 1H), 7.83 (s, 1H), 7.78-7.72 (m, 1H), 7.61 (d, J=8.0 Hz, 2H), 7.39 (t, J=7.9 Hz, 2H), 7.18 (s, 1H), 4.65-4.50 (m, 1H), 4.34 (t, J=7.3 Hz, 1H), 4.09 (d, J=3.3 Hz, 3H), 4.05-3.92 (m, 2H), 3.60 (quin, J=8.4 Hz, 1H), 3.46-3.32 (m, 2H), 2.98 (d, J=6.7 Hz, 2H), 2.91-2.81 (m, 1H), 2.61 (s, 3H), 2.35-2.22 (m, 2H), 2.02 (d, J=6.1 Hz, 2H); LCMS (ESI) m/z: [M+H]$^+$=485.2.

4-(4-(3-(1,3-dimethyl-1H-indazol-6-yl)-1,2,4-oxadiazol-5-yl)piperidine-1-carbonyl)-1-phenylpyrrolidin-2-one, Enantiomer 1

$^1$H NMR (400 MHz, CDCl$_3$) δ 8.12 (d, J=4.1 Hz, 1H), 7.86 (br d, J=8.5 Hz, 1H), 7.80-7.74 (m, 1H), 7.63 (d, J=7.9 Hz, 2H), 7.41 (t, J=8.0 Hz, 2H), 7.23-7.18 (m, 1H), 4.67-4.52 (m, 1H), 4.36 (br t, J=7.0 Hz, 1H), 4.11 (d, J=3.4 Hz, 3H), 4.07-3.94 (m, 2H), 3.62 (quin, J=8.5 Hz, 1H), 3.49-3.35 (m, 2H), 3.22-2.96 (m, 2H), 2.93-2.81 (m, 1H), 2.63 (s, 3H), 2.37-2.25 (m, 2H), 2.11-1.97 (m, 2H); LCMS (ESI) m/z: [M+H]$^+$=485.3.

4-(4-(3-(1,3-dimethyl-1H-indazol-6-yl)-1,2,4-oxadiazol-5-yl)piperidine-1-carbonyl)-1-phenylpyrrolidin-2-one, Enantiomer 2

$^1$H NMR (400 MHz, CDCl$_3$) δ 8.12 (d, J=3.9 Hz, 1H), 7.86 (d, J=8.4 Hz, 1H), 7.80-7.74 (m, 1H), 7.63 (d, J=8.3 Hz, 2H), 7.41 (t, J=8.0 Hz, 2H), 7.24-7.18 (m, 1H), 4.66-4.53 (m, 1H), 4.36 (br t, J=7.3 Hz, 1H), 4.11 (d, J=3.5 Hz, 3H), 4.07-3.94 (m, 2H), 3.62 (quin, J=8.5 Hz, 1H), 3.48-3.36 (m, 2H), 3.21-2.96 (m, 2H), 2.93-2.81 (m, 1H), 2.63 (s, 3H), 2.36-2.26 (m, 2H), 2.06 (br d, J=13.4 Hz, 2H); LCMS (ESI) m/z: [M+H]$^+$=485.3.

Examples 90 and 91 can be Synthesized in an Enantiospecific Fashion Using Appropriate Enantiopure Starting Materials, Following the Representative Procedure Below

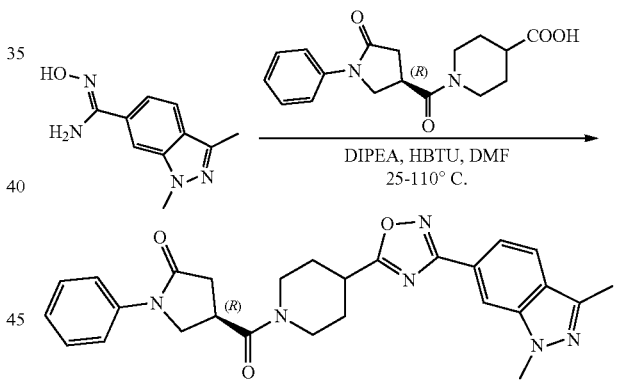

Preparation of (4R)-4-[4-[3-(1,3-dimethylindazol-6-yl)-1,2,4-oxadiazol-5-yl]piperidine-1-carbonyl]-1-phenyl-pyrrolidin-2-one

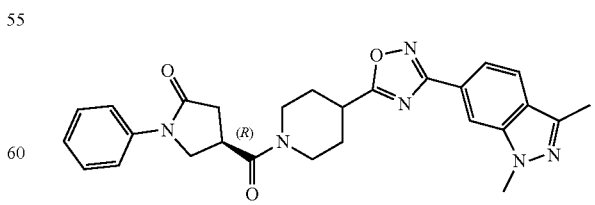

To a stirred solution of 1-[(3R)-5-oxo-1-phenyl-pyrrolidine-3-carbonyl]piperidine-4-carboxylic acid (115 mg, 363.52 µmol) and N'-hydroxy-1,3-dimethyl-indazole-6-carboxamidine (74 mg, 364 µmol) in DMF (1.50 mL) was added (2-(1H-benzotriazol-1-yl)-1,1,3,3-tetramethyluronium hexafluorophosphate) (137 mg, 364 μmol) and N-ethyl-N-(propan-2-yl)propan-2-amine (93 mg, 727 μmol, 126 μL) at 25° C. After 3 h, the mixture was warmed to 110° C. After 1 h, the mixture was purified by chromatography (Waters Xbridge 150×25 5 μm; mobile phase: [water (10 mM ammonium carbonate)-acetonitrile]; B %: 25%-60%, 12 min) to give (4R)-4-[4-[3-(1,3-dimethylindazol-6-yl)-1,2,4-oxadiazol-5-yl]piperidine-1-carbonyl]-1-phenyl-pyrrolidin-2-one (64 mg, 133 μmol, 37%) as a pink solid. $^1$H NMR (400 MHz, CHLOROFORM-d) δ=8.09 (d, J=4.0 Hz, 1H), 7.84-7.80 (d, 1H), 7.75-7.71 (d, 1H), 7.59 (d, J=7.9 Hz, 2H), 7.38 (t, J=7.9 Hz, 2H), 7.20-7.14 (t, 1H), 4.62-4.49 (m, 1H), 4.36-4.29 (m, 1H), 4.07 (d, J=3.3 Hz, 3H), 4.04-3.89 (m, 2H), 3.58 (quin, J=8.4 Hz, 1H), 3.45-3.30 (m, 2H), 3.18-2.92 (m, 2H), 2.90-2.80 (m, 1H), 2.59 (s, 3H), 2.27 (br t, J=13.2 Hz, 2H), 2.09-1.91 (m, 2H); LCMS (ESI) m/z: [M+H]$^+$=485.3.

Example 92: (4-(3-(4-ethoxy-3-methoxyphenyl)-1,2,4-oxadiazol-5-yl)piperidin-1-yl)(3-phenylisoxazol-5-yl)methanone

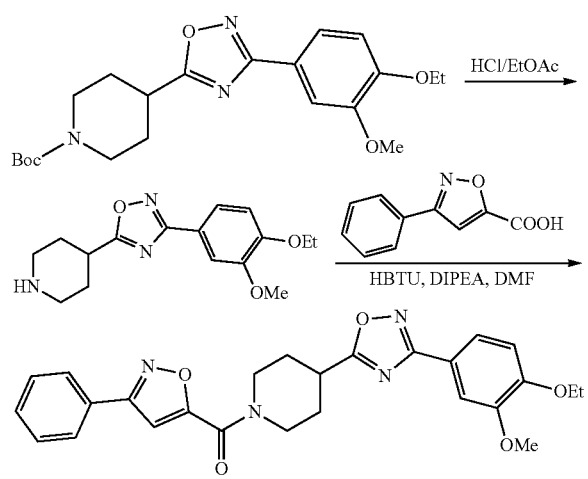

Step 1: Preparation of 3-(4-ethoxy-3-methoxyphenyl)-5-(piperidin-4-yl)-1,2,4-oxadiazole

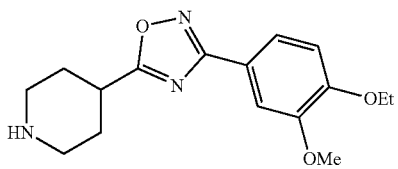 [SMILES: CCOc1ccc(-c2noc(C3CCNCC3)n2)cc1OC]

To a stirred solution of tert-butyl 4-(3-(4-ethoxy-3-methoxyphenyl)-1,2,4-oxadiazol-5-yl)piperidine-1-carboxylate (800 mg, 1.98 mmol) in ethyl acetate (5 mL) was added 4M hydrochloric acid/ethyl acetate (20 mL). The mixture was stirred at 20° C. for 0.5 h. The reaction mixture was filtered and the filter cake was dried in vacuo to give 3-(4-ethoxy-3-methoxyphenyl)-5-(piperidin-4-yl)-1,2,4-oxadiazole (450 mg, 1.48 mmol, 75%) as a white solid. $^1$H NMR (400 MHz, CDCl$_3$) δ 7.67 (dd, J=1.6, 8.3 Hz, 1H), 7.60-7.54 (m, 1H), 6.97 (d, J=8.4 Hz, 1H), 4.24-4.13 (m, 2H), 3.98 (s, 3H), 3.56 (br s, 2H), 3.39 (br s, 1H), 3.33-3.15 (m, 2H), 2.51 (br s, 2H), 2.48-2.33 (m, 2H), 2.19-1.83 (m, 1H), 1.53 (t, J=7.0 Hz, 3H).

Step 2: Preparation of (4-(3-(4-ethoxy-3-methoxyphenyl)-1,2,4-oxadiazol-5-yl)piperidin-1-yl)(3-phenylisoxazol-5-yl)methanone

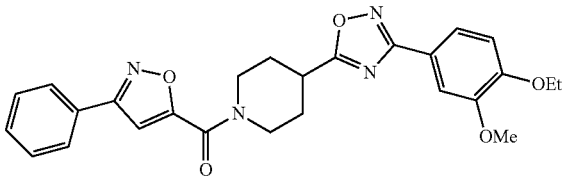 [SMILES: CCOc1ccc(-c2noc(C3CCN(C(=O)c4cc(-c5ccccc5)no4)CC3)n2)cc1OC]

To a stirred solution of 3-phenylisoxazole-5-carboxylic acid (75 mg, 396 μmol) in N,N-dimethylformamide (2 mL) was added 3-(4-ethoxy-3-methoxyphenyl)-5-(piperidin-4-yl)-1,2,4-oxadiazole (120 mg, 396 μmol), (2-(1H-benzotriazol-1-yl)-1,1,3,3-tetramethyluronium hexafluorophosphate) (150 mg, 396 μmol) and N-ethyl-N-(propan-2-yl)propan-2-amine (153 mg, 1.19 mmol, 207 μL). The mixture was stirred at 20° C. for 2 h. The reaction mixture was then purified by prep-HPLC (column: Waters Xbridge 150×2.5 mm 5 μm; mobile phase: [water (10 mM ammonium carbonate)-acetonitrile]; B %: 40%-70%, 12 min) to give (4-(3-(4-ethoxy-3-methoxyphenyl)-1,2,4-oxadiazol-5-yl)piperidin-1-yl)(3-phenylisoxazol-5-yl)methanone (41 mg, 87 μmol, 22%) as a white solid. $^1$H NMR (400 MHz, CDCl$_3$) δ 7.87 (br s, 2H), 7.70 (br d, J=7.8 Hz, 1H), 7.60 (br s, 1H), 7.53 (br s, 3H), 7.14 (s, 1H), 6.99 (br d, J=7.5 Hz, 1H), 4.59 (br s, 1H), 4.36 (br d, J=12.5 Hz, 1H), 4.21 (br d, J=6.4 Hz, 2H), 4.00 (s, 3H), 3.55 (br s, 1H), 3.46-3.25 (m, 2H), 2.32 (br s, 2H), 2.15 (br s, 2H), 1.54 (br t, J=6.8 Hz, 3H); LCMS (ESI) m/z: [M+H]$^+$=475.2.

Example 93: N-(2-(4-(3-(3-methyl-1H-indazol-6-yl)-1,2,4-oxadiazol-5-yl)piperidin-1-yl)-2-oxoethyl)benzamide

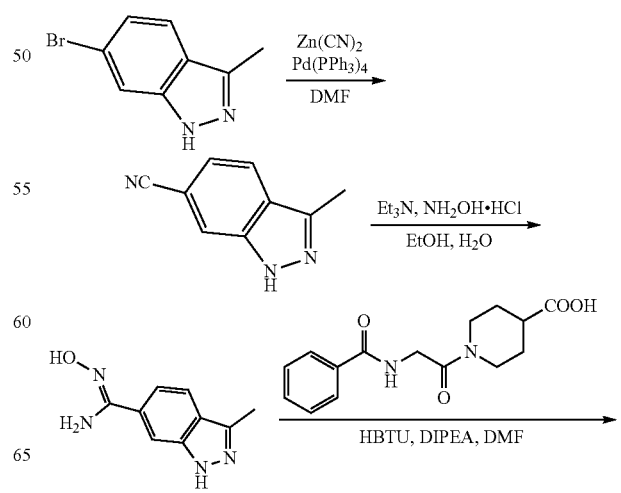

-continued

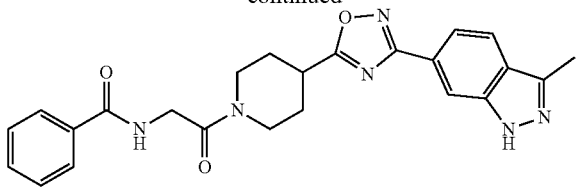

Step 1: Preparation of 3-methyl-1H-indazole-6-carbonitrile

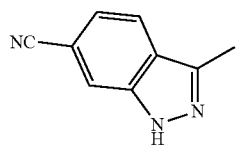

To a stirred solution of 6-bromo-3-methyl-1H-indazole (440 mg, 2.08 mmol) in N,N-dimethylformamide (5 mL) was added zinc cyanide (244 mg, 2.08 mmol) and tetrakis(triphenylphosphine)palladium(0) (240 mg, 208 μmol), then the mixture was degassed with nitrogen three times. The mixture stirred at 100° C. for 4 h under nitrogen, then cooled to 20° C., water (10 mL) added, and the reaction mixture was extracted with ethyl acetate (40 mL×3). The combined organic phases were washed with saturated aqueous sodium chloride solution (15 mL), dried over anhydrous sodium sulfate, filtered, and concentrated in vacuo to give crude product. Petroleum ether (20 mL) was added to the crude product, then the mixture was filtered and the filter cake dried in vacuo to give 3-methyl-1H-indazole-6-carbonitrile (220 mg, 1.40 mmol, 67%) as a brown solid. $^1$H NMR (400 MHz, DMSO-d6) δ 13.29-13.09 (m, 1H), 8.09-8.05 (m, 1H), 7.96-7.90 (m, 1H), 7.41 (d, J=8.3 Hz, 1H), 2.54 (s, 3H).

Step 2: Preparation of (Z)—N'-hydroxy-3-methyl-1H-indazole-6-carboximidamide

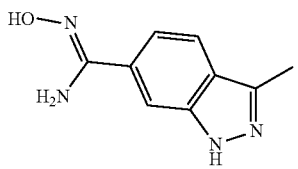

To a stirred solution of 3-methyl-1H-indazole-6-carbonitrile (200 mg, 1.27 mmol) in ethanol (1 mL) was added hydroxylamine hydrochloride (176 mg, 2.55 mmol), triethylamine (257 mg, 2.55 mmol, 352 μL) and water (100 μL). The mixture was stirred at 80° C. for 2 h. The reaction mixture was cooled and then concentrated under reduced pressure to remove ethanol. The residue was diluted with water (5 mL), filtered and the filter cake was dried under reduced pressure to give (Z)—N'-hydroxy-3-methyl-1H-indazole-6-carboximidamide (150 mg, 789 μmol, 62%) as a white solid. $^1$H NMR (400 MHz, DMSO-d6) δ 12.73 (s, 1H), 9.67 (s, 1H), 7.73 (s, 1H), 7.65 (d, J=8.5 Hz, 1H), 7.45 (d, J=8.5 Hz, 1H), 5.86 (s, 2H), 2.49 (s, 3H).

Step 3: Preparation of N-(2-(4-(3-(3-methyl-1H-indazol-6-yl)-1,2,4-oxadiazol-5-yl)piperidin-1-yl)-2-oxoethyl)benzamide

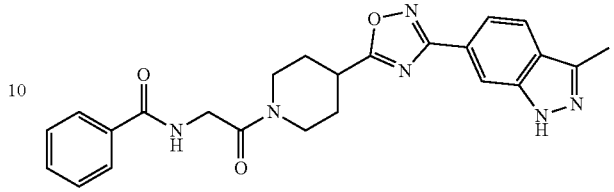

To a stirred solution of 1-(2-benzamidoacetyl)piperidine-4-carboxylic acid (120 mg, 413 μmol) in N,N-dimethylformamide (2 mL) was added (Z)—N'-hydroxy-3-methyl-1H-indazole-6-carboximidamide (78 mg, 413 μmol), (2-(1H-benzotriazol-1-yl)-1,1,3,3-tetramethyluronium hexafluorophosphate) (156 mg, 413 μmol) and N-ethyl-N-(propan-2-yl)propan-2-amine (160 mg, 1.24 mmol, 216 μL). The mixture was stirred at 20° C. for 2 h, then heated at 110° C. for 1 h. The reaction mixture was cooled then purified directly by prep-HPLC (column: Waters Xbridge 150×2.5 mm 5 μm; mobile phase: [water (10 mM ammonium carbonate)-acetonitrile]; B %: 20%-55%, 12 min) to give N-(2-(4-(3-(3-methyl-1H-indazol-6-yl)-1,2,4-oxadiazol-5-yl)piperidin-1-yl)-2-oxoethyl)benzamide (93 mg, 209 μmol, 51%) as a white solid. $^1$H NMR (400 MHz, DMSO-d6) δ 12.92 (s, 1H), 8.59-8.53 (m, 1H), 8.08 (s, 1H), 7.86 (d, J=8.4 Hz, 3H), 7.71-7.65 (m, 1H), 7.55-7.42 (m, 3H), 4.30 (d, J=13.2 Hz, 1H), 4.16 (d, J=5.7 Hz, 2H), 3.97 (d, J=14.6 Hz, 1H), 3.49-3.43 (m, 1H), 3.29-3.24 (m, 1H), 2.92 (t, J=11.2 Hz, 1H), 2.50 (s, 3H), 2.14 (t, J=13.0 Hz, 2H), 1.88-1.78 (m, 1H), 1.66 (d, J=9.7 Hz, 1H); LCMS (ESI) m/z: [M+H]$^+$ =445.3.

Example 94: N-(2-(4-(3-(1-methyl-1H-indazol-6-yl)-1,2,4-oxadiazol-5-yl)piperidin-1-yl)-2-oxoethyl)benzamide

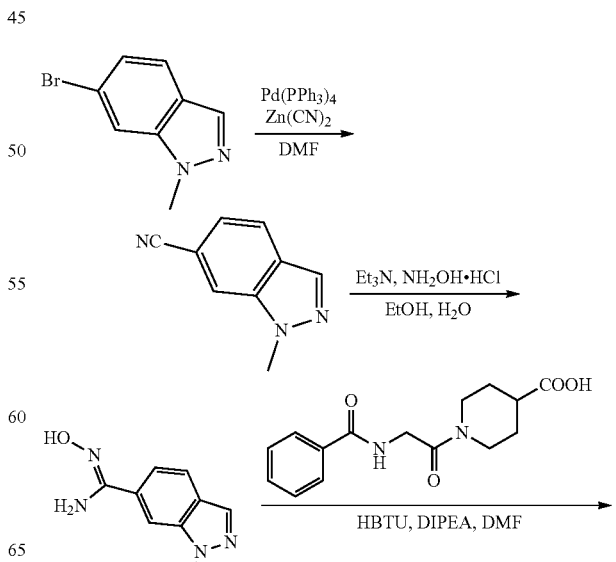

479
-continued

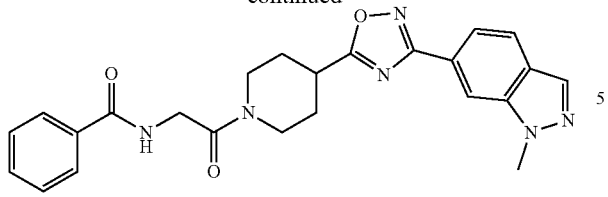

Step 1: Preparation of 1-methyl-1H-indazole-6-carbonitrile

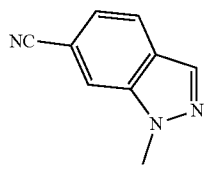

To a stirred solution of 6-bromo-1-methyl-1H-indazole (500 mg, 2.37 mmol) in N,N-dimethylformamide (8 mL) was added zinc cyanide (278 mg, 2.37 mmol) and tetrakis(triphenylphosphine)palladium(0) (273 mg, 236.90 μmol), the mixture was degassed with nitrogen three times. The mixture was stirred at 100° C. for 4 h under nitrogen, then cooled to 20° C., water (10 mL) added, and the reaction mixture extracted with ethyl acetate (40 mL×3). The combined organic phases were washed with saturated aqueous sodium chloride solution (15 mL), dried over anhydrous sodium sulfate, filtered and concentrated in vacuo to give crude product. The mixture was triturated with petroleum ether (20 mL) and dichloromethane (3 mL), then filtered and dried in vacuo to give 1-methyl-1H-indazole-6-carbonitrile (300 mg, 1.91 mmol, 81%) as a yellow solid. $^1$H NMR (400 MHz, CDCl$_3$) δ 8.10 (s, 1H), 7.88-7.83 (m, 1H), 7.82 (s, 1H), 7.39 (dd, J=1.1, 8.3 Hz, 1H), 4.16 (s, 3H).

Step 2: Preparation of (Z)—N'-hydroxy-1-methyl-1H-indazole-6-carboximidamide

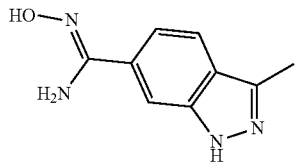

To a stirred solution of 1-methyl-1H-indazole-6-carbonitrile (250 mg, 1.59 mmol) in ethanol (1 mL) was added hydroxylamine hydrochloride (221 mg, 3.18 mmol), triethylamine (321 mg, 3.18 mmol, 440 μL) and water (100 μL). The mixture was heated at 80° C. for 2 h. The reaction mixture was concentrated under reduced pressure and the residue then triturated with water (4 mL), filtered and the filter cake was dried under reduced pressure to give (Z)—N'-hydroxy-1-methyl-1H-indazole-6-carboximidamide (500 mg) as a yellow solid. $^1$H NMR (400 MHz, DMSO-d6) δ 10.65 (br. s., 2H), 9.65-9.84 (m, 1H), 7.98 (d, J=18.1 Hz, 2H), 7.67 (d, J=8.8 Hz, 1H), 7.46-7.52 (m, 1H), 4.03 ppm (s, 3H).

Step 3: Preparation of N-(2-(4-(3-(1-methyl-1H-indazol-6-yl)-1,2,4-oxadiazol-5-yl)piperidin-1-yl)-2-oxoethyl)benzamide

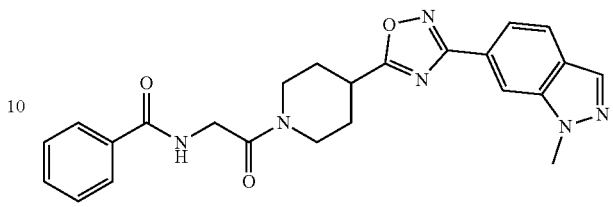

To a stirred solution of 1-(2-benzamidoacetyl)piperidine-4-carboxylic acid (120 mg, 413 μmol) in N,N-dimethylformamide (2 mL) was added (Z)—N'-hydroxy-1-methyl-1H-indazole-6-carboximidamide (125 mg, 661 μmol), (2-(1H-benzotriazol-1-yl)-1,1,3,3-tetramethyluronium hexafluorophosphate) (156 mg, 413 μmol) and N-ethyl-N-(propan-2-yl)propan-2-amine (160 mg, 1.24 mmol, 216 μL). The mixture was stirred at 20° C. for 1 h, then heated at 110° C. for 1 h. The reaction mixture was cooled then purified by prep-HPLC (column: Waters Xbridge 150×2.5 mm 5 μm; mobile phase: [water (10 mM ammonium carbonate)-acetonitrile]; B %: 33%-63%, 12 min) to give N-(2-(4-(3-(1-methyl-1H-indazol-6-yl)-1,2,4-oxadiazol-5-yl)piperidin-1-yl)-2-oxoethyl)benzamide (29 mg, 64 μmol, 15%) as a yellow solid. $^1$H NMR (400 MHz, CDCl$_3$) δ 8.19 (s, 1H), 8.06 (s, 1H), 7.92-7.82 (m, 4H), 7.58-7.45 (m, 3H), 7.36 (br. s., 1H), 4.56 (d, J=14.2 Hz, 1H), 4.34 (d, J=3.9 Hz, 2H), 4.19 (s, 3H), 4.00-3.92 (m, 1H), 3.44-3.34 (m, 2H), 3.19 (t, J=10.9 Hz, 1H), 2.36-2.26 (m, 2H), 2.14-1.98 (m, 2H); LCMS (ESI) m/z: [M+H]$^+$=445.2.

Example 95: N-(2-(4-(3-(1,3-dimethyl-1H-indazol-5-yl)-1,2,4-oxadiazol-5-yl)piperidin-1-yl)-2-oxoethyl)benzamide

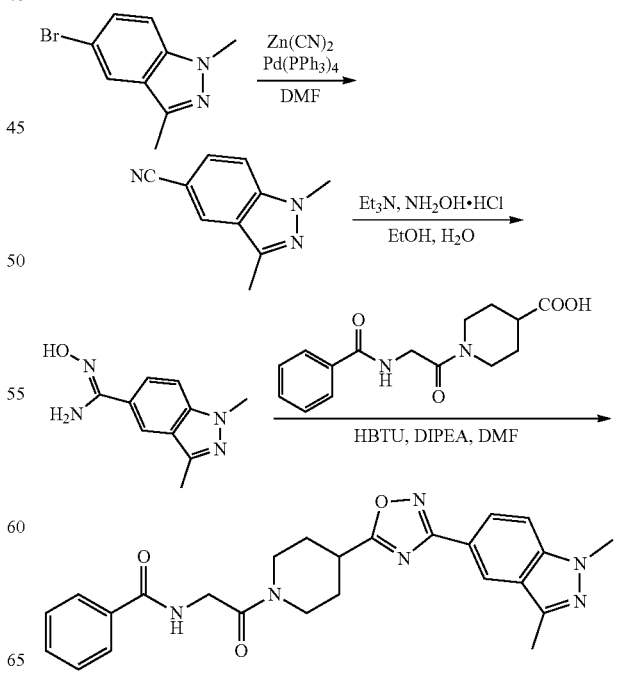

Step 1: Preparation of 1,3-dimethyl-1H-indazole-5-carbonitrile

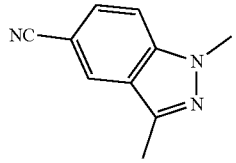

To a stirred solution of 5-bromo-1,3-dimethyl-1H-indazole (600 mg, 2.67 mmol) in N,N-dimethylformamide (10 mL) was added zinc cyanide (313 mg, 2.67 mmol, 169 μL) and tetrakis(triphenylphosphine)palladium(0) (308 mg, 267 μmol) under nitrogen. The mixture was stirred at 100° C. for 16 h, then cooled to 20° C., and diluted with water (15 mL). The reaction mixture was extracted with ethyl acetate (40 mL×3). The combined organic phases were washed with saturated aqueous sodium chloride solution (20 mL), dried over anhydrous sodium sulfate, filtered and concentrated in vacuo to give crude product. This was triturated with petroleum ether (30 mL) and dichloromethane (5 mL), filtered and the filter cake dried in vacuo to give 1,3-dimethyl-1H-indazole-5-carbonitrile (340 mg, 1.99 mmol, 74%) as a brown solid. $^1$H NMR (400 MHz, CDCl$_3$) δ 8.02 (s, 1H), 7.54 (d, J=8.8 Hz, 1H), 7.37 (d, J=8.8 Hz, 1H), 4.02 (s, 3H), 2.57 (s, 3H).

Step 2: Preparation of (Z)—N'-hydroxy-1,3-dimethyl-1H-indazole-5-carboximidamide

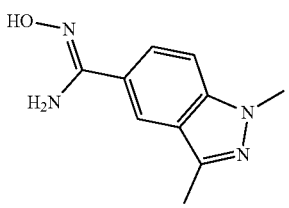

To a stirred solution of 1,3-dimethyl-1H-indazole-5-carbonitrile (340 mg, 1.99 mmol) in ethanol (6 mL) was added hydroxylamine hydrochloride (276 mg, 3.97 mmol), triethylamine (401 mg, 3.97 mmol, 550 μL) and water (600 μL). The mixture was stirred at 80° C. for 2 h. The reaction mixture was cooled and then concentrated under reduced pressure. The residue was triturated with water (4 mL), filtered and the filter cake was dried under reduced pressure to give (Z)—N'-hydroxy-1,3-dimethyl-1H-indazole-5-carboximidamide (250 mg, 1.22 mmol, 62%) as a white solid. $^1$H NMR (400 MHz, DMSO-d6) δ 9.50 (s, 1H), 7.99 (s, 1H), 7.72 (dd, J=1.5, 9.0 Hz, 1H), 7.48 (d, J=8.8 Hz, 1H), 5.82 (s, 2H), 3.92 (s, 3H), 2.46 (s, 3H).

Step 3: Preparation of N-(2-(4-(3-(1,3-dimethyl-1H-indazol-5-yl)-1,2,4-oxadiazol-5-yl)piperidin-1-yl)-2-oxoethyl)benzamide

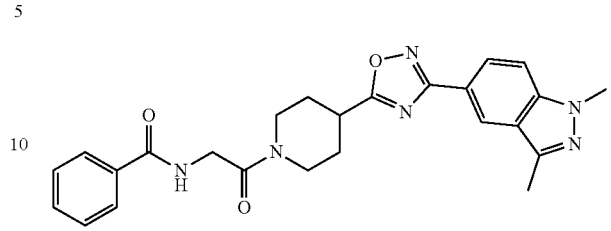

To a stirred solution of 1-(2-benzamidoacetyl)piperidine-4-carboxylic acid (120 mg, 413 μmol) in N,N-dimethylformamide (2 mL) was added N'-hydroxy-1,3-dimethyl-indazole-5-carboxamidine (84 mg, 413 μmol), (2-(1H-benzotriazol-1-yl)-1,1,3,3-tetramethyluronium hexafluorophosphate) (156 mg, 413 μmol) and N-ethyl-N-(propan-2-yl)propan-2-amine (160 mg, 1.24 mmol, 216 μL). The mixture was stirred at 20° C. for 2 h, and then heated at 110° C. for 2 h. The reaction mixture was cooled then purified by prep-HPLC (column: Waters Xbridge 150×2.5 mm 5 μm; mobile phase: [water (10 mM ammonium carbonate)-acetonitrile]; B %: 35%-64%, 12 min) to give N-(2-(4-(3-(1,3-dimethyl-1H-indazol-5-yl)-1,2,4-oxadiazol-5-yl)piperidin-1-yl)-2-oxoethyl)benzamide (54 mg, 118 μmol, 29%) as a white solid. $^1$H NMR (400 MHz, DMSO-d6) δ 8.55 (t, J=5.5 Hz, 1H), 8.34 (s, 1H), 7.96 (dd, J=1.3, 8.8 Hz, 1H), 7.86 (d, J=7.1 Hz, 2H), 7.70 (d, J=8.8 Hz, 1H), 7.55-7.42 (m, 3H), 4.31 (d, J=13.2 Hz, 1H), 4.16 (dd, J=2.2, 5.3 Hz, 2H), 4.03-3.92 (m, 4H), 3.49-3.40 (m, 1H), 3.34-3.30 (m, 1H), 2.92 (t, J=11.5 Hz, 1H), 2.52 (s, 3H), 2.14 (t, J=13.0 Hz, 2H), 1.83 (d, J=10.1 Hz, 1H), 1.71-1.62 (m, 1H); LCMS (ESI) m/z: [M+H]$^+$=459.3.

Example 96: 4-(4-(3-(1,3-dimethyl-1H-indazol-6-yl)-1,2,4-oxadiazol-5-yl)piperazine-1-carbonyl)-1-phenylpyrrolidin-2-one

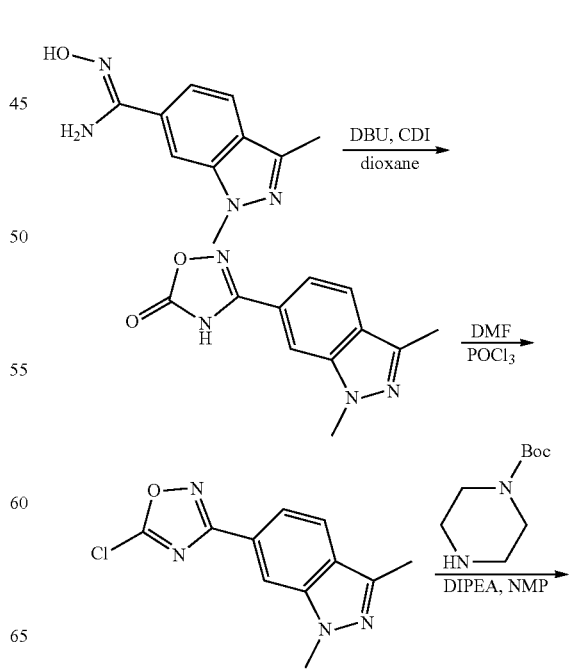

-continued

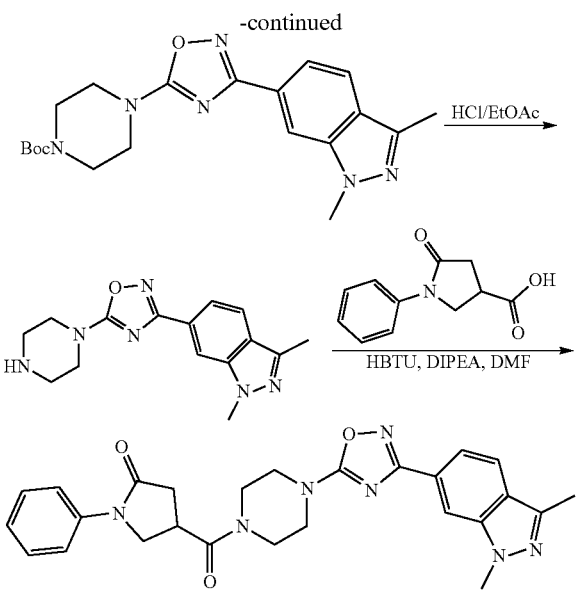

Step 1: Preparation of 3-(1,3-dimethyl-1H-indazol-6-yl)-1,2,4-oxadiazol-5(4H)-one

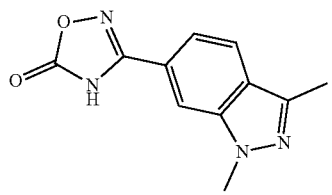 [SMILES: Cc1nn(C)c2cc(-c3noc(=O)[nH]3)ccc12]

To a stirred solution of (Z)—N'-hydroxy-1,3-dimethyl-1H-indazole-6-carboximidamide (180 mg, 881 μmol) in dioxane (3 mL) was added 1,8-diazabicyclo[5.4.0]undec-7-ene (147 mg, 970 μmol, 146 μL) and 1,1'-carbonyldiimidazole (214 mg, 1.32 mmol). The mixture was stirred at 110° C. for 16 h. The reaction mixture was concentrated in vacuo then purified by chromatography (silica, dichloromethane:methanol=50:1) to give 3-(1,3-dimethyl-1H-indazol-6-yl)-1,2,4-oxadiazol-5(4H)-one (220 mg) as a yellow solid. $^1$H NMR (400 MHz, Methanol-d4) δ 7.97-7.93 (m, 1H), 7.82-7.77 (m, 1H), 7.62 (d, J=1.1 Hz, 1H), 4.05 (s, 3H), 2.57 (s, 3H).

Step 2: Preparation of 5-chloro-3-(1,3-dimethyl-1H-indazol-6-yl)-1,2,4-oxadiazole

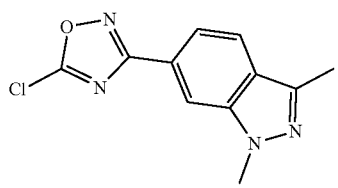 [SMILES: Cc1nn(C)c2cc(-c3noc(Cl)n3)ccc12]

A flask 3-(1,3-dimethyl-1H-indazol-6-yl)-1,2,4-oxadiazol-5(4H)-one (220 mg, 956 μmol) was charged with N,N-dimethylformamide (1 mL) then phosphoryl chloride (10 mL) was added dropwise. The mixture was heated at 110° C. for 16 h, then cooled and concentrated under reduced pressure, poured onto ice water (10 mL), and stirred for 10 min. The mixture was extracted with dichloromethane (20 mL×3), then the combined organic phases were washed with saturated aqueous sodium chloride solution (10 mL), dried over anhydrous sodium sulfate, filtered and concentrated to give 5-chloro-3-(1,3-dimethyl-1H-indazol-6-yl)-1,2,4-oxadiazole (100 mg) as a brown solid.

Step 3: Preparation of tert-butyl 4-(3-(1,3-dimethyl-1H-indazol-6-yl)-1,2,4-oxadiazol-5-yl)piperazine-1-carboxylate

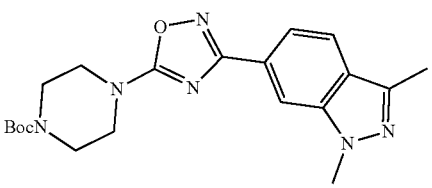 [SMILES: Cc1nn(C)c2cc(-c3noc(N4CCN(C(=O)OC(C)(C)C)CC4)n3)ccc12]

To a stirred solution of 5-chloro-3-(1,3-dimethyl-1H-indazol-6-yl)-1,2,4-oxadiazole (100 mg, 402.1 μmol) in N-methyl-2-pyrrolidone (3 mL) was added tert-butyl piperazine-1-carboxylate (74 mg, 402 μmol) and N-ethyl-N-(propan-2-yl)propan-2-amine (103 mg, 804 μmol, 140 μL). The mixture was stirred at 120° C. for 16 h. The reaction mixture was cooled, quenched by addition of water (5 mL) then the mixture was extracted with ethyl acetate (20 mL×3). The combined organic phases were washed with saturated aqueous sodium chloride solution (10 mL), dried over anhydrous sodium sulfate, filtered and concentrated. Purification by prep-TLC (silica, petroleumether:ethylacetate=1:1) gave tert-butyl 4-(3-(1,3-dimethyl-1H-indazol-6-yl)-1,2,4-oxadiazol-5-yl)piperazine-1-carboxylate (65 mg, 163 μmol, 41%) as a brown solid.

Step 4: Preparation of 3-(1,3-dimethyl-1H-indazol-6-yl)-5-(piperazin-1-yl)-1,2,4-oxadiazole

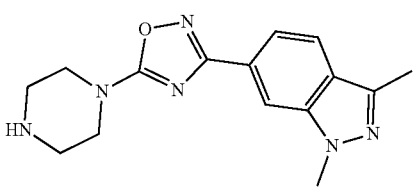 [SMILES: Cc1nn(C)c2cc(-c3noc(N4CCNCC4)n3)ccc12]

To a stirred solution of tert-butyl 4-[3-(1,3-dimethylindazol-6-yl)-1,2,4-oxadiazol-5-yl]piperazine-1-carboxylate (65 mg, 163 μmol) in ethyl acetate (1 mL) was added hydrochloric acid/ethyl acetate (4M, 5 mL). The mixture was stirred at 20° C. for 0.5 h. The reaction mixture was concentrated under reduced pressure to give 3-(1,3-dimethyl-1H-indazol-6-yl)-5-(piperazin-1-yl)-1,2,4-oxadiazole (40 mg, 134 μmol, 82%) as a white solid. LCMS (ESI) m/z: [M+H]$^+$=299.1.

Step 5: Preparation of 4-(4-(3-(1,3-dimethyl-1H-indazol-6-yl)-1,2,4-oxadiazol-5-yl)piperazine-1-carbonyl)-1-phenylpyrrolidin-2-one

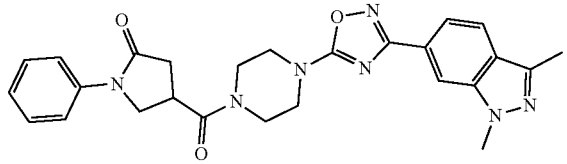 [SMILES: Cc1nn(C)c2cc(-c3noc(N4CCN(C(=O)C5CC(=O)N(c6ccccc6)C5)CC4)n3)ccc12]

To a stirred solution of 3-(1,3-dimethyl-1H-indazol-6-yl)-5-(piperazin-1-yl)-1,2,4-oxadiazole (35 mg, 117 μmol) in N,N-dimethylformamide (1 mL) was added 5-oxo-1-phenylpyrrolidine-3-carboxylic acid (24 mg, 117 μmol), (2-(1H-benzotriazol-1-yl)-1,1,3,3-tetramethyluronium hexafluorophosphate) (44 mg, 117 μmol) and N-ethyl-N-(propan-2-yl)propan-2-amine (45 mg, 352 μmol, 61 μL). The mixture was stirred at 20° C. for 1 h. The reaction mixture was purified directly by prep-HPLC (column: Waters Xbridge 150×2.5 mm 5 μm; mobile phase: [water (10 mM ammonium carbonate)-acetonitrile]; B %: 30%-60%, 12 min) to give 4-(4-(3-(1,3-dimethyl-1H-indazol-6-yl)-1,2,4-oxadiazol-5-yl)piperazine-1-carbonyl)-1-phenylpyrrolidin-2-one (26 mg, 54.58 μmol, 47%) as a white solid. $^1$H NMR (400 MHz, CDCl$_3$) δ 8.05 (s, 1H), 7.83-7.69 (m, 2H), 7.63 (br d, J=7.5 Hz, 2H), 7.42 (br t, J=7.5 Hz, 2H), 7.22 (br d, J=7.9 Hz, 1H), 4.37 (br t, J=8.0 Hz, 1H), 4.09 (s, 3H), 4.03-3.96 (m, 1H), 3.93-3.72 (m, 8H), 3.63 (br d, J=9.7 Hz, 1H), 3.04-2.85 (m, 2H), 2.62 (s, 3H); LCMS (ESI) m/z: [M+H]$^+$=486.3.

Example 97: N-(2-(4-(3-(4-ethoxy-3-fluorophenyl)-1,2,4-oxadiazol-5-yl)piperidin-1-yl)-2-oxoethyl)benzamide

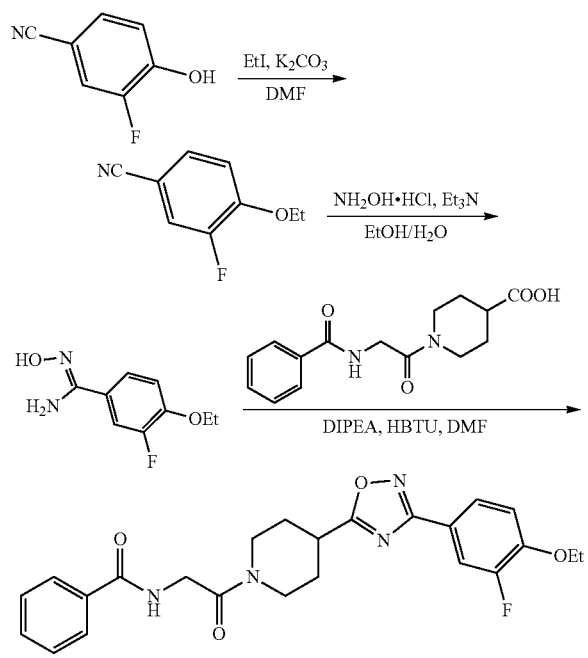

Step 1: Preparation of 4-ethoxy-3-fluorobenzonitrile

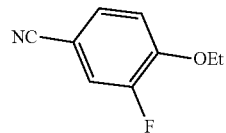 [SMILES: CCOc1ccc(C#N)cc1F]

To a stirred solution of 3-fluoro-4-hydroxybenzonitrile (800 mg, 5.83 mmol) in N,N-dimethylformamide (10 mL) was added iodoethane (1.09 g, 7.00 mmol, 559 μL) and potassium carbonate (1.61 g, 11.7 mmol) at 0° C. The reaction was warmed at 40° C. for 16 h. The reaction mixture was quenched with water (10 mL), then the mixture was extracted with ethyl acetate (40 mL×3). The combined organic phases were washed with saturated aqueous sodium chloride solution (10 mL), dried over anhydrous sodium sulfate, filtered and concentrated to give crude 4-ethoxy-3-fluorobenzonitrile (750 mg, 4.54 mmol, 78%) as a yellow solid. $^1$H NMR (400 MHz, CDCl$_3$) δ 7.43-7.30 (m, 2H), 6.98 (t, J=8.3 Hz, 1H), 4.15 (q, J=7.0 Hz, 2H), 1.47 (tt, J=1.2, 7.0 Hz, 3H).

Step 2: Preparation of (Z)-4-ethoxy-3-fluoro-N'-hydroxybenzimidamide

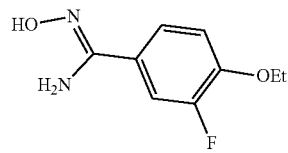

To a stirred solution of 4-ethoxy-3-fluorobenzonitrile (400 mg, 2.42 mmol) in ethanol (6 mL) was added hydroxylamine hydrochloride (336 mg, 4.84 mmol), triethylamine (490 mg, 4.84 mmol, 671 μL) and water (600 μL). The mixture was stirred at 80° C. for 2 h. The reaction mixture was cooled then concentrated under reduced pressure. The residue was triturated with water (5 mL), filtered and the filter cake was dried under reduced pressure to give (Z)-4-ethoxy-3-fluoro-N'-hydroxybenzimidamide (300 mg, 1.51 mmol, 63%) as a white solid. $^1$H NMR (400 MHz, DMSO-d6) δ 9.57 (s, 1H), 7.47-7.39 (m, 2H), 7.12 (t, J=8.9 Hz, 1H), 5.80 (s, 2H), 4.13-4.06 (m, 2H), 1.34-1.29 (m, 3H).

Step 3: Preparation of N-(2-(4-(3-(4-ethoxy-3-fluorophenyl)-1,2,4-oxadiazol-5-yl)piperidin-1-yl)-2-oxoethyl)benzamide

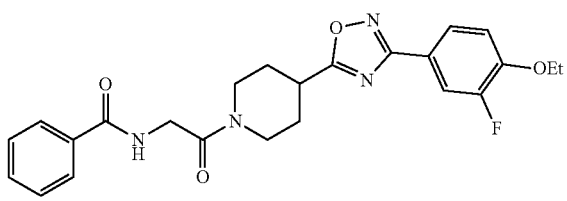 [SMILES: CCOc1ccc(-c2noc(C3CCN(C(=O)CNC(=O)c4ccccc4)CC3)n2)cc1F]

To a stirred solution of 1-(2-benzamidoacetyl)piperidine-4-carboxylic acid (100 mg, 344 μmol) in N,N-dimethylformamide (2 mL) was added (Z)-4-ethoxy-3-fluoro-N'-hydroxybenzimidamide (68 mg, 344 μmol), (2-(1H-benzotriazol-1-yl)-1,1,3,3-tetramethyluronium hexafluorophosphate) (130 mg, 344 μmol) and N-ethyl-N-(propan-2-yl)propan-2-amine (133 mg, 1.03 mmol, 180 μL). The mixture was stirred at 20° C. for 1 h, then heated at 110° C. for 1 h. The reaction mixture was cooled then purified by prep-HPLC (column: Waters Xbridge 150×2.5 mm 5 μm; mobile phase: [water (10 mM ammonium carbonate)-acetonitrile]; B %: 40%-70%, 12 min) to give N-(2-(4-(3-(4-ethoxy-3-fluorophenyl)-1,2,4-oxadiazol-5-yl)piperidin-1-yl)-2-oxoethyl)benzamide (43 mg, 96 μmol, 28%) as a pink solid. $^1$H NMR (400 MHz, CDCl$_3$) δ 7.88 (d, J=7.0 Hz, 2H), 7.85-7.79 (m, 2H), 7.58-7.44 (m, 3H), 7.35 (br s, 1H), 7.05 (t, J=8.5 Hz, 1H), 4.51 (br d, J=13.6 Hz, 1H), 4.33 (d, J=3.8 Hz, 2H), 4.20 (q, J=7.0 Hz, 2H), 3.93 (br d, J=13.7 Hz, 1H), 3.41-3.29 (m, 2H), 3.23-3.13 (m, 1H), 2.32-2.20 (m, 2H), 2.08-1.93 (m, 2H), 1.51 (t, J=7.0 Hz, 3H); LCMS (ESI) m/z: [M+H]$^+$=453.1.

Example 98: [4-[3-(4-ethoxy-3-methoxy-phenyl)-1,2,4-oxadiazol-5-yl]-1-piperidyl]-(2-phenyl-1H-imidazol-5-yl)methanone

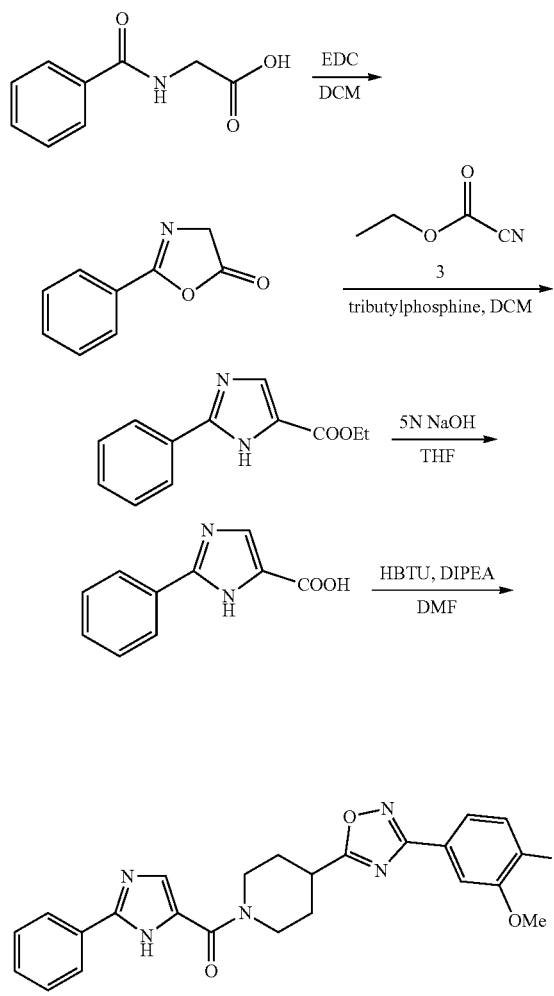

Step 1: Preparation of 2-phenyl-4H-oxazol-5-one

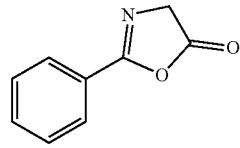 [SMILES: O=C1CN=C(c2ccccc2)O1]

A mixture of 2-benzamidoacetic acid (1.0 g, 5.58 mmol) and 1-ethyl-3-(3-dimethylaminopropyl)carbodiimide (953 mg, 6.14 mmol, 1.08 mL) in dichloromethane (25 mL) was degassed and purged with nitrogen 3 times, and then the mixture was stirred at 20° C. for 6 h under a nitrogen atmosphere. The mixture was concentrated in vacuum to get a crude product. The crude product, 2-phenyl-4H-oxazol-5-one (1.20 g) was used directly without further purification.

Step 2: Ethyl 2-phenyl-1H-imidazole-5-carboxylate

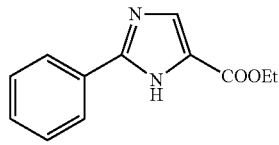 [SMILES: CCOC(=O)c1cnc(-c2ccccc2)[nH]1]

A mixture of 2-phenyl-4H-oxazol-5-one (1.0 g, 6.21 mmol), ethyl cyanoformate (676 mg, 6.83 mmol, 669 μL) and tributylphosphine (753 mg, 3.72 mmol, 918 μL) in dichloromethane (3 mL) was degassed and purged with nitrogen 3 times, and then the mixture was stirred at 20° C. for 6 h under a nitrogen atmosphere. The reaction mixture was quenched by addition of water (3 mL), then extracted with dichloromethane (10 mL×2). The combined organic phases were dried over anhydrous sodium sulfate, filtered and concentrated under reduced pressure to give a residue that was purified by chromatography (silica, petroleum ether/ethyl acetate=2:1) to give ethyl 2-phenyl-1H-imidazole-5-carboxylate (480 mg, 2.22 mmol, 36%) as a white solid.

Step 3: 2-phenyl-1H-imidazole-5-carboxylic acid

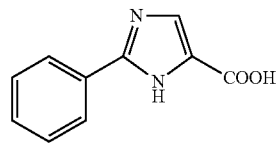 [SMILES: O=C(O)c1cnc(-c2ccccc2)[nH]1]

A mixture of ethyl 2-phenyl-1H-imidazole-5-carboxylate (300 mg, 1.39 mmol) and sodium hydroxide (166 mg, 4.17 mmol) in tetrahydrofuran (3 mL) and water (1.50 mL) was stirred at 20° C. for 2 h. The reaction mixture was extracted with dichloromethane (10 mL×3). The combined organic phases were washed with saturated aqueous sodium chloride solution (5 mL), dried over anhydrous sodium sulfate, filtered and concentrated under reduced pressure to give 2-phenyl-1H-imidazole-5-carboxylic acid (200 mg) that was used directly without further purification.

Step 4: [4-[3-(4-ethoxy-3-methoxy-phenyl)-1,2,4-oxadiazol-5-yl]-1-piperidyl]-(2-phenyl-1H-imidazol-5-yl)methanone

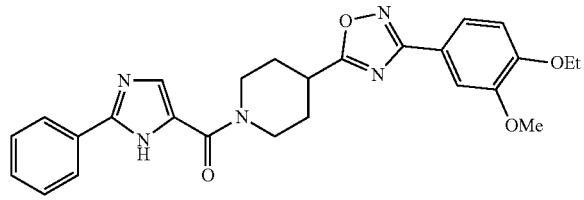 [SMILES: CCOc1ccc(-c2noc(C3CCN(C(=O)c4cnc(-c5ccccc5)[nH]4)CC3)n2)cc1OC]

A mixture of 2-phenyl-1H-imidazole-5-carboxylic acid (62 mg, 330 µmol), 3-(4-ethoxy-3-methoxy-phenyl)-5-(4-piperidyl)-1,2,4-oxadiazole (100 mg, 330 µmol), (2-(1H-benzotriazol-1-yl)-1,1,3,3-tetramethyluronium hexafluorophosphate) (125 mg, 330 µmol) and diisopropylethylamine (85 mg, 659 µmol, 115 µL) in N,N-dimethylformamide (3 mL) was degassed and purged with nitrogen 3 times, and then the mixture was stirred at 20° C. for 2 h under a nitrogen atmosphere. The mixture was purified by prep-HPLC (column: Waters Xbridge 150×25 5 µm; mobile phase: [water (10 mM ammonium carbonate)-acetonitrile]; B %: 40%-65%, 12 min) to give [4-[3-(4-ethoxy-3-methoxy-phenyl)-1,2,4-oxadiazol-5-yl]-1-piperidyl]-(2-phenyl-1H-imidazol-5-yl)methanone (25 mg, 105 µmol, 16%) as a white solid. $^1$H NMR (400 MHz, CHLOROFORM-d) δ=7.95 (br d, J=7.7 Hz, 2H), 7.65 (dd, J=1.8, 8.4 Hz, 1H), 7.54 (s, 2H), 7.47-7.32 (m, 3H), 6.92 (d, J=8.4 Hz, 1H), 5.56-5.27 (m, 1H), 4.77-4.46 (m, 1H), 4.14 (q, J=6.8 Hz, 2H), 3.99-3.88 (m, 3H), 3.66-3.09 (m, 3H), 2.24 (br d, J=9.7 Hz, 2H), 2.07 (br s, 1H), 1.84 (br s, 1H), 1.47 (t, J=6.8 Hz, 3H); LCMS(ESI) m/z: [M+H]$^+$=474.3.

Example 99: N-(2-(4-(3-(3-bromo-4-ethoxyphenyl)-1,2,4-oxadiazol-5-yl)piperidin-1-yl)-2-oxoethyl)benzamide

Step 1: Preparation of N-(2-(4-(3-(3-bromo-4-ethoxyphenyl)-1,2,4-oxadiazol-5-yl)piperidin-1-yl)-2-oxoethyl)benzamide

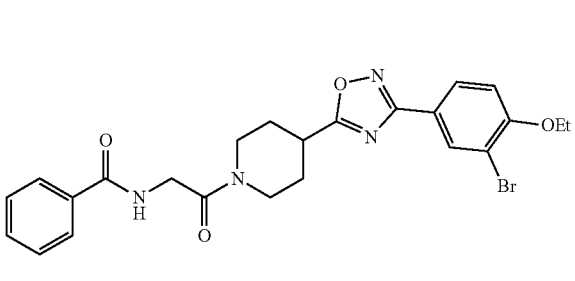

To a stirred solution of 1-(2-benzamidoacetyl)piperidine-4-carboxylic acid (100 mg, 344 µmol) in N,N-dimethylformamide (2 mL) was added (Z)-3-bromo-4-ethoxy-N'-hydroxybenzimidamide (89 mg, 344 µmol), (2-(1H-benzotriazol-1-yl)-1,1,3,3-tetramethyluronium hexafluorophosphate) (130 mg, 344 µmol) and N-ethyl-N-(propan-2-yl)propan-2-amine (133 mg, 1.03 mmol, 180 µL). The mixture was stirred at 20° C. for 1 h, then heated at 110° C. for 1 h. The reaction mixture was purified directly by prep-HPLC (column: Waters Xbridge 150×2.5 mm 5 µm; mobile phase: [water (10 mM ammonium carbonate)-acetonitrile]; B %: 45%-75%, 12 min) to give N-(2-(4-(3-(3-bromo-4-ethoxyphenyl)-1,2,4-oxadiazol-5-yl)piperidin-1-yl)-2-oxoethyl)benzamide (43 mg, 83 µmol, 24%) as a yellow solid. $^1$H NMR (400 MHz, CDCl$_3$) δ 8.30 (d, J=2.1 Hz, 1H), 8.00 (dd, J=2.1, 8.6 Hz, 1H), 7.91-7.85 (m, 2H), 7.58-7.44 (m, 3H), 7.35 (br s, 1H), 6.98 (d, J=8.7 Hz, 1H), 4.50 (br d, J=14.1 Hz, 1H), 4.33 (d, J=3.9 Hz, 2H), 4.20 (q, J=6.9 Hz, 2H), 3.93 (br d, J=13.8 Hz, 1H), 3.41-3.29 (m, 2H), 3.18 (br t, J=10.6 Hz, 1H), 2.32-2.20 (m, 2H), 2.09-1.93 (m, 2H), 1.53 (t, J=7.0 Hz, 3H); LCMS (ESI) m/z: [M+H]$^+$=513.2.

Example 100: (1-(3-(4-ethoxy-3-methoxyphenyl)-1,2,4-oxadiazol-5-yl)piperidin-4-yl)(3-phenylpiperidin-1-yl)methanone

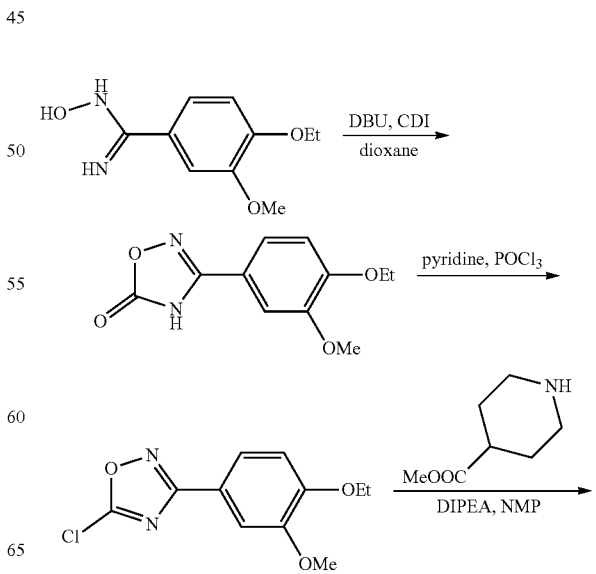

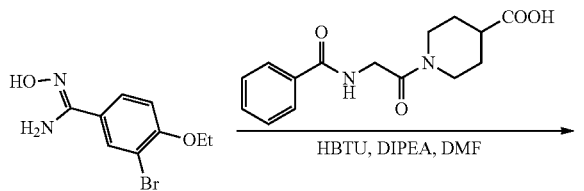

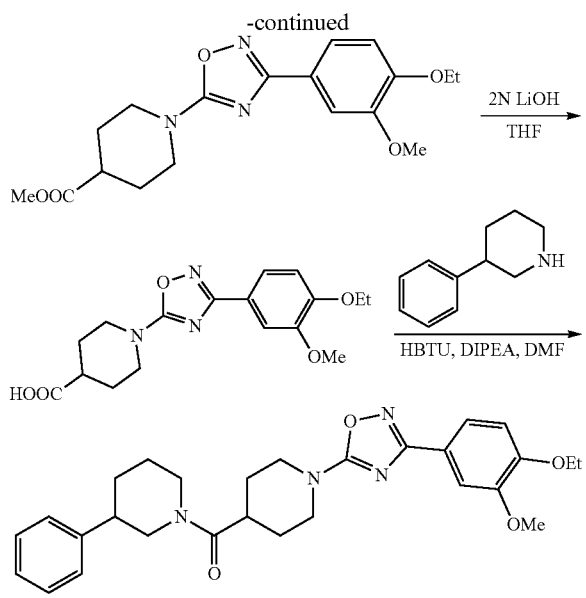

Step 1: Preparation of 3-(4-ethoxy-3-methoxyphenyl)-1,2,4-oxadiazol-5(4H)-one

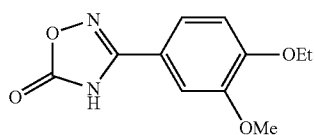 [SMILES: CCOc1ccc(-c2noc(=O)[nH]2)cc1OC]

To a stirred solution of 4-ethoxy-N-hydroxy-3-methoxybenzimidamide (1.0 g, 4.76 mmol) in dioxane (10 mL) was added 1,8-diazabicyclo[5.4.0]undec-7-ene (796 mg, 5.24 mmol, 788 µL) and 1,1'-carbonyldiimidazole (1.16 g, 7.14 mmol). The mixture was heated at 110° C. for 16 h. The reaction mixture was cooled, quenched with water (10 mL), and then extracted with dichloromethane (50 mL×3). The combined organic phases were washed with 1M aqueous hydrochloric acid (5 mL×2), then with saturated aqueous sodium chloride solution (10 mL), filtered and dried over anhydrous sodium sulfate. The organic layer was concentrated to give 3-(4-ethoxy-3-methoxyphenyl)-1,2,4-oxadiazol-5(4H)-one (1.02 g, 4.32 mmol, 91%) as a brown solid. $^1$H NMR (400 MHz, DMSO-d6) δ 12.78 (br s, 1H), 7.38-7.28 (m, 2H), 7.08 (d, J=8.4 Hz, 1H), 4.05 (q, J=7.1 Hz, 2H), 3.77 (s, 3H), 1.30 (t, J=6.9 Hz, 3H).

Step 2: Preparation of 5-chloro-3-(4-ethoxy-3-methoxyphenyl)-1,2,4-oxadiazole

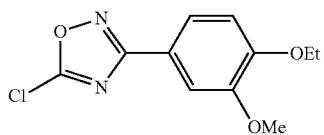 [SMILES: CCOc1ccc(-c2noc(Cl)n2)cc1OC]

A flask 3-(4-ethoxy-3-methoxyphenyl)-1,2,4-oxadiazol-5(4H)-one (1.02 g, 4.32 mmol) was equipped with calcium chloride tube, then phosphoryl chloride (12 mL) and pyridine (170 mg, 2.16 mmol, 174 µL) were added dropwise and the mixture was heated at 110° C. for 16 h. The reaction mixture was cooled then concentrated under reduced pressure to remove phosphoryl chloride, and the residue added to ice water (20 mL) and stirred for 10 min. The mixture was extracted with dichloromethane (40 mL×3), then the combined organic phases were washed with saturated aqueous sodium chloride solution (20 mL), dried over anhydrous sodium sulfate, filtered and concentrated to give crude 5-chloro-3-(4-ethoxy-3-methoxyphenyl)-1,2,4-oxadiazole (910 mg) as a yellow solid.

Step 3: Preparation of methyl 1-(3-(4-ethoxy-3-methoxyphenyl)-1,2,4-oxadiazol-5-yl)piperidine-4-carboxylate

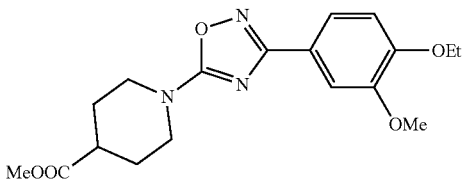 [SMILES: CCOc1ccc(-c2noc(N3CCC(C(=O)OC)CC3)n2)cc1OC]

To a stirred solution of 5-chloro-3-(4-ethoxy-3-methoxyphenyl)-1,2,4-oxadiazole (600 mg, 2.36 mmol) in N-methyl-2-pyrrolidone (8 mL) was added methyl piperidine-4-carboxylate (337 mg, 2.36 mmol) and N-ethyl-N-(propan-2-yl)propan-2-amine (610 mg, 4.72 mmol, 824 µL). The mixture was stirred at 120° C. for 16 h. The reaction mixture was quenched with water (10 mL), then the mixture was extracted with ethyl acetate (40 mL×3), then the combined organic phases were washed with saturated aqueous sodium chloride solution (10 mL), dried over anhydrous sodium sulfate, filtered and concentrated to give a residue that was purified by chromatography (silica, petroleumether:ethylacetate=50:1 to 10:1) to give methyl 1-(3-(4-ethoxy-3-methoxyphenyl)-1,2,4-oxadiazol-5-yl)piperidine-4-carboxylate (510 mg, 1.41 mmol, 60%) as a yellow solid. $^1$H NMR (400 MHz, DMSO-d6) δ 7.47 (dd, J=1.9, 8.3 Hz, 1H), 7.38 (d, J=2.0 Hz, 1H), 7.06 (d, J=8.4 Hz, 1H), 4.08 (q, J=7.0 Hz, 2H), 4.00 (td, J=3.5, 13.2 Hz, 2H), 3.82 (s, 3H), 3.64 (s, 3H), 3.31-3.24 (m, 2H), 2.68 (tt, J=3.9, 10.9 Hz, 1H), 1.98 (br dd, J=3.2, 13.5 Hz, 2H), 1.70-1.58 (m, 2H), 1.36 (t, J=7.0 Hz, 3H).

Step 4: Preparation of 1-(3-(4-ethoxy-3-methoxyphenyl)-1,2,4-oxadiazol-5-yl)piperidine-4-carboxylic acid

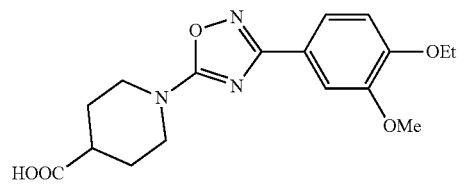 [SMILES: CCOc1ccc(-c2noc(N3CCC(C(=O)O)CC3)n2)cc1OC]

To a stirred solution of methyl 1-(3-(4-ethoxy-3-methoxyphenyl)-1,2,4-oxadiazol-5-yl)piperidine-4-carboxylate (490 mg, 1.36 mmol) in tetrahydrofuran (10 mL) was added lithium hydroxide (2 M, 2.04 mL). The mixture was stirred at 20° C. for 16 h. The reaction mixture was concentrated under reduced pressure to remove tetrahydrofuran, then the mixture was acidified with concentrated hydrochloric acid until pH 1. The mixture was extracted with dichloromethane (40 mL×3). The organic layer was washed with saturated aqueous sodium chloride solution (20 mL), dried over anhydrous sodium sulfate, filtered and concentrated to give crude 1-(3-(4-ethoxy-3-methoxyphenyl)-1,2,4-oxadiazol-5-yl)piperidine-4-carboxylic acid (400 mg, 1.15 mmol, 85%) as a white solid. $^1$H NMR (400 MHz, Methanol-d4) δ 7.52-7.45 (m, 2H), 6.99 (d, J=8.4 Hz, 1H), 4.15-4.05 (m, 4H), 3.86 (s, 3H), 3.32 (br d, J=3.1 Hz, 1H), 3.28-3.25 (m, 1H), 2.61 (tt, J=3.8, 10.8 Hz, 1H), 2.07-1.98 (m, 2H), 1.80-1.68 (m, 2H), 1.41 (t, J=6.9 Hz, 3H).

Step 5: Preparation of (1-(3-(4-ethoxy-3-methoxyphenyl)-1,2,4-oxadiazol-5-yl)piperidin-4-yl)(3-phenylpiperidin-1-yl)methanone

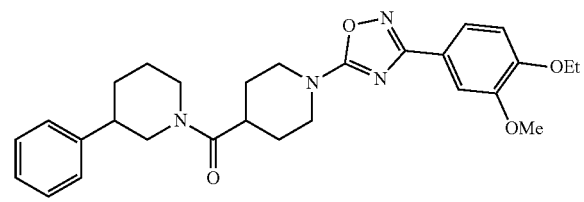 [SMILES: CCOc1ccc(-c2noc(N3CCC(C(=O)N4CCCC(c5ccccc5)C4)CC3)n2)cc1OC]

To a stirred solution of 1-(3-(4-ethoxy-3-methoxyphenyl)-1,2,4-oxadiazol-5-yl)piperidine-4-carboxylic acid (100 mg, 288 μmol) in N,N-dimethylformamide (500 μL) was added 3-phenylpiperidine (46 mg, 288 μmol), (2-(1H-benzotriazol-1-yl)-1,1,3,3-tetramethyluronium hexafluorophosphate) (109 mg, 288 μmol) and N-ethyl-N-(propan-2-yl)propan-2-amine (111 mg, 863.66 μmol, 150 μL). The mixture was stirred at 20° C. for 2 h. The reaction mixture was then purified by prep-HPLC (column: Waters Xbridge 150×2.5 mm 5 μm; mobile phase: [water (10 mM ammonium carbonate)-acetonitrile]; B %: 35%-60%, 12 min) to give (1-(3-(4-ethoxy-3-methoxyphenyl)-1,2,4-oxadiazol-5-yl)piperidin-4-yl)(3-phenylpiperidin-1-yl)methanone (80 mg, 162 μmol, 56%) as a white solid. $^1$H NMR (400 MHz, DMSO-d6) δ 7.45-7.40 (m, 1H), 7.36-7.16 (m, 6H), 7.02 (d, J=8.4 Hz, 1H), 4.49-4.36 (m, 1H), 4.09-3.92 (m, 5H), 3.78 (s, 3H), 3.28-2.92 (m, 4H), 2.70-2.50 (m, 2H), 1.89 (br d, J=11.7 Hz, 1H), 1.82-1.44 (m, 7H), 1.31 (t, J=6.9 Hz, 3H); LCMS (ESI) m/z: [M+H]$^+$=491.3.

Example 101: N-(2-(4-(3-(3-cyano-4-ethoxyphenyl)-1,2,4-oxadiazol-5-yl)piperidin-1-yl)-2-oxoethyl)benzamide

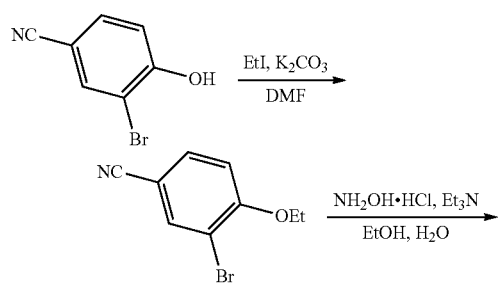

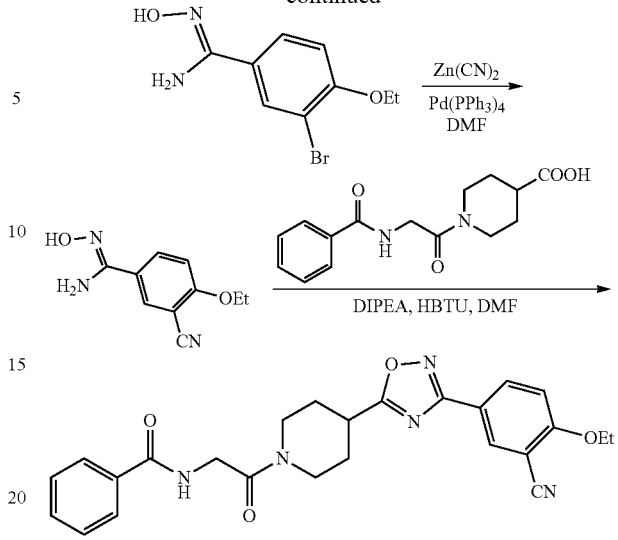

Step 1: Preparation of 3-bromo-4-ethoxybenzonitrile

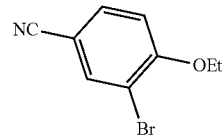

To a stirred solution of 3-bromo-4-hydroxybenzonitrile (1.0 g, 5.05 mmol) in N,N-dimethylformamide (10 mL) was added iodoethane (945 mg, 6.06 mmol, 484 μL) and potassium carbonate (1.40 g, 10.1 mmol) at 0° C. The reaction was warmed at 40° C. for 16 h. The reaction mixture was quenched by addition of water (15 mL), then the mixture was extracted with ethyl acetate (40 mL×3), then the combined organic phases were washed with saturated aqueous sodium chloride solution (20 mL), dried over anhydrous sodium sulfate, filtered and concentrated in vacuo to give 3-bromo-4-ethoxybenzonitrile (1.20 g) as a yellow solid. $^1$H NMR (400 MHz, CDCl$_3$) δ 7.80 (d, J=2.0 Hz, 1H), 7.55 (dd, J=2.0, 8.6 Hz, 1H), 6.89 (d, J=8.6 Hz, 1H), 4.14 (q, J=7.0 Hz, 2H), 1.49 (t, J=6.9 Hz, 3H).

Step 2: Preparation of (Z)-3-bromo-4-ethoxy-N'-hydroxybenzimidamide

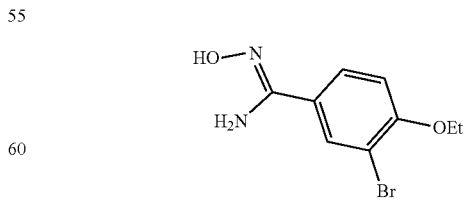

To a stirred solution of 3-bromo-4-ethoxybenzonitrile (1.15 g, 5.09 mmol) in ethanol (10 mL) was added hydroxylamine hydrochloride (706 mg, 10.2 mmol), triethylamine (1.03 g, 10.2 mmol, 1.41 mL) and water (1 mL). The mixture was heated at 80° C. for 1 h, then cooled and concentrated under reduced pressure to remove ethanol. The residue was triturated with water (5 mL) and filtered, and the filter cake was dried under reduced pressure to give (Z)-3-bromo-4-ethoxy-N'-hydroxybenzimidamide (1.31 g, 5.06 mmol, 99%) as a white solid. ¹H NMR (400 MHz, DMSO-d6) δ 9.55 (br s, 1H), 7.82 (d, J=2.2 Hz, 1H), 7.60 (dd, J=2.2, 8.6 Hz, 1H), 7.05 (d, J=8.8 Hz, 1H), 5.79 (s, 2H), 4.12-4.05 (m, 2H), 1.31 (t, J=7.1 Hz, 3H).

Step 3: Preparation of (Z)-3-cyano-4-ethoxy-N'-hydroxybenzimidamide

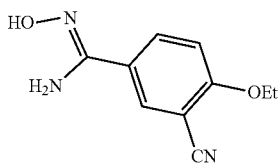 [SMILES: CCOc1ccc(/C(N)=N/O)cc1C#N]

To a stirred solution of zinc cyanide (226 mg, 1.93 mmol, 122 μL) in N,N-dimethylformamide (10 mL) was added (Z)-3-bromo-4-ethoxy-N'-hydroxybenzimidamide (500 mg, 1.93 mmol) and tetrakis(triphenylphosphine)palladium(0) (222 mg, 193 μmol), then the mixture was degassed with nitrogen three times. The mixture was heated at 110° C. for 16 h under nitrogen then cooled to 20° C., water (10 mL) was added, and the reaction mixture extracted with ethyl acetate (40 mL×3). The combined organic phases were washed with saturated aqueous sodium chloride solution (15 mL), dried over anhydrous sodium sulfate, filtered and concentrated in vacuo to give a residue that was purified by prep-HPLC (column: Waters Xbridge 150×2.5 mm 5 μm; mobile phase: [water (10 mM ammonium carbonate)-acetonitrile]; B %: 13%-43%, 12 min) to give (Z)-3-cyano-4-ethoxy-N'-hydroxybenzimidamide (60 mg, 292 μmol, 15%) as a white solid.

Step 4: Preparation of N-(2-(4-(3-(3-cyano-4-ethoxyphenyl)-1,2,4-oxadiazol-5-yl)piperidin-1-yl)-2-oxoethyl)benzamide

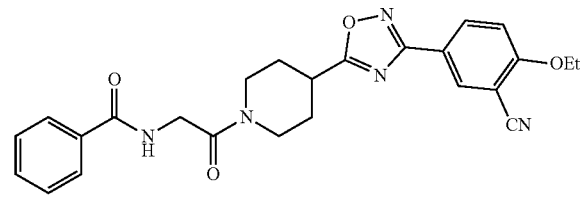

To a stirred solution of 1-(2-benzamidoacetyl)piperidine-4-carboxylic acid (70 mg, 241 μmol) in N,N-dimethylformamide (1 mL) was added (Z)-3-cyano-4-ethoxy-N'-hydroxybenzimidamide (49 mg, 241 μmol), (2-(1H-benzotriazol-1-yl)-1,1,3,3-tetramethyluronium hexafluorophosphate) (91 mg, 241 μmol) and N-ethyl-N-(propan-2-yl)propan-2-amine (93 mg, 723 μmol, 126 μL). The mixture was stirred at 20° C. for 1 h, then heated at 110° C. for 1 h. The reaction mixture was cooled then purified by prep-HPLC (column: Waters Xbridge 150×2.5 mm 5 μm; mobile phase: [water (10 mM ammonium carbonate)-acetonitrile]; B %: 40%-65%, 12 min) to give N-(2-(4-(3-(3-cyano-4-ethoxyphenyl)-1,2,4-oxadiazol-5-yl)piperidin-1-yl)-2-oxoethyl)benzamide (20 mg, 43 μmol, 18%) as a yellow solid. ¹H NMR (400 MHz, DMSO-d6) δ 8.55 (t, J=5.5 Hz, 1H), 8.26-8.17 (m, 2H), 7.84 (dd, J=1.2, 8.3 Hz, 2H), 7.57-7.34 (m, 4H), 4.26 (q, J=6.9 Hz, 3H), 4.14 (br d, J=5.5 Hz, 2H), 3.94 (br d, J=14.6 Hz, 1H), 3.48-3.40 (m, 1H), 3.29-3.22 (m, 1H), 2.90 (br t, J=11.4 Hz, 1H), 2.10 (br t, J=12.8 Hz, 2H), 1.87-1.72 (m, 1H), 1.68-1.55 (m, 1H), 1.37 (t, J=6.9 Hz, 3H); LCMS (ESI) m/z: [M+H]⁺=460.2.

Example 102: N-(2-(4-(3-(1,3-dimethyl-1H-indazol-6-yl)-1,2,4-oxadiazol-5-yl)piperazin-1-yl)-2-oxoethyl)benzamide

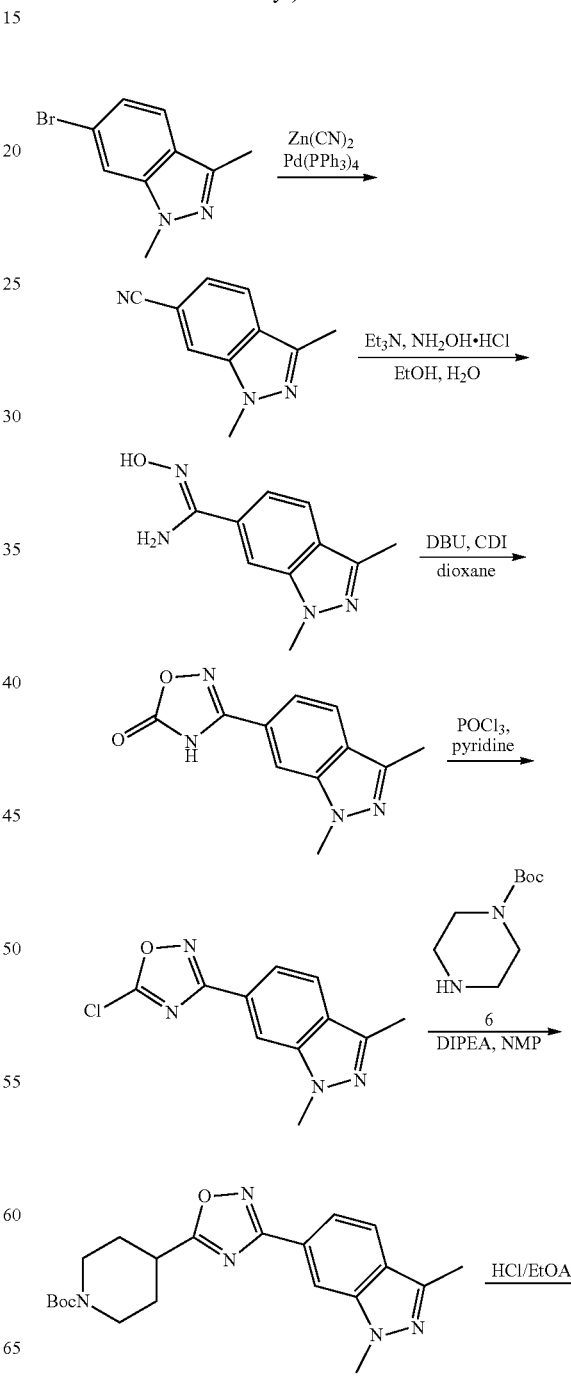

Step 1: Preparation of 1,3-dimethyl-1H-indazol-6-carbonitrile

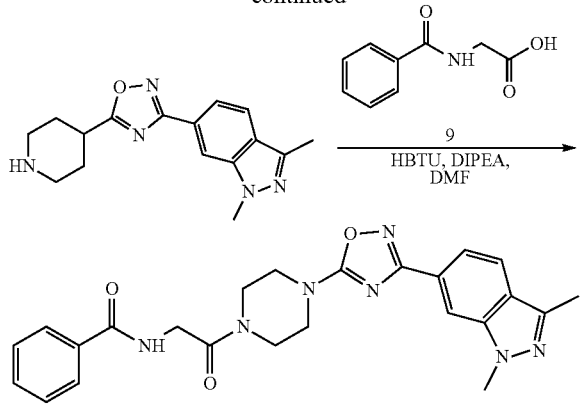

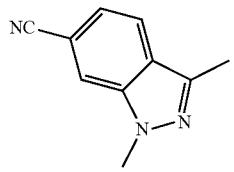

To a stirred solution of 6-bromo-1,3-dimethyl-1H-indazole (1.0 g, 4.44 mmol) in N,N-dimethylformamide (10 mL) was added zinc cyanide (521 mg, 4.44 mmol, 281 µL) and tetrakis(triphenylphosphine)palladium(0) (513 mg, 444 µmol), then the mixture was degassed with nitrogen three times. The mixture was stirred at 100° C. for 16 h under nitrogen, then cooled to 20° C., water (10 mL) added, and the reaction mixture extracted with ethyl acetate (40 mL×3). The combined organic phases were washed with saturated aqueous sodium chloride solution (15 mL), dried over anhydrous sodium sulfate, filtered and concentrated in vacuo to give a residue that was purified by chromatography (silica, petroleumether:ethylacetate=50:1 to 10:1) to give 1,3-dimethyl-1H-indazole-6-carbonitrile (660 mg, 3.86 mmol, 87%) as a white solid. $^1$H NMR (400 MHz, CDCl$_3$) δ 7.74-7.66 (m, 2H), 7.30 (d, J=8.4 Hz, 1H), 4.03 (s, 3H), 2.57 (s, 3H).

Step 2: Preparation of (Z)—N'-hydroxy-1,3-dimethyl-1H-indazole-6-carboximidamide

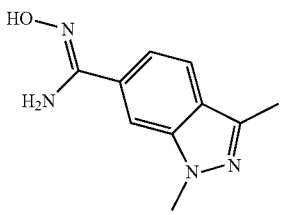

To a stirred solution of 1,3-dimethyl-1H-indazole-6-carbonitrile (660 mg, 3.86 mmol) in ethanol (8 mL) was added hydroxylamine hydrochloride (536 mg, 7.72 mmol), triethylamine (781 mg, 7.72 mmol, 1.07 mL) and water (800 µL). The mixture was heated at 80° C. for 2 h, then cooled and concentrated under reduced pressure. The residue was triturated with water (5 mL), filtered and the filter cake was dried under reduced pressure to give (Z)—N'-hydroxy-1,3-dimethyl-1H-indazole-6-carboximidamide (650 mg, 3.18 mmol, 82%) as a white solid. $^1$H NMR (400 MHz, DMSO-d6) δ 9.72 (br. s., 1H), 7.86 (s, 1H), 7.65 (d, J=8.5 Hz, 1H), 7.49 (dd, J=1.1, 8.5 Hz, 1H), 5.91 (s, 2H), 3.97 (s, 3H), 2.47 (s, 3H).

Step 3: Preparation of 3-(1,3-dimethyl-1H-indazol-6-yl)-1,2,4-oxadiazol-5(4H)-one

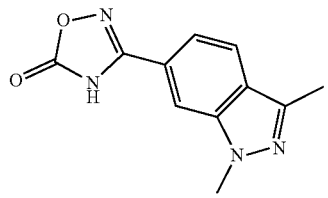 [SMILES: Cc1nn(C)c2cc(-c3noc(=O)[nH]3)ccc12]

To a stirred solution of (Z)—N'-hydroxy-1,3-dimethyl-1H-indazole-6-carboximidamide (510 mg, 2.50 mmol) in dioxane (8 mL) was added 1,8-diazabicyclo[5.4.0]undec-7-ene (418 mg, 2.75 mmol, 414 µL) and 1,1'-carbonyldiimidazole (608 mg, 3.75 mmol). The mixture was stirred at 110° C. for 16 h. The reaction mixture was cooled, quenched with water (10 mL), and then extracted with dichloromethane (50 mL×3). The combined organic layers were washed with 1M hydrochloric acid (5 mL×2), then washed with saturated aqueous sodium chloride solution (10 mL), dried over anhydrous sodium sulfate, filtered and concentrated to give 3-(1,3-dimethyl-1H-indazol-6-yl)-1,2,4-oxadiazol-5(4H)-one (430 mg, 1.87 mmol, 75%) as a yellow solid. $^1$H NMR (400 MHz, DMSO-d6) δ 13.29-12.78 (m, 1H), 8.03 (s, 1H), 7.87 (d, J=8.4 Hz, 1H), 7.48 (dd, J=1.1, 8.4 Hz, 1H), 3.98 (s, 3H), 2.48 (br s, 3H).

Step 4: Preparation of 5-chloro-3-(1,3-dimethyl-1H-indazol-6-yl)-1,2,4-oxadiazole

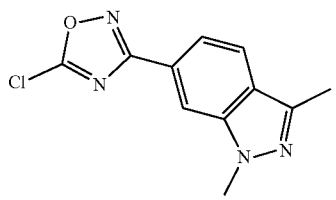 [SMILES: Cc1nn(C)c2cc(-c3noc(Cl)n3)ccc12]

A flask 3-(1,3-dimethyl-1H-indazol-6-yl)-1,2,4-oxadiazol-5(4H)-one (180 mg, 781.86 µmol) was equipped with calcium chloride tube then pyridine (123 mg, 1.56 mmol, 126 µL) and phosphoryl chloride (5 mL) were added dropwise. The mixture was heated at 110° C. for 16 h, then cooled and concentrated under reduced pressure to remove phosphoryl chloride, and then added to ice water (20 mL). The mixture was extracted with dichloromethane (40 mL×3), then the combined organic phases were washed with saturated aqueous sodium chloride solution (10 mL), dried over anhydrous sodium sulfate, filtered and concentrated to give 5-chloro-3-(1,3-dimethyl-1H-indazol-6-yl)-1,2,4-oxadiazole (250 mg) as a brown solid.

Step 5: Preparation of tert-butyl 4-(3-(1,3-dimethyl-1H-indazol-6-yl)-1,2,4-oxadiazol-5-yl)piperazine-1-carboxylate

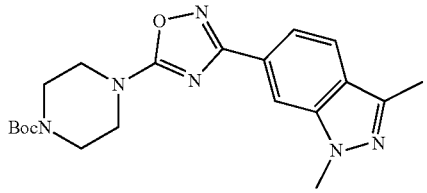 [SMILES: Cc1nn(C)c2cc(-c3noc(N4CCN(C(=O)OC(C)(C)C)CC4)n3)ccc12]

To a stirred solution of 5-chloro-3-(1,3-dimethyl-1H-indazol-6-yl)-1,2,4-oxadiazole (230 mg, 925 μmol) in N-methyl-2-pyrrolidone (3 mL) was added tert-butyl piperazine-1-carboxylate (172 mg, 925 μmol) and N-ethyl-N-(propan-2-yl)propan-2-amine (239 mg, 1.85 mmol, 323 μL). The mixture was heated at 120° C. for 2 h. The reaction mixture was cooled, quenched by addition of water (5 mL), then the mixture was extracted with ethyl acetate (20 mL×3). The combined organic phases were washed with saturated aqueous sodium chloride solution (10 mL), dried over anhydrous sodium sulfate, filtered and concentrated in vacuo. Purification by prep-TLC (silica, petroleumether:ethylacetate=1:1) gave tert-butyl 4-(3-(1,3-dimethyl-1H-indazol-6-yl)-1,2,4-oxadiazol-5-yl)piperazine-1-carboxylate (150 mg, 376 μmol, 41%) as a pink solid.

Step 6: Preparation of 3-(1,3-dimethyl-1H-indazol-6-yl)-5-(piperazin-1-yl)-1,2,4-oxadiazole

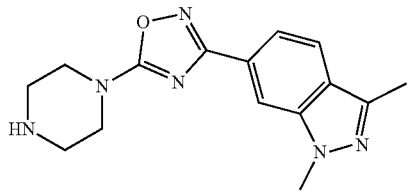 [SMILES: Cc1nn(C)c2cc(-c3noc(N4CCNCC4)n3)ccc12]

To a stirred solution of tert-butyl 4-(3-(1,3-dimethyl-1H-indazol-6-yl)-1,2,4-oxadiazol-5-yl)piperazine-1-carboxylate (150 mg, 376 μmol) in ethyl acetate (1 mL) was added hydrochloric acid/ethyl acetate (4M, 5 mL). The mixture was stirred at 20° C. for 2 h. The reaction mixture was concentrated under reduced pressure to give 3-(1,3-dimethyl-1H-indazol-6-yl)-5-(piperazin-1-yl)-1,2,4-oxadiazole (110 mg, 369 μmol, 98%) as a pink solid. LCMS (ESI) m/z: [M+H]$^+$=299.2.

Step 7: Preparation of N-(2-(4-(3-(1,3-dimethyl-1H-indazol-6-yl)-1,2,4-oxadiazol-5-yl)piperazin-1-yl)-2-oxoethyl)benzamide

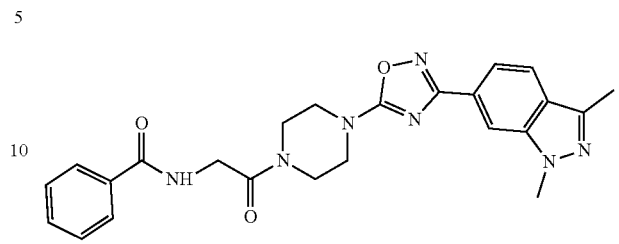

To a stirred solution of 3-(1,3-dimethyl-1H-indazol-6-yl)-5-(piperazin-1-yl)-1,2,4-oxadiazole (50 mg, 168 μmol) in N,N-dimethylformamide (1 mL) was added 2-benzamidoacetic acid (30 mg, 168 μmol), (2-(1H-benzotriazol-1-yl)-1,1,3,3-tetramethyluronium hexafluorophosphate) (63 mg, 168 μmol) and N-ethyl-N-(propan-2-yl)propan-2-amine (64 mg, 503 μmol, 87 μL). The mixture was stirred at 20° C. for 1 h. The reaction mixture was purified directly by prep-HPLC (column: Waters Xbridge 150×2.5 mm 5 μm; mobile phase: [water (10 mM ammonium carbonate)-acetonitrile]; B %: 30%-60%, 12 min) to give N-(2-(4-(3-(1,3-dimethyl-1H-indazol-6-yl)-1,2,4-oxadiazol-5-yl)piperazin-1-yl)-2-oxoethyl)benzamide (29 mg, 64 μmol, 38%) as a white solid. $^1$H NMR (400 MHz, CDCl$_3$) δ 8.00 (s, 1H), 7.84 (d, J=7.7 Hz, 2H), 7.76-7.66 (m, 2H), 7.55-7.41 (m, 3H), 7.27-7.25 (m, 1H), 4.33 (d, J=3.7 Hz, 2H), 4.05 (s, 3H), 3.89-3.75 (m, 6H), 3.66 (br d, J=5.1 Hz, 2H), 2.57 (s, 3H); LCMS (ESI) m/z: [M+H]$^+$=460.3.

Example 103: (4-(3-(1,3-dimethyl-1H-indazol-6-yl)-1,2,4-oxadiazol-5-yl)piperazin-1-yl)(3-phenylisoxazol-5-yl)methanone

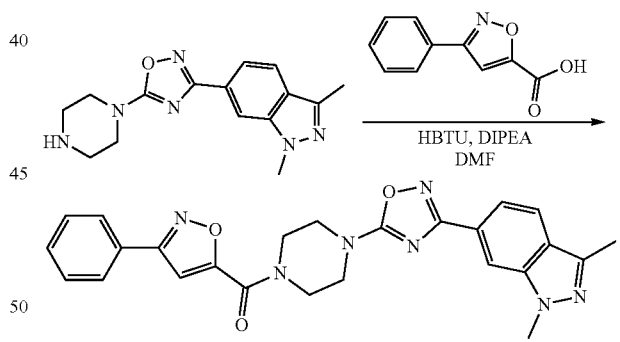

Step 1: Preparation of (4-(3-(1,3-dimethyl-1H-indazol-6-yl)-1,2,4-oxadiazol-5-yl)piperazin-1-yl)(3-phenylisoxazol-5-yl)methanone

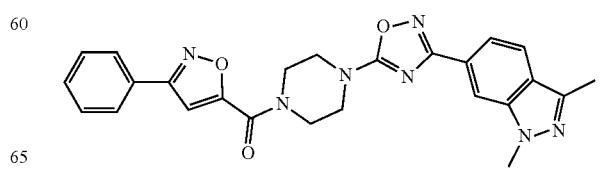

To a stirred solution of 3-(1,3-dimethyl-1H-indazol-6-yl)-5-(piperazin-1-yl)-1,2,4-oxadiazole (50 mg, 168 μmol) in N,N-dimethylformamide (1 mL) was added 3-phenylisoxazole-5-carboxylic acid (31 mg, 168 μmol), (2-(1H-benzotriazol-1-yl)-1,1,3,3-tetramethyluronium hexafluorophosphate) (63 mg, 168 μmol) and N-ethyl-N-(propan-2-yl)propan-2-amine (64 mg, 502.8 μmol, 87 μL). The mixture was stirred at 20° C. for 1 h. The reaction mixture was purified directly by prep-HPLC (column: Waters Xbridge 150×2.5 mm 5 μm; mobile phase: [water (10 mM ammonium carbonate)-acetonitrile]; B %: 35%-75%, 12 min) to give (4-(3-(1,3-dimethyl-1H-indazol-6-yl)-1,2,4-oxadiazol-5-yl)piperazin-1-yl)(3-phenylisoxazol-5-yl)methanone (26 mg, 56.9 μmol, 34%) as a white solid. $^1$H NMR (400 MHz, CDCl$_3$) δ 8.01 (s, 1H), 7.83 (td, J=2.8, 4.1 Hz, 2H), 7.76-7.73 (m, 1H), 7.71-7.67 (m, 1H), 7.51-7.47 (m, 3H), 7.18 (s, 1H), 4.05 (s, 3H), 4.03-3.93 (m, 4H), 3.89-3.84 (m, 4H), 2.57 (s, 3H); LCMS (ESI) m/z: [M+H]$^+$=470.3.

Example 104: N-(2-(4-(3-(benzo[c][1,2,5]thiadiazol-5-yl)-1,2,4-oxadiazol-5-yl)piperidin-1-yl)-2-oxoethyl)benzamide

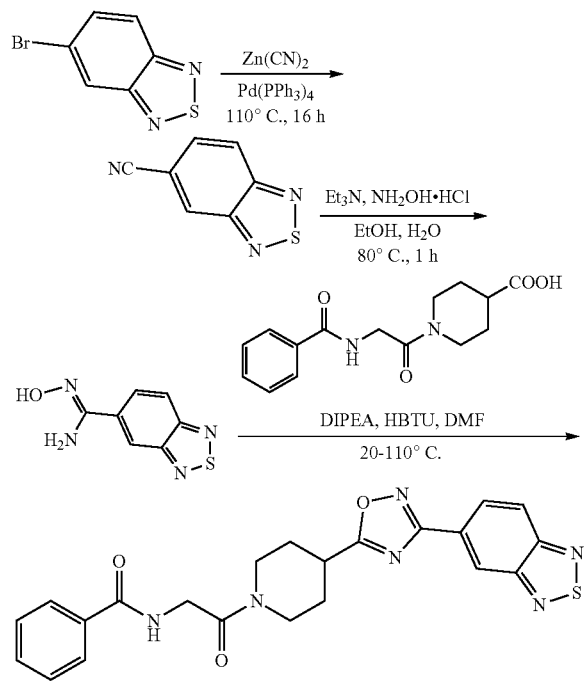

Step 1: Preparation of benzo[c][1,2,5]thiadiazole-5-carbonitrile

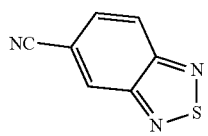 [SMILES: N#Cc1ccc2nsnc2c1]

To a stirred solution of 5-bromobenzo[c][1,2,5]thiadiazole (200 mg, 930 μmol) in N,N-dimethylformamide (2 mL) was added zinc cyanide (109 mg, 930 μmol, 59 μL) and tetrakis(triphenylphosphine)palladium(0) (107 mg, 93 μmol), the mixture was degassed with nitrogen three times. The mixture was heated at 110° C. for 16 h under nitrogen. After cooling to 20° C., water (5 mL) was added to the reaction, and the mixture extracted with ethyl acetate (20 mL×3). The combined organic phases were washed with saturated aqueous sodium chloride solution (10 mL), dried over anhydrous sodium sulfate, filtered and concentrated in vacuo to give crude product. The mixture was triturated with petroleum ether (20 mL) and dichloromethane (2 mL), then the mixture was filtered, and the filter cake dried in vacuo to give benzo[c][1,2,5]thiadiazole-5-carbonitrile (100 mg, 620 μmol, 67%) as a red solid. LCMS (ESI) m/z: [M+H]$^+$=162.0.

Step 2: Preparation of (Z)—N'-hydroxybenzo[c][1,2,5]thiadiazole-5-carboximidamide

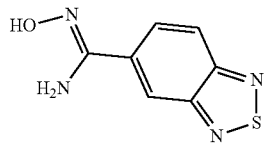 [SMILES: N/C(=N\O)c1ccc2nsnc2c1]

To a stirred solution of benzo[c][1,2,5]thiadiazole-5-carbonitrile (100 mg, 620 μmol) in ethanol (2 mL) was added hydroxylamine hydrochloride (86 mg, 1.24 mmol), triethylamine (125 mg, 1.24 mmol, 172 μL) and water (200 μL). The mixture was heated at 80° C. for 1 h. The reaction mixture was cooled and then concentrated under reduced pressure to remove ethanol. The residue was triturated with water (5 mL), filtered and the filter cake was dried under reduced pressure to give (Z)—N'-hydroxybenzo[c][1,2,5]thiadiazole-5-carboximidamide (70 mg, 360 μmol, 58%) as a brown solid. $^1$H NMR (400 MHz, DMSO-d6) δ 10.13 (s, 1H), 8.35 (d, J=0.9 Hz, 1H), 8.10 (dd, J=1.5, 9.3 Hz, 1H), 8.01-7.96 (m, 1H), 6.08 (s, 2H).

Step 3: Preparation of N-(2-(4-(3-(benzo[c][1,2,5]thiadiazol-5-yl)-1,2,4-oxadiazol-5-yl)piperidin-1-yl)-2-oxoethyl)benzamide

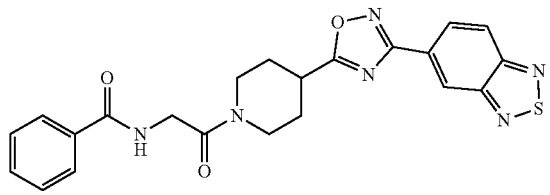 [SMILES: O=C(NCC(=O)N1CCC(c2nc(-c3ccc4nsnc4c3)no2)CC1)c1ccccc1]

To a stirred solution of 1-(2-benzamidoacetyl)piperidine-4-carboxylic acid (80 mg, 276 μmol) in N,N-dimethylformamide (2 mL) was added (Z)—N'-hydroxybenzo[c][1,2,5]thiadiazole-5-carboximidamide (53 mg, 276 μmol), (2-(1H-benzotriazol-1-yl)-1,1,3,3-tetramethyluronium hexafluorophosphate) (104 mg, 276 μmol) and N-ethyl-N-(propan-2-yl)propan-2-amine (106 mg, 827 μmol, 144 μL). The mixture was stirred at 20° C. for 1 h, then heated at 110° C. for 1 h. The reaction mixture was purified directly by prep-HPLC (column: Waters Xbridge 150×2.5 mm 5 μm; mobile phase: [water (10 mM ammonium carbonate)-acetonitrile]; B %: 45%-65%, 12 min) to give N-(2-(4-(3-(benzo[c][1,2,5]thiadiazol-5-yl)-1,2,4-oxadiazol-5-yl)piperidin-1-yl)-2-oxoethyl)benzamide (30 mg, 67 µmol, 24%) as a brown solid. ¹H NMR (400 MHz, DMSO-d6) δ 8.66 (t, J=1.2 Hz, 1H), 8.55 (t, J=5.7 Hz, 1H), 8.28-8.22 (m, 2H), 7.87-7.83 (m, 2H), 7.54-7.42 (m, 3H), 4.31 (br d, J=13.0 Hz, 1H), 4.16 (dd, J=1.5, 5.7 Hz, 2H), 3.98 (br d, J=13.5 Hz, 1H), 3.54-3.51 (m, 1H), 3.29 (br t, J=11.5 Hz, 1H), 2.93 (br t, J=11.2 Hz, 1H), 2.16 (br t, J=13.2 Hz, 2H), 1.90-1.78 (m, 1H), 1.73-1.62 (m, 1H); LCMS (ESI) m/z: [M+H]⁺=449.2.

Example 105: N-(2-(4-(3-(1,4-dimethylphthalazin-6-yl)-1,2,4-oxadiazol-5-yl)piperidin-1-yl)-2-oxoethyl)benzamide

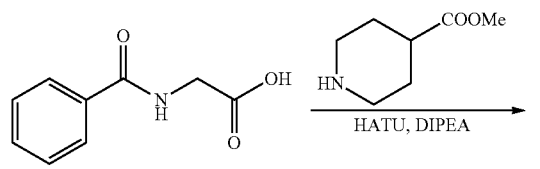

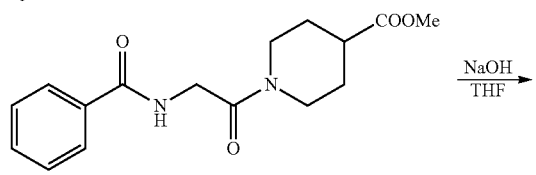

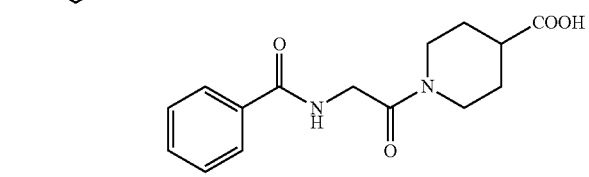

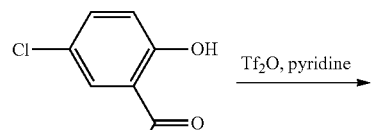

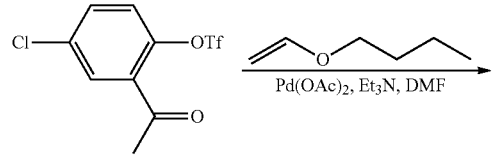

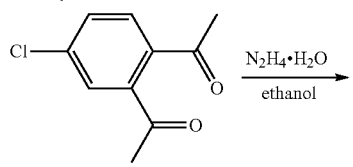

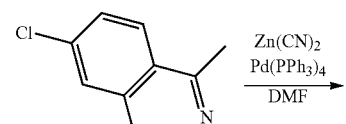

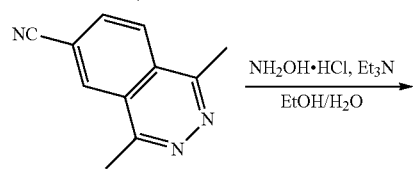

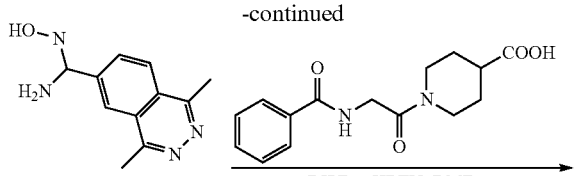

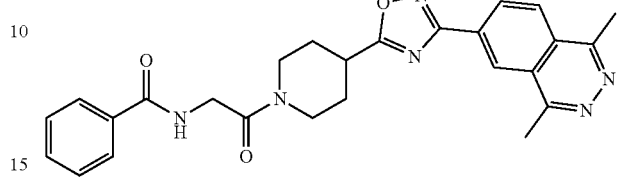

Step 1: Preparation of methyl 1-(2-benzamidoacetyl)piperidine-4-carboxylate

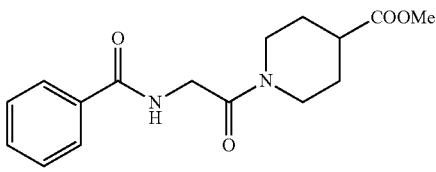 [SMILES: COC(=O)C1CCN(C(=O)CNC(=O)c2ccccc2)CC1]

To a stirred solution of 2-benzamidoacetic acid (5.0 g, 27.9 mmol) in N,N-dimethylformamide (50 mL) was added methyl piperidine-4-carboxylate (4.40 g, 30.7 mmol), 1-[bis(dimethylamino)methylene]-1H-1,2,3-triazolo[4,5-b]pyridinium 3-oxide hexafluorophosphate (10.6 g, 27.9 mmol) and N-ethyl-N-(propan-2-yl)propan-2-amine (10.8 g, 83.7 mmol, 14.6 mL). The mixture was stirred at 20° C. for 2 h, then quenched by addition of water (50 mL). The mixture was extracted with ethyl acetate (100 mL×3), then the combined organic phases were washed with saturated aqueous sodium chloride solution (40 mL), dried over anhydrous sodium sulfate, filtered and concentrated to give a residue that was purified by chromatography (silica, petroleumether:ethylacetate=5:1 to 1:1) to give methyl 1-(2-benzamidoacetyl)piperidine-4-carboxylate (9.17 g) as a yellow solid. ¹H NMR (400 MHz, Methanol-d4) δ 7.88-7.83 (m, 2H), 7.55-7.49 (m, 1H), 7.48-7.41 (m, 2H), 4.35-4.28 (m, 1H), 4.24 (d, J=5.3 Hz, 2H), 3.88 (d, J=14.1 Hz, 1H), 3.66 (s, 3H), 3.20 (d, J=2.2 Hz, 1H), 2.92-2.84 (m, 1H), 2.65 (tt, J=4.0, 10.8 Hz, 1H), 1.99-1.87 (m, 2H), 1.74-1.64 (m, 1H), 1.62-1.51 (m, 1H).

Step 2: Preparation of 1-(2-benzamidoacetyl)piperidine-4-carboxylic acid

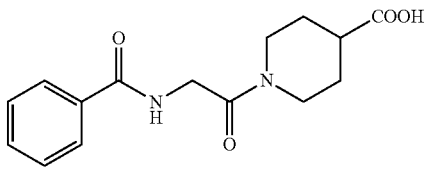 [SMILES: O=C(NCC(=O)N1CCC(C(=O)O)CC1)c1ccccc1]

To a stirred solution of methyl 1-(2-benzamidoacetyl)piperidine-4-carboxylate (9.17 g, 30.1 mmol) in tetrahydrofuran (90 mL) was added sodium hydroxide (2 M, 30.1 mL). The mixture was stirred at 20° C. for 2 h. The reaction mixture was concentrated under reduced pressure then acidified with concentrated hydrochloric acid until pH 1. The mixture was extracted with dichloromethane (80 mL×4). The organic phases were combined and then washed with saturated aqueous sodium chloride solution (30 mL), dried over anhydrous sodium sulfate, filtered and concentrated to give a crude residue (8.85 g). A portion of crude product (2.5 g) was purified by prep-HPLC (column: Daiso 250*50 mm, 10 μm; mobile phase: [water (0.1% TFA)-acetonitrile]; B %: 1%-30%, 20 min) to provide 1-(2-benzamidoacetyl)piperidine-4-carboxylic acid (0.95 g). The remaining crude product was used directly without purification. $^1$H NMR (400 MHz, Methanol-d4) δ 7.87-7.83 (m, 2H), 7.55-7.50 (m, 1H), 7.48-7.42 (m, 2H), 4.36 (td, J=3.2, 13.2 Hz, 1H), 4.25 (d, J=3.3 Hz, 2H), 3.94-3.86 (m, 1H), 3.22-3.14 (m, 1H), 2.89-2.80 (m, 1H), 2.46 (tt, J=3.9, 11.0 Hz, 1H), 2.00-1.87 (m, 2H), 1.74-1.52 (m, 2H).

Step 3: Preparation of 2-acetyl-4-chlorophenyl trifluoromethanesulfonate

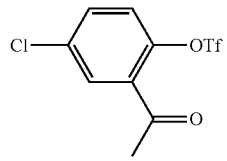

Triflic anhydride (9.92 g, 35.2 mmol, 5.80 mL) was added dropwise at 0° C. to a stirred solution of 1-(5-chloro-2-hydroxy-phenyl)ethanone (5.0 g, 29.3 mmol) in pyridine (50 mL) The reaction was warmed slowly to 15° C. and stirred for 15 h. The reaction solution was diluted with dichloromethane (100 mL), then poured into 1N aqueous hydrochloric acid (100 mL) at 0° C. and the phases separated. The organic phase was washed with 1N hydrochloric acid (50 mL×2), saturated aqueous sodium chloride solution (50 mL), dried over anhydrous sodium sulfate, filtered, and concentrated in vacuo to give a crude residue. Purification by chromatography (silica, petroleum ether:ethyl acetate from 100/1 to 30/1) gave 2-acetyl-4-chlorophenyl trifluoromethanesulfonate (7.50 g, 24.8 mmol, 85%) as a yellow liquid.

Step 4: Preparation of 1,1'-(4-chloro-1,2-phenylene)diethanone

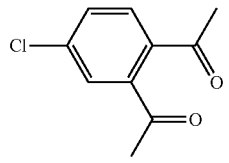

To a stirred solution of 2-acetyl-4-chlorophenyl trifluoromethanesulfonate (3.0 g, 9.91 mmol) in N,N-dimethylformamide (30 mL) was added 1-vinyloxybutane (4.96 g, 49.6 mmol, 6.36 mL), palladium(II) acetate(111 mg, 495.5 μmol), 3-diphenylphosphanylpropyl(diphenyl)phosphane (245 mg, 594.6 μmol) and TEA (1.20 g, 11.9 mmol, 1.65 mL), then the mixture was degassed with nitrogen three times. The mixture was heated at 80° C. for 16 h under nitrogen. After cooling to 20° C., 2M hydrochloric acid (20 mL) was added and the solution stirred at 20° C. for 2 h. Water (30 mL) was added and the mixture was extracted with ethyl acetate (80 mL×3). The combined organic phases were washed with saturated aqueous sodium chloride solution (20 mL), dried over anhydrous sodium sulfate, filtered and concentrated in vacuo to give a crude residue that was purified by chromatography (silica, petroleum ether:ethyl acetate=50:1 to 10:1) to give 1,1'-(4-chloro-1,2-phenylene)diethanone (800 mg, 4.07 mmol, 41%) as a red oil. $^1$H NMR (400 MHz, CDCl$_3$) δ 7.58-7.54 (m, 1H), 7.51-7.47 (m, 1H), 7.43 (t, J=1.9 Hz, 1H), 2.52 (d, J=2.0 Hz, 3H), 2.50 (d, J=2.0 Hz, 3H).

Step 5: Preparation of 6-chloro-1,4-dimethylphthalazine

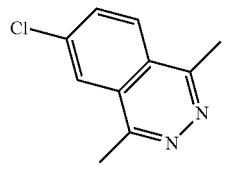

1,1'-(4-chloro-1,2-phenylene)diethanone (800 mg, 4.07 mmol) in ethanol (15 mL) was added to hydrazine hydrate (224 mg, 4.48 mmol, 217 μL) in ethanol (15 mL) at 0° C. over a period of 5 min under argon. The mixture was stirred at 20° C. for 18 h. The reaction mixture was concentrated under reduced pressure to ~15 mL, then extracted with dichloromethane (50 mL×3). The combined organic phases were washed water (20 mL×2), then the separated organic layer was washed saturated aqueous sodium chloride solution (20 mL), dried over anhydrous sodium sulfate, filtered and concentrated to give 6-chloro-1,4-dimethylphthalazine (662 mg, 3.44 mmol, 84%) as a red solid. $^1$H NMR (400 MHz, CDCl$_3$) δ 7.98-7.93 (m, 2H), 7.75 (dd, J=2.1, 8.8 Hz, 1H), 2.88 (d, J=5.1 Hz, 6H).

Step 6: Preparation of 1,4-dimethylphthalazine-6-carbonitrile

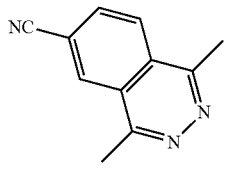

To a stirred solution of 6-chloro-1,4-dimethylphthalazine (640 mg, 3.32 mmol) in N,N-dimethylformamide (10 mL) was added zinc cyanide (390 mg, 3.32 mmol, 210 μL) and tetrakis(triphenylphosphine)palladium(0) (383 mg, 332 μmol) under nitrogen. The mixture was heated at 110° C. for 16 h, then cooled to 20° C. Water (15 mL) was added then the reaction mixture was extracted with ethyl acetate (40 mL×3). The combined organic phases were washed with saturated aqueous sodium chloride solution (20 mL), dried over anhydrous sodium sulfate, filtered and concentrated in vacuo to give a crude product. Trituration with petroleum ether (30 mL) and dichloromethane (5 mL) followed by filtration and drying the filter cake in vacuo gave 1,4-dimethylphthalazine-6-carbonitrile (400 mg, 2.18 mmol, 66%) as a brown solid. ¹H NMR (400 MHz, CDCl₃) δ 8.47 (s, 1H), 8.21 (d, J=8.5 Hz, 1H), 8.09 (dd, J=1.4, 8.5 Hz, 1H), 3.04 (s, 6H).

Step 7: Preparation of (Z)—N'-hydroxy-1,4-dimethylphthalazine-6-carboximidamide

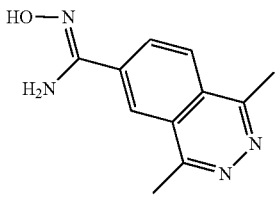 [SMILES: Cc1nnc(C)c2cc(/C(N)=N/O)ccc12]

To a stirred solution of 1,4-dimethylphthalazine-6-carbonitrile (380 mg, 2.07 mmol) in ethanol (1 mL) was added hydroxylamine hydrochloride (288 mg, 4.15 mmol), triethylamine (419 mg, 4.15 mmol, 575 µL) and water (100 µL). The mixture was heated at 80° C. for 1 h. The reaction mixture was cooled then concentrated under reduced pressure. The residue was triturated with water (5 mL), filtered and the filter cake was dried under reduced pressure to give (Z)—N'-hydroxy-1,4-dimethylphthalazine-6-carboximidamide (330 mg, 1.53 mmol, 74%) as a brown solid. ¹H NMR (400 MHz, DMSO-d6) δ 10.06 (s, 1H), 8.38 (d, J=1.3 Hz, 1H), 8.28 (dd, J=1.7, 8.7 Hz, 1H), 8.12 (d, J=8.8 Hz, 1H), 6.19 (s, 2H), 2.85 (d, J=17.0 Hz, 6H).

Step 8: Preparation of N-(2-(4-(3-(1,4-dimethylphthalazin-6-yl)-1,2,4-oxadiazol-5-yl)piperidin-1-yl)-2-oxoethyl)benzamide

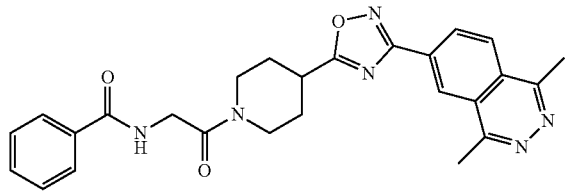 [SMILES: Cc1nnc(C)c2cc(-c3noc(C4CCN(C(=O)CNC(=O)c5ccccc5)CC4)n3)ccc12]

To a stirred solution of 1-(2-benzamidoacetyl)piperidine-4-carboxylic acid (100 mg, 344 µmol) in N,N-dimethylformamide (2 mL) was added N'-hydroxy-1,4-dimethyl-phthalazine-6-carboxamidine (74 mg, 344 µmol), (2-(1H-benzotriazol-1-yl)-1,1,3,3-tetramethyluronium hexafluorophosphate) (130 mg, 344 µmol) and N-ethyl-N-(propan-2-yl)propan-2-amine (133 mg, 1.03 mmol, 180 µL). The mixture was stirred at 20° C. for 1 h, then heated at 110° C. for 1 h. The reaction mixture was cooled, then purified by prep-HPLC (column: Waters Xbridge 150×2.5 mm 5 µm; mobile phase: [water (10 mM ammonium carbonate)-acetonitrile]; B %: 25%-55%, 12 min) to give N-(2-(4-(3-(1,4-dimethylphthalazin-6-yl)-1,2,4-oxadiazol-5-yl)piperidin-1-yl)-2-oxoethyl)benzamide (37 mg, 77 µmol, 22%) as a yellow solid. ¹H NMR (400 MHz, DMSO-d6) δ 8.71 (d, J=1.5 Hz, 1H), 8.59 (t, J=5.6 Hz, 1H), 8.54 (d, J=1.5, 8.6 Hz, 1H), 8.39 (d, J=8.6 Hz, 1H), 7.90-7.86 (m, 2H), 7.57-7.45 (m, 3H), 4.37 (br d, J=13.2 Hz, 1H), 4.25-4.13 (m, 2H), 4.02 (br d, J=13.5 Hz, 1H), 3.55 (tt, J=3.8, 11.1 Hz, 1H), 3.32-3.27 (m, 1H), 2.96 (s, 3H), 2.98-2.91 (m, 1H), 2.93 (s, 3H), 2.20 (br t, J=13.7 Hz, 2H), 1.95-1.82 (m, 1H), 1.77-1.65 (m, 1H); LCMS (ESI) m/z: [M+H]⁺=471.3.

Example 106: 2-(2-(4-(3-(4-ethoxy-3-methoxyphenyl)-1,2,4-oxadiazol-5-yl)piperidin-1-yl)-2-oxoethyl)isoindolin-1-one

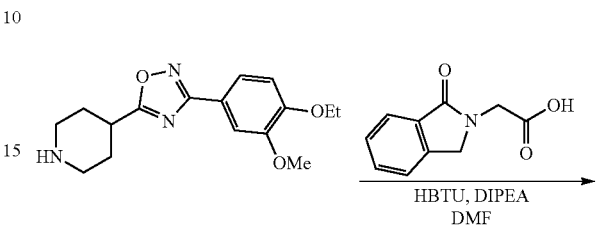

Step 1: Preparation of 2-(2-(4-(3-(4-ethoxy-3-methoxyphenyl)-1,2,4-oxadiazol-5-yl)piperidin-1-yl)-2-oxoethyl)isoindolin-1-one

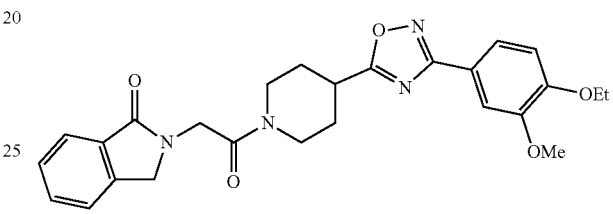

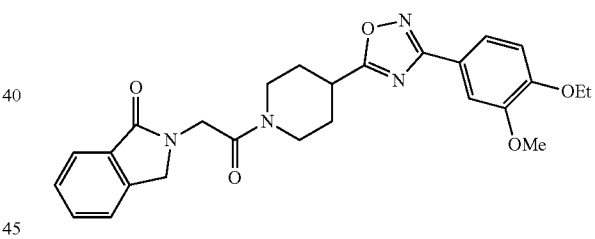

To a stirred solution of 3-(4-ethoxy-3-methoxyphenyl)-5-(piperidin-4-yl)-1,2,4-oxadiazole (50 mg, 165 µmol) in N,N-dimethylformamide (1 mL) was added 2-(1-oxoisoindolin-2-yl)acetic acid (31 mg, 165 µmol), (2-(1H-benzotriazol-1-yl)-1,1,3,3-tetramethyluronium hexafluorophosphate) (62 mg, 165 µmol) and N-ethyl-N-(propan-2-yl)propan-2-amine (63 mg, 494 µmol, 86 µL). The mixture was stirred at 20° C. for 1 h, then the reaction mixture was cooled then purified by prep-HPLC (column: Waters Xbridge 150×2.5 mm 5 µm; mobile phase: [water (10 mM ammonium carbonate)-acetonitrile]; B %: 30%-60%, 12 min) to give 2-(2-(4-(3-(4-ethoxy-3-methoxyphenyl)-1,2,4-oxadiazol-5-yl)piperidin-1-yl)-2-oxoethyl)isoindolin-1-one (41 mg, 86 µmol, 52%) as a gray solid. ¹H NMR (400 MHz, CDCl₃) δ 7.88 (d, J=8.2 Hz, 1H), 7.66 (dd, J=1.9, 8.3 Hz, 1H), 7.59-7.54 (m, 2H), 7.48 (t, J=6.4 Hz, 2H), 6.95 (d, J=8.4 Hz, 1H), 4.59 (d, J=3.4 Hz, 2H), 4.53-4.40 (m, 3H), 4.18 (q, J=7.0 Hz, 2H), 4.08 (br d, J=13.7 Hz, 1H), 3.96 (s, 3H), 3.43-3.24 (m, 2H), 3.11-3.02 (m, 1H), 2.28-2.15 (m, 2H), 2.05-1.90 (m, 2H), 1.51 (t, J=7.0 Hz, 3H); LCMS (ESI) m/z: [M+H]⁺=477.3.

Example 107: N-[2-[4-[3-(5-ethoxy-6-methoxy-2-pyridyl)-1,2,4-oxadiazol-5-yl]-1-piperidyl]-2-oxo-ethyl]benzamide

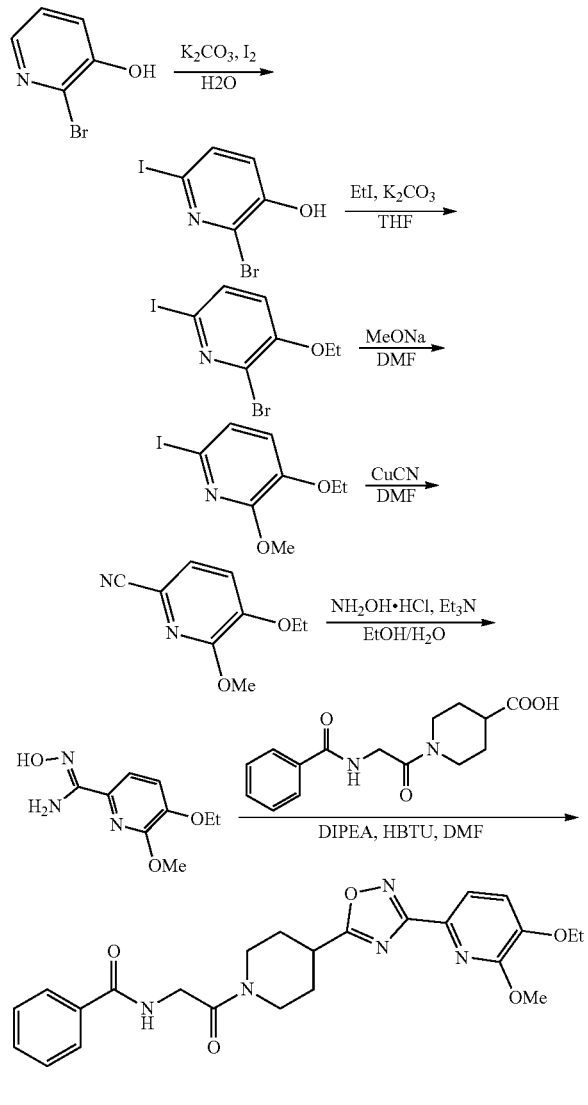

Step 1: 2-bromo-6-iodo-pyridin-3-ol

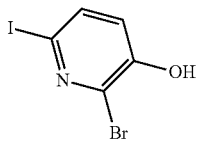

A mixture of 2-bromopyridin-3-ol (5.0 g, 28.7 mmol), iodine (8.02 g, 31.6 mmol, 6.37 mL), and potassium carbonate (7.94 g, 57.5 mmol) in water (66 mL) was degassed and purged with nitrogen 3 times, and then the mixture was stirred at 20° C. for 16 h under a nitrogen atmosphere. Excess iodine was quenched by addition of solid sodium bisulfite. The pH of the solution was adjusted to 5-6 using glacial acetic acid, and the solid formed was collected by filtration and dried in vacuum to give 2-bromo-6-iodo-pyridin-3-ol (10.0 g) that was used directly without further purification.

Step 2: 2-bromo-3-ethoxy-6-iodo-pyridine

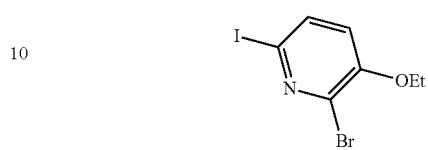

To a stirred solution of 2-bromo-6-iodo-pyridin-3-ol (10.0 g, 33.4 mmol) in tetrahydrofuran (200 mL) was added potassium carbonate (6.91 g, 50.0 mmol) and the mixture was stirred for 10 min at 0° C. in an ice bath. Iodoethane (6.24 g, 40.0 mmol, 3.20 mL) was added dropwise, then the reaction mixture was warmed to 40° C. After 16 h, the reaction mixture was quenched by addition of water (10 mL), and then extracted with ethyl acetate (10 mL×2). The combined organic phases were washed with saturated aqueous sodium chloride solution (10 mL), dried over anhydrous sodium sulfate, filtered and concentrated under reduced pressure to give 2-bromo-3-ethoxy-6-iodo-pyridine (7.50 g, 22.9 mmol, 69%) that was used directly without further purification.

Step 3: 3-ethoxy-6-iodo-2-methoxy-pyridine

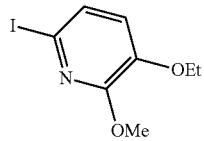 [SMILES: CCOc1ccc(I)nc1OC]

A mixture of 2-bromo-3-ethoxy-6-iodo-pyridine (7.0 g, 21.4 mmol) and sodium methoxide (1.73 g, 32.0 mmol) in N,N-dimethylformamide (3 mL) was degassed and purged with nitrogen 3 times, and then the mixture was heated at 100° C. for 16 h under a nitrogen atmosphere. The reaction mixture was quenched by addition of water (20 mL), then extracted with ethyl acetate (20 mL×3). The organic layer phases were combined and then washed with saturated aqueous sodium chloride solution (10 mL), dried over anhydrous sodium sulfate, filtered and concentrated under reduced pressure to give 3-ethoxy-6-iodo-2-methoxy-pyridine (5.0 g, 17.9 mmol). This was used directly without further purification.

Step 4: 5-ethoxy-6-methoxy-pyridine-2-carbonitrile

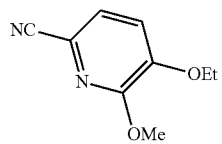 [SMILES: CCOc1ccc(C#N)nc1OC]

A mixture of 3-ethoxy-6-iodo-2-methoxy-pyridine (2.50 g, 8.96 mmol) and cooper(I) cyanide (962 mg, 10.75 mmol, 2.35 mL) in N,N-dimethylformamide (10 mL) was degassed and purged with nitrogen 3 times, and then the mixture was heated at 100° C. for 16 h under a nitrogen atmosphere. The reaction mixture was quenched by addition of water (20 mL), then extracted with ethyl acetate (20 mL×3). The organic extracts were combined, washed with saturated aqueous sodium chloride solution (10 mL), dried over anhydrous sodium sulfate, filtered and concentrated under reduced pressure to give 5-ethoxy-6-methoxy-pyridine-2-carbonitrile (1.40 g). This was used directly without further purification.

Step 5: 5-ethoxy-6-methoxy-pyridine-2-carbonitrile

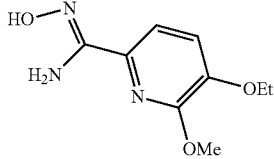 [SMILES: CCOc1ccc(/C(N)=N/O)nc1OC]

A mixture of 5-ethoxy-6-methoxy-pyridine-2-carbonitrile (1.0 g, 5.61 mmol), hydroxylamine hydrochloride (857 mg, 12.34 mmol) and triethylamine (1.25 g, 12.34 mmol, 1.71 mL) in ethanol (10 mL) was heated at 75° C. for 16 h under a nitrogen atmosphere. The reaction mixture was cooled, diluted with water (10 mL), and filtered. The filter cake was dried in vacuo to give 5-ethoxy-N'-hydroxy-6-methoxy-pyridine-2-carboxamidine (950 mg, 4.50 mmol, 80%) as a yellow solid. $^1$H NMR (400 MHz, CHLOROFORM-d) δ=7.40 (d, J=8.2 Hz, 1H), 6.99 (d, J=8.2 Hz, 1H), 5.45 (br s, 2H), 4.05 (q, J=6.9 Hz, 2H), 3.98 (s, 3H), 1.41 (t, J=7.0 Hz, 3H).

Step 6: N-[2-[4-[3-(5-ethoxy-6-methoxy-2-pyridyl)-1,2,4-oxadiazol-5-yl]-1-piperidyl]-2-oxo-ethyl]benzamide

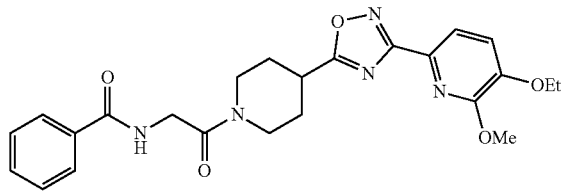 [SMILES: CCOc1ccc(-c2noc(C3CCN(C(=O)CNC(=O)c4ccccc4)CC3)n2)nc1OC]

To a stirred solution of 1-(2-benzamidoacetyl)piperidine-4-carboxylic acid (100 mg, 344 μmol) in N,N-dimethylformamide (2 mL) was added 5-ethoxy-N'-hydroxy-6-methoxy-pyridine-2-carboxamidine (72 mg, 344 μmol), (2-(1H-benzotriazol-1-yl)-1,1,3,3-tetramethyluronium hexafluorophosphate) (156 mg, 413 μmol) and N-ethyl-N-(propan-2-yl)propan-2-amine (133 mg, 1.03 mmol, 180 μL). The mixture was stirred at 20° C. for 1 h, then heated at 110° C. for 1 h. The crude product was purified by prep-HPLC (column: Waters Xbridge 150×25 5 μm; mobile phase: [water (10 mM ammonium carbonate)-acetonitrile]; B %: 30%-60%, 12 min) to give N-[2-[4-[3-(5-ethoxy-6-methoxy-2-pyridyl)-1,2,4-oxadiazol-5-yl]-1-piperidyl]-2-oxo-ethyl]benzamide (37 mg, 79.9 μmol, 23%) as a yellow solid. $^1$H NMR (400 MHz, CHLOROFORM-d) δ=7.91-7.85 (m, 2H), 7.70 (d, J=8.0 Hz, 1H), 7.57-7.52 (m, 1H), 7.51-7.44 (m, 2H), 7.36 (br s, 1H), 7.13 (d, J=8.2 Hz, 1H), 4.57-4.48 (m, 1H), 4.32 (d, J=3.9 Hz, 2H), 4.23-4.12 (m, 5H), 4.06-3.90 (m, 1H), 3.42-3.32 (m, 2H), 3.20-3.11 (m, 1H), 2.32-2.20 (m, 2H), 2.08-1.95 (m, 2H), 1.54 (t, J=7.0 Hz, 3H); LCMS(ESI) m/z: [M+H]$^+$=466.3.

Example 108: 4-[4-[3-(5-ethoxy-6-methoxy-2-pyridyl)-1,2,4-oxadiazol-5-yl]piperidine-1-carbonyl]-1-phenyl-pyrrolidin-2-one

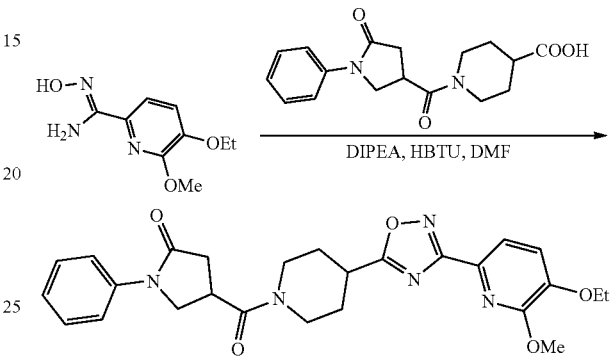

Step 1: 4-[4-[3-(5-ethoxy-6-methoxy-2-pyridyl)-1,2,4-oxadiazol-5-yl]piperidine-1-carbonyl]-1-phenyl-pyrrolidin-2-one

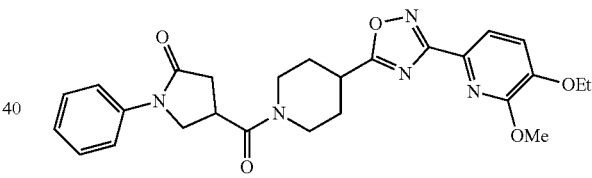

To a stirred solution of 5-ethoxy-N'-hydroxy-6-methoxy-pyridine-2-carboxamidine (66 mg, 316 μmol) in N,N-dimethylformamide (2 mL) was added 1-(5-oxo-1-phenyl-pyrrolidine-3-carbonyl)piperidine-4-carboxylic acid (100 mg, 316 μmol), (2-(1H-benzotriazol-1-yl)-1,1,3,3-tetramethyluronium hexafluorophosphate) (143 mg, 379 μmol) and N-ethyl-N-(propan-2-yl)propan-2-amine (122 mg, 948 μmol, 165 μL). The mixture was stirred at 20° C. for 1 h, then heated at 110° C. for 1 h. The mixture was cooled and the crude product was purified by prep-HPLC (column: Waters Xbridge 150×25 5 μm; mobile phase: [water (10 mM ammonium carbonate)-acetonitrile]; B %: 30%-70%, 12 min) to give 4-[4-[3-(5-ethoxy-6-methoxy-2-pyridyl)-1,2,4-oxadiazol-5-yl]piperidine-1-carbonyl]-1-phenyl-pyrrolidin-2-one (47 mg, 96 μmol, 3%) as a yellow solid. $^1$H NMR (400 MHz, CHLOROFORM-d) δ=7.71 (dd, J=4.6, 8.0 Hz, 1H), 7.62 (dd, J=1.1, 8.7 Hz, 2H), 7.43-7.38 (m, 2H), 7.22-7.17 (m, 1H), 7.13 (d, J=7.8 Hz, 1H), 4.63-4.48 (m, 1H), 4.34 (t, J=7.9 Hz, 1H), 4.22-4.15 (m, 5H), 4.03-3.93 (m, 2H), 3.60 (m, 1H), 3.46-3.33 (m, 2H), 3.15-2.95 (m, 2H), 2.91-2.82 (m, 1H), 2.27 (m, 2H), 2.08-1.94 (m, 2H), 1.54 (t, J=7.0 Hz, 3H); LCMS(ESI) m/z: [M+H]$^+$=492.3.

Example 109: N-[2-[4-[3-(2,2-difluoro-1,3-benzodioxol-5-yl)-1,2,4-oxadiazol-5-yl]-1-piperidyl]-2-oxo-ethyl]benzamide

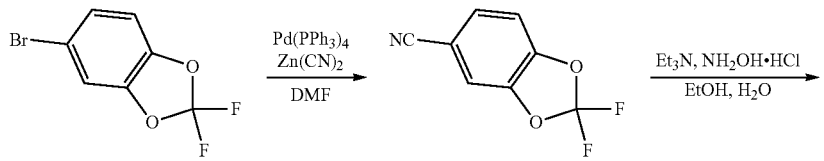

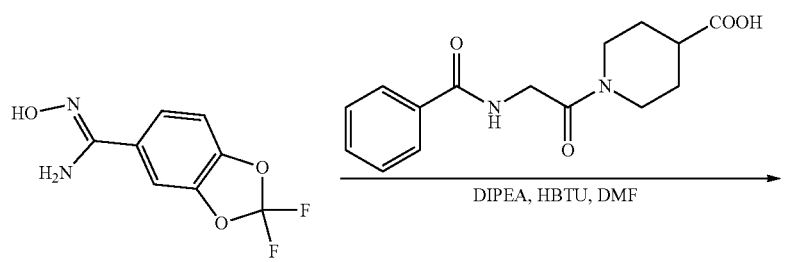

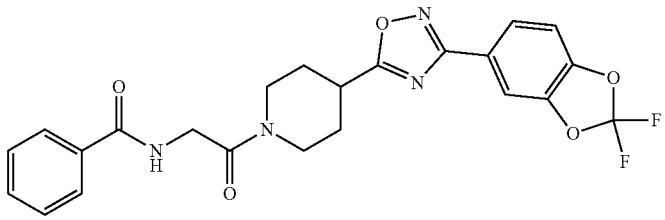

Step 1: 2,2-difluoro-1,3-benzodioxole-5-carbonitrile

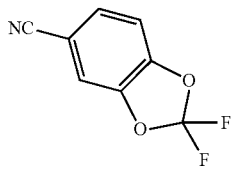 [SMILES: N#Cc1ccc2c(c1)OC(F)(F)O2]

A mixture of 5-bromo-2,2-difluoro-1,3-benzodioxole (500 mg, 2.11 mmol), zinc cyanide (247 mg, 2.11 mmol, 133 µL) and tetrakis(triphenylphosphine)palladium(0) (243 mg, 211 µmol) in N,N-dimethylformamide (4 mL) was degassed and purged with nitrogen 3 times, and then the mixture was heated at 100° C. for 16 h under a nitrogen atmosphere. The reaction mixture was cooled, diluted with water (5 mL), and extracted with ethyl acetate (10 mL×2). The combined organic phases were washed with saturated aqueous sodium chloride solution (10 mL), dried over anhydrous sodium sulfate, filtered and concentrated under reduced pressure to give 2,2-difluoro-1,3-benzodioxole-5-carbonitrile (300 mg, 1.64 mmol, 78%) as a solid. $^1$H NMR (400 MHz, CHLOROFORM-d) δ=7.38 (dd, J=1.5, 8.3 Hz, 1H), 7.27 (d, J=1.5 Hz, 1H), 7.08 (d, J=8.3 Hz, 1H).

Step 2: 2,2-difluoro-N'-hydroxy-1,3-benzodioxole-5-carboxamidine

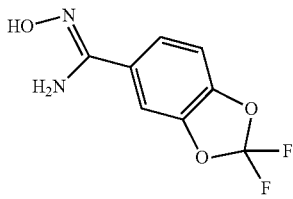 [SMILES: N/C(=N\O)c1ccc2c(c1)OC(F)(F)O2]

A mixture of 2,2-difluoro-1,3-benzodioxole-5-carbonitrile (300 mg, 1.64 mmol), triethylamine (331 mg, 3.28 mmol, 454 µL) and hydroxylamine hydrochloride (227 mg, 3.28 mmol) in water (500 µL) and ethanol (5 mL) was heated at 70° C. for 16 h. The reaction mixture was cooled, diluted with water (10 mL) and filtered. The collected solid was dried in vacuo to give 2,2-difluoro-N'-hydroxy-1,3-benzodioxole-5-carboxamidine (210 mg) as a solid.

Step 3: N-[2-[4-[3-(2,2-difluoro-1,3-benzodioxol-5-yl)-1,2,4-oxadiazol-5-yl]-1-piperidyl]-2-oxo-ethyl]benzamide

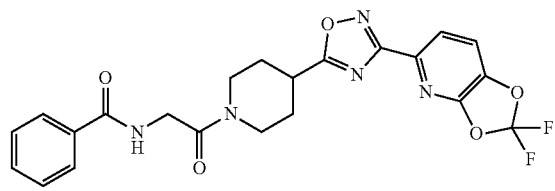 [SMILES: O=C(NCC(=O)N1CCC(c2nc(-c3ccc4c(n3)OC(F)(F)O4)no2)CC1)c1ccccc1]

A mixture of 2,2-difluoro-N'-hydroxy-1,3-benzodioxole-5-carboxamidine (74 mg, 344 μmol), 1-(2-benzamidoacetyl)piperidine-4-carboxylic acid (100 mg, 344 μmol), N-ethyl-N-(propan-2-yl)propan-2-amine (133 mg, 1.03 mmol, 180 μL) and (2-(1H-benzotriazol-1-yl)-1,1,3,3-tetramethyluronium hexafluorophosphate) (156 mg, 413 μmol) in N,N-dimethylformamide (2 mL) was stirred at 20° C. for 1 h under a nitrogen atmosphere. The mixture was heated at 120° C. for 1 h, then cooled and purified by prep-HPLC (column: Waters Xbridge 150×25 5 μm; mobile phase: [water (10 mM ammonium carbonate)-acetonitrile]; B %: 40%-70%, 12 min) to give N-[2-[4-[3-(2,2-difluoro-1,3-benzodioxol-5-yl)-1,2,4-oxadiazol-5-yl]-1-piperidyl]-2-oxo-ethyl]benzamide (58 mg, 124 μmol, 36%) as a white solid. $^1$H NMR (400 MHz, CHLOROFORM-d) δ=7.85-7.76 (m, 3H), 7.72 (d, J=1.5 Hz, 1H), 7.48-7.42 (m, 1H), 7.41-7.35 (m, 2H), 7.26 (br s, 1H), 7.10 (d, J=8.4 Hz, 1H), 4.53-4.37 (m, 1H), 4.23 (d, J=4.0 Hz, 2H), 3.84 (br d, J=13.9 Hz, 1H), 3.35-3.21 (m, 2H), 3.12-3.02 (m, 1H), 2.26-2.10 (m, 2H), 1.98-1.85 (m, 2H); LCMS (ESI) m/z: [M+H]$^+$: 471.2.

Example 110: N-(2-(4-(3-(4-ethyl-3,4-dihydro-2H-benzo[b][1,4]oxazin-7-yl)-1,2,4-oxadiazol-5-yl)piperidin-1-yl)-2-oxoethyl)benzamide

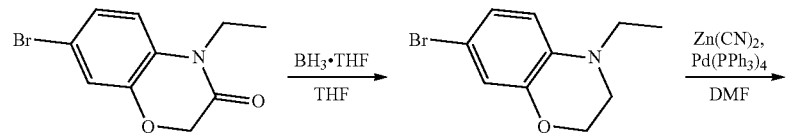

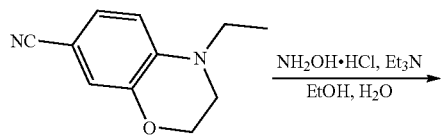

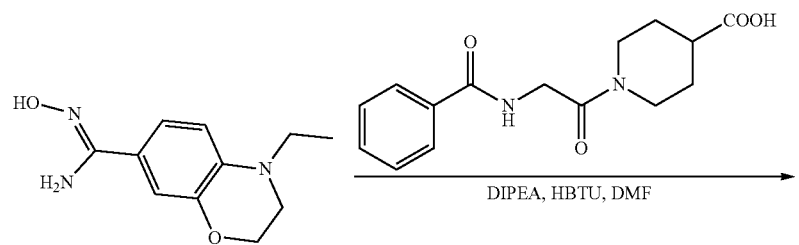

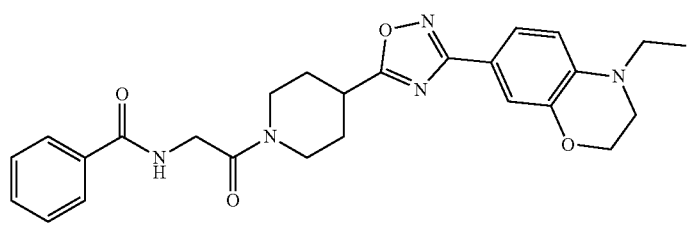

Step 1: Preparation of 7-bromo-4-ethyl-3,4-dihydro-2H-benzo[b][1,4]oxazine

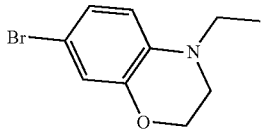

To a stirred solution of 7-bromo-4-ethyl-2H-benzo[b][1,4]oxazin-3(4H)-one (900 mg, 3.51 mmol) in tetrahydrofuran (10 mL) was added a solution of borane in tetrahydrofuran (1 M, 12.28 mL), and the mixture was stirred 20° C. for 1 h, then heated at 80° C. for 2 h. The reaction mixture was cooled then quenched by addition of methanol (15 mL). The mixture was concentrated under reduced pressure, then diluted with water (20 mL), extracted with ethyl acetate (60 mL×2), and the combined organic phases washed with saturated aqueous sodium chloride solution (20 mL), dried over anhydrous sodium sulfate, filtered and concentrated to give 7-bromo-4-ethyl-3,4-dihydro-2H-benzo[b][1,4]oxazine (750 mg, 3.10 mmol, 88%) as a yellow oil. $^1$H NMR (400 MHz, CDCl$_3$) δ 6.86-6.80 (m, 2H), 6.45 (d, J=8.3 Hz, 1H), 4.19-4.13 (m, 2H), 3.28-3.18 (m, 4H), 1.06 (t, J=7.1 Hz, 3H).

Step 2: Preparation of 4-ethyl-3,4-dihydro-2H-benzo[b][1,4]oxazine-7-carbonitrile

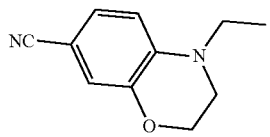

To a stirred solution of 7-bromo-4-ethyl-3,4-dihydro-2H-benzo[b][1,4]oxazine (80 mg, 330 μmol) in N,N-dimethylformamide (1 mL) was added zinc cyanide (38 mg, 330 μmol) and tetrakis(triphenylphosphine)palladium(0) (38 mg, 33 μmol), then the mixture was degassed with nitrogen three times. The mixture was heated at 110° C. for 16 h under nitrogen, then cooled to 20° C., and water (3 mL) added. The reaction mixture was extracted with ethyl acetate (20 mL×2). The combined organic phases were washed with saturated aqueous sodium chloride solution (5 mL), dried over anhydrous sodium sulfate, filtered and then concentrated in vacuo to give a crude residue that was purified by prep-TLC (petroleumether:ethylacetate=2:1) to give 4-ethyl-3,4-dihydro-2H-benzo[b][1,4]oxazine-7-carbonitrile (60 mg, 319 μmol, 96%) as a brown solid. $^1$H NMR (400 MHz, CDCl$_3$) δ 7.10 (td, J=1.4, 8.5 Hz, 1H), 7.00-6.92 (m, 1H), 6.59 (d, J=8.4 Hz, 1H), 4.20 (dt, J=0.9, 4.5 Hz, 2H), 3.42-3.33 (m, 4H), 1.16 (dt, J=0.9, 7.2 Hz, 3H).

Step 3: Preparation of (Z)-4-ethyl-N'-hydroxy-3,4-dihydro-2H-benzo[b][1,4]oxazine-7-carboximidamide

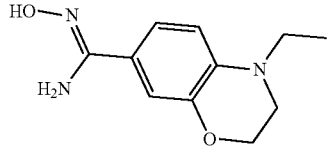 [SMILES: CCN1CCOc2cc(/C(N)=N/O)ccc21]

To a stirred solution of 4-ethyl-3,4-dihydro-2H-benzo[b][1,4]oxazine-7-carbonitrile (60 mg, 319 μmol) in ethanol (1 mL) was added hydroxylamine hydrochloride (44 mg, 638 μmol), triethylamine (64 mg, 638 μmol, 88 μL) and water (100 μL). The mixture was stirred at 80° C. for 5 h. The reaction mixture was cooled, concentrated under reduced pressure, and then diluted with water (5 mL). The mixture was extracted with ethyl acetate (20 mL×3). The combined organic phases were washed with saturated aqueous sodium chloride solution (10 mL), dried over anhydrous sodium sulfate, filtered, and concentrated in vacuo to give crude (Z)-4-ethyl-N'-hydroxy-3,4-dihydro-2H-benzo[b][1,4]oxazine-7-carboximidamide (60 mg, 271 μmol, 85%) as a white solid.

Step 4: Preparation of N-(2-(4-(3-(4-ethyl-3,4-dihydro-2H-benzo[b][1,4]oxazin-7-yl)-1,2,4-oxadiazol-5-yl)piperidin-1-yl)-2-oxoethyl)benzamide

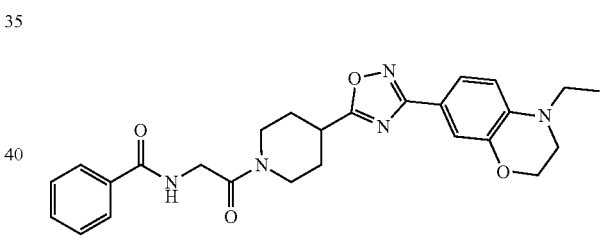

To a stirred solution of 1-(2-benzamidoacetyl)piperidine-4-carboxylic acid (60 mg, 207 μmol) in N,N-dimethylformamide (1 mL) was added (Z)-4-ethyl-N'-hydroxy-3,4-dihydro-2H-benzo[b][1,4]oxazine-7-carboximidamide (45 mg, 207 μmol), (2-(1H-benzotriazol-1-yl)-1,1,3,3-tetramethyluronium hexafluorophosphate) (78 mg, 207 μmol) and N-ethyl-N-(propan-2-yl)propan-2-amine (80 mg, 620 μmol, 108 μL). The mixture was stirred at 20° C. for 1 h, then heated at 110° C. for 1 h. The reaction mixture was purified directly by prep-HPLC (column: Luna C18 150×2.5 mm 5 μm; mobile phase: [water (0.225% TFA)-acetonitrile]; B %: 40%-65%, 16 min) to give N-(2-(4-(3-(4-ethyl-3,4-dihydro-2H-benzo[b][1,4]oxazin-7-yl)-1,2,4-oxadiazol-5-yl)piperidin-1-yl)-2-oxoethyl)benzamide (17 mg, 35.8 μmol, 17%) as a brown solid. $^1$H NMR (400 MHz, CDCl$_3$) δ 7.89-7.84 (m, 2H), 7.58-7.43 (m, 5H), 7.35 (br s, 1H), 6.72 (d, J=8.5 Hz, 1H), 4.45 (br d, J=13.8 Hz, 1H), 4.33-4.24 (m, 4H), 3.89 (br d, J=14.1 Hz, 1H), 3.45-3.25 (m, 6H), 3.18 (br t, J=10.4 Hz, 1H), 2.28-2.18 (m, 2H), 2.07-1.92 (m, 2H), 1.20 (t, J=7.2 Hz, 3H); LCMS (ESI) m/z: [M+H]$^+$=476.3.

Example 111: N-(2-(4-(3-(4-ethyl-3-oxo-3,4-dihydro-2H-benzo[b][1,4]oxazin-7-yl)-1,2,4-oxadiazol-5-yl)piperidin-1-yl)-2-oxoethyl)benzamide 7-bromo-4-ethyl-2H-benzo[b][1,4]oxazin-3(4H)-one (2.06 g, 8.04 mmol, 92%) as a yellow solid. $^1$H NMR (400 MHz, CDCl$_3$) δ 7.11-7.05 (m, 2H), 6.78 (d, J=8.9 Hz, 1H), 4.52 (s, 2H), 3.89 (q, J=7.2 Hz, 2H), 1.20 (t, J=7.2 Hz, 3H).

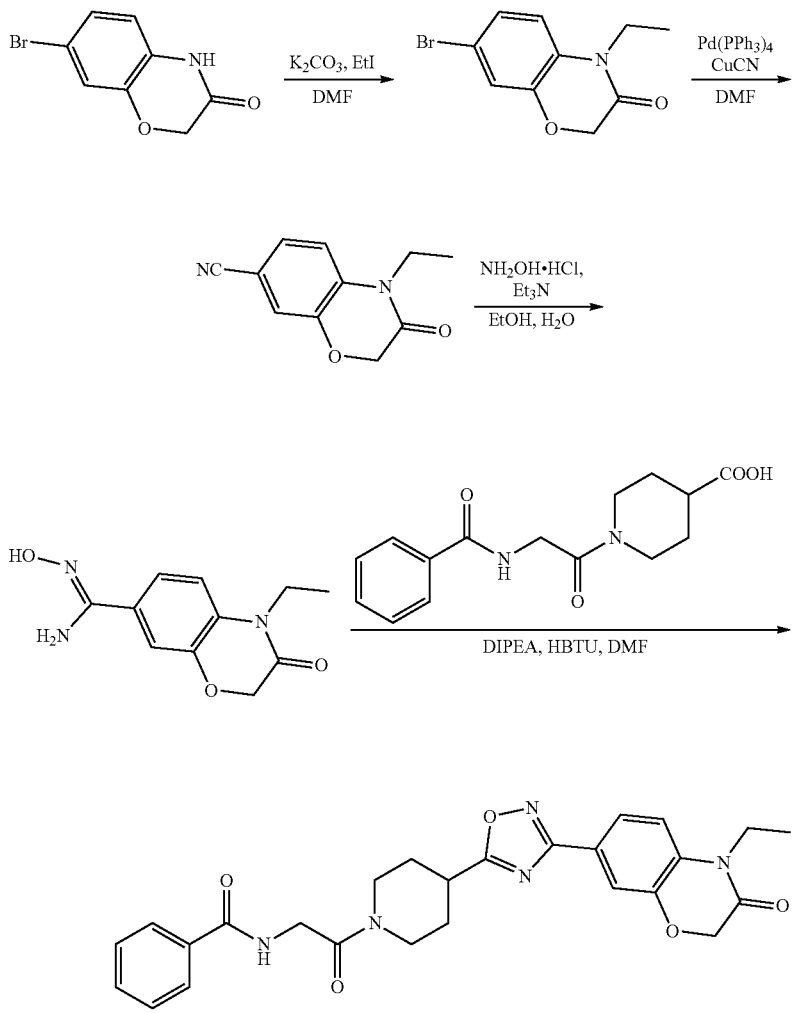

Step 1: Preparation of 7-bromo-4-ethyl-2H-benzo[b][1,4]oxazin-3(4H)-one

Step 2: Preparation of 4-ethyl-3-oxo-3,4-dihydro-2H-benzo[b][1,4]oxazine-7-carbonitrile

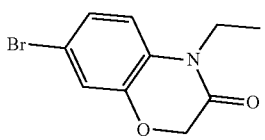

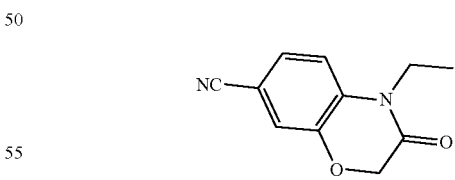

To a stirred solution of 7-bromo-4H-1,4-benzoxazin-3-one (2.0 g, 8.77 mmol) in N,N-dimethylformamide (20 mL) was added iodoethane (1.64 g, 10.52 mmol, 841 μL) and potassium carbonate (3.64 g, 26.3 mmol) at 0° C. The reaction was warmed at 40° C. for 2 h. The reaction mixture was cooled then quenched by addition of water (30 mL), and then the mixture was extracted with ethyl acetate (60 mL×3). The combined organic phases were washed with saturated aqueous sodium chloride solution (30 mL), dried over anhydrous sodium sulfate, filtered and concentrated to give To a stirred solution of 7-bromo-4-ethyl-2H-benzo[b][1,4]oxazin-3(4H)-one (800 mg, 3.12 mmol) in N,N-dimethylformamide (10 mL) was added copper(I) cyanide (559 mg, 6.25 mmol, 1.36 mL) and tetrakis(triphenylphosphine)palladium(0) (360 mg, 312 μmol). The mixture was degassed with nitrogen, then heated at 110° C. for 16 h under nitrogen. The reaction mixture was cooled to 20° C., then water (15 mL) was added and the reaction mixture extracted with ethyl acetate (40 mL×3). The combined organic phases were washed with saturated aqueous sodium chloride solution (20 mL), dried over anhydrous sodium sulfate, filtered and concentrated in vacuo to give a crude residue that was purified by chromatography (silica, petroleumether:ethylacetate=1:0 to 5:1) to give 4-ethyl-3-oxo-3,4-dihydro-2H-benzo[b][1,4]oxazine-7-carbonitrile (70 mg, 346 μmol, 11%) as a white solid. $^1$H NMR (400 MHz, CDCl$_3$) δ 7.38 (dd, J=1.9, 8.4 Hz, 1H), 7.30-7.29 (m, 1H), 7.08 (d, J=8.3 Hz, 1H), 4.68 (s, 2H), 4.04 (q, J=7.2 Hz, 2H), 1.32 (t, J=7.2 Hz, 3H).

Step 3: Preparation of (Z)-4-ethyl-N'-hydroxy-3-oxo-3,4-dihydro-2H-benzo[b][1,4]oxazine-7-carboximidamide

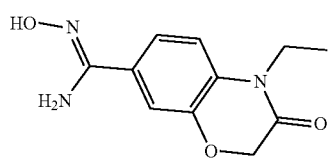 [SMILES: CCN1C(=O)COc2cc(/C(N)=N/O)ccc21]

To a stirred solution of 4-ethyl-3-oxo-3,4-dihydro-2H-benzo[b][1,4]oxazine-7-carbonitrile (70 mg, 346 μmol) in ethanol (1 mL) was added hydroxylamine hydrochloride (48 mg, 692 μmol), triethylamine (70 mg, 692 μmol, 95 μL) and water (100 μL). The mixture was heated at 80° C. for 5 h. The reaction mixture was cooled then concentrated under reduced pressure. The residue was diluted with water (5 mL), then the reaction mixture was extracted with ethyl acetate (20 mL×3). The combined organic phases were washed with saturated aqueous sodium chloride solution (10 mL), dried over anhydrous sodium sulfate, filtered and concentrated in vacuo to give (Z)-4-ethyl-N'-hydroxy-3-oxo-3,4-dihydro-2H-benzo[b][1,4]oxazine-7-carboximidamide (60 mg, 255 μmol, 74%) as a white solid.

Step 4: Preparation of N-(2-(4-(3-(4-ethyl-3-oxo-3,4-dihydro-2H-benzo[b][1,4]oxazin-7-yl)-1,2,4-oxadiazol-5-yl)piperidin-1-yl)-2-oxoethyl)benzamide

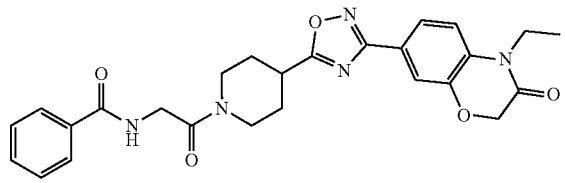 [SMILES: CCN1C(=O)COc2cc(-c3noc(C4CCN(C(=O)CNC(=O)c5ccccc5)CC4)n3)ccc21]

To a stirred solution of 1-(2-benzamidoacetyl)piperidine-4-carboxylic acid (60 mg, 206.7 μmol) in N,N-dimethylformamide (1 mL) was added (Z)-4-ethyl-N'-hydroxy-3-oxo-3,4-dihydro-2H-benzo[b][1,4]oxazine-7-carboximidamide (48 mg, 206.7 μmol), (2-(1H-benzotriazol-1-yl)-1,1,3,3-tetramethyluronium hexafluorophosphate) (78 mg, 206.7 μmol) and N-ethyl-N-(propan-2-yl)propan-2-amine (80 mg, 620 μmol, 108 μL). The mixture was stirred at 20° C. for 1 h, then heated at 110° C. for 1 h. The reaction mixture was cooled then purified by prep-HPLC (column: Luna C18 100×30 5 μm; mobile phase: [water (0.1% TFA)-methanol]; B %: 38%-68%, 12 min) to give N-(2-(4-(3-(4-ethyl-3-oxo-3,4-dihydro-2H-benzo[b][1,4]oxazin-7-yl)-1,2,4-oxadiazol-5-yl)piperidin-1-yl)-2-oxoethyl)benzamide (6 mg, 13 μmol, 6%) as a white solid. $^1$H NMR (400 MHz, CDCl$_3$) δ 7.86 (d, J=7.2 Hz, 2H), 7.77 (dd, J=1.8, 8.5 Hz, 1H), 7.71 (d, J=1.8 Hz, 1H), 7.56-7.43 (m, 3H), 7.34 (br s, 1H), 7.10 (d, J=8.4 Hz, 1H), 4.66 (s, 2H), 4.50 (br d, J=13.7 Hz, 1H), 4.31 (d, J=3.8 Hz, 2H), 4.04 (q, J=7.1 Hz, 2H), 3.92 (br d, J=14.7 Hz, 1H), 3.40-3.29 (m, 2H), 3.17 (br t, J=10.7 Hz, 1H), 2.31-2.19 (m, 2H), 2.00 (br t, J=13.4 Hz, 2H), 1.32 (t, J=7.2 Hz, 3H); LCMS (ESI) m/z: [M+H]$^+$=490.2.

Example 112: (1-(3-(4-ethoxy-3-methoxyphenyl)-1,2,4-oxadiazol-5-yl)piperidin-4-yl)(2-phenylmorpholino)methanone

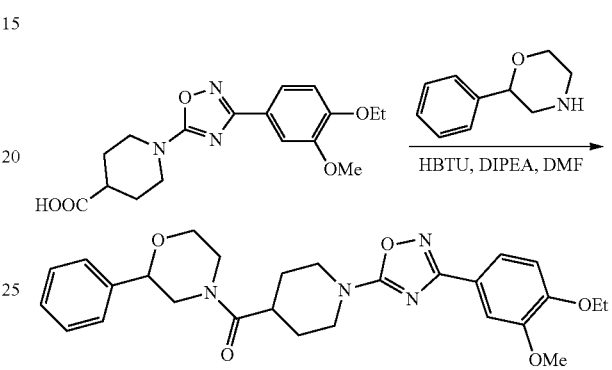

Step 1: Preparation of (1-(3-(4-ethoxy-3-methoxyphenyl)-1,2,4-oxadiazol-5-yl)piperidin-4-yl)(2-phenylmorpholino)methanone

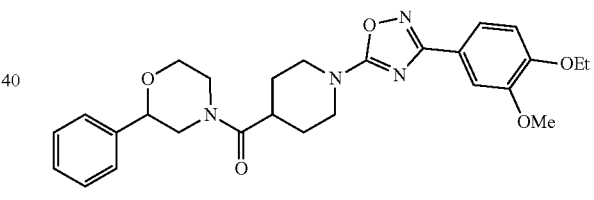

To a stirred solution of 1-(3-(4-ethoxy-3-methoxyphenyl)-1,2,4-oxadiazol-5-yl)piperidine-4-carboxylic acid (80 mg, 230 μmol) in N,N-dimethylformamide (1 mL) was added 2-phenylmorpholine (37 mg, 230 μmol), (2-(1H-benzotriazol-1-yl)-1,1,3,3-tetramethyluronium hexafluorophosphate) (87 mg, 230 μmol) and N-ethyl-N-(propan-2-yl)propan-2-amine (89 mg, 690.93 μmol, 120 μL). The mixture was stirred at 20° C. for 1 h. The reaction mixture was purified by prep-HPLC (column: Waters Xbridge 150×2.5 mm 5 μm; mobile phase: [water (10 mM ammonium carbonate)-acetonitrile]; B %: 30%-70%, 12 min) to give (1-(3-(4-ethoxy-3-methoxyphenyl)-1,2,4-oxadiazol-5-yl)piperidin-4-yl)(2-phenylmorpholino)methanone (94 mg, 191.6 μmol, 83%) as a yellow oil. $^1$H NMR (400 MHz, Methanol-d4) δ 7.55-7.41 (m, 3H), 7.40-7.26 (m, 4H), 6.99 (d, J=8.4 Hz, 1H), 4.51-4.36 (m, 2H), 4.26-4.13 (m, 2H), 4.12-3.98 (m, 4H), 3.86 (s, 3H), 3.75-3.58 (m, 1H), 3.46-3.30 (m, 1H), 3.28-3.17 (m, 2H), 3.04 (br s, 1H), 2.95-2.64 (m, 1H), 1.93-1.68 (m, 4H), 1.40 (t, J=6.9 Hz, 3H); LCMS (ESI) m/z: [M+H]$^+$=493.3.

Example 113: (1-(3-(4-ethoxy-3-methoxyphenyl)-1,2,4-oxadiazol-5-yl)piperidin-4-yl)(4-methyl-3-phenylpiperazin-1-yl)methanone

Example 114: N-(2-(4-(3-(1,3-dimethyl-1H-pyrazolo[4,3-c]pyridin-6-yl)-1,2,4-oxadiazol-5-yl)piperidin-1-yl)-2-oxoethyl)benzamide

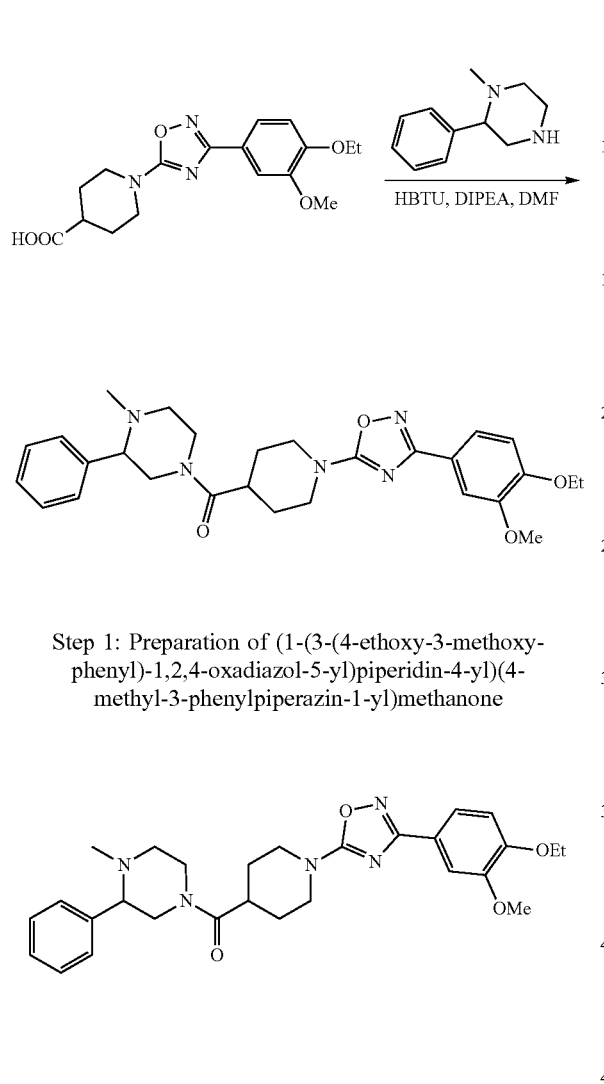

Step 1: Preparation of (1-(3-(4-ethoxy-3-methoxyphenyl)-1,2,4-oxadiazol-5-yl)piperidin-4-yl)(4-methyl-3-phenylpiperazin-1-yl)methanone To a stirred solution of 1-(3-(4-ethoxy-3-methoxyphenyl)-1,2,4-oxadiazol-5-yl)piperidine-4-carboxylic acid (70 mg, 201.5 μmol) in N,N-dimethylformamide (1 mL) was added 1-methyl-2-phenylpiperazine dihydrochloride (50 mg, 201.5 μmol,), (2-(1H-benzotriazol-1-yl)-1,1,3,3-tetramethyluronium hexafluorophosphate) (76 mg, 201.5 μmol) and N-ethyl-N-(propan-2-yl)propan-2-amine (78 mg, 604.6 μmol, 105 μL). The mixture was stirred at 20° C. for 1 h. The reaction mixture was purified directly by prep-HPLC (column: Waters Xbridge 150×2.5 mm 5 μm; mobile phase: [water (10 mM ammonium carbonate)-acetonitrile]; B %: 38%-68%, 12 min) to give (1-(3-(4-ethoxy-3-methoxyphenyl)-1,2,4-oxadiazol-5-yl)piperidin-4-yl)(4-methyl-3-phenylpiperazin-1-yl)methanone (60 mg, 117 μmol, 58%) as a yellow solid. $^1$H NMR (400 MHz, CDCl$_3$) δ 7.57 (br d, J=7.9 Hz, 1H), 7.50 (br s, 1H), 7.45-7.29 (m, 5H), 6.91 (d, J=8.3 Hz, 1H), 4.68-4.48 (m, 1H), 4.35-4.11 (m, 4H), 3.94 (s, 3H), 3.92-3.69 (m, 1H), 3.52-3.10 (m, 3H), 3.09-2.60 (m, 4H), 2.33-2.17 (m, 1H), 2.07 (br d, J=4.9 Hz, 3H), 2.04-1.73 (m, 4H), 1.49 (t, J=7.0 Hz, 3H); LCMS (ESI) m/z: [M+H]$^+$=506.4.

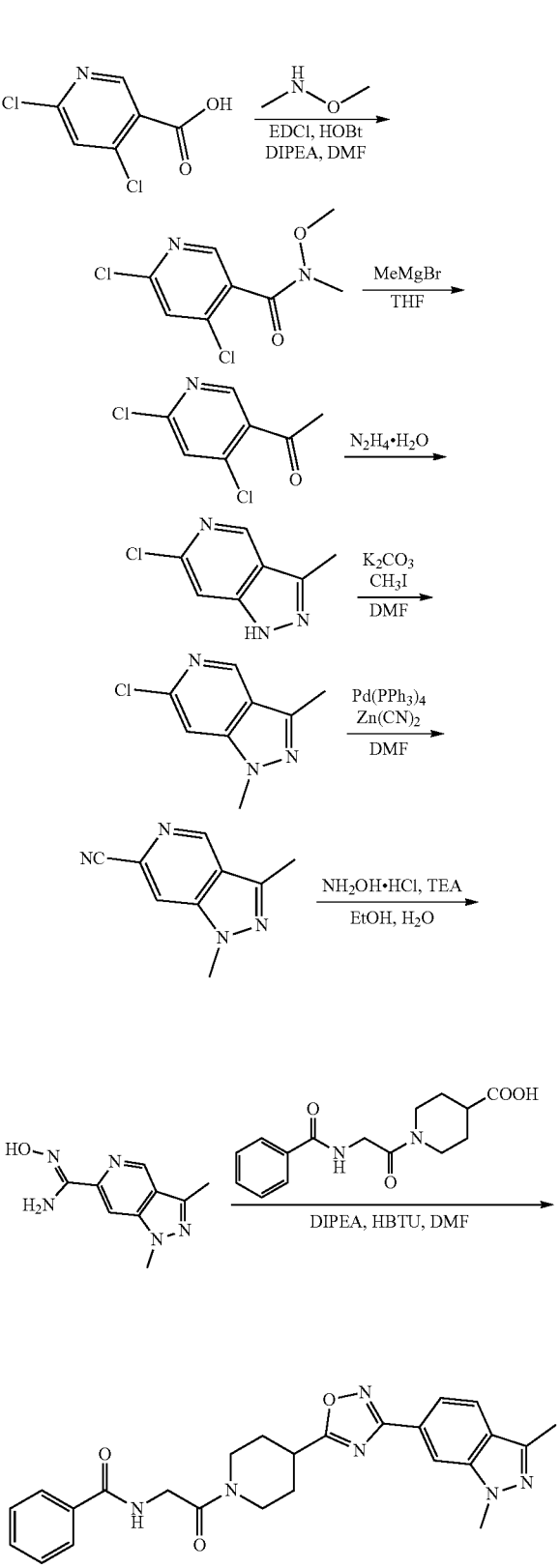

Step 1: Preparation of
4,6-dichloro-N-methoxy-N-methylnicotinamide

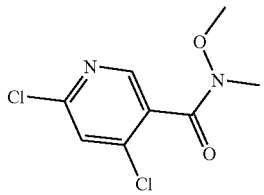

To a stirred solution of 4,6-dichloronicotinic acid (1.0 g, 5.21 mmol) in N,N-dimethylformamide (15 mL) was added N,O-dimethylhydroxylamine (1.02 g, 10.42 mmol), hydroxybenzotriazole (1.41 g, 10.4 mmol), 1-ethyl-3-(3-dimethylaminopropyl)carbodiimide (2.0 g, 10.4 mmol) and N-ethyl-N-(propan-2-yl)propan-2-amine (2.02 g, 15.6 mmol, 2.73 mL). The mixture was stirred at 20° C. for 48 h. The reaction mixture was quenched by addition of water (20 mL) then the mixture was extracted with ethyl acetate (50 mL×3). The combined organic phases were washed with saturated aqueous sodium chloride solution (20 mL), dried over anhydrous sodium sulfate, filtered and concentrated to give a crude residue that was purified by chromatography (silica, petroleumether:ethylacetate=50:1 to 5:1 to give 4,6-dichloro-N-methoxy-N-methylnicotinamide (660 mg, 2.81 mmol, 54%) as a yellow oil. $^1$H NMR (400 MHz, CDCl$_3$) δ 8.37 (s, 1H), 7.45 (s, 1H), 3.51 (br s, 3H), 3.40 (br s, 3H).

Step 2: Preparation of
1-(4,6-dichloropyridin-3-yl)ethanone

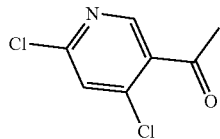

To a stirred solution of 4,6-dichloro-N-methoxy-N-methylnicotinamide (600 mg, 2.55 mmol) in tetrahydrofuran (10 mL) was added methylmagnesium bromide (3 M, 2.16 mL) at 0° C., then the mixture was stirred at 0° C. for 2 h. After addition of saturated aqueous ammonium chloride (20 mL), the mixture was concentrated to ~20 mL and the residue that remained was extracted with dichloromethane (40 mL×3). The combined organic layers were washed with saturated aqueous sodium chloride solution (20 mL), dried over anhydrous sodium sulfate, filtered and concentrated under reduced pressure to give 1-(4,6-dichloropyridin-3-yl)ethanone (430 mg, 2.26 mmol, 89%) as a yellow oil. $^1$H NMR (400 MHz, CDCl$_3$) δ 8.64 (s, 1H), 7.48 (s, 1H), 2.70 (s, 3H).

Step 3: Preparation of 6-chloro-3-methyl-1H-pyrazolo[4,3-c]pyridine

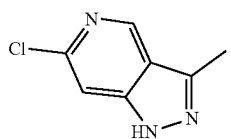

1-(4,6-dichloropyridin-3-yl)ethanone (430 mg, 2.26 mmol) in hydrazine hydrate (10 mL) was stirred at 20° C. for 4 h. The reaction mixture was diluted with water (10 mL), then the mixture was extracted with dichloromethane (40 mL×3). The combined organic phases were washed with water (10 mL×2), then saturated aqueous sodium chloride solution (20 mL), then dried over anhydrous sodium sulfate, filtered and concentrated to give crude 6-chloro-3-methyl-1H-pyrazolo[4,3-c]pyridine (370 mg, 2.21 mmol, 98%) as a yellow solid. $^1$H NMR (400 MHz, DMSO-d6) δ 13.23 (br s, 1H), 8.95 (br s, 1H), 7.59 (s, 1H), 2.61 (br s, 3H).

Step 4: Preparation of 6-chloro-1,3-dimethyl-1H-pyrazolo[4,3-c]pyridine

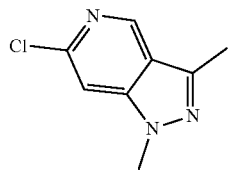

To a stirred solution of 6-chloro-3-methyl-1H-pyrazolo[4,3-c]pyridine (330 mg, 1.97 mmol) in N,N-dimethylformamide (5 mL) was added iodomethane (558 mg, 3.94 mmol, 245 μL) and potassium carbonate (816 mg, 5.91 mmol) at 0° C. The reaction was heated at 60° C. for 2 h. The reaction mixture was cooled then quenched with water (10 mL), and the mixture was extracted with ethyl acetate (20 mL×3). The combined organic phases were washed with saturated aqueous sodium chloride solution (10 mL), dried over anhydrous sodium sulfate, filtered and concentrated to give a crude residue that was purified by prep-TLC (Petroleum ether:ethyl acetate=1:1) to give 6-chloro-1,3-dimethyl-1H-pyrazolo[4,3-c]pyridine (120 mg, 661 μmol, 34%) as a yellow solid. $^1$H NMR (400 MHz, CDCl$_3$) δ 8.77 (s, 1H), 7.29-7.27 (m, 1H), 3.98 (s, 3H), 2.63 (s, 3H).

Step 5: Preparation of 1,3-dimethyl-1H-pyrazolo[4,3-c]pyridine-6-carbonitrile

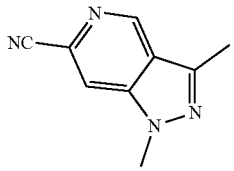

To a stirred solution of 6-chloro-1,3-dimethyl-1H-pyrazolo[4,3-c]pyridine (100 mg, 551 μmol) in N,N-dimethylformamide (2 mL) was added zinc cyanide (64 mg, 551 μmol) and tetrakis(triphenylphosphine)palladium(0) (63 mg, 55 μmol), then the mixture was degassed with nitrogen three times. The mixture was stirred at 110° C. for 16 h under nitrogen. The reaction was cooled to 20° C., then water (3 mL) was added and the mixture was extracted with ethyl acetate (20 mL×2). The combined organic phases were washed with saturated aqueous sodium chloride solution (5 mL), dried over anhydrous sodium sulfate, filtered and concentrated in vacuo to give a crude residue that was purified by prep-TLC (silica, petroleumether:ethylacetate=1:1). 1,3-dimethyl-1H-pyrazolo[4,3-c]pyridine-6-carbonitrile (50 mg, 290 μmol, 53%) as a white solid. LCMS (ESI) m/z: [M+H]⁺=173.1.

Step 6: Preparation of (Z)—N'-hydroxy-1,3-dimethyl-1H-pyrazolo[4,3-c]pyridine-6-carboximidamide

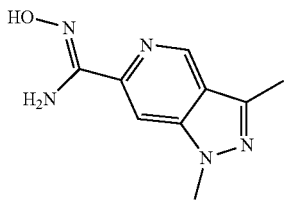

To a stirred solution of 1,3-dimethyl-1H-pyrazolo[4,3-c]pyridine-6-carbonitrile (50 mg, 290 μmol) in ethanol (1 mL) was added hydroxylamine hydrochloride (40 mg, 580.76 μmol), triethylamine (58 mg, 580.76 μmol, 80 μL) and water (100 μL). The mixture was stirred at 80° C. for 2 h. The reaction mixture was concentrated under reduced pressure then diluted with water (5 mL). The reaction mixture was extracted with ethyl acetate (20 mL×3). The combined organic phases were washed with saturated aqueous sodium chloride solution (50 mL), dried over anhydrous sodium sulfate, filtered and concentrated in vacuo to give crude (Z)—N'-hydroxy-1,3-dimethyl-1H-pyrazolo[4,3-c]pyridine-6-carboximidamide (60 mg) as a white solid. LCMS (ESI) m/z: [M+H]⁺=206.2.

Step 7: Preparation of N-(2-(4-(3-(1,3-dimethyl-1H-pyrazolo[4,3-c]pyridin-6-yl)-1,2,4-oxadiazol-5-yl)piperidin-1-yl)-2-oxoethyl)benzamide

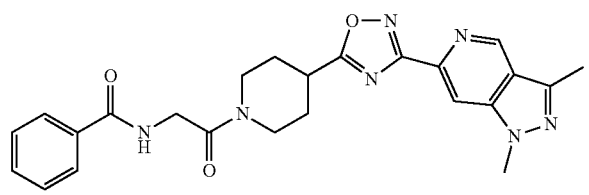 [SMILES: Cc1nn(C)c2cc(-c3noc(C4CCN(C(=O)CNC(=O)c5ccccc5)CC4)n3)ncc12]

To a stirred solution of 1-(2-benzamidoacetyl)piperidine-4-carboxylic acid (35 mg, 120.6 μmol) in N,N-dimethylformamide (1 mL) was added (Z)—N'-hydroxy-1,3-dimethyl-1H-pyrazolo[4,3-c]pyridine-6-carboximidamide (24 mg, 120.6 μmol), (2-(1H-benzotriazol-1-yl)-1,1,3,3-tetramethyluronium hexafluorophosphate) (45 mg, 120.6 μmol) and N-ethyl-N-(propan-2-yl)propan-2-amine (46 mg, 361.7 μmol, 63 μL). The mixture was stirred at 20° C. for 1 h, then heated at 110° C. for 1 h. The reaction mixture was cooled then purified by prep-HPLC (column: Waters Xbridge 150× 2.5 mm 5 μm; mobile phase: [water (10 mM ammonium carbonate)-acetonitrile]; B %: 20%-50%, 12 min) to give N-(2-(4-(3-(1,3-dimethyl-1H-pyrazolo[4,3-c]pyridin-6-yl)-1,2,4-oxadiazol-5-yl)piperidin-1-yl)-2-oxoethyl)benzamide (5 mg, 11 μmol, 9%) as a yellow solid. ¹H NMR (400 MHz, CDCl₃) δ 9.13 (d, J=1.1 Hz, 1H), 8.12 (d, J=1.0 Hz, 1H), 7.89-7.84 (m, 2H), 7.56-7.43 (m, 3H), 7.34 (br s, 1H), 4.55 (br d, J=13.7 Hz, 1H), 4.32 (d, J=3.9 Hz, 2H), 4.09 (s, 3H), 3.94 (br d, J=13.8 Hz, 1H), 3.44-3.32 (m, 2H), 3.14 (br t, J=10.9 Hz, 1H), 2.68 (s, 3H), 2.37-2.24 (m, 2H), 2.16-1.96 (m, 2H); LCMS (ESI) m/z: [M+H]⁺=460.1.

Example 115: N-[2-[4-[3-(1,3-dimethylpyrazolo[3,4-b]pyridin-6-yl)-1,2,4-oxadiazol-5-yl]-1-piperidyl]-2-oxo-ethyl]benzamide

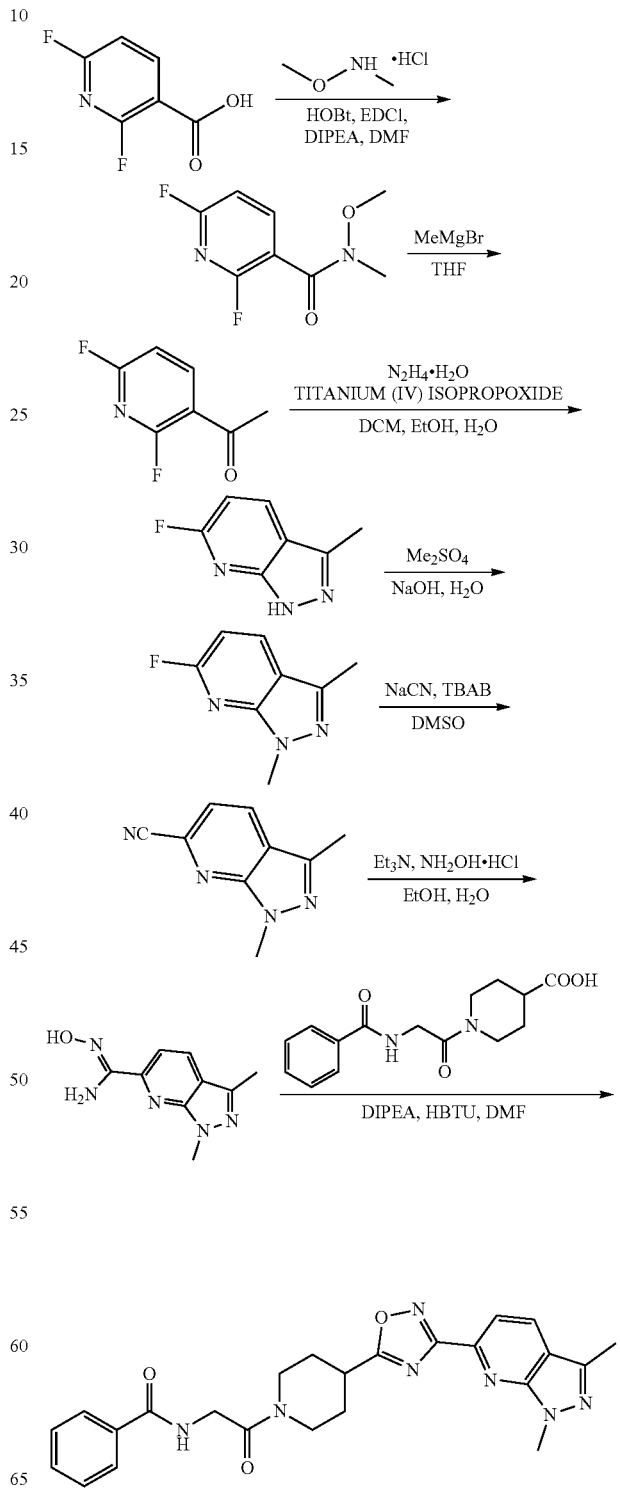

Step 1: 2,6-difluoro-N-methoxy-N-methyl-pyridine-3-carboxamide

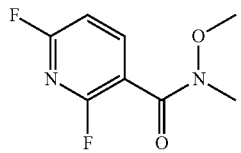

A mixture of 2,6-difluoropyridine-3-carboxylic acid (3.0 g, 18.9 mmol), N-methoxymethanamine hydrochloride (12.9 g, 132.0 mmol) hydroxybenzotriazole (10.2 g, 75.4 mmol), diisopropylethylamine (3.70 g, 28.7 mmol, 5.01 mL) and 1-ethyl-3-(3-dimethylaminopropyl)carbodiimide (7.20 g, 37.5 mmol) in N,N-dimethylformamide (50 mL) was stirred at 20° C. for 16 h under a nitrogen atmosphere. The reaction mixture was diluted with water (30 mL) and extracted with dichloromethane (20 mL×3). The combined organic phases were washed with saturated aqueous sodium chloride solution (20 mL×3), dried over anhydrous sodium sulfate, filtered and concentrated under reduced pressure to give 2,6-difluoro-N-methoxy-N-methyl-pyridine-3-carboxamide (2.80 g, 13.9 mmol, 73%) as a solid.

Step 2: 1-(2,6-difluoro-3-pyridyl)ethanone

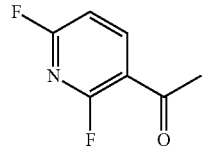

To a stirred solution of 2,6-difluoro-N-methoxy-N-methyl-pyridine-3-carboxamide (3.0 g, 14.8 mmol) in tetrahydrofuran (60 mL) was added dropwise methylmagnesium bromide (1.77 g, 14.84 mmol) at 0° C. The resulting mixture was stirred at 0° C. for 2 h, and then quenched by water at 0° C. The mixture was diluted with ethyl acetate (60 mL) and extracted with ethyl acetate (50 mL×2). The combined organic phases were washed with saturated aqueous sodium chloride solution (25 mL×2), dried over anhydrous sodium sulfate, filtered and concentrated under reduced pressure to give a residue. Purification by chromatography (silica, petroleum ether/ethyl acetate=2:1) gave 1-(2,6-difluoro-3-pyridyl)ethanone (2.20 g, 14.0 mmol, 94%) as a white solid.

Step 3: 3-ethoxy-6-iodo-2-methoxy-pyridine

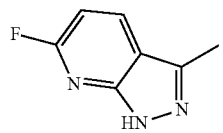

A solution of 1-(2,6-difluoro-3-pyridyl)ethanone (1.50 g, 9.55 mmol) in dichloromethane (55 mL) was treated with titanium(IV) isopropoxide (10.37 g, 36.48 mmol, 10.80 mL) at room temperature. The resulting mixture was stirred for 15 min, then hydrazine hydrate (2.06 g, 41.16 mmol, 2 mL) was added. Stirring continued for an additional 1.5 h, then water (5 mL) was added, and the resulting thick mixture was stirred vigorously for 20 min. The reaction mixture was filtered, and the solids were washed with dichloromethane (10 mL). The filtrate was concentrated in vacuo to provide the crude hydrazone intermediate as an oil. The crude hydrazine was dissolved in ethanol (15 mL), and the solution was heated at 80° C. for 24 h. The reaction mixture was quenched by addition of water (10 mL) at 20° C., and then extracted with dichloromethane (10 mL×3). The combined organic phases were washed with saturated aqueous sodium chloride solution (20 mL), dried over anhydrous sodium sulfate, filtered and concentrated under reduced pressure to give 6-fluoro-3-methyl-1H-pyrazolo[3,4-b]pyridine (1.20 g) which was used directly without further purification.

Step 4: 6-fluoro-1,3-dimethyl-pyrazolo[3,4-b]pyridine

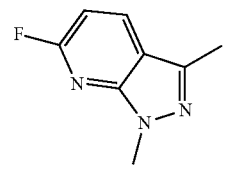

A mixture of 6-fluoro-3-methyl-1H-pyrazolo[3,4-b]pyridine (1.20 g, 7.94 mmol), dimethylsulfate (1.20 g, 9.53 mmol, 903 μL), sodium hydroxide (952 mg, 23.82 mmol) in water (30 mL) was degassed and purged with nitrogen 3 times, and then the mixture was stirred at 70° C. for 2 h under a nitrogen atmosphere. The reaction mixture was cooled, extracted with ethyl acetate (50 mL×2), then the combined organic phases were washed with saturated aqueous sodium chloride solution (20 mL×2), dried over anhydrous sodium sulfate, filtered and concentrated under reduced pressure to give a residue. The residue was purified by chromatography (silica, petroleum ether/ethyl acetate=2:1) to give 6-fluoro-1,3-dimethyl-pyrazolo[3,4-b]pyridine (400 mg, 2.42 mmol, 3%) as a yellow solid.

Step 5: 1,3-dimethylpyrazolo[3,4-b]pyridine-6-carbonitrile

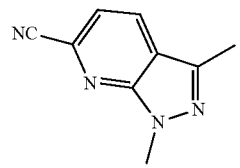

A mixture of 6-fluoro-1,3-dimethyl-pyrazolo[3,4-b]pyridine (350 mg, 2.12 mmol), tetra-n-butylammonium bromide (1.37 g, 4.24 mmol) and sodium cyanide (727 mg, 14.84 mmol) in dimethylsulfoxide (10 mL) was degassed and purged with nitrogen 3 times, and then the mixture was heated at 150° C. for 2 h under a nitrogen atmosphere. The reaction mixture was cooled then extracted with ethyl acetate (5 mL×2). The combined organic phases were washed with saturated aqueous sodium chloride solution (10 mL), dried over anhydrous sodium sulfate, then filtered and concentrated under reduced pressure to give a residue. The residue was purified by chromatography (silica, petroleum ether/ethyl acetate=2:1) to give 1,3-dimethylpyrazolo[3,4-b]pyridine-6-carbonitrile (150 mg, 871 μmol, 41%) as a yellow solid.

Step 6: N'-hydroxy-1,3-dimethyl-pyrazolo[3,4-b]pyridine-6-carboxamidine

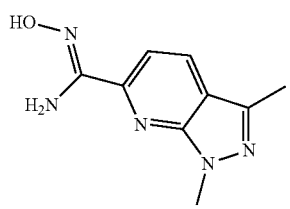

A mixture of 1,3-dimethylpyrazolo[3,4-b]pyridine-6-carbonitrile (150 mg, 871 μmol), hydroxylamine hydrochloride (121 mg, 1.74 mmol) and triethylamine (176 mg, 1.74 mmol, 241 μL) in ethanol (3 mL) and water (300 μL) was degassed and purged with nitrogen 3 times, and then the mixture was stirred at 70° C. for 5 h under a nitrogen atmosphere. The reaction mixture was filtered and concentrated under reduced pressure to give N'-hydroxy-1,3-dimethyl-pyrazolo[3,4-b]pyridine-6-carboxamidine (120 mg, 584.7 μmol, 67%) as a yellow solid.

Step 7: N-[2-[4-[3-(1,3-dimethylpyrazolo[3,4-b]pyridin-6-yl)-1,2,4-oxadiazol-5-yl]-1-piperidyl]-2-oxo-ethyl]benzamide

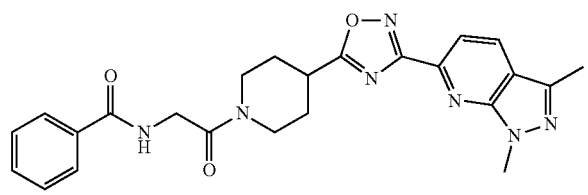 [SMILES: Cc1nn(C)c2nc(-c3noc(C4CCN(C(=O)CNC(=O)c5ccccc5)CC4)n3)ccc12]

A mixture of N'-hydroxy-1,3-dimethyl-pyrazolo[3,4-b]pyridine-6-carboxamidine (50 mg, 243.6 μmol), 1-(2-benzamidoacetyl)piperidine-4-carboxylic acid (84 mg, 292 μmol), (2-(1H-benzotriazol-1-yl)-1,1,3,3-tetramethyluronium hexafluorophosphate) (110 mg, 292 μmol) and N-ethyl-N-(propan-2-yl)propan-2-amine (94 mg, 730.92 μmol, 127 μL) in N,N-dimethylformamide (1 mL) was degassed and purged with nitrogen 3 times, and then the mixture was stirred at 20° C. for 1 h under a nitrogen atmosphere. The mixture was stirred at 120° C. for 1 h. The mixture was cooled then purified via Prep-HPLC (column: Waters Xbridge 150×25 5 μm; mobile phase: [water (10 mM ammonium carbonate)-acetonitrile]; B %: 20%-50%, 12 min) to give N-[2-[4-[3-(1,3-dimethylpyrazolo[3,4-b]pyridin-6-yl)-1,2,4-oxadiazol-5-yl]-1-piperidyl]-2-oxo-ethyl]benzamide (14 mg, 31.71 μmol, 13%) as a brown solid. $^1$H NMR (400 MHz, CHLOROFORM-d) δ 8.17-8.15 (d, J=8.3 Hz, 1H), 7.96-7.94 (d, J=8.2 Hz, 2H), 7.90-7.86 (m, 2H), 7.57-7.52 (m, 1H), 7.51-7.46 (m, 2H), 7.36 (br s, 1H), 4.60-4.56 (br d, J=13.9 Hz, 1H), 4.34-4.33 (d, J=4.0 Hz, 2H), 4.20 (s, 3H), 3.98-3.95 (br d, J=13.3 Hz, 1H), 3.49-3.33 (m, 2H), 3.22-3.10 (m, 1H), 2.64 (s, 3H), 2.38-2.26 (m, 2H), 2.15-1.99 (m, 2H); LCMS(ESI) m/z: [M+H]$^+$=460.3.

Example 116: 4-[4-[3-(1,3-dimethylpyrazolo[3,4-b]pyridin-6-yl)-1,2,4-oxadiazol-5-yl]piperidine-1-carbonyl]-1-phenyl-pyrrolidin-2-one

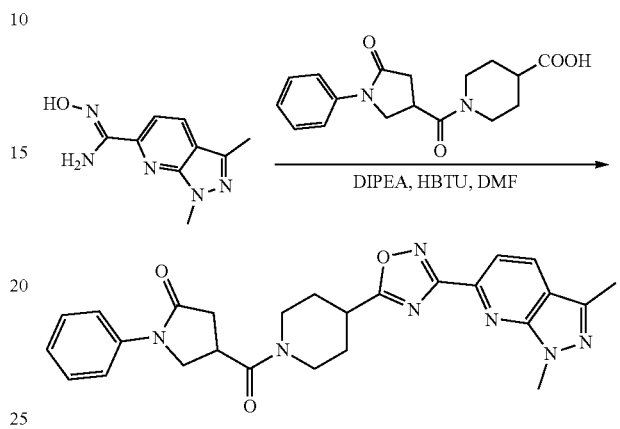

Prepared using a similar experimental procedure as for example 115.

4-[4-[3-(1,3-dimethylpyrazolo[3,4-b]pyridin-6-yl)-1,2,4-oxadiazol-5-yl]piperidine-1-carbonyl]-1-phenyl-pyrrolidin-2-one (4.06 mg, 8.36 μmol, 3.43% yield) was obtained as a white solid. $^1$H NMR (400 MHz, CHLOROFORM-d) δ 8.15-8.17 (d, J=8.4 Hz, 1H), 7.96-7.93 (dd, J=3.2, 8.2 Hz, 1H), 7.61-7.63 (d, J=7.7 Hz, 2H), 7.42-7.40 (t, J=8.0 Hz, 2H), 7.23-7.17 (m, 1H), 4.65-4.62 (br t, J=14.0 Hz, 1H), 4.36-4.32 (dd, J=7.3, 9.6 Hz, 1H), 4.21 (s, 3H), 4.07-3.94 (m, 2H), 3.69-3.58 (m, 1H), 3.50-3.37 (m, 2H), 3.16-2.96 (m, 2H), 2.91-2.84 (m, 1H), 2.64 (s, 3H), 2.33 (br t, J=13.9 Hz, 2H), 2.13-1.97 (m, 2H); LCMS(ESI) m/z: [M+H]$^+$=486.3.

Example 117: (4-(3-(1,3-dimethyl-1H-indazol-5-yl)-1,2,4-oxadiazol-5-yl)piperidin-1-yl)(piperidin-1-yl)methanone

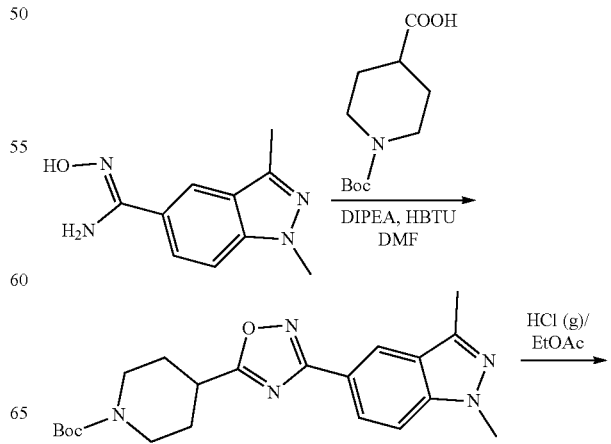

-continued

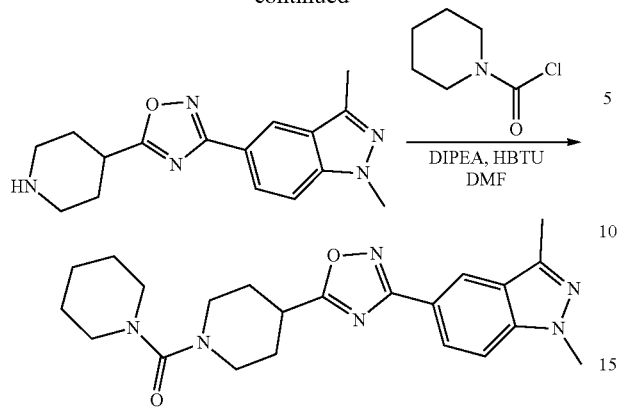

Step 1: Preparation of tert-butyl 4-(3-(1,3-dimethyl-1H-indazol-5-yl)-1,2,4-oxadiazol-5-yl)piperidine-1-carboxylate

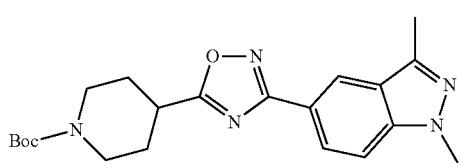 [SMILES: Cc1nn(C)c2ccc(-c3noc(C4CCN(C(=O)OC(C)(C)C)CC4)n3)cc12]

To a stirred solution of 1-(tert-butoxycarbonyl)piperidine-4-carboxylic acid (150 mg, 654 μmol) in N,N-dimethylformamide (2 mL) was added (Z)—N'-hydroxy-1,3-dimethyl-1H-indazole-5-carboximidamide (133 mg, 654 μmol), (2-(1H-benzotriazol-1-yl)-1,1,3,3-tetramethyluronium hexafluorophosphate) (248 mg, 654 μmol) and N-ethyl-N-(propan-2-yl)propan-2-amine (253 mg, 1.96 mmol, 342 μL). The mixture was stirred at 20° C. for 1 h, then heated at 120° C. for 1 h. The reaction mixture was quenched by addition of water (5 mL) then the mixture was extracted with ethyl acetate (20 mL×3), then the combined organic phases were washed with saturated aqueous sodium chloride solution (10 mL), dried over anhydrous sodium sulfate, filtered and concentrated to give a crude residue that was purified by prep-TLC (silica, petroleumether:ethylacetate=1:1) to furnish tert-butyl 4-(3-(1,3-dimethyl-1H-indazol-5-yl)-1,2,4-oxadiazol-5-yl)piperidine-1-carboxylate (190 mg, 478 μmol, 73%) as a white solid.

Step 2: Preparation of 3-(1,3-dimethyl-1H-indazol-5-yl)-5-(piperidin-4-yl)-1,2,4-oxadiazole

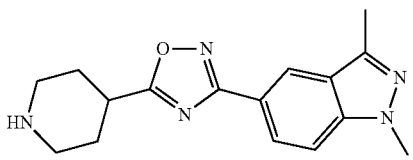 [SMILES: Cc1nn(C)c2ccc(-c3noc(C4CCNCC4)n3)cc12]

To a stirred solution of tert-butyl 4-(3-(1,3-dimethyl-1H-indazol-5-yl)-1,2,4-oxadiazol-5-yl)piperidine-1-carboxylate (190 mg, 478 μmol) in methanol (3 mL) was added methanolic hydrogen chloride solution (4M, 10 mL). The mixture was stirred at 20° C. for 0.5 h. The reaction mixture was concentrated under reduced pressure to provide 3-(1,3-dimethyl-1H-indazol-5-yl)-5-(piperidin-4-yl)-1,2,4-oxadiazole (140 mg, 471 μmol, 98%) as a white solid. $^1$H NMR (400 MHz, DMSO-d6) δ 9.04 (br s, 1H), 8.33 (d, J=0.7 Hz, 1H), 7.96 (dd, J=1.3, 8.8 Hz, 1H), 7.71 (d, J=8.8 Hz, 1H), 3.98 (s, 3H), 3.53-3.43 (m, 1H), 3.34 (br d, J=12.6 Hz, 2H), 3.11-3.00 (m, 2H), 2.52 (s, 3H), 2.26 (br d, J=10.8 Hz, 2H), 2.08-1.95 (m, 2H).

Step 3: Preparation of (4-(3-(1,3-dimethyl-1H-indazol-5-yl)-1,2,4-oxadiazol-5-yl)piperidin-1-yl)(piperidin-1-yl)methanone

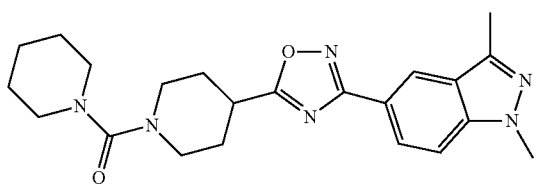 [SMILES: Cc1nn(C)c2ccc(-c3noc(C4CCN(C(=O)N5CCCCC5)CC4)n3)cc12]

To a stirred solution of 3-(1,3-dimethyl-1H-indazol-5-yl)-5-(piperidin-4-yl)-1,2,4-oxadiazole (130 mg, 437 μmol) in dichloromethane (500 μL) was added piperidine-1-carbonyl chloride (77 mg, 524.6 μmol, 65 μL) and triethylamine (132 mg, 1.31 mmol, 181 μL) at 0° C. The mixture was warmed and then stirred at 20° C. for 1 h. The reaction mixture was concentrated in vacuo to give a crude product that was purified by prep-HPLC (column: Waters Xbridge 150×2.5 mm 5 μm; mobile phase: [water (10 mM ammonium carbonate)-acetonitrile]; B %: 30%-70%, 12 min) to give (4-(3-(1,3-dimethyl-1H-indazol-5-yl)-1,2,4-oxadiazol-5-yl)piperidin-1-yl)(piperidin-1-yl)methanone (68 mg, 166.6 μmol, 38%) as a pale yellow solid. $^1$H NMR (400 MHz, CDCl$_3$) δ 8.42 (s, 1H), 8.08 (dd, J=1.4, 8.8 Hz, 1H), 7.40 (d, J=8.8 Hz, 1H), 4.03 (s, 3H), 3.80-3.70 (m, 2H), 3.28-3.14 (m, 5H), 3.05-2.93 (m, 2H), 2.62 (s, 3H), 2.18 (br dd, J=3.3, 13.6 Hz, 2H), 2.07-1.93 (m, 2H), 1.60 (br s, 6H); LCMS (ESI) m/z: [M+H]$^+$=409.1.

Example 118: 4-(4-(3-(5-ethoxy-4-methoxypyridin-2-yl)-1,2,4-oxadiazol-5-yl)piperidine-1-carbonyl)-1-phenylpyrrolidin-2-one

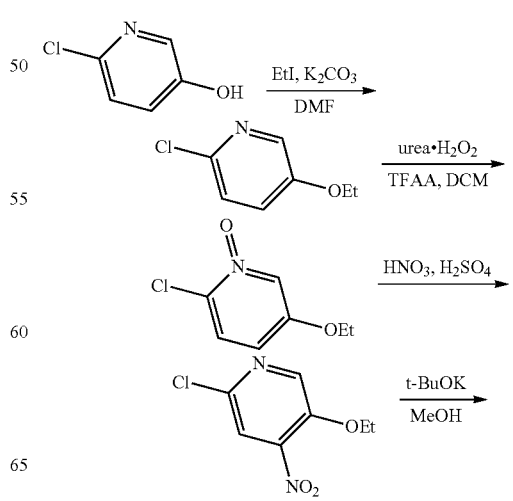

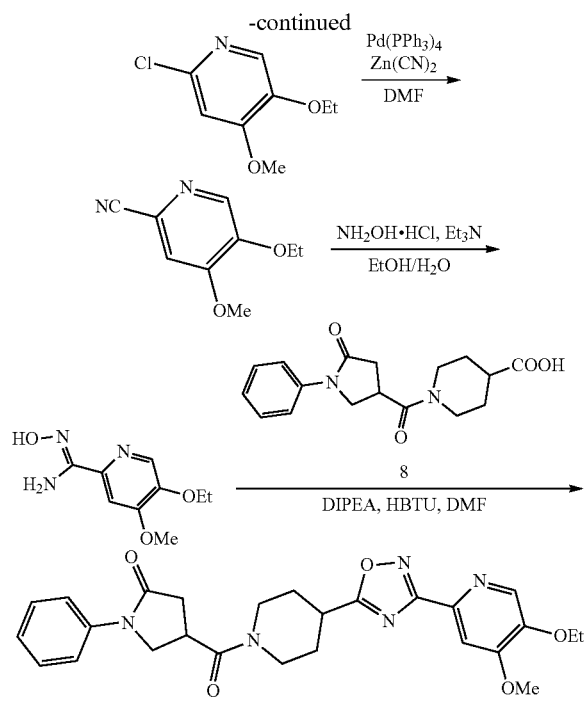

Step 1: Preparation of 2-chloro-5-ethoxypyridine

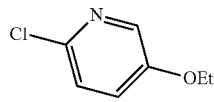

To a stirred solution of 6-chloropyridin-3-ol (3.0 g, 23.2 mmol) in N,N-dimethylformamide (30 mL) was added iodoethane (4.33 g, 27.8 mmol, 2.22 mL), and potassium carbonate (9.60 g, 69.6 mmol) at 0° C. The reaction was warmed and stirred at 40° C. for 2 h. The reaction mixture was quenched by addition of water (30 mL) then the mixture was extracted with ethyl acetate (60 mL×3). The combined organic phases were washed with saturated aqueous sodium chloride solution (30 mL), dried over anhydrous sodium sulfate, filtered and concentrated to give 2-chloro-5-ethoxypyridine (3.30 g, 20.9 mmol, 90%) as a yellow solid. $^1$H NMR (400 MHz, CDCl$_3$) δ 7.97 (d, J=2.9 Hz, 1H), 7.17-7.07 (m, 2H), 3.99 (q, J=7.0 Hz, 2H), 1.36 (t, J=7.0 Hz, 3H).

Step 2: Preparation of 2-chloro-5-ethoxypyridine 1-oxide

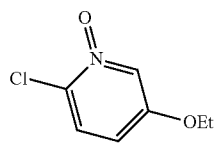 [SMILES: CCOc1ccc(Cl)[n+]([O-])c1]

Hydrogen peroxide-urea adduct (3.82 g, 40.61 mmol) was added in one portion to a solution of 2-chloro-5-ethoxypyridine (3.20 g, 20.3 mmol) in dichloromethane (30 mL) at 0° C., trifluoroacetic anhydride (7.68 g, 36.6 mmol, 5.08 mL) was added dropwise. The mixture was stirred at 20° C. for 16 h. The reaction mixture was quenched by addition of saturated aqueous sodium thiosulfate (30 mL). The mixture was extracted with dichloromethane (60 mL×3), then the combined organic phases were washed with saturated aqueous sodium chloride solution (30 mL), dried over anhydrous sodium sulfate, filtered and concentrated to give 2-chloro-5-ethoxypyridine 1-oxide (4.0 g) as a yellow oil. $^1$H NMR (400 MHz, CDCl$_3$) δ 8.35-8.28 (m, 1H), 7.44 (dt, J=3.0, 6.0 Hz, 1H), 7.13-7.04 (m, 1H), 4.13-4.00 (m, 2H), 1.50-1.40 (m, 3H).

Step 3: Preparation of 2-chloro-5-ethoxy-4-nitropyridine

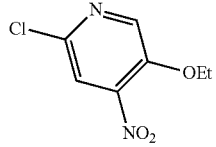 [SMILES: CCOc1cnc(Cl)cc1[N+](=O)[O-]]

To a stirred solution of 2-chloro-5-ethoxypyridine 1-oxide (1.80 g, 10.37 mmol) in concentrated sulfuric acid (12 mL) was added concentrated nitric acid (6.50 mL) at 0° C., the mixture was stirred at 25° C. for 1 hrs, then heated to 110° C. and stirred for 16 hrs. After cooling to 20° C., the mixture was poured onto ice, and then aqueous sodium hydroxide solution (40 wt. %) was added carefully to adjust the pH to 14. The mixture was extracted with dichloromethane (80 mL×3), then the combined organic phases were washed with saturated aqueous sodium chloride solution (30 mL), dried over anhydrous sodium sulfate, filtered and concentrated in vacuo to give 2-chloro-5-ethoxy-4-nitropyridine (810 mg, 4.00 mmol, 39%) as a yellow solid. $^1$H NMR (400 MHz, CDCl$_3$) δ 8.32 (s, 1H), 7.64 (s, 1H), 4.30 (q, J=6.9 Hz, 2H), 1.51 (t, J=7.0 Hz, 3H).

Step 4: Preparation of 2-chloro-5-ethoxy-4-methoxypyridine

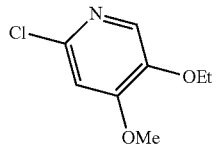 [SMILES: CCOc1cnc(Cl)cc1OC]

To a stirred solution of 2-chloro-5-ethoxy-4-nitro-pyridine (770 mg, 3.80 mmol) in methanol (8 mL) was added potassium tert-butoxide (644 mg, 4.18 mmol) at 0° C., then the mixture was warmed and stirred at 20° C. for 2 h. The reaction mixture was concentrated under reduced pressure then diluted with water (10 mL) of water. The mixture was extracted with dichloromethane (60 mL×3), then the combined organic phases were washed with saturated aqueous sodium chloride solution (20 mL), dried over anhydrous sodium sulfate, filtered and concentrated to give 2-chloro-5-ethoxy-4-methoxypyridine (660 mg, 3.52 mmol, 93%) as a yellow solid. $^1$H NMR (400 MHz, CDCl$_3$) δ 7.85 (s, 1H), 6.80 (s, 1H), 4.13 (q, J=7.0 Hz, 2H), 3.95-3.88 (m, 3H), 1.47 (t, J=7.0 Hz, 3H).

Step 5: Preparation of 5-ethoxy-4-methoxypicolinonitrile

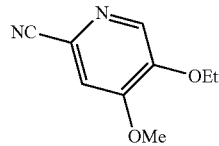 [SMILES: CCOc1cnc(C#N)cc1OC]

To a stirred solution of zinc cyanide (368 mg, 3.14 mmol) in N,N-dimethylformamide (8 mL) was added 2-chloro-5-ethoxy-4-methoxypyridine (590 mg, 3.14 mmol) and tetrakis(triphenylphosphine)palladium(0) (362 mg, 314 μmol) under nitrogen. The mixture was heated at 120° C. for 16 h. The reaction was cooled to 20° C., water (20 mL) was added to the reaction, and then the mixture was extracted with ethyl acetate (60 mL×3). The combined organic phases were washed with saturated aqueous sodium chloride solution (30 mL), dried over anhydrous sodium sulfate, filtered and concentrated in vacuo to give a crude residue that was purified by chromatography (silica, petroleum ether:ethyl acetate=1:0 to 5:1) to give 5-ethoxy-4-methoxypicolinonitrile (320 mg, 1.80 mmol, 57%) as a white solid. $^1$H NMR (400 MHz, CDCl$_3$) δ 8.19 (s, 1H), 7.18 (s, 1H), 4.25 (q, J=6.9 Hz, 2H), 3.96 (s, 3H), 1.52 (t, J=7.0 Hz, 3H).

Step 6: Preparation of (Z)-5-ethoxy-N'-hydroxy-4-methoxypicolinimidamide

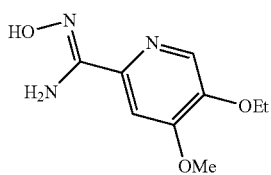 [SMILES: CCOc1cnc(/C(N)=N/O)cc1OC]

To a stirred solution of 5-ethoxy-4-methoxypicolinonitrile (320 mg, 1.80 mmol) in ethanol (5 mL) was added hydroxylamine hydrochloride (250 mg, 3.60 mmol), triethylamine (364 mg, 3.60 mmol, 499 μL) and water (0.50 mL). The mixture was stirred at 80° C. for 2 h. The reaction mixture was concentrated under reduced pressure then diluted with water (10 mL). The mixture was extracted with ethyl acetate (60 mL×3). The combined organic phases were washed with saturated aqueous sodium chloride solution (20 mL) then dried over anhydrous sodium sulfate, filtered and concentrated in vacuo to give (Z)-5-ethoxy-N'-hydroxy-4-methoxypicolinimidamide (330 mg, 1.56 mmol, 87%) as a white solid. $^1$H NMR (400 MHz, DMSO-d6) δ 9.71 (s, 1H), 8.10 (s, 1H), 7.39 (s, 1H), 5.75 (br s, 2H), 4.17-4.06 (m, 2H), 3.84 (s, 3H), 1.34 (t, J=6.9 Hz, 3H).

Step 7: Preparation of 4-(4-(3-(5-ethoxy-4-methoxypyridin-2-yl)-1,2,4-oxadiazol-5-yl)piperidine-1-carbonyl)-1-phenylpyrrolidin-2-one

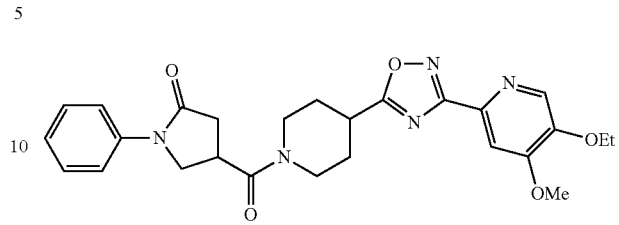

To a stirred solution of 1-(5-oxo-1-phenylpyrrolidine-3-carbonyl)piperidine-4-carboxylic acid (90 mg, 285 μmol) in N,N-dimethylformamide (2 mL) was added (Z)-5-ethoxy-N'-hydroxy-4-methoxypicolinimidamide (60 mg, 285 μmol), (2-(1H-benzotriazol-1-yl)-1,1,3,3-tetramethyluronium hexafluorophosphate) (107 mg, 285 μmol) and N-ethyl-N-(propan-2-yl)propan-2-amine (110 mg, 854 μmol, 149 μL). The mixture was stirred at 20° C. for 1 h, then heated at 110° C. for 1 h. The reaction mixture was cooled and then purified directly by prep-HPLC (column: Waters Xbridge 150×2.5 mm 5 μm; mobile phase: [water (10 mM ammonium carbonate)-acetonitrile]; B %: 30%-55%, 12 min) to give 4-(4-(3-(5-ethoxy-4-methoxypyridin-2-yl)-1,2,4-oxadiazol-5-yl)piperidine-1-carbonyl)-1-phenylpyrrolidin-2-one (34 mg, 70 μmol, 24%) as a yellow solid. $^1$H NMR (400 MHz, CDCl$_3$) δ 8.29 (s, 1H), 7.68-7.57 (m, 3H), 7.44-7.33 (m, 2H), 7.22-7.13 (m, 1H), 4.63-4.50 (m, 1H), 4.36-4.22 (m, 3H), 4.04-3.90 (m, 5H), 3.59 (td, J=8.6, 16.7 Hz, 1H), 3.43-3.30 (m, 2H), 3.12-2.93 (m, 2H), 2.88-2.79 (m, 1H), 2.33-2.20 (m, 2H), 2.13-1.93 (m, 2H), 1.52 (t, J=7.0 Hz, 3H); LCMS (ESI) m/z: [M+H]$^+$=492.1.

Example 119: (4-(3-(4-ethoxy-3-methoxyphenyl)-1,2,4-oxadiazol-5-yl)piperidin-1-yl)((2S,5R)-5-phenylpyrrolidin-2-yl)methanone

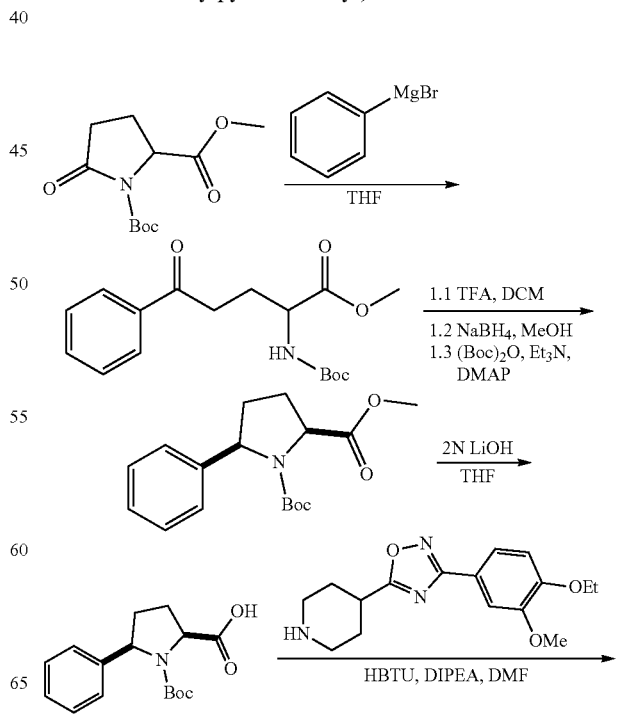

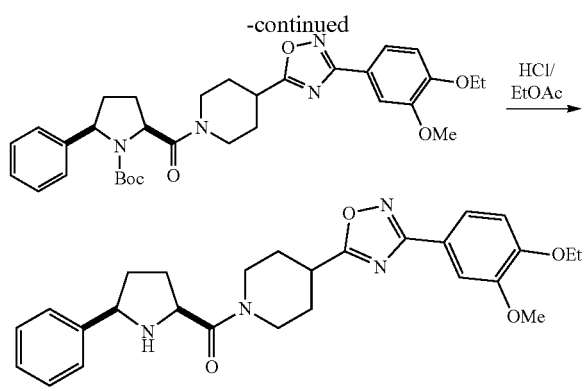

Step 1: Preparation of methyl 2-((tert-butoxycarbonyl)amino)-5-oxo-5-phenylpentanoate

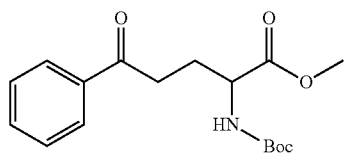 [SMILES: COC(=O)C(CCC(=O)c1ccccc1)NC(=O)OC(C)(C)C]

To a stirred solution of O1-tert-butyl O2-methyl 5-oxopyrrolidine-1,2-dicarboxylate (1.0 g, 4.11 mmol) in tetrahydrofuran (10 mL) was added phenylmagnesium bromide (1 M in THF, 4.93 mL) at −30° C. The reaction mixture was slowly warmed to 20° C. and stirred for 16 h. The reaction mixture was quenched by addition of saturated aqueous ammonium chloride (10 mL), and then extracted with ethyl acetate (40 mL×3). The combined organic phases were washed with saturated aqueous sodium chloride solution (20 mL), dried over anhydrous sodium sulfate, filtered and concentrated under reduced pressure to give a residue. The residue was purified by chromatography (silica, petroleumether:ethylacetate=1:0 to 20:1) to give methyl 2-((tert-butoxycarbonyl)amino)-5-oxo-5-phenylpentanoate (900 mg, 2.80 mmol, 68%) as a white solid. $^1$H NMR (400 MHz, CDCl$_3$) δ 7.95 (d, J=8.0 Hz, 2H), 7.60-7.53 (m, 1H), 7.50-7.43 (m, 2H), 5.17 (br s, 1H), 4.40 (brs, 1H), 3.75 (s, 3H), 3.19-2.99 (m, 2H), 2.37-2.26 (m, 1H), 2.15-2.02 (m, 1H), 1.42 (s, 9H).

Step 2: Preparation of (2S/R,5R/S)-1-tert-butyl 2-methyl 5-phenylpyrrolidine-1,2-dicarboxylate

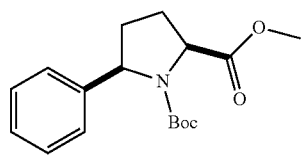

To a stirred solution of methyl 2-((tert-butoxycarbonyl)amino)-5-oxo-5-phenylpentanoate (800 mg, 2.49 mmol) in dichloromethane (10 mL) was added trifluoroacetic acid (5.68 g, 49.8 mmol, 3.69 mL) at 20° C. After 16 h, the solvent was removed under reduced pressure, then the residue was dissolved in methanol (10 mL) and cooled to 0° C. Sodium borohydride (188 mg, 4.98 mmol) was slowly added, then the mixture was warmed and stirred at 20° C. for 16 h. The mixture was concentrated in vacuo and the resulting orange oil was diluted with methanol (20 mL) and concentrated again a total of four times. The residue was suspended in dichloromethane (10 mL), then di-tert-butyl dicarbonate (815 mg, 3.74 mmol, 858 μL), triethylamine (377 mg, 3.74 mmol, 517 μL), 4-dimethylaminopyridine (3 mg, 24.90 μmol) were added and stirred at 20° C. for 16 h. Sat. aq. ammonium chloride (20 mL) was added and the layers were separated. The aqueous layer was extracted with dichloromethane (50 mL×3) and the combined organic layers were dried over anhydrous sodium sulfate, filtered and concentrated to give a crude residue that was purified by prep-HPLC (column: Waters Xbridge 150×2.5 mm 5 μm; mobile phase: [water (10 mM ammonium carbonate)-acetonitrile]; B %: 36%-66%, 12 min]) to give (2S/R,5R/S)-1-tert-butyl 2-methyl 5-phenylpyrrolidine-1,2-dicarboxylate (230 mg, 753 μmol, 30%) as a white solid. $^1$H NMR (400 MHz, CDCl$_3$) δ 7.56 (br d, J=7.5 Hz, 2H), 7.33 (t, J=7.5 Hz, 2H), 7.26-7.19 (m, 1H), 5.00 (br d, J=3.4 Hz, 0.4H), 4.75 (br t, J=7.0 Hz, 0.6H), 4.50 (br dd, J=4.7, 8.0 Hz, 0.6H), 4.36 (br t, J=7.4 Hz, 0.4H), 3.82 (s, 3H), 2.38-2.28 (m, 1H), 2.20 (ddd, J=6.5, 7.8, 12.5 Hz, 1H), 2.12-1.91 (m, 2H), 1.42 (s, 3.6H), 1.15 (s, 5.4H).

Step 3: Preparation of (2S/R,5R/S)-1-(tert-butoxycarbonyl)-5-phenylpyrrolidine-2-carboxylic acid

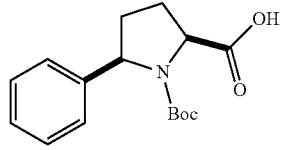

To a stirred solution of (2S/R,5R/S)-1-tert-butyl 2-methyl 5-phenylpyrrolidine-1,2-dicarboxylate (180 mg, 589 μmol) in tetrahydrofuran (2 mL) was added lithium hydroxide (2 M, 589 μL). The mixture was stirred at 20° C. for 16 h. The mixture was acidified to pH 1 by dropwise addition of concentrated hydrochloric acid. The mixture was extracted with ethyl acetate (40 mL×3). The organic layer was washed with saturated aqueous sodium chloride solution (20 mL), dried over anhydrous sodium sulfate, filtered and concentrated to give (2S/R,5R/S)-1-(tert-butoxycarbonyl)-5-phenylpyrrolidine-2-carboxylic acid (300 mg) as a white solid.

Step 4: Preparation of (2S/R,5R/S)-tert-butyl 2-(4-(3-(4-ethoxy-3-methoxyphenyl)-1,2,4-oxadiazol-5-yl)piperidine-1-carbonyl)-5-phenylpyrrolidine-1-carboxylate

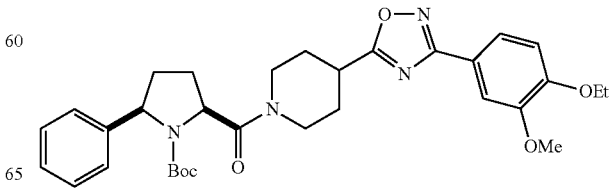

To a stirred solution of (2S,5R)-1-(tert-butoxycarbonyl)-5-phenylpyrrolidine-2-carboxylic acid (270 mg, 927 μmol) in N,N-dimethylformamide (3 mL) was added 3-(4-ethoxy-3-methoxyphenyl)-5-(piperidin-4-yl)-1,2,4-oxadiazole (281 mg, 927 μmol), (2-(1H-benzotriazol-1-yl)-1,1,3,3-tetramethyluronium hexafluorophosphate) (351 mg, 927 μmol) and N-ethyl-N-(propan-2-yl)propan-2-amine (359 mg, 2.78 mmol, 485 μL). The mixture was stirred at 20° C. for 1 h. Water (15 mL) was added to the reaction, then the reaction mixture was extracted with ethyl acetate (40 mL×3). The combined organic phases were washed with saturated aqueous sodium chloride solution (20 mL), then dried over anhydrous sodium sulfate, filtered and concentrated in vacuo to give (2S/R,5R/S)-tert-butyl 2-(4-(3-(4-ethoxy-3-methoxyphenyl)-1,2,4-oxadiazol-5-yl)piperidine-1-carbonyl)-5-phenylpyrrolidine-1-carboxylate (500 mg) as a yellow oil. This material was used directly without purification.

Step 5: Preparation of (4-(3-(4-ethoxy-3-methoxyphenyl)-1,2,4-oxadiazol-5-yl)piperidin-1-yl)((2S/R, 5R/S)-5-phenylpyrrolidin-2-yl)methanone

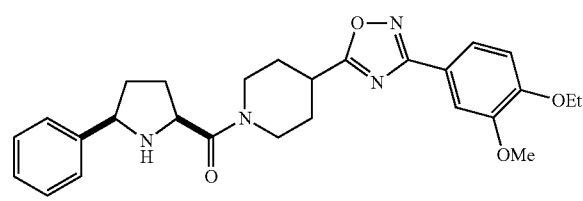 [SMILES: CCOc1ccc(-c2noc(C3CCN(C(=O)[C@@H]4CC[C@H](c5ccccc5)N4)CC3)n2)cc1OC]

To a stirred solution of (2S/R,5R/S)-tert-butyl 2-(4-(3-(4-ethoxy-3-methoxyphenyl)-1,2,4-oxadiazol-5-yl)piperidine-1-carbonyl)-5-phenylpyrrolidine-1-carboxylate (500 mg, 867 μmol) in ethyl acetate (5 mL) was added 4N hydrochloric acid in ethyl acetate (20 mL). The mixture was stirred at 20° C. for 0.5 h. The reaction mixture was concentrated under reduced pressure to provide the crude product. The crude product was purified by prep-HPLC (column: Waters Xbridge 150×2.5 mm 5 μm; mobile phase: [water (10 mM ammonium carbonate)-acetonitrile]; B %: 45%-65%, 12 min) to give (4-(3-(4-ethoxy-3-methoxyphenyl)-1,2,4-oxadiazol-5-yl)piperidin-1-yl)((2S/R,5R/S)-5-phenylpyrrolidin-2-yl)methanone (78 mg, 161.6 μmol, 19%) as a yellow solid. $^1$H NMR (400 MHz, Methanol-d4) δ 7.66 (ddd, J=2.0, 3.5, 8.3 Hz, 1H), 7.61 (br d, J=2.5 Hz, 1H), 7.48 (br d, J=7.8 Hz, 2H), 7.39 (t, J=7.4 Hz, 2H), 7.35-7.28 (m, 1H), 7.11-7.04 (m, 1H), 4.53 (br t, J=12.5 Hz, 1H), 4.24-4.05 (m, 5H), 3.92 (d, J=1.8 Hz, 3H), 3.49-3.38 (m, 2H), 3.18-3.06 (m, 1H), 2.45-2.20 (m, 4H), 2.04-1.66 (m, 4H), 1.45 (t, J=7.0 Hz, 3H); LCMS (ESI) m/z: [M+H]$^+$=477.1.

Example 120: 4-(4-(3-(1,3-dimethyl-1H-pyrazolo[4,3-c]pyridin-6-yl)-1,2,4-oxadiazol-5-yl)piperidine-1-carbonyl)-1-phenylpyrrolidin-2-one

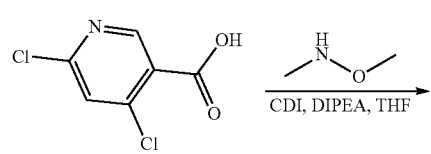

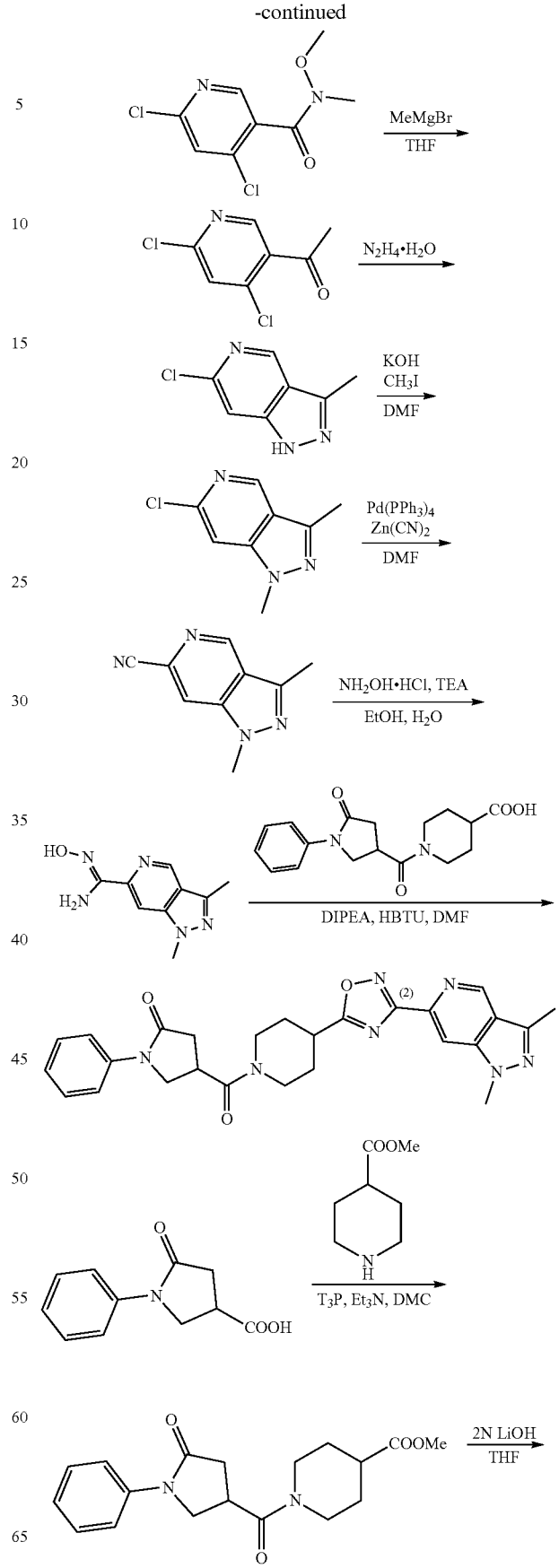

-continued

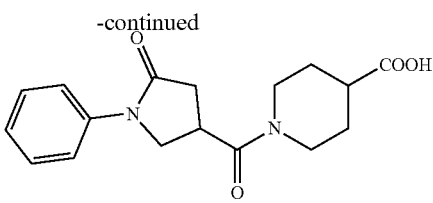

Step 1: Preparation of 4,6-dichloro-N-methoxy-N-methylnicotinamide

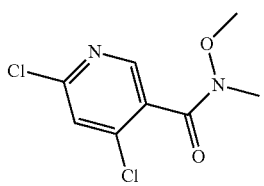

A solution of 4,6-dichloropyridine-3-carboxylic acid (13.5 g, 70.3 mmol) and 1,1'-carbonyldiimidazole (17.10 g, 105.5 mmol) in tetrahydrofuran (200 mL) was stirred for 0.5 h at 25° C. N-ethyl-N-(propan-2-yl)propan-2-amine (18.17 g, 140.62 mmol, 24.55 mL) and N,O-dimethylhydroxylamine hydrochloride (8.23 g, 84.4 mmol) were added and the resulting solution was stirred at 25° C. for 16 h. The reaction mixture was diluted with water (200 mL), then the mixture was extracted with ethyl acetate (200 mL×3). The combined organic layer was washed with water (50 mL×3) then saturated aqueous sodium chloride solution (50 mL), dried over anhydrous sodium sulfate, filtered and concentrated to give 4,6-dichloro-N-methoxy-N-methylnicotinamide (19.0 g) as a yellow oil. $^1$H NMR (400 MHz, CDCl$_3$) δ 8.35 (s, 1H), 7.44 (d, J=0.6 Hz, 1H), 3.49 (br s, 3H), 3.38 (br s, 3H).

Step 2: Preparation of 1-(4,6-dichloropyridin-3-yl)ethanone

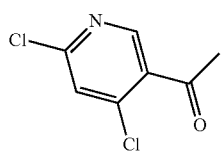

To a stirred solution of 4,6-dichloro-N-methoxy-N-methylnicotinamide (16.0 g, 68.1 mmol) in tetrahydrofuran (200 mL) was added a solution of methylmagnesium bromide in tetrahydrofuran (3 M, 57.6 mL) at 0° C., the mixture was stirred at 0° C. for 2 h. After addition of saturated aqueous ammonium chloride (100 mL), the mixture was concentrated to ~200 mL and the residue was extracted with dichloromethane (200 mL×3). The combined organic phases were washed with saturated aqueous sodium chloride solution (60 mL), dried over anhydrous sodium sulfate, filtered and concentrated under reduced pressure to give 1-(4,6-dichloropyridin-3-yl)ethanone (8.95 g, 47.1 mmol, 69%) as a yellow oil. $^1$H NMR (400 MHz, CDCl$_3$) δ 8.62 (s, 1H), 7.46 (s, 1H), 2.68 (s, 3H).

Step 3: Preparation of 6-chloro-3-methyl-1H-pyrazolo[4,3-c]pyridine

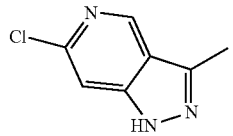

1-(4,6-dichloropyridin-3-yl)ethanone (8.40 g, 44.2 mmol) in hydrazine hydrate (60 mL) was stirred at 20° C. for 1 h. The reaction mixture was diluted with water (100 mL), then the mixture was extracted with dichloromethane (150 mL×3). The separated organic layer was washed water (40 mL×3) and saturated aqueous sodium chloride solution (50 mL), then dried over anhydrous sodium sulfate, filtered and concentrated to give 6-chloro-3-methyl-1H-pyrazolo[4,3-c]pyridine (6.10 g, 36.4 mmol, 82%) as a yellow solid. $^1$H NMR (400 MHz, DMSO-d6) δ 13.17 (br s, 1H), 8.88 (s, 1H), 7.53 (s, 1H), 2.55 (s, 3H).

Step 4: Preparation of 6-chloro-1,3-dimethyl-1H-pyrazolo[4,3-c]pyridine

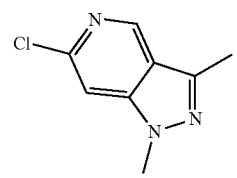

To a stirred solution of 6-chloro-3-methyl-1H-pyrazolo[4,3-c]pyridine (5.90 g, 35.2 mmol) in N,N-dimethylformamide (80 mL) was added iodomethane (9.99 g, 70.4 mmol, 4.38 mL), and potassium hydroxide (7.90 g, 140.8 mmol) at 0° C. The reaction was stirred at 60° C. for 2 h. The reaction mixture was cooled then quenched by addition of water (100 mL). The mixture was extracted with ethyl acetate (150 mL×3), then the combined organic phases were washed with saturated aqueous sodium chloride solution (100 mL), dried over anhydrous sodium sulfate, filtered and concentrated to give a crude residue that was purified by chromatography (silica, petroleumether:ethylacetate=1:0 to 5:1) to give 6-chloro-1,3-dimethyl-1H-pyrazolo[4,3-c]pyridine (2.73 g, 15.0 mmol, 43%) as a yellow solid. $^1$H NMR (400 MHz, CDCl$_3$) δ 8.70 (s, 1H), 7.22 (s, 1H), 3.93 (s, 3H), 2.58 (s, 3H).

Step 5: Preparation of 1,3-dimethyl-1H-pyrazolo[4,3-c]pyridine-6-carbonitrile

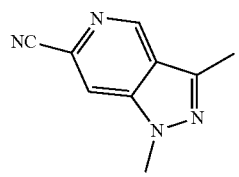

To a stirred solution of 6-chloro-1,3-dimethyl-1H-pyrazolo[4,3-c]pyridine (1.70 g, 9.36 mmol) in N,N-dimethylformamide (20 mL) was added zinc cyanide (1.10 g, 9.36 mmol, 594 µL) and tetrakis(triphenylphosphine)palladium (0) (1.08 g, 936 µmol) under nitrogen. The mixture was stirred at 110° C. for 16 h. The reaction was cooled to 20° C., water (30 mL) was added to the reaction, and then the reaction mixture was extracted with ethyl acetate (80 mL×2). The combined organic phases were washed with saturated aqueous sodium chloride solution (30 mL), dried over anhydrous sodium sulfate, filtered and concentrated in vacuo to give a crude residue that was purified by chromatography (silica, petroleumether:ethylacetate=50:1 to 1:1) to give 1,3-dimethyl-1H-pyrazolo[4,3-c]pyridine-6-carbonitrile (1.06 g, 6.16 mmol, 66%) as a white solid. ¹H NMR (400 MHz, CDCl₃) δ 9.03 (d, J=1.0 Hz, 1H), 7.73 (d, J=1.0 Hz, 1H), 4.07 (s, 3H), 2.67 (s, 3H).

Step 6: Preparation of (Z)—N'-hydroxy-1,3-dimethyl-1H-pyrazolo[4,3-c]pyridine-6-carboximidamide

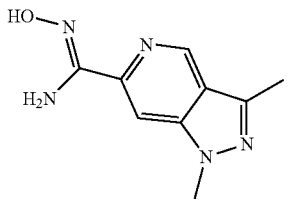

To a stirred solution of 1,3-dimethyl-1H-pyrazolo[4,3-c]pyridine-6-carbonitrile (1.06 g, 6.16 mmol) in ethanol (15 mL) was added hydroxylamine hydrochloride (855 mg, 12.3 mmol), triethylamine (1.25 g, 12.3 mmol, 1.71 mL) and water (1.50 mL). The mixture was heated at 80° C. for 2 h. The reaction mixture was concentrated under reduced pressure then the residue was triturated with water (5 mL), filtered and the filter cake was dried under reduced pressure to give (Z)—N'-hydroxy-1,3-dimethyl-1H-pyrazolo[4,3-c]pyridine-6-carboximidamide (1.0 g, 4.87 mmol, 79%) as a white solid. ¹H NMR (400 MHz, DMSO-d6) δ 9.73 (s, 1H), 9.02 (s, 1H), 7.91 (s, 1H), 5.91 (br s, 2H), 3.98 (s, 3H), 2.56 (s, 3H).

Step 7: Preparation of methyl 1-(5-oxo-1-phenylpyrrolidine-3-carbonyl)piperidine-4-carboxylate

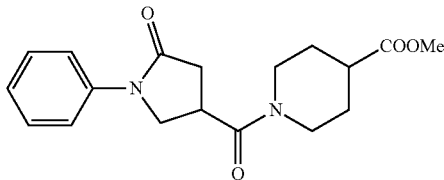 [SMILES: COC(=O)C1CCN(C(=O)C2CC(=O)N(c3ccccc3)C2)CC1]

To a stirred solution of 5-oxo-1-phenylpyrrolidine-3-carboxylic acid (3.0 g, 14.6 mmol) in dichloromethane (30 mL) was added methyl piperidine-4-carboxylate (2.09 g, 14.6 mmol), 2,4,6-tripropyl-1,3,5,2,4,6-trioxatriphosphinane 2,4,6-trioxide (9.30 g, 14.6 mmol, 8.69 mL, 50% purity in ethyl acetate) and triethylamine (1.48 g, 14.6 mmol, 2.03 mL). The mixture was stirred at 25° C. for 16 h. The reaction mixture was diluted by addition of water (20 mL) then extracted with dichloromethane (60 mL×3). The combined organic layer was washed with saturated aqueous sodium chloride solution (30 mL), dried over anhydrous sodium sulfate, filtered and concentrated to give methyl 1-(5-oxo-1-phenylpyrrolidine-3-carbonyl)piperidine-4-carboxylate (4.02 g, 12.2 mmol, 83%) as a yellow oil. ¹H NMR (400 MHz, CDCl₃) δ 7.59 (d, J=7.7 Hz, 2H), 7.38 (t, J=7.3 Hz, 2H), 7.21-7.12 (m, 1H), 4.43 (m, 1H), 4.29 (dd, J=7.3, 9.6 Hz, 1H), 3.97-3.81 (m, 2H), 3.72 (s, 3H), 3.55 (m, 1H), 3.28-3.17 (m, 1H), 3.01-2.75 (m, 3H), 2.62 (dt, J=6.3, 10.4 Hz, 1H), 2.08-1.94 (m, 2H), 1.80-1.64 (m, 2H).

Step 8: Preparation of 1-(5-oxo-1-phenylpyrrolidine-3-carbonyl)piperidine-4-carboxylic acid

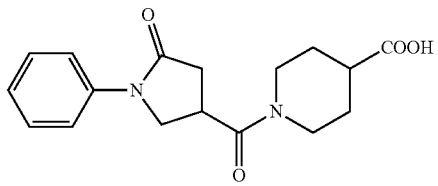 [SMILES: O=C(O)C1CCN(C(=O)C2CC(=O)N(c3ccccc3)C2)CC1]

To a stirred solution of methyl 1-(5-oxo-1-phenylpyrrolidine-3-carbonyl)piperidine-4-carboxylate (4.0 g, 12.11 mmol) in tetrahydrofuran (30 mL) was added aqueous lithium hydroxide (2 M, 12.11 mL). After 1 h, the reaction mixture was cooled to 0° C. then acidified with 2 M hydrochloric acid (6 mL). The mixture was extracted with ethyl acetate (80 mL×3). The combined organic extracts were washed with saturated aqueous sodium chloride solution (30 mL), dried over anhydrous sodium sulfate, filtered and concentrated to give 1-(5-oxo-1-phenylpyrrolidine-3-carbonyl)piperidine-4-carboxylic acid (3.60 g, 11.38 mmol, 94%) as a yellow solid. ¹H NMR (400 MHz, Methanol-d4) δ 7.59 (dd, J=4.0, 7.7 Hz, 2H), 7.38 (t, J=7.6 Hz, 2H), 7.23-7.15 (m, 1H), 4.41-4.30 (m, 1H), 4.15-3.96 (m, 3H), 3.85-3.75 (m, 1H), 3.30-3.22 (m, 1H), 2.99-2.77 (m, 3H), 2.63 (m, 1H), 2.06-1.93 (m, 2H), 1.74-1.53 (m, 2H).

Step 9: Preparation of 4-(4-(3-(1,3-dimethyl-1H-pyrazolo[4,3-c]pyridin-6-yl)-1,2,4-oxadiazol-5-yl)piperidine-1-carbonyl)-1-phenylpyrrolidin-2-one

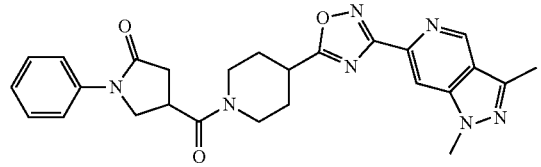 [SMILES: Cc1nn(C)c2cc(-c3noc(C4CCN(C(=O)C5CC(=O)N(c6ccccc6)C5)CC4)n3)ncc12]

To a stirred solution of (Z)—N'-hydroxy-1,3-dimethyl-1H-pyrazolo[4,3-c]pyridine-6-carboximidamide (84 mg, 410.9 µmol) in N,N-dimethylformamide (2 mL) was added 1-(5-oxo-1-phenylpyrrolidine-3-carbonyl)piperidine-4-carboxylic acid (130 mg, 410.9 µmol), (2-(1H-benzotriazol-1-yl)-1,1,3,3-tetramethyluronium hexafluorophosphate) (155 mg, 410.9 µmol) and N-ethyl-N-(propan-2-yl)propan-2-amine (159 mg, 1.23 mmol, 215 µL). The mixture was stirred at 20° C. for 1 h, then heated at 110° C. for 1 h. The reaction mixture was cooled then purified directly by prep- HPLC (column: Waters Xbridge 150×2.5 mm 5 μm; mobile phase: [water (10 mM ammonium carbonate)-acetonitrile]; B %: 25%-40%, 12 min) to give 4-(4-(3-(1,3-dimethyl-1H-pyrazolo[4,3-c]pyridin-6-yl)-1,2,4-oxadiazol-5-yl)piperidine-1-carbonyl)-1-phenylpyrrolidin-2-one (78 mg, 155 μmol, 38%) as a yellow solid. $^1$H NMR (400 MHz, CDCl$_3$) δ 9.13 (d, J=1.0 Hz, 1H), 8.12 (br d, J=3.9 Hz, 1H), 7.60 (br d, J=7.8 Hz, 2H), 7.39 (br t, J=8.0 Hz, 2H), 7.18 (br t, J=7.4 Hz, 1H), 4.59 (br t, J=13.8 Hz, 1H), 4.36-4.27 (m, 1H), 4.09 (d, J=3.8 Hz, 3H), 4.03-3.92 (m, 2H), 3.60 (m, 1H), 3.39 (br s, 2H), 3.14-2.94 (m, 2H), 2.90-2.80 (m, 1H), 2.68 (s, 3H), 2.37-2.23 (m, 2H), 2.12-1.96 (m, 2H); LCMS (ESI) m/z: [M+H]$^+$=486.1.

Example 121: N-(2-(4-(3-(5-ethoxy-4-methoxypyridin-2-yl)-1,2,4-oxadiazol-5-yl)piperidin-1-yl)-2-oxoethyl)benzamide

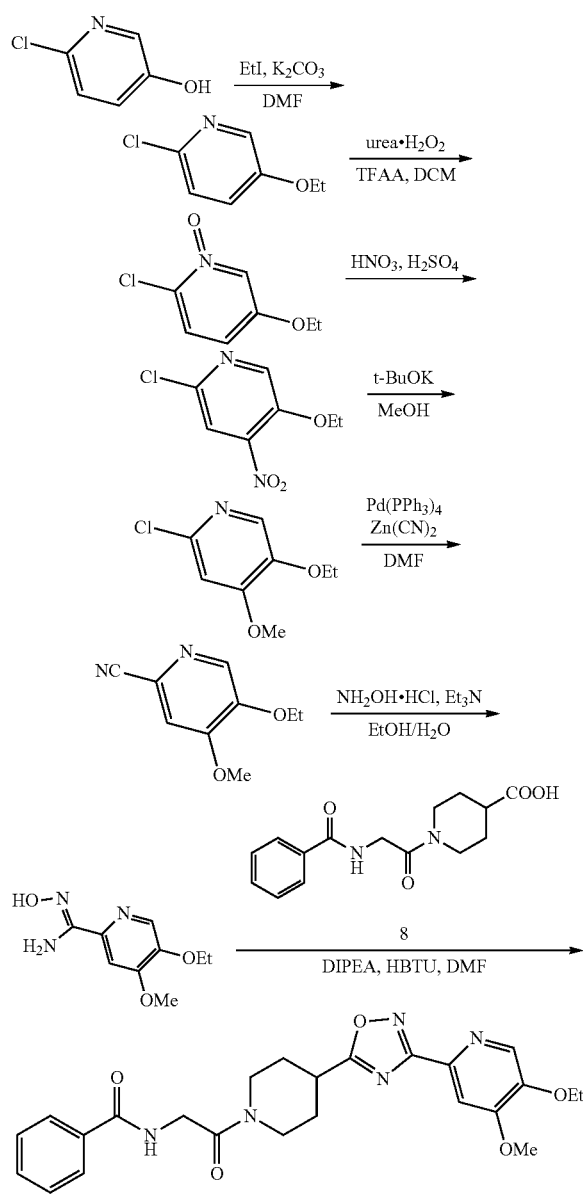

Step 1: Preparation of 2-chloro-5-ethoxypyridine

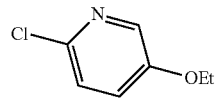

To a stirred solution of 6-chloropyridin-3-ol (21.0 g, 162.1 mmol) in N,N-dimethylformamide (200 mL) was added iodoethane (30.34 g, 194.5 mmol, 15.6 mL) and potassium carbonate (67.2 g, 486.3 mmol) at 0° C., then the reaction was warmed and stirred at 40° C. for 2 h. The reaction mixture was quenched by addition of water (200 mL), then the mixture was extracted with ethyl acetate (300 mL×3). The combined organic phases were washed with saturated aqueous sodium chloride solution (100 mL), dried over anhydrous sodium sulfate, filtered and concentrated to give 2-chloro-5-ethoxypyridine (26.0 g) as a yellow oil. This was used directly without further purification. $^1$H NMR (400 MHz, CDCl$_3$) δ 7.95 (d, J=2.9 Hz, 1H), 7.15-7.06 (m, 2H), 3.98 (q, J=7.0 Hz, 2H), 1.35 (t, J=7.0 Hz, 3H).

Step 2: Preparation of 2-chloro-5-ethoxypyridine 1-oxide

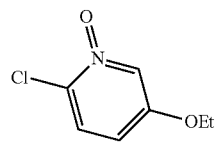 [SMILES: CCOc1ccc(Cl)[n+]([O-])c1]

Hydrogen peroxide-urea complex (31.04 g, 330 mmol) was added in one portion to a solution of 2-chloro-5-ethoxypyridine (26.0 g, 165 mmol) in dichloromethane (250 mL) at 0° C., then trifluoroacetic anhydride (62.4 g, 297 mmol, 41.3 0 mL) was added dropwise. The mixture was stirred at 20° C. for 16 h. The reaction mixture was quenched by addition of saturated aqueous sodium thiosulfate (150 mL). The mixture was extracted with dichloromethane (200 mL×3), then the combined organic phases were washed with saturated aqueous sodium chloride solution (100 mL), dried over anhydrous sodium sulfate, filtered and concentrated to give a crude residue that was purified by chromatography (silica, petroleum ether:ethyl acetate=1:0 to 1:2) to give 2-chloro-5-ethoxypyridine 1-oxide (22.0 g, 126.7 mmol, 77%) as a yellow solid. $^1$H NMR (400 MHz, CDCl$_3$) δ 8.05 (d, J=2.6 Hz, 1H), 7.29 (d, J=9.0 Hz, 1H), 6.81 (dd, J=2.6, 9.1 Hz, 1H), 3.97 (q, J=6.9 Hz, 2H), 1.37 (t, J=7.0 Hz, 3H).

Step 3: Preparation of 2-chloro-5-ethoxy-4-nitropyridine

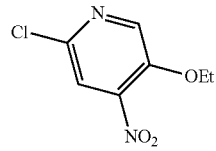

To a stirred solution of 2-chloro-5-ethoxypyridine 1-oxide (5.0 g, 28.8 mmol) in concentrated sulfuric acid (30 mL) was added dropwise concentrated nitric acid (15 mL) at 0° C., then the mixture was warmed, stirred at 25° C. for 1 h, and then heated to 110° C. for 16 h. After cooling to 20° C., the mixture was poured onto ice, and then aqueous sodium hydroxide solution (40 wt. %) was added carefully to adjust the pH to 14. The mixture was extracted with dichloromethane (100 mL×3), then the combined organic phases were washed with saturated aqueous sodium chloride solution (30 mL), dried over anhydrous sodium sulfate, filtered and concentrated to give 2-chloro-5-ethoxy-4-nitropyridine (3.10 g, 15.3 mmol, 53%) as a yellow solid. $^1$H NMR (400 MHz, CDCl$_3$) δ 8.32 (s, 1H), 7.64 (s, 1H), 4.30 (q, J=7.0 Hz, 2H), 1.50 (t, J=7.0 Hz, 3H).

Step 4: Preparation of
2-chloro-5-ethoxy-4-methoxypyridine

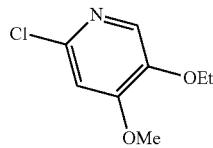 [SMILES: CCOc1cnc(Cl)cc1OC]

To a stirred solution of 2-chloro-5-ethoxy-4-nitro-pyridine (3.10 g, 15.3 mmol) in methanol (32 mL) was added potassium tert-butoxide (2.60 g, 16.8 mmol) at 0° C., the mixture was warmed and stirred at 20° C. for 2 h. The reaction was concentrated under reduced pressure then diluted with water (20 mL). The mixture was extracted with dichloromethane (60 mL×3), then the combined organic phases were washed with saturated aqueous sodium chloride solution (20 mL), dried over anhydrous sodium sulfate, filtered and concentrated to give 2-chloro-5-ethoxy-4-methoxypyridine (2.68 g, 14.28 mmol, 93%) as a yellow solid. $^1$H NMR (400 MHz, CDCl$_3$) δ 7.88-7.81 (m, 1H), 6.83-6.76 (m, 1H), 4.18-4.07 (m, 2H), 3.91 (dd, J=2.1, 2.8 Hz, 3H), 1.46 (m, 3H).

Step 5: Preparation of
5-ethoxy-4-methoxypicolinonitrile

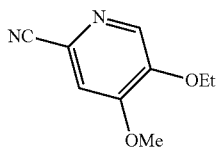 [SMILES: CCOc1cnc(C#N)cc1OC]

To a stirred solution of zinc cyanide (1.31 g, 11.2 mmol) in N,N-dimethylformamide (25 mL) was added 2-chloro-5-ethoxy-4-methoxypyridine (2.10 g, 11.2 mmol) and tetrakis(triphenylphosphine)palladium(0) (1.29 g, 1.12 mmol) under nitrogen. The mixture was heated at 110° C. for 16 h. The reaction was cooled to 20° C., then water (40 mL) was added and the reaction mixture extracted with ethyl acetate (80 mL×3). The combined organic phases were washed with saturated aqueous sodium chloride solution (50 mL), dried over anhydrous sodium sulfate, filtered and concentrated in vacuo to give a crude residue that was purified by chromatography (silica, petroleum ether:ethyl acetate=1:0 to 5:1) to give 5-ethoxy-4-methoxypicolinonitrile (1.20 g, 6.73 mmol, 60%) as a white solid. $^1$H NMR (400 MHz, CDCl$_3$) δ 8.18 (s, 1H), 7.18 (s, 1H), 4.24 (q, J=7.0 Hz, 2H), 3.96 (s, 3H), 1.51 (t, J=7.0 Hz, 3H).

Step 6: Preparation of (Z)-5-ethoxy-N'-hydroxy-4-methoxypicolinimidamide

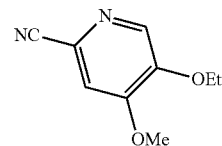 [SMILES: CCOc1cnc(C#N)cc1OC]

To a stirred solution of 5-ethoxy-4-methoxypicolinonitrile (1.20 g, 6.73 mmol) in ethanol (15 mL) was added hydroxylamine hydrochloride (935 mg, 13.5 mmol), triethylamine (1.36 g, 13.5 mmol, 1.87 mL) and water (1.50 mL). The mixture was heated at 80° C. for 2 h. The reaction mixture was cooled and then concentrated under reduced pressure. The residue was triturated with water (5 mL), filtered and the filter cake was dried under reduced pressure to give (Z)-5-ethoxy-N'-hydroxy-4-methoxypicolinimidamide (1.30 g, 6.15 mmol, 91%) as a white solid. $^1$H NMR (400 MHz, DMSO-d6) δ 9.70 (s, 1H), 8.10 (s, 1H), 7.38 (s, 1H), 5.72 (s, 2H), 4.12 (q, J=7.0 Hz, 2H), 3.84 (s, 3H), 1.34 (t, J=6.9 Hz, 3H).

Step 7: Preparation of N-(2-(4-(3-(5-ethoxy-4-methoxypyridin-2-yl)-1,2,4-oxadiazol-5-yl)piperidin-1-yl)-2-oxoethyl)benzamide

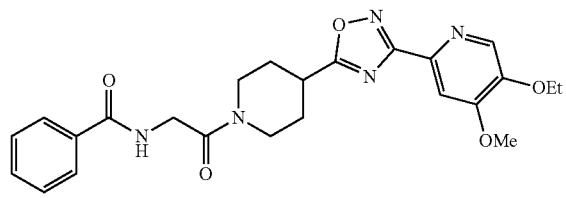 [SMILES: CCOc1cnc(-c2noc(C3CCN(C(=O)CNC(=O)c4ccccc4)CC3)n2)cc1OC]

To a stirred solution of 1-(2-benzamidoacetyl)piperidine-4-carboxylic acid (150 mg, 516.7 μmol) in N,N-dimethylformamide (2 mL) was added (Z)-5-ethoxy-N'-hydroxy-4-methoxypicolinimidamide (109 mg, 516.7 μmol), (2-(1H-benzotriazol-1-yl)-1,1,3,3-tetramethyluronium hexafluorophosphate) (195 mg, 516.7 μmol) and N-ethyl-N-(propan-2-yl)propan-2-amine (200 mg, 1.55 mmol, 270 μL). The mixture was stirred at 20° C. for 1 h, then heated at 110° C. for 1 h. The reaction mixture was cooled and then purified directly by prep-HPLC (column: Waters Xbridge 150×2.5 mm 5 μm; mobile phase: [water (10 mM ammonium carbonate)-acetonitrile]; B %: 25%-40%, 12 min) to give N-(2-(4-(3-(5-ethoxy-4-methoxypyridin-2-yl)-1,2,4-oxadiazol-5-yl)piperidin-1-yl)-2-oxoethyl)benzamide (32 mg, 67 μmol, 13%) as a yellow solid. $^1$H NMR (400 MHz, CDCl$_3$) δ 8.29 (s, 1H), 7.90-7.82 (m, 2H), 7.64 (s, 1H), 7.56-7.42 (m, 3H), 7.34 (br s, 1H), 4.52 (br d, J=13.6 Hz, 1H), 4.34-4.21 (m, 4H), 4.02 (s, 3H), 3.91 (br d, J=14.1 Hz, 1H), 3.41-3.28 (m, 2H), 3.12 (br t, J=11.0 Hz, 1H), 2.33-2.21 (m, 2H), 2.13-1.95 (m, 2H), 1.52 (t, J=7.0 Hz, 3H); LCMS (ESI) m/z: [M+H]$^+$=466.3.

Example 122: N-[2-[4-[3-(1,3-dimethyl-2-oxo-benzimidazol-5-yl)-1,2,4-oxadiazol-5-yl]-1-piperidyl]-2-oxo-ethyl]benzamide

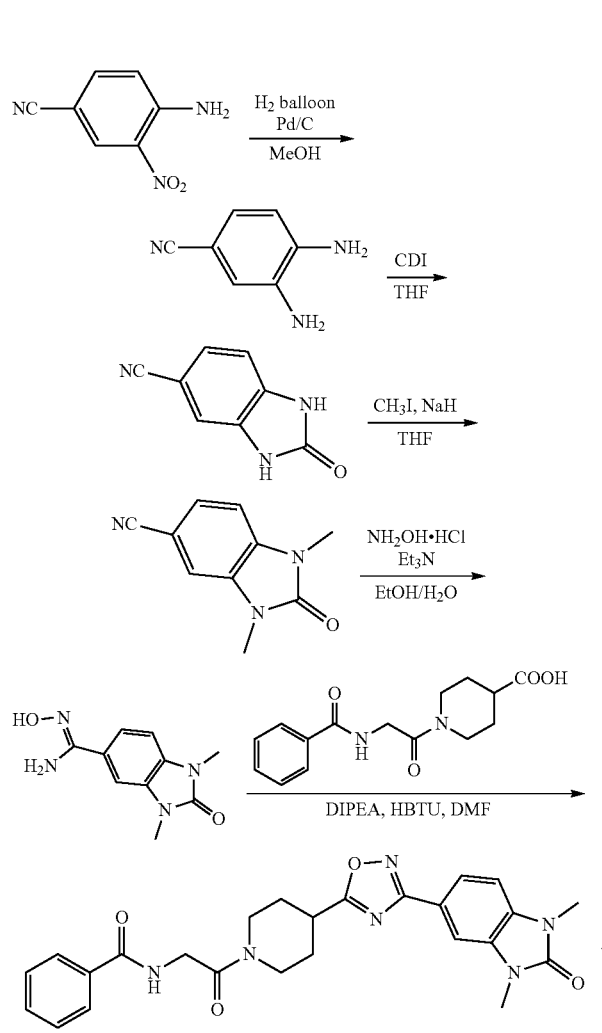

Step 1: Preparation of 3,4-diaminobenzonitrile

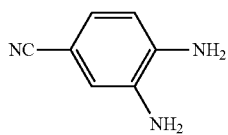

To a stirred solution of 4-amino-3-nitro-benzonitrile (2.00 g, 12.3 mmol) in methanol (20 mL) was added Pd/C (500 mg, 10% purity), then the flask was degassed and filled with hydrogen three times, and the reaction mixture stirred vigorously under hydrogen (balloon) for 18 h at 25° C. The mixture was evacuated and backfilled with nitrogen three times, then filtered through a pad of celite, and the filtrate concentrated in vacuo to give 3,4-diaminobenzonitrile (1.47 g, 11.04 mmol, 90%) as a green oil that was used in next step directly.

Step 2: Preparation of 2-oxo-1,3-dihydrobenzimidazole-5-carbonitrile

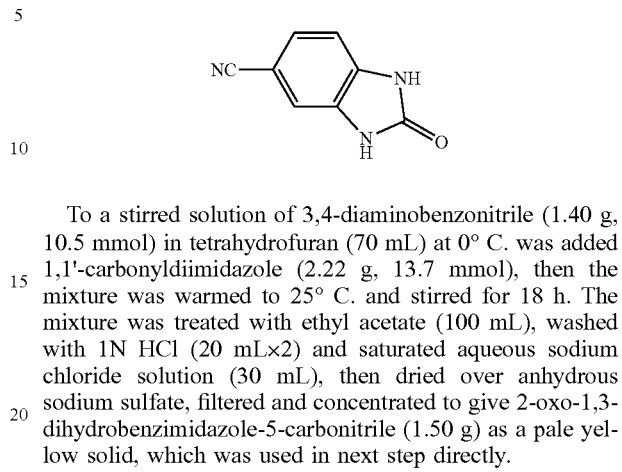

To a stirred solution of 3,4-diaminobenzonitrile (1.40 g, 10.5 mmol) in tetrahydrofuran (70 mL) at 0° C. was added 1,1'-carbonyldiimidazole (2.22 g, 13.7 mmol), then the mixture was warmed to 25° C. and stirred for 18 h. The mixture was treated with ethyl acetate (100 mL), washed with 1N HCl (20 mL×2) and saturated aqueous sodium chloride solution (30 mL), then dried over anhydrous sodium sulfate, filtered and concentrated to give 2-oxo-1,3-dihydrobenzimidazole-5-carbonitrile (1.50 g) as a pale yellow solid, which was used in next step directly.

Step 3: Preparation of 1,3-dimethyl-2-oxo-benzimidazole-5-carbonitrile

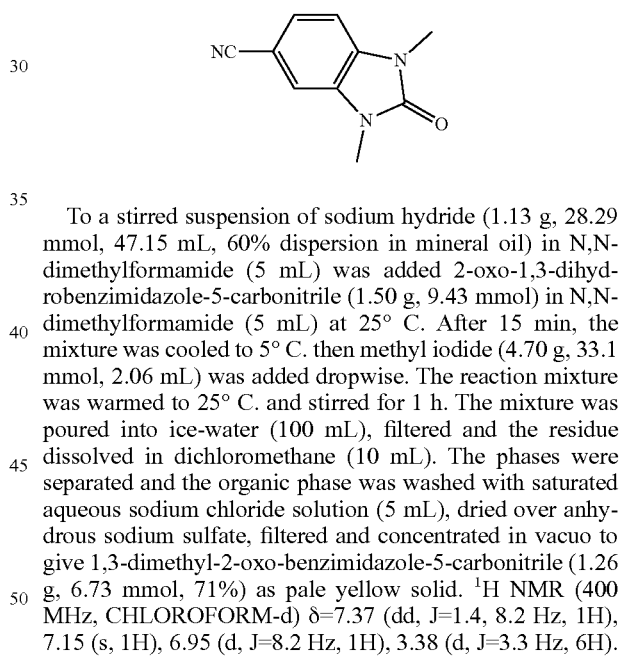

To a stirred suspension of sodium hydride (1.13 g, 28.29 mmol, 47.15 mL, 60% dispersion in mineral oil) in N,N-dimethylformamide (5 mL) was added 2-oxo-1,3-dihydrobenzimidazole-5-carbonitrile (1.50 g, 9.43 mmol) in N,N-dimethylformamide (5 mL) at 25° C. After 15 min, the mixture was cooled to 5° C. then methyl iodide (4.70 g, 33.1 mmol, 2.06 mL) was added dropwise. The reaction mixture was warmed to 25° C. and stirred for 1 h. The mixture was poured into ice-water (100 mL), filtered and the residue dissolved in dichloromethane (10 mL). The phases were separated and the organic phase was washed with saturated aqueous sodium chloride solution (5 mL), dried over anhydrous sodium sulfate, filtered and concentrated in vacuo to give 1,3-dimethyl-2-oxo-benzimidazole-5-carbonitrile (1.26 g, 6.73 mmol, 71%) as pale yellow solid. $^1$H NMR (400 MHz, CHLOROFORM-d) δ=7.37 (dd, J=1.4, 8.2 Hz, 1H), 7.15 (s, 1H), 6.95 (d, J=8.2 Hz, 1H), 3.38 (d, J=3.3 Hz, 6H).

Step 4: Preparation of N'-hydroxy-1,3-dimethyl-2-oxo-benzimidazole-5-carboxamidine

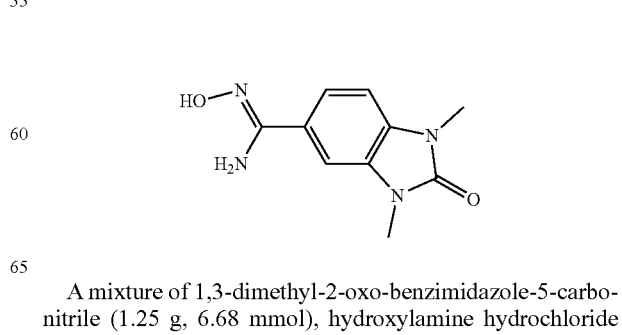

A mixture of 1,3-dimethyl-2-oxo-benzimidazole-5-carbonitrile (1.25 g, 6.68 mmol), hydroxylamine hydrochloride (928 mg, 13.4 mmol) and triethylamine (1.35 g, 13.4 mmol, 1.85 mL) in ethanol (15 mL) and water (1.50 mL) was degassed and purged with nitrogen 3 times, and then the mixture was stirred at 70° C. for 5 h under a nitrogen atmosphere. The resulting suspension was filtered then the filter cake was dissolved in ethyl acetate (20 mL), dried with anhydrous sodium sulfate, filtered and concentrated in vacuo to give N'-hydroxy-1,3-dimethyl-2-oxo-benzimidazole-5-carboxamidine (1.25 g, 5.68 mmol, 85%) as a white solid.

Step 5: Preparation of N-[2-[4-[3-(1,3-dimethyl-2-oxo-benzimidazol-5-yl)-1,2,4-oxadiazol-5-yl]-1-piperidyl]-2-oxo-ethyl]benzamide

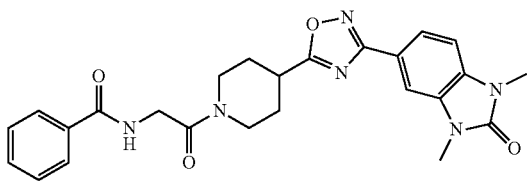 [SMILES: Cn1c(=O)n(C)c2cc(-c3noc(C4CCN(C(=O)CNC(=O)c5ccccc5)CC4)n3)ccc21]

To a stirred solution of N'-hydroxy-1,3-dimethyl-2-oxo-benzimidazole-5-carboxamidine (80 mg, 363 μmol) and 1-(2-benzamidoacetyl)piperidine-4-carboxylic acid (105 mg, 363 μmol) in N,N-dimethylformamide (1 mL) was added (2-(1H-benzotriazol-1-yl)-1,1,3,3-tetramethyluronium hexafluorophosphate) (137 mg, 363 μmol) and N-ethyl-N-(propan-2-yl)propan-2-amine (93 mg, 726.5 μmol, 126 μL) at 25° C. After stirring at 25° C. for 1 h, the mixture was warmed to 110° C. and stirred for 1 h. The mixture was cooled then purified by prep-HPLC (column: Waters Xbridge 150×25 5 μm; mobile phase: [water (10 mM ammonium carbonate)-acetonitrile]; B %: 25%-40%, 12 min) to give N-[2-[4-[3-(1,3-dimethyl-2-oxo-benzimidazol-5-yl)-1,2,4-oxadiazol-5-yl]-1-piperidyl]-2-oxo-ethyl]benzamide (38 mg, 78.7 μmol, 22%) as pale yellow solid. $^1$H NMR (400 MHz, DMSO-d6) δ=8.55 (t, J=5.7 Hz, 1H), 7.89-7.83 (m, 2H), 7.75 (dd, J=1.5, 8.2 Hz, 1H), 7.67 (d, J=1.3 Hz, 1H), 7.55-7.42 (m, 3H), 7.29 (d, J=8.2 Hz, 1H), 4.31 (br d, J=13.0 Hz, 1H), 4.16 (dd, J=3.6, 5.4 Hz, 2H), 3.97 (br d, J=13.9 Hz, 1H), 3.48-3.40 (m, 1H), 3.37 (d, J=10.4 Hz, 6H), 3.29-3.22 (m, 1H), 2.91 (br t, J=11.2 Hz, 1H), 2.13 (br t, J=12.9 Hz, 2H), 1.89-1.58 (m, 2H); LCMS (ESI) m/z: [M+H]$^+$=475.3.

Example 123: 1,3-dimethyl-5-[5-[1-(5-oxo-1-phenyl-pyrrolidine-3-carbonyl)-4-piperidyl]-1,2,4-oxadiazol-3-yl]benzimidazol-2-one Step 1: Preparation of 1,3-dimethyl-5-[5-[1-(5-oxo-1-phenyl-pyrrolidine-3-carbonyl)-4-piperidyl]-1,2,4-oxadiazol-3-yl]benzimidazol-2-one

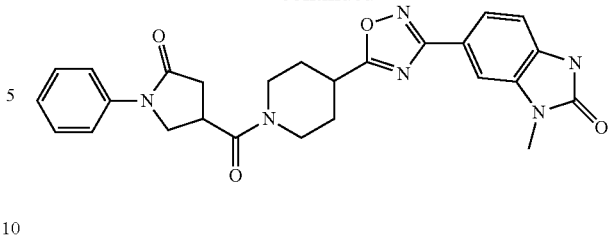

To a stirred solution of N'-hydroxy-1,3-dimethyl-2-oxo-benzimidazole-5-carboxamidine (120 mg, 544.9 μmol) and 1-(5-oxo-1-phenyl-pyrrolidine-3-carbonyl)piperidine-4-carboxylic acid (206 mg, 653.9 μmol) in N,N-dimethylformamide (2 mL) was added (2-(1H-benzotriazol-1-yl)-1,1,3,3-tetramethyluronium hexafluorophosphate) (206 mg, 544.9 μmol) and N-ethyl-N-(propan-2-yl)propan-2-amine (140 mg, 1.09 mmol, 190 μL) at 25° C. After stirring at 25° C. for 2 h, the mixture was heated at 120° C. for 1 h. The mixture was cooled then purified by prep-HPLC (column: Waters Xbridge 150×25 5 μm; mobile phase: [water (10 mM ammonium carbonate)-acetonitrile]; B %: 25%-55%, 12 min) to give 1,3-dimethyl-5-[5-[1-(5-oxo-1-phenyl-pyrrolidine-3-carbonyl)-4-piperidyl]-1,2,4-oxadiazol-3-yl]benzimidazol-2-one (57 mg, 110.5 μmol, 20%) as a yellow solid. $^1$H NMR (400 MHz, DMSO-d$_6$) δ=7.75 (td, J=1.5, 8.2 Hz, 1H), 7.69-7.62 (m, 3H), 7.38-7.32 (m, 2H), 7.29 (d, J=8.4 Hz, 1H), 7.15-7.08 (m, 1H), 4.35 (br d, J=12.8 Hz, 1H), 4.07-3.91 (m, 3H), 3.77-3.68 (m, 1H), 3.47-3.39 (m, 1H), 3.39-3.34 (m, 6H), 3.34-3.32 (m, 1H), 3.28 (s, 1H), 2.98-2.88 (m, 1H), 2.82-2.67 (m, 2H), 2.14 (br t, J=13.8 Hz, 2H), 1.90-1.63 (m, 2H). LCMS (ESI) m/z: [M+H]$^+$=501.3.

Example 124: 1-[(2,4-dimethoxyphenyl)methyl]-4-[4-[3-(1,3-dimethylindazol-6-yl)-1,2,4-oxadiazol-5-yl]piperidine-1-carbonyl]pyrrolidin-2-one

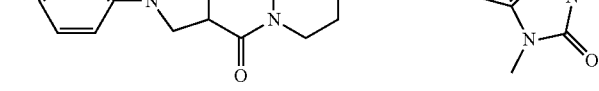

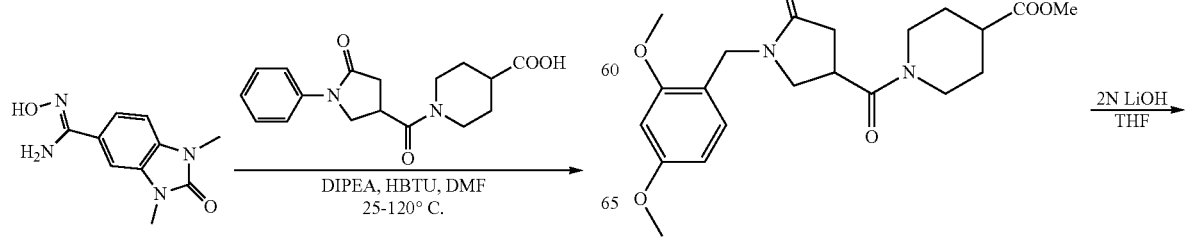

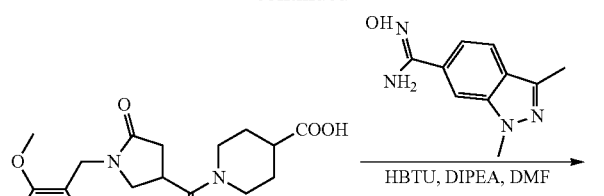

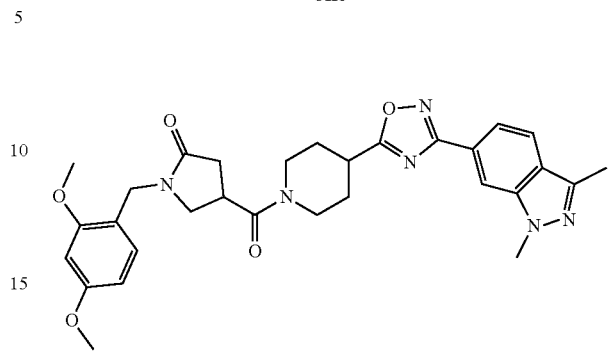

Step 1: Preparation of 1-[1-[(2,4-dimethoxyphenyl)methyl]-5-oxo-pyrrolidine-3-carbonyl]piperidine-4-carboxylic acid

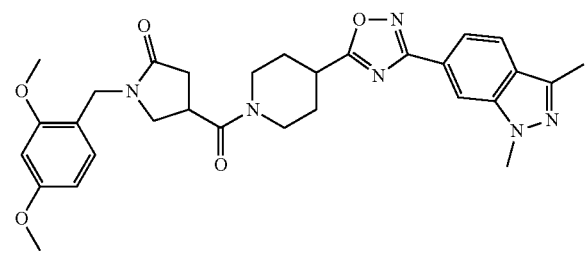

To a stirred solution of methyl 1-[1-[(2,4-dimethoxyphenyl)methyl]-5-oxo-pyrrolidine-3-carbonyl]piperidine-4-carboxylate (200 mg, 494 μmol) in tetrahydrofuran (2 mL) was added aqueous lithium hydroxide (2 M, 494 μL). The mixture was stirred at 20° C. for 2 h, then the mixture was acidified with 2N hydrochloric acid to pH 1. The mixture was extracted with ethyl acetate (20 mL×3), then the organic extracts were combined and washed with saturated aqueous sodium chloride solution (10 mL), dried over anhydrous sodium sulfate, filtered and concentrated to give 1-[1-[(2,4-dimethoxyphenyl)methyl]-5-oxo-pyrrolidine-3-carbonyl]piperidine-4-carboxylic acid (160 mg, 409.8 μmol, 83%) as a yellow solid.

Step 2: Preparation of 1-[(2,4-dimethoxyphenyl)methyl]-4-[4-[3-(1,3-dimethylindazol-6-yl)-1,2,4-oxadiazol-5-yl]piperidine-1-carbonyl]pyrrolidin-2-one

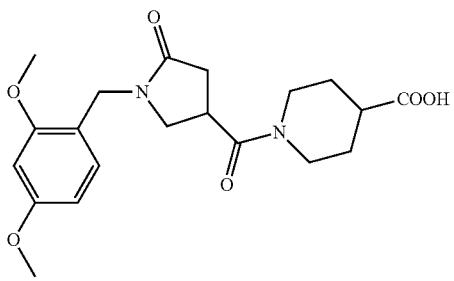 [SMILES: COc1ccc(CN2CC(C(=O)N3CCC(C(=O)O)CC3)CC2=O)c(OC)c1]

To a stirred solution of N'-hydroxy-1,3-dimethyl-indazole-6-carboxamidine (78 mg, 384 μmol) in N,N-dimethylformamide (2 mL) was added 1-[1-[(2,4-dimethoxyphenyl)methyl]-5-oxo-pyrrolidine-3-carbonyl]piperidine-4-carboxylic acid (150 mg, 384 μmol), (2-(1H-benzotriazol-1-yl)-1,1,3,3-tetramethyluronium hexafluorophosphate) (145 mg, 384 μmol) and N-ethyl-N-(propan-2-yl)propan-2-amine (148 mg, 1.15 mmol, 201 μL). The mixture was stirred at 20° C. for 1 h, then heated at 110° C. for 1 h. The reaction mixture was cooled then purified directly by prep-HPLC (column: Waters Xbridge 150×2.5 mm 5 μm; mobile phase: [water (10 mM ammonium carbonate)-acetonitrile]; B %: 30%-50%, 12 min) to give 1-[(2,4-dimethoxyphenyl)methyl]-4-[4-[3-(1,3-dimethylindazol-6-yl)-1,2,4-oxadiazol-5-yl]piperidine-1-carbonyl]pyrrolidin-2-one (35 mg, 64 μmol, 17%) as a pink solid. $^1$H NMR (400 MHz, CDCl$_3$) δ 8.09 (d, J=4.1 Hz, 1H), 7.85-7.80 (m, 1H), 7.77-7.71 (m, 1H), 7.17 (d, J=8.7 Hz, 1H), 6.49-6.43 (m, 2H), 4.59-4.38 (m, 3H), 4.08 (d, J=1.8 Hz, 3H), 3.98-3.86 (m, 1H), 3.84-3.77 (m, 6H), 3.71-3.62 (m, 1H), 3.46-3.24 (m, 4H), 3.13-2.96 (m, 1H), 2.85-2.75 (m, 1H), 2.67 (m, 1H), 2.60 (s, 3H), 2.21 (br s, 2H), 2.04-1.87 (m, 2H); LCMS (ESI) m/z: [M+H]$^+$=559.3.

Example 125: 1-cyclohexyl-4-[4-[3-(3,4-dimethoxyphenyl)-1,2,4-oxadiazol-5-yl]piperidine-1-carbonyl]pyrrolidin-2-one

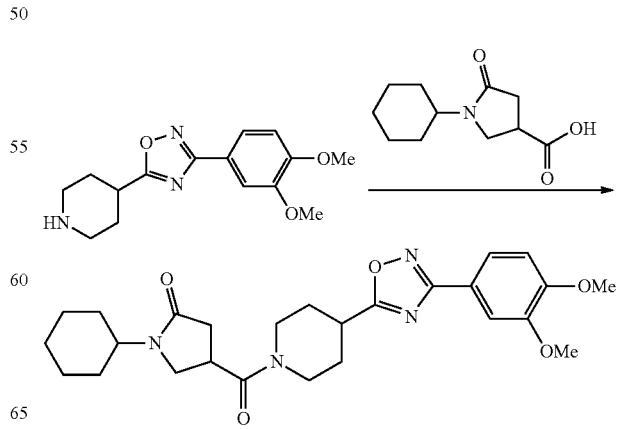

Step 1: Preparation of 1-cyclohexyl-4-[4-[3-(3,4-dimethoxyphenyl)-1,2,4-oxadiazol-5-yl]piperidine-1-carbonyl]pyrrolidin-2-one

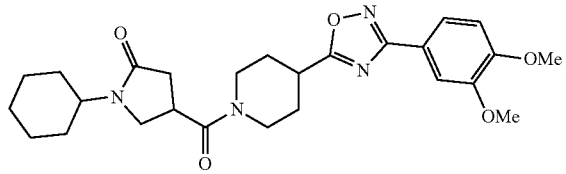 [SMILES: COc1ccc(-c2noc(C3CCN(C(=O)C4CC(=O)N(C5CCCCC5)C4)CC3)n2)cc1OC]

To a stirred solution of 3-(3,4-dimethoxyphenyl)-5-(4-piperidyl)-1,2,4-oxadiazole (100 mg, 345.6 μmol) and 1-cyclohexyl-5-oxo-pyrrolidine-3-carboxylic acid (73 mg, 345.6 μmol) in N,N-dimethylformamide (1.00 mL) was added (2-(1H-benzotriazol-1-yl)-1,1,3,3-tetramethyluronium hexafluorophosphate) (131 mg, 345.63 μmol) and N-ethyl-N-(propan-2-yl)propan-2-amine (89 mg, 691 μmol, 120 μL) at 25° C. The mixture was then stirred for an additional 2 h at 25° C. The reaction mixture was concentrated under reduced pressure to give a residue further purified by chromatography [Waters Xbridge 150×25 5 μm; mobile phase: [water (10 mM ammonium carbonate)-acetonitrile]; B %: 30%-50%, 12 min]. The title product, 1-cyclohexyl-4-[4-[3-(3,4-dimethoxyphenyl)-1,2,4-oxadiazol-5-yl]piperidine-1-carbonyl]pyrrolidin-2-one, was isolated as a white solid (97 mg, 201.6 μmol, 58%). $^1$H NMR (400 MHz, CHLOROFORM-d) δ=7.69 (dd, J=1.7, 8.3 Hz, 1H), 7.57 (d, J=1.8 Hz, 1H), 6.97 (d, J=8.4 Hz, 1H), 4.60-4.44 (dd, 1H), 3.97 (d, J=7.9 Hz, 6H), 3.77 (br t, J=7.0 Hz, 1H), 3.51-3.21 (m, 4H), 3.14-2.97 (m, 1H), 2.77-2.61 (m, 2H), 2.28-2.17 (m, 2H), 2.03-1.89 (m, 2H), 1.88-1.64 (m, 7H), 1.48-1.32 (m, 4H), 1.23-1.04 (m, 1H); LCMS (ESI) m/z: [M+H]$^+$=483.3.

Example 126: 4-[4-[3-(1,3-dimethylindazol-6-yl)-1,2,4-oxadiazol-5-yl]piperidine-1-carbonyl]pyrrolidin-2-one

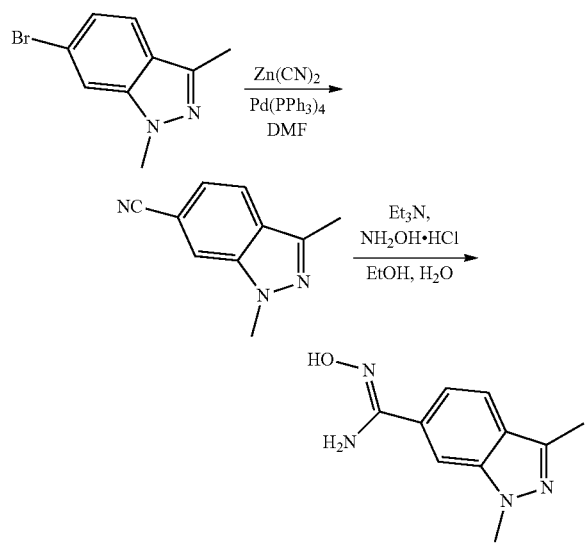

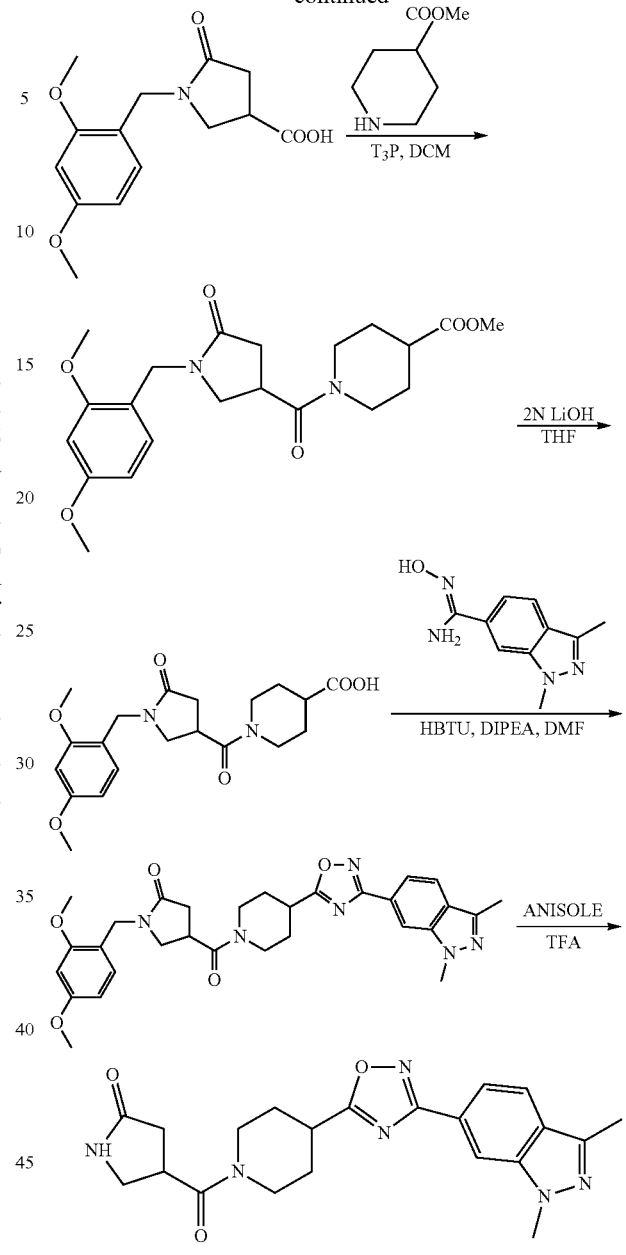

Step 1: Preparation of 1,3-dimethylindazole-6-carbonitrile

To a stirred solution of 6-bromo-1,3-dimethyl-indazole (3.0 g, 13.33 mmol) in N,N-dimethylformamide (30 mL) was added, under a nitrogen atmosphere, zinc cyanide (1.57 g, 13.33 mmol, 846 μL) and tetrakis(triphenylphosphine)

palladium(0) (1.54 g, 1.33 mmol). The mixture was then stirred at 110° C. for 16 h and then cooled to 20° C. Water (50 mL) was added to the reaction mixture which was extracted with ethyl acetate (80 mL×3). The organic extracts were combined, washed with saturated aqueous sodium chloride (50 mL), dried over anhydrous sodium sulfate, filtered and concentrated under reduced pressure to give the crude product further purified by chromatography (silica, petroleum ether:ethyl acetate=50:1 to 10:1. The title compound, 1,3-dimethylindazole-6-carbonitrile was isolated as a white solid (1.92 g, 11.21 mmol, 84%) $^1$H NMR (400 MHz, CDCl$_3$) δ 7.78-7.67 (m, 2H), 7.33 (dd, J=1.0, 8.3 Hz, 1H), 4.05 (s, 3H), 2.59 (s, 3H)

Step 2: Preparation of N'-hydroxy-1,3-dimethyl-indazole-6-carboxamidine

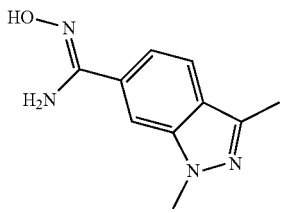

To a stirred solution of 1,3-dimethylindazole-6-carbonitrile (2.50 g, 14.60 mmol) in ethanol (30 mL) was added hydroxylamine hydrochloride (2.03 g, 29.20 mmol), triethylamine (2.95 g, 29.20 mmol, 4.05 mL) and water (3 mL). The mixture was stirred at 80° C. for 2 h, and then concentrated under reduced pressure. Water (5 mL) was added to the residue, the resulting solid was collected by filtration and used for the next step without further purification. The title compound, N'-hydroxy-1,3-dimethyl-indazole-6-carboxamidine, was isolated as a white solid (2.86 g, 14.00 mmol, 96%); $^1$H NMR (400 MHz, DMSO-d6) δ 9.70 (s, 1H), 7.85 (s, 1H), 7.63 (d, J=8.4 Hz, 1H), 7.47 (dd, J=1.2, 8.5 Hz, 1H), 5.89 (s, 2H), 3.96 (s, 3H), 2.46 (s, 3H).

Step 3: Preparation of methyl 1-[1-[(2,4-dimethoxyphenyl)methyl]-5-oxo-pyrrolidine-3-carbonyl]piperidine-4-carboxylate

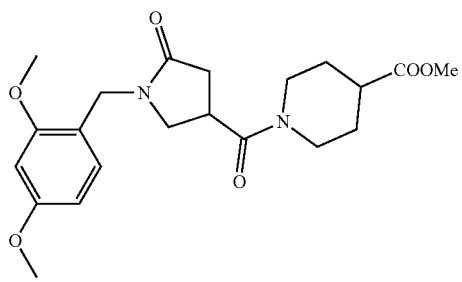 [SMILES: COC(=O)C1CCN(C(=O)C2CC(=O)N(Cc3ccc(OC)cc3OC)C2)CC1]

To a stirred solution of 1-[(2,4-dimethoxyphenyl)methyl]-5-oxo-pyrrolidine-3-carboxylic acid (1.0 g, 3.58 mmol) in dichloromethane (15 mL) was added methyl piperidine-4-carboxylate (512 mg, 3.58 mmol), 2,4,6-tripropyl-1,3,5,2,4,6-trioxatriphosphinane 2,4,6-trioxide in ethyl acetate (2.51 g, 3.94 mmol, 2.34 mL, 50% purity), triethylamine (724 mg, 7.16 mmol, 992 pt), and the reaction mixture was stirred at 20° C. for 2 h, Water (30 mL) was added to the mixture which was extracted with dichloromethane (50 mL×3)). The organic extracts were combined, washed with saturated aqueous sodium chloride (30 mL), dried over anhydrous sodium sulfate, filtered and concentrated to give methyl 1-[1-[(2,4-dimethoxyphenyl)methyl]-5-oxo-pyrrolidine-3-carbonyl]piperidine-4-carboxylate isolated as a yellow oil (1.37 g, 3.39 mmol, 95%) and used for the next step without further purification. $^1$H NMR (400 MHz, CDCl$_3$) δ 7.15 (br d, J=8.5 Hz, 1H), 6.51-6.39 (m, 2H), 4.50-4.33 (m, 3H), 3.80 (s, 6H), 3.75 (br d, J=5.0 Hz, 1H), 3.70 (s, 3H), 3.65-3.55 (m, 1H), 3.42-3.29 (m, 2H). 3.19-3.05 (m, 1H), 2.94-2.71 (m, 2H), 2.64-2.49 (m, 2H), 1.94 (br dd, J=3.3, 13.3 Hz, 2H). 1.62 (br s, 2H).

Step 4: Preparation of 1-[1-[(2,4-dimethoxyphenyl)methyl]-5-oxo-pyrrolidine-3-carbonyl]piperidine-4-carboxylic acid

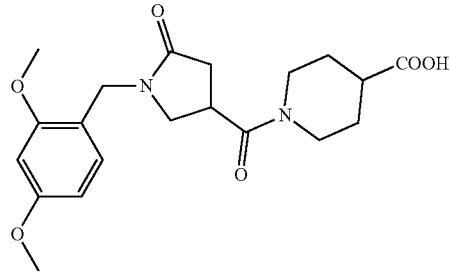 [SMILES: COc1ccc(CN2CC(C(=O)N3CCC(C(=O)O)CC3)CC2=O)c(OC)c1]

To a stirred solution of methyl 1-[1-[(2,4-dimethoxyphenyl)methyl]-5-oxo-pyrrolidine-3-carbonyl]piperidine-4-carboxylate (1.17 g, 2.89 mmol) in tetrahydrofuran (15 mL) was added lithium hydroxide (2 M solution in tetrahydrofuran, 2.89 mL). The reaction mixture was stirred at 20° C. for 1 h, and then acidified until pH 1 using a 2M aqueous solution of hydrochloric acid. The resulting mixture was extracted with ethyl acetate (80 mL×3). The organic extracts were combined, washed with saturated aqueous sodium chloride (30 mL), dried over anhydrous sodium sulfate, filtered and concentrated to give 1-[1-[(2,4-dimethoxyphenyl)methyl]-5-oxo-pyrrolidine-3-carbonyl]piperidine-4-carboxylic acid isolated as a white solid (1.0 g, 2.56 mmol, 89%) and used for the next step without further purification. $^1$H NMR (400 MHz, Methanol-d4) δ 7.09 (dd, J=2.9, 8.4 Hz, 1H), 6.52 (d, J=2.2 Hz, 1H), 6.47 (dd, J=2, 3, 8.3 Hz, 1H), 4.46-4.25 (m, 3H), 3.92-3.83 (m, 1H), 3.80 (d, J=1.3 Hz, 3H), 3.78-3.75 (m, 3H), 3.65-3.36 (m, 3H), 3.25-3.11 (m, 1H), 2.92-2.80 (m, 1H), 2.71-2.52 (m, 3H), 1.97-1.87 (m, 2H), 1.68-1.42 (m, 2H).

Step 5: Preparation of 1-[(2,4-dimethoxyphenyl)methyl]-4-[4-[3-(1,3-dimethylindazol-6-yl)-1,2,4-oxadiazol-5-yl]piperidine-1-carbonyl]pyrrolidin-2-one

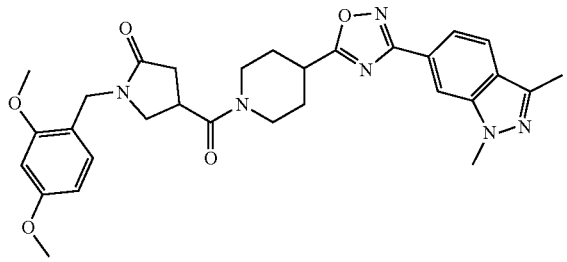 [SMILES: COc1ccc(CN2CC(C(=O)N3CCC(c4nc(-c5ccc6c(C)nn(C)c6c5)no4)CC3)CC2=O)c(OC)c1]

To a stirred solution of N'-hydroxy-1,3-dimethyl-indazole-6-carboxamidine (261 mg, 1.28 mmol) in N,N-dimethylformamide (6 mL) was added 1-[1-[(2,4-dimethoxyphenyl)methyl]-5-oxo-pyrrolidine-3-carbonyl]piperidine-4-carboxylic acid (500 mg, 1.28 mmol), (2-(1H-benzotriazol-1-yl)-1,1,3,3-tetramethyluronium hexafluorophosphate) (485 mg, 1.28 mmol) and N-ethyl-N-(propan-2-yl)propan-2-amine (496 mg, 3.84 mmol, 670 μL). The reaction mixture was stirred at 20° C. for 1 h, at 110° C. for 1 h. and then cooled to 20° C. Water (10 mL) was added to the mixture, which was extracted with ethyl acetate (40 mL×3). The organic extracts were combined, washed with saturated aqueous sodium chloride (10 mL), dried over anhydrous sodium sulfate, filtered and concentrated under reduced pressure to provide the crude product further purified by chromatography (Dichloromethane:Methanol=1:0 to 10:1). The title compound, 1-[(2,4-dimethoxyphenyl)methyl]-4-[4-[3-(1,3-dimethylindazol-6-yl)-1,2,4-oxadiazol-5-yl]piperidine-1-carbonyl]pyrrolidin-2-one was isolated as a yellow solid (500 mg, 895 μmol, 70%). $^1$H NMR (400 MHz, CDCl$_3$) δ 8.11 (d, J=5.0 Hz, 1H), 7.84 (d, J=8.5 Hz, 1H), 7.79-7.73 (m, 1H), 7.17 (d, J=8.9 Hz, 1H), 6.50-6.44 (m, 2H), 4.58-4.41 (m, 3H), 4.10 (s, 3H), 3.97-3.88 (m, 1H), 3.84-3.79 (m, 6H), 3.69 (br d, J=6.7 Hz, 1H), 3.47-3.27 (m, 4H), 3.16 (q, J=7.5 Hz, 1H), 2.83-2.76 (m, 1H), 2.71-2.64 (m, 1H), 2.62 (s, 3H), 2.25 (br s, 2H), 2.03-1.88 (m, 2H)

Step 6: Preparation of 4-[4-[3-(1,3-dimethylindazol-6-yl)-1,2,4-oxadiazol-5-yl]piperidine-1-carbonyl]pyrrolidin-2-one

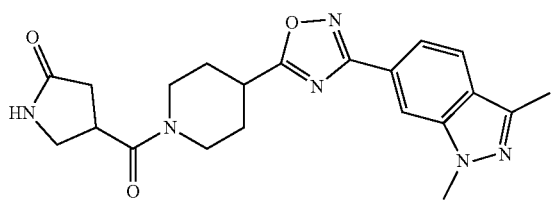 [SMILES: Cc1nn(C)c2cc(-c3noc(C4CCN(C(=O)C5CNC(=O)C5)CC4)n3)ccc12]

A mixture of 1-[(2,4-dimethoxyphenyl)methyl]-4-[4-[3-(1,3-dimethylindazol-6-yl)-1,2,4-oxadiazol-5-yl]piperidine-1-carbonyl]pyrrolidin-2-one (150 mg, 268.51 μmol), anisole (58 mg, 537 μmol, 58 μL) in trifluoro acetic acid (2 mL) was degassed, purged with nitrogen three times, and then stirred at 80° C. for 2 h under a nitrogen atmosphere. The reaction mixture was concentrated under reduced pressure to give the crude product further purified by chromatography (column: Waters Xbridge 150×25 5 μm; mobile phase: [water (10 mM ammonium carbonate)-acetonitrile]; B %: 15%-35%, 12 min). The title compound, 4-[4-[3-(1,3-dimethylindazol-6-yl)-1,2,4-oxadiazol-5-yl]piperidine-1-carbonyl]pyrrolidin-2-one, was isolated as a white solid (50 mg, 122.8 μmol, 46%) $^1$H NMR (400 MHz, CDCl$_3$) δ 8.10 (br s, 1H), 7.86-7.80 (m, 1H), 7.77-7.72 (m, 1H), 5.74 (br s, 1H), 4.55 (br t, J=14.1 Hz, 1H), 4.08 (s, 3H), 3.95 (br d, J=9.0 Hz, 1H), 3.82-3.75 (m, 1H), 3.66-3.53 (m, 2H), 3.43-3.29 (m, 2H), 3.15-3.02 (m, 1H), 2.77-2.67 (m, 1H), 2.60 (s, 3H), 2.59-2.52 (m, 1H), 2.33-2.18 (m, 2H), 2.08-1.92 (m, 2H); LCMS (ESI) m/z: [M+H]$^+$=409.3.

Example 127: [4-[3-(3,4-dimethoxyphenyl)-1,2,4-oxadiazol-5-yl]-1-piperidyl]-(4-isopropylphenyl)methanone

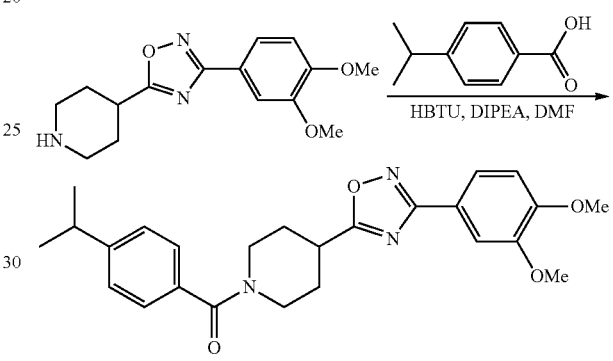

Step 1: Preparation of [4-[3-(3,4-dimethoxyphenyl)-1,2,4-oxadiazol-5-yl]-1-piperidyl]-(4-isopropylphenyl)methanone

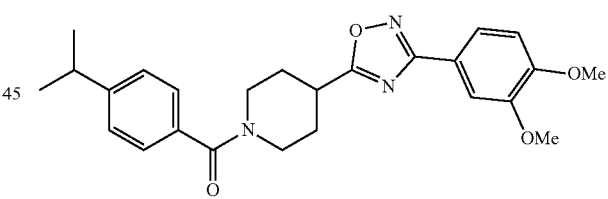

To a stirred solution of 3-(3,4-dimethoxyphenyl)-5-(4-piperidyl)-1,2,4-oxadiazole (80 mg, 276.50 μmol) and 4-isopropylbenzoic acid (54 mg, 331.80 μmol) in N,N-dimethylformamide (1.00 mL) was added (2-(1H-benzotriazol-1-yl)-1,1,3,3-tetramethyluronium hexafluorophosphate) (125 mg, 331.80 μmol) and N-ethyl-N-(propan-2-yl)propan-2-amine (71 mg, 553 μmol, 96 μL) at 25° C. The mixture was stirred at 25° C. for 2 h and then concentrated under reduced pressure to provide a residue purified by chromatography (Waters Xbridge 150×25 5 μm; mobile phase: [water (10 mM ammonium carbonate)-acetonitrile]; B %: 40%-70%, 12 min. The title compound, [4-[3-(3,4-dimethoxyphenyl)-1,2,4-oxadiazol-5-yl]-1-piperidyl]-(4-isopropylphenyl)methanone was isolated as a yellow solid (83 mg, 191.6 μmol, 69%) $^1$H NMR (400 MHz, CHLOROFORM-d) δ=7.71 (dd, J=1.9, 8.3 Hz, 1H), 7.59 (d, J=1.9 Hz, 1H), 7.40-7.36 (dd, 2H), 7.31-7.26 (t, 2H), 6.97 (d, J=8.4 Hz, 1H), 4.65 (br s, 1H), 3.97 (d, J=8.5 Hz, 6H), 3.36-3.15 (m, 3H), 2.95 (spt, J=6.9 Hz, 1H), 2.33-1.62 (m, 4H), 2.36-1.62 (m, 1H), 1.28 (d, J=6.9 Hz, 6H); LCMS (ESI) m/z: [M+H]⁺=436.3.

Example 128: 2-[2-[4-[3-(4-ethoxy-3-methoxy-phenyl)-1,2,4-oxadiazol-5-yl]-1-piperidyl]-1-(hydroxymethyl)-2-oxo-ethyl]isoindolin-1-one

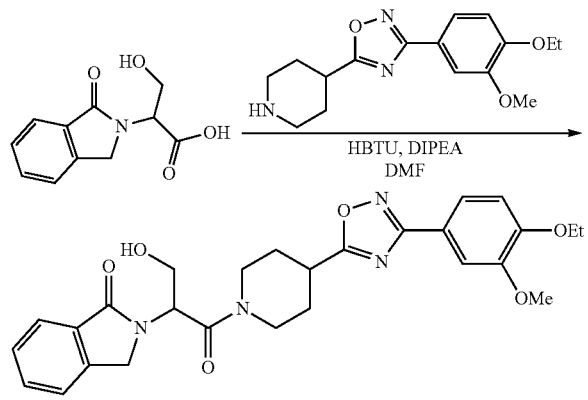

Example 129: 2-[2-[4-[3-(1,3-dimethylindazol-6-yl]-1,2,4-oxadiazol-5-yl]-1-piperidyl]-1-(hydroxymethyl)-2-oxo-ethyl]isoindolin-1-one

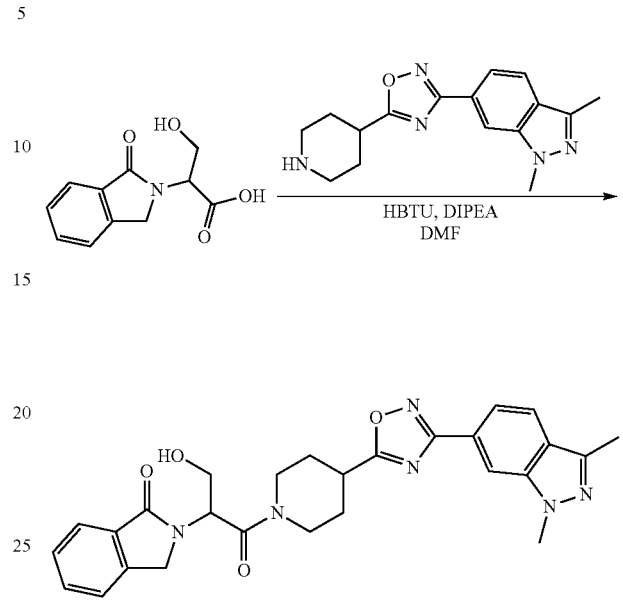

Step 1: Preparation of 2-[2-[4-[3-(4-ethoxy-3-methoxy-phenyl)-1,2,4-oxadiazol-5-yl]-1-piperidyl]-1-(hydroxymethyl)-2-oxo-ethyl]isoindolin-1-one Step 1: Preparation of 2-[2-[4-[3-(1,3-dimethylindazol-6-yl)-1,2,4-oxadiazol-5-yl]-1-piperidyl]-1-(hydroxymethyl)-2-oxo-ethyl]isoindolin-1-one

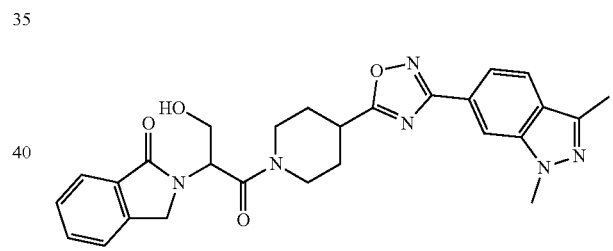

To a stirred solution of 3-hydroxy-2-(1-oxoisoindolin-2-yl)propanoic acid (120 mg, 542 µmol) in N,N-dimethylformamide (2 mL) was added 3-(4-ethoxy-3-methoxy-phenyl)-5-(4-piperidyl)-1,2,4-oxadiazole (153 mg, 452 µmol, 1.00 eq, hydrochloric acid), (2-(1H-benzotriazol-1-yl)-1,1,3,3-tetramethyluronium hexafluorophosphate) (205 mg, 542 µmol) and N-ethyl-N-(propan-2-yl)propan-2-amine (175 mg, 1.36 mmol, 236 µL), The mixture was stirred at 20° C. for 1 h, and then purified directly by prep-HPLC (column: Waters Xbridge 150×25 5 µm; mobile phase: [water (10 mM ammonium carbonate)-acetonitrile]; B %: 30%-60%, 12 min). The title compound, 2-[2-[4-[3-(4-ethoxy-3-methoxy-phenyl)-1,2,4-oxadiazol-5-yl]-1-piperidyl]-1-(hydroxymethyl)-2-oxo-ethyl]isoindolin-1-one was isolated as a white solid (139 mg, 274.8 µmol, 61%). ¹H NMR (400 MHz, CDCl₃) δ 7.88 (t, J=6.8 Hz, 1H), 7.68-7.44 (m, 5H), 6.92 (dd, J=8.4, 17.7 Hz, 1H), 5.38 (t, J=4.6 Hz, 1H), 4.84 (br d, J=17.2 Hz, 1H), 4.48-4.35 (m, 2H), 4.21-3.98 (m, 5H), 3.94 (d, J=17.1 Hz, 3H), 3.77-3.41 (m, 1H), 3.39-3.04 (m, 3H), 2.26-1.78 (m, 4H), 1.50 (q, J=6.8 Hz, 3H); LCMS (ESI) m/z: [M+H]⁺=507.3.

To a stirred solution of 3-hydroxy-2-(1-oxoisoindolin-2-yl)propanoic acid (120 mg, 542 µmol) in N,N-dimethylformamide (2 mL) was added 3-(1,3-dimethylindazol-6-yl)-5-(4-piperidyl)-1,2,4-oxadiazole, hydrochloride (150 mg, 452 µmol), (2-(1H-benzotriazol-1-yl)-1,1,3,3-tetramethyluronium hexafluorophosphate) (205 mg, 542 µmol) and N-ethyl-N-(propan-2-yl)propan-2-amine (175 mg, 1.36 mmol, 236 µL). The reaction mixture was stirred at 20° C. for 1 h and then purified directly by prep-HPLC (column: Waters Xbridge 150×25 5 µm; mobile phase: [water (10 mM ammonium carbonate)-acetonitrile]; B %: 25%-55%, 12 min). The title compound, 2-[2-[4-[3-(1,3-dimethylindazol-6-yl)-1,2,4-oxadiazol-5-yl]-1-piperidyl]-1-(hydroxymethyl)-2-oxo-ethyl]isoindolin-1-one was isolated as a white solid (68 mg, 137 µmol, 30%) ¹H NMR (400 MHz, CDCl₃) δ 8.10-7.97 (m, 1H), 7.91-7.65 (m, 3H), 7.62-7.44 (m, 3H), 5.40 (t, J=4.9 Hz, 1H), 4.82 (dd, J=3.0, 17.3 Hz, 1H), 4.51-4.37 (m, 2H), 4.16-3.99 (m, 6H), 3.65 (br s, 1H), 3.43-3.04 (m, 3H), 2.58 (d, J=6.7 Hz, 3H), 2.27-1.93 (m, 3.6H), 1.62-1.50 (m, 0.4H); LCMS (ESI) m/z: [M+H]⁺=501.3.

Example 130: 4-[4-[3-(6-ethoxy-5-methoxy-3-pyridyl)-1,2,4-oxadiazol-5-yl]piperidine-1-carbonyl]-1-phenyl-pyrrolidin-2-one

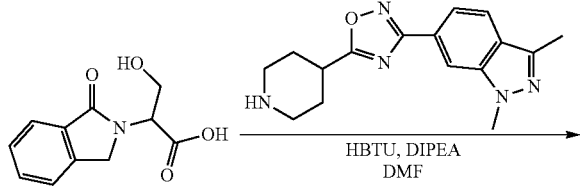

Step 1: Preparation of 4-[4-[3-(6-ethoxy-5-methoxy-3-pyridyl)-1,2,4-oxadiazol-5-yl]piperidine-1-carbonyl]-1-phenyl-pyrrolidin-2-one

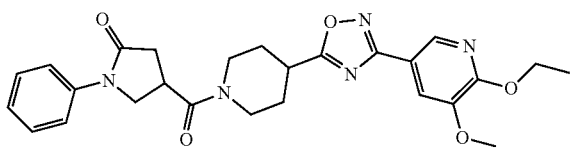 [SMILES: CCOc1ncc(-c2noc(C3CCN(C(=O)C4CC(=O)N(c5ccccc5)C4)CC3)n2)cc1OC]

A solution of (Z)-6-ethoxy-N'-hydroxy-5-methoxynicotinimidamide (100 mg, 474 μmol) in N,N-dimethylformamide (2.00 mL) was added 1-(5-oxo-1-phenylpyrrolidine-3-carbonyl)piperidine-4-carboxylic acid (150 mg, 474 μmol) N-ethyl-N-(propan-2-yl)propan-2-amine (183 mg, 1.42 mmol, 248 μL), and (2-(1H-benzotriazol-1-yl)-1,1,3,3-tetramethyluronium hexafluorophosphate) (197 mg, 521.58 μmol). The mixture was stirred at 25° C. for 12 h, and then at 110° C. for 1 h. The residue was purified directly by pre-HPLC (column: Waters Xbridge 150×2.5 mm 5 μm; mobile phase: [water (10 mM ammonium carbonate)-acetonitrile]; B %: 30%-50%, 12 min) to give 4-[4-[3-(6-ethoxy-5-methoxy-3-pyridyl)-1,2,4-oxadiazol-5-yl]piperidine-1-carbonyl]-1-phenyl-pyrrolidin-2-one (96 mg, 194.7 μmol, 41%), isolated as a yellow solid. $^1$H NMR (400 MHz, CHLOROFORM-d) δ=8.44 (s, 1H), 7.64-7.57 (m, 3H), 7.41-7.34 (m, 2H), 7.21-7.14 (m, 1H), 4.61-4.46 (m, 3H), 4.37-4.28 (m, 1H), 4.02-3.90 (m, 5H), 3.58 (td, J=8.4, 16.6 Hz, 1H), 3.44-3.26 (m, 2H), 3.17-2.91 (m, 2H), 2.89-2.78 (m, 1H), 2.31-2.17 (m, 2H), 2.06-1.87 (m, 2H), 1.47 (t, J=7.2 Hz, 3H) LCMS (ESI) [M+H]$^+$=492.1.

Example 131: 2-(2-(4-(3-(6-ethoxy-5-methoxypyridin-3-yl)-1,2,4-oxadiazol-5-yl)piperidin-1-yl)-2-oxoethyl)isoindolin-1-one

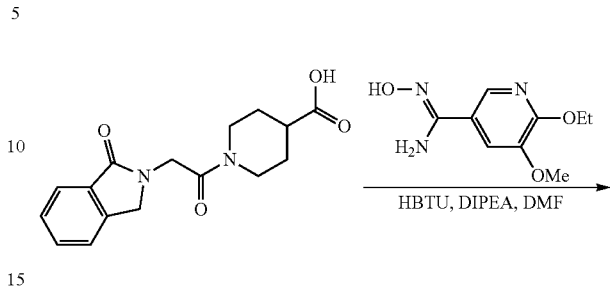

Step 1: Preparation of 2-(2-(4-(3-(6-ethoxy-5-methoxypyridin-3-yl)-1,2,4-oxadiazol-5-yl)piperidin-1-yl)-2-oxoethyl)isoindolin-1-one

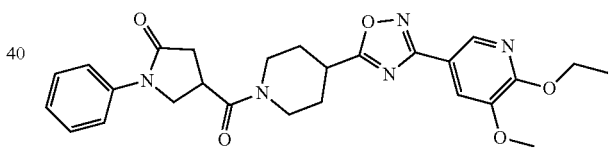

A solution of 6-ethoxy-N'-hydroxy-5-methoxy-pyridine-3-carboxamidine (104 mg, 496 μmol) in N,N-dimethylformamide (2 mL) was added 1-[2-(1-oxoisoindolin-2-yl)acetyl]piperidine-4-carboxylic acid (150 mg, 496 μmol), N-ethyl-N-(propan-2-yl)propan-2-amine (192 mg, 1.49 mmol, 259 μL) and (2-(1H-benzotriazol-1-yl)-1,1,3,3-tetramethyluronium hexafluorophosphate) (206 mg, 545.77 μmol). The mixture was stirred at 25° C. for 12 h, and then at 110° C. for 1 h. The mixture was purified by pre-HPLC (column: Waters Xbridge 150×25 5 μm; mobile phase: [water (10 mM ammonium carbonate)-acetonitrile]; B %: 25%-50%, 12 min) to give 2-[2-[4-[3-(6-ethoxy-5-methoxy-3-pyridyl)-1,2,4-oxadiazol-5-yl]-1-piperidyl]-2-oxo-ethyl]isoindolin-1-one (82 mg, 171 μmol, 34%), isolated as a pink solid. $^1$H NMR (400 MHz, CHLOROFORM-d) δ=8.46 (d, J=1.8 Hz, 1H), 7.89 (d, J=7.8 Hz, 1H), 7.65 (d, J=1.5 Hz, 1H), 7.62-7.56 (m, 1H), 7.50 (t, J=6.7 Hz, 2H), 4.64-4.44 (m, 7H), 4.11 (br d, J=13.7 Hz, 1H), 3.98 (s, 3H), 3.46-3.26 (m, 2H), 3.08 (br t, J=10.9 Hz, 1H), 2.24 (br d, J=14.0 Hz, 2H), 2.09-1.89 (m, 2H), 1.50 (t, J=7.1 Hz, 3H); LCMS (ESI) [M+H]$^+$=478.1.

Example 132: N-(2-(4-(3-(6-ethoxy-5-methoxypyridin-3-yl)-1,2,4-oxadiazol-5-yl)piperidin-1-yl)-2-oxoethyl)benzamide

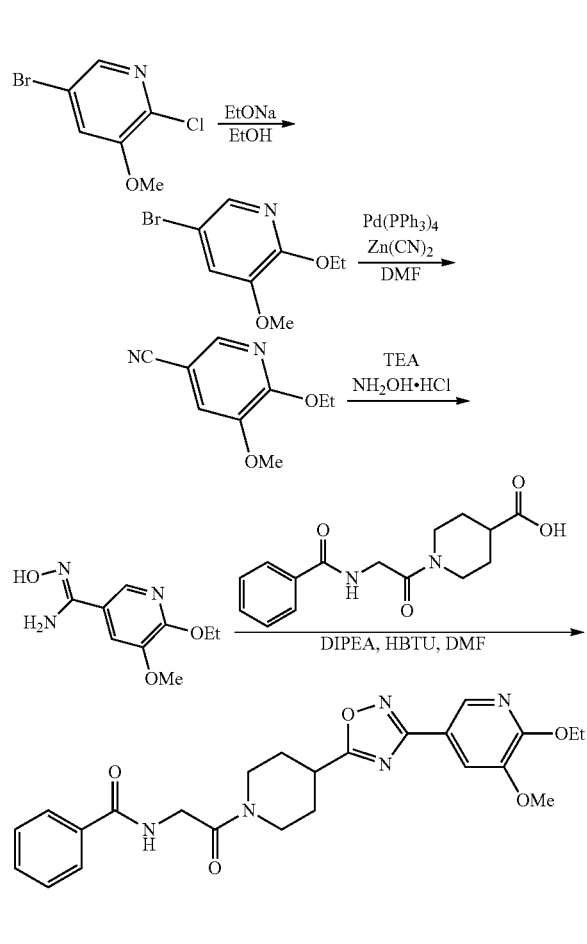

Step 1: Preparation of 5-bromo-2-ethoxy-3-methoxypyridine

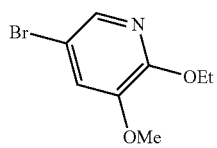 [SMILES: CCOc1ncc(Br)cc1OC]

A solution of sodium (465 mg, 20.23 mmol, 479 µL) in ethanol (5 mL) was stirred at 20° C. for 2 h. 5-Bromo-2-chloro-3-methoxypyridine (1.50 g, 6.74 mmol) was then added to the mixture which was stirred at 100° C. for 12 h. The reaction mixture was concentrated under reduced pressure. Water (50 mL) was then added to the residue. The mixture was extracted with dichloromethane (60 mL×3). The organic extracts were combined, dried over anhydrous sodium sulfate, filtered and concentrated under reduced pressure to provide 5-bromo-2-ethoxy-3-methoxypyridine, isolated as a white solid (1.70 g, crude), and used for the next step without further purification. $^1$H NMR (400 MHz, METHANOL-d4) δ=7.70 (d, J=2.0 Hz, 1H), 7.34 (d, J=2.2 Hz, 1H), 4.34 (q, J=7.1 Hz, 2H), 3.83 (s, 3H), 1.36 (t, J=7.1 Hz, 3H).

Step 2: Preparation of 6-ethoxy-5-methoxynicotinonitrile

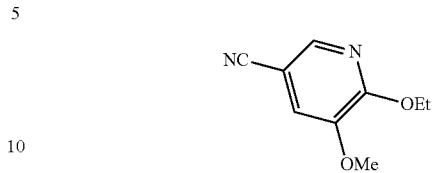

To a stirred solution of 5-bromo-2-ethoxy-3-methoxypyridine (1.70 g, 7.33 mmol) in N,N-dimethylformamide (10 mL) was added zinc cyanide (860 mg, 7.33 mmol, 464 µL), and tetrakis(triphenylphosphine)palladium(0) (847 mg, 733 µmol, 0.10 eq), the mixture was degassed with nitrogen for three times. The resulting mixture was stirred at 110° C. for 12 h under nitrogen atmosphere and then poured into water (30 mL). The mixture was then extracted with dichloromethane (50 mL×3). The organic extracts were combined, dried over anhydrous sodium sulfate, filtered and concentrated under reduced pressure to provide the crude product purified by chromatography (silica, petroleum ether:ethyl acetate=50:1 R$_f$=0.6). The title compound, 6-ethoxy-5-methoxy-pyridine-3-carbonitrile was isolated as a white solid (820 mg, 4.60 mmol, 63%) $^1$H NMR (400 MHz, METHANOL-d4) δ=8.08 (d, J=1.8 Hz, 1H), 7.49 (d, J=1.8 Hz, 1H), 4.48 (q, J=7.1 Hz, 2H), 3.92-3.88 (m, 3H), 1.42 (t, J=7.1 Hz, 3H).

Step 3: Preparation of (Z)-6-ethoxy-N'-hydroxy-5-methoxynicotinimidamide

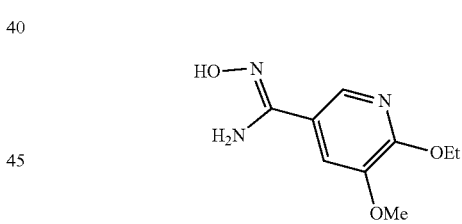

To a stirred solution of 6-ethoxy-5-methoxynicotinonitrile (820 mg, 4.60 mmol) in ethanol (20 mL) and water (2 mL) was added hydroxylamine hydrochloride (639 mg, 9.20 mmol) and triethylamine (931 mg, 9.20 mmol, 1.28 mL). The mixture was stirred at 80° C. for 2 h, cooled to room temperature, concentrated under reduced pressure and poured into water (5 mL). The resulting mixture was extracted with ethyl acetate (10 mL×3). The combined organic extracts were dried over sodium sulfate, filtered and concentrated under reduced pressure to give (Z)-6-ethoxy-N'-hydroxy-5-methoxynicotinimidamide (1.0 g, crude) as a white solid. $^1$H NMR (400 MHz, METHANOL-d4) δ=7.94 (d, J=2.0 Hz, 1H), 7.44 (d, J=2.0 Hz, 1H), 4.43-4.36 (m, 2H), 3.86 (s, 3H), 1.38 (t, J=7.1 Hz, 3H).

Step 4: Preparation of N-(2-(4-(3-(6-ethoxy-5-methoxypyridin-3-yl)-1,2,4-oxadiazol-5-yl)piperidin-1-yl)-2-oxoethyl)benzamide

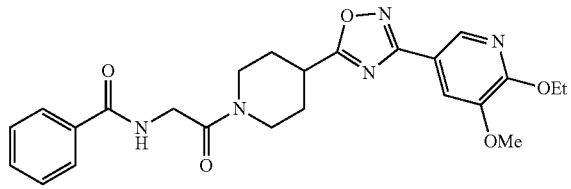 [SMILES: CCOc1ncc(-c2noc(C3CCN(C(=O)CNC(=O)c4ccccc4)CC3)n2)cc1OC]

To a stirred solution of (Z)-6-ethoxy-N'-hydroxy-5-methoxynicotinimidamide (109 mg, 516.69 µmol) in N,N-dimethylformamide (2 mL) was added 1-(2-benzamidoacetyl)piperidine-4-carboxylic acid (150 mg, 516.69 µmol), N-ethyl-N-(propan-2-yl)propan-2-amine (200 mg, 1.55 mmol, 270 µL) and (2-(1H-benzotriazol-1-yl)-1,1,3,3-tetramethyluronium hexafluorophosphate) (215 mg, 568 µmol). The mixture was stirred at 25° C. for 12 h, and at 110° C. for 1 h. The residue was purified directly by chromatography (column: Waters Xbridge 150×25 5 µm; mobile phase: [water (10 mM ammonium carbonate)-acetonitrile]; B %: 30%-50%, 12 min) to give N-(2-(4-(3-(6-ethoxy-5-methoxypyridin-3-yl)-1,2,4-oxadiazol-5-yl)piperidin-1-yl)-2-oxoethyl)benzamide (83 mg, 177.7 µmol, 34%) as a yellow solid. $^1$H NMR (400 MHz, CHLOROFORM-d) δ=8.44 (d, J=1.8 Hz, 1H), 7.88-7.82 (m, 2H), 7.62 (d, J=2.0 Hz, 1H), 7.55-7.49 (m, 1H), 7.48-7.42 (m, 2H), 7.32 (br s, 1H), 4.58-4.47 (m, 3H), 4.30 (d, J=4.0 Hz, 2H), 3.95 (s, 3H), 3.39-3.28 (m, 2H), 3.18-3.09 (m, 1H), 2.30-2.19 (m, 2H), 2.07-1.91 (m, 2H), 1.47 (t, J=7.1 Hz, 3H); LCMS (ESI) m/z: [M+H]$^+$=466.1.

Example 133: 3-methyl-5-[5-[1-[2-(1-oxoisoindolin-2-yl)acetyl]-4-piperidyl]-1,2,4-oxadiazol-3-yl]-1H-benzimidazol-2-one

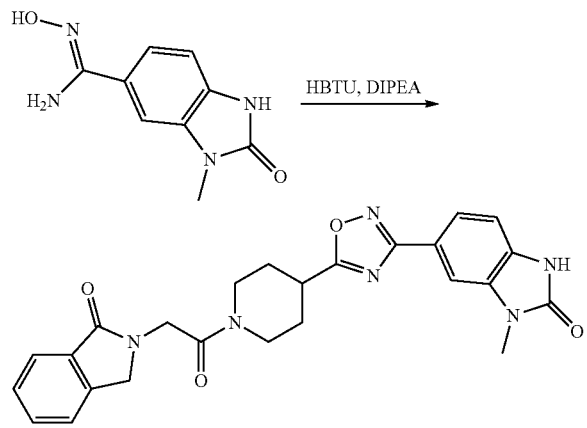

Step 1: 3-methyl-5-[5-[1-[2-(1-oxoisoindolin-2-yl)acetyl]-4-piperidyl]-1,2,4-oxadiazol-3-yl]-1H-benzimidazol-2-one A mixture of N'-hydroxy-3-methyl-2-oxo-1H-benzimidazole-5-carboxamidine (81.85 mg, 396.94 µmol, 1.20 eq), 1-[2-(1-oxoisoindolin-2-yl)acetyl]piperidine-4-carboxylic acid (100.00 mg, 330.78 µmol, 1.00 eq), (2-(1H-benzotriazol-1-yl)-1,1,3,3-tetramethyluronium hexafluorophosphate) (188.16 mg, 496.16 µmol, 1.50 eq), N-ethyl-N-(propan-2-yl)propan-2-amine (128.25 mg, 992.33 µmol, 173.31 µL, 3.00 eq) in N,N-dimethylformamide (2.00 mL) then the mixture was stirred at 20° C. for 15 h then the mixture was stirred at 110° C. for 1 h. The product was purified by column: Waters Xbridge 150×25 5 µm; mobile phase: [water (10 mM NH$_4$HCO$_3$)-acetonitrile]; B %: 20%-45%, 12 min to obtain compound 3-methyl-5-[5-[1-[2-(1-oxoisoindolin-2-yl)acetyl]-4-piperidyl]-1,2,4-oxadiazol-3-yl]-1H-benzimidazol-2-one (53.58 mg, 113.40 µmol, 34.28%) as a pink solid. 1H NMR (400 MHz, CHLOROFORM-d) δ=9.60 (br s, 1H), 7.79 (t, J=9.0 Hz, 2H), 7.61 (s, 1H), 7.51-7.46 (m, 1H), 7.42-7.37 (m, 2H), 7.10 (d, J=8.2 Hz, 1H), 4.52 (s, 2H), 4.45-4.37 (m, 3H), 4.02 (br d, J=13.6 Hz, 1H), 3.42 (s, 3H), 3.37-3.19 (m, 2H), 3.00 (br t, J=11.0 Hz, 1H), 2.21-2.10 (m, 2H), 1.99-1.85 (m, 2H); LCMS (ESI) m/z [M+H]$^+$=473.3.

Example 134: 3-methyl-5-[5-[1-(5-oxo-1-phenyl-pyrrolidine-3-carbonyl)-4-piperidyl]-1,2,4-oxadiazol-3-yl]-1H-benzimidazol-2-one

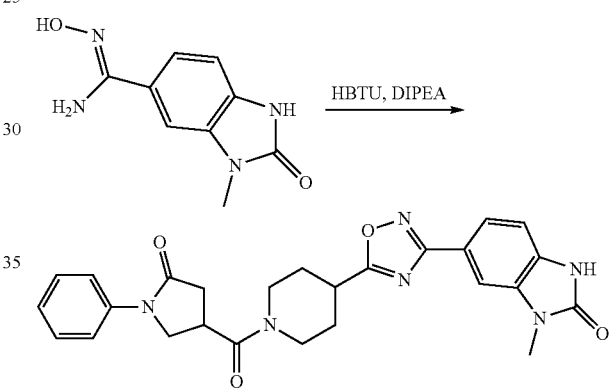

Step 1: Preparation of 3-methyl-5-[5-[1-(5-oxo-1-phenyl-pyrrolidine-3-carbonyl)-4-piperidyl]-1,2,4-oxadiazol-3-yl]-1H-benzimidazol-2-one Example 134 was synthesized according to the synthetic procedure reported for the preparation of Example 133. $^1$H NMR (400 MHz, CHLOROFORM-d) δ=9.82 (br s, 1H), 7.79 (br d, J=8.2 Hz, 1H), 7.62 (br s, 1H), 7.52 (d, J=8.2 Hz, 2H), 7.34-7.29 (m, 2H), 7.14-7.08 (m, 2H), 4.57-4.40 (m, 1H), 4.26 (br t, J=7.3 Hz, 1H), 3.97-3.84 (m, 2H), 3.52 (quin, J=8.4 Hz, 1H), 3.42 (d, J=1.6 Hz, 3H), 3.37-3.23 (m, 2H), 3.13-2.86 (m, 2H), 2.83-2.76 (m, 1H), 2.19 (br t, J=12.5 Hz, 2H), 2.00-1.82 (m, 2H). LCMS (ESI) m/z: [M+H]$^+$=487.3.

Example 135: N-[2-[4-[3-(3-methyl-1,2-benzoxazol-6-yl)-1,2,4-oxadiazol-5-yl]-1-piperidyl]-2-oxo-ethyl]benzamide

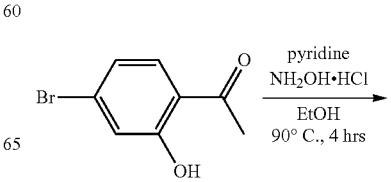

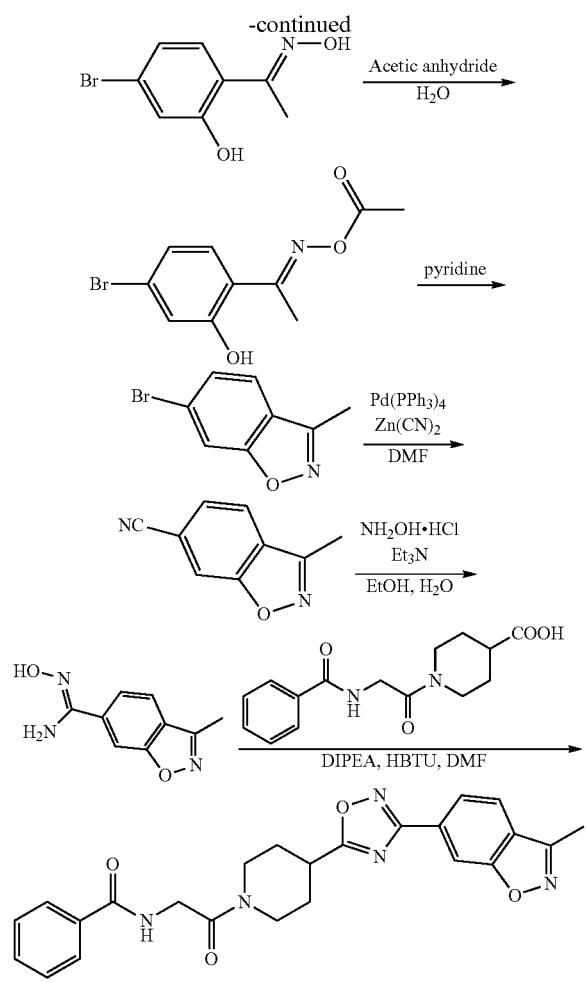

Step 1: Preparation of
1-(4-bromo-2-hydroxy-phenyl)ethanone oxime

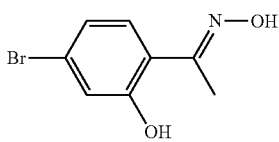

To a stirred solution of 1-(4-bromo-2-hydroxy-phenyl)ethanone (10.00 g, 46.50 mmol) and pyridine (49.66 g, 627.75 mmol, 50.67 mL) in ethanol (100 mL) was added hydroxylamine hydrochloride (16.16 g, 232.50 mmol) at 25° C. The mixture was heated to 90° C. for 4 h and was poured into a 2M aqueous solution of hydrochloric acid (250 mL). The mixture was then extracted with ethyl acetate (100 mL×4), washed with saturated aqueous sodium chloride solution (25 mL×1), dried with anhydrous Na₂SO₄, filtered and concentrated under vacuum to give 1-(4-bromo-2-hydroxy-phenyl)ethanone oxime (12.49 g, crude), isolated as pale yellow solid, and used for the next step without further purification. ¹H NMR (400 MHz, CHLOROFORM-d) δ=11.47 (br s, 1H), 8.65 (br d, J=4.3 Hz, 1H), 7.94 (br s, 1H), 7.31-7.28 (d, 1H), 7.17 (d, J=1.9 Hz, 1H), 7.06 (dd, J=2.0, 8.5 Hz, 1H), 2.37 (s, 3H)

Step 2: Preparation of [(E)-1-(4-bromo-2-hydroxy-phenyl)ethylideneamino]acetate

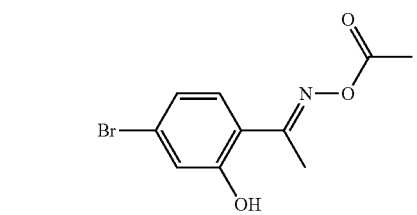

Acetic anhydride (25.50 mL) was added to 1-(4-bromo-2-hydroxy-phenyl)ethanone oxime (12.49 g, 54.29 mmol, 1.00 eq) one portion at 25° C., then the mixture was stirred at 25° C. for 30 mins. Water (100 mL) was then added to the suspension (a solid precipitated from the reaction mixture after 30 min stirring at room temperature), further stirred for 30 min at 25° C. The suspension was filtered and the resulting solid was washed with water (10 mL×3) and dissolved in ethyl acetate (20 mL). The organic solution was then dried with anhydrous Na₂SO₄, filtered and concentrated under vacuum to give [(E)-1-(4-bromo-2-hydroxy-phenyl) ethylideneamino] acetate (12.18 g, 44.8 mmol, 82%) as pale white solid. ¹H NMR (400 MHz, CHLOROFORM-d) δ=11.48 (s, 1H), 7.34 (d, J=8.7 Hz, 1H), 7.24 (d, J=1.9 Hz, 1H), 7.07 (dd, J=1.9, 8.6 Hz, 1H), 2.45 (s, 3H), 2.28 (s, 3H).

Step 3: Preparation of
6-bromo-3-methyl-1,2-benzoxazole

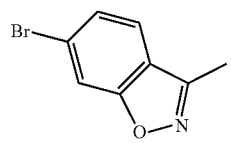

[(E)-1-(4-bromo-2-hydroxy-phenyl)ethylideneamino] acetate (11.00 g, 40.4 mmol) was added in one portion to pyridine (100 mL) and the resulting solution was refluxed at 130° C. for 15 h. The mixture was cooled to room temperature and poured into a 2M aqueous solution of hydrochloric acid (500 mL). The resulting mixture was extracted with methyl tert-butyl ether (200 mL×3). The organic extracts were washed with saturated aqueous sodium chloride solution (20 mL×1), dried with anhydrous Na₂SO₄, filtered and concentrated under vacuum to give the crude product further purified by chromatography (silica, petroleum ether/ethyl acetate=200/1 to 100/1). The desired compound (6-bromo-3-methyl-1,2-benzoxazole) was obtained as a yellow solid (7.50 g). ¹H NMR (400 MHz, DMSO-d₆) δ=8.05 (s, 1H), 8.08-8.03 (d, 1H), 8.08-8.03 (1H), 7.82 (d, J=8.4 Hz, 1H), 7.56 (dd, J=1.1, 8.3 Hz, 1H), 2.56 (s, 3H).

Step 4: Preparation of 3-methyl-1,2-benzoxazole-6-carbonitrile

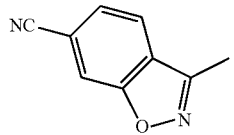

To a stirred solution of 6-bromo-3-methyl-1,2-benzoxazole (2.50 g, 11.8 mmol) and zinc cyanide (1.38 g, 11.8 mmol, 748 μL) in N,N-dimethylformamide (12 mL) was added tetrakis(triphenylphosphine)palladium(0) (1.36 g, 1.18 mmol) at 25° C., the mixture was degassed and purged with nitrogen 3 times, and then the mixture was stirred at 110° C. for 24 hrs under a nitrogen atmosphere. The suspension was filtered through a pad of Celite. The filtrate was then poured into water (50 mL), extracted with ethyl acetate (50 mL×3) and the organic layer was washed with saturated aqueous sodium chloride solution (20 mL×1), dried with anhydrous $Na_2SO_4$, and concentrated in vacuo. The residue was purified by chromatography (silica, petroleum ether/ethyl acetate=100/1 to 50:1) to give 3-methyl-1,2-benzoxazole-6-carbonitrile (240 mg, 1.52 mmol, 13%), isolated as a white solid. $^1$H NMR (400 MHz, CHLOROFORM-d) δ=7.89 (t, J=1.0 Hz, 1H), 7.76 (dd, J=0.7, 8.2 Hz, 1H), 7.60-7.57 (m, 1H), 2.63 (s, 3H).

Step 5: Preparation of N'-hydroxy-3-methyl-1,2-benzoxazole-6-carboxamidine

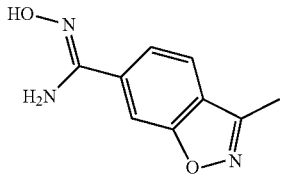

To a stirred solution of 3-methyl-1,2-benzoxazole-6-carbonitrile (240 mg, 1.52 mmol) in ethanol (4.00 mL) and water (400 μL) was added hydroxylamine hydrochloride (210 mg, 3.03 mmol) and triethylamine (307 mg, 3.03 mmol, 420 μL) at 25° C. The mixture was then stirred at 70° C. for 5 h and concentrated in vacuo to give N'-hydroxy-3-methyl-1,2-benzoxazole-6-carboxamidine (265 mg, 1.39 mmol, 91.60%) isolated as a white solid, and used for the next step without further purification.

Step 6: Preparation of N-[2-[4-[3-(3-methyl-1,2-benzoxazol-6-yl)-1,2,4-oxadiazol-5-yl]-1-piperidyl]-2-oxo-ethyl]benzamide

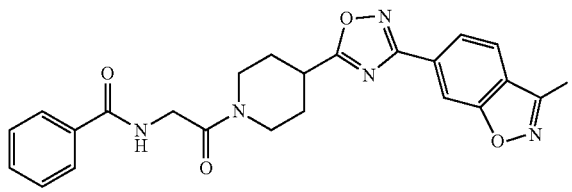 [SMILES: Cc1noc2cc(-c3noc(C4CCN(C(=O)CNC(=O)c5ccccc5)CC4)n3)ccc12]

To a stirred solution of N'-hydroxy-3-methyl-1,2-benzoxazole-6-carboxamidine (85 mg, 447.80 μmol) and 1-(2-benzamidoacetyl)piperidine-4-carboxylic acid (130 mg, 447.80 μmol) in N,N-dimethylformamide (2.00 mL) was added (2-(1H-benzotriazol-1-yl)-1,1,3,3-tetramethyluronium hexafluorophosphate) (169 mg, 447.80 μmol) and N-ethyl-N-(propan-2-yl)propan-2-amine (115 mg, 895.60 μmol, 156 μL) at 25° C. The mixture was then stirred at 25° C. for 4 h and warmed to 110° C. for 1 h. The mixture was concentrated in vacuo and the resulting residue was purified by chromatography (Boston Green ODS 150×30 mm 5 μm; mobile phase: [water (10 mM ammonium carbonate)-acetonitrile]; B %: 26%-56%, 11.5 min) to give N-[2-[4-[3-(3-methyl-1,2-benzoxazol-6-yl)-1,2,4-oxadiazol-5-yl]-1-piperidyl]-2-oxo-ethyl]benzamide (48 mg, 107.82 μmol, 24%, 99% purity), isolated as a pale yellow solid. $^1$H NMR (400 MHz, CHLOROFORM-d) δ=8.28 (s, 1H), 8.05 (d, J=8.3 Hz, 1H), 7.85 (d, J=7.5 Hz, 2H), 7.74 (d, J=7.9 Hz, 1H), 7.55-7.42 (m, 3H), 7.34 (br s, 1H), 4.51 (br d, J=13.6 Hz, 1H), 4.31 (d, J=3.9 Hz, 2H), 3.93 (br d, J=14.0 Hz, 1H), 3.41-3.32 (m, 2H), 3.16 (br t, J=10.7 Hz, 1H), 2.63 (s, 3H), 2.33-2.22 (m, 2H), 2.09-1.93 (m, 2H); LCMS (ESI) m/z: [M+H]$^+$:446.2.

Example 136: 4-[4-[3-(3-methyl-1,2-benzoxazol-6-yl)-1,2,4-oxadiazol-5-yl]piperidine-1-carbonyl]-1-phenyl-pyrrolidin-2-one

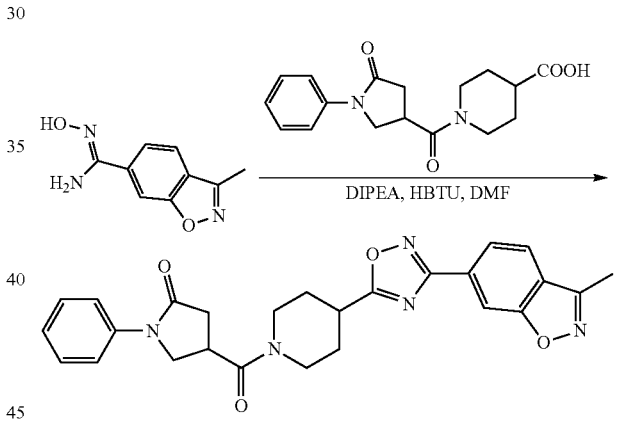

Step 1: Preparation of 4-[4-[3-(3-methyl-1,2-benzoxazol-6-yl)-1,2,4-oxadiazol-5-yl]piperidine-1-carbonyl]-1-phenyl-pyrrolidin-2-one

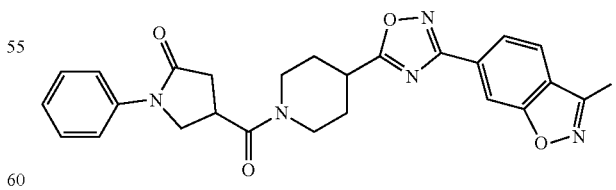

To a stirred solution of N'-hydroxy-3-methyl-1,2-benzoxazole-6-carboxamidine (78 mg, 410.94 μmol) and 1-(5-oxo-1-phenyl-pyrrolidine-3-carbonyl)piperidine-4-carboxylic acid (130 mg, 410.94 μmol) in N,N-dimethylformamide (2.00 mL) was added (2-(1H-benzotriazol-1-yl)-1,1,3,3-tetramethyluronium hexafluorophosphate) (155 mg, 410.94

μmol) and N-ethyl-N-(propan-2-yl)propan-2-amine (106 mg, 821.88 μmol, 143 μL) at 25° C. The mixture was then stirred at 25° C. for 4 h and warmed to 110° C. for 1 h. The mixture was concentrated in vacuo and the resulting residue was purified by chromatography (Boston Green ODS 150× 30 5 μm; mobile phase: [water (10 mM ammonium carbonate)-acetonitrile]; B %: 35%-65%, 11.5 min) to give 4-[4-[3-(3-methyl-1,2-benzoxazol-6-yl)-1,2,4-oxadiazol-5-yl] piperidine-1-carbonyl]-1-phenyl-pyrrolidin-2-one (42 mg, 89.8 μmol, 22%) isolated as a yellow solid. $^1$H NMR (400 MHz, CHLOROFORM-d) δ=8.28 (s, 1H), 8.06 (d, J=8.3 Hz, 1H), 7.74 (d, J=8.3 Hz, 1H), 7.60 (d, J=7.9 Hz, 2H), 7.38 (t, J=7.9 Hz, 2H), 7.20-7.14 (t, 1H), 4.61-4.48 (t, 1H), 4.35-4.29 (t, 1H), 4.04-3.92 (dd, 2H), 3.59 (quin, J=8.4 Hz, 1H), 3.46-3.31 (m, 2H), 3.20-3.05 (m, 1H), 3.03-2.92 (m, 1H), 2.89-2.80 (m, 1H), 2.63 (s, 3H), 2.28 (br t, J=12.3 Hz, 2H), 2.08-1.91 (m, 2H); LCMS (ESI) m/z: [M+H]$^+$=472.2.

Example 137: N-(2-(4-(3-(1,3-dimethyl-1H-pyrazolo[4,3-b]pyridin-6-yl)-1,2,4-oxadiazol-5-yl)piperidin-1-yl)-2-oxoethyl)benzamide

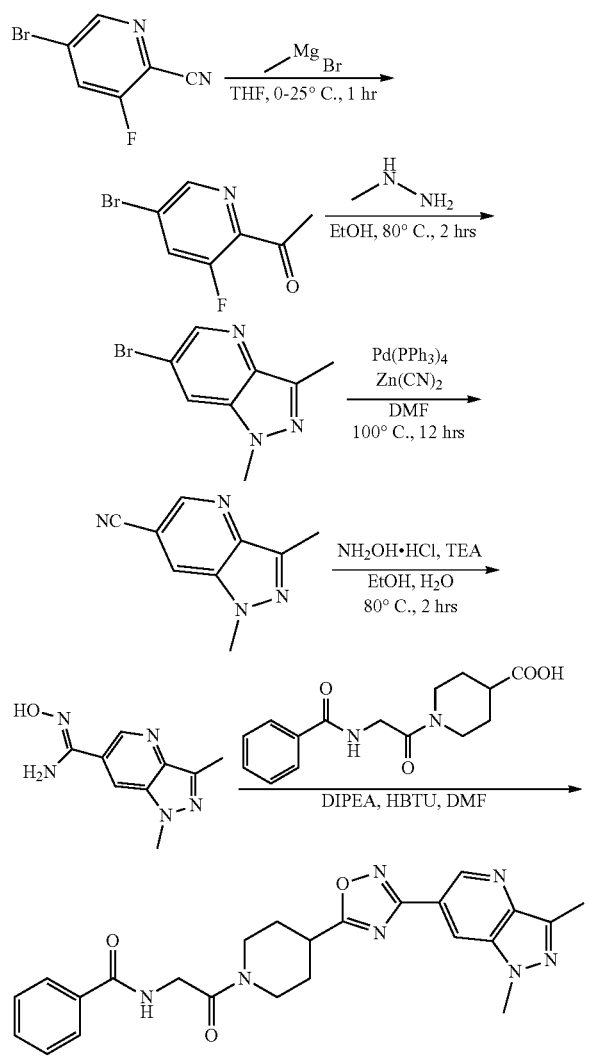

Step 1: Preparation of 1-(5-bromo-3-fluoropyridin-2-yl)ethanone

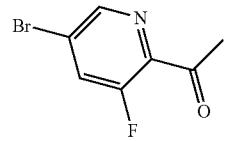

A 3M solution of ethylmagnesium bromide in tetrahydrofuran (4.97 mL) was added at 0° C. to a stirred solution of 5-bromo-3-fluoropicolinonitrile (2.0 g, 9.95 mmol) in tetrahydrofuran (20 mL). The mixture was then stirred at 25° C. for 1 h, and quenched by addition of an aqueous solution of ammonium hydroxide ammonium chloride solution (20 mL). The resulting mixture was extracted with ethyl acetate (2×20 mL). The combined organic extracts were washed with saturated aqueous sodium chloride solution (20 mL), dried over anhydrous anhydrous sodium sulfate, filtered and evaporated under reduced pressure to give the crude product further purified by chromatography (silica, petroleumether:ethylacetate=20:1 to 1:1). The desired compound (1-(5-bromo-3-fluoropyridin-2-yl)ethanone) was isolated as a yellow solid (580 mg, 1.49 mmol, 15%). $^1$H NMR. (400 MHz, CHLOROFORM-d) δ 8.56 (s, 1H). 7.74 (dd, J=1.8, 9.8 Hz, 1H), 2.68 (s, 3H).

Step 2 preparation of 6-bromo-1,3-dimethyl-1H-pyrazolo[4,3-b]pyridine

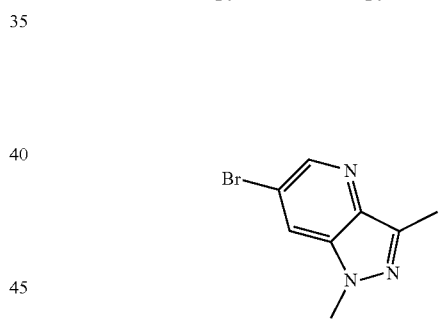

To a stirred solution of 1-(5-bromo-3-fluoropyridin-2-yl) ethanone (570 mg, 1.46 mmol) in ethanol (5 mL), was added methylhydrazine (1.68 g, 14.60 mmol, 1.91 mL), and the resulting mixture was heated at 80° C. for 2 h. The reaction mixture was then quenched with water (5 mL) and extracted with ethyl acetate (2×5 mL). The combined organic extracts were washed with saturated aqueous sodium chloride solution (5 mL), dried over anhydrous sodium sulfate, filtered and evaporated under reduced pressure to give the crude product further purified by prep-TLC (silica, petroleumether:ethylacetate=3:1). The title compound (6-bromo-1,3-dimethyl-1H-pyrazolo[4,3-b]pyridine) was isolated as a yellow solid (280 mg, 1.23 mmol, 84%)$^1$H NMR (400 MHz, CHLOROFORM-d) δ 8.54 (d, J=1.9 Hz, 1H), 7.86 (d, J=1.9 Hz, 1H), 3.99 (s, 3H), 2.64 (s, 3H).

Step 3 preparation of 1,3-dimethyl-1H-pyrazolo[4,3-b]pyridine-6-carbonitrile

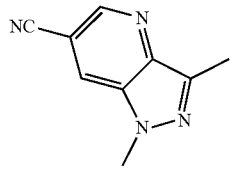

A solution of 6-bromo-1,3-dimethyl-1H-pyrazolo[4,3-b]pyridine (280 mg, 1.24 mmol), tetrakis(triphenylphosphine)palladium(0) (214 mg, 186 μmol), and zinc cyanide (87 mg, 744 μmol, 47 μL) in N,N-dimethylformamide (2 mL) under nitrogen was heated to 100° C. and stirred for 12 h at 100° C. The reaction mixture was cooled to room temperature, filtered and the filtrate was concentrated to give a residue poured into water (3 mL). The aqueous phase was extracted with ethyl acetate (3 mL×3). The combined organic extracts were then washed with saturated aqueous sodium chloride solution (5 mL×1), dried over anhydrous anhydrous sodium sulfate, filtered and concentrated in vacuo. The residue was purified by prep-TLC (silica, petroleumether:ethylacetate=1:1) to give 1,3-dimethyl-1H-pyrazolo[4,3-b]pyridine-6-carbonitrile (190 mg, 805.5 μmol, 65%) as a light yellow solid. $^1$H NMR (400 MHz, CHLOROFORM-d) δ 8.72 (d, J=1.5 Hz, 1H), 8.04 (d, J=1.5 Hz, 1H), 4.09 (s, 3H), 2.69 (s, 3H).

Step 4: Preparation of (Z)—N'-hydroxy-1,3-dimethyl-1H-pyrazolo[4,3-b]pyridine-6-carboximidamide

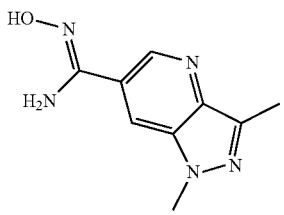

To a stirred solution of 1,3-dimethyl-1H-pyrazolo[4,3-b]pyridine-6-carbonitrile (170 mg, 987 μmol) in ethanol (2 mL) was added hydroxylamine hydrochloride (137 mg, 1.97 mmol), triethylamine (199 mg, 1.97 mmol, 273 μL) and water (200 μL). The reaction mixture was then stirred at 80° C. for 2 h. and concentrated under reduced pressure. The residue was diluted with water (5 mL). The resulting solid was filtered to give (Z)—N'-hydroxy-1,3-dimethyl-1H-pyrazolo[4,3-b]pyridine-6-carboximidamide (160 mg, 779.7 μmol, 79%) isolated as a light yellow solid, and used for the next step without further purification. $^1$H NMR (400 MHz, DMSO-$d_6$) δ 9.93 (s, 1H), 8.82 (d, J=1.8 Hz, 1H), 8.29 (d, J=2.0 Hz, 1H), 6.07 (br s, 2H), 4.00 (s, 3H), 2.51 (s, 3H).

Step 5: Preparation of N-(2-(4-(3-(1,3-dimethyl-1H-pyrazolo[4,3-b]pyridin-6-yl)-1,2,4-oxadiazol-5-yl)piperidin-1-yl)-2-oxoethyl)benzamide

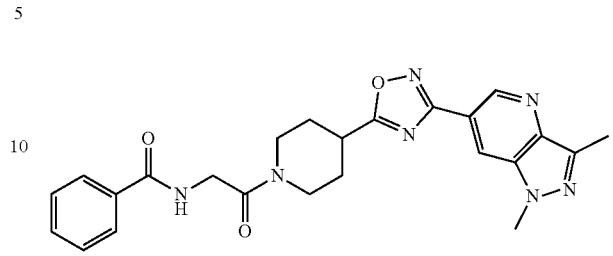

To a stirred solution of 1-(2-benzamidoacetyl)piperidine-4-carboxylic acid (150 mg, 516.69 μmol) in N,N-dimethylformamide (1.50 mL) was added (2-(1H-benzotriazol-1-yl)-1,1,3,3-tetramethyluronium hexafluorophosphate) (215 mg, 568 μmol), N-ethyl-N-(propan-2-yl)propan-2-amine (200 mg, 1.55 mmol, 270 μL) and (Z)—N'-hydroxy-1,3-dimethyl-1H-pyrazolo[4,3-b]pyridine-6-carboximidamide (106 mg, 516.69 μmol). The reaction mixture was stirred at 25° C. for 1 h, and then warmed to 110° C. for 1 h. The reaction mixture was concentrated under vacuum and the resulting residue was purified by prep-HPLC (column: Waters Xbridge 150×25 5 μm; mobile phase: [water (10 mM ammonium carbonate)-acetonitrile]; B %: 20%-45%, 12 min) to give N-(2-(4-(3-(1,3-dimethyl-1H-pyrazolo[4,3-b]pyridin-6-yl)-1,2,4-oxadiazol-5-yl)piperidin-1-yl)-2-oxoethyl)benzamide (116 mg, 252.7 μmol, 49%) isolated as a brown solid. $^1$H NMR (400 MHz, DMSO-$d_6$) δ 9.05 (d, J=1.8 Hz, 1H), 8.64 (d, J=1.8 Hz, 1H), 8.61-8.54 (m, 1H), 7.88 (br d, J=7.1 Hz, 2H), 7.57-7.45 (m, 3H), 4.35 (br d, J=13.0 Hz, 1H), 4.19 (br t, J=5.6 Hz, 2H), 4.10 (s, 3H), 4.01 (br d, J=13.2 Hz, 1H), 3.53 (br t, J=10.9 Hz, 1H), 3.58-3.48 (m, 1H), 3.32-3.24 (m, 1H), 2.96 (br t, J=11.8 Hz, 1H), 2.56 (s, 3H), 2.18 (br t, J=13.7 Hz, 2H), 1.88 (br d, J=10.1 Hz, 1H), 1.81-1.57 (m, 1H); LCMS (ESI) m/z: [M+H]$^+$=460.3.

Example 138: 4-(4-(3-(1,3-dimethyl-1H-pyrazolo[4,3-b]pyridin-6-yl)-1,2,4-oxadiazol-5-yl)piperidine-1-carbonyl)-1-phenylpyrrolidin-2-one

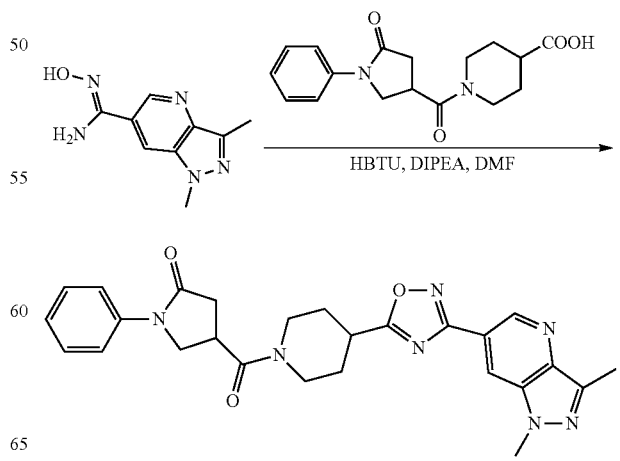

Step 1: Preparation of 4-(4-(3-(1,3-dimethyl-1H-pyrazolo[4,3-b]pyridin-6-yl)-1,2,4-oxadiazol-5-yl)piperidine-1-carbonyl)-1-phenylpyrrolidin-2-one

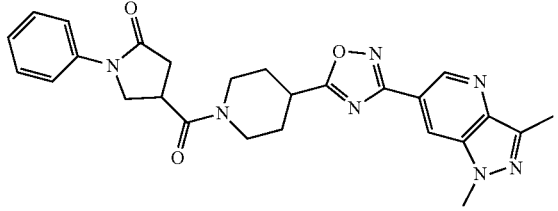 [SMILES: Cc1nn(C)c2cc(-c3noc(C4CCN(C(=O)C5CC(=O)N(c6ccccc6)C5)CC4)n3)cnc12]

To a stirred solution of 1-(5-oxo-1-phenylpyrrolidine-3-carbonyl)piperidine-4-carboxylic acid (150 mg, 474 μmol) in N,N-dimethylformamide (1.50 mL) was added (2-(1H-benzotriazol-1-yl)-1,1,3,3-tetramethyluronium hexafluorophosphate) (197 mg, 521.58 μmol), N-ethyl-N-(propan-2-yl)propan-2-amine (183 mg, 1.42 mmol, 248 μL) and (Z)—N'-hydroxy-1,3-dimethyl-1H-pyrazolo[4,3-b]pyridine-6-carboximidamide (97 mg, 474 μmol). The reaction mixture was stirred at 25° C. for 1 h and then warmed to 110° C. for 1 h. The reaction mixture was concentrated under vacuum and the resulting residue was purified by prep-HPLC (column: Waters Xbridge 150×25 5 μm; mobile phase: [water (10 mM ammonium carbonate)-acetonitrile]; B %: 20%-50%, 12 min) to give 4-(4-(3-(1,3-dimethyl-1H-pyrazolo[4,3-b]pyridin-6-yl)-1,2,4-oxadiazol-5-yl)piperidine-1-carbonyl)-1-phenylpyrrolidin-2-one (121 mg, 249 μmol, 52%) isolated as a yellow solid. $^1$H NMR (400 MHz, DMSO-d6) δ 9.05 (s, 1H), 8.64 (br s, 1H), 7.66 (br d, J=8.2 Hz, 2H), 7.41-7.34 (m, 2H), 7.17-7.11 (m, 1H), 4.39 (br d, J=13.5 Hz, 1H), 4.10 (s, 3H), 4.06 (br d, J=9.0 Hz, 2H), 4.00-3.93 (m, 1H), 3.80-3.71 (m, 1H), 3.52 (br t, J=10.9 Hz, 1H), 3.40-3.34 (m, 1H), 3.03-2.92 (m, 1H), 2.85-2.71 (m, 2H), 2.56 (s, 3H), 2.19 (t, J=14.3 Hz, 2H), 1.95-1.82 (m, 1H), 1.80-1.70 (m, 1H); LCMS (ESI) [M+H]$^+$=486.3.

Example 139: 4-[4-[4-[3-(1,3-dimethylindazol-6-yl)-1,2,4-oxadiazol-5-yl]piperidine-1-carbonyl]-2-oxo-pyrrolidin-1-yl]benzonitrile

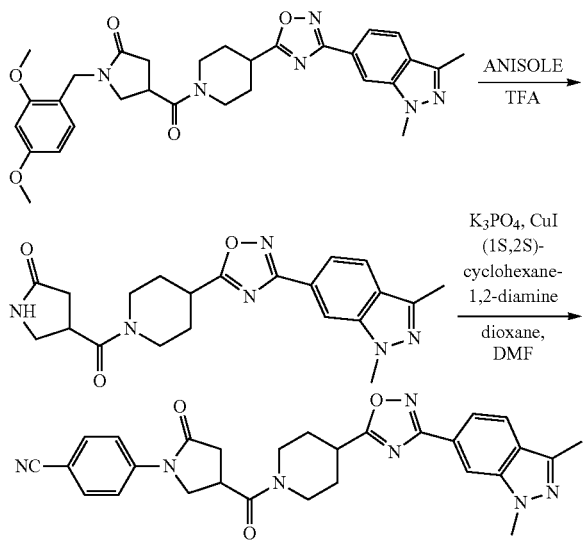

Step 1: Preparation of 4-[4-[3-(1,3-dimethylindazol-6-yl)-1,2,4-oxadiazol-5-yl]piperidine-1-carbonyl]pyrrolidin-2-one

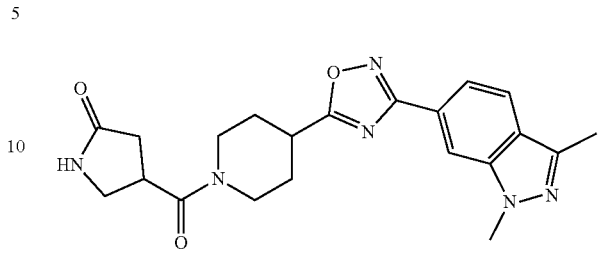

A mixture of 1-[(2,4-dimethoxyphenyl)methyl]-4-[4-[3-(1,3-dimethylindazol-6-yl)-1,2,4-oxadiazol-5-yl]piperidine-1-carbonyl]pyrrolidin-2-one (350 mg, 626.53 μmol), anisole (135 mg, 1.25 mmol, 135 μL) in trifluoroacetic acid (5 mL) was degassed and purged with nitrogen three times. The reaction mixture was stirred at 80° C. for 2 h under a nitrogen atmosphere and then concentrated under reduced pressure to to provide the crude product (500 mg) isolated as a yellow oil and used for the next step without further purification.

Step 2: Preparation of 4-[4-[4-[3-(1,3-dimethylindazol-6-yl)-1,2,4-oxadiazol-5-yl]piperidine-1-carbonyl]-2-oxo-pyrrolidin-1-yl]benzonitrile

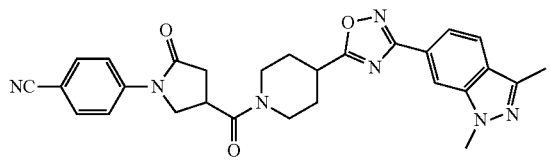 [SMILES: Cc1nn(C)c2cc(-c3noc(C4CCN(C(=O)C5CC(=O)N(c6ccc(C#N)cc6)C5)CC4)n3)ccc12]

A mixture of 4-[4-[3-(1,3-dimethylindazol-6-yl)-1,2,4-oxadiazol-5-yl]piperidine-1-carbonyl]pyrrolidin-2-one (200 mg, 489.66 μmol), 4-iodobenzonitrile (112 mg, 489.66 μmol), potassium phosphate tribasic (187 mg, 881 μmol), copper iodide (18 mg, 97.93 μmol) and (1S,2S)-cyclohexane-1,2-diamine (55 mg, 489.66 μmol, 60 μL) in dioxane (1 mL) and N,N-dimethylformamide (1 mL) was degassed and purged with nitrogen three times. The mixture was stirred at 110° C. for 16 h under a nitrogen atmosphere. After the reaction cooled to 20° C., water (10 mL) was added to the mixture which was extracted with ethyl acetate (30×3). The combined organic extracts were washed with saturated aqueous sodium chloride solution (10 mL), dried over anhydrous sodium sulfate, filtered and concentrated under vacuum to give the crude product further purified by prep-HPLC (column: Waters Xbridge 150×2.5 mm 5 μm; mobile phase: [water (10 mM ammonium carbonate)-acetonitrile]; B %: 15%-40%, 12 min). The title compound (4-[4-[4-[3-(1,3-dimethylindazol-6-yl)-1,2,4-oxadiazol-5-yl]piperidine-1-carbonyl]-2-oxo-pyrrolidin-1-yl]benzonitrile) was isolated as a pale yellow solid (17 mg, 34 μmol, 7%). $^1$H NMR (400 MHz, CDCl$_3$) δ 8.10 (br s, 1H), 7.87-7.72 (m, 4H), 7.67 (d, J=8.8 Hz, 2H), 4.63-4.47 (m, 1H), 4.36 (dd, 9.5 Hz, 1H), 4.09 (s, 3H), 4.03-3.93 (m, 2H), 3.62 (m, 1H), 3.48-3.32 (m, 2H), 3.20-3.04 (m, 1H), 3.02-2.88 (m, 2H), 2.61 (s, 3H), 2.30 (br t, J=14.4 Hz, 2H), 2.10-1.96 (m, 2H); LCMS (ESI) [M+H]$^+$=510.3.

Example 140: 2-[2-[4-[3-(4-ethoxy-3-methoxy-phenyl)-1,2,4-oxadiazol-5-yl]-1-piperidyl]-1-methyl-2-oxo-ethyl]isoindolin-1-one

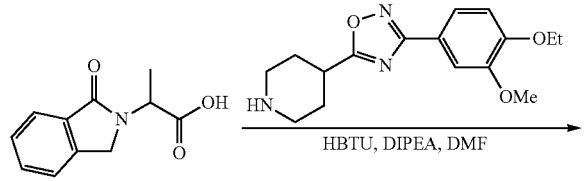

Step 1: Preparation of 2-[2-[4-[3-(4-ethoxy-3-methoxy-phenyl)-1,2,4-oxadiazol-5-yl]-1-piperidyl]-1-methyl-2-oxo-ethyl]isoindolin-1-one

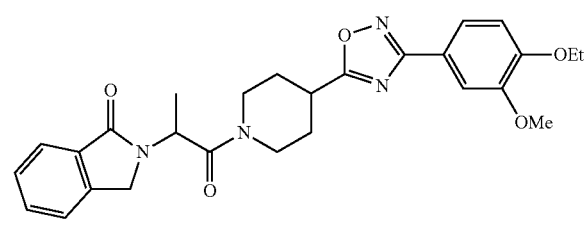

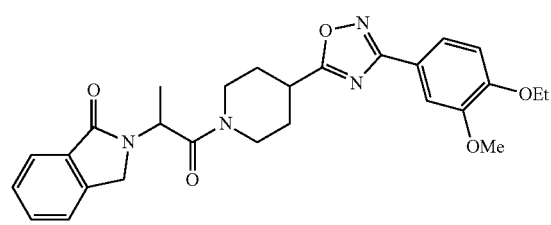 [SMILES: CCOc1ccc(-c2noc(C3CCN(C(=O)C(C)N4Cc5ccccc5C4=O)CC3)n2)cc1OC]

To a stirred solution of 3-(4-ethoxy-3-methoxy-phenyl)-5-(4-piperidyl)-1,2,4-oxadiazole (130 mg, 382.56 μmol, 1.00 eq, hydrochloric acid) in N,N-dimethylformamide (2 mL) was added 2-(1-oxoisoindolin-2-yl)propanoic acid (78 mg, 382.56 μmol), (2-(1H-benzotriazol-1-yl)-1,1,3,3-tetramethyluronium hexafluorophosphate) (174 mg, 459 μmol) and N-ethyl-N-(propan-2-yl)propan-2-amine (148 mg, 1.15 mmol, 200 μL). The mixture was stirred at 20° C. for 1 h. The reaction mixture was concentrated under vacuum and the residue was purified by prep-HPLC (column: Waters Xbridge 150×25 5 μm; mobile phase: [water (10 mM ammonium carbonate)-acetonitrile]; B %; 40%-70%, 12 min) to give 2-[2-[4-[3-(4-ethoxy-3-methoxy-phenyl)-1,2,4-oxadiazol-5-yl]-1-piperidyl]-1-methyl-2-oxo-ethyl]isoindolin-1-one (132 mg, 266 μmol, 70%), isolated as a yellow solid. H NMR (400 MHz, CDCl$_3$) δ 7.86 (br t, J=6.2 Hz, 1H), 7.69-7.43 (m, 5H), 6.93 (dd, J=8.4, 15.4 Hz, 1H), 5.55 (q, J=6.8 Hz, 1H), 4.57-4.36 (m, 3H), 4.29-4.11 (m, 3H), 3.95 (d, J=13.5 Hz, 3H), 3.42-3.19 (m, 2H), 3.14-3.00 (m, 1H), 2.16 (br dd, J=4.4, 8.8 Hz, 2H), 2.06-1.67 (m, 2H), 1.54-1.47 (m, 6H); LCMS (ESI) m/z: [M+H]$^+$=491.1.

Example 141: 2-[2-[4-[3-(1,3-dimethylindazol-6-yl)-1,2,4-oxadiazol-5-yl]-1-piperidyl]-1-methyl-2-oxo-ethyl]isoindolin-1-one

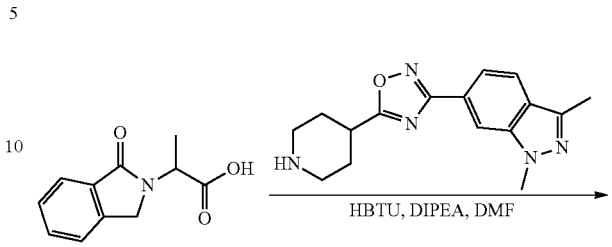

Step 1: Preparation of 2-[2-[4-[3-(1,3-dimethylindazol-6-yl)-1,2,4-oxadiazol-5-yl]-1-piperidyl]-1-methyl-2-oxo-ethyl]isoindolin-1-one

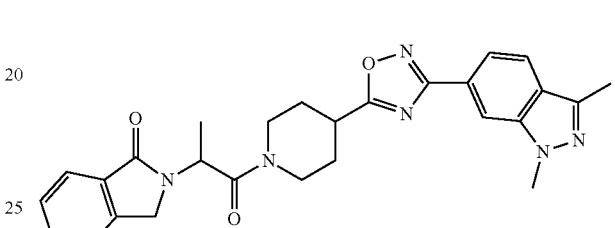

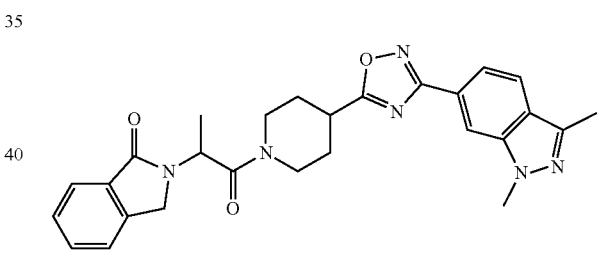

To a stirred solution of 2-(1-oxoisoindolin-2-yl)propanoic acid (79 mg, 389 μmol) in N,N-dimethylformamide (2 mL) was added 3-(1,3-dimethylindazol-6-yl)-5-(4-piperidyl)-1,2,4-oxadiazole (130 mg, 389 μmol), (2-(1H-benzotriazol-1-yl)-1,1,3,3-tetramethyluronium hexafluorophosphate) (177 mg, 467 μmol) and N-ethyl-N-(propan-2-yl)propan-2-amine (150 mg, 1.17 mmol, 204 μL). The mixture was stirred at 20° C. for 1 h. The reaction mixture was concentrated under vacuum and the residue was purified by prep-HPLC (column: Waters Xbridge 150×25 5 μm; mobile phase: [water (10 mM ammonium carbonate)-acetonitrile]; B %: 40%-70%, 12 min) to give 2-[2-[4-[3-(1,3-dimethylindazol-6-yl)-1,2,4-oxadiazol-5-yl]-1-piperidyl]-1-methyl-2-oxo-ethyl]isoindolin-1-one (118 mg, 243.5 μmol, 63%) isolated as a white solid. $^1$H NMR (400 MHz, CDCl$_3$) δ 8.12-8.01 (m, 1H), 7.90-7.67 (m, 3H), 7.60-7.44 (m, 3H), 5.56 (q, J=6.6 Hz, 1H), 4.58-4.40 (m, 3H), 4.27 (br t, J=13.7 Hz. 1H), 4.07 (d, J=9.9 Hz, 3H), 3.45-3.24 (m, 2H), 3.14-3.03 (m, 1H), 2.59 (d, J=6.6 Hz, 3H), 2.21 (br d, J=12.8 Hz. 2H), 2.10-1.70 (m, 2H), 1.52 (br dd, J=4.3, 6.3 Hz, 3H); LCMS (ESI) m/z: [M+H]$^+$=485.1.

Example 142: 2-(2-(4-(3-(5-ethoxy-6-methoxypyridin-2-yl)-1,2,4-oxadiazol-5-yl)piperidin-1-yl)-2-oxoethyl)isoindolin-1-one

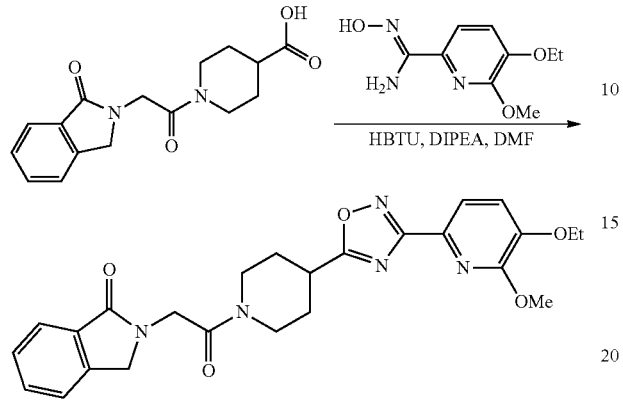

Step 1: 2-(2-(4-(3-(5-ethoxy-6-methoxypyridin-2-yl)-1,2,4-oxadiazol-5-yl)piperidin-1-yl)-2-oxoethyl)isoindolin-1-one Example 142 was synthesized according to the synthetic procedure reported for the preparation of Example 147. $^1$H NMR (400 MHz, CHLOROFORM-d) δ=7.87 (d, J=7.5 Hz, 1H), 7.67 (d, J=8.3 Hz, 1H), 7.58-7.53 (m, 1H), 7.47 (t, J=6.8 Hz, 2H), 7.10 (d, J=7.9 Hz, 1H), 4.58 (d, J=5.7 Hz, 2H), 4.52 (s, 1H), 4.48-4.41 (m, 2H), 4.19-4.12 (m, 5H), 4.04 (s, 1H), 3.44-3.26 (m, 2H), 3.05 (br t, J=11.0 Hz, 1H), 2.26-2.13 (m, 2H), 1.96 (br dd, J=10.1, 19.7 Hz, 2H), 1.52 (t, J=7.0 Hz, 3H); LCMS (ESI) m/z: [M+H]$^+$:478.1.

Example 143: N-[2-[4-[3-(3,4-dimethoxyphenyl)-1,2,4-oxadiazol-5-yl]-1-piperidyl]-2-oxo-ethyl]piperidine-1-carboxamide

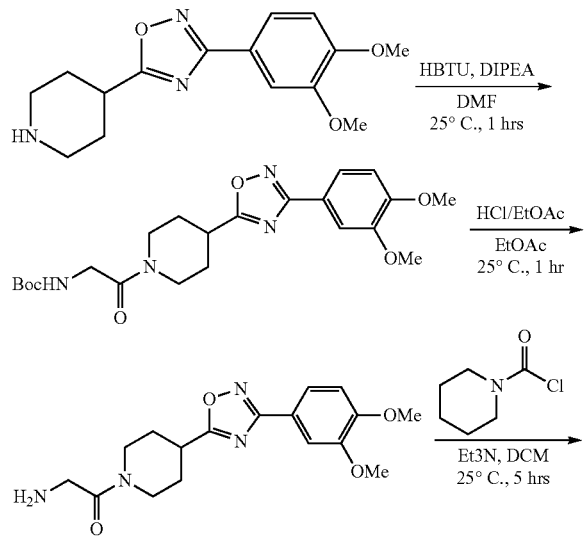

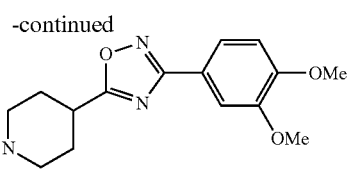

Step 1: Preparation of tert-butyl N-[2-[4-[3-(3,4-dimethoxyphenyl)-1,2,4-oxadiazol-5-yl]-1-piperidyl]-2-oxo-ethyl]carbamate

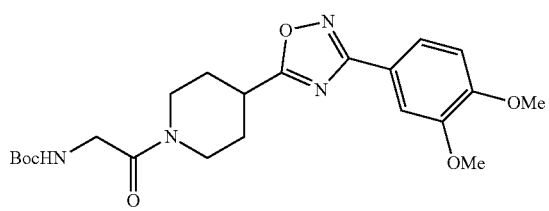 [SMILES: COc1ccc(-c2noc(C3CCN(C(=O)CNC(=O)OC(C)(C)C)CC3)n2)cc1OC]

To a stirred solution of 3-(3,4-dimethoxyphenyl)-5-(4-piperidyl)-1,2,4-oxadiazole hydrochloride (1.00 g, 3.07 mmol, 1.00 eq) and 2-(tert-butoxycarbonylamino) acetic acid (537 mg, 3.07 mmol), (2-(1H-benzotriazol-1-yl)-1,1,3,3-tetramethyluronium hexafluorophosphate) (1.16 g, 3.07 mmol) in N,N-dimethylformamide (10.00 mL) was added N-ethyl-N-(propan-2-yl)propan-2-amine (793 mg, 6.14 mmol, 1.07 mL) at 25° C. The mixture was then stirred at 25° C. for 1 h. The mixture was poured into water (20 mL) and extracted with ethyl acetate (20 mL×3). The organic extracts were washed with saturated aqueous sodium chloride solution (20 mL), dried with anhydrous Na$_2$SO$_4$, filtered and concentrated under vacuum to provide the crude product further purified by chromatography (silica, petroleum ether/ethyl acetate=100/1 to 50:1 to 1:1). The title compound (tert-butyl N-[2-[4-[3-(3,4-dimethoxyphenyl)-1,2,4-oxadiazol-5-yl]-1-piperidyl]-2-oxo-ethyl]carbamate) was isolated as a pale yellow oil (1.70 g, crude) (contained some residual ethyl acetate and dimethylformamide, and was used without further purification).

Step 2: 2-amino-1-[4-[3-(3,4-dimethoxyphenyl)-1,2,4-oxadiazol-5-yl]-1-piperidyl]ethanone

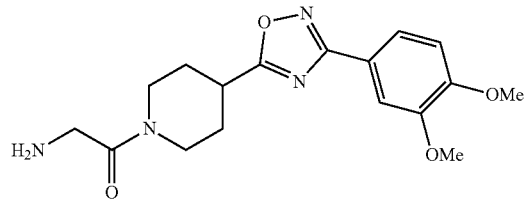 [SMILES: COc1ccc(-c2noc(C3CCN(C(=O)CN)CC3)n2)cc1OC]

To a stirred solution of tert-butyl N-[2-[4-[3-(3,4-dimethoxyphenyl)-1,2,4-oxadiazol-5-yl]-1-piperidyl]-2-oxo-ethyl]carbamate (800 mg, 1.79 mmol) in ethyl acetate (5.00 mL) was added a 4M hydrochloric acid in ethyl acetate (15.00 mL). The mixture was then stirred at 25° C. for 1 h, and then concentrated under vacuum to give 2-amino-1-[4-

[3-(3,4-dimethoxyphenyl)-1,2,4-oxadiazol-5-yl]-1-piperidyl]ethanone hydrochloride (660 mg, crude), isolated as a white solid and used for the next step without further purification.

Step 3: Preparation of N-[2-[4-[3-(3,4-dimethoxyphenyl)-1,2,4-oxadiazol-5-yl]-1-piperidyl]-2-oxo-ethyl]piperidine-1-carboxamide

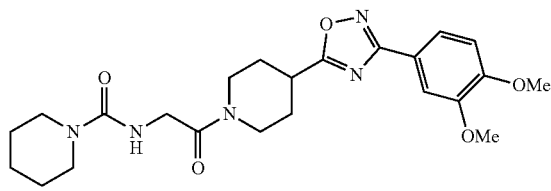 [SMILES: COc1ccc(-c2noc(C3CCN(C(=O)CNC(=O)N4CCCCC4)CC3)n2)cc1OC]

To a stirred solution of 2-amino-1-[4-[3-(3,4-dimethoxyphenyl)-1,2,4-oxadiazol-5-yl]-1-piperidyl]ethanone (200 mg, 522 µmol) and piperidine-1-carbonyl chloride (77 mg, 522 µmol, 65 µL) in dichloromethane (3.00 mL) was added triethylamine (158 mg, 1.57 mmol, 217 µL) at 25° C. The mixture was then stirred at 25° C. for 5 h. The reaction mixture was poured into 5 mL water and extracted with dichloromethane (5 mL×3). The combined organic extracts were concentrated under vacuum, dissolved in N,N-dimethylformamide (3 mL) and purified by chromatography (Boston Green ODS 150×30 5 µm; mobile phase: [water (10 mM ammonium carbonate)-acetonitrile]; B %: 30%-70%, 11.5 min to give N-[2-[4-[3-(3,4-dimethoxyphenyl)-1,2,4-oxadiazol-5-yl]-1-piperidyl]-2-oxo-ethyl]piperidine-1-carboxamide (113 mg, 248 µmol, 48%) isolated as a white solid. $^1$H NMR (400 MHz, CHLOROFORM-d) δ=7.68 (dd, J=1.8, 8.3 Hz, 1H), 7.56 (d, J=1.8 Hz, 1H), 6.95 (d, J=8.8 Hz, 1H), 5.57 (br s, 1H), 4.46 (br d, J=13.6 Hz, 1H), 4.10 (d, J=3.5 Hz, 2H), 3.95 (d, J=7.5 Hz, 6H), 3.86 (br d, J=14.0 Hz, 1H), 3.40-3.35 (m, 4H), 3.32-3.23 (m, 2H), 3.08 (br t, J=11.0 Hz, 1H), 2.25-2.15 (m, 2H), 2.03-1.88 (m, 2H), 1.62-1.51 (m, 6H); LCMS (ESI) m/z: [M+H]$^+$=458.1.

Example 144: N-[2-[4-[3-(3,4-dimethoxyphenyl)-1,2,4-oxadiazol-5-yl]-1-piperidyl]-2-oxo-ethyl]-2-methoxy-benzamide Step 1: Preparation of N-[2-[4-[3-(3,4-dimethoxyphenyl)-1,2,4-oxadiazol-5-yl]-1-piperidyl]-2-oxo-ethyl]-2-methoxy-benzamide

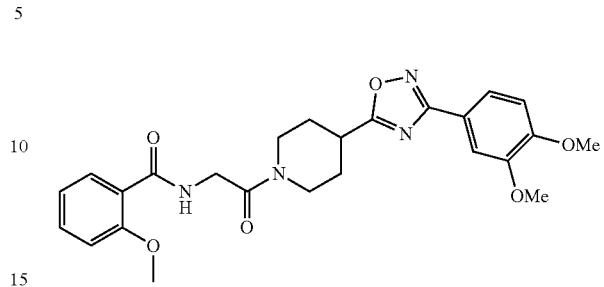

To a stirred solution of 2-amino-1-[4-[3-(3,4-dimethoxyphenyl)-1,2,4-oxadiazol-5-yl]-1-piperidyl]ethanone hydrochloride (200 mg, 522 µmol) and 2-methoxybenzoic acid (79 mg, 522 µmol) in dichloromethane (3.00 mL) was added 2,4,6-tripropyl-1,3,5,2,4,6-trioxatriphosphinane 2,4,6-trioxide in ethyl acetate (661.8 mg, 1.04 mmol, 681.51 µL, 50% purity) and triethylamine (158 mg, 1.57 mmol, 217 µL) at 25° C. The mixture was then stirred at 25° C. for 5 h. The reaction mixture was poured into water (5 mL) and extracted with dichloromethane (5 mL×3). The combined organic extracts were concentrated under vacuum. The resulting residue, dissolved in dimethylsulphoxide (3 mL), was purified by chromatography (Boston Green ODS 150*30 mm 5 µm; mobile phase: [water (10 mM ammonium carbonate)-acetonitrile]; B %: 42%-72%, 11.5 min) to give N-[2-[4-[3-(3,4-dimethoxyphenyl)-1,2,4-oxadiazol-5-yl]-1-piperidyl]-2-oxo-ethyl]-2-methoxy-benzamide (83 mg, 169.3 µmol, 32%) isolated as a white solid. $^1$H NMR (400 MHz, CHLOROFORM-d) δ=9.01 (br s, 1H), 8.21 (dd, J=1.8, 7.9 Hz, 1H), 7.68 (dd, J=2.2, 8.3 Hz, 1H), 7.56 (d, J=1.8 Hz, 1H), 7.49-7.43 (m, 1H), 7.11-6.93 (m, 3H), 4.51 (br d, J=13.6 Hz, 1H), 4.36 (d, J=3.9 Hz, 2H), 4.04 (s, 3H), 3.95 (t, J=7.9 Hz, 7H), 3.38-3.26 (m, 2H), 3.13 (br t, J=11.0 Hz, 1H), 2.28-2.17 (d, 2H), 2.07-1.91 (m, 2H); LCMS (ESI) m/z: [M+H]$^+$=481.1.

Example 145: N-[2-[4-[3-(3,4-dimethoxyphenyl)-1,2,4-oxadiazol-5-yl]-1-piperidyl]-2-oxo-ethyl]pyridine-2-carboxamide

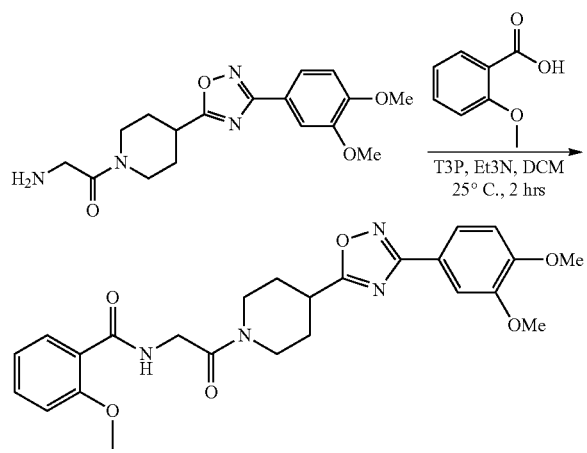

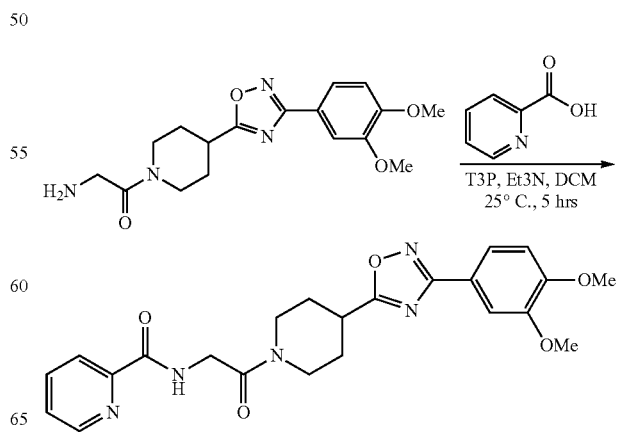

Step 1: Preparation of N-[2-[4-[3-(3,4-dimethoxyphenyl)-1,2,4-oxadiazol-5-yl]-1-piperidyl]-2-oxo-ethyl]pyridine-2-carboxamide

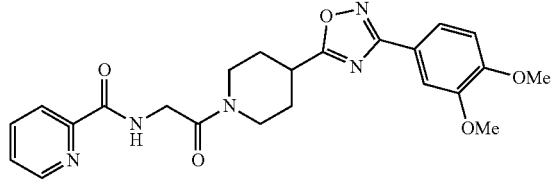

To a stirred solution of 2-amino-1-[4-[3-(3,4-dimethoxyphenyl)-1,2,4-oxadiazol-5-yl]-1-piperidyl]ethanone (200 mg, 522 µmol, 1.00 eq, HCl) and pyridine-2-carboxylic acid (64 mg, 522 µmol) in dichloromethane (3.00 mL) was added 2,4,6-tripropyl-1,3,5,2,4,6-trioxatriphosphinane 2,4,6-trioxide in ethyl acetate (661.81 mg, 1.04 mmol, 681.51 µL, 50% purity, 2 eq) and triethylamine (158 mg, 1.57 mmol, 217 µL) at 25° C., then the mixture was stirred at 25° C. for 5 h. The reaction mixture was poured into water (5 mL) and extracted with dichloromethane (5 mL×3). The combined organic extracts were concentrated under vacuum. The resulting residue, dissolved in dimethylsulphoxide (3 mL), was purified by prep-HPLC (Boston Green ODS 150×30 mm 5 µm; mobile phase: [water (10 mM ammonium carbonate)-acetonitrile]; B %: 35%-65%, 11.5 min) to give N-[2-[4-[3-(3,4-dimethoxyphenyl)-1,2,4-oxadiazol-5-yl]-1-piperidyl]-2-oxo-ethyl]pyridine-2-carboxamide (85 mg, 182.18 µmol, 35%) isolated as a white solid. $^1$H NMR (400 MHz, CHLOROFORM-d) δ=8.91 (br s, 1H), 8.61 (d, J=3.9 Hz, 1H), 8.17 (d, J=7.9 Hz, 1H), 7.84 (dt, J=1.8, 7.7 Hz, 1H), 7.68 (dd, J=1.8, 8.3 Hz, 1H), 7.56 (d, J=1.8 Hz, 1H), 7.46-7.40 (dd, 1H), 6.95 (d, J=8.3 Hz, 1H), 4.53 (br d, J=13.6 Hz, 1H), 4.33 (d, J=4.4 Hz, 2H), 3.95 (d, J=7.9 Hz, 6H), 3.91 (br s, 1H), 3.39-3.26 (m, 2H), 3.12 (br t, J=11.0 Hz, 1H), 2.29-2.18 (t, 2H), 2.07-1.91 (m, 2H); LCMS (ESI) m/z: [M+H]$^+$=452.1.

Example 146: 2-[2-[4-[3-(1,3-dimethylpyrazolo[3,4-b]pyridin-6-yl)-1,2,4-oxadiazol-5-yl]-1-piperidyl]-2-oxo-ethyl]isoindolin-1-one

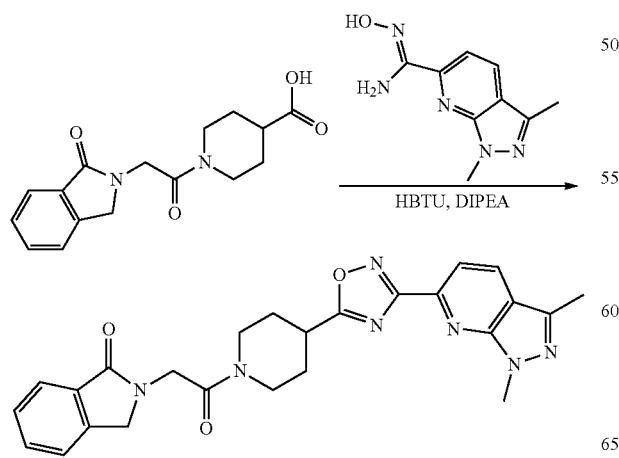

Step 1: 2-[2-[4-[3-(1,3-dimethylpyrazolo[3,4-b]pyridin-6-yl)-1,2,4-oxadiazol-5-yl]-1-piperidyl]-2-oxo-ethyl]isoindolin-1-one Example 146 was synthesized according to the synthetic procedure reported for the preparation of Example 147. $^1$H NMR (400 MHz, CHLOROFORM-d) δ=8.11 (d, J=8.4 Hz, 1H), 7.89 (d, J=8.2 Hz, 1H), 7.85 (d, J=8.2 Hz, 1H), 7.56-7.50 (m, 1H), 7.47-7.41 (m, 2H), 4.60-4.41 (m, 5H), 4.16 (s, 3H), 4.12-4.05 (m, 1H), 3.41-3.31 (m, 2H), 3.06-2.98 (m, 1H), 2.62-2.57 (m, 3H), 2.25 (br t, J=14.6 Hz, 2H), 2.05-1.94 (m, 2H); LCMS(ESI) m/z: [M+H]$^+$:472.3.

Example 147: 2-[2-[4-[3-(5-ethoxy-4-methoxy-2-pyridyl)-1,2,4-oxadiazol-5-yl]-1-piperidyl]-2-oxo-ethyl]isoindolin-1-one

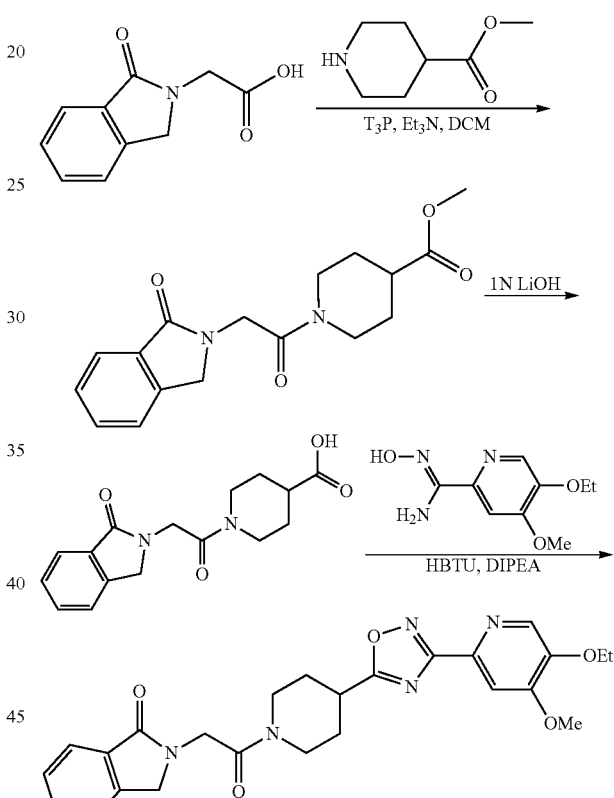

Step 1: methyl 1-[2-(1-oxoisoindolin-2-yl)acetyl]piperidine-4-carboxylate

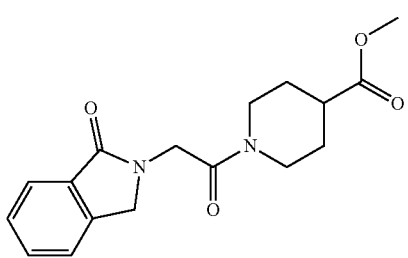 [SMILES: COC(=O)C1CCN(C(=O)CN2Cc3ccccc3C2=O)CC1]

A mixture of 2-(1-oxoisoindolin-2-yl)acetic acid (3.0 g, 15.69 mmol), methyl piperidine-4-carboxylate (2.47 g, 17.26 mmol), 2,4,6-tripropyl-1,3,5,2,4,6-trioxatriphosphinane 2,4,6-trioxide in ethyl acetate (12.98 g, 20.40 mmol, 12.13 mL, 50% purity) and triethylamine (31.76 g, 313.80 mmol, 43.51 mL) in dichloromethane (60 mL), was stirred at 20° C. for 16 h. The reaction mixture was then diluted with water (20 mL) and extracted with dichloromethane (60 mL). The organic layers were combined, washed with saturated aqueous sodium chloride solution (30 mL×2), dried over anhydrous sodium sulfate filtered and concentrated under reduced pressure to give the crude product further purified by chromatography (silica, petroleum ether/ethyl acetate=1:2). The title compound methyl 1-[2-(1-oxoisoindolin-2-yl)acetyl]piperidine-4-carboxylate was isolated as a yellow solid (4.30 g, 13.6 mmol, 87%).

Step 2: Preparation of 1-[2-(1-oxoisoindolin-2-yl)acetyl]piperidine-4-carboxylic acid

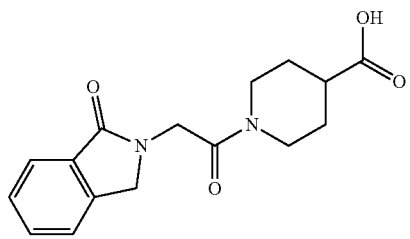 [SMILES: O=C(O)C1CCN(C(=O)CN2Cc3ccccc3C2=O)CC1]

A mixture of methyl 1-[2-(1-oxoisoindolin-2-yl)acetyl]piperidine-4-carboxylate (4.30 g, 13.59 mmol), Lithium hydroxide monohydrate (1 M, 13.59 mL) in tetrahydrofuran (50 mL) was stirred at 20° C. for 1 h, and then acidified to pH 3 by addition of a 1M aqueous hydrochloric acid solution. The mixture was extracted with dichloromethane 20 mL. The organic layers were combined, washed with saturated aqueous sodium chloride solution (25 mL×2), dried over anhydrous sodium sulfate, filtered and concentrated under reduced pressure to give 1-[2-(1-oxoisoindolin-2-yl)acetyl]piperidine-4-carboxylic acid (2.50 g, 8.27 mmol, 60.85%) isolated as a white solid, and used for the next step without further purification.

Step 3: 2-[2-[4-[3-(5-ethoxy-4-methoxy-2-pyridyl)-1,2,4-oxadiazol-5-yl]-1-piperidyl]-2-oxo-ethyl]isoindolin-1-one

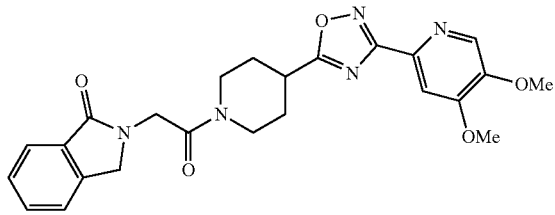 [SMILES: COc1cnc(-c2noc(C3CCN(C(=O)CN4Cc5ccccc5C4=O)CC3)n2)cc1OC]

A mixture of 1-[2-(1-oxoisoindolin-2-yl)acetyl]piperidine-4-carboxylic acid (150 mg, 496 μmol), 5-ethoxy-N'-hydroxy-4-methoxy-pyridine-2-carboxamidine (125 mg, 595 μmol), (2-(1H-benzotriazol-1-yl)-1,1,3,3-tetramethyluronium hexafluorophosphate) (282 mg, 744 μmol) and N-ethyl-N-(propan-2-yl)propan-2-amine (192 mg, 1.49 mmol, 259 μL) in N,N-dimethylformamide (2 mL) was stirred at 20° C. for 5 h, and at 110° C. for 1 h. The mixture was then cooled to room temperature and concentrated under vacuum to give a residue purified by chromatography (Boston Green ODS 150×30 5 μm; mobile phase: [water (10 mM ammonium carbonate)-acetonitrile]; B %: 25%-45%, 11.5 min). The title compound 2-[2-[4-[3-(5-ethoxy-4-methoxy-2-pyridyl)-1,2,4-oxadiazol-5-yl]-1-piperidyl]-2-oxo-ethyl]isoindolin-1-one was isolated as a white solid (76 mg, 160 μmol, 32%) as a white solid. $^1$H NMR (400 MHz, CHLOROFORM-d) δ=8.26 (s, 1H), 7.88-7.82 (m, 1H), 7.62 (s, 1H), 7.56-7.52 (m, 1H), 7.48-7.43 (m, 2H), 4.56 (d, J=9.3 Hz, 2H), 4.52-4.40 (m, 3H), 4.24 (q, J=7.1 Hz, 2H), 4.07 (br d, J=13.7 Hz, 1H), 4.00 (s, 3H), 3.40-3.26 (m, 2H), 3.05-2.97 (m, 1H), 2.27-2.16 (m, 2H), 2.07-1.93 (m, 2H), 1.50 (t, J=6.9 Hz, 3H); LCMS (ESI) m/z: [M+H]$^+$=478.3.

Example 148: (R)-5-(4-(3-(4-ethoxy-3-methoxyphenyl)-1,2,4-oxadiazol-5-yl)piperidine-1-carbonyl)-3-phenyloxazolidin-2-one

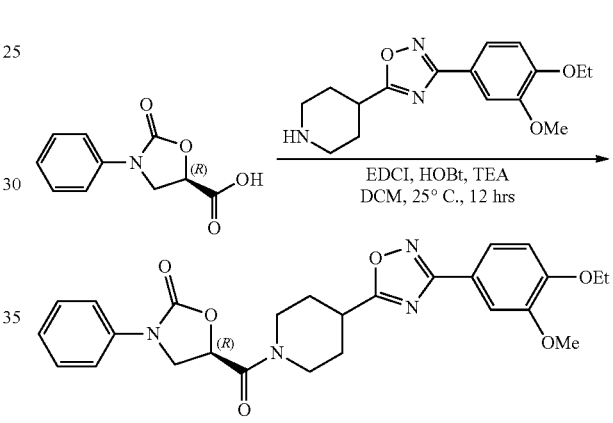

Step 1: Preparation of (R)-5-(4-(3-(4-ethoxy-3-methoxyphenyl)-1,2,4-oxadiazol-5-yl)piperidine-1-carbonyl)-3-phenyloxazolidin-2-one

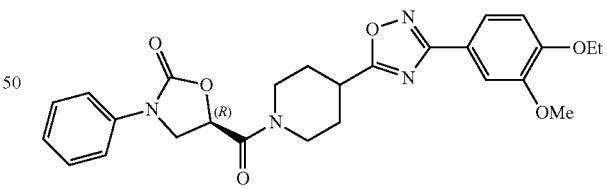

To a stirred solution of (R)-2-oxo-3-phenyloxazolidine-5-carboxylic acid (100 mg, 482.67 μmol) in dichloromethane (2 mL) was added 1-ethyl-3-(3-dimethylaminopropyl)carbodiimide (111 mg, 579 μmol), HOBt (78 mg, 579 μmol), triethylamine (146 mg, 1.45 mmol, 200 μL) and 3-(4-ethoxy-3-methoxyphenyl)-5-(piperidin-4-yl)-1,2,4-oxadiazole hydrochloride (164 mg, 482.67 μmol). The reaction mixture was stirred at 25° C. for 12 h and then concentrated under reduced pressure. The residue was purified by prep-HPLC (column: Boston Green ODS 150×30 Slim; mobile phase: [water (10 mM ammonium carbonate)-acetonitrile]; B %: 45%-75%, 11.5 min) to give (R)-5-(4-(3-(4-ethoxy-3- methoxyphenyl)-1,2,4-oxadiazol-5-yl)piperidine-1-carbonyl)-3-phenyloxazolidin-2-one (139 mg, 280 μmol, 58%) as a pale yellow solid. ¹H NMR (400 MHz, CHLOROFORM-d) δ 7.67 (d, J=8.3 Hz, 1H), 7.59-7.55 (m, 3H), 7.40 (t, J=7.7 Hz, 2H), 7.17 (t, J=6.9 Hz, 1H), 6.95 (dd, J=1.1, 8.6 Hz, 1H), 5.25 (ddd, J=3.1, 6.2, 9.1 Hz, 1H), 4.81 (dd, 8.6 Hz, 1H), 4.58 (br d, J=14.0 Hz, 0.5H), 4.37-4.21 (m, 1H), 4.17 (q, J=7.0 Hz, 2H), 4.07 (dt, 9.0 Hz, 1.5H), 3.96 (d, J=2.2 Hz, 3H), 3.59 (ddd, 10.3, 14.0 Hz, 0.5H), 3.41-3.17 (m, 2H), 3.09-3.00 (m, 0.5H), 2.34-1.95 (m, 4H), 1.54-1.47 (m, 3H); LCMS (ESI) m/z: [M+H]⁺=493.3.

Example 149: (S)-5-(4-(3-(1,3-dimethyl-1H-indazol-6-yl)-1,2,4-oxadiazol-5-yl)piperidine-1-carbonyl)-3-phenyloxazolidin-2-one

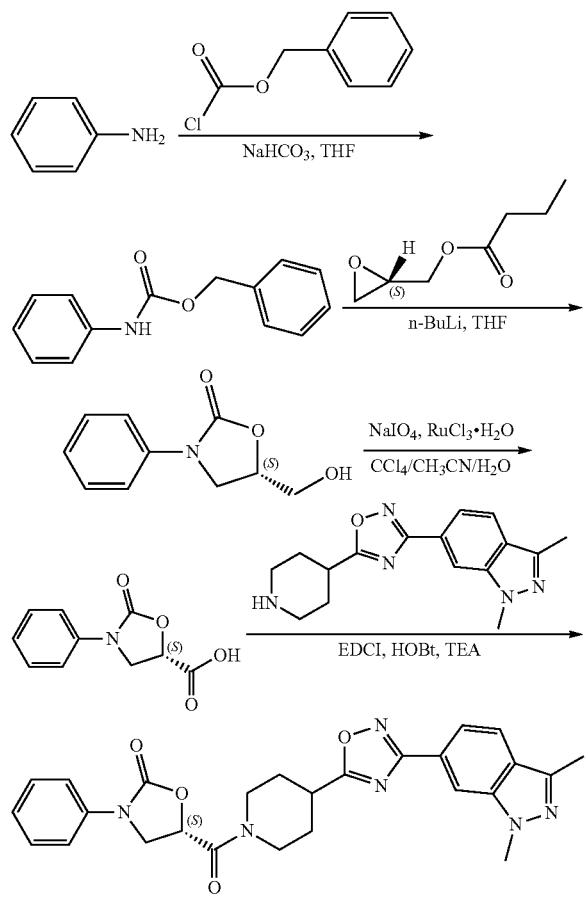

Step 1: Preparation of benzyl phenylcarbamate

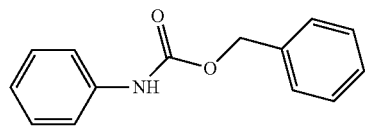 [SMILES: O=C(Nc1ccccc1)OCc1ccccc1]

To a stirred solution of aniline (5.0 g, 53.69 mmol, 4.90 mL) in tetrahydrofuran (100 mL) at 0° C. was added saturated aqueous sodium hydrogen carbonate (4.96 g, 59.06 mmol, 2.30 mL) followed by benzyl chloroformate (10.07 g, 59.06 mmol, 8.39 mL). The reaction mixture was stirred for 0.25 h at 0° C., warmed to 25° C. and stirring was continued for 0.75 h at 25° C. The reaction mixture was quenched with water (50 mL) and extracted with ethyl acetate (3×50 mL). The combined organic extracts were dried over anhydrous anhydrous sodium sulfate, filtered and concentrated under reduced pressure to provide benzyl phenylcarbamate (12.98 g, 53.7 mmol, 100%) isolated as a white solid, and used for the next step without further purification ¹H NMR (400 MHz, DMSO-d6) δ 9.76 (s, 1H), 7.53-7.23 (m, 9H), 6.99 (t, J=7.1 Hz, 1H), 5.15 (s, 2H).

Step 2 preparation of (S)-5-(hydroxymethyl)-3-phenyloxazolidin-2-one

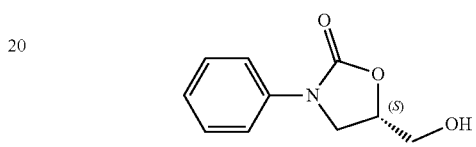

A solution of benzyl phenylcarbamate (3.0 g, 13.20 mmol) in dry tetrahydrofuran (30 mL) was cooled to −78° C. under dry nitrogen atmosphere. A solution of n-butyl lithium in tetrahydrofuran (2.5 M, 7.92 mL) was slowly added to the reaction mixture which was stirred for 0.75 h at −78° C. A solution of (S)-oxiran-2-ylmethyl butyrate (2.28 g, 15.84 mmol) in dry tetrahydrofuran (10 mL) was slowly added to the mixture which was stirred at −78° C. for 2 h and then slowly warmed to 25° C. Stirring was continued for 12 h at room temperature and the reaction mixture was quenched by the addition of saturated aqueous ammonium chloride (30 mL). Ethyl acetate (30 mL) and water (30 mL) were added to the mixture and the layers were separated. The aqueous layer was further extracted with ethyl acetate (3×30 mL). The combined organic extracts were washed with saturated aqueous sodium chloride solution (30 mL), dried over anhydrous anhydrous sodium sulfate, filtered, and evaporated under reduced pressure to give the crude product purified by chromatography (silica, petroleumether:ethylacetate=1:1). The title compound (S)-5-(hydroxymethyl)-3-phenyloxazolidin-2-one was isolated as a white solid (1.70 g, 8.80 mmol, 67%). ¹H NMR (400 MHz, METHANOL-d4) δ 7.57 (d, J=7.8 Hz, 2H), 7.43-7.31 (m, 2H), 7.14 (t, J=7.2 Hz, 1H). 4.78-4.71 (m, 1H), 4.13 (t, J=9.0 Hz, 1H), 3.94 (dd, J=6.6, 8.8 Hz, 1H), 3.85 (dd, J=3.4, 12.5 Hz, 1H), 3.70 (dd, 12.6 Hz, 1H).

Step 3 preparation of (S)-2-oxo-3-phenyloxazolidine-5-carboxylic acid

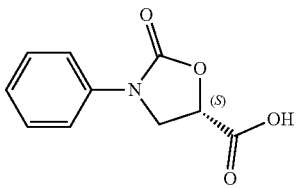

To an ice-cooled solution of NaIO₄ (3.88 g, 18.13 mmol, 1.01 mL) in water (30 mL) was added a solution of (S)-5-

(hydroxymethyl)-3-phenyloxazolidin-2-one (1.0 g, 5.18 mmol) in a mixture of acetonitrile (20 mL) and carbon tetrachloride (20 mL). Solid RuCl₃·H₂O (58 mg, 259 µmol) was added to the reaction mixture which was stirred at 0° C. for 0.5 h, warmed to 25° C. and then stirred at 25° C. for an additional 12 h. The suspension was then filtered and the filtered solid was washed thoroughly with dichloromethane (50 mL). The filtrate was concentrated under reduced pressure to provide a residue further dissolved in ethyl acetate (50 mL). The organic solution was washed with saturated aqueous sodium carbonate (2×20 mL). The organic layer was discarded. The aqueous layer was acidified with concentrated hydrochloric acid and extracted with ethyl acetate (3×30 mL). The combined organic phases were dried over anhydrous anhydrous sodium sulfate, filtered and concentrated under reduced pressure to afford the crude product (850 mg) crude. 500 mg of this crude product was purified by prep-HPLC (column: Luna C18 150×25 mm 5 µm; mobile phase: [water (0.225% FA)-acetonitrile]; B %: 30%-50%, 12 min) to give 150 mg of (S)-2-oxo-3-phenyloxazolidine-5-carboxylic acid as an off-white solid. ¹H NMR (400 MHz, CHLOROFORM-d) δ 7.57-7.45 (m, 2H), 7.44-7.34 (m, 2H), 7.24-7.10 (m, 1H), 5.12 (dd, J=5.3, 9.8 Hz, 1H), 4.37 (t, J=9.6 Hz, 1H) 4.19 (dd, J=5.3, 9.4 Hz, 1H).

Step 4: Preparation of (S)-5-(4-(3-(1,3-dimethyl-1H-indazol-6-yl)-1,2,4-oxadiazol-5-yl)piperidine-1-carbonyl)-3-phenyloxazolidin-2-one Example 150: N-[2-[4-[3-(1,3-dimethylindazol-6-yl)-1,2,4-oxadiazol-5-yl]-1-piperidyl]-2-oxo-ethyl]-4-methoxy-pyridine-2-carboxamide

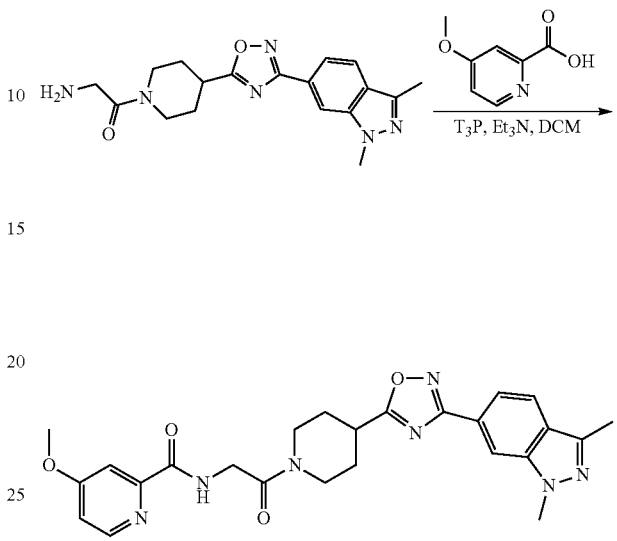

Step 1: Preparation of N-[2-[4-[3-(1,3-dimethylindazol-6-yl)-1,2,4-oxadiazol-5-yl]-1-piperidyl]-2-oxo-ethyl]-4-methoxy-pyridine-2-carboxamide

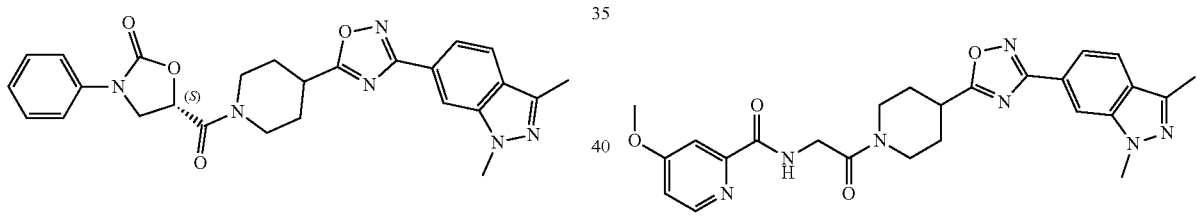

To a stirred solution of (S)-2-oxo-3-phenyloxazolidine-5-carboxylic acid (80 mg, 386 µmol) in hydroxybenzotriazole (62 mg, 463 µmol), triethylamine (117 mg, 1.16 mmol, 160 µL) and 3-(1,3-dimethyl-1H-indazol-6-yl)-5-(piperidin-4-yl)-1,2,4-oxadiazole, hydrochloride (128 mg, 386 µmol, hydrochloric acid). The reaction mixture was stirred at 25° C. for 12 h and was then concentrated under reduced pressure. The residue was purified by prep-HPLC (column: Boston Green ODS 150×30 5 µm; mobile phase: [water (10 mM ammonium carbonate)-acetonitrile]; B %: 43%-73%, 11.5 min) to give (S)-5-(4-(3-(1,3-dimethyl-1H-indazol-6-yl)-1,2,4-oxadiazol-5-yl)piperidine-1-carbonyl)-3-phenyloxazolidin-2-one (82 mg, 168.7 µmol, 44%) isolated as a white solid. ¹H NMR (400 MHz, CHLOROFORM-d) δ 8.11 (d, J=7.9 Hz, 1H), 7.84 (d, J=8.8 Hz, 1H). 7.74 (dd, J=3.5, 8.3 Hz, 1H), 7.58 (d, J=8.3 Hz, 2H), 7.41 (t, J=7.7 Hz, 2H), 7.20-7.16 (m, 1H), 5.26 (dd, J=7.5, 8.3 Hz, 1H), 4.83 (dd, J=6.4, 9.0 Hz, 1H), 4.66-4.57 (m, 0.5H), 4.38-4.27 (m, 1H), 4.09 (d, J=3.1 Hz, 4.5H), 3.66-3.59 (m, 0.5H), 3.45-3.32 (m, 2H). 3.08 (br t, J=11.2 Hz, 0.5H), 2.60 (s, 3H), 2.39-2.25 (m, 2H), 2.24-1.97 (m, 2H); LCMS (ESI) m/z: [M+H]⁺=487.3.

To a stirred solution of 2-amino-1-[4-[3-(1,3-dimethylindazol-6-yl)-1,2,4-oxadiazol-5-yl]-1-piperidyl]ethanone (130 mg, 366.81 µmol) in dichloromethane (3 mL) was added 4-methoxypyridine-2-carboxylic acid (56 mg, 366.81 µmol), 2,4,6-tripropyl-1,3,5,2,4,6-trioxatriphosphinane 2,4,6-trioxide in ethyl acetate (256 mg, 403 µmol, 239 µL, 50% purity) and triethylamine (111 mg, 1.10 mmol, 152 µL). The mixture was stirred at 20° C. for 1 h and then concentrated under reduced pressure. The resulting residue was purified by chromatography (column: Luna C18 100×30 5 µm; mobile phase: [water (10 mM ammonium carbonate)-acetonitrile]; B %: 20%-60%, 10 min) to give N-[2-[4-[3-(1,3-dimethylindazol-6-yl)-1,2,4-oxadiazol-5-yl]-1-piperidyl]-2-oxo-ethyl]-4-methoxy-pyridine-2-carboxamide (18 mg, 35 µmol, 10%) as a white solid. ¹H NMR (400 MHz, CDCl₃) δ 8.93 (br s, 1H), 8.41 (d, J=5.5 Hz, 1H), 8.10 (s, 1H), 7.86-7.80 (m, 1H), 7.77-7.69 (m, 2H), 6.93 (dd, J=2.4, 5.5 Hz, 1H), 4.56 (br d, J=14.1 Hz, 1H), 4.34 (d, J=4.4 Hz, 2H), 4.08 (s, 3H), 3.96 (br d, J=13.9 Hz, 1H), 3.92 (s, 3H), 3.41-3.31 (m, 2H), 3.14 (br t, J=11.6 Hz, 1H), 2.60 (s, 3H), 2.33-2.22 (m, 2H), 2.11-1.95 (m, 2H); LCMS (ESI) m/z: [M+H]⁺=490.2.

Example 151: N-(2-(4-(3-(1,3-dimethyl-1H-indazol-6-yl)-1,2,4-oxadiazol-5-yl)piperidin-1-yl)-2-oxo-ethyl)-5-methoxypicolinamide

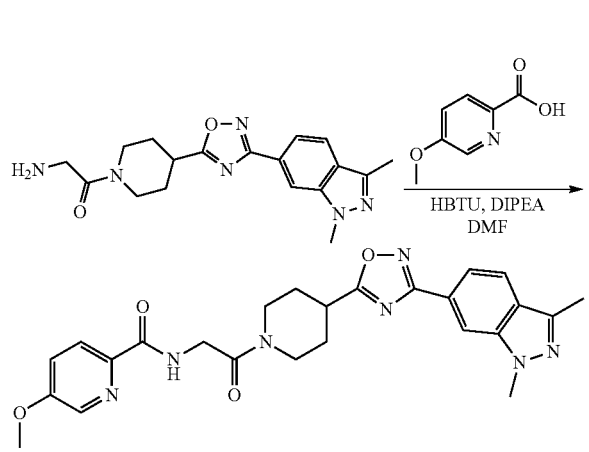

Example 151 was synthesized according to a procedure similar to the one described in Example 154. $^1$H NMR (400 MHz, CDCl$_3$) δ 8.72 (br s, 1H), 8.27 (d, J=2.6 Hz, 1H), 8.13 (d, J=8.6 Hz, 1H), 8.09 (s, 1H), 7.85-7.79 (m, 1H), 7.77-7.68 (m, 1H), 7.29 (d, J=2.6 Hz, 1H), 4.55 (br d, J=13.7 Hz, 1H), 4.33 (d, J=4.2 Hz, 2H), 4.08 (s, 3H), 3.96 (br d, J=13.9 Hz, 1H), 3.91 (s, 3H), 3.40-3.30 (m, 2H), 3.13 (br t, J=10.9 Hz, 1H), 2.60 (s, 3H), 2.27 (br t, J=11.8 Hz, 2H), 2.09-1.95 (m, 2H); LCMS (ESI) m/z: [M+H]$^+$=490.2.

Example 152: N-(2-(4-(3-(1,3-dimethyl-1H-indazol-6-yl)-1,2,4-oxadiazol-5-yl)piperidin-1-yl)-2-oxo-ethyl)-2-methoxybenzamide

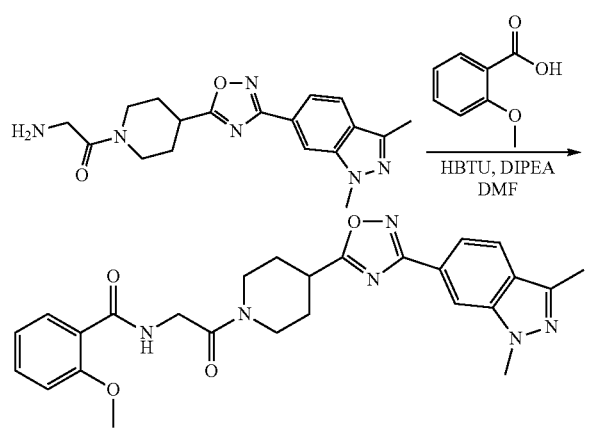

Example 152 was synthesized according to a procedure similar to the one described in Example 154. $^1$H NMR (400 MHz, CDCl$_3$) δ 9.03 (br s, 1H), 8.22 (dd, J=1.4, 7.8 Hz, 1H), 8.10 (s, 1H), 7.87-7.80 (m, 1H), 7.77-7.71 (m, 1H), 7.51-7.43 (m, 1H), 7.09 (t, J=7.6 Hz, 1H), 7.01 (d, J=8.2 Hz, 1H), 4.55 (br d, J=13.9 Hz, 1H), 4.38 (d, J=4.0 Hz, 2H), 4.08 (s, 3H), 4.05 (s, 3H), 3.96 (br d, J=14.1 Hz, 1H), 3.41-3.31 (m, 2H), 3.15 (br t, J=11.4 Hz, 1H), 2.60 (s, 3H), 2.28 (br t, J=10.6 Hz, 2H), 2.10-1.96 (m, 2H); LCMS (ESI) m/z: [M+H]$^+$=489.3.

Example 153: N-(2-(4-(3-(1,3-dimethyl-1H-indazol-6-yl)-1,2,4-oxadiazol-5-yl)piperidin-1-yl)-2-oxo-ethyl)picolinamide

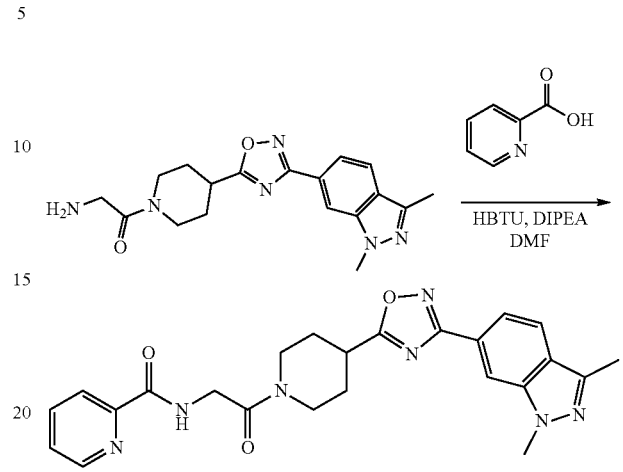

Example 153 was synthesized according to a procedure similar to the one described in Example 154. $^1$H NMR (400 MHz, CDCl$_3$) δ 8.93 (br s, 1H), 8.63 (d, J=4.0 Hz, 1H), 8.19 (d, J=7.7 Hz, 1H), 8.10 (s, 1H), 7.89-7.80 (m, 2H), 7.76-7.71 (m, 1H), 7.47-7.41 (m, 1H), 4.56 (br d, J=13.7 Hz, 1H), 4.35 (d, J=4.4 Hz, 2H), 4.09 (s, 3H), 3.96 (br d, J=13.9 Hz, 1H), 3.44-3.31 (m, 2H), 3.15 (br t, J=10.7 Hz, 1H), 2.60 (s, 3H), 2.34-2.23 (m, 2H), 2.11-1.95 (m, 2H); LCMS (ESI) m/z: [M+H]$^+$=460.2.

Example 154: N-[2-[4-[3-(1,3-dimethylindazol-6-yl)-1,2,4-oxadiazol-5-yl]-1-piperidyl]-2-oxo-ethyl]-6-methoxy-pyridine-2-carboxamide

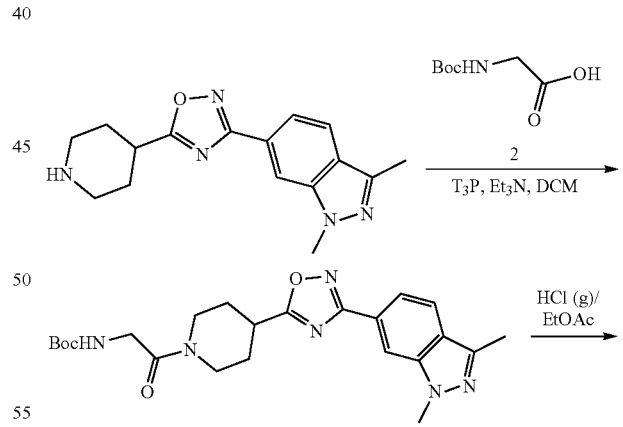

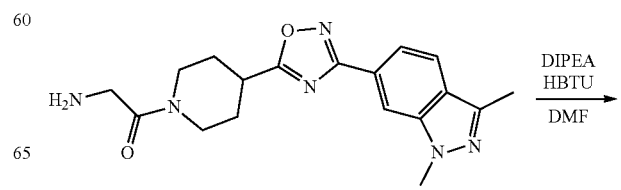

-continued

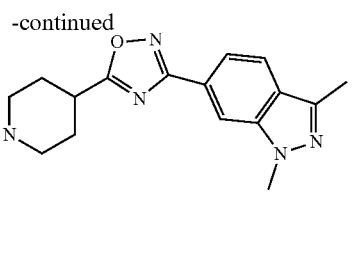

Step 1: Preparation of tert-butyl N-[2-[4-[3-(1,3-dimethylindazol-6-yl)-1,2,4-oxadiazol-5-yl]-1-piperidyl]-2-oxo-ethyl]carbamate

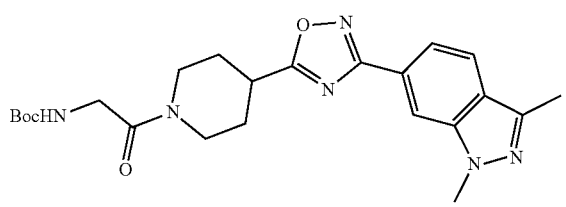 [SMILES: Cc1nn(C)c2cc(-c3noc(C4CCN(C(=O)CNC(=O)OC(C)(C)C)CC4)n3)ccc12]

To a stirred solution of 3-(1,3-dimethylindazol-6-yl)-5-(4-piperidyl)-1,2,4-oxadiazole (1.0 g, 3.00 mmol, 1.00 eq, hydrochloric acid salt) in dichloromethane (20 mL) was added 2-(tert-butoxycarbonylamino)acetic acid (525 mg, 3.00 mmol), 2,4,6-tripropyl-1,3,5,2,4,6-trioxatriphosphinane 2,4,6-trioxide in ethyl acetate (2.86 g, 4.50 mmol, 2.68 mL, 50% purity) and triethylamine (1.82 g, 18.00 mmol, 2.49 mL, 6.00 eq). The mixture was stirred at 20° C. for 16 h. Water (30 mL) was then added to the reaction mixture which was extracted with dichloromethane (60 mL×3). The combined organic extracts were washed with saturated aqueous sodium chloride (30 mL), dried over anhydrous sodium sulfate, filtered and concentrated under reduced pressure to provide the crude product further purified by chromatography (silica, petroleumether:ethylacetate=20:1 to 1:4). The title compound (tert-butyl N-[2-[4-[3-(1,3-dimethylindazol-6-yl)-1,2,4-oxadiazol-5-yl]-1-piperidyl]-2-oxo-ethyl]carbamate) was isolated as a white solid (1.0 g, 2.20 mmol, 73%). $^1$H NMR (400 MHz, CDCl$_3$) δ 8.10 (s, 1H), 7.86-7.80 (m, 1H), 7.77-7.72 (m, 1H), 5.53 (br s, 1H), 4.50 (br d, J=12.3 Hz, 1H), 4.09 (s, 3H), 4.02 (br d, J=3.5 Hz, 2H), 3.83 (br d, J=12.7 Hz, 1H), 3.38-3.23 (m, 2H), 3.10 (br t, J=11.6 Hz, 1H), 2.60 (s, 3H), 2.23 (br s, 2H), 2.06-1.94 (m, 2H), 1.47 (s, 9H).

Step 2: Preparation of 2-amino-1-[4-[3-(1,3-dimethylindazol-6-yl)-1,2,4-oxadiazol-5-yl]-1-piperidyl]ethanone

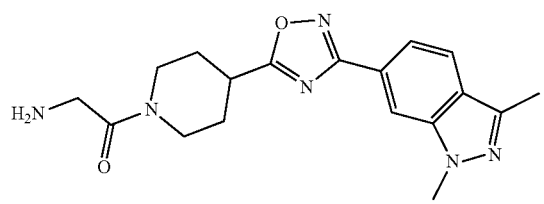 [SMILES: Cc1nn(C)c2cc(-c3noc(C4CCN(C(=O)CN)CC4)n3)ccc12]

To a stirred solution of tert-butyl N-[2-[4-[3-(1,3-dimethylindazol-6-yl)-1,2,4-oxadiazol-5-yl]-1-piperidyl]-2-oxo-ethyl]carbamate (980 mg, 2.16 mmol) in ethyl acetate (5 mL) was added a 4M solution of hydrochloric acid in ethyl acetate (50 mL). The mixture was stirred at 20° C. for 0.5 h and then concentrated under reduced pressure to give 2-amino-1-[4-[3-(1,3-dimethylindazol-6-yl)-1,2,4-oxadiazol-5-yl]-1-piperidyl]ethanone, hydrochloride (940 mg, crude)) isolated as a white solid and used for the next step without further purification. $^1$H NMR (400 MHz, Methanol-d4) δ 8.19 (s, 1H), 7.83 (d, J=0.9 Hz, 2H), 4.48 (br d, J=13.9 Hz, 1H), 4.06 (s, 3H), 4.04-3.95 (m, 2H), 3.86 (br d, J=13.9 Hz, 1H), 3.53-3.43 (m, 1H), 3.38 (br t, J=11.5 Hz, 1H), 3.13 (br t, J=11.2 Hz, 1H), 2.58 (s, 3H), 2.28 (br t, J=9.3 Hz, 2H), 2.01-1.84 (m, 2H).

Step 3: Preparation of N-[2-[4-[3-(1,3-dimethylindazol-6-yl)-1,2,4-oxadiazol-5-yl]-1-piperidyl]-2-oxo-ethyl]-6-methoxy-pyridine-2-carboxamide

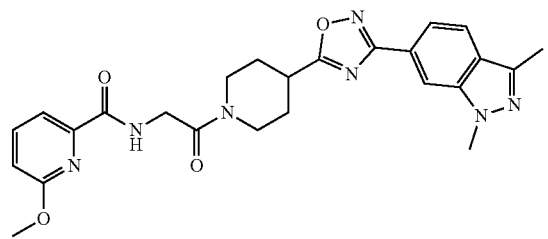

To a stirred solution of 2-amino-1-[4-[3-(1,3-dimethylindazol-6-yl)-1,2,4-oxadiazol-5-yl]-1-piperidyl]ethanone (130 mg, 366.81 μmol) in N,N-dimethylformamide (2 mL) was added 6-methoxypyridine-2-carboxylic acid (56 mg, 366.81 μmol), (2-(1H-benzotriazol-1-yl)-1,1,3,3-tetramethyluronium hexafluorophosphate) (166 mg, 440 μmol) and N-ethyl-N-(propan-2-yl)propan-2-amine (142 mg, 1.10 mmol, 192 μL). The mixture was stirred at 20° C. for 1 h and concentrated under reduced pressure. The resulting residue was purified by chromatography (column: Luna C18 100×30 5 μm; mobile phase: [water (10 mM ammonium carbonate)-acetonitrile]; B %: 25%-65%, 10 min) to give N-[2-[4-[3-(1,3-dimethylindazol-6-yl)-1,2,4-oxadiazol-5-yl]-1-piperidyl]-2-oxo-ethyl]-6-methoxy-pyridine-2-carboxamide (92 mg, 187.6 μmol, 51%) as a white solid. $^1$H NMR (400 MHz, CDCl$_3$) δ 8.82 (br s, 1H), 8.10 (s, 1H), 7.86-7.69 (m, 4H), 6.92 (d, J=8.2 Hz, 1H), 4.55 (br d, J=13.9 Hz, 1H), 4.34 (d, J=4.2 Hz, 2H), 4.08 (s, 3H), 4.05 (s, 3H), 4.01-3.92 (m, 1H), 3.43-3.32 (m, 2H), 3.17 (br t, J=11.1 Hz, 1H), 2.60 (s, 3H), 2.34-2.23 (m, 2H), 2.12-1.97 (m, 2H); LCMS (ESI) m/z: [M+H]$^+$=490.3.

Example 155: N-(2-(4-(3-(4-ethoxy-3-methoxyphenyl)-1,2,4-oxadiazol-5-yl)piperidin-1-yl)-2-oxoethyl)benzamide

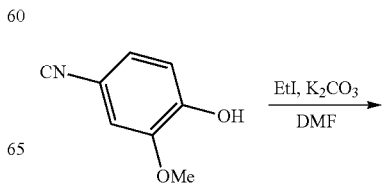

-continued

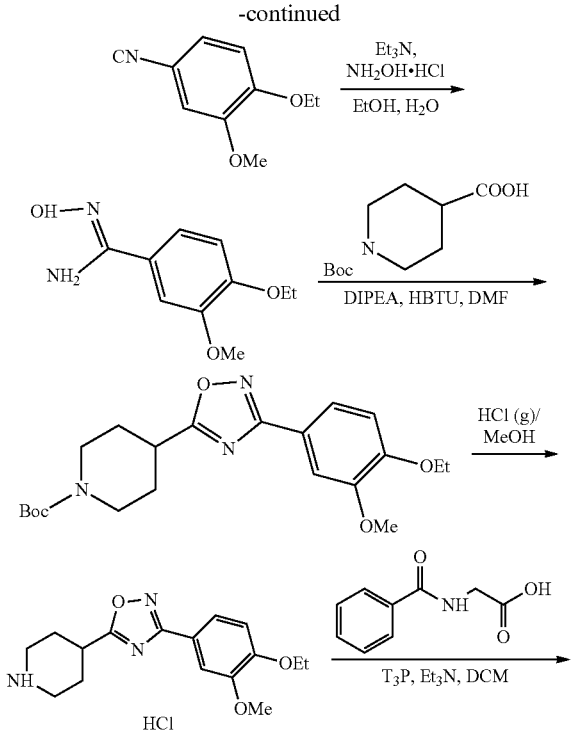

Step 1: Preparation of 4-ethoxy-3-methoxy-benzonitrile

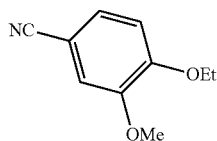 [SMILES: CCOc1ccc(C#N)cc1OC]

To a 0° C. stirred solution of 4-hydroxy-3-methoxy-benzonitrile (20 g, 134.09 mmol) in N,N-dimethylformamide (200 mL) was added iodoethane (25.10 g, 160.91 mmol, 12.87 mL), potassium carbonate (37.07 g, 268.18 mmol). The reaction mixture was stirred at 40° C. for 16 h and then quenched by addition of water (300 mL). The mixture was extracted with ethyl acetate (200 mL×3) and the combined organic extracts were washed with saturated aqueous sodium chloride solution (100 mL), dried over anhydrous sodium sulfate, filtered and concentrated under reduced pressure to give 4-ethoxy-3-methoxy-benzonitrile (25.0 g, crude), isolated as a yellow solid and used for the next step without further purification. $^1$H NMR (400 MHz, CDCl$_3$) δ 7.30-7.20 (m, 1H), 7.07 (d, J=1.8 Hz, 1H), 6.88 (d, J=8.4 Hz, 1H), 4.14 (q, J=7.0 Hz, 2H), 3.88 (s, 3H), 1.49 (t, J=7.0 Hz, 3H).

Step 2: Preparation of 4-ethoxy-N'-hydroxy-3-methoxy-benzamidine

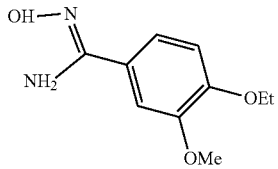 [SMILES: CCOc1ccc(/C(N)=N/O)cc1OC]

To a stirred solution of 4-ethoxy-3-methoxy-benzonitrile (25.0 g, 141.08 mmol) in ethanol (200 mL) was added hydroxylamine hydrochloride (19.61 g, 282.17 mmol), triethylamine (28.55 g, 282.17 mmol, 39.11 mL) and water (20 mL). The mixture was stirred at 80° C. for 2 h and then concentrated under reduced pressure. The resulting residue was diluted with water (30 mL) and filtered to provide 4-ethoxy-N'-hydroxy-3-methoxy-benzamidine isolated as a white solid (24.0 g, 114.2 mmol, 81%) and used for the next step without further purification. $^1$H NMR (400 MHz, DMSO-d6) δ 9.47 (br s, 1H), 7.25 (d, J=2.0 Hz, 1H), 7.20 (dd, J=2.0, 8.4 Hz, 1H), 6.92 (d, J=8.4 Hz, 1H), 5.75 (br s, 2H), 4.01 (q, J=7.0 Hz, 2H), 3.76 (s, 3H), 1.32 (t, J=7.0 Hz, 3H).

Step 3: Preparation of tert-butyl 4-[3-(4-ethoxy-3-methoxy-phenyl)-1,2,4-oxadiazol-5-yl]piperidine-1-carboxylate

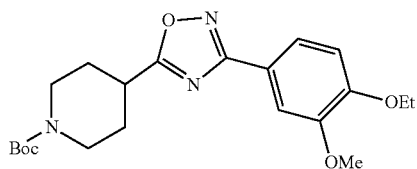 [SMILES: CCOc1ccc(-c2noc(C3CCN(C(=O)OC(C)(C)C)CC3)n2)cc1OC]

To a stirred solution of 4-ethoxy-N'-hydroxy-3-methoxy-benzamidine (10.0 g, 47.57 mmol) in N,N-dimethylformamide (100 mL) was added 1-tert-butoxycarbonylpiperidine-4-carboxylic acid (10.91 g, 47.57 mmol), 2-(1H-benzotriazol-1-yl)-1,1,3,3-tetramethyluronium hexafluorophosphate (18.04 g, 47.57 mmol) and N-ethyl-N-(propan-2-yl)propan-2-amine (18.44 g, 142.71 mmol, 24.92 mL), The mixture was stirred at 20° C. for 16 h and at 110° C. for 1 h. The reaction mixture was then cooled to room temperature, quenched by addition of water (100 mL) and extracted with ethyl acetate (100 mL×3). The combined organic layers were washed with saturated aqueous sodium chloride (50 mL), dried over anhydrous sodium sulfate, filtered and concentrated to give the crude product further was purified by chromatography (silica, petroleumether:ethylacetate=1:0 to 10:1). The title compound, tert-butyl 4-[3-(4-ethoxy-3-methoxy-phenyl)-1,2,4-oxadiazol-5-yl]piperidine-1-carboxylate, was isolated as a yellow solid (13.30 g, 33.0 mmol, 69%).

Step 4: Preparation of 3-(4-ethoxy-3-methoxy-phenyl)-5-(4-piperidyl)-1,2,4-oxadiazole

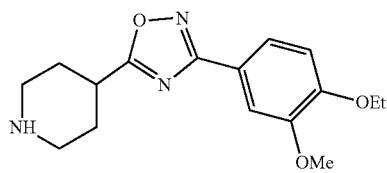 [SMILES: CCOc1ccc(-c2noc(C3CCNCC3)n2)cc1OC]

To a stirred solution of tert-butyl 4-[3-(4-ethoxy-3-methoxy-phenyl)-1,2,4-oxadiazol-5-yl]piperidine-1-carboxylate (13.30 g, 32.96 mmol) in ethyl acetate (300 mL) was added a 4M solution of hydrochloric acid in methanol (30 mL). The mixture was stirred at 20° C. for 2 h and filtered to give 3-(4-ethoxy-3-methoxy-phenyl)-5-(4-piperidyl)-1,2,4-oxadiazole hydrochloride (10.0 g, 29.4 mmol, 89%), isolated as a white solid and used for the next step without further purification.

Step 5: Preparation of N-[2-[4-[3-(4-ethoxy-3-methoxy-phenyl)-1,2,4-oxadiazol-5-yl]-1-piperidyl]-2-oxo-ethyl]benzamide

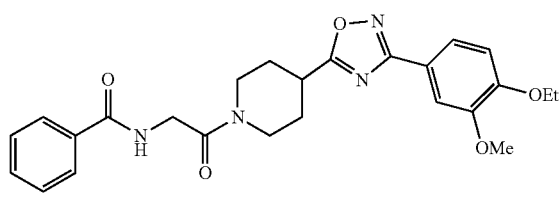 [SMILES: CCOc1ccc(-c2noc(C3CCN(C(=O)CNC(=O)c4ccccc4)CC3)n2)cc1OC]

To a stirred solution of 2-benzamidoacetic acid (1.16 g, 6.48 mmol) in dichloromethane (20 mL) was added 3-(4-ethoxy-3-methoxy-phenyl)-5-(4-piperidyl)-1,2,4-oxadiazole hydrochloride (2.0 g, 5.89 mmol), 2,4,6-tripropyl-1,3,5,2,4,6-trioxatriphosphinane 2,4,6-trioxide in ethyl acetate (4.87 g, 7.65 mmol, 4.55 mL, 50% in ethyl acetate) and triethylamine (2.38 g, 23.5 mmol, 3.26 mL). The mixture was stirred at 20° C. for 16 h. Water (20 mL) was then added to the mixture which was extracted with dichloromethane (80 mL×2). The combined organic extracts were washed with saturated aqueous sodium chloride solution, dried over anhydrous sodium sulfate, filtered and concentrated to give a residue dissolved in with ethyl acetate (40 mL). The organic solution was washed with 1N aqueous hydrochloric acid solution (15 mL×2), saturated sodium carbonate (15 mL×2), saturated aqueous sodium chloride solution (15 mL×2), dried over anhydrous sodium sulfate, filtered and concentrated to give the crude product. To a solution of the crude product in methyl tert-butyl ether (20 mL) was added petroleum ether (2 mL). The precipitate, formed after 2 h stirring at room temperature, was collected by filtration, washed with methyl tert-butyl ether (5 mL×2) and dried under reduced pressure to give N-[2-[4-[3-(4-ethoxy-3-methoxy-phenyl)-1,2,4-oxadiazol-5-yl]-1-piperidyl]-2-oxo-ethyl]benzamide (1.68 g, 3.60 mmol, 61%) as a white solid. $^1$H NMR (400 MHz, CDCl$_3$) δ 7.89-7.83 (m, 2H), 7.66 (dd, J=1.9, 8.3 Hz, 1H), 7.58-7.42 (m, 4H), 7.35 (br s, 1H), 6.95 (d, J=8.4 Hz, 1H), 4.50 (td, J=3.8, 13.6 Hz, 1H), 4.30 (d, J=4.0 Hz, 2H), 4.17 (q, J=7.0 Hz, 2H), 3.96 (s, 3H), 3.94-3.87 (m, 1H), 3.38-3.27 (m, 2H), 3.19-3.08 (m, 1H), 2.24 (m, 2H), 2.07-1.91 (m, 2H), 1.50 (t, J=7.0 Hz, 3H); LCMS (ESI) m/z: [M+H]$^+$=465.2.

Example 156. Characterization Data of Compounds of the Invention

The following compounds were synthesized by methods similar to those described above.

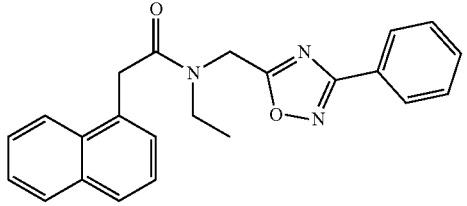 [SMILES: CCN(Cc1nc(-c2ccccc2)no1)C(=O)Cc1cccc2ccccc12]

$^1$H NMR (400 MHz, DMSO-d$_6$) δ 8.10-7.71 (m, 5H), 7.65-7.30 (m, 7H), 4.87 (br s, 2H), 4.26 (s, 2H), 3.69 (br s, 2H), 1.23 (br s, 3H); LCMS (ESI) [M+H]+: 372.1.

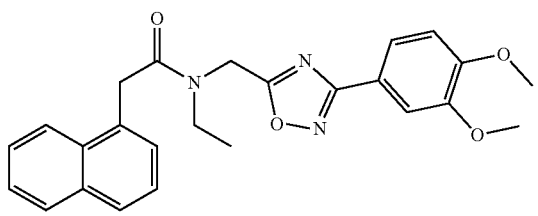 [SMILES: CCN(Cc1nc(-c2ccc(OC)c(OC)c2)no1)C(=O)Cc1cccc2ccccc12]

$^1$H NMR (400 MHz, DMSO-d$_6$) δ 8.07-8.00 (m, 1H), 7.99-7.91 (m, 1H), 7.86 (d, J=6.2 Hz, 1H), 7.66 (d, J=8.4 Hz, 1H), 7.58-7.52 (m, 3H), 7.49 (br s, 2H), 7.20 (d, J=8.4 Hz, 1H), 4.92 (br s, 2H), 4.32 (s, 2H), 3.91 (d, J=6.2 Hz, 6H), 3.74 (br s, 2H), 1.28 (br s, 3H); LCMS (ESI) [M+H]+: 432.1.

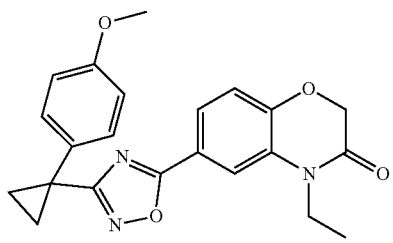 [SMILES: CCN1C(=O)COc2ccc(-c3nc(C4(c5ccc(OC)cc5)CC4)no3)cc21]

$^1$H NMR (400 MHz, DMSO-d$_6$) δ 7.71-7.59 (m, 1H), 7.33 (br d, J=8.6 Hz, 1H), 7.18 (d, J=8.4 Hz, 1H), 6.89 (br d, J=8.6 Hz, 2H), 4.76 (s, 2H), 4.06-3.91 (m, 2H), 3.74 (s, 3H), 1.60-1.49 (m, 2H), 1.34 (br d, J=2.2 Hz, 2H), 1.16 (br t, J=7.1 Hz, 3H); LCMS (ESI) [M+H]+: 392.2.

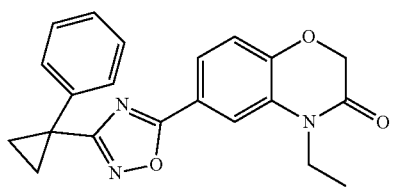 [SMILES: CCN1C(=O)COc2ccc(-c3nc(C4(c5ccccc5)CC4)no3)cc21]

$^1$H NMR (400 MHz, DMSO-d$_6$) δ 7.73-7.63 (m, 2H), 7.44-7.39 (m, 2H), 7.37-7.25 (m, 3H), 7.21-7.15 (m, 1H), 4.84-4.69 (s, 2H), 4.05-3.91 (m, 2H), 1.62-1.54 (m, 2H), 1.43-1.36 (m, 2H), 1.16 (s, 3H); LCMS (ESI) [M+H]+: 362.2.

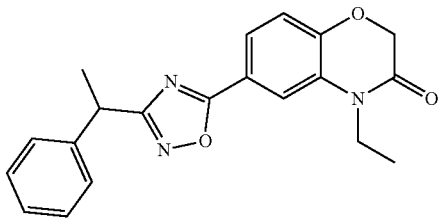 [SMILES: CCN1C(=O)COc2ccc(-c3nc(C(C)c4ccccc4)no3)cc21]

¹H NMR (400 MHz, CHLOROFORM-d) δ 7.71 (dd, J=1.8, 8.3 Hz, 1H), 7.63 (d, J=1.9 Hz, 1H), 7.37-7.31 (m, 2H), 7.27 (t, J=7.5 Hz, 2H), 7.22-7.16 (m, 2H), 7.00 (d, J=8.3 Hz, 1H), 4.60 (s, 2H), 4.28 (q, J=7.2 Hz, 1H), 3.99 (q, J=7.1 Hz, 2H), 1.69 (d, J=7.2 Hz, 3H), 1.25 (t, J=7.2 Hz, 3H); LCMS (ESI) [M+H]+: 350.2.

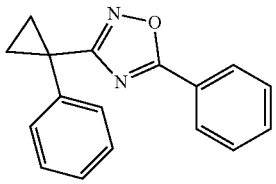 [SMILES: c1ccc(-c2nc(C3(c4ccccc4)CC3)no2)cc1]

¹H NMR (400 MHz, CHLOROFORM-d) δ 8.09-8.11 (m, 2H), 7.51-7.53 (m, 5H), 7.25-7.40 (m, 3H), 1.72-1.74 (t, 2H), 1.43-1.46 (t, 2H); LCMS (ESI) [M+H]+: 263.1.

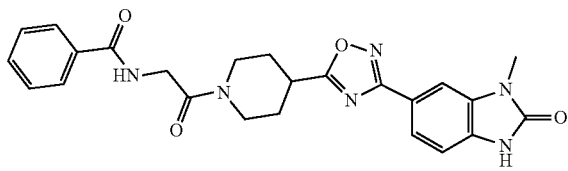 [SMILES: Cn1c(=O)[nH]c2ccc(-c3noc(C4CCN(C(=O)CNC(=O)c5ccccc5)CC4)n3)cc21]

¹H NMR (400 MHz, CHLOROFORM-d) δ 9.06 (br s, 1H), 7.88-7.80 (m, 3H), 7.69 (s, 1H), 7.53-7.44 (m, 3H), 7.40-7.30 (m, 1H), 7.18-7.16 (d, J=8.4 Hz, 1H), 4.54-4.50 (m, 1H), 4.33-4.32 (d, J=4.0 Hz, 2H), 3.95-3.91 (m, 1H), 3.49 (s, 3H), 3.39-3.13 (m, 1H), 2.30-2.23 (m, 2H), 2.05-1.98 (m, 2H); LCMS (ESI) [M+H]+: 461.1.

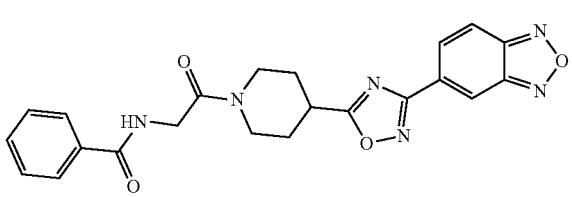 [SMILES: O=C(NCC(=O)N1CCC(c2nc(-c3ccc4nonc4c3)no2)CC1)c1ccccc1]

¹H NMR (400 MHz, CHLOROFORM-d) δ 8.64 (t, J=1.1 Hz, 1H), 8.11 (dd, J=1.2, 9.4 Hz, 1H), 7.96 (dd, J=1.0, 9.4 Hz, 1H), 7.87-7.81 (m, 2H), 7.54-7.48 (m, 1H), 7.47-7.41 (m, 2H), 7.31 (br s, 1H), 4.57-4.48 (m, 1H), 4.30 (d, J=3.7 Hz, 2H), 3.92 (br d, J=14.1 Hz, 1H), 3.41-3.31 (m, 2H), 3.20-3.09 (m, 1H), 2.27 (dt, J=3.7, 13.2 Hz, 2H), 2.00 (ddq, J=4.1, 10.6, 14.4 Hz, 2H); LCMS (ESI) [M+H]+: 433.1.

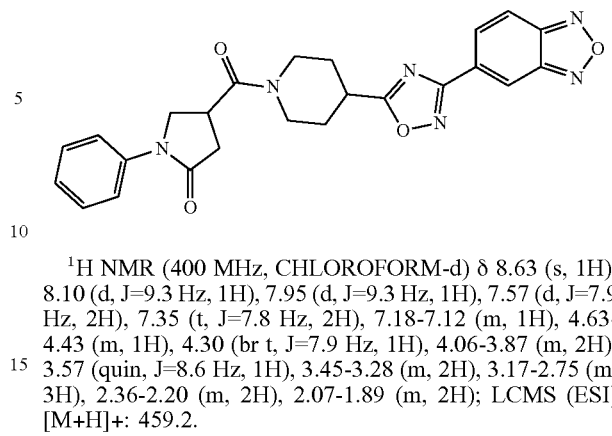

¹H NMR (400 MHz, CHLOROFORM-d) δ 8.63 (s, 1H), 8.10 (d, J=9.3 Hz, 1H), 7.95 (d, J=9.3 Hz, 1H), 7.57 (d, J=7.9 Hz, 2H), 7.35 (t, J=7.8 Hz, 2H), 7.18-7.12 (m, 1H), 4.63-4.43 (m, 1H), 4.30 (br t, J=7.9 Hz, 1H), 4.06-3.87 (m, 2H), 3.57 (quin, J=8.6 Hz, 1H), 3.45-3.28 (m, 2H), 3.17-2.75 (m, 3H), 2.36-2.20 (m, 2H), 2.07-1.89 (m, 2H); LCMS (ESI) [M+H]+: 459.2.

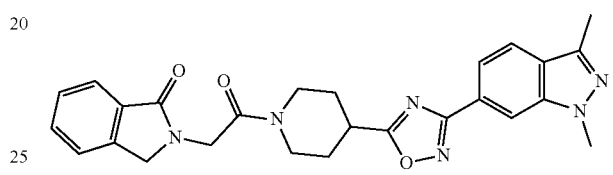

¹H NMR (400 MHz, METHANOL-d₄) δ 8.14 (s, 1H), 7.77-7.70 (m, 3H), 7.62-7.47 (m, 2H), 7.51-7.46 (m, 1H), 4.64-4.42 (m, 5H), 4.09-4.01 (m, 1H), 4.01 (s, 3H), 3.48-3.37 (m, 2H), 3.06 (br t, J=11.0 Hz, 1H), 2.53 (s, 3H), 2.32-2.18 (m, 2H), 2.07-1.84 (m, 2H); LCMS (ESI) [M+H]+: 471.3.

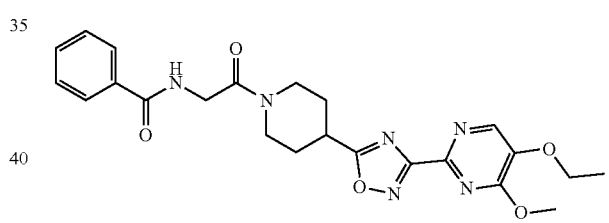

¹H NMR (400 MHz, CHLOROFORM-d) δ 8.18 (s, 1H), 7.85 (d, J=7.0 Hz, 2H), 7.54-7.42 (m, 3H), 7.32 (br s, 1H), 4.51 (br d, J=13.6 Hz, 1H), 4.29 (t, J=4.8 Hz, 2H), 4.26-4.17 (m, 5H), 3.90 (br d, J=14.0 Hz, 1H), 3.42-3.28 (m, 2H), 3.10 (br t, J=11.0 Hz, 1H), 2.33-2.22 (m, 2H), 2.13-1.95 (m, 2H), 1.52 (t, J=7.0 Hz, 3H); LCMS (ESI) [M+H]+: 467.3.

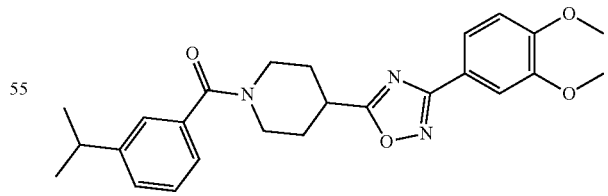

¹H NMR (400 MHz, CHLOROFORM-d) δ 7.68 (dd, J=1.8, 8.3 Hz, 1H), 7.56 (d, J=1.8 Hz, 1H), 7.36-7.27 (m, 3H), 7.24-7.20 (m, 1H), 6.95 (d, J=8.3 Hz, 1H), 4.76-4.53 (m, 1H), 3.86-3.93 (m, 1H), 3.94-3.96 (m, 1H), 4.30 (d, J=8.3 Hz, 6H), 3.34-3.14 (m, 2H), 3.34-3.11 (m, 1H), 2.93 (quin, J=7.0 Hz, 1H), 2.97-2.89 (m, 1H), 2.34-1.88 (m, 4H), 1.26 (d, J=7.0 Hz, 6H); LCMS (ESI) [M+H]+: 436.2.

605

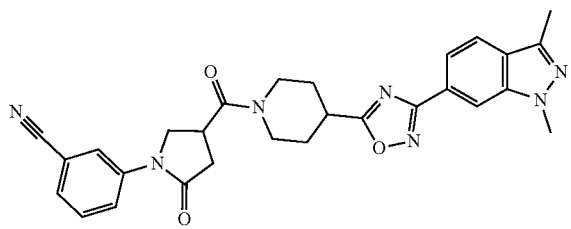 [SMILES: Cc1nn(C)c2cc(-c3noc(C4CCN(C(=O)C5CC(=O)N(c6cccc(C#N)c6)C5)CC4)n3)ccc12]

¹H NMR (400 MHz, CHLOROFORM-d) δ 8.10 (d, J=3.1 Hz, 1H), 8.01-7.88 (m, 2H), 7.87-7.80 (m, 1H), 7.78-7.71 (m, 1H), 7.53-7.42 (m, 2H), 4.63-4.49 (m, 1H), 4.34 (dd, J=7.1, 8.8 Hz, 1H), 4.09 (d, J=2.6 Hz, 3H), 4.04-3.92 (m, 2H), 3.63 (quin, J=8.2 Hz, 1H), 3.48-3.34 (m, 2H), 3.21-2.85 (m, 3H), 2.61 (s, 3H), 2.30 (br t, J=14.3 Hz, 2H), 2.11-1.94 (m, 2H); LCMS (ESI) [M+H]+: 510.0.

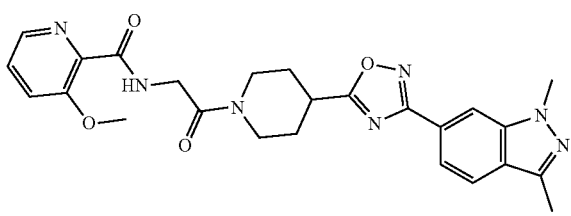 [SMILES: COc1cccnc1C(=O)NCC(=O)N1CCC(c2nc(-c3ccc4c(C)nn(C)c4c3)no2)CC1]

¹H NMR (400 MHz, CHLOROFORM-d) δ 8.69 (br s, 1H), 8.32 (dd, J=1.5, 4.2 Hz, 1H), 8.10 (s, 1H), 7.86-7.80 (m, 1H), 7.77-7.71 (m, 1H), 7.45-7.36 (m, 2H), 4.54 (br d, J=13.9 Hz, 1H), 4.37 (br d, J=3.5 Hz, 2H), 4.09 (s, 3H), 4.00 (s, 3H), 3.96 (br s, 1H), 3.41-3.31 (m, 2H), 3.14 (br t, J=11.1 Hz, 1H), 2.60 (s, 3H), 2.33-2.22 (m, 2H), 2.11-1.94 (m, 2H); LCMS (ESI) [M+H]+: 490.2.

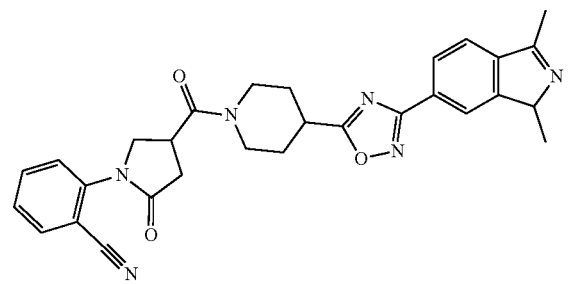 [SMILES: CC1=NC(C)c2cc(-c3noc(C4CCN(C(=O)C5CC(=O)N(c6ccccc6C#N)C5)CC4)n3)ccc21]

¹H NMR (400 MHz, CHLOROFORM-d) δ 8.10 (br d, J=7.1 Hz, 1H), 7.87-7.79 (m, 1H), 7.78-7.63 (m, 3H), 7.56-7.48 (m, 1H), 7.46-7.38 (m, 1H), 4.56 (br t, J=13.6 Hz, 1H), 4.32-4.22 (m, 1H), 4.17-3.96 (m, 5H), 3.74 (quin, J=8.2 Hz, 1H), 3.48-3.31 (m, 2H), 3.20-3.04 (m, 1H), 3.01-2.84 (m, 2H), 2.60 (s, 3H), 2.36-2.21 (m, 2H), 2.10-1.93 (m, 2H); LCMS (ESI) [M+H]+: 510.3.

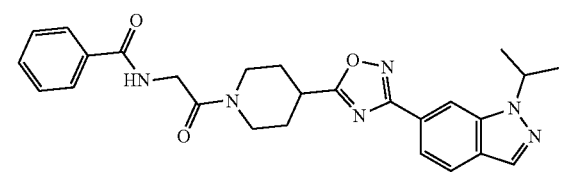 [SMILES: CC(C)n1ncc2ccc(-c3noc(C4CCN(C(=O)CNC(=O)c5ccccc5)CC4)n3)cc21]

606

¹H NMR (400 MHz, CHLOROFORM-d) δ 8.20 (s, 1H), 8.05 (s, 1H), 7.87-7.78 (m, 4H), 7.54-7.42 (m, 2H), 7.35 (br s, 1H), 5.00-4.91 (spt, J=6.8 Hz, 1H), 4.52-4.50 (br d, J=13.7 Hz, 1H), 4.35-4.27 (d, J=3.7 Hz, 2H), 3.94-3.91 (br d, J=13.9 Hz, 1H), 3.38-3.32 (m, 2H), 3.18-3.12 (br t, J=11.0 Hz, 1H), 2.35-2.21 (m, 2H), 2.09-1.96 (m, 2H), 1.63-1.62 (d, J=6.6 Hz, 6H); LCMS (ESI) [M+H]+: 473.2.

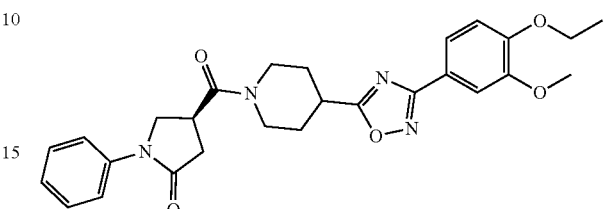

¹H NMR (400 MHz, CHLOROFORM-d) δ 7.67 (br d, J=8.2 Hz, 1H), 7.60-7.55 (m, 3H), 7.40 (t, J=7.7 Hz, 2H), 7.18 (t, J=6.9 Hz, 1H), 6.95 (d, J=8.4 Hz, 1H), 5.28-5.22 (m, 1H), 4.84-4.79 (m, 1H), 4.59 (br d, J=13.5 Hz, 0.5H), 4.36-4.22 (m, 1H), 4.18 (q, J=7.1 Hz, 2H), 4.13-4.03 (m, 1.5H), 3.97 (d, J=2.2 Hz, 3H), 3.64-3.54 (m, 0.5H), 3.41-3.27 (m, 2H), 3.09-3.01 (m, 0.5H), 2.35-2.15 (m, 2.5H), 2.11-1.93 (m, 1.5H), 1.51 (t, J=6.8 Hz, 3H); LCMS (ESI) [M+H]+: 492.8.

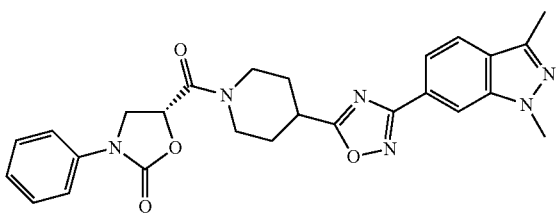 [SMILES: Cc1nn(C)c2cc(-c3noc(C4CCN(C(=O)[C@H]5CN(c6ccccc6)C(=O)O5)CC4)n3)ccc12]

¹H NMR (400 MHz, CHLOROFORM-d) δ 8.11 (d, J=7.5 Hz, 1H), 7.84 (dd, J=1.3, 8.3 Hz, 1H), 7.74 (dd, J=3.9, 8.3 Hz, 1H), 7.58 (d, J=7.9 Hz, 2H), 7.40 (t, J=7.7 Hz, 2H), 7.18 (t, J=7.3 Hz, 1H), 5.26 (t, J=7.7 Hz, 1H), 4.83 (dd, J=6.6, 8.8 Hz, 1H), 4.62 (d, J=13.6 Hz, 0.5H), 4.38-4.26 (m, 1H), 4.13-4.05 (m, 4.5H), 3.66-3.58 (m, 0.5H), 3.45-3.31 (m, 2H), 3.11-3.04 (m, 0.5H), 2.60 (s, 3H), 2.40-2.25 (m, 2H), 2.24-1.96 (m, 2H); LCMS (ESI) [M+H]+: 487.3.

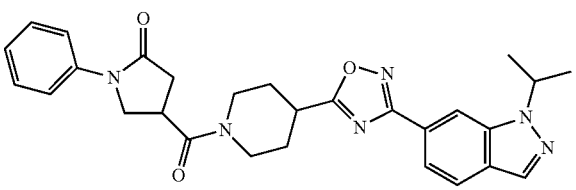 [SMILES: CC(C)n1ncc2ccc(-c3noc(C4CCN(C(=O)C5CC(=O)N(c6ccccc6)C5)CC4)n3)cc21]

¹H NMR (400 MHz, DMSO-d₆) δ 8.28 (s, 1H), 8.17 (s, 1H), 7.92-7.90 (d, J=8.4 Hz, 1H), 7.75-7.73 (d, J=8.4 Hz, 1H), 7.66-7.64 (br d, J=8.2 Hz, 2H), 7.38-7.33 (dt, J=3.7, 7.8 Hz, 2H), 7.13-7.11 (m, 1H), 5.15-5.11 (dt, J=3.5, 6.5 Hz, 1H), 4.39-4.35 (br d, J=13.2 Hz, 1H), 4.06-3.93 (m, 3H), 3.78-3.70 (m, 1H), 3.50-3.45 (br t, J=10.7 Hz, 1H), 3.36-3.33 (m, 1H), 2.98-2.93 (m, 1H), 2.81-2.71 (m, 2H), 2.20-2.13 (br t, J=14.0 Hz, 2H), 1.89-1.65 (m, 2H), 1.49-1.48 (d, J=6.4 Hz, 6H); LCMS (ESI) [M+H]+: 499.2.

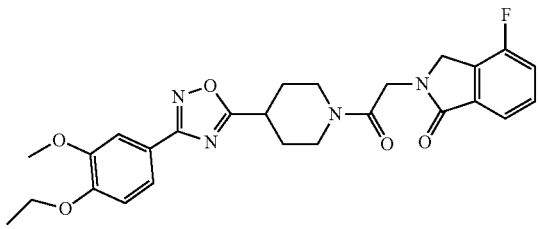 [SMILES: CCOc1ccc(-c2noc(C3CCN(C(=O)CN4Cc5c(F)cccc5C4=O)CC3)n2)cc1OC]

¹H NMR (400 MHz, CHLOROFORM-d) δ 7.69-7.62 (m, 2H), 7.55 (d, J=1.8 Hz, 1H), 7.45 (dt, J=4.6, 7.7 Hz, 1H), 7.27-7.24 (m, 1H), 7.27-7.19 (m, 1H), 6.94 (d, J=8.6 Hz, 1H), 4.63 (d, J=2.9 Hz, 2H), 4.55-4.39 (m, 3H), 4.16 (q, J=6.9 Hz, 2H), 4.02 (br d, J=13.7 Hz, 1H), 3.95 (s, 3H), 3.43-3.23 (m, 2H), 3.06 (br t, J=10.9 Hz, 1H), 2.29-2.15 (m, 2H), 2.08-1.88 (m, 2H), 1.50 (t, J=7.1 Hz, 3H); LCMS (ESI) [M+H]+: 495.1.

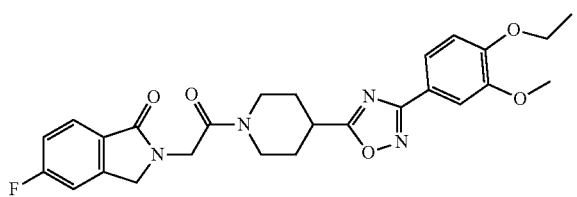 [SMILES: CCOc1ccc(-c2noc(C3CCN(C(=O)CN4Cc5cc(F)ccc5C4=O)CC3)n2)cc1OC]

¹H NMR (400 MHz, CHLOROFORM-d) δ 7.85 (dd, J=5.3, 8.4 Hz, 1H), 7.65 (dd, J=1.8, 8.4 Hz, 1H), 7.56 (d, J=1.8 Hz, 1H), 7.20-7.13 (m, 2H), 6.95 (d, J=8.4 Hz, 1H), 4.57 (d, J=3.7 Hz, 2H), 4.51-4.41 (m, 3H), 4.18 (q, J=7.0 Hz, 2H), 4.05 (br d, J=13.9 Hz, 1H), 3.96 (s, 3H), 3.42-3.24 (m, 2H), 3.07 (br t, J=10.9 Hz, 1H), 2.29-2.15 (m, 2H), 2.07-1.89 (m, 2H), 1.51 (t, J=6.9 Hz, 3H); LCMS (ESI) [M+H]+: 495.1.

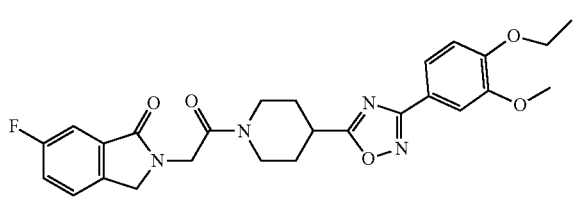 [SMILES: CCOc1ccc(-c2noc(C3CCN(C(=O)CN4Cc5ccc(F)cc5C4=O)CC3)n2)cc1OC]

¹H NMR (400 MHz, CHLOROFORM-d) δ 7.53 (dd, J=2.0, 8.4 Hz, 1H), 7.46-7.39 (m, 2H), 7.30 (dd, J=4.4, 8.2 Hz, 1H), 7.18-7.10 (m, 1H), 6.83 (d, J=8.4 Hz, 1H), 4.52-4.27 (m, 5H), 4.05 (q, J=7.0 Hz, 2H), 3.92 (br d, J=13.7 Hz, 1H), 3.84 (s, 3H), 3.32-3.10 (m, 2H), 2.94 (br t, J=10.8 Hz, 1H), 2.10 (br t, J=15.0 Hz, 2H), 1.95-1.76 (m, 2H), 1.39 (t, J=7.1 Hz, 3H); LCMS (ESI) [M+H]+: 495.1.

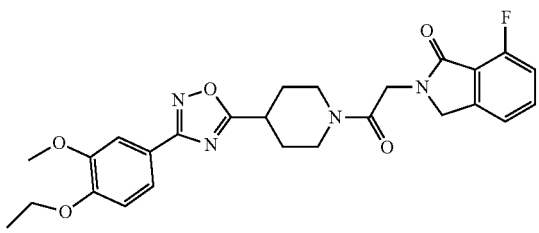 [SMILES: CCOc1ccc(-c2noc(C3CCN(C(=O)CN4Cc5cccc(F)c5C4=O)CC3)n2)cc1OC]

¹H NMR (400 MHz, CHLOROFORM-d) δ 7.66 (dd, J=2.0, 8.4 Hz, 1H), 7.58-7.49 (m, 2H), 7.24 (d, J=7.5 Hz, 1H), 7.10 (t, J=8.8 Hz, 1H), 6.95 (d, J=8.4 Hz, 1H), 4.59 (d, J=5.1 Hz, 2H), 4.53-4.38 (m, 3H), 4.17 (q, J=6.9 Hz, 2H), 4.07 (br d, J=13.9 Hz, 1H), 3.96 (s, 3H), 3.45-3.22 (m, 2H), 3.12-3.02 (m, 1H), 2.22 (br dd, J=14.2, 18.2 Hz, 2H), 2.09-1.88 (m, 2H), 1.51 (t, J=7.1 Hz, 3H); LCMS (ESI) [M+H]+: 495.3.

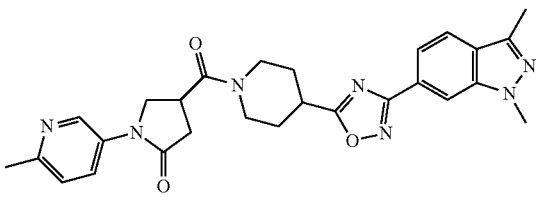 [SMILES: Cc1ccc(N2CC(C(=O)N3CCC(c4nc(-c5ccc6c(C)nn(C)c6c5)no4)CC3)CC2=O)cn1]

¹H NMR (400 MHz, CHLOROFORM-d) δ 8.56 (dd, J=2.3, 7.2 Hz, 1H), 8.13-8.02 (m, 2H), 7.86-7.79 (m, 1H), 7.77-7.71 (m, 1H), 7.17 (d, J=8.6 Hz, 1H), 4.64-4.47 (m, 1H), 4.32 (ddd, J=3.3, 6.6, 9.5 Hz, 1H), 4.08 (d, J=2.2 Hz, 3H), 4.04-3.91 (m, 2H), 3.63 (quin, J=8.3 Hz, 1H), 3.46-3.32 (m, 2H), 3.19-3.04 (m, 1H), 3.01-2.81 (m, 2H), 2.60 (s, 3H), 2.54 (s, 3H), 2.28 (br t, J=13.3 Hz, 2H), 2.11-1.95 (m, 2H); LCMS (ESI) [M+H]+: 500.3.

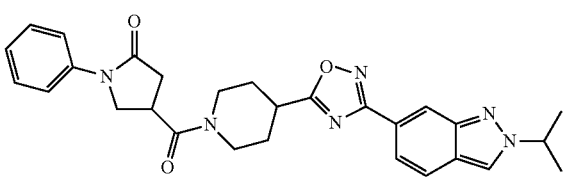 [SMILES: CC(C)n1cc2ccc(-c3noc(C4CCN(C(=O)C5CC(=O)N(c6ccccc6)C5)CC4)n3)cc2n1]

¹H NMR (400 MHz, CHLOROFORM-d) δ 8.51 (s, 1H), 7.98 (s, 1H), 7.73 (s, 2H), 7.59-7.57 (br d, J=8.2 Hz, 2H), 7.38-7.34 (t, J=7.9 Hz, 2H), 7.17-7.13 (m, 1H), 4.85-4.77 (m, 1H), 4.50-4.42 (br t, J=14.9 Hz, 1H), 4.33-4.23 (m, 1H), 4.01-3.89 (m, 2H), 3.62-3.54 (quin, J=8.5 Hz, 1H), 3.45-3.27 (m, 2H), 3.22-2.90 (m, 2H), 2.87-2.75 (m, 1H), 2.31-2.17 (m, 2H), 2.07-1.91 (m, 2H), 1.67-1.66 (d, J=6.8 Hz, 6H); LCMS (ESI) [M+H]+: 499.3.

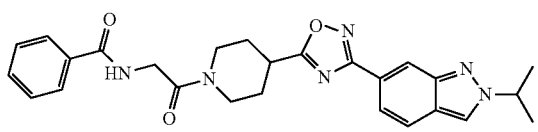 [SMILES: CC(C)n1cc2ccc(-c3noc(C4CCN(C(=O)CNC(=O)c5ccccc5)CC4)n3)cc2n1]

¹H NMR (400 MHz, DMSO-d₆) δ 8.57-8.52 (m, 2H), 8.27 (s, 1H), 7.88-7.84 (t, J=7.6 Hz, 3H), 7.62-7.60 (dd, J=1.2, 8.7 Hz, 1H), 7.55-7.43 (m, 3H), 4.92-4.82 (spt, J=6.7 Hz, 1H), 4.34-4.31 (br d, J=13.5 Hz, 1H), 4.18-4.16 (d, J=5.5 Hz, 2H), 4.00-3.96 (br d, J=13.9 Hz, 1H), 3.50-3.43 (m, 1H), 3.29-3.25 (m, 1H), 2.95-2.90 (br t, J=11.2 Hz, 1H), 2.18-2.12 (br t, J=12.3 Hz, 2H), 1.88-1.80 (q, J=10.6 Hz, 1H), 1.73-1.63 (m, 1H), 1.60-1.55 (d, J=6.6 Hz, 6H); LCMS (ESI) [M+H]+: 473.3.

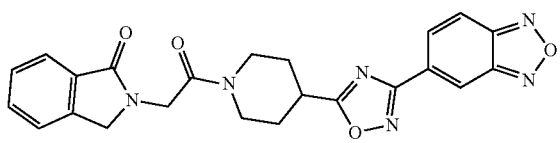 [SMILES: O=C(CN1Cc2ccccc2C1=O)N1CCC(c2nc(-c3ccc4nonc4c3)no2)CC1]

¹H NMR (400 MHz, CHLOROFORM-d) δ 8.63 (t, J=1.1 Hz, 1H), 8.11 (dd, J=1.3, 9.3 Hz, 1H), 7.96 (dd, J=1.0, 9.4 Hz, 1H), 7.88-7.83 (m, 1H), 7.59-7.53 (m, 1H), 7.50-7.43 (m, 2H), 4.58 (s, 2H), 4.53-4.43 (m, 3H), 4.11 (br d, J=14.1 Hz, 1H), 3.45-3.28 (m, 2H), 3.12-3.01 (m, 1H), 2.25 (br t, J=14.1 Hz, 2H), 2.07-1.87 (m, 2H); LCMS (ESI) [M+H]+: 445.2.

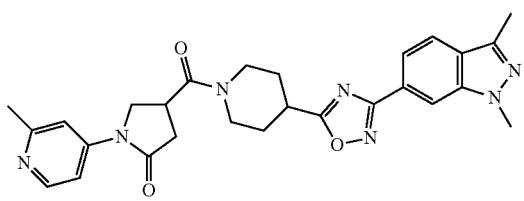 [SMILES: Cc1cc(N2CC(C(=O)N3CCC(c4nc(-c5ccc6c(C)nn(C)c6c5)no4)CC3)CC2=O)ccn1]

¹H NMR (400 MHz, CHLOROFORM-d) δ 8.44 (br d, J=5.5 Hz, 1H), 8.09 (s, 1H), 7.87-7.80 (m, 1H), 7.78-7.71 (m, 1H), 7.50 (br s, 1H), 7.40 (br d, J=5.3 Hz, 1H), 4.64-4.48 (m, 1H), 4.29 (dd, J=6.9, 9.6 Hz, 1H), 4.08 (s, 3H), 4.04-3.90 (m, 2H), 3.61 (quin, J=8.4 Hz, 1H), 3.40 (br d, J=10.8 Hz, 2H), 3.21-3.04 (m, 1H), 3.02-2.82 (m, 2H), 2.60 (s, 3H), 2.56 (s, 3H), 2.29 (br t, J=14.7 Hz, 2H), 2.11-1.96 (m, 2H); LCMS (ESI) [M+H]+: 500.2.

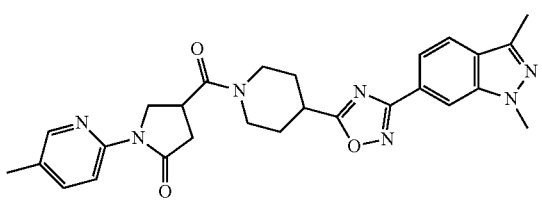 [SMILES: Cc1ccc(N2CC(C(=O)N3CCC(c4nc(-c5ccc6c(C)nn(C)c6c5)no4)CC3)CC2=O)nc1]

¹H NMR (400 MHz, CHLOROFORM-d) δ 8.27 (br dd, J=4.7, 8.3 Hz, 1H), 8.15 (br s, 1H), 8.10 (br s, 1H), 7.86-7.79 (m, 1H), 7.78-7.71 (m, 1H), 7.52 (br d, J=8.4 Hz, 1H), 4.57 (br t, J=12.7 Hz, 1H), 4.41 (dd, J=9.0, 10.8 Hz, 1H), 4.22-4.14 (m, 1H), 4.09 (s, 3H), 4.04 (br d, J=14.1 Hz, 1H), 3.57 (quin, J=8.2 Hz, 1H), 3.47-3.32 (m, 2H), 3.25 (br dd, J=7.7, 17.2 Hz, 1H), 3.16-3.04 (m, 1H), 2.86-2.76 (m, 1H), 2.60 (s, 3H), 2.36-2.21 (m, 5H), 2.12-1.93 (m, 2H); LCMS (ESI) [M+H]+: 500.3.

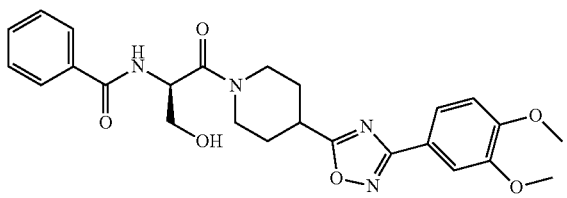 [SMILES: COc1ccc(-c2noc(C3CCN(C(=O)[C@@H](CO)NC(=O)c4ccccc4)CC3)n2)cc1OC]

¹H NMR (400 MHz, CHLOROFORM-d) δ 7.85-7.80 (m, 2H), 7.66 (br t, J=8.8 Hz, 1H), 7.58-7.49 (m, 3H), 7.47-7.41 (m, 2H), 6.94 (t, J=7.9 Hz, 1H), 5.18 (br d, J=2.6 Hz, 1H), 4.54-4.38 (m, 1H), 4.18 (br t, J=14.0 Hz, 1H), 3.97-3.92 (m, 7H), 3.89-3.83 (m, 1H), 3.46-3.36 (m, 1H), 3.34-3.23 (m, 1H), 3.19-3.03 (m, 1H), 2.23 (br s, 2H), 2.11-1.92 (m, 2H); LCMS (ESI) [M+H]+: 481.3.

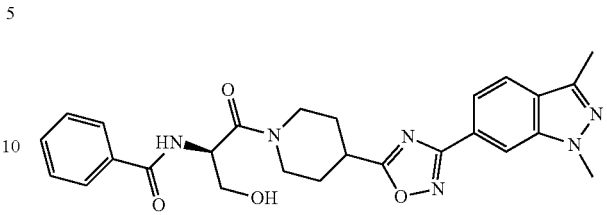

¹H NMR (400 MHz, METHANOL-d₄) δ 8.14 (br d, J=11.0 Hz, 1H), 7.89-7.84 (m, 2H), 7.77 (br d, J=7.0 Hz, 2H), 7.55-7.43 (m, 3H), 5.23 (t, J=6.1 Hz, 1H), 4.58-4.45 (m, 1H), 4.28 (br t, J=14.9 Hz, 1H), 4.02 (br d, J=5.3 Hz, 3H), 3.93-3.82 (m, 2H), 3.54-3.40 (m, 2H), 3.16-3.03 (m, 1H), 2.54 (s, 3H), 2.34-2.18 (m, 2H), 2.08-1.86 (m, 2H); LCMS (ESI) [M+H]+: 489.3.

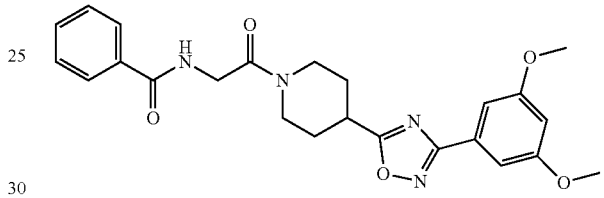

¹H NMR (400 MHz, CHLOROFORM-d) δ 7.86 (d, J=7.1 Hz, 2H), 7.58-7.42 (m, 3H), 7.35 (br s, 1H), 7.23 (d, J=2.2 Hz, 2H), 6.61 (t, J=2.2 Hz, 1H), 4.50 (br d, J=13.7 Hz, 1H), 4.31 (d, J=4.0 Hz, 2H), 3.91 (br d, J=14.3 Hz, 1H), 3.86 (s, 6H), 3.39-3.29 (m, 2H), 3.15 (br t, J=10.7 Hz, 1H), 2.30-2.20 (m, 2H), 2.08-1.93 (m, 2H); LCMS (ESI) [M+H]+: 451.3.

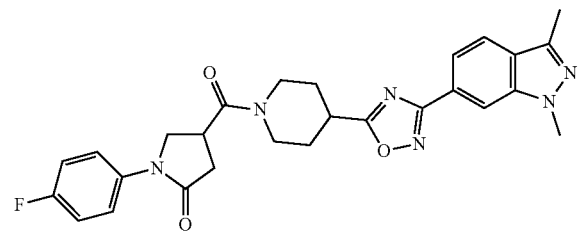 [SMILES: Cc1nn(C)c2cc(-c3noc(C4CCN(C(=O)C5CC(=O)N(c6ccc(F)cc6)C5)CC4)n3)ccc12]

¹H NMR (400 MHz, CHLOROFORM-d) δ 8.10 (d, J=4.9 Hz, 1H), 7.87-7.80 (m, 1H), 7.79-7.72 (m, 1H), 7.57 (br dd, J=4.6, 8.6 Hz, 2H), 7.08 (t, J=8.6 Hz, 2H), 4.65-4.48 (m, 1H), 4.36-4.29 (m, 1H), 4.09 (d, J=3.3 Hz, 3H), 4.05-3.87 (m, 2H), 3.60 (quin, J=8.3 Hz, 1H), 3.48-3.32 (m, 2H), 3.20-3.03 (m, 1H), 3.01-2.82 (m, 2H), 2.61 (s, 3H), 2.29 (br t, J=13.7 Hz, 2H), 2.10-1.94 (m, 2H); LCMS (ESI) [M+H]+: 503.3.

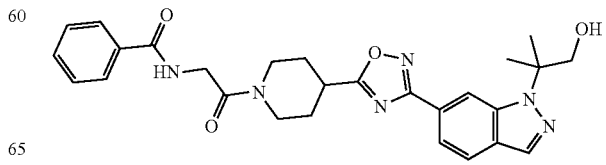

611

¹H NMR (400 MHz, CHLOROFORM-d) δ 8.34 (d, J=0.9 Hz, 1H), 7.93 (d, J=1.1 Hz, 1H), 7.83-7.75 (m, 4H), 7.49-7.35 (m, 3H), 7.27 (br s, 1H), 4.52-4.43 (m, 1H), 4.25 (dd, J=2.4, 3.7 Hz, 2H), 4.02 (br d, J=6.4 Hz, 2H), 3.91-3.81 (m, 2H), 3.34-3.24 (m, 2H), 3.11-3.02 (m, 1H), 2.21 (dt, J=3.4, 13.2 Hz, 2H), 2.05-1.87 (m, 2H), 1.69 (s, 6H); LCMS (ESI) [M+H]+: 503.2.

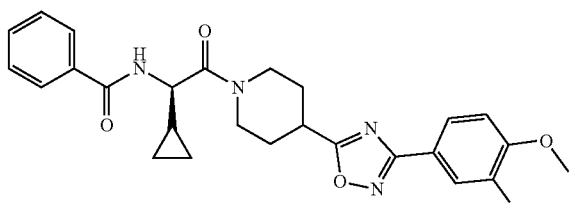

¹H NMR (400 MHz, CHLOROFORM-d) δ 7.83-7.78 (m, 2H), 7.67 (br t, J=8.6 Hz, 1H), 7.58-7.47 (m, 2H), 7.46-7.40 (m, 2H), 7.16 (br d, J=6.6 Hz, 1H), 6.97-6.90 (m, 1H), 5.09-4.96 (m, 1H), 4.59-4.38 (m, 1H), 4.23-4.06 (m, 1H), 3.99-3.91 (m, 6H), 3.49-3.25 (m, 2H), 3.21-3.04 (m, 1H), 2.34-2.13 (m, 2H), 2.10-1.90 (m, 2H), 1.25 (br d, J=5.7 Hz, 1H), 0.74-0.43 (m, 4H); LCMS (ESI) [M+H]+: 491.0.

612

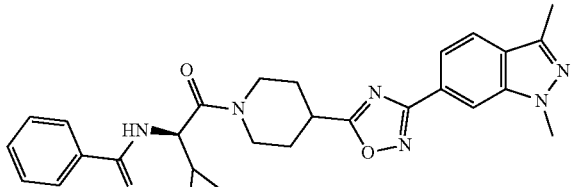

¹H NMR (400 MHz, CHLOROFORM-d) δ 8.08 (br d, J=6.6 Hz, 1H), 7.85-7.77 (m, 3H), 7.75-7.67 (m, 1H), 7.53-7.46 (m, 1H), 7.45-7.40 (m, 2H), 7.18 (br s, 1H), 5.09-4.96 (m, 1H), 4.59-4.43 (m, 1H), 4.23-4.10 (m, 1H), 4.06 (br d, J=5.3 Hz, 3H), 3.52-3.30 (m, 2H), 3.21-3.05 (m, 1H), 2.58 (d, J=2.2 Hz, 3H), 2.37-2.19 (m, 2H), 2.13-1.97 (m, 1H), 2.13-1.97 (m, 1H), 1.27 (br s, 1H), 0.63-0.43 (m, 4H); LCMS (ESI) [M+H]+: 499.3.

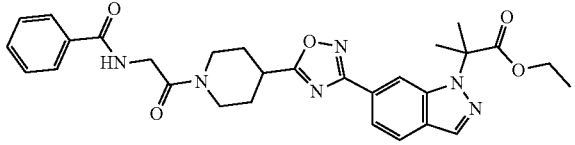 [SMILES: CCOC(=O)C(C)(C)n1ncc2ccc(-c3noc(C4CCN(C(=O)CNC(=O)c5ccccc5)CC4)n3)cc21]

¹H NMR (400 MHz, CHLOROFORM-d) δ 8.04 (d, J=5.7 Hz, 2H), 7.88-7.78 (m, 4H), 7.55-7.40 (m, 3H), 7.33 (br s, 1H), 4.51 (br d, J=13.7 Hz, 1H), 4.30 (d, J=3.7 Hz, 2H), 4.20 (q, J=7.1 Hz, 2H), 3.90 (br d, J=14.1 Hz, 1H), 3.39-3.28 (m, 2H), 3.12 (br t, J=11.1 Hz, 1H), 2.32-2.17 (m, 2H), 1.99 (s, 8H), 1.15 (t, J=7.2 Hz, 3H); LCMS (ESI) [M+H]+: 545.2.

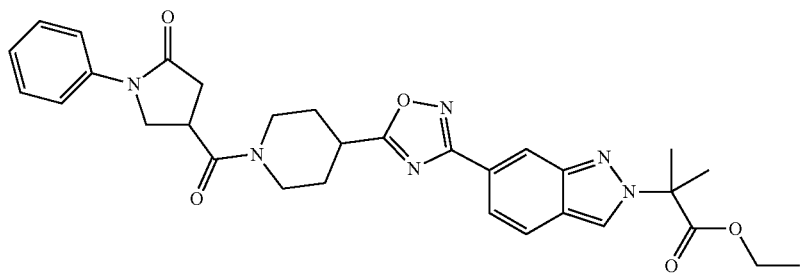 [SMILES: CCOC(=O)C(C)(C)n1cc2ccc(-c3noc(C4CCN(C(=O)C5CC(=O)N(c6ccccc6)C5)CC4)n3)cc2n1]

¹H NMR (400 MHz, CHLOROFORM-d) δ 8.53 (s, 1H), 8.12 (s, 1H), 7.76-7.71 (m, 2H), 7.58 (br d, J=7.9 Hz, 2H), 7.36 (t, J=7.9 Hz, 2H), 7.15 (t, J=7.3 Hz, 1H), 4.51-4.37 (m, 1H), 4.28 (q, J=8.3 Hz, 1H), 4.17 (q, J=7.2 Hz, 2H), 4.01-3.89 (m, 2H), 3.57 (quin, J=8.4 Hz, 1H), 3.45-3.28 (m, 2H), 3.23-3.09 (m, 1H), 3.02-2.91 (m, 1H), 2.86-2.76 (m, 1H), 2.31-2.16 (m, 2H), 2.00 (s, 8H), 1.17 (t, J=7.1 Hz, 3H); LCMS (ESI) [M+H]+: 571.2.

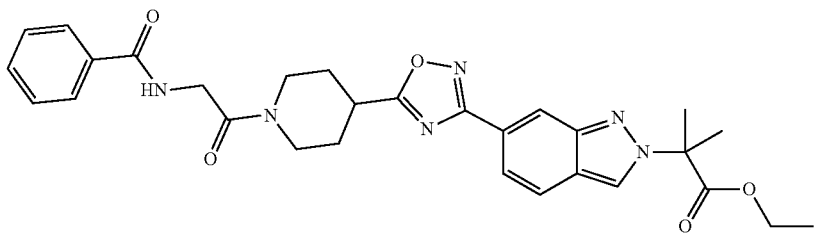 [SMILES: CCOC(=O)C(C)(C)n1cc2ccc(-c3noc(C4CCN(C(=O)CNC(=O)c5ccccc5)CC4)n3)cc2n1]

¹H NMR (400 MHz, CHLOROFORM-d) δ 8.55 (s, 1H), 8.15 (s, 1H), 7.86 (d, J=7.1 Hz, 2H), 7.76 (s, 2H), 7.56-7.42 (m, 3H), 7.36 (br s, 1H), 4.45 (br d, J=13.7 Hz, 1H), 4.32 (br s, 2H), 4.20 (q, J=7.1 Hz, 2H), 3.91 (br d, J=14.1 Hz, 1H), 3.42-3.29 (m, 2H), 3.22 (br t, J=10.6 Hz, 1H), 2.26 (br t, J=10.8 Hz, 2H), 2.10-1.94 (m, 8H), 1.20 (t, J=7.1 Hz, 3H); LCMS (ESI) [M+H]+: 545.2.

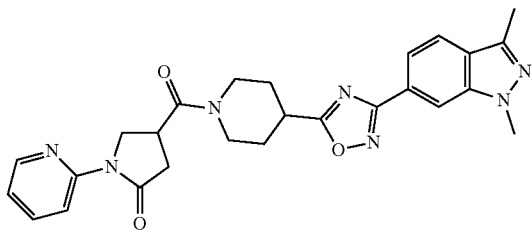 [SMILES: Cc1nn(C)c2cc(-c3noc(C4CCN(C(=O)C5CC(=O)N(c6ccccn6)C5)CC4)n3)ccc12]

¹H NMR (400 MHz, CHLOROFORM-d) δ 8.44-8.31 (m, 2H), 8.11 (s, 1H), 7.87-7.81 (m, 1H), 7.78-7.66 (m, 2H), 7.06 (br s, 1H), 4.64-4.52 (m, 1H), 4.44 (dd, J=9.0, 11.0 Hz, 1H), 4.25-4.17 (m, 1H), 4.09 (s, 3H), 4.04 (br d, J=13.0 Hz, 1H), 3.58 (quin, J=8.2 Hz, 1H), 3.48-3.32 (m, 2H), 3.27 (dd, J=7.7, 17.4 Hz, 1H), 3.17-3.05 (m, 1H), 2.88-2.78 (m, 1H), 2.61 (s, 3H), 2.36-2.22 (m, 2H), 2.14-1.94 (m, 2H); LCMS (ESI) [M+H]+: 486.3.

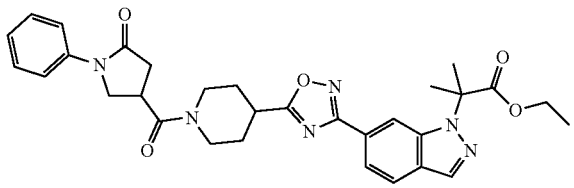 [SMILES: CCOC(=O)C(C)(C)n1ncc2ccc(-c3noc(C4CCN(C(=O)C5CC(=O)N(c6ccccc6)C5)CC4)n3)cc21]

¹H NMR (400 MHz, CHLOROFORM-d) δ 8.08-8.02 (m, 2H), 7.88-7.79 (m, 2H), 7.58 (d, J=7.9 Hz, 2H), 7.36 (t, J=7.9 Hz, 2H), 7.19-7.12 (m, 1H), 4.60-4.47 (m, 1H), 4.36-4.26 (m, 1H), 4.20 (br dd, J=3.4, 6.9 Hz, 2H), 3.94 (q, J=9.3 Hz, 2H), 3.58 (quin, J=8.4 Hz, 1H), 3.43-3.27 (m, 2H), 3.16-2.89 (m, 2H), 2.88-2.79 (m, 1H), 2.25 (br t, J=12.8 Hz, 2H), 1.99 (s, 8H), 1.18-1.10 (m, 3H); LCMS (ESI) [M+H]+: 571.2.

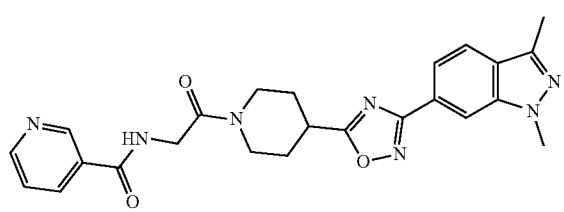 [SMILES: Cc1nn(C)c2cc(-c3noc(C4CCN(C(=O)CNC(=O)c5cccnc5)CC4)n3)ccc12]

¹H NMR (400 MHz, CHLOROFORM-d) δ 9.09 (d, J=1.6 Hz, 1H), 8.76 (dd, J=1.6, 4.9 Hz, 1H), 8.16 (td, J=2.0, 8.0 Hz, 1H), 8.10 (s, 1H), 7.87-7.80 (m, 1H), 7.78-7.71 (m, 1H), 7.46-7.37 (m, 2H), 4.58-4.48 (m, 1H), 4.33 (d, J=3.9 Hz, 2H), 4.08 (s, 3H), 3.93 (br d, J=13.8 Hz, 1H), 3.44-3.33 (m, 2H), 3.23-3.13 (m, 1H), 2.60 (s, 3H), 2.36-2.24 (m, 2H), 2.13-1.97 (m, 2H); LCMS (ESI) [M+H]+: 460.2.

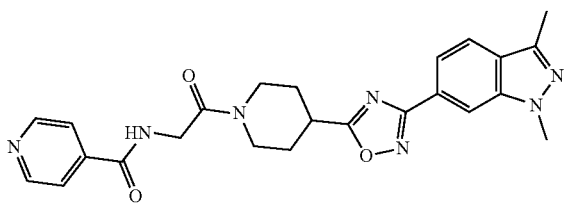 [SMILES: Cc1nn(C)c2cc(-c3noc(C4CCN(C(=O)CNC(=O)c5ccncc5)CC4)n3)ccc12]

¹H NMR (400 MHz, CHLOROFORM-d) δ 8.81-8.76 (m, 2H), 8.09 (s, 1H), 7.86-7.80 (m, 1H), 7.77-7.67 (m, 3H), 7.48 (br s, 1H), 4.58-4.48 (m, 1H), 4.31 (d, J=3.9 Hz, 2H), 4.08 (s, 3H), 3.92 (br d, J=14.1 Hz, 1H), 3.38 (ddd, J=3.4, 10.6, 14.0 Hz, 2H), 3.23-3.13 (m, 1H), 2.60 (s, 3H), 2.36-2.24 (m, 2H), 2.12-1.96 (m, 2H); LCMS (ESI) [M+H]+: 460.3.

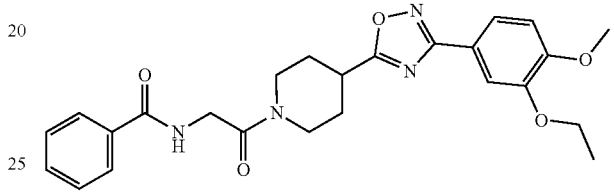

¹H NMR (400 MHz, CHLOROFORM-d) δ 7.89-7.83 (m, 2H), 7.67 (dd, J=1.9, 8.3 Hz, 1H), 7.60-7.42 (m, 4H), 7.35 (br s, 1H), 6.96 (d, J=8.4 Hz, 1H), 4.55-4.46 (m, 1H), 4.31 (d, J=3.9 Hz, 2H), 4.20 (q, J=7.0 Hz, 2H), 3.94 (s, 3H), 3.93-3.87 (m, 1H), 3.40-3.27 (m, 2H), 3.20-3.09 (m, 1H), 2.25 (dt, J=3.9, 12.8 Hz, 2H), 2.08-1.92 (m, 2H), 1.51 (t, J=7.0 Hz, 3H); LCMS (ESI) [M+H]+: 465.3.

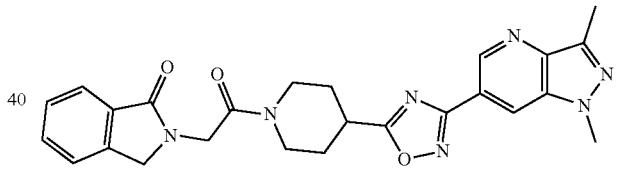

¹H NMR (400 MHz, CHLOROFORM-d) δ 9.16 (br d, J=1.8 Hz, 1H), 8.33 (d, J=1.5 Hz, 1H), 7.82 (br d, J=7.5 Hz, 1H), 7.55-7.48 (m, 1H), 7.45-7.39 (m, 2H), 4.54 (s, 2H), 4.49-4.41 (m, 3H), 4.05 (s, 4H), 3.41-3.24 (m, 2H), 3.03 (br t, J=11.8 Hz, 1H), 2.65 (s, 3H), 2.22 (br t, J=15.8 Hz, 2H), 2.07-1.86 (m, 4H); LCMS (ESI) [M+H]+: 472.1.

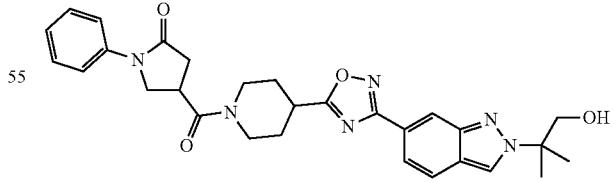

¹H NMR (400 MHz, CHLOROFORM-d) δ 8.48 (s, 1H), 8.08 (s, 1H), 7.74 (s, 2H), 7.58 (d, J=7.7 Hz, 2H), 7.36 (t, J=7.9 Hz, 2H), 7.18-7.11 (m, 1H), 4.53-4.40 (m, 1H), 4.33-4.24 (m, 1H), 4.00-3.89 (m, 4H), 3.57 (quin, J=8.4 Hz, 1H), 3.44-3.28 (m, 2H), 3.20-3.06 (m, 1H), 3.03-2.90 (m, 1H), 2.86-2.77 (m, 1H), 2.30-2.18 (m, 2H), 2.07-1.88 (m, 3H), 1.71 (s, 6H); LCMS (ESI) [M+H]+: 529.3.

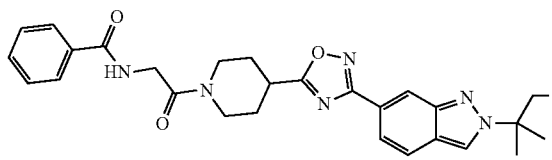

¹H NMR (400 MHz, CHLOROFORM-d) δ 8.50 (d, J=0.9 Hz, 1H), 8.10 (d, J=0.7 Hz, 1H), 7.86 (d, J=7.3 Hz, 2H), 7.77 (s, 2H), 7.56-7.50 (m, 1H), 7.49-7.43 (m, 2H), 7.36 (br s, 1H), 4.47 (br d, J=13.5 Hz, 1H), 4.31 (d, J=2.6 Hz, 2H), 4.06 (br s, 1H), 3.99-3.87 (m, 3H), 3.43-3.31 (m, 2H), 3.21 (br t, J=10.7 Hz, 1H), 2.33-2.21 (m, 2H), 2.11-1.94 (m, 2H), 1.73 (s, 6H); LCMS (ESI) [M+H]+: 503.3.

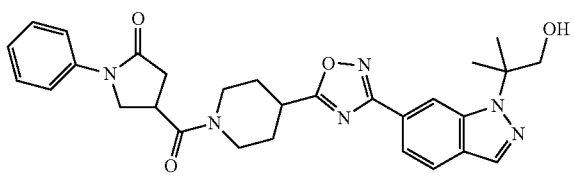 [SMILES: CC(C)(CO)n1ncc2ccc(-c3noc(C4CCN(C(=O)C5CC(=O)N(c6ccccc6)C5)CC4)n3)cc21]

¹H NMR (400 MHz, CHLOROFORM-d) δ 8.39 (s, 1H), 7.99 (s, 1H), 7.88-7.79 (m, 1H), 7.88-7.79 (m, 1H), 7.58 (d, J=7.9 Hz, 2H), 7.36 (t, J=7.8 Hz, 2H), 7.19-7.12 (m, 1H), 4.64-4.49 (m, 1H), 4.36-4.27 (m, 1H), 4.07 (br s, 2H), 4.02-3.85 (m, 3H), 3.57 (quin, J=8.5 Hz, 1H), 3.43-3.29 (m, 2H), 3.16-2.89 (m, 2H), 2.88-2.78 (m, 1H), 2.34-2.19 (m, 2H), 2.05-1.96 (m, 2H), 1.74 (d, J=2.0 Hz, 6H); LCMS (ESI) [M+H]+: 529.3.

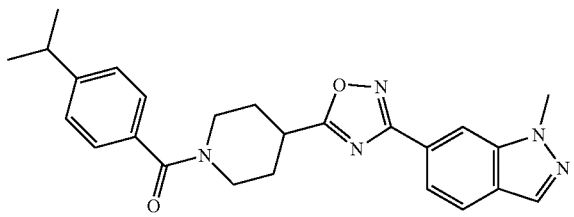 [SMILES: CC(C)c1ccc(C(=O)N2CCC(c3nc(-c4ccc5cnn(C)c5c4)no3)CC2)cc1]

¹H NMR (400 MHz, CHLOROFORM-d) δ 8.15 (s, 1H), 8.01 (s, 1H), 7.87-7.78 (m, 2H), 7.35 (d, J=8.2 Hz, 2H), 7.24 (s, 1H), 4.64 (br s, 1H), 4.14 (s, 3H), 4.09-3.71 (m, 1H), 3.37-3.27 (m, 1H), 3.20 (br s, 2H), 2.97-2.87 (m, 1H), 2.28-1.96 (m, 4H), 1.24 (d, J=6.8 Hz, 6H); LCMS (ESI) [M+H]+: 430.0.

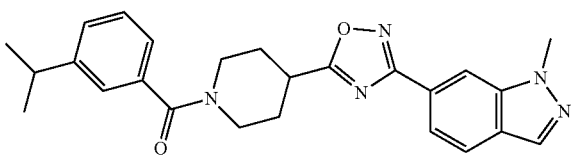 [SMILES: CC(C)c1cccc(C(=O)N2CCC(c3nc(-c4ccc5cnn(C)c5c4)no3)CC2)c1]

¹H NMR (400 MHz, CHLOROFORM-d) δ 8.15 (s, 1H), 8.01 (d, J=0.7 Hz, 1H), 7.87-7.78 (m, 2H), 7.34-7.26 (m, 3H), 7.21 (br d, J=7.3 Hz, 1H), 4.66 (br s, 1H), 4.14 (s, 3H), 3.97-3.78 (m, 1H), 3.36-3.12 (m, 3H), 2.96-2.87 (m, 1H), 2.32-1.90 (m, 4H), 1.25 (d, J=7.1 Hz, 6H); LCMS (ESI) [M+H]+: 430.0.

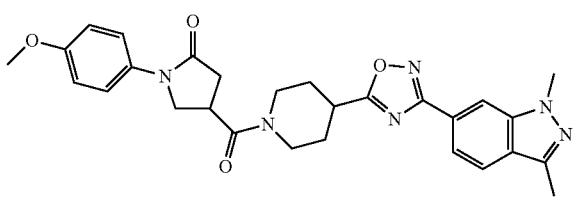 [SMILES: COc1ccc(N2CC(C(=O)N3CCC(c4nc(-c5ccc6c(C)nn(C)c6c5)no4)CC3)CC2=O)cc1]

¹H NMR (400 MHz, CHLOROFORM-d) δ 8.10 (br d, J=4.9 Hz, 1H), 7.86-7.81 (m, 1H), 7.77-7.72 (m, 1H), 7.49 (d, J=8.8 Hz, 2H), 6.92 (d, J=8.8 Hz, 2H), 4.64-4.51 (m, 1H), 4.30 (br s, 1H), 4.09 (d, J=3.5 Hz, 3H), 3.99 (br s, 1H), 3.91 (br t, J=8.8 Hz, 1H), 3.81 (s, 3H), 3.59 (quin, J=8.2 Hz, 1H), 3.47-3.31 (m, 2H), 3.19-3.03 (m, 1H), 3.00-2.79 (m, 2H), 2.61 (s, 3H), 2.34-2.23 (m, 2H), 2.01 (br d, J=10.8 Hz, 2H); LCMS (ESI) [M+H]+: 515.3.

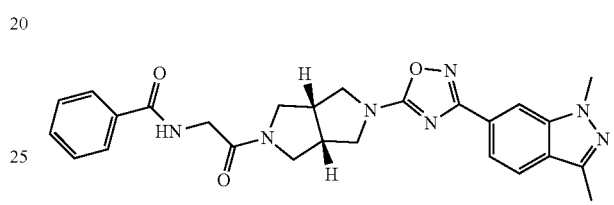

¹H NMR (400 MHz, CHLOROFORM-d) δ 8.02 (s, 1H), 7.84 (d, J=7.1 Hz, 2H), 7.79-7.66 (m, 2H), 7.55-7.41 (m, 3H), 7.22 (br s, 1H), 4.29-4.13 (m, 2H), 4.06 (s, 3H), 4.04-3.96 (m, 2H), 3.96-3.84 (m, 2H), 3.69-3.56 (m, 3H), 3.50 (dd, J=5.1, 10.8 Hz, 1H), 3.31-3.22 (m, 1H), 3.20-3.11 (m, 1H), 2.59 (s, 3H); LCMS (ESI) [M+H]+: 486.3.

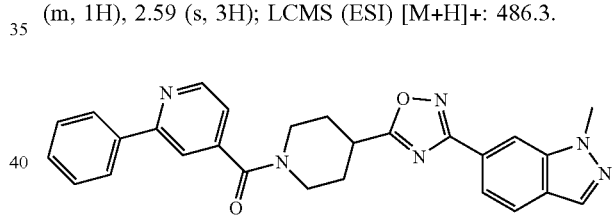

¹H NMR (400 MHz, CHLOROFORM-d) δ 8.79 (d, J=4.8 Hz, 1H), 8.16 (s, 1H), 8.05-7.99 (m, 3H), 7.87-7.80 (m, 2H), 7.75 (s, 1H), 7.52-7.44 (m, 3H), 7.25 (d, J=4.8 Hz, 1H), 4.67 (br d, J=11.4 Hz, 1H), 4.16 (s, 3H), 3.83 (br d, J=14.0 Hz, 1H), 3.41-3.21 (m, 3H), 2.34 (br s, 1H), 2.22-1.97 (m, 3H); LCMS (ESI) [M+H]+: 465.0.

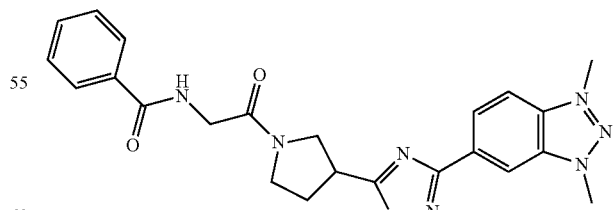

¹H NMR (400 MHz, CHLOROFORM-d) δ 8.12-8.08 (m, 1H), 7.89-7.80 (m, 3H), 7.77-7.72 (m, 1H), 7.56-7.42 (m, 3H), 7.25 (br d, J=3.1 Hz, 1H), 4.33-4.24 (m, 2H), 4.17-3.99 (m, 5H), 3.97-3.68 (m, 3H), 2.68-2.38 (m, 5H); LCMS (ESI) [M+H]+: 445.2.

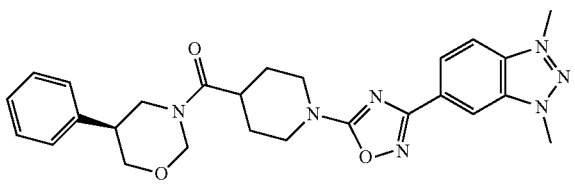

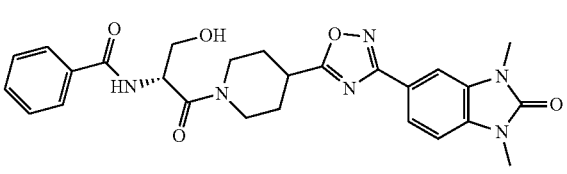

¹H NMR (400 MHz, CHLOROFORM-d) δ 8.02 (s, 1H), 7.79-7.74 (m, 1H), 7.73-7.67 (m, 1H), 7.46-7.30 (m, 5H), 4.71-4.51 (m, 1H), 4.44 (br d, J=10.4 Hz, 1H), 4.39-4.25 (m, 2H), 4.15 (br d, J=11.7 Hz, 1H), 4.07 (s, 3H), 3.90-3.65 (m, 2H), 3.51-3.17 (m, 3H), 2.98-2.70 (m, 2H), 2.59 (s, 3H), 2.11-1.79 (m, 4H); LCMS (ESI) [M+H]+: 487.3.

¹H NMR (400 MHz, METHANOL-d4) δ 7.93-7.70 (m, 4H), 7.55-7.35 (m, 3H), 7.25-7.10 (m, 1H), 5.23-5.19 (t, J=6.0 Hz, 1H), 4.60-4.40 (m, 1H), 4.30-4.15 (m, 1H), 3.90-3.75 (m, 2H), 3.55-3.35 (m, 8H), 3.20-2.95 (m, 1H), 2.30-2.10 (m, 2H), 2.10-1.95 (m, 1H), 1.95-1.75 (m, 1H); LCMS (ESI) [M+H]+: 505.2.

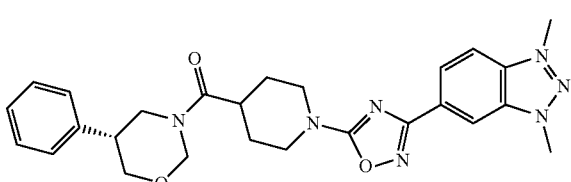

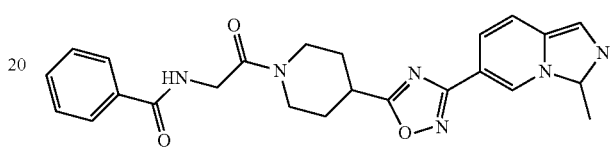

¹H NMR (400 MHz, CHLOROFORM-d) δ 8.02 (s, 1H), 7.79-7.73 (m, 1H), 7.72-7.65 (m, 1H), 7.47-7.30 (m, 5H), 4.71-4.51 (m, 1H), 4.44 (br d, J=10.4 Hz, 1H), 4.39-4.25 (m, 2H), 4.15 (br d, J=11.7 Hz, 1H), 4.06 (s, 3H), 3.90-3.66 (m, 2H), 3.51-3.17 (m, 3H), 2.98-2.71 (m, 2H), 2.59 (s, 3H), 2.11-1.79 (m, 4H); LCMS (ESI) [M+H]+: 487.3.

¹H NMR (400 MHz, CHLOROFORM-d) δ 8.47 (s, 1H), 7.84 (d, J=7.3 Hz, 2H), 7.54-7.41 (m, 4H), 7.38 (s, 1H), 7.26-7.22 (t, 2H), 4.53 (br d, J=13.9 Hz, 1H), 4.30 (t, J=3.7 Hz, 2H), 3.91 (br d, J=13.7 Hz, 1H), 3.38-3.27 (m, 2H), 3.11 (br t, J=11.1 Hz, 1H), 2.73 (s, 3H), 2.31-2.19 (t, 2H), 2.07-1.90 (m, 2H); LCMS (ESI) [M+H]+: 445.2.

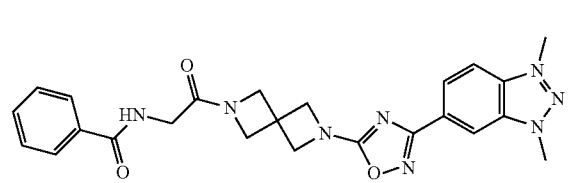

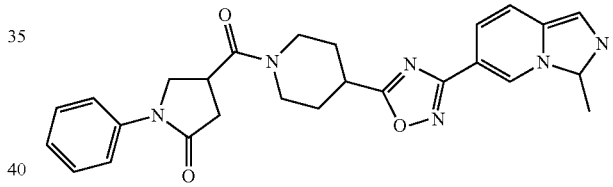

¹H NMR (400 MHz, CHLOROFORM-d) δ 8.01 (t, J=1.0 Hz, 1H), 7.89-7.80 (m, 2H), 7.72 (dq, J=1.0, 8.6 Hz, 2H), 7.60-7.50 (m, 1H), 7.50-7.43 (m, 2H), 6.98 (br s, 1H), 4.52 (s, 4H), 4.49 (s, 2H), 4.34 (s, 2H), 4.08 (d, J=4.6 Hz, 2H), 4.07 (s, 3H), 2.59 (s, 3H); LCMS (ESI) [M+H]+: 472.3.

¹H NMR (400 MHz, CHLOROFORM-d) δ 8.42 (br d, J=4.4 Hz, 1H), 7.53 (br d, J=8.2 Hz, 2H), 7.43 (d, J=9.5 Hz, 1H), 7.36-7.28 (dd, 3H), 7.20 (m, 1H), 7.14-7.07 (t, 1H), 4.59-4.43 (dd, 1H), 4.31-4.23 (m, 1H), 3.98-3.82 (m, 2H), 3.52 (quin, J=8.4 Hz, 1H), 3.39-3.21 (m, 2H), 3.15-2.73 (m, 3H), 2.68 (d, J=5.7 Hz, 3H), 2.27-2.13 (t, 2H), 1.99-1.81 (m, 2H); LCMS (ESI) [M+H]+: 471.3.

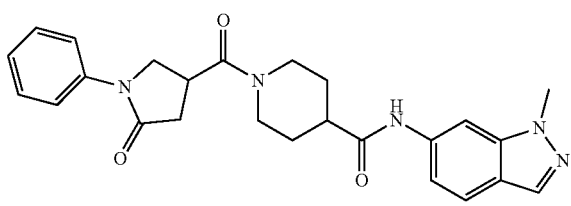 [SMILES: Cn1ncc2ccc(NC(=O)C3CCN(C(=O)C4CC(=O)N(c5ccccc5)C4)CC3)cc21]

¹H NMR (400 MHz, CHLOROFORM-d) δ 8.20 (s, 1H), 8.00 (s, 1H), 7.91 (d, J=0.9 Hz, 1H), 7.59 (dd, J=8.5, 12.0 Hz, 3H), 7.43-7.32 (m, 2H), 7.22-7.13 (m, 1H), 6.85 (td, J=1.5, 8.6 Hz, 1H), 4.71-4.53 (m, 1H), 4.27 (ddd, J=6.8, 9.6, 18.8 Hz, 1H), 4.03 (s, 3H), 4.00-3.91 (m, 2H), 3.57 (quin, J=8.3 Hz, 1H), 3.25-3.11 (m, 1H), 3.04-2.90 (m, 1H), 2.87-2.76 (m, 2H), 2.57 (dt, J=4.1, 10.9 Hz, 1H), 2.08-1.94 (m, 2H), 1.89-1.80 (m, 1H), 1.89-1.79 (m, 1H); LCMS (ESI) [M+H]+: 446.1.

¹H NMR (400 MHz, CHLOROFORM-d) δ 7.57 (br d, J=8.3 Hz, 1H), 7.49 (s, 1H), 7.43-7.31 (m, 5H), 6.90 (d, J=8.3 Hz, 1H), 4.65 (br d, J=13.6 Hz, 1H), 4.53 (br d, J=12.7 Hz, 1H), 4.42 (br d, J=10.5 Hz, 1H), 4.34-4.21 (m, 2H), 4.14 (q, J=7.0 Hz, 3H), 3.93 (s, 3H), 3.86-3.64 (m, 2H), 3.43 (br t, J=11.4 Hz, 1H), 3.27-3.16 (m, 2H), 2.91 (br t, J=11.4 Hz, 1H), 2.81-2.67 (m, 2H), 2.07-1.77 (m, 4H), 1.48 (t, J=7.0 Hz, 3H); LCMS (ESI) [M+H]+: 493.0.

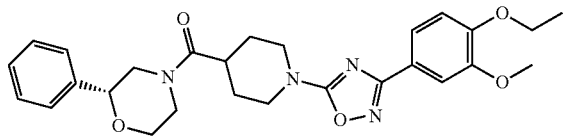 [SMILES: CCOc1ccc(-c2noc(N3CCC(C(=O)N4CCO[C@H](c5ccccc5)C4)CC3)n2)cc1OC]

¹H NMR (400 MHz, CHLOROFORM-d) δ 7.57 (br d, J=8.3 Hz, 1H), 7.49 (s, 1H), 7.43-7.32 (m, 5H), 6.90 (d, J=8.3 Hz, 1H), 4.66 (br d, J=13.6 Hz, 0.5H), 4.54 (br d, J=13.6 Hz, 0.5H), 4.42 (br d, J=10.1 Hz, 1H), 4.34-4.22 (m, 2H), 4.15 (q, J=7.0 Hz, 3H), 3.93 (s, 3H), 3.87-3.65 (m, 2H), 3.44 (br t, J=11.6 Hz, 0.5H), 3.27-3.17 (m, 2H), 2.91 (br t, J=11.8 Hz, 0.5H), 2.81-2.69 (m, 2H), 2.06-1.78 (m, 4H), 1.48 (t, J=7.0 Hz, 3H); LCMS (ESI) [M+H]+: 493.0.

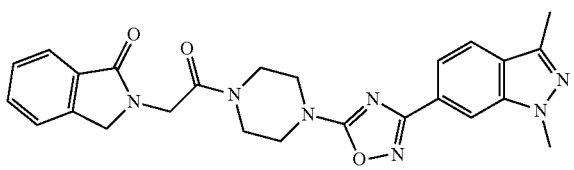 [SMILES: Cc1nn(C)c2cc(-c3noc(N4CCN(C(=O)CN5Cc6ccccc6C5=O)CC4)n3)ccc12]

¹H NMR (400 MHz, CHLOROFORM-d) δ 8.01 (s, 1H), 7.88 (d, J=7.5 Hz, 1H), 7.78-7.67 (m, 2H), 7.61-7.55 (m, 1H), 7.52-7.46 (m, 2H), 4.59 (s, 2H), 4.52 (s, 2H), 4.06 (s, 3H), 3.83-3.73 (m, 8H), 2.59 (s, 3H); LCMS (ESI) [M+H]+: 472.0.

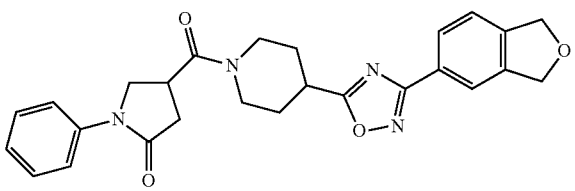 [SMILES: O=C(C1CC(=O)N(c2ccccc2)C1)N1CCC(c2nc(-c3ccc4c(c3)COC4)no2)CC1]

¹H NMR (400 MHz, CHLOROFORM-d) δ 8.00 (br d, J=7.5 Hz, 1H), 7.95 (br s, 1H), 7.59 (d, J=7.9 Hz, 2H), 7.41-7.33 (m, 3H), 7.19-7.14 (m, 1H), 5.16 (s, 4H), 4.58-4.47 (m, 1H), 4.31 (dd, J=7.2, 9.4 Hz, 1H), 4.00-3.89 (m, 2H), 3.62-3.55 (m, 1H), 3.44-3.28 (m, 2H), 3.18-2.92 (m, 2H), 2.87-2.80 (m, 1H), 2.32-2.18 (m, 2H), 2.06-1.90 (m, 2H); LCMS (ESI) [M+H]+: 459.2.

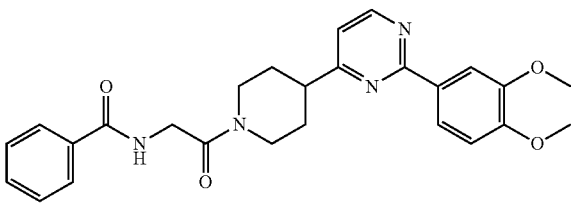 [SMILES: COc1ccc(-c2nccc(C3CCN(C(=O)CNC(=O)c4ccccc4)CC3)n2)cc1OC]

¹H NMR (400 MHz, DMSO-d₆) δ 8.75 (d, J=5.3 Hz, 1H), 8.57 (br t, J=5.7 Hz, 1H), 8.06-8.00 (m, 1H), 7.96 (s, 1H), 7.89 (d, J=7.0 Hz, 2H), 7.58-7.52 (m, 1H), 7.52-7.44 (m, 2H), 7.29 (d, J=5.3 Hz, 1H), 7.09 (d, J=8.8 Hz, 1H), 4.51 (br d, J=12.3 Hz, 1H), 4.27-4.12 (m, 2H), 4.06 (br d, J=13.6 Hz, 1H), 3.84 (d, J=4.4 Hz, 6H), 3.23 (br t, J=12.1 Hz, 1H), 3.04 (br t, J=11.8 Hz, 1H), 2.79 (br t, J=12.1 Hz, 1H), 2.00 (br t, J=12.1 Hz, 2H), 1.86-1.73 (m, 1H), 1.70-1.56 (m, 1H); LCMS (ESI) [M+H]+: 461.3.

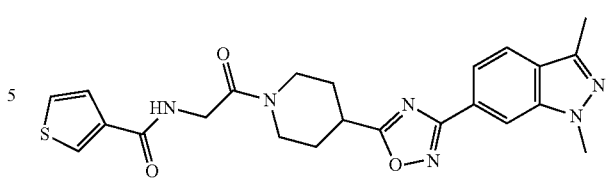

¹H NMR (400 MHz, CHLOROFORM-d) δ 8.10 (s, 1H), 7.95 (dd, J=1.2, 2.8 Hz, 1H), 7.86-7.80 (m, 1H), 7.78-7.72 (m, 1H), 7.46 (dd, J=1.1, 5.1 Hz, 1H), 7.36 (dd, J=3.1, 5.1 Hz, 1H), 7.15 (br s, 1H), 4.53 (br d, J=13.7 Hz, 1H), 4.29 (d, J=4.0 Hz, 2H), 4.09 (s, 3H), 3.93 (br d, J=14.3 Hz, 1H), 3.42-3.32 (m, 2H), 3.16 (br t, J=10.8 Hz, 1H), 2.60 (s, 3H), 2.29 (br t, J=10.9 Hz, 2H), 2.11-1.95 (m, 2H); LCMS (ESI) [M+H]+: 465.2.

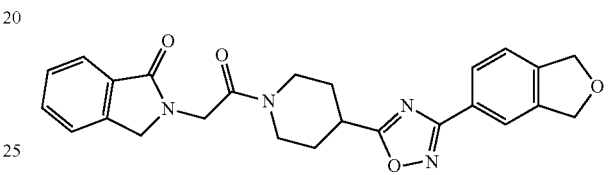

¹H NMR (400 MHz, CHLOROFORM-d) δ 7.99 (d, J=7.9 Hz, 1H), 7.94 (s, 1H), 7.86 (d, J=8.3 Hz, 1H), 7.57-7.52 (m, 1H), 7.49-7.43 (m, 2H), 7.34 (d, J=7.9 Hz, 1H), 5.16 (s, 4H), 4.60-4.39 (m, 5H), 4.07 (br d, J=14.0 Hz, 1H), 3.43-3.24 (m, 2H), 3.07 (br t, J=11.2 Hz, 1H), 2.21 (br t, J=13.8 Hz, 2H), 2.03-1.88 (m, 2H); LCMS (ESI) [M+H]+: 445.2.

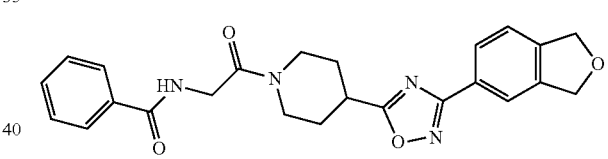

¹H NMR (400 MHz, CHLOROFORM-d) δ 7.99 (d, J=7.9 Hz, 1H), 7.94 (s, 1H), 7.85 (d, J=7.0 Hz, 2H), 7.54-7.48 (m, 1H), 7.48-7.42 (m, 2H), 7.35 (br d, J=7.9 Hz, 2H), 5.16 (s, 4H), 4.49 (br d, J=14.0 Hz, 1H), 4.30 (d, J=3.9 Hz, 2H), 3.90 (br d, J=14.0 Hz, 1H), 3.40-3.26 (m, 2H), 3.21-3.13 (m, 1H), 2.32-2.18 (m, 2H), 2.07-1.91 (m, 2H); LCMS (ESI) [M+H]+: 433.2.

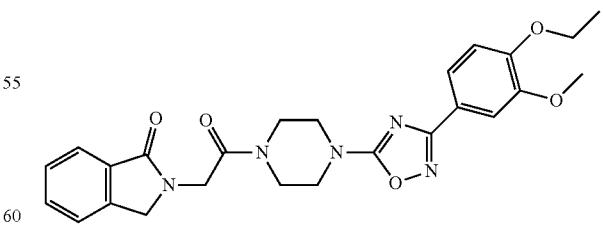

¹H NMR (400 MHz, CHLOROFORM-d) δ 7.87 (d, J=7.5 Hz, 1H), 7.59-7.54 (m, 2H), 7.51-7.45 (m, 3H), 6.91 (d, J=8.4 Hz, 1H), 4.58 (s, 2H), 4.51 (s, 2H), 4.15 (q, J=6.9 Hz, 2H), 3.94 (s, 3H), 3.79-3.68 (m, 8H), 1.49 (t, J=7.1 Hz, 3H); LCMS (ESI) [M+H]+: 478.2.

621

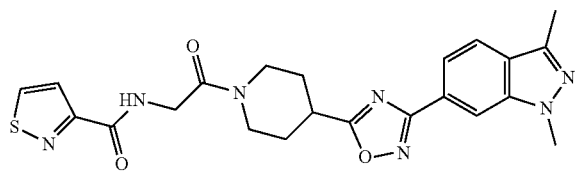 [SMILES: Cc1nn(C)c2cc(-c3noc(C4CCN(C(=O)CNC(=O)c5ccsn5)CC4)n3)ccc12]

¹H NMR (400 MHz, CHLOROFORM-d) δ 8.70 (d, J=4.6 Hz, 1H), 8.23 (br s, 1H), 8.10 (s, 1H), 7.89-7.80 (m, 2H), 7.77-7.70 (m, 1H), 4.55 (br d, J=14.1 Hz, 1H), 4.32 (d, J=4.4 Hz, 2H), 4.09 (s, 3H), 3.93 (br d, J=13.5 Hz, 1H), 3.41-3.32 (m, 2H), 3.15 (br t, J=11.4 Hz, 1H), 2.60 (s, 3H), 2.34-2.22 (m, 2H), 2.12-1.95 (m, 2H); LCMS (ESI) [M+H]+: 466.2.

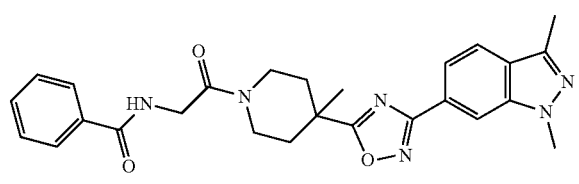 [SMILES: Cc1nn(C)c2cc(-c3noc(C4(C)CCN(C(=O)CNC(=O)c5ccccc5)CC4)n3)ccc12]

¹H NMR (400 MHz, CHLOROFORM-d) δ 8.11 (s, 1H), 7.88-7.81 (m, 3H), 7.78-7.72 (m, 1H), 7.55-7.50 (m, 1H), 7.49-7.43 (m, 2H), 7.35 (br s, 1H), 4.42-4.31 (m, 2H), 4.28-4.19 (m, 1H), 4.10 (s, 3H), 3.76 (br d, J=14.3 Hz, 1H), 3.46-3.36 (m, 1H), 3.21-3.11 (m, 1H), 2.61 (s, 3H), 2.58-2.45 (m, 2H), 1.84-1.74 (m, 2H), 1.61 (s, 3H); LCMS (ESI) [M+H]+: 473.3.

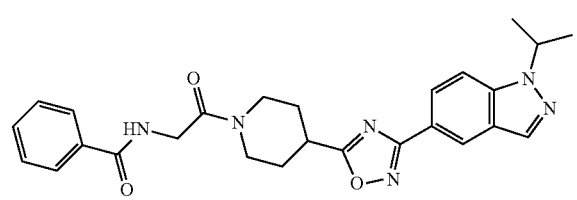 [SMILES: CC(C)n1ncc2cc(-c3noc(C4CCN(C(=O)CNC(=O)c5ccccc5)CC4)n3)ccc21]

¹H NMR (400 MHz, CHLOROFORM-d) δ 8.49 (s, 1H), 8.11-8.04 (m, 2H), 7.87-7.83 (m, 2H), 7.54-7.49 (m, 2H), 7.47-7.42 (m, 2H), 7.35 (br s, 1H), 4.88 (td, J=6.7, 13.3 Hz, 1H), 4.53-4.46 (m, 1H), 4.31 (d, J=3.7 Hz, 2H), 3.96-3.88 (m, 1H), 3.40-3.28 (m, 2H), 3.22-3.12 (m, 1H), 2.26 (dt, J=3.6, 13.0 Hz, 2H), 2.09-1.93 (m, 2H), 1.62 (d, J=6.6 Hz, 6H); LCMS (ESI) [M+H]+: 473.3.

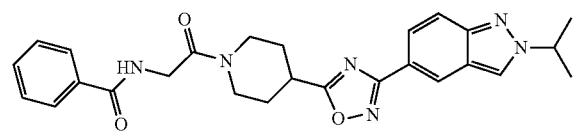 [SMILES: CC(C)n1cc2cc(-c3noc(C4CCN(C(=O)CNC(=O)c5ccccc5)CC4)n3)ccc2n1]

¹H NMR (400 MHz, CHLOROFORM-d) δ 8.45 (s, 1H), 8.06 (s, 1H), 7.95 (dd, J=1.3, 9.0 Hz, 1H), 7.85 (d, J=7.3 Hz, 2H), 7.79 (d, J=9.0 Hz, 1H), 7.54-7.49 (m, 1H), 7.47-7.42 (m, 2H), 7.35 (br s, 1H), 4.82 (quin, J=6.7 Hz, 1H), 4.49 (td, J=4.0, 13.7 Hz, 1H), 4.30 (d, J=4.0 Hz, 2H), 3.95-3.87 (m, 1H), 3.38-3.27 (m, 2H), 3.21-3.13 (m, 1H), 2.25 (dt, J=3.7, 12.9 Hz, 2H), 2.07-1.95 (m, 2H), 1.68 (d, J=6.6 Hz, 6H); LCMS (ESI) [M+H]+: 473.2.

622

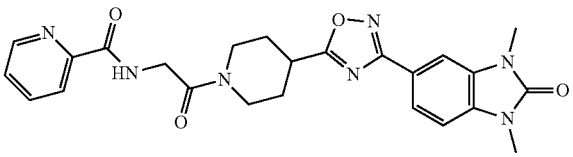 [SMILES: Cn1c(=O)n(C)c2cc(-c3noc(C4CCN(C(=O)CNC(=O)c5ccccn5)CC4)n3)ccc21]

¹H NMR (400 MHz, CHLOROFORM-d) δ 8.93 (br s, 1H), 8.64 (br d, J=4.3 Hz, 1H), 8.20 (d, J=7.9 Hz, 1H), 7.94-7.84 (m, 2H), 7.70 (s, 1H), 7.49-7.41 (m, 1H), 7.07 (d, J=8.2 Hz, 1H), 4.56 (br d, J=13.6 Hz, 1H), 4.36 (br d, J=4.4 Hz, 2H), 3.97 (br d, J=14.3 Hz, 1H), 3.50 (d, J=8.3 Hz, 6H), 3.43-3.32 (m, 2H), 3.16 (br t, J=11.2 Hz, 1H), 2.27 (br t, J=12.1 Hz, 2H), 2.11-1.91 (m, 2H); LCMS (ESI) [M+H]+: 476.3.

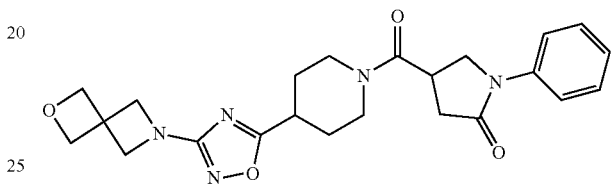

¹HNMR (400 MHz, CHLOROFORM-d) δ 7.60-7.54 (m, 2H), 7.36 (t, J=7.8 Hz, 2H), 7.19-7.10 (m, 1H), 4.81 (s, 4H), 4.52-4.39 (m, 1H), 4.27 (dd, J=7.3, 9.7 Hz, 1H), 4.20 (s, 4H), 3.95-3.84 (m, 2H), 3.53 (quin, J=8.4 Hz, 1H), 3.34-3.23 (m, 1H), 3.15-2.87 (m, 3H), 2.84-2.75 (m, 1H), 2.16-2.04 (m, 2H), 1.90-1.75 (m, 2H); LCMS (ESI) [M+H]+: 438.2.

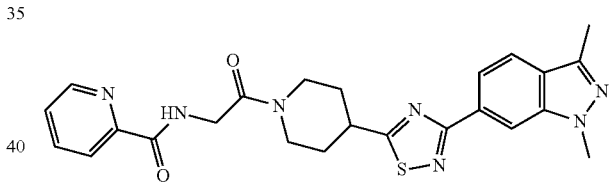

¹H NMR (400 MHz, CHLOROFORM-d) δ 8.94 (br s, 1H), 8.63 (br s, 1H), 8.36-8.27 (m, 1H), 8.19 (br d, J=7.3 Hz, 1H), 8.08 (br d, J=7.9 Hz, 1H), 7.90-7.81 (m, 1H), 7.73 (br d, J=7.7 Hz, 1H), 7.52-7.40 (m, 1H), 4.75 (br d, J=12.1 Hz, 1H), 4.36 (br s, 2H), 4.10 (br s, 3H), 4.02 (br d, J=12.6 Hz, 1H), 3.51 (br s, 1H), 3.36 (br t, J=11.2 Hz, 1H), 3.08-2.94 (m, 1H), 2.61 (br s, 3H), 2.32 (br d, J=14.8 Hz, 2H), 1.96 (br d, J=10.8 Hz, 2H); LCMS (ESI) [M+H]+: 476.2.

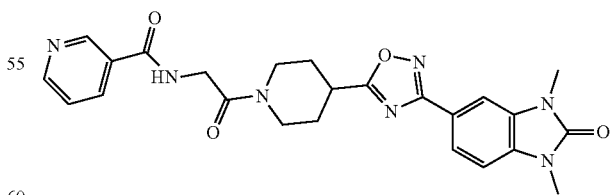

¹H NMR (400 MHz, CHLOROFORM-d) δ 9.10 (dd, J=0.7, 2.3 Hz, 1H), 8.77 (dd, J=1.7, 4.9 Hz, 1H), 8.17 (td, J=2.0, 7.9 Hz, 1H), 7.89 (dd, J=1.5, 8.2 Hz, 1H), 7.69 (d, J=1.3 Hz, 1H), 7.42 (ddd, J=0.8, 4.9, 7.9 Hz, 2H), 7.07 (d, J=8.2 Hz, 1H), 4.53 (td, J=3.8, 13.8 Hz, 1H), 4.33 (d, J=3.9 Hz, 2H), 3.96-3.89 (m, 1H), 3.49 (d, J=7.6 Hz, 6H), 3.42-

3.32 (m, 2H), 3.18 (ddd, J=3.1, 10.9, 13.6 Hz, 1H), 2.29 (dt, J=3.8, 13.8 Hz, 2H), 2.12-1.95 (m, 2H); LCMS (ESI) [M+H]+: 476.2.

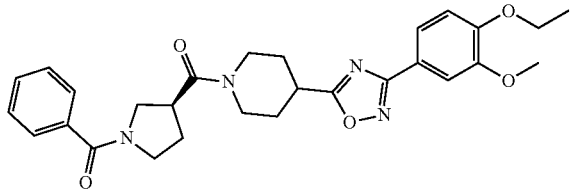 [SMILES: CCOc1ccc(-c2noc(C3CCN(C(=O)[C@H]4CCN(C(=O)c5ccccc5)C4)CC3)n2)cc1OC]

¹H NMR (400 MHz, CHLOROFORM-d) δ 7.67-7.58 (m, 1H), 7.55-7.46 (m, 3H), 7.42-7.32 (m, 3H), 6.91 (br d, J=8.4 Hz, 1H), 4.57-4.39 (m, 1H), 4.13 (q, J=7.1 Hz, 2H), 4.05-3.97 (m, 1H), 3.96-3.91 (m, 3H), 3.90-3.61 (m, 3H), 3.58-3.42 (m, 1H), 3.39-3.18 (m, 3H), 3.08-2.91 (m, 1H), 2.34-1.82 (m, 6H), 1.47 (t, J=6.9 Hz, 3H); LCMS (ESI) [M+H]+: 505.3.

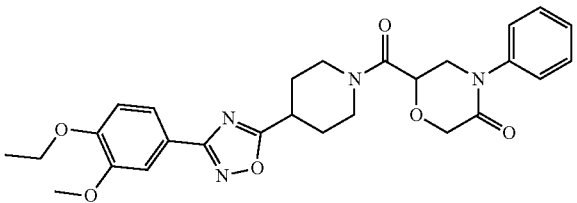 [SMILES: CCOc1ccc(-c2noc(C3CCN(C(=O)C4CN(c5ccccc5)C(=O)CO4)CC3)n2)cc1OC]

¹H NMR (400 MHz, CHLOROFORM-d) δ 7.63 (br s, 1H), 7.54 (br s, 1H), 7.45-7.39 (m, 2H), 7.38-7.34 (m, 2H), 7.32-7.27 (m, 1H), 6.93 (br d, J=8.4 Hz, 1H), 4.67 (br s, 1H), 4.45-4.39 (m, 1H), 4.26 (br dd, J=8.5, 12.7 Hz, 1H), 4.15 (q, J=6.6 Hz, 2H), 3.94 (br s, 3H), 3.77 (br d, J=12.8 Hz, 1H), 3.47 (br t, J=11.5 Hz, 0.5H), 3.35-3.15 (m, 2H), 2.97 (br t, J=12.1 Hz, 0.5H), 2.23 (br s, 2H), 2.12-1.87 (m, 2H), 1.49 (br t, J=6.9 Hz, 3H); LCMS (ESI) [M+H]+: 507.3.

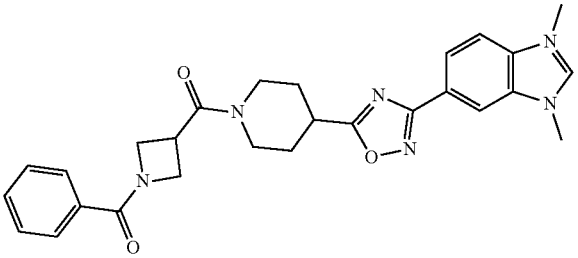

¹H NMR (400 MHz, CHLOROFORM-d) δ 8.09 (br d, J=8.6 Hz, 1H), 7.82 (br s, 1H), 7.77-7.70 (m, 1H), 7.65 (d, J=7.1 Hz, 2H), 7.51-7.38 (m, 3H), 4.75 (br s, 1H), 4.63-4.27 (m, 4H), 4.08 (br d, J=4.6 Hz, 3H), 3.70-3.59 (m, 2H), 3.39-2.99 (m, 3H), 2.60 (s, 3H), 2.24 (br d, J=11.0 Hz, 2H), 2.05-1.91 (m, 2H); LCMS (ESI) [M+H]+: 485.3.

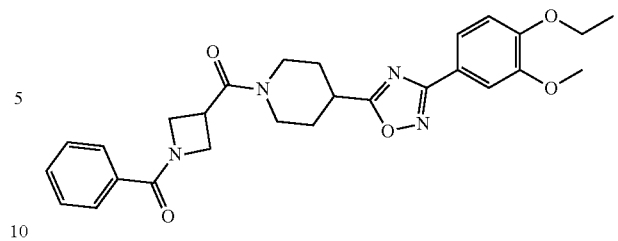

¹H NMR (400 MHz, CHLOROFORM-d) δ 7.65 (br d, J=7.1 Hz, 3H), 7.56 (br s, 1H), 7.51-7.39 (m, 3H), 6.95 (br d, J=8.2 Hz, 1H), 4.74 (br t, J=7.1 Hz, 1H), 4.59-4.25 (m, 4H), 4.17 (q, J=7.1 Hz, 2H), 3.97 (br s, 3H), 3.68-3.57 (m, 2H), 3.35-2.97 (m, 3H), 2.20 (br d, J=12.1 Hz, 2H), 2.03-1.87 (m, 2H), 1.51 (t, J=6.9 Hz, 3H); LCMS (ESI) [M+H]+: 491.3.

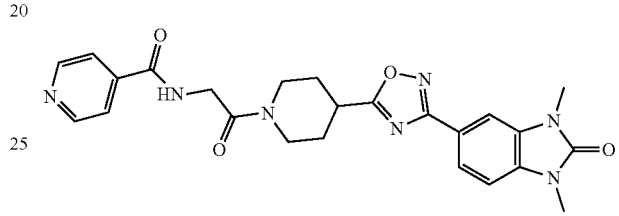

¹H NMR (400 MHz, CHLOROFORM-d) δ 8.80-8.74 (m, 2H), 7.87 (dd, J=1.5, 8.2 Hz, 1H), 7.70-7.66 (m, 3H), 7.46 (br s, 1H), 7.07-7.02 (m, 1H), 7.05 (d, J=8.2 Hz, 1H), 4.51 (td, J=3.7, 13.7 Hz, 1H), 4.30 (d, J=3.7 Hz, 2H), 3.93-3.86 (m, 1H), 3.47 (d, J=7.1 Hz, 6H), 3.40-3.29 (m, 2H), 3.21-3.13 (m, 1H), 2.27 (dt, J=3.5, 13.3 Hz, 2H), 2.09-1.94 (m, 2H); LCMS (ESI) [M+H]+: 476.2.

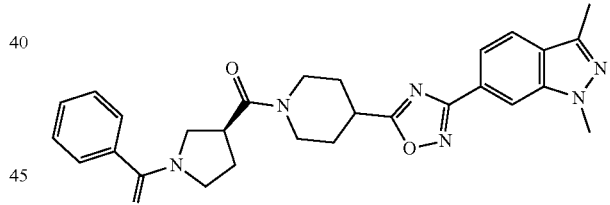

¹H NMR (400 MHz, CHLOROFORM-d) δ 8.11-8.04 (m, 1H), 7.84-7.76 (m, 1H), 7.74-7.70 (m, 1H), 7.56-7.48 (m, 2H), 7.43-7.35 (m, 3H), 4.62-4.46 (m, 1H), 4.10-4.02 (m, 4H), 4.00-3.67 (m, 3H), 3.62-3.45 (m, 1H), 3.41-3.20 (m, 3H), 3.12-2.94 (m, 1H), 2.58 (s, 3H), 2.38-1.86 (m, 6H); LCMS (ESI) [M+H]+: 499.3.

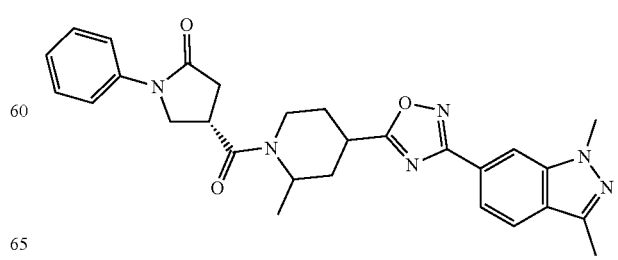

¹H NMR (400 MHz, DMSO-d₆) δ 8.22-8.17 (m, 1H), 7.91-7.86 (m, 1H), 7.76-7.64 (m, 3H), 7.41-7.34 (m, 2H), 7.18-7.11 (m, 1H), 4.99-4.34 (m, 1H), 4.13-3.86 (m, 6H), 3.77-3.64 (m, 1H), 3.49 (br s, 1H), 2.90-2.62 (m, 3H), 2.52-2.52 (m, 3H), 2.38-2.03 (m, 4H), 1.42-0.87 (m, 3H); LCMS (ESI) [M+H]+: 499.3.

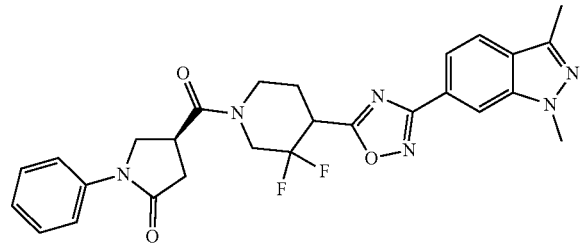 [SMILES: Cc1nn(C)c2cc(-c3noc(C4CCN(C(=O)[C@H]5CC(=O)N(c6ccccc6)C5)CC4(F)F)n3)ccc12]

¹H NMR (400 MHz, CHLOROFORM-d) δ 8.11 (br s, 1H), 7.85 (br d, J=8.4 Hz, 1H), 7.80-7.71 (m, 1H), 7.60 (br d, J=7.0 Hz, 2H), 7.47-7.33 (m, 2H), 7.19 (br d, J=5.1 Hz, 1H), 4.76-4.16 (m, 3H), 4.09 (br s, 3H), 4.03-3.39 (m, 5H), 3.08-2.80 (m, 2H), 2.61 (s, 3H), 2.52-2.23 (m, 2H); LCMS (ESI) [M+H]+: 521.2.

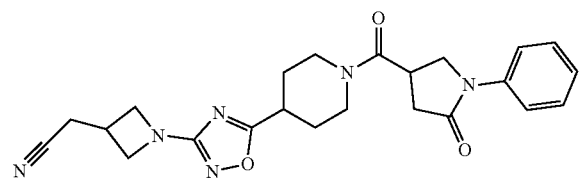 [SMILES: N#CCC1CN(c2noc(C3CCN(C(=O)C4CC(=O)N(c5ccccc5)C4)CC3)n2)C1]

¹H NMR (400 MHz, CHLOROFORM-d) δ 7.59 (d, J=8.2 Hz, 2H), 7.38 (t, J=7.8 Hz, 2H), 7.21-7.14 (m, 1H), 4.56-4.42 (m, 1H), 4.33-4.23 (m, 3H), 3.97-3.83 (m, 4H), 3.56 (quin, J=8.5 Hz, 1H), 3.37-3.27 (m, 1H), 3.19-2.90 (m, 4H), 2.87-2.78 (m, 1H), 2.75 (d, J=7.1 Hz, 2H), 2.14 (br t, J=12.5 Hz, 2H), 1.93-1.78 (m, 2H); LCMS (ESI) [M+H]+: 435.1.

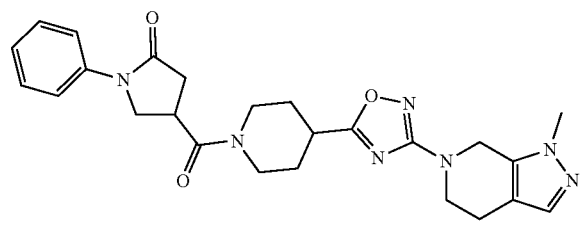 [SMILES: Cn1ncc2c1CN(c1noc(C3CCN(C(=O)C4CC(=O)N(c5ccccc5)C4)CC3)n1)CC2]

¹H NMR (400 MHz, CHLOROFORM-d) δ 7.59 (d, J=8.2 Hz, 2H), 7.38 (t, J=7.6 Hz, 2H), 7.32 (s, 1H), 7.22-7.13 (m, 1H), 4.55-4.41 (m, 3H), 4.31 (br t, J=8.3 Hz, 1H), 3.96-3.79 (m, 4H), 3.76 (s, 3H), 3.56 (quin, J=8.5 Hz, 1H), 3.38-3.27 (m, 1H), 3.18-2.90 (m, 3H), 2.89-2.74 (m, 3H), 2.14 (br t, J=13.0 Hz, 2H), 1.94-1.79 (m, 2H); LCMS (ESI) [M+H]+: 476.2.

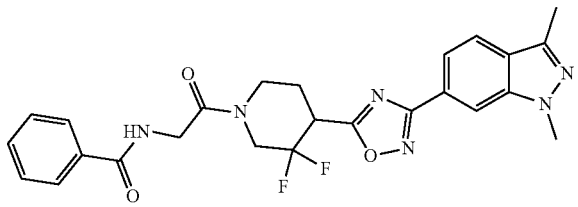 [SMILES: Cc1nn(C)c2cc(-c3noc(C4CCN(C(=O)CNC(=O)c5ccccc5)CC4(F)F)n3)ccc12]

¹H NMR (400 MHz, CHLOROFORM-d) δ 8.11 (s, 1H), 7.85 (t, J=7.3 Hz, 3H), 7.78-7.73 (m, 1H), 7.58-7.51 (m, 1H), 7.50-7.43 (m, 2H), 7.22 (br s, 1H), 4.65-4.49 (m, 0.5H), 4.44-4.18 (m, 3H), 4.09 (s, 3H), 4.07-4.01 (m, 0.5H), 3.94-3.70 (m, 2H), 3.67-3.50 (m, 1H), 2.61 (s, 3H), 2.47-2.31 (m, 2H); LCMS (ESI) [M+H]+: 495.3.

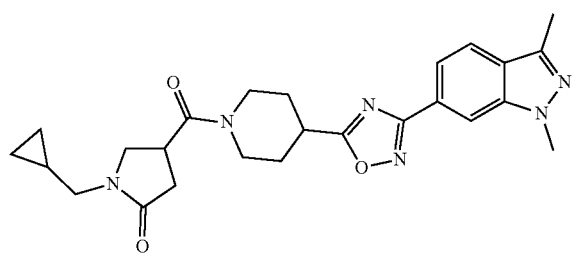 [SMILES: Cc1nn(C)c2cc(-c3noc(C4CCN(C(=O)C5CC(=O)N(CC6CC6)C5)CC4)n3)ccc12]

¹H NMR (400 MHz, CHLOROFORM-d) δ 7.88-7.80 (d, J=2, 1H), 7.60 (dd, J=1.1, 8.4 Hz, 1H), 7.52 (d, J=8.4 Hz, 1H), 4.40-4.26 (m, 1H), 3.88-3.84 (s, 3H), 3.80-3.64 (m, 2H), 3.40 (t, J=9.2 Hz, 1H), 3.25 (td, J=8.4, 16.6 Hz, 1H), 3.18-3.08 (m, 2H), 3.03-2.78 (m, 3H), 2.57-2.41 (m, 2H), 2.38 (s, 3H), 2.11-1.96 (m, 2H), 1.85-1.67 (m, 2H), 0.76-0.66 (m, 1H), 0.36-0.29 (m, 2H), 0.02 (q, J=4.8 Hz, 2H); LCMS (ESI) [M+H]+: 463.2.

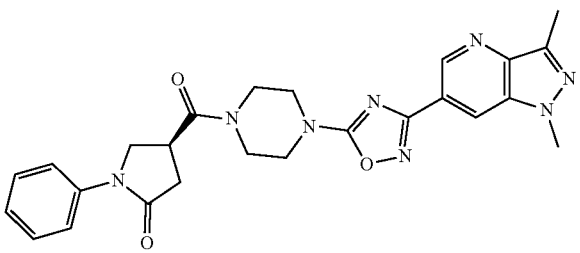 [SMILES: Cc1nn(C)c2cc(-c3noc(N4CCN(C(=O)[C@H]5CC(=O)N(c6ccccc6)C5)CC4)n3)cnc12]

¹H NMR (400 MHz, CHLOROFORM-d) δ 9.13 (d, J=1.8 Hz, 1H), 8.28 (d, J=1.8 Hz, 1H), 7.61-7.55 (m, 2H), 7.37 (t, J=7.9 Hz, 2H), 7.19-7.14 (m, 1H), 4.32 (dd, J=7.2, 9.4 Hz, 1H), 4.07 (s, 3H), 3.95 (t, J=9.2 Hz, 1H), 3.86-3.67 (m, 8H), 3.63-3.54 (m, 1H), 2.97-2.81 (m, 2H), 2.68 (s, 3H); LCMS (ESI) [M+H]+: 487.2.

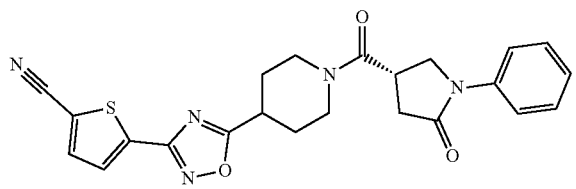 [SMILES: N#Cc1ccc(-c2noc(C3CCN(C(=O)[C@H]4CC(=O)N(c5ccccc5)C4)CC3)n2)s1]

¹H NMR (400 MHz, CHLOROFORM-d) δ 7.75 (br s, 1H), 7.64 (d, J=3.7 Hz, 1H), 7.58 (d, J=7.9 Hz, 2H), 7.37 (t, J=7.9 Hz, 2H), 7.20-7.13 (m, 1H), 4.61-4.46 (m, 1H), 4.30 (br t, J=8.4 Hz, 1H), 4.01-3.88 (m, 2H), 3.56 (quin, J=8.4 Hz, 1H), 3.43-3.25 (m, 2H), 3.12-2.88 (m, 2H), 2.87-2.79 (m, 1H), 2.23 (br t, J=12.8 Hz, 2H), 2.01-1.86 (m, 2H); LCMS (ESI) [M+H]+: 448.1.

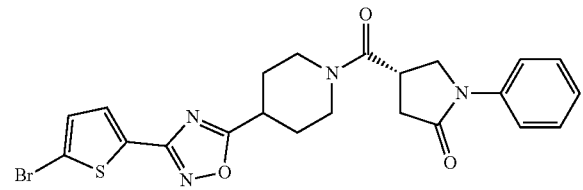 [SMILES: O=C([C@H]1CC(=O)N(c2ccccc2)C1)N1CCC(c2nc(-c3ccc(Br)s3)no2)CC1]

¹H NMR (400 MHz, CHLOROFORM-d) δ 7.54-7.43 (m, 3H), 7.34-7.26 (m, 2H), 7.12-7.03 (m, 2H), 4.44 (br t, J=15.5 Hz, 1H), 4.22 (br d, J=2.3 Hz, 1H), 3.94-3.83 (m, 2H), 3.55-3.45 (m, 1H), 3.35-3.15 (m, 2H), 3.05-2.83 (m, 2H), 2.81-2.71 (m, 1H), 2.15 (br t, J=13.6 Hz, 2H), 1.95-1.78 (m, 2H); LCMS (ESI) [M+H]+: 501.1.

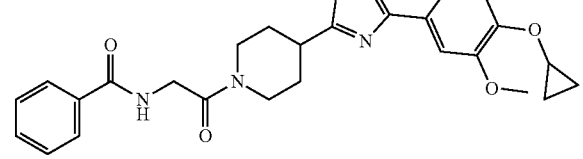

¹H NMR (400 MHz, CHLOROFORM-d) δ 7.93-7.82 (m, 2H), 7.69 (dd, J=1.9, 8.4 Hz, 1H), 7.61-7.42 (m, 4H), 7.38-7.31 (m, 2H), 4.57-4.45 (m, 1H), 4.31 (d, J=3.8 Hz, 2H), 3.94 (s, 3H), 3.93-3.86 (m, 1H), 3.85-3.78 (m, 1H), 3.41-3.26 (m, 2H), 3.22-3.09 (m, 1H), 2.34-2.18 (m, 2H), 2.10-1.92 (m, 2H), 0.95-0.81 (m, 4H); LCMS (ESI) [M+H]+: 477.2.

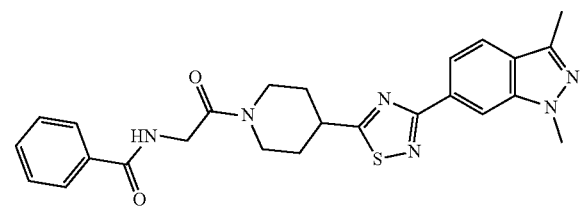 [SMILES: Cc1nn(C)c2cc(-c3nsc(C4CCN(C(=O)CNC(=O)c5ccccc5)CC4)n3)ccc12]

¹H NMR (400 MHz, CHLOROFORM-d) δ 8.31 (s, 1H), 8.08 (d, J=8.4 Hz, 1H), 7.87 (d, J=7.3 Hz, 2H), 7.73 (d, J=8.4 Hz, 1H), 7.56-7.50 (m, 1H), 7.49-7.44 (m, 2H), 7.36 (br s, 1H), 4.72 (br d, J=13.4 Hz, 1H), 4.40-4.27 (m, 2H), 4.10 (s, 3H), 4.00 (br d, J=13.9 Hz, 1H), 3.52 (tt, J=3.7, 11.0 Hz, 1H), 3.41-3.31 (m, 1H), 3.04 (br t, J=11.3 Hz, 1H), 2.61 (s, 3H), 2.35 (br t, J=15.7 Hz, 2H), 1.95 (dquin, J=3.9, 12.1 Hz, 2H); LCMS (ESI) [M+H]+: 475.2.

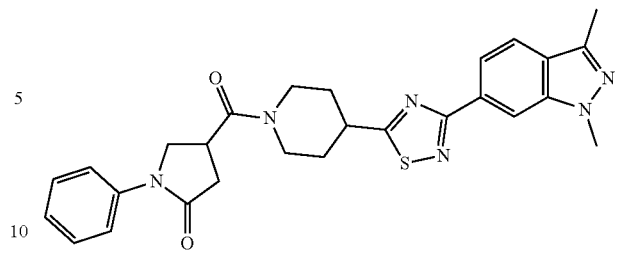

¹H NMR (400 MHz, CHLOROFORM-d) δ 8.31 (s, 1H), 8.08 (d, J=8.4 Hz, 1H), 7.73 (d, J=8.4 Hz, 1H), 7.61 (d, J=7.8 Hz, 2H), 7.39 (t, J=7.8 Hz, 2H), 7.22-7.15 (m, 1H), 4.75 (br t, J=14.6 Hz, 1H), 4.35 (q, J=8.1 Hz, 1H), 4.10 (d, J=2.2 Hz, 3H), 4.04 (br s, 1H), 3.96 (dt, J=3.1, 9.0 Hz, 1H), 3.60 (quin, J=8.5 Hz, 1H), 3.51 (dt, J=4.0, 11.0 Hz, 1H), 3.46-3.33 (m, 1H), 3.07-2.92 (m, 2H), 2.91-2.82 (m, 1H), 2.61 (s, 3H), 2.43-2.28 (m, 2H), 2.01-1.87 (m, 2H); LCMS (ESI) [M+H]+: 501.2.

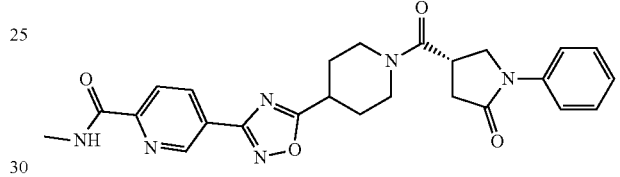

¹H NMR (400 MHz, CHLOROFORM-d) δ 9.24 (s, 1H), 8.53 (br d, J=8.1 Hz, 1H), 8.35 (d, J=8.1 Hz, 1H), 8.07 (br s, 1H), 7.62 (d, J=8.1 Hz, 2H), 7.40 (t, J=7.9 Hz, 2H), 7.22-7.17 (m, 1H), 4.64-4.50 (m, 1H), 4.37-4.30 (m, 1H), 4.05-3.94 (m, 2H), 3.61 (quin, J=8.4 Hz, 1H), 3.47-3.33 (m, 2H), 3.09 (d, J=5.1 Hz, 4H), 3.04-2.94 (m, 1H), 2.91-2.82 (m, 1H), 2.35-2.22 (m, 2H), 2.07-1.92 (m, 2H); LCMS (ESI) [M+H]+: 475.2.

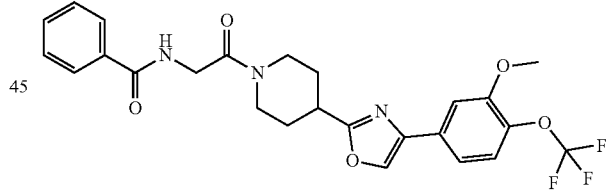

¹H NMR (400 MHz, CHLOROFORM-d) δ 7.89-7.83 (m, 2H), 7.73-7.67 (m, 2H), 7.57-7.50 (m, 1H), 7.50-7.43 (m, 2H), 7.38-7.31 (m, 2H), 4.53 (br d, J=14.6 Hz, 1H), 4.32 (d, J=3.3 Hz, 2H), 3.98 (s, 3H), 3.92 (br d, J=13.5 Hz, 1H), 3.40-3.30 (m, 2H), 3.19-3.09 (m, 1H), 2.32-2.20 (m, 2H), 2.08-1.93 (m, 2H); LCMS (ESI) [M+H]+: 505.1.

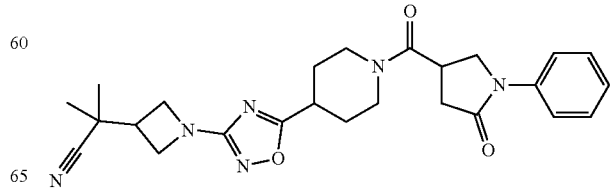

¹H NMR (400 MHz, CHLOROFORM-d) δ 7.60 (d, J=8.2 Hz, 2H), 7.39 (t, J=7.8 Hz, 2H), 7.21-7.14 (m, 1H), 4.49 (br t, J=14.6 Hz, 1H), 4.30 (dd, J=7.3, 9.7 Hz, 1H), 4.21-4.13 (m, 2H), 4.05-3.98 (m, 2H), 3.93 (br t, J=8.7 Hz, 2H), 3.57 (quin, J=8.5 Hz, 1H), 3.39-3.27 (m, 1H), 3.18-2.92 (m, 3H), 2.88-2.79 (m, 2H), 2.20-2.08 (m, 2H), 1.88 (br d, J=12.1 Hz, 2H), 1.35 (s, 6H); LCMS (ESI) [M+H]+: 463.2.

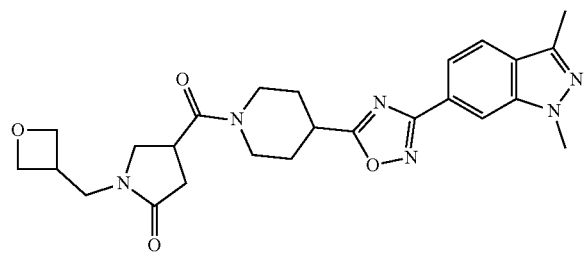 [SMILES: Cc1nn(C)c2cc(-c3noc(C4CCN(C(=O)C5CC(=O)N(CC6COC6)C5)CC4)n3)ccc12]

¹H NMR (400 MHz, CHLOROFORM-d) δ 8.09 (d, J=4.4 Hz, 1H), 7.86-7.79 (m, 1H), 7.77-7.71 (m, 1H), 4.87-4.78 (m, 2H), 4.61-4.45 (m, 3H), 4.09 (d, J=2.6 Hz, 3H), 3.92 (br d, J=8.4 Hz, 1H), 3.87-3.79 (m, 1H), 3.77-3.69 (m, 1H), 3.63-3.56 (m, 1H), 3.50-3.42 (m, 2H), 3.41-3.23 (m, 3H), 3.15-3.00 (m, 1H), 2.79-2.63 (m, 2H), 2.61 (s, 3H), 2.26 (br s, 2H), 2.06-1.90 (m, 2H); LCMS (ESI) [M+H]+: 479.2.

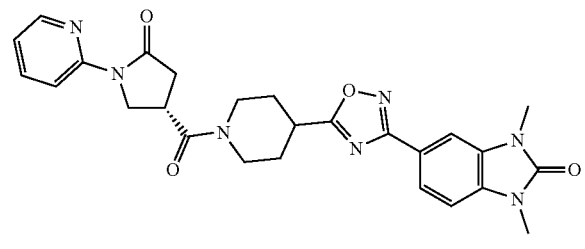 [SMILES: Cn1c(=O)n(C)c2cc(-c3noc(C4CCN(C(=O)[C@H]5CC(=O)N(c6ccccn6)C5)CC4)n3)ccc21]

¹H NMR (400 MHz, CHLOROFORM-d) δ 8.35-8.25 (m, 2H), 7.82 (br d, J=8.2 Hz, 1H), 7.66-7.59 (m, 2H), 7.02-6.95 (m, 2H), 4.52-4.42 (m, 1H), 4.35 (dd, J=8.9, 11.0 Hz, 1H), 4.18-4.08 (m, 1H), 3.95 (br d, J=13.6 Hz, 1H), 3.54-3.47 (m, 1H), 3.41 (d, J=8.8 Hz, 6H), 3.36-3.23 (m, 2H), 3.18 (dd, J=7.8, 17.2 Hz, 1H), 3.10-2.97 (m, 1H), 2.81-2.69 (m, 1H), 2.22-2.15 (m, 2H), 2.07-1.84 (m, 2H); LCMS (ESI) [M+H]+: 502.3.

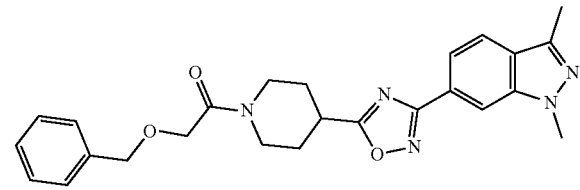 [SMILES: Cc1nn(C)c2cc(-c3noc(C4CCN(C(=O)COCc5ccccc5)CC4)n3)ccc12]

¹H NMR (400 MHz, CHLOROFORM-d) δ 8.10 (s, 1H), 7.87-7.80 (m, 1H), 7.78-7.71 (m, 1H), 7.43-7.29 (m, 5H), 4.63 (s, 2H), 4.51 (br d, J=13.0 Hz, 1H), 4.23 (d, J=2.8 Hz, 2H), 4.08 (s, 3H), 4.02 (br d, J=13.6 Hz, 1H), 3.36-3.23 (m, 2H), 3.04 (br t, J=11.8 Hz, 1H), 2.61 (s, 3H), 2.21 (br s, 2H), 2.04-1.92 (m, 2H); LCMS (ESI) [M+H]+: 446.2.

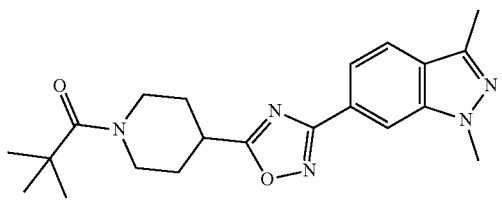 [SMILES: Cc1nn(C)c2cc(-c3noc(C4CCN(C(=O)C(C)(C)C)CC4)n3)ccc12]

¹H NMR (400 MHz, CHLOROFORM-d) δ 8.10 (s, 1H), 7.87-7.80 (m, 1H), 7.78-7.66 (m, 1H), 4.43 (br d, J=13.8 Hz, 2H), 4.08 (s, 3H), 3.36-3.26 (m, 1H), 3.16 (br t, J=11.8 Hz, 2H), 2.60 (s, 3H), 2.26-2.18 (m, 2H), 2.03-1.92 (m, 2H), 1.33 (s, 9H); LCMS (ESI) [M+H]+: 382.2.

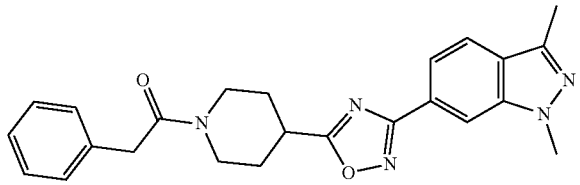 [SMILES: Cc1nn(C)c2cc(-c3noc(C4CCN(C(=O)Cc5ccccc5)CC4)n3)ccc12]

¹H NMR (400 MHz, CHLOROFORM-d) δ 8.00 (s, 1H), 7.77-7.70 (m, 1H), 7.67-7.62 (m, 1H), 7.30-7.23 (m, 2H), 7.23-7.16 (m, 3H), 4.48 (br d, J=13.4 Hz, 1H), 4.00 (s, 3H), 3.87 (br d, J=13.7 Hz, 1H), 3.72 (s, 2H), 3.22-3.12 (m, 2H), 2.97 (br t, J=11.1 Hz, 1H), 2.52 (s, 3H), 2.12 (br d, J=10.8 Hz, 1H), 1.97 (br d, J=10.8 Hz, 1H), 1.91-1.80 (m, 1H), 1.71-1.60 (m, 1H); LCMS (ESI) [M+H]+: 416.2.

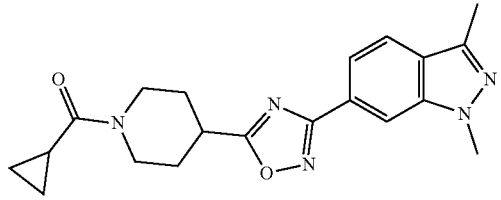 [SMILES: Cc1nn(C)c2cc(-c3noc(C4CCN(C(=O)C5CC5)CC4)n3)ccc12]

¹H NMR (400 MHz, CHLOROFORM-d) δ 8.10 (s, 1H), 7.87-7.80 (m, 1H), 7.77-7.70 (m, 1H), 4.55 (br s, 1H), 4.31 (br s, 1H), 4.08 (s, 3H), 3.49-3.27 (m, 2H), 3.01 (br s, 1H), 2.60 (s, 3H), 2.24 (br s, 2H), 2.01 (br s, 2H), 1.85-1.75 (m, 1H), 1.02 (br s, 2H), 0.80 (br dd, J=2.8, 7.6 Hz, 2H); LCMS (ESI) [M+H]+: 366.1.

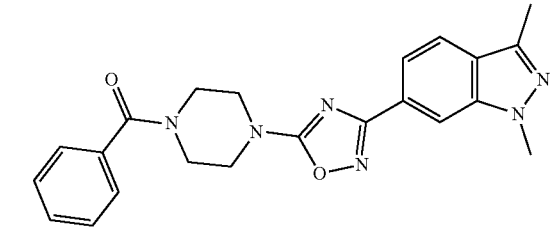

¹H NMR (400 MHz, CHLOROFORM-d) δ 8.04 (s, 1H), 7.80-7.70 (m, 2H), 7.53-7.45 (m, 5H), 4.08 (s, 3H), 3.96-3.65 (m, 8H), 2.61 (s, 3H); LCMS (ESI) [M+H]+: 403.1.

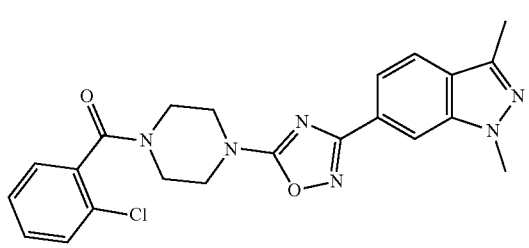

<sup>1</sup>H NMR (400 MHz, CHLOROFORM-d) δ 8.03 (s, 1H), 7.81-7.67 (m, 2H), 7.52-7.32 (m, 4H), 4.19-4.06 (m, 4H), 3.94-3.70 (m, 5H), 3.55-3.35 (m, 2H), 2.61 (s, 3H); LCMS (ESI) [M+H]+: 437.0.

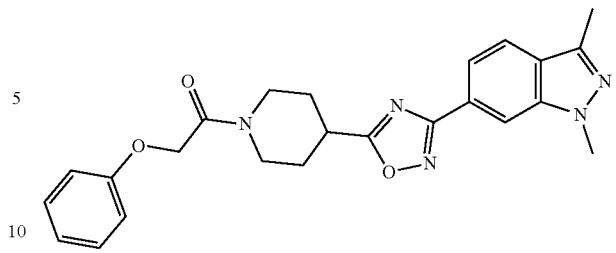

<sup>1</sup>H NMR (400 MHz, CHLOROFORM-d) δ 8.09 (s, 1H), 7.87-7.80 (m, 1H), 7.78-7.69 (m, 1H), 7.32 (t, J=7.7 Hz, 2H), 7.05-6.94 (m, 3H), 4.74 (s, 2H), 4.49 (br d, J=13.3 Hz, 1H), 4.14 (br s, 1H), 4.08 (s, 3H), 3.46-3.25 (m, 2H), 3.10 (br t, J=11.4 Hz, 1H), 2.60 (s, 3H), 2.22 (br s, 2H), 2.10-1.91 (m, 2H); LCMS (ESI) [M+H]+: 432.2.

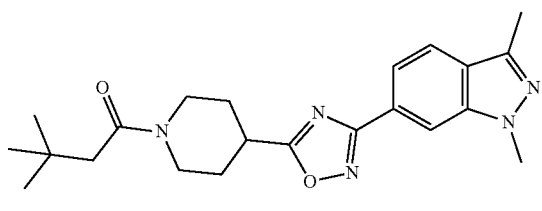 [SMILES: Cc1nn(C)c2cc(-c3noc(C4CCN(C(=O)CC(C)(C)C)CC4)n3)ccc12]

<sup>1</sup>H NMR (400 MHz, CHLOROFORM-d) δ 8.10 (s, 1H), 7.83 (d, J=8.3 Hz, 1H), 7.78-7.70 (m, 1H), 4.62 (br d, J=13.1 Hz, 1H), 4.08 (s, 3H), 4.05 (br d, J=15.3 Hz, 1H), 3.36-3.25 (m, 2H), 2.97 (br t, J=11.7 Hz, 1H), 2.60 (s, 3H), 2.32 (s, 2H), 2.22 (br d, J=12.2 Hz, 2H), 2.05-1.88 (m, 2H), 1.09 (s, 9H); LCMS (ESI) [M+H]+: 396.2.

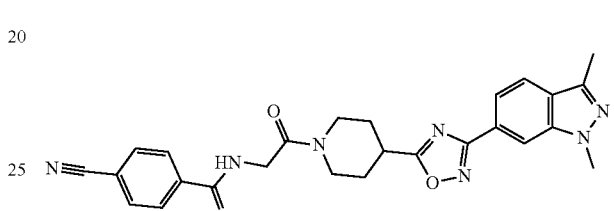

<sup>1</sup>H NMR (400 MHz, CHLOROFORM-d) δ 8.11 (s, 1H), 7.98 (d, J=8.2 Hz, 2H), 7.87-7.83 (m, 1H), 7.81-7.74 (m, 3H), 7.42 (br s, 1H), 4.54 (br d, J=13.6 Hz, 1H), 4.33 (d, J=3.7 Hz, 2H), 4.10 (s, 3H), 3.93 (br d, J=14.1 Hz, 1H), 3.40 (br t, J=10.7 Hz, 2H), 3.27-3.16 (m, 1H), 2.62 (s, 3H), 2.37-2.25 (m, 2H), 2.14-2.00 (m, 2H); LCMS (ESI) [M+H]+: 484.2.

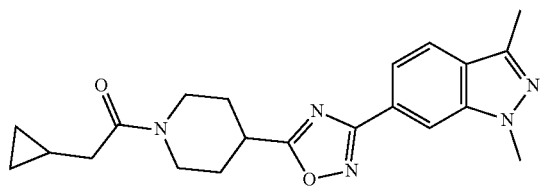 [SMILES: Cc1nn(C)c2cc(-c3noc(C4CCN(C(=O)CC5CC5)CC4)n3)ccc12]

<sup>1</sup>H NMR (400 MHz, CHLOROFORM-d) δ 8.10 (s, 1H), 7.87-7.79 (m, 1H), 7.77-7.69 (m, 1H), 4.59 (br d, J=13.1 Hz, 1H), 4.08 (s, 3H), 4.02-3.90 (m, 1H), 3.38-3.23 (m, 2H), 3.00 (br t, J=11.5 Hz, 1H), 2.60 (s, 3H), 2.34 (d, J=6.8 Hz, 2H), 2.23 (br d, J=13.1 Hz, 2H), 2.06-1.89 (m, 2H), 1.15-1.02 (m, 1H), 0.66-0.53 (m, 2H), 0.25-0.18 (m, 2H); LCMS (ESI) [M+H]+: 380.2.

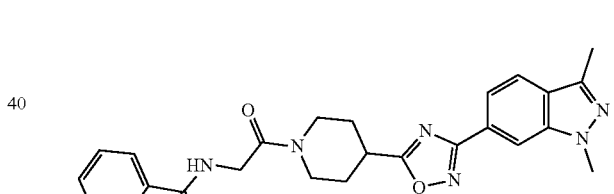

<sup>1</sup>H NMR (400 MHz, CHLOROFORM-d) δ 8.19 (s, 1H), 8.12-8.06 (m, 2H), 7.86-7.81 (m, 2H), 7.74 (s, 1H), 7.64-7.58 (m, 1H), 7.43 (br s, 1H), 4.58-4.50 (m, 1H), 4.33 (d, J=3.8 Hz, 2H), 4.10 (s, 3H), 3.98-3.89 (m, 1H), 3.46-3.33 (m, 2H), 3.28-3.15 (m, 1H), 2.62 (s, 3H), 2.31 (dt, J=3.3, 13.3 Hz, 2H), 2.14-1.98 (m, 2H); LCMS (ESI) [M+H]+: 484.2.

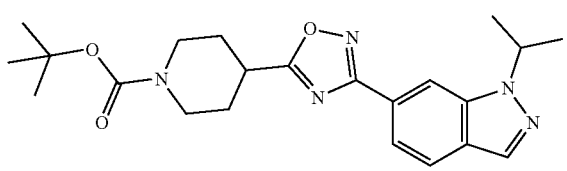 [SMILES: CC(C)n1ncc2ccc(-c3noc(C4CCN(C(=O)OC(C)(C)C)CC4)n3)cc21]

<sup>1</sup>H NMR (400 MHz, CHLOROFORM-d) δ 8.21 (s, 1H), 8.06 (s, 1H), 7.90-7.77 (m, 2H), 5.10-4.88 (m, 1H), 4.30-4.01 (m, 2H), 3.32-3.15 (m, 1H), 3.02 (t, J=12.0 Hz, 2H), 2.29-2.06 (m, 2H), 2.04-1.87 (m, 2H), 1.63 (d, J=6.8 Hz, 6H), 1.49 (s, 9H); LCMS (ESI) [M+H]+: 412.1.

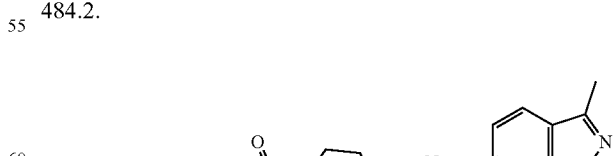

<sup>1</sup>H NMR (400 MHz, CHLOROFORM-d) δ 8.11 (s, 1H), 7.88-7.79 (m, 3H), 7.78-7.74 (m, 1H), 7.45 (d, J=8.3 Hz, 2H), 7.33 (br s, 1H), 4.54 (br d, J=13.4 Hz, 1H), 4.32 (d, J=3.5 Hz, 2H), 4.10 (s, 3H), 3.94 (br d, J=14.1 Hz, 1H), 3.39 (br t, J=10.6 Hz, 2H), 3.19 (br t, J=10.8 Hz, 1H), 2.62 (s, 3H), 2.35-2.23 (m, 2H), 2.13-1.99 (m, 2H); LCMS (ESI) [M+H]+: 493.1.

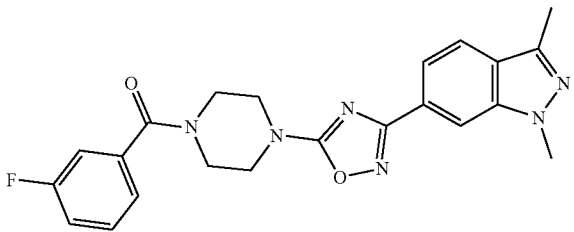 [SMILES: Cc1nn(C)c2cc(-c3noc(N4CCN(C(=O)c5cccc(F)c5)CC4)n3)ccc12]

¹H NMR (400 MHz, CHLOROFORM-d) δ 7.94 (s, 1H), 7.70-7.60 (m, 2H), 7.41-7.32 (m, 1H), 7.17-7.07 (m, 3H), 3.98 (s, 3H), 3.89-3.55 (m, 8H), 2.51 (s, 3H); LCMS (ESI) [M+H]+: 421.2.

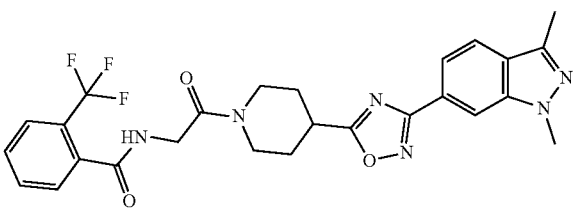 [SMILES: Cc1nn(C)c2cc(-c3noc(C4CCN(C(=O)CNC(=O)c5ccccc5C(F)(F)F)CC4)n3)ccc12]

¹H NMR (400 MHz, CHLOROFORM-d) δ 8.14 (s, 1H), 7.88 (d, J=8.3 Hz, 1H), 7.81-7.72 (m, 2H), 7.66-7.55 (m, 3H), 7.03 (br s, 1H), 4.52 (br d, J=13.4 Hz, 1H), 4.34 (d, J=3.9 Hz, 2H), 4.13 (s, 3H), 3.92 (br d, J=13.7 Hz, 1H), 3.38 (br t, J=10.6 Hz, 2H), 3.17 (br t, J=11.0 Hz, 1H), 2.65 (s, 3H), 2.30 (br t, J=13.9 Hz, 2H), 2.14-1.99 (m, 2H); LCMS (ESI) [M+H]+: 527.1.

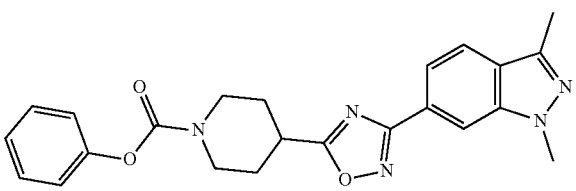 [SMILES: Cc1nn(C)c2cc(-c3noc(C4CCN(C(=O)Oc5ccccc5)CC4)n3)ccc12]

¹H NMR (400 MHz, CHLOROFORM-d) δ 8.12 (s, 1H), 7.85 (dd, J=1.0, 8.4 Hz, 1H), 7.78-7.71 (m, 1H), 7.43-7.34 (m, 2H), 7.25-7.19 (m, 1H), 7.14 (d, J=7.7 Hz, 2H), 4.43-4.25 (m, 2H), 4.09 (s, 3H), 3.32 (tt, J=3.9, 10.7 Hz, 2H), 3.20 (br s, 1H), 2.61 (s, 3H), 2.28 (br dd, J=3.3, 13.4 Hz, 2H), 2.09 (br d, J=10.8 Hz, 2H); LCMS (ESI) [M+H]+: 418.1.

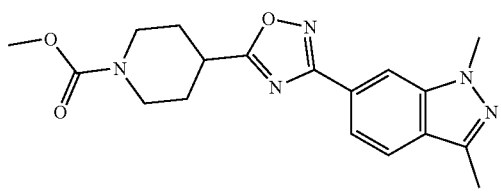 [SMILES: COC(=O)N1CCC(c2nc(-c3ccc4c(C)nn(C)c4c3)no2)CC1]

¹H NMR (400 MHz, CHLOROFORM-d) δ 8.10 (s, 1H), 7.83 (d, J=8.4 Hz, 1H), 7.78-7.69 (m, 1H), 4.20 (br s, 2H), 4.08 (s, 3H), 3.74 (s, 3H), 3.29-3.19 (m, 1H), 3.10 (br t, J=11.6 Hz, 2H), 2.60 (s, 3H), 2.18 (br d, J=11.0 Hz, 2H), 2.03-1.90 (m, 2H); LCMS (ESI) [M+H]+: 356.2.

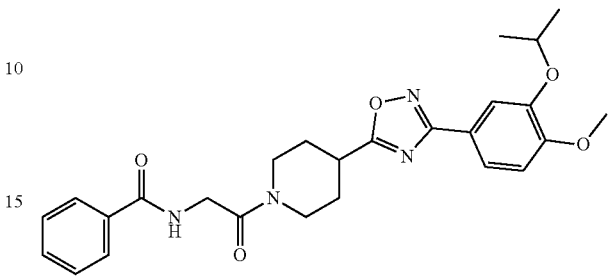

¹H NMR (400 MHz, CHLOROFORM-d) δ 7.86 (d, J=7.2 Hz, 2H), 7.67 (dd, J=1.8, 8.3 Hz, 1H), 7.60 (d, J=1.8 Hz, 1H), 7.56-7.50 (m, 1H), 7.49-7.43 (m, 2H), 7.34 (br s, 1H), 6.96 (d, J=8.4 Hz, 1H), 4.66 (spt, J=6.1 Hz, 1H), 4.55-4.45 (m, 1H), 4.31 (d, J=3.9 Hz, 2H), 3.92 (s, 3H), 3.90 (br d, J=3.7 Hz, 1H), 3.39-3.27 (m, 2H), 3.21-3.10 (m, 1H), 2.24 (dt, J=3.5, 12.9 Hz, 2H), 2.08-1.92 (m, 2H), 1.41 (d, J=6.0 Hz, 6H); LCMS (ESI) [M+H]+: 479.2.

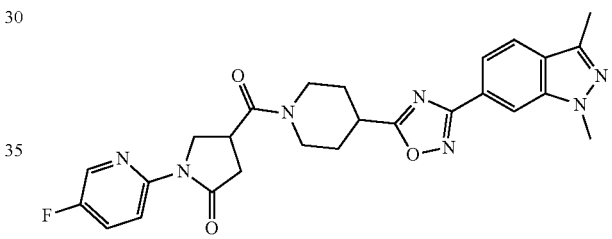

¹H NMR (400 MHz, CHLOROFORM-d) δ 8.45-8.39 (m, 1H), 8.18 (br s, 1H), 8.09 (s, 1H), 7.86-7.80 (m, 1H), 7.76-7.72 (m, 1H), 7.44 (br t, J=8.3 Hz, 1H), 4.61-4.51 (m, 1H), 4.41-4.34 (m, 1H), 4.20 (td, J=5.9, 11.3 Hz, 1H), 4.08 (s, 3H), 4.02 (br d, J=14.3 Hz, 1H), 3.57 (quin, J=8.0 Hz, 1H), 3.47-3.31 (m, 2H), 3.22 (dd, J=7.6, 17.3 Hz, 1H), 3.16-3.04 (m, 1H), 2.88-2.78 (m, 1H), 2.60 (s, 3H), 2.37-2.21 (m, 2H), 2.12-1.92 (m, 2H); LCMS (ESI) [M+H]+: 504.2.

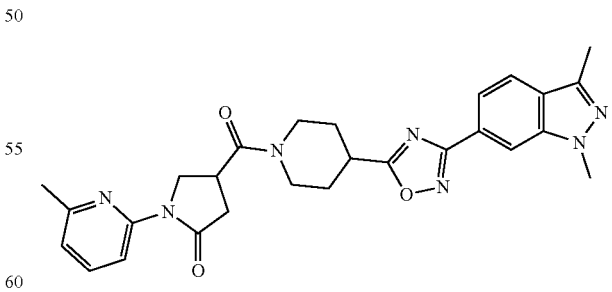

¹H NMR (400 MHz, CHLOROFORM-d) δ 8.15 (dd, J=4.9, 7.9 Hz, 1H), 8.10 (s, 1H), 7.85-7.80 (m, 1H), 7.76-7.72 (m, 1H), 7.57 (t, J=7.9 Hz, 1H), 6.89 (d, J=7.5 Hz, 1H), 4.64-4.49 (m, 1H), 4.47-4.39 (m, 1H), 4.20 (dd, J=7.1, 11.2 Hz, 1H), 4.08 (s, 3H), 4.03 (br s, 1H), 3.55 (quin, J=8.3 Hz, 1H), 3.47-3.31 (m, 2H), 3.26-3.01 (m, 2H), 2.85-2.76 (m, 1H), 2.60 (s, 3H), 2.46 (d, J=2.2 Hz, 3H), 2.26 (br d, J=14.1 Hz, 2H), 2.12-1.91 (m, 2H); LCMS (ESI) [M+H]+: 500.2.

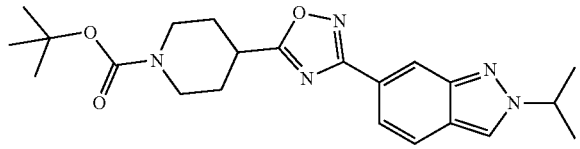 [SMILES: CC(C)n1cc2ccc(-c3noc(C4CCN(C(=O)OC(C)(C)C)CC4)n3)cc2n1]

¹H NMR (400 MHz, CHLOROFORM-d) δ 8.53 (s, 1H), 8.00 (s, 1H), 7.79-7.70 (m, 2H), 4.91-4.77 (m, 1H), 4.22-4.05 (m, 2H), 3.26-3.14 (m, 1H), 3.03 (br t, J=11.2 Hz, 2H), 2.22-2.08 (m, 2H), 1.98-1.85 (m, 2H), 1.69 (d, J=6.8 Hz, 6H), 1.94 (s, 9H); LCMS (ESI) [M+H]+: 412.2.

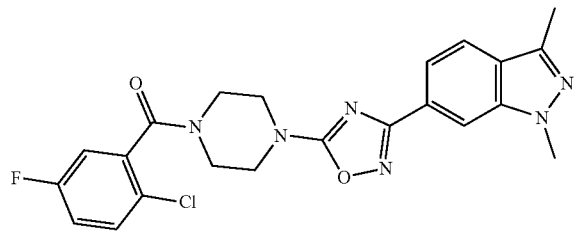 [SMILES: Cc1nn(C)c2cc(-c3noc(N4CCN(C(=O)c5cc(F)ccc5Cl)CC4)n3)ccc12]

¹H NMR (400 MHz, CHLOROFORM-d) δ 7.94 (s, 1H), 7.70-7.60 (m, 2H), 7.35 (dd, J=4.8, 8.8 Hz, 1H), 7.06-6.96 (m, 2H), 4.07-3.96 (m, 4H), 3.88-3.60 (m, 5H), 3.45-3.28 (m, 2H), 2.51 (s, 3H); LCMS (ESI) [M+H]+: 455.1.

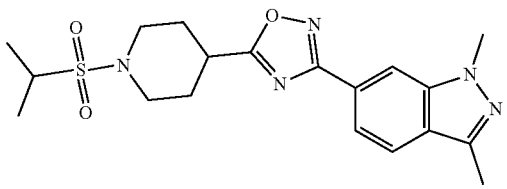 [SMILES: Cc1nn(C)c2cc(-c3noc(C4CCN(S(=O)(=O)C(C)C)CC4)n3)ccc12]

¹H NMR (400 MHz, CHLOROFORM-d) δ 8.10 (s, 1H), 7.83 (d, J=8.3 Hz, 1H), 7.78-7.69 (m, 1H), 4.09 (s, 3H), 3.89 (br d, J=13.1 Hz, 2H), 3.28-3.14 (m, 4H), 2.60 (s, 3H), 2.26 (br dd, J=2.9, 13.4 Hz, 2H), 2.17-2.05 (m, 2H), 1.38 (d, J=6.7 Hz, 6H); LCMS (ESI) [M+H]+: 404.1.

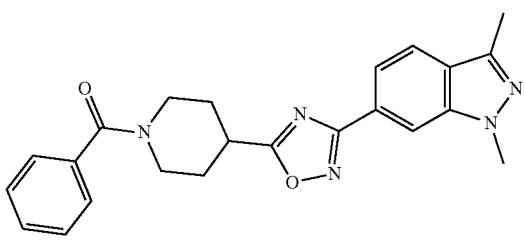

¹H NMR (400 MHz, CHLOROFORM-d) δ 8.10 (s, 1H), 7.90-7.81 (m, 1H), 7.78-7.70 (m, 1H), 7.44 (s, 5H), 4.82-4.37 (m, 1H), 4.09 (s, 3H), 3.91 (br s, 1H), 3.40-3.30 (m, 1H), 3.30-3.17 (m, 2H), 2.61 (s, 3H), 2.37-1.96 (m, 4H); LCMS (ESI) [M+H]+: 402.1.

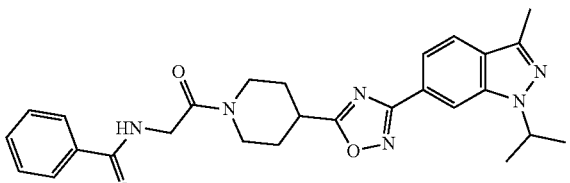

¹H NMR (400 MHz, CHLOROFORM-d) δ 8.13 (s, 1H), 7.89-7.84 (m, 2H), 7.83-7.78 (m, 1H), 7.75-7.70 (m, 1H), 7.55-7.49 (m, 1H), 7.49-7.42 (m, 2H), 7.33 (br s, 1H), 4.88 (m, 1H), 4.53 (m, J=3.7, 13.5 Hz, 1H), 4.32 (d, J=3.9 Hz, 2H), 3.99-3.87 (m, 1H), 3.43-3.29 (m, 2H), 3.23-3.09 (m, 1H), 2.61 (s, 3H), 2.28 (m, 2H), 2.13-1.92 (m, 2H), 1.60 (d, J=6.7 Hz, 6H); LCMS (ESI) [M+H]+: 487.2.

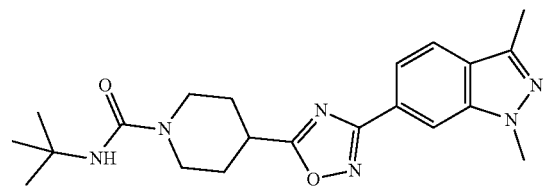 [SMILES: Cc1nn(C)c2cc(-c3noc(C4CCN(C(=O)NC(C)(C)C)CC4)n3)ccc12]

¹H NMR (400 MHz, CHLOROFORM-d) δ 8.10 (s, 1H), 7.83 (d, J=8.4 Hz, 1H), 7.77-7.70 (m, 1H), 4.35 (br s, 1H), 4.08 (s, 3H), 3.96 (br d, J=13.4 Hz, 2H), 3.26-3.16 (m, 1H), 3.08-2.99 (m, 2H), 2.60 (s, 3H), 2.19 (br d, J=10.3 Hz, 2H), 2.04-1.92 (m, 2H), 1.38 (s, 9H); LCMS (ESI) [M+H]+: 397.2.

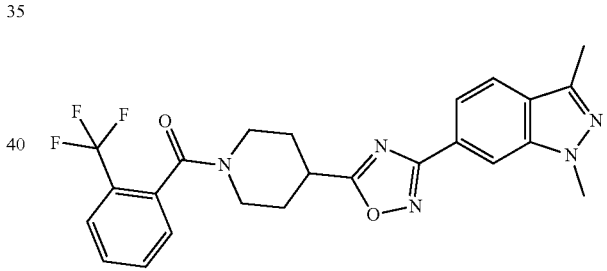

¹H NMR (400 MHz, CHLOROFORM-d) δ 8.10 (s, 1H), 7.88-7.80 (m, 1H), 7.74 (br d, J=7.9 Hz, 2H), 7.68-7.60 (m, 1H), 7.59-7.52 (m, 1H), 7.38 (dd, J=7.5, 17.2 Hz, 1H), 4.78-4.63 (m, 1H), 4.09 (s, 3H), 3.58-3.46 (m, 1H), 3.39-3.14 (m, 3H), 2.61 (s, 3H), 2.38-2.30 (m, 1H), 2.16-1.86 (m, 3H); LCMS (ESI) [M+H]+: 470.1.

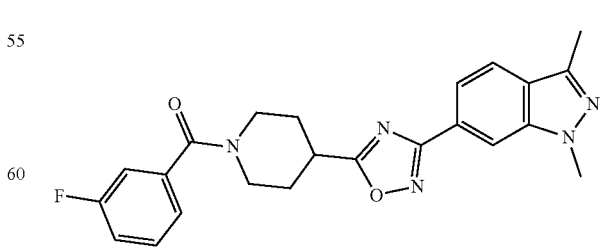

¹H NMR (400 MHz, CHLOROFORM-d) δ 8.10 (s, 1H), 7.84 (dd, J=1.0, 8.4 Hz, 1H), 7.79-7.70 (m, 1H), 7.48-7.37 (m, 1H), 7.22 (d, J=7.6 Hz, 1H), 7.19-7.10 (m, 2H), 4.65 (br s, 1H), 4.09 (s, 3H), 3.91 (br s, 1H), 3.45-3.16 (m, 3H), 2.61 (s, 3H), 2.42-1.91 (m, 4H); LCMS (ESI) [M+H]+: 420.1.

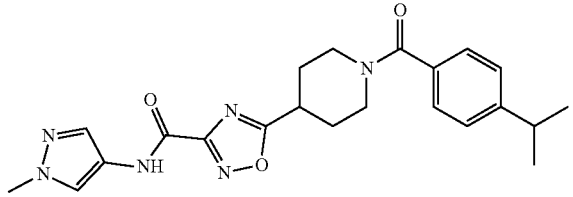 [SMILES: CC(C)c1ccc(C(=O)N2CCC(c3nc(C(=O)Nc4cnn(C)c4)no3)CC2)cc1]

¹H NMR (400 MHz, CHLOROFORM-d) δ 8.67 (s, 1H), 8.10 (s, 1H), 7.54 (s, 1H), 7.38-7.33 (m, 2H), 7.29-7.26 (m, 2H), 4.62 (br s, 1H), 4.10 (s, 1H), 3.93 (s, 3H), 3.34 (tt, J=4.0, 10.8 Hz, 1H), 3.19 (br s, 2H), 2.94 (spt, J=6.9 Hz, 1H), 2.18 (br d, J=4.6 Hz, 2H), 1.98 (br d, J=9.5 Hz, 2H), 1.27 (d, J=6.8 Hz, 6H); LCMS (ESI) [M+H]+: 423.2.

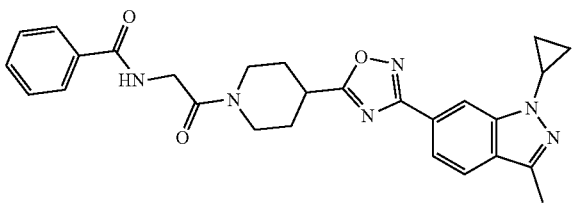 [SMILES: Cc1nn(C2CC2)c2cc(-c3noc(C4CCN(C(=O)CNC(=O)c5ccccc5)CC4)n3)ccc12]

¹H NMR (400 MHz, CHLOROFORM-d) δ 8.27 (s, 1H), 7.89-7.82 (m, 3H), 7.72 (d, J=8.6 Hz, 1H), 7.56-7.50 (m, 1H), 7.49-7.43 (m, 2H), 7.35 (br s, 1H), 4.59-4.49 (m, 1H), 4.32 (d, J=3.7 Hz, 2H), 3.94 (br d, J=13.9 Hz, 1H), 3.58 (tt, J=3.6, 6.9 Hz, 1H), 3.44-3.30 (m, 2H), 3.23-3.10 (m, 1H), 2.58 (s, 3H), 2.29 (dt, J=3.2, 13.1 Hz, 2H), 2.15-1.95 (m, 2H), 1.28-1.17 (m, 4H); LCMS (ESI) [M+H]+: 485.2.

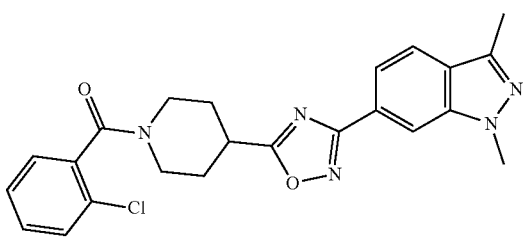 [SMILES: Cc1nn(C)c2cc(-c3noc(C4CCN(C(=O)c5ccccc5Cl)CC4)n3)ccc12]

¹H NMR (400 MHz, CHLOROFORM-d) δ 8.10 (d, J=2.6 Hz, 1H), 7.87-7.80 (m, 1H), 7.78-7.70 (m, 1H), 7.43 (br d, J=5.4 Hz, 1H), 7.40-7.28 (m, 3H), 4.80-4.63 (m, 1H), 4.08 (s, 3H), 3.67-3.53 (m, 1H), 3.41-3.12 (m, 3H), 2.60 (s, 3H), 2.34 (br d, J=13.1 Hz, 1H), 2.20-1.87 (m, 3H); LCMS (ESI) [M+H]+: 436.1.

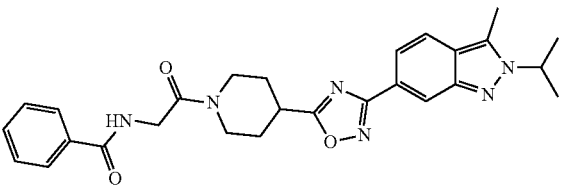 [SMILES: Cc1c2ccc(-c3noc(C4CCN(C(=O)CNC(=O)c5ccccc5)CC4)n3)cc2nn1C(C)C]

¹H NMR (400 MHz, CHLOROFORM-d) δ 8.50 (s, 1H), 7.85 (br d, J=7.3 Hz, 2H), 7.66 (m, 2H), 7.55-7.41 (m, 3H), 7.35 (br s, 1H), 4.78 (td, J=6.7, 13.3 Hz, 1H), 4.44 (br d, J=13.2 Hz, 1H), 4.30 (m, 2H), 3.90 (br d, J=13.5 Hz, 1H), 3.43-3.28 (m, 2H), 3.22 (br t, J=11.4 Hz, 1H), 2.72-2.56 (s, 3H), 2.33-2.17 (m, 2H), 2.13-1.91 (m, 2H), 1.64 (d, J=6.6 Hz, 6H); LCMS (ESI) [M+H]+: 487.2.

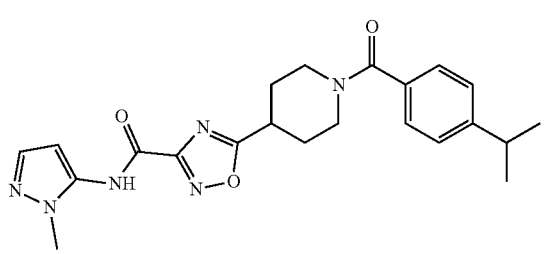

¹H NMR (400 MHz, CHLOROFORM-d) δ 8.52 (s, 1H), 7.49 (d, J=1.8 Hz, 1H), 7.38-7.34 (m, 2H), 7.28 (d, J=7.7 Hz, 2H), 6.43 (d, J=1.8 Hz, 1H), 4.84-4.39 (m, 1H), 4.35-3.91 (m, 1H), 3.85 (s, 3H), 3.37 (tt, J=4.0, 10.9 Hz, 1H), 3.28-3.10 (m, 2H), 2.95 (spt, J=6.9 Hz, 1H), 2.19 (br d, J=9.9 Hz, 2H), 2.08-1.87 (m, 2H), 1.27 (d, J=6.8 Hz, 6H); LCMS (ESI) [M+H]+: 423.2.

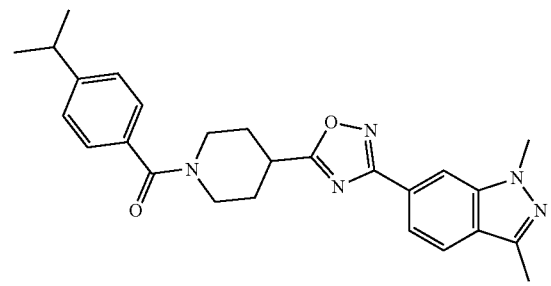 [SMILES: Cc1nn(C)c2cc(-c3noc(C4CCN(C(=O)c5ccc(C(C)C)cc5)CC4)n3)ccc12]

¹H NMR (400 MHz, CHLOROFORM-d) δ 8.11 (s, 1H), 7.85 (d, J=8.4 Hz, 1H), 7.79-7.67 (m, 1H), 7.39 (d, J=7.6 Hz, 2H), 7.29 (d, J=7.8 Hz, 2H), 4.63 (br s, 1H), 4.10 (s, 3H), 3.92 (br s, 1H), 3.45-3.13 (m, 3H), 2.96 (quind, J=6.8, 13.8 Hz, 1H), 2.62 (s, 3H), 2.38-1.94 (m, 4H), 1.28 (d, J=6.8 Hz, 6H); LCMS (ESI) [M+H]+: 444.2.

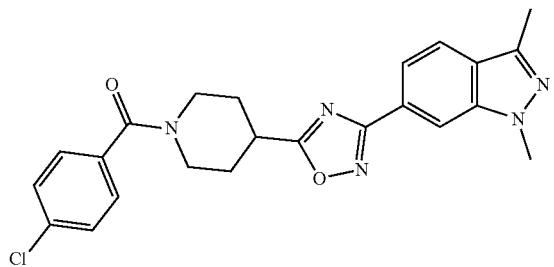 [SMILES: Cc1nn(C)c2cc(-c3noc(C4CCN(C(=O)c5ccc(Cl)cc5)CC4)n3)ccc12]

¹H NMR (400 MHz, CHLOROFORM-d) δ 8.10 (s, 1H), 7.88-7.81 (m, 1H), 7.78-7.71 (m, 1H), 7.46-7.37 (m, 4H), 4.60 (br s, 1H), 4.09 (s, 3H), 3.91 (br s, 1H), 3.44-3.13 (m, 3H), 2.61 (s, 3H), 2.40-1.88 (m, 4H); LCMS (ESI) [M+H]+: 436.1.

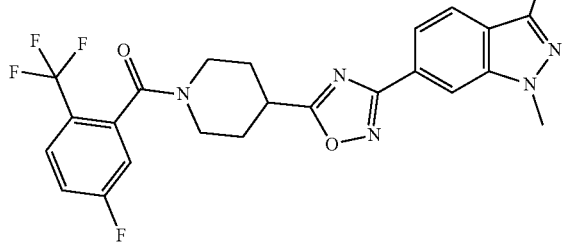

¹H NMR (400 MHz, CHLOROFORM-d) δ 8.10 (s, 1H), 7.88-7.80 (m, 1H), 7.78-7.69 (m, 2H), 7.27-7.20 (m, 1H), 7.09 (br dd, J=7.9, 16.6 Hz, 1H), 4.78-4.55 (m, 1H), 4.09 (s, 3H), 3.58-3.46 (m, 1H), 3.41-3.16 (m, 3H), 2.61 (s, 3H), 2.43-2.26 (m, 1H), 2.19-1.90 (m, 3H); LCMS (ESI) [M+H]+: 488.1.

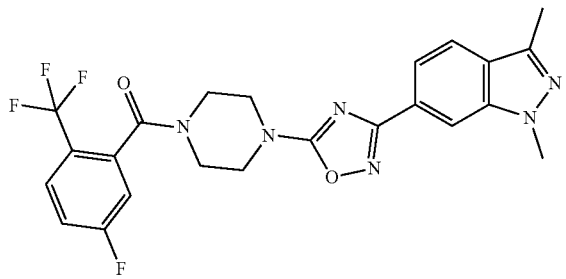 [SMILES: Cc1nn(C)c2cc(-c3noc(N4CCN(C(=O)c5cc(F)ccc5C(F)(F)F)CC4)n3)ccc12]

¹H NMR (400 MHz, CHLOROFORM-d) δ 7.93 (s, 1H), 7.72-7.60 (m, 3H), 7.21 (br d, J=2.3 Hz, 1H), 7.17 (d, J=2.2 Hz, 1H), 7.02 (dd, J=2.4, 7.9 Hz, 1H), 4.05-3.96 (m, 4H), 3.86-3.69 (m, 3H), 3.65-3.55 (m, 2H), 3.30 (t, J=5.2 Hz, 2H), 2.51 (s, 3H); LCMS (ESI) [M+H]+: 489.1.

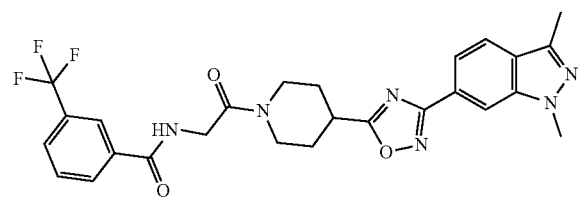 [SMILES: Cc1nn(C)c2cc(-c3noc(C4CCN(C(=O)CNC(=O)c5cccc(C(F)(F)F)c5)CC4)n3)ccc12]

¹H NMR (400 MHz, CHLOROFORM-d) δ 8.09-8.00 (m, 2H), 7.95 (d, J=7.8 Hz, 1H), 7.78-7.65 (m, 3H), 7.56-7.50 (m, 1H), 7.32 (br s, 1H), 4.49-4.41 (m, 1H), 4.25 (d, J=3.9 Hz, 2H), 4.01 (s, 3H), 3.89-3.81 (m, 1H), 3.34-3.26 (m, 2H), 3.16-3.07 (m, 1H), 2.52 (s, 3H), 2.22 (dt, J=3.5, 13.5 Hz, 2H), 2.04-1.90 (m, 2H); LCMS (ESI) [M+H]+: 527.1.

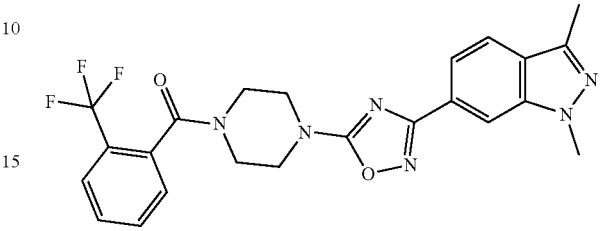

¹H NMR (400 MHz, CHLOROFORM-d) δ 8.02 (s, 1H), 7.82-7.69 (m, 3H), 7.69-7.57 (m, 2H), 7.39 (d, J=7.5 Hz, 1H), 4.15-4.06 (m, 4H), 3.96-3.79 (m, 3H), 3.71-3.61 (m, 2H), 3.40-3.33 (m, 2H), 2.60 (s, 3H); LCMS (ESI) [M+H]+: 471.1.

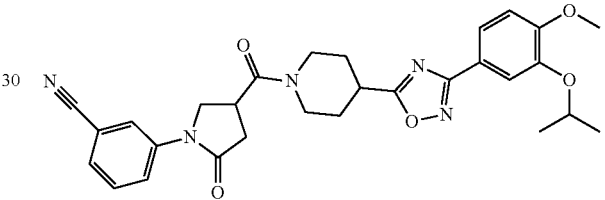

¹H NMR (400 MHz, CHLOROFORM-d) 8.02-7.83 (m, 2H), 7.66 (br d, J=8.4 Hz, 1H), 7.58 (s, 1H), 7.51-7.40 (m, 2H), 6.95 (d, J=8.6 Hz, 1H), 4.67-4.62 (m, 1H), 4.58-4.44 (m, 1H), 4.37-4.27 (m, 1H), 4.01-3.93 (m, 2H), 3.91 (s, 3H), 3.64-3.56 (m, 1H), 3.45-3.24 (m, 2H), 3.19-3.02 (m, 1H), 3.01-2.83 (m, 2H), 2.24 (br t, J=14.4 Hz, 2H), 2.09-1.88 (m, 2H), 1.40 (br d, J=5.7 Hz, 6H); LCMS (ESI) [M+H]+: 530.2.

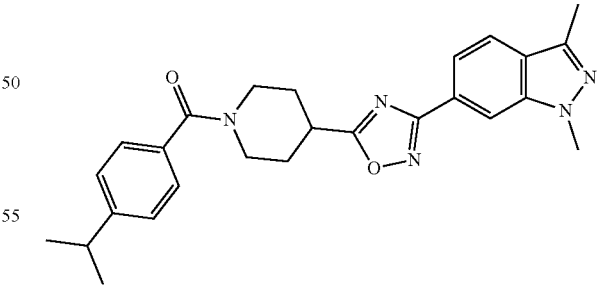

¹H NMR (400 MHz, CHLOROFORM-d) δ 8.41 (s, 1H), 8.08 (d, J=8.8 Hz, 1H), 7.44-7.33 (m, 3H), 7.27 (d, J=7.9 Hz, 2H), 4.63 (br s, 1H), 4.03 (s, 4H), 3.32 (br t, J=10.7 Hz, 1H), 3.21 (br s, 2H), 2.97-2.90 (m, 1H), 2.62 (s, 3H), 2.36-1.87 (m, 4H), 1.26 (d, J=6.8 Hz, 6H); LCMS (ESI) [M+H]+: 444.1.

641

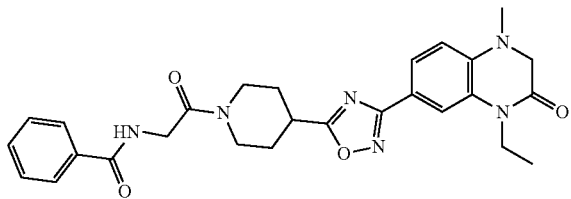 [SMILES: CCN1C(=O)CN(C)c2ccc(-c3noc(C4CCN(C(=O)CNC(=O)c5ccccc5)CC4)n3)cc21]

¹H NMR (400 MHz, CHLOROFORM-d) δ 7.86 (d, J=7.1 Hz, 2H), 7.75 (dd, J=1.5, 8.4 Hz, 1H), 7.65 (d, J=1.3 Hz, 1H), 7.57-7.50 (m, 1H), 7.49-7.43 (m, 2H), 7.35 (br s, 1H), 6.76 (d, J=8.4 Hz, 1H), 4.52 (br d, J=13.7 Hz, 1H), 4.31 (d, J=3.7 Hz, 2H), 4.17-4.05 (m, 2H), 3.92 (br d, J=14.1 Hz, 1H), 3.85 (s, 2H), 3.42-3.28 (m, 2H), 3.19-3.07 (m, 1H), 2.92 (s, 3H), 2.33-2.19 (m, 2H), 2.10-1.91 (m, 2H), 1.32 (t, J=7.1 Hz, 3H); LCMS (ESI) [M+H]+: 503.2.

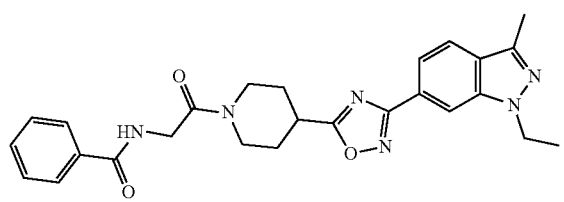 [SMILES: CCn1nc(C)c2ccc(-c3noc(C4CCN(C(=O)CNC(=O)c5ccccc5)CC4)n3)cc21]

¹H NMR (400 MHz, CHLOROFORM-d) δ 8.42 (s, 1H), 8.07 (dd, J=0.9, 8.8 Hz, 1H), 7.87 (d, J=7.3 Hz, 2H), 7.56-7.51 (m, 1H), 7.45 (dd, J=8.4, 17.2 Hz, 3H), 7.35 (br s, 1H), 4.53 (br d, J=13.7 Hz, 1H), 4.43-4.37 (m, 2H), 4.32 (d, J=3.7 Hz, 2H), 3.94 (br d, J=13.9 Hz, 1H), 3.41-3.32 (m, 1H), 3.36 (dt, J=4.1, 10.3 Hz, 1H), 3.17 (br t, J=10.9 Hz, 1H), 2.63 (s, 3H), 2.35-2.22 (m, 2H), 2.12-1.96 (m, 2H), 1.52 (t, J=7.3 Hz, 3H; LCMS (ESI) [M+H]+: 473.2.

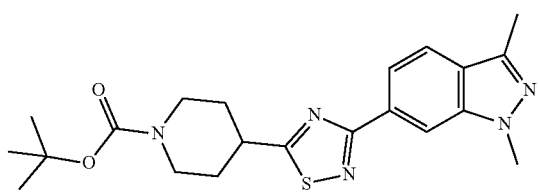 [SMILES: Cc1nn(C)c2cc(-c3nsc(C4CCN(C(=O)OC(C)(C)C)CC4)n3)ccc12]

¹H NMR (400 MHz, CHLOROFORM-d) δ 8.31 (s, 1H), 8.08 (d, J=8.4 Hz, 1H), 7.73 (d, J=8.4 Hz, 1H), 4.26 (br s, 2H), 4.09 (s, 3H), 3.41-3.31 (m, 1H), 2.98 (br t, J=12.0 Hz, 2H), 2.60 (s, 3H), 2.23 (br d, J=12.0 Hz, 2H), 1.85 (dq, J=4.0, 12.0 Hz, 2H), 1.50 (s, 9H); LCMS (ESI) [M+H]+: 414.1.

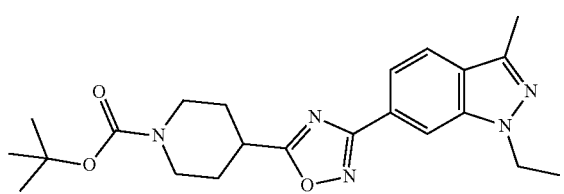 [SMILES: CCn1nc(C)c2ccc(-c3noc(C4CCN(C(=O)OC(C)(C)C)CC4)n3)cc21]

¹H NMR (400 MHz, CHLOROFORM-d) δ 8.34 (s, 1H), 7.99 (dd, J=1.2, 8.7 Hz, 1H), 7.34 (d, J=8.8 Hz, 1H), 4.31 (q, J=7.3 Hz, 2H), 4.08 (br d, J=10.1 Hz, 2H), 3.15-3.08 (m, 1H), 2.94 (br t, J=11.7 Hz, 2H), 2.55 (s, 3H), 2.07 (br dd, J=2.9, 13.2 Hz, 2H), 1.93-1.82 (m, 2H), 1.46-1.43 (m, 3H), 1.41 (s, 9H); LCMS (ESI) [M+H]+: 412.2.

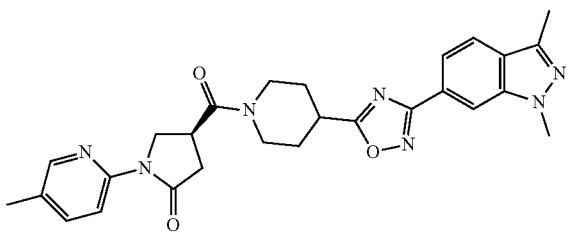 [SMILES: Cc1ccc(N2C[C@@H](C(=O)N3CCC(c4nc(-c5ccc6c(C)nn(C)c6c5)no4)CC3)CC2=O)nc1]

¹H NMR (400 MHz, CHLOROFORM-d) δ 8.28-8.24 (m, 1H), 8.14 (br s, 1H), 8.09 (d, J=3.5 Hz, 1H), 7.85-7.80 (m, 1H), 7.74-7.72 (m, 1H), 7.51 (br d, J=8.8 Hz, 1H), 4.56 (br t, J=13.4 Hz, 1H), 4.40 (dd, J=9.2, 11.0 Hz, 1H), 4.21-4.12 (m, 1H), 4.08 (s, 3H), 4.03 (br d, J=13.6 Hz, 1H), 3.62-3.51 (m, 1H), 3.46-3.30 (m, 2H), 3.25 (dd, J=7.9, 17.1 Hz, 1H), 3.15-3.01 (m, 1H), 2.86-2.74 (m, 1H), 2.59 (s, 3H), 2.35-2.20 (m, 5H), 2.12-1.91 (m, 2H); LCMS (ESI) [M+H]+: 500.2.

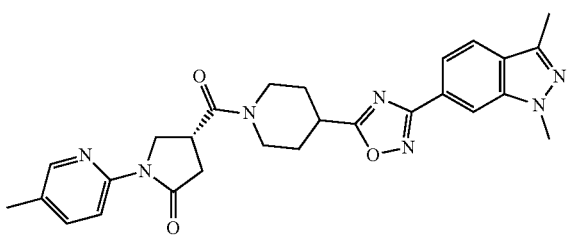 [SMILES: Cc1ccc(N2C[C@H](C(=O)N3CCC(c4nc(-c5ccc6c(C)nn(C)c6c5)no4)CC3)CC2=O)nc1]

¹H NMR (400 MHz, CHLOROFORM-d) δ 8.28-8.24 (m, 1H), 8.14 (br s, 1H), 8.09 (d, J=3.5 Hz, 1H), 7.85-7.80 (m, 1H), 7.76-7.71 (m, 1H), 7.51 (br d, J=8.3 Hz, 1H), 4.56 (br t, J=12.7 Hz, 1H), 4.40-4.37 (m, 1H), 4.21-4.13 (m, 1H), 4.08 (s, 3H), 4.03 (br d, J=13.2 Hz, 1H), 3.62-3.51 (m, 1H), 3.46-3.30 (m, 2H), 3.25 (dd, J=7.7, 17.3 Hz, 1H), 3.15-3.01 (m, 1H), 2.86-2.75 (m, 1H), 2.59 (s, 3H), 2.35-2.20 (m, 5H), 2.11-1.91 (m, 2H); LCMS (ESI) [M+H]+: 500.2.

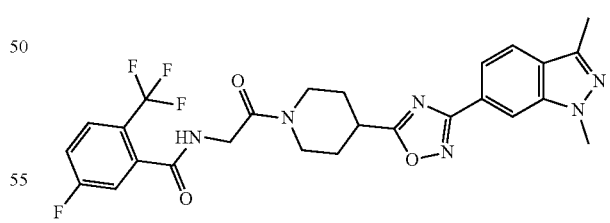

¹H NMR (400 MHz, CHLOROFORM-d) δ 8.02 (s, 1H), 7.75 (dd, J=0.9, 8.4 Hz, 1H), 7.69-7.62 (m, 2H), 7.22 (dd, J=2.4, 8.1 Hz, 1H), 7.19-7.14 (m, 1H), 6.97 (br s, 1H), 4.46-4.36 (m, 1H), 4.23 (d, J=4.0 Hz, 2H), 4.01 (s, 3H), 3.81 (br d, J=13.9 Hz, 1H), 3.34-3.24 (m, 2H), 3.13-3.04 (m, 1H), 2.53 (s, 3H), 2.27-2.15 (m, 2H), 2.05-1.91 (m, 2H); LCMS (ESI) [M+H]+: 545.1.

643

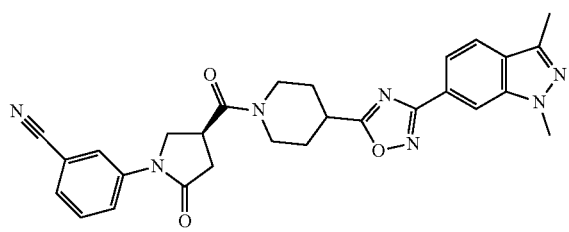 [SMILES: Cc1nn(C)c2cc(-c3noc(C4CCN(C(=O)[C@H]5CC(=O)N(c6cccc(C#N)c6)C5)CC4)n3)ccc12]

¹H NMR (400 MHz, CHLOROFORM-d) δ 8.11 (d, J=2.3 Hz, 1H), 8.02-7.89 (m, 2H), 7.87-7.82 (m, 1H), 7.79-7.73 (m, 1H), 7.54-7.43 (m, 2H), 4.66-4.48 (m, 1H), 4.35 (dd, J=6.6, 9.4 Hz, 1H), 4.10 (d, J=2.1 Hz, 3H), 4.06-3.92 (m, 2H), 3.64 (m, 1H), 3.52-3.33 (m, 2H), 3.25-3.07 (m, 1H), 3.06-2.86 (m, 2H), 2.62 (s, 3H), 2.39-2.23 (m, 2H), 2.15-1.95 (m, 2H); LCMS (ESI) [M+H]+: 510.2.

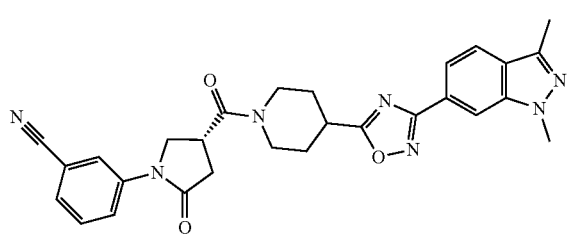 [SMILES: Cc1nn(C)c2cc(-c3noc(C4CCN(C(=O)[C@@H]5CC(=O)N(c6cccc(C#N)c6)C5)CC4)n3)ccc12]

¹H NMR (400 MHz, CHLOROFORM-d) δ 8.09 (d, J=2.3 Hz, 1H), 8.00-7.87 (m, 2H), 7.86-7.80 (m, 1H), 7.77-7.70 (m, 1H), 7.53-7.40 (m, 2H), 4.62-4.47 (m, 1H), 4.33 (dd, J=6.7, 9.4 Hz, 1H), 4.08 (d, J=2.3 Hz, 3H), 4.03-3.90 (m, 2H), 3.61 (td, J=8.3, 16.1 Hz, 1H), 3.51-3.31 (m, 2H), 3.13 (m, 1H), 3.02-2.83 (m, 2H), 2.60 (s, 3H), 2.38-2.20 (m, 2H), 2.12-1.92 (m, 2H); LCMS (ESI) [M+H]+: 510.2.

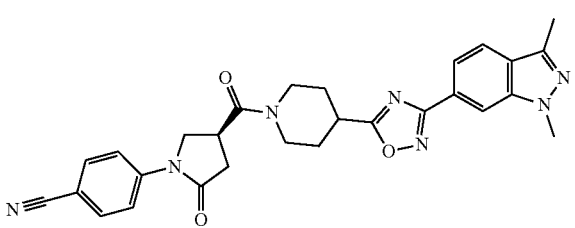 [SMILES: Cc1nn(C)c2cc(-c3noc(C4CCN(C(=O)[C@H]5CC(=O)N(c6ccc(C#N)cc6)C5)CC4)n3)ccc12]

¹H NMR (400 MHz, CHLOROFORM-d) δ 8.09 (s, 1H), 7.85-7.71 (m, 4H), 7.66 (d, J=8.8 Hz, 2H), 4.62-4.47 (m, 1H), 4.35 (dd, J=6.8, 9.6 Hz, 1H), 4.08 (s, 3H), 4.03-3.91 (m, 2H), 3.61 (m, 1H), 3.48-3.30 (m, 2H), 3.22-3.05 (m, 1H), 3.03-2.84 (m, 2H), 2.60 (s, 3H), 2.29 (br t, J=13.2 Hz, 2H), 2.12-1.92 (m, 2H); LCMS (ESI) [M+H]+: 510.2.

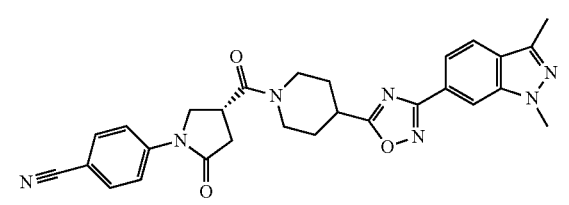 [SMILES: Cc1nn(C)c2cc(-c3noc(C4CCN(C(=O)[C@@H]5CC(=O)N(c6ccc(C#N)cc6)C5)CC4)n3)ccc12]

¹H NMR (400 MHz, CHLOROFORM-d) δ 8.09 (s, 1H), 7.85-7.72 (m, 4H), 7.66 (d, J=8.8 Hz, 2H), 4.65-4.47 (m,

644

1H), 4.35 (dd, J=6.8, 9.6 Hz, 1H), 4.08 (s, 3H), 4.03-3.89 (m, 2H), 3.61 (m, 1H), 3.48-3.31 (m, 2H), 3.22-3.05 (m, 1H), 3.03-2.85 (m, 2H), 2.60 (s, 3H), 2.29 (br t, J=13.3 Hz, 2H), 2.14-1.92 (m, 2H); LCMS (ESI) [M+H]+: 510.2.

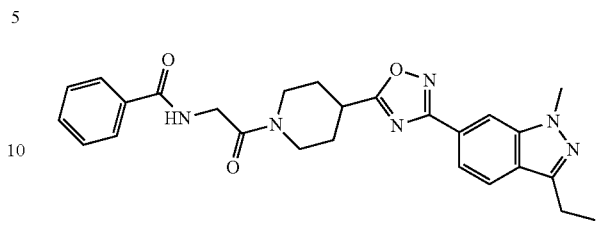

¹H NMR (400 MHz, CHLOROFORM-d) δ 8.11 (s, 1H), 7.90-7.77 (m, 4H), 7.57-7.45 (m, 3H), 7.36 (br s, 1H), 4.59-4.50 (m, 1H), 4.33 (d, J=3.8 Hz, 2H), 4.10 (s, 3H), 3.95 (br d, J=14.1 Hz, 1H), 3.38 (ddd, J=3.3, 10.6, 14.0 Hz, 2H), 3.22-3.12 (m, 1H), 3.07-3.00 (m, 1H), 3.04 (q, J=7.6 Hz, 1H), 2.30 (dt, J=3.3, 13.0 Hz, 2H), 2.11-1.97 (m, 2H), 1.44 (t, J=7.6 Hz, 3H); LCMS (ESI) [M+H]+: 473.2.

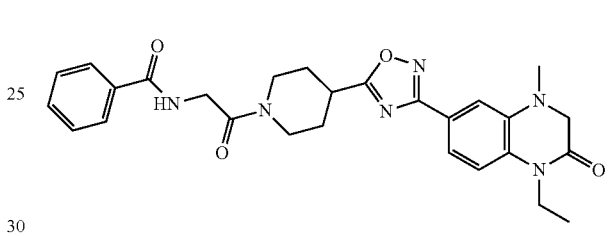

¹H NMR (400 MHz, CHLOROFORM-d) δ 7.86 (br d, J=6.8 Hz, 2H), 7.60 (dd, J=1.6, 8.4 Hz, 1H), 7.53 (t, J=7.2 Hz, 1H), 7.46 (t, J=7.2 Hz, 1H), 7.38 (d, J=1.2 Hz, 1H), 7.37-7.31 (m, 1H), 7.05 (d, J=8.4 Hz, 1H), 4.52 (td, J=3.6, 13.6 Hz, 1H), 4.31 (d, J=8.0 Hz, 2H), 4.05 (q, J=7.2 Hz, 2H), 3.92 (d, J=13.6 Hz, 1H), 3.42-3.27 (m, 2H), 3.20-3.07 (m, 1H), 2.93 (s, 3H), 2.34-2.17 (m, 2H), 2.08-1.90 (m, 2H), 1.31 (t, J=7.2 Hz, 3H); LCMS (ESI) [M+H]+: 503.3.

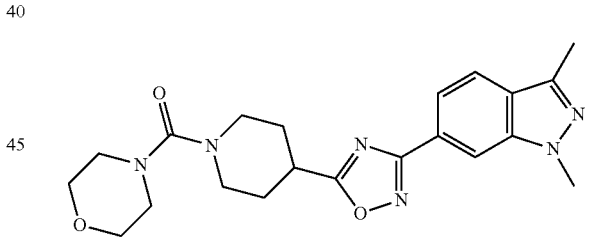

¹H NMR (400 MHz, CHLOROFORM-d) δ 8.09 (s, 1H), 7.87-7.79 (m, 1H), 7.78-7.66 (m, 1H), 4.08 (s, 3H), 3.79 (br d, J=13.4 Hz, 2H), 3.74-3.64 (m, 4H), 3.37-3.28 (m, 4H), 3.28-3.18 (m, 1H), 3.04 (br t, J=11.6 Hz, 2H), 2.60 (s, 3H), 2.20 (br d, J=10.9 Hz, 2H), 2.09-1.95 (m, 2H); LCMS (ESI) [M+H]+: 411.2.

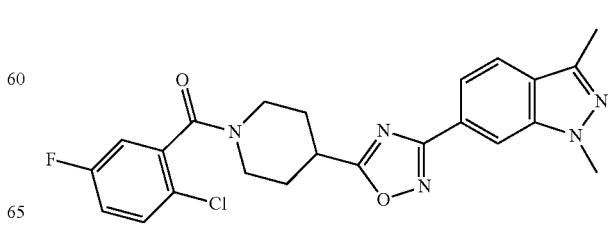

¹H NMR (400 MHz, CHLOROFORM-d) δ 8.10 (s, 1H), 7.87-7.80 (m, 1H), 7.78-7.70 (m, 1H), 7.45-7.32 (m, 1H), 7.16-6.98 (m, 2H), 4.76-4.60 (m, 1H), 4.09 (s, 3H), 3.59 (br t, J=12.8 Hz, 1H), 3.41-3.16 (m, 3H), 2.60 (s, 3H), 2.34 (br d, J=11.1 Hz, 1H), 2.24-1.87 (m, 3H); LCMS (ESI) [M+H]+: 454.1.

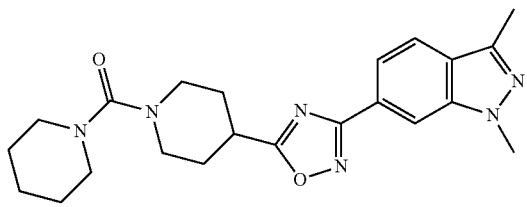 [SMILES: Cc1nn(C)c2cc(-c3noc(C4CCN(C(=O)N5CCCCC5)CC4)n3)ccc12]

¹H NMR (400 MHz, CHLOROFORM-d) δ 8.10 (s, 1H), 7.83 (d, J=8.4 Hz, 1H), 7.77-7.68 (m, 1H), 4.08 (s, 3H), 3.75 (br d, J=13.4 Hz, 2H), 3.30-3.15 (m, 5H), 2.99 (br t, J=11.8 Hz, 2H), 2.60 (s, 3H), 2.18 (br d, J=10.9 Hz, 2H), 2.08-1.95 (m, 2H), 1.60 (br s, 6H); LCMS (ESI) [M+H]+: 409.2.

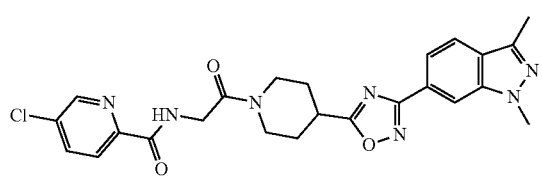 [SMILES: Cc1nn(C)c2cc(-c3noc(C4CCN(C(=O)CNC(=O)c5ccc(Cl)cn5)CC4)n3)ccc12]

¹H NMR (400 MHz, CHLOROFORM-d) δ 8.79 (br s, 1H), 8.55 (s, 1H), 8.14-8.07 (m, 2H), 7.81 (br d, J=8.4 Hz, 2H), 7.75-7.70 (m, 1H), 4.54 (br d, J=13.7 Hz, 1H), 4.32 (br d, J=4.2 Hz, 2H), 4.07 (s, 3H), 3.93 (br d, J=13.7 Hz, 1H), 3.41-3.30 (m, 2H), 3.13 (br t, J=11.6 Hz, 1H), 2.59 (s, 3H), 2.32-2.19 (m, 2H), 2.10-1.93 (m, 2H); LCMS (ESI) [M+H]+: 494.1.

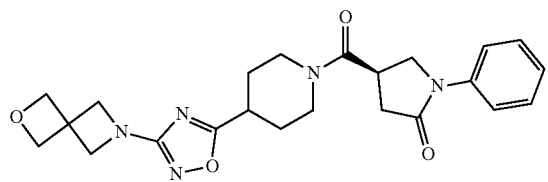 [SMILES: O=C([C@@H]1CC(=O)N(c2ccccc2)C1)N1CCC(c2nc(N3CC4(COC4)C3)no2)CC1]

¹H NMR (400 MHz, CHLOROFORM-d) δ 7.59 (br d, J=7.7 Hz, 2H), 7.38 (br t, J=7.4 Hz, 2H), 7.22-7.13 (m, 1H), 4.83 (s, 4H), 4.49 (br t, J=15.0 Hz, 1H), 4.33-4.27 (m, 1H), 4.22 (s, 4H), 3.97-3.87 (m, 2H), 3.61-3.50 (m, 1H), 3.31 (br d, J=8.2 Hz, 1H), 3.16-2.90 (m, 3H), 2.87-2.77 (m, 1H), 2.19-2.07 (m, 2H), 1.86 (br d, J=10.4 Hz, 2H); LCMS (ESI) [M+H]+: 438.2.

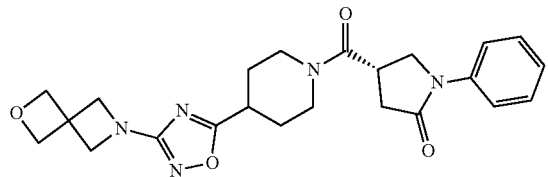 [SMILES: O=C([C@H]1CC(=O)N(c2ccccc2)C1)N1CCC(c2nc(N3CC4(COC4)C3)no2)CC1]

¹H NMR (400 MHz, CHLOROFORM-d) δ 7.59 (br d, J=7.5 Hz, 2H), 7.38 (br t, J=7.2 Hz, 2H), 7.22-7.13 (m, 1H), 4.83 (br s, 4H), 4.49 (br t, J=15.0 Hz, 1H), 4.30 (br t, J=8.2 Hz, 1H), 4.22 (br s, 4H), 3.97-3.87 (m, 2H), 3.61-3.51 (m, 1H), 3.31 (br d, J=6.8 Hz, 1H), 3.17-2.90 (m, 3H), 2.87-2.77 (m, 1H), 2.19-2.07 (m, 2H), 1.86 (br d, J=10.6 Hz, 2H); LCMS (ESI) [M+H]+: 438.2.

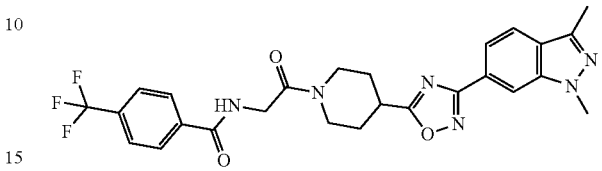

¹H NMR (400 MHz, CHLOROFORM-d) δ 8.11 (s, 1H), 7.99 (d, J=8.1 Hz, 2H), 7.84 (dd, J=0.9, 8.4 Hz, 1H), 7.75 (dd, J=5.0, 8.1 Hz, 3H), 7.43 (br s, 1H), 4.60-4.50 (m, 1H), 4.34 (d, J=3.8 Hz, 2H), 4.10 (s, 3H), 3.94 (br d, J=14.1 Hz, 1H), 3.45-3.33 (m, 2H), 3.25-3.14 (m, 1H), 2.62 (s, 3H), 2.37-2.25 (m, 2H), 2.14-1.99 (m, 2H); LCMS (ESI) [M+H]+: 527.1.

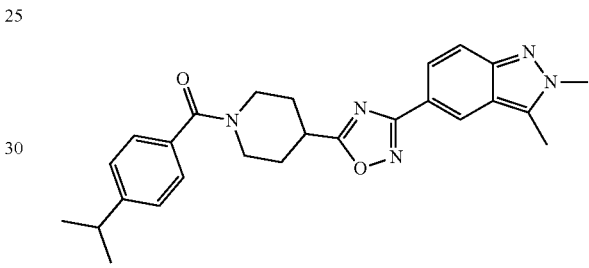

¹H NMR (400 MHz, CHLOROFORM-d) δ 8.29 (s, 1H), 7.86 (dd, J=1.5, 9.0 Hz, 1H), 7.61 (d, J=9.0 Hz, 1H), 7.29 (d, J=8.0 Hz, 2H), 7.20 (d, J=7.6 Hz, 2H), 4.54 (br s, 1H), 4.05 (s, 4H), 4.26-3.24 (m, 1H), 3.15 (br t, J=11.4 Hz, 2H), 2.90-2.81 (m, 1H), 2.60 (s, 3H), 2.22-1.86 (m, 4H), 1.19 (d, J=7.0 Hz, 6H); LCMS (ESI) [M+H]+: 444.2.

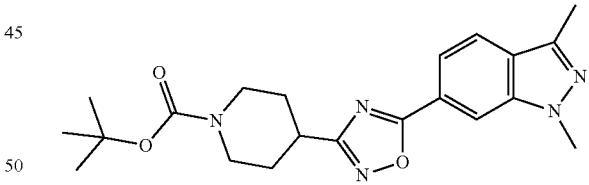

¹H NMR (400 MHz, CHLOROFORM-d) δ 8.15 (s, 1H), 7.86-7.83 (m, 1H), 7.79-7.76 (m, 1H), 4.16 (br s, 2H), 4.09 (s, 3H), 3.10-2.91 (m, 3H), 2.61 (s, 3H), 2.08 (br d, J=10.6 Hz, 2H), 1.94-1.82 (m, 2H), 1.48 (s, 9H); LCMS (ESI) [M+H]+: 398.2.

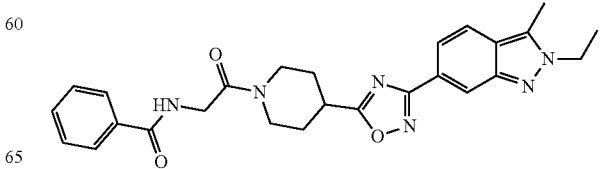

¹H NMR (400 MHz, CHLOROFORM-d) δ 8.38 (s, 1H), 7.95 (br d, J=9.2 Hz, 1H), 7.88 (br d, J=7.6 Hz, 2H), 7.72 (d, J=8.9 Hz, 1H), 7.57-7.44 (m, 3H), 7.36 (br s, 1H), 4.58-4.40 (m, 3H), 4.33 (br d, J=3.5 Hz, 2H), 3.94 (br d, J=13.6 Hz, 1H), 3.43-3.32 (m, 2H), 3.19 (br t, J=11.1 Hz, 1H), 2.70 (s, 3H), 2.33-2.23 (m, 2H), 2.13-1.99 (m, 2H), 1.60 (t, J=7.2 Hz, 3H); LCMS (ESI) [M+H]+: 473.2.

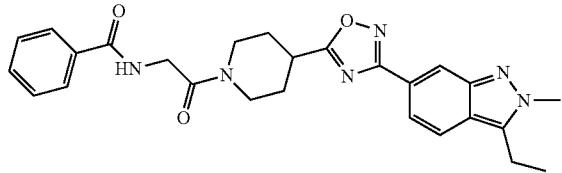 [SMILES: CCc1c2ccc(-c3noc(C4CCN(C(=O)CNC(=O)c5ccccc5)CC4)n3)cc2nn1C]

¹H NMR (400 MHz, CHLOROFORM-d) δ 8.43 (s, 1H), 7.88 (br d, J=7.7 Hz, 2H), 7.71 (s, 2H), 7.57-7.51 (m, 1H), 7.51-7.45 (m, 2H), 7.36 (br s, 1H), 4.51 (br d, J=13.8 Hz, 1H), 4.33 (br d, J=2.3 Hz, 2H), 4.18 (s, 3H), 3.94 (br d, J=13.9 Hz, 1H), 3.42-3.33 (m, 2H), 3.21 (br t, J=10.7 Hz, 1H), 3.13-3.07 (m, 2H), 2.34-2.24 (m, 2H), 2.12-2.00 (m, 2H), 1.40 (t, J=7.6 Hz, 3H); LCMS (ESI) [M+H]+: 473.2.

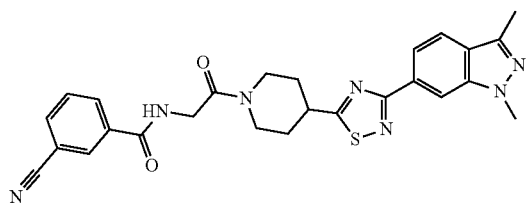 [SMILES: Cc1nn(C)c2cc(-c3nsc(C4CCN(C(=O)CNC(=O)c5cccc(C#N)c5)CC4)n3)ccc12]

¹H NMR (400 MHz, CHLOROFORM-d) δ 8.22 (s, 1H), 8.18 (s, 1H), 8.11-8.00 (m, 2H), 7.81 (d, J=7.6 Hz, 1H), 7.73 (d, J=8.4 Hz, 1H), 7.60 (t, J=7.6 Hz, 1H), 7.42 (br s, 1H), 4.90 (br d, J=13.2 Hz, 1H), 4.43-4.22 (m, 2H), 4.10 (s, 3H), 3.97 (d, J=14.0 Hz, 1H), 3.60-3.46 (m, 1H), 3.37 (t, J=12.0 Hz, 1H), 3.06 (t, J=11.6 Hz, 1H), 2.61 (s, 3H), 2.37 (t, J=11.6 Hz, 2H), 2.05-1.86 (m, 2H); LCMS (ESI) [M+H]+: 500.2.

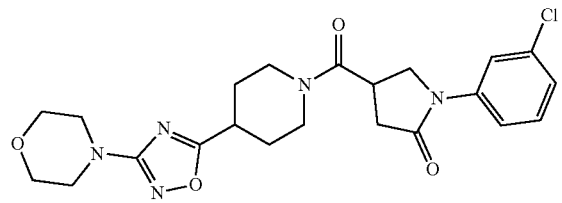 [SMILES: O=C(C1CC(=O)N(c2cccc(Cl)c2)C1)N1CCC(c2nc(N3CCOCC3)no2)CC1]

¹H NMR (400 MHz, CHLOROFORM-d) δ 7.67 (br s, 1H), 7.53 (br t, J=6.0 Hz, 1H), 7.30 (t, J=8.2 Hz, 1H), 7.15 (br d, J=7.9 Hz, 1H), 4.56-4.38 (m, 1H), 4.28 (dd, J=7.1, 9.5 Hz, 1H), 4.01-3.86 (m, 2H), 3.84-3.76 (m, 4H), 3.60-3.52 (m, 1H), 3.44 (br t, J=4.3 Hz, 4H), 3.39-3.28 (m, 1H), 3.20-2.90 (m, 3H), 2.89-2.78 (m, 1H), 2.23-2.08 (m, 2H), 1.96-1.77 (m, 2H); LCMS (ESI) [M+H]+: 460.2.

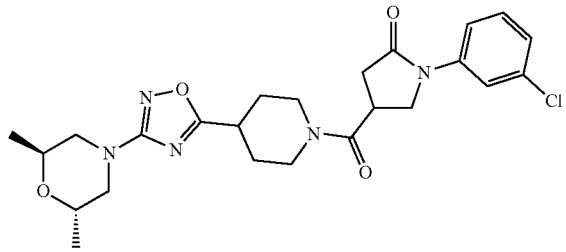 [SMILES: C[C@H]1CN(c2noc(C3CCN(C(=O)C4CC(=O)N(c5cccc(Cl)c5)C4)CC3)n2)C[C@H](C)O1]

¹H NMR (400 MHz, CHLOROFORM-d) δ 7.67 (s, 1H), 7.56-7.49 (m, 1H), 7.30 (t, J=8.2 Hz, 1H), 7.15 (d, J=8.2 Hz, 1H), 4.56-4.41 (m, 1H), 4.28 (dd, J=7.1, 9.5 Hz, 1H), 4.19-4.03 (m, 2H), 3.91 (br t, J=7.9 Hz, 2H), 3.63-3.46 (m, 3H), 3.40-3.27 (m, 1H), 3.21-2.90 (m, 5H), 2.89-2.76 (m, 1H), 2.15 (br t, J=13.2 Hz, 2H), 1.96-1.77 (m, 2H), 1.27 (d, J=6.4 Hz, 6H); LCMS (ESI) [M+H]+: 488.1.

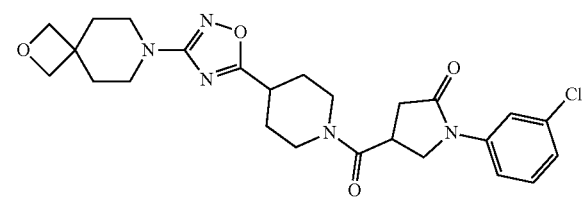 [SMILES: O=C(C1CC(=O)N(c2cccc(Cl)c2)C1)N1CCC(c2nc(N3CCC4(CC3)COC4)no2)CC1]

¹H NMR (400 MHz, CHLOROFORM-d) δ 7.67 (br s, 1H), 7.53 (br d, J=6.0 Hz, 1H), 7.30 (t, J=8.2 Hz, 1H), 7.15 (br d, J=7.1 Hz, 1H), 4.48 (s, 5H), 4.28 (dd, J=7.1, 9.5 Hz, 1H), 3.91 (br t, J=7.9 Hz, 2H), 3.56 (quin, J=8.3 Hz, 1H), 3.43-3.28 (m, 5H), 3.18-2.89 (m, 3H), 2.87-2.77 (m, 1H), 2.20-2.07 (m, 2H), 1.98-1.92 (m, 4H), 1.91-1.76 (m, 2H); LCMS (ESI) [M+H]+: 500.2.

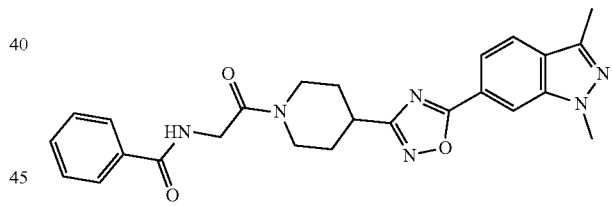

¹H NMR (400 MHz, CHLOROFORM-d) δ 8.15 (s, 1H), 7.89-7.82 (m, 3H), 7.80-7.75 (m, 1H), 7.55-7.49 (m, 1H), 7.48-7.42 (m, 2H), 7.36 (br s, 1H), 4.57 (br d, J=13.8 Hz, 1H), 4.31 (d, J=3.8 Hz, 2H), 4.09 (s, 3H), 3.92 (br d, J=13.9 Hz, 1H), 3.37-3.28 (m, 1H), 3.26-3.17 (m, 1H), 3.13-3.04 (m, 1H), 2.60 (s, 3H), 2.26-2.15 (m, 2H), 2.05-1.90 (m, 2H); LCMS (ESI) [M+H]+: 459.1.

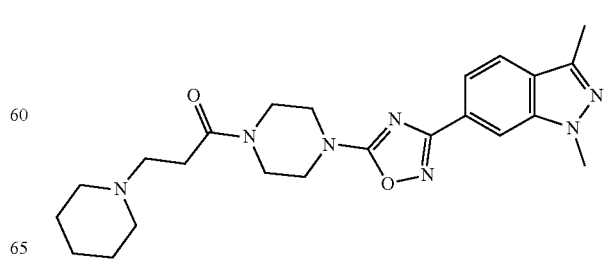

¹H NMR (400 MHz, CHLOROFORM-d) δ 8.11 (s, 1H), 7.89-7.84 (m, 1H), 7.79-7.75 (m, 1H), 4.20 (s, 3H), 3.81-3.73 (m, 4H), 3.44-3.36 (m, 4H), 3.27 (br s, 4H), 2.71 (s, 3H); LCMS (ESI) [M+H]+: 410.2.

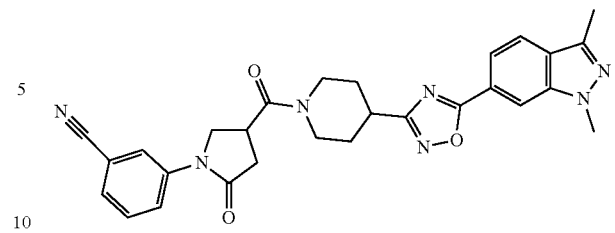

¹H NMR (400 MHz, CHLOROFORM-d) δ 8.18 (d, J=4.3 Hz, 1H), 8.00 (br d, J=4.6 Hz, 1H), 7.94 (br t, J=7.6 Hz, 1H), 7.89-7.84 (d, 1H), 7.83-7.77 (d, 1H), 7.54-7.43 (m, 2H), 4.61 (m, 1H), 4.35 (m, 1H), 4.12 (d, J=1.7 Hz, 3H), 4.05-3.92 (m, 2H), 3.65 (m, 1H), 3.47-3.34 (m, 1H), 3.31-3.19 (m, 1H), 3.16-2.86 (m, 3H), 2.63 (s, 3H), 2.31-2.16 (m, 2H), 2.09-1.89 (m, 2H); LCMS (ESI) [M+H]+: 510.2.

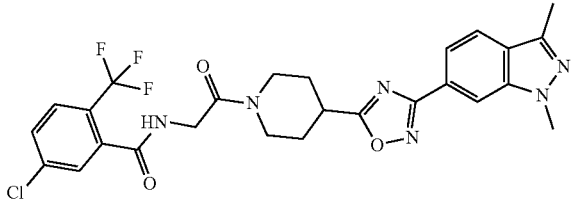 [SMILES: Cc1nn(C)c2cc(-c3noc(C4CCN(C(=O)CNC(=O)c5cc(Cl)ccc5C(F)(F)F)CC4)n3)ccc12]

¹H NMR (400 MHz, CHLOROFORM-d) δ 8.02 (s, 1H), 7.76 (d, J=8.3 Hz, 1H), 7.70-7.65 (m, 1H), 7.59 (d, J=8.4 Hz, 1H), 7.54-7.42 (m, 2H), 6.97 (br s, 1H), 4.42 (br d, J=13.6 Hz, 1H), 4.23 (d, J=3.9 Hz, 2H), 4.01 (s, 3H), 3.81 (br d, J=14.2 Hz, 1H), 3.34-3.23 (m, 2H), 3.09 (br t, J=11.1 Hz, 1H), 2.53 (s, 3H), 2.21 (br t, J=13.4 Hz, 2H), 2.05-1.91 (m, 2H); LCMS (ESI) [M+H]+: 561.1.

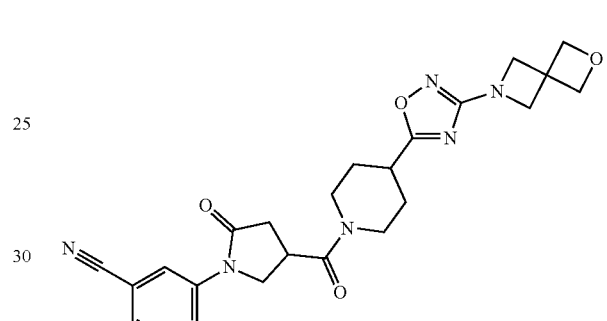

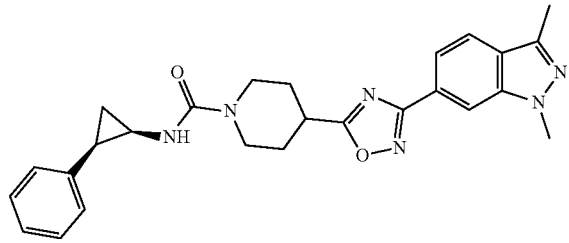 [SMILES: Cc1nn(C)c2cc(-c3noc(C4CCN(C(=O)N[C@@H]5C[C@@H]5c5ccccc5)CC4)n3)ccc12]

¹H NMR (400 MHz, CHLOROFORM-d) δ 7.96 (br d, J=10.6 Hz, 1H), 7.90 (br t, J=9.0 Hz, 1H), 7.52-7.41 (m, 2H), 4.83 (s, 4H), 4.47 (br t, J=14.4 Hz, 1H), 4.35-4.27 (m, 1H), 4.22 (s, 4H), 3.99-3.84 (m, 2H), 3.58 (quin, J=8.2 Hz, 1H), 3.40-3.26 (m, 1H), 3.19-2.82 (m, 4H), 2.14 (br t, J=14.0 Hz, 2H), 1.96-1.72 (m, 2H); LCMS (ESI) [M+H]+: 463.2.

¹H NMR (400 MHz, CHLOROFORM-d) δ 8.17-7.97 (m, 1H), 7.87-7.77 (m, 1H), 7.75-7.66 (m, 1H), 7.24 (br d, J=6.6 Hz, 2H), 7.20-7.12 (m, 3H), 4.89 (s, 1H), 4.06 (s, 3H), 3.99 (br d, J=13.5 Hz, 2H), 3.21 (br t, J=10.8 Hz, 1H), 3.06 (br t, J=11.5 Hz, 2H), 2.85 (br s, 1H), 2.58 (s, 3H), 2.18 (br d, J=11.5 Hz, 2H), 2.09-1.87 (m, 3H), 1.25-1.20 (m, 1H), 1.17-1.10 (m, 1H); LCMS (ESI) [M+H]+: 457.2.

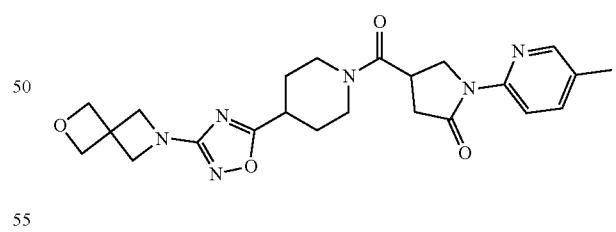

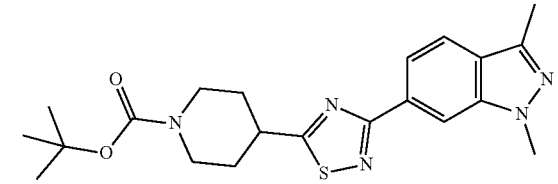 [SMILES: Cc1nn(C)c2cc(-c3nsc(C4CCN(C(=O)OC(C)(C)C)CC4)n3)ccc12]

¹H NMR (400 MHz, CHLOROFORM-d) δ 8.31 (s, 1H), 8.08 (d, J=8.4 Hz, 1H), 7.73 (d, J=8.4 Hz, 1H), 4.26 (br s, 2H), 4.09 (s, 3H), 3.41-3.31 (m, 1H), 2.98 (br t, J=12.0 Hz, 2H), 2.60 (s, 3H), 2.23 (br d, J=12.0 Hz, 2H), 1.85 (dq, J=4.0, 12.0 Hz, 2H), 1.50 (s, 9H); LCMS (ESI) [M+H]+: 414.1.

¹H NMR (400 MHz, CHLOROFORM-d) δ 8.25 (dd, J=3.9, 8.3 Hz, 1H), 8.13 (s, 1H), 7.50 (dd, J=1.8, 8.3 Hz, 1H), 4.82 (s, 4H), 4.52-4.41 (m, 1H), 4.36 (t, J=9.9 Hz, 1H), 4.21 (s, 4H), 4.13 (br t, J=7.7 Hz, 1H), 3.93 (br d, J=13.2 Hz, 1H), 3.51 (quin, J=8.1 Hz, 1H), 3.32 (br t, J=11.2 Hz, 1H), 3.21 (br dd, J=7.5, 17.1 Hz, 1H), 3.14-2.93 (m, 2H), 2.77 (br dd, J=9.2, 18.9 Hz, 1H), 2.29 (s, 3H), 2.18-2.05 (m, 2H), 1.94-1.74 (m, 2H); LCMS (ESI) [M+H]+: 453.2.

651

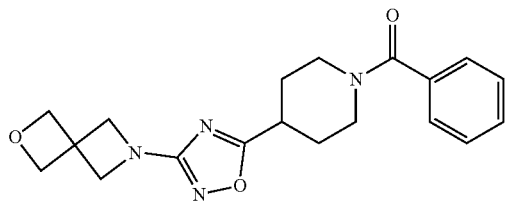 [SMILES: O=C(c1ccccc1)N1CCC(c2nc(N3CC4(COC4)C3)no2)CC1]

¹H NMR (400 MHz, CHLOROFORM-d) δ 7.48-7.36 (m, 5H), 4.83 (s, 4H), 4.74-4.45 (m, 1H), 4.22 (s, 4H), 3.81 (br d, J=15.4 Hz, 1H), 3.27-3.00 (m, 3H), 2.30-1.94 (m, 2H), 1.87 (br s, 2H); LCMS (ESI) [M+H]+: 355.2.

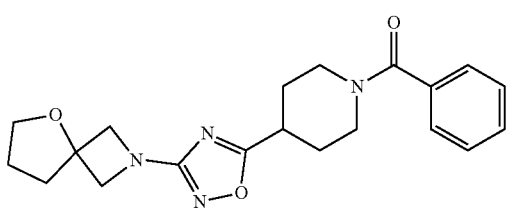 [SMILES: O=C(c1ccccc1)N1CCC(c2nc(N3CC4(CCCO4)C3)no2)CC1]

¹H NMR (400 MHz, CHLOROFORM-d) δ 7.49-7.35 (m, 5H), 4.59 (br s, 1H), 4.13 (d, J=8.6 Hz, 2H), 4.01 (d, J=8.6 Hz, 2H), 3.87 (t, J=6.8 Hz, 2H), 3.84-3.67 (m, 1H), 3.26-3.02 (m, 3H), 2.25-2.11 (m, 3H), 2.02-1.73 (m, 5H); LCMS (ESI) [M+H]+: 369.2.

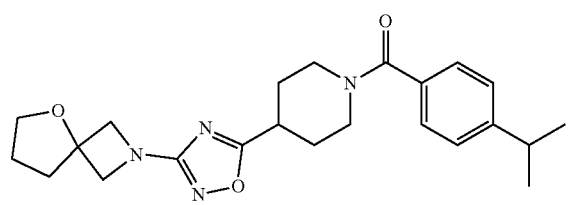 [SMILES: CC(C)c1ccc(C(=O)N2CCC(c3nc(N4CC5(CCCO5)C4)no3)CC2)cc1]

¹H NMR (400 MHz, METHANOL-d₄) δ 7.39-7.29 (m, 4H), 4.52 (br s, 1H), 4.08-3.97 (m, 4H), 3.86 (t, J=6.8 Hz, 3H), 3.23 (tt, J=4.0, 10.8 Hz, 3H), 2.96 (td, J=6.9, 13.8 Hz, 1H), 2.25-2.02 (m, 4H), 1.95 (quin, J=7.1 Hz, 2H), 1.81 (br s, 2H), 1.27 (d, J=6.8 Hz, 6H); LCMS (ESI) [M+H]+: 411.2.

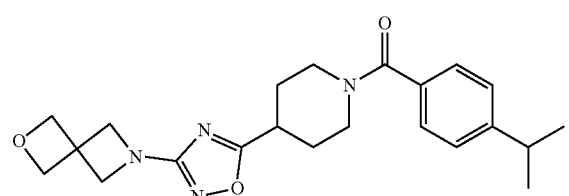

¹H NMR (400 MHz, CHLOROFORM-d) δ 7.38-7.31 (m, 2H), 7.27-7.24 (m, 2H), 4.83 (s, 4H), 4.71-4.40 (m, 1H), 4.22 (s, 4H), 4.09-3.68 (m, 1H), 3.31-3.03 (m, 3H), 2.94 (spt, J=6.9 Hz, 1H), 2.06 (br d, J=7.1 Hz, 2H), 1.88 (br s, 2H), 1.26 (d, J=7.1 Hz, 6H); LCMS (ESI) [M+H]+: 397.2.

652

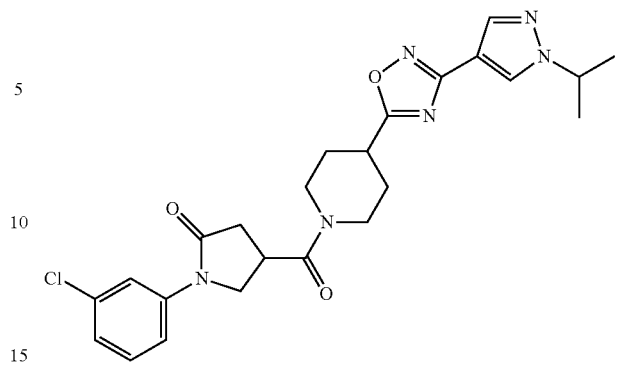

¹H NMR (400 MHz, CHLOROFORM-d) δ 8.05-7.92 (m, 2H), 7.71-7.60 (m, 1H), 7.50 (br t, J=7.4 Hz, 1H), 7.28 (t, J=8.2 Hz, 1H), 7.13 (dd, J=1.0, 8.0 Hz, 1H), 4.64-4.40 (m, 2H), 4.26 (dd, J=7.1, 9.3 Hz, 1H), 4.00-3.85 (m, 2H), 3.60-3.51 (m, 1H), 3.41-3.20 (m, 2H), 3.15-2.99 (m, 1H), 2.99-2.77 (m, 2H), 2.21 (br t, J=13.6 Hz, 2H), 2.02-1.84 (m, 2H), 1.54 (d, J=6.6 Hz, 6H); LCMS (ESI) [M+H]+: 483.1.

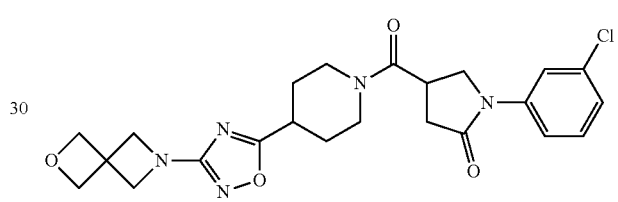

¹H NMR (400 MHz, CHLOROFORM-d) δ 7.68-7.64 (m, 1H), 7.52 (br t, J=6.2 Hz, 1H), 7.30 (t, J=8.2 Hz, 1H), 7.15 (d, J=7.9 Hz, 1H), 4.84 (s, 4H), 4.56-4.39 (m, 1H), 4.30-4.24 (m, 1H), 4.22 (s, 4H), 3.90 (dt, J=3.5, 8.9 Hz, 2H), 3.60-3.51 (m, 1H), 3.40-3.25 (m, 1H), 3.18-2.97 (m, 2H), 2.97-2.88 (m, 1H), 2.87-2.78 (m, 1H), 2.13 (t, J=12 Hz, 2H), 1.96-1.72 (m, 2H); LCMS (ESI) [M+H]+: 472.2.

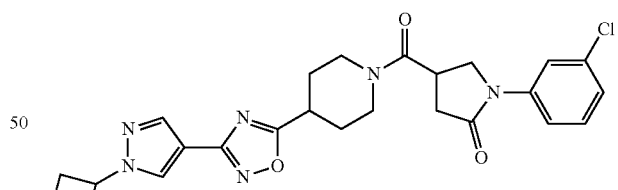

¹H NMR (400 MHz, DMSO-d₆) δ 8.51 (d, J=2.0 Hz, 1H), 8.06 (s, 1H), 7.86-7.80 (m, 1H), 7.55 (br d, J=8.2 Hz, 1H), 7.37 (dt, J=2.3, 8.1 Hz, 1H), 7.17 (br d, J=8.2 Hz, 1H), 5.68-5.61 (m, 1H), 4.96-4.83 (m, 4H), 4.31 (br d, J=12.6 Hz, 1H), 4.08-4.01 (m, 1H), 3.97 (br d, J=13.9 Hz, 1H), 3.91 (dd, J=5.7, 9.7 Hz, 1H), 3.76-3.65 (m, 1H), 3.44-3.34 (m, 1H), 3.29-3.21 (m, 1H), 2.90 (br t, J=13.8 Hz, 1H), 2.79-2.68 (m, 2H), 2.09 (br t, J=14.0 Hz, 2H), 1.87-1.56 (m, 2H); LCMS (ESI) [M+H]+: 497.1.

653

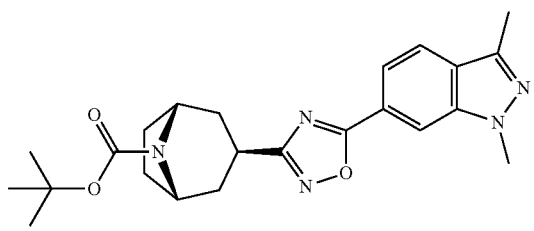 [SMILES: Cc1nn(C)c2cc(-c3nc([C@@H]4C[C@H]5CC[C@@H](C4)N5C(=O)OC(C)(C)C)no3)ccc12]

¹H NMR (400 MHz, CHLOROFORM-d) δ 8.10 (t, 1H), 7.79 (m, 2H), 4.38 (m, 2H), 4.09 (s, 3H), 3.59 (m, 1H), 2.61 (s, 3H), 2.06 (m, 5H), 1.81 (d, J=8 Hz, 2H), 1.51 (s, 9H); LCMS (ESI) [M+H]+: 424.

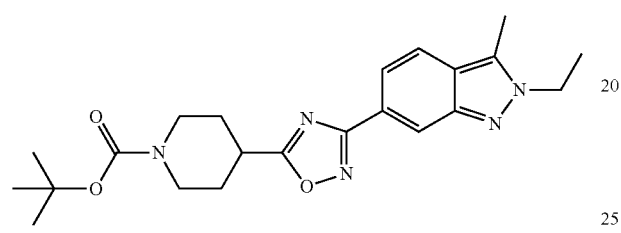

¹H NMR (400 MHz, CHLOROFORM-d) δ 8.29 (s, 1H), 7.86 (dd, J=1.5, 9.0 Hz, 1H), 7.62 (d, J=9.0 Hz, 1H), 4.35 (q, J=7.3 Hz, 2H), 4.06 (br s, 2H), 3.11 (tt, J=3.6, 10.8 Hz, 1H), 2.93 (br t, J=11.7 Hz, 2H), 2.60 (s, 3H), 2.06 (br dd, J=2.7, 13.1 Hz, 2H), 1.90-1.81 (m, 2H), 1.50 (t, J=7.3 Hz, 3H), 1.41 (s, 9H); LCMS (ESI) [M+H]+: 412.2.

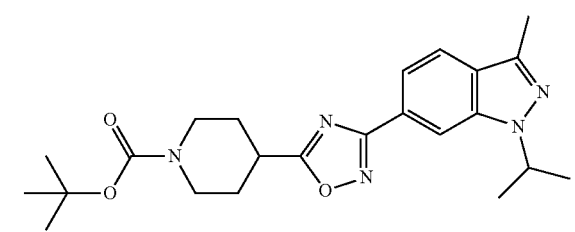 [SMILES: Cc1nn(C(C)C)c2cc(-c3noc(C4CCN(C(=O)OC(C)(C)C)CC4)n3)ccc12]

¹H NMR (400 MHz, CHLOROFORM-d) δ 8.13 (s, 1H), 7.84-7.78 (m, 1H), 7.75-7.69 (m, 1H), 4.88 (m, 1H), 4.16 (br s, 2H), 3.25-3.15 (m, 1H), 3.07-2.94 (m, 2H), 2.60 (s, 3H), 2.20-2.10 (m, 2H), 2.00-1.87 (m, 2H), 1.59 (d, J=6.6 Hz, 6H), 1.48 (s, 9H); LCMS (ESI) [M+H]+: 426.2.

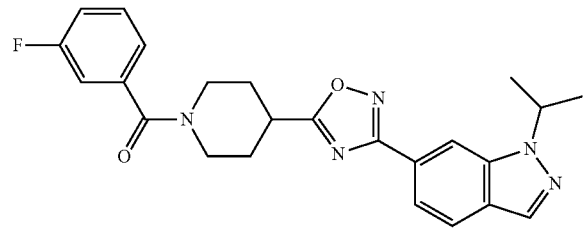 [SMILES: CC(C)n1ncc2ccc(-c3noc(C4CCN(C(=O)c5cccc(F)c5)CC4)n3)cc21]

¹H NMR (400 MHz, CHLOROFORM-d) δ 8.30 (s, 1H), 8.07 (s, 1H), 7.95-7.78 (m, 2H), 7.49-7.36 (m, 1H), 7.25-7.20 (m, 1H), 7.19-7.10 (m, 2H), 5.06-4.89 (m, 1H), 4.86-4.50 (m, 1H), 4.05-3.72 (m, 1H), 3.46-3.32 (m, 1H), 3.30-3.15 (m, 2H), 2.46-1.92 (m, 4H), 1.64 (d, J=6.8 Hz, 6H); LCMS (ESI) [M+H]+: 434.2.

654

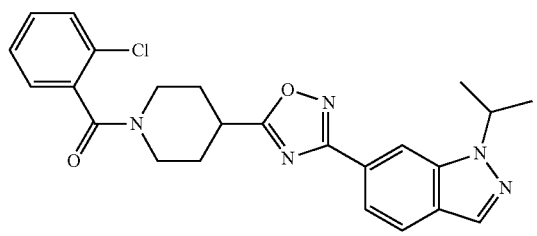 [SMILES: CC(C)n1ncc2ccc(-c3noc(C4CCN(C(=O)c5ccccc5Cl)CC4)n3)cc21]

¹H NMR (400 MHz, CHLOROFORM-d) δ 8.21 (s, 1H), 8.07 (s, 1H), 7.90-7.74 (m, 2H), 7.49-7.27 (m, 4H), 5.09-4.98 (m, 1H), 4.82-4.68 (m, 1H), 3.70-3.52 (m, 1H), 3.44-3.10 (m, 3H), 2.43-2.27 (m, 1H), 2.22-1.81 (m, 3H), 1.64 (d, J=6.4 Hz, 6H); LCMS (ESI) [M+H]+: 450.2.

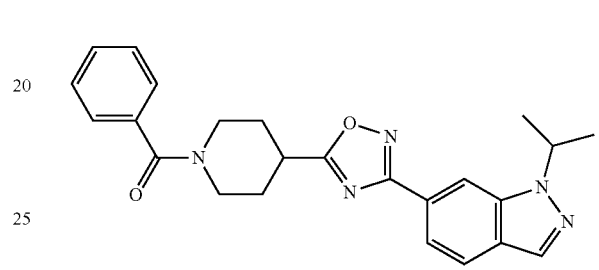

¹H NMR (400 MHz, CHLOROFORM-d) δ 8.22 (s, 1H), 8.07 (s, 1H), 7.84 (q, J=8.4 Hz, 2H), 7.45 (s, 5H), 5.06-4.90 (m, 1H), 4.77-4.54 (m, 1H), 4.10-3.77 (m, 1H), 3.45-3.30 (m, 1H), 3.30-3.07 (m, 2H), 2.45-1.93 (m, 4H), 1.64 (d, J=6.8 Hz, 6H); LCMS (ESI) [M+H]+: 416.2.

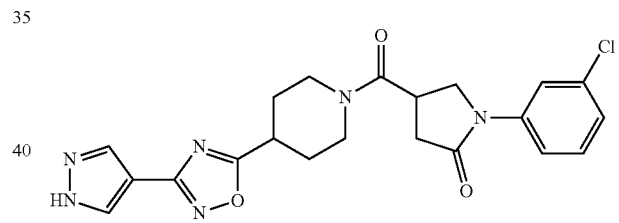

¹H NMR (400 MHz, CHLOROFORM-d) δ 11.23-10.26 (m, 1H), 8.16 (s, 2H), 7.72-7.63 (m, 1H), 7.53 (br t, J=7.3 Hz, 1H), 7.31 (t, J=8.1 Hz, 1H), 7.15 (d, J=7.9 Hz, 1H), 4.66-4.44 (m, 1H), 4.35-4.23 (m, 1H), 4.02-3.89 (m, 2H), 3.63-3.54 (m, 1H), 3.44-3.26 (m, 2H), 3.21-2.77 (m, 3H), 2.24 (br t, J=13.5 Hz, 2H), 2.06-1.87 (m, 2H); LCMS (ESI) [M+H]+: 441.1.

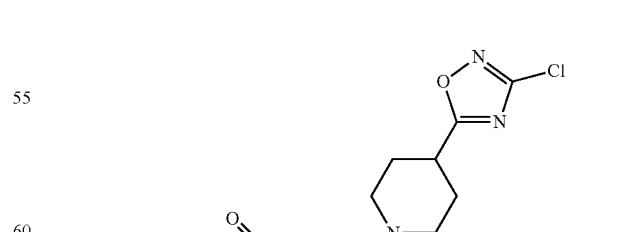

¹H NMR (400 MHz, CHLOROFORM-d) δ 7.67 (br d, J=10.1 Hz, 1H), 7.52 (br t, J=8.7 Hz, 1H), 7.30 (t, J=8.2 Hz, 1H), 7.15 (br d, J=7.9 Hz, 1H), 4.50 (br dd, J=14.2, 18.4 Hz, 1H), 4.34-4.18 (m, 1H), 4.04-3.85 (m, 2H), 3.60-3.52 (m, 1H), 3.44-3.22 (m, 2H), 3.16-3.00 (m, 1H), 3.00-2.77 (m, 2H), 2.31-2.13 (m, 2H), 2.03-1.79 (m, 2H); LCMS (ESI) [M+H]+: 409.0.

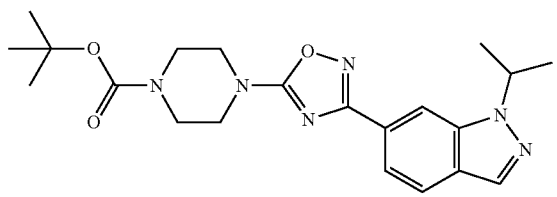 [SMILES: CC(C)n1ncc2ccc(-c3noc(N4CCN(C(=O)OC(C)(C)C)CC4)n3)cc21]

¹H NMR (400 MHz, CHLOROFORM-d) δ 8.12 (s, 1H), 8.03 (s, 1H), 7.77 (s, 2H), 4.94 (spt, J=6.6 Hz, 1H), 3.70 (br d, J=5.1 Hz, 4H), 3.62-3.55 (m, 4H), 1.61 (d, J=6.8 Hz, 6H), 1.49 (s, 9H); LCMS (ESI) [M+H]+: 413.2.

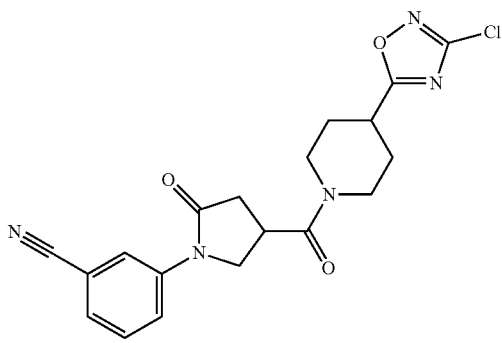 [SMILES: N#Cc1cccc(N2CC(C(=O)N3CCC(c4nc(Cl)no4)CC3)CC2=O)c1]

¹H NMR (400 MHz, CHLOROFORM-d) δ 8.03-7.94 (m, 1H), 7.89 (br dd, J=8.2, 19.2 Hz, 1H), 7.54-7.41 (m, 2H), 4.50 (br t, J=14.3 Hz, 1H), 4.36-4.24 (m, 1H), 4.02-3.87 (m, 2H), 3.60 (s, J=8.2 Hz, 1H), 3.46-3.24 (m, 2H), 3.18-3.01 (m, 1H), 3.00-2.82 (m, 2H), 2.22 (br t, J=14.0 Hz, 2H), 2.03-1.79 (m, 2H); LCMS (ESI) [M+H]+: 400.1.

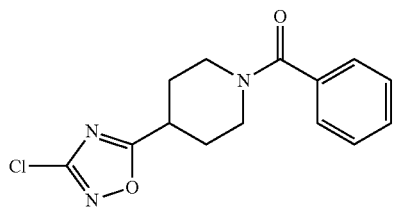 [SMILES: O=C(c1ccccc1)N1CCC(c2nc(Cl)no2)CC1]

¹H NMR (400 MHz, CHLOROFORM-d) δ 7.49-7.34 (m, 5H), 4.61 (br s, 1H), 3.86 (br s, 1H), 3.31-3.10 (m, 3H), 2.27-1.92 (m, 4H); LCMS (ESI) [M+H]+: 292.1.

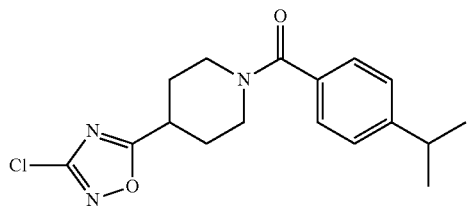 [SMILES: CC(C)c1ccc(C(=O)N2CCC(c3nc(Cl)no3)CC2)cc1]

¹H NMR (400 MHz, CHLOROFORM-d) δ 7.38-7.32 (m, 2H), 7.29-7.25 (m, 2H), 4.60 (br s, 1H), 3.94 (br s, 1H), 3.35-3.08 (m, 3H), 2.94 (spt, J=6.8 Hz, 1H), 2.15 (br s, 2H), 1.93 (br s, 2H), 1.26 (d, J=7.1 Hz, 6H); LCMS (ESI) [M+H]+: 334.2.

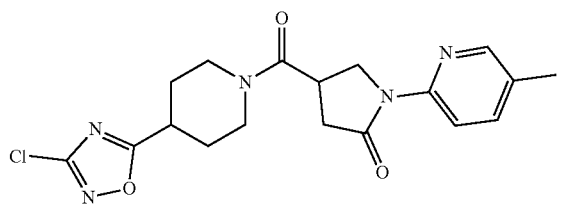 [SMILES: Cc1ccc(N2CC(C(=O)N3CCC(c4nc(Cl)no4)CC3)CC2=O)nc1]

¹H NMR (400 MHz, CHLOROFORM-d) δ 8.26 (t, J=8.6 Hz, 1H), 8.14 (br s, 1H), 7.51 (br d, J=7.9 Hz, 1H), 4.50 (br s, 1H), 4.38 (br t, J=10.1 Hz, 1H), 4.13 (dd, J=7.2, 11.2 Hz, 1H), 3.98 (br d, J=13.6 Hz, 1H), 3.57-3.48 (m, 1H), 3.37 (br t, J=11.8 Hz, 1H), 3.31-3.17 (m, 2H), 3.09-2.98 (m, 1H), 2.78 (dd, J=9.2, 17.1 Hz, 1H), 2.30 (s, 3H), 2.18 (br d, J=14.0 Hz, 2H), 1.99-1.83 (m, 2H); LCMS (ESI) [M+H]+: 390.3.

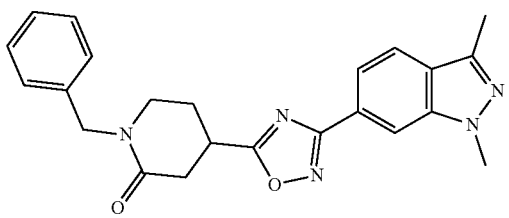 [SMILES: Cc1nn(C)c2cc(-c3noc(C4CCN(Cc5ccccc5)C(=O)C4)n3)ccc12]

¹H NMR (400 MHz, CHLOROFORM-d) δ 8.12 (s, 1H), 7.86-7.82 (d, J=1.2 Hz, 1H), 7.78-7.74 (d, J=8.4 Hz, 1H), 7.34-7.27 (m, 5H), 4.86 (d, J=14.7 Hz, 1H), 4.52 (d, J=14.7 Hz, 1H), 4.10 (s, 3H), 3.63 (tdd, J=3.6, 7.3, 13.5 Hz, 1H), 3.40-3.34 (m, 2H), 3.05 (d, J=7.5 Hz, 2H), 2.62 (s, 3H), 2.45-2.36 (m, 1H), 2.29-2.19 (m, 1H); LCMS (ESI) [M+H]+: 402.2.

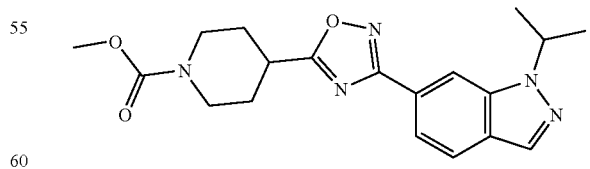

¹H NMR (400 MHz, CHLOROFORM-d) δ 8.20 (s, 1H), 8.05 (s, 1H), 7.90-7.75 (m, 2H), 4.95 (spt, J=6.6 Hz, 1H), 4.18 (br s, 2H), 3.72 (s, 3H), 3.22 (tt, J=3.9, 10.7 Hz, 1H), 3.08 (br t, J=11.7 Hz, 2H), 2.16 (br d, J=11.0 Hz, 2H), 2.03-1.86 (m, 2H), 1.62 (d, J=6.6 Hz, 6H); LCMS (ESI) [M+H]+: 370.2.

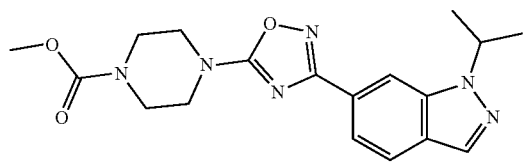 [SMILES: COC(=O)N1CCN(c2nc(-c3ccc4cnn(C(C)C)c4c3)no2)CC1]

¹H NMR (400 MHz, CHLOROFORM-d) δ 8.12 (s, 1H), 8.03 (s, 1H), 7.77 (s, 2H), 4.94 (spt, J=6.6 Hz, 1H), 3.76 (s, 3H), 3.72 (br s, 4H), 3.65 (br s, 4H), 1.61 (d, J=6.6 Hz, 6H); LCMS (ESI) [M+H]+: 371.2.

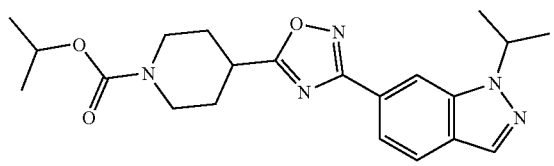 [SMILES: CC(C)OC(=O)N1CCC(c2nc(-c3ccc4cnn(C(C)C)c4c3)no2)CC1]

¹H NMR (400 MHz, CHLOROFORM-d) δ 8.21 (s, 1H), 8.06 (s, 1H), 7.83 (q, J=8.4 Hz, 2H), 5.07-4.87 (m, 2H), 4.20 (br s, 2H), 3.23 (tt, J=4.0, 10.8 Hz, 1H), 3.06 (br t, J=11.6 Hz, 2H), 2.25-2.09 (m, 2H), 2.05-1.87 (m, 2H), 1.64 (d, J=6.8 Hz, 6H), 1.28 (d, J=6.0 Hz, 6H); LCMS (ESI) [M+H]+: 398.2.

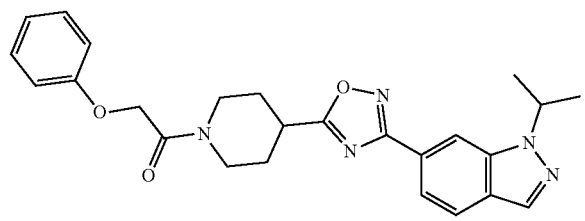 [SMILES: CC(C)n1ncc2ccc(-c3noc(C4CCN(C(=O)COc5ccccc5)CC4)n3)cc21]

¹H NMR (400 MHz, CHLOROFORM-d) δ 8.21 (s, 1H), 8.07 (s, 1H), 7.93-7.77 (m, 2H), 7.32 (br t, J=7.2 Hz, 2H), 7.09-6.92 (m, 3H), 5.09-4.90 (m, 1H), 4.74 (s, 2H), 4.49 (br d, J=13.6 Hz, 1H), 4.13 (br d, J=13.6 Hz, 1H), 3.57-3.25 (m, 2H), 3.10 (br t, J=11.6 Hz, 1H), 2.35-2.17 (m, 2H), 2.12-1.87 (m, 2H), 1.64 (d, J=5.6 Hz, J=6H); LCMS (ESI) [M+H]+: 446.2.

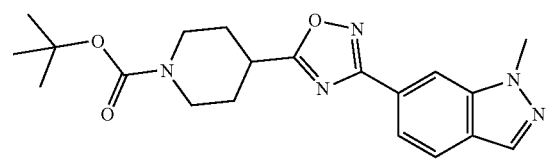 [SMILES: Cn1ncc2ccc(-c3noc(C4CCN(C(=O)OC(C)(C)C)CC4)n3)cc21]

¹H NMR (400 MHz, CHLOROFORM-d) δ 8.18 (s, 1H), 8.04 (s, 1H), 7.88 (d, J=8.4 Hz, 1H), 7.82 (d, J=8.4 Hz, 1H), 4.26-4.08 (m, 5H), 3.27-3.16 (m, 1H), 3.03 (br t, J=11.6 Hz, 2H), 2.16 (br d, J=10.0 Hz, 2H), 2.03-1.87 (m, 2H), 1.49 (s, 9H); LCMS (ESI) [M+H]+: 384.2.

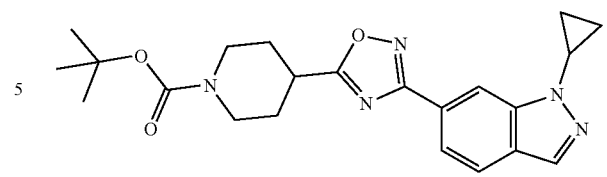

¹H NMR (400 MHz, CHLOROFORM-d) δ 8.34 (s, 1H), 7.98 (s, 1H), 7.92-7.84 (m, 1H), 7.83-7.75 (m, 1H), 4.24-4.07 (m, 2H), 3.72-3.62 (m, 1H), 3.27-3.15 (m, 1H), 3.09-2.93 (m, 2H), 2.16 (br d, J=11.0 Hz, 2H), 2.01-1.87 (m, 2H), 1.48 (s, 9H); LCMS (ESI) [M+H]+: 410.2.

¹H NMR (400 MHz, CHLOROFORM-d) δ 8.20 (s, 1H), 8.05 (s, 1H), 7.82 (q, J=8.5 Hz, 2H), 4.96 (spt, J=6.7 Hz, 1H), 4.16 (q, J=7.2 Hz, 4H), 3.22 (tt, J=3.9, 10.8 Hz, 1H), 3.07 (br t, J=11.7 Hz, 2H), 2.22-2.11 (m, 2H), 2.02-1.89 (m, 2H), 1.62 (d, J=6.6 Hz, 6H), 1.28 (t, J=7.2 Hz, 3H); LCMS (ESI) [M+H]+: 384.2.

¹H NMR (400 MHz, DMSO-d₆) δ 8.17 (s, 1H), 8.12 (s, 1H), 7.86 (d, J=8.4 Hz, 1H), 7.67 (dd, J=1.0, 8.5 Hz, 1H), 7.53-7.41 (m, 4H), 5.06 (quin, J=6.5 Hz, 1H), 3.78-3.62 (m, 8H), 1.53 (d, J=6.6 Hz, 6H); LCMS (ESI) [M+H]+: 417.1.

¹H NMR (400 MHz, CHLOROFORM-d) δ 8.23 (s, 1H), 8.09 (s, 1H), 7.91-7.81 (m, 2H), 7.47-7.39 (m, 4H), 5.07-4.92 (m, 1H), 4.65 (br s, 1H), 3.89 (br s, 1H), 3.44-3.15 (m, 3H), 2.40-1.94 (m, 4H), 1.65 (d, J=6.7 Hz, 6H); LCMS (ESI) [M+H]+: 450.2.

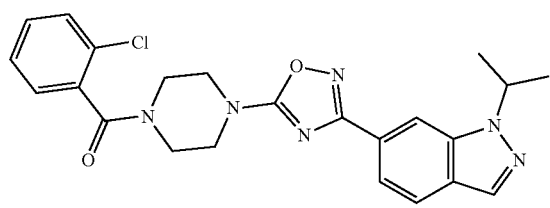 [SMILES: CC(C)n1ncc2ccc(-c3noc(N4CCN(C(=O)c5ccccc5Cl)CC4)n3)cc21]

$^1$H NMR (400 MHz, CHLOROFORM-d) δ 8.11 (s, 1H), 8.04 (s, 1H), 7.77 (s, 2H), 7.47-7.30 (m, 4H), 5.01-4.86 (m, 1H), 4.16-4.07 (m, 1H), 3.95-3.64 (m, 5H), 3.52-3.31 (m, 2H), 1.61 (d, J=6.8 Hz, 6H); LCMS (ESI) [M+H]+: 451.0.

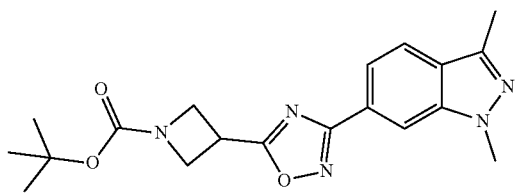 [SMILES: Cc1nn(C)c2cc(-c3noc(C4CN(C(=O)OC(C)(C)C)C4)n3)ccc12]

$^1$H NMR (400 MHz, CHLOROFORM-d) δ 8.13 (s, 1H), 7.89-7.81 (d, J=8.4 Hz, 1H), 7.78-7.69 (d, J=8.4 Hz, 1H), 4.48-4.33 (m, 4H), 4.15-4.02 (m, 4H), 2.61 (s, 3H), 1.49 (s, 9H); LCMS (ESI) [M+H]+: 370.1.

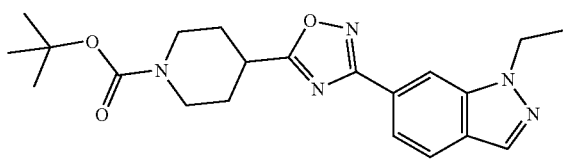 [SMILES: CCn1ncc2ccc(-c3noc(C4CCN(C(=O)OC(C)(C)C)CC4)n3)cc21]

$^1$H NMR (400 MHz, CHLOROFORM-d) δ 8.19 (s, 1H), 8.05 (s, 1H), 7.87 (d, J=7.2 Hz, 1H), 7.82 (d, J=8.4 Hz, 1H), 4.52 (q, J=7.2 Hz, 2H), 4.30-4.12 (m, 2H), 3.24-3.18 (m, 1H), 3.01 (t, J=5.6 Hz, 2H), 2.18-2.14 (m, 2H), 1.98-1.92 (m, 2H), 1.57 (t, J=7.2 Hz, 3H), 1.49 (s, 9H); LCMS (ESI) [M+H]+: 398.1.

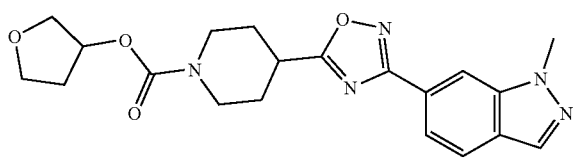 [SMILES: Cn1ncc2ccc(-c3noc(C4CCN(C(=O)OC5CCOC5)CC4)n3)cc21]

$^1$H NMR (400 MHz, CHLOROFORM-d) δ 8.17 (s, 1H), 8.04 (s, 1H), 7.92-7.85 (d, J=8.4 Hz, 1H), 7.84-7.78 (d, J=8.4 Hz, 1H), 5.36-5.26 (m, 1H), 4.36-4.06 (m, 5H), 4.00-3.82 (m, 4H), 3.29-3.18 (m, 1H), 3.16-3.00 (m, 2H), 2.30-2.17 (m, 3H), 2.11-1.88 (m, 3H); LCMS (ESI) [M+H]+: 398.1.

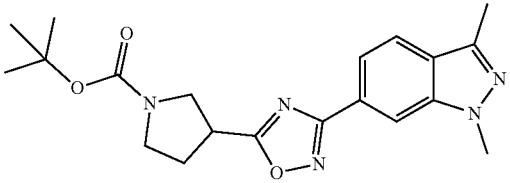 [SMILES: Cc1nn(C)c2cc(-c3noc(C4CCN(C(=O)OC(C)(C)C)C4)n3)ccc12]

$^1$H NMR (400 MHz, CHLOROFORM-d) δ 8.10 (s, 1H), 7.86-7.80 (d, J=8.4 Hz, 1H), 7.78-7.72 (d, J=8.4 Hz, 1H), 4.08 (s, 3H), 3.98-3.46 (m, 5H), 2.60 (s, 3H), 2.50-2.35 (m, 2H), 1.50 (s, 9H); LCMS (ESI) [M+H]+: 384.2.

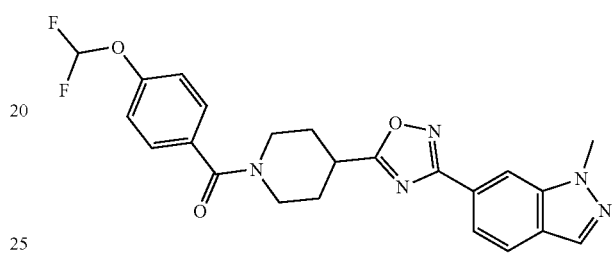

$^1$H NMR (400 MHz, DMSO-d$_6$) δ 8.23 (s, 1H), 8.11 (s, 1H), 7.90 (d, J=8.6 Hz, 1H), 7.75 (d, J=8.4 Hz, 1H), 7.49 (d, J=8.4 Hz, 2H), 7.39 (s, 0.2H), 7.25-7.22 (d, J=8.4 Hz, 2H), 7.22-7.20 (s, 0.6H), 7.03 (s, 0.2H), 4.14-3.93 (m, 5H), 3.54-3.43 (m, 1H), 3.23 (br t, J=11.2 Hz, 2H), 2.17 (br dd, J=2.5, 13.1 Hz, 2H), 1.93-1.82 (m, 2H); LCMS (ESI) [M+H]+: 454.2.

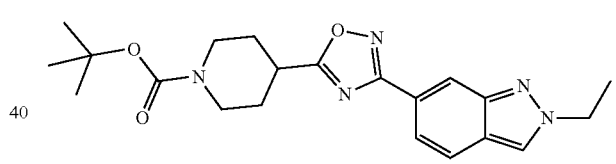

$^1$H NMR (400 MHz, CHLOROFORM-d) δ 8.50 (s, 1H), 7.97 (s, 1H), 7.79-7.71 (m, 2H), 4.51 (q, J=7.6 Hz, 2H), 4.13 (br d, J=8.8 Hz, 2H), 3.19 (tt, J=4.0, 10.8 Hz, 1H), 3.01 (br t, J=11.6 Hz, 2H), 2.14 (br dd, J=2.8, 13.2 Hz, 2H), 2.00-1.86 (m, 2H), 1.66 (t, J=7.6 Hz, 3H), 1.48 (s, 9H); LCMS (ESI) [M+H−56]+: 342.2, LCMS (ESI) [M+23]+: 420.2.

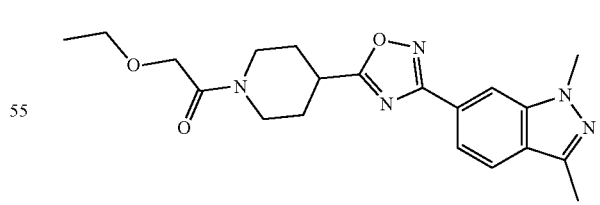

$^1$H NMR (400 MHz, CHLOROFORM-d) δ 8.09 (s, 1H), 7.85-7.80 (d, J=8.4 Hz, 1H), 7.76-7.71 (d, J=8.4 Hz, 1H), 4.51 (br d, J=13.0 Hz, 1H), 4.19 (d, J=6.8 Hz, 2H), 4.08 (s, 4H), 3.64-3.56 (m, 2H), 3.37-3.25 (m, 2H), 3.03 (br t, J=11.5 Hz, 1H), 2.60 (s, 3H), 2.24 (br d, J=12.3 Hz, 2H), 2.07-1.91 (m, 2H), 1.27 (t, J=7.1 Hz, 3H); LCMS (ESI) [M+H]+: 384.2.

661

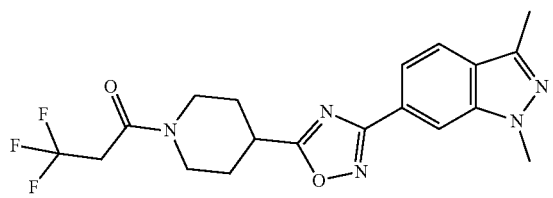 [SMILES: Cc1nn(C)c2cc(-c3noc(C4CCN(C(=O)CC(F)(F)F)CC4)n3)ccc12]

¹H NMR (400 MHz, DMSO-d₆) δ 8.10 (s, 1H), 7.85-7.81 (d, J=8.4 Hz, 1H), 7.77-7.72 (d, J=8.4 Hz, 1H), 4.55 (br d, J=13.5 Hz, 1H), 4.09 (s, 3H), 3.91 (br d, J=14.3 Hz, 1H), 3.46-3.25 (m, 4H), 3.20-3.07 (m, 1H), 2.61 (s, 3H), 2.33-2.21 (m, 2H), 2.11-1.95 (m, 2H); LCMS (ESI) [M+H]+: 408.2.

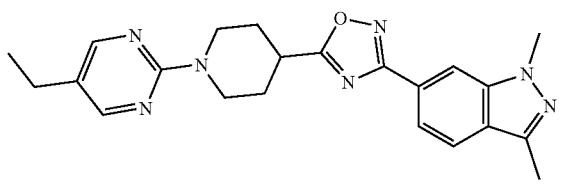 [SMILES: CCc1cnc(N2CCC(c3nc(-c4ccc5c(C)nn(C)c5c4)no3)CC2)nc1]

¹H NMR (400 MHz, CHLOROFORM-d) δ 8.21 (s, 2H), 8.10 (s, 1H), 7.83 (dd, J=1.1, 8.4 Hz, 1H), 7.73 (d, J=8.4 Hz, 1H), 4.76 (td, J=3.5, 13.5 Hz, 2H), 4.07 (s, 3H), 3.32 (tt, J=4.0, 11.0 Hz, 1H), 3.25-3.15 (m, 2H), 2.59 (s, 3H), 2.49 (q, J=7.5 Hz, 2H), 2.25 (br dd, J=3.0, 13.6 Hz, 2H), 2.07-1.95 (m, 2H), 1.21 (t, J=7.6 Hz, 3H); LCMS (ESI) [M+H]+: 404.2.

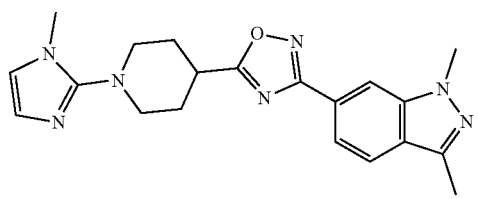 [SMILES: Cc1nn(C)c2cc(-c3noc(C4CCN(c5nccn5C)CC4)n3)ccc12]

¹H NMR (400 MHz, DMSO-d₆) δ 8.18 (s, 1H), 7.86 (d, J=8.4 Hz, 1H), 7.72 (d, J=8.4 Hz, 1H), 6.86 (d, J=1.3 Hz, 1H), 6.59 (d, J=1.3 Hz, 1H), 4.04 (s, 3H), 3.45 (s, 3H), 3.38-3.32 (m, 1H), 3.27-3.24 (m, 2H), 2.92 (br t, J=10.7 Hz, 2H), 2.21-2.12 (m, 2H), 2.08-1.96 (m, 2H); LCMS (ESI) [M+H]+: 378.3.

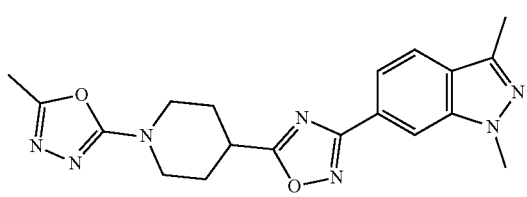 [SMILES: Cc1nnc(N2CCC(c3nc(-c4ccc5c(C)nn(C)c5c4)no3)CC2)o1]

¹H NMR (400 MHz, DMSO-d₆) δ 8.18 (s, 1H), 7.88-7.86 (d, J=8 Hz, 1H), 4.71-4.73 (d, J=8 Hz, 1H), 4.05 (s, 3H), 3.95-9.32 (m, 2H), 3.49-3.53 (m, 1H), 3.32-3.48 (m, 1H), 2.25-2.22 (m, 2H), 1.99-1.96 (m, 2H); LCMS (ESI) [M+H]+: 380.2.

662

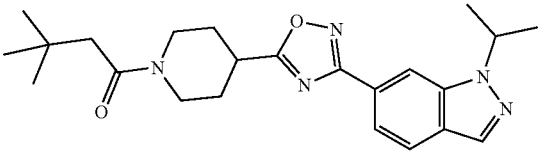 [SMILES: CC(C)n1ncc2ccc(-c3noc(C4CCN(C(=O)CC(C)(C)C)CC4)n3)cc21]

¹H NMR (400 MHz, CHLOROFORM-d) δ 8.20 (s, 1H), 8.05 (s, 1H), 7.82 (q, J=8.5 Hz, 2H), 5.05-4.90 (m, 1H), 4.62 (br d, J=13.7 Hz, 1H), 4.03 (br d, J=13.2 Hz, 1H), 3.36-3.22 (m, 2H), 2.95 (br t, J=11.1 Hz, 1H), 2.31 (s, 2H), 2.21 (br d, J=10.8 Hz, 2H), 2.07-1.86 (m, 2H), 1.62 (d, J=6.6 Hz, 6H), 1.08 (s, 9H); LCMS (ESI) [M+H]+: 410.1.

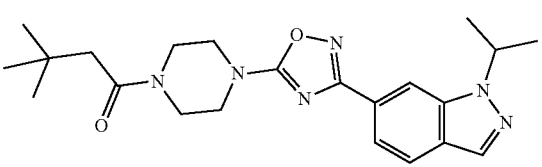 [SMILES: CC(C)n1ncc2ccc(-c3noc(N4CCN(C(=O)CC(C)(C)C)CC4)n3)cc21]

¹H NMR (400 MHz, CHLOROFORM-d) δ 8.06 (s, 1H), 7.98 (s, 1H), 7.70 (s, 2H), 4.88 (spt, J=6.6 Hz, 1H), 3.75 (br d, J=4.8 Hz, 2H), 3.67 (br d, J=4.9 Hz, 4H), 3.62 (br d, J=5.3 Hz, 2H), 2.26 (s, 2H), 1.55 (d, J=6.7 Hz, 6H), 1.02 (s, 9H); LCMS (ESI) [M+H]+: 411.2.

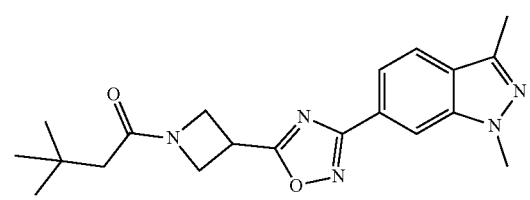 [SMILES: Cc1nn(C)c2cc(-c3noc(C4CN(C(=O)CC(C)(C)C)C4)n3)ccc12]

¹H NMR (400 MHz, CHLOROFORM-d) δ 8.12 (s, 1H), 7.87-7.81 (d, J=8.4 Hz, 1H), 7.78-7.72 (d, J=8.4 Hz, 1H), 4.65-4.40 (m, 4H), 4.17-4.11 (m, 1H), 4.09 (s, 3H), 2.61 (s, 3H), 2.06 (s, 2H), 1.09 (s, 9H); LCMS (ESI) [M+H]+: 368.2.

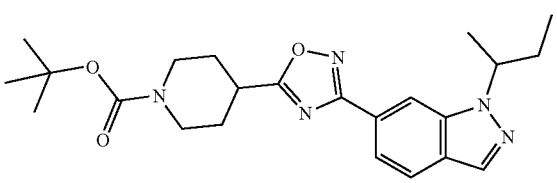 [SMILES: CCC(C)n1ncc2ccc(-c3noc(C4CCN(C(=O)OC(C)(C)C)CC4)n3)cc21]

¹H NMR (400 MHz, CHLOROFORM-d) δ 8.19 (s, 1H), 8.07 (s, 1H), 7.83 (q, J=8.4 Hz, 2H), 4.72-4.62 (m, 1H), 4.16 (br s, 2H), 3.25-3.16 (m, 1H), 3.01 (br t, J=11.7 Hz, 2H), 2.20-2.08 (m, 3H), 2.00-1.87 (m, 3H), 1.60 (d, J=6.6 Hz, 3H), 1.48 (s, 9H), 0.80 (t, J=7.4 Hz, 3H); LCMS (ESI) [M+H]+: 426.2.

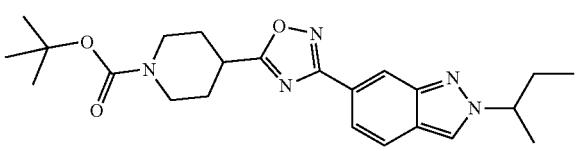 [SMILES: CCC(C)n1cc2ccc(-c3noc(C4CCN(C(=O)OC(C)(C)C)CC4)n3)cc2n1]

¹H NMR (400 MHz, CHLOROFORM-d) δ 8.53 (s, 1H), 7.96 (s, 1H), 7.77-7.70 (m, 2H), 4.54 (qd, J=6.9, 14.0 Hz, 1H), 4.10 (br s, 2H), 3.22-3.13 (m, 1H), 3.02 (br t, J=11.4 Hz, 2H), 2.17-2.04 (m, 3H), 2.00-1.85 (m, 3H), 1.66 (d, J=6.8 Hz, 3H), 1.48 (s, 9H), 0.84 (t, J=7.4 Hz, 3H); LCMS (ESI) [M+H]+: 426.2, LCMS (ESI) [M−55]+: 370.1.

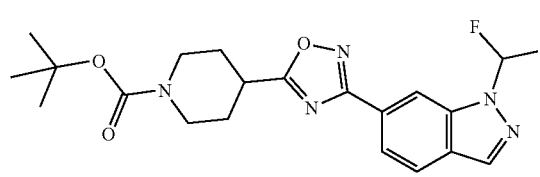

¹H NMR (400 MHz, CHLOROFORM-d) δ 8.51 (s, 1H), 8.15 (s, 1H), 8.04 (d, J=8.6 Hz, 1H), 7.87 (d, J=8.4 Hz, 1H), 7.66 (s, 0.2H), 7.51 (s, 0.5H), 7.36 (s, 0.3H), 4.15 (br s, 2H), 3.26-3.16 (m, 1H), 3.01 (br t, J=12.8 Hz, 2H), 2.15 (br d, J=10.4 Hz, 2H), 1.99-1.87 (m, 2H), 1.49 (s, 9H); LCMS (ESI) [M+H]+: 420.2, LCMS (ESI) [M+23]+: 442.1, LCMS (ESI) [M−100+23]+: 342.0.

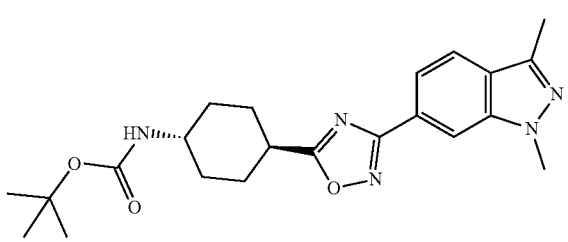 [SMILES: Cc1nn(C)c2cc(-c3noc([C@H]4CC[C@H](NC(=O)OC(C)(C)C)CC4)n3)ccc12]

¹H NMR (400 MHz, CHLOROFORM-d) δ 8.08 (s, 1H), 7.82-7.80 (d, J=8.4 Hz, 1H), 7.76-7.69 (d, J=8.4 Hz, 1H), 4.57-4.37 (m, 1H), 4.07 (s, 3H), 3.65-3.47 (m, 1H), 3.04-2.87 (m, 1H), 2.59 (s, 3H), 2.36-2.14 (m, 4H), 1.82 (dq, J=2.9, 12.9 Hz, 2H), 1.46 (s, 9H), 1.29 (dq, J=3.0, 12.5 Hz, 2H); LCMS (ESI) [M+H]+: 412.2.

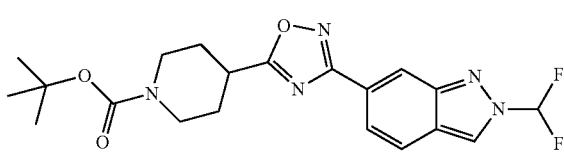 [SMILES: CC(C)(C)OC(=O)N1CCC(c2nc(-c3ccc4cn(C(F)F)nc4c3)no2)CC1]

¹H NMR (400 MHz, CHLOROFORM-d) δ 8.53 (s, 1H), 8.39 (s, 1H), 7.87-7.78 (m, 2H), 7.65 (s, 0.2H), 7.49 (s, 0.5H), 7.34 (s, 0.3H), 4.13 (br s, 2H), 3.24-3.15 (m, 1H), 3.07-2.96 (m, 2H), 2.15 (br d, J=10.8 Hz, 2H), 1.98-1.86 (m, 2H), 1.48 (s, 9H); LCMS (ESI) [M+23]+: 442.1, LCMS (ESI) [M−100]+: 320.0, LCMS (ESI) [M−55]+: 364.0.

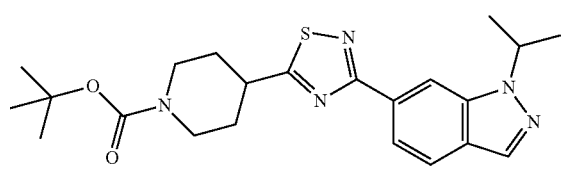 [SMILES: CC(C)n1ncc2ccc(-c3nsc(C4CCN(C(=O)OC(C)(C)C)CC4)n3)cc21]

¹H NMR (400 MHz, CHLOROFORM-d) δ 8.42 (s, 1H), 8.10 (d, J=8.4 Hz, 1H), 8.04 (s, 1H), 7.80 (d, J=8.4 Hz, 1H), 4.99 (td, J=6.7, 13.3 Hz, 1H), 4.35-4.14 (m, 2H), 3.43-3.29 (m, 1H), 2.97 (br t, J=12.0 Hz, 2H), 2.22 (br d, J=11.7 Hz, 2H), 1.85 (m, 2H), 1.63 (d, J=6.6 Hz, 6H), 1.49 (s, 9H); LCMS (ESI) [M+H]+: 428.2.

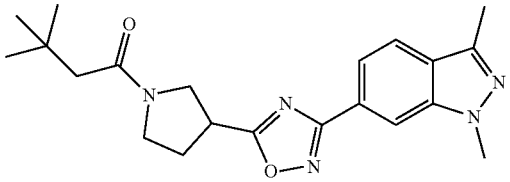 [SMILES: Cc1nn(C)c2cc(-c3noc(C4CCN(C(=O)CC(C)(C)C)C4)n3)ccc12]

¹H NMR (400 MHz, CHLOROFORM-d) δ 8.09 (s, 1H), 7.85-7.79 (m, 1H), 7.77-7.70 (m, 1H), 4.08 (d, J=1.8 Hz, 3H), 4.06-3.92 (m, 2H), 3.88-3.73 (m, 2H), 3.71-3.62 (m, 1H), 2.60 (s, 3H), 2.56-2.35 (m, 2H), 2.30-2.20 (m, 2H), 1.10 (d, J=1.8 Hz, 9H); LCMS (ESI) [M+H]+: 382.2.

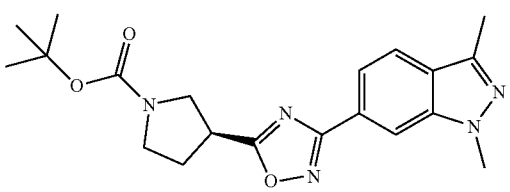 [SMILES: Cc1nn(C)c2cc(-c3noc([C@H]4CCN(C(=O)OC(C)(C)C)C4)n3)ccc12]

¹H NMR (400 MHz, CHLOROFORM-d) δ 8.12-8.08 (m, 1H), 7.83 (dd, J=1.1, 8.6 Hz, 1H), 7.76-7.72 (m, 1H), 4.09 (s, 3H), 3.99-3.49 (m, 5H), 2.60 (s, 3H), 2.50-2.34 (m, 2H), 1.50 (s, 9H); LCMS (ESI) [M+H]+: 384.1.

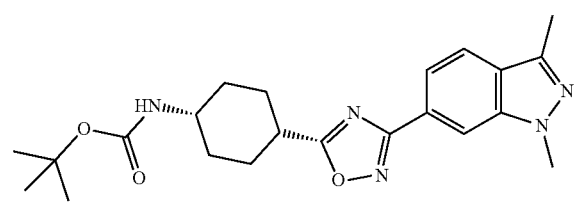

¹H NMR (400 MHz, CHLOROFORM-d) δ 8.11 (s, 1H), 7.87-7.81 (m, 1H), 7.74 (d, J=8.3 Hz, 1H), 4.64-4.62 (m, 1H), 4.09 (s, 3H), 3.77-3.74 (m, 1H), 3.23-3.20 (m, 1H), 2.61 (s, 3H), 2.15 (br s, 2H), 2.01 (dt, J=4.2, 8.9 Hz, 2H), 1.85 (br d, J=4.4 Hz, 2H), 1.73 (br s, 2H), 1.46 (s, 9H); LCMS (ESI) [M+H]+: 412.2.

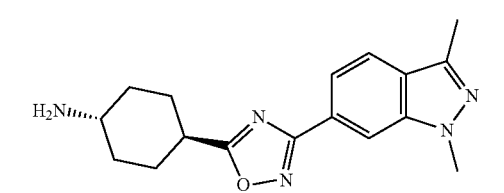 [SMILES: Cc1nn(C)c2cc(-c3noc([C@H]4CC[C@H](N)CC4)n3)ccc12]

¹H NMR (400 MHz, METHANOL-d₄) δ 8.16 (s, 1H), 7.85-7.74 (m, 2H), 4.04 (s, 3H), 3.27-3.06 (m, 2H), 2.56 (s, 3H), 2.44-2.30 (m, 2H), 2.21 (br d, J=10.6 Hz, 2H), 1.83 (m, 2H), 1.70-1.51 (m, 2H); LCMS (ESI) [M+H]+: 312.2.

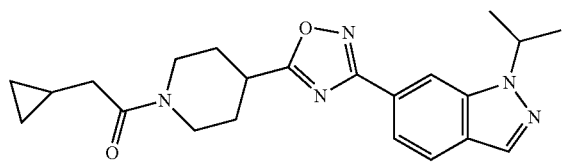 [SMILES: CC(C)n1ncc2ccc(-c3noc(C4CCN(C(=O)CC5CC5)CC4)n3)cc21]

¹H NMR (400 MHz, CHLOROFORM-d) δ 8.21 (s, 1H), 8.06 (s, 1H), 7.94-7.78 (m, 2H), 4.97 (td, J=6.7, 13.3 Hz, 1H), 4.59 (br d, J=13.7 Hz, 1H), 3.95 (br d, J=13.9 Hz, 1H), 3.39-3.21 (m, 2H), 3.00 (br t, J=11.4 Hz, 1H), 2.34 (d, J=6.8 Hz, 2H), 2.28-2.13 (m, 2H), 2.07-1.88 (m, 2H), 1.64 (d, J=6.6 Hz, 6H), 1.14-1.00 (m, 1H), 0.67-0.52 (m, 2H), 0.21 (q, J=4.9 Hz, 2H); LCMS (ESI) [M+H]+: 394.3.

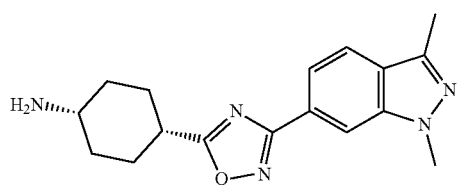 [SMILES: Cc1nn(C)c2cc(-c3noc([C@H]4CC[C@@H](N)CC4)n3)ccc12]

¹H NMR (400 MHz, METHANOL-d₄) δ 8.24 (s, 1H), 7.86 (s, 2H), 4.08 (s, 3H), 3.47 (br t, J=4.3 Hz, 1H), 3.36-3.32 (m, 1H), 2.60 (s, 3H), 2.49-2.39 (m, 2H), 2.12-1.98 (m, 4H), 1.84-1.68 (m, 2H); LCMS (ESI) [M+H]+: 312.2.

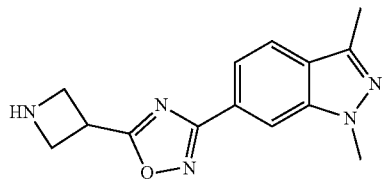 [SMILES: Cc1nn(C)c2cc(-c3noc(C4CNC4)n3)ccc12]

¹H NMR (400 MHz, METHANOL-d₄) δ 8.40 (br s, 1H), 8.22 (s, 1H), 7.83 (s, 2H), 4.63-4.45 (m, 5H), 4.05 (s, 3H), 2.57 (s, 3H); LCMS (ESI) [M+H]+: 270.1.

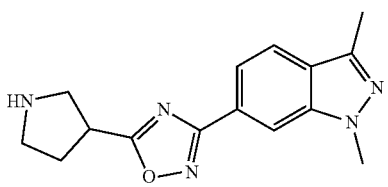 [SMILES: Cc1nn(C)c2cc(-c3noc(C4CCNC4)n3)ccc12]

¹H NMR (400 MHz, METHANOL-d₄) δ 8.25 (s, 1H), 7.87 (s, 2H), 4.15 (quin, J=7.2 Hz, 1H), 4.09 (s, 3H), 3.91-3.80 (m, 2H), 3.63-3.50 (m, 2H), 2.72-2.62 (m, 1H), 2.61 (s, 3H), 2.50 (qd, J=6.9, 13.8 Hz, 1H); LCMS (ESI) [M+H]+: 284.2.

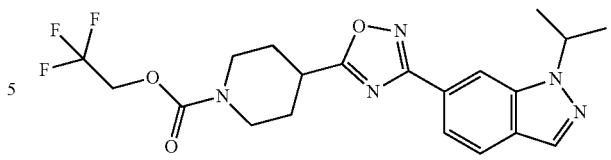

¹H NMR (400 MHz, CHLOROFORM-d) δ 8.20 (s, 1H), 8.06 (s, 1H), 7.87-7.79 (m, 2H), 4.96 (quind, J=6.7, 13.3 Hz, 1H), 4.52 (dq, J=2.0, 8.5 Hz, 2H), 4.19 (br t, J=17.3 Hz, 2H), 3.33-3.08 (m, 3H), 2.21 (br d, J=11.5 Hz, 2H), 2.07-1.92 (m, 2H), 1.62 (d, J=6.6 Hz, 6H); LCMS (ESI) [M+H]+: 438.1.

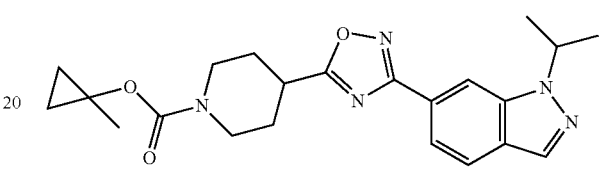

¹H NMR (400 MHz, CHLOROFORM-d) δ 8.20 (s, 1H), 8.05 (s, 1H), 7.90-7.75 (m, 2H), 4.95 (spt, J=6.6 Hz, 1H), 4.18 (br s, 2H), 3.72 (s, 3H), 3.22 (tt, J=3.9, 10.7 Hz, 1H), 3.08 (br t, J=11.7 Hz, 2H), 2.16 (br d, J=11.0 Hz, 2H), 2.03-1.86 (m, 2H), 1.62 (d, J=6.6 Hz, 6H); LCMS (ESI) [M+H]+: 370.2.

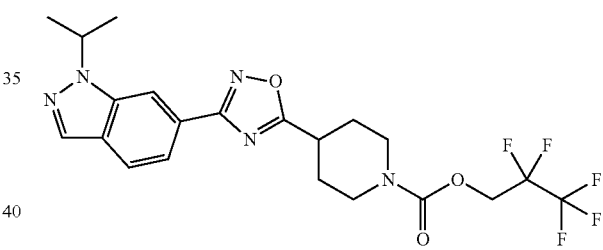

¹H NMR (400 MHz, CHLOROFORM-d) δ 8.23 (s, 1H), 8.08 (s, 1H), 7.91-7.79 (m, 2H), 4.99 (td, J=6.7, 13.3 Hz, 1H), 4.62 (br t, J=12.5 Hz, 2H), 4.31-4.08 (m, 2H), 3.36-3.09 (m, 4H), 2.23 (br s, 2H), 2.02 (br s, 2H), 1.65 (d, J=6.6 Hz, 6H); LCMS (ESI) [M+H]+: 488.0.

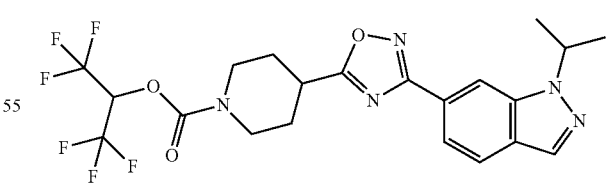

¹H NMR (400 MHz, CHLOROFORM-d) δ 8.23 (s, 1H), 8.08 (s, 1H), 7.91-7.80 (m, 2H), 5.81 (spt, J=6.1 Hz, 1H), 4.99 (spt, J=6.6 Hz, 1H), 4.34-4.07 (m, 2H), 3.42-3.14 (m, 3H), 2.26 (br d, J=3.5 Hz, 2H), 2.13-1.94 (m, 2H), 1.65 (d, J=6.7 Hz, 6H); LCMS (ESI) [M+H]+: 506.0.

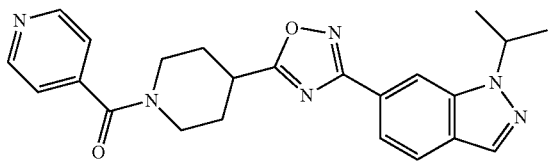 [SMILES: CC(C)n1ncc2ccc(-c3noc(C4CCN(C(=O)c5ccncc5)CC4)n3)cc21]

¹H NMR (400 MHz, CHLOROFORM-d) δ 8.72 (d, J=6.0 Hz, 2H), 8.20 (s, 1H), 8.06 (s, 1H), 7.91-7.77 (m, 2H), 7.32 (d, J=6.0 Hz, 2H), 4.96 (spt, J=6.6 Hz, 1H), 4.64 (br d, J=11.2 Hz, 1H), 3.76 (br d, J=11.9 Hz, 1H), 3.44-3.32 (m, 1H), 3.26 (br d, J=10.8 Hz, 2H), 2.32 (br s, 1H), 2.23-1.88 (m, 3H), 1.63 (d, J=6.8 Hz, 6H); LCMS (ESI) [M+H]+: 417.1.

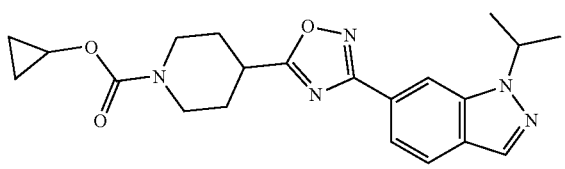 [SMILES: CC(C)n1ncc2ccc(-c3noc(C4CCN(C(=O)OC5CC5)CC4)n3)cc21]

¹H NMR (400 MHz, DMSO-d₆) δ 8.27 (s, 1H), 8.15 (s, 1H), 7.91 (d, J=8.6 Hz, 1H), 7.75 (d, J=8.6 Hz, 1H), 5.11 (spt, J=6.7 Hz, 1H), 4.14-4.00 (m, 1H), 3.94 (br d, J=13.5 Hz, 2H), 3.49-3.36 (m, 1H), 3.49-3.36 (m, 1H), 3.13-3.08 (m, 2H), 2.13 (br dd, J=3.3, 13.2 Hz, 2H), 1.86-1.70 (m, 2H), 1.53 (d, J=6.4 Hz, 6H), 0.72-0.60 (m, 4H); LCMS (ESI) [M+H]+: 396.2.

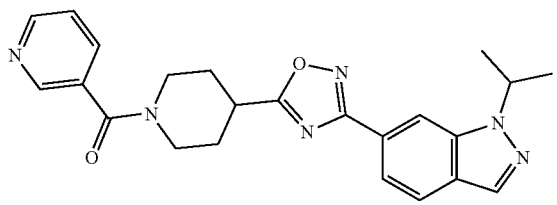 [SMILES: CC(C)n1ncc2ccc(-c3noc(C4CCN(C(=O)c5cccnc5)CC4)n3)cc21]

¹H NMR (400 MHz, DMSO-d₆) δ 8.68-8.63 (m, 2H), 8.28 (s, 1H), 8.16 (s, 1H), 7.92 (d, J=8.4 Hz, 1H), 7.86 (d, J=7.9 Hz, 1H), 7.76 (d, J=8.4 Hz, 1H), 7.48 (dd, J=4.9, 7.7 Hz, 1H), 5.11 (spt, J=6.6 Hz, 1H), 4.06 (br s, 2H), 3.59-3.46 (m, 1H), 3.29 (br t, J=11.2 Hz, 2H), 2.25-2.15 (m, 2H), 1.98-1.83 (m, 2H), 1.54 (d, J=6.6 Hz, 6H); LCMS (ESI) [M+H]+: 417.1.

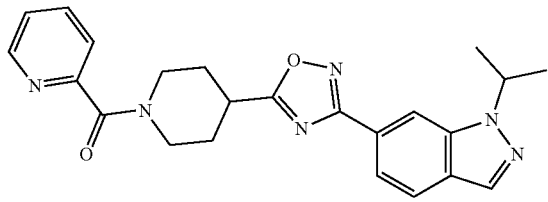 [SMILES: CC(C)n1ncc2ccc(-c3noc(C4CCN(C(=O)c5ccccn5)CC4)n3)cc21]

¹H NMR (400 MHz, CHLOROFORM-d) δ 8.60 (br d, J=4.4 Hz, 1H), 8.21 (s, 1H), 8.05 (s, 1H), 7.88-7.78 (m, 3H), 7.67 (br d, J=7.7 Hz, 1H), 7.40-7.33 (m, 1H), 4.96 (td, J=6.6, 13.2 Hz, 1H), 4.68 (br d, J=13.2 Hz, 1H), 4.11 (br d, J=13.2 Hz, 1H), 3.36 (br t, J=10.5 Hz, 2H), 3.24 (br t, J=11.5 Hz, 1H), 2.32 (br d, J=11.7 Hz, 1H), 2.24-2.01 (m, 3H), 1.62 (d, J=6.6 Hz, 6H); LCMS (ESI) [M+H]+: 417.1.

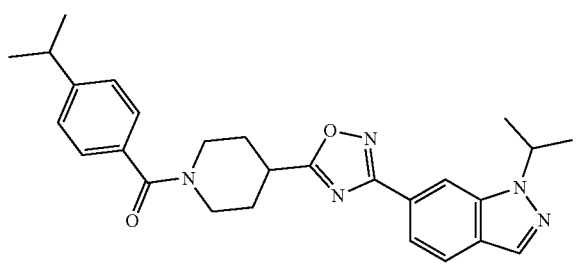 [SMILES: CC(C)c1ccc(C(=O)N2CCC(c3nc(-c4ccc5cnn(C(C)C)c5c4)no3)CC2)cc1]

¹H NMR (400 MHz, DMSO-d₆) δ 8.26 (s, 1H), 8.13 (s, 1H), 7.90 (d, J=8.4 Hz, 1H), 7.74 (d, J=8.4 Hz, 1H), 7.32 (q, J=8.2 Hz, 4H), 5.09 (spt, J=6.5 Hz, 1H), 4.06 (br s, 2H), 3.58-3.42 (m, 1H), 3.27-3.11 (m, 2H), 2.94 (spt, J=6.8 Hz, 1H), 2.16 (br dd, J=2.9, 13.0 Hz, 2H), 1.93-1.77 (m, 2H), 1.52 (d, J=6.6 Hz, 6H), 1.23 (d, J=6.8 Hz, 6H); LCMS (ESI) [M+H]+: 458.3.

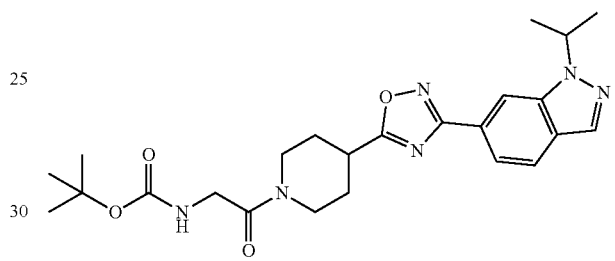

¹H NMR (400 MHz, CHLOROFORM-d) δ 8.20 (s, 1H), 8.09-8.06 (m, 1H), 7.90-7.76 (m, 2H), 5.52 (br s, 1H), 4.96 (dq, J=4.2, 6.5 Hz, 1H), 4.49 (br d, J=13.2 Hz, 1H), 4.01 (br s, 2H), 3.82 (br d, J=13.5 Hz, 1H), 3.39-3.22 (m, 2H), 3.08 (br t, J=12.0 Hz, 1H), 2.21 (br s, 2H), 2.06-1.89 (m, 2H), 1.63 (dd, J=2.6, 6.6 Hz, 6H), 1.46 (d, J=2.0 Hz, 9H); LCMS (ESI) [M+H]+: 349.2.

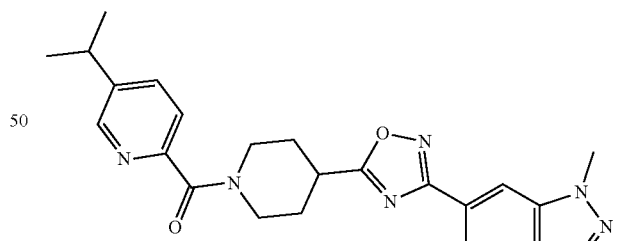

¹H NMR (400 MHz, CHLOROFORM-d) δ 8.49 (d, J=1.7 Hz, 1H), 8.20 (s, 1H), 8.05 (s, 1H), 7.91-7.82 (m, 2H), 7.70-7.62 (m, 2H), 4.71 (br d, J=13.4 Hz, 1H), 4.18 (s, 4H), 3.45-3.33 (m, 2H), 3.25 (br t, J=11.1 Hz, 1H), 3.02 (spt, J=6.9 Hz, 1H), 2.34 (br d, J=10.9 Hz, 1H), 2.23-2.11 (m, 3H), 1.33 (d, J=7.0 Hz, 6H); LCMS (ESI) [M+H]+: 431.1.

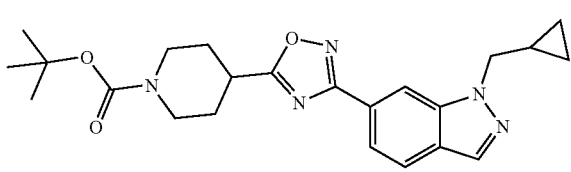 [SMILES: CC(C)(C)OC(=O)N1CCC(c2nc(-c3ccc4cnn(CC5CC5)c4c3)no2)CC1]

¹H NMR (400 MHz, CHLOROFORM-d) δ 8.20 (s, 1H), 8.06 (s, 1H), 7.89-7.81 (m, 2H), 4.35 (d, J=6.8 Hz, 2H), 4.25-4.11 (m, 2H), 3.25-3.18 (m, 1H), 3.09-2.97 (m, 2H), 2.21-2.12 (m, 2H), 2.01-1.89 (m, 2H), 1.50 (s, 9H), 1.41 (br d, J=4.9 Hz, 1H), 0.65-0.59 (m, 2H), 0.49-0.44 (m, 2H); LCMS (ESI) [M+H]+: 424.1.

¹H NMR (400 MHz, CHLOROFORM-d) δ 8.52 (s, 2H), 8.10 (s, 1H), 7.86-7.81 (d, J=8.4 Hz, 1H), 7.76-7.72 (d, J=8.4 Hz, 1H), 4.85 (td, J=3.7, 13.6 Hz, 2H), 4.08 (s, 3H), 3.45-3.25 (m, 3H), 2.60 (s, 3H), 2.29 (br dd, J=3.3, 13.6 Hz, 2H), 2.11-1.94 (m, 2H); LCMS (ESI) [M+H]+: 444.2.

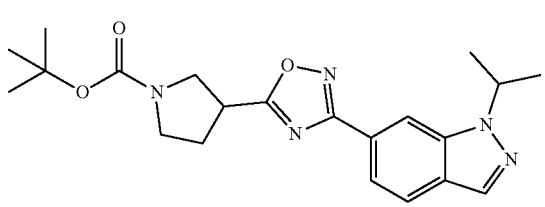 [SMILES: CC(C)n1ncc2ccc(-c3noc(C4CCN(C(=O)OC(C)(C)C)C4)n3)cc21]

¹H NMR (400 MHz, DMSO-d₆) δ 8.30 (s, 1H), 8.19 (s, 1H), 7.93 (d, J=8.4 Hz, 1H), 7.75 (dd, J=1.1, 8.4 Hz, 1H), 5.14 (quin, J=6.6 Hz, 1H), 3.93 (br d, J=7.3 Hz, 1H), 3.78 (br d, J=8.2 Hz, 1H), 3.68-3.60 (m, 1H), 3.52-3.44 (m, 1H), 3.40 (br d, J=7.5 Hz, 1H), 2.40 (br s, 1H), 2.24 (br d, J=6.8 Hz, 1H), 1.50 (d, J=6.4 Hz, 6H), 1.42 (s, 9H); LCMS (ESI) [M+H]+: 398.2.

¹H NMR (400 MHz, CHLOROFORM-d) δ 8.08 (s, 1H), 7.82-7.80 (d, J=8.0 Hz, 1H) 7.73-7.70 (d, J=8.0 Hz, 1H), 5.40-5.30 (m, 1H), 4.07 (s, 3H), 3.89 (m, 1H), 2.97 (tt, J=3.5, 12.2 Hz, 1H), 2.59 (s, 3H), 2.34-2.15 (m, 4H), 1.99 (s, 3H), 1.86 (m, 2H), 1.39-1.20 (m, 2H); LCMS (ESI) [M+H]+: 354.2.

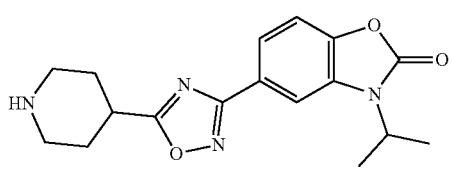 [SMILES: CC(C)n1c(=O)oc2ccc(-c3noc(C4CCNCC4)n3)cc21]

¹H NMR (400 MHz, DMSO-d₆) δ 9.05 (br s, 2H), 7.85 (d, J=1.3 Hz, 1H), 7.80 (dd, J=1.5, 8.4 Hz, 1H), 7.53 (d, J=8.4 Hz, 1H), 4.58 (spt, J=6.9 Hz, 1H), 3.52 (tt, J=3.8, 10.9 Hz, 1H), 3.38-3.33 (m, 2H), 3.07 (br t, J=11.2 Hz, 2H), 2.27 (br dd, J=2.9, 14.1 Hz, 2H), 2.10-1.98 (m, 2H), 1.49 (d, J=6.8 Hz, 6H); LCMS (ESI) [M+H]+: 329.1.

1H NMR (400 MHz, CHLOROFORM-d) δ 8.10 (s, 1H), 7.85 (d, J=8.4 Hz, 1H), 7.78-7.70 (m, 1H), 5.50-5.47 (br s, 1H), 4.09 (s, 3H), 4.08-3.99 (m, 1H), 3.31-3.23 (m, 1H), 2.61 (s, 3H), 2.27-2.16 (m, 2H), 2.08-2.00 (m, 2H), 1.99 (s, 3H), 1.95-1.84 (m, 2H), 1.73-1.64 (m, 2H); LCMS (ESI) [M+H]+: 354.2.

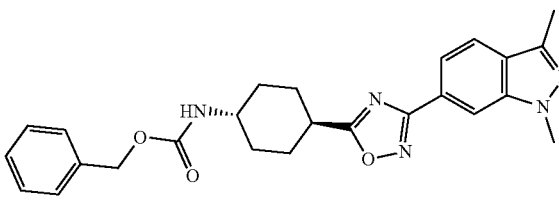

¹H NMR (400 MHz, CHLOROFORM-d) δ 8.08 (s, 1H), 7.85-7.79 (d, J=8.4 Hz 1H), 7.75-7.68 (d, J=8.4 Hz 1H), 7.42-7.29 (m, 5H), 5.11 (s, 2H), 4.68 (br d, J=5.5 Hz, 1H), 4.07 (s, 3H), 3.73-3.55 (m, 1H), 3.05-2.90 (m, 1H), 2.59 (s, 3H), 2.36-2.16 (m, 4H), 1.94-1.75 (m, 2H), 1.43-1.24 (m, 2H); LCMS (ESI) [M+H]+: 446.2.

¹H NMR (400 MHz, CHLOROFORM-d) δ 8.12 (s, 1H), 7.86 (d, J=8.4 Hz, 1H), 7.79-7.71 (m, 3H), 7.54-7.40 (m, 3H), 6.10 (br d, J=7.1 Hz, 1H), 4.26 (tt, J=4.1, 7.9 Hz, 1H), 4.09 (s, 3H), 3.32 (quin, J=5.2 Hz, 1H), 2.61 (s, 3H), 2.35-2.23 (m, 2H), 2.15-1.98 (m, 4H), 1.86-1.73 (m, 2H); LCMS (ESI) [M+H]+: 416.3.

671

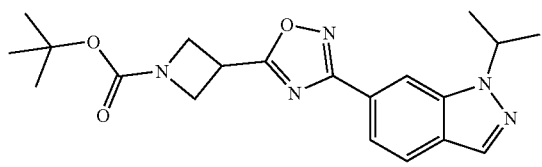 [SMILES: CC(C)n1ncc2ccc(-c3noc(C4CN(C(=O)OC(C)(C)C)C4)n3)cc21]

¹H NMR (400 MHz, CHLOROFORM-d) δ 8.25 (s, 1H), 8.07 (s, 1H), 7.85 (q, J=8.4 Hz, 2H), 4.98 (quin, J=6.7 Hz, 1H), 4.48-4.32 (m, 4H), 4.16-4.02 (m, 1H), 1.64 (d, J=6.8 Hz, 6H), 1.50-1.45 (m, 9H); LCMS (ESI) [M+H]+: 384.2.

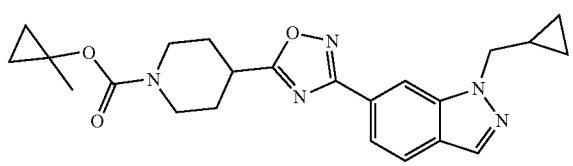 [SMILES: CC1(OC(=O)N2CCC(c3nc(-c4ccc5cnn(CC6CC6)c5c4)no3)CC2)CC1]

¹H NMR (400 MHz, DMSO-d₆) δ 8.28 (s, 1H), 8.14 (s, 1H), 7.92 (d, J=8.4 Hz, 1H), 7.75 (d, J=8.4 Hz, 1H), 4.41 (d, J=6.8 Hz, 2H), 3.93 (br d, J=13.5 Hz, 2H), 3.45-3.32 (m, 1H), 3.04-2.95 (m, 2H), 2.11 (br dd, J=3.2, 13.8 Hz, 2H), 1.84-1.67 (m, 2H), 1.51 (s, 3H), 1.39-1.26 (m, 1H), 0.89-0.77 (m, 2H), 0.64-0.59 (m, 2H), 0.56-0.50 (m, 2H), 0.44-0.38 (m, 2H); LCMS (ESI) [M+H]+: 422.2.

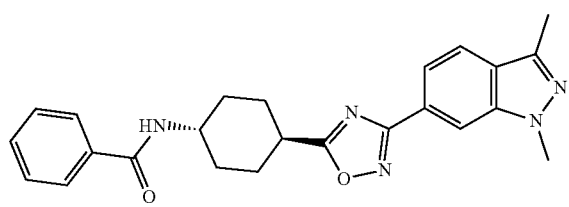 [SMILES: Cc1nn(C)c2cc(-c3noc([C@H]4CC[C@H](NC(=O)c5ccccc5)CC4)n3)ccc12]

¹H NMR (400 MHz, CHLOROFORM-d) δ 8.10 (s, 1H), 7.86-7.82 (m, 1H), 7.80-7.71 (m, 3H), 7.55-7.42 (m, 3H), 5.99 (br d, J=7.8 Hz, 1H), 4.20-4.03 (m, 4H), 3.03 (tt, J=3.2, 12.2 Hz, 1H), 2.60 (s, 3H), 2.41-2.28 (m, 4H), 2.03-1.84 (m, 2H), 1.52-1.36 (m, 2H); LCMS (ESI) [M+H]+: 416.3.

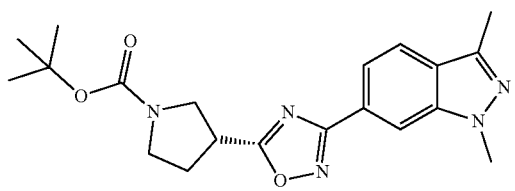

¹H NMR (400 MHz, CHLOROFORM-d) δ 8.10 (s, 1H), 7.86-7.81 (m, 1H), 7.77-7.70 (m, 1H), 4.08 (s, 3H), 3.96-3.49 (m, 5H), 2.60 (s, 3H), 2.51-2.32 (m, 2H), 1.50 (s, 9H); LCMS (ESI) [M+H]+: 384.2.

672

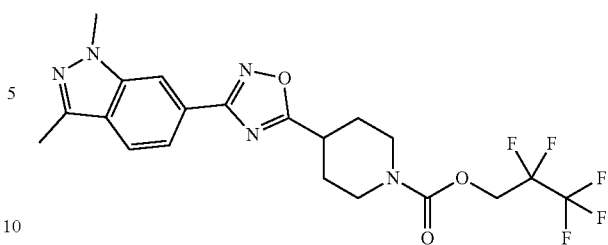

¹H NMR (400 MHz, CHLOROFORM-d) δ 8.09 (s, 1H), 7.83 (dd, J=1.0, 8.4 Hz, 1H), 7.76-7.72 (d, J=8.4 Hz, 1H), 4.61 (t, J=12.7 Hz, 2H), 4.27-4.10 (m, 2H), 4.08 (s, 3H), 3.32-3.10 (m, 3H), 2.60 (s, 3H), 2.24-2.15 (m, 2H), 2.00 (br d, J=4.9 Hz, 2H); LCMS (ESI) [M+H]+: 474.1.

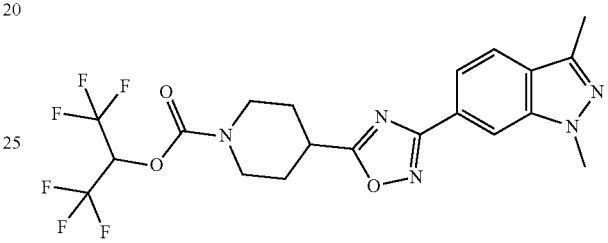

¹H NMR (400 MHz, CHLOROFORM-d) δ 8.10 (s, 1H), 7.86-7.81 (m, 1H), 7.77-7.71 (m, 1H), 5.79 (spt, J=6.2 Hz, 1H), 4.25-4.15 (m, 2H), 4.09 (s, 3H), 3.37-3.20 (m, 3H), 2.61 (s, 3H), 2.32-2.21 (m, 2H), 2.12-1.97 (m, 2H); LCMS (ESI) [M+H]+: 492.1.

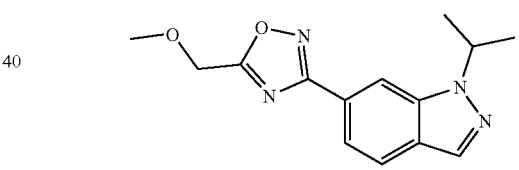

¹H NMR (400 MHz, CHLOROFORM-d) δ 8.27 (s, 1H), 8.07 (s, 1H), 7.92-7.86 (m, 1H), 7.85-7.80 (m, 1H), 5.01-4.91 (m, 1H), 4.80 (s, 2H), 3.60 (s, 3H), 1.63 (d, J=6.8 Hz, 6H); LCMS (ESI) [M+H]+: 273.1.

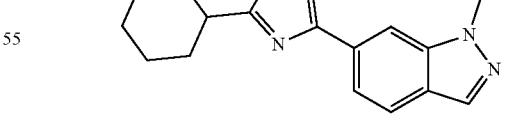

¹H NMR (400 MHz, CHLOROFORM-d) δ 8.29 (s, 1H), 8.06 (s, 1H), 7.93-7.86 (m, 1H), 7.83-7.77 (m, 1H), 4.96 (spt, J=6.8 Hz, 1H), 4.83 (dd, J=2.8, 10.7 Hz, 1H), 4.24 (br d, J=11.7 Hz, 1H), 3.84-3.62 (m, 1H), 2.22-2.11 (m, 1H), 2.09-1.91 (m, 2H), 1.86-1.74 (m, 2H), 1.73-1.65 (m, 1H), 1.62 (dd, J=1.1, 6.6 Hz, 6H); LCMS (ESI) [M+H]+: 313.1.

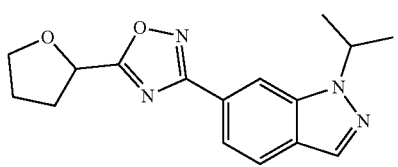 [SMILES: CC(C)n1ncc2ccc(-c3noc(C4CCCO4)n3)cc21]

¹H NMR (400 MHz, CHLOROFORM-d) δ 8.25 (s, 1H), 8.06 (s, 1H), 7.91-7.85 (m, 1H), 7.84-7.78 (m, 1H), 5.29 (dd, J=5.4, 7.8 Hz, 1H), 4.97 (spt, J=6.7 Hz, 1H), 4.27-4.14 (m, 1H), 4.11-3.99 (m, 1H), 2.55-2.42 (m, 1H), 2.40-2.31 (m, 1H), 2.28-2.04 (m, 2H), 1.63 (dd, J=1.1, 6.6 Hz, 6H); LCMS (ESI) [M+H]+: 299.1.

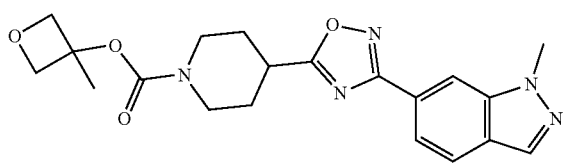 [SMILES: Cn1ncc2ccc(-c3noc(C4CCN(C(=O)OC5(C)COC5)CC4)n3)cc21]

¹H NMR (400 MHz, CHLOROFORM-d) δ 8.16 (s, 1H), 8.02 (s, 1H), 7.88-7.79 (m, 2H), 4.80 (d, J=7.0 Hz, 2H), 4.50 (d, J=7.0 Hz, 2H), 4.21-4.08 (m, 5H), 3.29-3.20 (m, 1H), 3.21-3.09 (m, 2H), 2.18 (br d, J=13.6 Hz, 2H), 2.02-1.92 (m, 2H), 1.75 (s, 3H); LCMS (ESI) [M+H]+: 398.1.

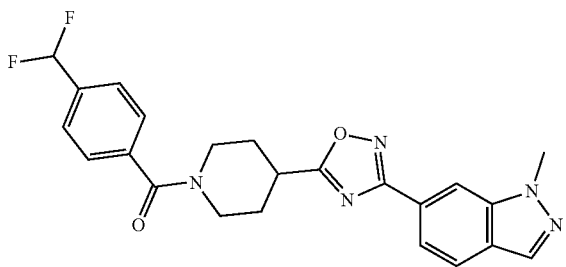 [SMILES: Cn1ncc2ccc(-c3noc(C4CCN(C(=O)c5ccc(C(F)F)cc5)CC4)n3)cc21]

¹H NMR (400 MHz, DMSO-d₆) δ 8.28 (d, J=0.9 Hz, 1H), 8.17 (d, J=0.9 Hz, 1H), 7.94 (dd, J=0.6, 8.4 Hz, 1H), 7.77 (dd, J=1.2, 8.4 Hz, 1H), 7.69-7.64 (m, 2H), 7.60-7.56 (m, 2H), 7.24-6.96 (t, J=55.6 Hz, 1H), 4.55-4.45 (m, 1H), 4.15 (s, 3H), 3.67-3.48 (m, 2H), 3.29-3.08 (m, 2H), 2.33-2.00 (m, 2H), 1.91-1.75 (m, 2H); LCMS (ESI) [M+H]+: 438.2.

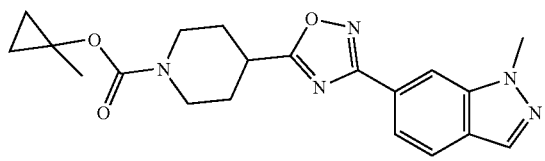 [SMILES: Cn1ncc2ccc(-c3noc(C4CCN(C(=O)OC5(C)CC5)CC4)n3)cc21]

¹H NMR (400 MHz, CHLOROFORM-d) δ 8.16 (s, 1H), 8.02 (s, 1H), 7.87-7.78 (m, 2H), 4.31-3.96 (m, 5H), 3.26-3.16 (m, 1H), 3.03 (br t, J=11.1 Hz, 2H), 2.15 (br d, J=11.5 Hz, 2H), 1.92 (br d, J=9.3 Hz, 2H), 1.56 (s, 3H), 0.91-0.84 (m, 2H), 0.67-0.55 (m, 2H); LCMS (ESI) [M+H]+: 382.1.

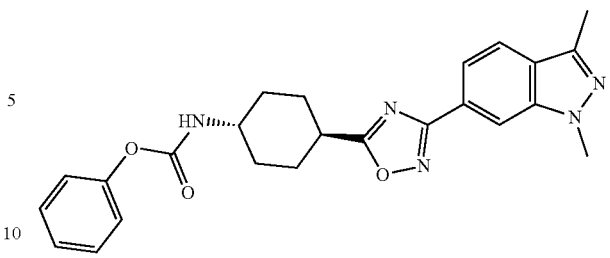

¹H NMR (400 MHz, CHLOROFORM-d) δ 8.09 (s, 1H), 7.83 (d, J=8.4 Hz, 1H), 7.76-7.69 (d, J=8.4 Hz, 1H), 7.42-7.32 (m, 2H), 7.25-7.08 (m, 3H), 4.96 (br d, J=7.6 Hz, 1H), 4.07 (s, 3H), 3.70 (br dd, J=4.1, 7.4 Hz, 1H), 3.01 (br t, J=12.2 Hz, 1H), 2.59 (s, 3H), 2.40-2.25 (m, 4H), 1.95-1.81 (m, 2H), 1.49-1.36 (m, 2H); LCMS (ESI) [M+H]+: 432.2.

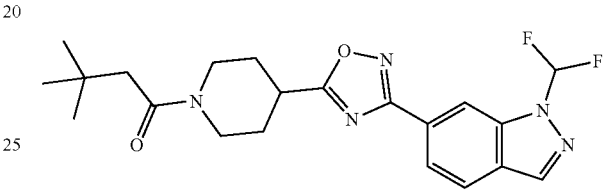

¹H NMR (400 MHz, CHLOROFORM-d) δ 8.51 (s, 1H), 8.15 (s, 1H), 8.03 (d, J=8.4 Hz, 1H), 7.87 (d, J=8.4 Hz, 1H), 7.66-7.36 (t, J=59.2 Hz, 1H), 4.62 (br d, J=13.6 Hz, 1H), 4.04 (br d, J=13.9 Hz, 1H), 3.35-3.24 (m, 2H), 3.01-2.90 (m, 1H), 2.31 (s, 2H), 2.22 (br d, J=12.7 Hz, 2H), 2.04-1.86 (m, 2H), 1.08 (s, 9H); LCMS (ESI) [M+H]+: 418.

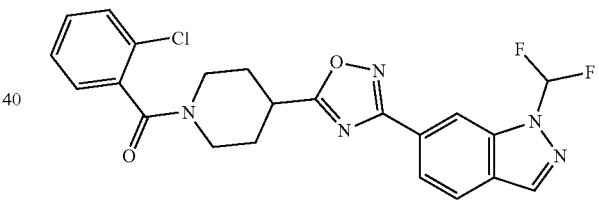

¹H NMR (400 MHz, CHLOROFORM-d) δ 8.51 (s, 1H), 8.15 (s, 1H), 8.07-8.01 (d, J=8.4 Hz, 1H), 7.87 (d, J=8.4 Hz, 1H), 7.67-7.37 (t, J=59.6 Hz, 1H), 7.45-7.40 (m, 1H), 7.36-7.27 (m, 3H), 4.78-4.63 (m, 1H), 3.64-3.53 (m, 1H), 3.40-3.13 (m, 3H), 2.34 (br dd, J=3.3, 13.6 Hz, 1H), 2.20-1.85 (m, 3H); LCMS (ESI) [M+H]+: 458.0.

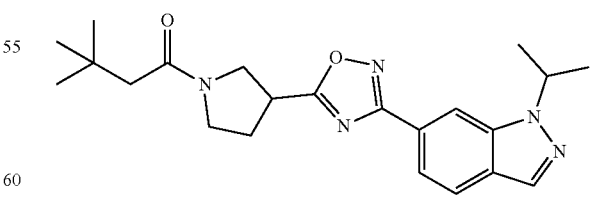

¹H NMR (400 MHz, CHLOROFORM-d) δ 7.97 (br s, 1H), 7.82 (br d, J=6.4 Hz, 1H), 7.66-7.50 (m, 2H), 4.78-4.64 (m, 1H), 3.87-3.34 (m, 5H), 2.35-2.09 (m, 2H), 2.06-1.93 (m, 2H), 1.45-1.31 (m, 6H), 0.95-0.75 (m, 9H); LCMS (ESI) [M+H]+: 396.2.

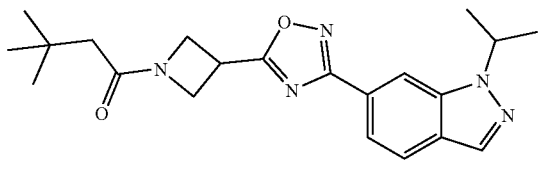 [SMILES: CC(C)n1ncc2ccc(-c3noc(C4CN(C(=O)CC(C)(C)C)C4)n3)cc21]

¹H NMR (400 MHz, CHLOROFORM-d) δ 8.31-8.21 (m, 1H), 8.15-8.04 (m, 1H), 7.91-7.77 (m, 2H), 4.99 (quind, J=6.6, 13.3 Hz, 1H), 4.69-4.39 (m, 4H), 4.14 (tt, J=6.0, 8.9 Hz, 1H), 2.14-2.00 (m, 2H), 1.65 (d, J=6.6 Hz, 6H), 1.15-1.03 (m, 9H); LCMS (ESI) [M+H]+: 382.1.

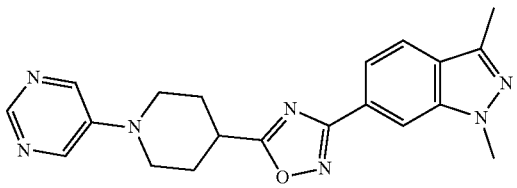

¹H NMR (300 MHz, CHLOROFORM-d) δ 8.74 (s, 1H), 8.46 (s, 2H), 8.12 (s, 1H), 7.91-7.80 (m, 1H), 7.76 (d, J=8.5 Hz, 1H), 4.10 (s, 3H), 3.83 (d, J=12.8 Hz, 2H), 3.12 (t, J=10.3 Hz, 2H), 2.61 (s, 3H), 2.37 (d, J=12.7 Hz, 2H), 2.29-2.16 (m, 2H); LCMS (ESI) [M+H]+: 376.1.

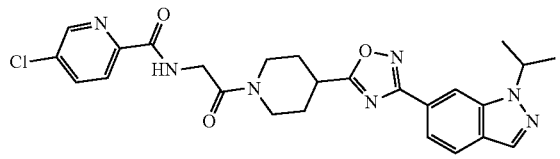 [SMILES: CC(C)n1ncc2ccc(-c3noc(C4CCN(C(=O)CNC(=O)c5ccc(Cl)cn5)CC4)n3)cc21]

¹H NMR (400 MHz, CHLOROFORM-d) δ 8.80 (br s, 1H), 8.57 (s, 1H), 8.21 (s, 1H), 8.14 (br d, J=8.4 Hz, 1H), 8.07 (s, 1H), 7.90-7.76 (m, 3H), 4.97 (td, J=6.6, 13.1 Hz, 1H), 4.56 (br d, J=13.0 Hz, 1H), 4.33 (br s, 2H), 3.94 (br d, J=14.1 Hz, 1H), 3.44-3.26 (m, 2H), 3.15 (br t, J=11.5 Hz, 1H), 2.28 (br t, J=12.5 Hz, 2H), 2.14-1.94 (m, 2H), 1.63 (br d, J=6.6 Hz, 6H); LCMS (ESI) [M+H]+: 508.2.

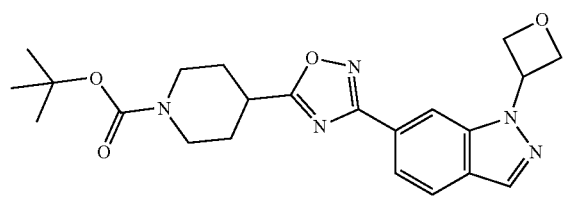

¹H NMR (300 MHz, CHLOROFORM-d) δ 8.21 (d, J=14.0 Hz, 2H), 7.96-7.82 (m, 2H), 5.91 (t, J=7.1 Hz, 1H), 5.35 (t, J=6.5 Hz, 2H), 5.17 (t, J=7.2 Hz, 2H), 4.16 (s, 2H), 3.02 (t, J=12.0 Hz, 2H), 2.17 (d, J=13.4 Hz, 2H), 2.07-1.77 (m, 2H), 1.50 (s, 8H); LCMS (ESI) [M+H]+: 426.

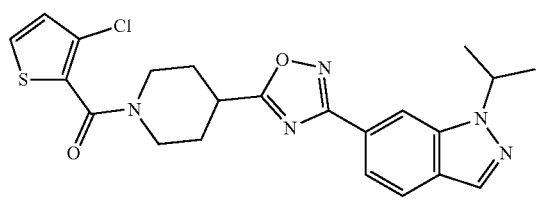 [SMILES: CC(C)n1ncc2ccc(-c3noc(C4CCN(C(=O)c5sccc5Cl)CC4)n3)cc21]

¹H NMR (400 MHz, DMSO-d₆) δ 8.26 (s, 1H), 8.14 (s, 1H), 7.90 (d, J=8.4 Hz, 1H), 7.79-7.71 (m, 1H), 7.08 (d, J=5.1 Hz, 1H), 5.09 (spt, J=6.7 Hz, 1H), 4.03 (br d, J=10.8 Hz, 2H), 3.56-3.45 (m, 1H), 3.36-3.22 (m, 2H), 2.21 (br dd, J=3.1, 13.2 Hz, 2H), 1.96-1.78 (m, 2H), 1.52 (d, J=6.6 Hz, 6H); LCMS (ESI) [M+H]+: 456.1.

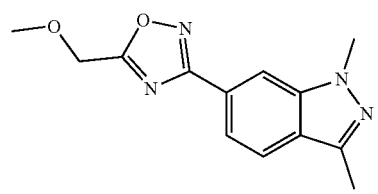 [SMILES: COCc1nc(-c2ccc3c(C)nn(C)c3c2)no1]

¹H NMR (400 MHz, CHLOROFORM-d) δ 8.16 (s, 1H), 7.86 (dd, J=1.3, 8.4 Hz, 1H), 7.75 (d, J=8.4 Hz, 1H), 4.80 (s, 2H), 4.08 (s, 3H), 3.60 (s, 3H), 2.60 (s, 3H); LCMS (ESI) [M+H]+: 259.1.

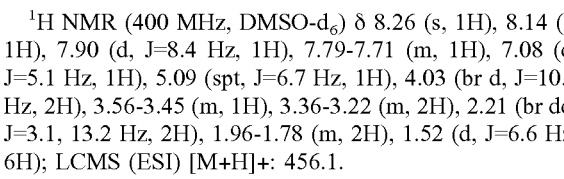

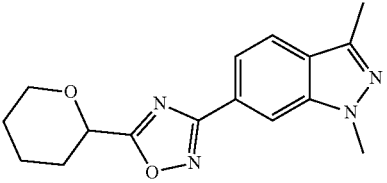 [SMILES: Cc1nn(C)c2cc(-c3noc(C4CCCCO4)n3)ccc12]

¹H NMR (400 MHz, DMSO-d₆) δ 8.30 (s, 1H), 8.20 (br s, 2H), 8.14-8.08 (m, 1H), 7.94 (br d, J=8.3 Hz, 1H), 7.75 (br d, J=8.3 Hz, 1H), 5.14 (td, J=6.3, 12.8 Hz, 1H), 4.36 (br d, J=12.8 Hz, 1H), 4.02-3.74 (m, 3H), 3.63-3.47 (m, 1H), 3.30-3.21 (m, 1H), 3.01 (br t, J=11.7 Hz, 1H), 2.18 (br d, J=12.1 Hz, 2H), 2.00-1.83 (m, 1H), 1.78-1.61 (m, 1H), 1.51 (br d, J=6.4 Hz, 6H); LCMS (ESI) [M+H]+: 369.1.

¹H NMR (400 MHz, CHLOROFORM-d) δ 8.18 (s, 1H), 7.87 (dd, J=1.1, 8.4 Hz, 1H), 7.73 (d, J=8.4 Hz, 1H), 4.83 (dd, J=2.6, 10.5 Hz, 1H), 4.24 (br d, J=11.8 Hz, 1H), 4.07 (s, 3H), 3.75-3.67 (m, 1H), 2.60 (s, 3H), 2.16 (br d, J=15.8 Hz, 1H), 2.08-1.91 (m, 2H), 1.84-1.64 (m, 3H); LCMS (ESI) [M+H]+: 299.1.

677

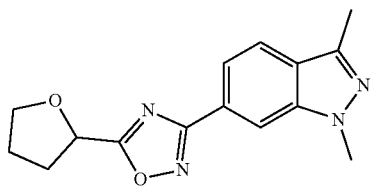 [SMILES: Cc1nn(C)c2cc(-c3noc(C4CCCO4)n3)ccc12]

¹H NMR (400 MHz, CHLOROFORM-d) δ 8.14 (s, 1H), 7.85 (dd, J=1.3, 8.3 Hz, 1H), 7.76-7.70 (m, 1H), 5.29 (dd, J=5.3, 7.9 Hz, 1H), 4.24-4.15 (m, 1H), 4.08 (s, 3H), 4.07-4.02 (m, 1H), 2.60 (s, 3H), 2.54-2.43 (m, 1H), 2.41-2.32 (m, 1H), 2.26-2.06 (m, 2H); LCMS (ESI) [M+H]+: 285.1.

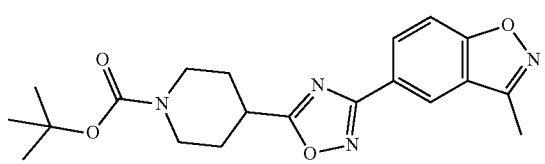 [SMILES: Cc1noc2ccc(-c3noc(C4CCN(C(=O)OC(C)(C)C)CC4)n3)cc12]

¹H NMR (400 MHz, CHLOROFORM-d) δ 8.40 (s, 1H), 8.30 (dd, J=1.5, 8.8 Hz, 1H), 7.69-7.61 (m, 1H), 4.20-4.05 (m, 2H), 3.20 (tt, J=3.9, 10.9 Hz, 1H), 3.02 (br t, J=11.3 Hz, 2H), 2.66 (s, 3H), 2.15 (br d, J=10.8 Hz, 2H), 1.98-1.88 (m, 2H), 1.49 (s, 9H); LCMS (ESI) [M+H]+: 385.1.

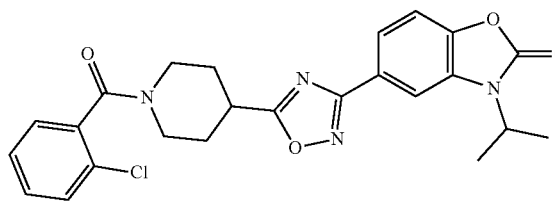

¹H NMR (400 MHz, CHLOROFORM-d) δ 7.86-7.78 (m, 1H), 7.71 (s, 1H), 7.44-7.28 (m, 3H), 7.25-7.19 (m, 2H), 4.70-4.57 (m, 1H), 4.52 (td, J=7.0, 13.9 Hz, 1H), 3.51 (br t, J=13.9 Hz, 1H), 3.28-3.19 (m, 2H), 3.16-3.05 (m, 1H), 2.25 (br d, J=13.4 Hz, 1H), 2.08-1.99 (m, 2H), 1.90-1.74 (m, 1H), 1.53 (d, J=6.8 Hz, 6H); LCMS (ESI) [M+H]+: 467.0.

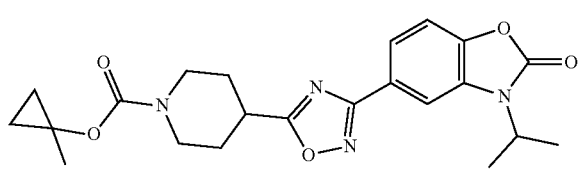 [SMILES: CC(C)n1c(=O)oc2ccc(-c3noc(C4CCN(C(=O)OC5(C)CC5)CC4)n3)cc21]

¹H NMR (400 MHz, CHLOROFORM-d) δ 7.88 (d, J=8.4 Hz, 1H), 7.78 (s, 1H), 7.29 (d, J=8.4 Hz, 1H), 4.59 (spt, J=6.9 Hz, 1H), 4.32-3.96 (m, 2H), 3.25-3.13 (m, 1H), 3.05-3.00 (m, 2H), 2.18-2.10 (m, 2H), 1.95-1.89 (m, 2H), 1.64-1.56 (m, 9H), 0.92-0.86 (m, 2H), 0.69-0.61 (m, 2H); LCMS (ESI) [M+H]+: 427.1.

678

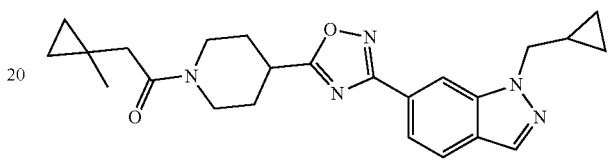

¹H NMR (400 MHz, METHANOL-d₄) δ 8.32 (s, 1H), 8.10 (s, 1H), 7.96-7.78 (m, 2H), 4.39 (d, J=6.8 Hz, 2H), 3.60-3.50 (m, 3H), 3.29-3.21 (m, 2H), 2.47 (br dd, J=3.3, 14.5 Hz, 2H), 2.29-2.10 (m, 2H), 1.44-1.28 (m, 1H), 0.64-0.53 (m, 2H), 0.46 (m, 2H); LCMS (ESI) [M+H]+: 324.1.

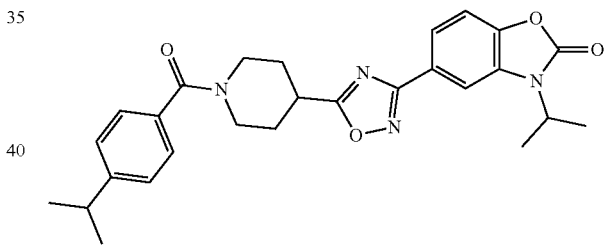

¹H NMR (400 MHz, CHLOROFORM-d) δ 8.20 (s, 1H), 8.06 (s, 1H), 7.92-7.78 (m, 2H), 4.61 (br d, J=14.1 Hz, 1H), 4.36 (d, J=6.8 Hz, 2H), 3.98 (br d, J=13.4 Hz, 1H), 3.37-3.22 (m, 2H), 3.05-2.90 (m, 1H), 2.40 (d, J=4.0 Hz, 2H), 2.23 (br d, J=13.3 Hz, 2H), 2.06-1.86 (m, 2H), 1.40 (br d, J=7.2 Hz, 1H), 1.18 (s, 3H), 0.67-0.55 (m, 2H), 0.49-0.40 (m, 6H); LCMS (ESI) [M+H]+: 420.2.

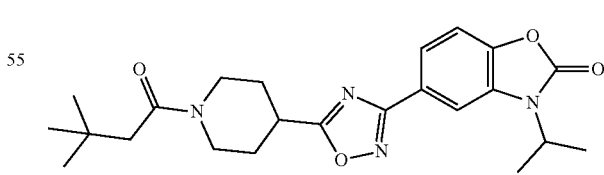

¹H NMR (400 MHz, CHLOROFORM-d) δ 7.85 (dd, J=1.2, 8.4 Hz, 1H), 7.75 (s, 1H), 7.36-7.30 (m, 2H), 7.24 (m, 3H), 4.60-4.50 (m, 2H), 3.98-3.94 (m, 1H), 3.33-3.08 (m, 3H), 2.91 (td, J=6.9, 13.8 Hz, 1H), 2.30-1.90 (m, 4H), 1.56 (d, J=7.0 Hz, 6H), 1.23 (d, J=7.0 Hz, 6H); LCMS (ESI) [M+H]+: 475.1.

¹H NMR (400 MHz, CHLOROFORM-d) δ 7.81 (dd, J=1.1, 8.3 Hz, 1H), 7.71 (s, 1H), 7.22 (d, J=8.3 Hz, 1H), 4.59-4.48 (m, 2H), 3.96 (br d, J=13.8 Hz, 1H), 3.28-3.15 (m, 2H), 2.87 (br t, J=11.2 Hz, 1H), 2.24 (d, J=1.7 Hz, 2H), 2.12 (br d, J=13.2 Hz, 2H), 1.94-1.79 (m, 2H), 1.52 (d, J=7.0 Hz, 6H), 1.00 (s, 9H); LCMS (ESI) [M+H]+: 427.1.

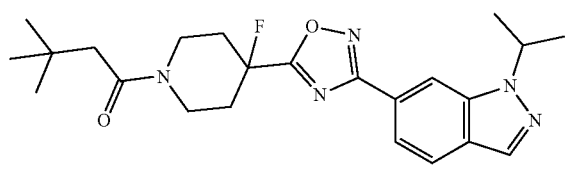 [SMILES: CC(C)n1ncc2ccc(-c3noc(C4(F)CCN(C(=O)CC(C)(C)C)CC4)n3)cc21]

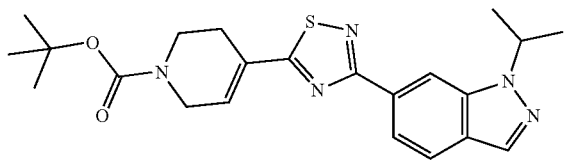 [SMILES: CC(C)n1ncc2ccc(-c3nsc(C4=CCN(C(=O)OC(C)(C)C)CC4)n3)cc21]

¹H NMR (400 MHz, CHLOROFORM-d) δ 8.22 (s, 1H), 8.06 (s, 1H), 7.87-7.80 (m, 2H), 4.96 (spt, J=6.7 Hz, 1H), 4.57 (br d, J=13.6 Hz, 1H), 3.93 (br d, J=14.5 Hz, 1H), 3.66-3.51 (m, 1H), 3.30-3.22 (m, 1H), 2.43-2.21 (m, 6H), 1.62 (d, J=7.0 Hz, 6H), 1.08 (s, 9H); LCMS (ESI) [M+H]+: 428.2.

¹H NMR (400 MHz, CHLOROFORM-d) δ 8.44 (s, 1H), 8.12 (d, J=8.4 Hz, 1H), 8.04 (s, 1H), 7.80 (d, J=8.4 Hz, 1H), 6.89 (br s, 1H), 4.99 (td, J=6.7, 13.3 Hz, 1H), 4.21 (m, 2H), 3.71 (br t, J=5.5 Hz, 2H), 2.77 (br s, J=1.6 Hz, 2H), 1.64 (d, J=6.6 Hz, 6H), 1.51 (s, 9H); LCMS (ESI) [M+H]+: 426.2.

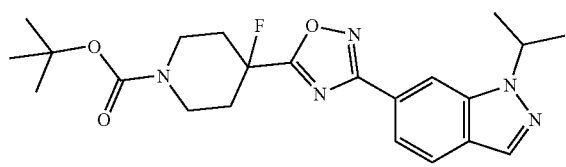

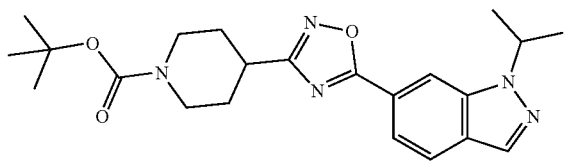 [SMILES: CC(C)n1ncc2ccc(-c3nc(C4CCN(C(=O)OC(C)(C)C)CC4)no3)cc21]

¹H NMR (400 MHz, CHLOROFORM-d) δ 8.25 (s, 1H), 8.08 (s, 1H), 7.90-7.82 (m, 2H), 5.02-4.95 (m, 1H), 4.08-4.00 (m, 2H), 3.40 (br d, J=9.8 Hz, 2H), 2.40-2.24 (m, 4H), 1.65 (d, J=6.7 Hz, 6H), 1.51 (s, 9H); LCMS (ESI) [M+H]+: 430.2.

¹H NMR (400 MHz, CHLOROFORM-d) δ 8.27 (s, 1H), 8.08 (s, 1H), 7.86 (m, 2H), 4.97 (td, J=6.6, 13.2 Hz, 1H), 4.20-4.12 (m, 2H), 3.12-2.87 (m, 3H), 2.08 (br d, J=11.2 Hz, 2H), 1.95-1.79 (m, 2H), 1.64 (d, J=6.6 Hz, 6H), 1.48 (s, 9H); LCMS (ESI) [M+H]+: 412.2.

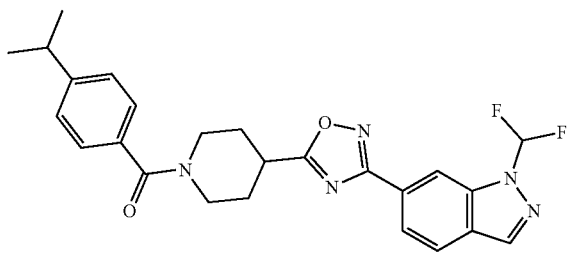

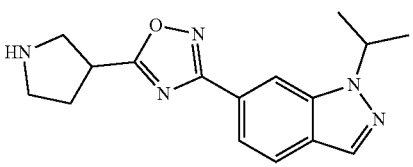 [SMILES: CC(C)n1ncc2ccc(-c3noc(C4CCNC4)n3)cc21]

¹H NMR (400 MHz, DMSO-d₆) δ 8.47 (s, 1H), 8.45 (s, 1H), 8.36-8.07 (t, J=58.8, 1H), 8.09-8.05 (m, 1H), 7.99-7.95 (m, 1H), 7.36-7.28 (m, 4H), 4.05 (br d, J=4.6 Hz, 2H), 3.54-3.41 (m, 1H), 3.26-3.17 (m, 2H), 2.98-2.88 (m, 1H), 2.17 (br dd, J=3.2, 13.3 Hz, 2H), 1.91-1.80 (m, 2H), 1.23 (d, J=6.8 Hz, 6H); LCMS (ESI) [M+H]+: 466.0.

¹H NMR (400 MHz, METHANOL-d₄) δ 8.36 (s, 1H), 8.13 (s, 1H), 7.97-7.82 (m, 2H), 5.08 (td, J=6.6, 13.2 Hz, 1H), 4.25-4.12 (m, 1H), 3.92-3.80 (m, 2H), 3.70-3.49 (m, 2H), 2.79-2.64 (m, 1H), 2.52 (qd, J=6.9, 13.6 Hz, 1H), 1.62 (d, J=6.6 Hz, 6H); LCMS (ESI) [M+H]+: 298.1.

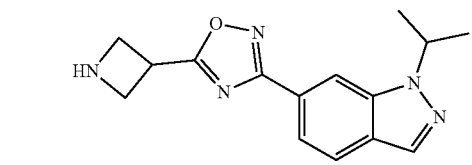 [SMILES: CC(C)n1ncc2ccc(-c3noc(C4CNC4)n3)cc21]

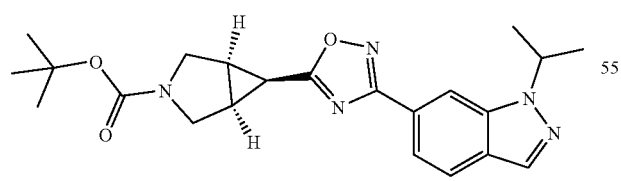

¹H NMR (400 MHz, DMSO-d₆) δ 9.33 (br s, 2H), 8.34 (s, 1H), 8.21 (s, 1H), 7.96 (d, J=8.4 Hz, 1H), 7.78 (d, J=8.4 Hz, 1H), 5.14 (td, J=6.6, 13.0 Hz, 1H), 4.64-4.45 (m, 1H), 4.41-4.28 (m, 4H), 1.51 (d, J=6.5 Hz, 6H); LCMS (ESI) [M+H]+: 284.1.

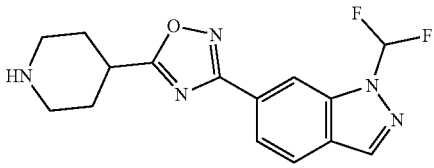 [SMILES: FC(F)n1ncc2ccc(-c3noc(C4CCNCC4)n3)cc21]

¹H NMR (400 MHz, CHLOROFORM-d) δ 8.16 (s, 1H), 8.05 (s, 1H), 7.84-7.77 (m, 2H), 4.94 (m, 1H), 3.92-3.72 (m, 2H), 3.61-3.48 (m, 2H), 2.40 (m, 2H), 2.17 (t, J=3.1 Hz, 1H), 1.62 (d, J=7.0 Hz, 6H), 1.47 (s, 9H); LCMS (ESI) [M+H]+: 410.2.

¹H NMR (400 MHz, DMSO-d₆) δ 9.04 (br s, 2H), 8.56 (s, 1H), 8.50-8.21 (t, J=58 Hz, 1H), 8.47 (s, 1H), 8.11 (d, J=8.4 Hz, 1H), 7.99 (d, J=8.4 Hz, 1H), 3.60-3.51 (m, 1H), 3.36 (br d, J=12.8 Hz, 2H), 3.09 (br t, J=11.0 Hz, 2H), 2.30 (br d, J=14.3 Hz, 2H), 2.14-2.01 (m, 2H); LCMS (ESI) [M+H]+: 320.1.

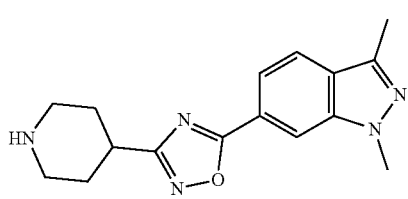 [SMILES: Cc1nn(C)c2cc(-c3nc(C4CCNCC4)no3)ccc12]

¹H NMR (400 MHz, DMSO-d₆) δ 9.31-8.98 (m, 2H), 8.36 (s, 1H), 7.94 (br d, J=8.4 Hz, 1H), 7.76 (d, J=8.4 Hz, 1H), 4.08 (s, 3H), 3.62-3.58 (m, 1H), 3.39-3.24 (m, 3H), 3.15-3.01 (m, 2H), 2.52 (s, 3H), 2.25-2.15 (m, 2H), 2.09-1.95 (m, 2H); LCMS (ESI) [M+H]+: 298.1.

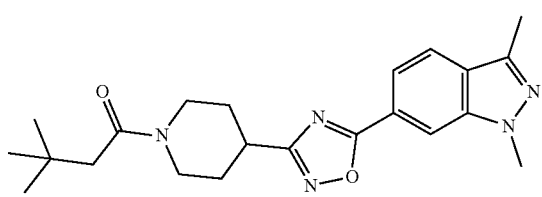 [SMILES: Cc1nn(C)c2cc(-c3nc(C4CCN(C(=O)CC(C)(C)C)CC4)no3)ccc12]

¹H NMR (400 MHz, CHLOROFORM-d) δ 8.15 (s, 1H), 7.86-7.82 (m, 1H), 7.79-7.75 (m, 1H), 4.66 (br d, J=13.8 Hz, 1H), 4.09 (s, 3H), 4.04 (br d, J=15.0 Hz, 1H), 3.26 (br t, J=11.7 Hz, 1H), 3.18-3.08 (m, 1H), 2.89 (br t, J=11.8 Hz, 1H), 2.60 (s, 3H), 2.31 (s, 2H), 2.14 (br dd, J=3.1, 13.6 Hz, 2H), 1.99-1.80 (m, 2H), 1.08 (s, 9H); LCMS (ESI) [M+H]+: 396.2.

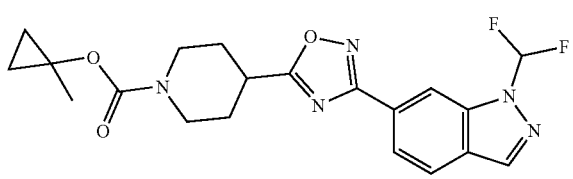 [SMILES: CC1(OC(=O)N2CCC(c3nc(-c4ccc5cnn(C(F)F)c5c4)no3)CC2)CC1]

¹H NMR (400 MHz, DMSO-d₆) δ 8.55 (s, 1H), 8.49-8.21 (t, J=58 Hz, 1H), 8.48 (s, 1H), 8.11 (d, J=8.2 Hz, 1H), 7.99 (dd, J=1.2, 8.4 Hz, 1H), 4.05-3.80 (m, 2H), 3.41 (tt, J=3.9, 11.0 Hz, 1H), 3.02 (br t, J=10.8 Hz, 2H), 2.16-2.07 (m, 2H), 1.79-1.66 (m, 2H), 1.49 (s, 3H), 0.83-0.78 (m, 2H), 0.67-0.57 (m, 2H); LCMS (ESI) [M+H]+: 418.1.

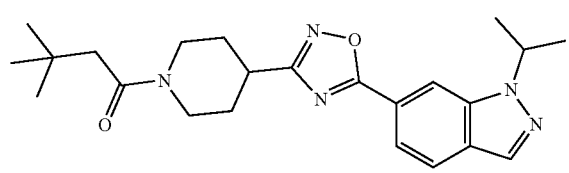 [SMILES: CC(C)n1ncc2ccc(-c3nc(C4CCN(C(=O)CC(C)(C)C)CC4)no3)cc21]

¹H NMR (400 MHz, CHLOROFORM-d) δ 8.28 (s, 1H), 8.10 (s, 1H), 7.87 (m, 2H), 4.98 (td, J=6.7, 13.3 Hz, 1H), 4.67 (br d, J=13.5 Hz, 1H), 4.06-4.00 (m, 1H), 3.27 (br t, J=11.6 Hz, 1H), 3.18-3.07 (m, 1H), 2.90 (br t, J=11.4 Hz, 1H), 2.33 (d, J=1.1 Hz, 2H), 2.16 (br dd, J=3.1, 13.2 Hz, 2H), 2.02-1.78 (m, 2H), 1.65 (d, J=6.8 Hz, 6H), 1.09 (s, 9H); LCMS (ESI) [M+H]+: 410.2.

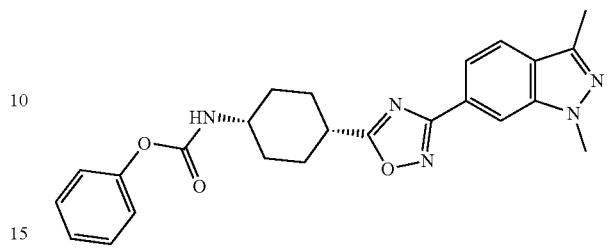

¹H NMR (400 MHz, CHLOROFORM-d) δ 8.12 (s, 1H), 7.85 (dd, J=1.2, 8.4 Hz, 1H), 7.78-7.72 (d, J=8.4 Hz, 1H), 7.41-7.32 (m, 2H), 7.24-7.17 (m, 1H), 7.14 (d, J=7.7 Hz, 2H), 5.11 (br d, J=6.5 Hz, 1H), 4.09 (s, 3H), 3.95-3.83 (m, 1H), 3.31-3.21 (m, 1H), 2.61 (s, 3H), 2.29-2.18 (m, 2H), 2.11-1.92 (m, 4H), 1.89-1.78 (m, 2H); LCMS (ESI) [M+H]+: 432.2.

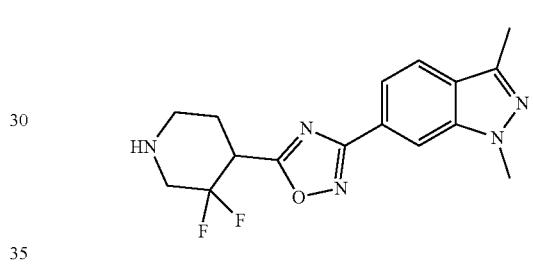

¹H NMR (400 MHz, METHANOL-d₄) δ 8.27 (s, 1H), 7.98-7.83 (m, 2H), 4.42-4.25 (m, 1H), 4.11 (s, 3H), 3.99 (td, J=8.6, 13.6 Hz, 1H), 3.88-3.74 (m, 1H), 3.69 (br d, J=13.6 Hz, 1H), 3.46-3.35 (m, 1H), 2.72-2.56 (m, 5H); LCMS (ESI) [M+H]+: 334.1.

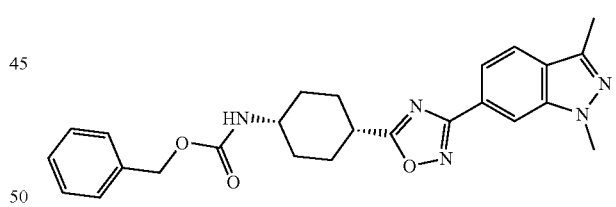

¹H NMR (400 MHz, CHLOROFORM-d) δ 8.10 (s, 1H), 7.84 (dd, J=1.2, 8.4 Hz, 1H), 7.73 (dd, J=0.6, 8.4 Hz, 1H), 7.42-7.30 (m, 5H), 5.11 (s, 2H), 4.86-4.82 (m, 1H), 4.08 (s, 3H), 3.86-3.82 (m, 1H), 3.27-3.18 (m, 1H), 2.60 (s, 3H), 2.22-2.10 (m, 2H), 2.07-1.97 (m, 2H), 1.91-1.87 (m, 2H), 1.81-1.69 (m, 2H); LCMS (ESI) [M+H]+: 446.2.

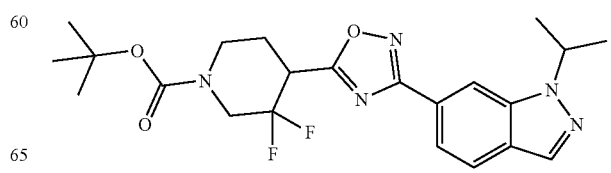

¹H NMR (400 MHz, CHLOROFORM-d) δ 8.15 (d, J=0.7 Hz, 1H), 7.99 (s, 1H), 7.82-7.77 (m, 1H), 7.76-7.72 (m, 1H), 4.89 (spt, J=6.7 Hz, 1H), 4.40-3.98 (m, 2H), 3.75-3.58 (m, 1H), 3.51-3.36 (m, 1H), 3.31-3.13 (m, 1H), 2.39-2.12 (m, 2H), 1.56 (d, J=6.6 Hz, 6H), 1.48-1.32 (m, 9H); LCMS (ESI) [M+H]+: 448.2.

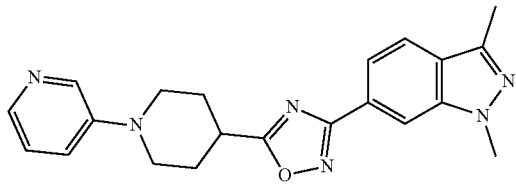 [SMILES: Cc1nn(C)c2cc(-c3noc(C4CCN(c5cccnc5)CC4)n3)ccc12]

¹H NMR (300 MHz, CHLOROFORM-d) δ 8.39 (s, 1H), 8.12 (s, 2H), 7.85 (dd, J=8.4, 1.3 Hz, 1H), 7.75 (dd, J=8.4, 0.9 Hz, 1H), 7.26-7.14 (m, 1H), 4.09 (s, 3H), 3.80 (d, J=12.7 Hz, 2H), 3.25 (m, 1H), 3.07 (d, J=14.2 Hz, 2H), 2.61 (s, 3H), 2.32 (s, 2H), 2.26-2.16 (m, 1H); LCMS (ESI) [M+H]+: 375.1.

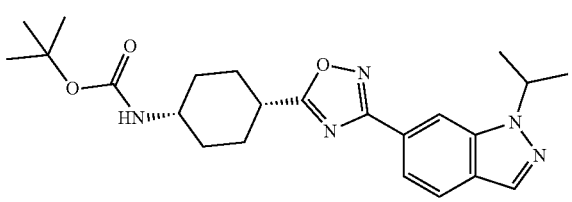 [SMILES: CC(C)n1ncc2ccc(-c3noc([C@H]4CC[C@@H](NC(=O)OC(C)(C)C)CC4)n3)cc21]

¹H NMR (400 MHz, CHLOROFORM-d) δ 8.22 (s, 1H), 8.07 (s, 1H), 7.88-7.80 (m, 2H), 4.98 (td, J=6.6, 13.4 Hz, 1H), 4.65-4.50 (m, 1H), 3.80-3.70 (m, 1H), 3.21 (br d, J=4.0 Hz, 1H), 2.16 (br d, J=7.9 Hz, 2H), 2.05-1.97 (m, 2H), 1.85 (br d, J=4.4 Hz, 2H), 1.75-1.70 (m, 2H), 1.64 (d, J=6.6 Hz, 6H), 1.46 (s, 9H); LCMS (ESI) [M+H]+: 426.2.

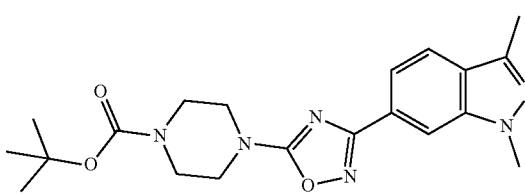

¹H NMR (400 MHz, CHLOROFORM-d) δ 8.04 (s, 1H), 7.79-7.76 (m, 1H), 7.73-7.70 (m, 1H), 4.08 (s, 3H), 3.76-3.70 (m, 4H), 3.65-3.59 (m, 4H), 2.61 (s, 3H), 1.52 (s, 9H); LCMS (ESI) [M+H]+: 399.1.

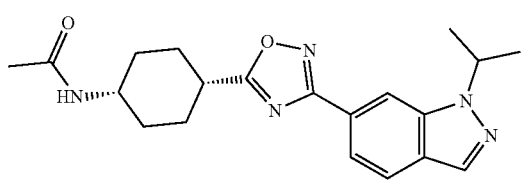 [SMILES: CC(=O)N[C@H]1CC[C@@H](c2nc(-c3ccc4cnn(C(C)C)c4c3)no2)CC1]

¹H NMR (400 MHz, CHLOROFORM-d) δ 8.20 (s, 1H), 8.06 (s, 1H), 7.88-7.78 (m, 2H), 5.50-5.35 (m, 1H), 4.96 (spt, J=6.7 Hz, 1H), 4.04 (td, J=3.9, 8.2 Hz, 1H), 3.30-3.22 (m, 1H), 2.25-2.16 (m, 2H), 2.03 (qd, J=4.6, 9.2 Hz, 2H), 1.98 (s, 3H), 1.93-1.84 (m, 2H), 1.70-1.60 (m, 8H); LCMS (ESI) [M+H]+: 368.2.

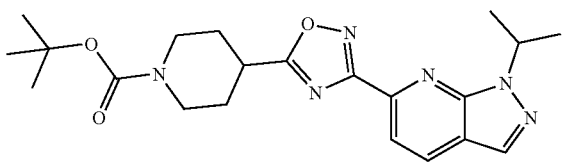 [SMILES: CC(C)n1ncc2ccc(-c3noc(C4CCN(C(=O)OC(C)(C)C)CC4)n3)nc21]

¹H NMR (400 MHz, CHLOROFORM-d) δ 8.18 (d, J=8.4 Hz, 1H), 8.09 (s, 1H), 7.95 (d, J=8.2 Hz, 1H), 5.52 (spt, J=6.7 Hz, 1H), 4.20-4.10 (m, 2H), 3.26 (tt, J=3.8, 11.1 Hz, 1H), 2.99 (br t, J=12.0 Hz, 2H), 2.16 (br d, J=10.4 Hz, 2H), 2.00-1.89 (m, 2H), 1.59 (d, J=6.6 Hz, 6H), 1.48 (s, 9H); LCMS (ESI) [M+H]+: 413.2.

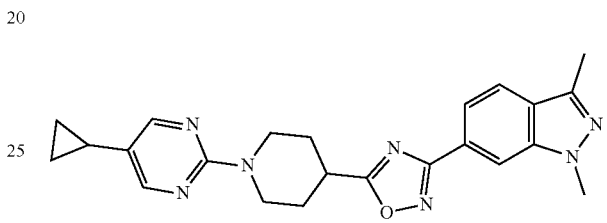

¹H NMR (400 MHz, CHLOROFORM-d) δ 8.15 (s, 2H), 8.10 (s, 1H), 7.83 (dd, J=1.2, 8.4 Hz, 1H), 7.73 (dd, J=0.6, 8.4 Hz, 1H), 4.74 (td, J=3.5, 13.6 Hz, 2H), 4.07 (s, 3H), 3.32 (tt, J=4.0, 11.0 Hz, 1H), 3.20 (ddd, J=2.8, 11.3, 13.7 Hz, 2H), 2.60 (s, 3H), 2.24 (br dd, J=3.2, 13.5 Hz, 2H), 2.07-1.92 (m, 2H), 1.73 (tt, J=5.1, 8.5 Hz, 1H), 0.97-0.86 (m, 2H), 0.63-0.57 (m, 2H); LCMS (ESI) [M+H]+: 416.1.

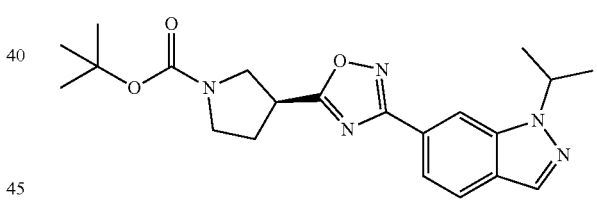

¹H NMR (400 MHz, DMSO-d₆) δ 8.29 (s, 1H), 8.19 (s, 1H), 7.92 (d, J=8.3 Hz, 1H), 7.75 (dd, J=1.0, 8.4 Hz, 1H), 5.14 (spt, J=6.5 Hz, 1H), 3.93 (br d, J=6.7 Hz, 1H), 3.78 (br d, J=7.2 Hz, 1H), 3.68-3.61 (m, 1H), 3.51-3.44 (m, 1H), 3.40 (br d, J=6.6 Hz, 1H), 2.46-2.33 (m, 1H), 2.24 (br d, J=7.1 Hz, 1H), 1.50 (d, J=6.6 Hz, 6H), 1.42 (s, 9H); LCMS (ESI) [M+H]+: 398.2.

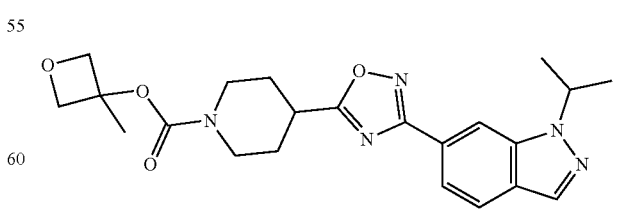

¹H NMR (400 MHz, CHLOROFORM-d) δ 8.23 (s, 1H), 8.08 (s, 1H), 7.92-7.81 (m, 2H), 4.98 (quind, J=6.7, 13.3 Hz, 1H), 4.83 (d, J=7.1 Hz, 2H), 4.53 (d, J=7.5 Hz, 2H), 4.17 (br s, 2H), 3.35-3.20 (m, 1H), 3.13 (br s, 2H), 2.22 (br d, J=11.1 Hz, 2H), 2.06-1.92 (m, 2H), 1.78 (s, 3H), 1.65 (d, J=6.7 Hz, 6H); LCMS (ESI) [M+H]+: 426.1.

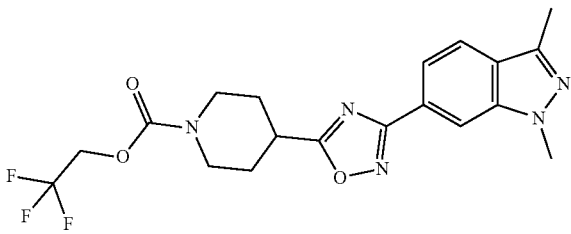 [SMILES: Cc1nn(C)c2cc(-c3noc(C4CCN(C(=O)OCC(F)(F)F)CC4)n3)ccc12]

¹H NMR (400 MHz, CHLOROFORM-d) δ 8.10 (s, 1H), 7.86-7.81 (m, 1H), 7.77-7.72 (m, 1H), 4.53 (dq, J=2.2, 8.4 Hz, 2H), 4.20 (br t, J=16.1 Hz, 2H), 4.08 (s, 3H), 3.32-3.23 (m, 1H), 3.22-3.10 (m, 2H), 2.60 (s, 3H), 2.22 (br d, J=11.9 Hz, 2H), 2.07-1.94 (m, 2H); LCMS (ESI) [M+H]+: 424.1.

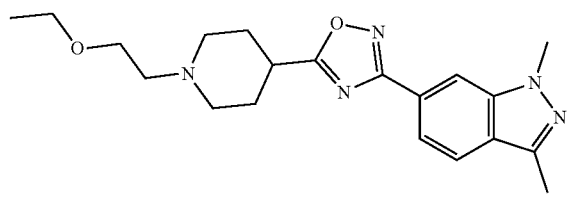 [SMILES: CCOCCN1CCC(c2nc(-c3ccc4c(C)nn(C)c4c3)no2)CC1]

¹H NMR (400 MHz, CHLOROFORM-d) δ 8.10 (s, 1H), 7.84 (dd, J=1.2, 8.4 Hz, 1H), 7.73 (dd, J=0.7, 8.4 Hz, 1H), 4.08 (s, 3H), 3.60 (t, J=5.9 Hz, 2H), 3.54 (q, J=7.0 Hz, 2H), 3.10-2.99 (m, 3H), 2.65 (t, J=6.0 Hz, 2H), 2.60 (s, 3H), 2.27 (dt, J=2.3, 11.3 Hz, 2H), 2.21-2.03 (m, 4H), 1.23 (t, J=7.0 Hz, 3H); LCMS (ESI) [M+H]+: 370.2.

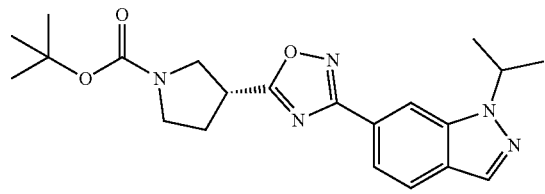 [SMILES: CC(C)n1ncc2ccc(-c3noc([C@@H]4CCN(C(=O)OC(C)(C)C)C4)n3)cc21]

¹H NMR (400 MHz, CHLOROFORM-d) δ 8.21 (s, 1H), 8.06 (s, 1H), 7.89-7.78 (m, 2H), 4.97 (td, J=6.6, 13.4 Hz, 1H), 4.02-3.43 (m, 5H), 2.52-2.32 (m, 2H), 1.64 (d, J=6.6 Hz, 6H), 1.50 (s, 9H); LCMS (ESI) [M+H]+: 398.2.

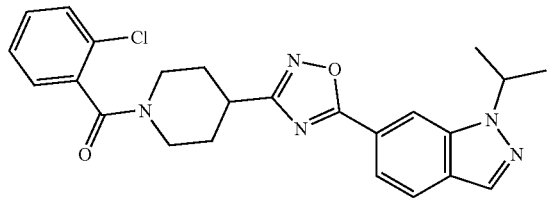 [SMILES: CC(C)n1ncc2ccc(-c3nc(C4CCN(C(=O)c5ccccc5Cl)CC4)no3)cc21]

¹H NMR (400 MHz, CHLOROFORM-d) δ 8.28 (s, 1H), 8.10 (s, 1H), 7.91-7.81 (m, 2H), 7.47-7.40 (m, 1H), 7.39-7.28 (m, 3H), 4.98 (td, J=6.6, 13.5 Hz, 1H), 4.76 (br t, J=12.5 Hz, 1H), 3.65-3.52 (m, 1H), 3.36-3.10 (m, 3H), 2.28 (br dd, J=3.5, 13.6 Hz, 1H), 2.15-1.95 (m, 2.5H), 1.94-1.79 (m, 0.5H), 1.65 (d, J=6.6 Hz, 6H); LCMS (ESI) [M+H]+: 450.1.

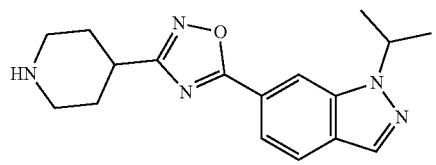 [SMILES: CC(C)n1ncc2ccc(-c3nc(C4CCNCC4)no3)cc21]

¹H NMR (400 MHz, DMSO-d₆) δ 9.13 (s, 2H), 8.49 (s, 1H), 8.25 (s, 1H), 7.99 (d, J=8.3 Hz, 1H), 7.80 (dd, J=1.1, 8.6 Hz, 1H), 5.22 (spt, J=6.4 Hz, 1H), 3.39-3.35 (m, 1H), 3.33-3.24 (m, 2H), 3.14-3.00 (m, 2H), 2.20 (br d, J=11.8 Hz, 2H), 2.08-1.92 (m, 2H), 1.50 (d, J=6.6 Hz, 6H); LCMS (ESI) [M+H]+: 312.1.

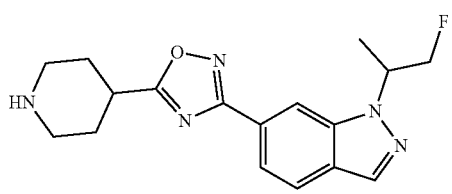 [SMILES: CC(CF)n1ncc2ccc(-c3noc(C4CCNCC4)n3)cc21]

¹H NMR (400 MHz, CHLOROFORM-d) δ 8.16 (s, 1H), 8.12 (s, 1H), 7.94-7.89 (m, 1H), 7.87-7.82 (m, 1H), 5.46 (q, J=7.2 Hz, 1H), 4.20-4.05 (m 2H), 3.72 (s, 3H), 3.21 (tt, J=3.9, 10.8 Hz, 1H), 3.02 (br t, J=11.9 Hz, 2H), 2.15 (br d, J=10.5 Hz, 2H), 1.98 (d, J=7.2 Hz, 3H), 1.97-1.87 (m, 2H), 1.49 (s, 9H); LCMS (ESI) [M+H]+: 456.2.

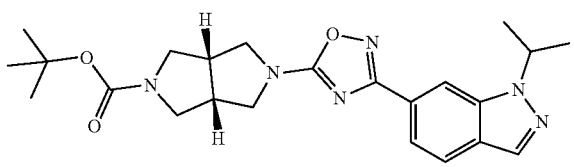 [SMILES: CC(C)n1ncc2ccc(-c3noc(N4C[C@H]5CN(C(=O)OC(C)(C)C)C[C@H]5C4)n3)cc21]

¹H NMR (400 MHz, CHLOROFORM-d) δ 8.13 (s, 1H), 8.04 (s, 1H), 7.77 (m, 2H), 4.95 (m, 1H), 3.99-3.87 (m, 2H), 3.74-3.56 (m, 4H), 3.47-3.24 (m, 2H), 3.07 (br s, 2H), 1.61 (d, J=7.0 Hz, 6H), 1.47 (s, 9H) LCMS (ESI) [M+H]+: 439.2.

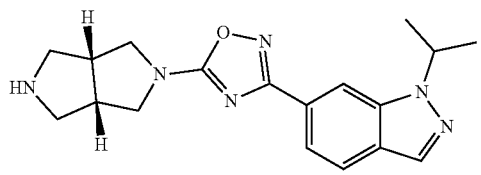 [SMILES: CC(C)n1ncc2ccc(-c3noc(N4C[C@H]5CNC[C@H]5C4)n3)cc21]

¹H NMR (400 MHz, METHANOL-d₄) δ 8.22 (s, 1H), 8.09 (s, 1H), 7.84 (dd, J=1.2, 8.4 Hz, 1H), 7.73 (dd, J=0.7, 8.4 Hz, 1H), 5.03 (m, 1H), 3.93 (br dd, J=7.4, 11.2 Hz, 2H), 3.75 (dd, J=3.1, 11.2 Hz, 2H), 3.65 (br dd, J=6.8, 11.6 Hz, 2H), 3.41-3.32 (m, 3H), 3.29 (m, 1H), 1.59 (d, J=6.6 Hz, 6H); LCMS (ESI) [M+H]+: 339.1.

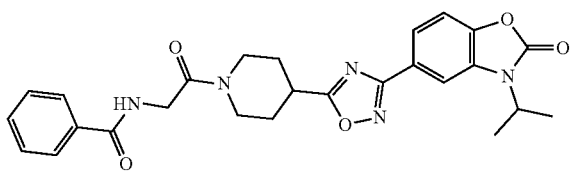 [SMILES: CC(C)n1c(=O)oc2ccc(-c3noc(C4CCN(C(=O)CNC(=O)c5ccccc5)CC4)n3)cc21]

¹H NMR (400 MHz, CHLOROFORM-d) δ 7.92-7.84 (m, 3H), 7.79 (d, J=1.1 Hz, 1H), 7.56-7.51 (m, 1H), 7.49-7.43 (m, 2H), 7.36-7.28 (m, 2H), 4.64-4.49 (m, 2H), 4.32 (t, J=3.2 Hz, 2H), 3.93 (br d, J=13.7 Hz, 1H), 3.40-3.30 (m, 2H), 3.14 (br t, J=11.0 Hz, 1H), 2.33-2.21 (m, 2H), 2.09-1.94 (m, 2H), 1.60 (d, J=6.8 Hz, 6H); LCMS (ESI) [M+H]+: 490.2.

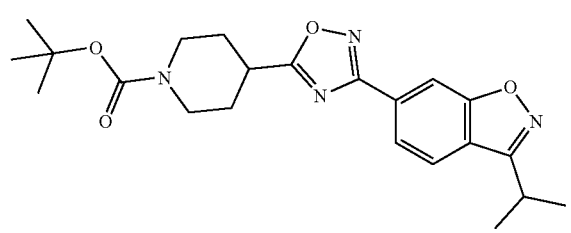 [SMILES: CC(C)c1noc2cc(-c3noc(C4CCN(C(=O)OC(C)(C)C)CC4)n3)ccc12]

¹H NMR (400 MHz, CHLOROFORM-d) δ 8.29 (s, 1H), 8.04 (dd, J=1.2, 8.3 Hz, 1H), 7.81 (dd, J=0.6, 8.2 Hz, 1H), 4.20-4.05 (m, 2H), 3.46 (spt, J=7.0 Hz, 1H), 3.21 (tt, J=3.9, 10.9 Hz, 1H), 3.02 (br t, J=11.6 Hz, 2H), 2.15 (br dd, J=3.0, 13.3 Hz, 2H), 1.92 (dtd, J=4.2, 11.1, 13.5 Hz, 2H), 1.53 (d, J=7.0 Hz, 6H), 1.49 (s, 9H); LCMS (ESI) [M+H]+: 413.2.

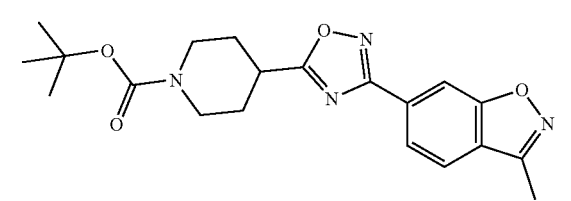 [SMILES: Cc1noc2cc(-c3noc(C4CCN(C(=O)OC(C)(C)C)CC4)n3)ccc12]

¹H NMR (400 MHz, CHLOROFORM-d) δ 8.28 (s, 1H), 8.05 (dd, J=1.1, 8.2 Hz, 1H), 7.73 (d, J=8.2 Hz, 1H), 4.20-4.05 (m, 2H), 3.20 (tt, J=3.9, 10.9 Hz, 1H), 3.01 (br t, J=11.9 Hz, 2H), 2.63 (s, 3H), 2.14 (br dd, J=3.0, 13.3 Hz, 2H), 1.97-1.85 (m, 2H), 1.48 (s, 9H); LCMS (ESI) [M−55]+: 329.1.

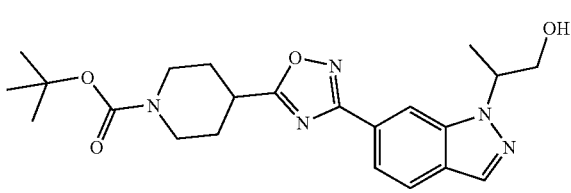 [SMILES: CC(CO)n1ncc2ccc(-c3noc(C4CCN(C(=O)OC(C)(C)C)CC4)n3)cc21]

¹H NMR (400 MHz, CHLOROFORM-d) δ 8.20 (s, 1H), 8.08 (s, 1H), 7.91-7.87 (m, 1H), 7.86-7.81 (m, 1H), 4.95-4.83 (m, 1H), 4.27-4.02 (m, 4H), 3.21 (tt, J=3.9, 10.9 Hz, 1H), 3.02 (br t, J=11.6 Hz, 2H), 2.82-2.78 (m, 1H), 2.16 (br dd, J=2.6, 13.3 Hz, 2H), 2.00-1.87 (m, 2H), 1.60 (d, J=6.7 Hz, 3H), 1.49 (s, 9H); LCMS (ESI) [M+H]+: 428.2.

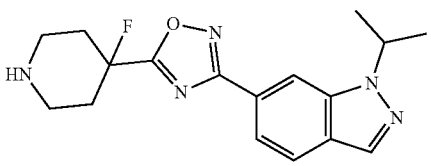 [SMILES: CC(C)n1ncc2ccc(-c3noc(C4(F)CCNCC4)n3)cc21]

¹H NMR (400 MHz, CHLOROFORM-d) δ 8.24 (s, 1H), 8.06 (s, 1H), 7.88-7.78 (m, 2H), 5.01-4.93 (m, 1H), 3.19-2.99 (m, 4H), 2.37-2.24 (m, 4H), 1.63 (d, J=6.6 Hz, 6H); LCMS (ESI) [M+H]+: 330.1.

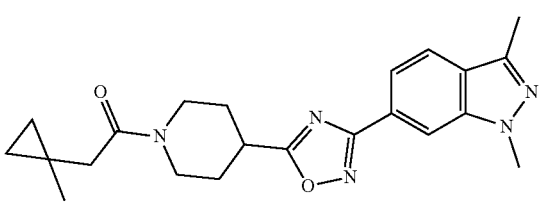 [SMILES: Cc1nn(C)c2cc(-c3noc(C4CCN(C(=O)CC5(C)CC5)CC4)n3)ccc12]

¹H NMR (400 MHz, CHLOROFORM-d) δ 7.69 (s, 1H), 7.45-7.41 (m, 1H), 7.36-7.32 (m, 1H), 4.20 (br d, J=13.5 Hz, 1H), 3.68 (s, 3H), 3.57 (br d, J=14.1 Hz, 1H), 2.92-2.84 (m, 2H), 2.58 (br t, J=11.8 Hz, 1H), 2.20 (s, 3H), 2.00 (d, J=3.1 Hz, 2H), 1.83 (br d, J=13.2 Hz, 2H), 1.62-1.50 (m, 2H), 0.78 (s, 3H), 0.08--0.03 (m, 4H); LCMS (ESI) [M+H]+: 394.2.

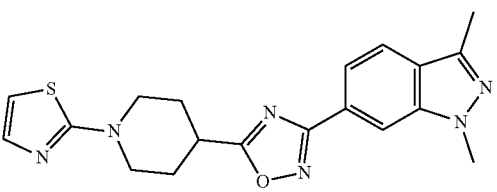 [SMILES: Cc1nn(C)c2cc(-c3noc(C4CCN(c5nccs5)CC4)n3)ccc12]

¹H NMR (300 MHz, CHLOROFORM-d) δ 8.11 (s, J=1.0 Hz, 1H), 7.85 (dd, J=8.4, 1.3 Hz, 1H), 7.75 (dd, J=8.4, 0.8 Hz, 1H), 7.22 (d, J=3.6 Hz, 1H), 6.62 (d, J=3.6 Hz, 1H), 4.14 (m, 2H), 4.09 (s, 3H), 3.32 (td, J=12.9, 11.9, 3.1 Hz, 2H), 2.61 (s, 3H), 2.38-2.25 (m, 2H), 2.25-2.10 (m, 2H); LCMS (ESI) [M+H]+: 381.1.

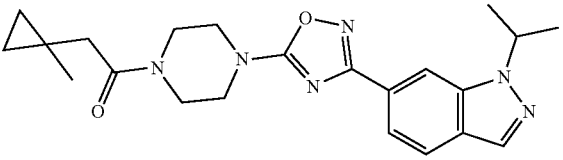 [SMILES: CC(C)n1ncc2ccc(-c3noc(N4CCN(C(=O)CC5(C)CC5)CC4)n3)cc21]

¹H NMR (400 MHz, CHLOROFORM-d) δ 8.13 (s, 1H), 8.05 (s, 1H), 7.78 (s, 2H), 4.95 (td, J=6.6, 13.3 Hz, 1H), 3.93-3.57 (m, 8H), 2.41 (s, 2H), 1.63 (d, J=6.7 Hz, 6H), 1.18 (s, 3H), 0.58-0.37 (m, 4H); LCMS (ESI) [M+H]+: 409.2.

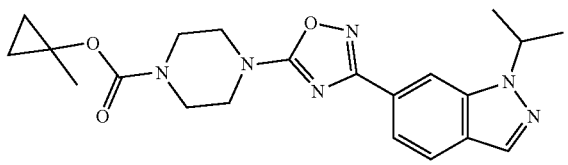 [SMILES: CC(C)n1ncc2ccc(-c3noc(N4CCN(C(=O)OC5(C)CC5)CC4)n3)cc21]

¹H NMR (400 MHz, CHLOROFORM-d) δ 8.13 (s, 1H), 8.05 (s, 1H), 7.78 (d, J=0.9 Hz, 2H), 5.03-4.86 (m, 1H), 3.84-3.49 (m, 8H), 1.62 (d, J=6.7 Hz, 6H), 1.59 (s, 3H), 0.95-0.88 (m, 2H), 0.72-0.64 (m, 2H); LCMS (ESI) [M+H]+: 411.2.

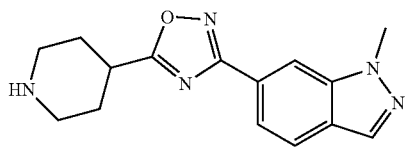

¹H NMR (400 MHz, METHANOL-d₄) δ 8.27 (s, 1H), 8.08 (s, 1H), 7.90-7.83 (m, 2H), 4.14 (s, 3H), 3.59-3.50 (m, 3H), 3.28-3.21 (m, 2H), 2.46 (br dd, J=3.6, 14.9 Hz, 2H), 2.24-2.13 (m, 2H); LCMS (ESI) [M+H]+: 284.1.

¹H NMR (400 MHz, CHLOROFORM-d) δ 8.13 (s, 1H), 8.04 (s, 1H), 7.79-7.75 (m, 2H), 5.01-4.90 (m, 1H), 3.96 (td, J=7.9, 10.8 Hz, 2H), 3.88-3.77 (m, 2H), 3.68-3.50 (m, 3H), 3.45 (dd, J=5.3, 10.7 Hz, 1H), 3.23-3.03 (m, 2H), 2.19 (s, 2H), 1.61 (d, J=6.6 Hz, 6H), 1.06 (s, 9H); LCMS (ESI) [M+H]+: 437.2.

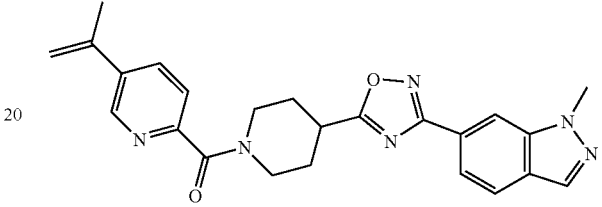

¹H NMR (400 MHz, CHLOROFORM-d) δ 8.63 (d, J=1.8 Hz, 1H), 8.10 (d, J=0.6 Hz, 1H), 7.96 (d, J=0.7 Hz, 1H), 7.81-7.73 (m, 3H), 7.59 (d, J=8.2 Hz, 1H), 5.42 (s, 1H), 5.19 (s, 1H), 4.62 (br d, J=13.4 Hz, 1H), 4.09 (s, 4H), 3.36-3.27 (m, 2H), 3.22-3.11 (m, 1H), 2.30-2.20 (m, 1H), 2.14-2.03 (m, 6H); LCMS (ESI) [M+H]+: 429.2.

¹H NMR (400 MHz, CHLOROFORM-d) δ 8.21 (s, 1H), 8.04 (s, 1H), 7.86-7.74 (m, 2H), 5.02-4.89 (m, 1H), 4.02 (d, J=11.5 Hz, 1H), 3.81 (d, J=11.5 Hz, 1H), 3.50 (dt, J=2.8, 11.9 Hz, 2H), 2.32-2.16 (m, 3H), 1.61 (dd, J=6.7, 11.7 Hz, 6H), 1.19 (s, 9H); LCMS (ESI) [M+H]+: 410.2.

¹H NMR (400 MHz, METHANOL-d₄) δ 8.25-8.12 (m, 1H), 7.83 (br s, 2H), 4.47 (br d, J=13.4 Hz, 1H), 4.14-4.01 (m, 6H), 3.63 (br s, 2H), 3.47-3.35 (m, 2H), 3.07-2.90 (m, 2H), 2.83 (br d, J=5.7 Hz, 2H), 2.59 (s, 3H), 2.34-2.18 (m, 2H), 2.03-1.83 (m, 2H), 1.45 (s, 9H); LCMS (ESI) [M+H]+: 495.3.

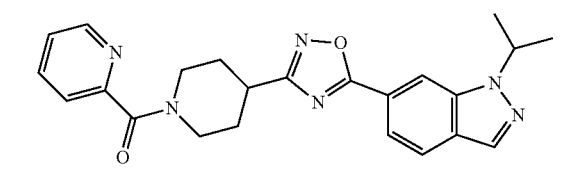 [SMILES: CC(C)n1ncc2ccc(-c3nc(C4CCN(C(=O)c5ccccn5)CC4)no3)cc21]

¹H NMR (400 MHz, CHLOROFORM-d) δ 8.62 (d, J=4.2 Hz, 1H), 8.29 (d, J=0.9 Hz, 1H), 8.10 (s, 1H), 7.87 (s, 2H), 7.82 (dt, J=1.8, 7.7 Hz, 1H), 7.67 (d, J=7.7 Hz, 1H), 7.36 (ddd, J=1.1, 4.9, 7.7 Hz, 1H), 4.99 (td, J=6.6, 13.4 Hz, 1H), 4.74 (br d, J=13.9 Hz, 1H), 4.08 (br d, J=12.6 Hz, 1H), 3.40-3.27 (m, 1H), 3.26-3.10 (m, 2H), 2.26 (br d, J=10.6 Hz, 1H), 2.16-1.95 (m, 3H), 1.65 (d, J=6.6 Hz, 6H); LCMS (ESI) [M+H]+: 417.1.

¹H NMR (400 MHz, CHLOROFORM-d) δ 8.23 (s, 1H), 8.11 (s, 1H), 7.92-7.86 (m, 1H), 7.86-7.79 (m, 1H), 5.17-5.02 (m, 1H), 4.91 (dd, J=8.0, 9.2 Hz, 0.5H), 4.84-4.74 (m, 1H), 4.67 (dd, J=4.9, 9.3 Hz, 0.5H), 4.16 (br s, 2H), 3.21 (tt, J=3.9, 10.9 Hz, 1H), 3.02 (br t, J=11.7 Hz, 2H), 2.22-2.09 (m, 2H), 2.02-1.87 (m, 2H), 1.66 (dd, J=1.6, 6.8 Hz, 3H), 1.49 (s, 9H); LCMS (ESI) [M+H]+: 430.1.

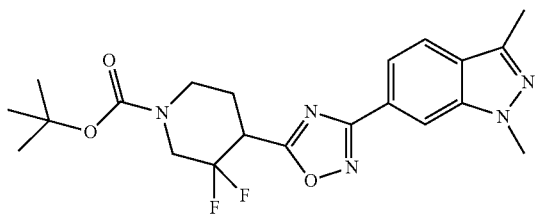 [SMILES: Cc1nn(C)c2cc(-c3noc(C4CCN(C(=O)OC(C)(C)C)CC4(F)F)n3)ccc12]

¹H NMR (400 MHz, CHLOROFORM-d) δ 8.14 (s, 1H), 7.89 (dd, J=0.9, 8.4 Hz, 1H), 7.77 (d, J=8.4 Hz, 1H), 4.31 (br s, 1H), 4.22-4.14 (m, 1H), 4.13 (s, 3H), 3.79-3.66 (m, 1H), 3.48 (br d, J=14.5 Hz, 1H), 3.27 (br t, J=10.6 Hz, 1H), 2.65 (s, 3H), 2.42-2.30 (m, 1H), 2.30-2.20 (m, 1H), 1.51 (s, 9H); LCMS (ESI) [M+H]+: 434.2.

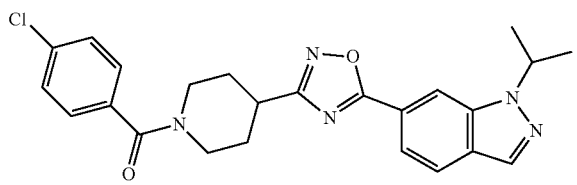 [SMILES: CC(C)n1ncc2ccc(-c3nc(C4CCN(C(=O)c5ccc(Cl)cc5)CC4)no3)cc21]

¹H NMR (400 MHz, DMSO-d₆) δ 8.44 (s, 1H), 8.21 (s, 1H), 7.98 (m, J=8.4 Hz, 1H), 7.80 (dd, J=0.9, 8.4 Hz, 1H), 7.53-7.48 (m, 2H), 7.47-7.42 (m, 2H), 5.18 (spt, J=6.7 Hz, 1H), 4.00-4.2 (m, 2H), 3.35-3.16 (m, 3H), 2.10 (br d, J=10.8 Hz, 2H), 1.90-1.71 (m, 2H), 1.54 (d, J=6.6 Hz, 6H); LCMS (ESI) [M+H]+: 450.1.

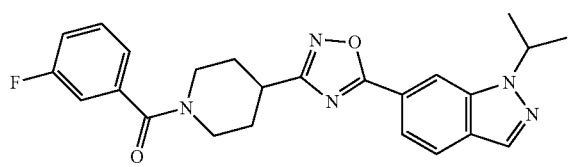 [SMILES: CC(C)n1ncc2ccc(-c3nc(C4CCN(C(=O)c5cccc(F)c5)CC4)no3)cc21]

¹H NMR (400 MHz, DMSO-d₆) δ 8.44 (s, 1H), 8.21 (s, 1H), 7.98 (m, J=8.6 Hz, 1H), 7.81 (dd, J=1.0, 8.5 Hz, 1H), 7.51 (dt, J=5.7, 7.9 Hz, 1H), 7.32-7.20 (m, 3H), 5.18 (spt, J=6.6 Hz, 1H), 4.00-4.20 (m, 2H), 3.36-3.16 (m, 3H), 2.11 (br d, J=10.6 Hz, 2H), 1.89-1.75 (m, 2H), 1.54 (d, J=6.6 Hz, 6H); LCMS (ESI) [M+H]+: 434.1.

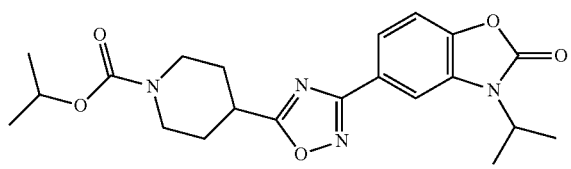 [SMILES: CC(C)OC(=O)N1CCC(c2nc(-c3ccc4oc(=O)n(C(C)C)c4c3)no2)CC1]

¹H NMR (400 MHz, CHLOROFORM-d) δ 7.89 (dd, J=1.5, 8.4 Hz, 1H), 7.79 (s, 1H), 7.29 (d, J=8.4 Hz, 1H), 4.96 (spt, J=6.2 Hz, 1H), 4.64-4.53 (m, 1H), 4.19 (br d, J=11.9 Hz, 2H), 3.20 (tt, J=3.9, 10.9 Hz, 1H), 3.11-2.99 (m, 2H), 2.15 (br dd, J=3.1, 13.2 Hz, 2H), 1.99-1.87 (m, 2H), 1.60 (d, J=6.8 Hz, 6H), 1.27 (d, J=6.2 Hz, 6H); LCMS (ESI) [M+H]+: 415.2.

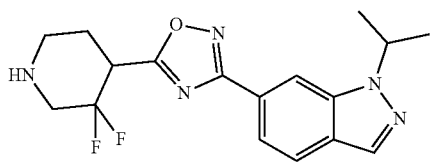 [SMILES: CC(C)n1ncc2ccc(-c3noc(C4CCNCC4(F)F)n3)cc21]

¹H NMR (400 MHz, METHANOL-d₄) δ 8.35 (s, 1H), 8.12 (s, 1H), 7.93-7.84 (m, 2H), 5.13-5.02 (m, 1H), 4.36-4.21 (m, 1H), 3.99 (td, J=8.5, 13.4 Hz, 1H), 3.86-3.63 (m, 2H), 3.43-3.34 (m, 1H), 2.68-2.56 (m, 2H), 1.60 (d, J=6.7 Hz, 6H); LCMS (ESI) [M+H]+: 348.1.

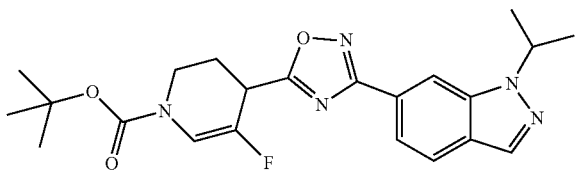 [SMILES: CC(C)n1ncc2ccc(-c3noc(C4CCN(C(=O)OC(C)(C)C)C=C4F)n3)cc21]

¹H NMR (400 MHz, CHLOROFORM-d) δ 8.14 (s, 1H), 7.99 (s, 1H), 7.80-7.72 (m, 2H), 7.03 (br d, J=10.3 Hz, 1H), 4.95-4.84 (m, 1H), 4.11 (q, J=5.0 Hz, 1H), 3.98-3.78 (m, 1H), 3.52-3.35 (m, 1H), 2.35-2.14 (m, 2H), 1.56 (d, J=6.6 Hz, 6H), 1.45 (s, 9H); LCMS (ESI) [M+H]+: 428.2.

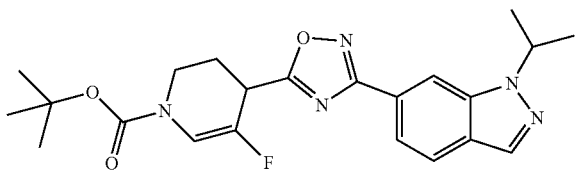 [SMILES: CC(C)n1ncc2ccc(-c3noc(C4CCN(C(=O)OC(C)(C)C)C=C4F)n3)cc21]

¹H NMR (400 MHz, CHLOROFORM-d) δ 8.31-8.23 (m, 1H), 8.09 (s, 1H), 7.94-7.89 (m, 1H), 7.86-7.80 (m, 1H), 5.08-4.93 (m, 1H), 4.28 (br s, 2H), 3.69 (br d, J=5.0 Hz, 2H), 2.85 (br s, 2H), 1.65 (dd, J=1.3, 6.7 Hz, 6H), 1.53 (d, J=1.3 Hz, 9H); LCMS (ESI) [M+H]+: 428.2.

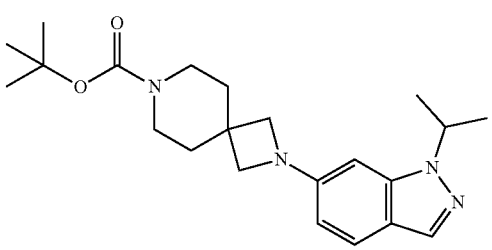 [SMILES: CC(C)n1ncc2ccc(N3CC4(CCN(C(=O)OC(C)(C)C)CC4)C3)cc21]

¹H NMR (400 MHz, CHLOROFORM-d) δ 7.84 (s, 1H), 7.53 (d, J=8.8 Hz, 1H), 6.40 (dd, J=8.8, 2.0 Hz, 1H), 6.22 (s, 1H), 4.79-4.61 (m, 1H), 3.71 (s, 4H), 3.43 (t, J=5.6 Hz, 4H), 1.81 (br t, J=5.2 Hz, 4H), 1.56 (d, J=6.8 Hz, 6H), 1.48 (s, 9H); LCMS (ESI) [M+H]+: 385.2.

693

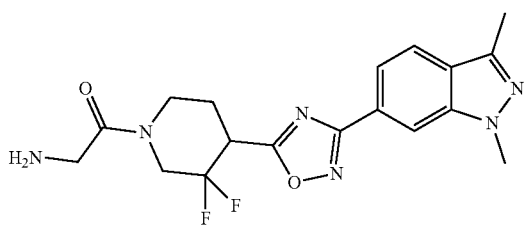 [SMILES: Cc1nn(C)c2cc(-c3noc(C4CCN(C(=O)CN)CC4(F)F)n3)ccc12]

¹H NMR (400 MHz, METHANOL-d₄) δ 8.29 (s, 1H), 7.97-7.85 (m, 2H), 4.80 (td, J=9.1, 13.6 Hz, 0.7H), 4.63 (br d, J=14.2 Hz, 0.4H), 4.34-4.16 (m, 2.4H), 4.13 (s, 3H), 4.10-3.98 (m, 1.5H), 3.96-3.79 (m, 0.6H), 3.66-3.48 (m, 1H), 3.33-3.25 (m, 0.4H), 2.64 (s, 3H), 2.56-2.26 (m, 2H); LCMS (ESI) [M+H]+: 391.1.

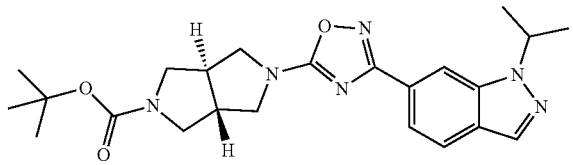 [SMILES: CC(C)n1ncc2ccc(-c3noc(N4C[C@@H]5CN(C(=O)OC(C)(C)C)C[C@H]5C4)n3)cc21]

¹H NMR (400 MHz, CHLOROFORM-d) δ 8.13 (d, J=0.9 Hz, 1H), 8.03 (s, 1H), 7.81-7.74 (m, 2H), 5.03-4.87 (m, 1H), 4.03-3.90 (m, 2H), 3.84-3.67 (m, 2H), 3.43-3.32 (m, 2H), 3.13 (t, J=10.3 Hz, 2H), 2.41 (m, 2H), 1.61 (d, J=6.7 Hz, 6H), 1.49 (s, 9H); LCMS (ESI) [M+H]+: 439.2.

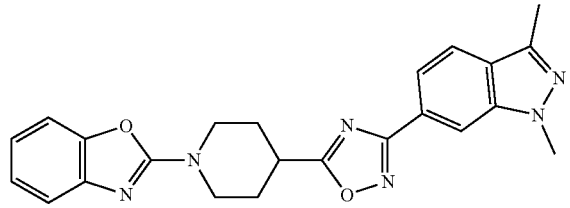 [SMILES: Cc1nn(C)c2cc(-c3noc(C4CCN(c5nc6ccccc6o5)CC4)n3)ccc12]

¹H NMR (300 MHz, CHLOROFORM-d) δ 8.11 (s, 1H), 7.85 (dd, J=8.4, 1.3 Hz, 1H), 7.75 (dd, J=8.5, 0.8 Hz, 1H), 7.39 (s, 1H), 7.21 (d, J=1.2 Hz, 1H), 7.15-7.04 (m, 1H), 4.45-4.32 (m, 2H), 4.09 (s, 3H), 3.53-3.30 (m, 3H), 2.61 (s, 3H), 2.43-2.28 (m, 2H), 2.28-2.12 (m, 2H); LCMS (ESI) [M+H]+: 415.3.

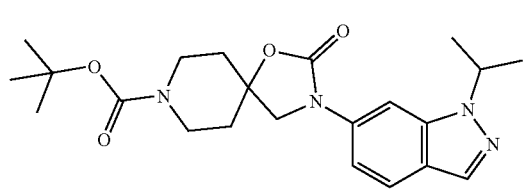 [SMILES: CC(C)n1ncc2ccc(N3CC4(CCN(C(=O)OC(C)(C)C)CC4)OC3=O)cc21]

¹H NMR (300 MHz, CHLOROFORM-d) δ 7.98 (t, J=0.7 Hz, 1H), 7.88-7.77 (m, 1H), 7.72 (d, J=8.8 Hz 1H), 7.20 (d, J=8.8, 1H), 4.90-4.76 (m, 1H), 3.95 (ms, 2H), 3.88 (s, 2H), 3.38 (t, J=12.4 Hz, 2H), 2.02 (m, 2H), 1.84 (m, 2H), 1.60 (d, J=6.7 Hz, 6H), 1.50 (s, 9H); LCMS (ESI) [M+H]+: 415.3.

694

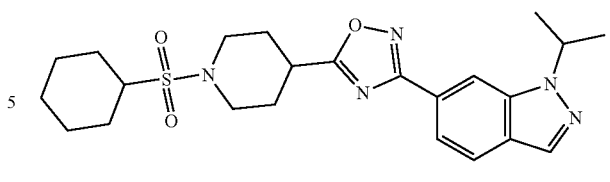

¹H NMR (300 MHz, DMSO-d₆) δ 8.31 (s, 1H), 8.19 (s, 1H), 7.93 (d, J=8.4 Hz, 1H), 7.75 (dd, J=8.4, 1.2 Hz, 1H), 5.16 (p, J=6.5 Hz, 1H), 3.71 (dt, J=13.2, 3.8 Hz, 2H), 3.39 (tt, J=10.9, 3.8 Hz, 1H), 3.13 (td, J=12.4, 12.0, 2.7 Hz, 3H), 2.19 (dd, J=13.7, 3.6 Hz, 2H), 2.01 (t, J=11.9 Hz, 2H), 1.92-1.72 (m, 4H), 1.62 (d, J=12.6 Hz, 1H), 1.50 (d, J=6.5 Hz, 6H), 1.45-1.21 (m, 5H); LCMS (ESI) [M+H]+: 458.4.

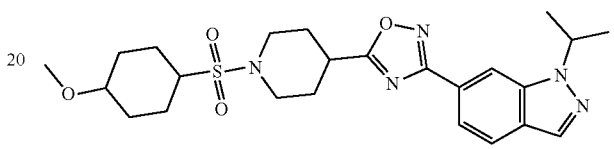

¹H NMR (300 MHz, DMSO-d₆) δ 8.31 (s, 1H), 8.19 (d, J=0.8 Hz, 1H), 7.93 (dd, J=8.4, 0.8 Hz, 1H), 7.75 (dd, J=8.5, 1.3 Hz, 1H), 5.15 (p, J=6.5 Hz, 1H), 3.71 (d, J=12.7 Hz, 3H), 3.47-3.35 (m, 2H), 3.21 (s, 2H), 3.13 (t, J=11.4 Hz, 2H), 2.19 (dd, J=13.9, 2.4 Hz, 3H), 1.95 (d, J=13.7 Hz, 2H), 1.88-1.60 (m, 7H), 1.50 (d, J=6.5 Hz, 6H), 1.44 (d, J=2.9 Hz, 1H); LCMS (ESI) [M+H]+: 488.4.

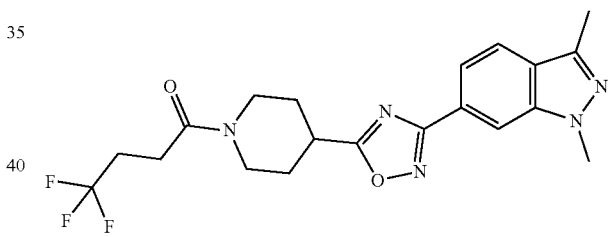

¹H NMR (400 MHz, CHLOROFORM-d) δ 8.09 (s, 1H), 7.85-7.81 (m, 1H), 7.76-7.72 (m, 1H), 4.54 (br d, J=13.9 Hz, 1H), 4.08 (s, 3H), 3.99-3.89 (m, 1H), 3.39-3.28 (m, 2H), 3.10-2.99 (m, 1H), 2.66-2.61 (m, 2H), 2.60 (s, 3H), 2.59-2.50 (m, 2H), 2.31-2.17 (m, 2H), 2.09-1.90 (m, 2H); LCMS (ESI) [M+H]+: 422.1.

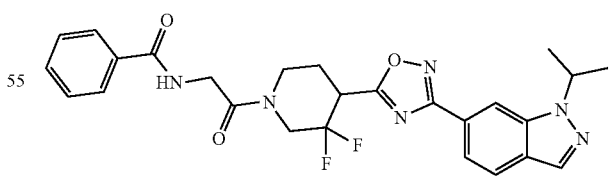

¹H NMR (400 MHz, CHLOROFORM-d) δ 8.14 (s, 1H), 8.00 (s, 1H), 7.83-7.72 (m, 4H), 7.50-7.43 (m, 1H), 7.42-7.34 (m, 2H), 7.14 (br s, 1H), 4.90 (td, J=6.6, 13.3 Hz, 1H), 4.51 (dt, J=6.7, 14.7 Hz, 0.5H), 4.38-4.08 (m, 3H), 3.96 (br s, 0.5H), 3.86-3.63 (m, 2H), 3.61-3.41 (m, 1H), 2.40-2.18 (m, 2H), 1.56 (d, J=6.6 Hz, 6H); LCMS (ESI) [M+H]+: 509.2.

695

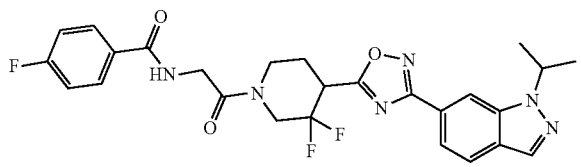 [SMILES: CC(C)n1ncc2ccc(-c3noc(C4CCN(C(=O)CNC(=O)c5ccc(F)cc5)CC4(F)F)n3)cc21]

¹H NMR (400 MHz, CHLOROFORM-d) δ 8.24 (s, 1H), 8.10 (s, 1H), 7.94-7.83 (m, 4H), 7.31-7.23 (m, 1H), 7.15 (br t, J=8.6 Hz, 2H), 5.07-4.93 (m, 1H), 4.70-4.50 (m, 0.5H), 4.45-4.16 (m, 3H), 4.06 (br d, J=13.4 Hz, 0.5H), 3.95-3.69 (m, 2H), 3.67-3.49 (m, 1H), 2.51-2.26 (m, 2H), 1.66 (br d, J=6.5 Hz, 6H); LCMS (ESI) [M+H]+: 527.2.

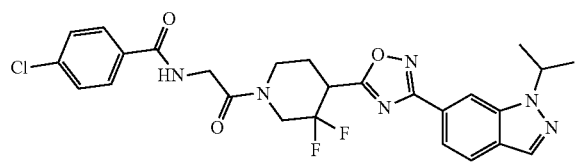 [SMILES: CC(C)n1ncc2ccc(-c3noc(C4CCN(C(=O)CNC(=O)c5ccc(Cl)cc5)CC4(F)F)n3)cc21]

¹H NMR (400 MHz, CHLOROFORM-d) δ 8.28-8.22 (m, 1H), 8.13 (br s, 1H), 7.95-7.79 (m, 4H), 7.49 (br d, J=8.2 Hz, 2H), 7.35-7.18 (m, 1H), 5.02 (br d, J=6.7 Hz, 1H), 4.62 (br s, 0.5H), 4.46-4.18 (m, 3H), 4.07 (br s, 0.5H), 3.99-3.50 (m, 3H), 2.56-2.28 (m, 2H), 1.69 (br d, J=6.6 Hz, 6H); LCMS (ESI) [M+H]+: 543.2.

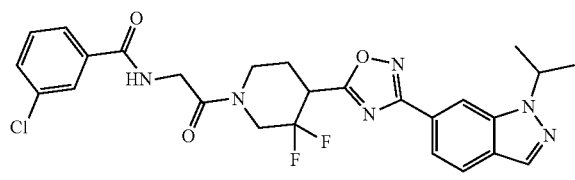 [SMILES: CC(C)n1ncc2ccc(-c3noc(C4CCN(C(=O)CNC(=O)c5cccc(Cl)c5)CC4(F)F)n3)cc21]

¹H NMR (400 MHz, CHLOROFORM-d) δ 8.14 (s, 1H), 8.00 (s, 1H), 7.86-7.71 (m, 3H), 7.64 (br d, J=7.6 Hz, 1H), 7.43 (br d, J=7.7 Hz, 1H), 7.37-7.28 (m, 1H), 4.98-4.80 (m, 1H), 4.50 (dt, J=6.2, 14.5 Hz, 0.5H), 4.37-4.22 (m, 2.5H), 4.22-4.08 (m, 0.5H), 3.96 (br d, J=13.6 Hz, 0.5H), 3.87-3.62 (m, 2H), 3.60-3.38 (m, 1H), 2.42-2.18 (m, 2H); LCMS (ESI) [M+H]+: 543.2.

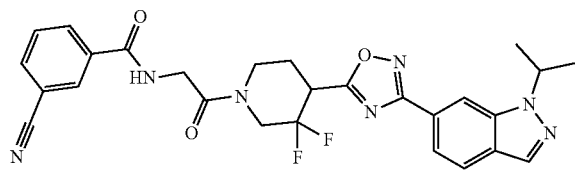 [SMILES: CC(C)n1ncc2ccc(-c3noc(C4CCN(C(=O)CNC(=O)c5cccc(C#N)c5)CC4(F)F)n3)cc21]

¹H NMR (400 MHz, CHLOROFORM-d) δ 8.14 (s, 1H), 8.09 (br d, J=4.6 Hz, 1H), 8.02-7.95 (m, 2H), 7.83-7.68 (m, 3H), 7.52 (br t, J=7.7 Hz, 1H), 7.38-7.21 (m, 1H), 4.90 (td, J=6.6, 13.2 Hz, 1H), 4.60-4.41 (m, 0.5H), 4.37-4.21 (m, 2.5H), 4.20-4.08 (m, 0.5H), 3.97 (br d, J=13.4 Hz, 0.5H), 3.89-3.62 (m, 2H), 3.61-3.42 (m, 1H), 2.42-2.22 (m, 2H), 1.56 (d, J=6.6 Hz, 6H); LCMS (ESI) [M+H]+: 534.2.

696

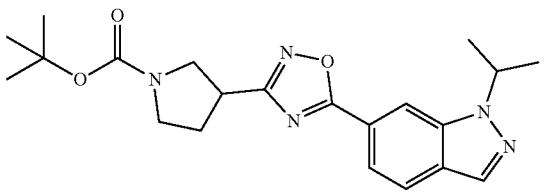 [SMILES: CC(C)n1ncc2ccc(-c3nc(C4CCN(C(=O)OC(C)(C)C)C4)no3)cc21]

¹H NMR (400 MHz, DMSO-d₆) δ 8.50 (s, 1H), 8.25 (s, 1H), 7.99 (m, J=8.4 Hz, 1H), 7.81 (dd, J=1.2, 8.5 Hz, 1H), 5.23 (spt, J=6.6 Hz, 1H), 3.78-3.66 (m, 2H), 3.60-3.52 (m, 1H), 3.52-3.43 (m, 1H), 3.38 (br t, J=8.4 Hz, 1H), 2.33 (br s, 1H), 2.25-2.07 (m, 1H), 1.50 (d, J=6.6 Hz, 6H), 1.42 (s, 9H); LCMS (ESI) [M+H]+: 398.2.

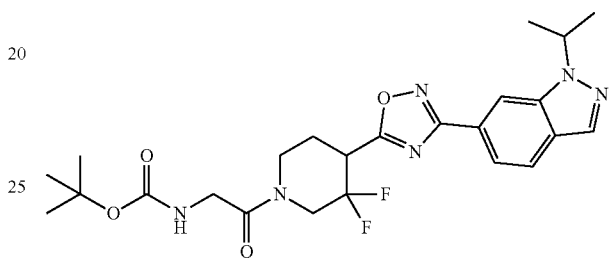

¹H NMR (400 MHz, CHLOROFORM-d) δ 8.21 (s, 1H), 8.06 (s, 1H), 7.88-7.79 (m, 2H), 5.51-5.37 (m, 1H), 4.97 (td, J=6.6, 13.2 Hz, 1H), 4.60-4.48 (m, 0.5H), 4.30 (m, 0.5H), 4.20-4.01 (m, 2.5H), 3.93 (m, 0.5H), 3.89-3.59 (m, 2H), 3.56-3.37 (m, 1H), 2.46-2.21 (m, 2H), 1.63 (d, J=6.6 Hz, 6H), 1.46 (s, 9H); LCMS (ESI) [M−55]+: 449.1.

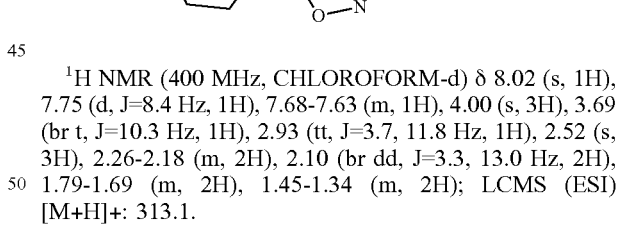

¹H NMR (400 MHz, CHLOROFORM-d) δ 8.02 (s, 1H), 7.75 (d, J=8.4 Hz, 1H), 7.68-7.63 (m, 1H), 4.00 (s, 3H), 3.69 (br t, J=10.3 Hz, 1H), 2.93 (tt, J=3.7, 11.8 Hz, 1H), 2.52 (s, 3H), 2.26-2.18 (m, 2H), 2.10 (br dd, J=3.3, 13.0 Hz, 2H), 1.79-1.69 (m, 2H), 1.45-1.34 (m, 2H); LCMS (ESI) [M+H]+: 313.1.

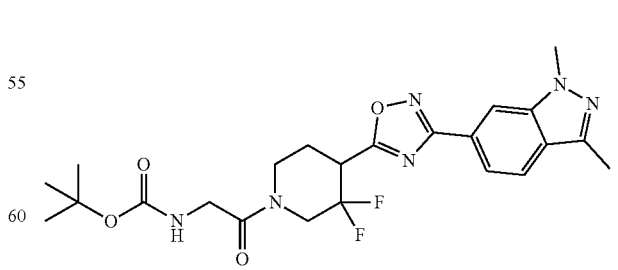

¹H NMR (400 MHz, CHLOROFORM-d) δ 8.09 (s, 1H), 7.86-7.81 (m, 1H), 7.77-7.70 (m, 1H), 5.55-5.39 (m, 1H), 4.55 (dt, J=6.6, 14.4 Hz, 0.5H), 4.35-4.26 (m, 0.5H), 4.22-4.10 (m, 1H), 4.08 (s, 3H), 4.07-3.90 (m, 2H), 3.89-3.60 (m,

2H), 3.58-3.39 (m, 1H), 2.60 (s, 3H), 2.43-2.25 (m, 2H), 1.47 (s, 9H); LCMS (ESI) [M+H]+: 435.1.

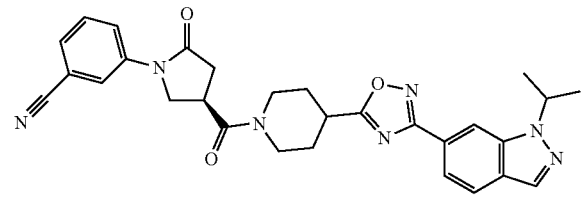 [SMILES: CC(C)n1ncc2ccc(-c3noc(C4CCN(C(=O)[C@@H]5CC(=O)N(c6cccc(C#N)c6)C5)CC4)n3)cc21]

¹H NMR (400 MHz, CHLOROFORM-d) δ 8.23 (br s, 1H), 8.09 (s, 1H), 8.02-7.82 (m, 4H), 7.54-7.44 (m, 2H), 5.05-4.92 (m, 1H), 4.66-4.51 (m, 1H), 4.36 (dd, J=6.6, 9.5 Hz, 1H), 4.06-3.93 (m, 2H), 3.69-3.60 (m, 1H), 3.49-3.35 (m, 2H), 3.23-3.07 (m, 1H), 3.02-2.90 (m, 2H), 2.31 (br t, J=14.1 Hz, 2H), 2.13-1.96 (m, 2H), 1.65 (dd, J=1.2, 6.7 Hz, 6H); LCMS (ESI) [M+H]+: 524.2.

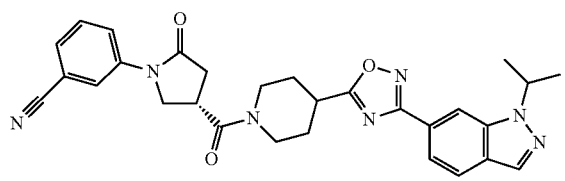 [SMILES: CC(C)n1ncc2ccc(-c3noc(C4CCN(C(=O)[C@H]5CC(=O)N(c6cccc(C#N)c6)C5)CC4)n3)cc21]

¹H NMR (400 MHz, CHLOROFORM-d) δ 8.14 (br s, 1H), 7.99 (s, 1H), 7.93-7.73 (m, 4H), 7.43-7.34 (m, 2H), 4.89 (qd, J=6.6, 13.3 Hz, 1H), 4.55-4.41 (m, 1H), 4.26 (dd, J=7.0, 8.9 Hz, 1H), 3.96-3.84 (m, 2H), 3.55 (td, J=8.3, 16.0 Hz, 1H), 3.40-3.26 (m, 2H), 3.13-2.97 (m, 1H), 2.94-2.81 (m, 2H), 2.22 (br t, J=14.3 Hz, 2H), 2.03-1.89 (m, 2H), 1.56 (br d, J=5.9 Hz, 6H); LCMS (ESI) [M+H]+: 524.2.

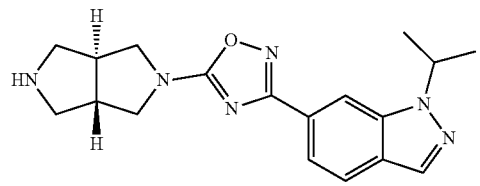 [SMILES: CC(C)n1ncc2ccc(-c3noc(N4C[C@@H]5CNC[C@H]5C4)n3)cc21]

¹H NMR (400 MHz, METHANOL-d₄) δ 8.23 (s, 1H), 8.11 (s, 1H), 7.86 (d, J=8.4 Hz, 1H), 7.75 (d, J=8.4 Hz, 1H), 5.12-4.98 (m, 1H), 4.07-3.96 (m, 2H), 3.63 (br dd, J=5.9, 10.5 Hz, 2H), 3.51 (br t, J=9.7 Hz, 2H), 3.17 (br t, J=10.8 Hz, 2H), 2.81-2.65 (m, 2H), 1.61 (d, J=6.7 Hz, 6H); LCMS (ESI) [M+H]+: 339.1.

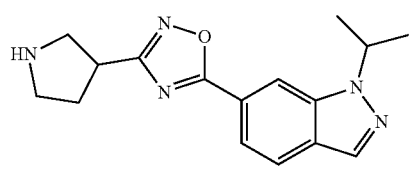 [SMILES: CC(C)n1ncc2ccc(-c3nc(C4CCNC4)no3)cc21]

¹H NMR (400 MHz, DMSO-d₆) δ 8.51 (s, 1H), 8.25 (s, 1H), 8.01 (m, J=8.4 Hz, 1H), 7.82 (dd, J=1.1, 8.6 Hz, 1H), 5.20 (spt, J=6.5 Hz, 1H), 3.86 (quin, J=7.6 Hz, 1H), 3.68 (dd, J=8.2, 11.7 Hz, 1H), 3.46 (dd, J=7.5, 11.7 Hz, 1H), 3.41-3.26 (m, 2H), 2.47-2.37 (m, 1H), 2.29-2.15 (m, 1H), 1.50 (d, J=6.6 Hz, 6H); LCMS (ESI) [M+H]+: 298.1.

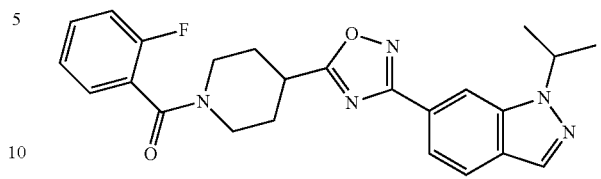

¹H NMR (400 MHz, CHLOROFORM-d) δ 8.22 (s, 1H), 8.07 (s, 1H), 7.88-7.79 (m, 2H), 7.47-7.39 (m, 2H), 7.26-7.22 (m, 1H), 7.16-7.10 (m, 1H), 4.98 (td, J=6.7, 13.3 Hz, 1H), 4.71 (br d, J=12.8 Hz, 1H), 3.72 (br d, J=13.6 Hz, 1H), 3.42-3.17 (m, 3H), 2.33 (br dd, J=3.3, 13.6 Hz, 1H), 2.23-2.03 (m, 3H), 1.64 (d, J=6.7 Hz, 5H), 1.66-1.62 (m, 1H); LCMS (ESI) [M+H]+: 434.2.

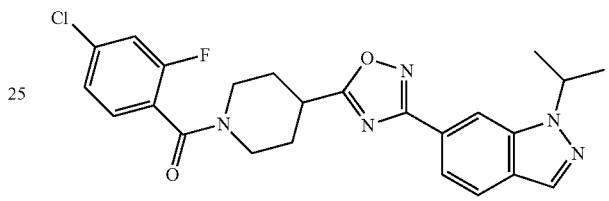

¹H NMR (400 MHz, CHLOROFORM-d) δ 8.21 (s, 1H), 8.07 (s, 1H), 7.88-7.80 (m, 2H), 7.41-7.36 (m, 1H), 7.25 (dd, J=1.8, 8.3 Hz, 1H), 7.18 (dd, J=1.9, 9.2 Hz, 1H), 4.97 (spt, J=6.7 Hz, 1H), 4.67 (br d, J=13.4 Hz, 1H), 3.70 (br d, J=13.8 Hz, 1H), 3.42-3.18 (m, 3H), 2.33 (br dd, J=3.4, 13.6 Hz, 1H), 2.24-1.95 (m, 3H), 1.66-1.62 (m, 1H), 1.64 (d, J=6.7 Hz, 5H); LCMS (ESI) [M+H]+: 468.1.

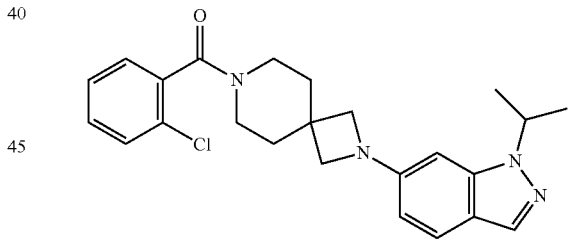

¹H NMR (400 MHz, CHLOROFORM-d) δ 7.85 (s, 1H), 7.54 (d, J=8.7 Hz, 1H), 7.46-7.40 (m, 1H), 7.38-7.28 (m, 3H), 6.40 (dd, J=1.6, 8.7 Hz, 1H), 6.23 (s, 1H), 4.70 (spt, J=6.6 Hz, 1H), 3.92-3.70 (m, 6H), 3.38-3.17 (m, 2H), 2.06-1.87 (m, 3H), 1.82-1.73 (m, 1H), 1.56 (d, J=6.6 Hz, 6H); LCMS (ESI) [M+H]+: 423.2.

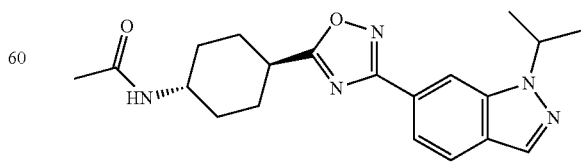

¹H NMR (400 MHz, CHLOROFORM-d) δ 8.13 (s, 1H), 7.98 (s, 1H), 7.80-7.71 (m, 2H), 5.27 (br d, J=7.9 Hz, 1H), 4.94-4.84 (m, 1H), 3.90-3.78 (m, 1H), 2.91 (tt, J=3.5, 12.2 Hz, 1H), 2.25-2.11 (m, 4H), 1.93 (s, 3H), 1.79 (dq, J=3.2, 13.0 Hz, 2H), 1.56 (d, J=6.7 Hz, 6H), 1.24 (dq, J=3.3, 12.5 Hz, 2H); LCMS (ESI) [M+H]+: 368.1.

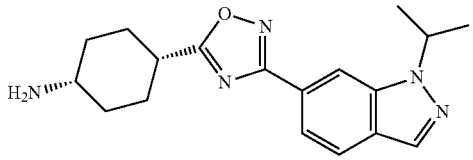 [SMILES: CC(C)n1ncc2ccc(-c3noc([C@H]4CC[C@@H](N)CC4)n3)cc21]

¹H NMR (400 MHz, DMSO-d₆) δ 8.30 (s, 1H), 8.19 (s, 1H), 7.94 (d, J=8.4 Hz, 1H), 7.77 (dd, J=1.1, 8.4 Hz, 1H), 5.17-5.07 (m, 1H), 3.43 (br t, J=4.5 Hz, 1H), 3.25-3.16 (m, 1H), 2.25 (br dd, J=4.6, 9.2 Hz, 2H), 1.97-1.88 (m, 4H), 1.66-1.57 (m, 2H), 1.50 (d, J=6.6 Hz, 6H); LCMS (ESI) [M+H]+: 326.2.

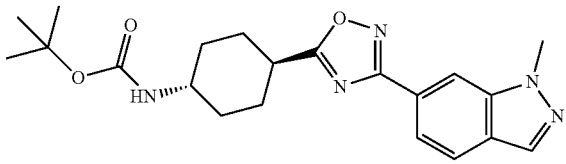 [SMILES: Cn1ncc2ccc(-c3noc([C@H]4CC[C@H](NC(=O)OC(C)(C)C)CC4)n3)cc21]

¹H NMR (400 MHz, CHLOROFORM-d) δ 8.22 (s, 1H), 8.07 (s, 1H), 7.89-7.81 (m, 2H), 4.99 (td, J=6.7, 13.3 Hz, 1H), 4.48 (br s, 1H), 3.57 (br s, 1H), 2.99 (tt, J=3.4, 12.2 Hz, 1H), 2.33-2.20 (m, 4H), 1.85 (dq, J=3.0, 13.0 Hz, 2H), 1.64 (d, J=6.6 Hz, 6H), 1.48 (s, 9H), 1.38-1.26 (m, 2H); LCMS (ESI) [M+H]+: 426.2.

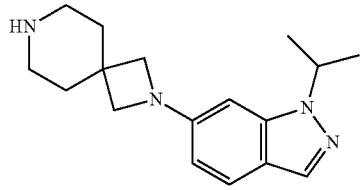

¹H NMR (400 MHz, CHLOROFORM-d) δ 7.84 (s, 1H), 7.52 (d, J=8.8 Hz, 1H), 6.40 (dd, J=8.8, 2.0 Hz, 1H), 6.22 (s, 1H), 4.79-4.61 (m, 1H), 3.69 (s, 4H), 3.10-2.66 (m, 5H), 1.83 (br t, J=5.2 Hz, 4H), 1.56 (d, J=6.8 Hz, 6H); LCMS (ESI) [M+H]+: 285.1.

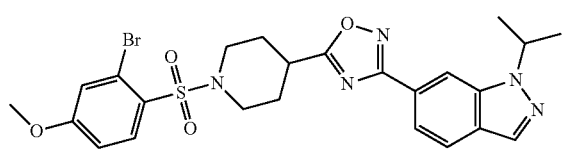 [SMILES: COc1ccc(S(=O)(=O)N2CCC(c3nc(-c4ccc5cnn(C(C)C)c5c4)no3)CC2)c(Br)c1]

¹H NMR (300 MHz, DMSO-d₆) δ 8.27 (d, J=1.2 Hz, 1H), 8.19 (s, 1H), 7.92 (d, J=8.5 Hz, 1H), 7.91 (d, J=2.3 Hz, 1H), 7.79 (dd, J=8.7, 2.3 Hz, 1H), 7.72 (dd, J=8.5, 1.3 Hz, 1H), 7.37 (d, J=8.8 Hz, 1H), 5.14 (p, J=6.6 Hz, 1H), 3.96 (s, 3H), 3.69 (d, J=11.9 Hz, 3H), 2.22 (d, J=12.9 Hz, 3H), 1.87 (q, J=10.5, 9.9 Hz, 2H), 1.50 (d, J=6.5 Hz, 6H); LCMS (ESI) [M+H]+: 560.2, 562.1.

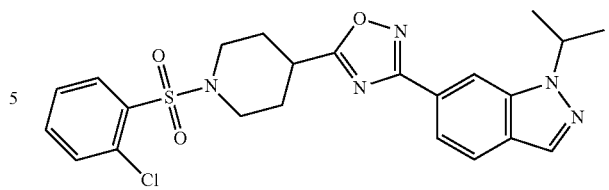

¹H NMR (300 MHz, DMSO-d₆) δ 8.29 (d, J=1.1 Hz, 1H), 8.19 (s, 1H), 8.02 (dd, J=7.7, 1.6 Hz, 1H), 7.92 (dd, J=8.5, 0.8 Hz, 1H), 7.76-7.66 (m, 3H), 7.59 (ddd, J=7.9, 6.8, 1.9 Hz, 1H), 5.15 (p, J=6.5 Hz, 1H), 3.78 (d, J=12.8 Hz, 2H), 3.39 (d, J=15.0 Hz, 1H), 3.09-2.93 (m, 2H), 2.21 (dd, J=13.4, 3.5 Hz, 2H), 1.93-1.74 (m, 1H), 1.50 (d, J=6.6 Hz, 6H); LCMS (ESI) [M+H]+: 486.3, 488.2.

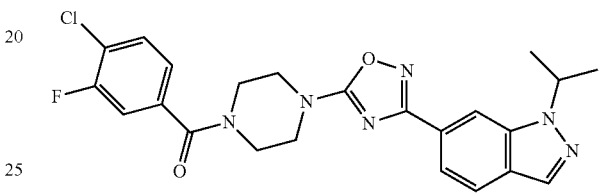

¹H NMR (400 MHz, DMSO-d₆) δ 8.28 (s, 1H), 8.15 (s, 1H), 7.92 (d, J=8.4 Hz, 1H), 7.76 (d, J=8.4 Hz, 1H), 7.65 (t, J=7.8 Hz, 1H), 7.48 (dd, J=1.9, 9.6 Hz, 1H), 7.30 (d, J=8.2 Hz, 1H), 5.10 (td, J=6.6, 13.2 Hz, 1H), 4.03 (br s, 1H), 4.20-3.86 (m, 1H), 3.58-3.43 (m, 1H), 3.25 (br t, J=11.2 Hz, 2H), 2.19 (br d, J=9.9 Hz, 2H), 1.99-1.81 (m, 2H), 1.54 (d, J=6.6 Hz, 6H); LCMS (ESI) [M+H]+: 468.1.

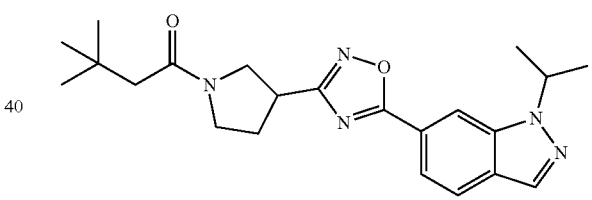

¹H NMR (400 MHz, CHLOROFORM-d) δ 8.29 (s, 1H), 8.11 (d, J=3.4 Hz, 1H), 7.88 (d, J=5.4 Hz, 2H), 5.07-4.90 (m, 1H), 4.09-3.95 (m, 1H), 3.94-3.77 (m, 2H), 3.76-3.57 (m, 2H), 2.55-2.31 (m, 2H), 2.29-2.24 (m, 2H), 1.66 (d, J=6.6 Hz, 6H), 1.11 (d, J=1.8 Hz, 9H); LCMS (ESI) [M+H]+: 396.2.

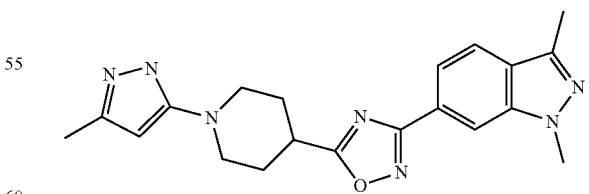

¹H NMR (400 MHz, CHLOROFORM-d) δ 8.08 (d, J=2.9 Hz, 1H), 7.82 (br dd, J=2.6, 8.4 Hz, 1H), 7.72 (dd, J=3.4, 8.3 Hz, 1H), 4.24-4.13 (m, 2H), 4.07 (d, J=3.7 Hz, 3H), 3.44-3.25 (m, 3H), 2.59-2.57 (m, 3H), 2.29-2.27 (m, 2H), 2.23 (d, J=4.0 Hz, 3H), 2.16-2.04 (m, 2H); LCMS (ESI) [M+H]+: 380.2.

701

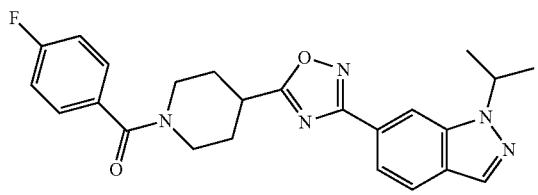 [SMILES: CC(C)n1ncc2ccc(-c3noc(C4CCN(C(=O)c5ccc(F)cc5)CC4)n3)cc21]

¹H NMR (400 MHz, DMSO-d₆) δ 8.28 (s, 1H), 8.16 (s, 1H), 7.92 (d, J=8.4 Hz, 1H), 7.76 (dd, J=1.0, 8.5 Hz, 1H), 7.55-7.47 (m, 2H), 7.30-7.22 (m, 2H), 5.11 (quin, J=6.6 Hz, 1H), 4.06 (br s, 2H), 3.57-3.45 (m, 1H), 3.32-3.18 (m, 2H), 2.19 (br dd, J=3.4, 13.1 Hz, 2H), 1.97-1.81 (m, 2H), 1.54 (d, J=6.6 Hz, 6H); LCMS (ESI) [M+H]+: 434.2.

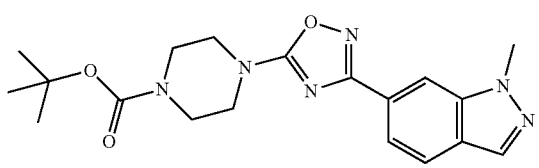 [SMILES: Cn1ncc2ccc(-c3noc(N4CCN(C(=O)OC(C)(C)C)CC4)n3)cc21]

¹H NMR (400 MHz, CHLOROFORM-d) δ 8.09 (d, J=0.9 Hz, 1H), 8.01 (d, J=0.9 Hz, 1H), 7.79-7.77 (m, 2H), 4.14 (s, 3H), 3.74-3.68 (m, 4H), 3.62-3.56 (m, 4H), 1.50 (s, 9H); LCMS (ESI) [M+H]+: 385.2.

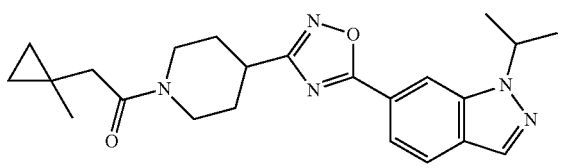 [SMILES: CC(C)n1ncc2ccc(-c3nc(C4CCN(C(=O)CC5(C)CC5)CC4)no3)cc21]

¹H NMR (400 MHz, CHLOROFORM-d) δ 8.28 (s, J=0.7 Hz, 1H), 8.10 (s, 1H), 7.91-7.82 (m, 2H), 4.98 (spt, J=6.6 Hz, 1H), 4.64 (br d, J=13.6 Hz, 1H), 3.98 (br d, J=13.6 Hz, 1H), 3.32-3.20 (m, 1H), 3.15 (tt, J=3.9, 10.9 Hz, 1H), 2.91 (br t, J=11.2 Hz, 1H), 2.40 (d, J=4.2 Hz, 2H), 2.16 (br d, J=11.1 Hz, 2H), 1.99-1.80 (m, 2H), 1.65 (d, J=6.7 Hz, 6H), 1.18 (s, 3H), 0.55-0.31 (m, 4H); LCMS (ESI) [M+H]+: 408.2.

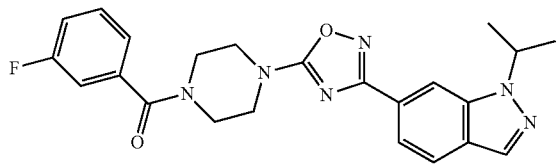 [SMILES: CC(C)n1ncc2ccc(-c3noc(N4CCN(C(=O)c5cccc(F)c5)CC4)n3)cc21]

¹H NMR (400 MHz, DMSO-d₆) δ 8.17 (d, J=10.8 Hz, 2H), 7.87 (d, J=8.4 Hz, 1H), 7.67 (dd, J=1.1, 8.4 Hz, 1H), 7.61-7.49 (m, 1H), 7.41-7.24 (m, 3H), 5.10 (td, J=6.6, 13.1 Hz, 1H), 3.94-3.43 (m, 8H), 1.50 (d, J=6.6 Hz, 6H); LCMS (ESI) [M+H]+: 435.2.

702

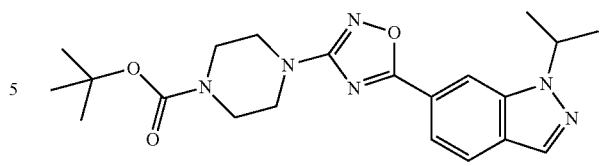

¹H NMR (400 MHz, CHLOROFORM-d) δ 8.22 (s, 1H), 8.09 (s, 1H), 7.84 (d, J=0.7 Hz, 2H), 4.97 (quin, J=6.7 Hz, 1H), 3.57 (br d, J=5.5 Hz, 8H), 1.65 (d, J=6.6 Hz, 6H), 1.51 (s, 9H); LCMS (ESI) [M+H]+: 413.2.

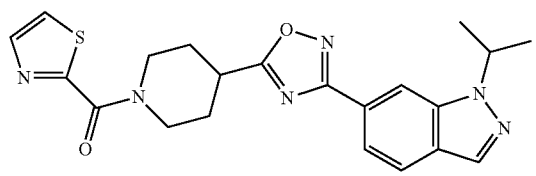 [SMILES: CC(C)n1ncc2ccc(-c3noc(C4CCN(C(=O)c5nccs5)CC4)n3)cc21]

¹H NMR (400 MHz, CHLOROFORM-d) δ 8.22 (s, 1H), 8.06 (s, 1H), 7.92 (d, J=3.1 Hz, 1H), 7.88-7.77 (m, 2H), 7.57 (d, J=3.3 Hz, 1H), 5.43 (br d, J=13.7 Hz, 1H), 4.97 (spt, J=6.7 Hz, 1H), 4.67 (br d, J=12.6 Hz, 1H), 3.80-3.60 (m, 1H), 3.48-3.36 (m, 1H), 3.34-3.18 (m, 1H), 2.31 (br s, 2H), 2.15 (br s, 2H), 1.64 (d, J=6.6 Hz, 6H); LCMS (ESI) [M+H]+: 423.1.

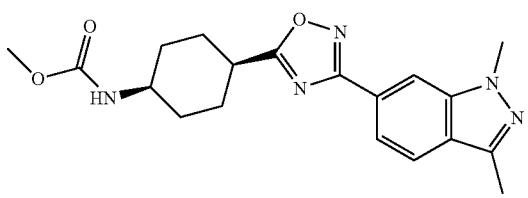 [SMILES: COC(=O)N[C@H]1CC[C@@H](c2nc(-c3ccc4c(C)nn(C)c4c3)no2)CC1]

¹H NMR (400 MHz, CHLOROFORM-d) δ 8.11 (s, 1H), 7.84 (dd, J=1.2, 8.4 Hz, 1H), 7.77-7.71 (m, 1H), 4.76 (br s, 1H), 4.09 (s, 3H), 3.81 (br s, 1H), 3.68 (s, 3H), 3.28-3.16 (m, 1H), 2.61 (s, 3H), 2.25-2.12 (m, 2H), 2.07-1.97 (m, 2H), 1.88 (dt, J=4.0, 8.7 Hz, 2H), 1.79-1.69 (m, 2H); LCMS (ESI) [M+H]+: 370.1.

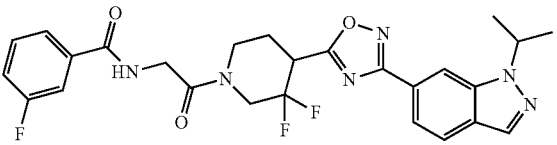 [SMILES: CC(C)n1ncc2ccc(-c3noc(C4CCN(C(=O)CNC(=O)c5cccc(F)c5)CC4(F)F)n3)cc21]

¹H NMR (400 MHz, CHLOROFORM-d) δ 8.21 (br s, 1H), 8.06 (br s, 1H), 7.91-7.77 (m, 2H), 7.65-7.55 (m, 2H), 7.43 (br d, J=5.7 Hz, 1H), 7.33-7.15 (m, 2H), 5.04-4.91 (m, 0.8H), 4.57 (br s, 0.4H), 4.44-4.31 (m, 2H), 4.28-4.14 (m, 0.5H), 4.02 (br s, 0.5H), 3.93-3.68 (m, 2H), 3.68-3.46 (m, 1H), 2.50-2.25 (m, 2H), 1.63 (br d, J=6.4 Hz, 6H); LCMS (ESI) [M+H]+: 527.2.

703

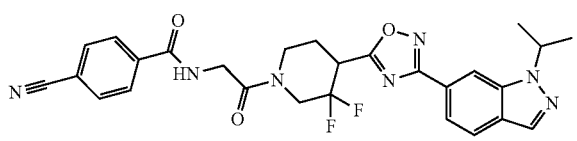 [SMILES: CC(C)n1ncc2ccc(-c3noc(C4CCN(C(=O)CNC(=O)c5ccc(C#N)cc5)CC4(F)F)n3)cc21]

¹H NMR (400 MHz, CHLOROFORM-d) δ 8.21 (s, 1H), 8.07 (s, 1H), 7.96-7.94 (d, J=8.0 Hz, 2H), 7.87-7.81 (m, 2H), 7.80-7.60 (d, J=8.0 Hz, 2H), 7.33-7.25 (m, 1H), 5.00-4.93 (m, 1H), 4.65-4.50 (m, 0.5H), 4.45-4.25 (m, 2.6H, 4.25-4.15 (m, 0.5 h), 4.08-3.98 (m, 0.5H), 3.95-3.80 (m, 1.5H), 3.80-3.05 (m, 0.5H), 3.65-3.50 (m, 1H), 2.50-2.33 (m, 2H), 1.64-1.62 (d, J=6.8 Hz, 6H); LCMS (ESI) [M+H]+: 534.2.

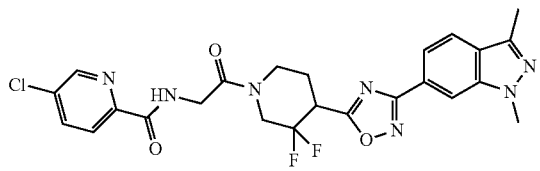 [SMILES: Cc1nn(C)c2cc(-c3noc(C4CCN(C(=O)CNC(=O)c5ccc(Cl)cn5)CC4(F)F)n3)ccc12]

¹H NMR (400 MHz, CHLOROFORM-d) δ 8.73 (br d, J=15.2 Hz, 1H), 8.57 (d, J=2.3 Hz, 1H), 8.20-8.11 (m, 2H), 7.92 (d, J=8.6 Hz, 1H), 7.87-7.78 (m, 2H), 4.64 (dt, J=6.8, 14.3 Hz, 0.5H), 4.39 (br t, J=5.4 Hz, 2.4H), 4.30-4.22 (m, 0.6H), 4.18 (s, 3H), 4.06 (br d, J=14.4 Hz, 0.6H), 3.93-3.70 (m, 2H), 3.62-3.49 (m, 1H), 2.69 (s, 3H), 2.50-2.29 (m, 2H); LCMS (ESI) [M+H]+: 530.1.

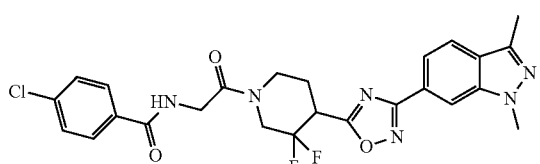

¹H NMR (400 MHz, CHLOROFORM-d) δ 8.17 (s, 1H), 7.95 (d, J=8.8 Hz, 1H), 7.84 (d, J=8.3 Hz, 1H), 7.79 (d, J=8.3 Hz, 2H), 7.48-7.39 (m, 2H), 7.28-7.19 (m, 1H), 4.64 (dt, J=7.3, 14.2 Hz, 0.5H), 4.48-4.32 (m, 2.3H), 4.26 (br s, 0.6H), 4.22 (s, 3H), 4.06 (br d, J=8.8 Hz, 0.7H), 3.95-3.69 (m, 2H), 3.61-3.47 (m, 1H), 2.73 (s, 3H), 2.50-2.30 (m, 2H); LCMS (ESI) [M+H]+: 529.1.

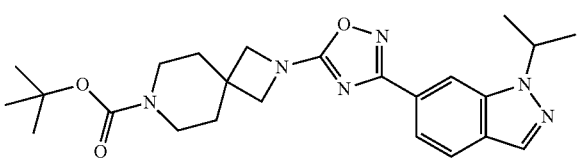 [SMILES: CC(C)n1ncc2ccc(-c3noc(N4CC5(CCN(C(=O)OC(C)(C)C)CC5)C4)n3)cc21]

¹H NMR (400 MHz, CHLOROFORM-d) δ 8.12 (d, J=0.8 Hz, 1H), 8.04 (s, 1H), 7.77 (d, J=0.8 Hz, 2H), 5.05-4.85 (m, 1H), 4.06 (s, 4H), 3.42 (t, J=5.6 Hz, 4H), 1.85 (t, J=5.6 Hz, 4H), 1.61 (d, J=6.4 Hz, 6H), 1.48 (s, 9H); LCMS (ESI) [M+H]+: 453.2.

704

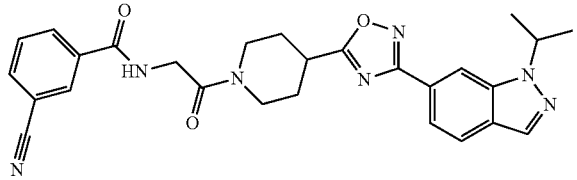 [SMILES: CC(C)n1ncc2ccc(-c3noc(C4CCN(C(=O)CNC(=O)c5cccc(C#N)c5)CC4)n3)cc21]

¹H NMR (400 MHz, CHLOROFORM-d) δ 8.19 (s, 1H), 8.16 (s, 1H), 8.08-8.04 (m, 2H), 7.87-7.78 (m, 3H), 7.59 (t, J=7.8 Hz, 1H), 7.41-7.35 (m, 1H), 4.96 (quin, J=6.7 Hz, 1H), 4.52 (br d, J=13.7 Hz, 1H), 4.31 (d, J=3.7 Hz, 2H), 3.91 (br d, J=13.9 Hz, 1H), 3.37 (ddd, J=3.3, 10.5, 13.9 Hz, 2H), 3.25-3.11 (m, 1H), 2.37-2.21 (m, 2H), 2.13-1.94 (m, 2H), 1.63 (d, J=6.6 Hz, 6H); LCMS (ESI) [M+H]+: 498.2.

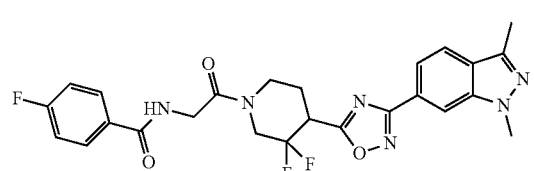

¹H NMR (400 MHz, CHLOROFORM-d) δ 8.11 (s, 1H), 7.93-7.81 (m, 3H), 7.79-7.72 (m, 1H), 7.25-7.10 (m, 3H), 4.59 (dt, J=6.7, 14.9 Hz, 0.5H), 4.43-4.30 (m, 2.5H), 4.24 (dt, J=6.3, 14.6 Hz, 0.5H), 4.10 (s, 3H), 4.05 (br d, J=13.9 Hz, 0.5H), 3.95-3.70 (m, 2H), 3.68-3.50 (m, 1H), 2.61 (s, 3H), 2.49-2.31 (m, 2H); LCMS (ESI) [M+H]+: 513.1.

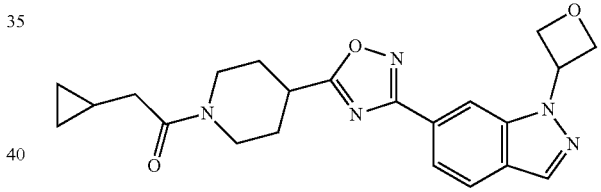

¹H NMR (400 MHz, CHLOROFORM-d) δ 8.06-7.90 (m, 2H), 7.75-7.57 (m, 2H), 5.76-5.60 (m, 1H), 5.12 (t, J=6.5 Hz, 2H), 4.95 (t, J=7.3 Hz, 2H), 4.38 (m, 1H), 3.74 (m, 1H), 3.17-2.98 (m, 2H), 2.86-2.69 (m, 1H), 2.12 (d, J=6.8 Hz, 2H), 2.07-1.95 (m, 2H), 1.84-1.66 (m, 2H), 0.93-0.80 (m, 1H), 0.44-0.33 (m, 2H), 0.05--0.05 (m, 2H); LCMS (ESI) [M+H]+: 408.2.

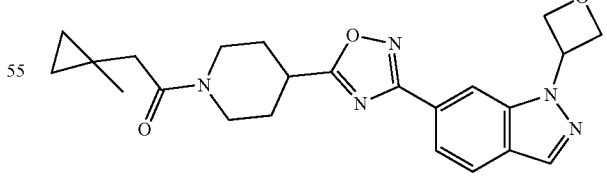

¹H NMR (400 MHz, CHLOROFORM-d) δ 8.21 (d, J=0.7 Hz, 1H), 8.17 (s, 1H), 7.93-7.81 (m, 2H), 5.96-5.83 (m, 1H), 5.33 (t, J=6.6 Hz, 2H), 5.16 (t, J=7.3 Hz, 2H), 4.60 (br d, J=13.4 Hz, 1H), 3.97 (br d, J=13.9 Hz, 1H), 3.36-3.20 (m, 2H), 2.96 (br t, J=11.2 Hz, 1H), 2.39 (m, 2H), 2.22 (br d, J=13.4 Hz, 2H), 2.05-1.85 (m, 2H), 1.17 (s, 3H), 0.55-0.32 (m, 4H); LCMS (ESI) [M+H]+: 422.2.

705

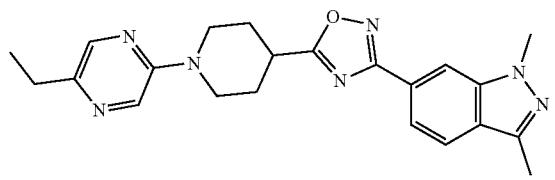 [SMILES: CCc1cnc(N2CCC(c3nc(-c4ccc5c(C)nn(C)c5c4)no3)CC2)cn1]

¹H NMR (400 MHz, CHLOROFORM-d) δ 8.15 (s, 1H), 8.10 (s, 1H), 7.99 (s, 1H), 7.85-7.80 (m, 1H), 7.73 (d, J=8.3 Hz, 1H), 4.32 (br d, J=13.2 Hz, 2H), 4.08 (s, 3H), 3.36-3.27 (m, 1H), 3.23-3.11 (m, 2H), 2.72 (q, J=7.7 Hz, 2H), 2.60 (s, 3H), 2.34-2.25 (m, 2H), 2.15-2.03 (m, 2H), 1.28 (t, J=7.7 Hz, 3H); LCMS (ESI) [M+H]+: 404.1.

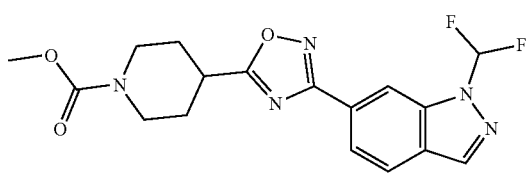 [SMILES: COC(=O)N1CCC(c2nc(-c3ccc4cnn(C(F)F)c4c3)no2)CC1]

¹H NMR (400 MHz, CHLOROFORM-d) δ 8.51 (s, 1H), 8.15 (d, J=0.7 Hz, 1H), 8.04 (dd, J=1.1, 8.4 Hz, 1H), 7.87 (d, J=8.4 Hz, 1H), 7.68-7.35 (t, J=59.2 Hz, 1H), 4.19 (br s, 2H), 3.73 (s, 3H), 3.23 (tt, J=3.9, 10.9 Hz, 1H), 3.08 (br t, J=11.6 Hz, 2H), 2.17 (br d, J=10.9 Hz, 2H), 2.01-1.89 (m, 2H); LCMS (ESI) [M+H]+: 378.1.

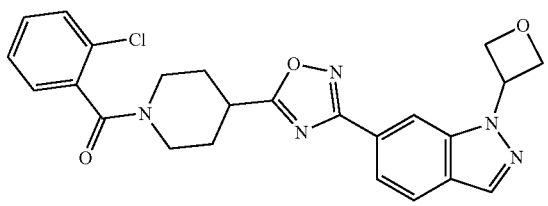 [SMILES: O=C(c1ccccc1Cl)N1CCC(c2nc(-c3ccc4cnn(C5COC5)c4c3)no2)CC1]

¹H NMR (400 MHz, CHLOROFORM-d) δ 8.15 (s, 1H), 8.10 (s, 1H), 7.85-7.82 (m, 1H), 7.80-7.75 (m, 1H), 7.40-7.33 (m, 1H), 7.32-7.20 (m, 3H), 5.92-5.74 (m, 1H), 5.26 (t, J=6.6 Hz, 2H), 5.09 (t, J=7.0 Hz, 2H), 4.76-4.55 (m, 1H), 3.61-3.44 (m, 1H), 3.36-3.01 (m, 3H), 2.27 (m, 1H), 2.15-1.93 (m, 2H), 1.93-1.77 (m, 1H); LCMS (ESI) [M+H]+: 464.1.

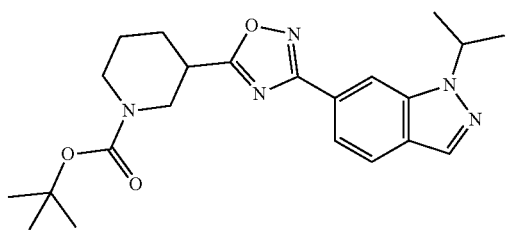 [SMILES: CC(C)n1ncc2ccc(-c3noc(C4CCCN(C(=O)OC(C)(C)C)C4)n3)cc21]

¹H NMR (400 MHz, DMSO-d₆) δ 8.25 (s, 1H), 8.14 (s, 1H), 7.90 (d, J=8.4 Hz, 1H), 7.74 (d, J=8.4 Hz, 1H), 5.11-5.05 (m, 1H), 4.07-3.99 (m, 1H), 3.66-3.56 (m, 1H), 3.49 (br dd, J=9.2, 13.3 Hz, 1H), 3.32-3.15 (m, 2H), 2.22-2.13 (m, 1H), 1.98-1.93 (m, 1H), 1.84-1.75 (m, 1H), 1.60-1.45 (m, 7H), 1.38 (s, 9H); LCMS (ESI) [M+H]+: 412.2.

706

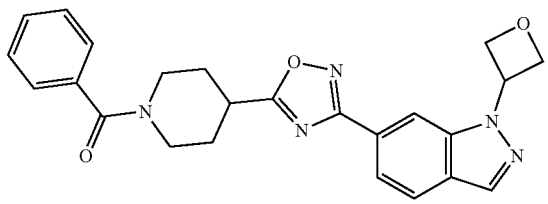 [SMILES: O=C(c1ccccc1)N1CCC(c2nc(-c3ccc4cnn(C5COC5)c4c3)no2)CC1]

¹H NMR (400 MHz, CHLOROFORM-d) δ 8.29-8.16 (m, 2H), 7.97-7.84 (m, 2H), 7.46 (m, 5H), 5.99-5.85 (m, 1H), 5.36 (t, J=6.7 Hz, 2H), 5.18 (t, J=7.3 Hz, 2H), 4.86-4.54 (m, 1H), 3.94 (m, 1H), 3.46-3.31 (m, 1H), 3.25 (br s, 2H), 2.39-1.82 (m, 4H); LCMS (ESI) [M+H]+: 430.1.

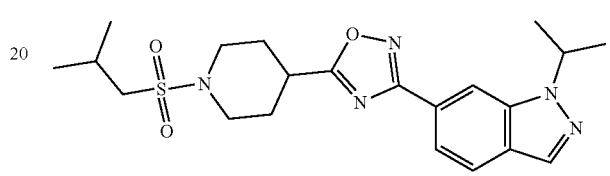

¹H NMR (300 MHz, DMSO-d₆) δ 8.31 (d, J=1.1 Hz, 1H), 8.19 (s, OH), 7.93 (dd, J=8.4, 0.8 Hz, 1H), 7.75 (dd, J=8.5, 1.3 Hz, 1H), 5.16 (h, J=6.6 Hz, 1H), 3.65 (dt, J=11.7, 3.3 Hz, 3H), 3.43-3.27 (m, 1H), 3.02 (td, J=12.6, 2.7 Hz, 3H), 2.95 (d, J=6.6 Hz, 2H), 2.23 (dd, J=13.6, 3.7 Hz, 2H), 2.12 (dq, J=13.3, 6.7 Hz, 1H), 1.97-1.78 (m, 2H), 1.50 (d, J=6.6 Hz, 6H), 1.05 (d, J=6.7 Hz, 6H); LCMS (ESI) [M+H]+: 432.3.

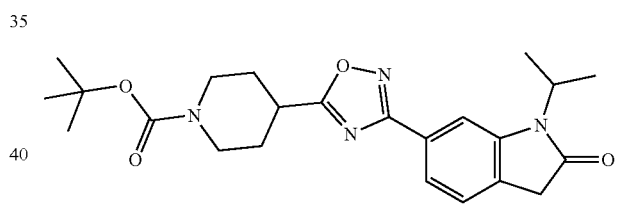

¹H NMR (400 MHz, CHLOROFORM-d) δ 7.77 (dd, J=1.1, 7.7 Hz, 1H), 7.67 (s, 1H), 7.35 (d, J=7.7 Hz, 1H), 4.68 (spt, J=7.0 Hz, 1H), 4.14 (m, 2H), 3.56 (s, 2H), 3.19 (tt, J=4.0, 10.9 Hz, 1H), 3.01 (br t, J=11.6 Hz, 2H), 2.14 (br dd, J=2.8, 13.3 Hz, 2H), 1.98-1.84 (m, 2H), 1.54 (d, J=7.1 Hz, 6H), 1.49 (s, 9H); LCMS (ESI) [M+H]+: 427.2.

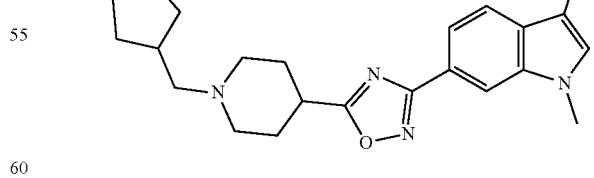

¹H NMR (400 MHz, CHLOROFORM-d) δ 8.10 (s, 1H), 7.86-7.81 (m, 1H), 7.74 (d, J=8.4 Hz, 1H), 4.42 (dd, J=7.2, 9.2 Hz, 1H), 4.16 (dd, J=5.3, 9.3 Hz, 1H), 4.08 (s, 3H), 3.09-2.89 (m, 3H), 2.87-2.76 (m, 1H), 2.68-2.61 (m, 1H), 2.60 (s, 3H), 2.45 (d, J=7.9 Hz, 2H), 2.37 (dd, J=5.7, 17.6 Hz, 1H), 2.31-2.13 (m, 4H), 2.11-1.98 (m, 2H)

707

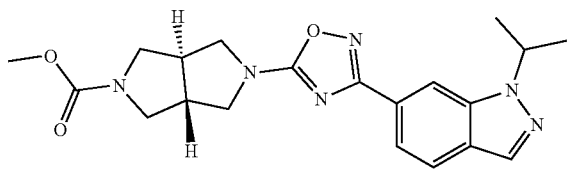 [SMILES: COC(=O)N1C[C@H]2CN(c3nc(-c4ccc5cnn(C(C)C)c5c4)no3)C[C@@H]2C1]

¹H NMR (400 MHz, CHLOROFORM-d) δ 8.13 (d, J=0.7 Hz, 1H), 8.04 (s, 1H), 7.77 (m, 2H), 4.95 (m, 1H), 3.99 (m, 2H), 3.84 (dd, J=6.3, 9.8 Hz, 1H), 3.80-3.71 (m, 4H), 3.39 (m, 2H), 3.17 (q, J=10.4 Hz, 2H), 2.53-2.34 (m, 2H), 1.61 (d, J=6.7 Hz, 6H); LCMS (ESI) [M+H]+: 397.1.

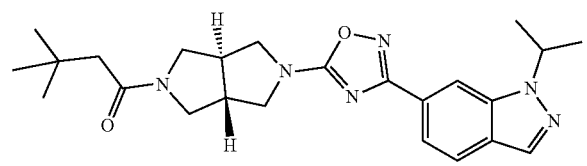 [SMILES: CC(C)n1ncc2ccc(-c3noc(N4C[C@@H]5CN(C(=O)CC(C)(C)C)C[C@H]5C4)n3)cc21]

¹H NMR (400 MHz, CHLOROFORM-d) δ 8.13 (d, J=0.9 Hz, 1H), 8.04 (s, 1H), 7.81-7.73 (m, 2H), 4.95 (m, 1H), 4.07-3.93 (m, 3H), 3.84 (dd, J=6.6, 8.9 Hz, 1H), 3.45-3.36 (m, 2H), 3.30 (dd, J=9.2, 10.8 Hz, 1H), 3.16 (t, J=11.0 Hz, 1H), 2.57-2.32 (m, 2H), 2.26-2.15 (m, 2H), 1.61 (d, J=6.6 Hz, 6H), 1.12-1.04 (m, 9H); LCMS (ESI) [M+H]+: 437.2.

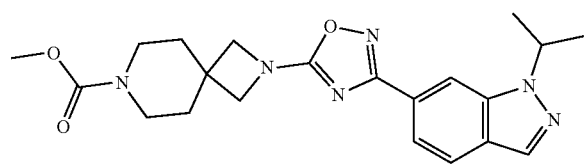 [SMILES: COC(=O)N1CCC2(CC1)CN(c1nc(-c3ccc4cnn(C(C)C)c4c3)no1)C2]

¹H NMR (400 MHz, CHLOROFORM-d) δ 8.12 (s, 1H), 8.04 (s, 1H), 7.77 (s, 2H), 5.00-4.88 (m, 1H), 4.07 (s, 4H), 3.71 (s, 3H), 3.47 (t, J=4.8 Hz, 4H), 1.86 (t, J=5.6 Hz, 4H), 1.61 (d, J=6.8 Hz, 6H); LCMS (ESI) [M+H]+: 411.1.

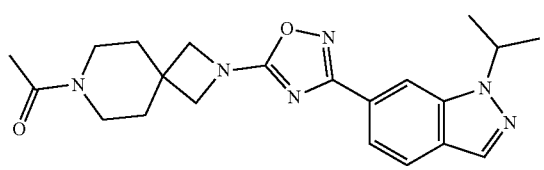 [SMILES: CC(=O)N1CCC2(CC1)CN(c1nc(-c3ccc4cnn(C(C)C)c4c3)no1)C2]

¹H NMR (400 MHz, CHLOROFORM-d) δ 8.12 (s. 1H), 8.05 (s, 1H), 7.76 (s, 2H), 5.01-4.90 (m, 1H), 4.15-4.04 (m, 4H), 3.61 (t, J=5.2 Hz, 2H), 3.45 (t, J=5.6 Hz, 2H), 2.13 (s, 3H), 1.89 (dt, J=16.6, 4.4 Hz, 4H), 1.61 (d, J=6.4 Hz, 6H); LCMS (ESI) [M+H]+: 395.1.

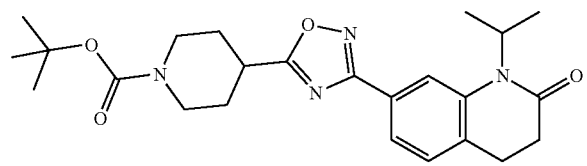 [SMILES: CC(C)N1C(=O)CCc2ccc(-c3noc(C4CCN(C(=O)OC(C)(C)C)CC4)n3)cc21]

708

¹H NMR (400 MHz, CHLOROFORM-d) δ 7.83 (s, 1H), 7.71 (dd, J=1.2, 7.6 Hz, 1H), 7.28 (d, J=7.6 Hz, 1H), 4.73 (spt, J=6.9 Hz, 1H), 4.25-4.00 (m, 2H), 3.18 (tt, J=3.9, 10.9 Hz, 1H), 3.00 (br t, J=11.7 Hz, 2H), 2.91-2.85 (m, 2H), 2.60 (dd, J=5.8, 8.3 Hz, 2H), 2.13 (br dd, J=2.8, 13.1 Hz, 2H), 1.96-1.85 (m, 2H), 1.58 (d, J=7.1 Hz, 6H), 1.49 (s, 9H); LCMS (ESI) [M−55]+: 385.1.

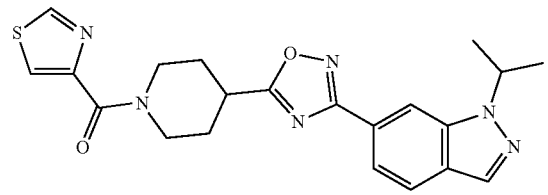 [SMILES: CC(C)n1ncc2ccc(-c3noc(C4CCN(C(=O)c5cscn5)CC4)n3)cc21]

¹H NMR (400 MHz, CHLOROFORM-d) δ 8.82 (d, J=2.2 Hz, 1H), 8.22 (s, 1H), 8.06 (s, 1H), 8.03 (d, J=2.2 Hz, 1H), 7.92-7.77 (m, 2H), 4.97 (spt, J=6.7 Hz, 1H), 4.63 (br d, J=7.3 Hz, 2H), 3.47 (br s, 1H), 3.38 (tt, J=4.2, 10.5 Hz, 1H), 3.24 (br s, 1H), 2.29 (br s, 2H), 2.19-2.07 (m, 2H), 1.63 (d, J=6.6 Hz, 6H); LCMS (ESI) [M+H]+: 423.1.

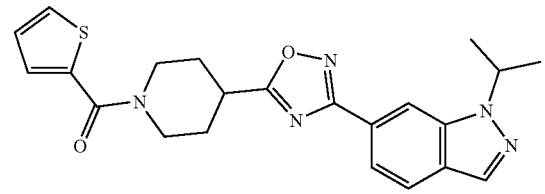 [SMILES: CC(C)n1ncc2ccc(-c3noc(C4CCN(C(=O)c5cccs5)CC4)n3)cc21]

¹H NMR (400 MHz, CHLOROFORM-d) δ 8.22 (s, 1H), 8.07 (s, 1H), 7.90-7.79 (m, 2H), 7.48 (dd, J=1.0, 5.0 Hz, 1H), 7.34 (dd, J=1.0, 3.6 Hz, 1H), 7.08 (dd, J=3.7, 4.9 Hz, 1H), 4.98 (td, J=6.6, 13.2 Hz, 1H), 4.47 (br d, J=12.8 Hz, 2H), 3.45-3.27 (m, 3H), 2.28 (br dd, J=3.4, 13.6 Hz, 2H), 2.15-2.01 (m, 2H), 1.64 (d, J=6.6 Hz, 6H); LCMS (ESI) [M+H]+: 422.1.

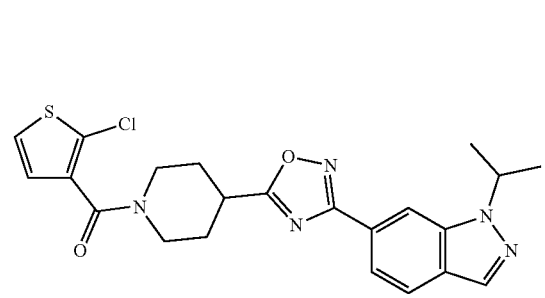 [SMILES: CC(C)n1ncc2ccc(-c3noc(C4CCN(C(=O)c5ccsc5Cl)CC4)n3)cc21]

¹H NMR (400 MHz, CHLOROFORM-d) δ 8.21 (s, 1H), 8.07 (s, 1H), 7.89-7.79 (m, 2H), 7.18 (d, J=5.7 Hz, 1H), 6.99 (d, J=5.7 Hz, 1H), 4.97 (td, J=6.6, 13.4 Hz, 1H), 4.66 (br d, J=12.8 Hz, 1H), 3.80 (br d, J=13.5 Hz, 1H), 3.43-3.16 (m, 3H), 2.40-2.17 (m, 2H), 2.17-1.93 (m, 2H), 1.64 (d, J=6.6 Hz, 6H); LCMS (ESI) [M+H]+: 456.1.

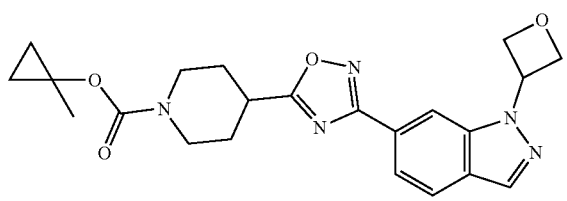 [SMILES: CC1(OC(=O)N2CCC(c3nc(-c4ccc5cnn(C6COC6)c5c4)no3)CC2)CC1]

¹H NMR (400 MHz, CHLOROFORM-d) δ 8.21 (d, J=0.6 Hz, 1H), 8.16 (s, 1H), 7.93-7.87 (m, 1H), 7.86-7.81 (m, 1H), 5.89 (quin, J=7.0 Hz, 1H), 5.33 (t, J=6.6 Hz, 2H), 5.15 (t, J=7.3 Hz, 2H), 4.32-3.96 (m, 2H), 3.20 (m, 1H), 3.08-2.96 (m, 2H), 2.15 (br d, J=12.5 Hz, 2H), 1.99-1.83 (m, 2H), 1.59 (br s, 1H), 1.57 (s, 3H), 0.93-0.83 (m, 2H), 0.72-0.59 (m, 2H); LCMS (ESI) [M+H]+: 424.2.

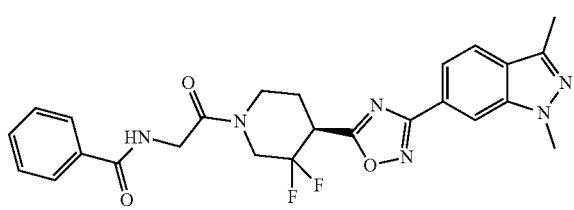 [SMILES: Cc1nn(C)c2cc(-c3noc([C@@H]4CCN(C(=O)CNC(=O)c5ccccc5)CC4(F)F)n3)ccc12]

¹H NMR (400 MHz, CHLOROFORM-d) δ 8.11 (s, 1H), 7.92-7.81 (m, 3H), 7.79-7.72 (m, 1H), 7.57-7.52 (m, 1H), 7.51-7.43 (m, 2H), 7.26-7.17 (m, 1H), 4.65-4.50 (m, 0.5H), 4.44-4.32 (m, 2.5H), 4.25 (dt, J=5.7, 14.8 Hz, 0.5H), 4.09 (s, 3H), 4.04 (br d, J=4.9 Hz, 0.5H), 3.96-3.69 (m, 2H), 3.68-3.50 (m, 1H), 2.61 (s, 3H), 2.50-2.23 (m, 2H); LCMS (ESI) [M+H]+: 495.1.

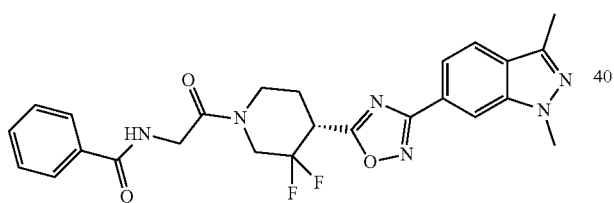

¹H NMR (400 MHz, CHLOROFORM-d) δ 8.11 (s, 1H), 7.90-7.81 (m, 3H), 7.78-7.73 (m, 1H), 7.58-7.51 (m, 1H), 7.50-7.43 (m, 2H), 7.30-7.19 (m, 1H), 4.65-4.49 (m, 0.5H), 4.45-4.31 (m, 2.5H), 4.25 (dt, J=5.6, 14.8 Hz, 0.5H), 4.09 (s, 3H), 4.08-4.00 (m, 0.5H), 3.98-3.70 (m, 2H), 3.66-3.51 (m, 1H), 2.61 (s, 3H), 2.50-2.31 (m, 2H); LCMS (ESI) [M+H]+: 495.1.

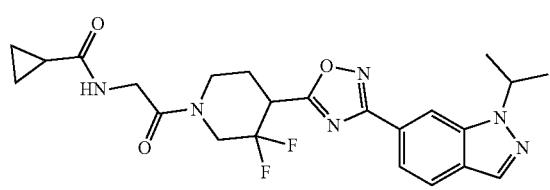 [SMILES: CC(C)n1ncc2ccc(-c3noc(C4CCN(C(=O)CNC(=O)C5CC5)CC4(F)F)n3)cc21]

¹H NMR (400 MHz, CHLOROFORM-d) δ 8.23 (s, 1H), 8.10 (s, 1H), 7.91-7.83 (m, 2H), 6.77-6.62 (m, 1H), 5.00 (td, J=6.6, 13.2 Hz, 1H), 4.58 (dt, J=6.8, 14.5 Hz, 0.5H), 4.34 (br d, J=13.9 Hz, 0.5H), 4.28-4.14 (m, 2.5H), 4.00 (br d, J=13.6 Hz, 0.5H), 3.94-3.45 (m, 3H), 2.36 (br d, J=16.4 Hz, 2H), 1.66 (d, J=6.7 Hz, 6H), 1.57-1.49 (m, 1H), 1.06-0.99 (m, 2H), 0.82 (td, J=3.6, 7.4 Hz, 2H); LCMS (ESI) [M+H]+: 473.2.

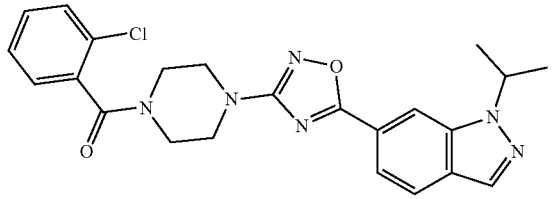 [SMILES: CC(C)n1ncc2ccc(-c3nc(N4CCN(C(=O)c5ccccc5Cl)CC4)no3)cc21]

¹H NMR (400 MHz, CHLOROFORM-d) δ 8.22 (s, 1H), 8.09 (s, 1H), 7.87-7.79 (m, 2H), 7.48-7.43 (m, 1H), 7.42-7.30 (m, 3H), 4.97 (td, J=6.8, 13.2 Hz, 1H), 4.13-4.00 (m, 1H), 3.97-3.84 (m, 1H), 3.72 (br s, 2H), 3.66-3.57 (m, 1H), 3.56-3.41 (m, 2H), 3.38 (br d, J=7.1 Hz, 1H), 1.64 (br d, J=6.6 Hz, 6H); LCMS (ESI) [M+H]+: 451.1.

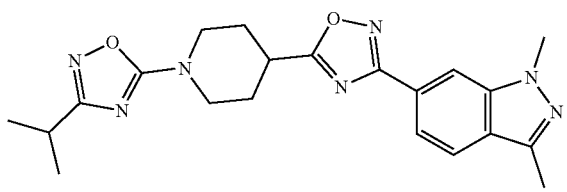 [SMILES: Cc1nn(C)c2cc(-c3noc(C4CCN(c5nc(C(C)C)no5)CC4)n3)ccc12]

¹H NMR (400 MHz, CHLOROFORM-d) δ 8.07 (s, 1H), 7.83-7.78 (m, 1H), 7.74-7.69 (m, 1H), 4.19 (td, J=3.8, 13.6 Hz, 2H), 4.06 (s, 3H), 3.40-3.23 (m, 3H), 2.94-2.84 (m, 1H), 2.58 (s, 3H), 2.27 (br dd, J=3.3, 13.7 Hz, 2H), 2.15-2.02 (m, 2H), 1.28 (d, J=6.8 Hz, 6H); LCMS (ESI) [M+H]+: 408.2.

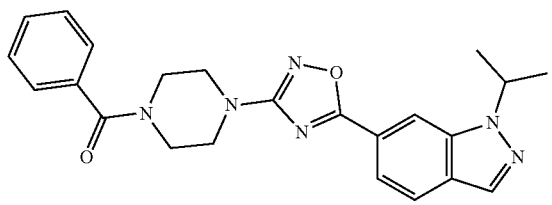 [SMILES: CC(C)n1ncc2ccc(-c3nc(N4CCN(C(=O)c5ccccc5)CC4)no3)cc21]

¹H NMR (400 MHz, DMSO-d₆) δ 8.37 (s, 1H), 8.19 (s, 1H), 7.95 (m, J=8.6 Hz, 1H), 7.75 (d, J=8.4 Hz, 1H), 7.54-7.37 (m, 5H), 5.15 (spt, J=6.6 Hz, 1H), 3.66 (br s, 4H), 3.58-3.50 (m, 4H), 1.53 (d, J=6.6 Hz, 6H); LCMS (ESI) [M+H]+: 417.2.

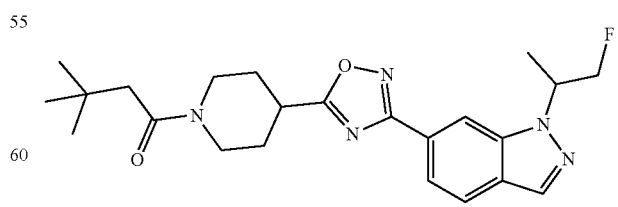

¹H NMR (400 MHz, CHLOROFORM-d) δ 8.23 (s, 1H), 8.11 (s, 1H), 7.91-7.86 (m, 1H), 7.85-7.81 (m, 1H), 5.16-5.03 (m, 1H), 4.91 (dd, J=7.9, 9.3 Hz, 0.5H), 4.82-4.76 (m, 1H), 4.67 (dd, J=4.9, 9.4 Hz, 0.5H), 4.61 (br s, 1H), 4.04 (br d, J=13.7 Hz, 1H), 3.36-3.24 (m, 2H), 2.97 (br t, J=12.1 Hz, 1H), 2.32 (s, 2H), 2.27-2.17 (m, 2H), 2.05-1.89 (m, 2H), 1.66 (dd, J=1.6, 6.8 Hz, 3H), 1.09 (s, 9H); LCMS (ESI) [M+H]+: 428.2.

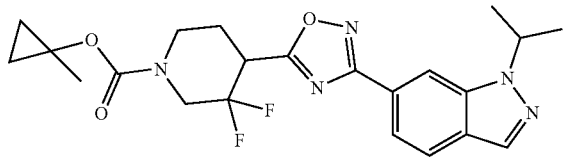 [SMILES: CC(C)n1ncc2ccc(-c3noc(C4CCN(C(=O)OC5(C)CC5)CC4(F)F)n3)cc21]

¹H NMR (400 MHz, CHLOROFORM-d) δ 8.23 (s, 1H), 8.07 (s, 1H), 7.90-7.81 (m, 2H), 4.98 (spt, J=6.6 Hz, 1H), 4.48-3.98 (m, 2H), 3.81-3.68 (m, 1H), 3.61-3.47 (m, 1H), 3.32 (br t, J=10.1 Hz, 1H), 2.42-2.20 (m, 2H), 1.64 (d, J=6.7 Hz, 6H), 1.59 (s, 3H), 0.96-0.90 (m, 2H), 0.72-0.65 (m, 2H); LCMS (ESI) [M+H]+: 446.1.

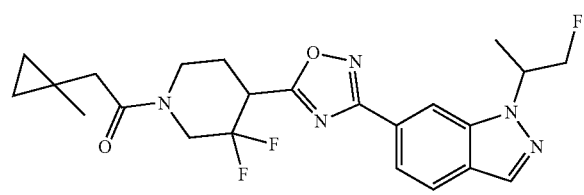 [SMILES: CC(CF)n1ncc2ccc(-c3noc(C4CCN(C(=O)CC5(C)CC5)CC4(F)F)n3)cc21]

¹H NMR (400 MHz, CHLOROFORM-d) δ 8.23 (s, 1H), 8.11 (s, 1H), 7.92-7.86 (m, 1H), 7.85-7.79 (m, 1H), 5.16-5.03 (m, 1H), 4.90 (dd, J=8.0, 9.4 Hz, 0.5H), 4.82-4.76 (m, 1H), 4.67 (dd, J=4.9, 9.4 Hz, 0.5H), 4.60 (br d, J=13.6 Hz, 1H), 3.97 (br d, J=13.4 Hz, 1H), 3.34-3.24 (m, 2H), 2.98 (br t, J=11.9 Hz, 1H), 2.40 (d, J=3.2 Hz, 2H), 2.22 (br d, J=13.1 Hz, 2H), 1.96 (quin, J=11.9 Hz, 2H), 1.66 (dd, J=1.5, 6.8 Hz, 3H), 1.18 (s, 3H), 0.50-0.44 (m, 2H), 0.44-0.38 (m, 2H); LCMS (ESI) [M+H]+: 426.2.

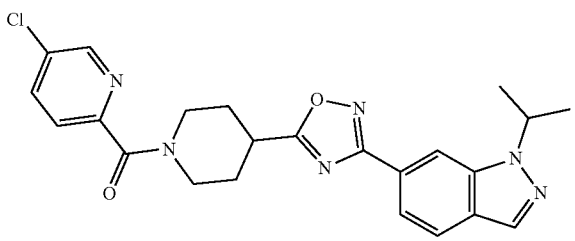 [SMILES: CC(C)n1ncc2ccc(-c3noc(C4CCN(C(=O)c5ccc(Cl)cn5)CC4)n3)cc21]

¹H NMR (400 MHz, CHLOROFORM-d) δ 8.57 (d, J=2.0 Hz, 1H), 8.22 (s, 1H), 8.07 (s, 1H), 7.89-7.78 (m, 3H), 7.69 (d, J=8.3 Hz, 1H), 4.98 (td, J=6.7, 13.4 Hz, 1H), 4.67 (br d, J=13.1 Hz, 1H), 4.16 (br d, J=13.4 Hz, 1H), 3.45-3.33 (m, 2H), 3.26 (br t, J=10.8 Hz, 1H), 2.33 (br d, J=10.9 Hz, 1H), 2.24-2.07 (m, 3H), 1.64 (d, J=6.7 Hz, 6H); LCMS (ESI) [M+H]+: 451.2.

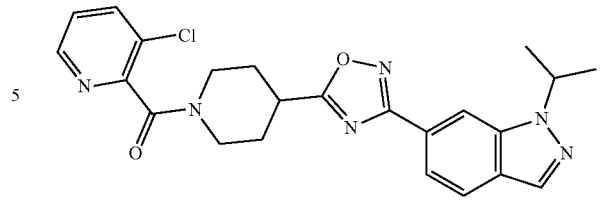

¹H NMR (400 MHz, CHLOROFORM-d) δ 8.56 (dd, J=1.2, 4.6 Hz, 1H), 8.22 (s, 1H), 8.07 (s, 1H), 7.91-7.75 (m, 3H), 7.33 (dd, J=4.6, 8.2 Hz, 1H), 4.98 (td, J=6.6, 13.3 Hz, 1H), 4.78-4.63 (m, 1H), 3.53 (td, J=3.8, 13.6 Hz, 1H), 3.42-3.19 (m, 3H), 2.35 (br dd, J=3.9, 13.6 Hz, 1H), 2.25-2.03 (m, 2H), 2.25-2.03 (m, 1H), 1.64 (d, J=6.6 Hz, 6H); [M+H]+: 451.1.

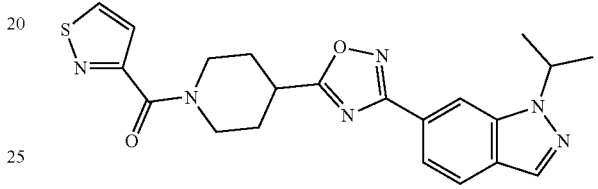

¹H NMR (400 MHz, CHLOROFORM-d) δ 8.71 (d, J=4.6 Hz, 1H), 8.22 (s, 1H), 8.07 (s, 1H), 7.89-7.79 (m, 2H), 7.68 (d, J=4.9 Hz, 1H), 4.98 (td, J=6.6, 13.4 Hz, 1H), 4.68 (br d, J=13.5 Hz, 1H), 4.57 (br d, J=13.9 Hz, 1H), 3.53-3.44 (m, 1H), 3.44-3.35 (m, 1H), 3.32-3.17 (m, 1H), 2.38-2.21 (m, 2H), 2.21-2.07 (m, 2H), 1.64 (d, J=6.6 Hz, 6H); LCMS (ESI) [M+H]+: 423.2.

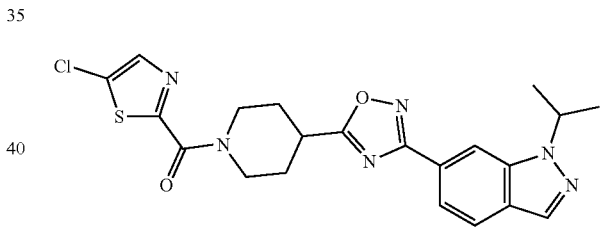

¹H NMR (400 MHz, CHLOROFORM-d) δ 8.21 (s, 1H), 8.07 (s, 1H), 7.89-7.80 (m, 2H), 7.68 (s, 1H), 5.41 (br d, J=12.3 Hz, 1H), 4.97 (td, J=6.6, 13.4 Hz, 1H), 4.60 (br d, J=11.5 Hz, 1H), 3.75-3.62 (m, 1H), 3.49-3.35 (m, 1H), 3.33-3.19 (m, 1H), 2.30 (br s, 2H), 2.14 (br s, 2H), 1.64 (d, J=6.6 Hz, 5H), 1.66-1.61 (m, 1H); LCMS (ESI) [M+H]+: 457.1.

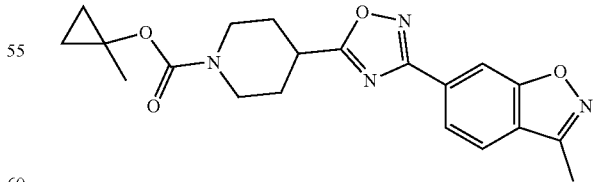

¹H NMR (400 MHz, CHLOROFORM-d) δ 8.27 (s, 1H), 8.05 (dd, J=1.1, 8.2 Hz, 1H), 7.73 (d, J=8.2 Hz, 1H), 4.16 (br s, 2H), 3.20 (tt, J=3.9, 10.8 Hz, 1H), 3.09-2.97 (m, 2H), 2.62 (s, 3H), 2.14 (br d, J=11.4 Hz, 2H), 1.98-1.84 (m, 2H), 1.56 (s, 3H), 0.91-0.85 (m, 2H), 0.67-0.61 (m, 2H); LCMS (ESI) [M+H]+: 383.1.

713

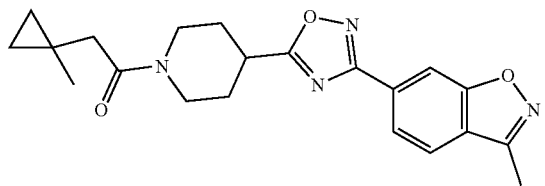 [SMILES: Cc1noc2cc(-c3noc(C4CCN(C(=O)CC5(C)CC5)CC4)n3)ccc12]

¹H NMR (400 MHz, CHLOROFORM-d) δ 8.28 (s, 1H), 8.05 (dd, J=1.1, 8.2 Hz, 1H), 7.73 (d, J=8.2 Hz, 1H), 4.58 (br d, J=13.7 Hz, 1H), 3.96 (br d, J=13.5 Hz, 1H), 3.34-3.22 (m, 2H), 2.97 (br t, J=11.2 Hz, 1H), 2.63 (s, 3H), 2.39 (s, 2H), 2.21 (br d, J=13.2 Hz, 2H), 2.03-1.85 (m, 2H), 1.16 (s, 3H), 0.48-0.38 (m, 4H); LCMS (ESI) [M+H]+: 381.1.

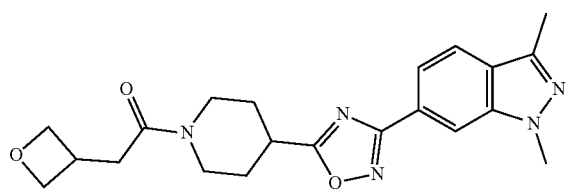 [SMILES: Cc1nn(C)c2cc(-c3noc(C4CCN(C(=O)CC5COC5)CC4)n3)ccc12]

¹H NMR (400 MHz, CHLOROFORM-d) δ 8.10 (s, 1H), 7.88-7.81 (m, 1H), 7.79-7.70 (m, 1H), 4.94 (t, J=7.0 Hz, 2H), 4.52 (br d, J=13.7 Hz, 1H), 4.43 (t, J=5.6 Hz, 2H), 4.09 (s, 3H), 3.98 (br d, J=13.6 Hz, 1H), 3.50-3.39 (m, 1H), 3.33 (br s, 2H), 3.00 (br s, 1H), 2.83 (d, J=7.7 Hz, 2H), 2.61 (s, 3H), 2.25 (br t, J=14.4 Hz, 2H), 2.09-1.89 (m, 2H); LCMS (ESI) [M+H]+: 396.2.

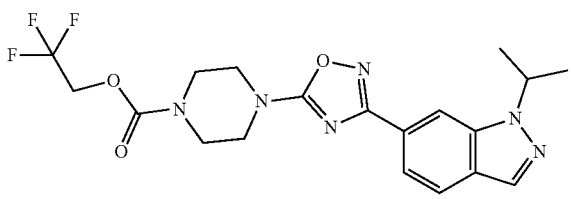 [SMILES: CC(C)n1ncc2ccc(-c3noc(N4CCN(C(=O)OCC(F)(F)F)CC4)n3)cc21]

¹H NMR (400 MHz, CHLOROFORM-d) δ 8.13 (d, J=0.7 Hz, 1H), 8.05 (s, 1H), 7.78 (d, J=0.9 Hz, 2H), 4.95 (spt, J=6.6 Hz, 1H), 4.56 (q, J=8.4 Hz, 2H), 3.78 (br s, 4H), 3.74-3.68 (m, 4H), 1.63 (d, J=6.7 Hz, 6H); LCMS (ESI) [M+H]+: 439.2.

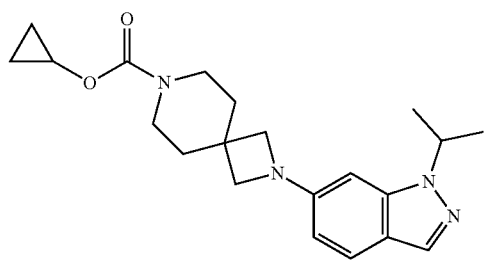 [SMILES: CC(C)n1ncc2ccc(N3CC4(CCN(C(=O)OC5CC5)CC4)C3)cc21]

¹H NMR (400 MHz, CHLOROFORM-d) δ 7.84 (s, 1H), 7.53 (d, J=8.8 Hz, 1H), 8.39 (dd, J=8.4, 1.6 Hz, 1H), 6.22 (s, 1H), 4.75-4.64 (m, 1H), 4.13-4.05 (m, 1H), 3.71 (s, 4H), 3.55-3.30 (m, 4H), 1.93-1.72 (m, 4H), 1.56 (d, J=6.8 Hz, 6H), 0.75-0.62 (m, 4H); LCMS (ESI) [M+H]+: 369.2.

714

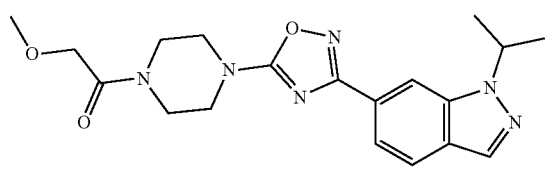 [SMILES: COCC(=O)N1CCN(c2nc(-c3ccc4cnn(C(C)C)c4c3)no2)CC1]

¹H NMR (400 MHz, CHLOROFORM-d) δ 8.13 (d, J=0.9 Hz, 1H), 8.05 (s, 1H), 7.78 (d, J=1.0 Hz, 2H), 4.95 (td, J=6.7, 13.3 Hz, 1H), 4.17 (s, 2H), 3.84-3.68 (m, 8H), 3.51-3.42 (m, 1H), 3.46 (s, 2H), 1.63 (d, J=6.6 Hz, 6H); LCMS (ESI) [M+H]+: 485.1.

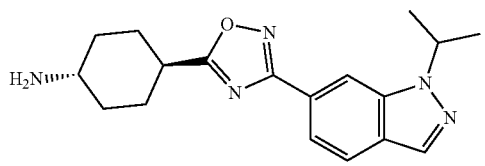 [SMILES: CC(C)n1ncc2ccc(-c3noc([C@H]4CC[C@H](N)CC4)n3)cc21]

¹H NMR (400 MHz, DMSO-d₆) δ 8.26 (s, 1H), 8.18 (s, 1H), 7.92 (d, J=8.4 Hz, 1H), 7.73 (dd, J=1.1, 8.4 Hz, 1H), 5.09 (spt, J=6.6 Hz, 1H), 3.16-3.05 (m, 2H), 2.24 (br d, J=11.4 Hz, 2H), 2.10 (br d, J=10.0 Hz, 2H), 1.76-1.65 (m, 2H), 1.54 (br dd, J=2.8, 12.6 Hz, 2H), 1.49 (d, J=6.6 Hz, 6H); LCMS (ESI) [M+H]+: 326.1.

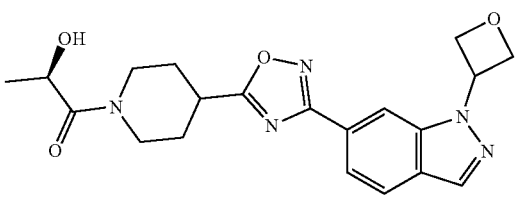 [SMILES: C[C@@H](O)C(=O)N1CCC(c2nc(-c3ccc4cnn(C5COC5)c4c3)no2)CC1]

¹H NMR (300 MHz, CHLOROFORM-d) δ 8.19 (dd, J=14.6, 1.0 Hz, 2H), 7.95-7.80 (m, 2H), 5.89 (p, J=7.1 Hz, 1H), 5.33 (t, J=6.9, 6.2 Hz, 2H), 5.16 (t, J=7.2 Hz, 2H), 4.51 (q, J=6.7 Hz, 2H), 3.83 (s, 1H), 3.37 (d, J=10.6 Hz, 1H), 3.32 (s, 1H), 3.19-3.05 (m, 1H), 2.80 (s, 1H), 2.25 (s, 1H), 1.64 (d, J=7.0 Hz, 1H), 1.57-1.42 (m, 1H), 1.38 (dd, J=8.8, 6.1 Hz, 3H), 1.25 (s, 1H), 1.06 (s, 1H); LCMS (ESI) [M+H]+: 398.3.

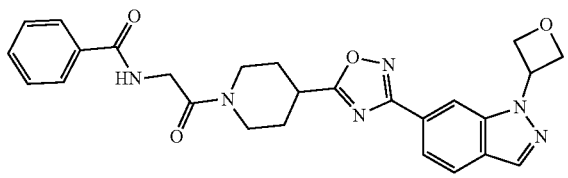 [SMILES: O=C(NCC(=O)N1CCC(c2nc(-c3ccc4cnn(C5COC5)c4c3)no2)CC1)c1ccccc1]

¹H NMR (300 MHz, CHLOROFORM-d) δ 8.26-8.14 (m, 2H), 7.96-7.80 (m, 4H), 7.59-7.40 (m, 3H), 7.33 (s, 1H), 5.88 (q, J=6.8 Hz, 1H), 5.33 (t, J=6.5 Hz, 2H), 5.16 (t, J=7.3 Hz, 2H), 4.54 (d, J=14.0 Hz, 1H), 4.32 (d, J=4.0 Hz, 2H), 3.93 (d, J=13.8 Hz, 1H), 3.43-3.28 (m, 2H), 3.15 (t, J=12.1 Hz, 1H), 2.02 (dd, J=14.6, 10.7 Hz, 2H), 1.47 (s, 1H), 1.25 (s, 2H); LCMS (ESI) [M+H]+: 487.3.

715

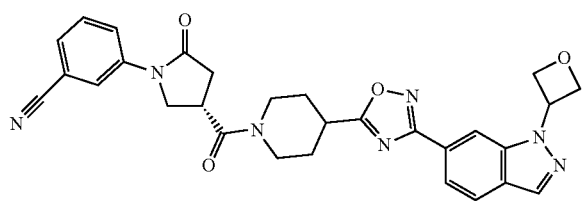 [SMILES: N#Cc1cccc(N2C[C@@H](C(=O)N3CCC(c4nc(-c5ccc6cnn(C7COC7)c6c5)no4)CC3)CC2=O)c1]

¹H NMR (300 MHz, CHLOROFORM-d) δ 8.27-8.14 (m, 2H), 8.01-7.81 (m, 4H), 7.55-7.40 (m, 2H), 5.90 (s, 1H), 5.33 (t, J=6.5 Hz, 2H), 5.16 (t, J=7.2 Hz, 2H), 4.57 (t, J=15.7 Hz, 1H), 4.34 (dd, J=9.5, 6.6 Hz, 1H), 3.95 (t, J=8.1 Hz, 2H), 3.62 (p, J=8.2 Hz, 1H), 3.40 (d, J=8.2 Hz, 1H), 3.37 (s, 1H), 3.21-2.87 (m, 3H), 2.28 (d, J=13.1 Hz, 2H), 2.06 (s, 1H), 1.25 (s, 1H); LCMS (ESI) [M+H]+: 538.3.

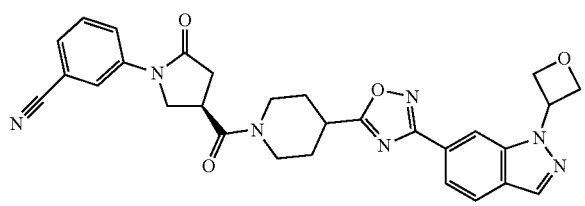 [SMILES: N#Cc1cccc(N2C[C@H](C(=O)N3CCC(c4nc(-c5ccc6cnn(C7COC7)c6c5)no4)CC3)CC2=O)c1]

¹H NMR (300 MHz, CHLOROFORM-d) δ 8.27-8.14 (m, 2H), 8.01-7.81 (m, 4H), 7.55-7.40 (m, 2H), 5.89 (s, 1H), 5.33 (t, J=6.5 Hz, 2H), 5.17 (t, J=7.1 Hz, 2H), 4.57 (s, 1H), 4.34 (dd, J=9.5, 6.6 Hz, 1H), 3.96 (t, J=8.5 Hz, 2H), 3.68-3.56 (m, 1H), 3.39 (s, 1H), 3.12 (s, 1H), 3.06-2.89 (m, 2H), 2.29 (s, 1H), 2.06 (s, 1H), 1.25 (s, 1H); LCMS (ESI) [M+H]+: 538.3.

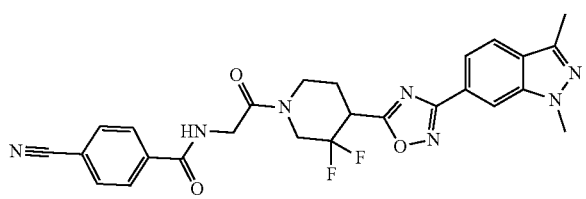 [SMILES: Cc1nn(C)c2cc(-c3noc(C4CCN(C(=O)CNC(=O)c5ccc(C#N)cc5)CC4(F)F)n3)ccc12]

¹H NMR (400 MHz, CHLOROFORM-d) δ 8.09 (s, 1H), 7.95 (d, J=8.2 Hz, 2H), 7.83 (dd, J=0.7, 8.4 Hz, 1H), 7.79-7.71 (m, 3H), 7.42-7.29 (m, 1H), 4.58 (dt, J=6.5, 14.7 Hz, 0.5H), 4.44-4.30 (m, 2.5H), 4.29-4.16 (m, 0.5H), 4.08 (s, 3H), 4.06-3.99 (m, 0.5H), 3.96-3.69 (m, 2H), 3.67-3.50 (m, 1H), 2.60 (s, 3H), 2.49-2.29 (m, 2H); LCMS (ESI) [M+H]+: 520.1.

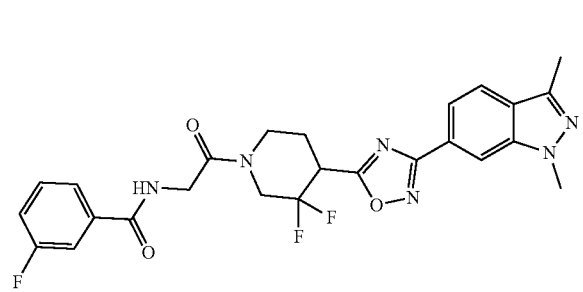 [SMILES: Cc1nn(C)c2cc(-c3noc(C4CCN(C(=O)CNC(=O)c5cccc(F)c5)CC4(F)F)n3)ccc12]

¹H NMR (400 MHz, CHLOROFORM-d) δ 8.03 (s, 1H), 7.76 (dd, J=1.1, 8.4 Hz, 1H), 7.70-7.64 (m, 1H), 7.57-7.46 (m, 2H), 7.36 (dt, J=5.6, 7.9 Hz, 1H), 7.21-7.11 (m, 2H), 4.57-4.42 (m, 0.5H), 4.34-4.22 (m, 2.6H), 4.21-4.10 (m, 0.6H), 4.01 (s, 3H), 3.99-3.90 (m, 0.5H), 3.87-3.62 (m, 2H), 3.60-3.42 (m, 1H), 2.53 (s, 3H), 2.41-2.22 (m, 2H); LCMS (ESI) [M+H]+: 513.2.

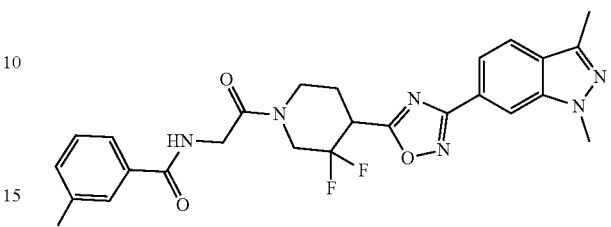

¹H NMR (400 MHz, CHLOROFORM-d) δ 8.14 (s, 1H), 7.91-7.85 (m, 2H), 7.81-7.76 (m, 1H), 7.74 (d, J=7.7 Hz, 1H), 7.53 (d, J=8.8 Hz, 1H), 7.46-7.40 (m, 1H), 7.23 (br d, J=19.8 Hz, 1H), 4.60 (dt, J=6.4, 14.7 Hz, 0.5H), 4.44-4.32 (m, 2.5H), 4.25 (dt, J=5.3, 14.7 Hz, 0.5H), 4.13 (s, 3H), 4.06 (br d, J=13.4 Hz, 0.5H), 3.97-3.71 (m, 2H), 3.69-3.52 (m, 1H), 2.65 (s, 3H), 2.48-2.33 (m, 2H); LCMS (ESI) [M+H]+: 529.1.

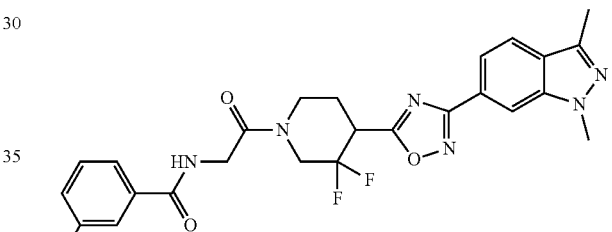

¹H NMR (400 MHz, CHLOROFORM-d) δ 8.17 (br d, J=5.3 Hz, 1H), 8.11 (s, 1H), 8.07 (br d, J=7.9 Hz, 1H), 7.87-7.80 (m, 2H), 7.76 (dd, J=0.7, 8.4 Hz, 1H), 7.64-7.59 (m, 1H), 7.35-7.26 (m, 1H), 4.58 (dt, J=6.3, 14.9 Hz, 0.5H), 4.44-4.30 (m, 2.5H), 4.24 (dt, J=5.6, 15.1 Hz, 0.5H), 4.09 (s, 3H), 4.04 (br d, J=14.5 Hz, 0.5H), 3.96-3.84 (m, 1.5H), 3.82-3.70 (m, 0.5H), 3.70-3.49 (m, 1H), 2.61 (s, 3H), 2.47-2.31 (m, 2H); LCMS (ESI) [M+H]+: 520.2.

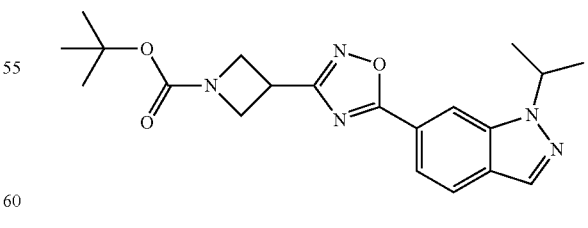

¹H NMR (400 MHz, CHLOROFORM-d) δ 8.32 (s, 1H), 8.11 (s, 1H), 7.95-7.79 (m, 2H), 5.00 (spt, J=6.6 Hz, 1H), 4.42-4.24 (m, 4H), 4.01 (tt, J=6.1, 8.8 Hz, 1H), 1.66 (d, J=6.6 Hz, 6H), 1.49 (s, 9H); LCMS (ESI) [M−55]+: 328.1.

717

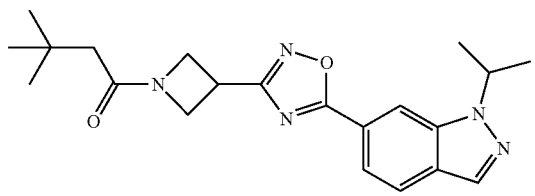 [SMILES: CC(C)n1ncc2ccc(-c3nc(C4CN(C(=O)CC(C)(C)C)C4)no3)cc21]

¹H NMR (400 MHz, CHLOROFORM-d) δ 8.31 (s, 1H), 8.11 (s, 1H), 7.88 (m, 2H), 4.99 (spt, J=6.7 Hz, 1H), 4.59-4.49 (m, 2H), 4.48-4.41 (m, 1H), 4.39-4.32 (m, 1H), 4.04 (tt, J=6.0, 8.8 Hz, 1H), 2.14-2.02 (m, 2H), 1.66 (d, J=6.6 Hz, 6H), 1.10 (s, 9H); LCMS (ESI) [M+H]+: 382.2.

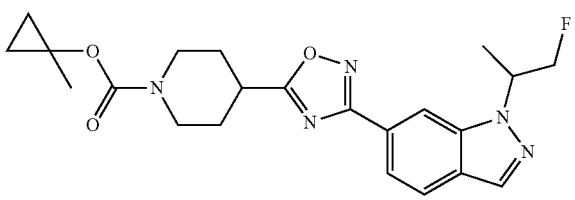 [SMILES: CC(CF)n1ncc2ccc(-c3noc(C4CCN(C(=O)OC5(C)CC5)CC4)n3)cc21]

¹H NMR (400 MHz, CHLOROFORM-d) δ 8.23 (s, 1H), 8.11 (s, 1H), 7.91-7.86 (m, 1H), 7.85-7.80 (m, 1H), 5.16-5.03 (m, 1H), 4.90 (t, J=8.6 Hz, 0.5H), 4.82-4.74 (m, 1H), 4.67 (dd, J=5.0, 9.4 Hz, 0.5H), 4.34-3.93 (br s, 2H), 3.21 (tt, J=3.9, 10.8 Hz, 1H), 3.11-2.97 (m, 2H), 2.16 (br d, J=12.0 Hz, 2H), 1.94 (br d, J=9.7 Hz, 2H), 1.66 (dd, J=1.5, 6.9 Hz, 3H), 1.58 (s, 3H), 0.95-0.84 (m, 2H), 0.69-0.60 (m, 2H); LCMS (ESI) [M+H]+: 428.1.

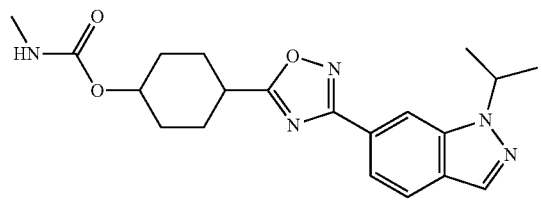 [SMILES: CNC(=O)OC1CCC(c2nc(-c3ccc4cnn(C(C)C)c4c3)no2)CC1]

¹H NMR (400 MHz, DMSO-d₆) δ 8.29 (s, 1H), 8.19 (s, 1H), 7.93 (d, J=8.4 Hz, 1H), 7.75 (d, J=8.4 Hz, 1H), 6.95 (br d, J=4.5 Hz, 1H), 5.14 (spt, J=6.5 Hz, 1H), 4.65-4.43 (m, 1H), 3.20-3.12 (m, 1H), 2.58 (d, J=4.5 Hz, 3H), 2.21 (br d, J=11.4 Hz, 2H), 2.04 (br dd, J=3.1, 12.5 Hz, 2H), 1.82-1.71 (m, 2H), 1.57-1.44 (m, 8H); LCMS (ESI) [M+H]+: 384.2.

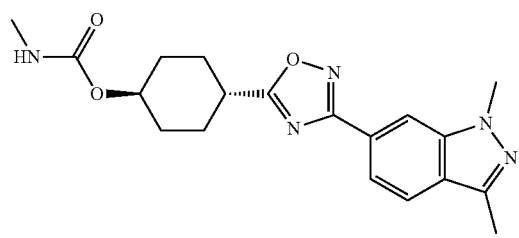 [SMILES: CNC(=O)O[C@H]1CC[C@H](c2nc(-c3ccc4c(C)nn(C)c4c3)no2)CC1]

¹H NMR (400 MHz, CHLOROFORM-d) δ 8.10 (s, 1H), 7.83 (dd, J=1.0, 8.4 Hz, 1H), 7.76-7.70 (m, 1H), 4.80-4.54 (m, 2H), 4.08 (s, 3H), 3.06-2.96 (m, 1H), 2.82 (d, J=4.8 Hz, 3H), 2.60 (s, 3H), 2.34-2.16 (m, 4H), 1.94-1.82 (m, 2H), 1.60-1.46 (m, 2H); LCMS (ESI) [M+H]+: 370.1.

718

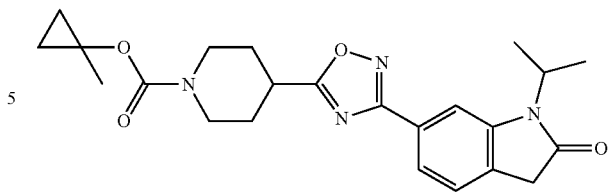

¹H NMR (400 MHz, CHLOROFORM-d) δ 7.77 (d, J=7.7 Hz, 1H), 7.66 (s, 1H), 7.35 (d, J=7.6 Hz, 1H), 4.72-4.65 (m, 1H), 4.25-4.00 (m, 2H), 3.56 (s, 2H), 3.24-3.15 (m, 1H), 3.03 (br t, J=11.1 Hz, 2H), 2.14 (br d, J=11.9 Hz, 2H), 1.92 (br d, J=9.5 Hz, 2H), 1.57 (s, 3H), 1.54 (d, J=7.0 Hz, 6H), 0.92-0.87 (m, 2H), 0.68-0.63 (m, 2H); LCMS (ESI) [M+H]+: 425.2.

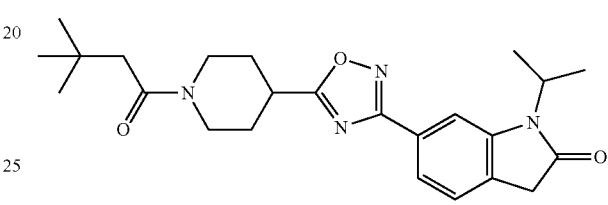

¹H NMR (400 MHz, CHLOROFORM-d) δ 7.77 (d, J=7.7 Hz, 1H), 7.66 (s, 1H), 7.35 (d, J=7.7 Hz, 1H), 4.72-4.65 (m, 1H), 4.62 (br d, J=14.1 Hz, 1H), 4.03 (br d, J=14.1 Hz, 1H), 3.56 (s, 2H), 3.34-3.22 (m, 2H), 2.95 (br t, J=11.5 Hz, 1H), 2.32 (s, 2H), 2.20 (br d, J=11.5 Hz, 2H), 2.03-1.84 (m, 2H), 1.54 (d, J=6.8 Hz, 6H), 1.08 (s, 9H); LCMS (ESI) [M+H]+: 425.2.

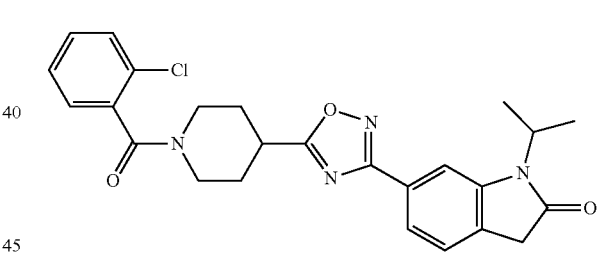

¹H NMR (400 MHz, METHANOL-d₄) δ 7.80 (d, J=7.7 Hz, 1H), 7.75 (s, 1H), 7.54 (d, J=7.7 Hz, 1H), 7.49-7.35 (m, 4H), 4.70-4.63 (m, 2H), 3.60-3.53 (m, 1H), 3.44-3.39 (m, 1H), 3.52-3.37 (m, 1H), 3.32-3.22 (m, 2H), 2.35 (br d, J=11.9 Hz, 1H), 2.17 (br d, J=13.0 Hz, 1H), 2.10-1.96 (m, 2H), 1.95-1.81 (m, 1H), 1.55 (d, J=7.1 Hz, 6H). LCMS (ESI) [M+H]+: 465.1.

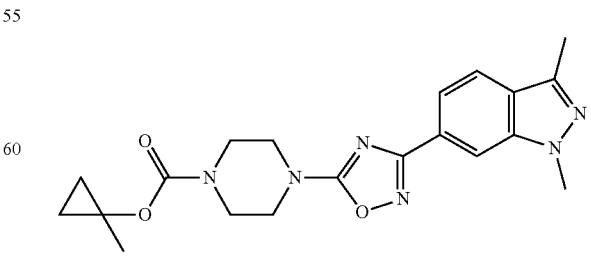

¹H NMR (400 MHz, CHLOROFORM-d) δ 7.94 (s, 1H), 7.70-7.61 (m, 2H), 3.99 (s, 3H), 3.67-3.49 (m, 8H), 2.51 (s,

3H), 1.51 (s, 3H), 0.88-0.79 (m, 2H), 0.64-0.56 (m, 2H); LCMS (ESI) [M+H]+: 397.1.

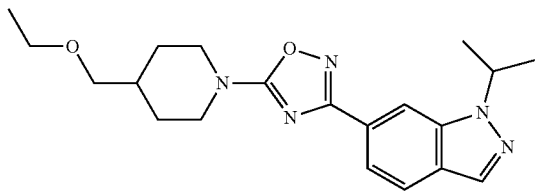 [SMILES: CCOCC1CCN(c2nc(-c3ccc4cnn(C(C)C)c4c3)no2)CC1]

$^1$H NMR (400 MHz, CHLOROFORM-d) δ 8.12 (s, 1H), 8.03 (s, 1H), 7.81-7.73 (m, 2H), 4.95 (m, 1H), 4.30 (m, 2H), 3.49 (q, J=7.1 Hz, 2H), 3.32 (d, J=6.0 Hz, 2H), 3.15 (dt, J=2.3, 12.8 Hz, 2H), 1.96-1.80 (m, 3H), 1.61 (d, J=6.6 Hz, 6H), 1.46-1.29 (m, 2H), 1.21 (t, J=6.9 Hz, 3H); LCMS (ESI) [M+H]+: 370.2.

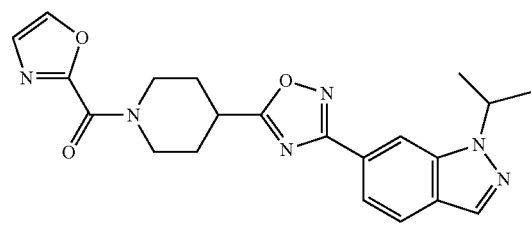 [SMILES: CC(C)n1ncc2ccc(-c3noc(C4CCN(C(=O)c5ncco5)CC4)n3)cc21]

$^1$H NMR (400 MHz, CHLOROFORM-d) δ 8.22 (s, 1H), 8.07 (s, 1H), 7.90-7.78 (m, 3H), 7.28 (s, 1H), 5.09-4.91 (m, 2H), 4.65 (br d, J=13.2 Hz, 1H), 3.70-3.58 (m, 1H), 3.47-3.36 (m, 1H), 3.34-3.23 (m, 1H), 2.30 (br d, J=3.5 Hz, 2H), 2.23-2.05 (m, 2H), 1.64 (d, J=6.6 Hz, 6H); LCMS (ESI) [M+H]+: 407.1.

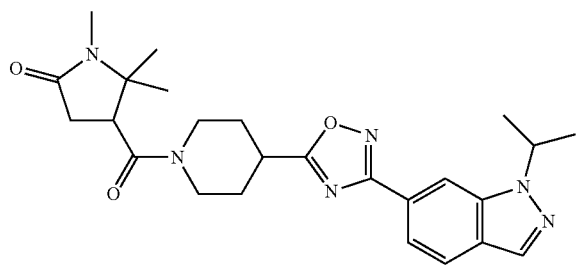 [SMILES: CC(C)n1ncc2ccc(-c3noc(C4CCN(C(=O)C5CC(=O)N(C)C5(C)C)CC4)n3)cc21]

$^1$H NMR (400 MHz, CHLOROFORM-d) δ 8.22 (s, 1H), 8.08 (s, 1H), 7.91-7.79 (m, 2H), 4.98 (td, J=6.6, 13.3 Hz, 1H), 4.74-4.49 (m, 1H), 4.25-4.03 (m, 1H), 3.53-3.29 (m, 3H), 3.23-2.97 (m, 2H), 2.77 (s, 3H), 2.48 (br dd, J=7.6, 17.0 Hz, 1H), 2.38-2.21 (m, 2H), 2.11-1.92 (m, 2H), 1.65 (d, J=6.6 Hz, 6H), 1.43 (s, 3H), 1.17 (d, J=5.0 Hz, 3H); LCMS (ESI) [M+H]+: 465.2.

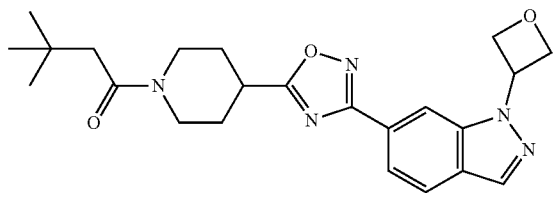

$^1$H NMR (400 MHz, CHLOROFORM-d) δ 8.22 (s, 1H), 8.17 (s, 1H), 7.94-7.89 (m, 1H), 7.88-7.83 (m, 1H), 5.90 (quin, J=7.0 Hz, 1H), 5.34 (t, J=6.6 Hz, 2H), 5.16 (t, J=7.3 Hz, 2H), 4.63 (br d, J=13.4 Hz, 1H), 4.05 (br d, J=13.4 Hz, 1H), 3.37-3.23 (m, 2H), 2.96 (br t, J=11.2 Hz, 1H), 2.32 (s, 2H), 2.22 (br d, J=12.8 Hz, 2H), 2.03-1.88 (m, 2H), 1.09 (s, 9H); LCMS (ESI) [M+H]+: 424.2.

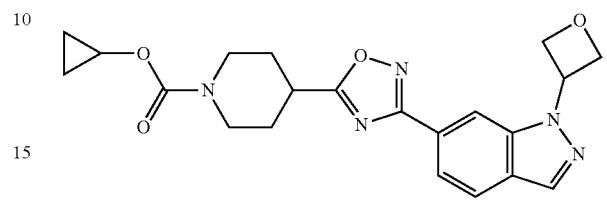

$^1$H NMR (400 MHz, CHLOROFORM-d) δ 8.22 (s, 1H), 8.17 (s, 1H), 7.94-7.88 (m, 1H), 7.88-7.82 (m, 1H), 5.90 (quin, J=7.0 Hz, 1H), 5.34 (t, J=6.5 Hz, 2H), 5.16 (t, J=7.3 Hz, 2H), 4.39-3.91 (m, 3H), 3.23 (tt, J=3.9, 10.9 Hz, 1H), 3.07 (ddd, J=2.9, 11.2, 13.8 Hz, 2H), 2.25-2.08 (m, 2H), 2.03-1.85 (m, 2H), 0.76-0.66 (m, 4H); LCMS (ESI) [M+H]+: 410.1.

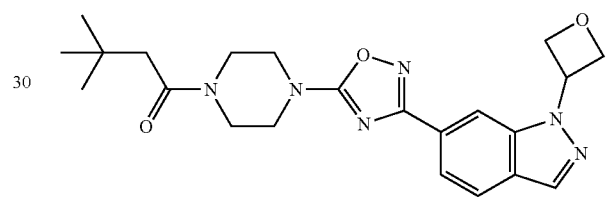

$^1$H NMR (400 MHz, CHLOROFORM-d) δ 8.15 (br d, J=2.9 Hz, 2H), 7.86-7.78 (m, 2H), 5.93-5.84 (m, 1H), 5.33 (m, 2H), 5.19-5.11 (m, 2H), 3.85-3.67 (m, 8H), 2.33 (d, J=2.4 Hz, 2H), 1.09 (d, J=2.4 Hz, 9H); LCMS (ESI) [M+H]+: 425.2.

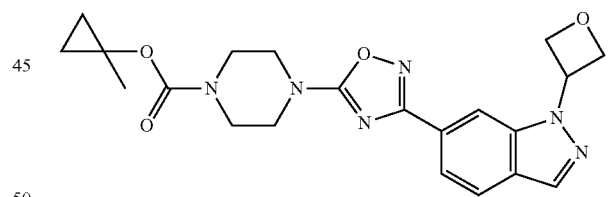

$^1$H NMR (400 MHz, CHLOROFORM-d) δ 8.14 (d, J=7.1 Hz, 2H), 7.84-7.78 (m, 2H), 5.88 (quin, J=7.1 Hz, 1H), 5.32 (t, J=6.6 Hz, 2H), 5.14 (t, J=7.3 Hz, 2H), 3.74-3.56 (m, 8H), 1.58 (s, 3H), 0.93-0.88 (t, J=6.4 Hz, 2H), 0.70-0.65 (t, J=6.4 Hz, 2H); LCMS (ESI) [M+H]+: 425.2.

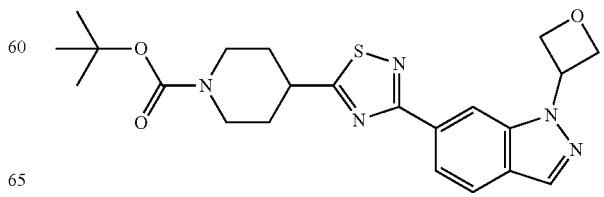

721

¹H NMR (400 MHz, CHLOROFORM-d) δ 8.46 (s, 1H), 8.21-8.14 (m, 2H), 7.85 (d, J=8.4 Hz, 1H), 5.94 (m, 1H), 5.37 (t, J=6.6 Hz, 2H), 5.18 (t, J=7.3 Hz, 2H), 4.26 (m, 2H), 3.38 (m, 1H), 3.00 (m, 2H), 2.25 (m, 2H), 1.87 (m, 2H), 1.52 (s, 9H); LCMS (ESI) [M+H]+: 442.1.

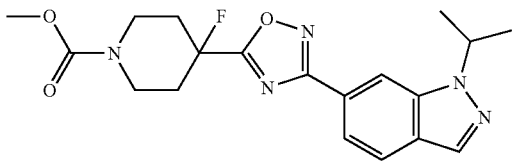 [SMILES: COC(=O)N1CCC(F)(c2nc(-c3ccc4cnn(C(C)C)c4c3)no2)CC1]

¹H NMR (400 MHz, CHLOROFORM-d) δ 8.23 (s, 1H), 8.07 (s, 1H), 7.89-7.80 (m, 2H), 5.02-4.93 (m, 1H), 4.10 (br s, 2H), 3.75 (s, 3H), 3.42 (br t, J=10.6 Hz, 2H), 2.41-2.23 (m, 4H), 1.63 (d, J=6.7 Hz, 6H); LCMS (ESI) [M+H]+: 388.1.

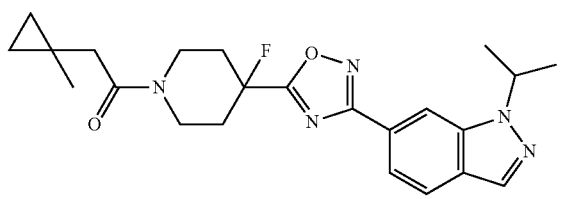 [SMILES: CC(C)n1ncc2ccc(-c3noc(C4(F)CCN(C(=O)CC5(C)CC5)CC4)n3)cc21]

¹H NMR (400 MHz, CHLOROFORM-d) δ 8.25 (s, 1H), 8.09 (s, 1H), 7.90-7.83 (m, 2H), 5.03-4.96 (m, 1H), 4.56 (br d, J=13.4 Hz, 1H), 3.89 (br d, J=13.9 Hz, 1H), 3.62 (br t, J=11.4 Hz, 1H), 3.29 (br t, J=11.2 Hz, 1H), 2.48-2.24 (m, 6H), 1.65 (d, J=6.6 Hz, 6H), 1.20 (s, 3H), 0.52-0.40 (m, 4H); LCMS (ESI) [M+H]+: 426.2.

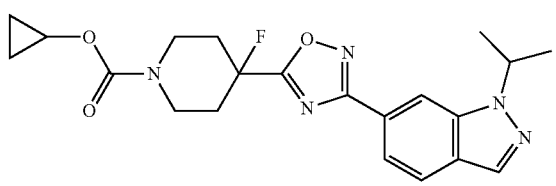 [SMILES: CC(C)n1ncc2ccc(-c3noc(C4(F)CCN(C(=O)OC5CC5)CC4)n3)cc21]

¹H NMR (400 MHz, CHLOROFORM-d) δ 8.15 (s, 1H), 7.99 (s, 1H), 7.80-7.73 (m, 2H), 4.95-4.84 (m, 1H), 4.19-3.78 (m, 3H), 3.39-3.24 (m, 2H), 2.34-2.11 (m, 4H), 1.55 (d, J=6.7 Hz, 6H), 0.67-0.61 (m, 4H); LCMS (ESI) [M+H]+: 414.1.

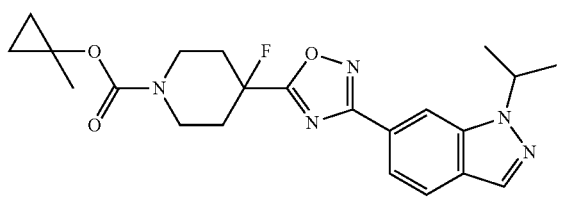 [SMILES: CC(C)n1ncc2ccc(-c3noc(C4(F)CCN(C(=O)OC5(C)CC5)CC4)n3)cc21]

¹H NMR (400 MHz, CHLOROFORM-d) δ 8.24 (s, 1H), 8.08 (s, 1H), 7.89-7.82 (m, 2H), 4.98 (spt, J=6.6 Hz, 1H), 4.22-3.89 (m, 2H), 3.46-3.32 (m, 2H), 2.40-2.23 (m, 4H), 1.65 (d, J=6.6 Hz, 6H), 1.59 (s, 3H), 1.05-0.86 (m, 2H), 0.71-0.65 (m, 2H); LCMS (ESI) [M+H]+: 428.1.

722

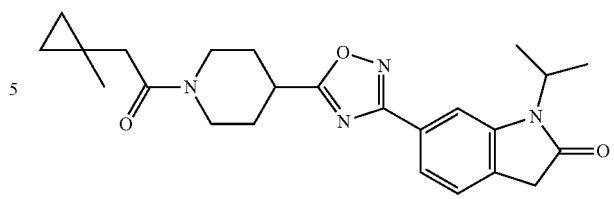

¹H NMR (400 MHz, CHLOROFORM-d) δ 7.77 (d, J=7.7 Hz, 1H), 7.66 (s, 1H), 7.35 (d, J=7.5 Hz, 1H), 4.72-4.65 (m, 1H), 4.59 (br d, J=13.5 Hz, 1H), 3.96 (br d, J=13.7 Hz, 1H), 3.56 (s, 2H), 3.33-3.23 (m, 2H), 2.97 (br t, J=11.4 Hz, 1H), 2.39 (d, J=4.4 Hz, 2H), 2.21 (br d, J=13.2 Hz, 2H), 2.01-1.87 (m, 2H), 1.54 (d, J=7.1 Hz, 6H), 1.17 (s, 3H), 0.48-0.38 (m, 4H); LCMS (ESI) [M+H]+: 423.2.

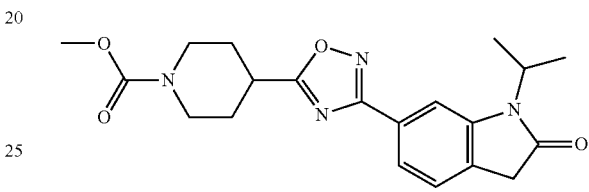

¹H NMR (400 MHz, CHLOROFORM-d) δ 7.77 (dd, J=1.0, 7.6 Hz, 1H), 7.66 (s, 1H), 7.35 (d, J=7.7 Hz, 1H), 4.68 (spt, J=7.0 Hz, 1H), 4.30-4.00 (m, 2H), 3.73 (s, 3H), 3.55 (s, 2H), 3.22 (tt, J=4.0, 10.8 Hz, 1H), 3.08 (br t, J=11.7 Hz, 2H), 2.16 (br d, J=10.8 Hz, 2H), 2.03-1.84 (m, 2H), 1.54 (d, J=7.1 Hz, 6H); LCMS (ESI) [M+H]+: 385.2.

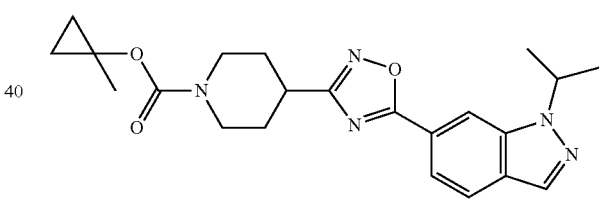

¹H NMR (400 MHz, CHLOROFORM-d) δ 8.27 (s, 1H), 8.10 (s, 1H), 7.87 (m, 2H), 5.06-4.92 (m, 1H), 4.37-3.97 (m, 2H), 3.14-2.90 (m, 3H), 2.09 (br d, J=10.8 Hz, 2H), 1.88 (br d, J=9.9 Hz, 2H), 1.65 (d, J=6.6 Hz, 6H), 1.58 (s, 3H), 0.97-0.83 (m, 2H), 0.70-0.59 (m, 2H); LCMS (ESI) [M+H]+: 410.2.

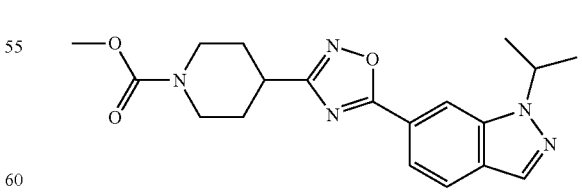

¹H NMR (400 MHz, CHLOROFORM-d) δ 8.28 (s, J=0.6 Hz, 1H), 8.10 (s, 1H), 7.92-7.82 (m, 2H), 4.98 (spt, J=6.7 Hz, 1H), 4.22 (br s, 2H), 3.74 (s, 3H), 3.16-2.97 (m, 3H), 2.11 (m, J=11.7 Hz, 2H), 1.99-1.82 (m, 2H), 1.65 (d, J=6.6 Hz, 6H); LCMS (ESI) [M+H]+: 370.1.

723

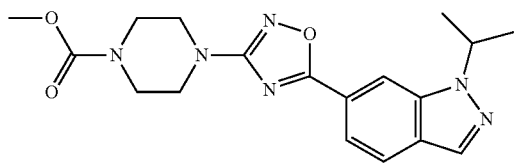 [SMILES: COC(=O)N1CCN(c2noc(-c3ccc4cnn(C(C)C)c4c3)n2)CC1]

¹H NMR (400 MHz, CHLOROFORM-d) δ 8.22 (s, 1H), 8.09 (s, 1H), 7.84 (m, 2H), 4.97 (spt, J=6.6 Hz, 1H), 3.76 (s, 3H), 3.69-3.44 (m, 8H), 1.64 (d, J=6.7 Hz, 6H); LCMS (ESI) [M+H]+: 371.1.

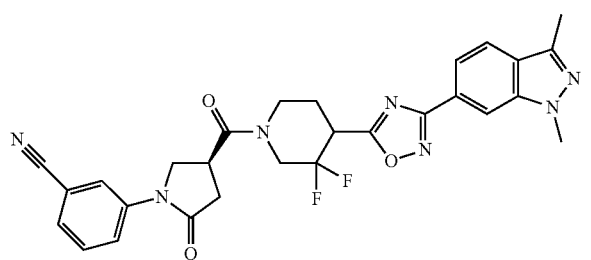 [SMILES: Cc1nn(C)c2cc(-c3noc(C4CCN(C(=O)[C@H]5CC(=O)N(c6cccc(C#N)c6)C5)CC4(F)F)n3)ccc12]

¹H NMR (400 MHz, CHLOROFORM-d) δ 8.12 (s, 1H), 8.03-7.82 (m, 3H), 7.78-7.73 (m, 1H), 7.53-7.43 (m, 2H), 4.65 (m 0.4H), 4.48 (m, 0.5H), 4.41-4.24 (m, 2H), 4.10 (br d, J=2.4 Hz, 3H), 4.00 (t, J=9.0 Hz, 1H), 3.95-3.75 (m, 2H), 3.73-3.45 (m, 2H), 3.07-2.89 (m, 2H), 2.62 (s, 3H), 2.49-2.32 (m, 2H); LCMS (ESI) [M+H]+: 546.2.

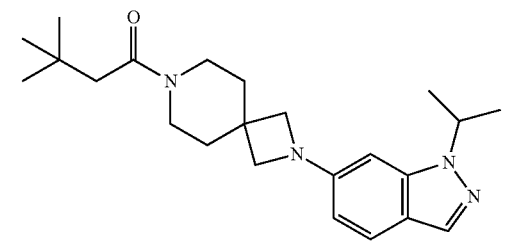 [SMILES: CC(C)n1ncc2ccc(N3CC4(CCN(C(=O)CC(C)(C)C)CC4)C3)cc21]

¹H NMR (400 MHz, CHLOROFORM-d) δ 7.85 (s, 1H), 7.54 (d, J=8.7 Hz, 1H), 6.40 (dd, J=1.6, 8.7 Hz, 1H), 6.23 (s, 1H), 4.83-4.60 (m, 1H), 3.73 (s, 4H), 3.69-3.44 (m, 4H), 2.30 (s, 2H), 1.85 (br dd, J=5.4, 8.8 Hz, 4H), 1.57 (d, J=6.6 Hz, 6H), 1.08 (s, 9H); LCMS (ESI) [M+H]+: 383.2.

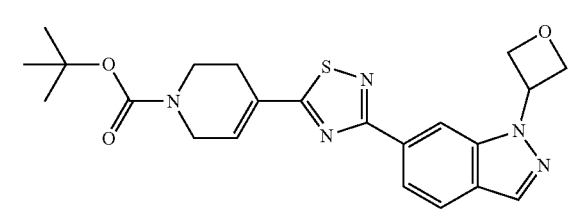

¹H NMR (400 MHz, CHLOROFORM-d) δ 8.38 (s, 1H), 8.14-8.04 (m, 2H), 7.76 (d, J=8.4 Hz, 1H), 6.83 (br s, 1H), 5.85 (t, J=6.9 Hz, 1H), 5.28 (t, J=6.5 Hz, 2H), 5.09 (t, J=7.3 Hz, 2H), 4.15 (d, J=2.4 Hz, 2H), 3.64 (t, J=5.4 Hz, 2H), 2.70 (m, 2H), 1.44 (s, 9H) LCMS (ESI) [M+H]+: 440.1.

724

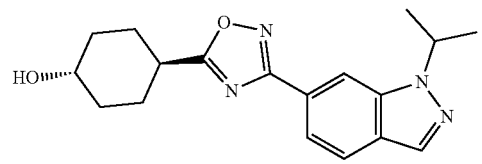 [SMILES: CC(C)n1ncc2ccc(-c3noc([C@H]4CC[C@H](O)CC4)n3)cc21]

¹H NMR (400 MHz, CHLOROFORM-d) δ 8.22 (s, 1H), 8.08 (s, 1H), 7.89-7.81 (m, 2H), 5.04-4.93 (m, 1H), 3.84-3.73 (m, 1H), 3.03 (tt, J=3.7, 11.9 Hz, 1H), 2.33-2.26 (m, 2H), 2.24-2.15 (m, 2H), 1.88-1.77 (m, 2H), 1.64 (d, J=6.7 Hz, 6H), 1.55-1.44 (m, 2H); LCMS (ESI) [M+H]+: 327.1.

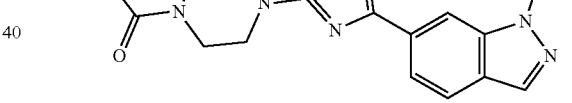

¹H NMR (400 MHz, CHLOROFORM-d) δ 8.22 (s, 1H), 8.17 (s, 1H), 7.94-7.88 (m, 1H), 7.87-7.81 (m, 1H), 5.90 (quin, J=7.0 Hz, 1H), 5.34 (t, J=6.5 Hz, 2H), 5.16 (t, J=7.3 Hz, 2H), 4.31-4.08 (m, 2H), 3.74 (s, 3H), 3.23 (tt, J=3.9, 10.9 Hz, 1H), 3.09 (br t, J=11.5 Hz, 2H), 2.18 (br dd, J=2.8, 13.3 Hz, 2H), 2.02-1.89 (m, 2H); LCMS (ESI) [M+H]+: 384.1.

¹HNMR (400 MHz, CHLOROFORM-d) δ 8.14 (d, J=4.5 Hz, 2H), 7.81-7.81 (m, 2H), 5.87 (quin, J=7.0 Hz, 1H), 5.32 (t, J=6.5 Hz, 2H), 5.14 (t, J=7.3 Hz, 2H), 3.76 (s, 3H), 3.72 (m, 4H), 3.65 (m, 4H); LCMS (ESI) [M+H]+: 385.1.

¹H NMR (400 MHz, CHLOROFORM-d) δ 8.12 (s, 1H), 8.03 (s, 1H), 7.81-7.73 (m, 2H), 4.95 (m, 1H), 4.33 (m, 2H), 3.57 (d, J=6.2 Hz, 2H), 3.16 (dt, J=2.8, 13.0 Hz, 2H), 1.90 (br d, J=12.6 Hz, 2H), 1.84-1.73 (m, 1H), 1.61 (d, J=6.6 Hz, 6H), 1.45-1.33 (m, 2H); LCMS (ESI) [M+H]+: 342.1.

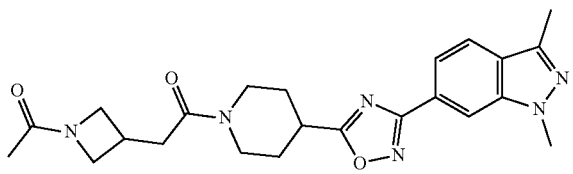 [SMILES: CC(=O)N1CC(CC(=O)N2CCC(c3nc(-c4ccc5c(C)nn(C)c5c4)no3)CC2)C1]

¹H NMR (400 MHz, CHLOROFORM-d) δ 8.08 (s, 1H), 7.84-7.79 (m, 1H), 7.75-7.71 (m, 1H), 4.50 (br dd, J=10.0, 13.3 Hz, 1H), 4.37 (t, J=8.5 Hz, 1H), 4.19 (t, J=9.3 Hz, 1H), 4.07 (s, 3H), 3.92 (br d, J=13.5 Hz, 1H), 3.79 (dd, J=5.6, 8.5 Hz, 1H), 3.67 (br dd, J=5.7, 9.5 Hz, 1H), 3.31 (br t, J=10.9 Hz, 2H), 3.06-2.96 (m, 2H), 2.80-2.62 (m, 2H), 2.59 (s, 3H), 2.29-2.18 (m, 2H), 2.05-1.91 (m, 2H), 1.85 (s, 3H); LCMS (ESI) [M+H]+: 437.5.

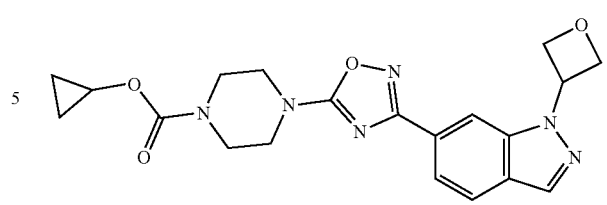

¹H NMR (400 MHz, CHLOROFORM-d) δ 8.14 (d, J=6.1 Hz, 2H), 7.84-7.78 (m, 2H), 5.88 (quin, J=7.1 Hz, 1H), 5.33 (t, J=6.6 Hz, 2H), 5.14 (t, J=7.3 Hz, 2H), 4.16-4.10 (m, 1H), 3.79-3.56 (m, 8H), 0.78-0.67 (m, 4H); LCMS (ESI) [M+H]+: 411.1.

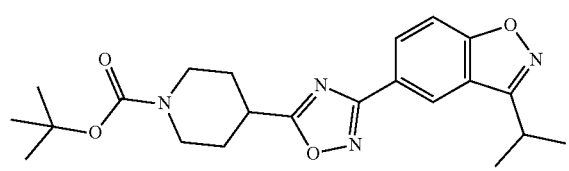 [SMILES: CC(C)c1noc2ccc(-c3noc(C4CCN(C(=O)OC(C)(C)C)CC4)n3)cc12]

¹H NMR (400 MHz, CHLOROFORM-d) δ 8.45 (s, 1H), 8.28 (d, J=8.7 Hz, 1H), 7.65 (d, J=8.8 Hz, 1H), 4.16 (br s, 2H), 3.48 (td, J=7.0, 14.0 Hz, 1H), 3.28-3.13 (m, 1H), 3.02 (br t, J=11.6 Hz, 2H), 2.15 (br d, J=10.4 Hz, 2H), 2.03-1.86 (m, 2H), 1.54 (d, J=7.0 Hz, 6H), 1.49 (s, 9H); LCMS (ESI) [M+H]+: 413.1.

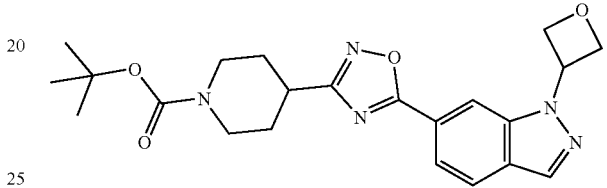

¹H NMR (400 MHz, CHLOROFORM-d) δ 8.30 (s, 1H), 8.21 (s, 1H), 7.98-7.83 (m, 2H), 5.91 (m, J=7.0 Hz, 1H), 5.40-5.30 (m, 2H), 5.24-5.11 (m, 2H), 4.29-4.06 (m, 2H), 3.06 (tt, J=3.7, 11.2 Hz, 1H), 2.97 (br t, J=11.9 Hz, 2H), 2.16-2.01 (m, 2H), 1.97-1.79 (m, 2H), 1.49 (s, 9H); LCMS (ESI) [M−55]+: 370.1.

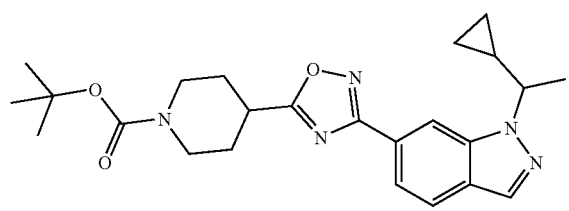 [SMILES: CC(C1CC1)n1ncc2ccc(-c3noc(C4CCN(C(=O)OC(C)(C)C)CC4)n3)cc21]

¹H NMR (400 MHz, DMSO-d₆) δ 8.29 (s, 1H), 8.20 (s, 1H), 7.92 (d, J=8.4 Hz, 1H), 7.74 (dd, J=1.2, 8.5 Hz, 1H), 4.46-4.29 (m, 1H), 3.98 (br d, J=13.2 Hz, 2H), 3.48-3.35 (m, 1H), 2.99 (br s, 2H), 2.10 (br dd, J=3.1, 13.2 Hz, 2H), 1.80-1.64 (m, 2H), 1.59 (d, J=6.6 Hz, 3H), 1.47-1.36 (m, 10H), 0.64-0.55 (m, 1H), 0.44 (qd, J=4.8, 9.5 Hz, 1H), 0.38-0.30 (m, 1H), 0.25 (qd, J=4.9, 9.6 Hz, 1H); LCMS (ESI) [M+H]+: 438.2.

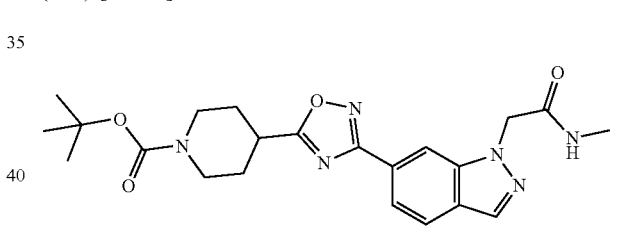

¹H NMR (400 MHz, CHLOROFORM-d) δ 8.21 (d, J=8.4 Hz, 2H), 8.00-7.94 (m, 1H), 7.92-7.83 (m, 1H), 5.90-5.75 (m, 1H), 5.16 (s, 2H), 4.25-4.10 (m, 2H), 3.29-2.96 (m, 3H), 2.80 (d, J=4.8 Hz, 3H), 2.18 (br d, J=11.1 Hz, 2H), 2.05-1.85 (m, 2H), 1.51 (s, 9H); LCMS (ESI) [M−100+H]+: 341.1.

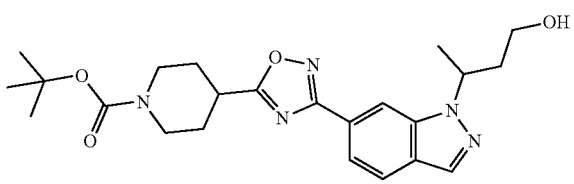 [SMILES: CC(CCO)n1ncc2ccc(-c3noc(C4CCN(C(=O)OC(C)(C)C)CC4)n3)cc21]

¹H NMR (400 MHz, CHLOROFORM-d) δ 8.25 (s, 1H), 8.07 (s, 1H), 7.88-7.84 (d, J=12 Hz, 1H), 7.83-7.79 (d, J=12 Hz, 1H), 5.15-5.01 (m, 1H), 4.16-4.13 (m, 2H), 3.64-3.62 (m, 1H), 3.45-3.34 (m, 1H), 3.21-3.18 (m, 1H), 2.98-3.02 (m, 2H), 2.39-2.36 (m, 1H), 2.24-2.09 (m, 3H), 1.99-1.86 (m, 3H), 1.63 (d, J=6.6 Hz, 3H), 1.49 (s, 9H); LCMS (ESI) [M+H]+: 442.2.

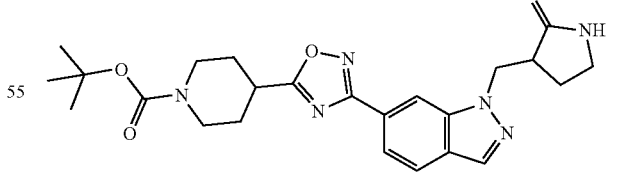

¹H NMR (400 MHz, CHLOROFORM-d) δ 8.32 (s, 1H), 8.08 (s, 1H), 7.91-7.88 (m, 1H), 7.85-7.81 (m, 1H), 5.61 (br s, 1H), 4.92 (dd, J=4.3, 14.4 Hz, 1H), 4.63 (dd, J=8.5, 14.4 Hz, 1H), 4.17 (m, 2H), 3.39-3.16 (m, 3H), 3.14-2.95 (m, 3H), 2.31-2.07 (m, 4H), 2.02-1.89 (m, 2H); LCMS (ESI) [M+H]+: 367.1.

727

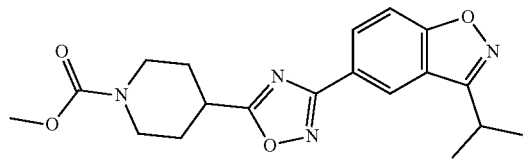 [SMILES: COC(=O)N1CCC(c2nc(-c3ccc4onc(C(C)C)c4c3)no2)CC1]

¹H NMR (400 MHz, CHLOROFORM-d) δ 8.45 (s, 1H), 8.28 (dd, J=1.6, 8.8 Hz, 1H), 7.65 (d, J=8.9 Hz, 1H), 4.19 (br s, 2H), 3.74 (s, 3H), 3.48 (td, J=6.9, 14.0 Hz, 1H), 3.29-3.18 (m, 1H), 3.09 (br t, J=12.5 Hz, 2H), 2.17 (br d, J=13.6 Hz, 2H), 2.02-1.88 (m, 2H), 1.55 (s, 3H), 1.54 (s, 3H); LCMS (ESI) [M+H]+: 371.1.

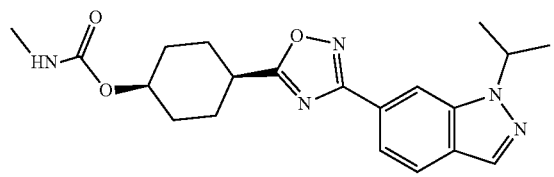 [SMILES: CNC(=O)O[C@H]1CC[C@@H](c2nc(-c3ccc4cnn(C(C)C)c4c3)no2)CC1]

¹H NMR (400 MHz, CHLOROFORM-d) δ 8.22 (s, 1H), 8.06 (s, 1H), 7.89-7.80 (m, 2H), 5.04-4.93 (m, 2H), 4.65 (br s, 1H), 3.18-3.09 (m, 1H), 2.82 (d, J=4.9 Hz, 3H), 2.23-1.97 (m, 6H), 1.77 (br d, J=11.1 Hz, 2H), 1.63 (d, J=6.6 Hz, 6H); LCMS (ESI) [M+H]+: 384.1.

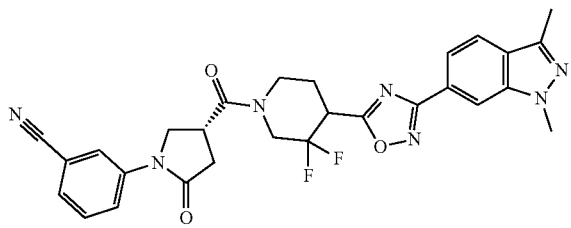 [SMILES: Cc1nn(C)c2cc(-c3noc(C4CCN(C(=O)[C@@H]5CC(=O)N(c6cccc(C#N)c6)C5)CC4(F)F)n3)ccc12]

¹H NMR (400 MHz, CHLOROFORM-d) δ 8.11 (s, 1H), 8.01-7.83 (m, 3H), 7.79-7.73 (m, 1H), 7.52-7.43 (m, 2H), 4.64 (dt, J=6.5, 14.2 Hz, 1H), 4.47 (br d, J=13.3 Hz, 1H), 4.41-4.25 (m, 2H), 4.10 (br d, J=2.8 Hz, 3H), 3.99 (t, J=9.0 Hz, 1H), 3.94-3.75 (m, 2H), 3.71-3.43 (m, 2H), 3.05-2.87 (m, 2H), 2.61 (s, 3H), 2.48-2.30 (m, 2H); LCMS (ESI) [M+H]+: 546.2.

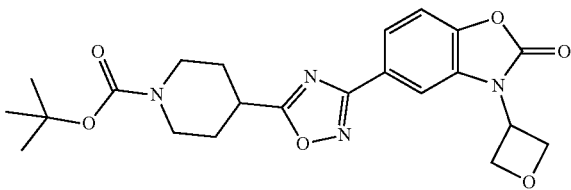 [SMILES: CC(C)(C)OC(=O)N1CCC(c2nc(-c3ccc4oc(=O)n(C5COC5)c4c3)no2)CC1]

¹H NMR (400 MHz, CHLOROFORM-d) δ 8.22 (s, 1H), 7.98 (d, J=8.4 Hz, 1H), 7.36 (d, J=8.4 Hz, 1H), 5.55-5.48 (m, 1H), 5.24-5.21 (m, 2H), 5.15-5.11 (m, 2H), 4.22-4.05 (m, 2H), 3.19 (tt, J=3.8, 11.0 Hz, 1H), 3.00 (br t, J=11.8 Hz, 2H), 2.14 (br d, J=10.6 Hz, 2H), 1.98-1.85 (m, 2H), 1.49 (s, 9H); LCMS (ESI) [M−55]+: 387.1.

728

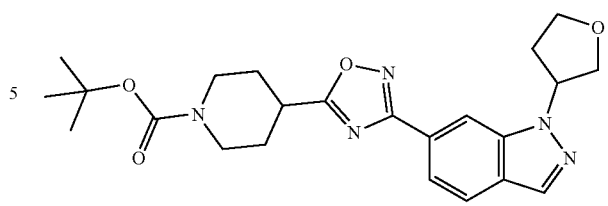

¹H NMR (400 MHz, CHLOROFORM-d) δ 8.24 (s, 1H), 8.08 (s, 1H), 7.93-7.87 (m, 1H), 7.86-7.79 (m, 1H), 5.43-5.33 (m, 1H), 4.34-4.12 (m, 5H), 4.05 (q, J=7.3 Hz, 1H), 3.21 (br t, J=10.9 Hz, 1H), 3.02 (br t, J=11.7 Hz, 2H), 2.55 (q, J=6.7 Hz, 2H), 2.16 (br d, J=13.0 Hz, 2H), 2.01-1.86 (m, 2H), 1.49 (s, 9H); LCMS (ESI) [M+H]+: 440.5.

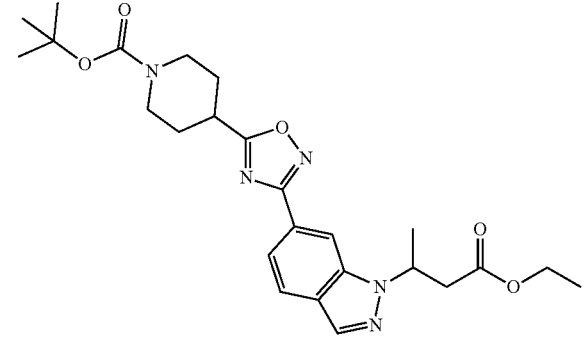 [SMILES: CCOC(=O)CC(C)n1ncc2ccc(-c3noc(C4CCN(C(=O)OC(C)(C)C)CC4)n3)cc21]

¹H NMR (400 MHz, CHLOROFORM-d) δ 8.28 (s, 1H), 8.07 (s, 1H), 7.88-7.84 (d, J=8.4 Hz, 1H), 7.82-7.77 (d, J=8.4 Hz, 1H), 5.35-5.23 (m, 1H), 4.18-4.16 (m, 2H), 4.05-3.96 (m, 2H), 3.25-3.14 (m, 2H), 3.03 (br t, J=11.9 Hz, 2H), 2.93 (dd, J=6.1, 16.0 Hz, 1H), 2.16 (br d, J=10.8 Hz, 2H), 2.01-1.89 (m, 2H), 1.64 (d, J=6.6 Hz, 3H), 1.50 (s, 9H), 1.10 (t, J=7.2 Hz, 3H); LCMS (ESI) [M+H]+: 484.2.

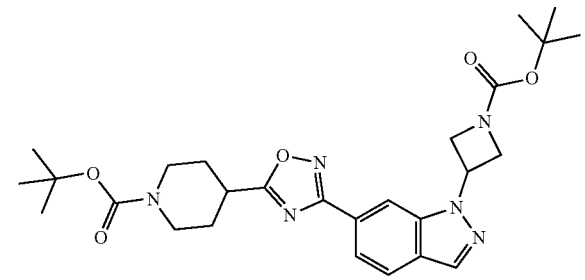 [SMILES: CC(C)(C)OC(=O)N1CCC(c2nc(-c3ccc4cnn(C5CN(C(=O)OC(C)(C)C)C5)c4c3)no2)CC1]

¹H NMR (400 MHz, CHLOROFORM-d) δ 8.17 (s, 1H), 8.14 (s, 1H), 7.93-7.87 (m, 1H), 7.86-7.80 (m, 1H), 5.54-5.42 (m, 1H), 4.60-4.52 (m, 2H), 4.51-4.43 (m, 2H), 4.22-4.07 (m, 2H), 3.20 (tt, J=3.9, 10.9 Hz, 1H), 3.01 (br t, J=12.0 Hz, 2H), 2.15 (br dd, J=2.6, 13.2 Hz, 2H), 2.00-1.83 (m, 2H), 1.49 (d, J=2.6 Hz, 18H); LCMS (ESI) [M−100+H]+: 425.2.

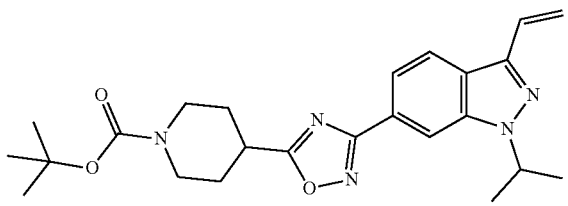 [SMILES: C=Cc1nn(C(C)C)c2cc(-c3noc(C4CCN(C(=O)OC(C)(C)C)CC4)n3)ccc12]

¹H NMR (400 MHz, CHLOROFORM-d) δ 8.18 (s, 1H), 8.00 (d, J=8.4 Hz, 1H), 7.93-7.85 (m, 1H), 7.07 (dd, J=11.5, 18.0 Hz, 1H), 6.09 (d, J=18.1 Hz, 1H), 5.63-5.46 (m, 1H), 5.05-4.85 (m, 1H), 4.16 (br s, 2H), 3.21 (ddd, J=4.2, 6.9, 10.8 Hz, 1H), 3.02 (br t, J=11.6 Hz, 2H), 2.16 (br d, J=11.1 Hz, 2H), 2.00-1.88 (m, 2H), 1.63 (d, J=6.7 Hz, 6H), 1.49 (s, 9H); LCMS (ESI) [M+H]+: 438.5.

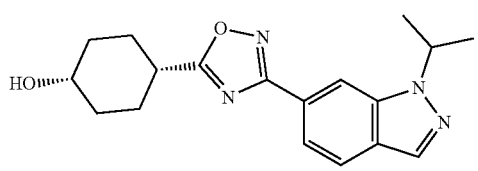 [SMILES: CC(C)n1ncc2ccc(-c3noc([C@H]4CC[C@@H](O)CC4)n3)cc21]

¹H NMR (400 MHz, CHLOROFORM-d) δ 8.23 (s, 1H), 8.06 (s, 1H), 7.90-7.80 (m, 2H), 4.98 (spt, J=6.6 Hz, 1H), 4.05 (br d, J=2.9 Hz, 1H), 3.19-3.03 (m, 1H), 2.32-2.21 (m, 2H), 1.98 (qd, J=4.5, 13.7 Hz, 2H), 1.91-1.77 (m, 4H), 1.64 (d, J=6.6 Hz, 6H), 1.43 (d, J=3.4 Hz, 1H); LCMS (ESI) [M+H]+: 327.1

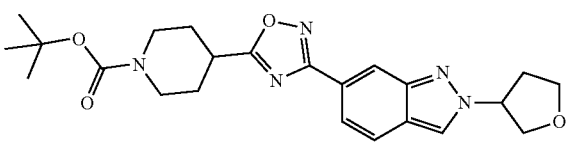 [SMILES: CC(C)(C)OC(=O)N1CCC(c2nc(-c3ccc4cn(C5CCOC5)nc4c3)no2)CC1]

¹H NMR (400 MHz, CHLOROFORM-d) δ 8.51 (s, 1H), 8.07 (s, 1H), 7.80-7.76 (m, 1H), 7.75-7.72 (m, 1H), 5.36-5.26 (m, 1H), 4.32-4.08 (m, 5H), 4.06-3.99 (m, 1H), 3.24-3.14 (m, 1H), 3.03 (br t, J=11.8 Hz, 2H), 2.69-2.58 (m, 1H), 2.54-2.44 (m, 1H), 2.15 (br d, J=11.4 Hz, 2H), 1.99-1.87 (m, 2H), 1.49 (s, 9H); LCMS (ESI) [M+H]+: 440.5.

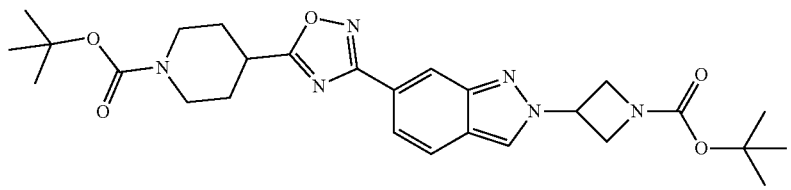 [SMILES: CC(C)(C)OC(=O)N1CCC(c2nc(-c3ccc4cn(C5CN(C(=O)OC(C)(C)C)C5)nc4c3)no2)CC1]

¹H NMR (400 MHz, CHLOROFORM-d) δ 8.53 (d, J=0.7 Hz, 1H), 8.10 (s, 1H), 7.82-7.77 (m, 1H), 7.76-7.71 (m, 1H), 5.35 (m, 1H), 4.55-4.45 (m, 4H), 4.21-4.04 (m, 2H), 3.25-3.12 (m, 1H), 3.02 (br t, J=11.7 Hz, 2H), 2.14 (br dd, J=2.9, 13.2 Hz, 2H), 2.00-1.83 (m, 2H), 1.48 (d, J=1.5 Hz, 18H); LCMS (ESI) [M+23]+: 547.2, LCMS (ESI) [M−100+H]+: 425.2, LCMS (ESI) [M−100−55+H]+: 369.1.

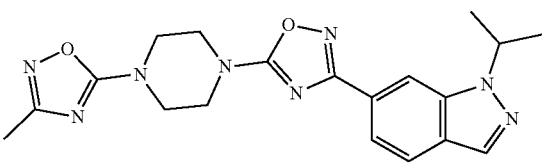 [SMILES: Cc1noc(N2CCN(c3nc(-c4ccc5cnn(C(C)C)c5c4)no3)CC2)n1]

¹H NMR (400 MHz, CHLOROFORM-d) δ 8.15 (s, 1H), 8.07 (s, 1H), 7.79 (m, 2H), 5.04-4.88 (m, 1H), 3.85 (m, 8H), 2.28 (s, 3H), 1.64 (d, J=6.7 Hz, 6H); LCMS (ESI) [M+H]+: 395.1.

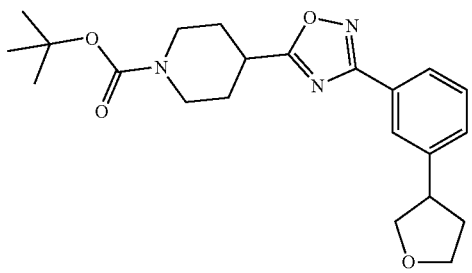 [SMILES: CC(C)(C)OC(=O)N1CCC(c2nc(-c3cccc(C4CCOC4)c3)no2)CC1]

¹H NMR (400 MHz, CHLOROFORM-d) δ 7.98-7.90 (m, 2H), 7.46-7.36 (m, 2H), 4.22-4.05 (m, 4H), 3.94 (q, J=7.9 Hz, 1H), 3.80-3.73 (m, 1H), 3.48 (quin, J=7.8 Hz, 1H), 3.17 (m, 1H), 2.99 (br t, J=11.4 Hz, 2H), 2.41 (m, 1H), 2.18-1.99 (m, 3H), 1.97-1.83 (m, 2H), 1.48 (s, 9H); LCMS (ESI) [M−100+H]+: 300.1.

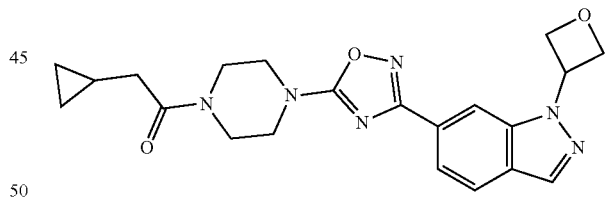

¹H NMR (400 MHz, CHLOROFORM-d) δ 8.14 (d, J=3.4 Hz, 2H), 7.85-7.78 (m, 2H), 5.88 (quin, J=7.1 Hz, 1H), 5.33 (t, J=6.6 Hz, 2H), 5.14 (t, J=7.3 Hz, 2H), 3.83-3.62 (m, 8H), 2.35 (d, J=6.7 Hz, 2H), 1.12-1.02 (m, 1H), 0.65-0.58 (m, 2H), 0.25-0.18 (m, 2H); LCMS (ESI) [M+H]+: 409.2.

731

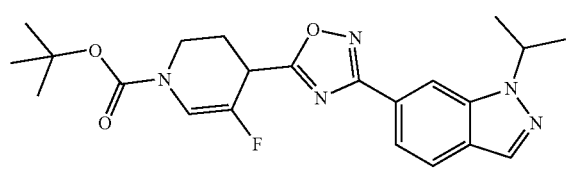 [SMILES: CC(C)n1ncc2ccc(-c3noc(C4CCN(C(=O)OC(C)(C)C)C=C4F)n3)cc21]

¹H NMR (400 MHz, CHLOROFORM-d) δ 8.43 (s, 1H), 8.13 (s, 1H), 7.96 (d, J=8.3 Hz, 1H), 7.82 (d, J=8.4 Hz, 1H), 7.68-7.34 (t, J=59.6 Hz, 1H), 3.70 (m, 4H), 3.62-3.57 (m, 4H), 1.50 (s, 9H); LCMS (ESI) [M−55]+: 365.1.

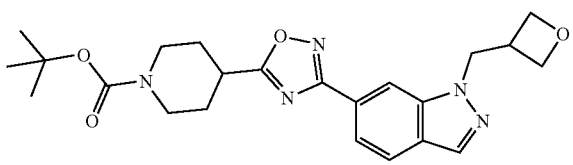 [SMILES: CC(C)(C)OC(=O)N1CCC(c2nc(-c3ccc4cnn(CC5COC5)c4c3)no2)CC1]

¹H NMR (400 MHz, CHLOROFORM-d) δ 8.20 (s, 1H), 8.04 (d, J=0.7 Hz, 1H), 7.91-7.86 (m, 1H), 7.84-7.80 (m, 1H), 4.85 (dd, J=6.5, 7.5 Hz, 2H), 4.76 (d, J=7.5 Hz, 2H), 4.62 (t, J=6.1 Hz, 2H), 4.26-4.05 (m, 2H), 3.72-3.60 (m, 1H), 3.21 (tt, J=3.9, 11.0 Hz, 1H), 3.02 (br t, J=11.6 Hz, 1H), 3.08-2.96 (m, 1H), 2.16 (br dd, J=2.4, 13.6 Hz, 2H), 2.01-1.87 (m, 2H), 1.49 (s, 9H); LCMS (ESI) [M+H]+: 440.2.

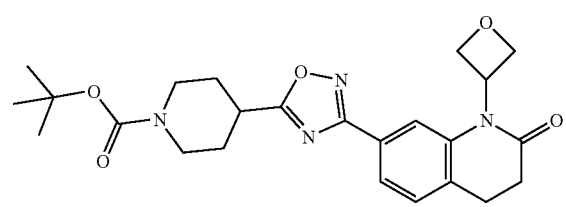 [SMILES: CC(C)(C)OC(=O)N1CCC(c2nc(-c3ccc4c(c3)N(C3COC3)C(=O)CC4)no2)CC1]

¹H NMR (400 MHz, CHLOROFORM-d) δ 7.76 (d, J=7.7 Hz, 1H), 7.35 (d, J=7.9 Hz, 1H), 7.05 (s, 1H), 5.22-5.09 (m, 1H), 5.02 (t, J=7.1 Hz, 2H), 4.70 (t, J=7.3 Hz, 2H), 4.21-4.08 (m, 2H), 3.17 (tt, J=3.8, 10.9 Hz, 1H), 3.06-2.94 (m, 4H), 2.62 (t, J=7.2 Hz, 2H), 2.12 (br d, J=11.0 Hz, 2H), 1.97-1.83 (m, 2H), 1.49 (s, 9H); LCMS (ESI) [M+H]+: 455.2.

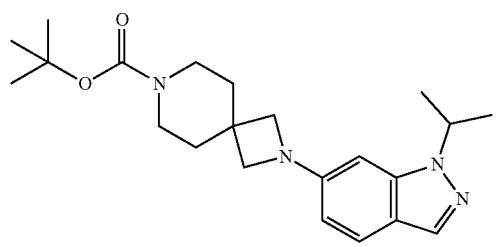 [SMILES: CC(C)n1ncc2ccc(N3CC4(CCN(C(=O)OC(C)(C)C)CC4)C3)cc21]

¹H NMR (400 MHz, CHLOROFORM-d) δ 8.34 (s, 1H), 8.24 (s, 1H), 8.00-7.89 (m, 2H), 5.93 (quin, J=6.9 Hz, 1H), 5.35 (t, J=6.5 Hz, 2H), 5.20 (t, J=7.2 Hz, 2H), 4.53-4.04 (m, 2H), 3.69-3.38 (m, 2H), 3.35-3.22 (m, 1H), 2.41-2.14 (m, 2H), 1.53 (s, 9H); LCMS (ESI) [M+H]+: 462.1.

732

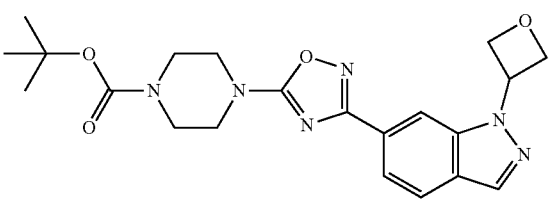 [SMILES: CC(C)(C)OC(=O)N1CCN(c2nc(-c3ccc4cnn(C5COC5)c4c3)no2)CC1]

¹H NMR (400 MHz, CHLOROFORM-d) δ 8.14 (d, J=4.4 Hz, 2H), 7.85-7.78 (m, 2H), 5.88 (quin, J=7.1 Hz, 1H), 5.33 (t, J=6.6 Hz, 2H), 5.14 (t, J=7.3 Hz, 2H), 3.75-3.67 (m, 4H), 3.63-3.57 (m, 4H), 1.50 (s, 9H); LCMS (ESI) [M+H]+: 427.1.

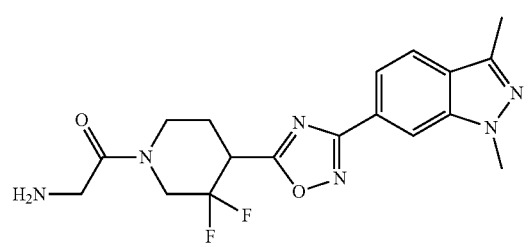 [SMILES: Cc1nn(C)c2cc(-c3noc(C4CCN(C(=O)CN)CC4(F)F)n3)ccc12]

¹H NMR (400 MHz, CHLOROFORM-d) δ 8.24 (s, 1H), 8.02 (d, J=7.7 Hz, 1H), 7.64 (br d, J=8.1 Hz, 1H), 7.40-7.33 (m, 1H), 4.14 (br s, 2H), 3.18 (tt, J=3.8, 10.9 Hz, 1H), 3.01 (br t, J=11.6 Hz, 2H), 2.13 (br d, J=10.9 Hz, 2H), 1.98-1.82 (m, 2H), 1.49 (s, 9H); LCMS (ESI) [M−55]+: 352.0.

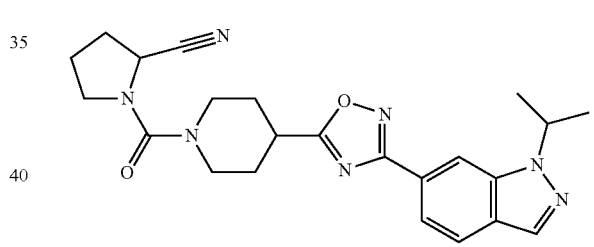

¹H NMR (400 MHz, CHLOROFORM-d) δ 8.22 (s, 1H), 8.07 (s, 1H), 7.84 (q, J=8.4 Hz, 1H), 7.90-7.80 (m, 1H), 4.98 (td, J=6.7, 13.4 Hz, 1H), 4.86 (t, J=6.8 Hz, 1H), 3.93 (br t, J=12.8 Hz, 2H), 3.59-3.41 (m, 2H), 3.34-3.22 (m, 1H), 3.20-3.03 (m, 2H), 2.38-2.28 (m, 1H), 2.36-1.92 (m, 7H), 1.64 (d, J=6.6 Hz, 6H); LCMS (ESI) [M+H]+: 434.2.

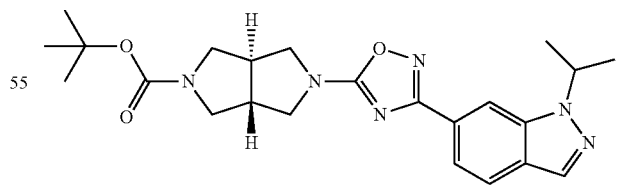

¹H NMR (400 MHz, CHLOROFORM-d) δ 8.22 (s, 1H), 8.07 (s, 1H), 7.90-7.79 (m, 2H), 4.98 (td, J=6.7, 13.3 Hz, 1H), 3.68 (br d, J=13.4 Hz, 2H), 3.50 (t, J=6.6 Hz, 2H), 3.19 (tt, J=4.0, 11.1 Hz, 1H), 2.99-2.82 (m, 2H), 2.26-2.13 (m, 2H), 2.06-1.94 (m, 2H), 1.91-1.82 (m, 2H), 1.80-1.74 (m, 2H), 1.64 (d, J=6.7 Hz, 6H), 1.46 (s, 6H); LCMS (ESI) [M+H]+: 437.2.

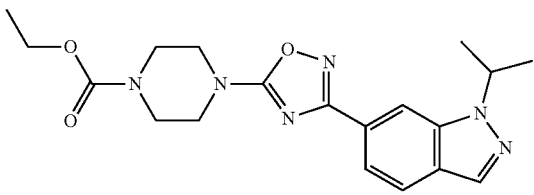 [SMILES: CCOC(=O)N1CCN(c2nc(-c3ccc4cnn(C(C)C)c4c3)no2)CC1]

¹H NMR (400 MHz, CHLOROFORM-d) δ 8.13 (s, 1H), 8.05 (s, 1H), 7.78 (s, 2H), 4.96 (td, J=6.6, 13.3 Hz, 1H), 4.21 (q, J=7.1 Hz, 2H), 3.79-3.61 (m, 8H), 1.63 (d, J=6.7 Hz, 6H), 1.31 (t, J=7.1 Hz, 3H); LCMS (ESI) [M+H]+: 385.1.

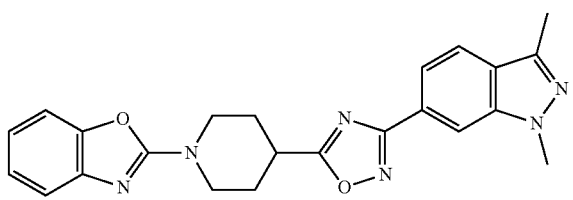 [SMILES: Cc1nn(C)c2cc(-c3noc(C4CCN(c5nc6ccccc6o5)CC4)n3)ccc12]

¹H NMR (400 MHz, CHLOROFORM-d) δ 8.13 (s, 1H), 8.05 (s, 1H), 7.78 (s, 2H), 4.95 (td, J=6.6, 13.3 Hz, 1H), 3.92-3.68 (m, 8H), 3.18 (s, 2H), 2.31 (s, 6H), 1.63 (d, J=6.6 Hz, 6H); LCMS (ESI) [M+H]+: 398.2.

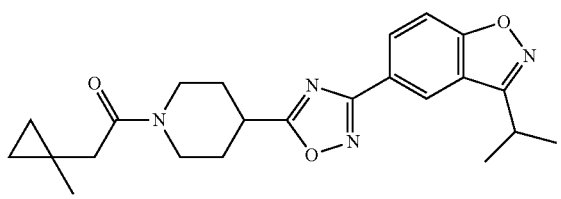 [SMILES: CC(C)c1noc2ccc(-c3noc(C4CCN(C(=O)CC5(C)CC5)CC4)n3)cc12]

¹H NMR (400 MHz, CHLOROFORM-d) δ 8.45 (s, 1H), 8.28 (dd, J=1.4, 8.7 Hz, 1H), 7.66 (d, J=8.7 Hz, 1H), 4.60 (br d, J=13.3 Hz, 1H), 3.97 (br d, J=13.6 Hz, 1H), 3.48 (td, J=6.9, 14.0 Hz, 1H), 3.37-3.22 (m, 2H), 2.97 (br t, J=11.1 Hz, 1H), 2.40 (d, J=4.0 Hz, 2H), 2.22 (br d, J=12.6 Hz, 2H), 2.04-1.86 (m, 2H), 1.55 (s, 6H), 1.18 (s, 3H), 0.49-0.40 (m, 4H); LCMS (ESI) [M+H]+: 409.2.

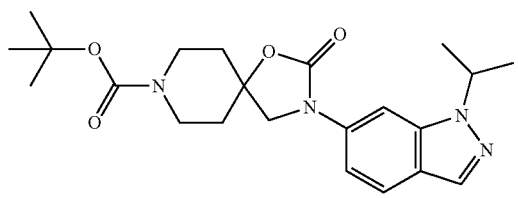 [SMILES: CC(C)n1ncc2ccc(N3CC4(CCN(C(=O)OC(C)(C)C)CC4)OC3=O)cc21]

¹H NMR (400 MHz, CHLOROFORM-d) δ 9.20 (s, 1H), 8.24 (s, 1H), 8.09 (m, J=8.2 Hz, 1H), 7.85 (br d, J=8.2 Hz, 1H), 4.58 (br d, J=14.1 Hz, 1H), 4.03 (br d, J=13.7 Hz, 1H), 3.28 (br d, J=11.7 Hz, 3H), 2.98 (br t, J=11.8 Hz, 1H), 2.32 (s, 2H), 2.21 (br d, J=12.6 Hz, 2H), 2.05-1.80 (m, 2H), 1.37 (m, 2H), 1.18 (d, J=4.0 Hz, 2H), 1.09 (s, 9H); LCMS (ESI) [M+H]+: 436.20.

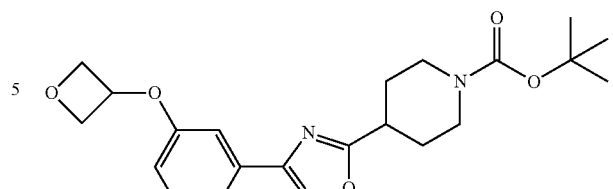

¹H NMR (400 MHz, CHLOROFORM-d) δ 7.71 (d, J=7.7 Hz, 1H), 7.43-7.35 (m, 2H), 6.89 (dd, J=2.5, 8.3 Hz, 1H), 5.32-5.26 (m, 1H), 5.02 (t, J=6.8 Hz, 2H), 4.79 (dd, J=5.3, 7.2 Hz, 2H), 4.13 (br d, J=9.9 Hz, 2H), 3.17 (tt, J=3.9, 10.9 Hz, 1H), 3.00 (br t, J=11.8 Hz, 2H), 2.12 (br dd, J=2.8, 13.3 Hz, 2H), 1.94-1.83 (m, 2H), 1.49 (s, 9H); LCMS (ESI) [M−55]+: 346.1.

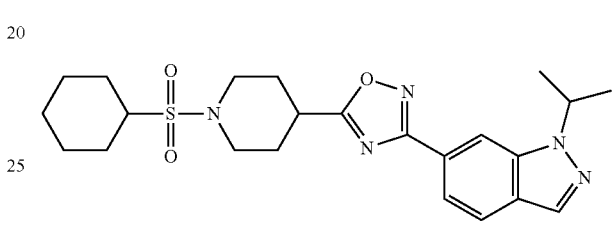

¹H NMR (400 MHz, CHLOROFORM-d) δ 8.18 (s, 1H), 8.04 (s, 1H), 7.79 (s, 2H), 5.01-4.90 (m, 1H), 4.24 (br s, 2H), 3.12-3.04 (m, 1H), 2.99-2.88 (m, 2H), 2.15-2.06 (m, 2H), 1.89-1.80 (m, 2H), 1.61 (d, J=6.6 Hz, 6H), 1.49 (s, 9H); LCMS (ESI) [M+H]+: 411.2.

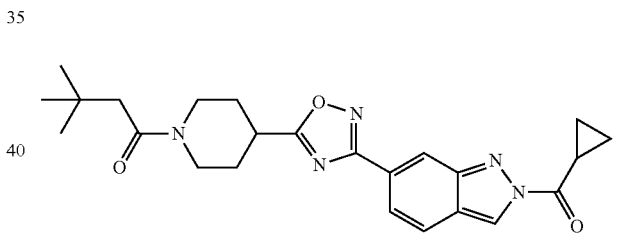

¹H NMR (400 MHz, CHLOROFORM-d) δ 8.79 (s, 1H), 8.54 (s, 1H), 7.79 (m, 2H), 4.60 (m, J=13.0 Hz, 1H), 4.04 (m, J=13.5 Hz, 1H), 3.47 (s, 1H), 3.39-3.22 (m, 2H), 3.00 (t, J=11.7 Hz, 1H), 2.33 (m, 2H), 2.22 (m, J=13.5 Hz, 2H), 2.07-1.82 (m, 2H), 1.44 (m, 2H), 1.32 (m, 2H), 1.09 (s, 9H); LCMS (ESI) [M+H]+: 436.2.

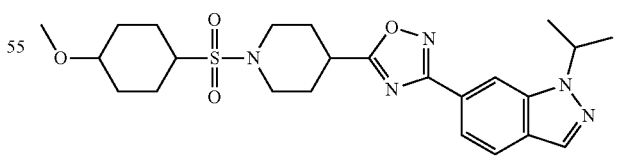

¹H NMR (400 MHz, CHLOROFORM-d) δ 8.30 (s, 1H), 8.21 (s, 1H), 8.01-7.82 (m, 2H), 5.91 (quin, J=7.0 Hz, 1H), 5.33 (t, J=6.6 Hz, 2H), 5.19 (t, J=7.2 Hz, 2H), 4.27 (m, 1H), 4.16-3.98 (m, 2H), 3.18-2.93 (m, 3H), 2.08 (m, 2H), 1.90 (m, 2H), 0.78-0.65 (m, 4H); LCMS (ESI) [M+H]+: 410.1.

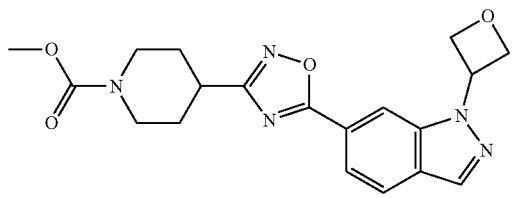 [SMILES: COC(=O)N1CCC(c2noc(-c3ccc4cnn(C5COC5)c4c3)n2)CC1]

¹H NMR (400 MHz, CHLOROFORM-d) δ 8.30 (s, 1H), 8.21 (s, 1H), 7.98-7.86 (m, 2H), 5.97-5.81 (m, 1H), 5.33 (t, J=6.6 Hz, 2H), 5.18 (t, J=7.2 Hz, 2H), 4.21 (m, 2H), 3.74 (s, 3H), 3.20-2.92 (m, 3H), 2.11 (m, J=11.8 Hz, 2H), 1.96-1.79 (m, 2H); LCMS (ESI) [M+H]+: 384.1.

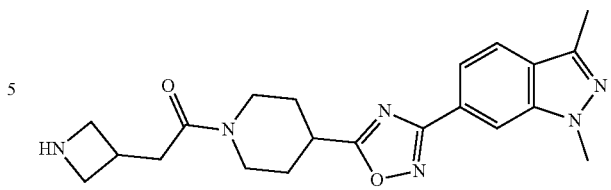

¹H NMR (400 MHz, CHLOROFORM-d) δ 8.56 (br s, 1H), 8.02 (s, 1H), 7.77-7.72 (m, 1H), 7.68-7.63 (m, 1H), 4.38 (br d, J=13.4 Hz, 1H), 4.20-4.07 (m, 2H), 4.01 (s, 3H), 3.85 (br d, J=14.4 Hz, 1H), 3.66 (br s, 2H), 3.30-3.10 (m, 3H), 2.93 (br t, J=10.5 Hz, 1H), 2.84-2.73 (m, 2H), 2.52 (s, 3H), 2.21-2.08 (m, 2H), 1.96-1.81 (m, 2H); LCMS (ESI) [M+H]+: 395.2.

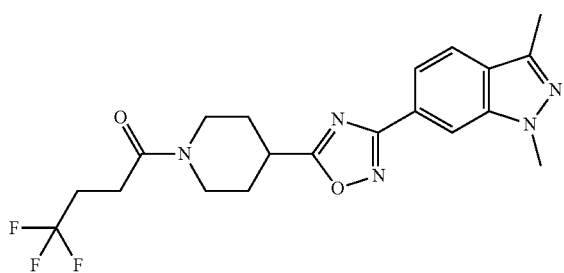 [SMILES: Cc1nn(C)c2cc(-c3noc(C4CCN(C(=O)CCC(F)(F)F)CC4)n3)ccc12]

¹H NMR (400 MHz, CHLOROFORM-d) δ 8.10 (s, 1H), 7.97 (s, 1H), 7.73-7.66 (m, 2H), 4.94-4.78 (m, 1H), 4.19 (br s, 2H), 3.66 (s, 3H), 3.09-2.86 (m, 3H), 2.06 (br d, J=10.9 Hz, 2H), 1.87-1.71 (m, 2H), 1.54 (d, J=6.6 Hz, 6H); LCMS (ESI) [M+H]+: 369.1.

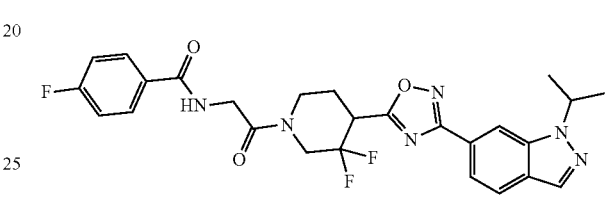

¹H NMR (400 MHz, CHLOROFORM-d) δ 8.35 (s, 1H), 8.21 (s, 1H), 7.98-7.90 (m, 1H), 7.89-7.81 (m, 1H), 5.99-5.86 (m, 1H), 5.35 (t, J=6.6 Hz, 2H), 5.24-5.12 (m, 2H); LCMS (ESI) [M+H]+: 219.0.

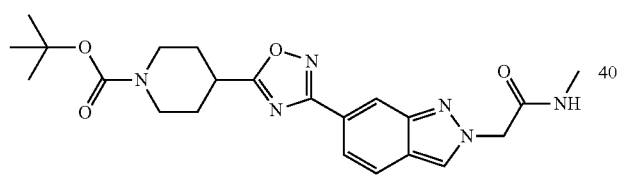

¹H NMR (400 MHz, CHLOROFORM-d) δ 8.54 (s, 1H), 8.08 (s, 1H), 7.91-7.71 (m, 2H), 6.65 (br s, 1H), 5.15 (s, 2H), 4.25-4.07 (m, 2H), 3.22 (br t, J=10.8 Hz, 1H), 3.12-2.97 (m, 2H), 2.83 (d, J=4.9 Hz, 3H), 2.17 (br d, J=11.1 Hz, 2H), 2.04-1.87 (m, 2H), 1.51 (s, 9H); LCMS (ESI) [M+H]+: 441.2.

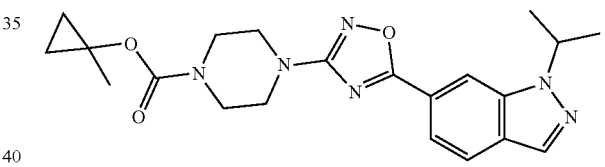

¹H NMR (400 MHz, CHLOROFORM-d) δ 8.21 (s, 1H), 8.08 (s, 1H), 7.82 (m, 2H), 5.08-4.88 (m, 1H), 3.55 (m, 8H), 1.63 (d, J=6.6 Hz, 6H), 1.57 (s, 3H), 0.96-0.85 (m, 2H), 0.68-0.60 (m, 2H); LCMS (ESI) [M+H]+: 411.1.

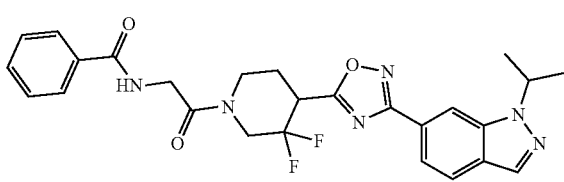 [SMILES: CC(C)n1ncc2ccc(-c3noc(C4CCN(C(=O)CNC(=O)c5ccccc5)CC4(F)F)n3)cc21]

¹H NMR (400 MHz, CHLOROFORM-d) δ 8.11 (s, 1H), 7.94 (s, 1H), 7.73-7.62 (m, 2H), 7.37-7.25 (m, 5H), 4.84-4.64 (m, 2H), 3.87-3.67 (m, 1H), 3.16-2.88 (m, 3H), 2.12-1.74 (m, 4H), 1.47 (br d, J=6.6 Hz, 6H); LCMS (ESI) [M+H]+: 415.2.

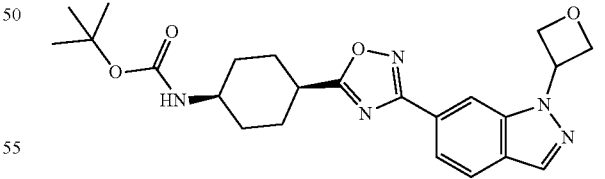

¹H NMR (400 MHz, CHLOROFORM-d) δ 8.23 (d, J=0.9 Hz, 1H), 8.18 (s, 1H), 7.94-7.90 (m, 1H), 7.87-7.84 (m, 1H), 5.92 (quin, J=7.1 Hz, 1H), 5.35 (t, J=6.7 Hz, 2H), 5.17 (t, J=7.4 Hz, 2H), 4.61 (br s, 1H), 3.76 (br s, 1H), 3.26-3.16 (m, 1H), 2.21-2.10 (m, 2H), 2.06-1.96 (m, 2H), 1.92-1.81 (m, 2H), 1.77-1.66 (m, 2H), 1.46 (s, 9H); LCMS (ESI) [M+H]+: 440.2.

737

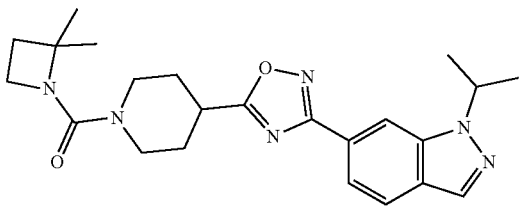 [SMILES: CC(C)n1ncc2ccc(-c3noc(C4CCN(C(=O)N5CCC5(C)C)CC4)n3)cc21]

¹H NMR (400 MHz, CHLOROFORM-d) δ 8.22 (s, 1H), 8.06 (s, 1H), 7.88-7.80 (m, 2H), 4.97 (quin, J=6.6 Hz, 1H), 3.99-3.90 (m, 4H), 3.22 (tt, J=3.9, 10.9 Hz, 1H), 3.01-2.92 (m, 2H), 2.16 (br dd, J=3.2, 13.4 Hz, 2H), 2.05-1.95 (m, 4H), 1.64 (d, J=6.6 Hz, 6H), 1.53 (s, 6H); LCMS (ESI) [M+H]+: 423.2.

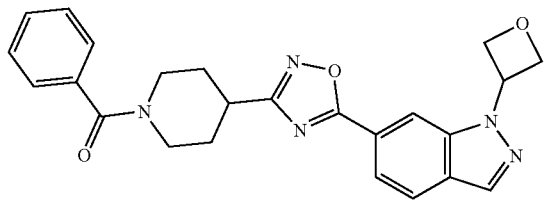 [SMILES: O=C(c1ccccc1)N1CCC(c2noc(-c3ccc4cnn(C5COC5)c4c3)n2)CC1]

¹H NMR (400 MHz, DMSO-d$_6$) δ 8.49 (s, 1H), 8.37 (s, 1H), 8.03 (d, J=8.6 Hz, 1H), 7.86 (d, J=8.4 Hz, 1H), 7.50-7.39 (m, 5H), 6.28-6.15 (m, 1H), 5.08 (d, J=6.8 Hz, 4H), 4.07 (br s, 2H), 3.32-3.15 (m, 3H), 2.11 (br d, J=11.5 Hz, 2H), 1.89-1.74 (m, 2H); LCMS (ESI) [M+H]+: 430.1.

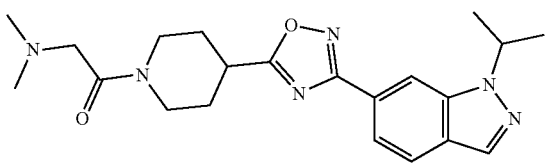 [SMILES: CC(C)n1ncc2ccc(-c3noc(C4CCN(C(=O)CN(C)C)CC4)n3)cc21]

¹H NMR (400 MHz, CHLOROFORM-d) δ 8.21 (s, 1H), 8.07 (s, 1H), 7.84 (q, J=8.4 Hz, 2H), 4.97 (td, J=6.5, 13.4 Hz, 1H), 4.54 (br d, J=12.7 Hz, 1H), 4.22 (br d, J=13.8 Hz, 1H), 3.31 (br t, J=10.5 Hz, 2H), 3.25-3.10 (m, 2H), 3.01 (br t, J=11.0 Hz, 1H), 2.33 (s, 6H), 2.23 (br d, J=13.6 Hz, 2H), 2.07-1.89 (m, 2H), 1.64 (d, J=6.7 Hz, 6H); LCMS (ESI) [M+H]+: 397.1.

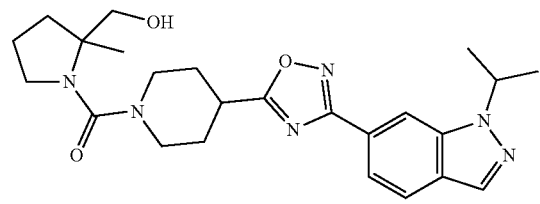 [SMILES: CC(C)n1ncc2ccc(-c3noc(C4CCN(C(=O)N5CCCC5(C)CO)CC4)n3)cc21]

¹H NMR (400 MHz, CHLOROFORM-d) δ 8.22 (s, 1H), 8.06 (s, 1H), 7.89-7.78 (m, 2H), 5.66 (dd, J=1.7, 9.5 Hz, 1H), 4.97 (td, J=6.6, 13.3 Hz, 1H), 3.80-3.67 (m, 3H), 3.63-3.45 (m, 3H), 3.23 (tt, J=4.1, 10.9 Hz, 1H), 3.07-2.90 (m, 2H), 2.22 (br t, J=10.7 Hz, 2H), 2.13-1.91 (m, 2H), 1.90-1.73 (m, 4H), 1.63 (d, J=6.6 Hz, 6H), 1.43 (s, 3H); LCMS (ESI) [M+H]+: 453.2.

738

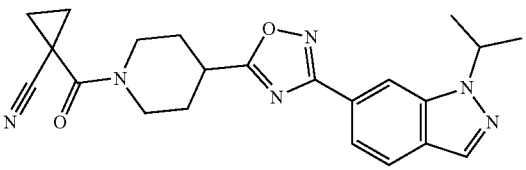 [SMILES: CC(C)n1ncc2ccc(-c3noc(C4CCN(C(=O)C5(C#N)CC5)CC4)n3)cc21]

¹H NMR (400 MHz, DMSO-d$_6$) δ 8.28 (s, 1H), 8.15 (s, 1H), 7.91 (d, J=8.4 Hz, 1H), 7.76 (d, J=8.4 Hz, 1H), 5.11 (td, J=6.7, 13.1 Hz, 1H), 4.26 (br d, J=13.9 Hz, 2H), 3.62-3.47 (m, 1H), 3.39-3.26 (m, 2H), 2.29-2.20 (m, 2H), 1.89 (q, J=10.4 Hz, 2H), 1.62-1.56 (m, 2H), 1.53 (m, 8H); LCMS (ESI) [M+H]+: 405.1.

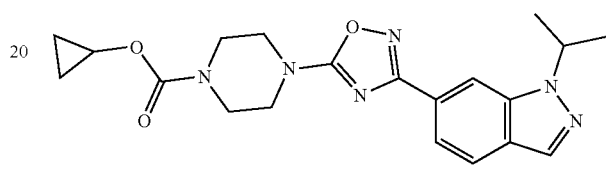

¹H NMR (400 MHz, CHLOROFORM-d) δ 8.13 (s, 1H), 8.05 (s, 1H), 7.78 (d, J=0.7 Hz, 2H), 4.95 (td, J=6.7, 13.3 Hz, 1H), 4.21-4.05 (m, 1H), 3.80-3.52 (m, 8H), 1.62 (d, J=6.6 Hz, 6H), 0.79-0.67 (m, 4H); LCMS (ESI) [M+H]+: 397.1.

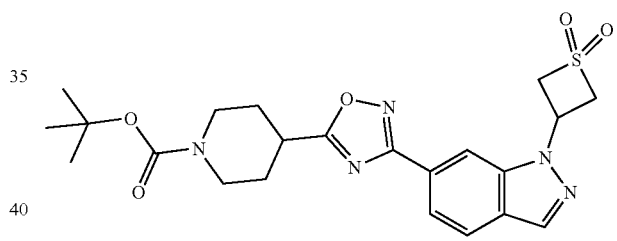

¹H NMR (400 MHz, CHLOROFORM-d) δ 8.11 (d, J=4.5 Hz, 2H), 7.91-7.85 (m, 1H), 7.81-7.77 (m, 1H), 5.53-5.42 (m, 1H), 4.93-4.83 (m, 2H), 4.66-4.56 (m, 2H), 4.08 (br s, 2H), 3.14 (tt, J=3.8, 10.9 Hz, 1H), 2.95 (br t, J=11.6 Hz, 2H), 2.14-2.03 (m, 2H), 1.93-1.80 (m, 2H), 1.42 (s, 9H); LCMS (ESI) [M+H]+: 418.1.

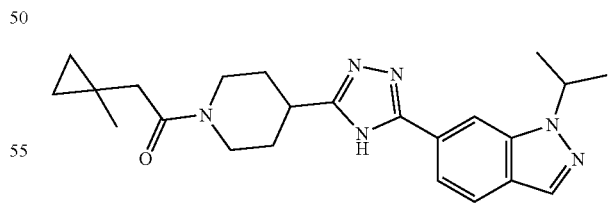

¹H NMR (400 MHz, CHLOROFORM-d) δ 8.21 (s, 1H), 8.05 (s, 1H), 7.87-7.76 (m, 2H), 4.96 (td, J=6.6, 13.2 Hz, 1H), 4.76 (br d, J=13.3 Hz, 1H), 4.03 (br d, J=13.6 Hz, 1H), 3.30-3.13 (m, 2H), 2.85 (br t, J=11.7 Hz, 1H), 2.51-2.35 (m, 2H), 2.28-2.10 (m, 2H), 2.02-1.84 (m, 2H), 1.61 (d, J=6.6 Hz, 6H), 1.19 (s, 2H), 1.20-1.17 (m, 1H), 0.50-0.38 (m, 4H); LCMS (ESI) [M+H]+: 407.2.

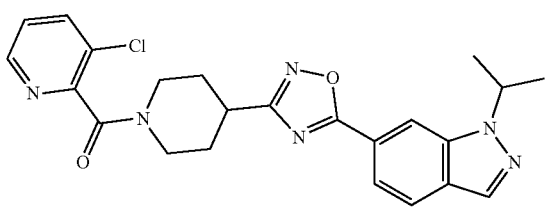 [SMILES: CC(C)n1ncc2ccc(-c3nc(C4CCN(C(=O)c5ncccc5Cl)CC4)no3)cc21]

¹H NMR (400 MHz, CHLOROFORM-d) δ 8.55 (dd, J=1.0, 4.7 Hz, 1H), 8.29 (s, 1H), 8.09 (s, 1H), 7.86 (s, 2H), 7.78 (dd, J=1.0, 8.2 Hz, 1H), 7.32 (dd, J=4.6, 8.2 Hz, 1H), 4.99 (td, J=6.7, 13.3 Hz, 1H), 4.78-4.71 (m, 1H), 3.55-3.46 (m, 1H), 3.30-3.14 (m, 3H), 2.28 (br dd, J=3.5, 13.6 Hz, 1H), 2.14-2.02 (m, 3H), 1.65 (d, J=6.7 Hz, 6H); LCMS (ESI) [M+H]+: 451.1.

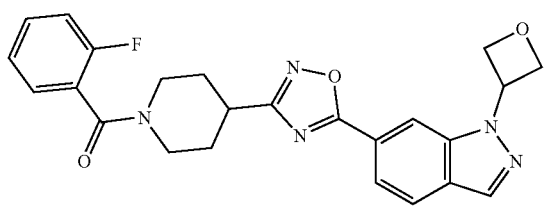 [SMILES: O=C(c1ccccc1F)N1CCC(c2noc(-c3ccc4cnn(C5COC5)c4c3)n2)CC1]

¹H NMR (400 MHz, DMSO-d₆) δ 8.53 (s, 1H), 8.41 (s, 1H), 8.02 (d, J=8.4 Hz, 1H), 7.84 (dd, J=1.2, 8.5 Hz, 1H), 7.55-7.47 (m, 1H), 7.44 (br t, J=6.7 Hz, 1H), 7.35-7.27 (m, 2H), 6.29 (quin, J=6.9 Hz, 1H), 5.04 (d, J=7.1 Hz, 4H), 4.53 (br d, J=13.2 Hz, 1H), 3.49 (br d, J=13.7 Hz, 1H), 3.31-3.23 (m, 2H), 3.15-3.06 (m, 1H), 2.16 (br d, J=11.5 Hz, 1H), 2.02 (br d, J=12.1 Hz, 1H), 1.82-1.65 (m, 2H); LCMS (ESI) [M+H]+: 448.1.

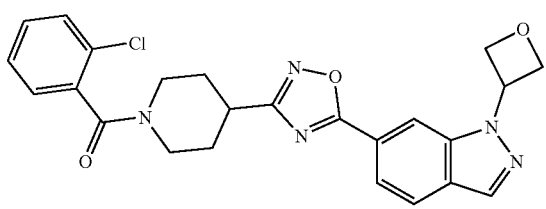 [SMILES: O=C(c1ccccc1Cl)N1CCC(c2noc(-c3ccc4cnn(C5COC5)c4c3)n2)CC1]

¹H NMR (400 MHz, DMSO-d₆) δ 8.53 (s, 1H), 8.42 (s, 1H), 8.03 (d, J=8.4 Hz, 1H), 7.84 (d, J=8.4 Hz, 1H), 7.55 (br d, J=6.8 Hz, 1H), 7.49-7.36 (m, 3H), 6.34-6.23 (m, 1H), 5.04 (d, J=6.8 Hz, 4H), 4.54 (br d, J=12.1 Hz, 1H), 3.37 (br d, J=2.4 Hz, 1H), 3.32-3.16 (m, 2H), 3.16-3.05 (m, 1H), 2.20-2.09 (m, 1H), 2.07-1.95 (m, 1H), 1.85-1.72 (m, 2H), 1.72-1.61 (m, 1H); LCMS (ESI) [M+H]+: 464.1.

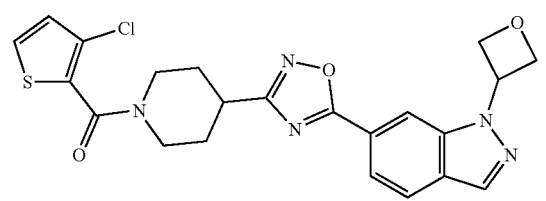 [SMILES: O=C(c1sccc1Cl)N1CCC(c2noc(-c3ccc4cnn(C5COC5)c4c3)n2)CC1]

¹H NMR (400 MHz, DMSO-d₆) δ 8.48 (s, 1H), 8.37 (s, 1H), 8.02 (d, J=8.4 Hz, 1H), 7.85 (d, J=8.4 Hz, 1H), 7.78 (d, J=5.3 Hz, 1H), 7.10 (d, J=5.3 Hz, 1H), 6.21 (m, 1H), 5.08 (d, J=6.8 Hz, 4H), 4.15-3.95 (m, 2H), 3.35-3.23 (m, 3H), 2.14 (br dd, J=3.2, 13.3 Hz, 2H), 1.89-1.75 (m, 2H); LCMS (ESI) [M+H]+: 470.0.

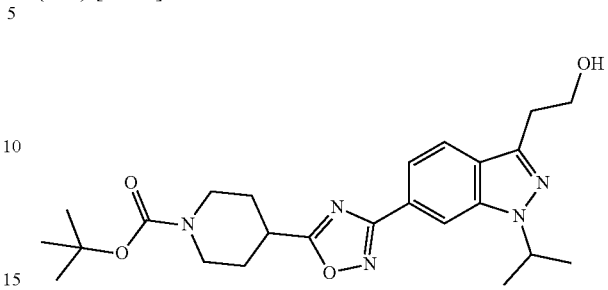

¹H NMR (400 MHz, CHLOROFORM-d) δ 8.17 (s, 1H), 7.90-7.81 (m, 1H), 7.79-7.67 (m, 1H), 4.91 (td, J=6.6, 13.3 Hz, 1H), 4.16 (br s, 2H), 4.09 (q, J=5.9 Hz, 2H), 3.28-3.18 (m, 3H), 3.11 (t, J=6.3 Hz, 1H), 3.02 (br t, J=11.7 Hz, 2H), 2.16 (br d, J=11.5 Hz, 2H), 2.02-1.87 (m, 2H), 1.60 (d, J=6.6 Hz, 6H), 1.49 (s, 9H); LCMS (ESI) [M+H]+: 456.2.

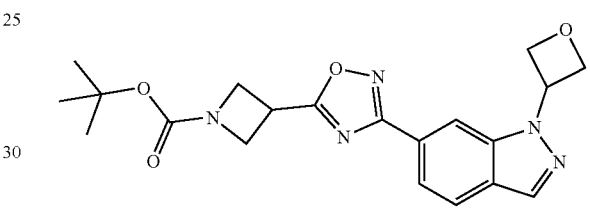

¹H NMR (400 MHz, CHLOROFORM-d) δ 8.25 (s, 1H), 8.17 (s, 1H), 7.94-7.89 (m, 1H), 7.88-7.82 (m, 1H), 5.96-5.85 (m, 1H), 5.33 (t, J=6.5 Hz, 2H), 5.17 (t, J=7.3 Hz, 2H), 4.47-4.32 (m, 4H), 4.14-4.04 (m, 1H), 1.48 (s, 9H); LCMS (ESI) [M+H]+: 398.1.

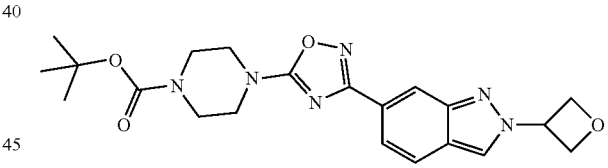

¹H NMR (400 MHz, CHLOROFORM-d) δ 8.46 (d, J=0.9 Hz, 1H), 8.18-8.11 (m, 1H), 7.72 (m, 2H), 5.79-5.71 (m, 1H), 5.25-5.16 (m, 4H), 3.72-3.67 (m, 4H), 3.62-3.56 (m, 4H), 1.50 (s, 9H); LCMS (ESI) [M+H]+: 427.1.

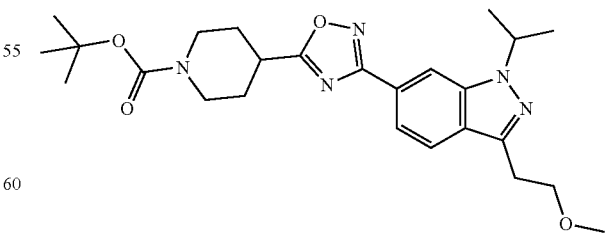

¹H NMR (400 MHz, CHLOROFORM-d) δ 8.14 (s, 1H), 7.81 (s, 2H), 4.90 (quin, J=6.7 Hz, 1H), 4.15 (br s, 2H), 3.88-3.75 (m, 2H), 3.40 (s, 3H), 3.29 (t, J=7.1 Hz, 2H), 3.24-3.14 (m, 1H), 3.02 (br t, J=11.1 Hz, 2H), 2.15 (br d, J=13.3 Hz, 2H), 2.01-1.88 (m, 2H), 1.63-1.57 (m, 6H), 1.49 (s, 9H); LCMS (ESI) [M+H]+: 470.2.

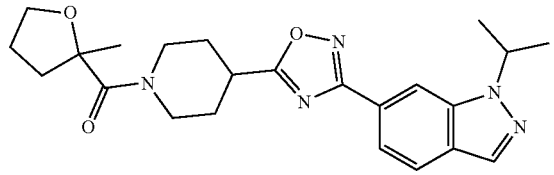 [SMILES: CC(C)n1ncc2ccc(-c3noc(C4CCN(C(=O)C5(C)CCCO5)CC4)n3)cc21]

¹H NMR (400 MHz, DMSO-d₆) δ 8.27 (s, 1H), 8.15 (s, 1H), 7.91 (d, J=8.4 Hz, 1H), 7.75 (d, J=8.4 Hz, 1H), 5.11 (td, J=6.6, 13.2 Hz, 1H), 4.56-4.37 (m, 2H), 3.97-3.85 (m, 1H), 3.75 (q, J=7.4 Hz, 1H), 3.53-3.41 (m, 1H), 3.24-3.11 (m, 2H), 2.72-2.63 (m, 1H), 2.16 (br s, 2H), 1.91-1.71 (m, 4H), 1.64-1.56 (m, 1H), 1.53 (d, J=6.6 Hz, 6H), 1.42 (s, 3H); LCMS (ESI) [M+H]+: 424.2.

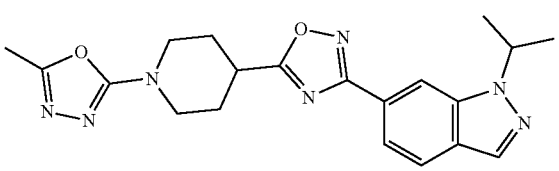 [SMILES: Cc1nnc(N2CCC(c3nc(-c4ccc5cnn(C(C)C)c5c4)no3)CC2)o1]

¹H NMR (400 MHz, CHLOROFORM-d) δ 8.21 (s, 1H), 8.06 (s, 1H), 7.90-7.78 (m, 2H), 4.97 (td, J=6.7, 13.3 Hz, 1H), 4.06 (td, J=3.8, 13.4 Hz, 2H), 3.36-3.22 (m, 3H), 2.42 (s, 3H), 2.29 (br dd, J=3.4, 13.7 Hz, 2H), 2.20-2.05 (m, 2H), 1.65-1.62 (m, 6H); LCMS (ESI) [M+H]+: 394.1.

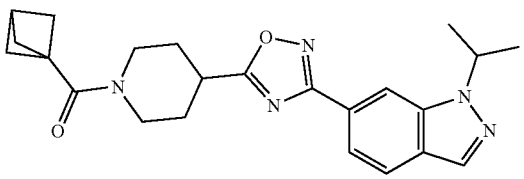 [SMILES: CC(C)n1ncc2ccc(-c3noc(C4CCN(C(=O)C56CC(C5)C6)CC4)n3)cc21]

¹H NMR (400 MHz, CHLOROFORM-d) δ 8.21 (s, 1H), 8.07 (s, 1H), 7.89-7.78 (m, 2H), 5.03-4.90 (m, 1H), 4.51 (br d, J=13.2 Hz, 1H), 4.27 (br d, J=13.4 Hz, 1H), 3.40-3.24 (m, 2H), 3.03-2.90 (m, 1H), 2.53 (s, 1H), 2.27-2.15 (m, 8H), 2.03-1.89 (m, 2H), 1.64 (d, J=6.6 Hz, 6H); LCMS (ESI) [M+H]+: 406.1.

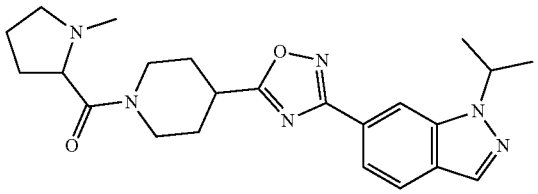 [SMILES: CC(C)n1ncc2ccc(-c3noc(C4CCN(C(=O)C5CCCN5C)CC4)n3)cc21]

¹H NMR (400 MHz, CHLOROFORM-d) δ 8.21 (s, 1H), 8.07 (s, 1H), 7.92-7.77 (m, 2H), 4.97 (td, J=6.6, 13.2 Hz, 1H), 4.74-4.49 (m, 1H), 4.40-4.16 (m, 1H), 3.31 (br s, 2H), 3.23-2.91 (m, 3H), 2.38 (s, 3H), 2.30-2.13 (m, 4H), 2.04-1.76 (m, 5H), 1.64 (d, J=6.6 Hz, 6H); LCMS (ESI) [M+H]+: 423.2.

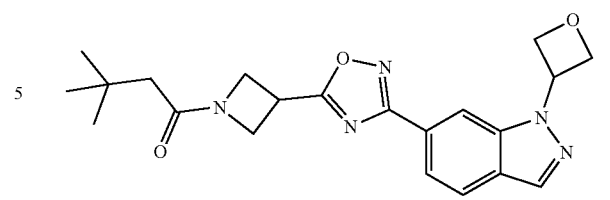

¹H NMR (400 MHz, CHLOROFORM-d) δ 8.24 (d, J=0.7 Hz, 1H), 8.17 (s, 1H), 7.94-7.82 (m, 2H), 5.95-5.83 (m, 1H), 5.33 (t, J=6.5 Hz, 2H), 5.17 (t, J=7.3 Hz, 2H), 4.66-4.36 (m, 4H), 4.18-4.07 (m, 1H), 2.05 (s, 2H), 1.09 (s, 9H); LCMS (ESI) [M+H]+: 369.2.

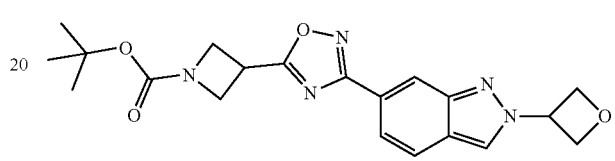

¹H NMR (400 MHz, CHLOROFORM-d) δ 8.56 (s, 1H), 8.17 (s, 1H), 7.84-7.73 (m, 2H), 5.76 (m, 1H), 5.28-5.14 (m, 4H), 4.45-4.30 (m, 4H), 4.14-4.03 (m, 1H), 1.48 (s, 9H); LCMS (ESI) [M+H]+: 398.1.

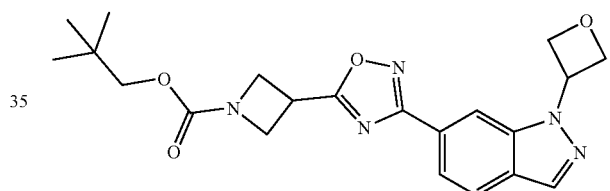

¹H NMR (400 MHz, CHLOROFORM-d) δ 8.24 (d, J=0.7 Hz, 1H), 8.17 (s, 1H), 7.94-7.90 (m, 1H), 7.88-7.83 (m, 1H), 5.96-5.85 (m, 1H), 5.33 (t, J=6.6 Hz, 2H), 5.21-5.11 (t, J=7.3 Hz, 2H), 4.53-4.40 (m, 4H), 4.15 (m, 1H), 3.80 (s, 2H), 0.96 (s, 9H); LCMS (ESI) [M+H]+: 412.2.

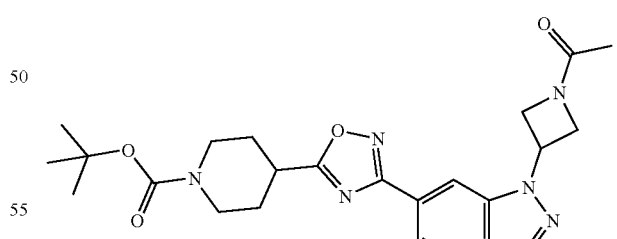

¹H NMR (400 MHz, CHLOROFORM-d) δ 8.53 (s, 1H), 8.07 (s, 1H), 7.82-7.77 (m, 1H), 7.77-7.71 (m, 1H), 5.40 (m, 1H), 4.79 (dd, J=5.3, 8.8 Hz, 1H), 4.73-4.65 (m, 1H), 4.63-4.55 (m, 2H), 4.13 (br d, J=8.2 Hz, 2H), 3.25-3.13 (m, 1H), 3.02 (br t, J=11.5 Hz, 2H), 2.14 (br d, J=11.2 Hz, 2H), 1.99 (s, 3H), 1.97-1.85 (m, 2H), 1.48 (s, 9H); LCMS (ESI) [M−100+H]+: 367.1.

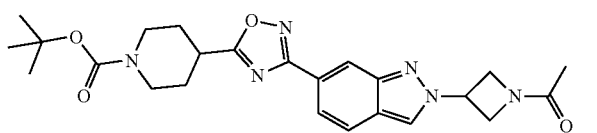 [SMILES: CC(=O)N1CC(n2cc3ccc(-c4noc(C5CCN(C(=O)OC(C)(C)C)CC5)n4)cc3n2)C1]

¹H NMR (400 MHz, CHLOROFORM-d) δ 8.16 (s, 2H), 7.95-7.89 (m, 1H), 7.87-7.82 (m, 1H), 5.54 (m, 1H), 4.80 (dd, J=5.4, 8.7 Hz, 1H), 4.72-4.63 (m, 1H), 4.62-4.51 (m, 2H), 4.23-4.07 (m, 2H), 3.26-3.14 (m, 1H), 3.02 (br t, J=11.5 Hz, 2H), 2.15 (m, 2H), 1.99 (s, 3H), 1.98-1.86 (m, 2H), 1.48 (s, 9H); LCMS (ESI) [M−100+H]+: 367.1.

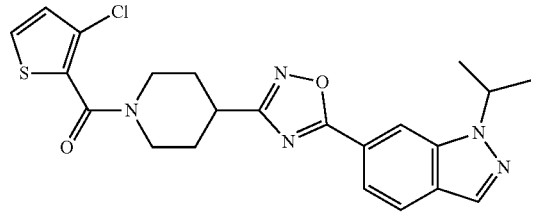

¹H NMR (400 MHz, DMSO-d₆) δ 8.43 (s, 1H), 8.19 (s, 1H), 7.96 (d, J=8.4 Hz, 1H), 7.81-7.75 (m, 2H), 7.08 (d, J=5.3 Hz, 1H), 5.22-5.10 (m, 1H), 4.02 (br s, 2H), 3.33-3.20 (m, 3H), 2.13 (m, 2H), 1.86-1.75 (m, 2H), 1.52 (d, J=6.6 Hz, 6H); LCMS (ESI) [M+H]+: 456.1.

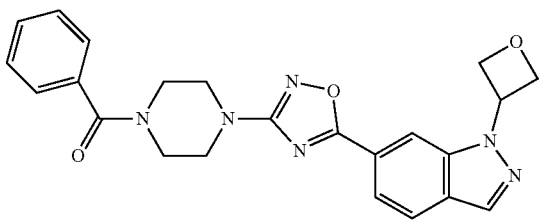 [SMILES: O=C(c1ccccc1)N1CCN(c2noc(-c3ccc4cnn(C5COC5)c4c3)n2)CC1]

¹H NMR (400 MHz, CHLOROFORM-d) δ 8.25 (s, 1H), 8.20 (s, 1H), 7.88 (m, 2H), 7.46 (s, 5H), 5.90 (quin, J=6.9 Hz, 1H), 5.33 (t, J=6.6 Hz, 2H), 5.18 (t, J=7.3 Hz, 2H), 3.61 (m, 8H); LCMS (ESI) [M+H]+: 431.1.

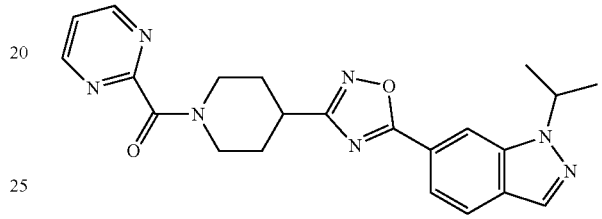

¹H NMR (400 MHz, CHLOROFORM-d) δ 8.85 (d, J=5.0 Hz, 2H), 8.30 (s, 1H), 8.09 (s, 1H), 7.86 (d, J=0.9 Hz, 2H), 7.37 (t, J=5.0 Hz, 1H), 4.99 (spt, J=6.6 Hz, 1H), 4.78-4.68 (m, 1H), 3.73-3.65 (m, 1H), 3.33-3.17 (m, 3H), 2.29-2.21 (m, 1H), 2.16-2.04 (m, 3H), 1.65 (d, J=6.6 Hz, 6H); LCMS (ESI) [M+H]+: 418.2.

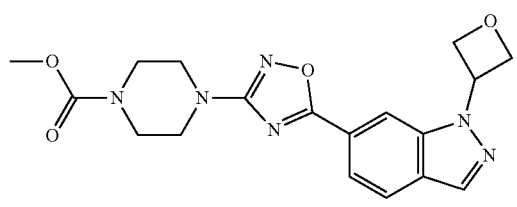 [SMILES: COC(=O)N1CCN(c2noc(-c3ccc4cnn(C5COC5)c4c3)n2)CC1]

¹H NMR (400 MHz, CHLOROFORM-d) δ 8.24 (s, 1H), 8.19 (s, 1H), 7.94-7.82 (m, 2H), 5.90 (quin, J=7.0 Hz, 1H), 5.33 (t, J=6.5 Hz, 2H), 5.18 (t, J=7.2 Hz, 2H), 3.76 (s, 3H), 3.69-3.41 (m, 8H); LCMS (ESI) [M+H]+: 385.1.

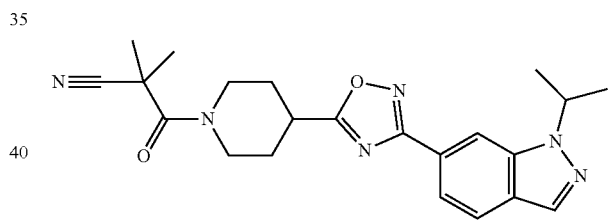

¹H NMR (400 MHz, DMSO-d₆) δ 8.28 (s, 1H), 8.16 (s, 1H), 7.92 (d, J=8.4 Hz, 1H), 7.76 (d, J=8.6 Hz, 1H), 5.12 (quin, J=6.6 Hz, 1H), 4.31 (br d, J=14.1 Hz, 2H), 3.62-3.49 (m, 1H), 3.33 (br t, J=12.1 Hz, 2H), 2.25 (br d, J=10.4 Hz, 2H), 1.98-1.82 (m, 2H), 1.59 (s, 6H), 1.54 (d, J=6.6 Hz, 6H); LCMS (ESI) [M+H]+: 407.1.

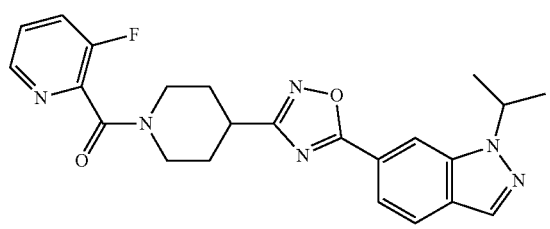 [SMILES: CC(C)n1ncc2ccc(-c3nc(C4CCN(C(=O)c5ncccc5F)CC4)no3)cc21]

¹H NMR (400 MHz, CHLOROFORM-d) δ 8.49 (d, J=4.6 Hz, 1H), 8.29 (s, 1H), 8.10 (s, 1H), 7.87 (s, 2H), 7.55-7.49 (m, 1H), 7.40 (td, J=4.4, 8.6 Hz, 1H), 4.99 (spt, J=6.7 Hz, 1H), 4.78-4.68 (m, 1H), 3.67 (br d, J=13.8 Hz, 1H), 3.32-3.17 (m, 3H), 2.27 (br dd, J=3.5, 13.6 Hz, 1H), 2.15-2.01 (m, 3H), 1.65 (d, J=6.7 Hz, 6H); LCMS (ESI) [M+H]+: 435.2.

¹H NMR (400 MHz, CHLOROFORM-d) δ 8.23 (s, 1H), 8.18 (s, 1H), 7.94-7.89 (m, 1H), 7.88-7.83 (m, 1H), 7.41 (d, J=5.3 Hz, 1H), 6.95 (d, J=5.3 Hz, 1H), 5.90 (quin, J=7.1 Hz, 1H), 5.34 (t, J=6.5 Hz, 2H), 5.20-5.14 (m, 2H), 4.77-3.73 (m, 2H), 3.50-3.16 (m, 3H), 2.28 (br d, J=11.6 Hz, 2H), 2.18-2.03 (m, 2H); LCMS (ESI) [M+H]+: 470.1.

745

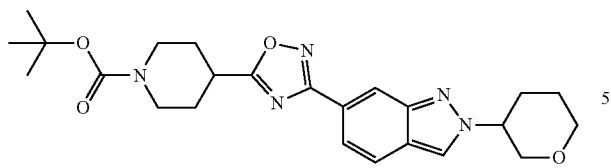

$^1$H NMR (400 MHz, CHLOROFORM-d) δ 8.51 (s, 1H), 8.14 (s, 1H), 7.79-7.73 (m, 2H), 4.69-4.61 (m, 1H), 4.23 (dd, J=4.0, 11.4 Hz, 1H), 4.14 (br d, J=6.2 Hz, 2H), 4.03-3.91 (m, 2H), 3.72-3.63 (m, 1H), 3.19 (tt, J=3.9, 10.8 Hz, 1H), 3.03 (br t, J=11.4 Hz, 2H), 2.41-2.32 (m, 2H), 2.15 (br d, J=10.3 Hz, 2H), 1.98-1.79 (m, 4H), 1.49 (s, 9H); LCMS (ESI) [M+H]+: 454.2.

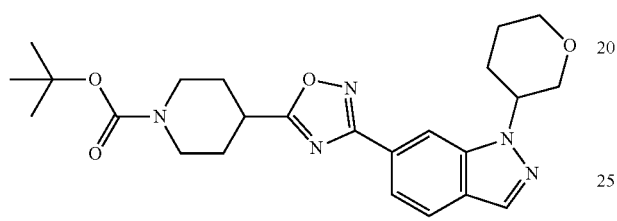

$^1$H NMR (400 MHz, CHLOROFORM-d) δ 8.24 (s, 1H), 8.06 (s, 1H), 7.91-7.86 (m, 1H), 7.84-7.79 (m, 1H), 4.79-4.68 (m, 1H), 4.24-4.02 (m, 4H), 3.85 (t, J=10.7 Hz, 1H), 3.60-3.50 (m, 1H), 3.22 (tt, J=3.9, 10.9 Hz, 1H), 3.03 (br t, J=11.6 Hz, 2H), 2.48-2.35 (m, 1H), 2.27 (br d, J=12.5 Hz, 1H), 2.17 (br d, J=10.6 Hz, 2H), 2.02-1.89 (m, 4H), 1.50 (s, 9H); LCMS (ESI) [M+H]+: 454.2.

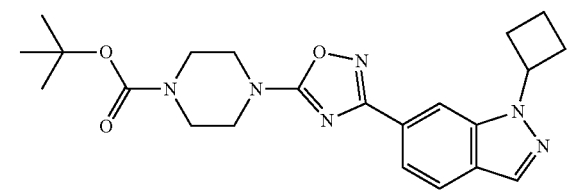 [SMILES: CC(C)(C)OC(=O)N1CCN(c2nc(-c3ccc4cnn(C5CCC5)c4c3)no2)CC1]

$^1$H NMR (400 MHz, CHLOROFORM-d) δ 8.11 (d, J=0.9 Hz, 1H), 8.06 (s, 1H), 7.79-7.74 (m, 2H), 5.16 (quin, J=8.3 Hz, 1H), 3.77-3.65 (m, 4H), 3.63-3.53 (m, 4H), 2.89-2.75 (m, 2H), 2.61-2.50 (m, 2H), 2.06-1.86 (m, 2H), 1.50 (s, 9H); LCMS (ESI) [M+H]+: 425.2.

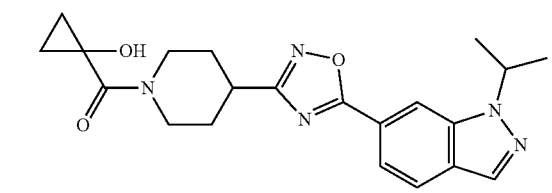 [SMILES: CC(C)n1ncc2ccc(-c3nc(C4CCN(C(=O)C5(O)CC5)CC4)no3)cc21]

$^1$H NMR (400 MHz, CHLOROFORM-d) δ 8.28 (br d, J=2.6 Hz, 1H), 8.10 (br d, J=3.4 Hz, 1H), 7.86 (br d, J=4.2 Hz, 2H), 5.06-4.91 (m, 1H), 4.60 (br d, J=12.2 Hz, 2H), 3.36-3.03 (m, 3H), 2.27-2.13 (m, 2H), 2.05-1.90 (m, 2H), 1.70-1.62 (m, 6H), 1.17-1.08 (m, 2H), 0.99 (br s, 2H); LCMS (ESI) [M+H]+: 396.2.

746

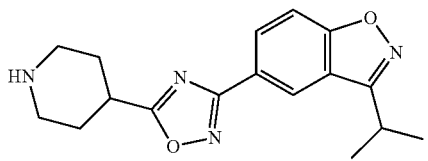 [SMILES: CC(C)c1noc2ccc(-c3noc(C4CCNCC4)n3)cc12]

$^1$H NMR (400 MHz, METHANOL-d$_4$) δ 8.53 (s, 1H), 8.35-8.27 (m, 1H), 7.75 (d, J=8.8 Hz, 1H), 3.60-3.45 (m, 4H), 3.30-3.21 (m, 2H), 2.47 (br dd, J=3.2, 14.4 Hz, 2H), 2.25-2.11 (m, 2H), 1.51 (d, J=7.1 Hz, 6H; LCMS (ESI) [M+H]+: 313.1.

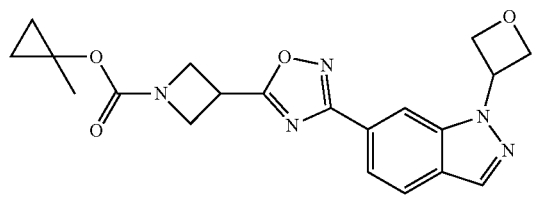 [SMILES: CC1(OC(=O)N2CC(c3nc(-c4ccc5cnn(C6COC6)c5c4)no3)C2)CC1]

$^1$H NMR (400 MHz, CHLOROFORM-d) δ 8.24 (s, 1H), 8.17 (s, 1H), 7.94-7.89 (m, 1H), 7.88-7.83 (m, 1H), 5.90 (quin, J=7.0 Hz, 1H), 5.33 (t, J=6.5 Hz, 2H), 5.17 (t, J=7.3 Hz, 2H), 4.50-4.31 (m, 4H), 4.18-4.03 (m, 1H), 1.57 (s, 3H), 0.96-0.85 (m, 2H), 0.68-0.61 (m, 2H); LCMS (ESI) [M+H]+: 396.1.

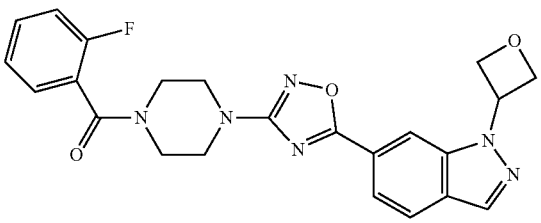 [SMILES: O=C(c1ccccc1Cl)N1CCN(c2noc(-c3ccc4cnn(C5COC5)c4c3)n2)CC1]

$^1$H NMR (400 MHz, CHLOROFORM-d) δ 8.25 (s, J=0.9 Hz, 1H), 8.20 (s, 1H), 7.88 (m, J=0.9 Hz, 2H), 7.50-7.40 (m, 2H), 7.28 (d, J=0.9 Hz, 0.3H), 7.26-7.22 (m, 0.7H), 7.14 (t, J=9.2 Hz, 1H), 5.96-5.81 (m, 1H), 5.33 (t, J=6.6 Hz, 2H), 5.18 (t, J=7.5 Hz, 2H), 3.98 (br s, 2H), 3.71 (br t, J=4.8 Hz, 2H), 3.62-3.41 (m, 4H); LCMS (ESI) [M+H]+: 449.1.

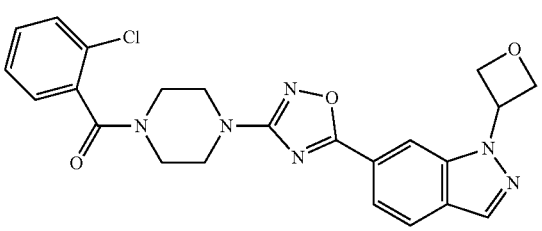

$^1$H NMR (400 MHz, CHLOROFORM-d) δ 8.25 (s, 1H), 8.20 (s, 1H), 7.88 (m, 2H), 7.48-7.42 (m, 1H), 7.41-7.31 (m, 3H), 5.89 (quin, J=7.0 Hz, 1H), 5.33 (t, J=6.6 Hz, 2H), 5.23-5.14 (m, 2H), 4.13-4.02 (m, 1H), 3.98-3.85 (m, 1H), 3.78-3.69 (m, 1H), 3.68-3.57 (m, 1H), 3.57-3.41 (m, 2H), 3.40-3.32 (m, 1H); LCMS (ESI) [M+H]+: 465.1.

747

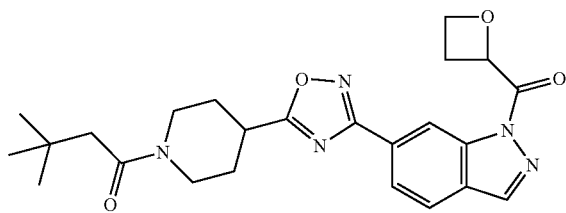 [SMILES: CC(C)(C)CC(=O)N1CCC(c2nc(-c3ccc4cnn(C(=O)C5CCO5)c4c3)no2)CC1]

¹H NMR (400 MHz, CHLOROFORM-d) δ 9.23 (s, 1H), 8.19 (d, J=0.9 Hz, 1H), 8.13 (dd, J=1.3, 8.3 Hz, 1H), 7.86 (dd, J=0.7, 8.3 Hz, 1H), 6.22 (dd, J=6.8, 9.0 Hz, 1H), 4.93-4.76 (m, 2H), 4.57 (br d, J=13.2 Hz, 1H), 4.05 (br d, J=12.2 Hz, 1H), 3.41-3.19 (m, 3H), 3.10-2.87 (m, 2H), 2.35 (s, 2H), 2.24 (br dd, J=3.5, 13.4 Hz, 2H), 2.03 (m, 2H), 1.09 (s, 9H); LCMS (ESI) [M+H]+: 452.2.

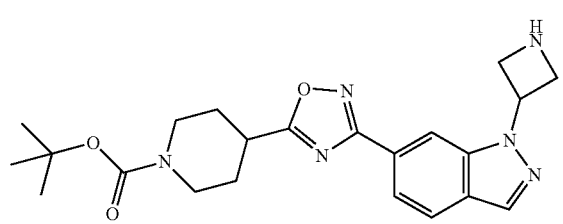 [SMILES: CC(C)(C)OC(=O)N1CCC(c2nc(-c3ccc4cnn(C5CNC5)c4c3)no2)CC1]

¹H NMR (400 MHz, METHANOL-d₄) δ 8.54 (br d, J=4.3 Hz, 1H), 8.36 (s, 1H), 8.33 (s, 1H), 7.97-7.89 (m, 2H), 5.98 (quin, J=7.2 Hz, 1H), 4.72-4.57 (m, 4H), 4.14 (m, 2H), 3.42-3.34 (m, 1H), 3.20-3.01 (m, 2H), 2.19 (m, 2H), 1.94-1.79 (m, 2H), 1.56-1.46 (s, 9H); LCMS (ESI) [M+H]+: 425.2.

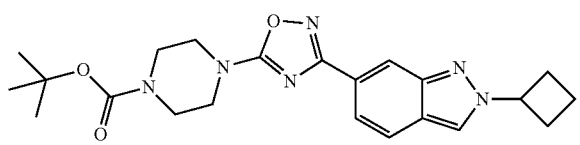 [SMILES: CC(C)(C)OC(=O)N1CCN(c2nc(-c3ccc4cn(C5CCC5)nc4c3)no2)CC1]

¹H NMR (400 MHz, CHLOROFORM-d) δ 8.43 (d, J=1.0 Hz, 1H), 7.98 (s, 1H), 7.68 (d, J=0.9 Hz, 2H), 5.07 (quin, J=8.4 Hz, 1H), 3.71-3.64 (m, 4H), 3.62-3.54 (m, 4H), 2.83-2.67 (m, 2H), 2.66-2.51 (m, 2H), 2.06-1.89 (m, 2H), 1.49 (s, 9H); LCMS (ESI) [M+H]+: 425.2.

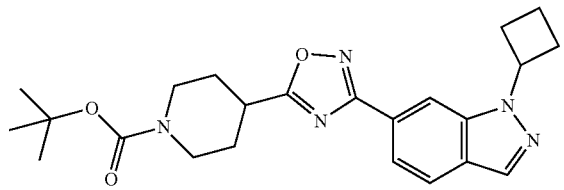 [SMILES: CC(C)(C)OC(=O)N1CCC(c2nc(-c3ccc4cnn(C5CCC5)c4c3)no2)CC1]

¹H NMR (400 MHz, CHLOROFORM-d) δ 8.19 (s, 1H), 8.07 (s, 1H), 7.88-7.74 (m, 2H), 5.17 (quin, J=8.3 Hz, 1H), 4.15 (br s, 2H), 3.20 (tt, J=3.9, 11.0 Hz, 1H), 3.01 (br t, J=12.0 Hz, 2H), 2.91-2.76 (m, 2H), 2.63-2.50 (m, 2H), 2.15 (br d, J=10.8 Hz, 2H), 2.06-1.84 (m, 4H), 1.48 (s, 9H); LCMS (ESI) [M+H]+: 424.2.

748

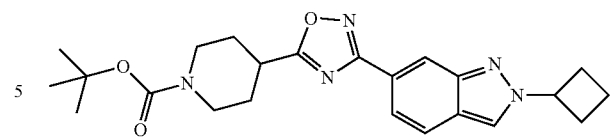

¹H NMR (400 MHz, CHLOROFORM-d) δ 8.52 (d, J=1.1 Hz, 1H), 8.00 (s, 1H), 7.77-7.70 (m, 2H), 5.08 (quin, J=8.3 Hz, 1H), 4.20-4.07 (m, 2H), 3.21-3.12 (m, 1H), 3.02 (br t, J=11.5 Hz, 2H), 2.82-2.58 (m, 4H), 2.14 (br d, J=9.9 Hz, 2H), 2.06-1.85 (m, 4H), 1.48 (s, 9H); LCMS (ESI) [M+H]+: 424.2.

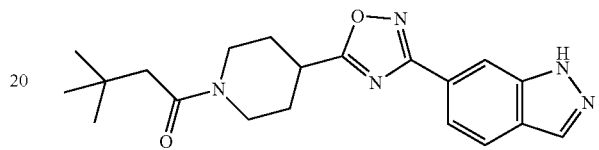

¹H NMR (400 MHz, CHLOROFORM-d) δ 10.59 (br s, 1H), 8.29 (s, J=0.9 Hz, 1H), 8.15 (s, J=0.9 Hz, 1H), 7.89 (m, J=1.0, 8.5 Hz, 2H), 4.62 (br d, J=13.7 Hz, 1H), 4.04 (br d, J=13.9 Hz, 1H), 3.45-3.20 (m, 2H), 2.99 (br t, J=11.0 Hz, 1H), 2.33 (m, 2H), 2.22 (m, J=13.5 Hz, 2H), 2.00-1.85 (m, 2H), 1.09 (s, 9H); LCMS (ESI) [M+H]+: 368.1.

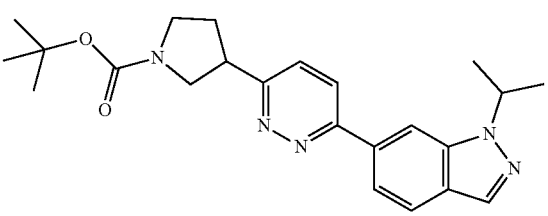 [SMILES: CC(C)n1ncc2ccc(-c3ccc(C4CCN(C(=O)OC(C)(C)C)C4)nn3)cc21]

¹H NMR (400 MHz, CHLOROFORM-d) δ 8.41 (br s, 1H), 8.07 (s, 1H), 7.93 (d, J=8.8 Hz, 1H), 7.86 (d, J=8.3 Hz, 1H), 7.71 (dd, J=1.1, 8.6 Hz, 1H), 7.47 (br d, J=8.8 Hz, 1H), 4.99 (spt, J=6.7 Hz, 1H), 4.05-3.90 (m, 1H), 3.86-3.60 (m, 3H), 3.58-3.45 (m, 1H), 2.51-2.22 (m, 2H), 1.64 (d, J=6.6 Hz, 6H), 1.49 (s, 9H); LCMS (ESI) [M+H]+: 408.2.

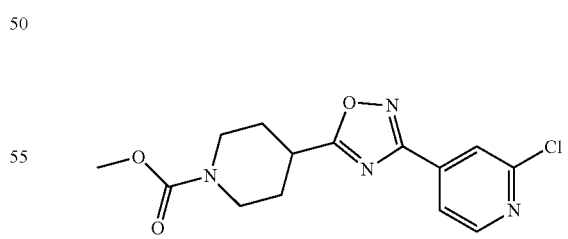

¹H NMR (400 MHz, CHLOROFORM-d) δ 8.55 (d, J=5.1 Hz, 1H), 8.00 (s, 1H), 7.88 (dd, J=1.3, 5.1 Hz, 1H), 4.18 (br s, 2H), 3.73 (s, 3H), 3.23 (tt, J=3.9, 10.9 Hz, 1H), 3.08 (br t, J=11.7 Hz, 2H), 2.20-2.12 (m, 2H), 1.99-1.86 (m, 2H); LCMS (ESI) [M+H]+: 323.0.

749

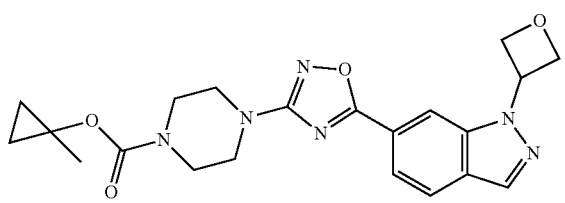 [SMILES: CC1(OC(=O)N2CCN(c3noc(-c4ccc5cnn(C6COC6)c5c4)n3)CC2)CC1]

¹H NMR (400 MHz, CHLOROFORM-d) δ 8.24 (s, J=0.7 Hz, 1H), 8.20 (s, 1H), 7.88 (m, 2H), 5.90 (quin, J=7.0 Hz, 1H), 5.33 (t, J=6.5 Hz, 2H), 5.22-5.11 (m, 2H), 3.56 (br s, 8H), 1.58 (s, 3H), 0.95-0.85 (m, 2H), 0.72-0.61 (m, 2H); LCMS (ESI) [M+H]+: 425.1.

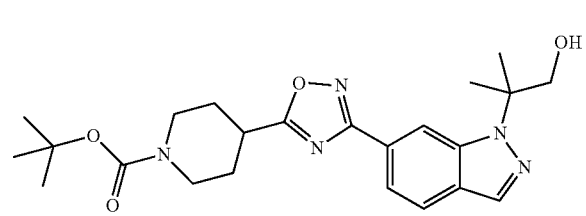 [SMILES: CC(C)(C)OC(=O)N1CCC(c2nc(-c3ccc4cnn(C(C)(C)CO)c4c3)no2)CC1]

¹H NMR (400 MHz, DMSO-d₆) δ 8.46 (d, J=0.9 Hz, 1H), 8.15 (d, J=0.9 Hz, 1H), 7.97-7.88 (m, 1H), 7.73 (dd, J=1.2, 8.4 Hz, 1H), 5.07 (t, J=5.7 Hz, 1H), 3.98 (br d, J=13.0 Hz, 2H), 3.81 (d, J=5.7 Hz, 2H), 3.43-3.36 (m, 1H), 2.98 (br s, 2H), 2.11 (br dd, J=2.9, 13.3 Hz, 2H), 1.79-1.63 (m, 8H), 1.42 (s, 9H); LCMS (ESI) [M+H]+: 442.1.

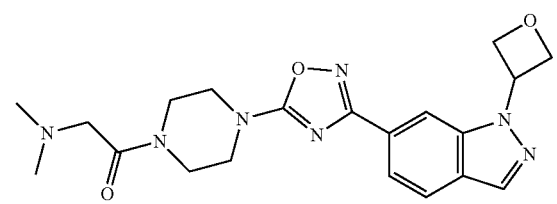 [SMILES: CN(C)CC(=O)N1CCN(c2nc(-c3ccc4cnn(C5COC5)c4c3)no2)CC1]

¹H NMR (400 MHz, CHLOROFORM-d) δ 8.16-8.12 (m, 2H), 7.85-7.78 (m, 2H), 5.92-5.84 (m, 1H), 5.33 (t, J=6.7 Hz, 2H), 5.14 (t, J=7.3 Hz, 2H), 3.84-3.71 (m, 8H), 3.17 (s, 2H), 2.30 (s, 6H); LCMS (ESI) [M+H]+: 412.2.

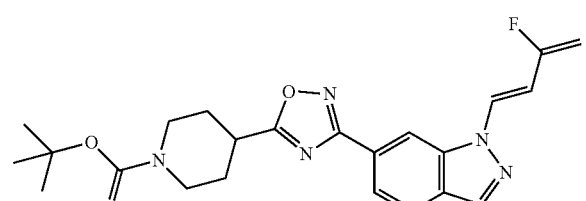

¹H NMR (400 MHz, CHLOROFORM-d) δ 8.31 (s, 1H), 8.20 (s, 1H), 7.97 (d, J=8.4 Hz, 1H), 7.84 (d, J=8.4 Hz, 1H), 7.69 (d, J=13.7 Hz, 1H), 6.85-6.73 (m, 1H), 4.78 (dd, J=2.9, 17.0 Hz, 1H), 4.67-4.52 (m, 1H), 4.16 (br s, 2H), 3.21 (tt, J=3.8, 10.9 Hz, 1H), 3.01 (br t, J=11.4 Hz, 2H), 2.16 (br d, J=11.2 Hz, 2H), 2.00-1.86 (m, 2H), 1.48 (s, 9H); LCMS (ESI) [M+H]+: 440.2.

750

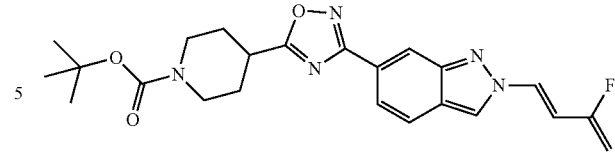

¹H NMR (400 MHz, CHLOROFORM-d) δ 8.48 (s, 1H), 8.07 (s, 1H), 7.79-7.70 (m, 2H), 7.51 (d, J=13.7 Hz, 1H), 7.14-7.02 (m, 1H), 4.92 (dd, J=2.9, 16.3 Hz, 1H), 4.81-4.66 (d, J=48 Hz, 1H), 4.13 (br s, 2H), 3.25-3.14 (m, 1H), 3.02 (br t, J=11.7 Hz, 2H), 2.14 (br d, J=11.0 Hz, 2H), 1.98-1.85 (m, 2H), 1.48 (s, 9H); LCMS (ESI) [M−55]+: 384.1.

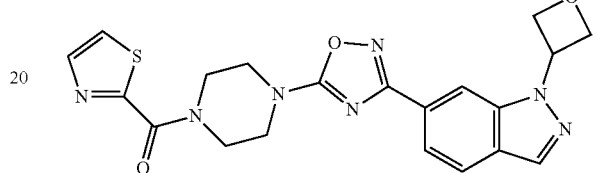

¹H NMR (400 MHz, CHLOROFORM-d) δ 8.15 (s, 2H), 7.93 (d, J=3.2 Hz, 1H), 7.86-7.79 (m, 2H), 7.60 (d, J=3.2 Hz, 1H), 5.93-5.84 (m, 1H), 5.33 (t, J=6.6 Hz, 2H), 5.15 (t, J=7.3 Hz, 2H), 4.66 (m, 2H), 3.98 (m, 2H), 3.87 (br t, J=4.9 Hz, 4H); LCMS (ESI) [M+H]+: 438.1.

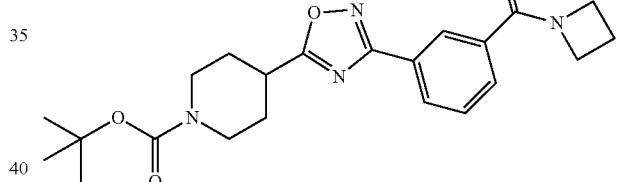

¹H NMR (400 MHz, CHLOROFORM-d) δ 8.25 (t, J=1.5 Hz, 1H), 8.09 (td, J=1.4, 7.8 Hz, 1H), 7.73 (td, J=1.4, 7.8 Hz, 1H), 7.47 (t, J=7.8 Hz, 1H), 4.34-4.14 (m, 4H), 4.05 (br d, J=9.0 Hz, 2H), 3.14-3.06 (m, 1H), 2.94 (br t, J=11.7 Hz, 2H), 2.35-2.23 (m, 2H), 2.05 (br dd, J=3.2, 13.3 Hz, 2H), 1.88-1.74 (m, 2H), 1.41 (s, 9H); LCMS (ESI) [M−100+1]+: 313.1, LCMS (ESI) [M+23]+: 435.1.

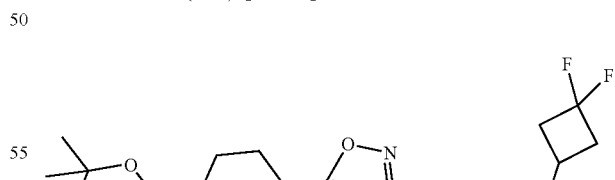

¹H NMR (400 MHz, CHLOROFORM-d) δ 8.17 (s, 1H), 8.11 (s, 1H), 7.92-7.88 (dd, J=8.8, 1H), 7.85-7.81 (d, J=8.8, 1H), 5.19-5.05 (m, 1H), 4.14 (m, 2H), 3.51-3.35 (m, 3.28-3.15 (m, 3H), 3.02 (br t, J=11.6 Hz, 2H), 2.15 (br dd, J=2.6, 13.4 Hz, 2H), 2.00-1.87 (m, 2H), 1.49 (s, 9H); LCMS (ESI) [M−55]+: 404.1.

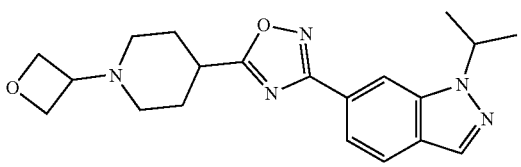 [SMILES: CC(C)n1ncc2ccc(-c3noc(C4CCN(C5COC5)CC4)n3)cc21]

¹H NMR (400 MHz, CHLOROFORM-d) δ 8.13 (s, 1H), 8.04 (s, 1H), 7.81-7.74 (m, 2H), 4.95 (td, J=6.6, 13.4 Hz, 1H), 4.81 (dd, J=6.2, 7.7 Hz, 2H), 4.51 (t, J=6.3 Hz, 2H), 4.33 (br d, J=13.2 Hz, 2H), 3.17 (dt, J=2.6, 12.9 Hz, 2H), 2.86-2.74 (m, 1H), 2.03-1.91 (m, 1H), 1.77 (br d, J=11.9 Hz, 2H), 1.62 (d, J=6.6 Hz, 6H), 1.25 (dq, J=4.4, 12.5 Hz, 2H); LCMS (ESI) [M+H]+: 368.2.

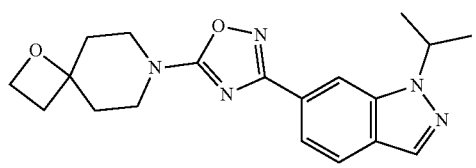 [SMILES: CC(C)n1ncc2ccc(-c3noc(N4CCC5(CCO5)CC4)n3)cc21]

¹H NMR (400 MHz, CHLOROFORM-d) δ 8.13 (s, 1H), 8.04 (s, 1H), 7.80-7.75 (m, 2H), 4.95 (quin, J=6.7 Hz, 1H), 4.60 (t, J=7.7 Hz, 2H), 3.85 (td, J=4.9, 13.6 Hz, 2H), 3.68 (ddd, J=3.3, 9.8, 13.3 Hz, 2H), 2.47 (t, J=7.8 Hz, 2H), 2.13 (td, J=4.2, 13.3 Hz, 2H), 1.92 (ddd, J=4.4, 9.6, 13.6 Hz, 2H), 1.62 (d, J=6.6 Hz, 6H); LCMS (ESI) [M+H]+: 354.2.

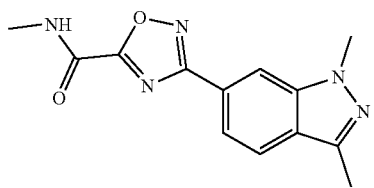 [SMILES: CNC(=O)c1nc(-c2ccc3c(C)nn(C)c3c2)no1]

¹H NMR (400 MHz, DMSO-d₆) δ 9.44 (br s, 1H), 8.25 (s, 1H), 7.92 (br d, J=8.3 Hz, 1H), 7.76 (br d, J=8.3 Hz, 1H), 4.05 (s, 3H), 2.85 (br d, J=3.5 Hz, 3H), 2.52 (br s, 3H); LCMS (ESI) [M+H]+: 272.1.

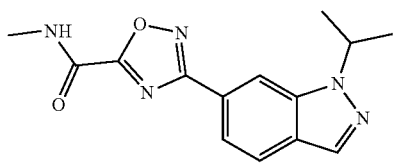 [SMILES: CNC(=O)c1nc(-c2ccc3cnn(C(C)C)c3c2)no1]

¹H NMR (400 MHz, CHLOROFORM-d) δ 8.25 (s, 1H), 8.06 (s, 1H), 7.90-7.78 (m, 2H), 7.19 (br s, 1H), 5.03-4.87 (m, 1H), 3.21-3.06 (m, 3H), 1.63 (br d, J=6.6 Hz, 6H); LCMS (ESI) [M+H]+: 286.1.

Example 157. Description of Yeast Models

α-synuclein and ApoE4 yeast strains were previously engineered to express the human α-synuclein or ApoE4 genes under control of the yeast galactose-regulated promoter, GAL1, as described in International Patent Publication No. WO2016/040794 and U.S. Pat. Nos. 7,452,670 and 7,045,290, the procedures for the production of such strains of which are herein incorporated by reference. The induced expression of α-synuclein and ApoE4 confers cytotoxicity, thus enabling the identification of compounds that can restore cell viability. This instantaneous/synchronous induction of α-synuclein and ApoE4 can be achieved due to the following expression control. In glucose-containing media, gene expression from the GAL1 promoter is 'off' and actively repressed by additional epigenetic factors. In raffinose, expression is 'off', but the promoter not actively repressed. Upon transition to galactose-containing media, the promoter is instantaneously turned 'on' to achieve robust and synchronous induction of α-synuclein or ApoE4 expression. This highly regulated induction provides a robust window for the determination of both efficacy (amplitude of protective effect) and potency (concentration of protective effect) of cytoprotective compounds.

Compound Profiling

Fresh powders (~5 mg) of newly synthesized compounds were dissolved to 10 mM in 100% DMSO using a Janus (Perkin Elmer) robotic workstation. Re-suspended compound stocks were subsequently arrayed into 384 well compound plates using automated pipetting. All other wells not receiving stock compound were filled with 10 μL of 100% DMSO using an automated plate filler (Multidrop Combi). An 11 point, 2-fold serial dilution was then performed using the robotic platform. Compound assay plates were covered with foil and stored at −20° C. until use.

Each strain was handled according to standard protocols and cultured in media composed of CSM (complete synthetic media), YNB (yeast nitrogenous base), and a 2% (w/v) carbon source (either glucose, raffinose, or galactose). Single use frozen aliquots of each strain were generated by growing cells in CSM/glucose media to an $OD_{600}$ of 0.6-0.8, concentrating the yeast to 12.5 $OD_{600}$ units per 30 μL of CSM/glucose media supplemented with 20% glycerol, and freezing 30 μL aliquots at −80° C.

In a standard yeast assay, a single-use aliquot of cells was thawed on ice and diluted into CSM/glucose (5 mL). Cultures were grown for 8 hours at 30° C. This pre-growth enables the yeast to exit the thaw and begin to grow without expressing aSyn or ApoE4. After 8 hours, cell density ($OD_{600}$) was determined and cultures diluted to an $OD_{600}$ of 0.01 in CSM/raffinose for an overnight culture phase at 30° C. During this period, the active glucose repression of the GAL1 promoter was relieved; however, expression of the α-Syn/ApoE4 genes were not yet induced. After ~16 hours of growth, cultures attain an $OD_{600}$ of 0.4-0.8 and were ready to apply to assay plates containing compound.

Compound profiling assays were executed in clear-bottom 384 well plates. First, compound plates were thawed at room temperature for 45', centrifuged at 1,000×g for 1 minute, and the foil removed. Clear 384 well assay plates were then filled with 15 μL of CSM/galactose. Both compound and media-containing plates were arranged on the Janus workstation and a compound pin tool (384×100 nL slotted pins) used to deliver 100 nL of compounds to each well according to the well map of the compound plate. Based on the previous serial dilution, the final concentration of compound ranged from 33.3 μL to 12.5 nM. The pin tool was washed iteratively with both 50% DMSO and 100% ethanol between each assay plate. After delivering compound to each assay plate, the overnight CSM/raffinose aSyn or ApoE4 cultures were added at a 2× cell density (0.04 for aSyn and 0.08 for ApoE4) in CSM/galactose to achieve a final assay $OD_{600}$ of 0.02 and 0.04 for aSyn and ApoE, respectively. The cultures (15 μL per well) were then dispensed to the compound-containing 384 well assay plates using an automated plate filler. Plates were incubated in a humidified 30° C. incubator for 40 or 24 hours for aSyn and ApoE4, respectively. The $OD_{600}$ of each assay plate was then read with a microplate reader (e.g., Perkin Elmer Envision).

The efficacy and potency of compounds were calculated according to the following. Raw data ($OD_{600}$ values) were first background corrected to account for $OD_{600}$ contributed by the plate and media itself. The efficacy (percent above DMSO, herein referred to as "Emax") was calculated according to the equation: (Experimental well−DMSO control well)/(DMSO control well)*100. For each individual compound with positive activity (>30% above DMSO—or 3 standard deviations from the DMSO negative control wells), the dose-response data were normalized to a scale of 0-100% to enable potency (herein referred to as "EC50") determination. Normalized dose-response data was fit with a logistic regression curve using Spotfire (TIBCO), or similar curve-fitting software package. EC50 values were then reported along with EMax to provide both efficacy and potency measures for each analog and enable further compound design. As shown in Table 3, compounds of the invention are able to reduce the toxicity of the expressed alpha-synuclein and/or ApoE4 proteins.

TABLE 3

Yeast rescue data for examples 1-155 showing that compounds of the invention were able to reduce toxicity in yeast strains expressing the human proteins α-synuclein and/or ApoE4.

| Compound # | α-Syn EC50 (nM) | α-Syn Emax (%) | ApoE4 EC50 (nM) | ApoE4 Emax (%) |
| --- | --- | --- | --- | --- |
| 1 | n/a | 155 | n/a | 320 |
| 2 | 8569 | 80 | | |
| 3 | 17843 | 307 | n/a | 200 |
| 4 | 8428 | 59 | 11756 | 76 |
| 6 | 10194 | 460 | 15110 | 815 |
| 7 | 40 | 594 | 176 | 782 |
| 8 | 13764 | 188 | n/a | 111 |
| 9 | 12113 | 167 | n/a | 301 |
| 10 | 4870 | 392 | 4614 | 736 |
| 11 | 5892 | 309 | n/a | 600 |
| 12 | 16197 | 43 | | |
| 13 | 58 | 712 | 368 | 837 |
| 14 | 1164 | 463 | 1830 | 771 |
| 15 | 1711 | 628 | 3627 | 866 |
| 16 | 17823 | 249 | 21200 | 418 |
| 17 | 17395 | 330 | n/a | 246 |
| 18 | 266 | 452 | 1512 | 826 |
| 19 | 2425 | 574 | 5627 | 891 |
| 20 | 15131 | 181 | 16216 | 529 |
| 21 | n/a | 276 | n/a | 447 |
| 22 | 8423 | 334 | n/a | 372 |
| 23 | 7680 | 182 | 6513 | 466 |
| 24 | 5126 | 76 | 13342 | 301 |
| 25 | 751 | 619 | 1855 | 889 |
| 26 | 42 | 608 | 377 | 811 |
| 27 | 59 | 589 | 390 | 761 |
| 28 | 66 | 576 | 1594 | 836 |
| 29 | 13928 | 38 | | |
| 31 | 7506 | 438 | 9813 | 721 |
| 32 | 9883 | 41 | | |
| 33 | 111 | 260 | 717 | 281 |
| 34 | 11112 | 562 | n/a | 596 |
| 35 | 52 | 626 | 1122 | 911 |
| 36 | 1757 | 629 | 2154 | 908 |
| 37 | 2205 | 608 | 6530 | 849 |
| 38 | 3296 | 336 | 6014 | 750 |
| 39 | 18143 | 216 | | |
| 40 | 86 | 443 | | |
| 41 | 10899 | 211 | n/a | 400 |
| 42 | 12462 | 255 | n/a | 399 |
| 43 | 14607 | 222 | 17730 | 517 |
| 44 | 10870 | 579 | 13312 | 676 |
| 45 | 26019 | 121 | 29268 | 19 |
| 46 | 10930 | 35 | | |
| 47 | 16513 | 88 | | |
| 48 | 1471 | 615 | 2944 | 874 |
| 49 | 1469 | 636 | 4336 | 942 |
| 50 | 7857 | 85 | n/a | 133 |
| 51 | 10924 | 137 | n/a | 286 |
| 52 | 9059 | 82 | 14485 | 154 |
| 53 | 6603 | 81 | 16643 | 296 |
| 54 | 9095 | 95 | 17308 | 240 |
| 55 | 23816 | 47 | 7902 | 29 |
| 56 | 1665 | 549 | 8325 | 793 |
| 57 | 9005 | 503 | 12060 | 797 |
| 58 | 7943 | 23 | | |
| 59 | 15667 | 82 | n/a | 47 |
| 60 | 32 | 605 | 119 | 795 |
| 61 | 19706 | 229 | 19380 | 465 |
| 62 | 21699 | 204 | 21427 | 430 |
| 63 | 17170 | 68 | 13385 | 250 |
| 64 | 13746 | 228 | 15275 | 330 |
| 65 | 36 | 643 | 987 | 779 |
| 66 | 11067 | 350 | 21212 | 790 |
| 67 | 7377 | 255 | 17364 | 420 |
| 68 | 1864 | 652 | 3123 | 775 |
| 69 | n/a | 294 | n/a | 387 |
| 70 | n/a | 605 | n/a | 580 |
| 71 | 8093 | 151 | 8969 | 235 |
| 72 | 12665 | 35 | | |
| 73 | 15760 | 151 | n/a | 303 |
| 74 | 17866 | 155 | n/a | 411 |
| 76 | 9921 | 76 | 14827 | 162 |
| 77 | n/a | 345 | n/a | 436 |
| 78 | 14604 | 38 | | |
| 79 | 9907 | 627 | 18845 | 631 |
| 80 | 3322 | 188 | 6014 | 262 |
| 82 | | | 16773 | 40 |
| 83 | 9309 | 151 | n/a | 567 |
| 84 | 60 | 463 | 956 | 866 |
| 85 | 12610 | 486 | 17049 | 602 |
| 86 | 18 | 772 | 64 | 633 |
| 87 | 1929 | 579 | | |
| 88 | 9037 | 130 | | |
| 89 | 165 | 580 | | |
| 90 | 1646 | 281 | | |
| 91 | 107 | 452 | | |
| 92 | 2499 | 187 | | |
| 93 | 1800 | 626 | | |
| 94 | 40 | 1083 | | |
| 95 | 91 | 827 | | |
| 96 | 26 | 343 | 228 | 840 |
| 97 | 707 | 132 | 3884 | 704 |
| 98 | 8009 | 386 | 9747 | 650 |
| 99 | 1032 | 209 | 2749 | 663 |
| 100 | 1191 | 385 | 2106 | 651 |
| 101 | 1175 | 122 | | |
| 102 | 284 | 411 | | |
| 103 | 2023 | 75 | | |
| 104 | 1872 | 253 | | |
| 105 | 3180 | 391 | | |
| 106 | 100 | 415 | | |
| 107 | 2899 | 312 | | |
| 108 | 11149 | 316 | | |
| 109 | 3041 | 35 | | |
| 110 | 4493 | 374 | | |
| 111 | 339 | 289 | | |
| 112 | 320 | 258 | | |
| 113 | 15628 | 55 | | |
| 114 | 17316 | 373 | | |
| 115 | 887 | 326 | | |
| 116 | 9038 | 345 | | |
| 117 | 7502 | 124 | | |

TABLE 3-continued

Yeast rescue data for examples 1-155 showing that compounds of the invention were able to reduce toxicity in yeast strains expressing the human proteins α-synuclein and/or ApoE4.

| Compound # | α-Syn EC50 (nM) | α-Syn Emax (%) | ApoE4 EC50 (nM) | ApoE4 Emax (%) |
|---|---|---|---|---|
| 118 | 15667 | 65 | | |
| 119 | 20897 | 61 | | |
| 120 | 19502 | 139 | | |
| 121 | 15527 | 388 | | |
| 122 | 139 | 414 | | |
| 123 | 69 | 343 | | |
| 124 | 17661 | 395 | | |
| 125 | 16712 | 200 | | |
| 127 | 7416 | 349 | | |
| 128 | 252 | 306 | | |
| 129 | 47 | 360 | | |
| 130 | 1443 | 328 | | |
| 131 | 167 | 352 | | |
| 132 | 1006 | 253 | | |
| 133 | 6381 | 281 | | |
| 134 | 13976 | 357 | | |
| 135 | 593 | 144 | | |
| 136 | 4080 | 67 | | |
| 137 | 1052 | 376 | | |
| 138 | 1280 | 353 | | |
| 139 | 21 | 437 | | |
| 140 | 49 | 322 | | |
| 141 | 19 | 259 | | |
| 142 | 7644 | 319 | | |
| 143 | 16891 | 73 | | |
| 144 | 521 | 537 | | |
| 145 | 100 | 432 | | |
| 146 | 1941 | 516 | | |
| 147 | 17902 | 453 | | |
| 148 | 13652 | 258 | | |
| 149 | 60 | 458 | | |
| 150 | 99 | 473 | | |
| 151 | 45 | 405 | | |
| 152 | 134 | 474 | | |
| 153 | 20 | 271 | | |
| 154 | 57 | 410 | | |
| 155 | 11 | 556 | 2159 | 865 |

Example 158: U2OS Transient Overexpression Induced Cytotoxicity Assay

U2OS (Sigma-Aldrich), a human bone osteosarcoma epithelial cell line, is regularly maintained in McCoy's 5A medium (ATCC) supplemented with 10% FBS (ThermoFisher) between passage 11-21 and sub-cultured twice a week for the assay.

On the day of experiment, cells are about 80% confluence and trypsinized using 0.25% trypsin-EDTA (ThermoFisher Inc.) for 5 minutes at 37c. Based on a ratio of 2 ug DNA/2e5 cells, required cells are spun down at 800 rpm for 5 minutes at room temperature. Cells are then re-suspended in SE solution (Lonza Inc.) at a density of 2e4 cells/μl. Nucleofection is performed using 4D-Nucleofector™ System (Lonza Inc.) under program code CM130. Cells are allowed to recover in the cuvette at room temperature for 10-15 minutes before further handling. Pre-warmed medium is added and cells suspension is thoroughly but gently mixed before plating. Cells are seeded at 2e4 cells/100 μl/well into 96 well PLD-coated white plate (Corning) using customized Viaflow program (Integra Biosciences). Serial dilution of drugs is carried out in DMSO. Drug solution is prepared at 6× fold, 20 ul of which is added to cells 4 hours after transfection. The final DMSO concentration is 0.3%. Microclimate lid (Labcyte) is strongly recommended to reduce evaporation and variation. Seventy-two hours post transfection, cells are lysed using CellTiter-Glow (Promega) and ATP content is determined using a luminescence plate reader (Perkin Elmer). % Maximum fold rescue at each concentration is calculated as follows:

$$\% \text{ Fold} = \frac{(RLU^{ASYN} \text{ drug}) \cdot 100}{RLU^{ASYN} \text{ DMSO}}$$

FK506 (tacrolimus), a macrolide calcineurin inhibitor, is used as reference compound in the assay. FK506 has been shown to rescue aSyn toxicity in yeast models, and this activity has translated to rodent in vivo models of neurodegeneration.

% Rescue (normalized by max fold rescue of FK506)=(% Fold$^{\alpha Syn}$ drug−100)*100/(% Max fold$^{\alpha Syn}$ FK506−100).

As shown in Table 4, the compounds of the invention were able to rescue human bone osteosarcoma epithelial U2OS cells that were transiently overexpressing the toxic alpha-synuclein protein, reducing the level of induced cytotoxicity:

TABLE 4

| | % Rescue (normalized by FK506 max rescue) | | | |
|---|---|---|---|---|
| Example # | 1 (μM) | 0.3 (μM) | 0.1 (μM) | 0.01 (μM) |
| 40 | 77 | 105 | 137 | 107 |
| 155 | 10 | 44 | 83 | −23 |

Example 159: Stearoyl-CoA Desaturase (SCD) is the Target of 1,2,4-Oxadiazoles A. Materials and Methods Strain Construction and OLE1 Replacement with SCD1 or SCD5

Strain GMYF was constructed from the ABC16/Green monster strain described in Suzuki et al. *Nat. Methods* 8(2):159-164, 2011. In this strain, YAP1 was deleted using a HIS3-MX6 cassette, and FLR1 was deleted using a NAT-MX6 cassette using standard methods. The knockout cassettes were PCR-amplified from plasmid templates (see, e.g., Bahler et al. *Yeast* 14(10):943-951, 1998; Longtine et al. *Yeast* 14(10):953-961, 1998) and transformed into yeast using lithium acetate-based transformation (Gietz et al. *Methods Mol. Biol.* 1205:1-12, 2014). The yap1::his3 deletion strain was selected on media lacking histidine and flr1::NAT on plates containing 100 μg/mL nourseothricin. All strains were confirmed by diagnostic PCR. Strain W303 pdr1Δ pdr3Δ was constructed from W303-1A (American Type Culture Collection (ATCC) 208352) by deleting PDR1 and PDR3 with kan-MX6 cassettes separately in MATa and MATα W303a isolates, mating, sporulating, and identifying double deletion haploids by tetrad dissection and identification of non-parental ditype tetrads. Strain W-erg3 was derived from W303 pdr1Δ pdr3Δ by deleting SNQ2 with NAT-MX6, YAP1 with HIS3-MX6, and ERG3 with BleMX.

Strain ApoE-mga2Δ was generated by amplifying 1000 base pairs (bp) upstream and downstream of the MGA2 ORF in a strain in which MGA2 was deleted using a G418 (GENETICIN®) resistance cassette (kanMX) (Piotrowski et al. *Proc. Natl. Acad. Sci. USA* 112(12):E1490-1497, 2015) and transforming the resulting deletion cassette into the ApoE4 strain in the BY4741 (ATCC 201388) genetic background. The ApoE strain is described, for example, in International Patent Application Publication No. WO 2016/040794, which is incorporated herein by reference in its entirety.

The alpha-synuclein expression strain was made in the same manner as described in Su et al. *Dis. Model Mech.* 3(3-4):194-208, 2010, except that the alpha-synuclein construct lacked the green fluorescent protein (GFP) tag.

Strain ole1Δ (yeast ole1 deletion mutant) was constructed by deleting OLE1 with NAT-MX6 in BY4741, amplifying the deletion cassette from the genomic DNA of the resulting strain with primers flanking the ORF by 1000 bp upstream and downstream, transforming the resulting deletion cassette into W303 pdr1Δ pdr3Δ, and plating transformants on YPD media containing G418 (200 µg/mL) and nourseothricin (100 µg/mL) with 0.01% TWEEN®-20 and 0.5 mM oleic and palmitoleic acids.

To generate yeast strains expressing SCD1 or SCD5 as the sole desaturase, the human SCD1 and SCD5 genes were cloned from cDNAs (Harvard PlasmID database Clone ID HsCD00340237 for SCD1 and HsCD00342695 for SCD5) into yeast plasmid pRS316 (ATCC 77145) between the yeast TDH3 promoter and the CYC1 terminator. The coding sequence of yeast OLE1 was also cloned into this plasmid). These clones were then transformed into the ole1Δ strain and plated on CSM-Ura media (CSM lacking uracil) with 2% glucose (w/v) and independent colonies were isolated and amplified.

Compound Profiling Methods

All compound profiling experiments were performed using the same basic protocol. Different genetic backgrounds (e.g., gene deletions) or conditions (e.g., addition of oleic and palmitoleic acid) were replaced as indicated below.

Yeast were cultured using standard techniques in complete synthetic media (CSM) and yeast nitrogen base supplemented with 2% (w/v) carbon source (glucose, raffinose, or galactose) to regulate the expression of the toxic disease protein. An initial starter culture was inoculated in 3 mL CSM-Glucose media and incubated overnight in a 30° C. shaker incubator (225 rpm). Saturated morning cultures were then diluted 1:20 in fresh CSM-Raffinose media and grown for 6 h to an $OD_{600}$ (optical density) of ~0.4-0.8 at 30° C. with shaking.

Compound stocks (10 mM in 100% DMSO) were arrayed into 384 round well, v-bottom polypropylene plates and diluted according to indicated dilution factors. Compound administration was performed in two separate steps. First, 15 µL of CSM-Galactose (induces expression of toxic protein) was dispensed into clear 384 well assay plates using a MULTIDROP™ Combi reagent dispenser. The diluted compound stock plates were then applied to the assay plates using an automated workstation (Perkin Elmer JANUS™) outfitted with a 384 pin tool containing slotted pins that deliver 100 nL of compound. The cultures described above were then diluted to a 2× concentration (0.03 and 0.08 for alpha-synuclein and ApoE, final $OD_{600}$ of 0.015 and 0.04) in CSM-Galactose. For wild-type and Ole1/SCD1/SCD5 plasmid-containing strains, the 2× cell density was 0.02. In all experiments, 15 µL culture was then dispensed into the pinned assay plate to achieve 30 µL of the 1× $OD_{600}$ culture and a top drug concentration of 33.3 µM. For 96-well assays (FIGS. 1A and 1B), compound dilutions in DMSO were generated in 96 well plates and 1 µL was manually pipetted into 96 well clear bottom assay plates.

For experiments with oleic and palmitoleic acid supplementation (FIGS. 2A, 2B, 4, and 5), TWEEN®-20 was first added to culture media at a concentration of 0.01%. Oleic and palmitoleic acid were both then added at the indicated concentrations (0.08 to 0.5 mM) and mixed thoroughly prior to compound pinning or the addition of yeast.

For experiments using a plasmid-borne copy of Ole1, SCD1, or SCD5 (FIGS. 3B, 6, and 7), media lacking uracil (SX-Ura, where X is glucose, raffinose, or galactose), was used for all steps of the compound profiling protocol to ensure its maintenance throughout the assay.

After yeast delivery, assay plates were incubated under humidified conditions at 30° C. for 24 to 40 h. ApoE4 rescue experiments were stopped at 24 h, aSyn experiments at 40 h, Ole1 at 24 h, and SCD1/SCD5 at 40 h. The growth of yeast was monitored by reading the $OD_{600}$ of each well using a microplate reader (Perkin Elmer EnVision™). Data were analyzed as follows. For model rescue experiments, raw data were processed by background subtracting and calculating a fold-change relative to DMSO control [(EXP-0.035)/(DMSO-0.035)—where 0.035 is the $OD_{600}$ contributed by an empty well containing 30 µL of media alone]. For growth inhibition of wild-type cells, raw data were processed by background subtracting and converting values to a percent of the nontreated condition for that strain [(EXP-0.035)/(DMSO-0.035)×100%].

Compound Sources

Compounds were sourced as follows: cycloheximide (Sigma Aldrich), A939572 (Abcam), CAY10566 (Abcam), MF-438 (Calbiochem), MK-8245 (Selleckchem), oleic acid (Sigma Aldrich), palmitoleic acid (Acros organics), mycophenolic acid (Sigma Aldrich), and tunicamycin (Cayman Chemical).

Drug Resistant Mutant Selection

Strains GMYF and W-erg3 were grown to saturation in CSM-glucose, centrifuged, resuspended in phosphate-buffered Saline (PBS), and plated at a density of $10^7$ cells/plate on solid 15 cm petri dishes containing CSM with 2% galactose (w/v), 2% (w/v) agar, and 10 µM Compound 155, and incubated at 30° C. Resistant colonies were isolated after 5-7 days, re-streaked on the same media, and resistance reconfirmed. Cultures of validated strains were then inoculated for genomic DNA isolation using a YeaStar™ yeast genomic DNA kit (Zymo Research).

Libraries were prepared for sequencing Lasing the lumina NEXTERA™ library prep kit and sequenced via Illumina HiSeq™ 2500 1×50 bp (single end reads). Sequences were aligned to the *S. cerevisiae* reference genome (S288CCR64-1-1, *Saccharomyces* Genome Database (SGD)) using Burrows-Wheeler Aligner (BWA, see, e.g., Li et al. *Bioinformatics* 25:1754-1760, 2009; Li et al. *Bioinformatics* 2010, Epub (PMID 20080505)). The BWA output SAI files were converted to SAM ides using BWA. The SAM ides were sorted using SAMtools 1.3.1 (Li et al. *Bioinformatics* 25:2079-2079, 2009). Variants (single-nucleotide polymorphisms (SNPs), indels) were identified using Freebayes (see, e.g., arXiv:1207.3907). Variant locations were summarized using snpEFF (Cingolani et al. *Fly* (Austin) 6(2):80-92, 2012).

Quantitative Lipid Profiling Overnight cultures of yeast strain W303 pdr1Δ pdr3Δ were diluted into CSM media with 2% (w/v) raffinose, $OD_{600}$ 0.25, and grown for 4 h before resuspending at an $OD_{600}$ of 0.2 in CSM media with 2% (w/v) galactose and adding Compound 95 or DMSO at the indicated concentrations. Cells were grown for the indicated timepoints before centrifugation, washing once in PBS, and freezing pellets. Lipids were extracted from pellets by resuspending the pellets in 600 µL methanol, 300 µL water, and 400 µL chloroform, followed by cell lysis by vortexing with glass beads for 1 min. Samples were then centrifuged at 10,000×g for 10 min, and the bottom layer that formed (organic/lipids) was moved into a new tube and evaporated. Samples were then analyzed by LC/MS/MS using a Thermo Scientific Q Exactive™ Orbitrap™ coupled to a Dionex UltiMate® 3000 ultra-high performance liquid chromatography system, following the method described in Tafesse et al. *PLoS Pathog.* 11(10): e1005188, 2015.

B. Results

Figure 1B:
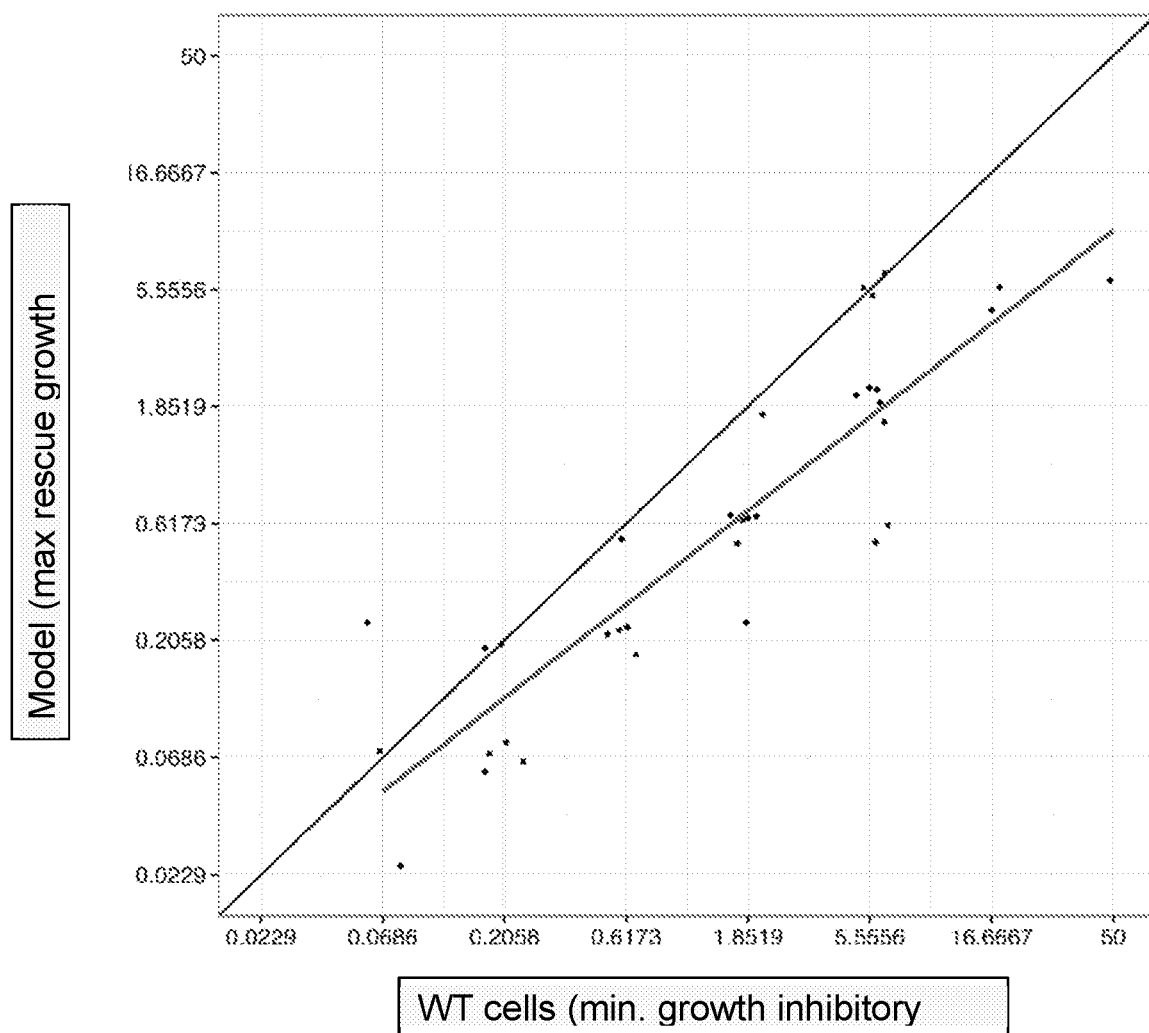

The effect of 1,2,4-oxiadiazoles on cell growth was assessed in a control condition and in a yeast model for ApoE4 toxicity (see International Patent Application Publication No. WO 2016/040794). The control condition was growth of the ApoE4 strain under non-inducing conditions using raffinose as the carbon source. The 1,2,4-oxadiazoles exhibited a bell-shaped rescue curve in the ApoE4 model (FIG. 1A, top panel). At higher concentrations, these compounds inhibited the growth in the control condition (FIG. 1B, bottom panel). The potency of model rescue correlated well with the potency of growth inhibition across the entire series of 1,2,4-oxadiazoles tested (FIG. 1B). These relationships indicate that the growth inhibition arises from an "on-target" activity, i.e., over activation or inhibition of a target that results in slowed growth.

Figure 9:
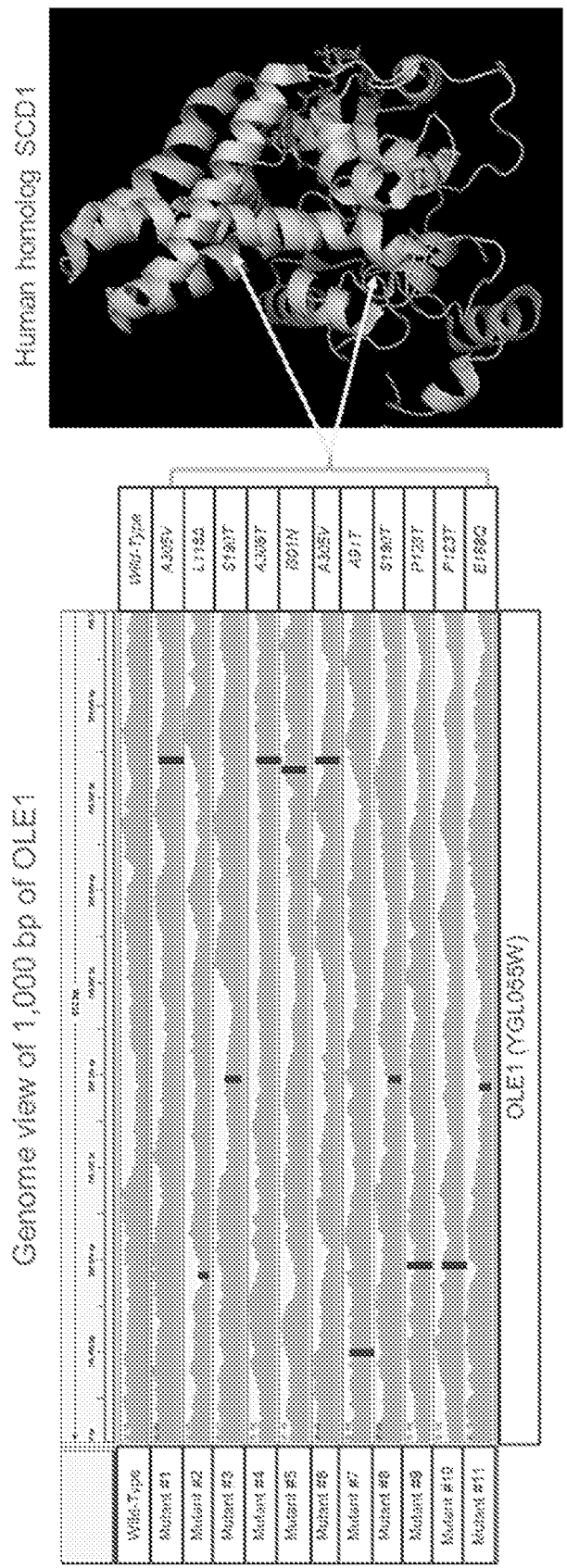
FIG. 9 shows OLE1 mutations conferring resistance to growth inhibition to 1,2,4-oxadiazoles identified by genome sequencing of resistant mutants. Cells were plated on media containing 10 µM of the 1,2,4-oxadiazole Compound 155 and resistant colonies that emerged were isolated, and genomic DNA was prepared from mutants and the parental, drug-sensitive control strain. Genomic DNA sequence was aligned to the *Saccharomyces cerevisiae* reference and unique mutations in the 1,2,4-oxadiazole-resistant mutants were identified. The position of the mutations, the amino acid changes they encode, and the fold resistance (increase in minimal inhibitory concentration) of Compound 155 are shown.

Drug-resistant mutants can be used to identify the target of the compounds, for example, by preventing or reducing drug binding, and therefore allowing growth under inhibitory doses of 1,2,4-oxadiazole concentrations. Twenty drug-resistant mutants were isolated, and the mutants were subjected to whole-genome sequencing in order to identify genetic lesions associated with the drug resistance. Surprisingly, all mutations identified in the drug resistant mutants localized to OLE1 (YGL055W), the sole stearoyl-CoA desaturase (SCD; also referred to as Δ9-desaturase) in yeast (FIG. 9). The drug resistant mutants specifically conferred resistance to 1,2,4-oxadiazoles, but were not cross-resistant to other toxic compounds. The ole1 mutations identified included indels and substitution mutations, including A305V, L118Δ, S190T, A305T, I301N, A91T, S190T, P123T, and E118Q. These mutations are relative to the wild-type OLE1 sequence provided below.

```
                                        (SEQ ID NO: 1)
MPTSGTTIELIDDQFPKDDSASSGIVDEVDLTEANILATGLNKKAPRIVNG

FGSLMGSKEMVSVEFDKKGNEKKSNLDRLLEKDNQEKEEAKTKIHISEQPW

TLNNWHQHLNWLNMVLVCGMPMIGWYFALSGKVPLHLNVFLFSVFYYAVGG

VSITAGYHRLWSHRSYSAHWPLRLFYAIFGCASVEGSAKWWGHSHRIHHRY

TDTLRDPYDARRGLWYSHMGWMLLKPNPKYKARADITDMTDDWTIRFQHRH

YILLMLLTAFVIPTLICGYFFNDYMGGLIYAGFIRVFVIQQATFCINSLAH

YIGTQPFDDRRTPRDNWITAIVTFGEGYHNFHHEFPTDYRNAIKWYQYDPT

KVIIYLTSLVGLAYDLKKFSQNAIEEALIQQEQKKINKKKAKINWGPVLTD

LPMWDKQTFLAKSKENKGLVIISGIVHDVSGYISEHPGGETLIKTALGKDA

TKAFSGGVYRHSNAAQNVLADMRVAVIKESKNSAIRMASKRGEIYETGKFF
```

Figure 2A:
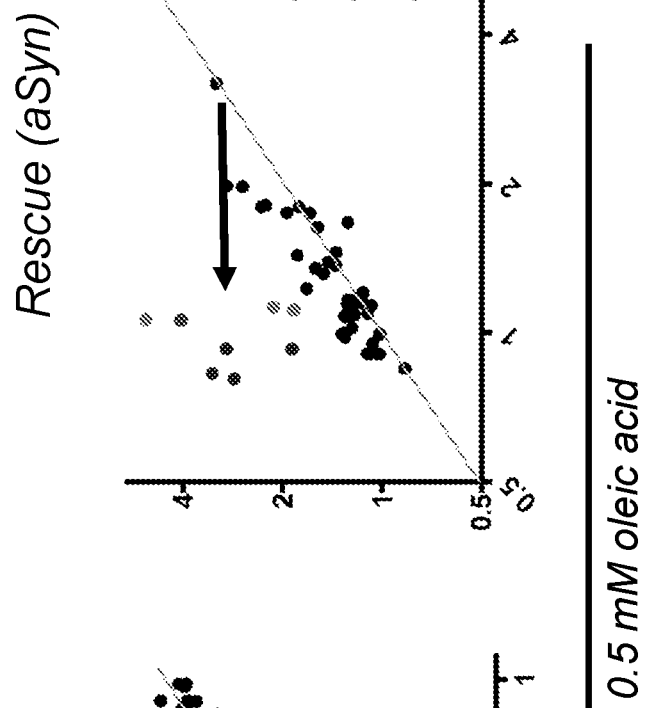
FIGS. 2A and 2B are graphs showing that exogenous oleic acid reverses growth inhibition and model rescue by Ole1/SCD-targeting 1,2,4-oxadiazoles. Growth was measured by reading $OD_{600}$ in a microplate reader and normalized to solvent control DMSO samples.
Figure 2B:
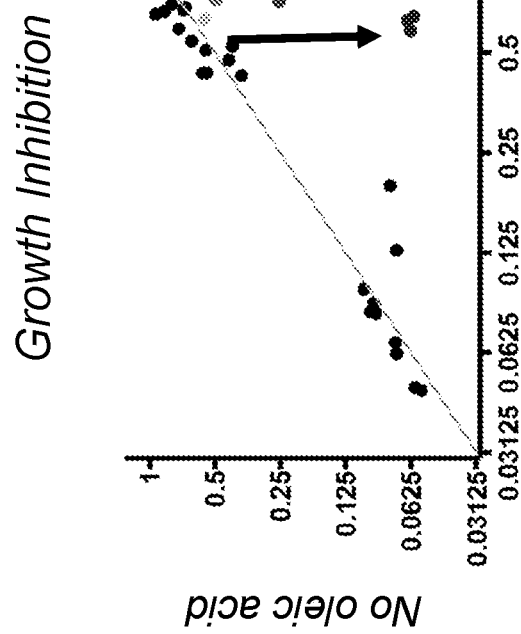

These data strongly suggest that Ole1 is the target of 1,2,4-oxadiazoles. Additionally, addition of exogenous oleic acid reversed both growth inhibition of wild-type cells and rescue of toxicity in a yeast disease model of alpha-synuclein toxicity (FIGS. 2A and 2B, respectively). Likewise, these effects were specific for 1,2,4-oxadiazoles, but not other toxic compounds.

Figure 3A:
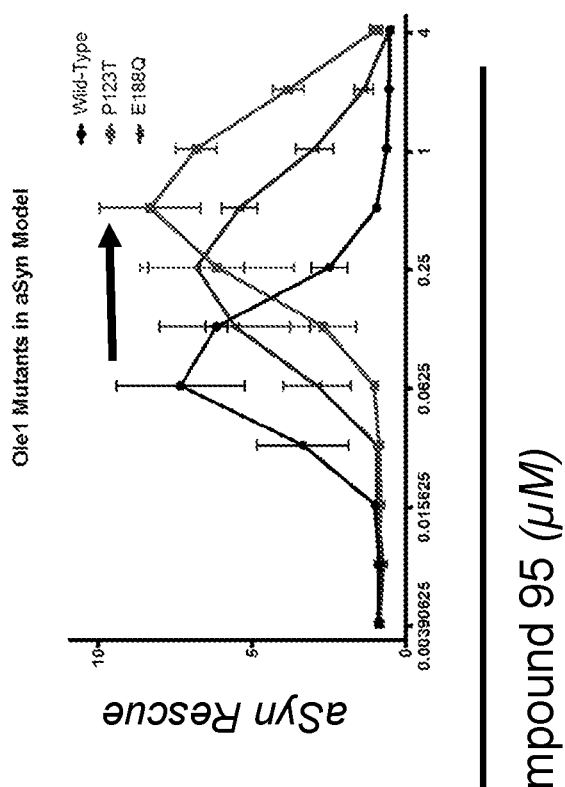
FIGS. 3A and 3B are graphs showing that point mutations in yeast OLE1 confer resistance to growth inhibition and alpha-synuclein model rescue by 1,2,4-oxadiazoles. Growth was measured by reading $OD_{600}$ in a microplate reader.
Figure 3B:
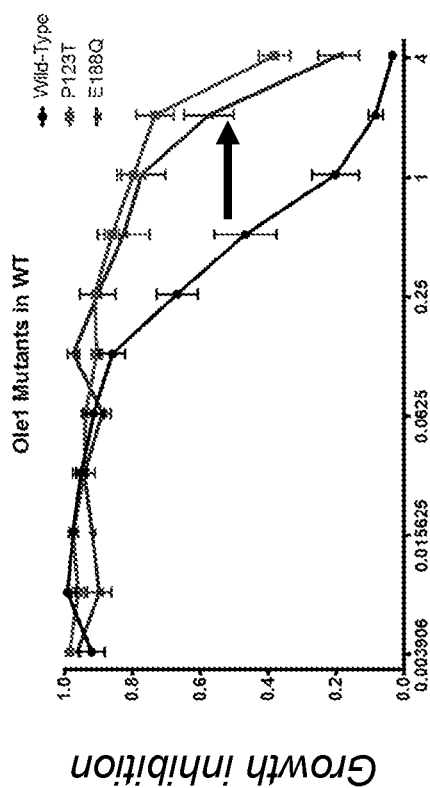

Drug-resistant Ole1 mutations reduced 1,2,4-oxadiazole-induced growth inhibition in control conditions (FIG. 3A). The same mutations also increased the EC50 (concentration that gives half-maximal response) in the context of the alpha-synuclein model, which is consistent with reduced binding to the target. These shifts in does response were specific for 1,2,4-oxadiazoles. These data further support that Ole1/SCD is the target for both growth inhibition and rescue of toxicity in disease models.

Figure 4:
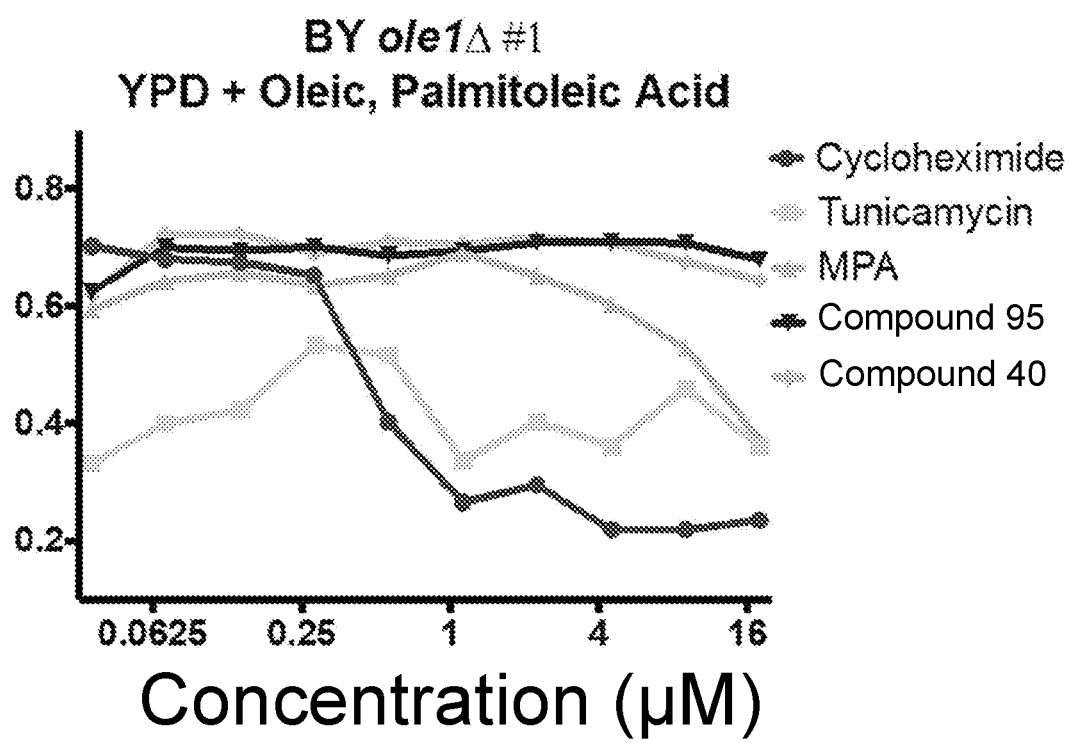
FIG. 4 is a graph showing that a ole1Δ deletion mutant is resistant to the growth-inhibitory effects of 1,2,4-oxadiazoles, but not other compounds. Twenty-four hour growth (presented as raw $OD_{600}$) of the ole1Δ deletion strain in yeast extract-peptone-dextrose (YPD) media is shown, with drugs added at the indicated concentrations.
Figure 5:
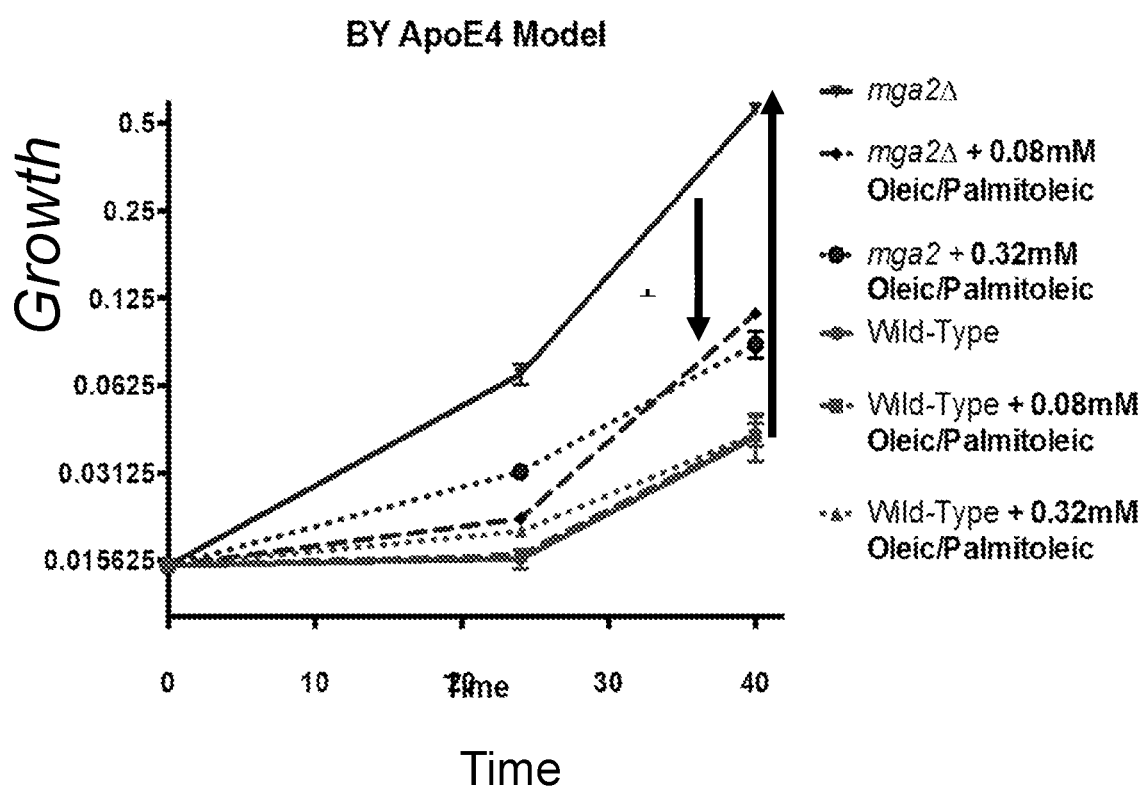
FIG. 5 is a graph showing that reducing OLE1 expression by deleting MGA2 rescues the growth of the ApoE4 yeast model. Yeast cells expressing ApoE4 were deleted for the MGA2 gene and their growth was assessed over time (compared to their isogenic, MGA2 wild-type counterpart). Growth was assessed by $OD_{600}$. Where indicated, 0.08 or 0.32 mM of oleic and palmitoleic acids (each) as added to the growth media in 0.01% tween (final).

The OLE1 gene is essential in *Saccharomyces cerevisiae*. However, strains deleted for OLE1 (ole1Δ) are viable if their growth media is supplemented with oleic/palmitoleic acid. The ole1Δ strain supplemented with exogenous fatty acids was fully resistant to 1,2,4-oxadiazoles (FIG. 4). In other words, in the absence of the target, Ole1, the 1,2,4-oxadiazoles do not have growth inhibition activity. Independently, a chemical genetics approach identified MGA2, the transcription factor that regulates Ole1. Genetic deletion of MGA2 (mga2Δ) phenocopied the effects of 1,2,4-oxadiazoles (FIG. 5). mga2Δ cells have reduced Ole1 levels, which itself rescues toxicity in the yeast disease models (e.g., the ApoE4 model). Supplementation of the growth media with oleic acid reversed this effect, similar to the results described above. Consistent with these data, treatment of yeast cells with the 1,2,4-oxadiazole Compound 95 inhibited lipid desaturation (FIGS. 8A-8D). Overall, these data provide still further evidence that Ole1/SCD is the target of 1,2,4-oxadiazoles.

Figure 6:
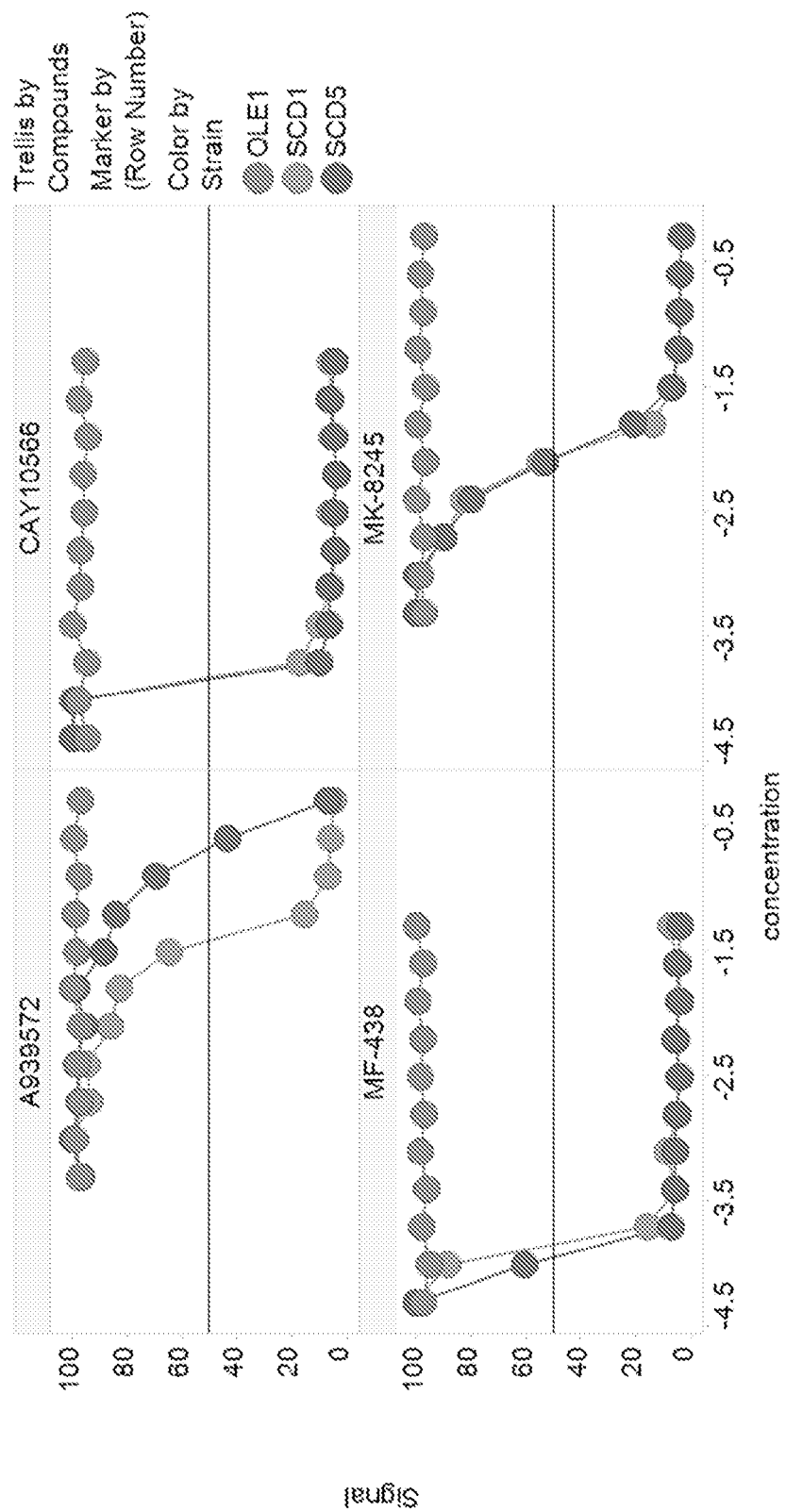
FIG. 6 is a series of graphs showing that commercial Scd inhibitors target human SCD1/SCD5 in yeast. Yeast surviving solely on yeast OLE1, or human SCD1 or SCD5, were treated with four commercial Scd inhibitors at indicated concentrations. Data are expressed as a percent of the DMSO-treated condition. All four compounds potently reduced growth of both SCD1-expressing yeast and SCD5-expressing yeast, but not the strain expressing Ole1. This growth inhibition was reversed by oleic/palmitoleic acid competition, similar to the results shown in FIGS. 2A and 2B.

Humanized yeast strains expressing the human SCD proteins SCD1 or SCD5 were generated by genetic deletion of OLE1 and expressing human SCD1 or SCD5 on a plasmid. Yeast expressing OLE1 were resistant to known SCD1/SCD5 inhibitors such as A939572, CAY10566, MF-438, and MK-8245 (FIG. 6), suggesting that they do not target the yeast enzyme. In marked contrast, in the SCD1 and SCD5 humanized strains, the known SCD1/SCD5 inhibitors were extremely potent, with low nanomolar half-maximal inhibitory concentration (IC50) values (FIG. 6).

Figure 7:
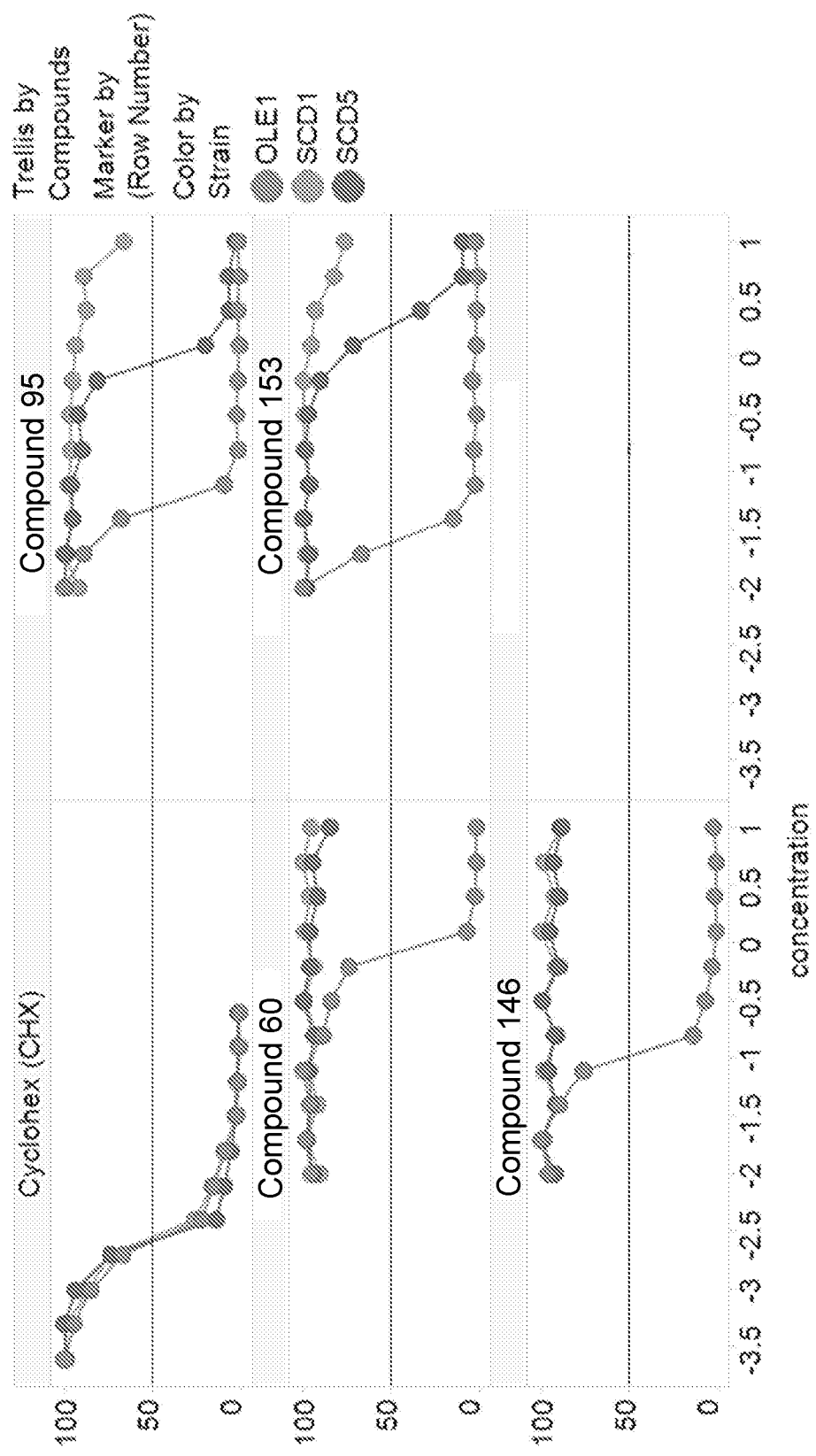
FIG. 7 is a series of graphs showing that 1,2,4-oxadiazoles target human SCD1 and SCD5. Three "SCD" strains expressing yeast OLE1 or human SCD1 or SCD5 were treated with five representative 1,2,4-oxadiazoles and a cycloheximide toxicity control at concentrations indicated on the $\log_{10}$ x-axis. The y-axis indicates the percent of the DMSO-treated condition. All of the 1,2,4-oxadiazole compounds potently inhibited Ole1-expressing yeast and showed variable growth inhibition of the SCD1 or SCD5 yeast strains. These data confirm that 1,2,4-oxadiazoles target the human protein and link Scd inhibition to rescue of neurodegenerative disease models. Approximately one half of all (250) 1,2,4-oxadiazoles tested inhibited SCD1 or SCD5 in a manner that was reversed by oleic/palmitoleic acid treatment. Cycloheximide, a translation inhibitor (top left panel), inhibited growth of all three strains with the same potency, indicating differences in growth inhibition was due to targeting the human protein.
Figure 8A:
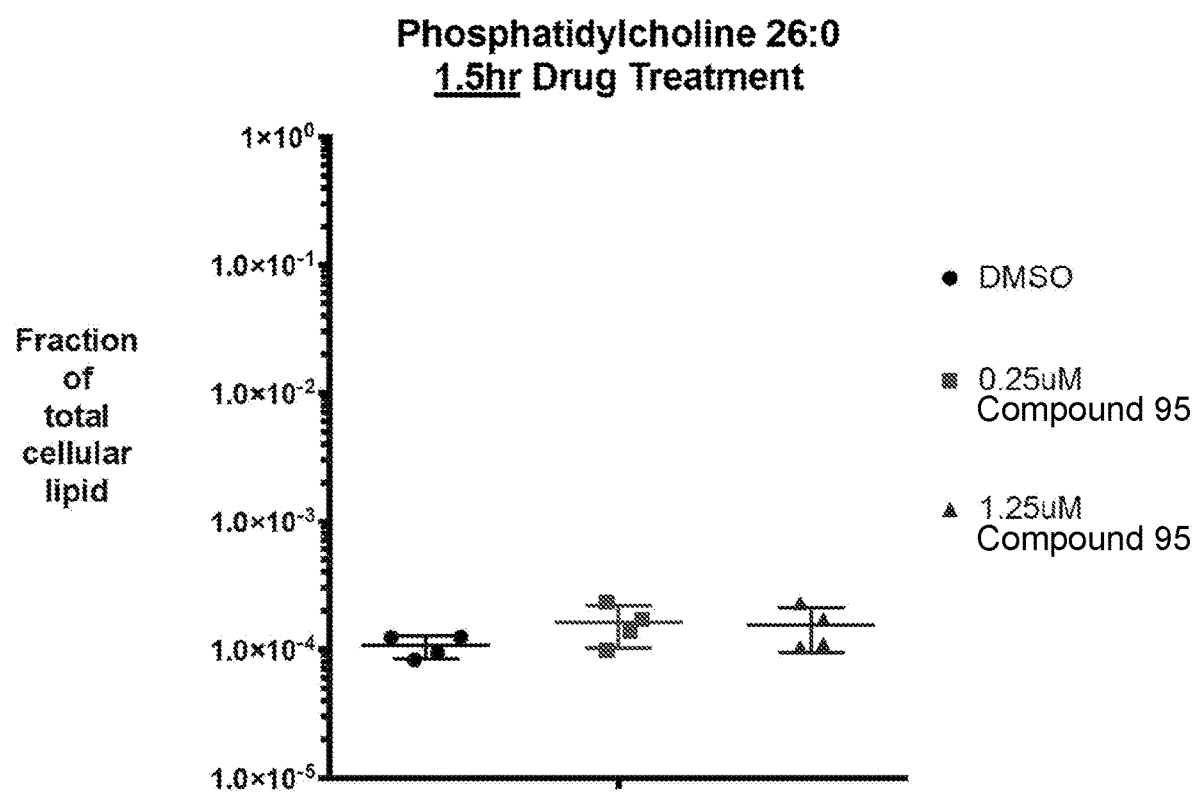
FIGS. 8A-8D are graphs showing that treatment of yeast cells with the 1,2,4-oxadiazole Compound 95 inhibits lipid desaturation. Exponentially-growing wild-type yeast cells were treated with the indicated doses of the 1,2,4-oxadiazole Compound 95 for the indicated times before cellular lysis, lipid extraction, and analysis by global LC-MS/MS profiling. The relative abundance (fraction of total cellular lipid signal) after 1.5 h and 8 h of the most abundant saturated lipid, phosphatidylcholine 26:0, is depicted in FIGS. 8A and 8B, respectively. The relative abundance after 1.5 h and 8 h drug treatment of the most abundant lipid with 2 or more degrees of unsaturation, phosphatidylcholine 16:1; 18:1, is depicted in FIGS. 8C and 8D, respectively. The data indicate a >300-fold increase in the abundance of the saturated lipid phosphatidylcholine 26:0 after 8 h treatment with Compound 95, and a >12-fold decrease in the abundance of the unsaturated lipid phosphatidylcholine 16:1, 18:1, indicating that Compound 95 blocks cellular fatty acid desaturase activity (Ole1 is the only fatty acid desaturase in yeast).
Figure 8B:
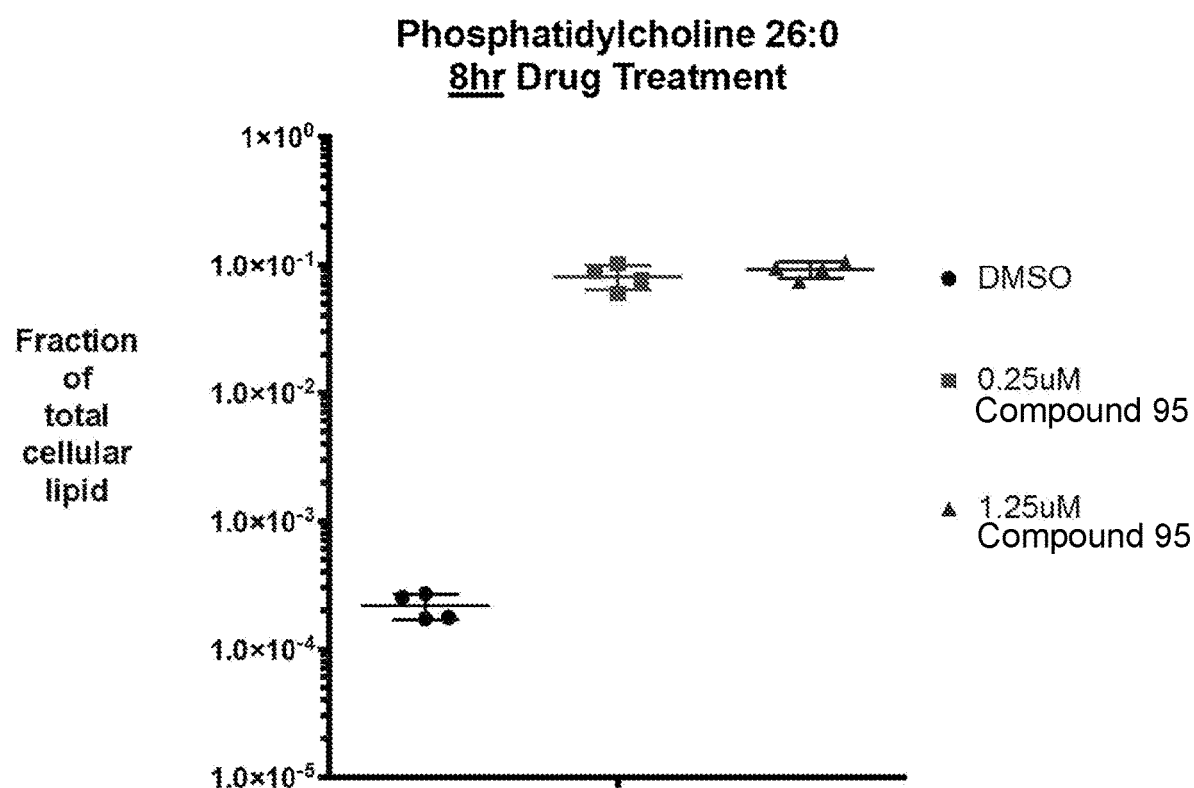
Figure 8C:
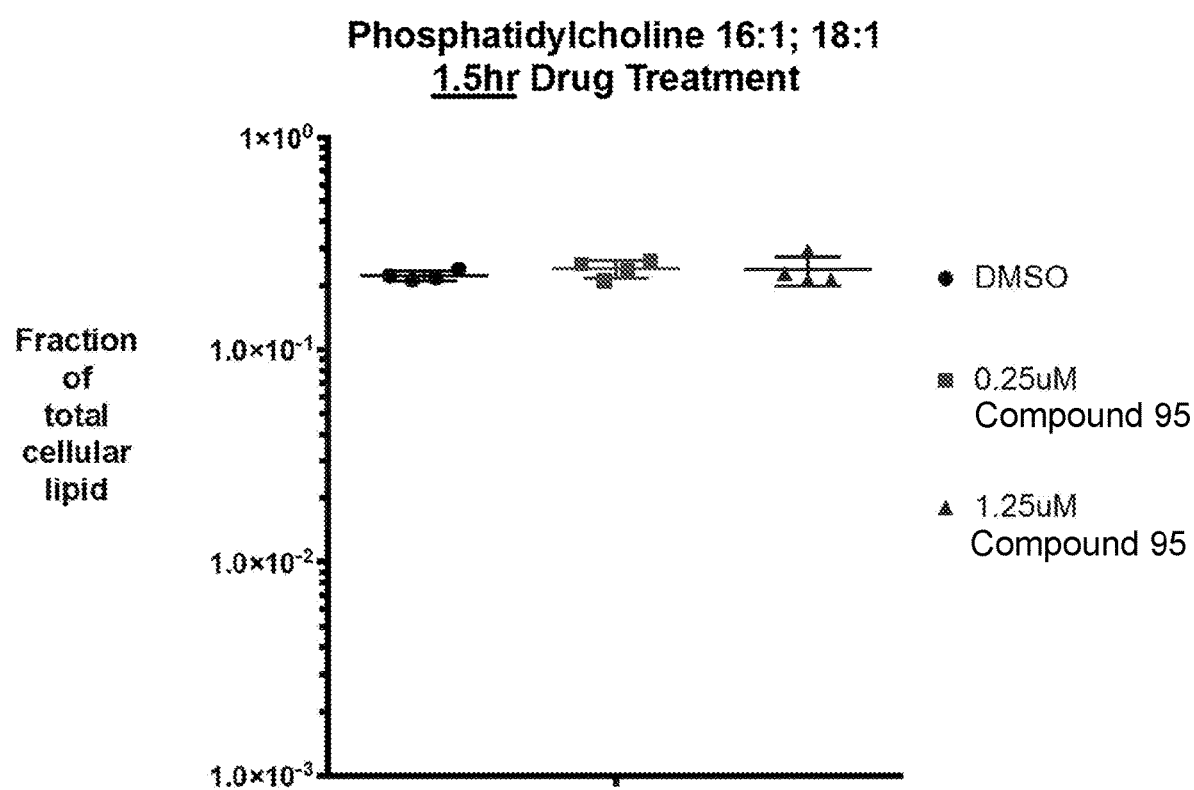
Figure 8D:
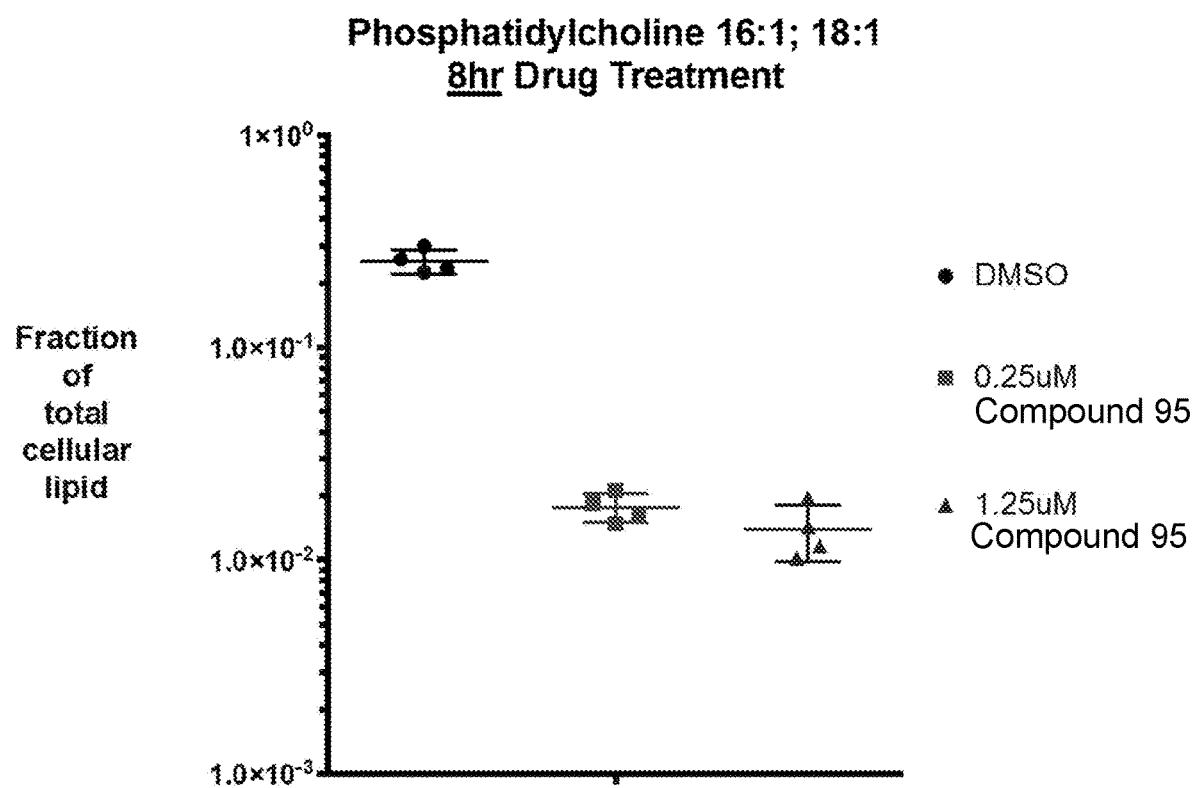

The effect of 1,2,4-oxadiazoles was also evaluated in both of the humanized SCD1 and SCD5 models. 1,2,4-oxadiazoles inhibited the growth of the SCD1 and/or SCD1 yeast strains, and differences in the structure-activity relationship (SAR) between the three SCD proteins was observed (FIG. 7). Some compounds inhibited the growth of both the SCD1 and the SCD5 strains. Other compounds appeared to target only the yeast enzyme. Out of a total of 250 1,2,4-oxadiazoles tested, approximately 50% exhibited activity against the human enzymes. The divergent SAR provides additional strong evidence for SCD being the target of 1,2,4-oxadiazoles.

Finally, treatment of yeast cells with the 1,2,4-oxadiazole Compound 95 inhibited lipid desaturation (FIGS. 8A-8D), providing additional confirmatory evidence that SCD is the target of 1,2,4-oxadiazoles.

Taken together, these data demonstrate that Ole1/SCD is the target of 1,2,4-oxadiazoles, and that these compounds inhibit Ole1/SCD.

Example 160. Inhibition of Ole1, SDC1, and SCD5 by Compounds of the Invention

Using the methods described above, the inhibition of Ole1, SCD1, and SCD5 was tested for compounds of the invention. The results are shown in Table 5.

TABLE 5

Inhibition of Ole1, SCD1, and SCD5 by Compounds of the Invention

| Compound # | OLE1 % Max Inhibition | OLE1 IC50 | SCD1 % Max Inhibition | SCD1 IC50 (μM) | SCD5 % Max Inhibition | SCD5 IC50 (μM) |
|---|---|---|---|---|---|---|
| 156 | 63.63 | 37.08 | 72.58 | >45 | 22.37 | >45 |
| 157 | 91.55 | >45 | 80.54 | >45 | 72.54 | >45 |
| 158 | 89.93 | >45 | 78.34 | >45 | 91.96 | >45 |
| 159 | 46.92 | >45 | 70.17 | 38.85 | 10.25 | 13.86 |
| 160 | 71.55 | 36.23 | 63.44 | 40.70 | 28.51 | 24.31 |
| 1 | 77.42 | 40.32 | 13.31 | >45 | 6.34 | >45 |
| 2 | 89.46 | >45 | 39.07 | >45 | 6.07 | >45 |
| 3 | 82.44 | 38.49 | 22.77 | >45 | 18.19 | >45 |
| 4 | 97.53 | >45 | 82.28 | >45 | 5.61 | >45 |
| 494 | 92.28 | >45 | 79.67 | >45 | 73.76 | >45 |
| 5 | 4.18 | >45 | 72.44 | >45 | 38.42 | 24.45 |
| 6 | 64.04 | 39.15 | 72.55 | >45 | 77.35 | 41.10 |
| 7 | 3.03 | >45 | 50.66 | 39.16 | 8.11 | >45 |
| 8 | 16.92 | >45 | 1.03 | >45 | 2.16 | >45 |
| 493 | 91.16 | >45 | 68.84 | >45 | 60.28 | 30.20 |
| 9 | 104.24 | >45 | 115.64 | >45 | 62.24 | >45 |
| 10 | 18.99 | >45 | 18.39 | >45 | 6.06 | >45 |
| 11 | 78.50 | >45 | 74.99 | >45 | 35.13 | >45 |
| 12 | 98.37 | >45 | 70.29 | >45 | 77.40 | >45 |
| 13 | 5.69 | >45 | 70.42 | >45 | 25.88 | >45 |
| 14 | 14.56 | >45 | 90.98 | >45 | 51.85 | 27.53 |
| 15 | 9.81 | >45 | 21.78 | >45 | 0.80 | >45 |
| 16 | 82.88 | >45 | 66.57 | 37.11 | 3.55 | >45 |
| 17 | 94.17 | >45 | 71.38 | >45 | 23.21 | >45 |
| 18 | 5.70 | >45 | 74.70 | 41.00 | 22.66 | >45 |
| 19 | 12.81 | >45 | 28.21 | >45 | 4.13 | >45 |
| 20 | 112.10 | >45 | 38.25 | >45 | 6.14 | >45 |
| 21 | 105.47 | >45 | 87.64 | 39.94 | 12.90 | >45 |
| 22 | 51.46 | 40.47 | 64.47 | 41.00 | 74.04 | 30.02 |
| 23 | 92.36 | >45 | 61.05 | 33.58 | 40.64 | >45 |
| 24 | 99.70 | >45 | 66.31 | >45 | 67.98 | 30.03 |
| 25 | 3.45 | >45 | 70.78 | >45 | 51.67 | 39.44 |
| 26 | 23.82 | >45 | 82.66 | >45 | 50.25 | 24.46 |
| 27 | 1.78 | >45 | 0.90 | >45 | −0.86 | >45 |
| 27 | 2.82 | >45 | 13.09 | >45 | 3.95 | >45 |
| 28 | 4.80 | >45 | 98.15 | >45 | 79.98 | >45 |
| 29 | 91.00 | >45 | 69.52 | >45 | 74.10 | >45 |
| 30 | 100.46 | >45 | 80.58 | >45 | 74.17 | >45 |
| 31 | 79.60 | >45 | 81.19 | >45 | 24.26 | 25.37 |
| 32 | 108.22 | >45 | 84.16 | >45 | 80.17 | >45 |
| 33 | 1.55 | >45 | 8.14 | >45 | 24.10 | >45 |
| 34 | 76.89 | >45 | 42.55 | >45 | 5.37 | >45 |
| 35 | 3.66 | >45 | 79.23 | >45 | 68.57 | >45 |
| 36 | 17.70 | >45 | 64.67 | 30.02 | 63.86 | >45 |
| 37 | 9.99 | >45 | 81.44 | >45 | 74.18 | >45 |
| 38 | 20.26 | >45 | 72.81 | >45 | 64.24 | 41.03 |
| 39 | 110.89 | >45 | 77.01 | >45 | 79.10 | >45 |
| 40 | 1.26 | >45 | 41.70 | >45 | 0.43 | >45 |
| 40 | 0.80 | >45 | 47.19 | >45 | 4.73 | >45 |
| 40 | 4.9 | >45 | 57.7 | >45 | 13.7 | >45 |
| 41 | 85.45 | >45 | 55.28 | 38.72 | 43.51 | >45 |
| 42 | 95.43 | >45 | 90.77 | >45 | 47.40 | >45 |
| 43 | 107.35 | >45 | 76.52 | >45 | 65.66 | >45 |
| 492 | 106.45 | >45 | 83.92 | >45 | 75.64 | >45 |
| 44 | 93.69 | >45 | 17.96 | >45 | 10.99 | >45 |
| 46 | 87.95 | >45 | 70.27 | >45 | 72.35 | >45 |
| 47 | 109.20 | >45 | 73.30 | >45 | 74.25 | >45 |
| 48 | 8.16 | >45 | 63.58 | 39.27 | 75.26 | >45 |
| 49 | 34.89 | >45 | 61.29 | >45 | 63.18 | >45 |
| 491 | 107.15 | >45 | 118.81 | >45 | 83.61 | >45 |
| 50 | 98.10 | >45 | 67.05 | 41.00 | 46.80 | >45 |
| 51 | 102.56 | >45 | 76.83 | >45 | 6.59 | >45 |
| 52 | 11.78 | >45 | 1.65 | >45 | −1.01 | >45 |
| 53 | 98.51 | >45 | 79.96 | >45 | 2.94 | >45 |
| 54 | 85.34 | >45 | 82.41 | >45 | 47.60 | >45 |
| 55 | 114.12 | >45 | 74.99 | 33.67 | 74.78 | >45 |
| 56 | 10.04 | >45 | 59.58 | >45 | 70.33 | 30.00 |
| 57 | 82.47 | >45 | 80.82 | >45 | 63.17 | 41.10 |
| 490 | 96.38 | >45 | 63.84 | 38.76 | 50.39 | 35.13 |
| 58 | 92.35 | >45 | 101.47 | >45 | 66.93 | >45 |
| 489 | 94.30 | >45 | 68.84 | 41.00 | 61.11 | 41.10 |
| 488 | 90.53 | >45 | 75.87 | >45 | 72.82 | >45 |
| 59 | 105.25 | >45 | 79.13 | >45 | 59.32 | >45 |
| 60 | 2.91 | >45 | 72.03 | >45 | 57.19 | 41.10 |

TABLE 5-continued

Inhibition of Ole1, SCD1, and SCD5 by Compounds of the Invention

| Compound # | OLE1 % Max Inhibition | OLE1 IC50 | SCD1 % Max Inhibition | SCD1 IC50 (µM) | SCD5 % Max Inhibition | SCD5 IC50 (µM) |
|---|---|---|---|---|---|---|
| 61 | 71.50 | 40.87 | 2.37 | >45 | 13.18 | >45 |
| 62 | 86.77 | >45 | 28.73 | >45 | 5.75 | >45 |
| 63 | 101.06 | >45 | 62.04 | 33.67 | 9.39 | >45 |
| 64 | 115.95 | >45 | 32.39 | >45 | 42.05 | >45 |
| 65 | 4.02 | >45 | 83.43 | >45 | 73.43 | >45 |
| 66 | 99.71 | >45 | 94.04 | >45 | 19.53 | >45 |
| 67 | 85.79 | >45 | 54.45 | 40.71 | 4.32 | >45 |
| 68 | 9.74 | >45 | 22.28 | >45 | 3.75 | >45 |
| 69 | 105.31 | >45 | 60.59 | >45 | 8.06 | >45 |
| 70 | 74.02 | >45 | 39.36 | >45 | 22.44 | >45 |
| 71 | 97.50 | >45 | 67.35 | >45 | 46.73 | >45 |
| 72 | 85.17 | >45 | 41.97 | 27.27 | 52.89 | 32.98 |
| 73 | 83.83 | >45 | 61.02 | 33.67 | 5.84 | >45 |
| 74 | 85.96 | >45 | 51.32 | 31.26 | 5.68 | >45 |
| 75 | 91.51 | >45 | 80.18 | >45 | 63.65 | 30.05 |
| 487 | 103.20 | >45 | 83.76 | >45 | 70.73 | 40.19 |
| 486 | 103.51 | >45 | 76.95 | >45 | 72.76 | >45 |
| 485 | 75.19 | >45 | 62.60 | >45 | 65.42 | 30.03 |
| 484 | 92.09 | >45 | 75.84 | >45 | 81.46 | >45 |
| 78 | 87.89 | 38.34 | 86.39 | >45 | 86.12 | >45 |
| 79 | 104.92 | >45 | 81.83 | >45 | 76.87 | >45 |
| 80 | 46.71 | >45 | 98.34 | >45 | 15.53 | >45 |
| 81 | 13.12 | >45 | 13.86 | >45 | 3.39 | >45 |
| 82 | 107.01 | >45 | 83.67 | >45 | 75.72 | >45 |
| 83 | 3.73 | >45 | 7.65 | >45 | 1.65 | >45 |
| 85 | 64.87 | >45 | 88.05 | >45 | 16.38 | >45 |
| 86 | 2.85 | >45 | 84.44 | >45 | 66.85 | 33.33 |
| 88 | 16.29 | >45 | 63.82 | 33.46 | 5.70 | >45 |
| 89 | 119.71 | >45 | 106.83 | >45 | 87.41 | >45 |
| 90 | 23.20 | >45 | 107.22 | >45 | 3.66 | >45 |
| 91 | 3.64 | >45 | 97.20 | >45 | 32.20 | >45 |
| 92 | 107.87 | >45 | 80.31 | >45 | 83.38 | >45 |
| 93 | 5.46 | >45 | 97.21 | >45 | 8.16 | >45 |
| 94 | 29.00 | >45 | 90.84 | >45 | 61.78 | 39.28 |
| 95 | 5.72 | >45 | 58.05 | 39.20 | 7.46 | >45 |
| 96 | 3.94 | >45 | 12.37 | >45 | 1.38 | >45 |
| 97 | 10.45 | >45 | 81.79 | >45 | 78.75 | 30.01 |
| 98 | 92.44 | >45 | 74.79 | >45 | 52.40 | 41.10 |
| 99 | 64.73 | >45 | 13.74 | >45 | 8.85 | >45 |
| 100 | 23.98 | >45 | 54.37 | 32.84 | 6.56 | >45 |
| 101 | 12.74 | >45 | 29.81 | >45 | 29.09 | >45 |
| 102 | 24.90 | >45 | 60.33 | >45 | 6.56 | >45 |
| 103 | 5.27 | >45 | 93.33 | >45 | 68.60 | >45 |
| 104 | 110.40 | >45 | 76.89 | >45 | 77.11 | >45 |
| 105 | 34.19 | >45 | 41.38 | >45 | 13.93 | >45 |
| 106 | 35.35 | >45 | 78.19 | >45 | 71.22 | >45 |
| 107 | 4.55 | >45 | 73.32 | >45 | 74.80 | >45 |
| 108 | 72.04 | >45 | 72.79 | >45 | 64.66 | >45 |
| 109 | 87.87 | >45 | 84.36 | >45 | 89.75 | >45 |
| 110 | 96.31 | >45 | 66.85 | >45 | 65.07 | >45 |
| 111 | 38.26 | >45 | 76.39 | >45 | 32.73 | >45 |
| 112 | 3.16 | >45 | 66.76 | >45 | 21.21 | >45 |
| 113 | 5.55 | >45 | 55.33 | 40.72 | 27.28 | >45 |
| 114 | 90.17 | >45 | 74.54 | >45 | 77.66 | >45 |
| 115 | 101.68 | >45 | 77.36 | >45 | 77.85 | >45 |
| 116 | 12.75 | >45 | 71.12 | >45 | 8.35 | >45 |
| 117 | 92.97 | >45 | 95.94 | >45 | 54.63 | 36.14 |
| 118 | 87.29 | >45 | 93.37 | >45 | 32.21 | 27.53 |
| 119 | 111.86 | >45 | 86.22 | >45 | 93.93 | >45 |
| 120 | 119.08 | >45 | 99.80 | >45 | 96.39 | >45 |
| 121 | 111.12 | >45 | 94.06 | >45 | 98.38 | >45 |
| 122 | 109.89 | >45 | 92.73 | >45 | 90.04 | >45 |
| 123 | 3.12 | >45 | 73.59 | >45 | 9.69 | >45 |
| 124 | 4.55 | >45 | 88.87 | >45 | 96.23 | >45 |
| 319 | 74.25 | >45 | 97.10 | >45 | 4.96 | >45 |
| 319 | 63.83 | >45 | 89.16 | >45 | 10.94 | >45 |
| 125 | 92.36 | >45 | 77.68 | >45 | 94.83 | >45 |
| 126 | 73.29 | >45 | 69.80 | >45 | 79.08 | 30.00 |
| 127 | 99.27 | >45 | 66.46 | >45 | 88.59 | >45 |
| 128 | 81.43 | >45 | 1.12 | >45 | 1.89 | >45 |
| 128 | 60.60 | 45 | 23.56 | >45 | 3.32 | >45 |
| 129 | 3.25 | >45 | 75.60 | >45 | 93.05 | >45 |
| 130 | 2.75 | >45 | 97.82 | >45 | 99.82 | >45 |
| 131 | 39.81 | 25.79 | 96.48 | >45 | 98.92 | >45 |

TABLE 5-continued

Inhibition of Ole1, SCD1, and SCD5 by Compounds of the Invention

| Compound # | OLE1 % Max Inhibition | OLE1 IC50 | SCD1 % Max Inhibition | SCD1 IC50 (μM) | SCD5 % Max Inhibition | SCD5 IC50 (μM) |
|---|---|---|---|---|---|---|
| 132 | 7.45 | >45 | 115.10 | >45 | 94.34 | >45 |
| 133 | 26.72 | >45 | 61.21 | 37.29 | 74.75 | >45 |
| 134 | 93.94 | >45 | 107.77 | >45 | 98.55 | >45 |
| 135 | 99.53 | >45 | 92.42 | >45 | 91.64 | >45 |
| 136 | 73.60 | >45 | 34.33 | >45 | 17.07 | >45 |
| 137 | 96.83 | >45 | 90.19 | >45 | 50.61 | 22.33 |
| 138 | 3.94 | >45 | 54.49 | 37.32 | 4.57 | >45 |
| 139 | 25.30 | >45 | 87.50 | >45 | 75.11 | >45 |
| 140 | 3.96 | >45 | 77.37 | >45 | 3.46 | >45 |
| 140 | 4.98 | >45 | 75.00 | 45 | 10.16 | 1.30 |
| 141 | 1.77 | >45 | 86.53 | >45 | 78.91 | >45 |
| 142 | 1.11 | >45 | 80.83 | >45 | 26.00 | >45 |
| 143 | 95.01 | >45 | 79.38 | >45 | 96.06 | >45 |
| 144 | 100.96 | >45 | 79.00 | >45 | 84.27 | >45 |
| 145 | 51.17 | 15.85 | 78.31 | >45 | 86.51 | >45 |
| 146 | 3.28 | >45 | 60.81 | 37.75 | 25.62 | >45 |
| 147 | 9.34 | >45 | 74.14 | >45 | 86.70 | >45 |
| 148 | 99.90 | >45 | 79.55 | >45 | 86.53 | >45 |
| 149 | 90.68 | >45 | 69.75 | >45 | 38.72 | >45 |
| 150 | 5.16 | >45 | 74.48 | >45 | 86.15 | >45 |
| 151 | 2.67 | >45 | 75.63 | >45 | 20.68 | >45 |
| 152 | 2.37 | >45 | 83.39 | >45 | 60.91 | >45 |
| 153 | 2.75 | >45 | 75.76 | >45 | 87.51 | >45 |
| 154 | 1.20 | >45 | 68.90 | >45 | 3.25 | >45 |
| 155 | 1.65 | >45 | 98.25 | >45 | 67.35 | 33.77 |
| 162 | 100.35 | >45 | 84.54 | >45 | 76.89 | >45 |
| 163 | 71.84 | >45 | 55.99 | 36.51 | 24.77 | >45 |
| 164 | 96.96 | >45 | 102.20 | >45 | 73.90 | >45 |
| 165 | 2.01 | >45 | 94.44 | >45 | 80.23 | >45 |
| 166 | 105.73 | >45 | 90.07 | >45 | 68.87 | >45 |
| 167 | 57.28 | 38.39 | 6.11 | >45 | 2.38 | >45 |
| 168 | 4.90 | >45 | 114.58 | >45 | 1.99 | >45 |
| 168 | 8.34 | >45 | 74.07 | 45 | 14.85 | >45 |
| 169 | 99.67 | >45 | 78.78 | >45 | 84.20 | >45 |
| 170 | 67.97 | 40.39 | 103.19 | >45 | 85.13 | >45 |
| 171 | 6.77 | >45 | 74.21 | 40.42 | −0.14 | >45 |
| 172 | 3.99 | >45 | 89.39 | >45 | 68.80 | 41.10 |
| 173 | 99.75 | >45 | 78.07 | >45 | 42.09 | 29.77 |
| 174 | 89.17 | >45 | 79.07 | >45 | 10.95 | >45 |
| 175 | 3.00 | >45 | 77.47 | >45 | 77.96 | >45 |
| 176 | 3.62 | >45 | 107.22 | >45 | 83.50 | >45 |
| 177 | 40.70 | >45 | 97.88 | >45 | 86.13 | >45 |
| 178 | 7.39 | >45 | 114.07 | >45 | 85.67 | >45 |
| 179 | 76.70 | 38.71 | 106.53 | >45 | 85.02 | >45 |
| 180 | 107.78 | >45 | 102.85 | >45 | 82.28 | >45 |
| 181 | 20.70 | >45 | 88.32 | >45 | 81.40 | >45 |
| 182 | 124.27 | >45 | 113.27 | >45 | 79.82 | >45 |
| 183 | 101.71 | >45 | 101.67 | >45 | 84.88 | >45 |
| 184 | 3.07 | >45 | 86.33 | >45 | 2.41 | >45 |
| 184 | 0.87 | >45 | 50.65 | 45 | 11.92 | >45 |
| 185 | 93.51 | >45 | 97.91 | >45 | 72.91 | >45 |
| 186 | 35.40 | >45 | 86.16 | >45 | 73.51 | 30.01 |
| 187 | 97.42 | >45 | 72.13 | >45 | 2.91 | >45 |
| 188 | 4.70 | >45 | 78.63 | >45 | 4.51 | >45 |
| 189 | 98.14 | >45 | 88.10 | >45 | 68.58 | >45 |
| 190 | 100.94 | >45 | 83.53 | >45 | 19.31 | >45 |
| 191 | 89.31 | >45 | 81.79 | >45 | 6.72 | >45 |
| 192 | 95.03 | >45 | 84.60 | >45 | 76.82 | >45 |
| 193 | 89.35 | >45 | 80.72 | >45 | 85.76 | >45 |
| 194 | 60.71 | >45 | 74.07 | >45 | 63.24 | >45 |
| 195 | 3.86 | >45 | 75.08 | >45 | 9.78 | >45 |
| 196 | 93.87 | >45 | 86.58 | >45 | 75.88 | >45 |
| 197 | 4.80 | >45 | 66.87 | >45 | 61.44 | >45 |
| 198 | 2.96 | >45 | 71.25 | >45 | 36.45 | >45 |
| 199 | 24.34 | >45 | 27.85 | >45 | 3.87 | >45 |
| 200 | 2.69 | >45 | 79.67 | >45 | 64.72 | 41.10 |
| 201 | 85.29 | >45 | 79.67 | >45 | 65.14 | 32.88 |
| 202 | 94.93 | >45 | 74.09 | >45 | 74.20 | >45 |
| 203 | 100.03 | >45 | 84.83 | >45 | 80.12 | >45 |
| 204 | 79.30 | >45 | 30.36 | >45 | 0.25 | >45 |
| 204 | 50.38 | >45 | 21.99 | >45 | 2.95 | >45 |
| 205 | 94.02 | >45 | 31.70 | >45 | 1.01 | >45 |
| 206 | 5.25 | >45 | 93.66 | >45 | 19.89 | >45 |
| 207 | 5.39 | >45 | 86.42 | >45 | 72.56 | >45 |

TABLE 5-continued

Inhibition of Ole1, SCD1, and SCD5 by Compounds of the Invention

| Compound # | OLE1 % Max Inhibition | OLE1 IC50 | SCD1 % Max Inhibition | SCD1 IC50 (µM) | SCD5 % Max Inhibition | SCD5 IC50 (µM) |
|---|---|---|---|---|---|---|
| 208 | 96.63 | >45 | 14.04 | >45 | 5.68 | >45 |
| 209 | 3.74 | >45 | 101.51 | >45 | 78.88 | >45 |
| 210 | 2.27 | >45 | 30.48 | >45 | 3.39 | >45 |
| 211 | 2.65 | >45 | 39.99 | >45 | 6.95 | >45 |
| 212 | 100.82 | >45 | 76.79 | >45 | 76.28 | >45 |
| 213 | 94.72 | >45 | 86.35 | >45 | 85.33 | >45 |
| 214 | 15.08 | >45 | 65.73 | 41.00 | 74.58 | >45 |
| 215 | 48.68 | >45 | 88.23 | >45 | 78.96 | >45 |
| 216 | 61.84 | 35.11 | 83.82 | >45 | 75.59 | >45 |
| 217 | 10.39 | >45 | 57.90 | 36.93 | 12.62 | >45 |
| 218 | 4.63 | >45 | 48.31 | >45 | 25.15 | >45 |
| 219 | 3.50 | >45 | 95.22 | >45 | 89.83 | >45 |
| 220 | 3.10 | >45 | 87.27 | >45 | 13.65 | >45 |
| 221 | 113.54 | >45 | 100.56 | >45 | 93.18 | >45 |
| 222 | 3.59 | >45 | 40.42 | >45 | 1.92 | >45 |
| 223 | 2.22 | >45 | 68.23 | 40.65 | 67.37 | 40.97 |
| 224 | 2.54 | >45 | 26.70 | >45 | 1.12 | >45 |
| 225 | 20.97 | >45 | 94.06 | >45 | 88.95 | >45 |
| 226 | 1.24 | >45 | 33.20 | >45 | 0.69 | >45 |
| 227 | 1.24 | >45 | 63.76 | 38.33 | 6.17 | >45 |
| 228 | 21.30 | >45 | 51.80 | 41.00 | 2.72 | >45 |
| 229 | 89.56 | >45 | 66.51 | >45 | 71.18 | >45 |
| 230 | 2.63 | >45 | 78.48 | >45 | 44.00 | >45 |
| 231 | 29.53 | >45 | 80.00 | >45 | 3.11 | >45 |
| 232 | 4.20 | >45 | 81.04 | >45 | 51.17 | 41.10 |
| 233 | 18.46 | >45 | 73.65 | >45 | 74.91 | >45 |
| 234 | 84.80 | >45 | 68.91 | >45 | 76.83 | >45 |
| 235 | 84.04 | >45 | 74.46 | >45 | 87.47 | >45 |
| 236 | 8.46 | >45 | 77.23 | >45 | 3.14 | >45 |
| 237 | 18.53 | >45 | 71.76 | >45 | 45.34 | 32.63 |
| 238 | 4.93 | >45 | 70.06 | >45 | 69.63 | 30.00 |
| 239 | 29.21 | >45 | 75.58 | >45 | 6.02 | >45 |
| 240 | 4.30 | >45 | 66.85 | >45 | 12.95 | >45 |
| 241 | 6.15 | >45 | 91.61 | >45 | 16.97 | >45 |
| 242 | 95.59 | >45 | 101.23 | >45 | 79.22 | >45 |
| 243 | 94.60 | >45 | 94.50 | >45 | 72.11 | >45 |
| 244 | 3.34 | >45 | 15.54 | >45 | 2.85 | >45 |
| 244 | 1.29 | >45 | 8.51 | >45 | 2.47 | >45 |
| 245 | 95.26 | >45 | 77.70 | >45 | 66.96 | >45 |
| 246 | 13.06 | >45 | 77.22 | >45 | 66.03 | >45 |
| 247 | 98.49 | >45 | 79.89 | >45 | 72.46 | >45 |
| 248 | 73.12 | >45 | 3.09 | >45 | 13.59 | >45 |
| 249 | 88.69 | >45 | 80.12 | >45 | 61.88 | 41.67 |
| 250 | 4.41 | >45 | 86.09 | >45 | 14.48 | >45 |
| 251 | 7.80 | >45 | 83.15 | >45 | 20.59 | >45 |
| 252 | 27.85 | >45 | 80.73 | >45 | 39.69 | >45 |
| 253 | 106.42 | >45 | 62.07 | >45 | 63.11 | >45 |
| 254 | 92.77 | >45 | 69.80 | >45 | 83.13 | >45 |
| 255 | 96.25 | >45 | 72.70 | >45 | 64.50 | 30.02 |
| 256 | 4.16 | >45 | 76.04 | >45 | 72.11 | >45 |
| 261 | 94.41 | >45 | 73.42 | >45 | 82.31 | >45 |
| 262 | 23.99 | >45 | 41.84 | >45 | 10.38 | >45 |
| 263 | 8.71 | >45 | 18.81 | >45 | 7.20 | >45 |
| 264 | 15.52 | >45 | 56.37 | 40.76 | 7.97 | >45 |
| 265 | 103.04 | >45 | 76.74 | >45 | 10.96 | >45 |
| 265 | 83.99 | 45 | 54.38 | 45 | 3.97 | >45 |
| 266 | 7.17 | >45 | 12.42 | >45 | 9.90 | >45 |
| 267 | 4.64 | >45 | 58.58 | 37.75 | 11.33 | >45 |
| 268 | 4.39 | >45 | 79.03 | >45 | 8.68 | >45 |
| 268 | 0.14 | >45 | 65 | 45 | 2.67 | >45 |
| 269 | 6.62 | >45 | 38.78 | >45 | 8.38 | >45 |
| 269 | 4.57 | >45 | 25.11 | >45 | 5.30 | >45 |
| 270 | 63.00 | 41.85 | 82.42 | >45 | 12.30 | >45 |
| 271 | 11.7 | >45 | 67.9 | >45 | 53.6 | >45 |
| 272 | 40.3 | >45 | 70.8 | >45 | 51.9 | >45 |
| 273 | 78.7 | >45 | 67.9 | >45 | 55.0 | >45 |
| 274 | 75.9 | >45 | 75.3 | >45 | 67.0 | >45 |
| 275 | 11.24 | >45 | 76.51 | >45 | 78.05 | >45 |
| 276 | 6.27 | >45 | 61.16 | >45 | 18.81 | 14.51 |
| 277 | 94.36 | >45 | 76.49 | >45 | 74.99 | >45 |
| 278 | 21.08 | >45 | 32.22 | >45 | 10.55 | >45 |
| 279 | 83.07 | >45 | 43.86 | >45 | 21.97 | >45 |
| 280 | 17.18 | >45 | 11.48 | >45 | 8.86 | >45 |
| 281 | 60.23 | 33.84 | 84.97 | >45 | 18.03 | >45 |

TABLE 5-continued

Inhibition of Ole1, SCD1, and SCD5 by Compounds of the Invention

| Compound # | OLE1 % Max Inhibition | OLE1 IC50 | SCD1 % Max Inhibition | SCD1 IC50 (µM) | SCD5 % Max Inhibition | SCD5 IC50 (µM) |
|---|---|---|---|---|---|---|
| 281 | 32.09 | >45 | 68.90 | 45 | 12.39 | >45 |
| 282 | 110.18 | >45 | 90.54 | >45 | 56.23 | 28.87 |
| 283 | 24.43 | >45 | 34.91 | 34.65 | 9.83 | >45 |
| 284 | 12.40 | >45 | 4.81 | >45 | 6.80 | >45 |
| 285 | 105.26 | >45 | 45.62 | >45 | 30.09 | >45 |
| 286 | 5.18 | >45 | 13.04 | >45 | 8.76 | >45 |
| 286 | 4.35 | >45 | 14.44 | >45 | 9.55 | >45 |
| 287 | 93.89 | >45 | 72.51 | >45 | 66.81 | >45 |
| 288 | 7.14 | >45 | 8.71 | >45 | 7.52 | >45 |
| 289 | 45.87 | >45 | 62.01 | >45 | 77.71 | >45 |
| 290 | 20.6 | >45 | 3.3 | >45 | 8.8 | >45 |
| 291 | 15.6 | >45 | 5.0 | >45 | 8.5 | >45 |
| 291 | 3.95 | >45 | 0.30 | >45 | 3.29 | >45 |
| 292 | 13.6 | >45 | 9.5 | >45 | 10.2 | >45 |
| 293 | 66.4 | 34.9 | 12.3 | >45 | 11.9 | >45 |
| 294 | 4.5 | >45 | 16.6 | >45 | 7.8 | >45 |
| 294 | 2.84 | >45 | 23.31 | >45 | 6.57 | >45 |
| 295 | 18.4 | >45 | 14.4 | >45 | 9.2 | >45 |
| 296 | 99.1 | >45 | 86.6 | >45 | 22.6 | >45 |
| 297 | 42.0 | 25.2 | 5.7 | >45 | 9.2 | >45 |
| 298 | 6.6 | >45 | 92.3 | >45 | 21.3 | >45 |
| 299 | 17.5 | >45 | 89.6 | >45 | 30.1 | >45 |
| 299 | 13.58 | >45 | 62.80 | 45 | 22.61 | >45 |
| 300 | 79.7 | >45 | 78.1 | >45 | 36.0 | >45 |
| 301 | 99.4 | >45 | 96.2 | >45 | 21.0 | >45 |
| 302 | 6.7 | >45 | 71.1 | 36.1 | 9.4 | >45 |
| 302 | 5.26 | >45 | 50.17 | 45 | 10.64 | >45 |
| 303 | 14.2 | >45 | 94.3 | >45 | 15.6 | >45 |
| 303 | 8.50 | >45 | 65 | 45 | 20.68 | >45 |
| 304 | 14.7 | >45 | 74.9 | >45 | 51.6 | >45 |
| 305 | 6.6 | >45 | 73.2 | >45 | 18.4 | >45 |
| 305 | 4.23 | >45 | 55.27 | 45 | 5.95 | >45 |
| 306 | 33.2 | >45 | 67.6 | >45 | 17.6 | >45 |
| 306 | 36.88 | >45 | 63.32 | 45 | 5.23 | >45 |
| 307 | 7.8 | >45 | 78.2 | >45 | 52.5 | >45 |
| 307 | 4.08 | >45 | 70.58 | 45 | 27.45 | >45 |
| 308 | 63.7 | >45 | 81.6 | >45 | 15.5 | >45 |
| 308 | 49.30 | 27.20 | 61.05 | 45 | 6.81 | >45 |
| 309 | 8.0 | >45 | 80.6 | >45 | 14.7 | >45 |
| 310 | 7.1 | >45 | 71.2 | >45 | 66.6 | >45 |
| 311 | 90.8 | >45 | 72.9 | >45 | 60.5 | >45 |
| 316 | 89.26 | 45 | 69.01 | 45 | 80 | 45 |
| 317 | 8.3 | >45 | 30.0 | >45 | 20.6 | >45 |
| 318 | 89.1 | >45 | 77.6 | >45 | 33.7 | >45 |
| 319 | 86.3 | >45 | 81.7 | >45 | 19.6 | >45 |
| 319 | 84.75 | 45 | 75.42 | 45 | 4.56 | >45 |
| 320 | 28.5 | >45 | 74.7 | >45 | 76.0 | >45 |
| 321 | 14.0 | >45 | 71.6 | >45 | 74.1 | >45 |
| 322 | 9.0 | >45 | 73.6 | >45 | 29.8 | >45 |
| 323 | 89.1 | >45 | 76.1 | >45 | 73.5 | >45 |
| 324 | 90.5 | >45 | 74.9 | >45 | 68.7 | >45 |
| 325 | 79.2 | >45 | 73.7 | >45 | 67.2 | >45 |
| 326 | 7.5 | >45 | 77.1 | >45 | 26.5 | >45 |
| 327 | 74.8 | >45 | 66.5 | >45 | 68.0 | >45 |
| 328 | 21.9 | >45 | 86.6 | >45 | 80.5 | >45 |
| 329 | 12.5 | >45 | 16.2 | >45 | 13.4 | >45 |
| 331 | 13.7 | >45 | 41.9 | >45 | 24.9 | >45 |
| 332 | 77.0 | >45 | 59.7 | >45 | 31.5 | >45 |
| 333 | 81.2 | >45 | 55.6 | >45 | 62.3 | >45 |
| 334 | 84.4 | >45 | 49.3 | >45 | 66.7 | >45 |
| 335 | 81.5 | >45 | 54.0 | >45 | 61.2 | >45 |
| 336 | 86.7 | >45 | 56.9 | >45 | 74.1 | >45 |
| 337 | 86.4 | >45 | 49.6 | >45 | 61.6 | >45 |
| 338 | 85.2 | >45 | 60.0 | >45 | 76.3 | >45 |
| 339 | 85.7 | >45 | 56.1 | >45 | 75.4 | >45 |
| 340 | 88.9 | >45 | 55.0 | >45 | 65.9 | >45 |
| 341 | 91.7 | >45 | 45.2 | >>45 | 45.6 | >45 |
| 342 | 80.9 | >45 | 75.9 | >45 | 43.5 | >45 |
| 343 | 84.7 | >45 | 59.1 | >45 | 23.2 | >45 |
| 344 | 7.14 | >45 | n/a | n/a | 1.1 | >45 |
| 345 | 6.63 | >45 | n/a | n/a | 2.2 | >45 |
| 346 | 12.12 | >45 | n/a | n/a | 1.1 | >45 |
| 348 | 74.78 | >45 | n/a | n/a | 59.2 | 45 |
| 349 | 84.00 | >45 | n/a | n/a | 0.2 | >45 |

TABLE 5-continued

Inhibition of Ole1, SCD1, and SCD5 by Compounds of the Invention

| Compound # | OLE1 % Max Inhibition | OLE1 IC50 | SCD1 % Max Inhibition | SCD1 IC50 (μM) | SCD5 % Max Inhibition | SCD5 IC50 (μM) |
|---|---|---|---|---|---|---|
| 350 | 71.00 | >45 | n/a | n/a | 56.3 | 45 |
| 351 | 68.60 | >45 | n/a | n/a | 57.3 | 45 |
| 352 | 71.57 | >45 | n/a | n/a | 44.5 | >45 |
| 354 | NT | NT | 30.16 | >45 | 4.29 | >45 |
| 355 | NT | NT | 71.31 | >45 | 3.68 | >45 |
| 356 | NT | NT | 51.18 | >45 | 2.88 | >45 |
| 357 | NT | NT | 64.32 | >45 | 2.31 | >45 |
| 358 | NT | NT | 59.61 | >45 | 4.53 | >45 |
| 359 | NT | NT | 55.70 | >45 | 0.81 | >45 |
| 360 | NT | NT | 64.03 | >45 | 2.38 | >45 |
| 361 | NT | NT | 67.22 | >45 | 0.95 | >45 |
| 362 | NT | NT | 67.00 | >45 | 2.26 | >45 |
| 363 | NT | NT | 64.44 | >45 | 1.99 | >45 |
| 364 | NT | NT | 70.82 | >45 | 2.22 | >45 |
| 365 | NT | NT | 58.08 | >45 | 23.74 | >45 |
| 495 | NT | NT | — | >45 | — | 1.917 |
| 496 | NT | NT | — | >45 | — | 0.445 |
| 497 | NT | NT | — | >45 | — | 11.33 |
| 498 | NT | NT | — | >45 | — | >45 |
| 499 | NT | NT | — | >45 | — | 1.103 |
| 500 | NT | NT | — | >45 | — | >45 |
| 501 | NT | NT | — | 12.16 | — | 21.27 |
| 502 | NT | NT | — | >45 | — | 38.94 |
| 503 | NT | NT | — | >45 | — | 0.316 |
| 504 | NT | NT | — | >45 | — | 14.84 |
| 505 | NT | NT | — | >45 | — | 0.669 |
| 506 | NT | NT | — | >45 | — | 0.81 |
| 507 | NT | NT | — | >45 | — | 2.443 |
| 508 | NT | NT | — | >45 | — | >45 |
| 509 | NT | NT | — | >45 | — | >45 |
| 510 | NT | NT | — | >45 | — | 4.16 |
| 511 | NT | NT | — | >45 | — | 3.39 |
| 512 | NT | NT | — | >45 | — | >45 |
| 513 | NT | NT | — | >45 | — | >45 |
| 514 | NT | NT | — | >45 | — | >45 |
| 515 | NT | NT | — | 16.53 | — | >45 |
| 516 | NT | NT | — | >45 | — | >45 |
| 517 | NT | NT | — | >45 | — | >45 |
| 518 | NT | NT | — | >45 | — | 2.95 |
| 519 | NT | NT | — | >45 | — | >45 |
| 520 | NT | NT | — | >45 | — | >45 |
| 521 | NT | NT | — | >45 | — | 8.794 |
| 522 | NT | NT | — | >45 | — | >45 |
| 523 | NT | NT | — | >45 | — | >45 |
| 524 | NT | NT | — | >45 | — | 2.499 |
| 745 | NT | NT | — | >45 | — | >45 |
| 525 | NT | NT | — | >45 | — | >45 |
| 526 | NT | NT | — | >45 | — | >45 |
| 527 | NT | NT | — | 0.958 | — | 1.46 |
| 528 | NT | NT | — | >45 | — | >45 |
| 529 | NT | NT | — | >45 | — | >45 |
| 530 | NT | NT | — | >45 | — | >45 |
| 531 | NT | NT | — | >45 | — | >45 |
| 532 | NT | NT | — | >45 | — | 2.15 |
| 533 | NT | NT | — | >45 | — | 3.331 |
| 534 | NT | NT | — | >45 | — | 36.8 |
| 535 | NT | NT | — | >45 | — | >45 |
| 536 | NT | NT | — | >45 | — | >45 |
| 537 | NT | NT | — | >45 | — | >45 |
| 538 | NT | NT | — | >45 | — | >45 |
| 539 | NT | NT | — | >45 | — | >45 |
| 540 | NT | NT | — | >45 | — | >45 |
| 541 | NT | NT | — | >45 | — | >45 |
| 542 | NT | NT | — | >45 | — | 7.331 |
| 543 | NT | NT | — | >45 | — | 45 |
| 544 | NT | NT | — | >45 | — | 10.03 |
| 545 | NT | NT | — | >45 | — | 18.95 |
| 546 | NT | NT | — | >45 | — | 0.019 |
| 547 | NT | NT | — | >45 | — | 44.3 |
| 548 | NT | NT | — | >45 | — | 0.01 |
| 549 | NT | NT | — | >45 | — | 1.211 |
| 550 | NT | NT | — | >45 | — | >45 |
| 551 | NT | NT | — | >45 | — | >45 |
| 552 | NT | NT | — | >45 | — | >45 |

TABLE 5-continued

Inhibition of Ole1, SCD1, and SCD5 by Compounds of the Invention

| Compound # | OLE1 % Max Inhibition | OLE1 IC50 | SCD1 % Max Inhibition | SCD1 IC50 (μM) | SCD5 % Max Inhibition | SCD5 IC50 (μM) |
|---|---|---|---|---|---|---|
| 553 | NT | NT | — | 5.708 | — | 0.885 |
| 554 | NT | NT | — | 4.079 | — | 1.071 |
| 555 | NT | NT | — | >45 | — | >45 |
| 556 | NT | NT | — | >45 | — | >45 |
| 557 | NT | NT | — | >45 | — | 6.03 |
| 558 | NT | NT | — | >45 | — | 1.072 |
| 559 | NT | NT | — | >45 | — | 1.191 |
| 560 | NT | NT | — | >45 | — | >45 |
| 561 | NT | NT | — | >45 | — | 29.43 |
| 562 | NT | NT | — | >45 | — | 1.496 |
| 563 | NT | NT | — | >45 | — | >45 |
| 564 | NT | NT | — | >45 | — | 4.234 |
| 565 | NT | NT | — | >45 | — | >45 |
| 567 | NT | NT | — | >45 | — | >45 |
| 568 | NT | NT | — | >45 | — | >45 |
| 569 | NT | NT | — | >45 | — | >45 |
| 570 | NT | NT | — | >45 | — | 26.35 |
| 571 | NT | NT | — | >45 | — | >45 |
| 572 | NT | NT | — | >45 | — | 14.99 |
| 573 | NT | NT | — | >45 | — | 5.601 |
| 574 | NT | NT | — | >45 | — | 2.282 |
| 575 | NT | NT | — | >45 | — | 4.681 |
| 576 | NT | NT | — | >45 | — | 0.028 |
| 577 | NT | NT | — | >45 | — | >45 |
| 578 | NT | NT | — | 8.457 | — | 1.487 |
| 579 | NT | NT | — | >45 | — | >45 |
| 580 | NT | NT | — | 14.08 | — | 0.022 |
| 581 | NT | NT | — | >45 | — | >45 |
| 582 | NT | NT | — | >45 | — | 0.176 |
| 583 | NT | NT | — | >45 | — | 0.989 |
| 584 | NT | NT | — | >45 | — | 5.338 |
| 585 | NT | NT | — | >45 | — | 1.807 |
| 586 | NT | NT | — | >45 | — | 3.768 |
| 587 | NT | NT | — | >45 | — | 4.92 |
| 588 | NT | NT | — | >45 | — | 1.861 |
| 589 | NT | NT | — | >45 | — | 0.356 |
| 590 | NT | NT | — | >45 | — | >45 |
| 591 | NT | NT | — | >45 | — | >45 |
| 592 | NT | NT | — | >45 | — | >45 |
| 593 | NT | NT | — | >45 | — | >45 |
| 594 | NT | NT | — | >45 | — | 11.8 |
| 595 | NT | NT | — | >45 | — | >45 |
| 596 | NT | NT | — | >45 | — | >45 |
| 597 | NT | NT | — | >45 | — | >45 |
| 598 | NT | NT | — | >45 | — | >45 |
| 599 | NT | NT | — | >45 | — | >45 |
| 600 | NT | NT | — | >45 | — | >45 |
| 601 | NT | NT | — | >45 | — | 5.686 |
| 602 | NT | NT | — | 15.94 | — | 2.744 |
| 603 | NT | NT | — | 7.258 | — | 2.411 |
| 604 | NT | NT | — | >45 | — | 6.12 |
| 605 | NT | NT | — | 31.84 | — | 0.513 |
| 606 | NT | NT | — | >45 | — | 0.737 |
| 607 | NT | NT | — | >45 | — | 0.511 |
| 608 | NT | NT | — | >45 | — | >45 |
| 609 | NT | NT | — | >45 | — | >45 |
| 610 | NT | NT | — | >45 | — | 2.157 |
| 611 | NT | NT | — | >45 | — | 7.479 |
| 612 | NT | NT | — | >45 | — | 2.385 |
| 613 | NT | NT | — | >45 | — | >45 |
| 614 | NT | NT | — | >45 | — | 13.92 |
| 615 | NT | NT | — | 0.848 | — | 1.878 |
| 616 | NT | NT | — | >45 | — | >45 |
| 617 | NT | NT | — | >45 | — | 0.121 |
| 618 | NT | NT | — | >45 | — | 0.101 |
| 619 | NT | NT | — | >45 | — | 0.291 |
| 620 | NT | NT | — | >45 | — | 0.013 |
| 621 | NT | NT | — | >45 | — | 0.042 |
| 622 | NT | NT | — | >45 | — | 1.614 |
| 623 | NT | NT | — | >45 | — | 0.854 |
| 624 | NT | NT | — | >45 | — | 0.222 |
| 625 | NT | NT | — | >45 | — | 0.122 |
| 626 | NT | NT | — | >45 | — | 2.75 |
| 627 | NT | NT | — | >45 | — | 6.686 |

TABLE 5-continued

Inhibition of Ole1, SCD1, and SCD5 by Compounds of the Invention

| Compound # | OLE1 % Max Inhibition | OLE1 IC50 | SCD1 % Max Inhibition | SCD1 IC50 (μM) | SCD5 % Max Inhibition | SCD5 IC50 (μM) |
|---|---|---|---|---|---|---|
| 628 | NT | NT | — | >45 | — | 0.01 |
| 629 | NT | NT | — | >45 | — | 0.03 |
| 630 | NT | NT | — | 10.24 | — | 0.014 |
| 631 | NT | NT | — | >45 | — | >45 |
| 632 | NT | NT | — | >45 | — | >45 |
| 633 | NT | NT | — | >45 | — | 0.214 |
| 634 | NT | NT | — | >45 | — | 45 |
| 635 | NT | NT | — | >45 | — | 0.397 |
| 636 | NT | NT | — | >45 | — | 1.801 |
| 637 | NT | NT | — | >45 | — | >45 |
| 638 | NT | NT | — | >45 | — | >45 |
| 639 | NT | NT | — | >45 | — | 4.791 |
| 640 | NT | NT | — | >45 | — | 3.98 |
| 641 | NT | NT | — | >45 | — | 6.72 |
| 642 | NT | NT | — | >45 | — | 0.211 |
| 643 | NT | NT | — | >45 | — | 0.01 |
| 644 | NT | NT | — | >45 | — | >45 |
| 645 | NT | NT | — | 17.92 | — | 4.473 |
| 646 | NT | NT | — | >45 | — | 1.184 |
| 647 | NT | NT | — | >45 | — | 9.371 |
| 648 | NT | NT | — | >45 | — | >45 |
| 649 | NT | NT | — | >45 | — | 0.259 |
| 650 | NT | NT | — | 4.359 | — | 0.013 |
| 651 | NT | NT | — | >45 | — | 18.43 |
| 652 | NT | NT | — | >45 | — | >45 |
| 653 | NT | NT | — | >45 | — | >45 |
| 654 | NT | NT | — | >45 | — | >45 |
| 655 | NT | NT | — | >45 | — | >45 |
| 656 | NT | NT | — | >45 | — | >45 |
| 657 | NT | NT | — | >45 | — | 9.109 |
| 658 | NT | NT | — | >45 | — | 0.089 |
| 659 | NT | NT | — | >45 | — | 4.201 |
| 660 | NT | NT | — | >45 | — | 14.62 |
| 661 | NT | NT | — | >45 | — | 1.541 |
| 662 | NT | NT | — | >45 | — | >45 |
| 663 | NT | NT | — | >45 | — | 0.01 |
| 664 | NT | NT | — | 23.48 | — | 0.023 |
| 665 | NT | NT | — | >45 | — | 5.006 |
| 666 | NT | NT | — | >45 | — | >45 |
| 667 | NT | NT | — | >45 | — | 0.87 |
| 668 | NT | NT | — | >45 | — | 0.719 |
| 669 | NT | NT | — | >45 | — | >45 |
| 670 | NT | NT | — | >45 | — | 3.789 |
| 671 | NT | NT | — | >45 | — | >45 |
| 672 | NT | NT | — | >45 | — | 0.441 |
| 673 | NT | NT | — | >45 | — | 33.85 |
| 674 | NT | NT | — | >45 | — | >45 |
| 675 | NT | NT | — | >45 | — | 0.01 |
| 676 | NT | NT | — | >45 | — | 0.013 |
| 677 | NT | NT | — | >45 | — | >45 |
| 678 | NT | NT | — | >45 | — | 3.868 |
| 679 | NT | NT | — | >45 | — | >45 |
| 680 | NT | NT | — | >45 | — | >45 |
| 681 | NT | NT | — | >45 | — | >45 |
| 682 | NT | NT | — | >45 | — | 0.01 |
| 683 | NT | NT | — | >45 | — | 10.15 |
| 684 | NT | NT | — | >45 | — | >45 |
| 685 | NT | NT | — | >45 | — | 0.184 |
| 686 | NT | NT | — | >45 | — | >45 |
| 687 | NT | NT | — | >45 | — | >45 |
| 688 | NT | NT | — | >45 | — | 1.504 |
| 689 | NT | NT | — | >45 | — | 0.657 |
| 690 | NT | NT | — | >45 | — | 0.131 |
| 691 | NT | NT | — | >45 | — | >45 |
| 692 | NT | NT | — | >45 | — | 0.492 |
| 693 | NT | NT | — | >45 | — | 1.666 |
| 694 | NT | NT | — | >45 | — | >45 |
| 695 | NT | NT | — | >45 | — | 2.394 |
| 696 | NT | NT | — | >45 | — | 0.08 |
| 697 | NT | NT | — | >45 | — | 0.059 |
| 698 | NT | NT | — | >45 | — | 0.026 |
| 699 | NT | NT | — | >45 | — | 7.647 |
| 700 | NT | NT | — | >45 | — | 0.703 |
| 701 | NT | NT | — | >45 | — | >45 |

TABLE 5-continued

Inhibition of Ole1, SCD1, and SCD5 by Compounds of the Invention

| Compound # | OLE1 % Max Inhibition | OLE1 IC50 | SCD1 % Max Inhibition | SCD1 IC50 (μM) | SCD5 % Max Inhibition | SCD5 IC50 (μM) |
|---|---|---|---|---|---|---|
| 702 | NT | NT | — | >45 | — | >45 |
| 703 | NT | NT | — | >45 | — | 0.121 |
| 704 | NT | NT | — | >45 | — | 1.677 |
| 705 | NT | NT | — | 14.37 | — | 0.174 |
| 706 | NT | NT | — | >45 | — | >45 |
| 707 | NT | NT | — | >45 | — | 14.53 |
| 708 | NT | NT | — | >45 | — | >45 |
| 709 | NT | NT | — | >45 | — | 4.774 |
| 710 | NT | NT | — | >45 | — | 0.05 |
| 711 | NT | NT | — | >45 | — | >45 |
| 712 | NT | NT | — | >45 | — | 0.016 |
| 713 | NT | NT | — | 5.583 | — | 0.01 |
| 714 | NT | NT | — | >45 | — | 0.23 |
| 715 | NT | NT | — | >45 | — | 0.048 |
| 716 | NT | NT | — | >45 | — | >45 |
| 717 | NT | NT | — | >45 | — | 1.698 |
| 718 | NT | NT | — | >45 | — | 0.635 |
| 719 | NT | NT | — | >45 | — | >45 |
| 720 | NT | NT | — | >45 | — | 1.966 |
| 721 | NT | NT | — | >45 | — | 1.653 |
| 722 | NT | NT | — | >45 | — | 1.374 |
| 723 | NT | NT | — | >45 | — | >45 |
| 724 | NT | NT | — | >45 | — | 1.249 |
| 725 | NT | NT | — | 5.99 | — | 0.011 |
| 726 | NT | NT | — | 5.65 | — | 0.01 |
| 727 | NT | NT | — | >45 | — | >45 |
| 728 | NT | NT | — | >45 | — | 0.126 |
| 729 | NT | NT | — | >45 | — | >45 |
| 730 | NT | NT | — | >45 | — | 0.718 |
| 731 | NT | NT | — | >45 | — | >45 |
| 732 | NT | NT | — | >45 | — | 31.82 |
| 733 | NT | NT | — | >45 | — | 2.727 |
| 734 | NT | NT | — | >45 | — | >45 |
| 735 | NT | NT | — | 3.99 | — | 0.01 |
| 736 | NT | NT | — | 32.65 | — | 0.26 |
| 737 | NT | NT | — | >45 | — | >45 |
| 738 | NT | NT | — | >45 | — | >45 |
| 739 | NT | NT | — | >45 | — | >45 |
| 740 | NT | NT | — | >45 | — | 1.43 |
| 741 | NT | NT | — | >45 | — | 7.756 |
| 742 | NT | NT | — | >45 | — | 5.048 |
| 743 | NT | NT | — | >45 | — | 14.78 |
| 744 | NT | NT | — | >45 | — | >45 |

TABLE 6

Inhibition of SCD1 and SCD5 by Compounds of the Invention

| # | SCD1 IC50 (μM) | SCD5 IC50 (μM) |
|---|---|---|
| 747 | >45 | 26.801 |
| 748 | >45 | 2.140 |
| 749 | >45 | 20.798 |
| 750 | 3.25 | 0.010 |
| 751 | >45 | >45 |
| 752 | >45 | >45 |
| 753 | >45 | 0.585 |
| 754 | >45 | 16.472 |
| 755 | >45 | 5.413 |
| 756 | >45 | 4.363 |
| 757 | >45 | 4.951 |
| 758 | >45 | 5.271 |
| 759 | >45 | >45 |
| 760 | >45 | >45 |
| 761 | >45 | >45 |
| 762 | >45 | 5.253 |
| 763 | 29.49 | 18.001 |
| 764 | >45 | 16.700 |
| 765 | 32.91 | 19.277 |
| 766 | >45 | >45 |
| 767 | >45 | 0.010 |
| 768 | >45 | >45 |
| 769 | >45 | >45 |
| 770 | >45 | >45 |
| 771 | >45 | >45 |
| 772 | >45 | >45 |
| 773 | >45 | 21.475 |
| 774 | >45 | >45 |
| 775 | >45 | 0.022 |
| 776 | >45 | 0.025 |
| 777 | 4.16 | 0.010 |
| 778 | >45 | 0.012 |
| 779 | >45 | 15.285 |
| 780 | >45 | 0.027 |
| 781 | >45 | 4.800 |
| 782 | >45 | 0.149 |
| 783 | >45 | >45 |
| 784 | 0.95 | 0.010 |
| 785 | 9.21 | 0.041 |
| 786 | >45 | >45 |
| 787 | 31.50 | 0.108 |
| 788 | >45 | 6.218 |

TABLE 6-continued

Inhibition of SCD1 and SCD5 by Compounds of the Invention

| # | SCD1 IC50 (µM) | SCD5 IC50 (µM) |
|---|---|---|
| 789 | >45 | 0.010 |
| 790 | >45 | 0.053 |
| 791 | >45 | 0.010 |
| 792 | 8.83 | 0.010 |
| 793 | >45 | >45 |
| 794 | >45 | >45 |
| 795 | >45 | 0.010 |
| 796 | >45 | 1.589 |
| 797 | >45 | 0.133 |
| 798 | >45 | >45 |
| 799 | >45 | 0.010 |
| 801 | >45 | 0.363 |
| 802 | >45 | 14.209 |
| 803 | 12.88 | 0.679 |
| 804 | >45 | >45 |
| 805 | >45 | 9.360 |
| 806 | >45 | >45 |
| 807 | >45 | 0.247 |
| 808 | >45 | 5.816 |
| 809 | >45 | 0.124 |
| 810 | >45 | 2.497 |
| 811 | >45 | 0.679 |
| 812 | >45 | 0.010 |
| 813 | >45 | 0.010 |
| 814 | >45 | >45 |
| 815 | >45 | >45 |
| 816 | >45 | 7.186 |
| 817 | 4.13 | 0.010 |
| 818 | >45 | 0.560 |
| 819 | >45 | 3.725 |
| 820 | >45 | 3.744 |
| 821 | >45 | 5.058 |
| 822 | >45 | 0.111 |
| 823 | >45 | 0.119 |
| 824 | >45 | 0.932 |
| 825 | >45 | 9.490 |
| 826 | >45 | 1.990 |
| 827 | >45 | >45 |
| 828 | >45 | 0.067 |
| 829 | >45 | 2.202 |
| 830 | >45 | >45 |
| 831 | >45 | 1.202 |
| 832 | >45 | 11.644 |
| 833 | >45 | >45 |
| 834 | >45 | >45 |
| 835 | >45 | >45 |
| 836 | >45 | 1.438 |
| 837 | >45 | 12.527 |
| 838 | >45 | 0.021 |
| 839 | >45 | 0.035 |
| 840 | >45 | 20.683 |
| 841 | >45 | 0.209 |
| 842 | >45 | 0.010 |
| 843 | >45 | 0.033 |
| 844 | >45 | 0.015 |
| 845 | >45 | 0.637 |
| 846 | >45 | 0.040 |
| 847 | >45 | >45 |
| 848 | >45 | 0.010 |
| 849 | >45 | 0.644 |
| 850 | >45 | 0.010 |
| 851 | >45 | 0.065 |
| 852 | >45 | 5.358 |
| 853 | >45 | 0.010 |
| 854 | 14.57 | 0.010 |
| 855 | >45 | >45 |
| 856 | >45 | >45 |
| 857 | >45 | 26.801 |
| 858 | >45 | 0.262 |
| 859 | >45 | >4 |
| 860 | >45 | 0.478 |
| 861 | 14.96 | 0.010 |
| 862 | 33.83 | 0.010 |
| 863 | >45 | >45 |
| 864 | >45 | >45 |
| 865 | >45 | 0.010 |
| 866 | >45 | 4.607 |
| 867 | >45 | 1.915 |
| 868 | >45 | 0.967 |
| 869 | >45 | 1.64 |
| 870 | >45 | 4.26 |
| 871 | >45 | 9.54 |
| 872 | >45 | 8.06 |
| 873 | >45 | 41.27 |
| 874 | >45 | 0.05 |
| 875 | >45 | 0.02 |
| 876 | >45 | 0.01 |
| 877 | >45 | 0.08 |
| 878 | >45 | 0.005 |
| 879 | 5.50 | 0.01 |
| 880 | >45 | 0.010 |
| 881 | >45 | 0.01 |
| 882 | 6.56 | 1.91 |
| 883 | >45 | 1.00 |
| 884 | >45 | 0.01 |
| 885 | 25.38 | 0.01 |
| 886 | 10.62 | 0.06 |
| 887 | >45 | 0.01 |
| 888 | >45 | 0.01 |
| 889 | 13.31 | 1.90 |
| 890 | 22.69 | 0.01 |
| 891 | >45 | 0.01 |
| 892 | >45 | 0.01 |
| 893 | >45 | 0.01 |
| 894 | >45 | 0.07 |
| 895 | >45 | 0.01 |
| 896 | >45 | 0.01 |
| 897 | >45 | 0.06 |
| 898 | >45 | 0.07 |
| 899 | >45 | 25.98 |
| 900 | >45 | 13.08 |
| 901 | >45 | >45 |
| 902 | >45 | 0.01 |
| 903 | >45 | 0.01 |
| 904 | >45 | 7.62 |
| 905 | >45 | >45 |
| 906 | >45 | 0.89 |
| 907 | >45 | 0.04 |
| 908 | >45 | 0.19 |
| 909 | >45 | 2.85 |
| 910 | >45 | 0.01 |
| 911 | >45 | >45 |
| 912 | >45 | 1.98 |
| 913 | >45 | 13.79 |
| 914 | >45 | 6.17 |
| 915 | >45 | 10.12 |
| 916 | 1.96 | 0.01 |
| 917 | >45 | 0.10 |
| 918 | >45 | 0.80 |
| 919 | >45 | 0.18 |
| 920 | 11.67 | 0.10 |
| 921 | >45 | 3.40 |
| 922 | >45 | 6.56 |
| 923 | >45 | >45 |
| 924 | >45 | 4.09 |
| 925 | >45 | >45 |
| 926 | >45 | >45 |
| 927 | >45 | 0.14 |
| 928 | >45 | 0.01 |
| 929 | >45 | 4.42 |
| 930 | >45 | 0.20 |
| 931 | >45 | >45 |
| 932 | >45 | 0.01 |
| 933 | >45 | 0.20 |
| 934 | >45 | 0.01 |
| 935 | >45 | >45 |
| 936 | >45 | 3.45 |
| 937 | >45 | >45 |
| 938 | >45 | >45 |
| 939 | >45 | 10.91 |
| 940 | >45 | 31.18 |
| 941 | >45 | 20.36 |

TABLE 6-continued

Inhibition of SCD1 and SCD5 by Compounds of the Invention

| # | SCD1 IC50 (μM) | SCD5 IC50 (μM) |
|---|---|---|
| 942 | >45 | 9.16 |
| 943 | >45 | >45 |
| 944 | >45 | 2.22 |
| 945 | >45 | 5.29 |
| 946 | >45 | 4.11 |
| 947 | >45 | >45 |
| 948 | >45 | >45 |
| 949 | >45 | >45 |
| 950 | >45 | >45 |
| 951 | >45 | >45 |
| 952 | 15.60 | 9.22 |
| 953 | >45 | 0.01 |
| 954 | >45 | 2.86 |
| 955 | >45 | >45 |
| 956 | >45 | 2.46 |
| 957 | 27.91 | 0.01 |
| 958 | >45 | 34.53 |
| 959 | >45 | >45 |
| 960 | 20.36 | 0.01 |
| 961 | >45 | >45 |
| 962 | >45 | 0.01 |
| 963 | >45 | 0.16 |
| 964 | 0.31 | 0.03 |
| 965 | >45 | 0.01 |
| 966 | >45 | 0.15 |

Other Embodiments

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

Other embodiments are in the claims.

What is claimed is:

1. A compound having the structure:

$R^1(L^1)_n L^2$-B-Het-$R^5$ wherein B has the structure:

[chemical structure], or [chemical structure];

Het is

[chemical structure] or [chemical structure];

n is 0 or 1;
o is 0, 1, or 2;
p and r are, independently, 0 or 1;
$X^1$ is N or $CR^6$;
$X^2$ is N;
$L^1$ is —O—;
$L^2$ is $CR^2R^3$;
$R^1$ is optionally substituted phenyl, optionally substituted $C_3$-$C_7$ cycloalkyl, optionally substituted $C_3$-$C_7$ cycloalkyl $C_1$-$C_6$ alkyl, or $C_2$-$C_9$ heterocycle optionally substituted with $C_1$-$C_6$ alkyl or $C_1$-$C_6$ heteroalkyl;
$R^2$ and $R^3$ are each, independently, hydrogen or $R^2$ and $R^3$ combine with the carbon to which they are attached to form a carbonyl;
each $R^4$ is, independently, halogen, hydroxyl, optionally substituted $C_1$-$C_6$ alkyl, or two $R^4$ combine with the carbon to which they are attached to form a carbonyl;
$R^5$ is a bicyclic heteroaryl comprising a 6-membered ring, wherein $R^5$ is unsubstituted or is substituted with 1 to 4 substituents selected from the group consisting of $C_1$-$C_6$ alkyl and $C_2$-$C_9$ heterocyclyl; and
each $R^6$ is, independently, hydrogen, halogen, or optionally substituted $C_1$-$C_6$ alkyl,
or a pharmaceutically acceptable salt thereof.

2. The compound of claim 1, wherein B has the structure:

[chemical structure].

3. The compound of claim 2, wherein B has the structure:

[chemical structure].

4. The compound of claim 2, wherein B has the structure:

[chemical structure], [chemical structure], or

[chemical structure].

5. The compound of claim 1, wherein $R^1$ is $C_2$-$C_9$ heterocycle optionally substituted with $C_1$-$C_6$ alkyl or $C_1$-$C_6$ heteroalkyl.

6. The compound of claim 5, wherein $C_2$-$C_9$ heterocycle optionally substituted with $C_1$-$C_6$ alkyl or $C_1$-$C_6$ heteroalkyl is

[chemical structures]

7. The compound of claim 2, having the structure:

[chemical structure]

wherein $R^2$ and $R^3$ are each, independently, hydrogen or $R^2$ and $R^3$ combine with the carbon to which they are attached to form a carbonyl;
each $R^4$ is, independently, fluoro, methyl, or two $R^4$ combine with the carbon to which they are attached to form a carbonyl;
$R^5$ is $C_2$-$C_9$ bicyclic heteroaryl comprising a 6-membered ring, wherein $R^5$ is substituted with 1 to 4 substituents selected from the group consisting of $C_1$-$C_6$ alkyl, and $C_2$-$C_9$ heterocyclyl; and
each $R^6$ is, independently, hydrogen or methyl.

8. The compound of claim 1, wherein $R^5$ is an indazole having the structure:

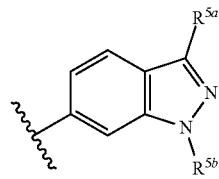

wherein $R^{5a}$ is hydrogen or optionally substituted $C_1$-$C_6$ alkyl, and
$R^{5b}$ is $C_1$-$C_6$ alkyl; or $C_2$-$C_9$ heterocyclyl.

9. A pharmaceutical composition comprising the compound of claim 1, and a pharmaceutically acceptable excipient.

10. The compound of claim 8, wherein $R^{5b}$ is methyl or iso-propyl.

11. The compound of claim 8, wherein $R^{5b}$ is oxetane.

12. The compound of claim 1, wherein the compound is selected from the group consisting of:

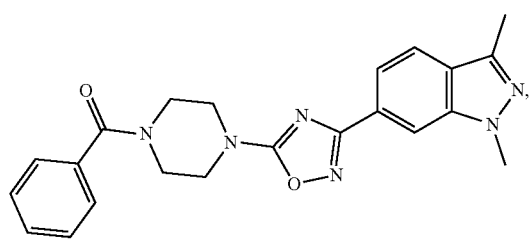

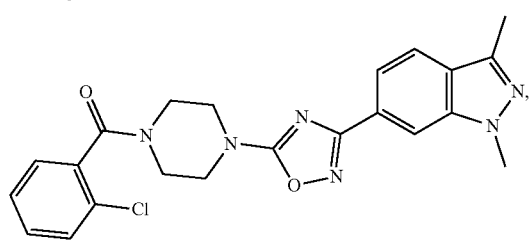

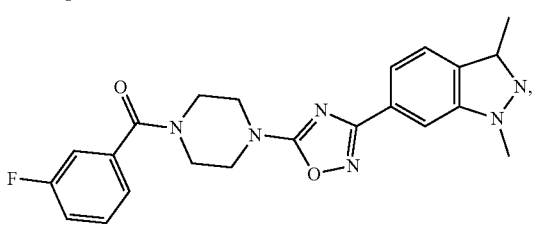

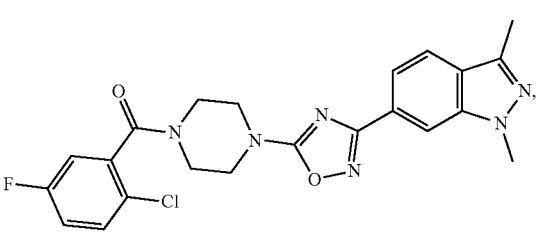

-continued

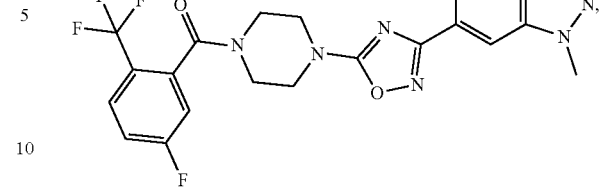

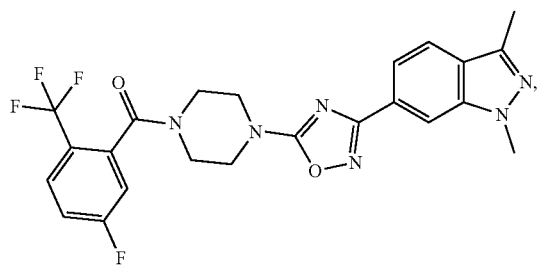

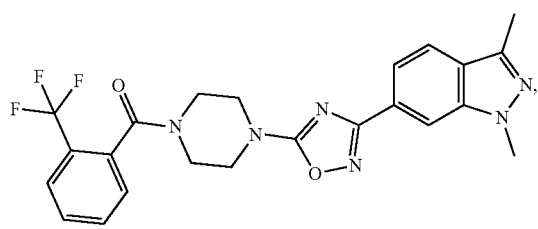

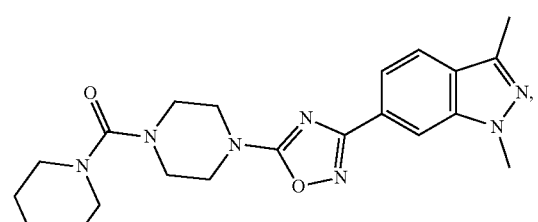

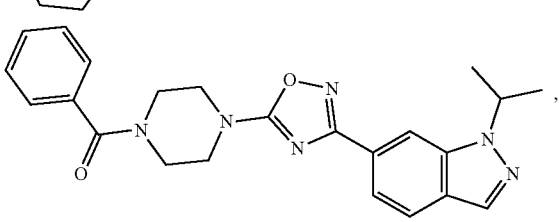

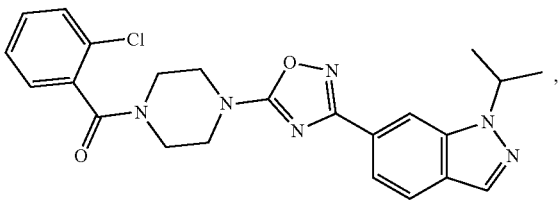

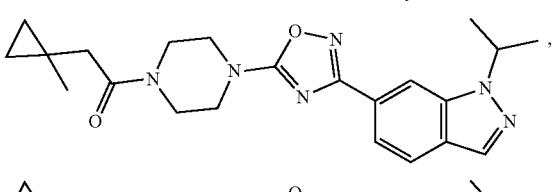

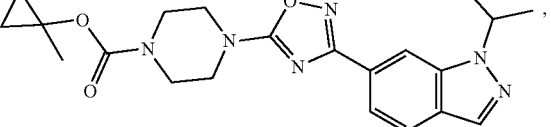

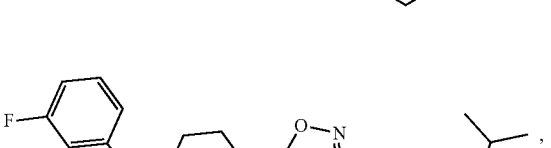

789
-continued
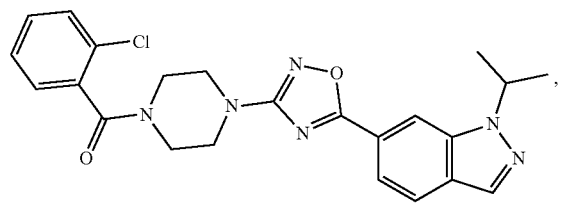
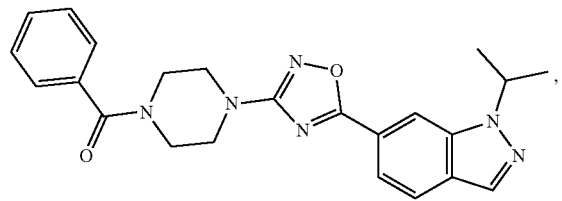
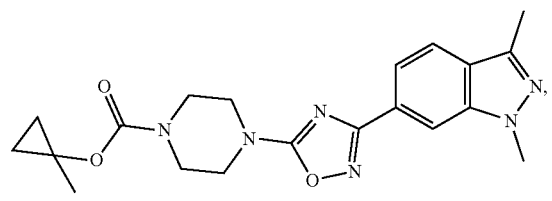
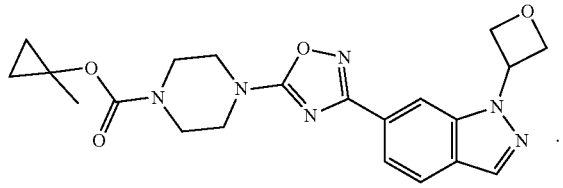
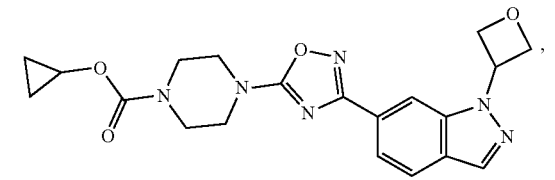
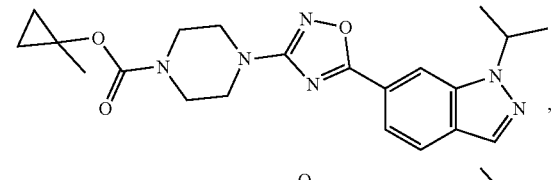
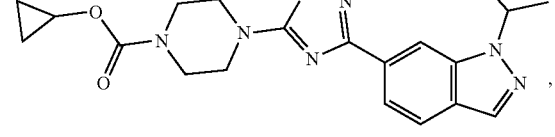
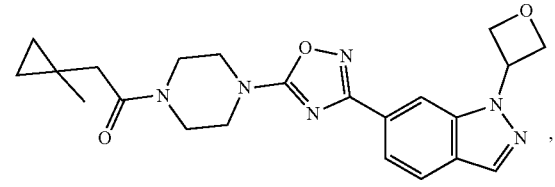
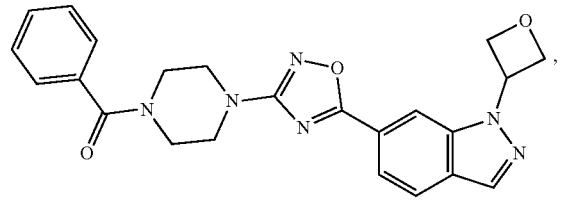
790
-continued
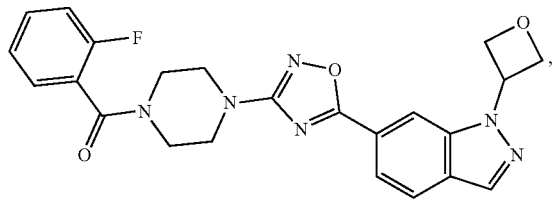
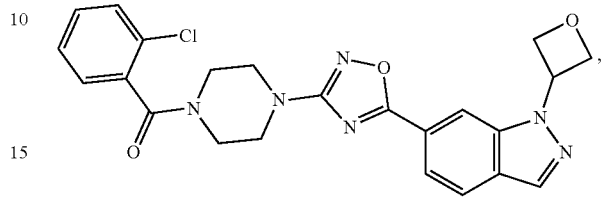
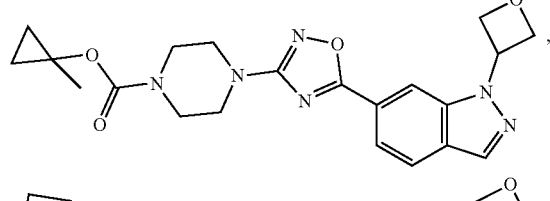
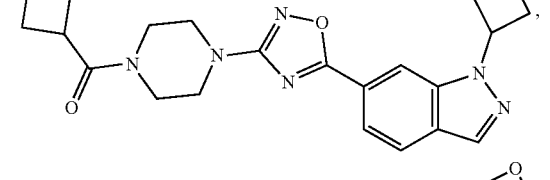
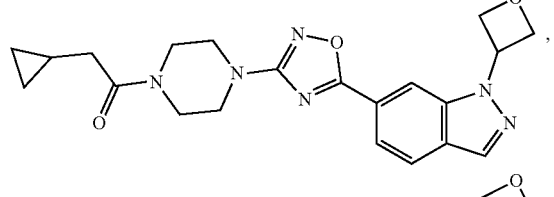
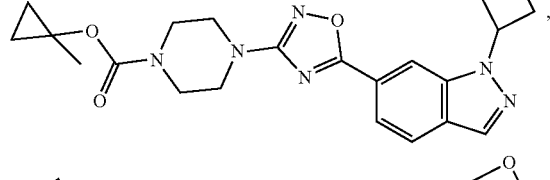
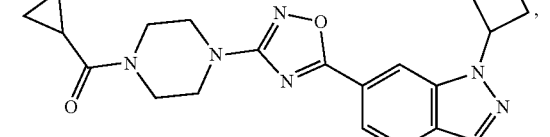
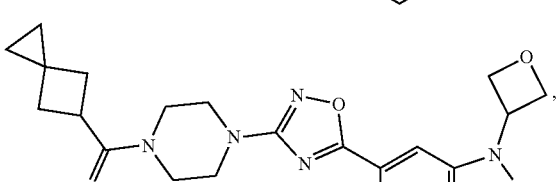
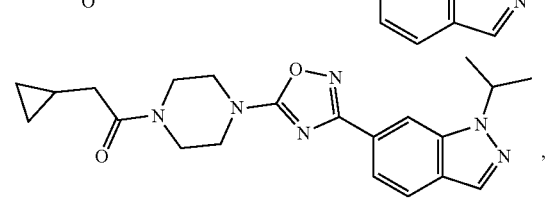

791
-continued
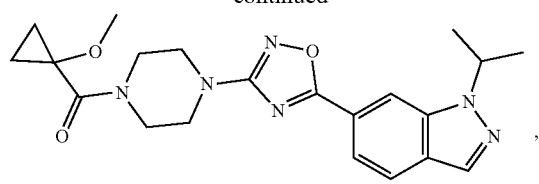
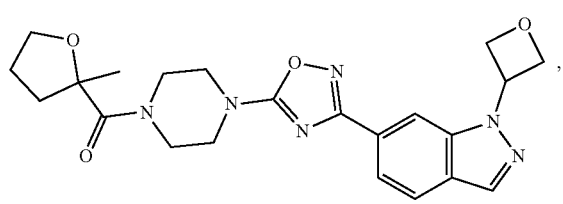
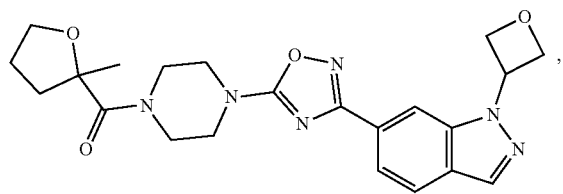
792
-continued
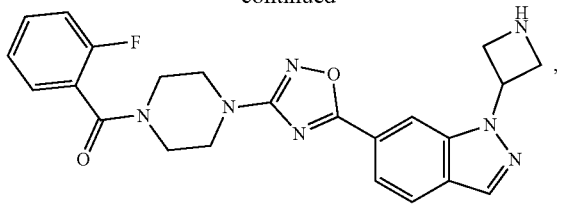
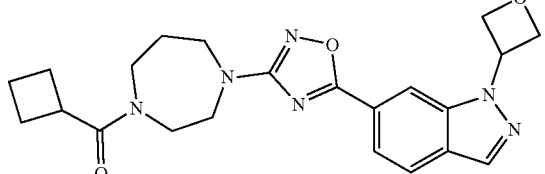
and
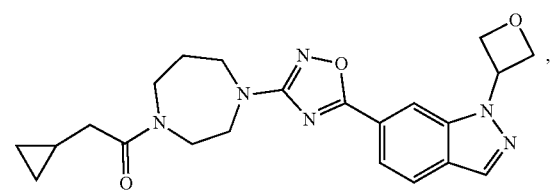
and pharmaceutically acceptable salts thereof.
* * * * *